(12) United States Patent
Sperry et al.

(10) Patent No.: US 11,286,268 B1
(45) Date of Patent: Mar. 29, 2022

(54) EIF4E-INHIBITING COMPOUNDS AND METHODS

(71) Applicant: EFFECTOR THERAPEUTICS, INC., San Diego, CA (US)

(72) Inventors: Samuel Sperry, Encinitas, CA (US); Alan X. Xiang, Irvine, CA (US); Justin T. Ernst, San Diego, CA (US); Siegfried H. Reich, La Jolla, CA (US); Paul A. Sprengeler, Escondido, CA (US); Mike Shaghafi, San Diego, CA (US); Theo Michels, San Diego, CA (US); Christian Nilewski, La Jolla, CA (US); Chinh Viet Tran, San Diego, CA (US); Garrick Kenneth Packard, San Diego, CA (US); Alan Grubbs, Spring Valley, CA (US); Kaveri Urkalan, San Diego, CA (US); Takasuke Mukaiyama, San Diego, CA (US)

(73) Assignee: eFFECTOR Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/916,820

(22) Filed: Jun. 30, 2020

Related U.S. Application Data

(60) Provisional application No. 62/869,662, filed on Jul. 2, 2019.

(51) Int. Cl.
*C07D 519/00* (2006.01)
*C07D 495/04* (2006.01)

(52) U.S. Cl.
CPC .......... *C07D 519/00* (2013.01); *C07D 495/04* (2013.01)

(58) Field of Classification Search
CPC ............................ C07D 519/00; C07D 495/04
See application file for complete search history.

(56) References Cited

U.S. PATENT DOCUMENTS 9,993,494 B2   6/2018  Appleman et al.

FOREIGN PATENT DOCUMENTS

WO        2014179237  A1   11/2014
WO     WO2014/179237    *  11/2014

OTHER PUBLICATIONS

Chen et al., "Structure-Guided Design, Synthesis, and Evaluation of Guanine-Derived Inhibitors of the eIF4E mRNA-Cap Interaction," J Med. Chem. 55, 3837-51, 2012.
Giri et al., "Synthesis and evaluation of quinazolinone derivatives as inhibitors of NF-?B, AP-1 mediated transcription and eIF-4E mediated translational activation: Inhibitors of multi-pathways involved in cancer," Eur. J. Med. Chem. 45, 3558-63, 2010.
PCT/US2020/040299 Search Report and Written Opinion, dated Aug. 21, 2020.
Rörsch et al., "Structure-Activity Relationship of Nonacidic Quinazolinone Inhibitors of Human Microsomal Prostaglandin Synthase 1 (mPGES?1)," J. Med. Chem. 55, 3792-803, 2012.

* cited by examiner

*Primary Examiner* — Dennis Heyer
(74) *Attorney, Agent, or Firm* — Banner & Witcoff, Ltd.

(57) ABSTRACT

The present invention provides synthesis, pharmaceutically acceptable formulations and uses of compounds in accordance with Formula I, or a stereoisomer, tautomer or pharmaceutically acceptable salt thereof.

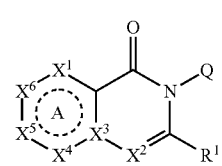

(I)

For Formula I compounds $X^1$, $X^2$, $X^3$, $X^4$, $X^5$, $X^6$, Q, $L^1$, $L^2$, Y, $R^1$, $R^2$, $R^3$, $R^4$, $R^5$, $R^6$, $R^7$, $R^8$ and rings A, B and C are as defined in the specification. The inventive Formula I compounds are inhibitors of eIF4e and find utility in any number of therapeutic applications, including but not limited to treatment of inflammation and various cancers.

28 Claims, 2 Drawing Sheets

EIF4E-INHIBITING COMPOUNDS AND METHODS

FIELD

The present invention generally relates to compounds having activity as inhibitors of eukaryotic initiation factor 4e (eIF4e), as well as to related compositions and methods for utilizing the inventive compounds as therapeutic agents for treatment of eIF4e dependent diseases, including the treatment of cancer.

BACKGROUND

Eukaryotic initiation factor 4E (eIF4E) is a general translation factor, but it has the potential to enhance preferentially the translation of messenger RNAs (mRNAs) that lead to production of malignancy-associated proteins. This selectivity may relate to an increased requirement for eIF4E and its binding partners for the translation of mRNAs containing extensive secondary structure in their 5'-untranslated regions (5'-UTRs). These mRNAs include those encoding certain proteins that control cell cycle progression and tumorigenesis. Under normal cellular conditions the translation of these malignancy-associated mRNAs is suppressed as the availability of active eIF4E is limited; however, their levels can increase when eIF4E is over-expressed or hyperactivated. Elevated levels of eIF4E have been found in many types of tumors and cancer cell lines including cancers of the colon, breast, bladder, lung, prostate, gastrointestinal tract, head and neck, Hodgkin's lymphomas and neuroblastomas.

Initiation of cap-dependent translation is thought to depend on the assembly of eIF4F, an initiation factor complex including eIF4E, the scaffold protein eIF4G, and the RNA helicase eIF4A. Because eIF4E is the only one of these proteins that binds directly to the mRNA cap structure, it is the key factor for the assembly of eIF4F at the 5' cap. The scaffold protein, eIF4G, also recruits the 40S ribosomal subunit to the mRNA via its interaction with eIF3 and binds eIF4B, a protein that aids the RNA-helicase function of eIF4A, thus facilitating the translation of mRNAs that contain structured 5'-UTRs. The availability of eIF4E as part of the eIF4F complex is a limiting factor in controlling the rate of translation, and therefore eIF4E is an important regulator of mRNA translation.

Regulation of eIF4E activity forms a node of convergence of the PI3K/Akt/mTOR and Ras/Raf/MAPK signaling pathways. The PI3K (phosphoinositide 3-kinase)/PTEN (phosphatase and tensin homologue deleted on chromosome ten)/Akt/mTOR (mammalian target of rapamycin) pathway is often involved in tumorigenesis and in sensitivity and resistance to cancer therapy. Deregulated signaling through the PI3K/PTEN/Akt/mTOR pathway is often the result of genetic alterations in critical components of this pathway and/or mutations at upstream growth factor receptors or signaling components. PI3K initiates a cascade of events when activated by, for example, extracellular growth factors, mitogens, cytokines and/or receptors, PDK1 activates Akt, which in turn phosphorylates and inactivates the tumor suppressor complex comprising TSC1 and 2 (tuberous sclerosis complex 1/2), resulting in the activation of mTORC1 (target of rapamycin complex 1) by Rheb-GTP. Activation of PDK1 and Akt by PI3Ks is negatively regulated by PTEN. PTEN is a critical tumor suppressor gene and is often mutated or silenced in human cancers. Its loss results in activation of Akt and increases downstream mTORC1 signaling. The involvement of mTOR complex1 (mTORC1) in neoplastic transformation appears to depend on its regulatory role toward the eIF4F complex; overexpression of eIF4E can confer resistance to rapamycin. mTORC1 regulates the eIF4F complex assembly that is critical for the translation of mRNAs associated with cell growth, prevention of apoptosis and transformation. mTORC1 achieves this by phosphorylation and inactivation of 4E-BPs and the subsequent dissociation of 4E-BPs from eIF4E. This then enables eIF4E to interact with the scaffold protein eIF4G, permitting assembly of the eIF4F complex for the translation of structured mRNAs. mTORC1 also promotes activation of the translational activator, S6K, which phosphorylates the ribosomal protein S6 and other substrates, including eIF4B. mTORC1 signaling is inhibited by rapamycin and its analogues (rapalogs), although these compounds act allosterically, rather than directly inhibiting mTOR kinase activity.

Given the importance of the PI3K/Akt/mTOR pathway in regulating mRNA translation of genes that encode for pro-oncogenic proteins and activated mTORC1 signaling in a high proportion of cancers, these kinases have been actively pursued as oncology drug targets. A number of pharmacological inhibitors have been identified, some of which have reached advanced clinical stages. However, it has recently become clear that the mTOR pathway participates in a complicated feedback loop that can impair activation of Akt. It has been shown that prolonged treatment of cancer cells or patients with mTOR inhibitors causes elevated PI3K activity that leads to phosphorylation of Akt and eIF4E, and promotes cancer cell survival. eIF4E, acting downstream of Akt and mTOR, recapitulates Akt's action in tumorigenesis and drug resistance, and Akt signaling via eIF4E is an important mechanism of oncogenesis and drug resistance in vivo.

In addition to the PI3K/Akt/mTOR pathway, eIF4E is also the target of the Ras/Raf/MAP signaling cascade which is activated by growth factors and for the stress-activated p38 MAP kinase pathway. Erk1/2 and p38 then phosphorylate MAP kinase-interacting kinase 1 (Mnk1) and MAP kinase-interacting kinase 2 (Mnk2). The Erk pathway is also activated in many cancers, reflecting, for example, activating mutations in Ras (found in around 20% of tumors) or loss of function of the Ras GTPase-activator protein NF1. Mnk1 and Mnk2 are threonine/serine protein kinases and specifically phosphorylate serine 209 (Ser209) of eIF4E within the eIF4F complex, by virtue of the interaction between eIF4E and the Mnks, which serves to recruit Mnks to act on eIF4E. Mice with mutated eIF4E, in which Ser209 is replaced by alanine, show no eIF4E phosphorylation and significantly attenuated tumor growth. Significantly, while Mnk activity is necessary for eIF4E-mediated oncogenic transformation, it is dispensable for normal development. Pharmacologically inhibiting Mnks thus presents an attractive therapeutic strategy for cancer.

Despite increased understanding of Mnk structure and function, little progress has been made with regard to the discovery of pharmacological Mnk inhibitors and relatively few Mnk inhibitors have been reported: CGP052088 (Tschopp et al., *Mol Cell Biol Res Commun.* 3(4):205-211, 2000); CGP57380 (Rowlett et al., *Am JPhysiol Gastrointest Liver Physiol.* 294(2):G452-459, 2008); and Cercosporamide (Konicek et al., *Cancer Res.* 71(5):1849-1857, 2011). These compounds, however, have mainly been used for the purpose of Mnk target validation. More recently, investigators have proposed further compounds for treating diseases influenced by the inhibition of kinase activity of Mnk1 and/or Mnk2, including, for example, the compounds disclosed in International Patent Application Publication WO 2014/044691 and the various patent documents cited therein, the 4-(dihydropyridinon-3-yl)amino-5-methylthieno[2,3,-d]pyrimidines disclosed by Yu et al., *European Journal of Med. Chem.*, 95: 116-126, 2015, and the 6'-((6-aminopyrimidin-4-yl)amino)-8'-methyl-2'H-spiro[cyclohexane-1,3'-imidazo[1,5-a]pyridine]-1',5'-dione and the various compounds disclosed in International Patent Application Publication WO 2015/200481.

Accordingly, while advances have been made in this field there remains a significant need in the art for compounds that specifically inhibit eFI4E activity, particularly with regard to eIF4E's role in regulation of cancer pathways, as well as for associated composition and methods. The present invention fulfils this need and provides further related advantages.

SUMMARY

The present invention is directed to compounds that inhibit or modulate the activity of eIF4E, as well as stereoisomers, tautomers and pharmaceutically acceptable salts of such compounds. The present invention also is directed to pharmaceutically acceptable compositions containing such compounds and associated methods for treating conditions that would benefit from eIF4E inhibition, such as cancer.

In one embodiment the invention is directed to compounds according to Formula I

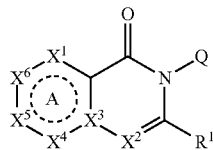

(I)

or stereoisomers, tautomers, or pharmaceutically acceptable salts thereof, wherein:

$X^1$ is $CR^2$, —C-$L^1$-Y or N;

$X^2$, $X^5$ and $X^6$ are independently $CR^2$ or N,
  wherein $X^5$ and $X^6$ together with 3 or 4 carbon or nitrogen atoms combine to form a 5- or 6-membered cycloalkyl or heterocyclyl,
  or when $X^2$ is $CR^2$, $R^1$ and $R^2$ together with the atoms they attached to form a 6-membered aryl or heteroaryl;

$X^3$ is C, or $X^3$ is C or N when $X^4$ is a bond;

$X^4$ is a bond, $CR^2$ or N,
  wherein $X^4$ and $X^5$ together with 3 or 4 carbon or nitrogen atoms combine to form a 5- or 6-membered heteroaryl;

Q is H or -$L^1$-Y;

$L^1$ is —(CH)—, —(CH$_2$)$_2$—, —(CH$_2$)$_3$—, —CH((C$_1$-C$_8$)alkyl)(CH$_2$)—, —CH((C$_1$-C$_8$)alkyl)(CH$_2$)$_2$—, —(CH$_2$)$_2$—O—, —CH$_2$CH=CH—, —CH$_2$C≡C— or —CH$_2$(cyclopropyl)-;

Y is

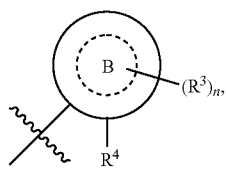

wherein
Ring B is a six-membered aryl, heteroaryl or heterocyclyl;

$R^1$ is H, OH, halo, CN, (C$_1$-C$_8$)alkyl, (C$_1$-C$_8$)haloalkyl, (C$_3$-C$_6$)cycloalkyl or NR$^5$R$^5$;

$R^2$ is independently H, halo, CN, NO, NO$_2$, C≡H, (C$_1$-C$_8$)alkyl, (C$_1$-C$_8$)haloalkyl, CH$_2$SR$^5$, OR$^5$, NHR$^5$, NR$^5$R$^5$, [(C$_1$-C$_8$)alkylene]heterocyclyl, [(C$_1$-C$_8$)alkylene]heteroaryl, [(C$_1$-C$_8$)alkylene]NHR$^5$, [(C$_1$-C$_8$)alkylene]NR$^5$R$^5$, [(C$_1$-C$_8$)alkylyne]NR$^5$R$^5$, C(O)R$^5$, C(O)OR$^5$, C(O)NHR$^5$, C(O)NR$^5$R$^5$, SR$^5$, S(O)R$^5$, SO$_2$R$^5$, SO$_2$NHR$^5$, SO$_2$NR$^5$R$^5$, NH(CO)R$^6$, NR$^5$(CO)R$^6$, aryl, heteroaryl, cycloalkyl or heterocyclyl;

$R^3$ is independently OH, halo, CN, NO$_2$, (C$_1$-C$_6$)alkyl, (C$_1$-C$_6$)haloalkyl, (C$_1$-C$_6$)alkoxy, C≡H, NHR$^7$, NR$^7$R$^7$, CO$_2$H, CO$_2$R$^7$, [(C$_1$-C$_3$)alkylene] (C$_1$-C$_3$)alkoxy, [(C$_1$-C$_3$)alkylene]CO$_2$H, (C$_3$-C$_5$)cycloalkyl, =O. =S, SR$^7$, SO$_2$R$^7$, NH(CO)R$^7$ or NR$^7$(CO)R$^7$;

$R^4$ is H, OH, halo, CN, (C$_1$-C$_3$)alkyl, (C$_1$-C$_3$)haloalkyl, (C$_1$-C$_3$)alkoxy, SR$^7$ or Z, wherein
is

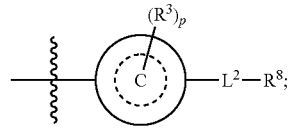

Ring C is cycloalkyl, heterocyclyl, aryl or heteroaryl;

$L^2$ is —C(R$^6$)(R$^6$)—, —C(R$^6$)(R$^6$)C(R$^6$)(R$^6$)—, —C(R$^6$)=C(R$^6$)—, —N(R$^5$)C(R$^6$)(R$^6$)—, —OC(R$^6$)(R$^6$)—, —C(=O)—, —C(=O)N(R$^5$)C(R$^6$)(R$^6$)— or a bond;

$R^5$ is independently H, (C$_1$-C$_3$)alkyl, (C$_1$-C$_3$)haloalkyl, (C$_3$-C$_5$)cycloalkyl, CO$_2$H, [(C$_1$-C$_3$)alkylene]heteroaryl, [(C$_1$-C$_3$)alkylene]aryl, [(C$_1$-C$_3$)alkylene]CO$_2$H, heterocyclyl, aryl or heteroaryl,
  or wherein two R$^5$ substituents together with a nitrogen atom form a 4-, 5-, 6- or 7-membered heterocyclyl;

$R^6$ is independently H, OH, halo, CN, (C$_1$-C$_3$)alkyl, (C$_1$-C$_3$)haloalkyl, (C$_1$-C$_3$)alkoxy, NHR$^7$, NR$^7$R$^7$, CO$_2$H, [(C$_1$-C$_3$)alkylene]CO$_2$H, (C$_3$-C$_5$)cycloalkyl, SR$^7$, NH(CO)R$^7$ or NR$^7$(CO)R$^7$;

$R^7$ is independently H, (C$_1$-C$_8$)alkyl, (C$_1$-C$_8$)haloalkyl, cycloalkyl, heterocyclyl, aryl or heteroaryl;

$R^8$ is H, OH, CO$_2$H, CO$_2$R$^7$, CF$_2$C(R$^6$)$_2$OH, C(R$^6$)$_2$OH, C(CF$_3$)$_2$OH, SO$_2$H, SO$_3$H, CF$_2$SO$_2$C(R$^6$)$_3$, CF$_2$SO$_2$N(H)R$^5$, SO$_2$N(H)R$^5$, SO$_2$N(H)C(O)R$^6$, C(O)N(H)SO$_2$R$^5$, C(O)haloalkyl, C(O)N(H)OR$^5$, C(O)N(R$^5$)OH, C(O)N(H)R$^5$, C(O)NR$^5$C(O)N(R$^5$)$_2$, P(O)(OR$^5$)OH, P(O)(O)N(H)R$^5$, P(O)(C(R$^6$)$_3$)C(R$^6$)$_3$, B(OH)$_2$, heterocyclyl or heteroaryl;

n is 0, 1, 2 or 3;

p is 0, 1, 2 or 3;

wherein any alkyl, alkylene, cycloalkyl, heterocyclyl, heteroaryl or aryl is optionally substituted with 1, 2 or 3 groups selected from OH, CN, SH, SCH$_3$, SO$_2$CH$_3$, SO$_2$NH$_2$, SO$_2$NH(C$_1$-C$_4$)alkyl, halogen, NH$_2$, NH(C$_1$-C$_4$)alkyl, N[(C$_1$-C$_4$)alkyl]$_2$, NH(aryl), C(O)NH$_2$, C(O)NH(alkyl), CH$_2$C(O)NH(alkyl), COOH, COOMe, acetyl, (C$_1$-C$_8$) alkyl, (C$_1$-C$_8$)haloalkyl, O(C$_1$-C$_8$)alkyl, O(C$_1$-C$_8$)haloalkyl, (C$_2$-C$_8$)alkenyl, (C$_2$-C$_8$)alkynyl, thioalkyl, cyanomethylene, alkylaminyl, alkylene-C(O)NH$_2$, alkylene-C(O)—NH(Me), NHC(O)alkyl, CH$_2$—C(O)—(C$_1$-C$_8$)alkyl, C(O)—(C$_1$-C$_8$) alkyl and alkylcarbonylaminyl, or a cycloalkyl, heterocyclyl, aryl or heteroaryl optionally substituted with OH, halogen, (C$_1$-C$_8$)alkyl, (C$_1$-C$_8$)haloalkyl, O(C$_1$-C$_8$)alkyl or O(C$_1$-C$_8$)haloalkyl, wherein when $X^4$ is a bond ring A forms a 5-membered heteroaryl wherein $X^1$, $X^5$ and $X^6$ can in addition to the above defined substituents be $NR^2$, and $X^1$ can in addition be —$N$-$L^1$-$Y$; and wherein either Q is -$L^1$-Y, or $X^1$ is —C-$L^1$-Y or —N-$L^1$-Y.

The present invention also provides a pharmaceutical composition comprising (i) a therapeutically effective amount of at least one compound according to Formula I, Formula II, Formula III, Formula IV, Formula V, or Formula VI or a stereoisomer, a tautomer or a pharmaceutically acceptable salt thereof; (ii) in combination with a pharmaceutically acceptable carrier, diluent or excipient.

Also provided by the present invention is a method for attenuating or inhibiting the activity of eIF4E in at least one cell overexpressing eIF4E, comprising contacting the at least one cell with a compound according to Formula I or a stereoisomer, tautomer or pharmaceutically acceptable salt thereof.

According to the inventive method at least one cell is a colon cancer cell, a gastric cancer cell, a thyroid cancer cell, a lung cancer cell, a leukemia cell, a B-cell lymphoma, a T-cell lymphoma, a hairy cell lymphoma, Hodgkin's lymphoma cell, non-Hodgkin's lymphoma cell, Burkitt's lymphoma cell, a pancreatic cancer cell, a melanoma cell, a multiple melanoma cell, a brain cancer cell, a CNS cancer cell, a renal cancer cell, a prostate cancer cell, an ovarian cancer cell, or a breast cancer cell.

According to yet another embodiment the invention provides a method for treating a eIF4E dependent condition in a mammal in need thereof comprising administering to the mammal (i) a therapeutically effective amount of at least one compound according to Formula I, Formula II, Formula III, Formula IV, Formula V, or Formula VI or a stereoisomer, tautomer or pharmaceutically acceptable salt thereof, or (ii) a pharmaceutical composition in accordance with the invention.

Compounds and pharmaceutically acceptable formulations in accordance with the invention are useful for treating an eIF4E dependent condition such as colon cancer, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, multiple melanoma, brain cancer, CNS cancer, renal cancer, prostate cancer, ovarian cancer, or breast cancer.

The above embodiments and other aspects of the invention are readily apparent in the detailed description that follows. Various references are set forth herein which describe in more detail certain background information, procedures, compounds and/or compositions, and are each hereby incorporated by reference in their entirety.

DETAILED DESCRIPTION

Figure 1:
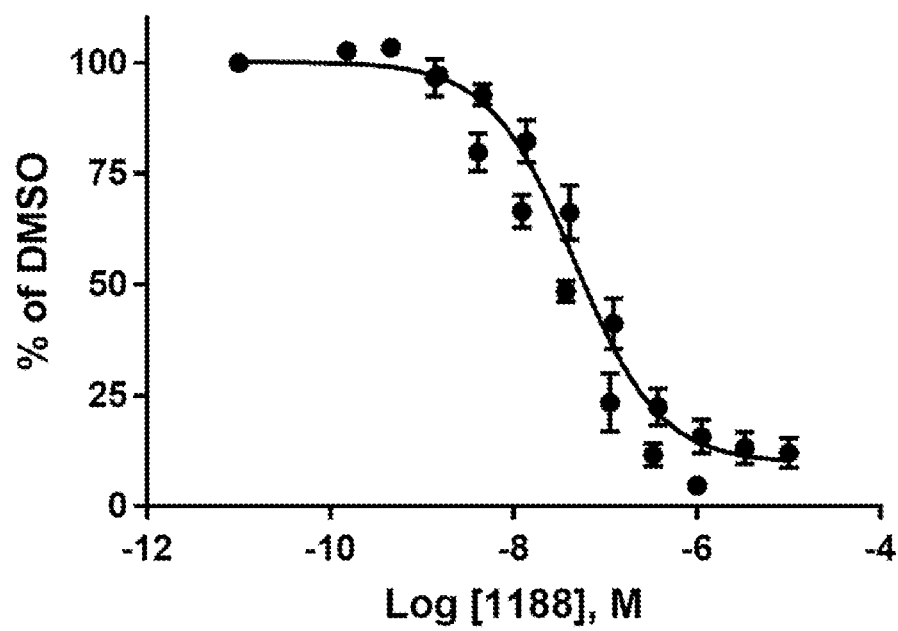
FIG. 1, graph showing the results of a cell proliferation assay using compound 1188.

In the following description certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

"Amino" refers to the —$NH_2$ substituent.

"Aminocarbonyl" refers to the —$C(O)NH_2$ substituent.

"Carboxyl" refers to the —$CO_2H$ substituent.

"Carbonyl" refers to a —C(O)—, —(CO)— or —C(=O)— group. All notations are used interchangeably within the specification.

"Cyano" refers to the —C≡N substituent.

"Cyanoalkylene" refers to the -(alkylene)C≡N substituent.

"Acetyl" refers to the —$C(O)CH_3$ substituent.

"Hydroxy" or "hydroxyl" refers to the —OH substituent.

"Hydroxyalkylene" refers to the -(alkylene)OH substituent.

"Oxo" refers to a =O substituent.

"Thio" or "thiol" refer to a —SH substituent.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.

"Lower alkyl" has the same meaning as alkyl defined above but having from one to four carbon atoms ($C_1$-$C_4$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula —OR$_a$ where R$_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Alkylaminyl" refers to a radical of the formula —NHR$_a$ or —NR$_a$R$_a$ where each R$_a$ is, independently, an alkyl radical having the indicated number of carbon atoms as defined above.

"Cycloalkylaminyl" refers to a radical of the formula —NHR$_a$ or —NR$_a$R$_a$ where R$_a$ is a cycloalkyl radical as defined herein.

"Alkylcarbonylaminyl" refers to a radical of the formula —NHC(O)R$_a$ or -NR$_a$C(O)R$_a$, where R$_a$ is an alkyl radical having the indicated number of carbon atoms as defined herein.

"Cycloalkylcarbonylaminyl" refers to a radical of the formula —NHC(O)R$_a$ or —NR$_a$C(O)R$_a$ where R$_a$ is a cycloalkyl radical as defined herein.

"Alkylaminocarbonyl" refers to a radical of the formula —C(O)NHR$_a$ or —C(O)NR$_a$R$_a$, where each R$_a$ is independently, an alkyl radical having the indicated number of carbon atoms as defined herein.

"Cyclolkylaminocarbonyl" refers to a radical of the formula —C(O)NHR$_a$, where R$_a$ is a cycloalkyl radical as defined herein.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group.

"Arylene" denotes divalent aryl, and "substituted arylene" refers to divalent substituted aryl.

"Aralkyl" or "araalkylene" may be used interchangeably and refer to a radical of the formula —R$_b$—R$_c$, where R$_b$ is an alkylene chain as defined herein and R$_c$ is one or more aryl radicals as defined herein, for example, benzyl, diphenylmethyl and the like.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Cycloalkylalkylene" or "cycloalkylalkyl" may be used interchangeably and refer to a radical of the formula —R$_b$R$_c$ where R$_b$ is an alkylene chain as defined herein and R$_c$ is a cycloalkyl radical as defined herein. In certain embodiments, R$_b$ is further substituted with a cycloalkyl group, such that the cycloalkylalkylene comprises two cycloalkyl moieties. Cyclopropylalkylene and cyclobutylalkylene are exemplary cycloalkylalkylene groups, comprising at least one cyclopropyl or at least one cyclobutyl group, respectively.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3-to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused, bridged or spiro ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, oxirane, oxetane, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heterocyclylalkyl" or "heterocyclylalkylene" refers to a radical of the formula —$R_b R_f$ where $R_b$ is an alkylene chain as defined herein and $R_f$ is a heterocyclyl radical as defined above, and if the heterocyclyl is a nitrogen-containing heterocyclyl, the heterocyclyl may be attached to the alkyl radical at the nitrogen atom.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" or "heteroarylalkylene" refers to a radical of the formula —$R_b R_g$ where $R_b$ is an alkylene chain as defined above and $R_g$ is a heteroaryl radical as defined above.

"Thioalkyl" refers to a radical of the formula —$SR_a$ where $R_a$ is an alkyl radical as defined above containing one to twelve carbon atoms, at least 1-10 carbon atoms, at least 1-8 carbon atoms, at least 1-6 carbon atoms, or at least 1-4 carbon atoms.

"Heterocyclylaminyl" refers to a radical of the formula —$NHR_f$ where $R_f$ is a heterocyclyl radical as defined above.

"Thione" refers to a =S group attached to a carbon atom of a saturated or unsaturated ($C_3$-$C_8$)cyclic or a ($C_1$-$C_8$) acyclic moiety.

"Sulfoxide" refers to a —S(O)— group in which the sulfur atom is covalently attached to two carbon atoms.

"Sulfone" refers to a —$S(O)_2$— or —($SO_2$)— group in which a hexavalent sulfur is attached to each of the two oxygen atoms through double bonds and is further attached to two carbon atoms through single covalent bonds.

The term "oxime" refers to a —$C(R_a)$=N—$OR_a$ radical where $R_a$ is hydrogen, lower alkyl, an alkylene or arylene group as defined above.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4- diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease. In the context of the present invention the terms "treat", "treating" and "treatment" also refer to:
(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy or synergies with another therapeutic agent.

The term "inhibit" or "inhibitor" refers to an alteration, interference, reduction, down regulation, blocking, suppression, abrogation or degradation, directly or indirectly, in the expression, amount or activity of a target gene, target protein, or signaling pathway relative to (1) a control, endogenous or reference target or pathway, or (2) the absence of a target or pathway, wherein the alteration, interference, reduction, down regulation, blocking, suppression, abrogation or degradation is statistically, biologically, or clinically significant. The term "inhibit" or "inhibitor" includes gene "knock out" and gene "knock down" methods, such as by chromosomal editing.

The terms "modulate", "modulation" and the like refer to the ability of a compound to increase or decrease the function, or activity of, for example, eukaryotic initiation factor 4E (eIF4E). "Modulation", in its various forms, is intended to encompass inhibition, antagonism, partial antagonism, activation, agonism and/or partial agonism of the activity associated with eIF4E. eIF4E inhibitors are compounds that bind to, partially or totally block stimulation, decrease, prevent, delay activation, inactivate, desensitize, or down regulate signal transduction. The ability of a compound to modulate eIF4E activity can be demonstrated in an enzymatic assay or a cell-based assay.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug, a compound which upon administration to a patient, must undergo chemical conversion by metabolic processes before becoming an active pharmacological agent. Exemplary prodrugs of compounds in accordance with Formula I are esters, acetamides, and amides.

Compounds of the Invention

The present invention generally is directed to compounds encompassed by the genus of Formula I, or stereoisomers, tautomers or pharmaceutically acceptable salts thereof.

In one embodiment, the invention is directed to compounds according to Formula II

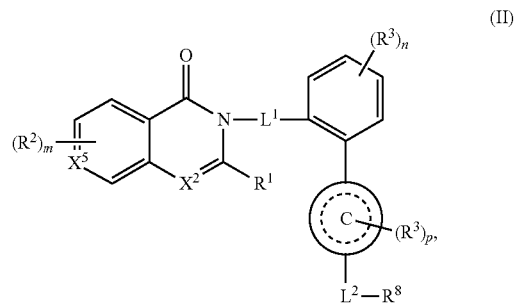

or stereoisomers, tautomers, or pharmaceutically acceptable salts thereof, wherein:

$X^2$ and $X^5$ are independently $CR^2$ or N,
or when $X^2$ is $CR^2$, $R_1$ and $R^2$ together with the atoms they attached to form a 6-membered aryl or heteroaryl;

$L^1$ is —(CH$_2$)—, —(CH$_2$)$_2$—, —(CH$_2$)$_3$—, —CH((C$_1$-C$_8$)alkyl)(CH$_2$)—, —CH((C$_1$-C$_8$)alkyl)(CH$_2$)$_2$—, —(CH$_2$)$_2$—O—, —CH$_2$CH=CH—, —CH$_2$C≡C— or —CH$_2$(cyclopropyl)-;

$L^2$ is —C(R$^6$)(R$^6$)—, —C(R$^6$)(R$^6$)C(R$^6$)(R$^6$)—, —C(R$^6$)=C(R$^6$)—, —N(R$^5$)C(R$^6$)(R$^6$)—, —OC(R$^6$)(R$^6$)—, —C(=O)—, —C(=O)N(R$^5$)C(R$^6$)(R$^6$)— or a bond;

Ring C is cycloalkyl, heterocyclyl, aryl or heteroaryl;

$R^1$ is H, OH, halo, CN, (C$_1$-C$_8$)alkyl, (C$_1$-C$_8$)haloalkyl, (C$_3$-C$_6$)cycloalkyl or NR$^5$R$^5$;

$R^2$ is independently H, halo, CN, NO, $NO_2$, C≡H, $(C_1$-$C_8)$alkyl, $(C_1$-$C_8)$haloalkyl, $CH_2SR^5$, $OR^5$, $NHR^5$, $NR^5R^5$, $[(C_1$-$C_8)$alkylene]heterocyclyl, $[(C_1$-$C_8)$alkylene]heteroaryl, $[(C_1$-$C_8)$alkylene]$NHR^5$, $[(C_1$-$C_8)$alkylene]$NR^5R^5$, $[(C_1$-$C_8)$alkylyne]$NR^5R^5$, $C(O)R^5$, $C(O)OR^5$, $C(O)NHR^5$, $C(O)NR^5R^5$, $SR^5$, $S(O)R^5$, $SO_2R^5$, $SO_2NHR^5$, $SO_2NR^5R^5$, $NH(CO)R^6$, $NR^5(CO)R^6$, aryl, heteroaryl, cycloalkyl or heterocyclyl;

$R^3$ is independently OH, halo, CN, $NO_2$, $(C_1$-$C_6)$alkyl, $(C_1$-$C_6)$haloalkyl, $(C_1$-$C_6)$alkoxy, C≡H, $NHR^7$, $NR^7R^7$, $CO_2H$, $CO_2R^7$, $[(C_1$-$C_3)$alkylene] $(C_1$-$C_3)$alkoxy, $[(C_1$-$C_3)$alkylene]$CO_2H$, $(C_3$-$C_5)$cycloalkyl, =O. =S, $SR^7$, $SO_2R^7$, $NH(CO)R^7$ or $NR^7(CO)R^7$;

$R^5$ is independently H, $(C_1$-$C_3)$alkyl, $(C_1$-$C_3)$haloalkyl, $(C_3$-$C_5)$cycloalkyl, $CO_2H$, $[(C_1$-$C_3)$alkylene]heteroaryl, $[(C_1$-$C_3)$alkylene]aryl, $[(C_1$-$C_3)$alkylene]$CO_2H$, heterocyclyl, aryl or heteroaryl, or wherein two $R^5$ substituents together with a nitrogen atom form a 4-, 5-, 6-, or 7-membered heterocyclyl;

$R^6$ is independently H, OH, halo, CN, $(C_1$-$C_3)$alkyl, $(C_1$-$C_3)$haloalkyl, $(C_1$-$C_3)$alkoxy, $NHR^7$, $NR^7R^7$, $CO_2H$, $[(C_1$-$C_3)$alkylene]$CO_2H$, $(C_3$-$C_5)$cycloalkyl, $SR^7$, $NH(CO)R^7$ or $NR^7(CO)R^7$;

$R^7$ is independently H, $(C_1$-$C_8)$alkyl, $(C_1$-$C_8)$haloalkyl, cycloalkyl, heterocyclyl, aryl or heteroaryl;

$R^8$ is H, OH, $CO_2H$, $CO_2R^7$, $CF_2C(R^6)_2OH$, $C(R^6)_2OH$, $C(CF_3)_2OH$, $SO_2H$, $SO_3H$, $CF_2SO_2C(R^6)_3$, $CF_2SO_2N(H)R^5$, $SO_2N(H)R^5$, $SO_2N(H)C(O)R^6$, $C(O)N(H)SO_2R^5$, $C(O)$haloalkyl, $C(O)N(H)OR^5$, $C(O)N(R^5)OH$, $C(O)N(H)R^5$, $C(O)NR^5C(O)N(R^5)_2$, $P(O)(OR^5)OH$, $P(O)(O)N(H)R^5$, $P(O)(C(R^6)_3)C(R^6)_3$, $B(OH)_2$, heterocyclyl or heteroaryl;

m is 0, 1, 2 or 3;

n is 0, 1, 2 or 3;

p is 0, 1, 2 or 3;

wherein any alkyl, alkylene, cycloalkyl, heterocyclyl, heteroaryl or aryl is optionally substituted with 1, 2 or 3 groups selected from OH, CN, SH, $SCH_3$, $SO_2CH_3$, $SO_2NH_2$, $SO_2NH(C_1$-$C_4)$alkyl, halogen, $NH_2$, $NH(C_1$-$C_4)$alkyl, $N[(C_1$-$C_4)$alkyl]$_2$, NH(aryl), $C(O)NH_2$, $C(O)NH$(alkyl), $CH_2C(O)NH$(alkyl), COOH, COOMe, acetyl, $(C_1$-$C_8)$alkyl, $(C_1$-$C_8)$haloalkyl, $O(C_1$-$C_8)$alkyl, $O(C_1$-$C_8)$haloalkyl, $(C_2$-$C_5)$alkenyl, $(C_2$-$C_5)$alkynyl, thioalkyl, cyanomethylene, alkylaminyl, alkylene-$C(O)NH_2$, alkylene-$C(O)$—NH(Me), NHC(O)alkyl, $CH_2$—C(O)—$(C_1$-$C_8)$alkyl, C(O)—$(C_1$-$C_8)$alkyl and alkylcarbonylaminyl, or a cycloalkyl, heterocyclyl, aryl or heteroaryl optionally substituted with OH, halogen, $(C_1$-$C_8)$alkyl, $(C_1$-$C_8)$haloalkyl, $O(C_1$-$C_8)$alkyl or $O(C_1$-$C_8)$haloalkyl.

In another embodiment the invention is directed to compounds of Formula III

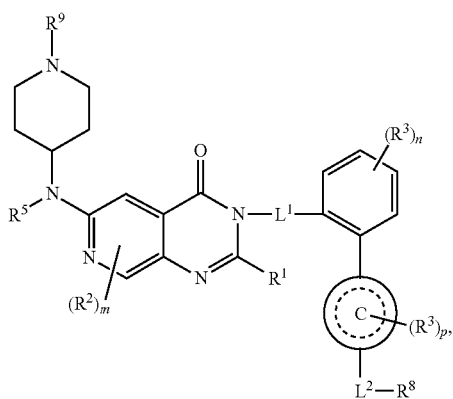

(III)

or stereoisomers, tautomers, or pharmaceutically acceptable salts thereof, wherein:

$L^1$ is —$(CH_2)$—, —$(CH_2)_2$—, —$(CH_2)_3$—, —CH$((C_1$-$C_8)$alkyl)$(CH_2)$—, —CH$((C_1$-$C_8)$alkyl)$(CH_2)_2$—, —$(CH_2)_2$—O—, —$CH_2CH$=CH—, —$CH_2$C≡C— or —$CH_2$(cyclopropyl)-;

$L^2$ is —$C(R^6)(R^6)$—, —$C(R^6)(R^6)C(R^6)(R^6)$—, —$C(R^6)$=$C(R^6)$—, —$N(R^5)C(R^6)(R^6)$—, —$OC(R^6)(R^6)$—, —C(=O)—, —C(=O)$N(R^5)C(R^6)(R^6)$— or a bond;

Ring C is a heteroaryl;

$R^1$ is H, OH, halo, CN, $(C_1$-$C_8)$alkyl, $(C_1$-$C_8)$haloalkyl, $(C_3$-$C_6)$cycloalkyl or $NR^5R^5$;

$R^2$ is independently H, halo, CN, NO, $NO_2$, C≡H, $(C_1$-$C_8)$alkyl, $(C_1$-$C_8)$haloalkyl, $CH_2SR^5$, $OR^5$, $NHR^5$, $NR^5R^5$, $[(C_1$-$C_8)$alkylene]heterocyclyl, $[(C_1$-$C_8)$alkylene]heteroaryl, $[(C_1$-$C_8)$alkylene]$NHR^5$, $[(C_1$-$C_8)$alkylene]$NR^5R^5$, $[(C_1$-$C_8)$alkylyne]$NR^5R^5$, $C(O)R^5$, $C(O)OR^5$, $C(O)NHR^5$, $C(O)NR^5R^5$, $SR^5$, $S(O)R^5$, $SO_2R^5$, $SO_2NHR^5$, $SO_2NR^5R^5$, $NH(CO)R^6$, $NR^5(CO)R^6$, aryl, heteroaryl, cycloalkyl or heterocyclyl;

$R^3$ is independently OH, halo, CN, $NO_2$, $(C_1$-$C_6)$alkyl, $(C_1$-$C_6)$haloalkyl, $(C_1$-$C_6)$alkoxy, C≡H, $NHR^7$, $NR^7R^7$, $CO_2H$, $CO_2R^7$, $[(C_1$-$C_3)$alkylene] $(C_1$-$C_3)$alkoxy, $[(C_1$-$C_3)$alkylene]$CO_2H$, $(C_3$-$C_5)$cycloalkyl, =O. =S, $SR^7$, $SO_2R^7$, $NH(CO)R^7$ or $NR^7(CO)R^7$;

$R^5$ is independently H, $(C_1$-$C_3)$alkyl, $(C_1$-$C_3)$haloalkyl, $(C_3$-$C_5)$cycloalkyl or heterocyclyl;

$R^6$ is independently H, OH, halo, CN, $(C_1$-$C_3)$alkyl, $(C_1$-$C_3)$haloalkyl, $(C_1$-$C_3)$alkoxy, $NHR^7$, $NR^7R^7$, $CO_2H$, $[(C_1$-$C_3)$alkylene]$CO_2H$, $(C_3$-$C_5)$cycloalkyl, $SR^7$, $NH(CO)R^7$ or $NR^7(CO)R^7$;

$R^7$ is independently H, $(C_1$-$C_8)$alkyl, $(C_1$-$C_8)$haloalkyl, cycloalkyl, heterocyclyl, aryl or heteroaryl;

$R^8$ is H, OH, $CO_2H$, $CO_2R^7$, $CF_2C(R^6)_2OH$, $C(R^6)_2OH$, $C(CF_3)_2OH$, $SO_2H$, $SO_3H$, $CF_2SO_2C(R^6)_3$, $CF_2SO_2N(H)R^5$, $SO_2N(H)R^5$, $SO_2N(H)C(O)R^6$, $C(O)N(H)SO_2R^5$, $C(O)$haloalkyl, $C(O)N(H)OR^5$, $C(O)N(R^5)OH$, $C(O)N(H)R^5$, $C(O)NR^5C(O)N(R^5)_2$, $P(O)(OR^5)OH$, $P(O)(O)N(H)R^5$, $P(O)(C(R^6)_3)C(R^6)_3$, $B(OH)_2$, heterocyclyl or heteroaryl;

$R^9$ is H, $(C_1$-$C_8)$alkyl, $(C_1$-$C_8)$haloalkyl, cycloalkyl or heterocyclyl;

m is 0, 1, or 2;

n is 0, 1, 2 or 3;

p is 0, 1, 2 or 3;

wherein any alkyl, alkylene, cycloalkyl, heterocyclyl, heteroaryl or aryl is optionally substituted with 1, 2 or 3 groups selected from OH, CN, SH, $SCH_3$, $SO_2CH_3$, $SO_2NH_2$, $SO_2NH(C_1$-$C_4)$alkyl, halogen, $NH_2$, $NH(C_1$-$C_4)$alkyl, $N[(C_1$-$C_4)$alkyl]$_2$, NH(aryl), $C(O)NH_2$, $C(O)NH$(alkyl), $CH_2C(O)NH$(alkyl), COOH, COOMe, acetyl, $(C_1$-$C_8)$alkyl, $(C_1$-$C_8)$haloalkyl, $O(C_1$-$C_8)$alkyl, $O(C_1$-$C_8)$haloalkyl, $(C_2$-$C_5)$alkenyl, $(C_2$-$C_5)$alkynyl, thioalkyl, cyanomethylene, alkylaminyl, alkylene-$C(O)NH_2$, alkylene-$C(O)$—NH(Me), NHC(O)alkyl, $CH_2$—C(O)—$(C_1$-$C_8)$alkyl, C(O)—$(C_1$-$C_8)$alkyl and alkylcarbonylaminyl.

In one embodiment, the invention is directed to compounds according to Formula IV

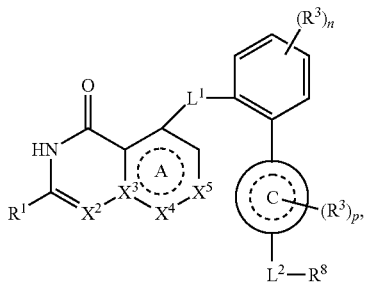
(IV)

or stereoisomers, tautomers, or pharmaceutically acceptable salts thereof, wherein:

$X^2$ and $X^5$ are independently $CR^2$ or N,
or when $X^2$ is $CR^2$, $R^1$ and $R^2$ together with the atoms they attached to form a 6-membered aryl or heteroaryl;
$X^3$ is C, or $X^3$ is C or N when $X^4$ is a bond;
$X^4$ is a bond, $CR^2$ or N,
wherein $X^4$ and $X^5$ together with 3 or 4 carbon or nitrogen atoms combine to form a 5- or 6-membered heteroaryl;
$L^1$ is —$(CH_2)$—, —$(CH_2)_2$—, —$(CH_2)_3$—, —$CH((C_1-C_8)alkyl)(CH_2)$—, —$CH((C_1-C_8)alkyl)(CH_2)_2$—, —$(CH_2)_2$—O—, —$CH_2CH$=CH—, —$CH_2C$≡C— or —$CH_2(cyclopropyl)$-;
$L^2$ is —$C(R^6)(R^6)$—, —$C(R^6)(R^6)C(R^6)(R^6)$—, —$C(R^6)$=$C(R^6)$—, —$N(R^5)C(R^6)(R^6)$—, —$OC(R^6)(R^6)$—, —$C(=O)$—, —$C(=O)N(R^5)C(R^6)(R^6)$—;
Ring C is cycloalkyl, heterocyclyl, aryl or heteroaryl;
$R^1$ is H, OH, halo, CN, $(C_1-C_8)$alkyl, $(C_1-C_8)$haloalkyl, $(C_3-C_6)$cycloalkyl or $NR^5R^5$;
$R^2$ is independently H, halo, CN, NO, $NO_2$, C≡H, $(C_1-C_8)$alkyl, $(C_1-C_8)$haloalkyl, $CH_2SR^5$, $OR^5$, $NHR^5$, $NR^5R^5$, $[(C_1-C_8)$alkylene]heterocyclyl, $[(C_1-C_8)$alkylene]heteroaryl, $[(C_1-C_8)$alkylene]$NHR^5$, $[(C_1-C_8)$alkylene]$NR^5R^5$, $[(C_1-C_8)$alkylyne]$NR^5R^5$, $C(O)R^5$, $C(O)OR^5$, $C(O)NHR^5$, $C(O)NR^5R^5$, $SR^5$, $S(O)R^5$, $SO_2R^5$, $SO_2NHR^5$, $SO_2NR^5R^5$, $NH(CO)R^6$, $NR^5(CO)R^6$, aryl, heteroaryl, cycloalkyl or heterocyclyl;
$R^3$ is independently OH, halo, CN, $NO_2$, $(C_1-C_6)$alkyl, $(C_1-C_6)$haloalkyl, $(C_1-C_6)$alkoxy, C≡H, $NHR^7$, $NR^7R^7$, $CO_2H$, $CO_2R^7$, $[(C_1-C_3)$alkylene]$(C_1-C_3)$alkoxy, $[(C_1-C_3)$alkylene]$CO_2H$, $(C_3-C_5)$cycloalkyl, =O. =S, $SR^7$, $SO_2R^7$, $NH(CO)R^7$ or $NR^7(CO)R^7$;
$R^5$ is independently H, $(C_1-C_3)$alkyl, $(C_1-C_3)$haloalkyl, $(C_3-C_5)$cycloalkyl, $CO_2H$, $[(C_1-C_3)$alkylene]heteroaryl, $[(C_1-C_3)$alkylene]aryl, $[(C_1-C_3)$alkylene]$CO_2H$, heterocyclyl, aryl or heteroaryl,
or wherein two $R^5$ substituents together with a nitrogen atom form a 4-, 5-, 6- or 7-membered heterocyclyl;
$R^6$ is independently H, OH, halo, CN, $(C_1-C_3)$alkyl, $(C_1-C_3)$haloalkyl, $(C_1-C_3)$alkoxy, $NHR^7$, $NR^7R^7$, $CO_2H$, $[(C_1-C_3)$alkylene]$CO_2H$, $(C_3-C_5)$cycloalkyl, $SR^7$, $NH(CO)R^7$ or $NR^7(CO)R^7$;
$R^7$ is independently H, $(C_1-C_8)$alkyl, $(C_1-C_8)$haloalkyl, cycloalkyl, heterocyclyl, aryl or heteroaryl;
$R^8$ is H, OH, $CO_2H$, $CO_2R^7$, $CF_2C(R^6)_2OH$, $C(R^6)_2OH$, $C(CF_3)_2OH$, $SO_2H$, $SO_3H$, $CF_2SO_2C(R^6)_3$, $CF_2SO_2N(H)R^5$, $SO_2N(H)R^5$, $SO_2N(H)C(O)R^6$, $C(O)N(H)SO_2R^5$, $C(O)$ haloalkyl, $C(O)N(H)OR^5$, $C(O)N(R^5)OH$, $C(O)N(H)R^5$, $C(O)NR^5C(O)N(R^5)_2$, $P(O)(OR^5)OH$, $P(O)(O)N(H)R^5$, $P(O)(C(R^6)_3)C(R^6)_3$, $B(OH)_2$, heterocyclyl or heteroaryl;
n is 0, 1, 2 or 3;
p is 0, 1, 2 or 3;
wherein any alkyl, alkylene, cycloalkyl, heterocyclyl, heteroaryl or aryl is optionally substituted with 1, 2 or 3 groups selected from OH, CN, SH, $SCH_3$, $SO_2CH_3$, $SO_2NH_2$, $SO_2NH(C_1-C_4)$alkyl, halogen, $NH_2$, $NH(C_1-C_4)$alkyl, $N[(C_1-C_4)$alkyl]$_2$, NH(aryl), $C(O)NH_2$, $C(O)NH(alkyl)$, $CH_2C(O)NH(alkyl)$, COOH, COOMe, acetyl, $(C_1-C_8)$alkyl, $(C_1-C_8)$haloalkyl, $O(C_1-C_8)$alkyl, $O(C_1-C_8)$haloalkyl, $(C_2-C_5)$alkenyl, $(C_2-C_5)$alkynyl, thioalkyl, cyanomethylene, alkylaminyl, alkylene-$C(O)NH_2$, alkylene-$C(O)$—NH(Me), NHC(O)alkyl, $CH_2$—$C(O)$—$(C_1-C_8)$alkyl, $C(O)$—$(C_1-C_8)$ alkyl and alkylcarbonylaminyl, or a cycloalkyl, heterocyclyl, aryl or heteroaryl optionally substituted with OH, halogen, $(C_1-C_8)$alkyl, $(C_1-C_8)$haloalkyl, $O(C_1-C_8)$alkyl or $O(C_1-C_8)$haloalkyl,
wherein when $X^4$ is a bond, ring A forms a 5-membered heteroaryl wherein $X_1$ and $X^5$ can in addition to C be N.

In another embodiment the invention is directed to compounds of Formula V

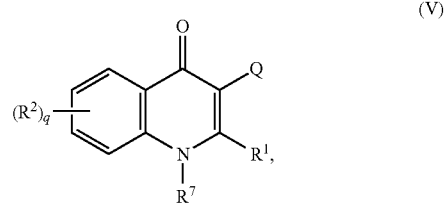
(V)

or stereoisomers, tautomers, or pharmaceutically acceptable salts thereof, wherein:

Q is -$L^1$-Y;
$L^1$ is —$(CH_2)$—, —$(CH_2)_2$—, —$(CH_2)_3$—, —$CH((C_1-C_8)alkyl)(CH_2)$—, —$CH((C_1-C_8)alkyl)(CH_2)_2$—, —$(CH_2)_2$—O—, —$CH_2CH$=CH—, —$CH_2C$≡C— or —$CH_2(cyclopropyl)$-;
Y is

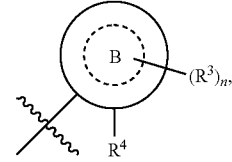

Ring B is a six-membered aryl, heteroaryl or heterocyclyl;
$R^1$ is H, OH, halo, CN, $(C_1-C_8)$alkyl, $(C_1-C_8)$haloalkyl, $(C_3-C_6)$cycloalkyl or $NR^5R^5$;
$R^2$ is independently H, halo, CN, NO, $NO_2$, C≡H, $(C_1-C_8)$alkyl, $(C_1-C_8)$haloalkyl, $CH_2SR^5$, $OR^5$, $NHR^5$, $NR^5R^5$, $[(C_1-C_8)$alkylene]heterocyclyl, $[(C_1-C_8)$alkylene]heteroaryl, $[(C_1-C_8)$alkylene]$NHR^5$, $[(C_1-C_8)$alkylene]$NR^5R^5$, $[(C_1-C_8)$alkylyne]$NR^5R^5$, $C(O)R^5$, $C(O)OR^5$, $C(O)NHR^5$, $C(O)NR^5R^5$, $SR^5$, $S(O)R^5$, $SO_2R^5$, $SO_2NHR^5$, $SO_2NR^5R^5$, $NH(CO)R^6$, $NR^5(CO)R^6$, aryl, heteroaryl, cycloalkyl or heterocyclyl;
$R^3$ is independently OH, halo, CN, $NO_2$, $(C_1-C_6)$alkyl, $(C_1-C_6)$haloalkyl, $(C_1-C_6)$alkoxy, C≡H, $NHR^7$, $NR^7R^7$, $CO_2H$, $CO_2R^7$, $[(C_1-C_3)$alkylene]$(C_1-C_3)$alkoxy, $[(C_1-C_3)$alkylene]$CO_2H$, $(C_3-C_5)$cycloalkyl, =O. =S, $SR^7$, $SO_2R^7$, $NH(CO)R^7$ or $NR^7(CO)R^7$;

R⁴ is H, OH, halo, CN, (C₁-C₃)alkyl, (C₁-C₃)haloalkyl, (C₁-C₃)alkoxy, SR⁷ or Z, wherein Z is

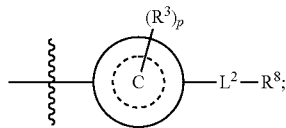

Ring C is cycloalkyl, heterocyclyl, aryl or heteroaryl;

L² is —C(R⁶)(R⁶)—, —C(R⁶)(R⁶)C(R⁶)(R⁶)—, —C(R⁶)=C(R⁶)—, —N(R⁵)C(R⁶)(R⁶)—, —OC(R⁶)(R⁶)—, —C(=O)—, —C(=O)N(R⁵)C(R⁶)(R⁶)— or a bond;

R⁵ is independently H, (C₁-C₃)alkyl, (C₁-C₃)haloalkyl, (C₃-C₅)cycloalkyl, CO₂H, [(C₁-C₃)alkylene]heteroaryl, [(C₁-C₃)alkylene]aryl, [(C₁-C₃)alkylene]CO₂H, heterocyclyl, aryl or heteroaryl, or wherein two R⁵ substituents together with a nitrogen atom form a 4-, 5-, or 6-membered heterocyclyl;

R⁶ is independently H, OH, halo, CN, (C₁-C₃)alkyl, (C₁-C₃)haloalkyl, (C₁-C₃)alkoxy, NHR⁷, NR⁷R⁷, CO₂H, [(C₁-C₃)alkylene]CO₂H, (C₃-C₅)cycloalkyl, SR⁷, NH(CO)R⁷ or NR⁷(CO)R⁷;

R⁷ is independently H, (C₁-C₈)alkyl, (C₁-C₈)haloalkyl, cycloalkyl, heterocyclyl, aryl or heteroaryl;

R⁸ is H, OH, CO₂H, CO₂R⁷, CF₂C(R⁶)₂OH, C(R⁶)₂OH, C(CF₃)₂OH, SO₂H, SO₃H, CF₂SO₂C(R⁶)₃, CF₂SO₂N(H)R⁵, SO₂N(H)R⁵, SO₂N(H)C(O)R⁶, C(O)N(H)SO₂R⁵, C(O)haloalkyl, C(O)N(H)OR⁵, C(O)N(R⁵)OH, C(O)N(H)R⁵, P(O)(OR⁵)OH, P(O)(O)N(H)R⁵, P(O)(C(R⁶)₃)C(R⁶)₃, B(OH)₂, heterocyclyl or heteroaryl;

n is 0, 1, 2 or 3;

p is 0, 1, 2 or 3;

q is 0, 1, 2, 3 or 4;

wherein any alkyl, alkylene, cycloalkyl, heterocyclyl, heteroaryl or aryl is optionally substituted with 1, 2 or 3 groups selected from OH, CN, SH, SCH₃, SO₂CH₃, SO₂NH₂, SO₂NH(C₁-C₄)alkyl, halogen, NH₂, NH(C₁-C₄)alkyl, N[(C₁-C₄)alkyl]₂, NH(aryl), C(O)NH₂, C(O)NH(alkyl), CH₂C(O)NH(alkyl), COOH, COOMe, acetyl, (C₁-C₈)alkyl, (C₁-C₈)haloalkyl, O(C₁-C₈)alkyl, O(C₁-C₈)haloalkyl, (C₂-C₅)alkenyl, (C₂-C₅)alkynyl, thioalkyl, cyanomethylene, alkylaminyl, alkylene-C(O)NH₂, alkylene-C(O)—NH(Me), NHC(O)alkyl, CH₂—(O)—(C₁-C₈)alkyl, C(O)—(C₁-C₈)alkyl and alkylcarbonylaminyl, or a cycloalkyl, heterocyclyl, aryl or heteroaryl optionally substituted with OH, halogen, (C₁-C₈)alkyl, (C₁-C₈)haloalkyl, O(C₁-C₈)alkyl or O(C₁-C₈)haloalkyl.

In another embodiment the invention is directed to compounds of Formula VI

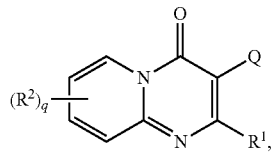

or stereoisomers, tautomers, or pharmaceutically acceptable salts thereof, wherein:

Q is -L₁-Y;

L¹ is —(CH₂)—, —(CH₂)₂—, —(CH₂)₃—, —CH((C₁-C₈)alkyl)(CH₂)—, —CH((C₁-C₈)alkyl)(CH₂)₂—, —(CH₂)₂—O—, —CH₂CH=CH—, —CH₂C≡C— or —CH₂(cyclopropyl)-;

Y is

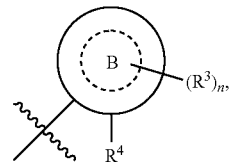

Ring B is a six-membered aryl, heteroaryl or heterocyclyl;

R¹ is H, OH, halo, CN, (C₁-C₈)alkyl, (C₁-C₈)haloalkyl, (C₃-C₆)cycloalkyl or NR⁵R⁵;

R² is independently H, halo, CN, NO, NO₂, C≡H, (C₁-C₈)alkyl, (C₁-C₈)haloalkyl, CH₂SR⁵, OR⁵, NHR⁵, NR⁵R⁵, [(C₁-C₈)alkylene]heterocyclyl, [(C₁-C₈)alkylene]heteroaryl, [(C₁-C₈)alkylene]NHR⁵, [(C₁-C₈)alkylene]NR⁵R⁵, [(C₁-C₈)alkylyne]NR⁵R⁵, C(O)R⁵, C(O)OR⁵, C(O)NHR⁵, C(O)NR⁵R⁵, SR⁵, S(O)R⁵, SO₂R⁵, SO₂NHR⁵, SO₂NR⁵R⁵, NH(CO)R⁶, NR⁵(CO)R⁶, aryl, heteroaryl, cycloalkyl or heterocyclyl;

R³ is independently OH, halo, CN, NO₂, (C₁-C₆)alkyl, (C₁-C₆)haloalkyl, (C₁-C₆)alkoxy, C≡H, NHR⁷, NR⁷R⁷, CO₂H, CO₂R⁷, [(C₁-C₃)alkylene] (C₁-C₃)alkoxy, [(C₁-C₃)alkylene]CO₂H, (C₃-C₅)cycloalkyl, =O. =S, SR⁷, SO₂R⁷, NH(CO)R⁷ or NR⁷(CO)R⁷;

R⁴ is H, OH, halo, CN, (C₁-C₃)alkyl, (C₁-C₃)haloalkyl, (C₁-C₃)alkoxy, SR⁷ or Z, wherein Z is

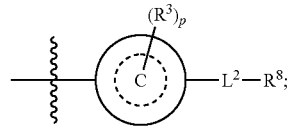

Ring C is cycloalkyl, heterocyclyl, aryl or heteroaryl;

L² is —C(R⁶)(R⁶)—, —C(R⁶)(R⁶)C(R⁶)(R⁶)—, —C(R⁶)=C(R⁶)—, —N(R⁵)C(R⁶)(R⁶)—, —OC(R⁶)(R⁶)—, —C(=O)—, —C(=O)N(R⁵)C(R⁶)(R⁶)— or a bond;

R⁵ is independently H, (C₁-C₃)alkyl, (C₁-C₃)haloalkyl, (C₃-C₅)cycloalkyl, CO₂H, [(C₁-C₃)alkylene]heteroaryl, [(C₁-C₃)alkylene]aryl, [(C₁-C₃)alkylene]CO₂H, heterocyclyl, aryl or heteroaryl, or wherein two R⁵ substituents together with a nitrogen atom form a 4-, 5-, or 6-membered heterocyclyl;

R⁶ is independently H, OH, halo, CN, (C₁-C₃)alkyl, (C₁-C₃)haloalkyl, (C₁-C₃)alkoxy, NHR⁷, NR⁷R⁷, CO₂H, [(C₁-C₃)alkylene]CO₂H, (C₃-C₅)cycloalkyl, SR⁷, NH(CO)R⁷ or NR⁷(CO)R⁷;

R⁷ is independently H, (C₁-C₈)alkyl, (C₁-C₈)haloalkyl, cycloalkyl, heterocyclyl, aryl or heteroaryl;

R⁷ is H, OH, CO₂H, CO₂R⁷, CF₂C(R⁶)₂OH, C(R⁶)₂OH, C(CF₃)₂OH, SO₂H, SO₃H, CF₂SO₂C(R⁶)₃, CF₂SO₂N(H)R⁵, SO₂N(H)R⁵, SO₂N(H)C(O)R⁶, C(O)N(H)SO₂R⁵, C(O)haloalkyl, C(O)N(H)OR⁵, C(O)N(R⁵)OH, C(O)N(H)R⁵, C(O)NR⁵C(O)N(R⁵)₂, P(O)(OR⁵)OH, P(O)(O)N(H)R⁵, P(O)(C(R⁶)₃)C(R⁶)₃, B(OH)₂, heterocyclyl or heteroaryl;

n is 0, 1, 2 or 3;
p is 0, 1, 2 or 3;
q is 0, 1, 2, 3 or 4;

wherein any alkyl, alkylene, cycloalkyl, heterocyclyl, heteroaryl or aryl is optionally substituted with 1, 2 or 3 groups selected from OH, CN, SH, SCH₃, SO₂CH₃, SO₂NH₂, SO₂NH(C₁-C₄)alkyl, halogen, NH₂, NH(C₁-C₄)alkyl, N[(C₁-C₄)alkyl]₂, NH(aryl), C(O)NH₂, C(O)NH(alkyl), CH₂C(O)NH(alkyl), COOH, COOMe, acetyl, (C₁-C₈)alkyl, (C₁-C₈)haloalkyl, O(C₁-C₈)alkyl, O(C₁-C₈)haloalkyl, (C₂-C₅)alkenyl, (C₂-C₅)alkynyl, thioalkyl, cyanomethylene, alkylaminyl, alkylene-C(O)NH₂, alkylene-C(O)—NH(Me), NHC(O)alkyl, CH₂—C(O)—(C₁-C₈)alkyl, C(O)—(C₁-C₈)alkyl and alkylcarbonylaminyl, or a cycloalkyl, heterocyclyl, aryl or heteroaryl optionally substituted with OH, halogen, (C₁-C₈)alkyl, (C₁-C₈)haloalkyl, O(C₁-C₈)alkyl or O(C₁-C₈)haloalkyl.

In one embodiment X² of Formulae I, II, and IV is N.
In one embodiment X³ of Formulae I and IV is C.
In one embodiment X⁴ of Formulae I and IV is CR² or N.
In one embodiment X⁵ of Formulae I and IV is CR².
In one embodiment L¹ of Formulae I, II, III, IV, V and VI is —(CH₂)₂—O—, —CH₂CH=CH— or —CH₂C≡C—. In another embodiment L¹ is —(CH₂)₂—O—.
In one embodiment L² of Formulae I, II, III, IV, V and VI is a bond.
In one embodiment Ring B of Formulae I, V and VI is aryl.
In one embodiment Ring C of Formulae I, II, III, IV, V and VI is heteroaryl.
In one embodiment Ring C of Formulae I, II, III, IV, V and VI is

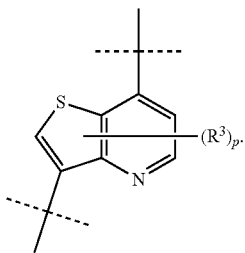

In one embodiment Ring C of Formula III is

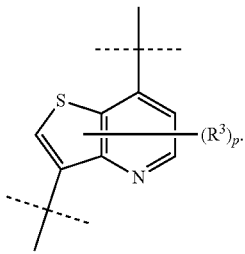

In one embodiment R¹ of Formulae I, II, III, IV, V and VI is H, (C₁-C₈)alkyl or (C₁-C₈)haloalkyl.

In one embodiment R¹ of Formula IV is NHR⁵ or N[(C₁-C₃)alkyl](R⁵).

In one embodiment R² of Formulae I, II, III, IV, V and VI is halo, CN, (C₁-C₈)alkyl, (C₁-C₈)haloalkyl or OR⁵. In another embodiment R² is halo, CN or (C₁-C₈)haloalkyl.

In one embodiment R³ of Formulae I, II, III, IV, V and VI is halo, CN, (C₁-C₃)alkyl or (C₁-C₃)haloalkyl.

In one embodiment R⁴ of Formulae I, V and VI is Z, wherein Z is

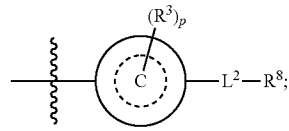

In one embodiment R⁵ of Formulae I, II, III, V and VI is H, (C₁-C₃)alkyl or (C₁-C₃)haloalkyl. In another embodiment R⁵ of Formula IV is aryl. In another embodiment R⁵ of Formulae I, II, III, IV, V, and VI is H, (C₁-C₃)alkyl or (C₁-C₃)haloalkyl.

In one embodiment R⁶ of Formulae I, II, III, IV, V and VI is H, OH, halo, CN, (C₁-C₃)alkyl, (C₁-C₃)haloalkyl or (C₁-C₃)alkoxy.

In one embodiment R⁷ of Formulae I, II, III, IV, V and VI is H, (C₁-C₈)alkyl or (C₁-C₈)haloalkyl.

In one embodiment R⁸ of Formulae I, II, III, IV, V and VI is CO₂H or C(O)N(H)SO₂R⁵.

In one embodiment R⁹ of Formula III is (C₁-C₈)alkyl or (C₁-C₈)haloalkyl.

In one embodiment R⁹ of Formula III is cycloalkyl or heterocyclyl.

In one embodiment "m" of Formulae I and II=2 or 3. In another embodiment "n" of Formulae I, II, IV, V and VI=1 or 2. In yet another embodiment "p" of Formulae I, II, III, IV, V and VI=0 or 1.

In one embodiment the optional substituents of alkyl, cycloalkyl, heterocyclyl, heteroaryl or aryl are OH, CN, halogen, (C₁-C₈)alkyl, O(C₁-C₈)alkyl, haloalkyl, alkylene-C(O)NH₂ or alkylene-C(O)—NH(Me).

In one embodiment the optional substituents of alkyl, cycloalkyl, heterocyclyl, heteroaryl or aryl are cycloalkyl, heterocyclyl, aryl or heteroaryl optionally substituted with OH, halogen, (C₁-C₈)alkyl, (C₁-C₈)haloalkyl, O(C₁-C₈)alkyl or O(C₁-C₈)haloalkyl.

In one embodiment, the compounds according to Formulae I, II, III, IV, V and VI are selected from compounds 1-1250.

The inventive compounds according to Formulae I, II, III, IV, V and VI may be isotopically-labeled by having one or more atoms replaced by an atom having a different atomic mass or mass number. Examples of isotopes that can be incorporated into compounds according to Formulae I, II, III, IV, V and VI include isotopes of hydrogen, carbon, nitrogen, oxygen, phosphorous, fluorine, chlorine, or iodine. Illustrative of such isotopes are ²H, ³H, ¹¹C, ¹³C, ¹⁴C, ¹³N, ¹⁵N, ¹⁵O, ¹⁸O, ³¹P, ³²P, ³⁵S ¹⁸F, ³⁶Cl, ¹²³I, and ¹²⁵I, respectively. These radiolabeled compounds can be used to measure the biodistribution, tissue concentration and the kinetics of transport and excretion from biological tissues including a subject to which such a labeled compound is administered. Labeled compounds are also used to determine therapeutic effectiveness, the site or mode of action, and the binding affinity of a candidate therapeutic to a pharmacologically important target. Certain radioactive-labeled compounds according to Formulae I, II, III, IV, V and VI, therefore, are useful in drug and/or tissue distribution studies. The radioactive isotopes tritium, i.e. ³H, and carbon-14, i.e. ¹⁴C, are particularly useful for this purpose in view of their ease of incorporation and ready means of detection.

Substitution with heavier isotopes such as deuterium, i.e. $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}$C, $^{18}$F, $^{15}$O and $^{13}$N, provides labeled analogs of the inventive compounds that are useful in Positron Emission Tomography (PET) studies, e.g., for examining substrate receptor occupancy. Isotopically-labeled compounds according to Formulae I, II, III, IV, V and VI can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of compounds according to Formulae I, II, III, IV, V and VI. Such products may result from, for example, the oxidation, reduction, hydrolysis, amidation, esterification, and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabeled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabeled compound.

The invention also provides pharmaceutically acceptable salt forms of compounds in Formulae I, II, III, IV, V and VI. Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases the compound of the invention may merely retain adventitious water or be a mixture of water plus some adventitious solvent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Compounds of the invention or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule. For example:

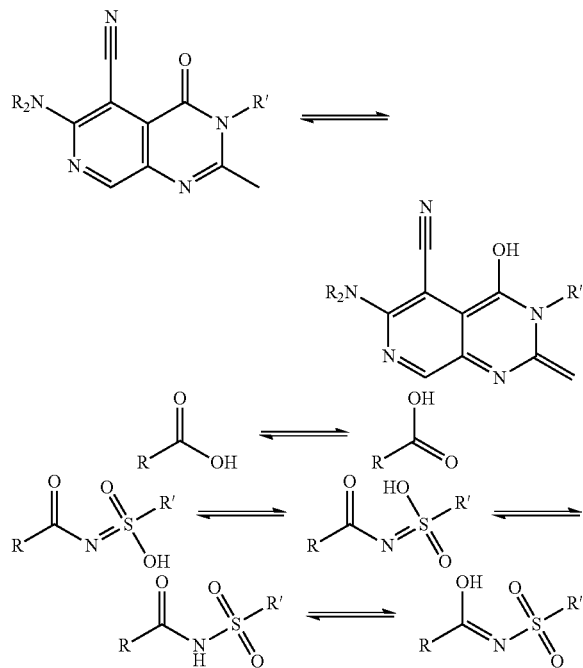

The compounds provided in this disclosure may be depicted as different tautomers, and when compounds have tautomeric forms, all tautomeric forms are intended to be within the scope of the invention, and the naming of a compound does not exclude any tautomer of that compound.

The inventive compounds are synthesized using conventional synthetic methods, and more specifically using the general methods noted below.

Pharmaceutical Formulations

In one embodiment compounds according to Formulae I, II, III, IV, V and VI are formulated as pharmaceutically acceptable compositions that contain compounds of Formulae I, II, III, IV, V and VI in an amount effective to treat a particular disease or condition of interest upon administration of the pharmaceutical composition to a mammal. Pharmaceutical compositions in accordance with the present invention can comprise compounds of Formulae I, II, III, IV, V and VI in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of Formulae I, II, III, IV, V and VI is administered to a mammal in an amount sufficient to inhibit eIF4E activity upon administration, and preferably with acceptable toxicity to the same. eIF4E activity of Formulae I, II, III, IV, V and VI compounds can be determined by one skilled in the art, for example, as described in the Examples below. Appropriate concentrations and dosages can be readily determined by one skilled in the art.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a eIF4E related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention or pharmaceutically acceptable salt thereof may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments the disclosed compounds are useful for inhibiting the activity of eIF4E and/or can be useful in analyzing eIF4E signaling activity in model systems and/or for preventing, treating, or ameliorating a symptom associated with a disease, disorder, or pathological condition involving eIF4E, preferably one afflicting humans. A compound which inhibits the activity of eIF4E will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by eIF4E, such as, for example, haematological tumors, solid tumors, and/or metastases thereof, including leukemias and myelodysplastic syndrome, malignant lymphomas, for example, B-cell lymphoma, T-cell lymphoma, hairy cell lymphoma, Hodgkin's lymphoma, non-Hodgins lymphoma and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjögren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, Goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Yet further, the inventive compounds and their pharmaceutical compositions are candidate therapeutics for the prophylaxis and/or therapy of fibrotic diseases, such as various forms of fibrosis, fibromas or any disease giving rise to fibrosis whether as a main or a secondary symptom. Exemplary fibrotic diseases include without limitation, viral hepatitis, hepatic fibrosis, schistosomiasis, steatohepatitis (alcoholic or non-alcoholic), cirrhosis, idiopathic pulmonary fibrosis (IPF), systemic sclerosis (scleroderma), nephrogenic systemic fibrosis (NSF), diabetes, untreated hypertension, heart attack, hypertension, atherosclerosis, restenosis, macular degeneration, retinal and vitreal retinopathy, keloids, hypertrophic scars, Crohn's disease and Alzheimer's disease.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

Accordingly, certain embodiments are directed to a method for treating a eIF4E dependent condition in a mammal in need thereof, the method comprising administering an effective amount of a pharmaceutical composition as described above (i.e., a pharmaceutical composition comprising one or more compounds of Formulae I, II, III, IV, V and VI) to a mammal.

As described above deregulation of protein synthesis is a common event in human cancers. A key regulator of translational control is eIF4E whose activity is a key determinant of tumorigenicity. Inhibitors of eIF4E are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; T-cell lymphoma, B-cell lymphoma, hairy cell lymphoma, Burkitt's lymphoma, plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma;

mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment, the present disclosure provides methods for treating solid tumor, colon cancer, rectal cancer, colorectal cancer, bladder cancer, gastric cancer, esophageal cancer, head and neck cancer, myelodysplastic syndrome, brain cancer, CNS cancer, malignant glioma, glioblastoma, hepatocellular cancers, hepatocellular carcinoma, thyroid cancer, lung cancer, non-small cell lung cancer, a hematological cancer, acute and chronic leukemia, B-cell lymphoma, Waldenström's macroglobulinemia, T-cell lymphoma, hairy cell lymphoma, diffuse large B cell lymphoma, Hodgkin's lymphoma, non-Hodgkin's lymphoma, Burkitt lymphoma, pancreatic cancer, melanoma, myeloma, multiple myeloma, pancreatic carcinoma, renal cell carcinoma, renal cancer, cervical cancer, urothelial cancer, prostate cancer, castration-resistant prostate cancer, ovarian cancer, breast cancer, triple-negative breast cancer, hormone receptor positive breast cancer or HER2+ breast cancer. According to such a method, a therapeutically effective amount of at least one compound according to Formulae I, II, III, IV, V and VI or a stereoisomer, tautomer or pharmaceutically acceptable salt thereof can be administered to a subject who has been diagnosed with a cell proliferative disease, such as a cancer. Alternatively, a pharmaceutical composition comprising at least one compound according to Formulae I, II, III, IV, V and VI or a stereoisomer, tautomer or pharmaceutically acceptable salt thereof can be administered to a subject who has been diagnosed with cancer.

In certain embodiments the compounds in accordance with the invention are administered to a subject with cancer in conjunction with other conventional cancer therapies such as radiation treatment or surgery. Radiation therapy is well-known in the art and includes X-ray therapies, such as gamma-irradiation, and radiopharmaceutical therapies.

In certain embodiments the inventive eIF4E inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

In certain embodiments, an additional therapeutic agent that may be used in combination with an eIF4E inhibitor is an inhibitor of an immunosuppression component, which may be an inhibitor of an immune checkpoint molecule or gene, a metabolic enzyme, an immunosuppressive cytokine, $T_{reg}$ cells, or any combination thereof. As used herein, the term "immunosuppression component" refers to one or more cells, proteins, molecules, compounds or complexes providing inhibitory signals to assist in controlling or suppressing an immune response. For example, immunosuppression components include those molecules that partially or totally block immune stimulation; decrease, prevent or delay immune activation; or increase, activate, or up regulate immune suppression. "Controlling or suppressing an immune response," as used herein, means reducing any one or more of antigen presentation, T cell activation, T cell proliferation, T cell effector function, cytokine secretion or production, and target cell lysis. Such modulation, control or suppression can promote or permit the persistence of a hyperproliferative disease or disorder (e.g., cancer, chronic infections).

Immune checkpoint molecules include immune checkpoint ligands such as, PD-L1, PD-L2, CD80, CD86, B7-H3, B7-H4, HVEM, adenosine, GAL9, VISTA, CEACAM-1, CEACAM-3, CEACAM-5, PVRL2, and immune checkpoint receptors such as, PD-1, CTLA-4, BTLA, KIR, LAG3, TIM3, A2aR, CD244/2B4, CD160, TIGIT, LAIR-1, and PVRIG/CD112R). Metabolic enzymes include arginase and indoleamine 2,3-dioxygenase (IDO)), and immunosuppressive cytokines include IL-10, IL-4, IL-1RA, and IL-35. In certain embodiments, an inhibitor of immunosuppression component is a small molecule, an antisense molecule, a ribozyme, an RNAi molecule (e.g., siRNA), an antibody or antigen binding fragment thereof, or fusion polypeptide (e.g., Fc fusion protein).

An antibody specific for PD-1 may be pidilizumab, nivolumab, pembrolizumab, MEDI0680 (formerly AMP-514), AMP-224, or BMS-936558.

An antibody specific for PD-L1 may be MDX-1105 (BMS-936559), durvalumab (formerly MEDI4736), atezolizumab (formerly MPDL3280A), or avelumab (formerly MSB0010718C). A compound specific for PD-L1 may be BMS-1001 or BMS-1166.

A CTLA4 inhibitor may be a CTLA4 specific antibody, such as tremelimumab or ipilimumab, or a CTLA4-Ig fusion protein (e.g., abatacept, belatacept).

A LAG3 inhibitor may be LAG525, IMP321, IMP701, 9H12, or BMS-986016.

An IDO inhibitor may be levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments an eIF4E inhibitor in accordance with the present invention is used simultaneously, in the same formulation or in separate formulations, or sequentially with an additional agent(s) as part of a combination therapy regimen.

eIF4E inhibitors according to Formulae I, II, III, IV, V and VI including their corresponding salts and pharmaceutically acceptable compositions of Formulae I, II, III, IV, V and VI compounds are also effective as therapeutic agents for treating or preventing cytokine mediated disorders, such as inflammation in a patient, preferably in a human. In one embodiment, a compound or composition in accordance with the invention is particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

The inventive compounds their corresponding salts and pharmaceutically acceptable compositions are candidate therapeutics for treating brain related disorders which include without limitation autism, Fragile X-syndrome, Parkinson's disease and Alzheimer's disease. Treatment is effected by administering to a subject in need of treatment a compound of Formulae I, II, III, IV, V and VI, its pharmaceutically acceptable salt form, or a pharmaceutically acceptable composition of a compound of Formulae I, II, III, IV, V and VI or its salt.

The invention also supports the use of the inventive compounds or a pharmaceutically acceptable formulation of the inventive compound as an inhibitor of eIF4E activity. Such inhibition is achieved by contacting a cell expressing eIF4E with a compound or a pharmaceutically acceptable formulation, to lower or inhibit eIF4E activity, to provide therapeutic efficacy for a eIF4E dependent condition in a mammal in need thereof.

Therapeutically effective dosages of a compound according to Formulae I, II, III, IV, V and VI or a composition containing a compound of Formulae I, II, III, IV, V and VI will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

General Methods for Synthesizing Compounds

Compounds described in this disclosure have a left-hand side and a right-hand side, illustrated below for Formula (II):

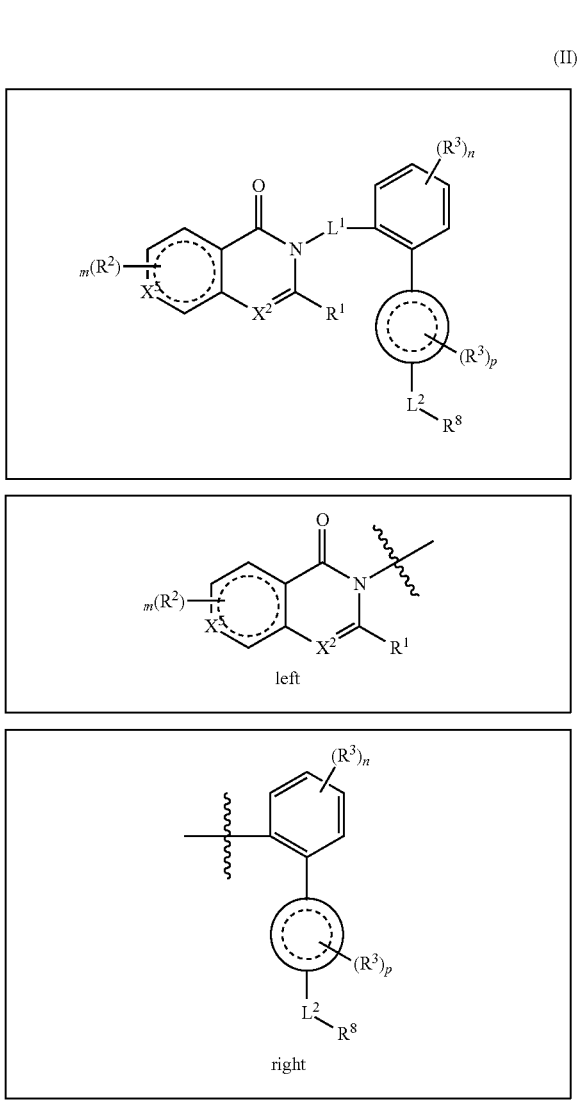

left right

In general, the compounds described in this disclosure can be synthesized by constructing the left-hand side and the right-hand and coupling the two sides together, as described in the general methods below. Many of the reactions carried out on the left-hand side prior to coupling, such as cyanation, can be postponed until the coupling is completed. Similarly, some of the reactions listed as post-coupling protocols can be performed prior to the coupling reaction to give the same result.

Example 1. General Methods for Synthesizing 7-Aza-Thienylpyridine and Derivative Compounds The 7-aza-thienylpyridine compounds in Table 1 can be synthesized using methods described in Example 1. For some compounds, some of the reactions described in Example 2 and/or Example 3, below, can be used to prepare the compounds.

Example 1A. Methods of Synthesizing the Left-Hand Side

Example 1A.1

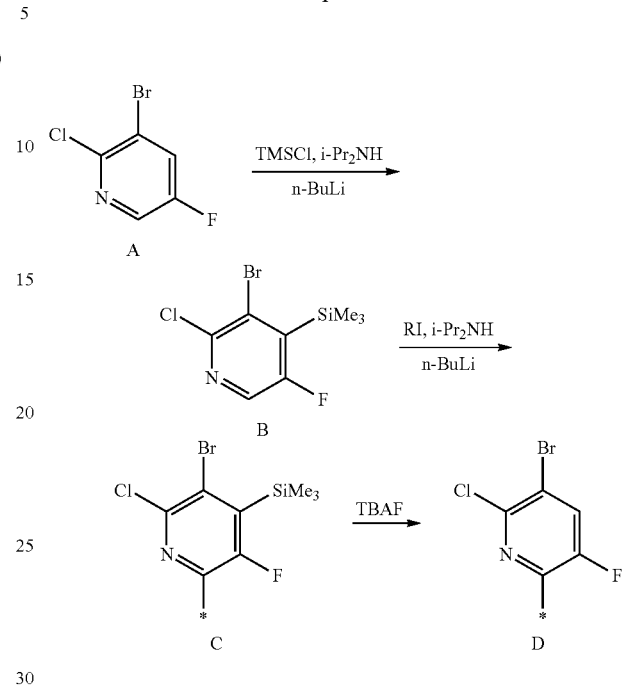

To dry N-isopropylpropan-2-amine (1.2 equiv.) in THF (0.3 M) at 0° C. is added n-butyllithium (2.5 M in hexane) (1.2 equiv.) slowly and the mixture is stirred for 10 min. The LDA solution in THF is used directly. To a solution of 3-bromo-2-chloro-5-fluoro-pyridine (A, 1 equiv.) in THF (0.3 M) at −78° C. is added the LDA solution and the resulting dark mixture is stirred for 45 min. Chloro(trimethyl)silane (1.7 equiv.) is added and the mixture is allowed to warm to rt within ca. 15 h. The reaction mixture is quenched with water, the layers separated, and the aqueous layer extracted with ethylacetate. The organic layers are combined, evaporated with silica gel and the free-flowing silica gel is loaded on a column and (3-bromo-2-chloro-5-fluoro-6-methyl-4-pyridyl)-trimethyl-silane (B) is purified by silica gel chromatography.

To a solution of (3-bromo-2-chloro-5-fluoro-4-pyridyl)-trimethyl-silane (B, 1 equiv.) in THF (0.25 M) at −78° C. is added LDA solution (1.2 equiv.) prepared as above and the resulting dark mixture is stirred for 45 min. Iodomethane (10 equiv.) is added and the mixture is allowed to warm to rt within ca. 15 h. The reaction mixture is quenched with water, the layers separated, and the aqueous layer further extracted with ethylacetate. The organic layers are combined, evaporated with silica gel and the free-flowing silica gel loaded on a column and (3-bromo-2-chloro-5-fluoro-6-methyl-4-pyridyl)-trimethyl-silane (C) is purified via silica gel chromatography.

(3-bromo-2-chloro-5-fluoro-6-methyl-4-pyridyl)-trimethyl-silane (C, 1 equiv.) is dissolved in THF (0.67 M), cooled to 0° C., and tetrabutylammonium fluoride (in THF) (1.2 equiv.) is added and the mixture stirred at 0° C. After 10 min the reaction is quenched with NH$_4$Cl(aq) and diluted with EtOAc. The organic phase is washed with water twice, dried, filtered, concentrated, and loaded on a column and 3-bromo-2-chloro-5-fluoro-6-methylpyridine (D) is purified via silica gel chromatography.

Example 1A.2

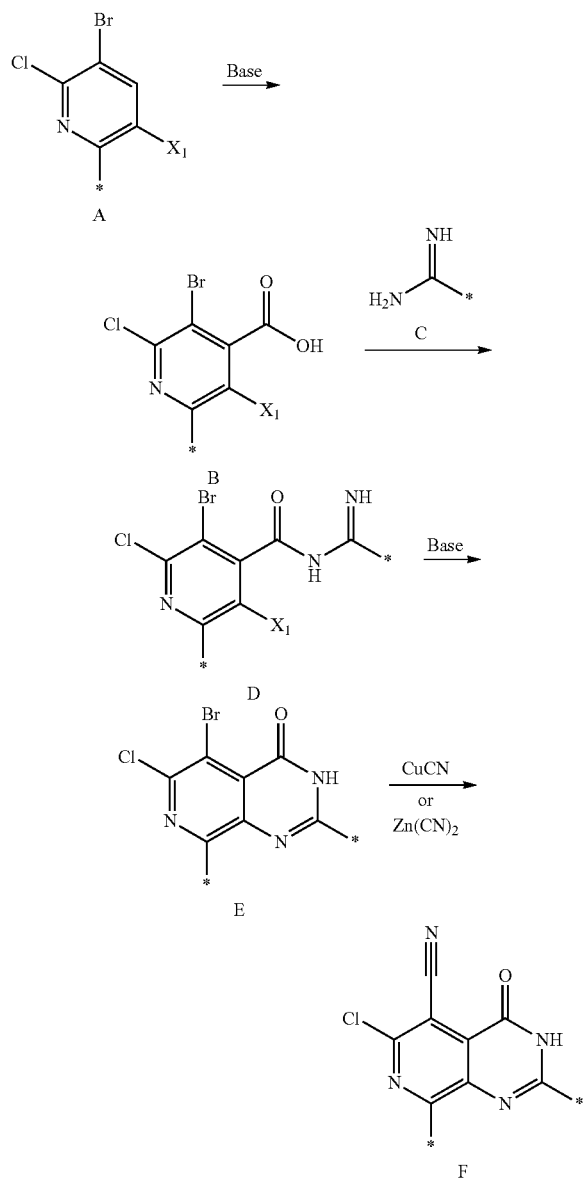

To a solution of 3-bromo-2-chloro-5-fluoro-6-methylpyridine (A, 1 equiv.) in tetrahydrofuran (0.40 M) at −96° C. (internal temperature), lithium diisopropylamide solution (1.2 equiv.; 2 M in tetrahydrofuran) is added over a period of 60 min, maintaining internal temperature between −96 to −84° C. and the reaction mixture is maintained at −96 to −90° C. for 2 h. Carbon dioxide gas is purged into the reaction mixture for 35 minutes, maintaining internal temperature at −95 to −78° C. Progress of the reaction is monitored by TLC and the reaction mixture is warmed to −50 to −45° C., quenched with saturated aqueous ammonium chloride solution, and stirred for 10 min. The solution is acidified to pH 2.0-1.5 with 6 N hydrochloric acid, diluted with ethyl acetate and the organic layer washed with water. The aqueous layer is extracted with ethyl acetate and the combined organic layers are concentrated under reduced pressure, stirred in dichloromethane and the solid precipitated is filtered, washed with dichloromethane, and dried under vacuum to afford 3-bromo-2-chloro-5-fluoro-6-methylisonicotinic acid (B).

To a solution of 3-bromo-2-chloro-5-fluoro-6-methylisonicotinic acid (B, 1 equiv.) in N,N-dimethylformamide (0.32 M), acetamidine hydrochloride (C, 1.4 equiv.) is added and reaction mixture is cooled at 0° C. N,N-di-isopropylethylamine (5 equiv.) and HATU (1.1 equiv.) are added and reaction mixture is stirred at room temperature for 1 h. The reaction mixture is diluted with water, extracted with ethyl acetate and the combined organic layers are dried over anhydrous sodium sulphate, filtered and concentrated to afford 3-bromo-2-chloro-5-fluoro-N-(1-iminoethyl)-6-methylisonicotinamide (D).

To a stirred solution of 3-bromo-2-chloro-5-fluoro-N-(1-iminoethyl)-6-methylisonicotinamide (D, 1 equiv.) in tetrahydrofuran (2 M), sodium hydride (60%) (1 equiv.) is added at 0° C. and stirred for 1 h at 0° C. The reaction mass is slowly warmed to room temperature and stirred for 16 h. The reaction mass is cooled to 0° C., acidified with 2 N hydrochloric acid (pH~2), and the resulting solid filtered, washed with 10% methanol in diethyl ether and dried to afford 5-bromo-6-chloro-2,8-dimethylpyrido[3,4-d]pyrimidin-4(3H)-one (E).

To a stirred solution of 5-bromo-6-chloro-2,8-dimethylpyrido[3,4-d]pyrimidin-4(3H)-one (E, 1 equiv.) in N,N-dimethylformamide (0.056 M), copper(I) cyanide (1.2 equiv.) is added at room temperature. The reaction is heated to 100° C. and stirred for 16 h. The reaction is quenched with 1 N hydrochloric acid, and the solid is filtered, washed with diethyl ether, and purified by via chromatography to afford 6-chloro-2,8-dimethyl-4-oxo-3,4-dihydropyrido[3,4-d]pyrimidine-5-carbonitrile (F).

5-bromo-6-chloro-2,8-dimethylpyrido[3,4-d]pyrimidin-4(3H)-one (E, 1 equiv.), copper(I) cyanide (1.2 equiv.), and NMP (0.072 M) are combined in a sealable vessel with a stir bar. The resulting mixture is sealed, stirred, and heated at 90° C. for 20 h. Upon cooling to room temperature, the reaction mixture is diluted with 1% TFA in acetonitrile, filtered, and purified via chromatography to afford 6-chloro-2,8-dimethyl-4-oxo-3,4-dihydropyrido[3,4-d]pyrimidine-5-carbonitrile (F).

To a solution of 5-bromo-6-chloro-2,8-dimethylpyrido[3,4-d]pyrimidin-4(3H)-one (E, 1 equiv.) in N,N-dimethylacetoamide (0.07 M) is added dicyanozinc (1.4 equiv.) and tetrakis(triphenylphosphine)palladium (2.0 equiv.) at room temperature. The mixture is degassed with argon for 5 min, and stirred for 5 h at 130° C. Upon cooling to room temperature, the mixture is diluted with dimethyl sulfoxide and acetonitrile and purified by chromatography to afford 6-chloro-2,8-dimethyl-4-oxo-3,4-dihydropyrido[3,4-d]pyrimidine-5-carbonitrile (F).

Example 1A.3

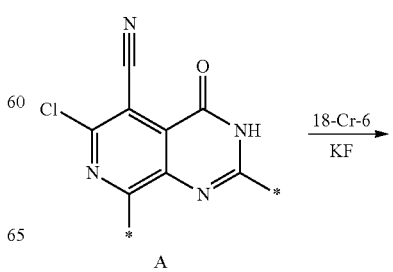

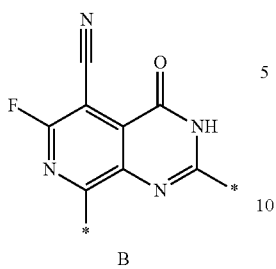

B

A solution of 6-chloro-2-methyl-4-oxo-3,4-dihydropyrido[3,4-d]pyrimidine-5-carbonitrile (A, 1 equiv.) in dimethyl sulfoxide (0.23 M) is purged with argon gas for 10 minutes. 18-Crown-6 ether (1.5 equiv.) and potassium fluoride (5 equiv.) are added to the reaction mixture and purging is continued for 5 minutes and stirred in a preheated oil bath at 160° C. for 2 h. The reaction mixture is cooled, poured on to ice cold water, extracted with ethyl acetate, and the ethyl acetate layer washed with brine solution, dried over anhydrous sodium sulphate, concentrated, and triturated with diethyl ether to get 6-fluoro-2-methyl-4-oxo-3,4-dihydropyrido[3,4-d]pyrimidine-5-carbonitrile (B).

Example 1A.4

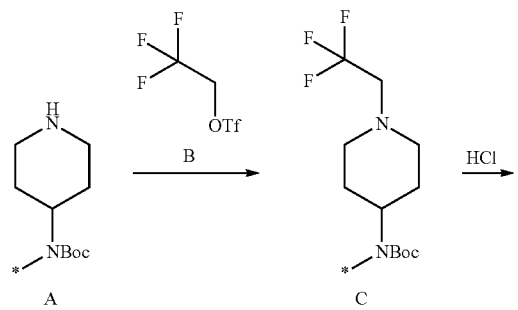

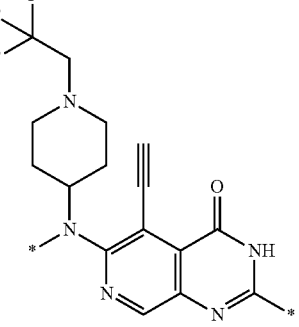

F

To a solution of tert-butyl methyl(piperidin-4-yl)carbamate (A, 1 equiv.) and N,N-diisopropylethylamine (10 equiv.) in acetonitrile (0.35 M), 2,2,2-trifluoroethyl trifluoromethanesulfonate (2, 1.25 equiv.) is added dropwise and the mixture stirred at room temperature for 16 h. The reaction mixture is diluted with water, extracted with dichloromethane, and the organic layer dried over anhydrous sodium sulphate, filtered, concentrated, and purified by flash column chromatography to afford tert-butyl methyl(1-(2,2,2-trifluoroethyl)piperidin-4-yl)carbamate (C).

A solution of tert-butyl methyl(1-(2,2,2-trifluoroethyl)piperidin-4-yl)carbamate (C, 1 equiv.) in hydrochloride (4 M solution in 1,4-dioxane, 0.34 M) is stirred at room temperature for 4 h. The reaction mixture is concentrated to afford N-methyl-1-(2,2,2-trifluoroethyl)piperidin-4-amine hydrochloride (D).

A solution of 6-chloro-2-methyl-4-oxo-3,4-dihydropyrido[3,4-d]pyrimidine-5-carbonitrile (E, 1 equiv.) and N-methyl-1-(2,2,2-trifluoroethyl)piperidin-4-amine hydrochloride (D, 3 equiv.) in N,N-dimethylacetamide (0.24 M), potassium fluoride (8 equiv.) and 18-crown-6 (1 equiv.) are added and the reaction mixture heated at 130° C. for 16 h. The reaction mixture is cooled, diluted with water, extracted with ethyl acetate, and the organic layer washed with water, dried over anhydrous sodium sulphate, filtered, concentrated, and purified by flash column chromatography to afford 2-methyl-6-(methyl(1-(2,2,2-trifluoroethyl)piperidin-4-yl)amino)-4-oxo-3,4-dihydropyrido[3,4-d]pyrimidine-5-carbonitrile (F).

Example 1A.5

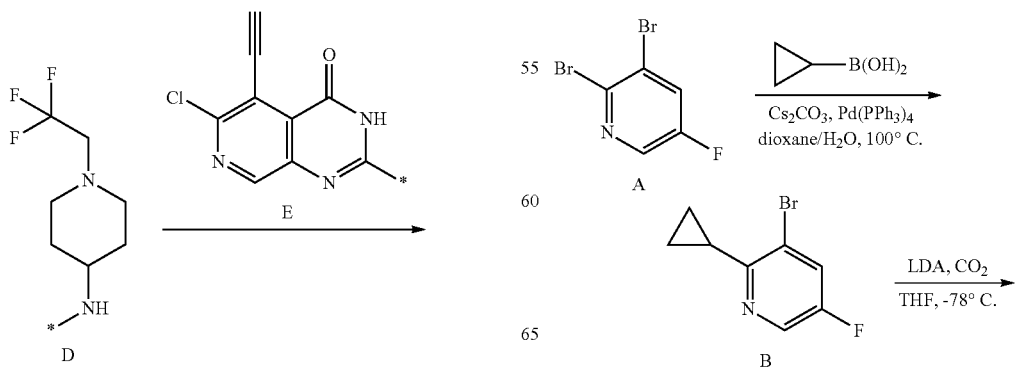

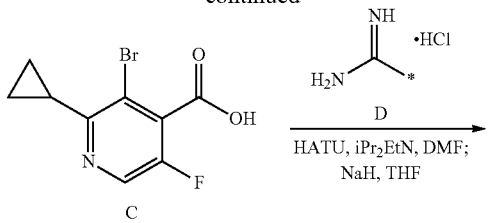

1,4-Dioxane (24 mL) and water (8 mL) is added to a mixture of 2,3-dibromo-5-fluoropyridine (A, 3000 mg, 11.8 mmol), cyclopropylboronic acid (1112 mg, 12.9 mmol), and cesium carbonate (8436 mg, 25.9 mmol). The mixture is bobbled with argon bubbling for 5 min. Tetrakis(triphenylphosphine)palladium (680 mg, 0.590 mmol) is added to the mixture, and the mixture is vacuumed and backfilled with argon three times. The resulting clear yellow reaction mixture is stirred for 72 h at 110° C. The mixture is diluted with ethyl acetate, and washed with brine, dried over anhydrous magnesium sulfate, and concentrated in vacuo after filtration. Purification by silica gel column chromatography (0 to 5% ethyl acetate in hexane) gave 3-bromo-2-cyclopropyl-5-fluoropyridine (B).

n-Butyllithium (2.5 M in hexane, 2.1 mL, 5.30 mmol) is added to a stirred solution of diisopropylamine (0.81 mL, 5.80 mmol) in THF (5 mL) at 0° C. under argon. The resulting light yellow solution is stirred for 10 min at 0° C. and then added slowly to a stirred solution of 3-bromo-2-cyclopropyl-5-fluoropyridine (B, 1000 mg, 4.60 mmol) in tetrahydrofuran (20 mL) at −78° C. under argon. The resulting yellow reaction mixture is stirred at −78° C. under argon for 30 min and then carbon dioxide gas is bubbled in for 2 min. The mixture is stirred at −78° C. for 10 min and then warmed to room temperature over 5 min. The reaction is diluted with 0.1 N sodium hydroxide, and extracted with diethyl ether. Water layer is acidified by 3 M hydrogen chloride, and extracted with ethyl acetate twice, dried over anhydrous magnesium sulfate, and concentrated in vacuo after filtration to afford 3-bromo-2-cyclopropyl-5-fluoroisonicotinic acid (C).

To a N,N-dimethylformamide (14 mL) solution of 3-bromo-2-cyclopropyl-5-fluoroisonicotinic acid (C, 730. mg, 2.81 mmol) is added 1-[bis(dimethylamino)methylene]-1H-1,2,3-triazolo[4,5-b]pyridinium 3-oxide hexafluorophosphate (1387 mg, 3.60 mmol) and N,N-diisopropylethylamine (2.0 mL, 11.2 mmol) at 0° C. The mixture is stirred for 5 min at room temperature, and acetamidine hydrochloride (D, 345 mg, 3.60 mmol) is added to the mixture. After stirring the mixture for 17 h at room temperature, ice-cold water is added to the mixture, and extracted with ethyl acetate twice. The combined extracts are washed with aqueous solution of ammonium chloride, aqueous solution of sodium bicarbonate, and brine, dried over anhydrous magnesium sulfate, and concentrated in vacuo after filtration. The residue is dissolved tetrahydrofuran (18 mL), and sodium hydride (60% in mineral oil, 225 mg, 5.60 mmol) is added to the mixture at 0° C. After stirring the mixture for 18 h, ice-cold water is added to the mixture, and extracted with ethyl acetate three times, dried over anhydrous magnesium sulfate, and concentrated in vacuo after filtration. The residue is triturated with dichloromethane, and filtered to afford 5-bromo-6-cyclopropyl-2-methylpyrido[3,4-d]pyrimidin-4(3H)-one (E).

Example 1A.6

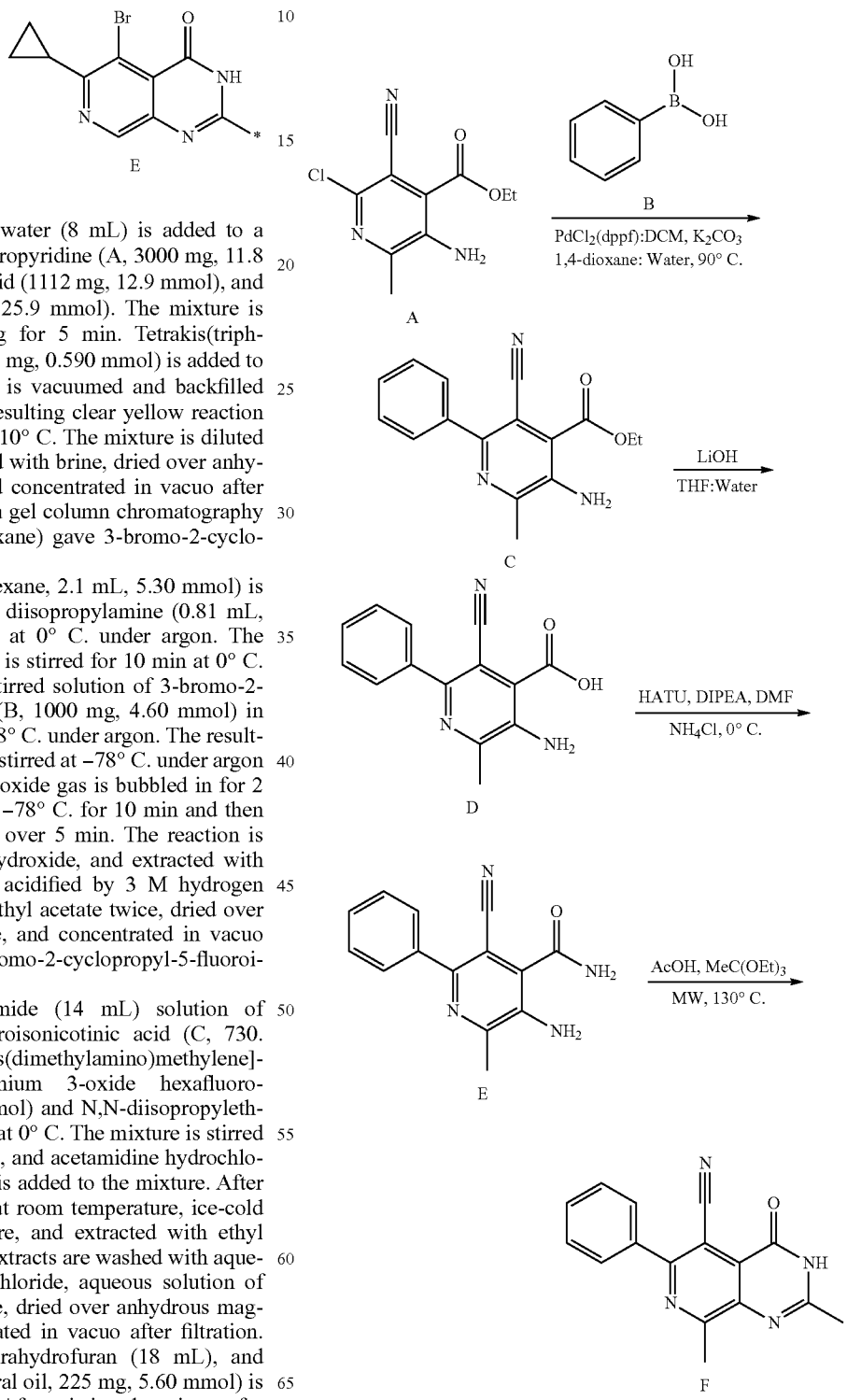

To a solution of ethyl 3-amino-6-chloro-5-cyano-2-methylisonicotinate (A, 0.90 g, 3.75 mmol) in 1,4-dioxane and water (4:1, 10.0 mL), phenylboronic acid (B, 0.68 g, 5.62 mmol) and potassium carbonate (1.53 g 11.25 mmol) are added. The reaction mixture is purged with argon for 5 min. Then, [1,1-bis(diphenylphospino)ferrocene] dichloropalladium(II) (complex with dichloromethane, 0.031 g, 0.037 mmol) is added and the reaction mixture is heated at 90° C.

acetic acid (4:1, 4 mL) is heated at 130° C. for 2 h under microwave. After this time, the reaction mixture is cooled, diluted with hexanes, and filtered to afford 2,8-dimethyl-4-oxo-6-phenyl-3,4-dihydropyrido[3,4-d]pyrimidine-5-carbonitrile (F).

Example 1A.7

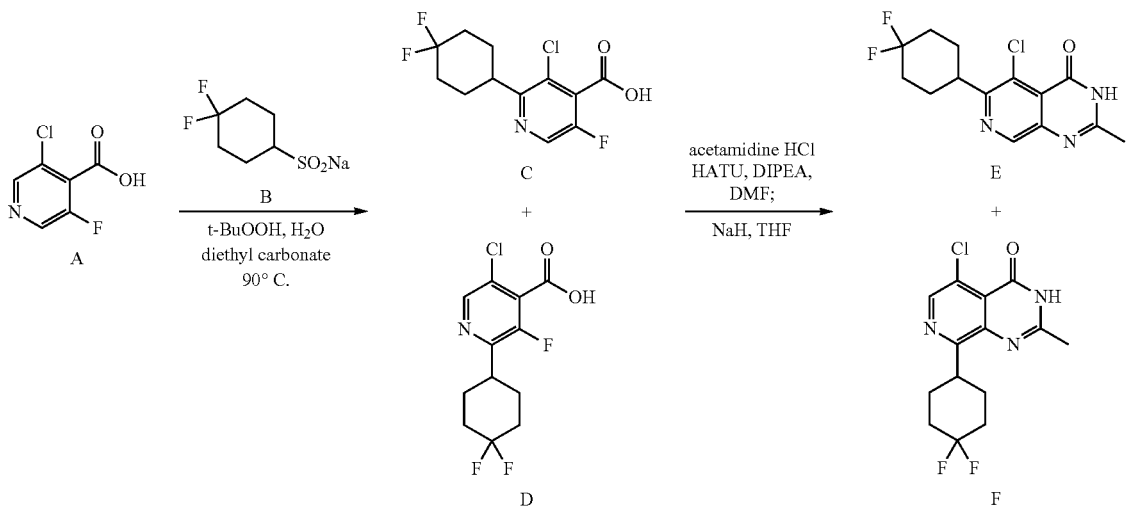

for 5 h. After this time, the reaction mixture is cooled, diluted with water, and extracted with ethyl acetate. The organic layer is dried over anhydrous sodium sulfate, filtered, and concentrated to obtain the crude product. This is purified by silica gel (100-200 mesh) column chromatography using 30-40% ethyl acetate in hexane to afford ethyl 3-amino-5-cyano-2-methyl-6-phenylisonicotinate (C).

To a solution of ethyl 3-amino-5-cyano-2-methyl-6-phenylisonicotinate (C, 0.6 g, 2.13 mmol) in tetrahydrofuran and water (4:1, 6 mL) at room temperature, lithium hydroxide (0.44 g, 10.67 mmol) is added. This reaction mixture is stirred at room temperature for 2 h. After this time, the reaction mixture is diluted with water, acidified with 1 N hydrochloric acid, and extracted with ethyl acetate. The organic layer is dried over anhydrous sodium sulfate, filtered, and concentrated to obtain the crude product. This is washed with diethyl ether to afford 3-amino-5-cyano-2-methyl-6-phenylisonicotinic acid (D).

To a solution of 3-amino-5-cyano-2-methyl-6-phenylisonicotinic acid (D, 0.5 g, 1.97 mmol) in N,N-dimethylformamide (5.0 mL), ammonium chloride (0.31 g, 5.92 mmol) and 1-[bis(dimethylamino)methylene]-1H-1,2,3-triazolo[4,5-b]pyridinium 3-oxid hexafluorophosphate (0.840 g, 2.21 mmol) are added. This reaction mixture is cooled to 0° C., N,N-di-isopropylethylamine (2.7 mL, 14.70 mmol) is added, and the reaction mixture is stirred at 0° C. for 10 min. Then, the reaction mixture is diluted with water and extracted with ethyl acetate. The organic layer is dried over anhydrous sodium sulfate, filtered, and concentrated to obtain the crude product. This is purified by silica gel (100-200 mesh) column chromatography using 30-40% ethyl acetate in hexanes to afford 3-amino-5-cyano-2-methyl-6-phenylisonicotinamide (E).

A solution of 3-amino-5-cyano-2-methyl-6-phenylisonicotinamide (E, 0.4 g, 1.19 mmol), in triethylorthoacetate and To a stirred mixture of 3-chloro-5-fluoroisonicotinic acid (A, 1 equiv.) in diethyl carbonate (0.29 M) and water (0.44 M) under argon is added sodium 4,4-difluorocyclohexane-1-sulfinate (B, 3 equiv.) and the mixture is cooled to 0° C. tert-Butyl hydroperoxide (70 wt. % in water) (10 equiv.) is added and the mixture is stirred for 5 min then heated at 90° C. under argon with an oil bath for 3 h. Volatiles are removed on a rotary evaporator. The residue is taken up in a mixture of water, acetonitrile and TFA, filtered, and purified via preparatory HPLC to afford a mixture of 3-chloro-2-(4,4-difluorocyclohexyl)-5-fluoroisonicotinic acid (C) and 5-chloro-2-(4,4-difluorocyclohexyl)-3-fluoroisonicotinic acid (D).

HATU (1.1 equiv.) is added to a stirred solution of 3-chloro-2-(4,4-difluorocyclohexyl)-5-fluoroisonicotinic acid (C) and 5-chloro-2-(4,4-difluorocyclohexyl)-3-fluoroisonicotinic acid (D 1 equiv.) in DMF (0.46 M) at room temperature under argon. After 2 min N,N-diisopropylethylamine (1.1 equiv.) is added. After stirring at room temperature for 35 min a solution of acetamidine hydrochloride (2 equiv.) and N,N-diisopropylethylamine (2.2 equiv.) in DMF (5.6 M) (this is heated with a heat gun and sonicated to get all of the acetamidine dissolved) is added. The resulting solution is stirred vigorously at room temperature under argon for 1.5 h. The reaction mixture is diluted with ethyl acetate and washed three times with brine. The organics are dried over magnesium sulfate, filtered, concentrated on a rotary evaporator, and dried under high vacuum to afford a viscous amber oil. The oil is dissolved in THF (0.046 M) with stirring under argon. Sodium hydride (2.2 equiv.) is added and the reaction mixture is stirred vigorously at room temperature under argon for 21 h. A solution of ammonium chloride (5 equiv.) in water (0.14 M) is added with vigorous stirring. The resulting mixture is partitioned between ethyl acetate and brine. The organics are dried over magnesium sulfate, filtered, and concentrated on a rotary evaporator. The residue is taken up in NMP, acetonitrile, and TFA, filtered, and purified via preparatory HPLC to afford 5-chloro-6-(4,4-difluorocyclohexyl)-2-methylpyrido[3,4-d]pyrimidin-4(3H)-one (E) and 5-chloro-8-(4,4-difluorocyclohexyl)-2-methylpyrido[3,4-d]pyrimidin-4(3H)-one (F)

Example 1A.8 solved in DMF (20 mL) with stirring at 90° C. under argon. Copper(I) cyanide (338 mg, 3.77 mmol) is added and the resulting clear red solution is stirred and heated at 90° C. under argon for 1 h 40 min. While still hot the reaction mixture is diluted with ethyl acetate and filtered through Celite into ethyl acetate (600 mL). The filter cake is washed with ethyl acetate. The filtrate is shaken with water to give an emulsion which is filtered. The filtrate is partitioned

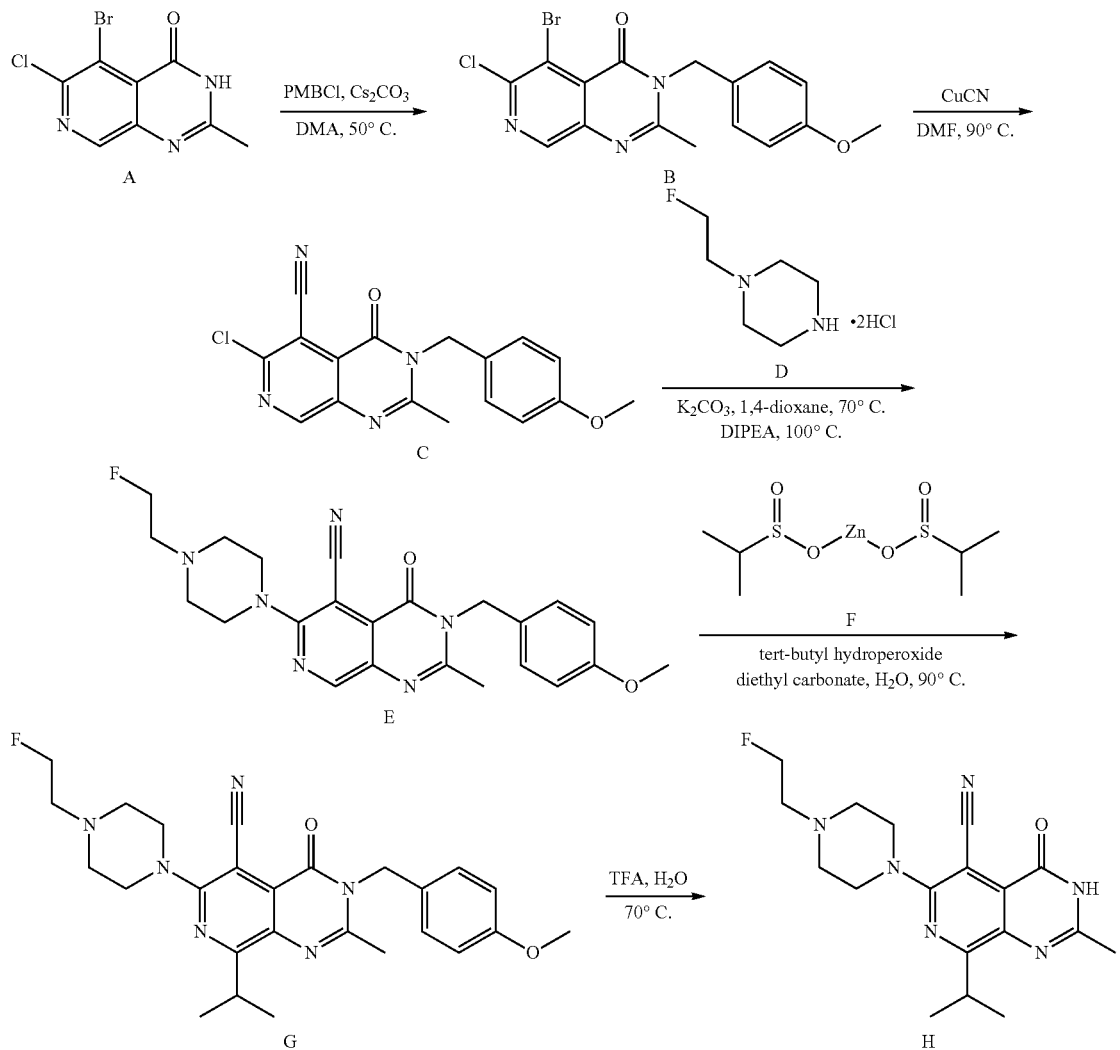

4-Methoxybenzyl chloride (1.27 mL, 9.38 mmol) is added to a stirred mixture of 5-bromo-6-chloro-2-methylpyrido[3,4-d]pyrimidin-4(3H)-one (A, 1.98 g, 7.21 mmol) and cesium carbonate (3.29 g, 10.1 mmol) in DMA (14 mL) at room temperature under argon. The resulting mixture is stirred vigorously and heated at 50° C. under argon for 2 h. The reaction mixture is diluted with ethyl acetate (1.5 L), washed once with water, and twice with brine. The organics are dried over magnesium sulfate, filtered, concentrated on a rotary evaporator with silica gel, and purified via silica gel chromatography (0-40% ethyl acetate in dichloromethane) to afford 5-bromo-6-chloro-3-(4-methoxybenzyl)-2-methylpyrido[3,4-d]pyrimidin-4(3H)-one (B).

5-Bromo-6-chloro-3-(4-methoxybenzyl)-2-methylpyrido[3,4-d]pyrimidin-4(3H)-one (B, 1.24 g, 3.14 mmol) is disbetween ethyl acetate and brine. The organics are washed twice with brine, dried over magnesium sulfate, filtered, concentrated on a rotary evaporator with silica gel, and purified via silica gel chromatography (0-100% ethyl acetate in dichloromethane) to afford 6-chloro-3-(4-methoxybenzyl)-2-methyl-4-oxo-3,4-dihydropyrido[3,4-d]pyrimidine-5-carbonitrile (C).

6-Chloro-3-(4-methoxybenzyl)-2-methyl-4-oxo-3,4-dihydropyrido[3,4-d]pyrimidine-5-carbonitrile (C, 100 mg, 0.293 mmol), 1-(2-fluoroethyl)piperazine bis HCl salt (D, 120 mg, 0.587 mmol), potassium carbonate (183 mg, 1.32 mmol), and NMP (1.5 mL) are combined in a sealable vessel with a stir bar. The resulting mixture is sealed, stirred vigorously, and heated at 70° C. with an oil bath for 40 min. N,N-diisopropylethylamine (0.26 mL, 1.47 mmol) is added and the resulting mixture is sealed, stirred vigorously, and heated at 100° C. with an oil bath for 1 h. After cooling to room temperature, the reaction mixture is diluted with methanol and acetic acid (0.34 mL, 5.87 mmol). The resulting mixture is filtered and purified via preparatory HPLC (10-45% acetonitrile in water with 0.1% TFA). Fractions containing the desired product are combined and concentrated on a rotary evaporator down to ~20 mL and then lyophilized to dryness to afford a yellow oil. The oil is dissolved in acetonitrile and loaded onto a 2-gram Strata X-C ion exchange column from Phenomenex. The column is washed sequentially with water, acetonitrile, methanol, and then 5% ammonium hydroxide in methanol. Eluent containing the desired product is concentrated on a rotary evaporator and dried under high vacuum to afford 6-(4-(2-fluoroethyl)piperazin-1-yl)-3-(4-methoxybenzyl)-2-methyl-4-oxo-3,4-dihydropyrido[3,4-d]pyrimidine-5-carbonitrile (E).

To a stirred mixture of 6-(4-(2-fluoroethyl)piperazin-1-yl)-3-(4-methoxybenzyl)-2-methyl-4-oxo-3,4-dihydropyrido[3,4-d]pyrimidine-5-carbonitrile (E, 28.2 mg, 0.065 mmol) in diethyl carbonate (0.4 mL) and water (0.2 mL) under argon is added bis((isopropylsulfinyl)oxy)zinc (F, 54.2 mg, 0.194 mmol) followed by tert-butyl hydroperoxide (70 wt. % in water) (0.092 mL, 0.666 mmol). The mixture is stirred and heated at 90° C. under argon with an oil bath for 10 min. The reaction mixture is diluted with NMP, acetic acid, and methanol, filtered, and purified via preparatory HPLC (15-65% acetonitrile in water with 0.1% TFA). Fractions containing the desired product are loaded onto a Strata X-C ion exchange column from Phenomenex. The column is washed sequentially with water, acetonitrile, methanol, and then 5% ammonium hydroxide in methanol. Eluent containing the desired product is concentrated on a rotary evaporator and dried under high vacuum to afford 6-(4-(2-fluoroethyl)piperazin-1-yl)-8-isopropyl-3-(4-methoxybenzyl)-2-methyl-4-oxo-3,4-dihydropyrido[3,4-d]pyrimidine-5-carbonitrile (G).

q6-(4-(2-Fluoroethyl)piperazin-1-yl)-8-isopropyl-3-(4-methoxybenzyl)-2-methyl-4-oxo-3,4-dihydropyrido[3,4-d]pyrimidine-5-carbonitrile (G, 23.8 mg, 0.050 mmol), TFA (2 mL), and water (0.1 mL) are combined in a sealable vessel with a stir bar, sealed, stirred, and heated at 70° C. for 1 h. Volatiles are removed on a rotary evaporator. The residue is taken up in NMP and methanol, filtered, and purified via preparatory HPLC (10-40% acetonitrile in water with 0.1% TFA). Fractions containing the desired product are loaded onto a Strata X-C ion exchange column from Phenomenex. The column is washed sequentially with water, acetonitrile, methanol, and then 5% ammonium hydroxide in methanol. Eluent containing the desired product is concentrated on a rotary evaporator and dried under high vacuum to afford 6-(4-(2-fluoroethyl)piperazin-1-yl)-8-isopropyl-2-methyl-4-oxo-3,4-dihydropyrido[3,4-d]pyrimidine-5-carbonitrile (H).

Example 1A.9

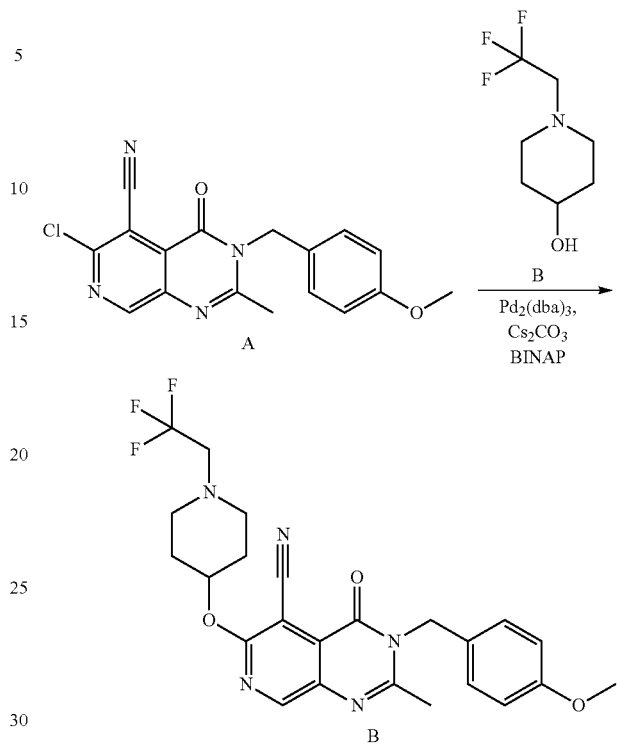

To a 1,4-dioxane (5.6 mL) solution of 6-chloro-3-(4-methoxybenzyl)-2-methyl-4-oxo-3,4-dihydropyrido[3,4-d]pyrimidine-5-carbonitrile (A, 192 mg, 0.560 mmol) is added 1-(2,2,2-trifluoroethyl)piperidin-4-ol (B, 206 mg, 1.13 mmol), cesium carbonate (367 mg, 1.13 mmol), 2,2'-bis(diphenylphosphino)-1,1'-binaphthyl (105 mg, 0.169 mmol), and tris(dibenzylideneacetone)dipalladium (103 mg, 0.113 mmol) at room temperature. The mixture is bubbled with argon for 5 min, and stirred for 2 h at 100° C. The mixture is diluted with ethyl acetate and filtered through a pad of Celite. The filtrate is concentrated in vacuo. Purification by silica gel column chromatography (0-80% ethyl acetate in hexane) gave crude 3-(4-methoxybenzyl)-2-methyl-4-oxo-6-((1-(2,2,2-trifluoroethyl)piperidin-4-yl)oxy)-3,4-dihydropyrido[3,4-d]pyrimidine-5-carbonitrile (C).

Example 1A.10

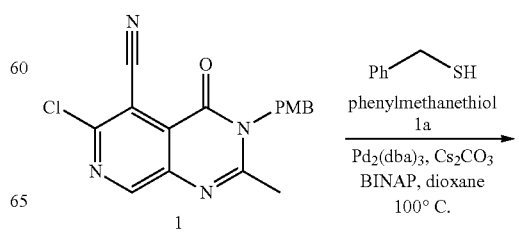

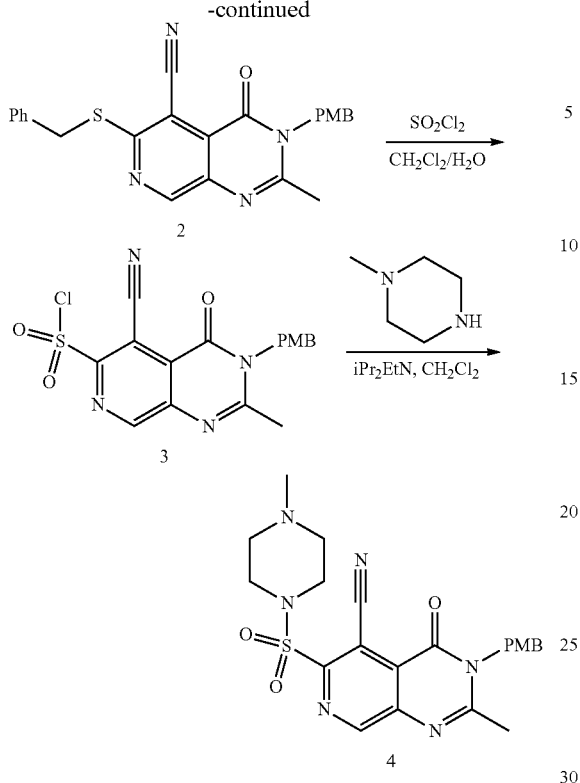

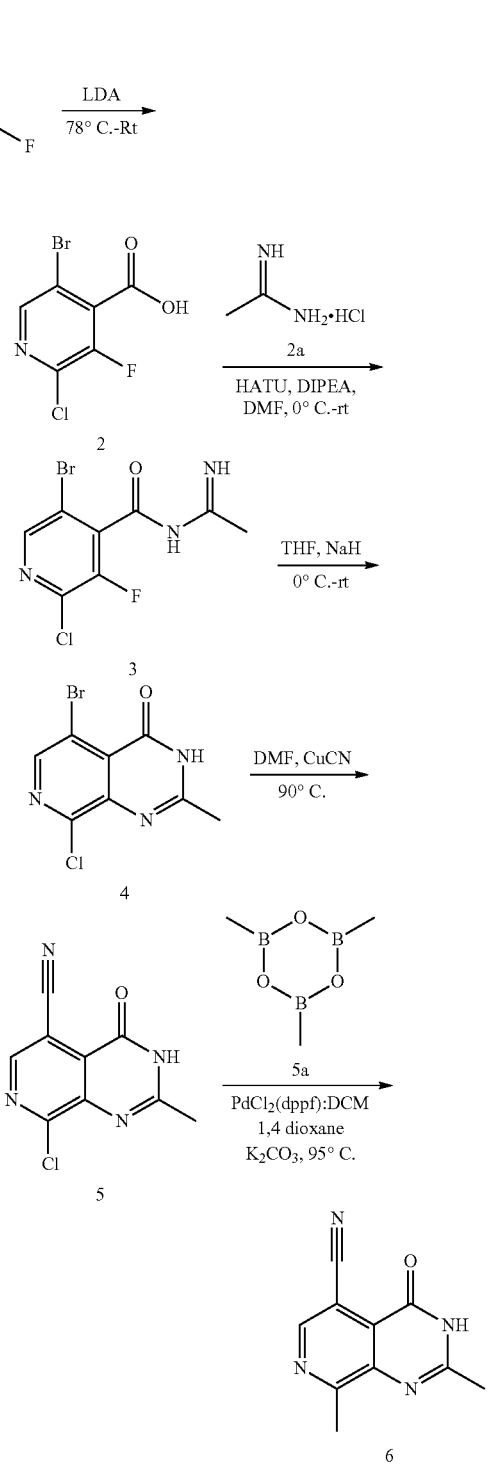

To a 1,4-dioxane (3.9 mL) solution of 6-chloro-3-(4-methoxybenzyl)-2-methyl-4-oxo-3,4-dihydropyrido[3,4-d]pyrimidine-5-carbonitrile (1, 134 mg, 0.390 mmol) is added phenylmethanethiol (1a, 0.09 mL, 0.790 mmol), cesium carbonate (256 mg, 0.790 mmol), 2,2'-bis(diphenylphosphino)-1,1'-binaphthyl (73 mg, 0.118 mmol), and tris(dibenzylideneacetone)dipalladium (72 mg, 0.0790 mmol) at room temperature. The mixture is bubbled with argon for 5 min, and stirred for 2 h at 100° C. The mixture is diluted with ethyl acetate, and washed with 5% breech in water, dried over anhydrous magnesium sulfate, and concentrated in vacuo after filtration. Purification by preparative HPLC ($C_{18}$ column, 15-85% acetonitrile in water+0.1% trifluoroacetic acid) gave 6-(benzylthio)-3-(4-methoxybenzyl)-2-methyl-4-oxo-3,4-dihydropyrido[3,4-d]pyrimidine-5-carbonitrile (2).

To a dichloromethane (2 mL) and water (0.4 mL) solution of 6-(benzylthio)-3-(4-methoxybenzyl)-2-methyl-4-oxo-3,4-dihydropyrido[3,4-d]pyrimidine-5-carbonitrile (2, 74 mg, 0.173 mmol) is added sulfuryl chloride (0.1 mL, 1.21 mmol) at 0° C. The mixture is stirred for 1 h at room temperature. Organic layer is separated and dried over anhydrous magnesium sulfate, and concentrated in vacuo after filtration to give crude 5-cyano-3-(4-methoxybenzyl)-2-methyl-4-oxo-3,4-dihydropyrido[3,4-d]pyrimidine-6-sulfonyl chloride (3).

To a dichloromethane (1.7 mL) solution of 5-cyano-3-(4-methoxybenzyl)-2-methyl-4-oxo-3,4-dihydropyrido[3,4-d]pyrimidine-6-sulfonyl chloride (3, 70 mg, 0.173 mmol) is added 1-methylpiperazine (0.06 mL, 0.520 mmol) and diisopropylethylamine (0.09 mL, 0.520 mmol) at 0° C. After stirring the mixture for 1 h at room temperature, the mixture is diluted with aqueous sodium bicarbonate. Organic materials are extracted with ethyl acetate twice, dried over anhydrous magnesium sulfate, and concentrated in vacuo after filtration. Purification by preparative IPLC ($C_{18}$ column, 15-60% acetonitrile in water+0.1% trifluoroacetic acid) gave 3-(4-methoxybenzyl)-2-methyl-6-((4-methylpiperazin-1-yl)sulfonyl)-4-oxo-3,4-dihydropyrido[3,4-d]pyrimidine-5-carbonitrile (4).

Example 1A.11

A solution of 5-bromo-2-chloro-3-fluoropyridine (1, 30.0 g, 143.6 mmol) in tetrahydrofuran (300 mL) is cooled to −78° C. and lithiumdiisopropylamide (2 M in THF, 78.9 mL, 157.9 mmol) is added dropwise. This reaction mixture is stirred at −78° C. for 1 h. Then, the reaction mixture is purged with carbon dioxide gas for 15 min allowed to warm at room temperature. The reaction mixture is quenched with ammonium chloride solution and diluted with water. The aqueous layer is washed with ethyl acetate, acidified with 6 N hydrochloric acid solution, and extracted with 15% methanol in dichloromethane. The organic layer is dried over anhydrous sodium sulfate, filtered, and concentrated to afford 5-bromo-2-chloro-3-fluoroisonicotinic acid (2).

To solution of 5-bromo-2-chloro-3-fluoroisonicotinic acid (2, 18.0 g, 71.1 mmol) in N,N-dimethylformamide (30 mL) at 0° C., acetamidine hydrochloride (2a, 13.4 g, 142.3 mmol) is added. Then N,N-diisopropylethylamine (110 mL, 711.0 mmol) and 1-[bis(dimethylamino)methylene]-1H-1,2,3-triazolo[4,5-b]pyridinium 3-oxid hexafluorophosphate (40.5 g, 106.6 mmol) are added and the reaction mixture is stirred at room temperature for 2 h. After this time, reaction mixture is diluted with water and extracted with ethyl acetate. The organic layer is dried over anhydrous sodium sulfate, filtered, and concentrated to afford crude 5-bromo-2-chloro-3-fluoro-N-(1-iminoethyl)isonicotinamide (3).

A solution of crude 5-bromo-2-chloro-3-fluoro-N-(1-iminoethyl)isonicotinamide (3, 18.0 g) in tetrahydrofuran (200 mL) is cooled to 0° C., then 60% sodium hydride in mineral oil (7.30 g NaH, 184.3 mmol) is added portionwise and the reaction mixture is stirred at room temperature for 12 h. After this time, the reaction mixture is poured into ice-cold water. The aqueous layer is washed with 5% methanol in dichloromethane, acidified with 6 N hydrochloric acid solution, and extracted with 10% methanol in dichloromethane. The organic layer from this extraction is dried over anhydrous sodium sulfate, filtered, and concentrated to obtain the crude product which is washed with diethyl ether to afford 5-bromo-8-chloro-2-methylpyrido[3,4-d]pyrimidin-4(3H)-one (4).

To a solution of 5-bromo-8-chloro-2-methylpyrido[3,4-d]pyrimidin-4(3H)-one (4, 8.0 g, 29.3 mmol) in N,N-dimethylformamide (80.0 mL), copper(I) cyanide (4.1 g, 46.8 mmol) is added. The reaction mixture is heated at 90° C. for 3 h. After this time, the reaction mixture is cooled, diluted with water, acidified with 6 N hydrochloric acid solution, and extracted with ethyl acetate. The organic layer is concentrated to obtain the crude product which is purified by silica gel (100-200 mesh) column chromatography using 40-50% ethyl acetate in hexanes as eluent to afford 8-chloro-2-methyl-4-oxo-3,4-dihydropyrido[3,4-d]pyrimidine-5-carbonitrile (5).

To a solution of 8-chloro-2-methyl-4-oxo-3,4-dihydropyrido[3,4-d]pyrimidine-5-carbonitrile (5, 1.0 g, 4.55 mmol) in 1,4-dioxane (15.0 mL) at room temperature, 2,4,6-trimethyl-1,3,5,2,4,6-trioxatriborinane (5a, 1.0 mL, 7.5 mmol), potassium carbonate (2.0 g, 15.0 mmol), and water (2 mL) are added. This reaction mixture is degassed with nitrogen for 10 min. Then, [1,1-bis(diphenylphosphino)ferrocene] dichloropalladium(II),complex with dichloromethane (0.183 g, 0.225 mmol) is added and reaction mixture is heated at 95° C. for 12 h. After this time, the reaction mixture is cooled and concentrated under reduced pressure to obtain the crude product which is purified by silica gel (100-200 mesh) column chromatography using 10% methanol in dichloromethane as eluent to afford 2,8-dimethyl-4-oxo-3,4-dihydropyrido[3,4-d]pyrimidine-5-carbonitrile (6).

Example 1A.12

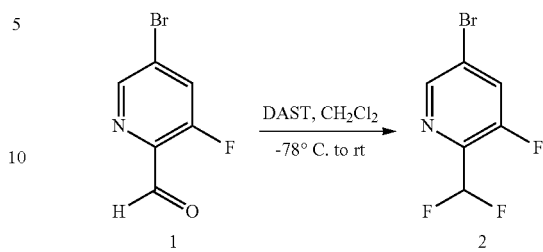

Diethylaminosulfur trifluoride (1.44 mL, 10.4 mmol) is added to a stirred solution of 5-bromo-3-fluoropicolinaldehyde (1, 0.97 g, 4.75 mmol) in DCM (20 mL) at −78° C. under argon. The cold bath is removed, and the reaction mixture is allowed to warm to room temperature under argon for 1.5 h. The reaction mixture is poured into a stirred mixture of saturated aqueous sodium bicarbonate and ice. The resulting mixture is stirred vigorously at room temperature for 1 h to fully quench the reaction mixture. The phases are separated, and the aqueous phase extracted with dichloromethane. The combined organics are dried over sodium sulfate, filtered, concentrated on a rotary evaporator, and purified via silica gel chromatography (0-10% ethyl acetate in hexanes) Fractions containing the desired product are combined and concentrated on a rotary evaporator at room temperature. The residue is diluted with dry THF (5 mL) and concentrated on a rotary evaporator. The residue is dried under high vacuum for 2 min to afford 5-bromo-2-(difluoromethyl)-3-fluoropyridine (2).

Example 1A.13

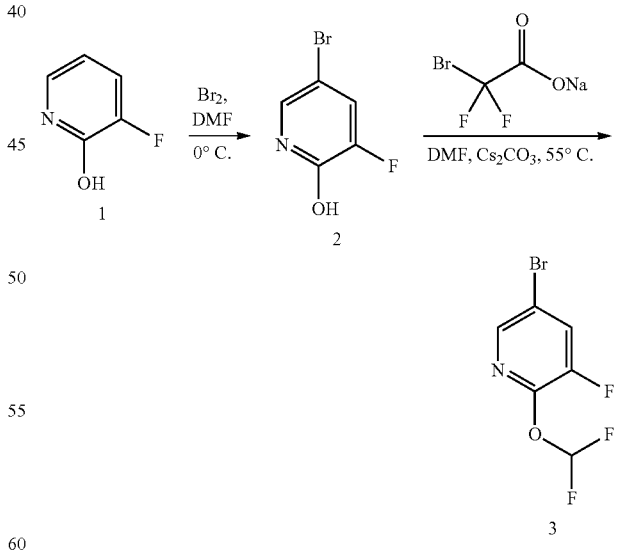

A solution of 3-fluoropyridin-2-ol (1, 20.0 g, 176.9 mmol) in N,N-dimethylformamide (220.0 mL) is cooled at 0° C., bromine (10.30 mL, 194.6 mmol) is added drop wise and reaction mixture is stirred at 0° C. for 2 h. After completion reaction mixture is diluted with water and extracted with ethyl acetate. The organic layer is washed with sodium bicarbonate and brine, dried over anhydrous sodium sulphate, filtered and concentrated to get crude compound. Crude compound is purified by column chromatography using silica gel (100-200 mesh) and 2-3% methanol in dichloromethane to afford 5-bromo-3-fluoropyridin-2-ol (2).

To a solution of 5-bromo-3-fluoropyridin-2-ol (2, 11.0 g, 57.29 mmol) in N,N-dimethylformamide (110 mL), cesium carbonate (24.59 g 74.47 mmol) and sodium 2-bromo-2,2-difluoroacetate (17.04 g, 85.93 mmol) are added and reaction mixture is heated at 55° C. After completion, reaction mixture is diluted with water and extracted with diethyl ether. The organic layer is dried over anhydrous sodium sulphate, filtered and concentrated to get crude compound. Crude compound obtained is concentrated under reduced pressure to obtain crude product which is purified by column chromatography using silica gel (100-200 mesh) and 1-2% ethyl acetate in hexane to afford 5-bromo-2-(difluoromethoxy)-3-fluoropyridine (3).

Example 1A.14

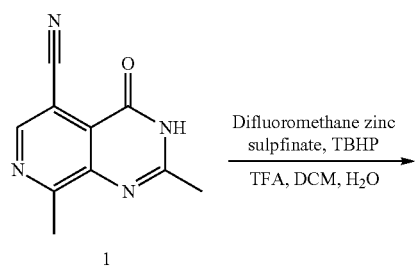

To a solution of 2,8-dimethyl-4-oxo-3,4-dihydropyrido[3,4-d]pyrimidine-5-carbonitrile (1, 0.16 g, 0.8 mmol) and zinc difluoromethanesulpfinate (0.472 g, 1.6 mmol) in a mixture of dichloromethane and water (4:1, 2 mL), trifluoroaceticacid (0.06 mL, 0.8 mmol) and tert-butyl hydroperoxide (0.23 mL, 2.4 mmol) are added. This mixture is stirred at room temperature for 16 h. After this time, the reaction mixture is concentrated under reduced pressure, diluted with water, and extracted with dichloromethane. The combined organic layer is washed with water and then brine, dried over anhydrous sodium sulfate, filtered, and concentrated. The crude product is purified by silica gel (100-200 mesh) flash chromatography using 40% ethyl acetate in hexanes as eluent. The desired fractions are concentrated under reduced pressure to afford 6-(difluoromethyl)-2,8-dimethyl-4-oxo-3,4-dihydropyrido[3,4-d]pyrimidine-5-carbonitrile (2).

Example 1A.15

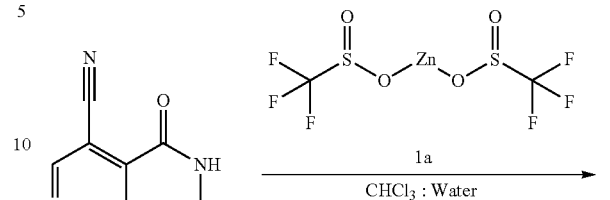

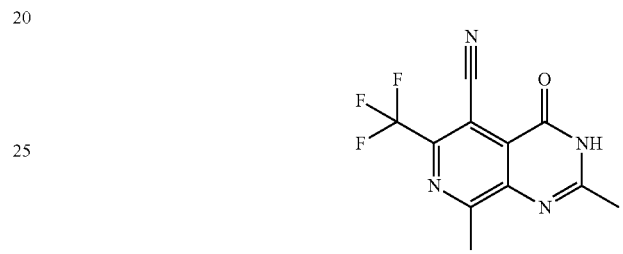

A solution of 2,8-dimethyl-4-oxo-3,4-dihydropyrido[3,4-d]pyrimidine-5-carbonitrile (1, 0.200 g, 0.99 mmol) and bis(((trifluoromethyl)sulfinyl)oxy)zinc (1a, 0.662 g 1.99 mmol) is stirred in chloroform (2.0 mL) and water (2.0 mL), tert-butyl hydrogen peroxide (70%) (0.38 mL, 2.99 mmol) is added at 0° C. The reaction mixture is stirred at room temperature for 15 h. After this time, the reaction mixture is diluted water and extracted with ethyl acetate. The organic layer is dried over anhydrous sodium sulfate, filtered, and concentrated to obtain the crude product. The crude is purified by silica gel (100-200 mesh) column chromatography using 70-80% ethyl acetate in hexanes as eluent. The desired fractions are concentrated under reduced pressure to afford 2,8-dimethyl-4-oxo-6-(trifluoromethyl)-3,4-dihydropyrido[3,4-d]pyrimidine-5-carbonitrile (2).

Example 1A.16

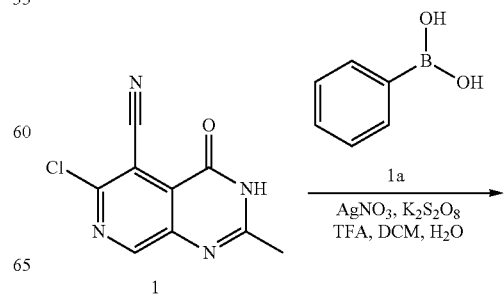

-continued

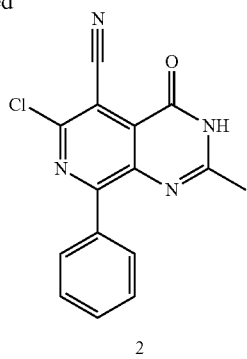

2

To a solution of 6-chloro-2-methyl-4-oxo-3,4-dihydropyrido[3,4-d]pyrimidine-5-carbonitrile (1, 1.0 g, 4.54 mmol), in dichloromethane:water (1:1) (20.0 mL) is added 2,2,2-trifluoroacetic acid (10.4 mL, 13.63 mmol). Reaction mixture is stirred at room temperature for 15 min before the addition of phenylboronic acid (1a, 1.65 g, 13.63 mmol) and stirred for 40 min. Silver nitrate (0.154 g, 0.90 mmol) and Potassium persulfate (2.45 g, 9.09 mmol). is added and reaction mixture is stirred for 24 h at room temperature. After completion, reaction mixture is diluted with water and extracted with dichloromethane. The organic layer is dried over anhydrous sodium sulphate, filtered and concentrated to get crude compound. The crude is washed with 30% diethyl ether in pentene to afford 6-chloro-2-methyl-4-oxo-8-phenyl-3,4-dihydropyrido[3,4-d]pyrimidine-5-carbonitrile (2).

Example 1A.17

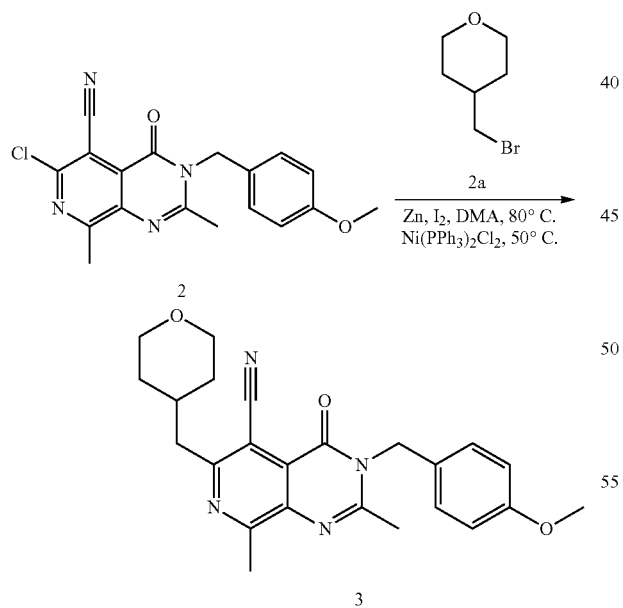

Zinc powder (<10 micron) (37.7 mg, 0.58 mmol) is weighed out in a dry 1 dram vial and placed under argon. DMA (0.4 mL) is added followed by iodine (3.6 mg, 0.014 mmol). The resulting mixture is stirred vigorously at room temperature under argon until the red color of iodine faded (5 min). 4-(bromomethyl)tetrahydro-2H-pyran (2a, 0.072 mL, 0.56 mmol) is added and the resulting mixture is sealed, stirred vigorously, and heated at 80° C. for 23 h. After cooling to room temperature the reaction mixture is placed under argon and 6-chloro-3-(4-methoxybenzyl)-2,8-dimethyl-4-oxo-3,4-dihydropyrido[3,4-d]pyrimidine-5-carbonitrile (2, 49.9 mg, 0.14 mmol) and bis(triphenylphosphine)nickel(II) dichloride (9.2 mg, 0.014 mmol) are added. The resulting mixture is stirred vigorously at room temperature under argon for 2.5 h and then at 50° C. for 2 h. The reaction mixture is diluted with NMP and methanol, filtered, and purified via preparatory HPLC (15-70% acetonitrile in water with 0.1% TFA). Fractions containing the desired product are combined and lyophilized to dryness to afford 3-(4-methoxybenzyl)-2,8-dimethyl-4-oxo-6-((tetrahydro-2H-pyran-4-yl)methyl)-3,4-dihydropyrido[3,4-d]pyrimidine-5-carbonitrile (3).

Example 1A.18

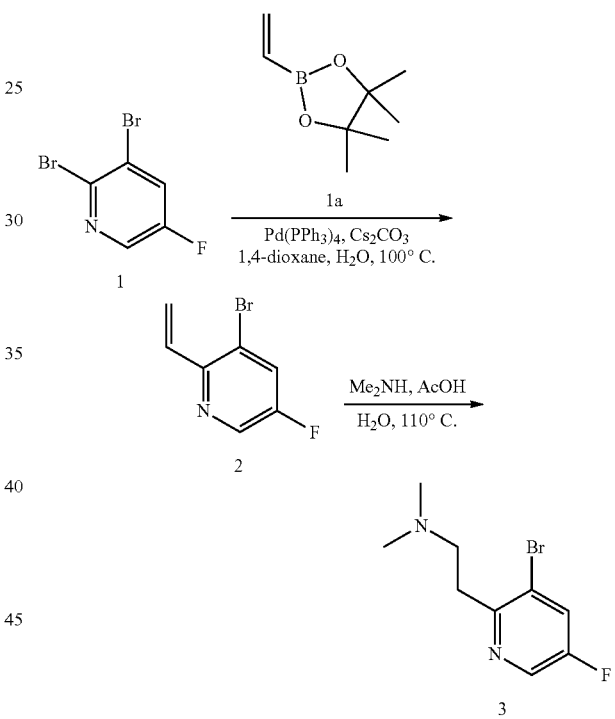

2,3-Dibromo-5-fluoropyridine (1, 3.15 g, 12.4 mmol), 4,4,5,5-tetramethyl-2-vinyl-1,3,2-dioxaborolane (1a, 1.93 mL, 13.6 mmol), cesium carbonate (8.86 g, 27.2 mmol), 1,4-dioxane (24 mL) and water (6 mL) are combined in a 100 mL round bottom flask with a stirbar. The atmosphere in the flask is removed under vacuum and replaced with argon twice. Tetrakis(triphenylphosphine)palladium(0) (0.71 g, 0.62 mmol) is added and the atmosphere in the flask is removed under vacuum and replaced with argon twice. The resulting clear yellow reaction mixture is stirred vigorously and heated at 100° C. under argon for 12 h. After cooling to room temperature the reaction mixture is partitioned between brine and ethyl acetate. The organics are dried over magnesium sulfate, filtered, concentrated on a rotary evaporator, and purified via silica gel chromatography (2-15% ethyl acetate in hexanes) to afford 3-bromo-5-fluoro-2-vinylpyridine (2).

Dimethylamine (40 wt. % in water) (34.1 mL, 108 mmol) is added to a stirred solution of 3-bromo-5-fluoro-2-vinylpyridine (2, 2.18 g, 10.8 mmol) in acetic acid (14.2 mL, 248 mmol). The resulting mixture is sealed, stirred vigorously, and heated at 110° C. for 68 h. After cooling to room temperature the reaction mixture is poured onto a stirred mixture of sodium hydroxide (9.93 g, 248 mmol) and sodium bicarbonate (4.53 g, 54.0 mmol) in ice water. The resulting mixture is extracted three times with dichloromethane. The combined organics are dried over magnesium sulfate, filtered, concentrated on a rotary evaporator, and purified via silica gel chromatography (0-20% methanol in dichloromethane). Fractions containing the desired product are combined and concentrated on a rotary evaporator. The residue is concentrated down from THF twice and dried under high vacuum to afford 2-(3-bromo-5-fluoropyridin-2-yl)-N,N-dimethylethan-1-amine (3).

Example 1A.19

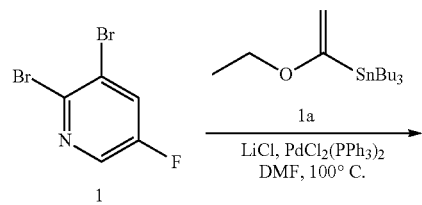

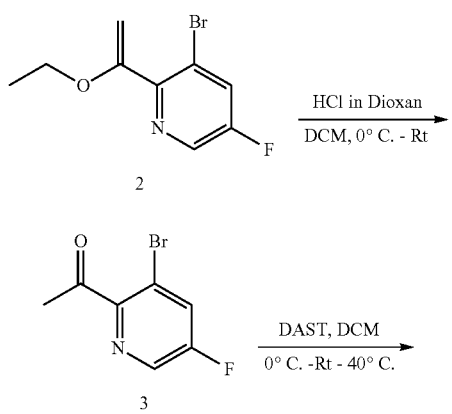

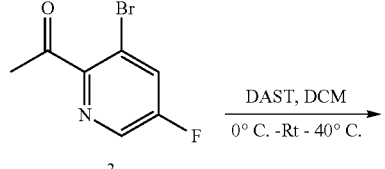

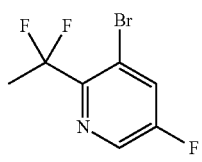

A solution of 2,3-dibromo-5-fluoropyridine (1, 10.0 g, 39.2 mmol), tributyl(1-ethoxyvinyl)stannane (1a, 15.5 mL, 43.1 mmol) and lithium chloride (4.9 g, 117.6 mmol) in N,N-dimethylformamide (100 mL) is degassed under nitrogen for 10 minutes. Then, bis(triphenylphosphine)palladium (II) dichloride (1.3 g, 1.9 mmol) is added and the mixture is heated at 100° C. for 4 h. The reaction mixture is cooled, diluted with water and extracted with diethyl ether. The combined organic layer is washed with water, dried over anhydrous sodium sulphate, filtered and concentrated. The crude product is purified by column chromatography using silica gel (100-200 mesh) and 0-2% ethyl acetate in hexane to afford 3-bromo-2-(1-ethoxyvinyl)-5-fluoropyridine (2).

A solution of 3-bromo-2-(1-ethoxyvinyl)-5-fluoropyridine (2, 5.7 g, 23.1 mmol) in dichloromethane (60 mL) is cooled to 0° C., hydrochloric acid in 1,4-dioxane (4 m, 10 mL) is added and the mixture is stirred at room temperature for 3 h. The reaction mixture is poured into ice cold water, neutralized with sodium bicarbonate and extracted with dichloromethane. The organic layer is dried over anhydrous sodium sulphate, filtered and concentrated. The crude product is purified by column chromatography using silica gel (100-200 mesh) and 0-5% ethyl acetate in hexane to afford 1-(3-bromo-5-fluoropyridin-2-yl)ethan-1-one (3).

A solution of 1-(3-bromo-5-fluoropyridin-2-yl)ethan-1-one (3, 3.8 g, 17.4 mmol) in dichloromethane (40 mL) is cooled to 0° C., diethylaminosulfur trifluoride (23.3 mL, 174.0 mmol) is added; the mixture is stirred at room temperature for 48 h and then heated at 40° C. for 72 h. The reaction mixture is cooled, poured into crushed ice (very slowly, in portions), neutralized with sodium bicarbonate and extracted with dichloromethane. The organic layer is dried over anhydrous sodium sulphate, filtered and concentrated. The crude is purified by column chromatography using silica gel (100-200 mesh) and 0-1% ethyl acetate in hexane to afford 3-bromo-2-(1,1-difluoroethyl)-5-fluoropyridine (4).

Example 1A.20

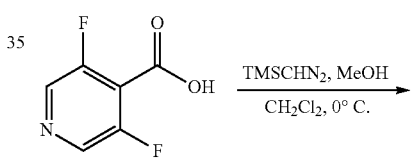

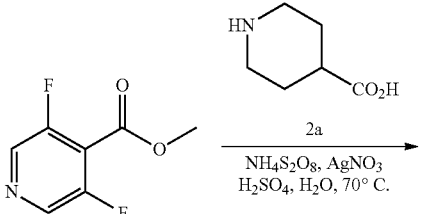

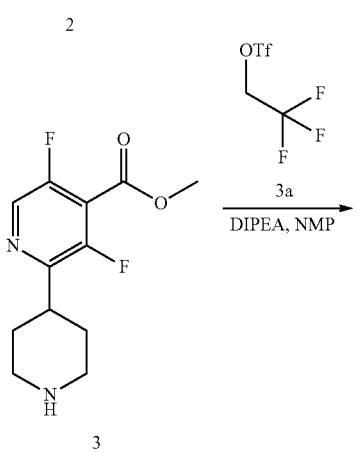

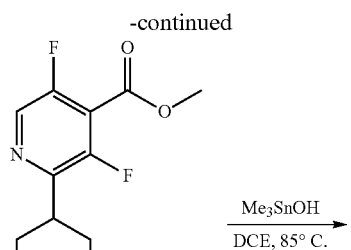

is slurried with 20% methanol in dichloromethane and filtered through Celite. The filter cake is washed thoroughly with 20% methanol in dichloromethane. The filtrate is concentrated on a rotary evaporator with silica gel and purified via silica gel chromatography (0-20% methanol in dichloromethane) to afford methyl 3,5-difluoro-2-(piperidin-4-yl)isonicotinate (3).

2,2,2-Trifluoroethyl trifluoromethanesulfonate (3a, 1.05 mL, 7.32 mmol) is added to a stirred solution of methyl 3,5-difluoro-2-(piperidin-4-yl)isonicotinate (3, 625 mg, 2.44 mmol) and N,N-diisopropylethylamine (3.40 mL, 19.5 mmol) in NMP (10 mL) at room temperature under argon. The resulting mixture is stirred at room temperature under argon for 3 h. The reaction mixture is diluted with ethyl acetate, washed three times with brine, dried over magnesium sulfate, filtered, concentrated on a rotary evaporator, and purified via silica gel chromatography (0-50% ethyl acetate in hexanes) to afford methyl 3,5-difluoro-2-(1-(2,2,2-trifluoroethyl)piperidin-4-yl)isonicotinate (4).

Methyl 3,5-difluoro-2-(1-(2,2,2-trifluoroethyl)piperidin-4-yl)isonicotinate (4, 505 mg, 1.49 mmol), trimethyltin hydroxide (1.08 g, 5.97 mmol), and DCE (10 mL) are combined in a 100 mL round bottom flask with a stirbar. The resulting mixture is stirred vigorously and heated at 80° C. under a reflux condenser under argon for 1 h and then at 85° C. for 3 h. Volatiles are removed on a rotary evaporator. The residue is taken up in 20% methanol in dichloromethane and purified via silica gel chromatography (0-20% methanol in dichloromethane) to afford 3,5-difluoro-2-(1-(2,2,2-trifluoroethyl)piperidin-4-yl)isonicotinic acid (5).

Example 1A.21

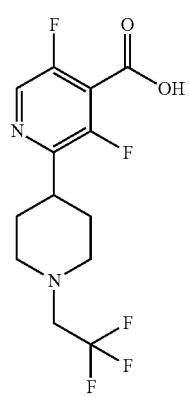

(Trimethylsilyl)diazomethane (2 M in diethyl ether) (19.5 mL, 39.1 mmol) is added slowly to a stirred mixture (not all dissolved) of 3,5-difluoroisonicotinic acid (1, 5.18 g, 32.6 mmol) in wet Methanol (200 mL) at 0° C. The resulting cloudy mixture is stirred vigorously at 0° C. under air. Bubbling is observed during the addition and continued for 45 min. Dichloromethane (100 mL) is added followed by more (trimethylsilyl)diazomethane (2 M in diethyl ether) (19.5 mL, 39.1 mmol). The resulting clear solution is stirred vigorously at 0° C. under air for 30 min. More (trimethylsilyl)diazomethane (2 M in diethyl ether) (19.5 mL, 39.1 mmol) is added and then more (trimethylsilyl)diazomethane (2 M in diethyl ether) (19.5 mL, 39.1 mmol) is added again until LCMS indicated complete conversion of the starting material. Volatiles are removed on a rotary evaporator. The residue is taken up in dichloromethane and purified via silica gel chromatography (0-50% ethyl acetate in hexanes) (dried under high vacuum for only a few seconds) to afford methyl 3,5-difluoroisonicotinate (2).

A solution of piperidine-4-carboxylic acid (2a 1.20 g, 9.27 mmol), ammonium persulfate (2.33 g, 10.2 mmol), and silver nitrate (590 mg, 3.47 mmol) in water (8 mL) is added to a stirred mixture of methyl 3,5-difluoroisonicotinate (2, 802 mg, 4.63 mmol) in 3% sulfuric acid in water (8 mL) at 70° C. The resulting brown mixture is heated at 70° C. with vigorous stirring for 10 min (bubbling is observed) and then cooled to room temperature. The reaction mixture is heated at 70° C. and more piperidine-4-carboxylic acid (1.20 g, 9.27 mmol), ammonium persulfate (2.33 g, 10.2 mmol), and silver nitrate (590 mg, 3.47 mmol) in water (8 mL) is added. The reaction mixture is heated at 70° C. for 10 min and then cooled to room temperature. Repeat this a total of four times. The reaction mixture is basified with potassium carbonate. All volatiles are removed on a rotary evaporator. The residue

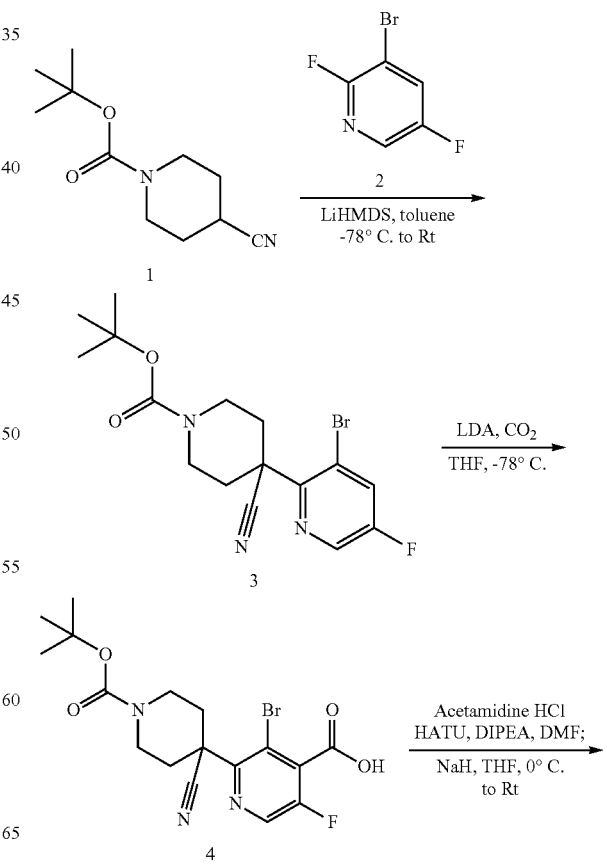

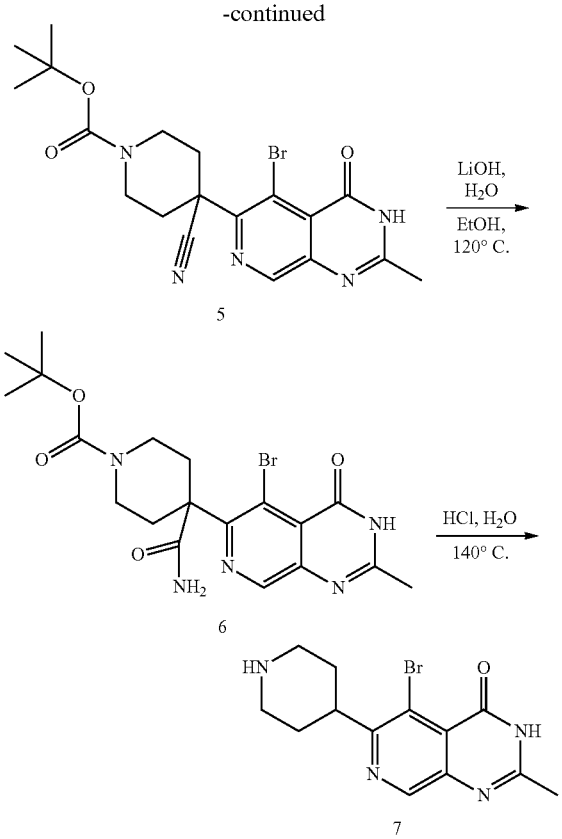

Lithium bis(trimethylsilyl)amide (1M in toluene) (2.23 mL, 2.23 mmol) is added slowly to a stirred solution of tert-butyl 4-cyanopiperidine-1-carboxylate (1, 469 mg, 2.23 mmol) and 3-bromo-2,5-difluoropyridine (2, 433 mg, 2.23 mmol) in toluene (5 mL) at −78° C. under argon. The cold bath is removed and the resulting orange solution is allowed to warm to room temperature with stirring under argon and allowed to stir at room temperature for 2 h. 0.2 M HCl in water (22.3 mL, 4.46 mmol) is added with vigorous stirring. The resulting mixture is extracted with ethyl acetate. The organics are washed with brine, dried over magnesium sulfate, filtered, concentrated on a rotary evaporator, and purified via silica gel chromatography (0-50% ethyl acetate in hexanes) to afford tert-butyl 4-(3-bromo-5-fluoropyridin-2-yl)-4-cyanopiperidine-1-carboxylate (3).

n-Butyllithium (2.5 M in hexane) (0.48 mL, 1.20 mmol) is added to a stirred solution of diisopropylamine (0.18 mL, 1.30 mmol) in THF (4 mL) at 0° C. under argon. The resulting light yellow solution is stirred for 10 min at 0° C. and then added slowly to a stirred solution of tert-butyl 4-(3-bromo-5-fluoropyridin-2-yl)-4-cyanopiperidine-1-carboxylate (3, 401 mg, 1.04 mmol) in THF (7 mL) at −78° C. under argon. The resulting orange reaction mixture is stirred at −78° C. under argon for 30 min and then carbon dioxide gas is bubbled in for ~1 min. (orange color fades) After 10 min 0.1 N sodium hydroxide in water (1 mL) is added to quench the reaction mixture. The resulting mixture is partitioned between 0.1 N sodium hydroxide in water (20 mL) and diethyl ether. The organics are extracted twice more with 0.1 N sodium hydroxide in water (5 mL). The organics are discarded. The water layer is acidified with 1 N HCl in water and then extracted four times with ethyl acetate. The organics are washed with brine, dried over magnesium sulfate, filtered, concentrated on a rotary evaporator, and dried under high vacuum to afford 3-bromo-2-(1-(tert-butoxycarbonyl)-4-cyanopiperidin-4-yl)-5-fluoroisonicotinic acid (4).

HATU (366 mg, 0.964 mmol) is added to a stirred solution of 3-bromo-2-(1-(tert-butoxycarbonyl)-4-cyanopiperidin-4-yl)-5-fluoroisonicotinic acid (4, 393 mg, 0.918 mmol) in DMF (6 mL) at room temperature under argon. After 2 min N,N-diisopropylethylamine (0.19 mL, 1.10 mmol) is added. The resulting orange mixture is stirred at room temperature under argon for 20 min. A solution of acetamidine hydrochloride (174 mg, 1.84 mmol) and N,N-diisopropylethylamine (0.80 mL, 4.59 mmol) in DMF (3 mL) (this is heated with a heat gun and sonicated to get all of the acetamidine dissolved) is added. The resulting orange mixture is stirred vigorously at room temperature under argon for 2 h. The reaction mixture is diluted with ethyl acetate, washed four times with brine, dried over magnesium sulfate, filtered, and concentrated on a rotary evaporator. Dry THF (10 mL) is added and volatiles are removed on a rotary evaporator again. The residue is dried under high vacuum for 10 min. The residue is dissolved with stirring in THF (15 mL) and cooled to 0° C. under argon. Sodium hydride (44.1 mg, 1.84 mmol) is added. The cold bath is removed and the resulting cloudy orange mixture is stirred vigorously at room temperature under argon for 2.5 h. A solution of ammonium chloride (147 mg, 2.75 mmol) in water (2 mL) is added and then the resulting mixture is partitioned between ethyl acetate and brine. The organics are dried over magnesium sulfate, filtered, concentrated on a rotary evaporator, and purified via silica gel chromatography (20-100% ethyl acetate in hexanes) to afford tert-butyl 4-(5-bromo-2-methyl-4-oxo-3,4-dihydropyrido[3,4-d]pyrimidin-6-yl)-4-cyanopiperidine-1-carboxylate (5).

tert-Butyl 4-(5-bromo-2-methyl-4-oxo-3,4-dihydropyrido[3,4-d]pyrimidin-6-yl)-4-cyanopiperidine-1-carboxylate (5, 313 mg, 0.698 mmol), ethanol (17 mL), and lithium hydroxide (1 M in water) (6.98 mL, 6.98 mmol) are combined in a sealable vessel with a stirbar. The resulting mixture is sealed, stirred vigorously, and heated at 120° C. with an oil bath for 44 h. After cooling to room temperature the reaction mixture is diluted with methanol and concentrated on a rotary evaporator. The residue is taken up in NMP, methanol, and acetic acid (0.60 mL, 10.5 mmol), filtered, and purified via preparatory HPLC (15-60% acetonitrile in water with 0.1% TFA). Fractions containing the desired product are combined and lyophilized to dryness to afford tert-butyl 4-(5-bromo-2-methyl-4-oxo-3,4-dihydropyrido[3,4-d]pyrimidin-6-yl)-4-carbamoylpiperidine-1-carboxylate (6).

A stirred mixture of tert-butyl 4-(5-bromo-2-methyl-4-oxo-3,4-dihydropyrido[3,4-d]pyrimidin-6-yl)-4-carbamoylpiperidine-1-carboxylate TFA salt (6, 186 mg, 0.321 mmol) in 6 M HCl in water (7 mL) is heated at 140° C. with an oil bath for 2 min and then sealed, stirred vigorously, and heated at 140° C. with an oil bath for 2 h. More 6 M HCl in water (3 mL) is added and heating at 140° C. with an oil bath continued for another 21 h. After cooling to room temperature the reaction mixture is diluted with methanol, filtered, and purified via preparatory HPLC (5-18% acetonitrile in water with 0.1% TFA). Fractions containing the desired product are loaded onto a Strata X-C ion exchange column from Phenomenex. The column is washed sequentially with water, acetonitrile, methanol, and then 5% ammonium hydroxide in methanol. Eluent containing the desired product is concentrated on a rotary evaporator and dried under high vacuum to afford 5-bromo-2-methyl-6-(piperidin-4-yl)pyrido[3,4-d]pyrimidin-4(3H)-one (7).

Example 1A.22

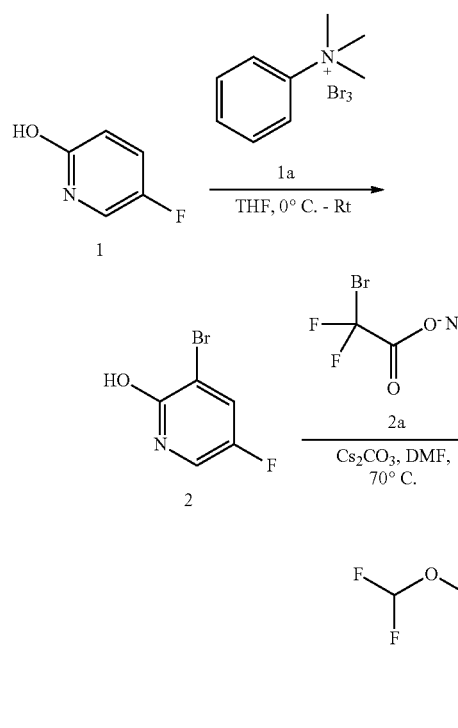

To a solution of 5-fluoropyridin-2-ol (1, 9.00 g, 0.079 mol) in tetrahydrofuran (290 mL) at 0° C., Trimethylphenylammonium tribromide (29.9 g, 0.079 mol) is added slowly and reaction mixture is stirred at room temperature for 16 h. After 16 h, the reaction mixture is partitioned between ethyl acetate and water. Aqueous layer is separated and re-extracted with ethyl acetate. The combined organic layer is washed with 5% sodium metabisulphite solution, saturated brine solution, dried over anhydrous sodium sulphate, filtered and concentrated to get crude product. The crude product is purified by column chromatography using silica gel (100-200 mesh) and 0-30% ethyl acetate in hexanes afford 3-bromo-5-fluoropyridin-2-ol (2) as off white solid. Yield: 4.90 g, 27%; MS (ESI) m/z 189.99 [M−1]⁻.

To a solution of 3-bromo-5-fluoropyridin-2-ol (2, 4.10 g, 0.021 mol) in N,N-dimethylformamide (40 mL), cesium carbonate (3.48 g, 0.031 mol) and sodium 2-bromo-2,2-difluoroacetate (2a, 5.05 g, 0.025 mmol) are added and the reaction mixture is heated at 70° C. for 4 h. After completion, reaction mixture cooled down and partitioned between diethyl ether and water. Aqueous layer is separated and re-extracted with diethyl ether. The combined organic layer is washed with water, saturated brine solution, dried over anhydrous sodium sulphate, filtered and concentrated to get crude product. The crude product is purified by column chromatography using silica gel (100-200 mesh) and hexane as eluent to afford 3-bromo-2-(difluoromethoxy)-5-fluoropyridine (3)

Example 1B. Methods of Synthesizing the Right-Hand Side

Example 1B.1

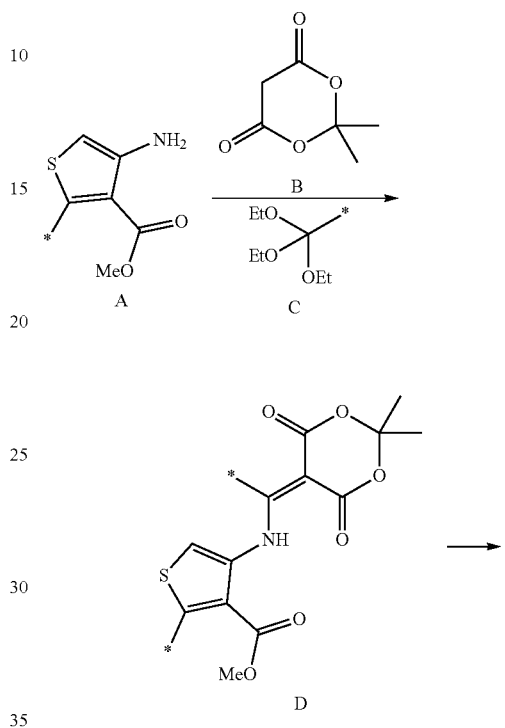

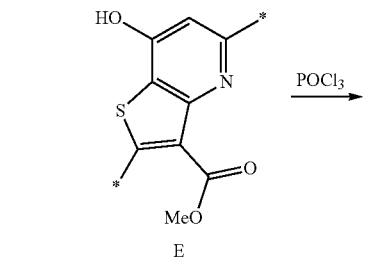

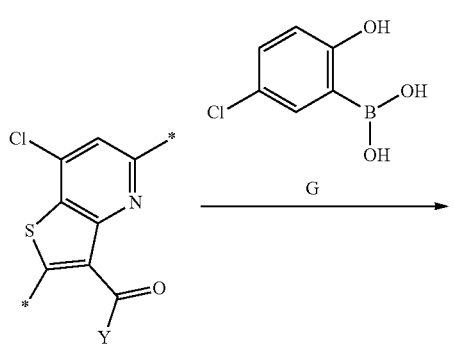

F1 Y = OMe
F2 Y = OH
F3 Y = O-t-Bu

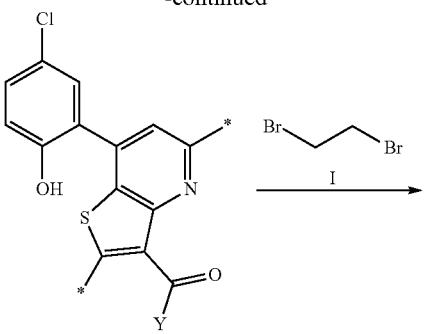

H1 Y = OMe
H2 Y = O-t-Bu

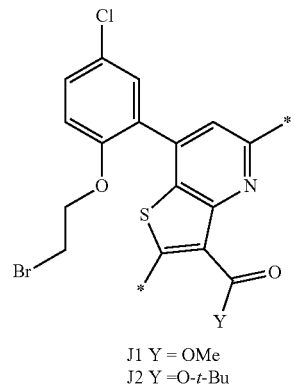

J1 Y = OMe
J2 Y = O-t-Bu

A solution of 2,2-dimethyl-1,3-dioxane-4,6-dione (B, 1.1 equiv.) and 1,1,1-triethoxyethane (C, 0.7 M) is stirred and heated at 90° C. for 2 h. methyl 4-aminothiophene-3-carboxylate (A, 1 equiv.) is added portionwise at 90° C. under argon atmosphere and heating at 90° C. continued for 6 h. The reaction mixture is cooled to room temperature, water added, and the mixture extracted with ethyl acetate. The organic layer is dried over anhydrous sodium sulfate, filtered and concentrated in vacuo. The crude product is triturated with diethyl ether to afford methyl 4-((1-(2,2-dimethyl-4,6-dioxo-1,3-dioxan-5-ylidene)ethyl)amino)thiophene-3-carboxylate (D).

A solution of methyl 4-((1-(2,2-dimethyl-4,6-dioxo-1,3-dioxan-5-ylidene)ethyl)amino)thiophene-3-carboxylate (D, 1 equiv.) in Dowtherm A (0.5 M), is heated at 235° C. for 4 h. After completion, the reaction mass is cooled to room temperature, the precipitated solid isolated by filtration and dried in vacuo. The solid obtained is washed with diethyl ether to afford methyl 7-hydroxy-5-methylthieno[3,2-b]pyridine-3-carboxylate (E).

To a solution of methyl 7-hydroxy-5-methylthieno[3,2-b]pyridine-3-carboxylate (E, 1 equiv.) in 1,2-dichloroethane (0.22 M) are added phosphoryl trichloride (3 equiv.) and a catalytic amount of N,N-dimethylformamide at room temperature and the reaction mixture heated at 90° C. for 6 h. The reaction mixture is concentrated under reduced pressure, diluted with ice cold water, and the solution basified with 10% aqueous sodium hydroxide solution to pH ~7-8 followed by extracted with ethyl acetate. The organic layer is dried over anhydrous sodium sulfate, filtered, concentrated, and purified by column chromatography to afford methyl 7-chloro-5-methylthieno[3,2-b]pyridine-3-carboxylate (F1).

To a solution of methyl 7-chloro-5-methylthieno[3,2-b]pyridine-3-carboxylate (F1, 1 equiv.) in mixture of methanol (1.7 M), water (1.7 M) and tetrahydrofuran (0.64 M) is added lithium hydroxide monohydrate (2 equiv.) at room temperature and the resulting mixture is stirred for 2 h. The solid is filtered, the filtrate is concentrated and combined with the solid. The combined solids are acidified with saturated citric acid solution (up to pH=1) and filtered. The resulting solid is washed with methanol followed by diethyl ether and dried under high vacuum to afford 7-chloro-5-methylthieno[3,2-b]pyridine-3-carboxylic acid (F2).

To a solution of 7-chloro-5-methylthieno[3,2-b]pyridine-3-carboxylic acid (F2, 1 equiv.) in tert-butyl alcohol (0.4 M) is added 4-dimethylaminopyridine (1 equiv.) and Boc-anhydride (3 equiv.) at room temperature. The mixture is stirred for 48 h at 90° C. and the reaction mixture is concentrated under reduced pressure. The crude product is purified by column chromatography over silica gel to afford tert-butyl 7-chloro-5-methylthieno[3,2-b]pyridine-3-carboxylate (F3).

To a solution of tert-butyl 7-chloro-5-methylthieno[3,2-b]pyridine-3-carboxylate (F3, 1 equiv.) and (5-chloro-2-hydroxyphenyl)boronic acid (G, 1.2 equiv.), in 1,4-dioxane (0.5 M) and water (1.2 M) is added potassium carbonate solution (2 equiv.) at room temperature and the reaction mixture degassed with argon for 20 minutes. [1,1'-bis(diphenylphosphino)ferrocene]palladium(II) dichloride (0.05 equiv.) is added and mixture heated at 90° C. for 2 h. The reaction mixture is cooled to room temperature and filtered and the solid, washed with water followed by methanol, and dried under vacuum to afford tert-butyl 7-(5-chloro-2-hydroxyphenyl)-5-methylthieno[3,2-b]pyridine-3-carboxylate (H).

To a solution of tert-butyl 7-(5-chloro-2-hydroxyphenyl)-5-methylthieno[3,2-b]pyridine-3-carboxylate (H, 1 equiv.) in acetone (0.28 M) are added potassium carbonate (3.5 equiv.) and 1,2-dibromoethane (I, 5.0 equiv.) at room temperature and the reaction mixture heated at 40° C. for 12 h. An additional 5.0 equiv. of 1,2-dibromoethane is then added at room temperature and the mixture heated to 45° C. The reaction mixture is filtered through a sintered funnel, washed with acetone, and the filtrate concentrated and purified by column chromatography to afford tert-butyl 7-(2-(2-bromoethoxy)-5-chlorophenyl)-5-methylthieno[3,2-b]pyridine-3-carboxylate (J).

Example 1B.2

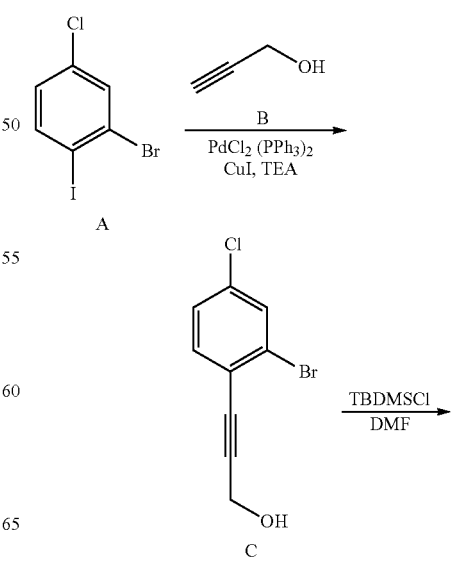

-continued

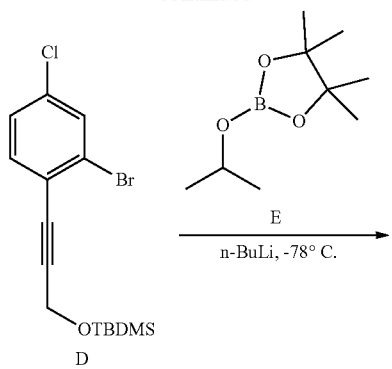

Example 1B.3

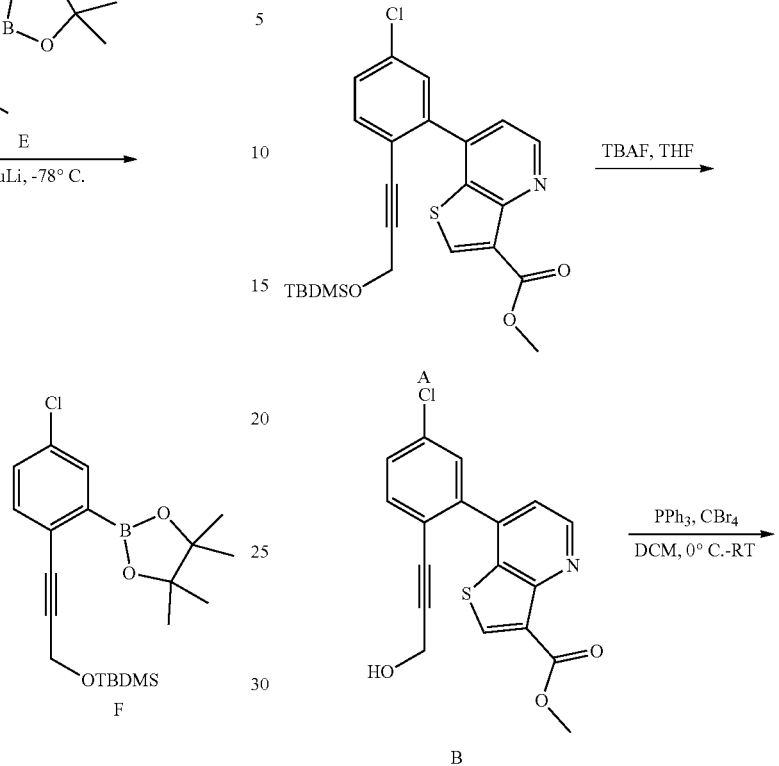

A solution of 2-bromo-4-chloro-1-iodobenzene (A, 1 equiv.) and prop-2-yn-1-ol (B, 1.3 equiv.) in triethylamine (0.3 M) is degassed with argon for 10 min. Copper(I) iodide (0.15 equiv.) and bis(triphenylphosphine)palladium chloride (0.08 equiv.) are added and the reaction mixture stirred at room temperature for 16 h. The reaction mass is concentrated under reduced pressure and the crude compound purified by Combi-flash to afford 3-(2-bromo-4-chlorophenyl)prop-2-yn-1-ol (C).

To a solution of 3-(2-bromo-4-chlorophenyl)prop-2-yn-1-ol (C, 1 equiv.) in tetrahydrofuran (0.8 M) are added imidazole (3 equiv.), 4-dimethylaminopyridine (0.045 equiv.) and tert-butyldimethylchlorosilane (1.2 equiv.) at room temperature and the reaction mixture stirred for 24 h. The reaction mass is diluted with water, extracted with ethyl acetate and the organic layer separated, dried over anhydrous sodium sulphate, and purified by Combi-flash to afford ((3-(2-bromo-4-chlorophenyl)prop-2-yn-1-yl)oxy)(tert-butyl)dimethylsilane (D).

To a solution of ((3-(2-bromo-4-chlorophenyl)prop-2-yn-1-yl)oxy)(tert-butyl)dimethylsilane (D, 1 equiv.) in tetrahydrofuran (0.14 M) is added dropwise n-butyllithium (1.23 M in hexanes, 1.3 equiv.) at −78° C. and the mixture stirred at −78° C. for 1 h. 2-Isopropoxy-4,4,5,5-tetramethyl-1,3,2-dioxaborolane (E, 1.2 equiv.) is added dropwise at −78° C. and stirring continued for 1 h. The reaction is quenched with chilled water, extracted with ethyl acetate, and the organic layer separated, dried over anhydrous sodium sulphate, concentrated, and purified by Combi-flash to afford tert-butyl((3-(4-chloro-2-(4,4,5,5-tetramethyl-1,3,2-dioxaborolan-2-yl)phenyl)prop-2-yn-1-yl)oxy)dimethylsilane (F).

To a solution of methyl 7-(2-(3-((tert-butyldimethylsilyl)oxy)prop-1-yn-1-yl)-5-chlorophenyl)thieno[3,2-b]pyridine-3-carboxylate (A, 1 equiv.) in tetrahydrofuran (0.21 M) is added tetra-n-butylammonium fluoride (1.2 equiv.) at room temperature and the mixture stirred for 2 h. The reaction mass is diluted with ethyl acetate, washed with cold water and the organic layer separated, dried over anhydrous sodium sulphate, concentrated, and triturated with diethyl ether to afford methyl 7-(5-chloro-2-(3-hydroxyprop-1-yn-1-yl)phenyl)thieno[3,2-b]pyridine-3-carboxylate (B).

To a solution of methyl 7-(5-chloro-2-(3-hydroxyprop-1-yn-1-yl)phenyl)thieno[3,2-b]pyridine-3-carboxylate (B, 1 equiv.) in dichloromethane (10.0 mL) is added triphenylphosphine (1.5 equiv.) at room temperature and the reaction mixture cooled to 0° C. Carbontetrabromide (1.5 equiv.) is added and the reaction mixture stirred for 3 h at room temperature. The reaction mass is concentrated and purified by Combi-flash to afford methyl 7-(2-(3-bromoprop-1-yn-1-yl)-5-chlorophenyl)thieno[3,2-b]pyridine-3-carboxylate (C).

Example 1B.4

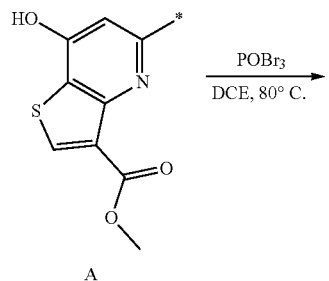

A

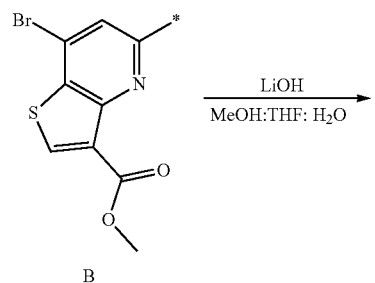

B

A solution of methyl 7-hydroxy-5-methylthieno[3,2-b]pyridine-3-carboxylate (A, 1 equiv.) and phosphorous oxybromide (10 equiv.) in 1,2 dichloroethane (0.45 M) is heated at 80° C. for 16 h. The reaction mixture is cooled to room temperature, quenched with aqueous solution of sodium bicarbonate, extracted with dichloromethane, and the combined organic layer washed with brine, dried over anhydrous sodium sulphate, filtered, concentrated, and purified by column chromatography to afford methyl 7-bromo-5-methylthieno[3,2-b]pyridine-3-carboxylate (B).

A solution of methyl 7-bromo-5-methylthieno[3,2-b]pyridine-3-carboxylate (B, 1 equiv.) and lithium hydroxide (3 equiv.) in methanol:tetrahydrofuran:water solvent mixture (1:2:1, 0.25 M) is stirred at room temperature for 16 h. The reaction is diluted with water, cooled to 0° C. and acidified with 1 N hydrochloric acid to pH ~5. The precipitate is filtered, washed with pentane and dried to afford 7-bromo-5-methylthieno[3,2-b]pyridine-3-carboxylic acid (C)

To a solution of 7-bromo-5-methylthieno[3,2-b]pyridine-3-carboxylic acid (C, 1 equiv.) and methanesulfonamide (D, 1.5 equiv.) in dichloromethane (0.16 M), N-ethyl-N'-(3-dimethylaminopropyl)carbodiimide hydrochloride (2 equiv.) and N,N-dimethylpyridin-4-amine (2.5 equiv.) are added at room temperature and the mixture stirred for 16 h. The reaction is diluted with water, cooled to 0° C., acidified with 1 N hydrochloric acid to pH ~2 and extracted with dichloromethane. The combined organic layer is dried over anhydrous sodium sulphate, concentrated, and purified by column chromatography to afford 7-bromo-5-methyl-N-(methylsulfonyl)thieno[3,2-b]pyridine-3-carboxamide (E).

Example 1B.5

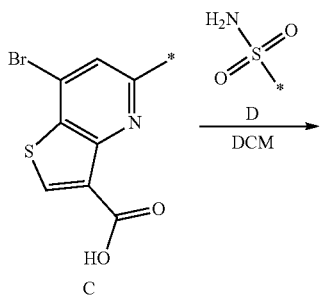

C

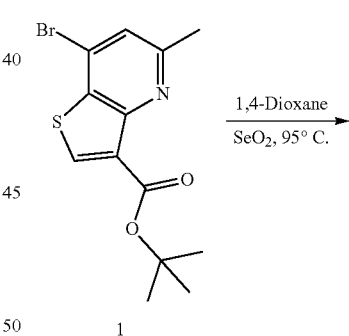

1

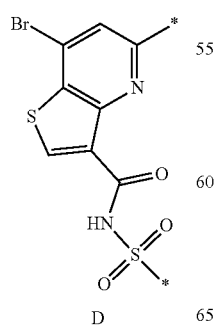

D

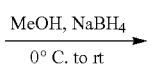

2

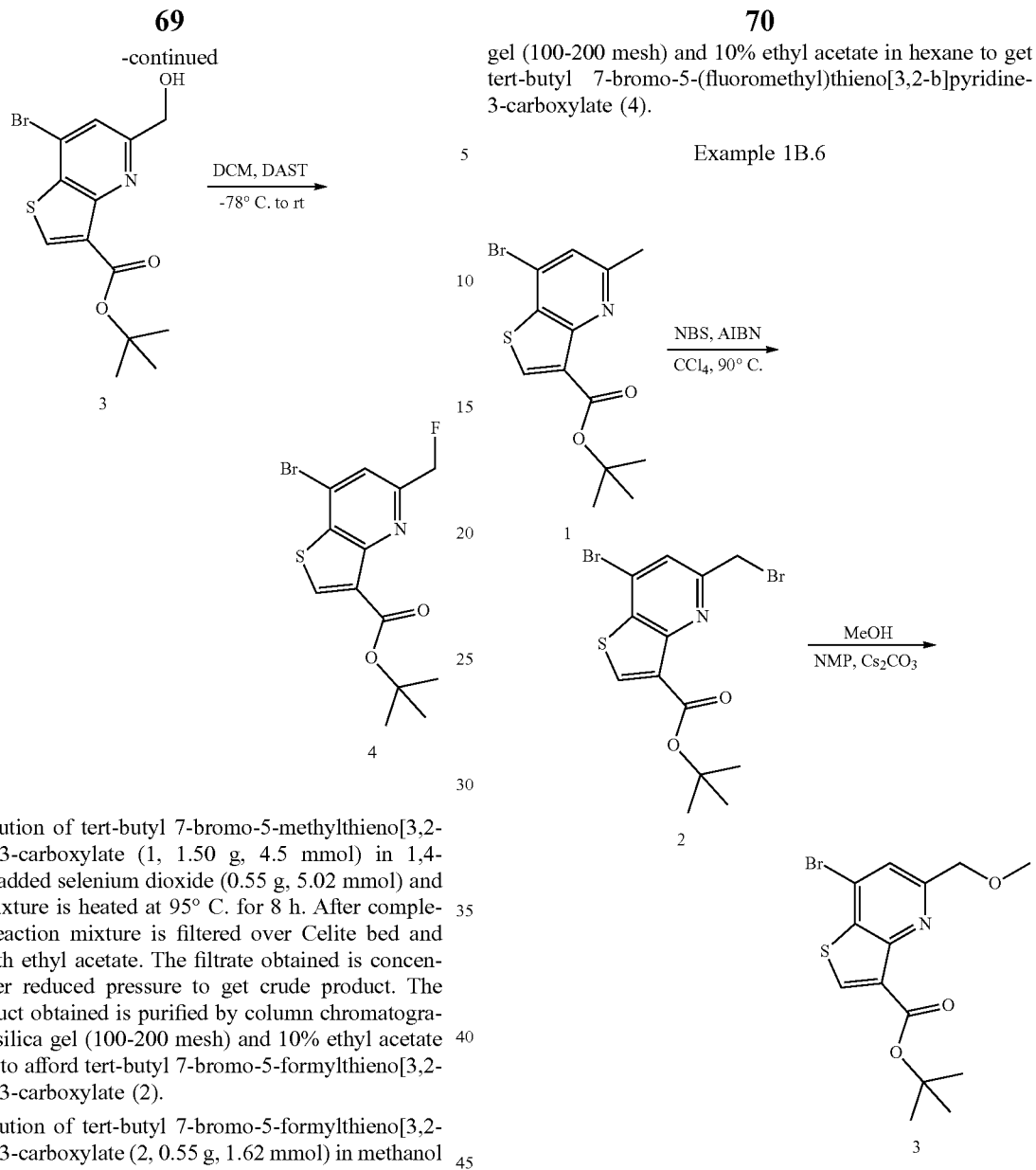

To a solution of tert-butyl 7-bromo-5-methylthieno[3,2-b]pyridine-3-carboxylate (1, 1.50 g, 4.5 mmol) in 1,4-dioxane is added selenium dioxide (0.55 g, 5.02 mmol) and reaction mixture is heated at 95° C. for 8 h. After completion, the reaction mixture is filtered over Celite bed and washed with ethyl acetate. The filtrate obtained is concentrated under reduced pressure to get crude product. The crude product obtained is purified by column chromatography using silica gel (100-200 mesh) and 10% ethyl acetate in hexanes to afford tert-butyl 7-bromo-5-formylthieno[3,2-b]pyridine-3-carboxylate (2).

To a solution of tert-butyl 7-bromo-5-formylthieno[3,2-b]pyridine-3-carboxylate (2, 0.55 g, 1.62 mmol) in methanol (6 mL) at 0° C. is added sodium borohydride (0.12 g, 3.25 mmol) and reaction mixture is stirred at same temperature for 1 hour. After completion, the reaction mixture is quenched with ice water and concentrated under reduced pressure. The crude material is dissolved in ethyl acetate, washed with water, brine solution, dried over anhydrous sodium sulphate, filtered and concentrated to get crude compound. The crude compound obtained is purified by column chromatography using silica gel (100-200 mesh) and 20% ethyl acetate in hexanes to afford tert-butyl 7-bromo-5-(hydroxymethyl)thieno[3,2-b]pyridine-3-carboxylate (3).

To a solution of tert-butyl 7-bromo-5-(hydroxymethyl)thieno[3,2-b]pyridine-3-carboxylate (3, 0.325 g, 0.94 mmol) in dichloromethane (5 mL) at −78° C., DAST (0.18 mL, 1.41 mmol) is added and reaction mixture is stirred at −78° C. for 1 hour. After completion, reaction mixture is quenched with ice cold water and extracted with dichloromethane. The organic layer is washed saturated solution of sodium bicarbonate, dried over anhydrous sodium sulphate, filtered and concentrated to get crude compound. The crude compound obtained is purified by column chromatography using silica gel (100-200 mesh) and 10% ethyl acetate in hexane to get tert-butyl 7-bromo-5-(fluoromethyl)thieno[3,2-b]pyridine-3-carboxylate (4).

Example 1B.6

A solution of tert-butyl 7-bromo-5-methylthieno[3,2-b]pyridine-3-carboxylate (1, 500.0 mg, 1.523 mmol), Azobisisobutyronitrile (24.98 mg, 0.152 mmol) and N-Bromosuccinimide (271.13 mg, 1.523 mmol) in carbon tetrachloride (10 mL) is stirred at 90° C. for 5 h. After completion, reaction mixture is concentrated under reduced pressure and is diluted with dichloromethane and silica gel is added. The solvent is evaporated. The crude silica mixture is purified by Isco column chromatography using 0-10% methanol in dichloromethane as eluent. The desired fractions are concentrated under reduced pressure to afford tert-butyl 7-bromo-5-(bromomethyl)thieno[3,2-b]pyridine-3-carboxylate (2)

To a stirred solution of tert-butyl 7-bromo-5-(bromomethyl)thieno[3,2-b]pyridine-3-carboxylate (2, 0.200 g, 0.491 mmol) in methanol (0.2 mL) and N-methylpyrrolidone (2.0 mL) is added cesium carbonate (0.480 g, 1.474 mmol) at RT and reaction mixture is stirred at room temperature for 8 h. After completion, the reaction mixture is diluted with dichloromethane and then silica gel is added. The solvent is then evaporated and the free flow silica gel is then loaded on the column and purified via silica gel chromatography eluting with methanol in dichloromethane to afford tert-butyl 7-bromo-5-(methoxymethyl)thieno[3,2-b]pyridine-3-carboxylate (3).

Example 1B.7

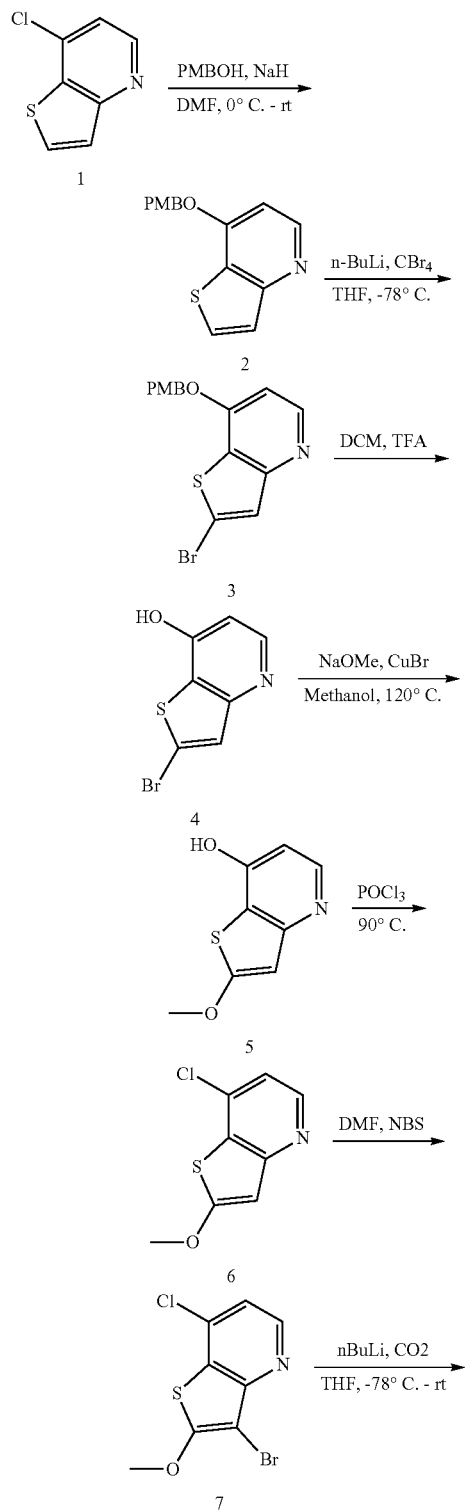

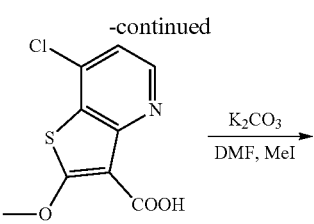

To a stirred solution of 4-methoxybenzyl alcohol (8.1 g, 59.1 mmol) in N,N-dimethylformamide (100 mL) at 0° C., sodium hydride (3.1 g, 65.0 mmol) is added. This reaction mixture is stirred at 0° C. for 30 min. Then, 7-chlorothieno[3,2-b]pyridine (1, 10 g, 59.1 mmol) is added at 0° C. and reaction mixture is stirred for 16 h at room temperature. After this time, the mixture is poured into ice. The resulting precipitate is collected by filtration and dried under reduced pressure to afford 7-((4-methoxybenzyl)oxy)thieno[3,2-b]pyridine (2).

To a stirred solution of 7-((4-methoxybenzyl)oxy)thieno[3,2-b]pyridine (2, 8.0 g, 29.5 mmol) in dry tetrahydrofuran (250 mL), n-butyllithium (2.3 M in hexanes, 38.0 mL, 64.9 mmol) is added dropwise at −78° C. This reaction mixture is stirred at the same temperature for 45 min. Then, carbon tetrabromide (9.7 g, 29.5 mmol) is added at −78° C. and the mixture is stirred at same temperature for 1 h. After this time, the reaction is quenched with saturated aqueous ammonium chloride solution and extracted with ethyl acetate. The organic layer is washed with water, dried over anhydrous sodium sulfate, filtered, and concentrated. The crude product is purified by silica gel (100-200 mesh) column chromatography using 15% ethyl acetate in hexanes as eluent. The desired fractions are concentrated under reduced pressure to afford 2-bromo-7-((4-methoxybenzyl)oxy)thieno[3,2-b]pyridine (3).

A solution of 2-bromo-7-((4-methoxybenzyl)oxy)thieno[3,2-b]pyridine (3, 6.5 g, 18.62 mmol) in a mixture of trifluoroacetic acid and dichloromethane (1:1, 40 mL) is stirred at room temperature for 8 h. After this time, the reaction mixture is concentrated under reduced pressure. The crude product is recrystallized with ether and pentanes to afford 2-bromothieno[3,2-b]pyridin-7-ol (4).

To a solution of 2-bromothieno[3,2-b]pyridin-7-ol (4, 3.5 g, 15.28 mmol) in methanol (30 mL), 30% sodium methoxide in methanol (14.0 g, in methanol, 76.4 mmol) and copper(I) bromide (0.200 g, 1.5 mmol) are added. This reaction mixture is stirred at 120° C. for 30 h. After this time, the reaction mixture is concentrated under reduced pressure, acidified with 2 N hydrochloric acid to pH~6, and extracted with 10% methanol in dichloromethane. The organic layer is dried over anhydrous sodium sulfate, filtered, and concentrated to afford 2-methoxythieno[3,2-b]pyridin-7-ol (5).

A mixture of 2-methoxythieno[3,2-b]pyridin-7-ol (5, 1.7 g, 9.39 mmol) and phosphoryl chloride (10 mL) is heated and stirred at 900° C. for 6 h. After this time, the reaction mixture is quenched with ice, treated with aqueous 50% sodium hydroxide solution, and extracted with ethyl acetate. The organic layer is washed with water and then saturated brine, dried over anhydrous sodium sulfate, and concentrated under reduced pressure. The crude product is purified by Combiflash using 30% ethyl acetate in hexanes as eluent. The desired fractions are concentrated under reduced pressure to afford 7-chloro-2-methoxythieno[3,2-b]pyridine (6).

To a solution of 3-bromo-7-chloro-2-methoxythieno[3,2-b]pyridine (6, 0.8 g, 4.02 mmol) in N,N-dimethylformamide (10 mL) at room temperature, N-bromosuccinimide (1.4 g, 8.04 mmol) is added. This reaction mixture is stirred for 30 min. Then, the reaction mixture is poured into ice and extracted with ethyl acetate. The organic layer is washed with brine, dried over anhydrous sodium sulfate, filtered, and concentrated to dryness under reduced pressure. The crude product is purified by Combiflash (12 g, RediSep column) using 10% ethyl acetate in hexanes as eluent. The desired fractions are concentrated under reduced pressure to afford 3-bromo-7-chloro-2-methoxythieno[3,2-b]pyridine (7).

To a stirred solution of 3-bromo-7-chloro-2-methoxythieno[3,2-b]pyridine (7, 0.7 g, 2.52 mmol) in dry tetrahydrofuran (10 mL), n-butyllithium (2.3 M in hexanes, 1.97 mL, 4.54 mmol) is added dropwise at −78° C. This reaction mixture is stirred at the same temperature for 45 min. Dry carbon dioxide gas is bubbled through the reaction mixture, which is slowly warmed up to room temperature and stirred for 16 h. The reaction mixture is quenched with 10% aqueous citric acid solution and extracted with 10% methanol in dichloromethane. The organic layer is dried over anhydrous sodium sulfate, filtered, and concentrated to afford 7-chloro-2-methoxythieno[3,2-b]pyridine-3-carboxylic acid (8).

To a solution of 7-chloro-2-methoxythieno[3,2-b]pyridine-3-carboxylic acid (8, 0.5 g, 2.05 mmol) in N,N-dimethylformamide (5.0 mL) at room temperature, potassium carbonate (0.85 g, 6.17 mmol) and methyl iodide (0.32 g, 2.26 mmol) are added. This reaction mixture is stirred for 16 h. After this time, the reaction mixture is poured into ice and extracted with ethyl acetate. The organic layer is washed with brine, dried over anhydrous sodium sulfate, filtered, and concentrated to dryness under reduced pressure. The crude product is purified by Combiflash (12 g, RediSep column) using 2% methanol in dichloromethane as eluent. The desired fractions are concentrated under reduced pressure to afford methyl 7-chloro-2-methoxythieno[3,2-b]pyridine-3-carboxylate (9).

Example 1B.8

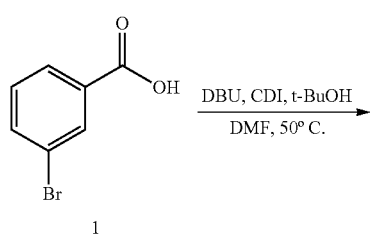

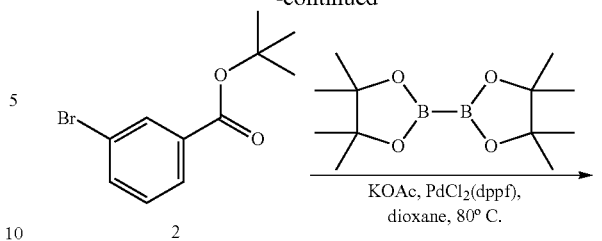

To a stirred solution of 3-bromobenzoic acid (1, 100.0 g, 497.5 mmol) in N,N-dimethylformamide (800 mL), carbodiimidazole (112.9 gm, 696.5 mmol) is added at room temperature and the reaction mixture is heated and stirred at 50° C. for 1 h. 1,8-Diazabicyclo[5.4.0]undec-7-ene (105.8 gm, 696.5 mmol) and tert-butanol (184.37 gm, 2487.5 mmol) are added at 50° C. and the reaction mixture is continued to stir at 50° C. for 16 h. After completion, the reaction mass is quenched with water and extracted with ethyl acetate. The organic layer is separated, dried over anhydrous sodium sulphate and concentrated under reduced pressure. The crude product obtained is purified by column chromatography using 100-200 silica gel and 2% ethyl acetate in hexanes as eluent. The desired fractions are concentrated under reduced pressure to afford tert-butyl 3-bromobenzoate (2).

A stirred solution of tert-butyl 3-bromobenzoate (2, 113.0 g, 439.4 mmol), 4,4,4',4',5,5,5',5'-octamethyl-2,2'-bi(1,3,2-dioxaborolane) (3, 167.43 gm, 659.1 mmol) and potassium acetate (107.65 gm, 1098.5 mmol) in dioxane (600 mL) is degassed with argon for 30 min. Then [1,1'-bis(diphenylphosphino)ferrocene]dichloropalladium(II) is added and the reaction mixture is heated and stirred at 85° C. for 16 h. After completion, the reaction mass is quenched with water and extracted with ethyl acetate. The organic layer is separated, dried over anhydrous sodium sulphate and concentrated under reduced pressure to obtain the crude mass. This crude compound is purified by column chromatography using 100-200 silica gel and 3% ethyl acetate in hexanes as eluent. The desired fractions are concentrated under reduced pressure to afford tert-butyl 3-(4,4,5,5-tetramethyl-1,3,2-dioxaborolan-2-yl)benzoate (4).

A stirred solution of 4-chloro-2-iodophenol (5, 60.0 g, 235.8 mmol), tert-butyl 3-(4,4,5,5-tetramethyl-1,3,2-dioxaborolan-2-yl)benzoate (4, 100.37 g, 330.1 mmol) and potassium carbonate (97.76 g, 707.4 mmol) in a mixture of dioxane and water (4:1, 1.0 Lit) is degassed with argon for 30 min. Palladium(II)bis(triphenylphosphine) dichloride is added at room temperature and stirred the reaction mixture at 100° C. for 6 h. After completion, the reaction mass is quenched with water and extracted with ethyl acetate. The organic layer is separated, dried over anhydrous sodium sulphate and concentrated under reduced pressure. The crude compound obtained is purified by column chromatography using 100-200 silica gel and 4% ethyl acetate in hexanes as eluent. The desired fractions are concentrated under reduced pressure to afford tert-butyl 5'-chloro-2'-hydroxy-[1,1'-biphenyl]-3-carboxylate (6).

To a stirred solution of tert-butyl 5'-chloro-2'-hydroxy-[1,1'-biphenyl]-3-carboxylate (6, 55.0 g, 180.5 mmol) in 1 N aqueous solution of sodium hydroxide (1.1 Lit), tetrabutylammoniumbromide (8.72 g, 27.07 mmol) and potassium iodide (4.49 g, 27.07 mmol) are added at room temperature and the reaction mass is heated to 90° C. 1,2-Dibromoethane (7, 57.82 mL, 667.89 mmol) is added slowly at 90° C. and the reaction mixture is stirred at 90° C. for 16 h. After completion, the reaction mass is extracted with dichloromethane. The organic layer is dried over sodium sulfate, filtered and concentrated under reduced pressure to obtain the crude mass. The crude compound is purified by column chromatography using 100-200 silica gel and 2% ethyl acetate in hexanes to afford tert-butyl 2'-(2-bromoethoxy)-5'-chloro-[1,1'-biphenyl]-3-carboxylate (8).

Example 1B.9

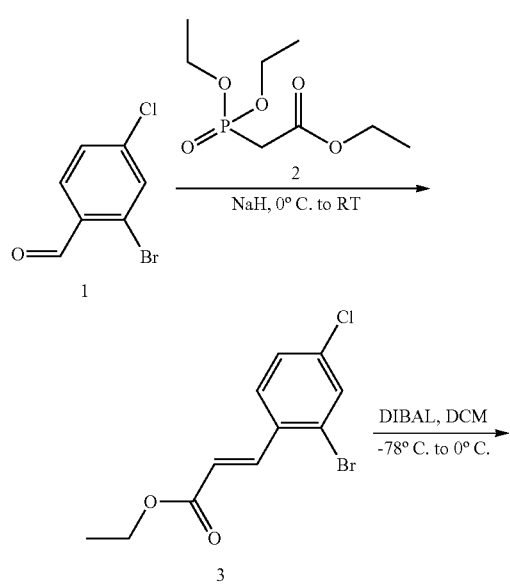

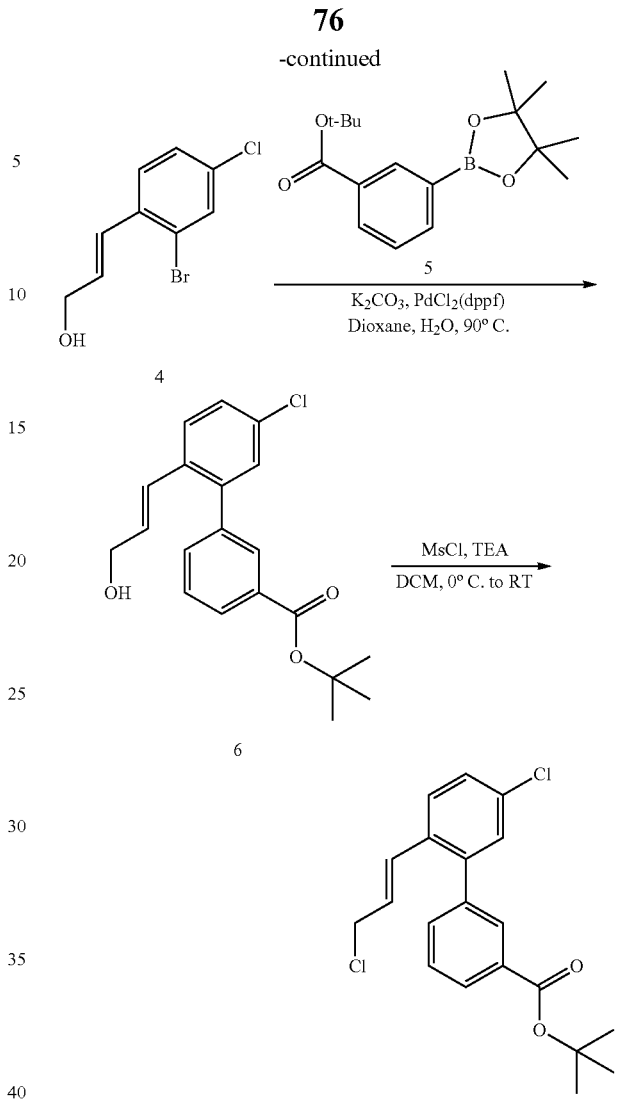

To a stirred solution of ethyl 2-(diethoxyphosphoryl)acetate (2, 23.01 g, 102.7 mmol) in tetrahydrofuran (100 mL) at 0° C., sodium hydride (60%) (5.47 g, 136.9 mmol) is added and the reaction mixture is stirred at 0° C. for 1 h. 2-bromo-4-chlorobenzaldehyde (1, 15.0 g, 68.4 mmol) in tetrahydrofuran (3 mL) is added slowly and the reaction mixture is stirred at 0° C. for 2 h. After completion, the reaction mass is quenched with water and extracted with ethyl acetate. The organic layer is separated, dried over anhydrous sodium sulphate and concentrated under reduced pressure to get the crude mass. The crude material is purified by Combi-flash using 3% ethyl acetate in hexanes as eluent. The desired fractions are concentrated under reduced pressure to afford ethyl (E)-3-(2-bromo-4-chlorophenyl)acrylate (3).

To a stirred solution of ethyl (E)-3-(2-bromo-4-chlorophenyl)acrylate (3, 2.0 g, 17.3 mmol) in dichloromethane (15.0 mL), diisobutylaluminium hydride (1 M in toluene) (31.1 mL, 31.1 mmol) is added and stirred at −78° C. for 1 h. The reaction mixture is slowly allowed to room temperature and stirred for 1 h. After completion, the reaction mass is quenched with aqueous ammonium chloride solution and extracted with dichloromethane. The organic layer is separated, dried over anhydrous sodium sulphate and concentrated under reduced pressure to get the crude mass which is purified by Combi-flash using 13% ethyl acetate in hexanes as eluent. The desired fractions are concentrated under reduced pressure to afford (E)-3-(2-bromo-4-chlorophenyl)prop-2-en-1-ol (4).

A stirred solution of (E)-3-(2-bromo-4-chlorophenyl)prop-2-en-1-ol (4, 1.5 g, 6.07 mmol), tert-butyl 3-(4,4,5,5-tetramethyl-1,3,2-dioxaborolan-2-yl)benzoate (5, 2.03 g, 6.68 mmol), and potassium carbonate (2.51 g, 18.2 mmol) in a mixture of dioxane and water (4:1) (24.0 mL) is degassed with argon for 30 min. [1,1'-Bis(diphenylphosphino)ferrocene]palladium(II) dichloride (0.222 g, 0.3 mmol) is added and the reaction mixture is heated at 90° C. for 12 h. After completion, the reaction mass is quenched with water and extracted with ethyl acetate. The organic layer is separated, dried over anhydrous sodium sulphate and concentrated under reduced pressure to get the crude mass. The crude compound is purified by Combi-flash using 15% ethyl acetate in hexanes as eluent. The desired fractions are concentrated under reduced pressure to afford tert-butyl (E)-5'-chloro-2'-(3-hydroxyprop-1-en-1-yl)-[1,1'-biphenyl]-3-carboxylate (6).

To a stirred solution of tert-butyl (E)-5'-chloro-2'-(3-hydroxyprop-1-en-1-yl)-[1,1'-biphenyl]-3-carboxylate (6, 1.5 g, 4.34 mmol) and triethylamine (1.82 mL, 13.04 mmol) in dichloromethane at 0° C., methanesulfonyl chloride (0.67 mL, 8.69 mmol) is added and the reaction mixture is slowly allowed to room temperature and stirred for 16 h. After completion, the reaction mass is quenched with water and extracted with dichloromethane. The organic layer is separated, dried over anhydrous sodium sulphate and concentrated to get the crude material. The crude compound is purified by Combi-flash using 10% ethyl acetate in hexanes as eluent to afford tert-butyl (E)-5'-chloro-2'-(3-chloroprop-1-en-1-yl)-[1,1'-biphenyl]-3-carboxylate (7).

Example 1B.10

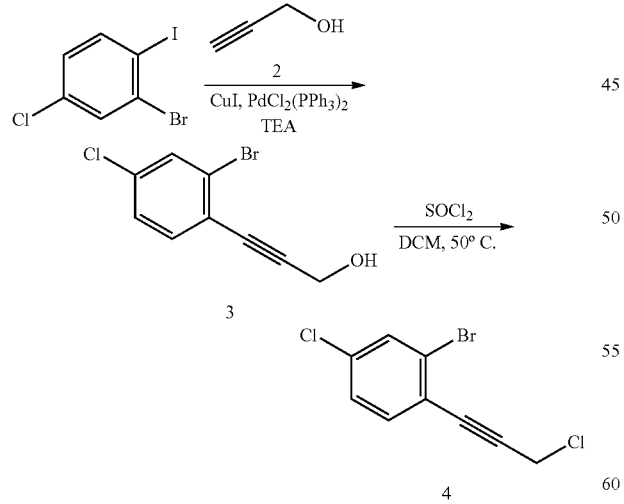

A stirred solution of 2-bromo-4-chloro-1-iodobenzene (1, 1.0 g, 3.15 mmol), prop-2-yn-1-ol (2, 0.2 mL, 3.47 mmol) & copper(I) iodide (0.024 g, 0.126 mmol) in triethyl amine (30 mL) is degassed with argon for 20 min. Dichlorobis(triphenylphosphine)palladium(II) (0.110 g, 0.15 mmol) is added and the reaction mixture is stirred at room temperature for 16 h. After completion, the reaction mass is quenched with water and extracted with ethyl acetate. The organic layer is separated, dried over anhydrous sodium sulphate and concentrated under reduced pressure to obtain the crude material. This crude compound is purified by Combi-flash using 10% ethyl acetate in hexanes as eluent. The desired fractions are concentrated under reduced pressure to afford 3-(2-bromo-4-chlorophenyl)prop-2-yn-1-ol (3) as yellow solid. Yield: 0.725 g, 93%, MS no ionization.

To a stirred solution of 3-(2-bromo-4-chlorophenyl)prop-2-yn-1-ol (3, 0.72 g, 2.93 mmol) in dichloromethane (10 mL), thionyl chloride (0.85 mL, 11.75 mmol) is added at 0° C. and the reaction mixture is heated and stirred at 50° C. for 16 h. After completion, the reaction mass concentrated under reduced pressure to obtain the crude which is purified by Combi-flash using 3% ethyl acetate in hexanes as eluent. The desired fractions are concentrated under reduced pressure to afford 2-bromo-4-chloro-1-(3-chloroprop-1-yn-1-yl)benzene (4)

Example 1C. General Coupling Methods

Example 1C₁

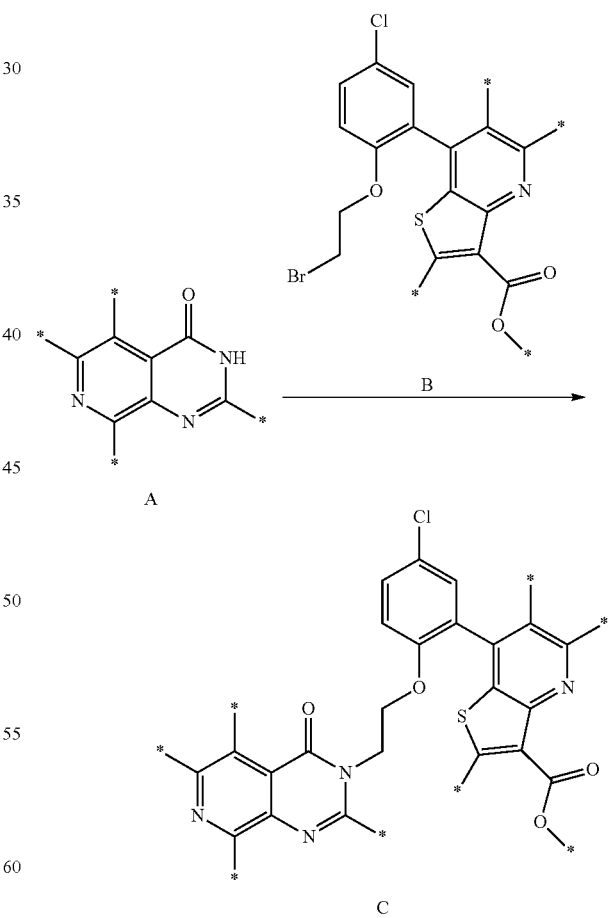

To a solution of 6-chloro-2-methyl-4-oxo-3,4-dihydropyrido[3,4-d]pyrimidine-5-carbonitrile (A, 1 equiv.) in N,N-dimethylformamide (0.2 M solution) is added potassium carbonate (3 equiv.) and tert-butyl 7-(2-(2-bromoethoxy)-5- chlorophenyl)thieno[3,2-b]pyridine-3-carboxylate (B, 1 equiv.) and the reaction mixture is heated at 60° C. for 16 h. The reaction mixture is then cooled, diluted with water, and extracted 2× with ethyl acetate. The combined organic layer is washed with water, dried over anhydrous sodium sulfate, filtered, and concentrated in vacuo. Purification by silica gel column chromatography affords tert-butyl 7-(5-chloro-2-(2-(6-chloro-5-cyano-2-methyl-4-oxopyrido[3,4-d]pyrimidin-3(4H)-yl)ethoxy)phenyl)thieno[3,2-b]pyridine-3-carboxylate (C).

Example 1C2

To a solution of 6-chloro-2-methyl-4-oxo-3,4-dihydropyrido[3,4-d]pyrimidine-5-carbonitrile (A, 1 equiv.) in N,N-dimethylformamide (0.14 M) is added tert-butyl 7-(2-(2-bromoethoxy)-5-chlorophenyl)thieno[3,2-b]pyridine-3-carboxylate (B, 1.3 equiv.), potassium iodide (0.2 equiv.), and ground potassium carbonate (3 equiv.) at room temperature. The mixture is stirred for 16 h at 50° C., diluted with water, and extracted 2× with ethyl acetate with ethyl acetate. The combined organic layer is washed with water, dried over anhydrous magnesium sulfate, and concentrated in vacuo. Purification by silica gel column chromatography gives tert-butyl 7-(5-chloro-2-(2-(6-chloro-5-cyano-2-methyl-4-oxopyrido[3,4-d]pyrimidin-3(4H)-yl)ethoxy)phenyl)thieno[3,2-b]pyridine-3-carboxylate (C).

Example 1C.3. Alternative Coupling Method

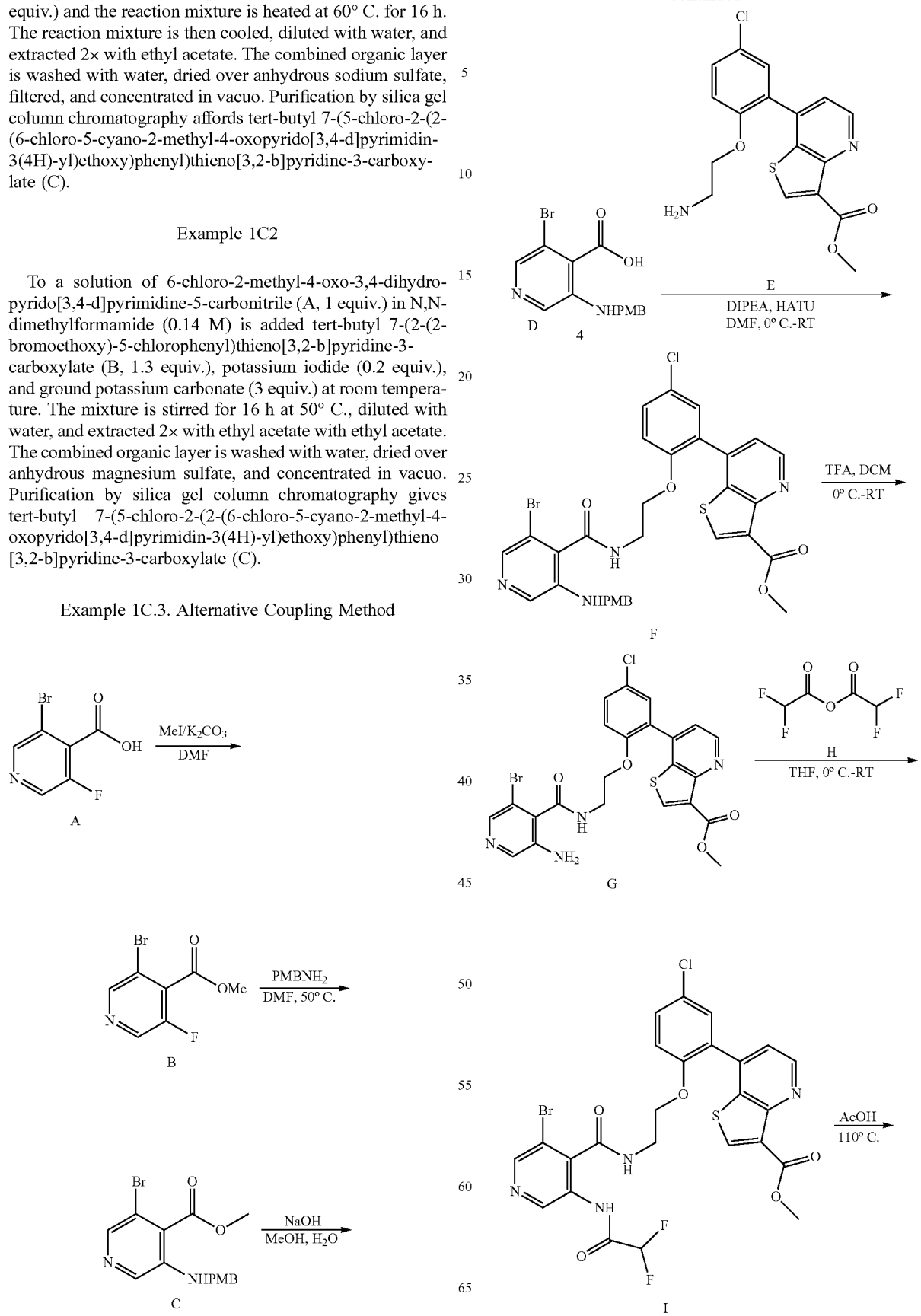

-continued

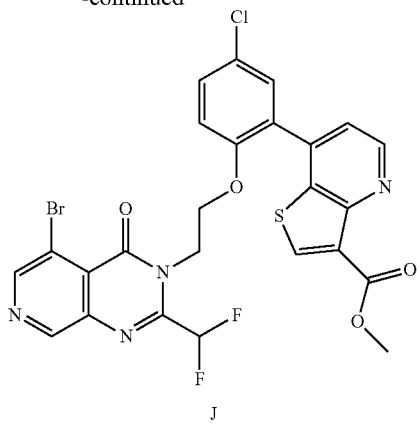

J

To a solution of 3-bromo-5-fluoroisonicotinic acid (A, 5.0 g, 21.92 mmol) in dimethylformamide (15 mL), potassium carbonate (6.07 g, 43.84 mmol) and iodomethane (2.05 mL, 32.88 mmol) are added at room temperature and stirred the reaction mixture for 2 h at room temperature. After completion, the reaction mass is diluted with ethyl acetate and washed with cold water. The organic layer is separated, dried over anhydrous sodium sulphate, filtered and concentrated to give crude. The crude is purified by flash chromatography eluting the compound with ethyl acetate in hexanes (1-10%). The desired fractions are concentrated under reduced pressure to afford methyl 3-bromo-5-fluoroisonicotinate (B).

To a solution of methyl 3-bromo-5-fluoroisonicotinate (B, 4.0 g, 17.17 mmol) in dimethylformamide (15 mL), potassium carbonate (7.0 g, 51.51 mmol) is added followed by drop wise addition of 4-methoxy benzyl amine (3.52 mL, 25.0 mmol at room temperature The reaction mixture is stirred for 16 h at 50° C. After completion, the reaction mass is diluted with ethyl acetate and washed with cold water. The organic layer is separated and dried over anhydrous sodium sulphate, filtered and concentrated to give crude. The crude is purified by flash column chromatography eluting the compound with ethyl acetate in hexanes (10-20%). The desired fractions are concentrated under reduced pressure to afford methyl 3-bromo-5-((4-methoxybenzyl)amino)isonicotinate (C).

To a solution of methyl 3-bromo-5-((4-methoxybenzyl)amino)isonicotinate (C, 2.8 g, 8.0 mmol) in methanol (5.0 mL) and water (5.0 mL) is added sodium hydroxide (0.64 g, 26.0 mmol) and stirred the reaction mixture for 6 h at room temperature. After completion, the reaction mass is concentrated to evaporate methanol. The aqueous layer is cooled to 0° C. and acidified with 2 N hydrochloric acid (pH ~4). The precipitated solid is filtered and dried to afford 3-bromo-5-((4-methoxybenzyl)amino)isonicotinic acid (D).

To a solution of 3-bromo-5-((4-methoxybenzyl)amino) isonicotinic acid (D, 0.9 g, 26.0 mmol) in dimethylformamide (15 mL), methyl 7-(2-(2-aminoethoxy)-5-chlorophenyl)thieno[3,2-b]pyridine-3-carboxylate (E, 1.16 g, 32.0 mmol) and 1-[bis(dimethylamino)methylene]-1H-1,2,3-triazolo[4,5-b]pyridinium 3-oxide hexafluorophosphate (1.48 g, 39.0 mmol) are added at 0° C. Diisopropylethylamine is added drop wise at 0° C. and stirred the reaction mixture at room temperature for 3 h. After completion, the reaction mass is diluted with ethyl acetate and washed with cold water. The organic layer is separated, dried over anhydrous sodium sulphate, filtered and concentrated under reduced pressure to give crude. The crude is purified by flash column chromatography eluting the compound with methanol in dichloromethane (2-5%). The desired fractions are concentrated under reduced pressure to afford methyl 7-(2-(2-(3-bromo-5-((4-methoxybenzyl)amino)isonicotinamido) ethoxy)-5-chlorophenyl)thieno[3,2-b]pyridine-3-carboxylate (F).

To a solution of methyl 7-(2-(2-(3-bromo-5-((4-methoxybenzyl)amino)isonicotinamido)ethoxy)-5-chlorophenyl) thieno[3,2-b]pyridine-3-carboxylate (F, 1.8 g, 26.0 mmol) in dichloromethane (10 mL) is added triflouroacetic acid (10 mL) at 0° C. and is stirred the reaction mixture at room temperature for 2 h. After completion, the reaction mass is concentrated to give crude. The crude is triturated with diethyl ether to afford methyl 7-(2-(2-(3-amino-5-bromoisonicotinamido)ethoxy)-5-chlorophenyl)thieno[3,2-b]pyridine-3-carboxylate (G).

To a solution of methyl 7-(2-(2-(3-amino-5-bromoisonicotinamido)ethoxy)-5-chlorophenyl)thieno[3,2-b]pyridine-3-carboxylate (G, 1.2 g, 2.1 mmol) in tetrahydofuran (10 mL), 2,2-difluoroacetic anhydride (H, 0.26 mL, 2.1 mmol) is added at 0° C. and stirred the reaction mixture at room temperature for 1 h. After completion, the reaction mass is concentrated to give crude. The crude is purified by washing and triturating with diethyl ether to afford methyl 7-(2-(2-(3-bromo-5-(2,2-difluoroacetamido)isonicotinamido) ethoxy)-5-chlorophenyl)thieno[3,2-b]pyridine-3-carboxylate (I).

A solution of methyl 7-(2-(2-(3-bromo-5-(2,2-difluoroacetamido)isonicotinamido)ethoxy)-5-chlorophenyl)thieno[3,2-b]pyridine-3-carboxylate (I, 1.0 g, 1.56 mmol) in acetic acid (10 mL) is heated and stirred at 110° C. for 24 h. After completion, acetic acid is removed under reduced pressure to give crude. The crude is purified by flash column chromatography eluting the compound with ethyl acetate in hexanes (50-70%). The desired fractions are concentrated under reduced pressure to afford methyl 7-(2-(2-(5-bromo-2-(difluoromethyl)-4-oxopyrido[3,4-d]pyrimidin-3(4H)-yl) ethoxy)-5-chlorophenyl)thieno[3,2-b]pyridine-3-carboxylate (J).

Example 1D. Post Coupling Modification Methods

Example 1D.1

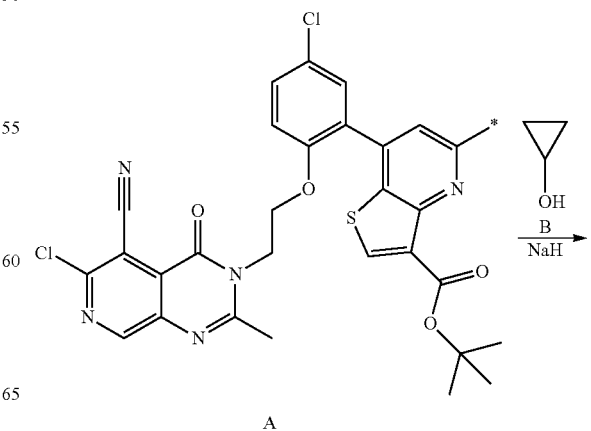

A

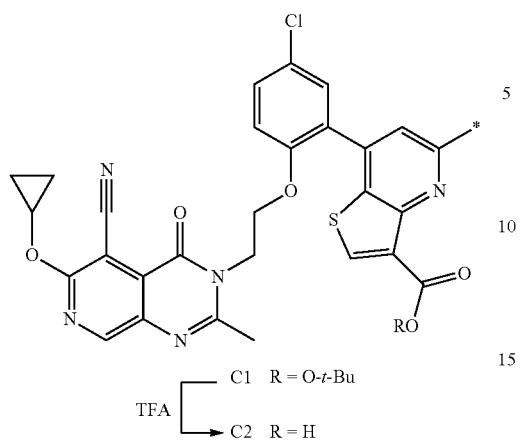

C1  R = O-t-Bu

TFA → C2  R = H

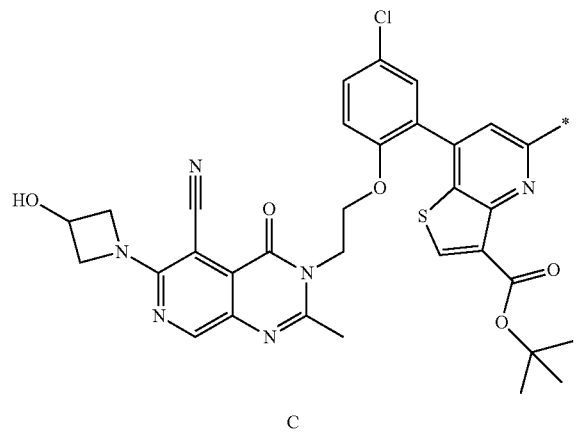

C

To a solution of cyclopropanol (B, 2.5 equiv.) in tetrahydrofuran (0.6 M), sodium hydride (3 equiv.) is added and the reaction mixture stirred at 0° C. for 10 min. tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.) is added to the reaction mixture at room temperature and heated at 120° C. for 6 h. The reaction mixture is cooled to room temperature, diluted with water, extracted with ethyl acetate, and the ethyl acetate layer dried over sodium sulfate, concentrated, and purified over a plug of silica gel to afford tert-butyl 7-(5-chloro-2-(2-(5-cyano-6-cyclopropoxy-2-methyl-4-oxopyrido[3,4-d]pyrimidin-3(4H)-yl)ethoxy)phenyl)-5-methylthieno[3,2-b]pyridine-3-carboxylate (C1).

To a solution of tert-butyl 7-(5-chloro-2-(2-(5-cyano-6-cyclopropoxy-2-methyl-4-oxopyrido[3,4-d]pyrimidin-3(4H)-yl)ethoxy)phenyl)-5-methylthieno[3,2-b]pyridine-3-carboxylate (C1, 1 equiv.) in dichloromethane (0.1 M), triflouroacetic acid (0.1 M) is added at 0° C. The reaction is slowly brought to room temperature and stirred for 16 h. The reaction is concentrated under reduced pressure, washed with diethyl ether, and purified by preparative HPLC to afford 7-(5-chloro-2-(2-(5-cyano-6-cyclopropoxy-2-methyl-4-oxopyrido[3,4-d]pyrimidin-3(4H)-yl)ethoxy)phenyl)-5-methylthieno[3,2-b]pyridine-3-carboxylic acid ($C_2$)

Example 1D.2

To a solution of tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.), and azetidin-3-ol hydrochloride (B, 2 equiv.) in DMF (0.16 M), potassium carbonate (5 equiv.) is added at room temperature followed by heating at 100° C. with stirring for 16 h. The reaction mixture is diluted with water, extracted with ethyl acetate, and the organic layers washed with water and brine solution, dried over sodium sulfate, concentrated, and purified by flash chromatography to afford tert-butyl 7-(5-chloro-2-(2-(5-cyano-6-(3-hydroxyazetidin-1-yl)-2-methyl-4-oxopyrido[3,4-d]pyrimidin-3(4H)-yl)ethoxy)phenyl)-5-methylthieno[3,2-b]pyridine-3-carboxylate (C).

Example 1D.3

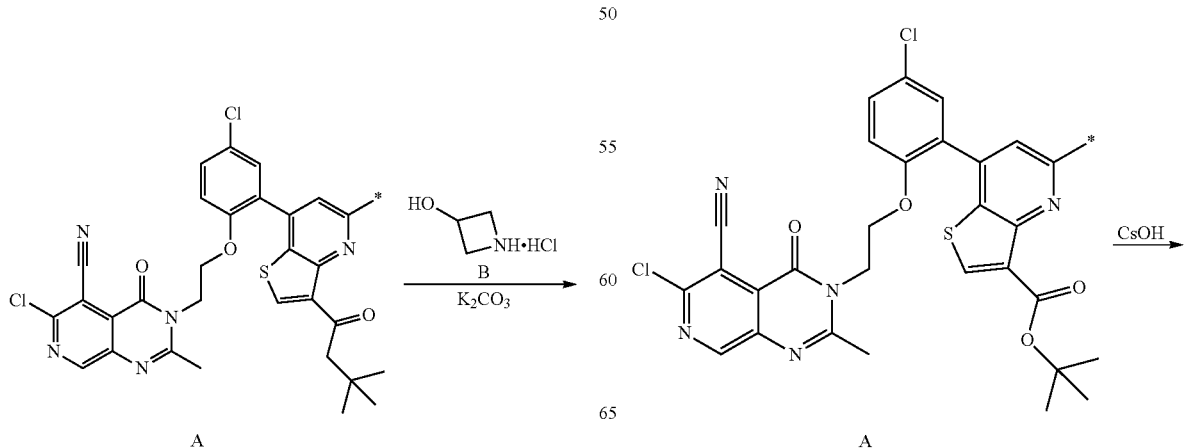

A → A

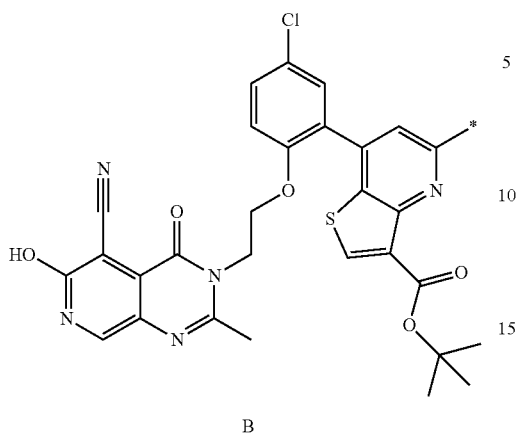

B

A solution of tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.), and cesium hydroxide (3 equiv.) in 1,4-dioxane (0.12 M) is degassed under nitrogen for 5 minutes. Tris(dibenzylideneacetone)dipalladium(0) (0.05 equiv.) and 5-(di-tert-butylphosphino)-1', 3', 5'-triphenyl-1'H-[1,4']bipyrazole (0.03 equiv.) are added and the mixture heated at 90° C. for 16 h. The reaction mixture is cooled, diluted with water, extracted with ethyl acetate, and the combined organic layer, dried over anhydrous sodium sulphate, filtered and concentrated to afford tert-butyl 7-(5-chloro-2-(2-(5-cyano-6-hydroxy-2-methyl-4-oxopyrido[3,4-d]pyrimidin-3(4H)-yl)ethoxy)phenyl)-5-methylthieno[3,2-b]pyridine-3-carboxylate (B).

Example 1D.4

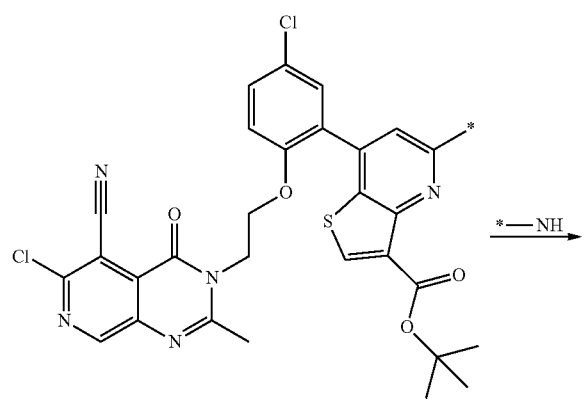

A

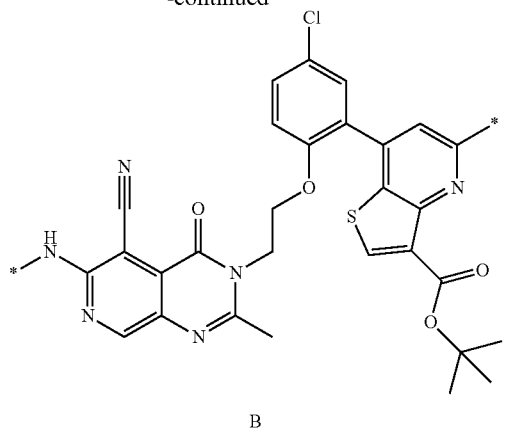

B

A solution tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.) in methanolic ammonia (20%, 0.05 M) is heated in a sealed tube at 120° C. for 16 h. The reaction mixture is concentrated to afford tert-butyl 7-(2-(2-(6-amino-5-cyano-2-methyl-4-oxopyrido[3,4-d]pyrimidin-3(4H)-yl)ethoxy)-5-chlorophenyl)-5-methylthieno[3,2-b]pyridine-3-carboxylate (B).

Example 1D.5

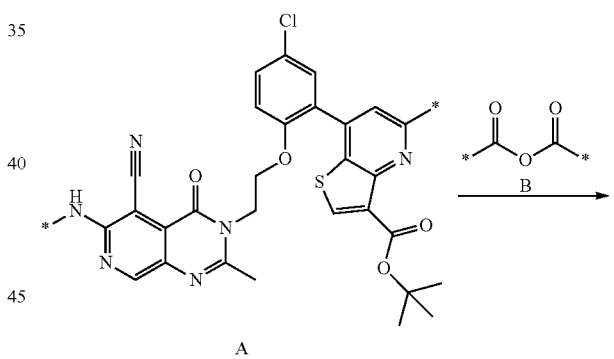

A

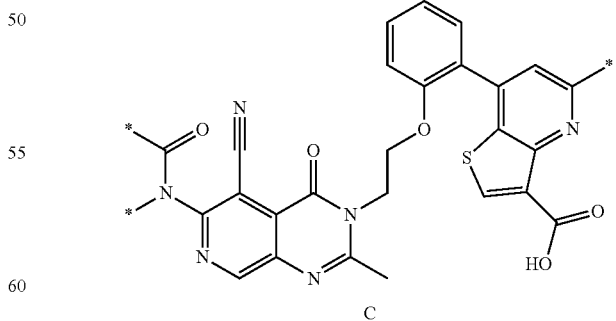

C

To a solution tert-butyl 7-(5-chloro-2-(2-(5-cyano-2-methyl-6-(methylamino)-4-oxopyrido[3,4-d]pyrimidin-3(4H)-yl)ethoxy)phenyl)-5-methylthieno[3,2-b]pyridine-3-carboxylate (A, 1 equiv.) in acetic anhydride (B, 0.06 M), acetic acid (0.24 M) is added at room temperature and the mixture is heated at 120° C. for 27 h. The reaction mixture is quenched on ice, extracted with ethyl acetate, and the organic layer dried over anhydrous sodium sulfate, filtered, concentrated, and purified by preparative HPLC to afford 7-(5-chloro-2-(2-(5-cyano-2-methyl-6-(N-methylacetamido)-4-oxopyrido[3,4-d]pyrimidin-3(4H)-yl)ethoxy)phenyl)-5-methylthieno[3,2-b]pyridine-3-carboxylic acid (C).

Example 1D.6

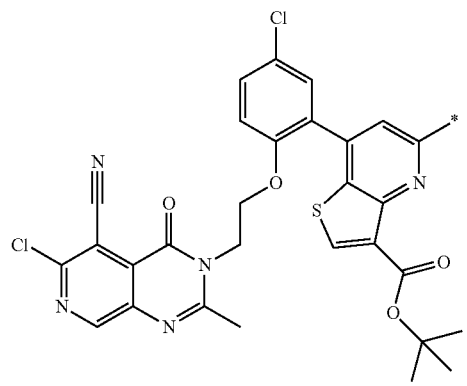

A

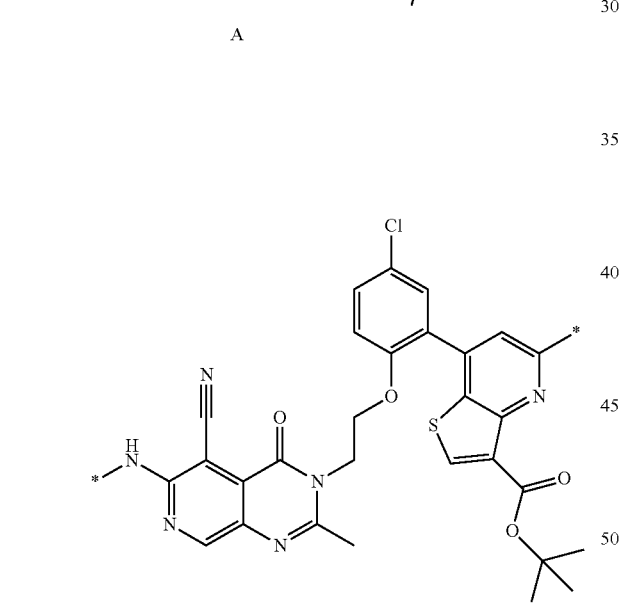

B

A solution tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.) in methanolic ammonia (20%, 0.05 M) is heated in a sealed tube at 120° C. for 16 h. The reaction mixture is concentrated to afford tert-butyl 7-(2-(2-(6-amino-5-cyano-2-methyl-4-oxopyrido[3,4-d]pyrimidin-3(4H)-yl)ethoxy)-5-chlorophenyl)-5-methylthieno[3,2-b]pyridine-3-carboxylate (B).

Example 1D.7

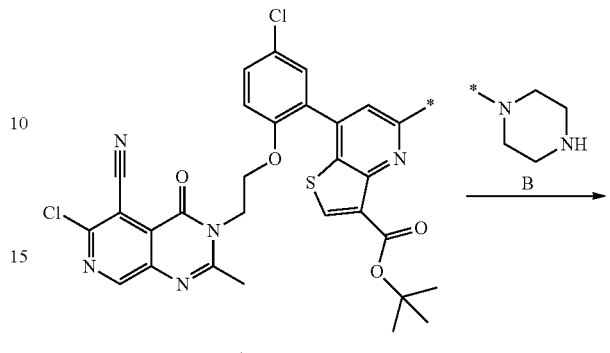

A

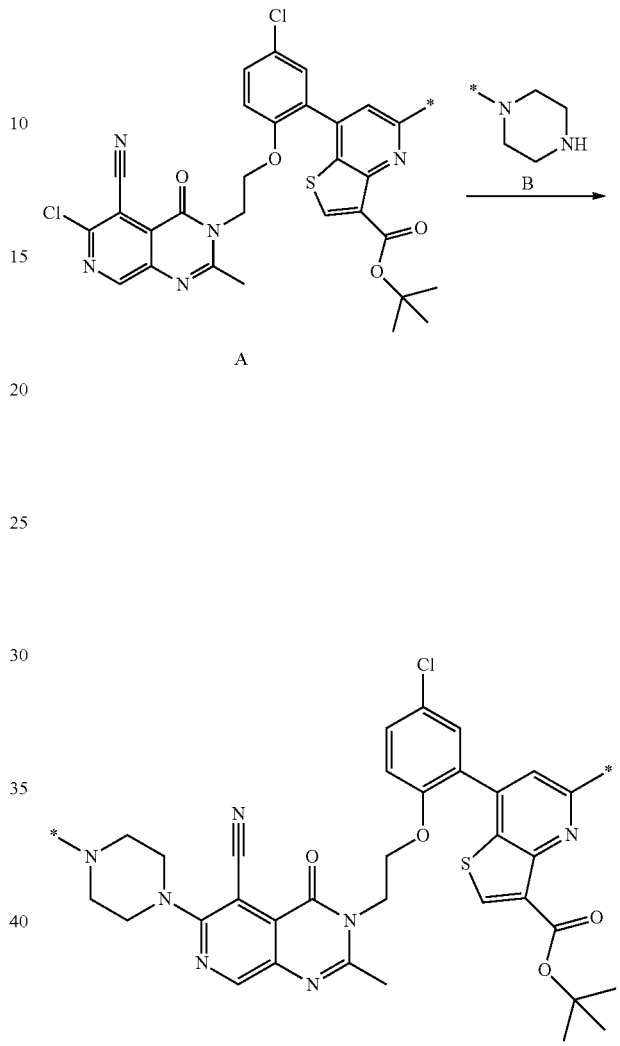

C

To a solution of tert-butyl 7-(5-chloro-2-(2-(6-chloro-5-cyano-2-methyl-4-oxopyrido[3,4-d]pyrimidin-3(4H)-yl)ethoxy)phenyl)-5-ethylthieno[3,2-b]pyridine-3-carboxylate (A, 1 equiv.) in N,N-dimethylformamide (0.05 M), 1-methylpiperazine (B, 3 equiv.), potassium fluoride (5 equiv.) and 18 crown-6 (1 equiv.) are added and the mixture heated at 90° C. for 3 h. The reaction mixture is cooled, diluted with water, extracted with ethyl acetate, and the combined organic layer dried over anhydrous sodium sulphate, filtered, and concentrated to afford tert-butyl 7-(5-chloro-2-(2-(5-cyano-2-methyl-6-(4-methylpiperazin-1-yl)-4-oxopyrido[3,4-d]pyrimidin-3(4H)-yl)ethoxy)phenyl)-5-ethylthieno[3,2-b]pyridine-3-carboxylate (C).

Example 1D.8

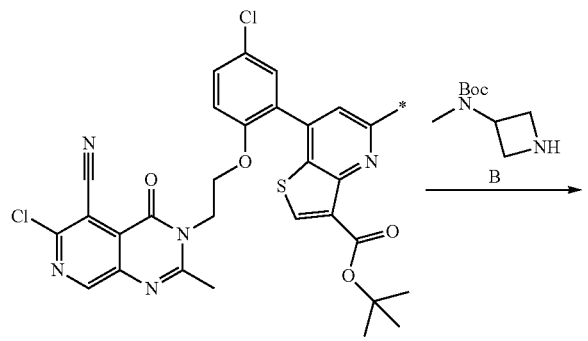

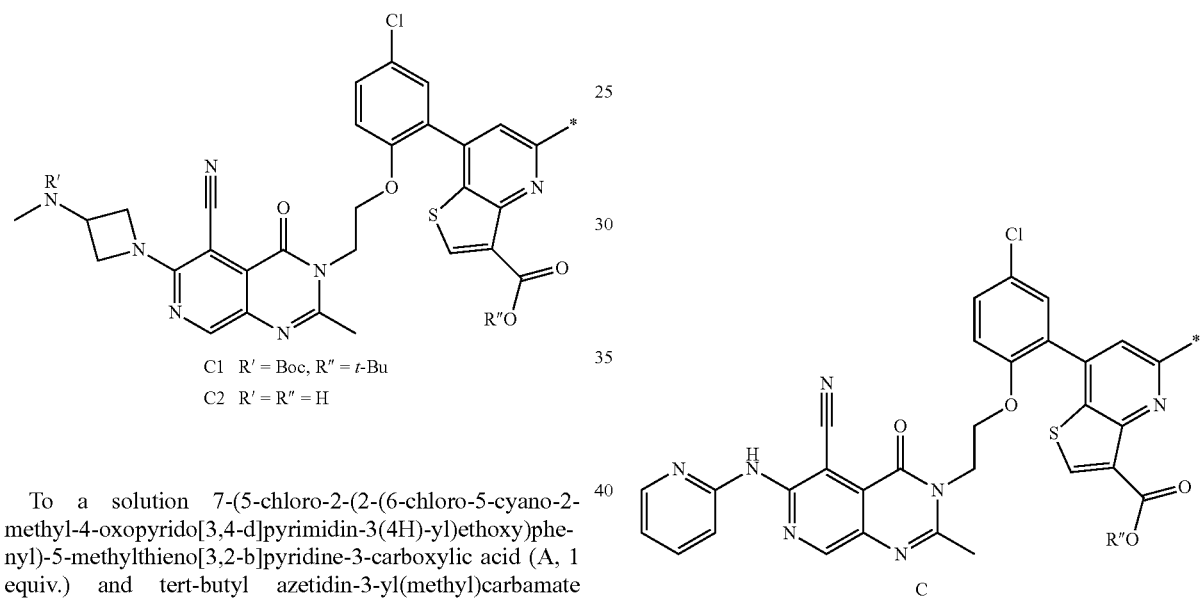

To a solution 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylic acid (A, 1 equiv.) and tert-butyl azetidin-3-yl(methyl)carbamate hydrochloride (B, 2 equiv.) in 1,4-dioxane (0.088 M) is added caesium carbonate (0.172 g, 0.530 mmol) and the reaction mixture heated at 90° C. for 3 h. The reaction mixture is diluted with water, extracted with ethyl acetate, and the organic layer dried over anhydrous sodium sulphate, filtered, concentrated, and purified by column chromatography to afford 7-(2-(2-(6-(3-((tert-butoxycarbonyl)(methyl)amino)azetidin-1-yl)-5-cyano-2-methyl-4-oxopyrido[3,4-d]pyrimidin-3(4H)-yl)ethoxy)-5-chlorophenyl)-5-methylthieno[3,2-b]pyridine-3-carboxylic acid (C1).

To a solution of 7-(2-(2-(6-(3-((tert-butoxycarbonyl)(methyl)amino)azetidin-1-yl)-5-cyano-2-methyl-4-oxopyrido[3,4-d]pyrimidin-3(4H)-yl)ethoxy)-5-chlorophenyl)-5-methylthieno[3,2-b]pyridine-3-carboxylic acid (C1, 1 equiv.) in dichloromethane (0.045 M), 2,2,2-trifluoroacetic acid (0.14 M) is added at 0° C. and the reaction mixture stirred for 16 h at room temperature. The reaction mixture is concentrated and purified by preparative HPLC to afford 7-(5-chloro-2-(2-(5-cyano-2-methyl-6-(3-(methylamino)azetidin-1-yl)-4-oxopyrido[3,4-d]pyrimidin-3(4H)-yl)ethoxy)phenyl)-5-methylthieno[3,2-b]pyridine-3-carboxylic acid (C2)

Example 1D.9

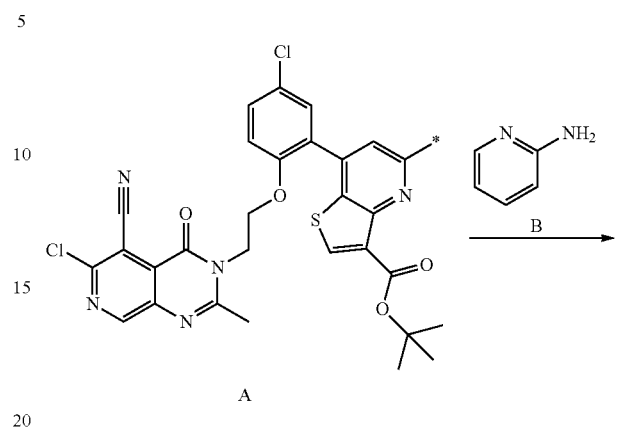

tert-Butyl 7-(2-(2-(6-bromo-5-cyano-2-methyl-4-oxo-7-(trifluoromethyl)quinazolin-3(4H)-yl)ethoxy)-5-chlorophenyl)-5-methylthieno[3,2-b]pyridine-3-carboxylate (A, 1 equiv.), 3-aminopyridine (B, 1.1 equiv.), xantphos (0.2 equiv.), cesium carbonate (3 equiv.), and tris(dibenzylideneacetone)dipalladium(0) (0.2 equiv.) are suspended in 1,4-dioxane (0.047 M) in a screw capped vial equipped with a stir bar. The reaction mixture is sparged with argon for 3 min, then sealed and heated at 100° C. in a heating block for 75 min. The reaction mixture is cooled to room temperature and taken up in a 1:1 N,N dimethylformamide:methanol solution and filtered through a syringe filter. Preparatory HPLC affords tert-butyl 7-(5-chloro-2-(2-(5-cyano-2-methyl-4-oxo-6-(pyridin-3-ylamino)-7-(trifluoromethyl)quinazolin-3(4H)-yl)ethoxy)phenyl)-5-methylthieno[3,2-b]pyridine-3-carboxylate (C).

Example 1D.10

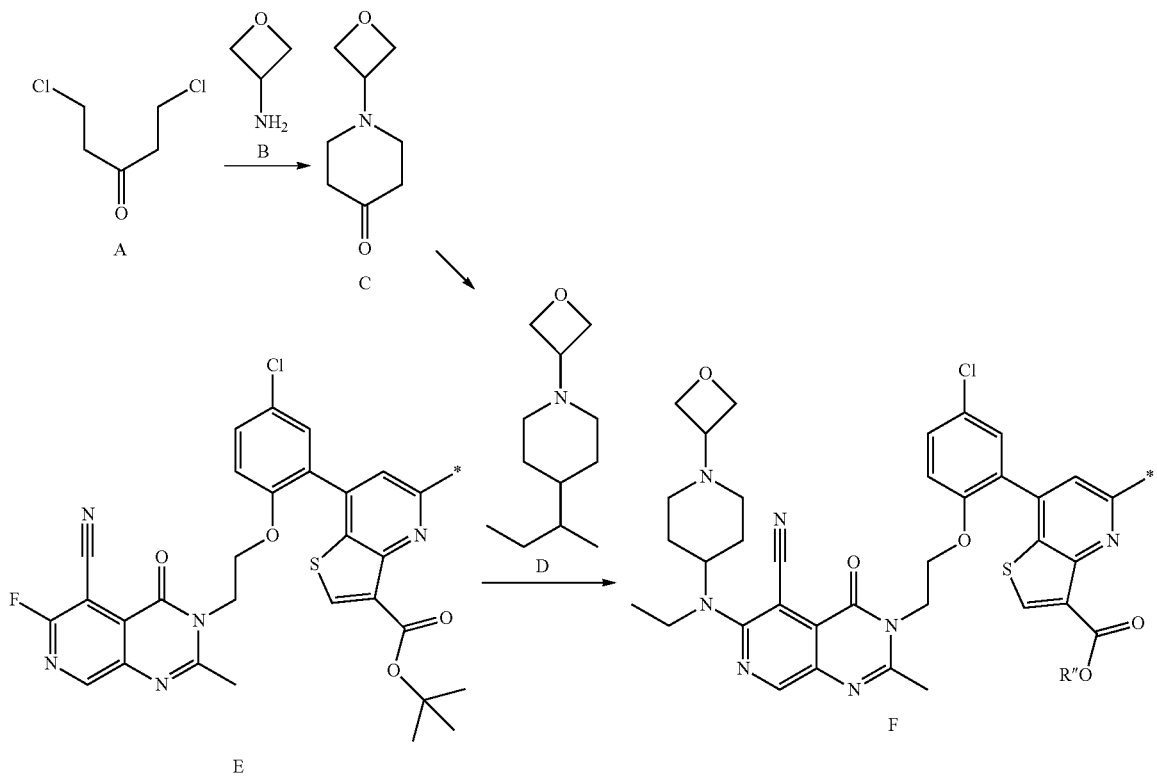

To a stirred solution of oxetan-3-amine (B, 1 equiv.), sodium carbonate (3.5 equiv.) in methanol (0.68 M) and 1,5-dichloropentan-3-one (A, 1 equiv.) are added at room temperature and the reaction mixture is heated at 75° C. for 3 h. The reaction mixture is cooled to room temperature, diluted with water, extracted with ethyl acetate, and the ethyl acetate layer is dried over sodium sulfate, concentrated, and purified over a plug of silica gel to afford 1-(oxetan-3-yl)piperidin-4-one (C).

To a solution of 1-(oxetan-3-yl)piperidin-4-one (C, 0.8 g, 5.16 mmol) in dichloromethane (0.5 M) are added ethylamine (2 M in tetrahydrofuran, 1.3 equiv.) and acetic acid (10 M) at room temperature. The reaction mixture is stirred for 60 min and sodium triacetoxyborohydride (1.3 equiv.) is added at 0° C. and stirred for 16 h at room temperature. The reaction is quenched with 10% aqueous sodium hydroxide solution, extracted with methanol in dichloromethane (5%), and the organic layer washed with sodium chloride solution, dried over anhydrous sodium sulfate, filtered and concentrated to afford N-ethyl-1-(oxetan-3-yl)piperidin-4-amine (D).

To a solution of tert-butyl 7-(5-chloro-2-(3-(5-cyano-6-fluoro-2-methyl-4-oxopyrido[3,4-d]pyrimidin-3(4H)-yl) prop-1-yn-1-yl)phenyl)thieno[3,2-b]pyridine-3-carboxylate (E, 1 equiv.) in acetonitrile (0.1 M), are added N-ethyl-1-(oxetan-3-yl)piperidin-4-amine (D, 2 equiv.) and N,N-diisopropylethylamine (3 equiv.) at room temperature and the reaction mixture is stirred for 30 h at 100° C. The reaction is cool to room temperature, quenched with water, extracted with ethyl acetate, and the organic layer washed with sodium chloride solution, dried over anhydrous sodium sulfate, filtered, concentrated and purified by Combi flash to afford tert-butyl 7-(5-chloro-2-(3-(5-cyano-6-(ethyl(1-(oxetan-3-yl)piperidin-4-yl)amino)-2-methyl-4-oxopyrido[3,4-d]pyrimidin-3(4H)-yl)prop-1-yn-1-yl)phenyl)thieno[3,2-b]pyridine-3-carboxylate (F).

Example 1D.11

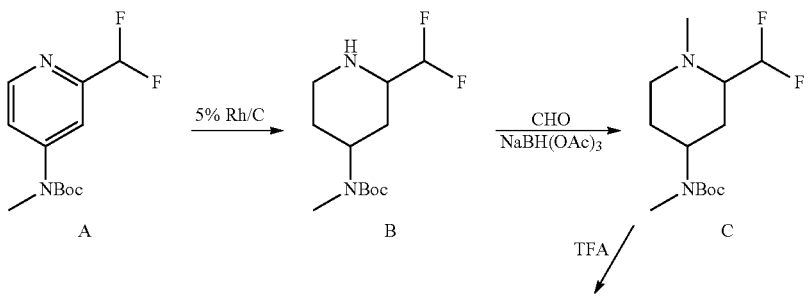

-continued

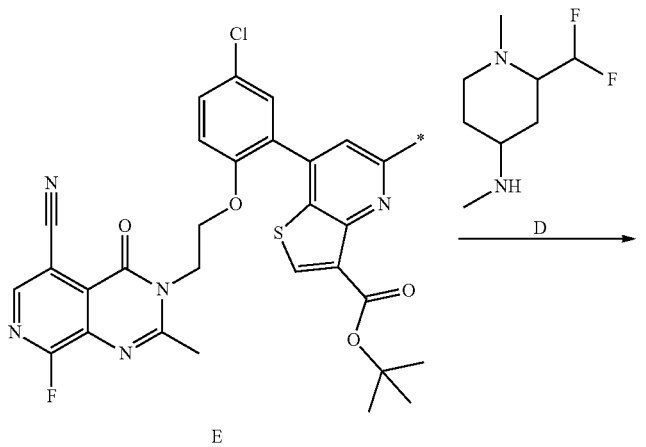

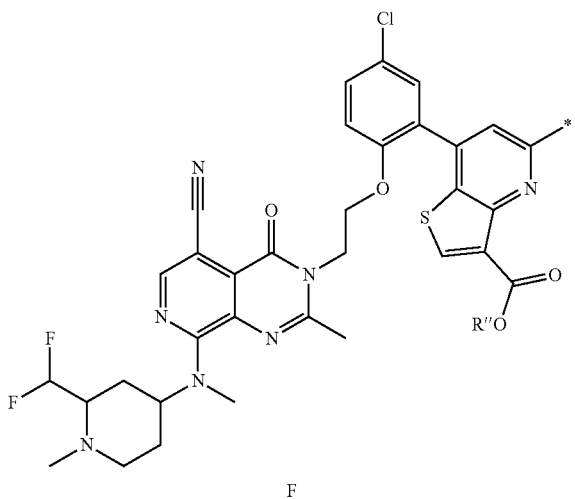

To a solution of tert-butyl (2-(difluoromethyl)pyridin-4-yl)(methyl)carbamate (A, 1 equiv.) and acetic acid (10 equiv.) in methanol (0.029 M), 5% rhodium on carbon (0.5 equiv.) is added at room temperature and the mixture heated at 80° C. under 80 psi for 15 hr. The reaction mixture is filtered and concentrated to afford tert-butyl (2-(difluoromethyl)piperidin-4-yl)(methyl)carbamate (B).

To a solution of tert-butyl (2-(difluoromethyl)piperidin-4-yl)(methyl)carbamate (B, 1 equiv.) in THF (0.19 M) are added formaldehyde (37% solution in water, 10 equiv.), acetic acid (9 equiv.) and molecular sieves (~3× by weight). The mixture is stirred for 30 min at room temperature, sodium triacetoxyboranuide (361 mg, 1.7 mmol) is added and the mixture stirred for 30 min. The reaction mixture is diluted with methanol and the residue passed through a strata ion exchange column, eluting with water three times, then acetonitrile three times, then methanol three times. tert-Butyl (2-(difluoromethyl)-1-methylpiperidin-4-yl) (methyl)carbamate (C) is eluted by washing the column with a solution of dichloromethane, methanol, and ammonium hydroxide (50:40:10).

tert-Butyl (2-(difluoromethyl)-1-methylpiperidin-4-yl) (methyl)carbamate (C, 1 equiv.) in trifluoroacetic acid (0.006 M) is stirred at room temperature for 30 min and the reaction mixture is concentrated to afford 2-(difluoromethyl)-N,1-dimethylpiperidin-4-amine (D).

A mixture of 7-(5-chloro-2-(2-(5-cyano-8-fluoro-2-methyl-4-oxopyrido[3,4-d]pyrimidin-3(4H)-yl)ethoxy)phenyl)thieno[3,2-b]pyridine-3-carboxylic acid (E, 1 equiv.), 2-(difluoromethyl)-N,1-dimethylpiperidin-4-amine (D, 5 equiv.) and NMP (0.037 M) in DIPEA (7 equiv.) is stirred at room temperature for 30 min. The reaction mixture is filtered and purified by HPLC to afford 7-(5-chloro-2-(2-(5-cyano-8-((2-(difluoromethyl)-1-methylpiperidin-4-yl) (methyl)amino)-2-methyl-4-oxopyrido[3,4-d]pyrimidin-3(4H)-yl)ethoxy)phenyl)thieno[3,2-b]pyridine-3-carboxylic acid (F).

Example 1D.12

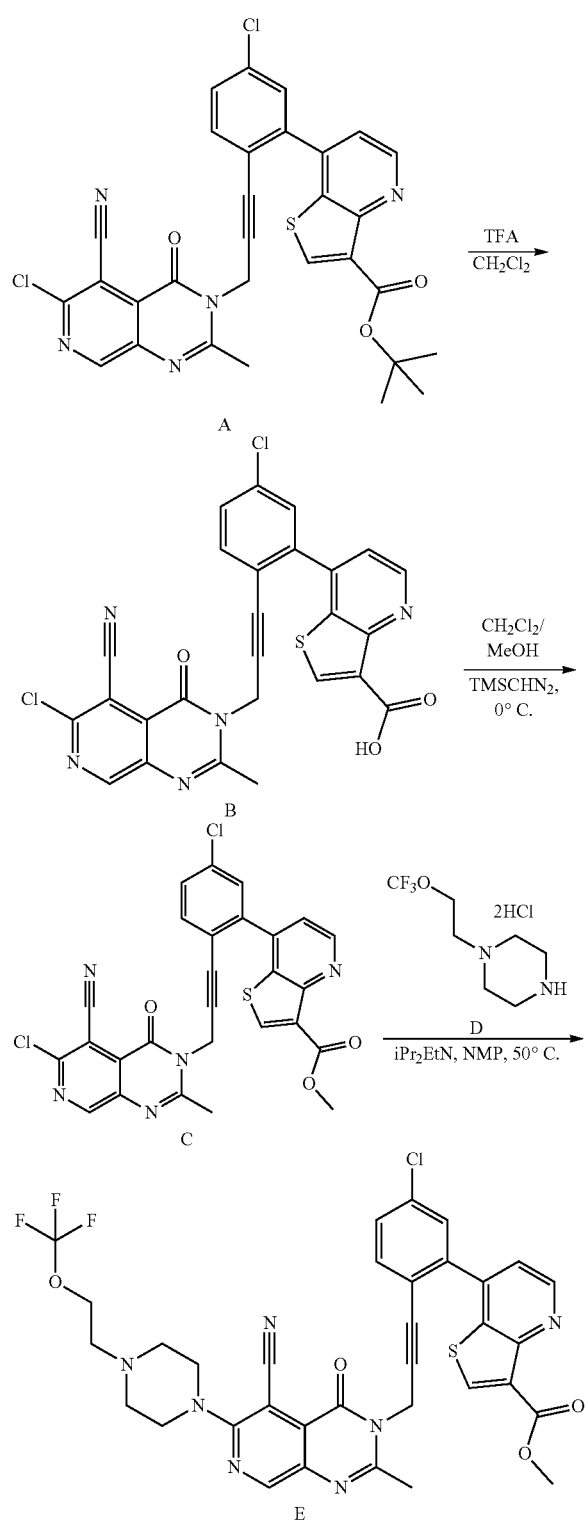

To a dichloromethane (40 mL) solution of tert-butyl 7-(5-chloro-2-(3-(6-chloro-5-cyano-2-methyl-4-oxopyrido[3,4-d]pyrimidin-3(4H)-yl)prop-1-yn-1-yl)phenyl)thieno[3,2-b]pyridine-3-carboxylate (A, 1 equiv.) is added trifluoroacetic acid (0.25 M) at 0° C. and stirred for 17 h at room temperature. The mixture is concentrated in vacuo, aqueous sodium bicarbonate solution added, and washed with diethyl ether. The water layer is acidified with 3 N hydrogen chloride solution and stirred for 15 min. Filtration affords 7-(5-chloro-2-(3-(6-chloro-5-cyano-2-methyl-4-oxopyrido[3,4-d]pyrimidin-3(4H)-yl)prop-1-yn-1-yl)phenyl)thieno[3,2-b]pyridine-3-carboxylic acid (B).

To a 7-(5-chloro-2-(3-(6-chloro-5-cyano-2-methyl-4-oxopyrido[3,4-d]pyrimidin-3(4H)-yl)prop-1-yn-1-yl)phenyl)thieno[3,2-b]pyridine-3-carboxylic acid (B, 1160 mg, 2.12 mmol) solution in dichloromethane (0.11 M) and methanol (0.42 M) is added trimethylsilyldiazomethane (4 equiv.) at 0° C. Upon stirring for 10 min at 0° C., the reaction is quenched with acetic acid (3.5 M), concentrated and purified by silica gel column chromatography to afford methyl 7-(5-chloro-2-(3-(6-chloro-5-cyano-2-methyl-4-oxopyrido[3,4-d]pyrimidin-3(4H)-yl)prop-1-yn-1-yl)phenyl)thieno[3,2-b]pyridine-3-carboxylate (C).

To a methyl 7-(5-chloro-2-(3-(6-chloro-5-cyano-2-methyl-4-oxopyrido[3,4-d]pyrimidin-3(4H)-yl)prop-1-yn-1-yl)phenyl)thieno[3,2-b]pyridine-3-carboxylate (C, 433 mg, 0.770 mmol) in N-methyl-2-pyrrolidone (0.21 M) is added 1-(2-(trifluoromethoxy)ethyl)piperazine dihydrochloride (D, 1.5 equiv.) at room temperature and the mixture stirred for 2 h at 50° C. followed by 17 h at room temperature. The mixture is diluted with methanol, filtered, and the filtrate purified by preparative HPLC to give methyl 7-(5-chloro-2-(3-(5-cyano-2-methyl-4-oxo-6-(4-(2-(trifluoromethoxy)ethyl)piperazin-1-yl)pyrido[3,4-d]pyrimidin-3(4H)-yl)prop-1-yn-1-yl)phenyl)thieno[3,2-b]pyridine-3-carboxylate (E).

Example 1D.13

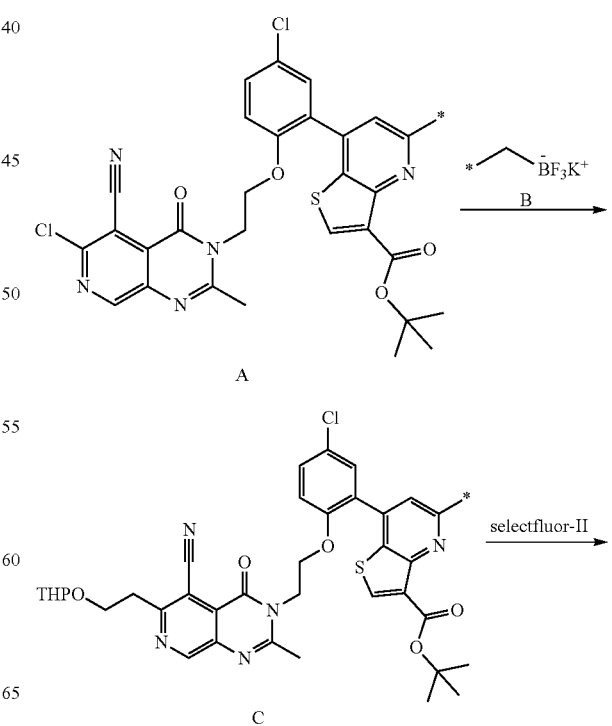

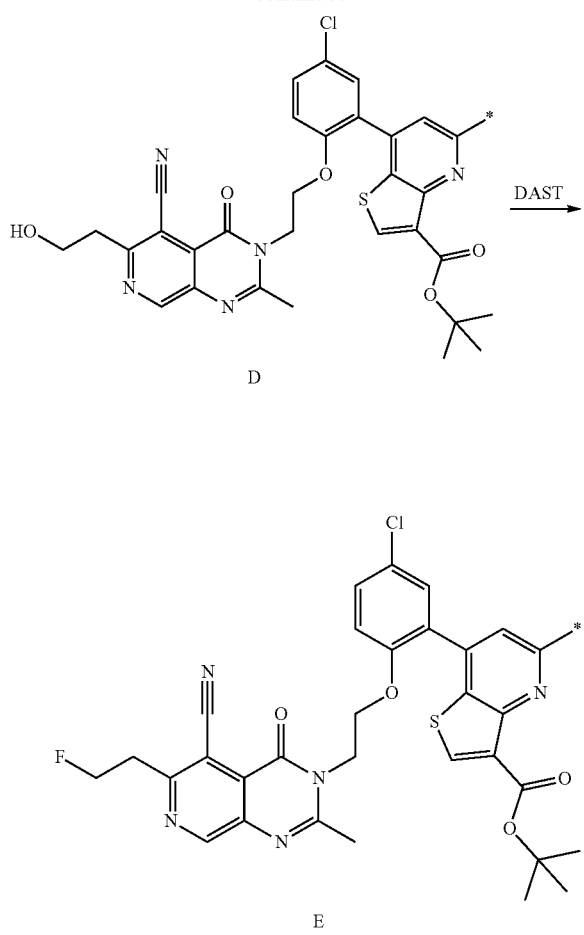

D

To a solution of tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.) and potassium trifluoro(2-((tetrahydro-2H-pyran-2-yl)oxy)ethyl)borate (B, 1.4 equiv.) in a mixture of toluene and water (2:1, 0.7 M) is added cesium carbonate (2 equiv.) and the reaction mixture degassed with argon for 15 min. [1,1'-Bis(diphenylphosphino)ferrocene]palladium(II) dichloride (0.1 equiv.) is added and heated at 100° C. for 16 h. The reaction mass is filtered through Celite, washed with ethyl acetate, and the filtrate dried over anhydrous sodium sulfate, concentrated, and purified by Combiflash to afford tert-butyl 7-(5-chloro-2-(2-(5-cyano-2-methyl-4-oxo-6-(2-((tetrahydro-2H-pyran-2-yl)oxy)ethyl)pyrido[3,4-d]pyrimidin-3(4H)-yl)ethoxy)phenyl)-5-methylthieno[3,2-b]pyridine-3-carboxylate (C).

To a stirred solution of tert-butyl 7-(5-chloro-2-(2-(5-cyano-2-methyl-4-oxo-6-(2-((tetrahydro-2H-pyran-2-yl)oxy)ethyl)pyrido[3,4-d]pyrimidin-3(4H)-yl)ethoxy)phenyl)-5-methylthieno[3,2-b]pyridine-3-carboxylate (C, 1 equiv.) in a mixture of acetonitrile and water (3:1, 0.018 M), selectfluor-II (2 equiv.) is added at 0° C. and the mixture stirred at room temperature for 48 h. The reaction mixture is partitioned between water and ethyl acetate and the organic layer dried over sodium sulfate and concentrated to afford tert-butyl 7-(5-chloro-2-(2-(5-cyano-6-(2-hydroxyethyl)-2-methyl-4-oxopyrido[3,4-d]pyrimidin-3(4H)-yl)ethoxy)phenyl)-5-methylthieno[3,2-b]pyridine-3-carboxylate (D).

To a solution of tert-butyl 7-(5-chloro-2-(2-(5-cyano-6-(2-hydroxyethyl)-2-methyl-4-oxopyrido[3,4-d]pyrimidin-3(4H)-yl)ethoxy)phenyl)-5-methylthieno[3,2-b]pyridine-3-carboxylate (D, 1 equiv.) in dichloromethane (0.4 M), diethylaminosulfur trifluoride (1.5 equiv.) is added at 0° C. and the mixture stirred at room temperature for 3 h. The reaction mass is quenched with 10% aqueous sodium hydroxide solution at 0° C., extracted with dichloromethane, and the organic layer dried over anhydrous sodium sulfate and concentrated to afford tert-butyl 7-(5-chloro-2-(2-(5-cyano-6-(2-fluoroethyl)-2-methyl-4-oxopyrido[3,4-d]pyrimidin-3(4H)-yl)ethoxy)phenyl)-5-methylthieno[3,2-b]pyridine-3-carboxylate (E).

Example 1D.14

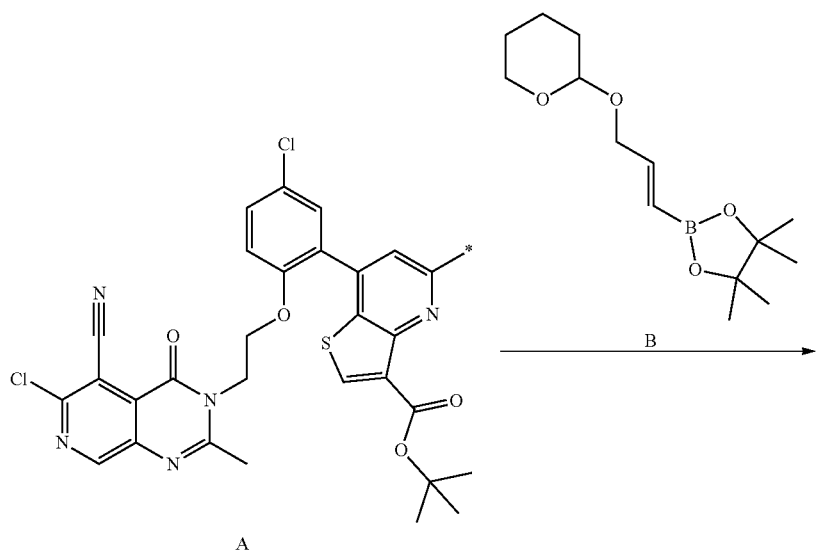

A

-continued
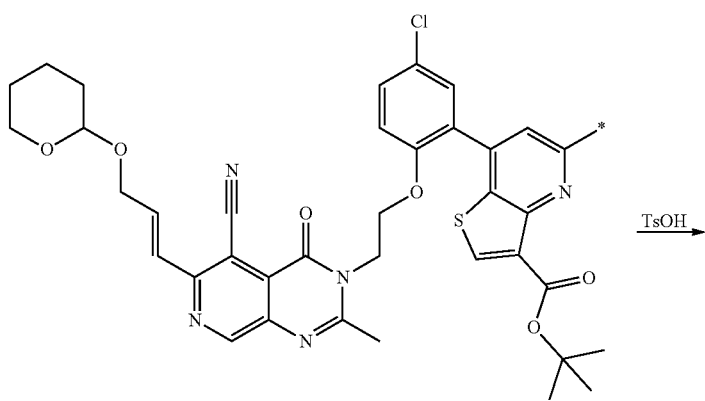
C
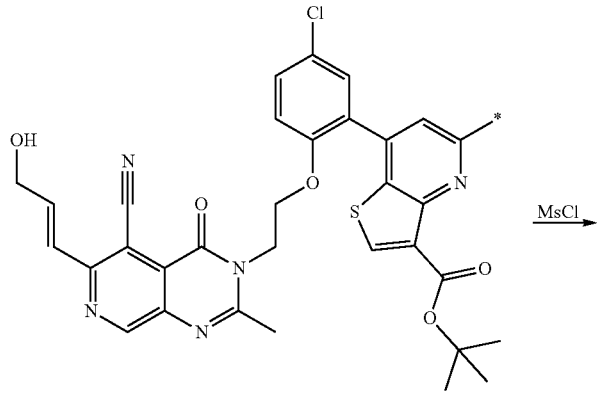
D
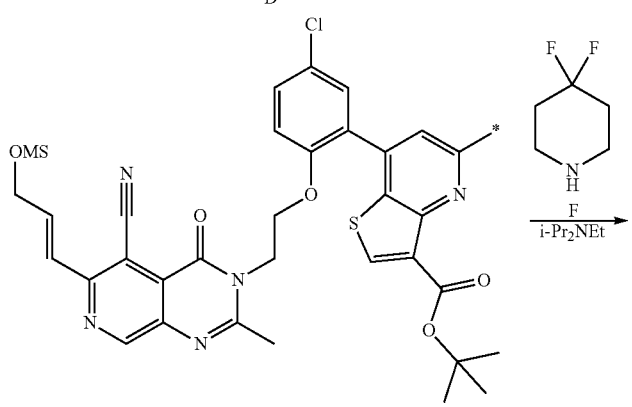
E
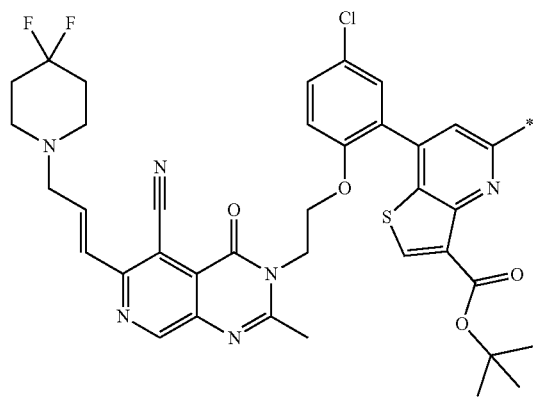
G tert-Butyl 7-(5-chloro-2-(2-(6-chloro-5-cyano-2-methyl-4-oxopyrido[3,4-d]pyrimidin-3(4H)-yl)ethoxy)phenyl)thieno[3,2-b]pyridine-3-carboxylate (A, 1 equiv.), PdCl$_2$(PPh$_3$)$_2$ (0.18 equiv.), and (E)-4,4,5,5-tetramethyl-2-(3-((tetrahydro-2H-pyran-2-yl)oxy)prop-1-en-1-yl)-1,3,2-dioxaborolane (B, 1.6 equiv.) are suspended in 1,4-dioxane (0.054 M) in an oven dried microwave vial equipped with a stir bar. Aqueous potassium carbonate (2.0 M, 4 equiv.) is added, and the sealed vial is sparged with argon for 5 min and heated at 100° C. in a microwave reactor for 4 h. The reaction mixture is diluted with saturated aqueous sodium bicarbonate and ethyl acetate and the aqueous phase extracted with ethyl acetate three times. The combined organic material is washed with brine, dried over magnesium sulfate, filtered, and purified via silica gel chromatography to afford tert-butyl (E)-7-(5-chloro-2-(2-(5-cyano-2-methyl-4-oxo-6-(3-((tetrahydro-2H-pyran-2-yl)oxy)prop-1-en-1-yl)pyrido[3,4-d]pyrimidin-3(4H)-yl)ethoxy)phenyl)thieno[3,2-b]pyridine-3-carboxylate (C).

tert-Butyl (E)-7-(5-chloro-2-(2-(5-cyano-2-methyl-4-oxo-6-(3-((tetrahydro-2H-pyran-2-yl)oxy)prop-1-en-1-yl)pyrido[3,4-d]pyrimidin-3(4H)-yl)ethoxy)phenyl)thieno[3,2-b]pyridine-3-carboxylate (C, 1 equiv.) is suspended in methanol (0.05 M) and tetrahydrofuran (0.05 M) and water (0.05 M) in a screw capped vial equipped with a stir bar and the reaction mixture stirred at room temperature while p-toluenesulfonic acid (0.35 equiv.) is added in 1 portion. After 30 min the temperature is raised to 55° C. and stirred an additional 1 h. Water (0.1 M) is added and, after 1 h, the temperature raised to 80° C. and heated at this temperature for 8 h. The reaction mixture is cooled to room temperature and volatile solvent is then removed in vacuo. The reaction mixture is diluted with saturated aqueous sodium bicarbonate and ethyl acetate, the layers separated, and the aqueous phase extracted with ethyl acetate three times. The combined organic material is washed with brine, dried over magnesium sulfate, and the solids filtered and concentrated to afford tert-butyl (E)-7-(5-chloro-2-(2-(5-cyano-6-(3-hydroxyprop-1-en-1-yl)-2-methyl-4-oxopyrido[3,4-d]pyrimidin-3(4H)-yl)ethoxy)phenyl)thieno[3,2-b]pyridine-3-carboxylate (D).

tert-Butyl (E)-7-(5-chloro-2-(2-(5-cyano-6-(3-hydroxyprop-1-en-1-yl)-2-methyl-4-oxopyrido[3,4-d]pyrimidin-3(4H)-yl)ethoxy)phenyl)thieno[3,2-b]pyridine-3-carboxylate (D, 1 equiv.) is dissolved in dichloromethane (0.086 M) in an oven-dried screw capped vial equipped with a stir bar. The reaction mixture is stirred at 0° C. while N,N-diisopropylethylamine (6 equiv.) is added slowly. Methanesulfonyl chloride (2.6 equiv.) is then added dropwise at which time the ice bath is removed. After 30 min the reaction mixture is diluted with dichloromethane, washed with saturated aqueous sodium bicarbonate and brine, dried over magnesium sulfate, filtered and the solvent removed in vacuo, affording tert-butyl (E)-7-(5-chloro-2-(2-(5-cyano-2-methyl-6-(3-((methylsulfonyl)oxy)prop-1-en-1-yl)-4-oxopyrido[3,4-d]pyrimidin-3(4H)-yl)ethoxy)phenyl)thieno[3,2-b]pyridine-3-carboxylate (E).

tert-Butyl (E)-7-(5-chloro-2-(2-(5-cyano-2-methyl-6-(3-((methylsulfonyl)oxy)prop-1-en-1-yl)-4-oxopyrido[3,4-d]pyrimidin-3(4H)-yl)ethoxy)phenyl)thieno[3,2-b]pyridine-3-carboxylate (E, 54.5 mg, 0.07 mmol) is dissolved in 1,2-dichloroethane (0.05 M) in a screw capped vial equipped with a stir bar and the reaction mixture stirred at 10° C. while 4,4-difluoropiperidine (F, 3.3 equiv.) is added dropwise. N,N-Diisopropylethylamine (6.6 equiv.) is added dropwise and after 5 min the reaction mixture is warmed to room temperature. After 15 min the temperature is raised to 45° C. and stirring continued for 3 h. The reaction mixture is cooled to room temperature and the solvent is then removed in vacuo. The residue is taken up in DMF and filtered through a syringe filter. Preparatory HPLC afforded the desired product, which is isolated by passing HPLC fractions through a strata ion exchange column, then washing with a solution of dichloromethane, methanol, and ammonium hydroxide. The solvent is to afford tert-butyl (E)-7-(5-chloro-2-(2-(5-cyano-6-(3-(4,4-difluoropiperidin-1-yl)prop-1-en-1-yl)-2-methyl-4-oxopyrido[3,4-d]pyrimidin-3(4H)-yl)ethoxy)phenyl)thieno[3,2-b]pyridine-3-carboxylate (G).

Example 1D.15

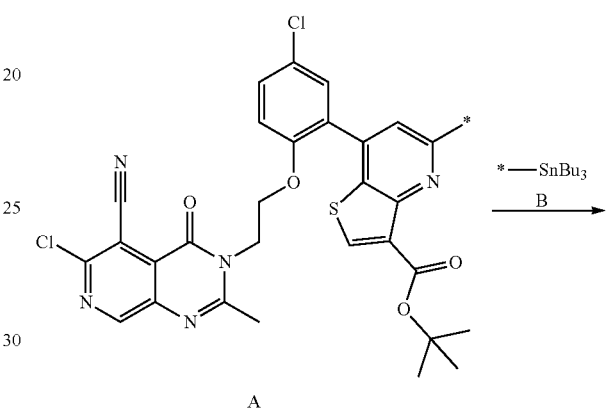

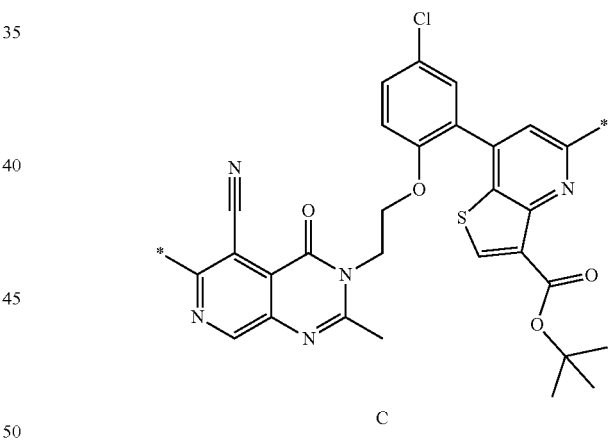

To a solution of tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.), tributyl(methoxymethyl)stannane (B, 1.5 equiv.) in 1-methyl-2-pyrrolidinone (0.1 M) is degassed using argon for 10 min and tetrakis(triphenylphosphine) palladium (0) (0.055 g, 0.048 mmol) is added at room temperature and heated at 130° C. for 10 h. The reaction mixture is cooled to room temperature, diluted with water and, extracted with ethyl acetate, and the ethyl acetate layer dried over sodium sulfate, concentrated, and purified by preparative HPLC to afford tert-butyl 7-(5-chloro-2-(2-(5-cyano-6-(methoxymethyl)-2-methyl-4-oxopyrido[3,4-d]pyrimidin-3(4H)-yl)ethoxy)phenyl)-5-methylthieno[3,2-b]pyridine-3-carboxylate (C).

103
Example 1D.16

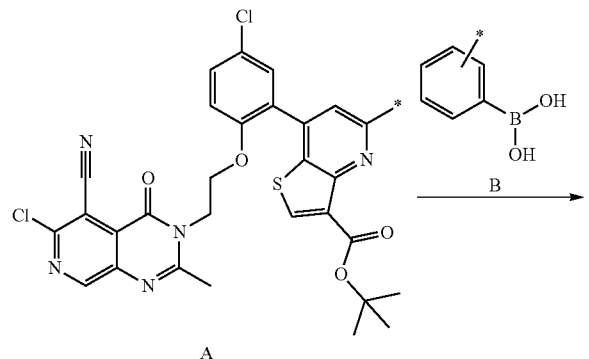

104
Example 1D.17

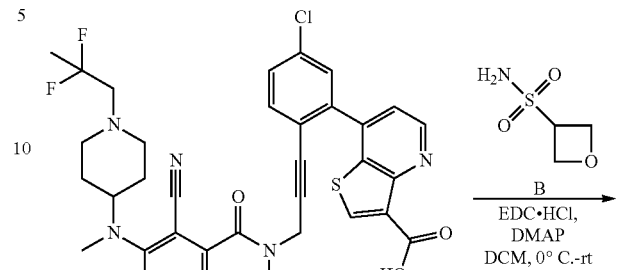

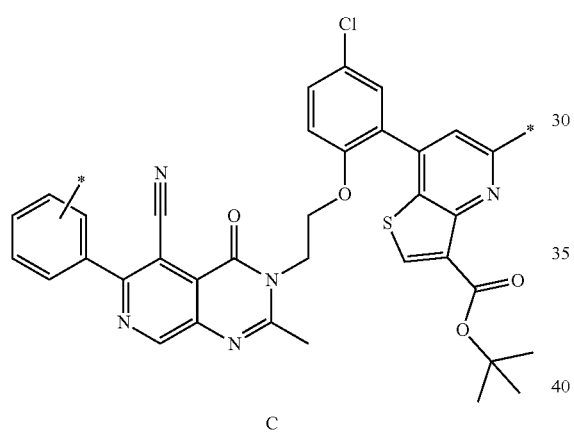

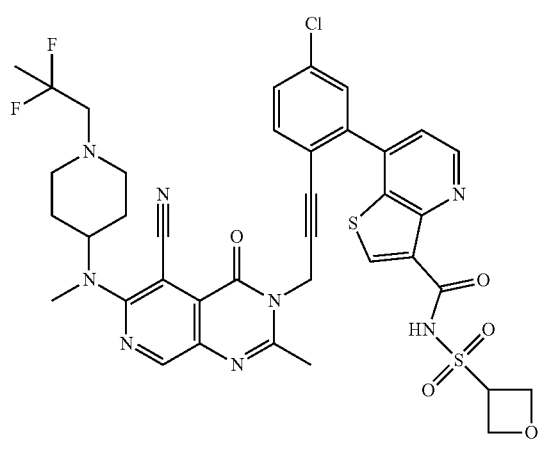

To a solution of tert-butyl 7-(5-chloro-2-(2-(6-chloro-5-cyano-2-methyl-4-oxopyrido[3,4-d]pyrimidin-3(4H)-yl)ethoxy)phenyl)-5-methylthieno[3,2-b]pyridine-3-carboxylate (A, 1 equiv.) and (2-fluorophenyl)boronic acid (B, 1.5 equiv.) in 1,4-dioxane is added 2 M aqueous potassium carbonate solution (3 equiv.) and reaction mixture degassed with argon gas for 10 min. [1,1'-Bis(diphenylphosphino)ferrocene] dichlopalladium(II)dichlomethane complex (0.05 equiv.) is added and degassed with argon gas for 5 min and the reaction mixture is heated at 90° C. for 3 h. The reaction mixture is diluted with water, extracted with ethyl acetate, and the organic layer dried over anhydrous sodium sulphate, filtered, concentrated, and purified by column chromatography to afford tert-butyl 7-(5-chloro-2-(2-(5-cyano-6-(2-fluorophenyl)-2-methyl-4-oxopyrido[3,4-d]pyrimidin-3(4H)-yl)ethoxy)phenyl)-5-methylthieno[3,2-b]pyridine-3-carboxylate (C).

To a solution of 7-(5-chloro-2-(3-(5-cyano-6-((1-(2,2-difluoropropyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylic acid (A, 1 equiv.) and oxetane-3-sulfonamide (B, 2.5 equiv.) in dichloromethane (0.07 M) is added 1-ethyl-3-(3-dimethylaminopropyl)carbodiimide hydrochloride (2 equiv.) and 4-(dimethylamino)pyridine (2.5 equiv.) at 0° C. and stirred at room temperature for 12 h. The reaction mixture is diluted with water, extracted with dichloromethane, and the organic layer dried over anhydrous sodium sulphate, filtered, concentrated, and purified by preparative HPLC to afford 7-(5-chloro-2-(3-(5-cyano-6-((1-(2,2-difluoropropyl)piperidin-4-yl)(methyl)amino)-2-methyl-4-oxopyrido[3,4-d]pyrimidin-3(4H)-yl)prop-1-yn-1-yl)phenyl)-N-(oxetan-3-ylsulfonyl)thieno[3,2-b]pyridine-3-carboxamide (C).

Example 1D.18

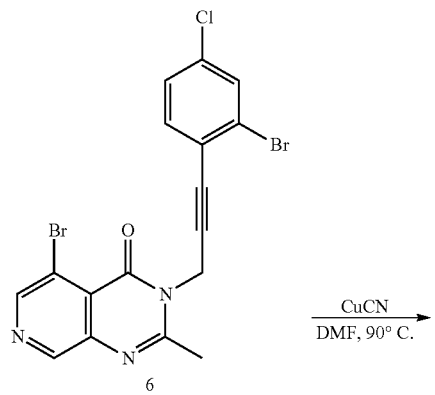

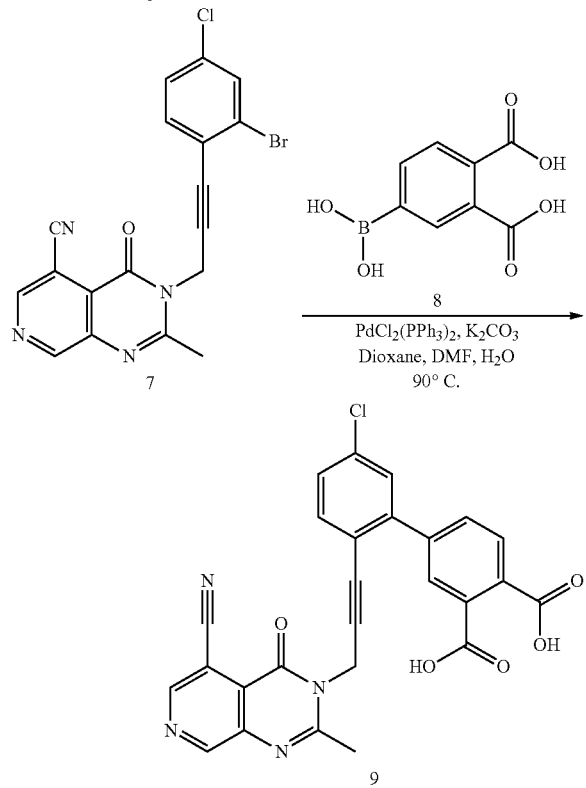

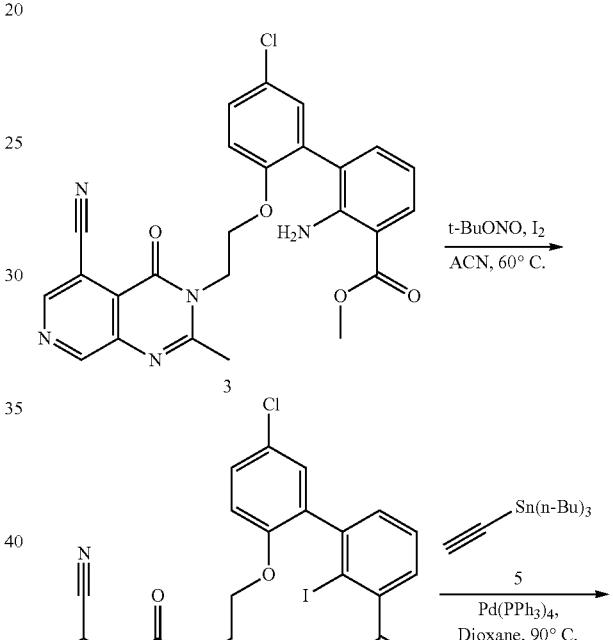

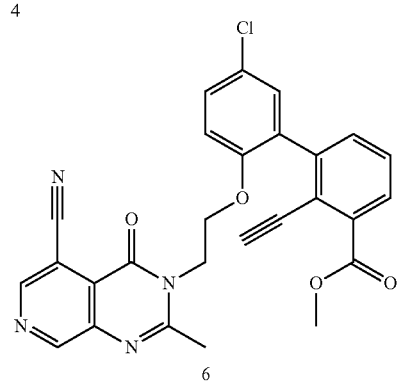

To a stirred solution of 5-bromo-3-(3-(2-bromo-4-chlorophenyl)prop-2-yn-1-yl)-2-methylpyrido[3,4-d]pyrimidin-4(3H)-one (6, 0.6 g, 1.28 mmol) in N,N-dimethylformamide, copper(I) cyanide (0.138 g, 1.53 mmol) is added and the reaction mixture is heated and stirred at 90° C. for 16 h. After completion, the reaction mass is diluted with ethyl acetate and washed with cold water. The organic layer is separated, dried over anhydrous sodium sulphate and concentrated under reduced pressure. The crude compound is purified by Combi-flash using 50% ethyl acetate in hexanes as eluent. The desired fractions are concentrated under reduced pressure to afford 3-(3-(2-bromo-4-chlorophenyl)prop-2-yn-1-yl)-2-methyl-4-oxo-3,4-dihydropyrido[3,4-d]pyrimidine-5-carbonitrile (7).

A stirred solution of 3-(3-(2-bromo-4-chlorophenyl)prop-2-yn-1-yl)-2-methyl-4-oxo-3,4-dihydropyrido[3,4-d]pyrimidine-5-carbonitrile (7, 0.1 g, 0.24 mmol), 4-boronophthalic acid (8, 0.075 g, 0.36 mmol) and potassium carbonate (0.099 g, 0.72 mmol) in a mixture of dioxane, N,N-dimethylformamide and water (1.2 mL, 0.6 mL, 0.2 mL respectively) is degassed with argon for 25 min. Dichlorobis(triphenylphosphine)palladium(II) is added and the reaction mixture is heated and stirred at 90° C. for 2 h. After completion, volatiles are removed under reduced pressure to obtain the residue. This residue is diluted with water, acidified with 1 N aqueous hydrochloric acid and extracted with ethyl acetate. The organic layer is separated, dried over anhydrous sodium sulphate and concentrated under reduced pressure to obtain the compound. This compound is purified by preparative HPLC to afford 5'-chloro-2'-(3-(5-cyano-2-methyl-4-oxopyrido[3,4-d]pyrimidin-3(4H)-yl)prop-1-yn-1-yl)-[1,1'-biphenyl]-3,4-dicarboxylic acid (9).

Example 1D.18

To a solution of methyl 2-amino-5'-chloro-2'-(2-(5-cyano-2-methyl-4-oxopyrido[3,4-d]pyrimidin-3(4H)-yl)ethoxy)-[1,1'-biphenyl]-3-carboxylate (3, 1.5 g, 3.06 mmol) in acetonitrile (40 mL), tert-butyl nitrite (0.50 g, 4.8 mmol) is added at room temperature. Suspension of copper(I) iodide (0.93 g, 3.06 mmol) in acetonitrile (10 mL) is added drop wise over a period of 10 min at room temperature. The reaction mixture is stirred at 60° C. for 4 h. After completion, the reaction mixture is diluted with water and extracted with ethyl acetate. The organic layer is washed with aqueous sodium thiosulphate, dried over anhydrous sodium sulphate, filtered and concentrated under reduced pressure to afford crude. The crude is purified by flash column chromatography using 0-40% ethyl acetate in hexane to afford methyl 5'-chloro-2'-(2-(5-cyano-2-methyl-4-oxopyrido[3,4-d]pyrimidin-3(4H)-yl)ethoxy)-2-iodo-[1,1'-biphenyl]-3-carboxylate (4).

A solution of methyl 5'-chloro-2'-(2-(5-cyano-2-methyl-4-oxopyrido[3,4-d]pyrimidin-3(4H)-yl)ethoxy)-2-iodo-[1,1'-biphenyl]-3-carboxylate (4, 0.57 g, 0.95 mmol) in dioxane (20 mL) is degassed for 10 min using argon. Tributyl(ethynyl)stannane (5, 0.6 g, 1.86 mmol) and tetrakis(triphenylphosphine)palladium(0) (0.076 g, 0.066 mmol) are added and the reaction mixture is stirred at 90° C. for 16 h. After completion, reaction mixture is diluted with water and extracted with ethyl acetate. The organic layer is dried over anhydrous sodium sulfate filtered and concentrated to dryness under reduced pressure. The crude is purified by flash column chromatography using 0-40% ethyl acetate in hexanes to afford methyl 5'-chloro-2'-(2-(5-cyano-2-methyl-4-oxopyrido[3,4-d]pyrimidin-3(4H)-yl)ethoxy)-2-ethynyl-[1,1'-biphenyl]-3-carboxylate (6).

Compounds made using one or more of the general methods described above are shown in Table 1. Where provided, characterization data is to the right of the compounds.

TABLE 1

7-Aza-Thienylpyridine and Derivative Compounds

| Compound | | Characterization |
|---|---|---|
| 34 | 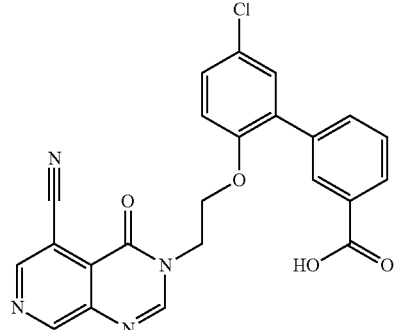 | MS (ESI) m/z 447.30 [M + 1]+; 1H NMR (400 MHz, DMSO-d6) δ 12.98 (s, 1H), 9.23 (s, 1H), 9.07 (s, 1H), 8.20 (s, 1H), 7.88 (s, 1H), 7.84 (d, J = 7.68, 1H), 7.61 (d, J = 7.72, 1H), 7.45-7.39 (m, 2H), 7.33 (d, J = 2.5 Hz, 1H), 7.21 (d, J = 8.84Hz, 1H), 4.35 (s, 4H) |
| 35 | 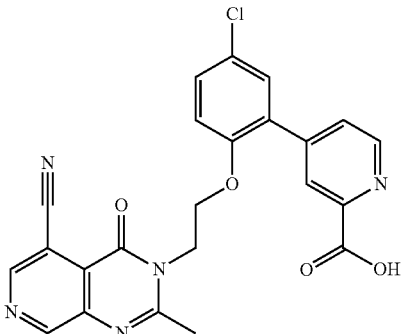 | MS (ESI) m/z 462.39 [M + 1]+; 1H NMR (400 MHz, DMSO-d6) δ 9.19 (s, 1H), 9.03 (s, 1H), 8.63 (d, J = 4.8 Hz, 1H), 7.94 (d, J = 0.8 Hz, 1H), 7.59 (dd, J = 4.8 Hz, 1H), 7.48 (dd, J = 4.4 Hz, 1H), 7.409 (d, J = 2.8 Hz, 1H), 7.249 (d, J = 8.8 Hz, 1H), 4.386 (s, 4H), 2.22 (s, 3H) |
| 36 | 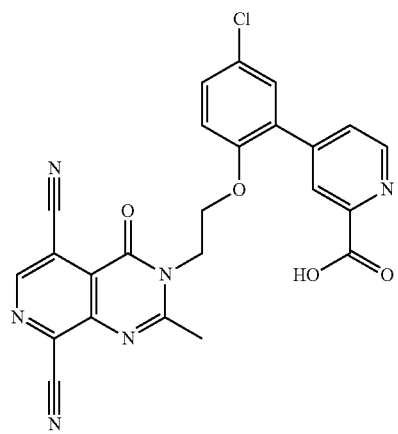 [SMILES: Cc1nc2c(C#N)ncc(C#N)c2c(=O)n1CCOc1ccc(Cl)cc1-c1ccnc(C(=O)O)c1] | MS (ESI) m/z 486.38 [M + 1]+; 1H NMR (400 MHz, DMSO-d6) δ 9.16 (s, 1H), 7.87 (d, J = 7.68 Hz, 1H), 7.83 (s, 1H), 7.49 (d, J = 7.68 Hz, 1H), 7.43-7.38 (m, 2H), 7.27 (d, J = 2.6 Hz, 1H), 7.20 (d, J = 8.88 Hz, 1H), 4.39-4.35 (dd, J = 12.52 Hz, 4H), 2.29 (s, 3H) |

TABLE 1-continued

7-Aza-Thienylpyridine and Derivative Compounds

| Compound | | Characterization |
|---|---|---|
| 38 |  | MS (ESI) m/z 529.45 [M + 1]+; 1H NMR (400 MHz, DMSO-d6) δ 12.98 (s, 1H), 9.13 (s, 1H), 7.87-7.85 (m, 2H), 7.56 (d, J = 7.76 Hz, 1H), 7.42-7.38 (m, 2H), 7.29 (d, J = 2.64 Hz, 1H), 7.21 (d, J = 8.92 Hz, 1H), 4.37 (m, 4H), 2.24 (s, 3H) |
| 39 | 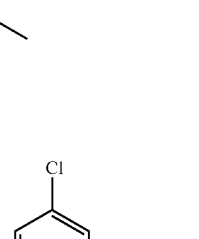 | MS (ESI) m/z 554.13 [M + 1]+; 1H NMR (400 MHz, DMSO-d6) δ 9.22 (s, 1H), 9.19 (s, 1H), 8.79 (d, J = 4.8 Hz, 1H), 8.45 (s, 1H), 7.61 (dd, J = 2.64, 8.88, 1H), 7.48 (d, J = 4.8 Hz, 1H), 7.45 (d, J = 2.68 Hz, 1H), 7.37 (d, J = 8.96 Hz, 1H), 6.72-6.46 (t, J = 51.6 Hz, 1H), 4.41 (d, J = 4.64 Hz, 2H), 4.36 (d, J = 4.52 Hz, 2H) |
| 44 | 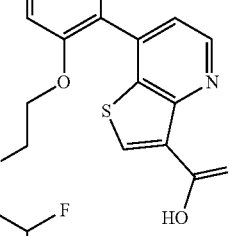 | MS (ESI) m/z 457.42 [M + 1]+; 1H NMR (400 MHz, DMSO-d6) δ 13.06 (s, 1H), 9.18 (s, 1H), 9.04 (s, 1H), 7.9-7.83 (m, 1H), 7.76 (s, 1H), 7.72 (d, J = 8.4 Hz, 1H), 7.52-7.44 (m, 3H), 7.36 (d, J = 2.2 Hz, 1H), 6.42-6.35 (m, 1H), 6.22 (d, J = 16.04 Hz, 1H), 4.82 (d, J = 4.8 Hz, 2H), 2.58 (s, 3H) |
| 45 | 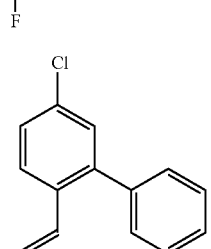 | MS (ESI) m/z 510.44 [M − 1]−; 1H NMR (400 MHz, DMSO-d6) δ 9.01 (s, 1H), 8.98 (s, 1H), 8.96 (d, J = 4.56 Hz, 1H), 8.17 (d, J = 7.52 Hz, 1H), 7.64 (s, 1H), 7.56 (dd, J = 8.92 Hz, 1H), 7.44 (d, J = 4.56 Hz, 1H), 7.30 (d, J = 2.56 Hz, 1H), 7.26 (d, J = 8.96 Hz, 1H), 7.19 (d, J = 7.6 Hz, 1H), 4.33-4.29 (m, 2H), 4.24-4.17 (m, 1H), 4.12-4.06 (m, 1H), 1.84 (s, 3H) |

TABLE 1-continued

7-Aza-Thienylpyridine and Derivative Compounds

| Compound | | Characterization |
|---|---|---|
| 48 | 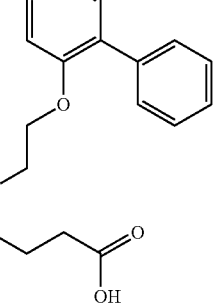 | MS (ESI) m/z 475.16 [M + 1]+; 1H NMR (400 MHz, DMSO-d6) δ 12.16 (s, 1H), 9.18 (s, 1H), 9.05 (s, 1H), 7.36 (dd, J = 8.8 Hz, 1H), 7.28 (t, 2H), 7.24-7.18 (m, 5 H), 4.57 (t, 2H), 4.33 (t, 2H), 2.87 (t, 2H) 2.57 (t, 2H) |
| 49 | 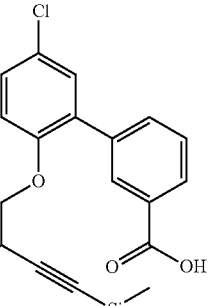 | MS (ESI) m/z 553.18 [M + 1]+; 1H NMR (400 MHz, DMSO-d6) d 12.17 (bs, 1H), 8.84 (d, J = 4.76 Hz, 1H), 8.41 (s, 1H), 7.72 (dd, J = 10.68 Hz, 7.56 Hz, 1H),7.60 (dd, J = 8.08, 2.60 Hz, 1H), 7.48 (d, J = 4.76 Hz, 1H), 7.41 (d, J = 2.52 Hz, 1H), 7.36 (d, J = 8.08 Hz, 1H), 4.39 (t, J = 4.64 Hz, 2H). 4.23 (t, J = 4.68 Hz, 2H), 1.77 (s, 3H) |
| 50 | 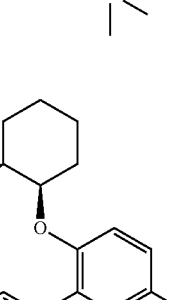 | MS (ESI) m/z 619.07 [M + 1]+; 1H NMR (400 MHz, DMSO-d6) δ 8.86 (d, J = 4.4 Hz, 1H), 8.24 (s, 1H), 8.08 (s, 1H), 7.60 (dd, J = 8.8, 2.6 Hz, 1H), 7.51 (d, J = 4.8 Hz, 1H), 7.43 (d, J = 2.6 Hz, 1H), 7.36 (d, J = 8.8 Hz, 1H), 4.41 (t, J = 4.7 Hz, 2H), 4.25 (t, J = 4.7 Hz, 2H), 1.69 (s, 3H) |
| 140 | 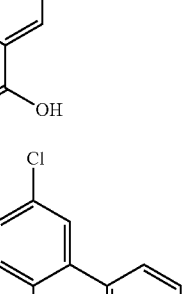 | MS (ESI) m/z 518.50 [M + 1]+; 1H NMR (400 MHz, DMSO-d6) δ 9.029 (d, J = 1.24 Hz, 2H), 8.835 (d, J = 4.76 Hz, 1H), 8.379 (s, 1H), 7.596 (dd, J = 2.6, 8.96 Hz, 1H), 7.48 (d, J = 4.72 Hz, 1H), 7.439 (d, J = 2.52 Hz, 1H), 7.35 (d, J = 9.0 Hz, 1H), 4.403 (t, J = 4.68 Hz, 2H), 4.255 (t, J = 6.04 Hz, 2H), 1.787 (s, 3H) |

TABLE 1-continued

7-Aza-Thienylpyridine and Derivative Compounds

| Compound | | Characterization |
|---|---|---|
| 147 | 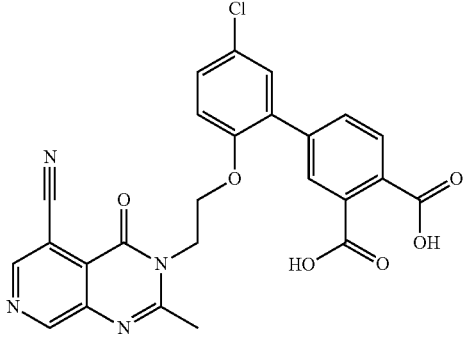 [SMILES: Cc1nc2cncc(C#N)c2c(=O)n1CCOc1ccc(Cl)cc1-c1ccc(C(=O)O)c(C(=O)O)c1] | MS (ESI) m/z 505 [M + 1]+;<br>1H NMR (400 MHz,<br>DMSO-d6) δ 9.16 (s, 1H), 9.00 (s, 1H), 8.139 (m, J = 8.04 Hz, 2H), 7.44 (m, J = 7.92 Hz, 2H), 7.28 (d, J = 2.76 Hz, 1H), 7.19 (d, J = 8.92 Hz, 1H), 4.35 (s, 4H), 2.22 (s, 3H) |
| 149 | 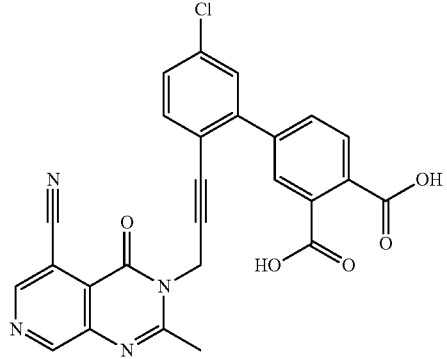 [SMILES: Cc1nc2cncc(C#N)c2c(=O)n1CC#Cc1ccc(Cl)cc1-c1ccc(C(=O)O)c(C(=O)O)c1] | MS (ESI) m/z 497.38 [M − 1]−; 1H NMR (400 MHz, DMSO-d6) δ 9.158 (s, 1H), 9.033 (s, 1H), 8.291 (s, 1H), 8.117 (d, J = 8.2 Hz, 1H), 7.63 (d, J = 8.28 Hz, 1H), 7.6 (dd, J = 1.96, 8.12 Hz, 1H), 7.53 (d, J = 1.96 Hz, 1H), 7.49 (dd, J = 2.2, 8.4 Hz, 1H), 5.05 (s, 2H), 2.35 (s, 3H) |
| 150FA | 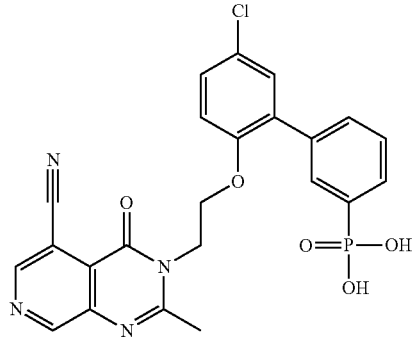 [SMILES: Cc1nc2cncc(C#N)c2c(=O)n1CCOc1ccc(Cl)cc1-c1cccc(P(=O)(O)O)c1] | MS (ESI) m/z 497 [M + 1]+;<br>1H NMR (400 MHz,<br>DMSO-d6) δ 9.20 (s, 1H), 9.03 (s, 1H), 7.68-7.63 (m, 2H), 7.47-7.38 (m, 3H), 7.23 (d, J = 2.6 Hz, 1H), 7.18 (d, J = 8.88 Hz, 1H), 4.37-4.22 (m, 4H), 2.25 (s, 3H) |
| 150FB | 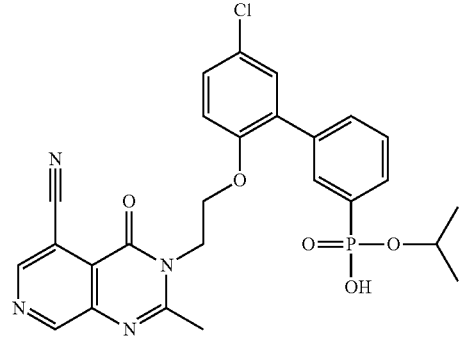 [SMILES: Cc1nc2cncc(C#N)c2c(=O)n1CCOc1ccc(Cl)cc1-c1cccc(P(=O)(O)OC(C)C)c1] | MS (ESI) m/z 539 [M + 1]+;<br>1H NMR (400 MHz,<br>DMSO-d6) δ 9.19 (s, 1H), 9.03 (s, 1H), 7.25 (d, J = 2.6 Hz, 1H), 7.19 (d, J = 8.8 Hz, 1H),7.63-7.67 (m, 2H), 7.50 (d, J = 6.5 Hz, 1H), 7.41-7.44 (m, 1H), 7.41 (dd, J = 2.8 Hz, J'= 2.6 Hz, 1H), 4.36 (s, 4H), 4.41-4.48 (m, 1H), 2.24 (s, 3H), 1.19 (d, J = 6.2 Hz, 6H) |

TABLE 1-continued

7-Aza-Thienylpyridine and Derivative Compounds

| Compound | | Characterization |
|---|---|---|
| 150FC | 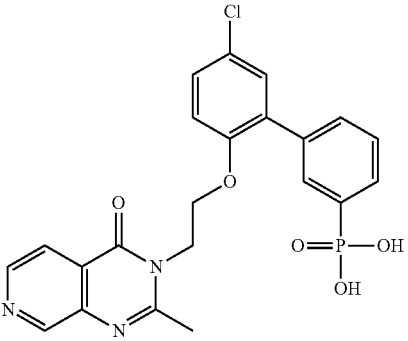 [SMILES: Cc1nc2cnccc2c(=O)n1CCOc1ccc(Cl)cc1-c1cccc(P(=O)(O)O)c1] | MS (ESI) m/z 472 [M + 1]+; 1H NMR (400 MHz, DMSO-d6) δ 8.9 (s, 1H), 8.62 (d, J = 5.2 Hz, 1H), 7.91 (d, J = 5.16 Hz, 1H), 7.63-7.72 (m, 2H), 7.40-7.44 (m, 3H), 7.24 (d, J = 2.64 Hz, 1H), 7.19 (d, J = 8.84, 1H), 4.33-4.37 (m, 4H), 2.28 (s, 3H) |
| 151 | 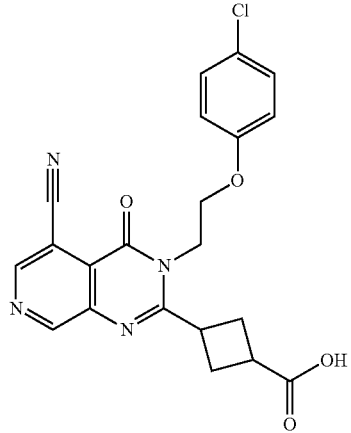 [SMILES: N#Cc1cncc2nc(C3CC(C(=O)O)C3)n(CCOc3ccc(Cl)cc3)c(=O)c12] | MS (ESI) m/z 696.11 [M + 1]+; 1H NMR (400 MHz, DMSO-d6) δ 12.69 (bs, 1H), 68.92 (d, J = 4.4 Hz, 1H), 6 8.34 (s, 1H), 6 8.09 (s, 1H), 6 7.63-7.57 (m, 2H), 67.45 (d, J = 2.0 Hz, 1H), 6 7.36 (d, J = 8.8 Hz, 1H), 6 4.42 (t, 4.8 Hz, 2H), 6 4.24 (t, J = 4.8, 2H), 6 3.56 (s, 3H), 6 1.65 (s, 3H) |
| 152 | 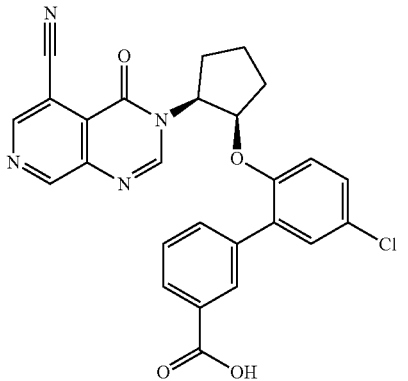 [SMILES: N#Cc1cncc2ncn([C@H]3CCC[C@H]3Oc3ccc(Cl)cc3-c3cccc(C(=O)O)c3)c(=O)c12] | MS (ESI) m/z 579.03 [M + 1]+; 1H NMR (400 MHz, DMSO-d6) δ 12.96 (b, 1H), 8.74(d, J = 4.72 Hz, 1H), 8.62 (s, 1H), 8.13 (d, J = 9.76 Hz, 1H), 7.76 (d, J = 9.76 Hz, 1H), 7.68 (t, J = 2.04 Hz, 1H), 7.53 (d, J = 4.72 Hz, 1H), 7.3 (t, J = 53.68 Hz, 1H), 4.88 (s, 2H), 2.22(s, 3H) |
| 155 | 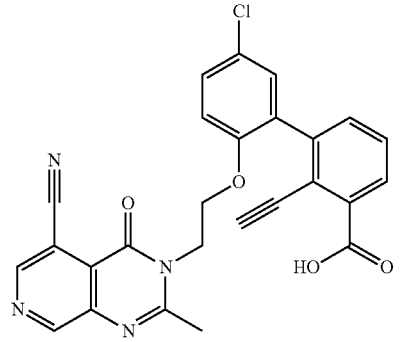 [SMILES: C#Cc1c(C(=O)O)cccc1-c1cc(Cl)ccc1OCCn1c(C)nc2cncc(C#N)c2c1=O] | MS (ESI) m/z 485.13 [M + 1]+; 1H NMR (400 MHz, DMSO-d6) δ 12.89 (bs, 1H), 9.17 (s, 1H), 9.00 (s, 1H), 7.88 (m, 1H), 7.46-7.36 (m, 3H), 7.16-7.12 (m, 2H), 4.32 (bs, 4H), 3.67 (s, 1H), 1.98 (s, 3H) |

TABLE 1-continued

7-Aza-Thienylpyridine and Derivative Compounds

| Compound | | Characterization |
|---|---|---|
| 157 | 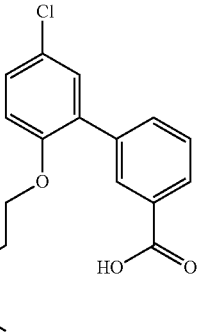 | MS (ESI) m/z 511.48 [M + 1]+; 1H NMR (400 MHz, DMSO-d6) δ 12.87 (s, 1H), 9.23 (s, 1H), 7.88-7.86 (dd, J = 1.28, J = 6.8 Hz, 1H), 7.80 (d, J = 1.6 Hz, 1H), 7.53 (d, J = 7.6 Hz, 1H), 7.45-7.17 (m, 5H), 4.36 (s, 4H), 2.19 (s, 3H) |
| 183 | 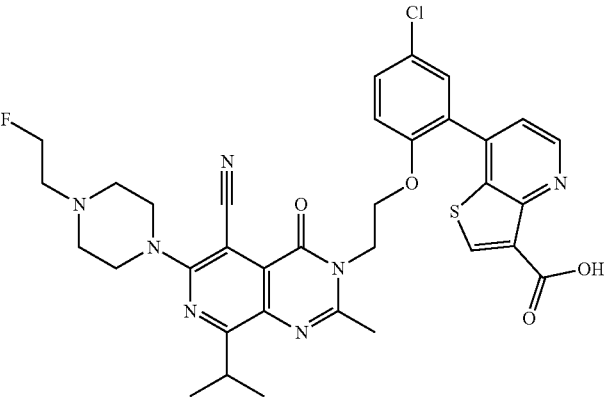 [SMILES: Cc1nc2c(C(C)C)nc(N3CCN(CCF)CC3)c(C#N)c2c(=O)n1CCOc1ccc(Cl)cc1-c1ccnc2c(C(=O)O)csc12] | MS (ESI) m/z 690.4 [M + 1]+; 1H NMR (400 MHz, DMSO-d6) δ 10.15 (s, 1H), 8.79 (d, J = 4.8 Hz, 1H), 8.59 (s, 1H), 7.60 (dd, J = 8.9, 2.7 Hz, 1H), 7.46 (d, J = 4.8 Hz, 1H), 7.44 (d, J = 2.6 Hz, 1H), 7.38 (d, J = 9.0 Hz, 1H), 4.89 (dt, J = 47.1, 4.7 Hz, 2H), 4.44-4.33 (m, 3H), 4.23 (t, J = 5.1 Hz, 2H), 3.93 (hept, J = 6.8 Hz, 1H), 3.79-3.52 (m, 7H), 1.87 (s, 3H), 1.25 (d, J = 6.8 Hz, 6H) |
| 184 | 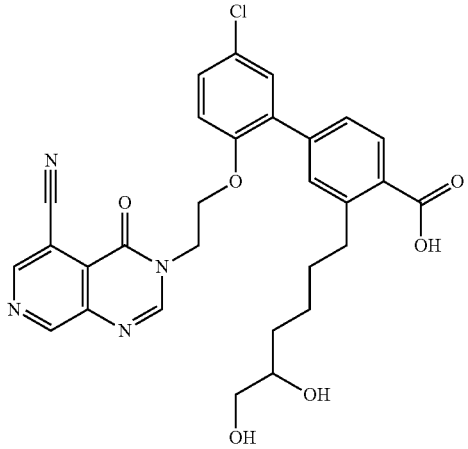 [SMILES: N#Cc1cncc2ncn(CCOc3ccc(Cl)cc3-c3ccc(C(=O)O)c(CCCCC(O)CO)c3)c(=O)c12] | MS (ESI) m/z 561.16 [M + 1]+; 1H NMR (400 MHz, DMSO-d6) δ 9.26 (s, 1H), 9.08 (s, 1H), 8.32 (s, 1H), 7.63 (d, J = 8.4 Hz, 1H), 7.39-7.16 (m, 5H), 4.34 (d, J = 3.6 Hz, 6H), 3.25-3.18 (m, 3H), 2.89 (s, 2H), 1.42 (d, J = 15 Hz, 4H), 1.27-1.18 (m, 2H) |
| 260 | 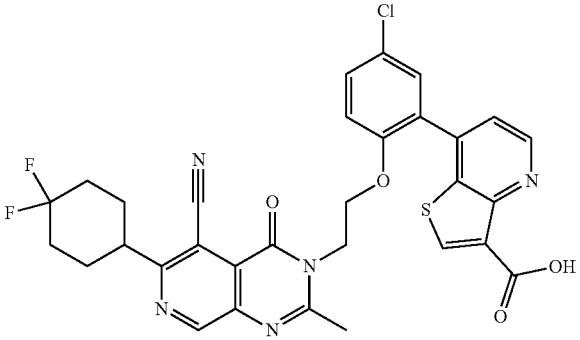 [SMILES: Cc1nc2cnc(C3CCC(F)(F)CC3)c(C#N)c2c(=O)n1CCOc1ccc(Cl)cc1-c1ccnc2c(C(=O)O)csc12] | MS (ESI) m/z 636.1 [M + 1]+; 1H NMR (400 MHz, DMSO-d6) δ 8.99 (s, 1H), 8.82 (d, J = 4.9 Hz, 1H), 8.40 (s, 1H), 7.60 (dd, J = 8.9, 2.7 Hz, 1H), 7.48 (d, J = 4.8 Hz, 1H), 7.44 (d, J = 2.7 Hz, 1H), 7.36 (d, J = 9.0 Hz, 1H), 4.40 (t, J = 5.0 Hz, 2H), 4.25 (t, J = 5.0 Hz, 2H), 3.50-3.41 (m, 1H), 2.24-1.94 (m, 8H), 1.83 (s, 3H) |

TABLE 1-continued

7-Aza-Thienylpyridine and Derivative Compounds

| Compound | | Characterization |
|---|---|---|
| 284 | 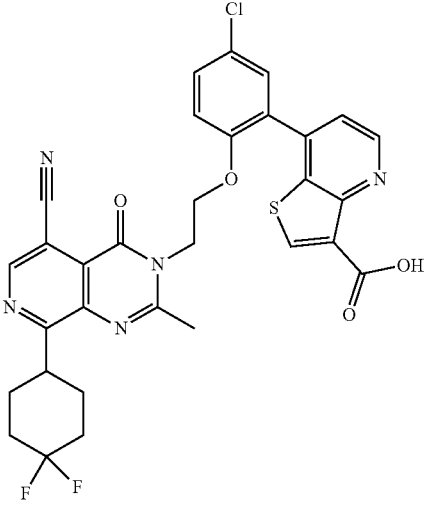 [SMILES: Cc1nc2c(C3CCC(F)(F)CC3)ncc(C#N)c2c(=O)n1CCOc1ccc(Cl)cc1-c1ccnc2c(C(=O)O)csc12] | MS (ESI) m/z 636.1 [M + 1]+; 1H NMR (400 MHz, DMSO-d6) δ 8.94 (s, 1H), 8.80 (d, J = 4.8 Hz, 1H), 8.60 (s, 1H), 7.59 (dd, J = 8.9, 2.7 Hz, 1H), 7.49 (d, J = 4.8 Hz, 1H), 7.45 (d, J = 2.7 Hz, 1H), 7.36 (d, J = 9.0 Hz, 1H), 4.42 (t, J = 4.9 Hz, 2H), 4.25 (t, J = 4.9 Hz, 2H), 3.94-3.82 (m, 1H), 2.23-1.94 (m, 6H), 1.86 (td, J = 12.7, 12.1, 4.2 Hz, 2H), 1.80 (s, 3H) |
| 338 | 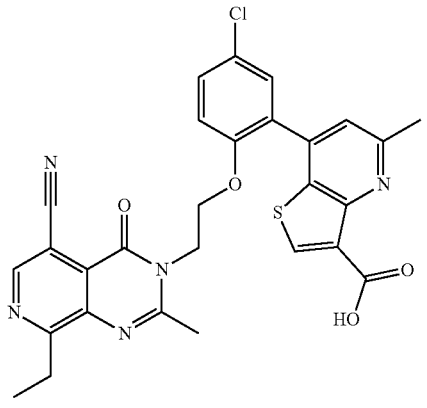 [SMILES: CCc1ncc(C#N)c2c(=O)n(CCOc3ccc(Cl)cc3-c3cc(C)nc4c(C(=O)O)csc34)c(C)nc12] | MS (ESI) m/z 560.1 [M + 1]+; 1H-NMR (400 MHz, d6-DMSO) d/ppm = 8.89 (s, 1H), 8.49 (s, 1H), 7.59 (dd, J = 8.9, 2.6 Hz, 1H), 7.43-7.41 (m, 2H), 7.36 (d, J = 8.9 Hz, 1H), 4.43 (t, J = 4.8 Hz, 2H), 4.26 (t, J = 4.8 Hz, 2H), 3.19 (q, J = 7.5 Hz, 2H), 2.69 (s, 3H), 1.93 (s, 3H), 1.27 (t, J = 7.5 Hz, 3H) |
| 339 | 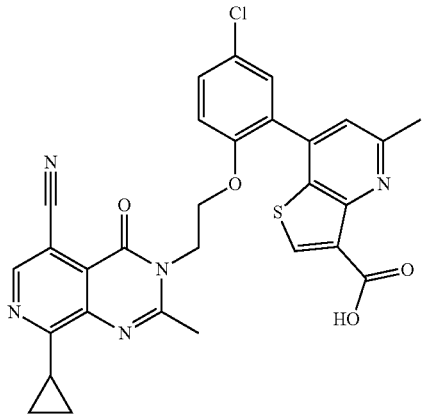 [SMILES: Cc1cc(-c2cc(Cl)ccc2OCCn2c(C)nc3c(C4CC4)ncc(C#N)c3c2=O)c2scc(C(=O)O)c2n1] | MS (ESI) m/z 572.1; 1H-NMR (400 MHz, d6-DMSO) d/ppm = 8.77 (s, 1H), 8.59 (s, 1H), 7.59 (dd, J = 8.9, 2.6 Hz, 1H), 7.42 (d, J = 2.6 Hz, 1H), 7.41 (s, 1H), 7.36 (d, J = 8.9 Hz, 1H), 4.42 (t, J = 5.0 Hz, 2H), 4.27 (t, J = 5.0 Hz, 2H), 3.21-3.11 (m, 1H), 2.68 (s, 3H), 1.92 (s, 3H), 1.33-1.26 (m, 1H), 1.21-1.15 (m, 1H) |

TABLE 1-continued

7-Aza-Thienylpyridine and Derivative Compounds

| Compound | | Characterization |
|---|---|---|
| 340 | 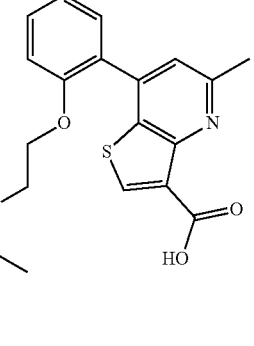 | MS (ESI) m/z 600.2 [M + 1]+; 1H-NMR (400 MHz, d6-DMSO) d/ppm = 9.11 (s, 1H), 8.63 (s, 1H), 7.60 (dd, J = 8.9, 2.7 Hz, 1H), 7.46-7.44 (m, 2H), 7.36 (d, J = 8.9 Hz, 1H), 4.44 (t, J = 4.9 Hz, 2H), 4.30 (t, J = 4.9 Hz, 2H), 2.70 (s, 3H), 2.05 (s, 3H) |
| 365 | 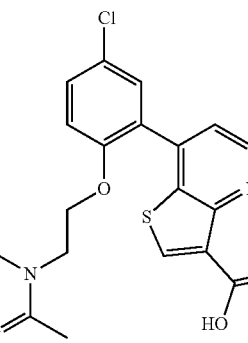 | MS (ESI) m/z 603.3 [M + 1]+; 1H NMR (400 MHz, DMSO-d6) δ 9.58 (s, 1H), 8.96 (s, 1H), 8.34 (s, 1H), 7.60 (dd, J = 8.9, 2.7 Hz, 1H), 7.42 (s, 1H), 7.41 (d, J = 2.7 Hz, 1H), 7.36 (d, J = 9.0 Hz, 1H), 4.41 (t, J = 5.0 Hz, 2H), 4.28 (t, J = 5.1 Hz, 2H), 3.69-3.61 (m, 2H), 3.58-3.50 (m, 2H), 2.93 (s, 3H), 2.92 (s, 3H), 2.72 (s, 3H), 1.92 (s, 3H) |
| 372 | 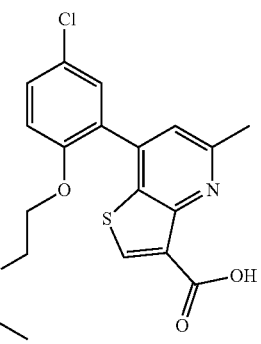 | MS (ESI) m/z 582.2 [M + 1]+; 1H NMR (400 MHz, DMSO-d6) δ 9.12 (s, 1H), 8.59 (s, 1H), 7.59 (dd, J = 8.9, 2.7 Hz, 1H), 7.52 (t, J = 53.5 Hz, 1H), 7.44 (d, J = 2.6 Hz, 1H), 7.40 (s, 1H), 7.35 (d, J = 9.0 Hz, 1H), 4.42 (t, J = 5.0 Hz, 2H), 4.27 (t, J = 5.0 Hz, 2H), 2.66 (s, 3H), 1.90 (s, 3H) |
| 384 | 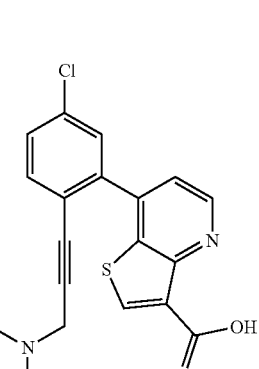 | MS (ESI) m/z 552.1 [M + 1]+; 1H NMR (400 MHz, DMSO-d6) δ 8.99 (s, 1H), 8.75 (d, J = 4.8 Hz, 1H), 8.62 (s, 1H), 7.80-7.73 (m, 1H), 7.72-7.65 (m, 2H), 7.55 (d, J = 4.8 Hz, 1H), 4.86 (s, 2H), 2.67-2.61 (m, 1H), 2.09 (s, 3H), 1.29-1.15 (m, 4H) |

TABLE 1-continued

7-Aza-Thienylpyridine and Derivative Compounds

| Compound | | Characterization |
|---|---|---|
| 385 | 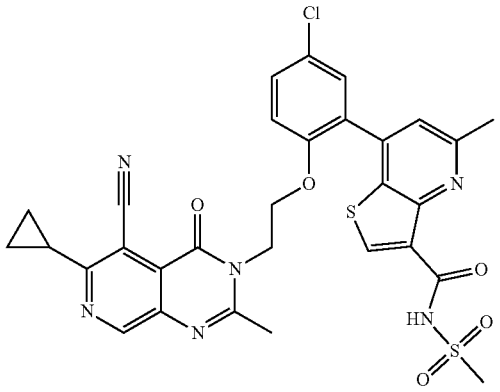 [SMILES: Cc1cc(-c2cc(Cl)ccc2OCCn2c(C)nc3cnc(C4CC4)c(C#N)c3c2=O)c2scc(C(=O)NS(C)(=O)=O)c2n1] | MS (ESI) m/z 649.1 [M + 1]+; 1H NMR (400 MHz, DMSO-d6) δ 12.91 (s, 1H), 8.84 (s, 1H), 8.56 (s, 1H), 7.60 (dd, J = 8.9, 2.7 Hz, 1H), 7.43 (s, 1H), 7.40 (d, J = 2.7 Hz, 1H), 7.37 (d, J = 9.0 Hz, 1H), 4.41 (t, J = 5.1 Hz, 2H), 4.25 (t, J = 5.1 Hz, 2H), 3.57 (s, 3H), 2.68 (s, 3H), 2.61 (tt, J = 7.6, 4.9 Hz, 1H), 1.87 (s, 3H), 1.31-1.13 (m, 4H) |
| 400 | 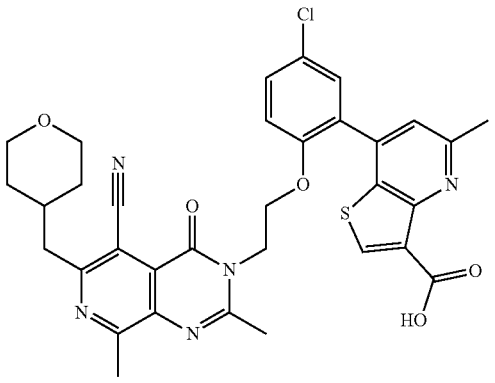 [SMILES: Cc1cc(-c2cc(Cl)ccc2OCCn2c(C)nc3c(C)nc(CC4CCOCC4)c(C#N)c3c2=O)c2scc(C(=O)O)c2n1] | MS (ESI) m/z 644.5 [M + 1]+; 1H NMR (400 MHz, DMSO-d6) δ 8.47 (s, 1H), 7.59 (dd, J = 8.9, 2.6 Hz, 1H), 7.44-7.38 (m, 2H), 7.37 (d, J = 9.0 Hz, 1H), 4.42 (t, J = 5.0 Hz, 2H), 4.25 (t, J = 5.0 Hz, 2H), 3.87-3.78 (m, 2H), 3.26 (td, J = 11.7, 2.1 Hz, 2H), 2.96 (d, J = 7.1 Hz, 2H), 2.73 (s, 3H), 2.69 (s, 3H), 2.15-2.02 (m, 1H), 1.92 (s, 3H), 1.56-1.47 (m, 2H), 1.33 (qd, J = 12.0, 4.4 Hz, 2H) |
| 418 | 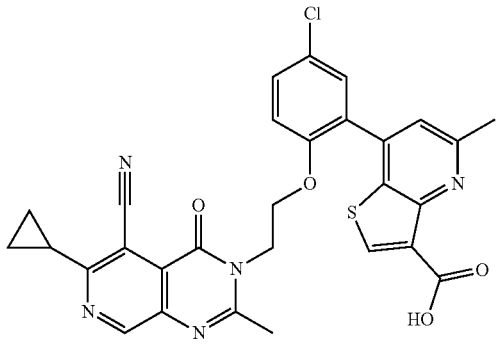 [SMILES: Cc1cc(-c2cc(Cl)ccc2OCCn2c(C)nc3cnc(C4CC4)c(C#N)c3c2=O)c2scc(C(=O)O)c2n1] | MS (ESI) m/z 572.5 [M + 1]+; 1H NMR (400 MHz, DMSO-d6) δ 8.84 (s, 1H), 8.42 (s, 1H), 7.59 (dd, J = 8.8, 2.6 Hz, 1H), 7.42 (s, 1H), 7.41 (d, J = 2.6 Hz, 1H), 7.36 (d, J = 9.0 Hz, 1H), 4.40 (t, J = 5.0 Hz, 2H), 4.25 (t, J = 5.0 Hz, 2H), 2.70 (s, 3H), 2.65-2.56 (m, 1H), 1.86 (s, 3H), 1.27-1.14 (m, 4H) |
| 419 | 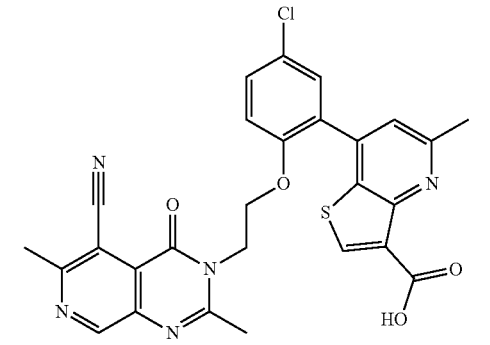 | MS (ESI) m/z 546.7 [M + 1]+; 1H NMR (400 MHz, DMSO-d6) δ 8.89 (s, 1H), 8.38 (s, 1H), 7.59 (dd, J = 8.9, 2.7 Hz, 1H), 7.42 (s, 1H), 7.41 (d, J = 2.6 Hz, 1H), 7.35 (d, J = 8.9 Hz, 1H), 4.40 (t, J = 5.0 Hz, 2H), 4.25 (t, J = 5.0 Hz, 2H), 2.79 (s, 3H), 2.71 (s, 3H), 1.88 (s, 3H) |

TABLE 1-continued

7-Aza-Thienylpyridine and Derivative Compounds

| Compound | Characterization |
|---|---|
| 420 | MS (ESI) m/z 588.1 [M + 1]+; 1H NMR (400 MHz, DMSO-d6) δ 8.92 (s, 1H), 8.46 (s, 1H), 7.59 (dd, J = 8.9, 2.7 Hz, 1H), 7.43 (s, 1H), 7.42 (d, J = 2.5 Hz, 1H), 7.36 (d, J = 9.0 Hz, 1H), 4.39 (t, J = 5.1 Hz, 2H), 4.24 (t, J = 5.1 Hz, 2H), 2.71 (s, 3H), 1.86 (s, 3H), 1.58 (s, 9H) |
| 432 | MS (ESI) m/z 574.6 [M + 1]+; 1H NMR (400 MHz, DMSO-d6) δ 8.98 (s, 1H), 8.42 (s, 1H), 7.59 (dd, J = 8.9, 2.6 Hz, 1H), 7.42 (d, J = 2.6 Hz, 1H), 7.42 (s, 1H), 7.35 (d, J = 9.0 Hz, 1H), 4.39 (t, J = 4.9 Hz, 2H), 4.25 (t, J = 5.0 Hz, 2H), 3.64 (hept, J = 6.8 Hz, 1H), 2.70 (s, 3H), 1.87 (s, 3H), 1.33 (d, J = 6.7 Hz, 6H) |
| 435 | MS (ESI) m/z 587.6 [M + 1]+; 1H NMR (400 MHz, DMSO-d6) δ 8.52-8.47 (m, 2H), 7.56 (dd, J = 8.9, 2.7 Hz, 1H), 7.40-7.35 (m, 2H), 7.31 (d, J = 9.0 Hz, 1H), 4.37-4.29 (m, 6H), 4.16 (t, J = 5.1 Hz, 3H), 2.68 (s, 3H), 2.40-2.28 (m, 2H), 1.79 (s, 3H) |
| 441 | MS (ESI) m/z 655.5 [M + 1]+; 1H NMR (400 MHz, DMSO-d6) δ 8.65 (d, J = 2.7 Hz, 1H), 8.48 (s, 1H), 8.06 (dd, J = 9.1, 2.8 Hz, 1H), 7.60 (dd, J = 8.9, 2.7 Hz, 1H), 7.49-7.34 (m, 3H), 4.46 (t, J = 5.0 Hz, 2H), 4.30 (t, J = 5.1 Hz, 2H), 2.79 (s, 3H), 2.72 (s, 3H), 2.35 (s, 3H), 2.00 (s, 3H) |

TABLE 1-continued
7-Aza-Thienylpyridine and Derivative Compounds
| Compound | | Characterization |
|---|---|---|
| 448 | 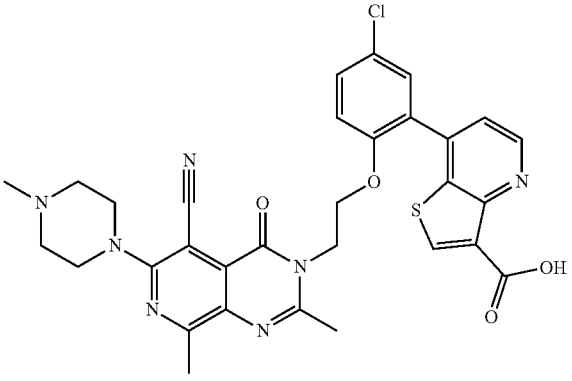 [SMILES: Cc1nc(N2CCN(C)CC2)c(C#N)c2c(=O)n(CCOc3ccc(Cl)cc3-c3ccnc4c(C(=O)O)csc34)c(C)nc12] | MS (ESI) m/z 630.2 [M + 1]+; 1H NMR (400 MHz, DMSO-d6) δ 9.89 (s, 1H), 8.82 (d, J = 4.8 Hz, 1H), 8.48 (s, 1H), 7.61 (dd, J = 9.0, 2.7 Hz, 1H), 7.47 (d, J = 4.8 Hz, 1H), 7.41-7.37 (m, 2H), 4.43 (t, J = 5.1 Hz, 2H), 4.33 (d, J = 14.1 Hz, 2H), 4.24 (t, J = 5.1 Hz, 2H), 3.60 (d, J = 11.9 Hz, 2H), 3.33-3.19 (m, 2H), 2.91 (d, J = 3.1 Hz, 3H), 2.66 (s, 3H), 1.89 (s, 3H) |
| 450 | 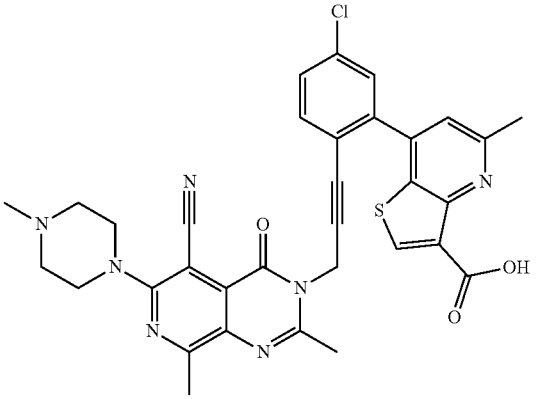 | MS (ESI) m/z 638.1 [M + 1]+; 1H NMR (400 MHz, DMSO-d6) δ 9.86 (s, 1H), 8.64 (s, 1H), 7.75 (d, J = 8.4 Hz, 1H), 7.69 (dd, J = 8.4, 2.2 Hz, 1H), 7.63 (d, J = 2.1 Hz, 1H), 7.46 (s, 1H), 4.81 (s, 2H), 4.35 (d, J = 14.1 Hz, 2H), 3.62 (d, J = 12.0 Hz, 2H), 3.48-3.23 (m, 6H), 2.92 (d, J = 3.5 Hz, 3H), 2.74 (s, 3H), 2.66 (s, 3H), 2.17 (s, 3H) |
| 459 | 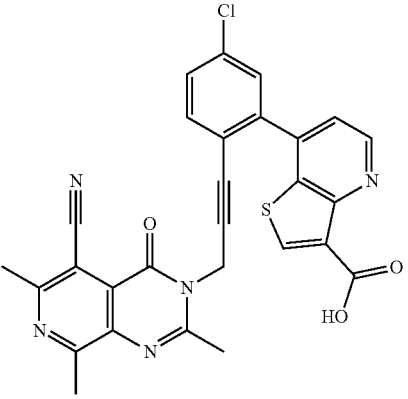 | MS (ESI) m/z 560.1 [M + 1]+; 1H NMR (400 MHz, DMSO-d6) δ 8.73 (d, J = 4.8 Hz, 1H), 8.63 (s, 1H), 7.76 (d, J = 8.2 Hz, 1H), 7.72-7.63 (m, 2H), 7.53 (d, J = 4.8 Hz, 1H), 4.85 (s, 2H), 2.78 (d, J = 10.6 Hz, 6H), 2.15 (s, 3H) |

TABLE 1-continued
7-Aza-Thienylpyridine and Derivative Compounds
| Compound | | Characterization |
|---|---|---|
| 474 | 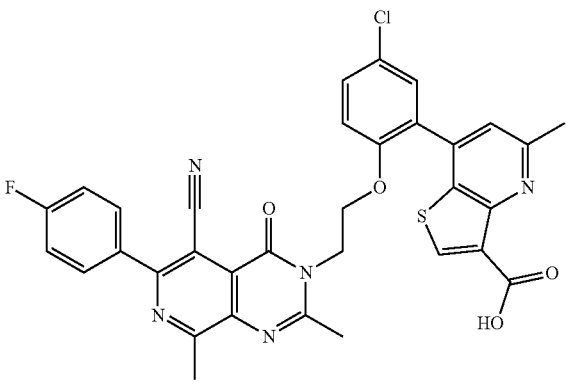 [SMILES: Cc1cc(-c2cc(Cl)ccc2OCCn2c(C)nc3c(C)nc(-c4ccc(F)cc4)c(C#N)c3c2=O)c2scc(C(=O)O)c2n1] | LCMS: 640.2 [M + H]+; 1H NMR (400 MHz, DMSO-d6) δ 8.50 (s, 1H), 7.99-7.89 (m, 2H), 7.60 (dd, J = 8.9, 2.7 Hz, 1H), 7.48-7.31 (m, 5H), 4.45 (t, J = 5.0 Hz, 2H), 4.28 (t, J = 5.1 Hz, 2H), 2.79 (s, 3H), 2.71 (s, 3H), 1.97 (s, 3H) |
| 475 | 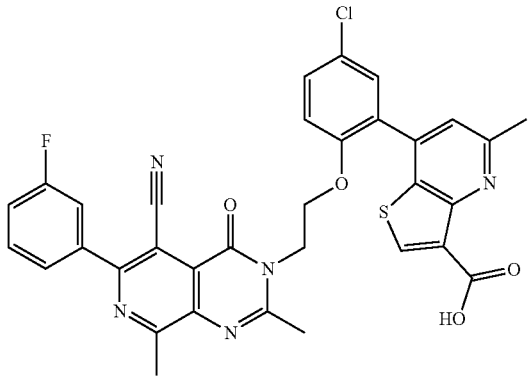 [SMILES: Cc1cc(-c2cc(Cl)ccc2OCCn2c(C)nc3c(C)nc(-c4cccc(F)c4)c(C#N)c3c2=O)c2scc(C(=O)O)c2n1] | LCMS: 640.2 [M + H]+; 1H NMR (400 MHz, DMSO-d6) δ 8.48 (s, 1H), 7.79-7.68 (m, 2H), 7.66-7.57 (m, 2H), 7.45-7.34 (m, 4H), 4.45 (t, J = 5.1 Hz, 2H), 4.29 (t, J = 5.0 Hz, 2H), 2.80 (s, 3H), 2.71 (s, 3H), 1.99 (s, 3H) |
| 476 | 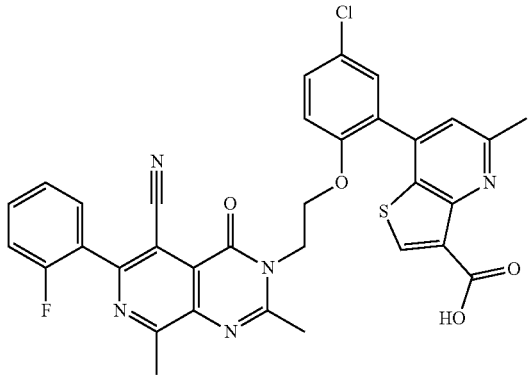 | LCMS: 640.2 [M + H]+; 1H NMR (400 MHz, DMSO-d6) δ 8.57 (s, 1H), 7.72 (td, J = 7.7, 1.9 Hz, 1H), 7.67-7.57 (m, 2H), 7.47-7.34 (m, 5H), 4.44 (t, J = 5.0 Hz, 2H), 4.28 (t, J = 5.0 Hz, 2H), 2.80 (s, 3H), 2.71 (s, 3H), 1.96 (s, 3H) |
| 477 | 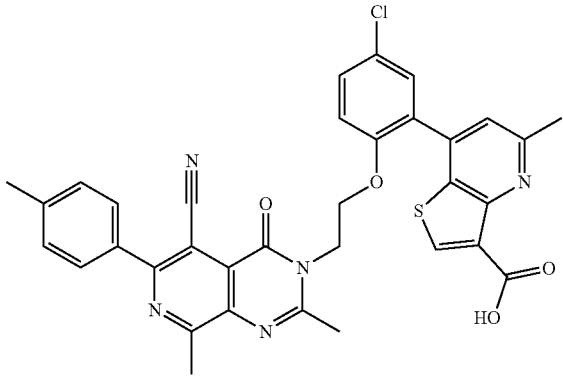 | LCMS: 636.7 [M + H]+; 1H NMR (400 MHz, DMSO-d6) δ 8.52 (s, 1H), 7.81-7.75 (m, 2H), 7.60 (dd, J = 8.9, 2.7 Hz, 1H), 7.46-7.32 (m, 5H), 4.45 (t, J = 5.0 Hz, 2H), 4.28 (t, J = 5.1 Hz, 2H), 2.78 (d, J = 0.7 Hz, 3H), 2.71 (s, 3H), 2.42 (s, 3H), 1.94 (s, 3H) |

TABLE 1-continued

7-Aza-Thienylpyridine and Derivative Compounds

| Compound | | Characterization |
|---|---|---|
| 478 | 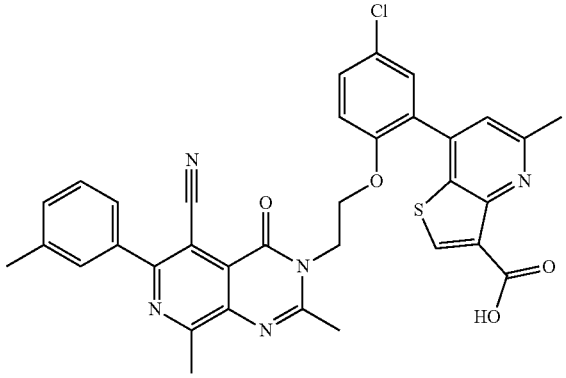 | LCMS: 636.8 [M + H]+; 1H NMR (400 MHz, DMSO-d6) δ 8.50 (s, 1H), 7.70-7.63 (m, 2H), 7.60 (dd, J = 8.9, 2.7 Hz, 1H), 7.48-7.33 (m, 5H), 4.45 (t, J = 5.0 Hz, 2H), 4.28 (t, J = 5.0 Hz, 2H), 2.79 (s, 3H), 2.71 (s, 3H), 2.43 (s, 3H), 1.94 (s, 3H) |
| 479 | 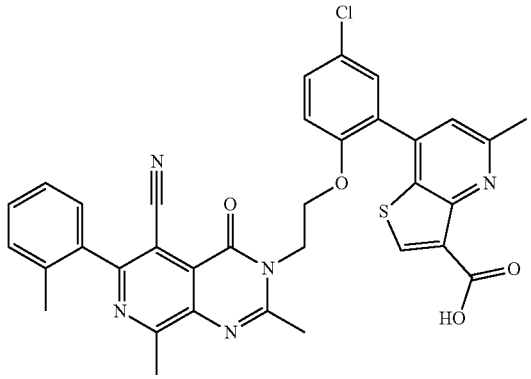 [SMILES: Cc1cc(-c2cc(Cl)ccc2OCCn2c(C)nc3c(C)nc(-c4ccccc4C)c(C#N)c3c2=O)c2scc(C(=O)O)c2n1] | LCMS: 636.8 [M + H]+; 1H NMR (400 MHz, DMSO-d6) δ 8.52 (s, 1H), 7.60 (dd, J = 8.9, 2.7 Hz, 1H), 7.44 (dq, J = 3.9, 2.0 Hz, 4H), 7.42-7.31 (m, 3H), 4.44 (t, J = 5.0 Hz, 2H), 4.28 (d, J = 4.9 Hz, 2H), 2.77 (s, 3H), 2.71 (s, 3H), 2.18 (s, 3H), 1.90 (s, 3H) |
| 480 | 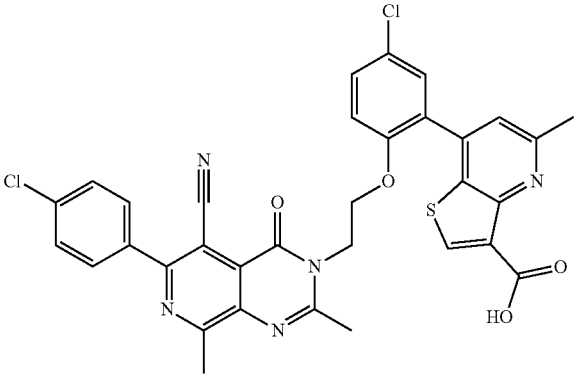 [SMILES: Cc1cc(-c2cc(Cl)ccc2OCCn2c(C)nc3c(C)nc(-c4ccc(Cl)cc4)c(C#N)c3c2=O)c2scc(C(=O)O)c2n1] | LCMS: 656.4 [M + H]+; 1H NMR (400 MHz, DMSO-d6) δ 8.49 (s, 1H), 7.92 (d, J = 2.1 Hz, 1H), 7.91 (d, J = 2.1 Hz, 1H), 7.68-7.63 (m, 2H), 7.60 (dd, J = 8.9, 2.7 Hz, 1H), 7.45-7.36 (m, 3H), 4.45 (t, J = 5.0 Hz, 2H), 4.29 (t, J = 4.9 Hz, 2H), 2.79 (s, 3H), 2.70 (s, 3H), 1.97 (s, 3H) |
| 481 | 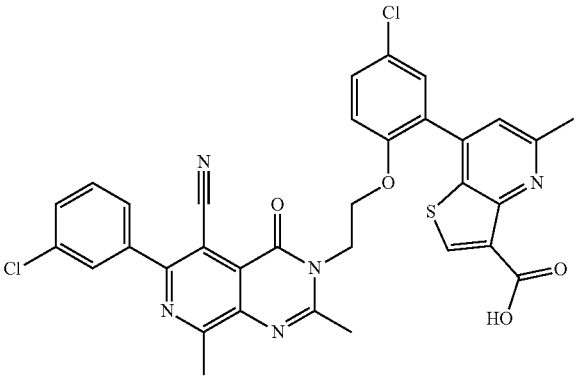 [SMILES: Cc1cc(-c2cc(Cl)ccc2OCCn2c(C)nc3c(C)nc(-c4cccc(Cl)c4)c(C#N)c3c2=O)c2scc(C(=O)O)c2n1] | LCMS: 656.6 [M + H]+; 1H NMR (400 MHz, DMSO-d6) δ 8.46 (s, 1H), 7.94 (td, J = 1.9, 0.6 Hz, 1H), 7.85 (dt, J = 7.1, 1.7 Hz, 1H), 7.67-7.57 (m, 3H), 7.45-7.36 (m, 3H), 4.46 (t, J = 5.1 Hz, 2H), 4.29 (t, J = 5.0 Hz, 2H), 2.79 (s, 3H), 2.72 (s, 3H), 1.99 (s, 3H) |

TABLE 1-continued

7-Aza-Thienylpyridine and Derivative Compounds

| Compound | | Characterization |
|---|---|---|
| 482 | 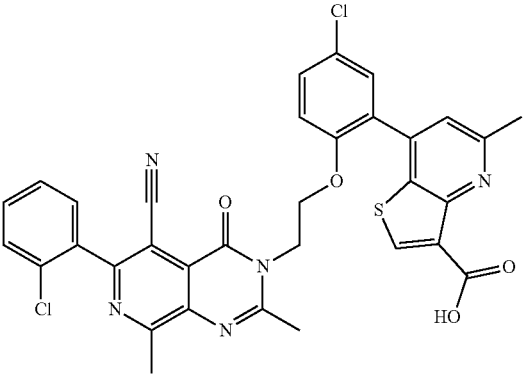 | LCMS: 656.7 [M + H]+; 1H NMR (400 MHz, DMSO-d6) δ 8.54 (s, 1H), 7.70-7.63 (m, 2H), 7.62-7.52 (m, 3H), 7.46-7.41 (m, 2H), 7.38 (d, J = 9.0 Hz, 1H), 4.44 (t, J = 5.0 Hz, 2H), 4.28 (s, 2H), 2.79 (s, 3H), 2.71 (s, 3H), 1.94 (s, 3H) |
| 491 | 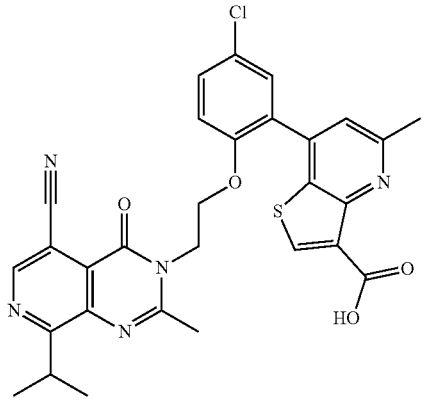 [SMILES: Cc1cc(-c2cc(Cl)ccc2OCCn2c(C)nc3c(C(C)C)ncc(C#N)c3c2=O)c2scc(C(=O)O)c2n1] | MS (ESI) m/z 574.5 [M + 1]+; 1H NMR (400 MHz, DMSO-d6) δ 8.92 (s, 1H), 8.59 (s, 1H), 7.59 (dd, J = 8.9, 2.7 Hz, 1H), 7.50-7.41 (m, 2H), 7.35 (d, J = 9.0 Hz, 1H), 4.42 (t, J = 5.0 Hz, 2H), 4.26 (t, J = 5.1 Hz, 2H), 4.12-4.00 N (m, 1H), 2.68 (s, 3H), 1.94 (s, 3H), 1.26 (d, J = 6.8 Hz, 6H) |
| 492 | 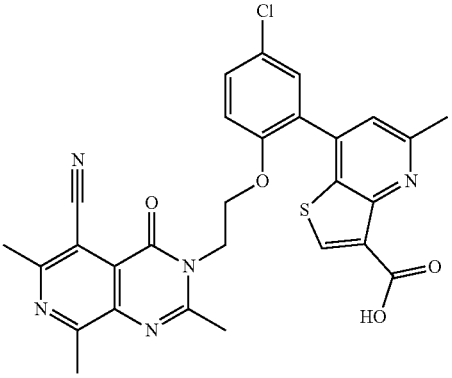 | MS (ESI) m/z 560.1 [M + 1]+; 1H NMR (400 MHz, DMSO-d6) δ 8.48 (s, 1H), 7.59 (dd, J = 8.9, 2.7 Hz, 1H), 7.42-7.35 (m, 4H), 4.43 (t, J = 5.1 Hz, 2H), 4.26 (t, J = 5.1 Hz, 2H), 2.72 (d, J = 3.2 Hz, 6H), 2.70 (s, 3H), 1.96 (s, 3H) |
| 597 | 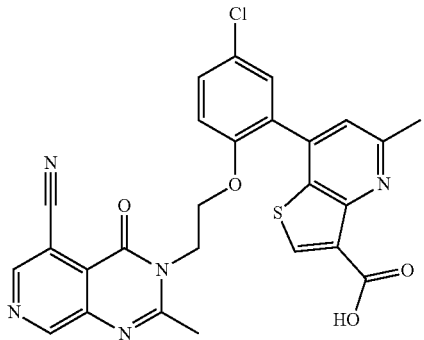 [SMILES: Cc1cc(-c2cc(Cl)ccc2OCCn2c(C)nc3cncc(C#N)c3c2=O)c2scc(C(=O)O)c2n1] | MS (ESI) m/z 532.14 [M + 1]+; 1H NMR (400 MHz, DMSO-d6) δ 9.0 (d, J = 5.6 Hz, 1H), 8.38 (s, 1H), 7.59 (dd, J = 8.8, 2.5 Hz, 1H), 7.41 (d, J = 2.1 Hz, 2H), 7.35 (d, J = 9.0 Hz, 1H), 4.4 (t, J = 4.2 Hz, 2H), 4.26 (t, J = 4.8 Hz, 2H), 2.7 (s, 3H), 1.85 (s, 3H) |

TABLE 1-continued

7-Aza-Thienylpyridine and Derivative Compounds

| Compound | Characterization |
|---|---|
| 600 | MS (ESI) m/z 609.11 [M + 1; 1H NMR (400 MHz, DMSO-d6) δ 12.94 (s, 1H), 9.01 (d, J = 5.44, 1H), 8.51 (s, 1H), 7.62-7.56 (m, 1H), 7.49-7.31 (m, 3H), 4.41 (s, 2H), 4.26 (s, 2H), 3.58 (s, 3H), 2.69 (s, 3H), 1.91 (s, 3H) |
| 601 | MS (ESI) m/z 526.12 [M + 1]+; 1H NMR (400 MHz, DMSO-d6) δ 9.14 (s, 1H), 9.08 (s, 1H), 8.61 (s, 1H), 7.75 (d, J = 8.2 Hz, 1H), 7.69-7.66 (m, 2H), 7.46 (s, 1H), 4.87 (s, 2H), 2.61 (s, 3H), 2.16 (s, 3H) |
| 602 | MS (ESI) m/z 598.13 [M + 1]+; 1H NMR (400 MHz, DMSO-d6) δ 8.78 (s, 1H), 8.40 (s, 1H), 7.85 (t, J = 72.0 Hz, 1H), 7.59 (d, J = 8.92 Hz, 1H), 7.42 (bs, 2H), 7.35 (d, J = 8.96 Hz, 1H), 4.40 (t, J = 5.12 Hz, 2H), 4.25 (t, J = 4.44 Hz, 2H), 2.71 (s, 3H), 1.82 (s, 3H) |
| 603 | MS (ESI) m/z 642.4 [M + 1]+; 1H NMR (400 MHz, DMSO-d6) δ 10.85 (s, 1H), 8.82 (d, J = 4.8 Hz, 1H), 8.53 (s, 1H), 7.60 (dd, J = 8.9, 2.7 Hz, 1H), 7.47 (d, J = 4.8 Hz, 1H), 7.42 (d, J = 2.7 Hz 1H), 7.39 (d, J = 9.0 Hz 1H), 4.55-4.38 (m, 3H), 4.30-4.15 (m, 2H), 3.66-3.44 (m, 4H), 3.27-3.12 (m, 1H), 3.05-2.83 (m, 4H), 2.64 (s, 3H), 1.85 (s, 3H), 1.44-1.22 (m, 2H) |

TABLE 1-continued

7-Aza-Thienylpyridine and Derivative Compounds

| Compound | | Characterization |
|---|---|---|
| 604 | | MS (ESI) m/z 598.18 [M + 1]+; 1H-NMR (400 MHz, DMSO-d6) δ 8.66 (s ,1H), 8.54 (s, 1H), 7.82 (t, J = 71.4 Hz, 1H), 7.60 (dd, J = 2.52, 8.84 Hz, 1H), 7.42 (d, J = 2.5 Hz, 1H), 7.40 (s, 1H), 7.36 (d, J = 8.8 Hz, 1H), 4.42 (t, J = 5.46 Hz, 2H), 4.29 (t, J = 5.46 Hz, 2H), 2.71 (s, 3H), 2.01 (s, 3H) |
| 624 | | MS (ESI) m/z 512.02 [M + 1]+; 1H NMR (400 MHz, DMSO-d6) δ 9.15 (s, 1H), 9.06 (s, 1H), 8.74 (d, J = 4.76 Hz, 1H), 8.61 (s, 1H), 7.76 (d, J = 8.96, 1H), 7.70-7.65 (m, 2H), 7.54 (d, J = 4.76, 1H), 4.87 (s, 2H), 2.13 (s, 3H) |
| 656 | | MS (ESI) m/z 636.2 [M + 1]+; 1H NMR (400 MHz, DMSO-d6) δ 10.83 (s, OH), 8.78 (d, J = 4.8 Hz, 1H), 8.67 (s, 1H), 7.76 (d, J = 8.3 Hz, 1H), 7.69 (dd, J = 8.3, 2.2 Hz, 1H), 7.66 (d, J = 2.1 Hz, 1H), 7.54 (d, J = 4.8 Hz, 1H), 4.91-4.76 (m, 2H), 4.57 (d, J = 14.5 Hz, 1H), 3.73-3.12 (m, 4H), 3.08-2.87 (m, 4H), 2.71 (s, 3H), 2.10 (s, 3H), 1.51 (s, 1H), 1.41-1.29 (m, 1H) |

TABLE 1-continued

7-Aza-Thienylpyridine and Derivative Compounds

| Compound | | Characterization |
|---|---|---|
| 673 | 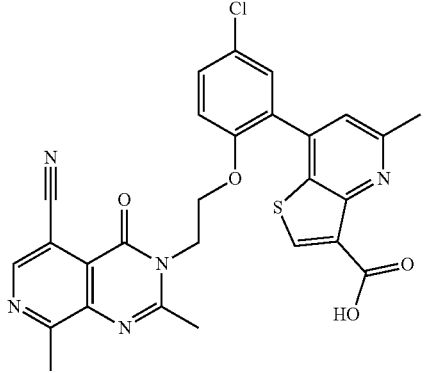 [SMILES: Cc1cc(-c2cc(Cl)ccc2OCCn2c(C)nc3c(C)ncc(C#N)c3c2=O)c2scc(C(=O)O)c2n1] | LCMS (ESI) m/z 546.0 [M + 1]+; 1H NMR (400 MHz, DMSO-d6) δ 8.80 (s, 1H), 8.44 (s, 1H), 7.56 (dd, J = 8.9, 2.7 Hz, 1H), 7.41-7.35 (m, 2H), 7.33 (d, J = 9.0 Hz, 1H), 4.40 (s, 2H), 4.23 (s, 2H), 2.72 (s, 3H), 2.67 (s, 3H), 1.88 (s, 3H) |
| 674 | 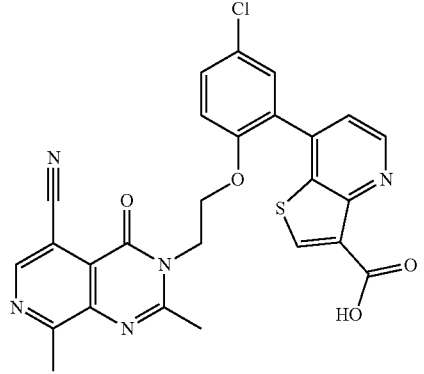 [SMILES: Cc1ncc(C#N)c2c(=O)n(CCOc3ccc(Cl)cc3-c3ccnc4c(C(=O)O)csc34)c(C)nc12] | LCMS (ESI) m/z 531.1 [M + 1]+; 1H NMR (400 MHz, DMSO-d6) δ 8.85 (s, 1H), 8.82 (dd, J = 4.8, 1.0 Hz, 1H), 8.48 (d, J = 2.0 Hz, 1H), 7.64-7.56 (m, 1H), 7.52-7.40 (m, 2H), 7.36 (dd, J = 9.0, 4.8 Hz, 1H), 4.43 (t, J = 5.0 Hz, 2H), 4.25 (t, J = 4.9 Hz, 2H), 2.76 (s, 3H), 1.85-1.78 (m, 3H) |
| 707 | 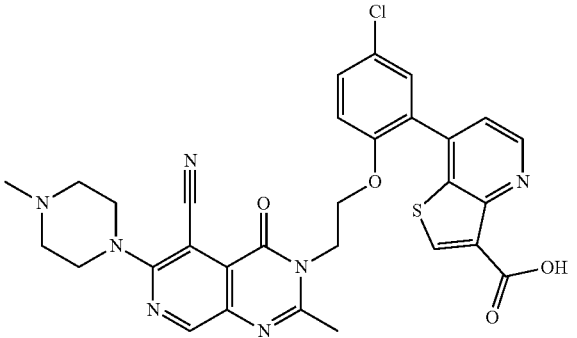 [SMILES: Cc1nc2cnc(N3CCN(C)CC3)c(C#N)c2c(=O)n1CCOc1ccc(Cl)cc1-c1ccnc2c(C(=O)O)csc12] | MS (ESI) m/z 616.2 [M + 1]+; 1H NMR (400 MHz, DMSO-d6) δ 9.89 (s, 1H), 8.83 (d, J = 4.8 Hz, 1H), 8.70 (s, 1H), 8.43 (s, 1H), 7.60 (dd, J = 8.9, 2.7 Hz, 1H), 7.47 (d, J = 4.8 Hz, 1H), 7.41 (d, J = 2.7 Hz, 1H), 7.37 (d, J = 9.0 Hz, 1H), 4.40 (t, J = 4.9 Hz, 2H), 4.32 (d, J = 14.2 Hz, 2H), 4.24 (t, J = 5.0 Hz, 2H), 3.61 (d, J = 12.0 Hz, 2H), 3.45 (t, J = 13.1 Hz, 2H), 3.32-3.21 (m, 2H), 2.91 (d, J = 3.5 Hz, 3H), 1.84 (s, 3H) |
| 721 |  | MS (ESI) m/z 560.99 [M + 1]+; 1H NMR (400 MHz, DMSO-d6) δ 12.73 (bs, 1H), 8.85 (s, 1H), 7.68 (s, 1H), 7.47 (dd, J = 2.64, 8.88 Hz, 1H), 7.28 (d, J = 2.60 Hz, 1H), 7.24 (d, J = 8.88 Hz, 1H), 7.19 (d, J = 8.00 Hz, 1H), 6.98 (d, J = 8.16 Hz, 1H), 4.34 (t, J = 4.60 Hz, 2H), 4.24 (t, J = 4.32 Hz, 2H), 3.93 (s, 3H), 2.79 (s, 3H), 1.86 (s, 3H) |

TABLE 1-continued
7-Aza-Thienylpyridine and Derivative Compounds
| Compound | | Characterization |
|---|---|---|
| 722 | 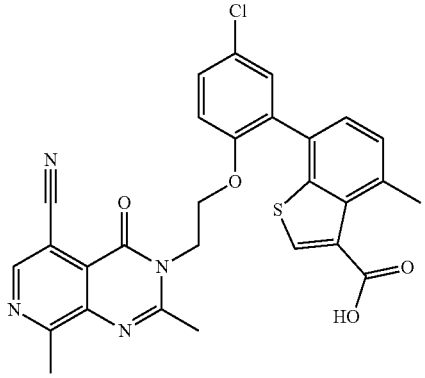 [SMILES: Cc1ncc(C#N)c2c(=O)n(CCOc3ccc(Cl)cc3-c3ccc(C)c4c(C(=O)O)csc34)c(C)nc12] | MS (ESI) m/z 544.96 [M + 1]+; 1H NMR (400 MHz, DMSO-d6) δ 12.92 (s, 1H), 8.84 (s, 1H), 7.92 (s, 1H), 7.49 (dd, J = 2.48 Hz, J = 8.84 Hz, 1H), 7.28-7.24 (m, 3H), 7.13 (d, J = 7.32 Hz, 1H), 4.35 (t, J = 4.56 Hz, 2H), 4.21 (t, J = 4.48 Hz, 2H), 2.79 (s, 3H), 2.67 (s, 3H), 1.76 (s, 3H) |
| 723 | 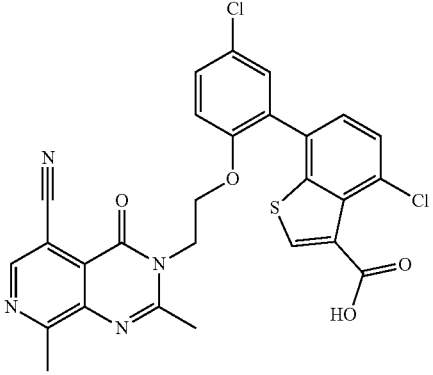 [SMILES: Cc1ncc(C#N)c2c(=O)n(CCOc3ccc(Cl)cc3-c3ccc(Cl)c4c(C(=O)O)csc34)c(C)nc12] | MS (ESI) m/z 564.90 [M + 1]+; 1H NMR (400 MHz, DMSO-d6) δ 13.15 (bs, 1H), 8.52 (s, 1H), 7.97 (s, 1H), 7.53-7.48 (m, 2H), 7.34 (d, J = 2.4Hz , 1H), 7.28 (d, J = 8.8 Hz, 1H), 7.23 (d, J = 7.6 Hz, 1H), 4.36 (t, J = 4.44 Hz, 2H), 4.22 (t, J = 4.4 Hz, 2H), 2.81 (s, 3H), 1.79 (s, 3H) |
| 725 | 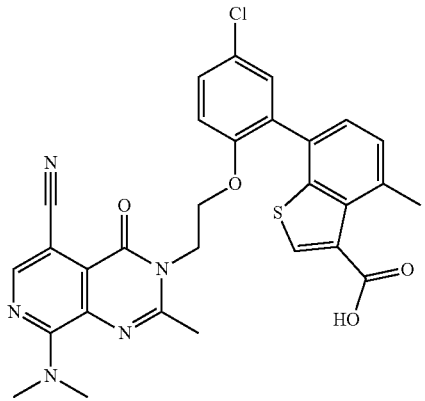 [SMILES: Cc1ccc(-c2cc(Cl)ccc2OCCn2c(C)nc3c(N(C)C)ncc(C#N)c3c2=O)c2scc(C(=O)O)c12] | MS (ESI) m/z 574 [M + 1]+; 1H NMR (400 MHz, DMSO-d6) δ 12.92 (bs, 1H), 8.35 (s, 1H), 7.96 (s, 1H), 7.49 (dd, J = 8.84, 2.48 Hz, 1H), 7.27-7.21 (m, 3H), 7.12 (d, J = 7.32 Hz, 1H), 4.33 (t, J = 4.56 Hz, 2H), 4.17 (t, J = 4.44 Hz, 2H) 3.41 (s, 6H), 2.65 (s, 3H), 1.67 ( s, 3H) |

TABLE 1-continued
7-Aza-Thienylpyridine and Derivative Compounds
| Compound | | Characterization |
|---|---|---|
| 726 | 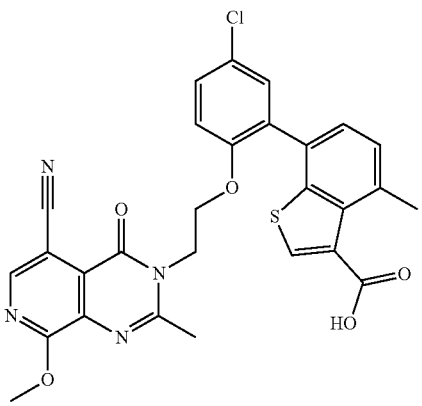 [SMILES: COc1ncc(C#N)c2c(=O)n(CCOc3ccc(Cl)cc3-c3ccc(C)c4c(C(=O)O)csc34)c(C)nc12] | MS (ESI) m/z 560.99 [M + 1]+; 1H NMR (400 MHz, DMSO-d6) δ 12.83 (s, 1H), 8.58 (s, 1H), 7.94 (s, 1H), 7.48 (dd, J = 8.88, 2.64 Hz, 1H), 7.28-7.22 (m, 3H), 7.37 (d, J = 7.36 Hz, 1H), 4.34 (s, 2H), 4.20 (s, 2H), 4.09 (s, 3H), 2.67 (s, 3H), 1.80 (s, 3H) |
| 727 | 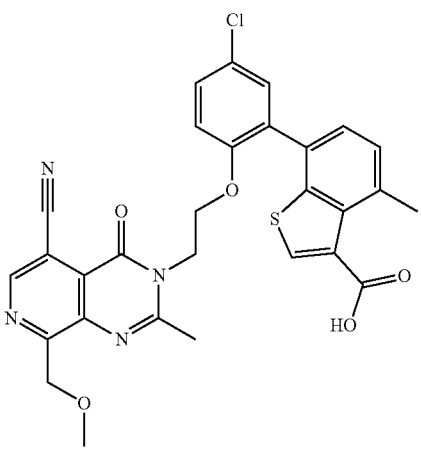 [SMILES: COCc1ncc(C#N)c2c(=O)n(CCOc3ccc(Cl)cc3-c3ccc(C)c4c(C(=O)O)csc34)c(C)nc12] | MS (ESI) m/z 574.98 [M + 1]+; 1H NMR (400 MHz, DMSO-d6) δ 12.98 (s, 1H), 8.96 (s, 1H), 7.93 (s, 1H), 7.48 (dd, J = 8.88, 2.56 Hz, 1H), 7.28-7.24 (m, 3H), 7.12 (d, J = 7.36 Hz, 1H), 4.95 (s, 2H), 4.34 (t, J = 4.4 Hz, 2H), 4.20 (t, J = 4.84 Hz, 2H), 3.41 (s, 3H), 2.66 (s, 3H), 1.74 (s, 3H) |
| 728 | 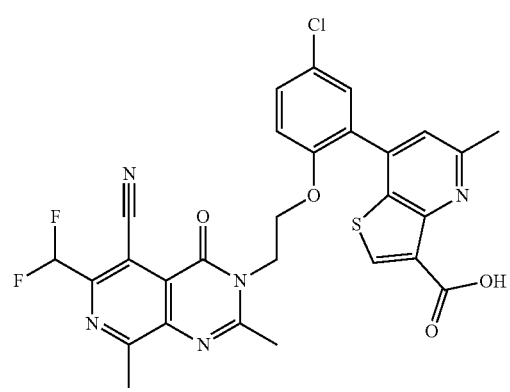 [SMILES: Cc1cc(-c2cc(Cl)ccc2OCCn2c(C)nc3c(C)nc(C(F)F)c(C#N)c3c2=O)c2scc(C(=O)O)c2n1] | MS (ESI) m/z 595.96 [M + 1]+; 1H NMR (400 MHz, DMSO-d6) δ 8.49 (s, 1H) 7.60 (dd, J = 8.88, 2.76 1H), 7.42-7.08 (m, 4H), 4.43 (t, J = 4.68 Hz, 2H), 4.27 (t, J = 4.44 Hz, 2H), 2.79 (s, 3H), 2.70 (s, 3H), 1.91 (s, 3H) |

TABLE 1-continued

7-Aza-Thienylpyridine and Derivative Compounds

| Compound | | Characterization |
|---|---|---|
| 730 | 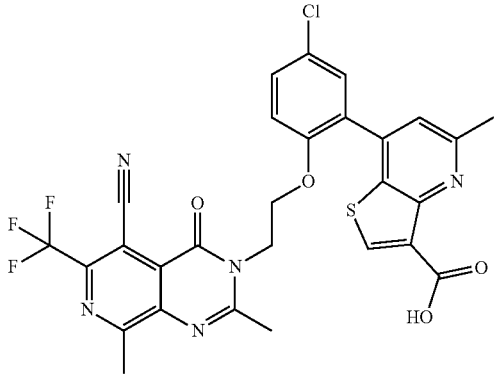 [SMILES: Cc1cc(-c2cc(Cl)ccc2OCCn2c(C)nc3c(C)nc(C(F)(F)F)c(C#N)c3c2=O)c2scc(C(=O)O)c2n1] | MS (ESI) m/z 614.03 [M + 1]+; 1H NMR (400 MHz, DMSO-d6) δ 13.50 (bs, 1H), 8.48 (s, 1H), 7.59 (d, J = 8.72 Hz, 1H), 7.42 (d, J = 4.8 Hz, 2H), 7.37 (d, J = 8.8 Hz, 1H), 4.44 (bs, 2H), 4.29 (bs, 2H), 2.80 (s, 3H), 2.71 (s, 1H), 1.94 (s, 1H |
| 731 | 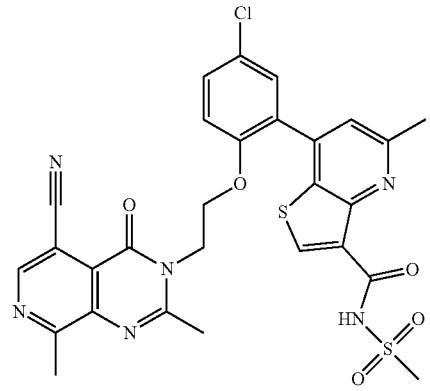 [SMILES: Cc1cc(-c2cc(Cl)ccc2OCCn2c(C)nc3c(C)ncc(C#N)c3c2=O)c2scc(C(=O)NS(C)(=O)=O)c2n1] | MS (ESI) m/z 622.99 [M + 1]+; 1H NMR (400 MHz, DMSO-d6) δ 12.89 (s, 1H), 8.83 (s, 1H), 8.63 (s, 1H), 7.61 (dd, J = 2.44, 8.84 Hz, 1H), 7.45 (s,1H), 7.39 (d, J = 9.4 Hz, 2H), 4.43 (t, J = 4.48 Hz, 2H), 4.28 (t, J = 4.6 Hz, 2H), 3.56 (s, 3H), 2.75 (s, 3H), 2.69 (s, 3H), 2.01 (s, 3H) |
| 732 | 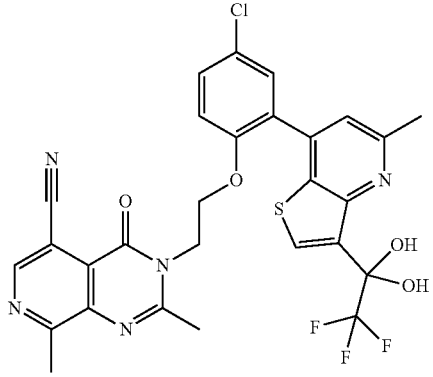 [SMILES: Cc1cc(-c2cc(Cl)ccc2OCCn2c(C)nc3c(C)ncc(C#N)c3c2=O)c2scc(C(O)(O)C(F)(F)F)c2n1] | MS (ESI) m/z 616.2 [M + 1]+; 1H NMR (400 MHz, DMSO-d6 at high temperature) δ 8.96 (s, 1H), 8.75 (s, 1H), 7.56-7.52 (dd, J = 6.4 Hz, 9.2 Hz, 1H), 7.38 (d, J = 2.8 Hz, 1H), 7.36 (s, 1H), 7.27 (bs, 1H), 4.43 (t, J = 5.2 Hz, 2H), 4.28 (t, J = 4.8 Hz, 2H), 2.73 (s, 3H), 2.63 (s, 3H), 2.00 (s, 3H) |
| 733 | 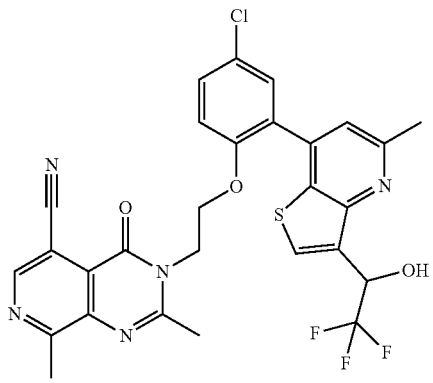 [SMILES: Cc1cc(-c2cc(Cl)ccc2OCCn2c(C)nc3c(C)ncc(C#N)c3c2=O)c2scc(C(O)C(F)(F)F)c2n1] | MS (ESI) m/z 599.99 [M + 1]+; 1H NMR (400 MHz, DMSO-d6) δ 8.51 (s, 1H), 8.11 (s, 1H), 7.55-7.52 (dd, J = 2.4, 8.8 Hz, 1H), 7.41 (d, J = 2.4 Hz, 1H), 7.31 (d, J = 9.2 Hz, 1H), 7.19 (s, 1H), 5.74-5.69 (m, 1H), 4.38 (t, J = 4.4 Hz, 2H), 4.26 (t, J = 4.4 Hz, 2H), 2.79 (s, 3H), 2.57 (s, 3H), 1.79 (s, 3H) |

TABLE 1-continued

7-Aza-Thienylpyridine and Derivative Compounds

| Compound | | Characterization |
|---|---|---|
| 734 | 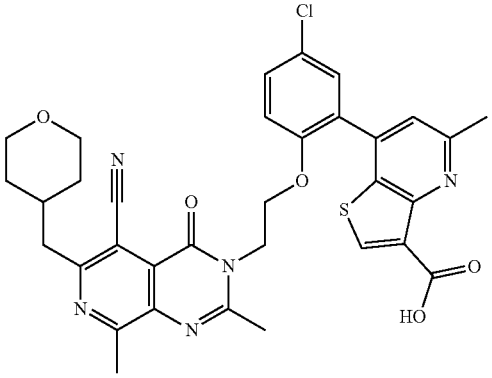 [SMILES: Cc1cc(-c2cc(Cl)ccc2OCCn2c(C)nc3c(C)nc(CC4CCOCC4)c(C#N)c3c2=O)c2scc(C(=O)O)c2n1] | MS (ESI) m/z 644.20 [M + 1]+; 1H NMR (400 MHz, DMSO-d6) δ 8.48 (s, 1H), 7.59 (dd, J = 8.88, 2.44 Hz, 1H), 7.41 (s, 2H), 7.36 (d, J = 8.96, 1H), 4.42 (t, J = 4.52 Hz, 2H), 4.25 (t, J = 4.4 Hz, 2H), 3.79 (t, J = 10.28 Hz, 2H), 3.26 (t, J = 11.36 Hz, 2H), 2.96 (d, J = 6.92 Hz, 2H), 2.73 (s, 3H), 2.69 (s, 3H), 2.09 (bs, 1H), 1.92 (s, 3H), 1.51 (d, J = 11.16 Hz, 2H), 1.39-1.28 (m, 2H) |
| 737 | 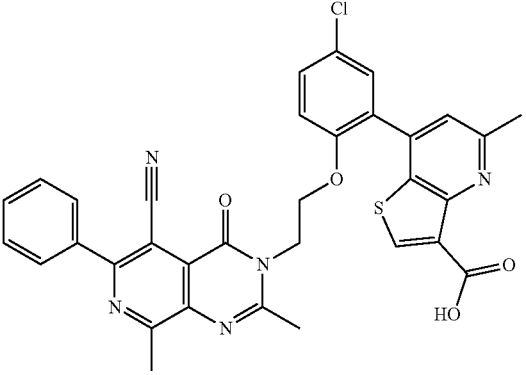 [SMILES: Cc1cc(-c2cc(Cl)ccc2OCCn2c(C)nc3c(C)nc(-c4ccccc4)c(C#N)c3c2=O)c2scc(C(=O)O)c2n1] | MS (ESI) m/z 622.05 [M + 1]+; 1H NMR (400 MHz, DMSO-d6) δ 13.51 (bs, 1H), 8.50 (s, 1H), 7.55 (bs, 2H), 7.64-7.7.45 (m, 4H), 7.42-7.36 (m, 3H), 4.44 (bs, 2H), 4.28 (bs, 2H), 2.78 (s, 3H), 2.69 (s, 3H), 1.94 (s, 3H) |
| 742 | 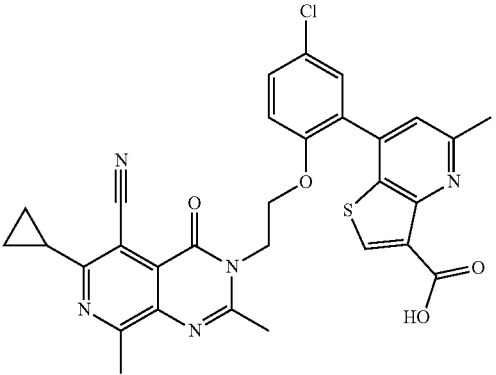 [SMILES: Cc1cc(-c2cc(Cl)ccc2OCCn2c(C)nc3c(C)nc(C4CC4)c(C#N)c3c2=O)c2scc(C(=O)O)c2n1] | MS (ESI) m/z 586.06 [M + 1]+; 1H NMR (400 MHz, DMSO-d6): δ 13.5 (bs, 1H), 8.49 (s, 1H), 7.60-7.57 (dd, J = 2.4, 8.8 Hz, 1H), 7.39-7.35 (m, 3H), 4.42 (t, J = 4.4 Hz, 2H), 4.25 (t, J = 3.6 Hz), 2.68 (s, 3H), 2.66 (s, 3H), 1.90 (s, 3H), 1.18-1.16 (m, 4H) |
| 749 | 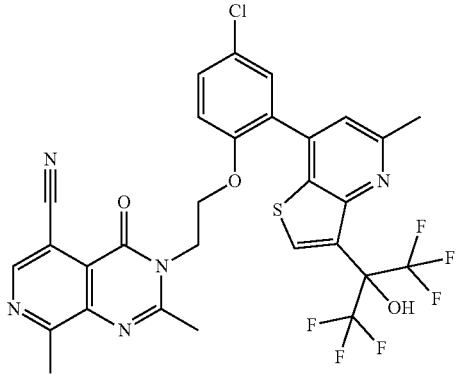 [SMILES: Cc1cc(-c2cc(Cl)ccc2OCCn2c(C)nc3c(C)ncc(C#N)c3c2=O)c2scc(C(O)(C(F)(F)F)C(F)(F)F)c2n1] | MS (ESI) m/z 668.00 [M + 1]+; 1H NMR (400 MHz, DMSO-d6) 611.6 (bs, 1H), 8.86 (s, 1H), 8.47 (s, 1H), 7.58-7.55 (m, 1H), 7.51 (d, J = 2.4 Hz, 1H), 7.39 (s, 1H), 7.34 (d, J = 8.8 Hz, 1H), 4.41 (t, J = 4.8 Hz, 2H), 4.27 (t, J = 5.20 Hz, 2H), 2.77 (s, 3H), 2.59 (s, 3H), 1.73 (s, 3H) |

TABLE 1-continued

7-Aza-Thienylpyridine and Derivative Compounds

| Compound | | Characterization |
|---|---|---|
| 756 |  | MS (ESI) m/z 541.2 [M + 1]+; 1H-NMR (400 MHz, DMSO-d6) δ 13.42 (bs, 1H), 9.11 (bs, 1H), 8.89 (s, 1H), 7.76 (d, J = 2.16 Hz, 1H), 7.74-7.62 (m, 2H), 7.53-7.38 (m, 2H), 7.11 (t, J = 7.80 Hz, 1H), 4.46 (s, 2H), 4.23 (s, 2H), 2.62-2.57 (m, 1H), 1.89 (s, 3H), 1.29-1.08 (m, 4H) |
| 757 |  | MS (ESI) m/z 548.02 [M + 1]+; 1H NMR (400 MHz, DMSO-d6) δ 13.54 (bs, 1H), 9.02 (s, 1H), 8.44 (d, J = 4.8 Hz 1H), 7.45 (dd, J = 2.8, 8.8 Hz, 1H), 7.26-7.20 (m, 3H), 4.31 (s, 4H), 2.62-2.58 (m, 1H), 2.02 (s, 3H), 1.93 ( s, 3H), 1.20 (d, J = 8.0 Hz ,2H), 1.12 (s, 2H) |
| 762 |  | MS (ESI) m/z 607.99 [M + 1]+; 1H NMR (400 MHz, DMSO-d6) δ 12.93 (s, 1H), 9.16 (s, 1H), 8.84 (d, J = 5.80, 2H), 7.91 (d, J = 5.92 Hz, 2H), 7.80 (s, 1H), 7.50 (dd, J = 8.84, 2.56 Hz, 1H), 7.29-7.26 (m, 3H), 7.15 (d, J = 7.32 Hz, 1H), 4.36 (t, J = 5.64, 2H), 4.25 (t, J = 3.80, 2H), 2.68 (s, 3H), 1.79 (s, 3H) |
| 763 |  | MS (ESI) m/z 622.01 [M + 1]+; 1H NMR (400 MHz, DMSO-d6) δ 12.9 (bs, 1H), 9.19 (s, 1H), 8.76 (d, J = 5.24, 1H), 7.89 (s, 1H), 7.85 (s, 1H), 7.77 (s, 1H), 7.51 (dd, J = 8.84, 2.52 Hz, 1H), 7.29-7.26 (m, 3H), 7.15 (d, J = 7.32 Hz, 1H), 4.36 (t, J = 3.96 Hz, 2H), 4.25 (t, J = 4.96 Hz 2H), 2.68 (s, 3H), 2.65 (s, 3H), 1.78 (s, 3H) |

TABLE 1-continued

7-Aza-Thienylpyridine and Derivative Compounds

| Compound | | Characterization |
|---|---|---|
| 770 | 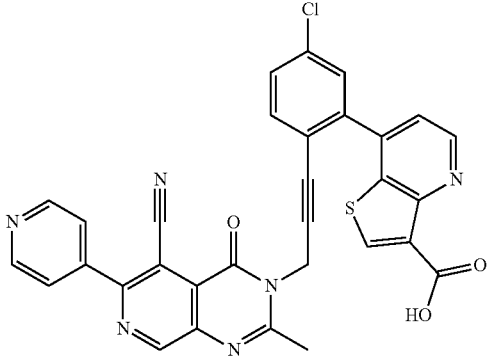 [SMILES: Cc1nc2cnc(-c3ccncc3)c(C#N)c2c(=O)n1CC#Cc1ccc(Cl)cc1-c1ccnc2c(C(=O)O)csc12] | MS (ESI) m/z 588.72 [M + 1]+; 1H NMR (400 MHz, DMSO-d6) δ 9.25 (s, 1H), 8.88 (d, J = 5.64 Hz, 2H), 8.79 (d, J = 4.76 Hz, 1H), 8.63 (s, 1H), 8.00 (d, J = 5.72 Hz, 2H), 7.77 (d, J = 8.08 Hz, 1H), 7.70-7.68 (m, J = 8.0 Hz, 2H) 7.55 (d, J = 4.76 Hz, 1H), 4.89 (s, 2H), 2.22 (s, 3H) |
| 771 | 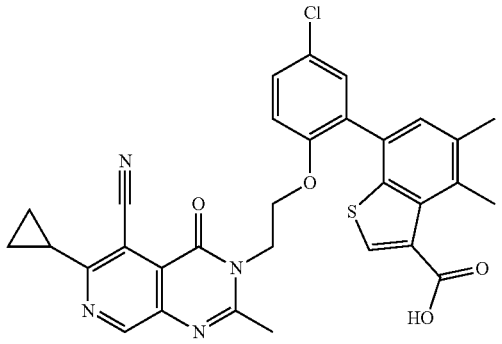 [SMILES: Cc1cc(-c2cc(Cl)ccc2OCCn2c(C)nc3cnc(C4CC4)c(C#N)c3c2=O)c2scc(C(=O)O)c2c1C] | MS (ESI) m/z 585.00 [M + 1]+; 1H NMR (400 MHz, DMSO-d6) δ 12.94 (bs, 1H), 8.94 (s, 1H), 7.76 (s, 1H), 7.48 (dd, J = 2.52, 8.76 Hz, 1H), 7.26-7.24 (m, 2H), 7.06 (s, 1H), 4.32 (t, J = 4.48 Hz, 2H), 4.20 (t, J = 5.08 Hz, 2H), 2.62-2.59 (m, 1H), 2.49 (s, 3H), 2.33 (s, 3H), 1.75 (s, 3H), 1.22 (bs, 2H), 1.14 (bs, 2H) |
| 772 | 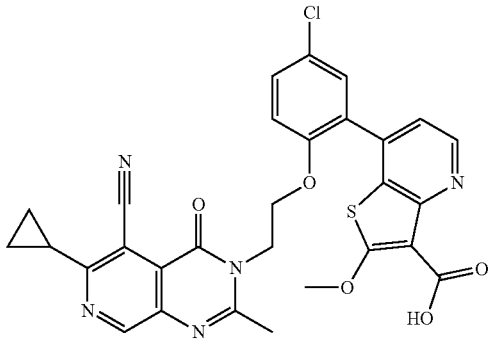 [SMILES: COc1sc2c(-c3cc(Cl)ccc3OCCn3c(C)nc4cnc(C5CC5)c(C#N)c4c3=O)ccnc2c1C(=O)O] | MS (ESI) m/z 588.02 [M + 1]+; 1H NMR (400 MHz, DMSO-d6) δ 8.84 (s, 1H), 8.70 (d, J = 5.12 Hz, 1H), 7.59 (dd, J = 8.88, 2.48 Hz, 1H), 7.42-7.39 (m, 2H), 7.35 (d, J = 8.96 Hz, 1H), 4.44 (t, J = 4.25 Hz, 2H), 4.29 (t, J = 4.28 Hz, 2H), 3.66 (s, 3H), 2.62-2.59 (m, 1H), 1.87 (s, 3H), 1.24-1.19 (m, 4H) |
| 773 | 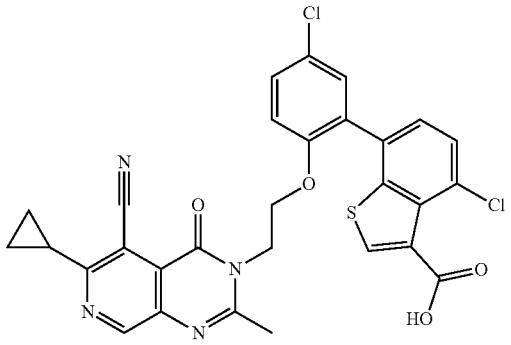 [SMILES: Cc1nc2cnc(C3CC3)c(C#N)c2c(=O)n1CCOc1ccc(Cl)cc1-c1ccc(Cl)c2c(C(=O)O)csc12] | MS (ESI) m/z 590.98 [M + 1]+; 1H NMR (400 MHz, DMSO-d6) δ 13.16 (bs, 1H), 8.98 (s, 1H), 7.83 (s, 1H), 7.53-7.49 (m, 2H), 7.33-7.22 (m, 3H), 4.34 (t, J = 4.8 Hz, 2H), 4.22 (t, J = 4.4 Hz, 2H), 2.60-2.58 (m, 1H), 1.77 (s, 3H), 1.22-1.15 (m, 4H) |

TABLE 1-continued

7-Aza-Thienylpyridine and Derivative Compounds

| Compound | | Characterization |
|---|---|---|
| 791 | 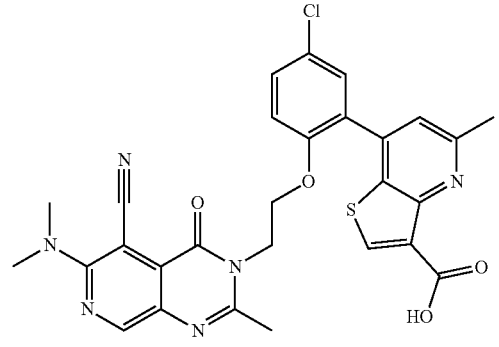 | MS (ESI) m/z 574.95 [M + 1]+; 1H NMR (400 MHz, DMSO-d6) δ 13.57 (bs, 1H), 8.56 (s, 1H), 8.48 (s, 1H), 7.58 (dd, J = 8.8, 2.48 Hz, 1H), 7.41 (d, J = 2.52 Hz, 1H), 7.38 (s, 1H), 7.35 (d, J = 9.4 Hz, 1H), 4.39-4.36 (m, 2H), 4.21-4.18 (m, 2H), 3.25 (s, 6H), 2.70 (s, 3H), 1.80 (s, 3H) |
| 792 | 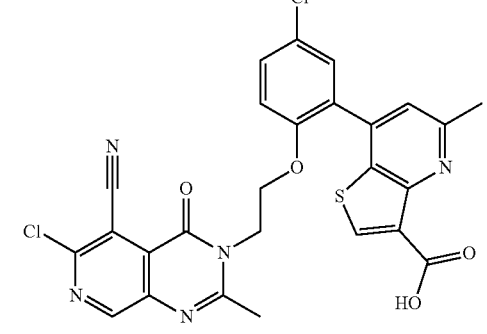 | MS (ESI) m/z 565.91 [M + 1]+; 1H NMR (400 MHz, DMSO-d6) δ 8.84 (s, 1H), 8.39 (s, 1H), 7.59 (dd, J = 8.84, 2.52 Hz, 1H), 7.42 (s, 2H), 7.34 (d, J = 8.96 Hz, 1H), 4.42-4.37 (m, 2H), 4.29-4.24 (m, 2H), 2.71 (s, 3H),.1.81(s, 3H) |
| 793 | 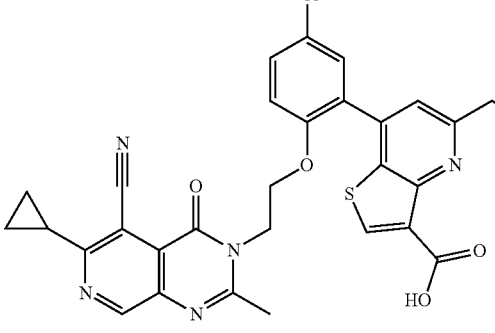 | MS (ESI) m/z 585.97 [M + 1]+; 1H NMR (400 MHz, DMSO-d6) δ 8.82 (s, 1H), 8.39 (s, 1H), 7.61 (dd, J = 8.88, 2.68 Hz, 1H), 7.45-7.43 (m, 2H), 7.37 (d, J = 8.96 Hz, 1H), 4.41 (t, J = 5.08 Hz, 2H), 4.25 (t, J = 5.24 Hz, 2H), 3.02 (q, J = 7.56,7.52 Hz, 2H), 2.67 (bs, 1H), 1.83 (s, 3H), 1.35 (t, J = 7.52 Hz, 3H), 1.24-1.19 (m, 4H) |
| 794 | 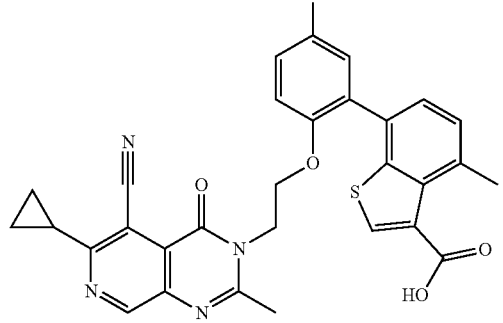 | MS (ESI) m/z 571.07 [M + 1]+; 1H NMR (400 MHz, DMSO-d6) δ 13.00 (bs, 1H), 8.94 (s, 1H), 7.80 (s, 1H), 7.50 (dd, J = 8.84, 2.4 Hz, 1H), 7.26-7.21 (m, 3H), 7.12 (d, J = 7.32 Hz, 1H), 4.34 (t, J = 4.8 Hz, 2H), 4.21 (t, J = 4.44 Hz, 2H), 2.66 (s, 3H), 2.62-2.57 (m, 1H), 1.73 (s, 3H), 1.22-1.15 (m, 4H) |

TABLE 1-continued

7-Aza-Thienylpyridine and Derivative Compounds

| Compound | | Characterization |
|---|---|---|
| 807 | 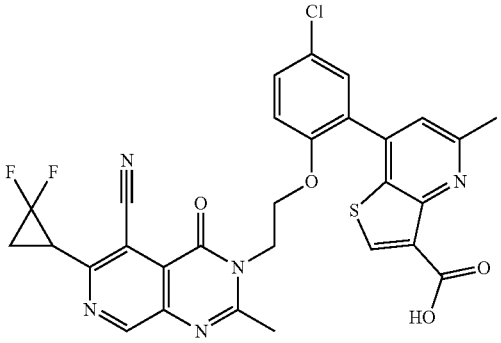 [SMILES: Cc1cc(-c2cc(Cl)ccc2OCCn2c(C)nc3cnc(C4CC4(F)F)c(C#N)c3c2=O)c2scc(C(=O)O)c2n1] | MS (ESI) m/z 608.7 [M + 1]+; 1H NMR (400 MHz, DMSO-d6) δ 8.97 (s, 1H), 8.41 (s, 1H), 7.60 (dd, J = 8.9, 2.7 Hz, 1H), 7.45-7.40 (m, 2H), 7.35 (d, J = 9.0 Hz, 1H), 4.45-4.35 (m, 2H), 4.26 (dtt, J = 14.9, 10.4, 5.0 Hz, 2H), 3.54 (td, J = 11.5, 7.9 Hz, 1H), 2.70 (s, 3H), 2.54-2.44 (m,1H), 2.37-2.23 (m, 1H), 1.86 (s, 3H) |
| 809 | 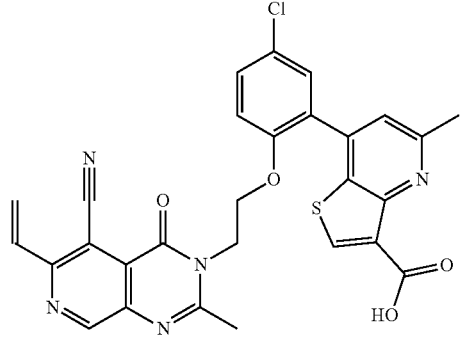 [SMILES: C=Cc1ncc2nc(C)n(CCOc3ccc(Cl)cc3-c3cc(C)nc4c(C(=O)O)csc34)c(=O)c2c1C#N] | MS (ESI) m/z 558.4 [M + 1]+; 1H NMR (400 MHz, DMSO-d6) δ 8.97 (d, J = 0.6 Hz, 1H), 8.41 (s, 1H), 7.59 (dd, J = 8.9, 2.7 Hz, 1H), 7.42 (d, J = 2.7 Hz, 1H), 7.42 (s, 1H), 7.35 (d, J = 9.0 Hz, 1H), 7.33-7.24 (m, 1H), 6.66 (dd, J = 16.7, 1.9 Hz, 1H), 5.88 (dd, J = 10.6, 1.9 Hz, 1H), 4.40 (t, J = 5.1 Hz, 2H), 4.26 (t, J = 5.0 Hz, 2H), 2.70 (s, 3H), 1.83 (s, 3H) |
| 813 | 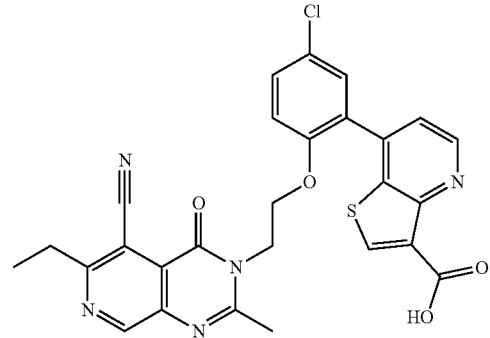 [SMILES: CCc1ncc2nc(C)n(CCOc3ccc(Cl)cc3-c3ccnc4c(C(=O)O)csc34)c(=O)c2c1C#N] | MS (ESI) m/z 546.6 [M + 1]+; 1H NMR (400 MHz, DMSO-d6) δ 8.96 (s, 1H), 8.83 (d, J = 4.9 Hz, 1H), 8.41 (s, 1H), 7.60 (dd, J = 8.9, 2.7 Hz, 1H), 7.49 (d, J = 4.8 Hz, 1H), 7.44 (d, J = 2.6 Hz, 1H), 7.36 (d, J = 9.0 Hz, 1H), 4.40 (t, J = 5.0 Hz, 2H), 4.25 (t, J = 5.0 Hz, 2H), 3.11 (q, J = 7.5 Hz, 2H), 1.81 (s, 3H), 1.34 (t, J = 7.5 Hz, 3H) |
| 814 | 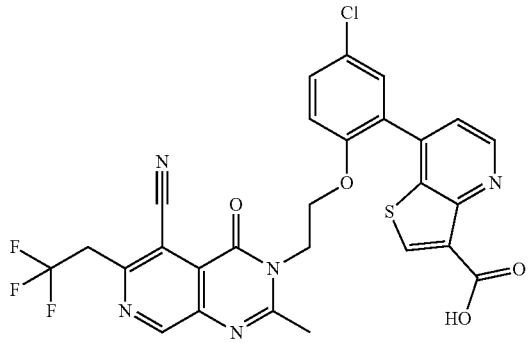 | MS (ESI) m/z 600.3 [M + 1]+; 1H NMR (400 MHz, DMSO-d6) δ 9.06 (s, 1H), 8.82 (d, J = 4.8 Hz, 1H), 8.43 (s, 1H), 7.60 (dd, J = 9.0, 2.6 Hz, 1H), 7.47 (d, J = 4.8 Hz, 1H), 7.44 (d, J = 2.6 Hz, 1H), 7.35 (d, J = 8.9 Hz, 1H), 4.40 (t, J = 5.0 Hz, 2H), 4.27 (t, J = 5.0 Hz, 2H), 4.16 (q, J = 10.7 Hz, 2H), 1.83 (s, 3H) |

TABLE 1-continued

7-Aza-Thienylpyridine and Derivative Compounds

| Compound | | Characterization |
|---|---|---|
| 815 | 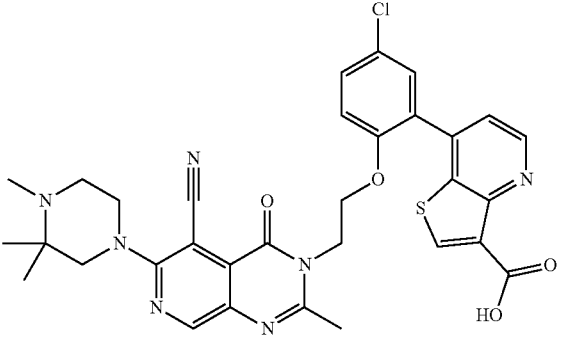 [SMILES: Cc1nc2cnc(N3CCN(C)C(C)(C)C3)c(C#N)c2c(=O)n1CCOc1ccc(Cl)cc1-c1ccnc2c(C(=O)O)csc12] | MS (ESI) m/z 644.6 [M + 1]+; 1H NMR (400 MHz, DMSO-d6) δ 8.83 (d, J = 4.8 Hz, 1H), 8.71 (s, 1H), 8.37 (s, 1H), 7.60 (dd, J = 8.9, 2.7 Hz, 1H), 7.47 (d, J = 4.8 Hz, 1H), 7.42 (d, J = 2.7 Hz, 1H), 7.36 (d, J = 9.0 Hz, 1H), 4.40 (t, J = 5.0 Hz, 2H), 4.23 (t, J = 5.0 Hz, 2H), 4.20-4.24 (m, 2H), 3.60-3.40 (m, 2H), 3.30 (d, J = 14.1 Hz, 2H), 2.81 (d, J = 4.7 Hz, 3H), 1.79 (s, 3H), 1.43 (s, 3H), 1.38 (s, 3H) |
| 816 | 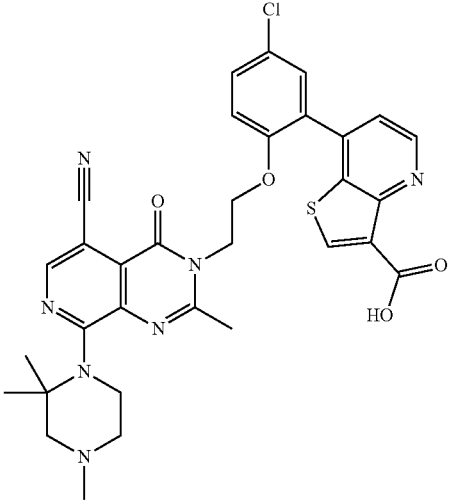 [SMILES: Cc1nc2c(N3CCN(C)CC3(C)C)ncc(C#N)c2c(=O)n1CCOc1ccc(Cl)cc1-c1ccnc2c(C(=O)O)csc12] | MS (ESI) m/z 644.6 [M + 1]+; 1H NMR (400 MHz, DMSO-d6) δ 8.78 (d, J = 4.8 Hz, 1H), 8.72 (s, 1H), 8.58 (s, 1H), 7.60 (dd, J = 8.9, 2.7 Hz, 1H), 7.46 (s, 1H), 7.46 (d, J = 2.2 Hz, 1H), 7.37 (d, J = 9.0 Hz, 1H), 4.45-4.38 (m, 2H), 4.37- 4.28 (m, 2H), 4.22 (t, J = 5.1 Hz, 2H), 3.29-3.08 (m, 4H), 2.96 (d, J = 3.9 Hz, 3H), 1.76 (s, 3H), 1.68 (s, 3H), 1.48 (s, 3H) |
| 817 | 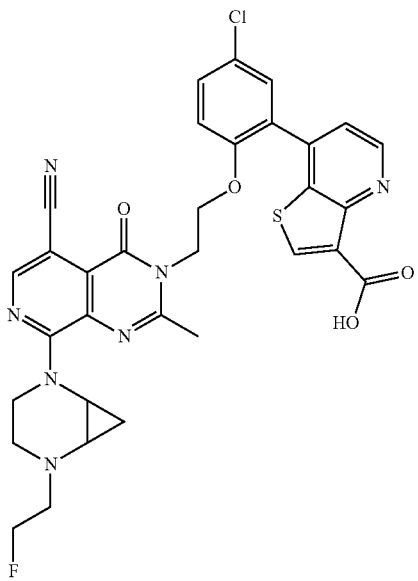 [SMILES: Cc1nc2c(N3CCN(CCF)C4CC43)ncc(C#N)c2c(=O)n1CCOc1ccc(Cl)cc1-c1ccnc2c(C(=O)O)csc12] | MS (ESI) m/z 660.8 [M + 1]+; 1H NMR (400 MHz, DMSO-d6) δ 8.81 (d, J = 4.8 Hz, 1H), 8.47 (d, J = 9.3 Hz, 2H), 7.60 (dd, J = 8.9, 2.7 Hz, 1H), 7.48 (d, J = 4.8 Hz, 1H), 7.42 (d, J = 2.6 Hz, 1H), 7.38 (d, J = 9.0 Hz, 1H), 4.91 (bs, 2H), 4.78 (bs, 2H), 4.49-4.38 (m, 2H), 4.30-4.14 (m, 2H), 3.55-2.82 (br, 4H), 1.79 (s, 3H), 1.32-0.83 (m, 4H) |

TABLE 1-continued

7-Aza-Thienylpyridine and Derivative Compounds

| Compound | | Characterization |
|---|---|---|
| 818 | 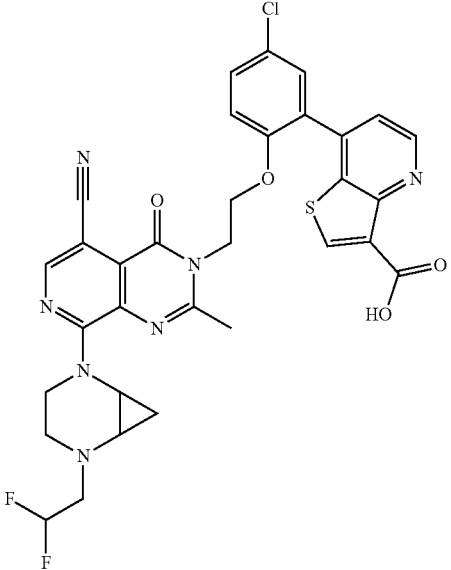 [SMILES: Cc1nc2c(N3CCN(CC(F)F)C4CC43)ncc(C#N)c2c(=O)n1CCOc1ccc(Cl)cc1-c1ccnc2c(C(=O)O)csc12] | MS (ESI) m/z 678.6 [M + 1]+; 1H NMR (400 MHz, DMSO-d6) δ 8.81 (d, J = 4.8 Hz, 1H), 8.49 (s, 1H), 8.40 (s, 1H), 7.60 (dd, J = 8.9, 2.7 Hz, 1H), 7.48 (d, J = 4.9 Hz, 1H), 7.42 (d, J = 2.7 Hz, 1H), 7.37 (d, J = 9.0 Hz, 1H), 6.26 (tt, J = 55.6, 4.2 Hz, 1H), 4.49-4.35 (m, 2H), 4.29-4.12 (m, 2H), 3.25-2.72 (m, 8H), 1.75 (s, 3H), 0.64-0.53 (m, 2H) |
| 819 | 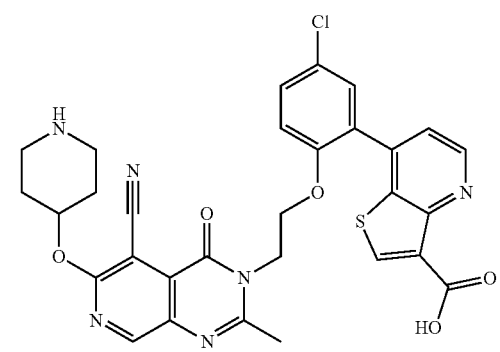 [SMILES: Cc1nc2cnc(OC3CCNCC3)c(C#N)c2c(=O)n1CCOc1ccc(Cl)cc1-c1ccnc2c(C(=O)O)csc12] | MS (ESI) m/z 617.4 [M + 1]+; 1H NMR (400 MHz, DMSO-d6) δ 8.79 (d, J = 4.8 Hz, 1H), 8.60 (s, 1H), 8.36 (s, 1H), 7.59 (dd, J = 8.9, 2.7 Hz, 1H), 7.47 (d, J = 4.8 Hz, 1H), 7.44 (d, J = 2.7 Hz, 1H), 7.36 (d, J = 9.0 Hz, 1H), 4.59-4.58 (m, 2H), 4.40 (t, J = 5.1 Hz, 2H), 4.20 (t, J = 5.1 Hz, 2H), 3.84-3.76 (m, 1H), 3.66-3.54 (m, 2H), 1.91-1.84 (m, 2H), 1.78 (s, 3H), 1.53-1.41 (m, 2H) |
| 820 | 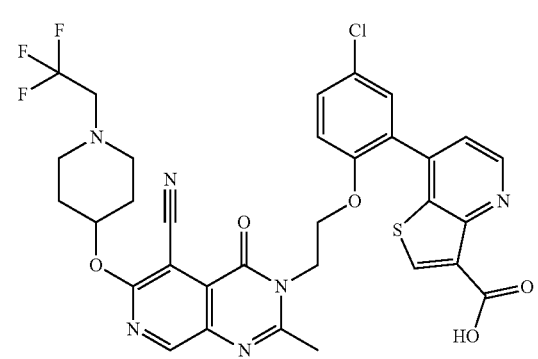 [SMILES: Cc1nc2cnc(OC3CCN(CC(F)(F)F)CC3)c(C#N)c2c(=O)n1CCOc1ccc(Cl)cc1-c1ccnc2c(C(=O)O)csc12] | MS (ESI) m/z 699.5 [M + 1]+; 1H NMR (400 MHz, DMSO-d6) δ 8.84 (dd, J = 4.9, 0.9 Hz, 1H), 8.71 (s, 1H), 8.42 (d, J = 1.5 Hz, 1H), 7.60 (dd, J = 9.0, 2.7 Hz, 1H), 7.50 (dd, J = 4.9, 2.6 Hz, 1H), 7.43 (d, J = 2.6 Hz, 1H), 7.36 (d, J = 9.0 Hz, 1H), 5.37-5.27 (m, 1H), 4.39 (t, J = 5.0 Hz, 2H), 4.22 (t, J = 5.0 Hz, 2H), 3.43-3.26 (m, 2H), 3.02-2.90 (m, 2H), 2.81-2.69 (m, 2H), 2.12-2.01 (m, 2H), 1.90-1.79 (m, 2H), 1.75 (s, 3H) |

TABLE 1-continued

7-Aza-Thienylpyridine and Derivative Compounds

| Compound | | Characterization |
|---|---|---|
| 821 | 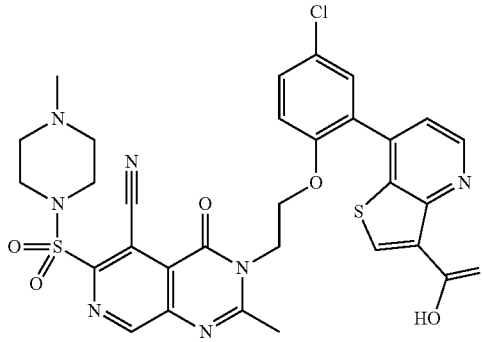 | MS (ESI) m/z 680.3 [M + 1]+; 1H NMR (400 MHz, DMSO-d6) δ 9.04 (s, 1H), 8.85 (d, J = 4.8 Hz, 1H), 8.39 (s, 1H), 7.61 (dd, J = 8.9, 2.7 Hz, 1H), 7.50 (d, J = 4.8 Hz, 1H), 7.46 (d, J = 2.7 Hz, 1H), 7.37 (d, J = 9.0 Hz, 1H), 4.42 (t, J = 5.0 Hz, 2H), 4.29 (t, J = 5.0 Hz, 2H), 4.05 (br, 2H), 3.62-3.16 (br, 6H), 2.89 (s, 3H), 1.77 (s, 3H) |
| 822 | 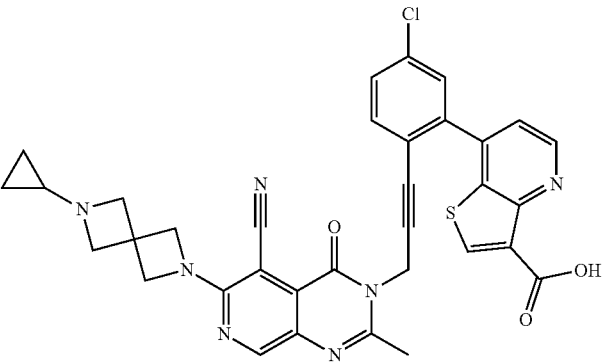 [SMILES: Cc1nc2cnc(N3CC4(C3)CN(C3CC3)C4)c(C#N)c2c(=O)n1CC#Cc1ccc(Cl)cc1-c1ccnc2c(C(=O)O)csc12] | MS (ESI) m/z 648.6 [M + 1]+; 1H NMR (400 MHz, DMSO-d6) δ 8.76-8.71 (m, 2H), 8.66 (s, 1H), 7.75 (dd, J = 8.0, 0.9 Hz, 1H), 7.71-7.64 (m, 2H), 7.54 (d, J = 4.8 Hz, 1H), 4.81 (s, 2H), 4.59 (bd, J = 16.5 Hz, 4H), 4.41 (s, 4H), 3.08 (br, 1H), 2.09 (s, 3H), 0.81-0.76 (m, 4H) |
| 823 | 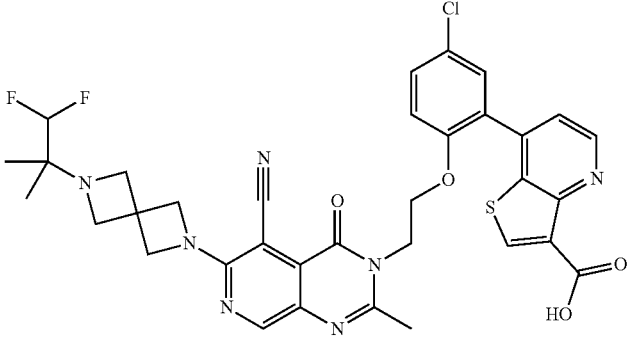 [SMILES: Cc1nc2cnc(N3CC4(C3)CN(C(C)(C)C(F)F)C4)c(C#N)c2c(=O)n1CCOc1ccc(Cl)cc1-c1ccnc2c(C(=O)O)csc12] | MS (ESI) m/z 706.5 [M + 1]+; 1H NMR (400 MHz, DMSO-d6) δ 8.82 (d, J = 4.8 Hz, 1H), 8.61 (s, 1H), 8.47 (s, 1H), 7.60 (dd, J = 8.9, 2.7 Hz, 1H), 7.46 (d, J = 4.8 Hz, 1H), 7.42 (d, J = 2.7 Hz, 1H), 7.36 (d, J = 9.0 Hz, 1H), 6.22 (t, J = 53.9 Hz, 1H), 4.56 (br, 6H), 4.38 (t, J = 5.0 Hz, 2H), 4.25 (br, 2H), 4.20 (t, J = 5.0 Hz, 2H), 1.79 (s, 3H), 1.32 (s, 6H) |
| 824 | 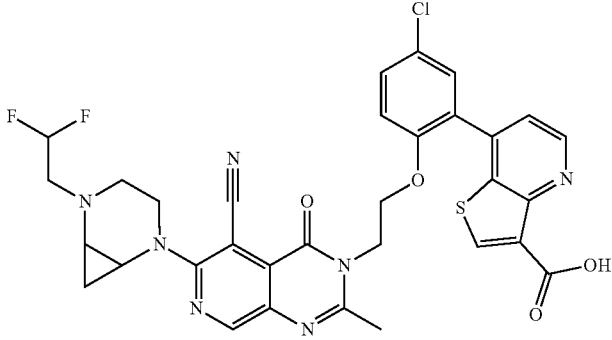 [SMILES: Cc1nc2cnc(N3CCN(CC(F)F)C4CC43)c(C#N)c2c(=O)n1CCOc1ccc(Cl)cc1-c1ccnc2c(C(=O)O)csc12] | MS (ESI) m/z 678.4 [M + 1]+; 1H NMR (400 MHz, DMSO-d6) δ 8.85 (d, J = 4.9 Hz, 1H), 8.60 (s, 1H), 8.50 (s, 1H), 7.60 (dd, J = 8.9, 2.7 Hz, 1H), 7.51 (d, J = 4.9 Hz, 1H), 7.45 (d, J = 2.7 Hz, 1H), 7.37 (d, J = 9.0 Hz, 1H), 6.26 (tt, J = 55.5, 4.2 Hz, 1H), 4.44-4.37 (m, 2H), 4.26-4.14 (m, 2H), 3.44 (dd, J = 7.8, 6.6, 4.1 Hz, 2H), 3.19-2.84 (m, 6H), 1.74 (s, 3H), 0.81 (q, J = 6.6 Hz, 1H), 0.69-0.63 (m, 1H) |

TABLE 1-continued

7-Aza-Thienylpyridine and Derivative Compounds

| Compound | | Characterization |
|---|---|---|
| 825 | 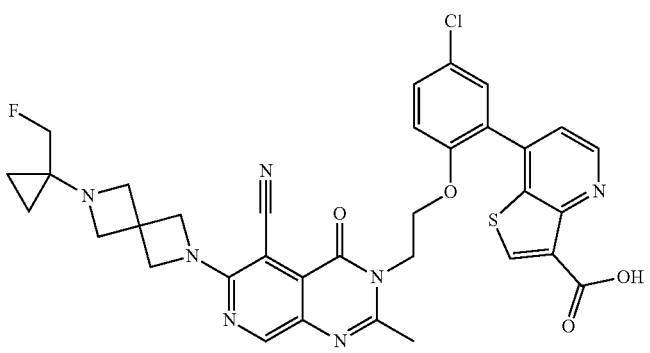 [SMILES: Cc1nc2cnc(N3CC4(C3)CN(C3(CF)CC3)C4)c(C#N)c2c(=O)n1CCOc1ccc(Cl)cc1-c1ccnc2c(C(=O)O)csc12] | MS (ESI) m/z 686.4 [M + 1]+; 1H NMR (400 MHz, DMSO-d6) δ 8.78 (d, J = 4.8 Hz, 1H), 8.57 (s, 1H), 8.44 (s, 1H), 7.57 (dd, J = 8.9, 2.7 Hz, 1H), 7.43 (d, J = 4.8 Hz, 1H), 7.39 (d, J = 2.7 Hz, 1H), 7.32 (d, J = 9.0 Hz, 1H), 4.65 (d, J = 48.5 Hz, 2H), 4.45 (br, 4H), 4.35 (t, J = 5.2 Hz, 2H), 4.27 (br, 4H), 4.17 (t, J = 5.2 Hz, 2H), 1.76 (s, 3H), 1.29 (br, 2H), 0.97 (br, 2H) |
| 826 | 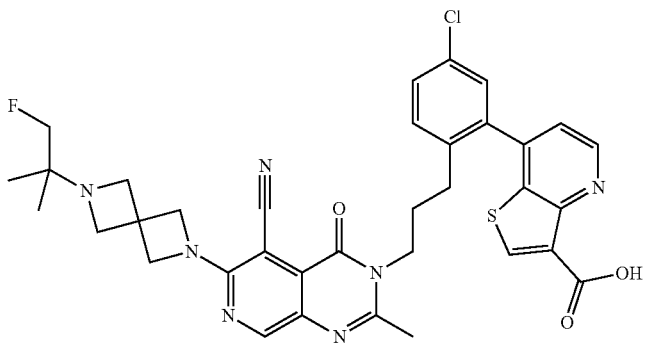 [SMILES: Cc1nc2cnc(N3CC4(C3)CN(C(C)(C)CF)C4)c(C#N)c2c(=O)n1CCCc1ccc(Cl)cc1-c1ccnc2c(C(=O)O)csc12] | MS (ESI) m/z 688.7 [M + 1]+; 1H NMR (400 MHz, DMSO-d6) δ 8.82 (d, J = 4.9 Hz, 1H), 8.61 (s, 1H), 8.48 (s, 1H), 7.64-7.58 (dd, J = 8.9, 2.6 Hz, 1H), 7.47 (d, J = 4.8 Hz, 1H), 7.43 (d, J = 4.4 Hz, 1H), 7.36 (d, J = 9.0 Hz, 1H), 4.71-4.42 (m, 8H), 4.38 (t, J = 5.2 Hz, 2H), 4.28-4.16 (m, 4H), 1.80 (s, 3H), 1.26 (s, 6H) |
| 827 | 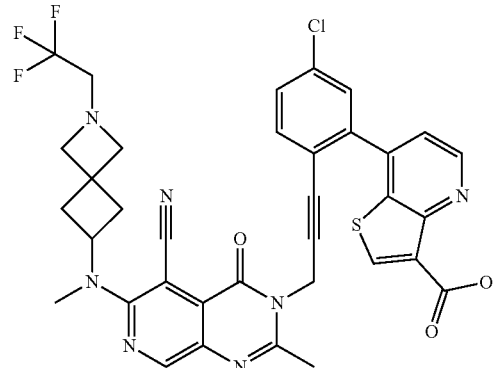 | MS (ESI) m/z 718.4 [M + 1]+; 1H NMR (400 MHz, DMSO-d6) δ 8.75 (d, J = 4.8 Hz, 1H), 8.72 (s, 1H), 8.66 (s, 1H), 7.76 (d, J = 9.0 Hz, 1H), 7.71-7.67 (m, 2H), 7.55 (d, J = 4.8 Hz, 1H), 4.82 (s, 2H), 4.59-4.47 (m, 2H), 4.33-3.54 (br, 8H), 3.14 (s, 3H), 2.63 (br, 1H), 2.06 (s, 3H) |
| 828 | 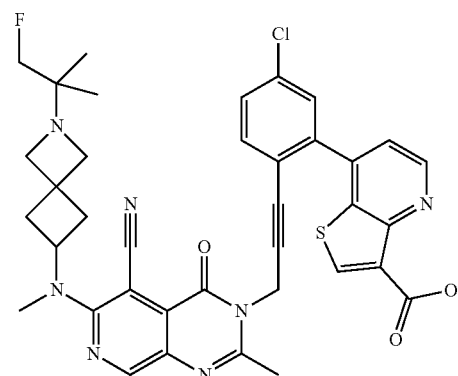 | MS (ESI) m/z 710.4 [M + 1]+; 1H NMR (400 MHz, DMSO-d6) δ 8.75 (d, J = 4.8 Hz, 1H), 8.72 (s, 1H), 8.65 (s, 1H), 7.78-7.74 (m, 1H), 7.71-7.67 (m, 2H), 7.55 (d, J = 4.8 Hz, 1H), 4.82 (s, 2H), 4.53-4.45 (m, 1H), 4.49 (d, J = 47.2 Hz, 2H), 4.42-4.36 (m, 1H), 4.31-4.24 (m, 1H), 4.15-4.07 (m, 1H), 3.99-3.92 (m, 1H), 3.15 (s, 3H), 2.79-2.40 (m, 4H), 2.06 (s, 3H), 1.24 (d, J = 1.9 Hz, 6H) |

TABLE 1-continued

7-Aza-Thienylpyridine and Derivative Compounds

| Compound | Characterization |
|---|---|
| 829 | MS (ESI) m/z 682.5 [M + 1]+; 1H NMR (400 MHz, DMSO-d6) δ 8.82 (d, J = 4.8 Hz, 1H), 8.58 (s, 1H), 8.46 (s, 1H), 7.60 (dd, J = 8.9, 2.7 Hz, 1H), 7.47 (d, J = 4.8 Hz, 1H), 7.43 (d, J = 2.7 Hz, 1H), 7.35 (d, J = 9.0 Hz, 1H), 4.45 (s, 2H), 4.37 (t, J = 5.1 Hz, 2H), 4.34 (s, 2H), 4.19 (t, J = 5.1 Hz, 2H), 3.98-3.87 (m, 1H), 2.76 (s, 3H), 2.69-2.42 (m, 4H), 1.76 (s, 3H), 1.10-0.99 (m, 1H), 0.93-0.72 (m, 4H) |
| 830 | MS (ESI) m/z 676.6 [M + 1]+; 1H NMR (400 MHz, DMSO-d6) δ 8.75 (d, J = 4.8 Hz, 1H), 8.71 (s, 1H), 8.66 (s, 1H), 7.77-7.74 (m, 1H), 7.71-7.66 (m, 2H), 7.54 (d, J = 4.8 Hz, 1H), 4.80 (s, 2H), 4.48 (s, 2H), 4.36 (s, 2H), 3.99-3.88 (m, 1H), 2.76 (s, 3H), 2.70-2.42 (m, 4H), 2.08 (s, 3H), 1.09-0.99 (m, 1H), 0.92-0.72 (m, 4H) |
| 831 | MS (ESI) m/z = 586.3 [M + 1]+; 1H-NMR (400 MHz, d6-DMSO) δ/ppm = 8.89 (s, 1H), 8.40 (s, 1H), 7.59 (dd, J = 9.0, 2.6, 1H), 7.43-7.41 (m, 2H), 7.35 (d, J = 9.0 Hz, 1H), 4.39 (t, J = 5.2 Hz, 2H), 4.39 (t, J = 5.2 Hz, 2H), 2.71 (s, 3H), 1.86 (s, 3H), 1.47 (s, 3H), 1.12-1.07 (m, 2H), 0.92-0.88 (m, 2H) |
| 837 | MS (ESI) m/z = 652.1 [M + 1]+; 1H;-NMR (400 MHz, d6-DMSO) δ/ppm = 8.79 (d, J = 4.8 Hz, 1H), 8.48 (s, 1H), 8.46 (s, 1H), 7.57 (dd, J = 8.9, 2.7 Hz, 1H), 7.44 (d, J = 4.8 Hz, 1H), 7.38 (d, J = 2.7 Hz, 1H), 7.35 (d, J = 8.9 Hz, 1H), 4.94-4.81 (m, 2H), 4.40 (t, J = 4.6 Hz, 2H), 4.28-4.19 (m, 4H), 3.88-3.77 (m, 2H), 1.80 (s, 3H) [remaining CH2-protons presumably obscured by water-peak] |

TABLE 1-continued

7-Aza-Thienylpyridine and Derivative Compounds

| Compound | | Characterization |
|---|---|---|
| 838 | 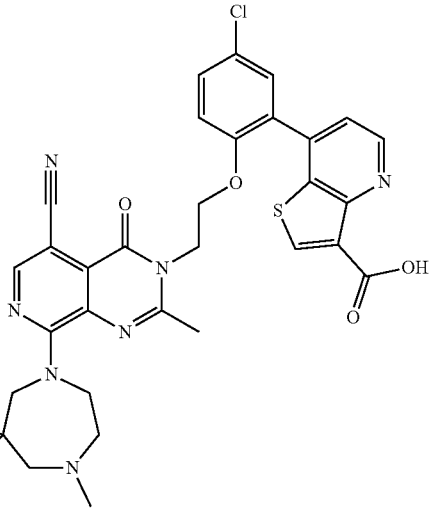 | MS (ESI) m/z = 666.4 [M + 1]+; 1H-NMR (400 MHz, d6-DMSO) δ/ppm = 8.81 (d, J = 4.8 Hz, 1H), 8.53 (s, 1H), 8.47 (s, 1H), 7.60 (dd, J = 8.8, 2.7 Hz, 1H), 7.47 (d, J = 4.8 Hz, 1H), 7.42 (d, J = 2.7 Hz, 1H), 7.38 (d, J = 8.8 Hz, 1H), 4.85 (bt, J = 12.4 Hz, 2H), 4.42 (t, J = 5.0 Hz, 2H), 4.24 (t, J = 5.0 Hz, 2H), 4.24-4.14 (b, 2H), 2.87-2.71 (b, 3H), 1.83 (s, 3H), remaining protons appear to be obscured by water peak |
| 839 | 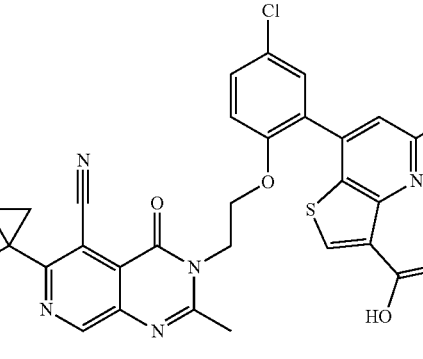 | MS (ESI) m/z = 640.0 [M + 1]+; 1H-NMR (400 MHz, d6-DMSO) δ/ppm = 9.00 (s, 1H), 8.38 (s, 1H), 7.59 (dd, J = 8.9, 2.8 Hz, 1H), 7.42 (d, J = 2.8 Hz, 1H), 7.41 (s, 1H), 7.35 (d, J = 8.9 Hz, 1H), 4.40 (t, J = 4.9 Hz, 2H), 4.26 (t, J = 4.9 Hz, 2H), 2.70 (s, 3H), 1.90 (s, 3H), 1.63-1.58 (m, 2H), 1.54-1.48 (m, 2H) |
| 840 | 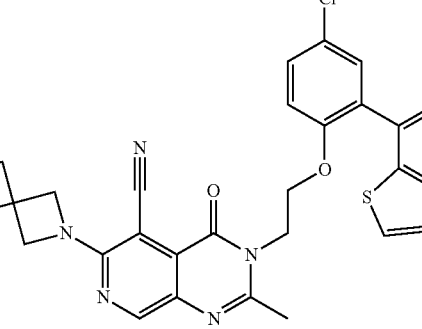 | MS (ESI) m/z = 696.3 [M + 1]+; 1H-NMR (400 MHz, d6-DMSO) δ/ppm = 8.78 (d, J = 4.8 Hz, 1H), 8.55 (s, 1H), 8.44 (s, 1H), 7.56 (dd, J = 8.9, 2.7 Hz, 1H), 7.42 (d, J = 4.8 Hz, 1H), 7.39 (d, J = 8.9 Hz, 1H), 4.44 (s, 4H), 4.34 (t, J = 5.0 Hz, 2H), 4.15 (t, J = 5.0 Hz, 2H), 3.89-3.51 (b), 3.12-2.76 (b), 1.73 (s, 3H) |

TABLE 1-continued

7-Aza-Thienylpyridine and Derivative Compounds

| Compound | | Characterization |
|---|---|---|
| 842 | 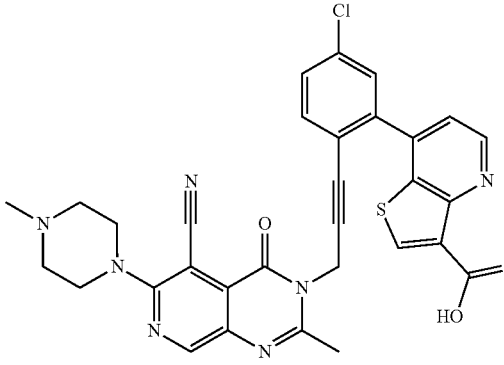 | MS (ESI) m/z = 610.3 [M + 1]+; 1H-NMR (400 MHz, d6-DMSO) δ/ppm = 9.98-9.88 (b, 1H), 8.84 (s, 1H), 8.75 (d, J = 4.8 Hz, 1H), 8.64 (s, 1H), 7.75 (d, J = 8.4 Hz, 1H), 7.71-7.65 (m, 2H), 7.53 (d, J = 4.8 Hz, 1H), 4.83 (s, 2H), 4.36 (bd, J = 14 Hz, 2H), 3.36-3.24 (m, 2H), 2.91 (s, 3H), 2.13 (s, 3H); remaining signals are obscured by water peak |
| 843 | 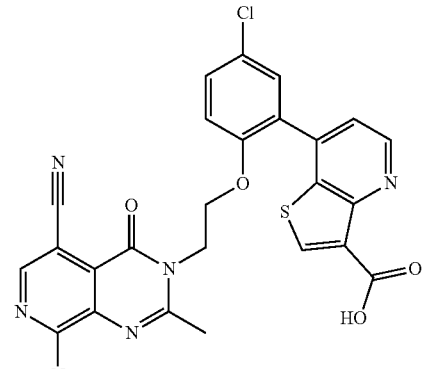 | MS (ESI) m/z = 712.5 [M + 1]+; 1H-NMR (400 MHz, d6-DMSO) δ/ppm = 9.98-9.79 (b, 1H), 8.81 (d, J = 4.9 Hz, 1H), 8.52 (s, 1H), 8.49 (s, 1H), 7.61 (dd, J = 8.9, 2.8 Hz, 1H), 7.48 (d, J = 4.9 Hz, 1H), 7.42 (d, J = 2.8 Hz, 1H), 7.39 (d, J = 8.9 Hz, 1H), 5.21-5.08 (m, 2H), 4.43 (t, J = 5.0 Hz, 2H), 4.23 (t, J = 5.0 Hz, 2H), 3.76-3.62 (m, partially obscured by water peak), 3.38-3.14 (m, partially obscured by water peak), 2.49-2.36 (m, 2H), 2.03-1.93 (m, 2H), 1.83 (s, 3H) |
| 844 | 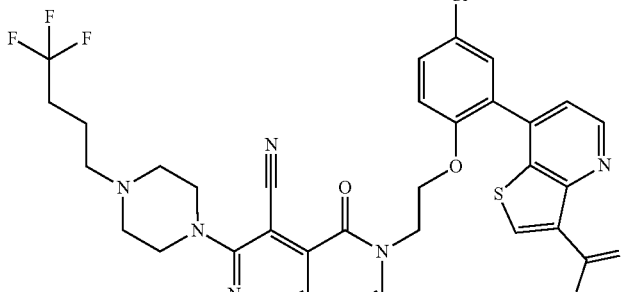 | MS (ESI) m/z = 712.3 [M + 1]+; 1H-NMR (400 MHz, d6-DMSO) δ/ppm = 9.98-9.78 (b, 1H), 8.83 (d, J = 4.9 Hz, 1H), 8.70 (s, 1H), 8.43 (s, 1H), 7.60 (dd, J = 8.9, 2.7 Hz, 1H), 7.48 (d, J = 4.9 Hz, 1H), 7.41 (d, J = 2.7 Hz, 1H), 7.38 (d, J = 8.9 Hz, 1H), 4.41 (t, J = 4.8 Hz, 2H), 4.38-4.28 (m, 2H), 4.24 (t, J = 4.8 Hz, 2H), 3.32-3.21 (m, partially obscured by water peak), 2.47-2.33 (m, 2H), 2.02-1.91 (m, 2H), 1.85 (s, 3H); remaining signals obscured by water peak |

TABLE 1-continued

7-Aza-Thienylpyridine and Derivative Compounds

| Compound | | Characterization |
|---|---|---|
| 845 | 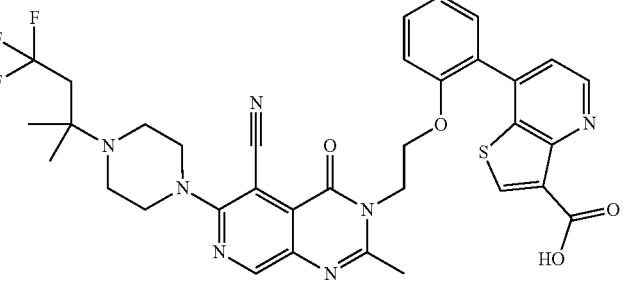 | MS (ESI) m/z = 726.3 [M + 1]+; 1H-NMR (400 MHz, d6-DMSO) δ/ppm = 10.29-9.70 (b, 1H), 8.83 (d, J = 4.7 Hz, 1H), 8.71 (s, 1H), 8.44 (s, 1H), 7.61 (dd, J = 8.9, 2.7 Hz, 1H), 7.48 (d, J = 4.7 Hz, 1H), 7.42 (d, J = 2.7 Hz, 1H), 7.37 (d, J = 8.9 Hz, 1H), 4.41 (t, J = 4.5 Hz, 2H), 4.24 (t, J = 4.5 Hz, 2H), 4.50-3.20 (broad signals, partially obscured by water peak), 2.99 (bq, J = 11 Hz, 2H), 1.85 (s, 3H), 1.52 (s, 6H) |
| 846 | 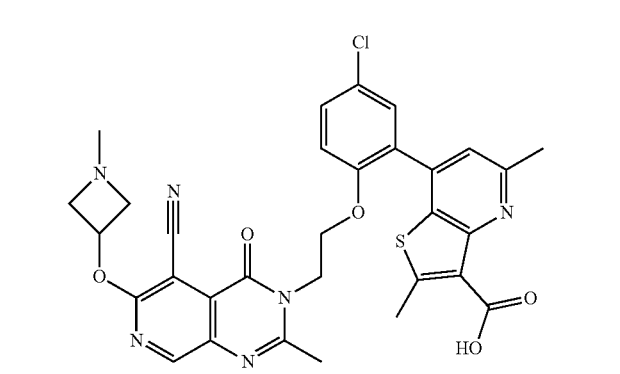 [SMILES: Cc1cc(-c2cc(Cl)ccc2OCCn2c(C)nc3cnc(OC4CN(C)C4)c(C#N)c3c2=O)c2sc(C)c(C(=O)O)c2n1] | MS (ESI) m/z 631.1 [M + 1]+; 1H NMR (400 MHz, DMSO-d6) δ 10.31 (s, 1H), 9.85 (s, 1H), 8.73 (d, J = 8.1 Hz, 1H), 7.60 (dd, J = 8.9, 2.7 Hz, 1H), 7.42 (s, 1H), 7.40-7.33 (m, 2H), 5.69 (d, J = 7.2 Hz, 1H), 5.60-5.42 (m, 1H), 4.78 (s, 1H), 4.59-4.46 (m, 2H), 4.41 (t, J = 5.2 Hz, 2H), 4.29 (q, J = 5.9, 5.4 Hz, 3H), 3.04-2.96 (m, 3H), 2.71 (s, 3H), 2.54 (d, J = 6.4 Hz, 3H), 2.11 (d, J = 22.1 Hz, 3H) |
| 848 |  | MS (ESI) m/z 671.9 [M + 1]+; 1H NMR (400 MHz, DMSO-d6) δ 8.55 (s, 1H), 7.56 (dd, J = 8.9, 2.7 Hz, 1H), 7.38-7.29 (m, 4H), 4.61-4.42 (m, 1H), 4.36 (t, J = 5.0 Hz, 2H), 4.20 (t, J = 5.0 Hz, 2H), 3.18-3.09 (m, 2H), 3.04 (s, 3H), 2.78 (d, J = 4.6 Hz, 3H), 2.67 (s, 4H), 2.17-1.94 (m, 3H), 1.92 (s, 3H) |
| 850 |  | LCMS: 574.6 [M + H]+; 1H NMR (400 MHz, DMSO-d6) δ 8.46 (s, 1H), 7.56 (dd, J = 8.9, 2.7 Hz, 1H), 7.40-7.28 (m, 3H), 4.39 (t, J = 5.1 Hz, 2H), 4.22 (t, J = 5.0 Hz, 2H), 3.00 (q, J = 7.6 Hz, 2H), 2.70 (s, 3H), 2.66 (s, 3H), 1.90 (s, 3H), 1.28 (t, J = 7.5 Hz, 3H) |

TABLE 1-continued

7-Aza-Thienylpyridine and Derivative Compounds

| Compound | | Characterization |
|---|---|---|
| 851 | 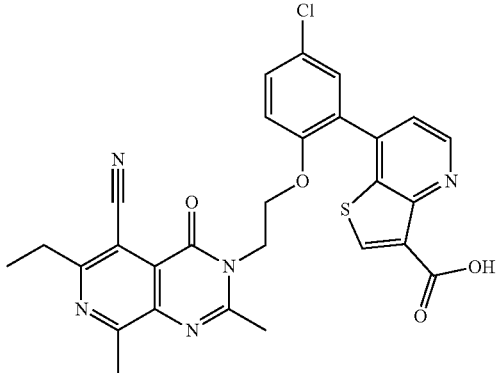 [SMILES: CCc1nc(C)c2nc(C)n(CCOc3ccc(Cl)cc3-c3ccnc4c(C(=O)O)csc34)c(=O)c2c1C#N] | LCMS: 560.4 [M + H]+; 1H NMR (400 MHz, DMSO-d6) δ 8.78 (d, J = 4.8 Hz, 1H), 8.46 (s, 1H), 7.56 (dd, J = 8.9, 2.7 Hz, 1H), 7.43 (d, J = 4.8 Hz, 1H), 7.39 (d, J = 2.7 Hz, 1H), 7.33 (d, J = 9.0 Hz, 1H), 4.39 (t, J = 5.0 Hz, 2H), 4.21 (t, J = 5.0 Hz, 2H), 3.01 (q, J = 7.5 Hz, 2H), 2.71 (s, 3H), 1.80 (s, 3H), 1.28 (t, J = 7.5 Hz, 3H) |
| 854 | 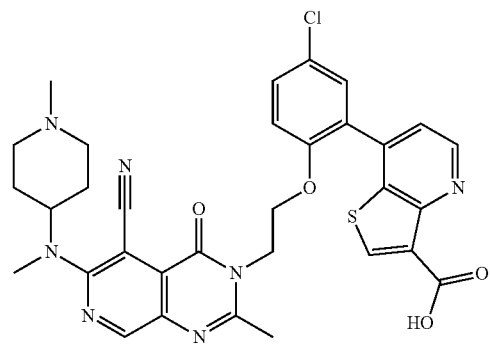 [SMILES: Cc1nc2cnc(N(C)C3CCN(C)CC3)c(C#N)c2c(=O)n1CCOc1ccc(Cl)cc1-c1ccnc2c(C(=O)O)csc12] | MS (ESI) m/z 644.3 [M + 1]+; 1H NMR (400 MHz, DMSO-d6) δ 8.82 (d, J = 4.8 Hz, 1H), 8.61 (s, 1H), 8.40 (s, 1H), 7.60 (dd, J = 8.9, 2.7 Hz, 1H), 7.47 (d, J = 4.8 Hz, 1H), 7.42 (d, J = 2.7 Hz, 1H), 7.36 (d, J = 9.0 Hz, 1H), 4.39 (t, J = 5.0 Hz, 2H), 4.21 (s, 2H), 3.08 (s, 3H), 2.81 (d, J = 4.7 Hz, 3H), 2.07 (d, J = 8.4 Hz, 5H), 1.77 (s, 3H) |
| 857 | 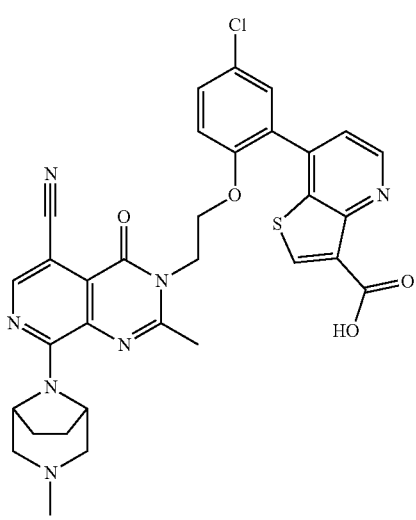 [SMILES: Cc1nc2c(N3C4CCC3CN(C)C4)ncc(C#N)c2c(=O)n1CCOc1ccc(Cl)cc1-c1ccnc2c(C(=O)O)csc12] | LCMS: 642.7 [M + H]+; 1H NMR (400 MHz, DMSO-d6) δ 9.57 (s, 1H), 8.80 (d, J = 4.8 Hz, 1H), 8.59 (s, 1H), 8.46 (s, 1H), 7.61 (dd, J = 8.9, 2.7 Hz, 1H), 7.49-7.34 (m, 3H), 4.43 (t, J = 5.0 Hz, 2H), 4.24 (d, J = 5.0 Hz, 2H), 3.35 (t, J = 10.8 Hz, 3H), 2.79 (d, J = 3.4 Hz, 3H), 2.23 (s, 2H), 2.08 (d, J = 8.1 Hz, 2H), 1.86 (s, 3H) |

TABLE 1-continued

7-Aza-Thienylpyridine and Derivative Compounds

| Compound | | Characterization |
|---|---|---|
| 860 | 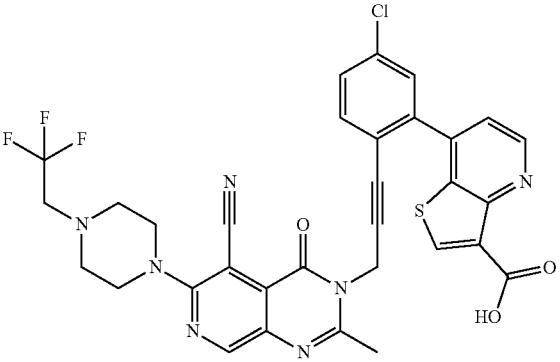 | LCMS: 678.5 [M + H]+; 1H NMR (400 MHz, DMSO-d6) δ 8.81-8.73 (m, 2H), 8.66 (s, 1H), 7.76 (d, J = 9.0 Hz, 1H), 7.69 (dd, J = 6.2, 2.3 Hz, 2H), 7.54 (d, J = 4.8 Hz, 1H), 4.82 (s, 2H), 3.69 (t, J = 4.7 Hz, 4H), 3.30 (q, J = 10.2 Hz, 2H), 2.84 (t, J = 4.8 Hz, 4H), 2.07 (s, 3H) |
| 861 | 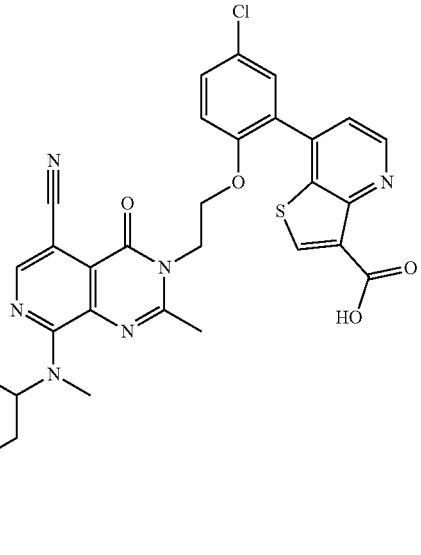 | LCMS: 712.7 [M + H]+; 1H NMR (400 MHz, DMSO-d6) δ 8.79 (d, J = 4.8 Hz, 1H), 8.50 (s, 1H), 8.37 (s, 1H), 7.60 (dd, J = 9.0, 2.7 Hz, 1H), 7.47 (d, J = 4.8 Hz, 1H), 7.43 (d, J = 2.6 Hz, 1H), 7.37 (d, J = 9.0 Hz, 1H), 4.69 (s, 1H), 4.43 (t, J = 5.1 Hz, 2H), 4.22 (d, J = 5.1 Hz, 2H), 3.22 (s, 1H), 3.13 (s, 3H), 3.04 (d, J = 11.2 Hz, 2H), 2.00-1.81 (m, 1H), 1.78 (s, 3H) |
| 862 | 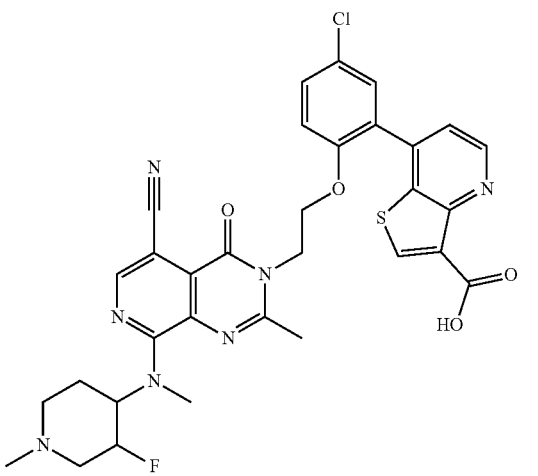 [SMILES: Cc1nc2c(N(C)C3CCN(C)CC3F)ncc(C#N)c2c(=O)n1CCOc1ccc(Cl)cc1-c1ccnc2c(C(=O)O)csc12] | LCMS: 662.5 [M + H]+; 1H NMR (400 MHz, DMSO-d6) δ 9.80 (s, 1H), 8.80 (d, J = 4.8 Hz, 1H), 8.45 (d, J = 9.3 Hz, J = 8.9, 2.7 Hz, 1H), 7.48-7.41 (m, 2H), 7.39 (d, J = 9.0 Hz, 1H), 5.50 (s, 1H),J = 11.4 Hz, 1H), 5.02 (d, J = 12.3 Hz, 1H), 4.44 (q, J = 4.8 Hz, 2H), J = 5.1 Hz, 2H), 3.85 (d, J = 12.3 Hz, 1H), 3.26 (d, J = 1.6 Hz, 3H), 2.87 (d, J = 4.1. 12H), 7.61 (dd, 5.38 (s, 1H), 5.10 (d, 4.25 (t, Hz, 3H), 2.20-2.03 (m, 1H), 1.80 (s, 3H) |

TABLE 1-continued

7-Aza-Thienylpyridine and Derivative Compounds

| Compound | | Characterization |
|---|---|---|
| 863 | | LCMS: 670.2 [M + H]+; 1H NMR (400 MHz, DMSO-d6) δ 9.64 (s, 1H), 9.51 (s, 1H), 8.82-8.75 (m, 1H), 8.44-8.38 J = 8.9, 2.6 Hz, 1H), 7.49 (t, J = 5.0 Hz, 1H), 7.44 (dd, J = 9.0, 2.7 Hz, 1H),J = 9.0 Hz, 1H), 5.18 (dq, J = 11.7, 5.8 Hz, 1H), 5.05 (s, 1H), 4.44 (q, J = 5.2 Hz, 2H), J = 5.0 Hz, 2H), 4.05-3.78 (m, 2H), 3.17 (d, J = 9.9 Hz, 1H), 3.07 (s, 3H), 2.72-J = 3.4 Hz, 5H) |
| 864 | | LCMS: 694.5 [M + H]+; 1H NMR (400 MHz, DMSO-d6) δ 8.75 (d, J = 4.9 Hz, 1H), 8.40 (d, J = 2.3 Hz, 2H), 7.58 (dd, J = 8.9, 2.7 Hz, 1H), 7.44 (d, J = 4.8 Hz, 1H), 7.40-7.32 (m, 2H), 6.55 (t, J = 52.5 Hz, 2H), 4.89 (s, 1H), 4.48-4.32 (m, 2H), 4.21 (t, J = 5.3 Hz, 2H), 3.10 (s, 3H), 2.91 (s, 4H), 2.33-2.08 (m, 4H), 2.05-1.88 (m, 3H), 1.74 (s, 3H) |
| 865 | | LCMS: 712.6 [M + H]+; 1H NMR (400 MHz, DMSO-d6) δ 8.83 (d, J = 4.8 Hz, 1H), 8.60 (s, 1H), 8.45 (s, 1H), 7.60 (dd, J = 8.9, 2.7 Hz, 1H), 7.48 (d, J = 4.8 Hz, 1H), 7.43 (d, J = 2.7 Hz, 1H), 7.36 (d, J = 9.0 Hz, 1H), 4.38 (t, J = 5.0 Hz, 2H), 4.33-4.13 (m, 3H), 3.07 (s, 3H), 2.73-2.52 (m, 3H), 2.03-1.82 (m, 2H), 1.77 (d, J = 28.9 Hz, 5H), 1.25 (d, J = 16.2 Hz, 1H) |

TABLE 1-continued

7-Aza-Thienylpyridine and Derivative Compounds

| Compound | | Characterization |
|---|---|---|
| 866 | 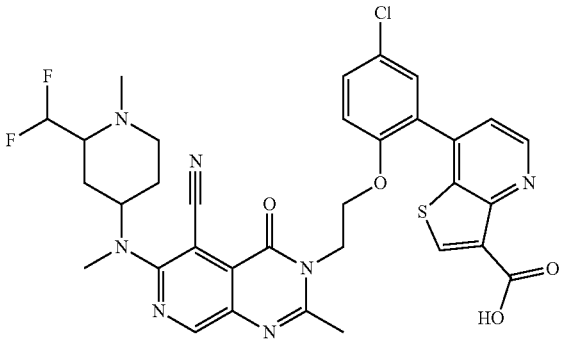 [SMILES: Cc1nc2cnc(N(C)C3CCN(C)C(C(F)F)C3)c(C#N)c2c(=O)n1CCOc1ccc(Cl)cc1-c1ccnc2c(C(=O)O)csc12] | LCMS: 694.5 [M + H]+; 1H NMR (400 MHz, DMSO-d6) δ 8.83 (d, J = 4.8 Hz, 1H), 8.63 (s, 1H), 8.42 (s, 1H), 7.60 (dd, J = 8.9, 2.7 Hz, 1H), 7.47 (d, J = 4.8 Hz, 1H), 7.43 (d, J = 2.7 Hz, 1H), 7.36 (d, J = 9.0 Hz, 1H), 6.49 (d, J = 52.7 Hz, 1H), 4.64 (d, J = 15.0 Hz, 1H), 4.39 (t, J = 5.0 Hz, 2H), 4.22 (t, J = 5.1 Hz, 2H), 3.09 (s, 3H), 2.94 (s, 3H), 1.76 (s, 3H) |
| 868 | 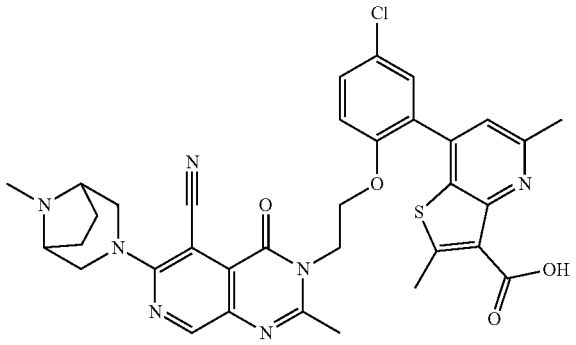 | MS (ESI) m/z 670.5 [M + 1]+; 1H NMR (400 MHz, DMSO-d6) δ 9.50 (s, 1H), 8.64 (s, 1H), 7.56 (dd, J = 8.9, 2.7 Hz, 1H), 7.38-7.30 (m, 3H), 4.90 (s, 2H), 4.36 (t, J = 5.1 Hz, 2H), 4.22 (t, J = 5.1 Hz, 2H), 3.56 (d, J = 12.1 Hz, 2H), 3.30 (t, J = 10.9 Hz, 2H), 2.80 (s, 2H), 2.67 (s, 3H), 2.02 (d, J = 2.5 Hz, 4H), 1.93 (s, 3H) |
| 869 | 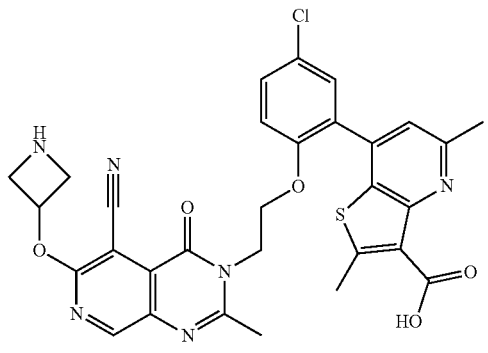 [SMILES: Cc1cc(-c2cc(Cl)ccc2OCCn2c(C)nc3cnc(OC4CNC4)c(C#N)c3c2=O)c2sc(C)c(C(=O)O)c2n1] | LCMS: 1.54 Min, 617.5 [M + H]-; 1H NM:R (400 MHz, DMSO-d6) δ 9.07 (s, 1H), 8.80 (s, 1H), 8.72 (s, 1H), 7.60 (dd, J = 8.9, 2.7 Hz, 1H), 7.44-7.33 (m, 3H), 5.62 (p, J = 6.2 Hz, 1H), 4.58-4.45 (m, 2H), 4.41 (t, J = 5.1 Hz, 2H), 4.25 (dt, J = 20.4, 5.8 Hz, 4H), 2.71 (s, 3H), 2.54 (s, 3H), 2.11 (s, 3H) |
| 871 | 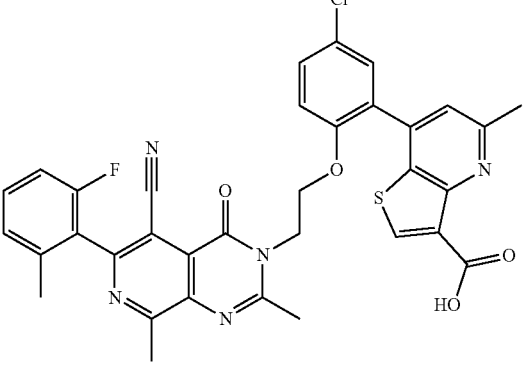 | LCMS (ESI) m/z 654.8 [M + 1]+; 1H NMR (400 MHz, DMSO-d6) δ 8.50 (s, 1H), 7.57 (dd, J = 8.9, 2.7 Hz, 1H), 7.51-7.39 (m, 3H), 7.34 (d, J = 9.0 Hz, 1H), 7.26-7.14 (m, 2H), 4.43 (td, J = 8.9, 7.7, 3.7 Hz, 1H), 4.37 (dd, J = 10.3, 4.5 Hz, 1H), 4.23 (t, J = 5.1 Hz, 2H), 2.75 (s, 3H), 2.68 (s, 3H), 2.12 (s, 3H), 1.83 (s, 3H) |

TABLE 1-continued

7-Aza-Thienylpyridine and Derivative Compounds

| Compound | | Characterization |
|---|---|---|
| 872 | 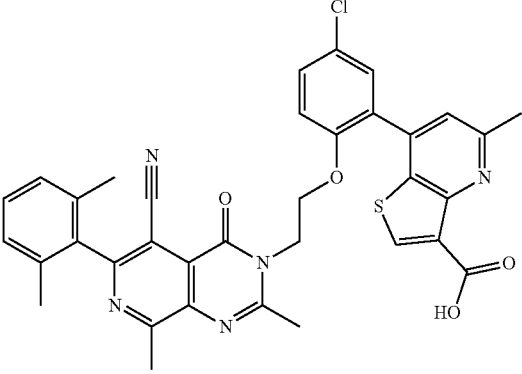 [SMILES: Cc1cc(-c2cc(Cl)ccc2OCCn2c(C)nc3c(C)nc(-c4c(C)cccc4C)c(C#N)c3c2=O)c2scc(C(=O)O)c2n1] | LCMS (ESI) m/z 650.8 [M + 1]+; 1H NMR (400 MHz, DMSO-d6) δ 8.47 (s, 1H), 7.60 (dd, J = 8.9, 2.7 Hz, 1H), 7.49-7.45 (m, 2H), 7.38 (d, J = 9.0 Hz, 1H), 7.30 (dd, J = 8.2, 6.9 Hz, 1H), 7.21-7.16 (m, 2H), 4.45 (t, J = 5.0 Hz, 2H), 4.26 (t, J = 5.0 Hz, 2H), 2.77 (s, 3H), 2.72 (s, 3H), 2.00 (s, 6H), 1.84 (s, 3H) |
| 873 | 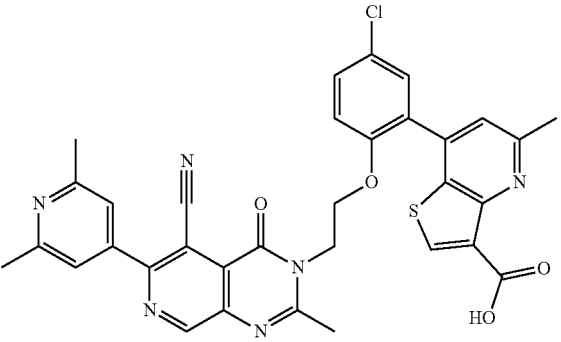 | LCMS (ESI) m/z 637.0 [M + 1]+; 1H NMR (400 MHz, DMSO-d6) δ 8.48 (s, 1H), 7.60 (dd, J = 8.9, 2.7 Hz, 1H), 7.49-7.43 (m, 2H), 7.38 (d, J = 9.0 Hz, 1H), 7.30 (dd, J = 8.2, 6.9 Hz, 1H), 7.19 (d, J = 8.0 Hz, 2H), 4.45 (t, J = 5.0 Hz, 2H), 4.26 (t, J = 4.9 Hz, 2H), 2.77 (s, 3H), 2.72 (s, 3H), 2.00 (s, 6H) |
| 874 | 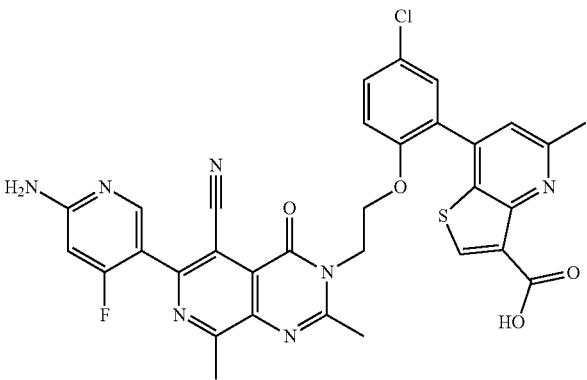 [SMILES: Cc1cc(-c2cc(Cl)ccc2OCCn2c(C)nc3c(C)nc(-c4cnc(N)cc4F)c(C#N)c3c2=O)c2scc(C(=O)O)c2n1] | LCMS (ESI) m/z 656.0 [M + 1]+; 1H NMR (400 MHz, DMSO-d6) δ 9.36 (s, 1H), 8.54 (s, 1H), 8.30 (dd, J = 9.3, 5.7 Hz, 1H), 7.66-7.57 (m, 2H), 7.48-7.33 (m, 3H), 6.96 (ddd, J = 8.2, 5.8, 2.3 Hz, 1H), 4.43 (t, J = 5.0 Hz, 2H), 4.24 (t, J = 5.0 Hz, 2H), 2.72 (d, J = 4.6 Hz, 6H), 1.87 (s, 3H) |
| 875 | 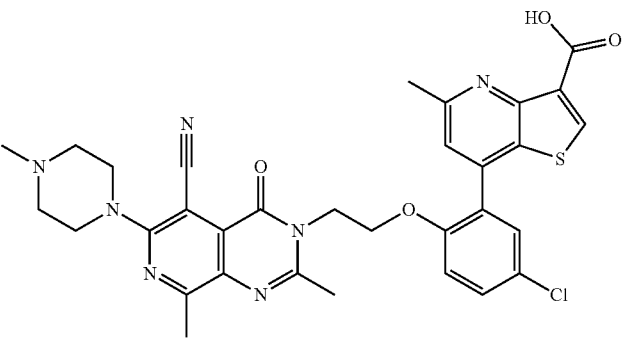 [SMILES: Cc1cc(-c2cc(Cl)ccc2OCCn2c(C)nc3c(C)nc(N4CCN(C)CC4)c(C#N)c3c2=O)c2scc(C(=O)O)c2n1] | LCMS (ESI) m/z 644.1 [M + 1]+; 1H NMR (400 MHz, Chloroform-d) δ 8.48 (s, 1H), 7.61 (dd, J = 8.9, 2.7 Hz, 1H), 7.43 (s, 1H), 7.42-7.37 (m, 2H), 4.42 (d, J = 5.3 Hz, 2H), 4.33 (s, 1H), 4.30 (s, 1H), 4.25 (d, J = 5.0 Hz, 2H), 3.61 (d, J = 12.2 Hz, 2H), 3.44 (d, J = 13.6 Hz, 4H), 3.24 (d, J = 11.0 Hz, 1H), 2.92 (d, J = 4.4 Hz, 3H), 2.73 (s, 3H), 2.66 (s, 4H), 1.98 (s, 3H) |

TABLE 1-continued

7-Aza-Thienylpyridine and Derivative Compounds

| Compound | | Characterization |
|---|---|---|
| 878 | 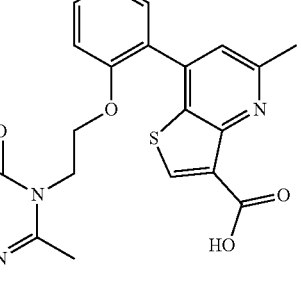 | LCMS (ESI) m/z 630.1 [M + 1]+; 1H NMR (400 MHz, DMSO-d6) δ 8.83 (s, 1H), 8.44 (s, 1H), 7.57 (dd, J = 8.9, 2.7 Hz, 1H), 7.41-7.31 (m, 2H), 4.39 (d, J = 10.4 Hz, 1H), 4.39 (s, 1H), 4.20 (s, 1H), 3.79 (t, J = 4.9 Hz, 2H), 3.28 (s, 2H), 2.68 (s, 2H), 2.62 (s, 2H), 1.94 (s, 2H) |
| 882 | 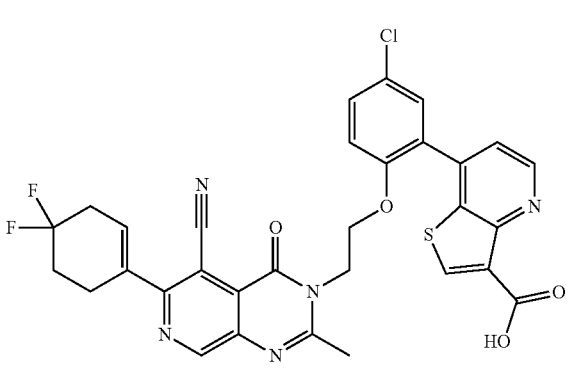 [SMILES: Cc1nc2cnc(C3=CCC(F)(F)CC3)c(C#N)c2c(=O)n1CCOc1ccc(Cl)cc1-c1ccnc2c(C(=O)O)csc12] | LCMS (ESI) m/z 634.2 [M + 1]+; 1H NMR (400 MHz, DMSO-d6) δ 8.91 (s, 1H), 8.80 (d, J = 4.8 Hz, 1H), 8.35 (s, 1H), 7.56 (dd, J = 8.9, 2.7 Hz, 1H), 7.47-7.38 (m, 2H), 7.32 (d, J = 9.0 Hz, 1H), 6.27 (s, 1H), 4.37 (t, J = 5.0 Hz, 2H), 4.21 (t, J = 4.9 Hz, 2H), 2.87-2.75 (m, 4H), 2.22 (dq, J = 14.1, 6.8 Hz, 2H), 1.75 (s, 3H). |
| 883 | 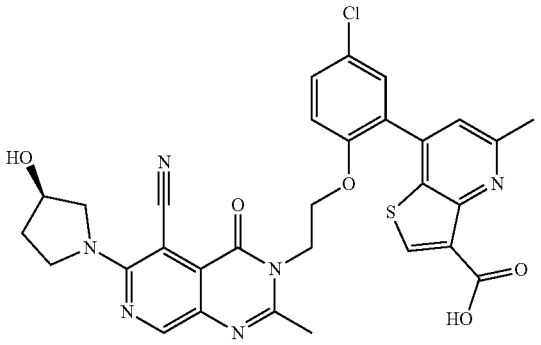 [SMILES: Cc1cc(-c2cc(Cl)ccc2OCCn2c(C)nc3cnc(N4CC[C@@H](O)C4)c(C#N)c3c2=O)c2scc(C(=O)O)c2n1] | LCMS (ESI) m/z 617.1 [M + 1]+.; 1H NMR (400 MHz, DMSO-d6) δ 8.53 (s, 1H), 8.47 (d, J = 0.8 Hz, 1H), 7.55 (dd, J = 8.9, 2.7 Hz, 1H), 7.41-7.34 (m, 2H), 7.39-7.28 (m, 2H), 7.44-4.40 (m, 2H), 4.34 (t, J = 5.1 Hz, 2H), 4.16 (t, J = 5.1 Hz, 2H), 3.86 (dd, J = 11.5, 4.8 Hz, 2H), 3.73 (ddd, J = 11.1, 8.1, 3.4 Hz, 1H), 3.54 (d, J = 11.6 Hz, 1H), 2.67 (s, 3H), 2.05-1.94 (m, 1H), 1.90 (s, 2H), 1.76 (s, 3H) |
| 884 | 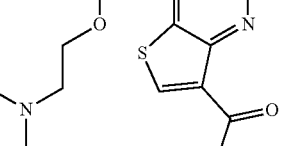 | LCMS (ESI) m/z 614.9 [M + 1]+; 1H NMR (400 MHz, DMSO-d6) δ 8.61 (s, 1H), 8.45 (s, 1H), 7.56 (dd, J = 8.9, 2.7 Hz, 1H), 7.39-7.29 (m, 3H), 4.36 (t, J = 5.1 Hz, 2H), 4.24 (s, 2H), 4.22 – 4.14 (m, 4H), 2.71 (t, J = 7.7 Hz, 2H), 2.68 (s, 3H), 1.86 (s, 3H) |

TABLE 1-continued

7-Aza-Thienylpyridine and Derivative Compounds

| Compound | | Characterization |
|---|---|---|
| 885 | 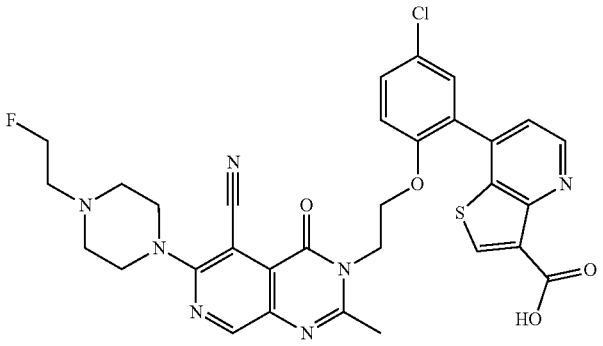 | LCMS (ESI) m/z 662.1 [M + 1]+; 1H NMR (400 MHz, DMSO-d6) δ 8.79 (d, J = 4.8 Hz, 1H), 8.46 (s, 1H), 7.57 (dd, J = 9.0, 2.6 Hz, 1H), 7.44 (d, J = 4.8 Hz, 1H), 7.39-7.32 (m, 2H), 4.98-4.74 (m, 2H), 4.40 (t, J = 5.1 Hz, 2H), 4.29 (s, 2H), 4.21 (t, J = 5.1 Hz, 2H), 3.64 (s, 2H), 3.56 (s, 2H), 3.47 (s, 2H), 3.31 (s, 2H), 2.66 (s, 3H), 1.86 (s, 3H) |
| 886 | 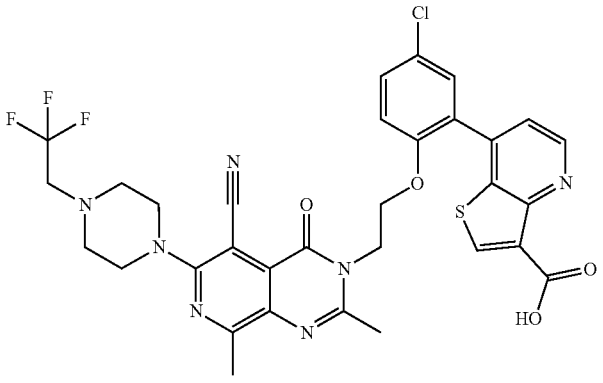 [SMILES: Cc1nc(N2CCN(CC(F)(F)F)CC2)c(C#N)c2c(=O)n(CCOc3ccc(Cl)cc3-c3ccnc4c(C(=O)O)csc34)c(C)nc12] | LCMS (ESI) m/z 698.3 [M + 1]+; 1H NMR (400 MHz, DMSO-d6) δ 8.82 (d, J = 4.9 Hz, 1H), 8.54 (s, 1H), 7.60 (dd, J = 8.8, 2.8 Hz, 1H), 7.48 (d, J = 4.8 Hz, 1H), 7.41 (d, J = 2.7 Hz, 1H), 7.37 (d, J = 9.0 Hz, 1H), 4.41 (s, 2H), 4.21 (s, 2H), 3.65 (s, 5H), 3.29 (q, J = 10.2 Hz, 2H), 2.82 (s, 4H), 2.64 (s, 3H), 1.80 (s, 3H) |
| 888 | 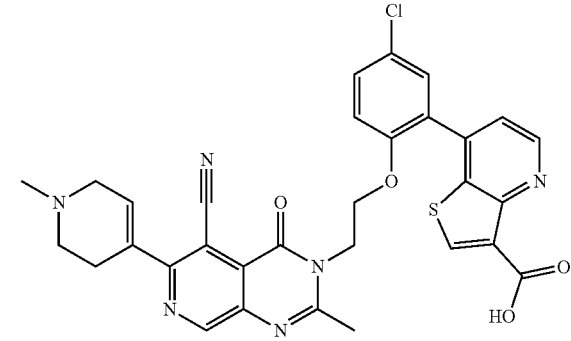 [SMILES: Cc1nc2cnc(C3=CCN(C)CC3)c(C#N)c2c(=O)n1CCOc1ccc(Cl)cc1-c1ccnc2c(C(=O)O)csc12] | LCMS (ESI) m/z 613.4 [M + 1]+; 1H NMR (400 MHz, DMSO-d6) δ 9.92 (s, 1H), 8.98 (s, 1H), 8.83 (d, J = 4.8 Hz, 1H), 8.36 (s, 1H), 7.60 (dd, J = 8.9, 2.7 Hz, 1H), 7.46 (dd, J = 13.2, 3.7 Hz, 2H), 7.36 (d, J = 9.0 Hz, 1H), 6.51 (s, 1H), 4.40 (d, J = 5.3 Hz, 2H), 4.27 (d, J = 5.0 Hz, 2H), 4.14 (d, J = 17.9 Hz, 1H), 3.91 (s, 1H), 3.69 (d, J = 11.9 Hz, 1H), 3.35 (s, 1H), 2.95 (d, J = 4.5 Hz, 6H), 1.81 (s, 3H) |
| 889 | 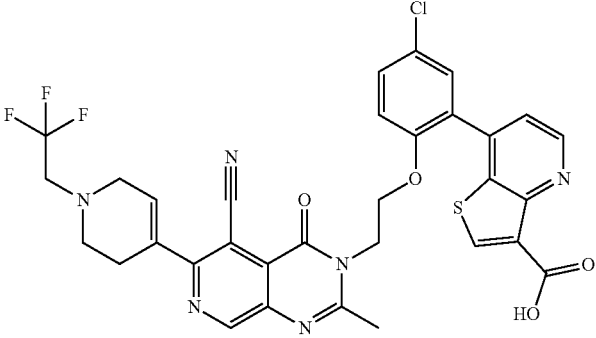 [SMILES: Cc1nc2cnc(C3=CCN(CC(F)(F)F)CC3)c(C#N)c2c(=O)n1CCOc1ccc(Cl)cc1-c1ccnc2c(C(=O)O)csc12] | 1H NMR (400 MHz, DMSO-d6) δ 8.91 (s, 1H), 8.80 (d, J = 4.8 Hz, 1H), 8.37 (s, 1H), 7.56 (d, J = 8.8 Hz, 1H), 7.43 (d, J = 15.4 Hz, 2H), 7.32 (d, J = 9.0 Hz, 1H), 6.40 (s, 1H), 4.37 (s, 2H), 4.21 (s, 2H), 3.35 (d, J = 9.9 Hz, 1H), 2.91 (s, 3H), 2.66 (s, 1H), 1.75 (s, 3H) |

TABLE 1-continued

7-Aza-Thienylpyridine and Derivative Compounds

| Compound | | Characterization |
|---|---|---|
| 890 | 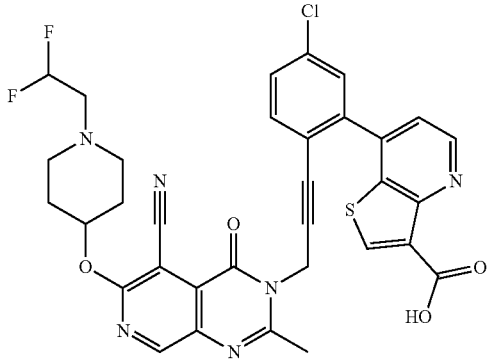 | LCMS (ESI) m/z 469.5 [M + 1]+; 1H NMR (400 MHz, DMSO-d6) δ 8.87 (s, 1H), 8.76 (d, J = 4.8 Hz, 1H), 8.61 (s, 1H), 7.76 (d, J = 8.2 Hz, 1H), 7.76-7.65 (m, 2H), 7.55 (d, J = 4.8 Hz, 1H), 6.51 (t, J = 54 Hz, 1H), 5.43 (s, 1H), 4.84 (s, 2H), 2.28 (s, 2H), 2.18 (s, 1H), 2.12 (s, 3H) |
| 891 | 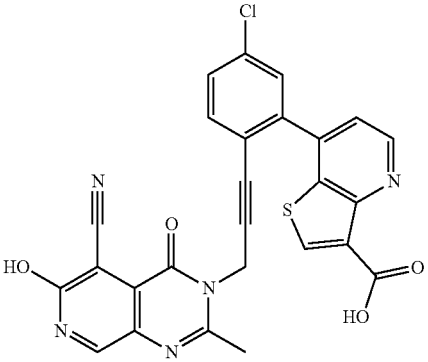 [SMILES: Cc1nc2cnc(O)c(C#N)c2c(=O)n1CC#Cc1ccc(Cl)cc1-c1ccnc2c(C(=O)O)csc12] | LCMS (ESI) m/z 528.1 [M + 1]+; 1H NMR (400 MHz, DMSO-d6) δ 8.80 (d, J = 4.8 Hz, 1H), 8.69 (s, 1H), 7.76 (d, J = 9.1 Hz, 1H), 7.72-7.64 (m, 2H), 7.56 (d, J = 4.8 Hz, 1H), 4.78 (s, 2H), 1.92 (s, 3H) |
| 892 | 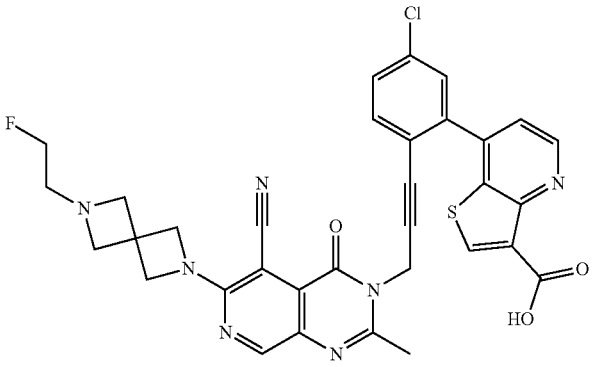 [SMILES: Cc1nc2cnc(N3CC4(CN(CCF)C4)C3)c(C#N)c2c(=O)n1CC#Cc1ccc(Cl)cc1-c1ccnc2c(C(=O)O)csc12] | LCMS (ESI) m/z 654.1 [M + 1]+; 1H NMR (400 MHz, DMSO-d6) 610.05 (s, 1H), 8.73-8.67 (m, 2H), 8.63 (s, 1H), 7.72 (dd, J = 8.1, 0.8 Hz, 1H), 7.73-7.61 (m, 2H), 7.51 (d, J = 4.8 Hz, 1H), 4.78 (s, 2H), 4.74-4.67 (m, 1H), 4.64-4.55 (m, 3H), 4.49 (s, 2H), 4.40 (t, J = 6.9 Hz, 4H), 3.59 (d, J = 4.6 Hz, 1H), 3.52 (s, 1H), 2.07 (s, 3H), 1.21 (s, 1H) |
| 893 | 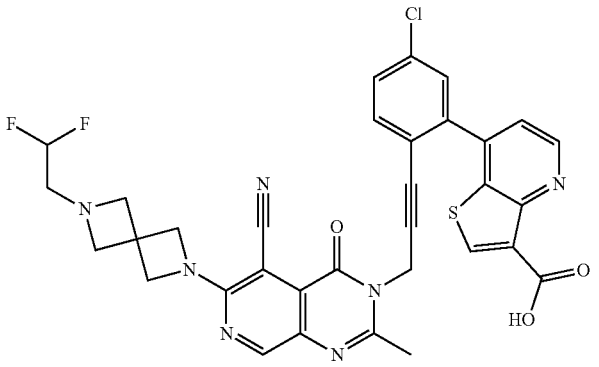 [SMILES: Cc1nc2cnc(N3CC4(CN(CC(F)F)C4)C3)c(C#N)c2c(=O)n1CC#Cc1ccc(Cl)cc1-c1ccnc2c(C(=O)O)csc12] | LCMS (ESI) m/z 672.2 [M + 1]+; 1H NMR (400 MHz, DMSO-d6) δ 8.75-8.67 (m, 2H), 8.63 (s, 1H), 7.72 (dd, J = 8.1, 0.8 Hz, 1H), 7.69-7.61 (m, 2H), 7.51 (d, J = 4.8 Hz, 1H), 6.34 (t, J = 52 Hz, 1 H), 4.78 (s, 2H), 4.50 (s, 5H), 4.45 (s, 3H), 3.81 (s, 1H), 2.94 (s, 2H), 2.35 (s, 6H), 2.07 (s, 3H) |

TABLE 1-continued

7-Aza-Thienylpyridine and Derivative Compounds

| Compound | Characterization |
|---|---|
| 894 | LCMS (ESI) m/z 720.1 [M + 1]+; 1H NMR (400 MHz, DMSO-d6) δ 10.05(s, 1H), 8.75-8.71 (m, 2H), 8.66 (s, 1H), 7.78-7.73 (m, 1H), 7.72-7.64 (m, 2H), 7.54 (d, J = 4.8 Hz, 1H), 4.81 (s, 2H), 4.65 (s, 2H), 4.52 (s, 2H), 4.44 (d, J = 3.7 Hz, 4H), 4.37-4.29 (m, 2H), 3.61 (s, 2H), 2.10 (s, 3H) |
| 895 | MS (ESI) m/z 650.4 [M + 1]+; 1H NMR (400 MHz, DMSO-d6) δ 9.78 (s, 1H), 8.85 (s, 1H), 8.75 (d, J = 4.8 Hz, 1H), 8.65 (s, 1H), 7.75 (d, J = 8.4 Hz, 1H), 7.69 (dd, J = 8.4, 2.2 Hz, 1H), 7.66 (d, J = 2.1 Hz, 1H), 7.53 (d, J = 4.8 Hz, 1H), 4.84 (s, 2H), 4.38 (d, J = 14.1 Hz, 2H), 3.75 (d, J = 12.0 Hz, 2H), 3.60-3.48 (m, 2H), 3.33-3.23 (m, 2H), 3.17-3.11 (m, 2H), 2.14 (s, 3H), 1.18-1.08 (m, 1H), 0.72-0.66 (m, 2H), 0.45-0.37 (m, 2H) |
| 897 | MS (ESI) m/z 562.07 [M + 1]+; 1H NMR (400 MHz, DMSO-d6) δ 13.59 (bs, 1H), 8.72 (s, 1H), 8.42 (s, 1H), 7.58 (dd, J = 2.56, 8.72 Hz, 1H), 7.40 (bs, 2H), 7.34 (d, J = 8.92 Hz, 1H), 4.39 (t, J = 4.00 Hz, 2H), 4.39 (t, J = 4.52 Hz, 2H), 4.11 (s, 3H), 2.70 (s, 3H), 1.85 (s, 3H) |
| 898 | MS (ESI) m/z 586.06 [M + 1]+; 1H NMR (400 MHz, DMSO-d6) δ 13.5 (bs, 1H), 8.49 (s, 1H), 7.60-7.57 (dd, J = 4.0, 8.8 Hz, 1H), 7.39 (m, 3H), 4.44 (t, J = 6.0 Hz, 2H), 4.25 (t, J = 3.6 Hz, 2H), 2.68 (s, 6H), 1.90 (s, 3H), 1.18-1.16 (m, 4H) |

TABLE 1-continued

7-Aza-Thienylpyridine and Derivative Compounds

| Compound | | Characterization |
|---|---|---|
| 900 | 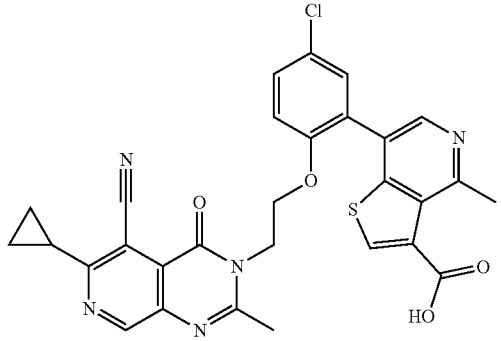 [SMILES: Cc1ncc(-c2cc(Cl)ccc2OCCn2c(C)nc3cnc(C4CC4)c(C#N)c3c2=O)c2scc(C(=O)O)c12] | MS (ESI) m/z 572.02 [M + 1]+; 1H NMR (400 MHz, DMSO-d6) δ 13.39 (bs, 1H), 8.91 (s, 1H), 8.35 (s, 1H), 8.07 (s, 1H), 7.60-7.57 (dd, J = 7.48, 2.56 Hz, 1H), 7.41 (d, J = 2.52 Hz, 1H), 7.33 (d, J = 8.92 Hz, 1H), 4.41-4.35 (m, 2H), 4.30-4.20 (m, 2H), 3.01 (s, 3H), 2.67-2.60 (m, 1H), 1.81 (s, 3H), 1.28-1.12 (m, 4H) |
| 910 | 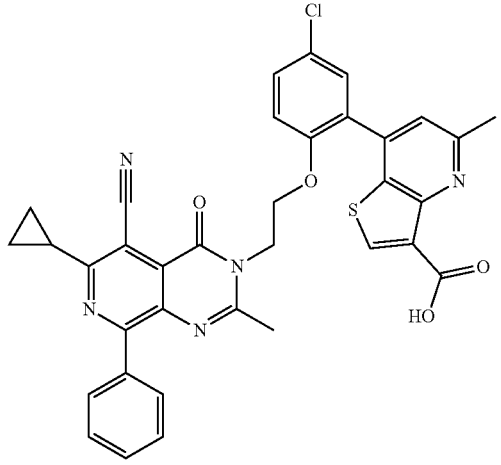 [SMILES: Cc1cc(-c2cc(Cl)ccc2OCCn2c(C)nc3c(-c4ccccc4)nc(C4CC4)c(C#N)c3c2=O)c2scc(C(=O)O)c2n1] | MS (ESI) m/z 648.05 [M + 1]+; 1H NMR (400 MHz, DMSO-d6) δ 13.41 (bs, 1H), 8.64 (s, 1H), 8.08 (d, J = 3.32 Hz, 2H), 7.58 (dd, J = 2.48, 8.84 Hz, 1H), 7.53 (d, J = 2.48 Hz, 3H), 7.42-7.35 (d, J = 2.48 Hz, 1H), 7.35-7.38 (m, 2H), 4.43 (t, J = 5.80 Hz, 2H), 4.28 (t, J = 4.52 Hz, 2H), 2.66-2.55 (m, 1H), 2.55 (s, 3H), 1.95 (s, 3H), 1.23 (d, J = 4.28 Hz, 4H) |
| 911 | 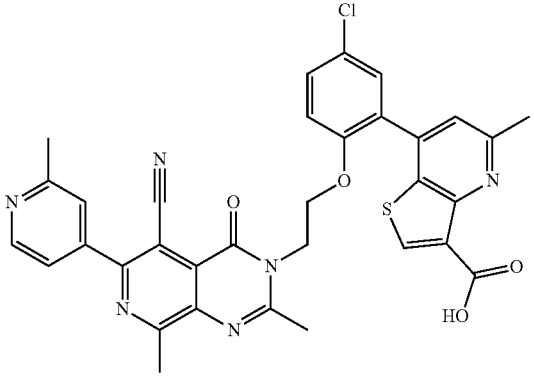 [SMILES: Cc1cc(-c2nc(C)c3nc(C)n(CCOc4ccc(Cl)cc4-c4cc(C)nc5c(C(=O)O)csc45)c(=O)c3c2C#N)ccn1] | MS (ESI) m/z 637.07 [M + 1]+; 1H NMR (400 MHz, DMSO-d6) δ 8.72 (d, J = 5.2 Hz, 1H), 8.47 (s, 1H), 7.83 (s, 1H), 7.79 (d, J = 4.48 Hz, 1H), 7.60 (dd, J = 2.52, 8.84 Hz, 1H), 7.42-7.34 (m, 3H), 4.45 (t, J = 6.12 Hz, 2H), 4.30 (t, J = 5.72 Hz, 2H), 2.80 (s, 3H), 2.71 (s, 3H), 2.65 (s, 3H), 2.01 (s, 3H) |
| 912 | 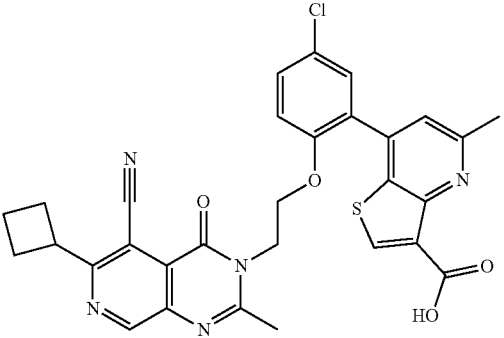 | MS (ESI) m/z 586.20 [M + 1]+; 1H NMR (400 MHz, DMSO-d6) δ 8.90 (s, 1H), 8.54 (s, 1H), 7.58 (dd, J = 8.92, 2.44 Hz, 1H), 7.42 (d, J = 2.52 Hz, 1H), 7.40 (s, 1H), 7.35 (d, J = 8.92 Hz, 1H), 4.95 (t, J = 8.68, 1H), 4.41 (t, J = 5.8 Hz, 2H), 4.24 (t, J = 5.84 Hz, 2H), 2.68 (s, 3H), 2.37-2.32 (m, 3H), 2.13-2.08 (m, 2H), 1.91 (s, 3H), 1.91 (bs, 2H) |

TABLE 1-continued

7-Aza-Thienylpyridine and Derivative Compounds

| Compound | | Characterization |
|---|---|---|
| 913 | 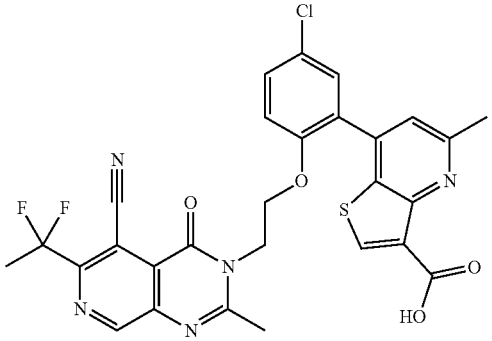 [SMILES: Cc1cc(-c2cc(Cl)ccc2OCCn2c(C)nc3cnc(C(C)(F)F)c(C#N)c3c2=O)c2scc(C(=O)O)c2n1] | MS (ESI) m/z 596.04 [M + 1]+; 1H NMR (400 MHz, DMSO-d6) δ 13.55 (bs, 1H), 9.00 (s, 1H), 8.42 (s, 1H), 7.58 (d, J = 8.68 Hz, 1H), 7.41 (s, 2H), 7.35 (d, J = 8.88 Hz, 1H), 4.40 (t, J = 4.88 Hz, 2H), 4.27 (t, J = 5.4 Hz, 2H), 2.70 (s, 3H), 2.16 (t, J = 19.28 Hz, 3H), 1.89 (s, 3H) |
| 914 | 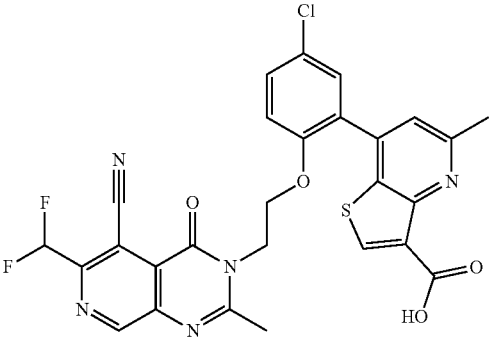 [SMILES: Cc1cc(-c2cc(Cl)ccc2OCCn2c(C)nc3cnc(C(F)F)c(C#N)c3c2=O)c2scc(C(=O)O)c2n1] | MS (ESI) m/z 582.03 [M + 1]+; 1H NMR (400 MHz, DMSO-d6) δ 9.06 (s, 1H), 8.40 (s, 1H), 7.59 (dd, J = 8.8, 2.5 Hz, 1H), 7.43-7.16 (m, 4H), 4.40 (t, J = 6.0 Hz, 2H), 4.28 (t, J = 2.6 Hz, 2H), 2.70 (s, 2H), 1.84 (s, 3H) |
| 915 | 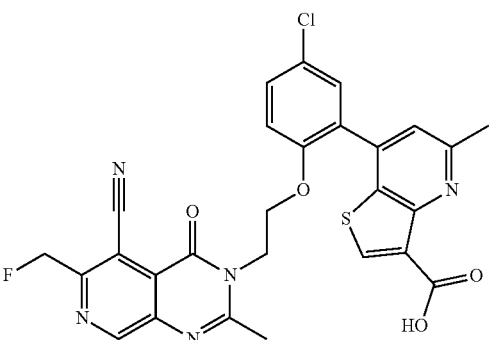 | MS (ESI) m/z 617.10 [M + 1]+; 1H NMR (400 MHz, DMSO-d6) δ 13.53 (bs, 1H), 9.02 (s, 1H), 8.36 (s, 1H), 7.59 (dd, J = 8.88 Hz, 2.52 Hz, 1H), 7.41-7.39 (m, 2H), 7.34 (d, J = 8.96 Hz, 1H), 5.72 (d, J = 47.16 Hz, 2H), 4.40 (t, J = 7.44 Hz, 2H), 4.27 (t, J = 4.48 Hz, 2H), 2.69 (s, 3H), 1.88 (s, 3H) |
| 916 | 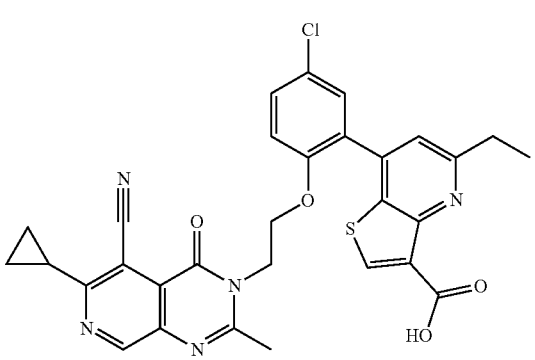 [SMILES: CCc1cc(-c2cc(Cl)ccc2OCCn2c(C)nc3cnc(C4CC4)c(C#N)c3c2=O)c2scc(C(=O)O)c2n1] | MS (ESI) m/z 585.97 [M + 1]+; 1H NMR (400 MHz, DMSO-d6) δ 8.82 (s, 1H), 8.39 (s, 1H), 7.61 (dd, J = 8.88Hz, 2.68 Hz, 1H), 7.45-7.43 (m, 2H), 7.37 (d, J = 8.96 Hz, 1H), 4.42-4.39 (m, 2H), 4.26- 4.23 (m, 2H), 3.02 (q, J = 7.56 Hz, J = 7.52 Hz, 2H), 2.67 (s, 1H), 1.83 (s, 3H), 1.35 (t, J = 7.52 Hz, 3H), 1.24-1.19 (m, 4H) |

TABLE 1-continued

7-Aza-Thienylpyridine and Derivative Compounds

| Compound | Characterization |
|---|---|
| 917 | MS (ESI) m/z 590.02 [M + 1]+; 1H NMR (400 MHz, DMSO-d6) δ 13.01 (s, 1H), 8.86 (s, 1H), 8.43 (s, 1H), 7.60 (dd, J = 2.48, 8.88 Hz, 1H), 7.51 (s, 1H), 7.43 (d, J = 2.52 Hz, 1H), 7.35 (d, J = 8.96, 1H), 5.69 (d, J = 46.8 Hz, 2H), 4.40 (t, J = 3.96 Hz, 2H), 4.23 (t, J = 4.40 Hz, 2H), 2.61-2.57 (m, 1H), 1.77 (s, 3H), 1.23-1.15 (m, 4H) |
| 922 | MS (ESI) m/z 540.10 [M + 1]+; 1H NMR (400 MHz, DMSO-d6) δ 12.96 (s, 1H), 8.87 (s, 1H), 7.74 (s, 1H) 7.67 (d, J = 2.3 Hz, 1H), 7.62 (dd, J = 8.84, 2.40 Hz, 1H), 7.35 (d, J = 8.92 Hz, 1H), 4.44 (s, 4H), 2.68 (s, 3H), 2.58-2.57 (m, 1H), 1.20-1.14 (m, 4H) |
| 923 | MS (ESI) m/z 560.11 [M + 1]+; 1H NMR (400 MHz, DMSO-d6) δ 8.95 (s, 1H), 8.35 (s, 1H), 7.59-7.56 (dd, J = 2.4, 8.4 Hz, 1H), 7.41-7.33 (m, 3H), 4.40 (t, J = 4.8 Hz, 2H), 4.26 (t, J = 4.8 Hz, 2H), 3.12 (m, 2H), 2.68 (s, 3H), 1.88 (s, 3H), 1.35 (t, J = 7.2 Hz, 3H) |
| 924 | MS (ESI) m/z 690 [M + 1]+; 1H NMR (400 MHz, DMSO-d6) δ 13.4 (s, 1H), 8.50 (s, 1H), 7.94 (d, J = 7.8 Hz, 1H), 7.89 (t, J = 7.2 Hz, 1H), 7.81 (t, J = 8.4 Hz, 1H), 7.61 (dd, J = 2.4, 8.8 Hz, 1H), 7.43 (s, 2H), 7.38 (d, J = 8.82 Hz, 1H), 4.44 (bs, 2H), 4.27 (bs, 2H), 2.80 (s, 3H), 2.71 (s, 3H), 1.92 (s, 3H) |

TABLE 1-continued

7-Aza-Thienylpyridine and Derivative Compounds

| Compound | | Characterization |
|---|---|---|
| 925 | 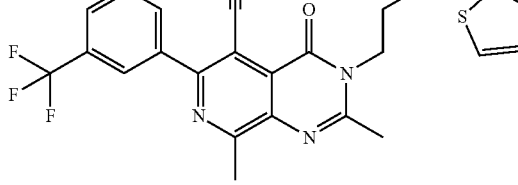 | MS (ESI) m/z 690.02 [M + 1]+; 1H NMR (400 MHz, DMSO-d6) δ 8.45 (s, 1H), 8.24 (s, 1H), 8.19 (d, J = 7.76 Hz, 1H), 7.94 (d, J = 7.6 Hz, 1H), 7.84 (t, J = 7.8 Hz, 1H), 7.60 (dd, J = 2.56, 8.8 Hz, 1H), 7.43 (s, 1H), 7.39 (d, J = 2.2 Hz, 2H), 4.46 (t, J = 3.6 Hz, 2H), 4.30 (t, J = 4.4 Hz, 2H), 2.80 (s, 3H), 2.71 (s, 3H), 2.00 (s, 3H) |
| 926 | 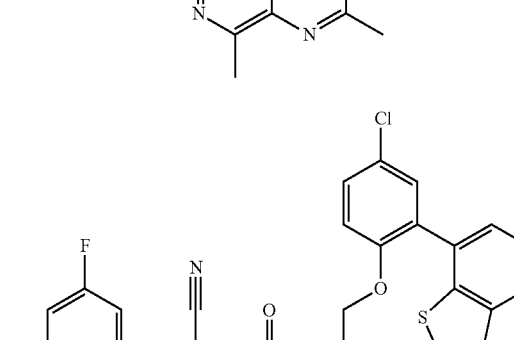 | MS (ESI) m/z 690.02 [M + 1]+; 1H NMR (400 MHz, DMSO-d6) δ 13.44 (bs, 1H), 8.49 (s, 1H), 8.10 (d, J = 8.08 Hz, 2H), 7.95 (d, J = 8.20 Hz, 2H), 7.60 (dd, J = 8.88, 2.60 Hz, 1H), 7.43 (s, 1H), 7.42-7.37 (m, 2H), 4.45 (t, J = 4.64 Hz, 2H), 4.30 (t, J = 4.36 Hz, 2H), 2.80 (s, 3H), 2.71 (s, 3H), 1.99 (s, 3H) |
| 927 | 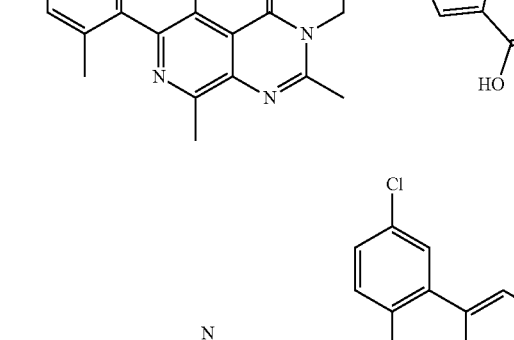 | MS (ESI) m/z 654.03 [M + 1]+; 1H NMR (400 MHz, DMSO-d6) δ 13.50 (bs, 1H), 8.48 (s, 1H), 7.60 (dd, J = 2.4, 8.7 Hz, 1H), 7.43-7.37 (m, 5H), 7.30-7.26 (m, 1H), 4.44 (t, J = 5.2 Hz, 2H), 4.27 (t, J = 5.8 Hz, 2H), 2.77 (s, 3H), 2.71 (s, 3H), 2.13 (s, 3H), 1.93 (s, 3H) |
| 928 | 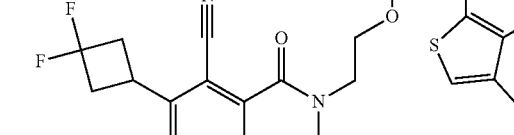 | MS (ESI) m/z 622.13 [M + 1]+; 1H NMR (400 MHz, DMSO-d6) δ 9.03 (s, 1H), 8.35 (s, 1H), 7.58 (dd, J = 2.52, 8.8 Hz, 1H), 7.39 (t, J = 2.68 Hz, 2H), 7.35 (d, J = 9 Hz, 1H), 4.39 (t, J = 4.4 Hz, 2H), 4.26 (t, J = 4.28 Hz, 2H), 4.04-3.95 (m, 1H), 3.11-3.05 (m, 4H), 2.70 (s, 3H), 1.91 (s, 3H) |

TABLE 1-continued

7-Aza-Thienylpyridine and Derivative Compounds

| Compound | | Characterization |
|---|---|---|
| 929 | 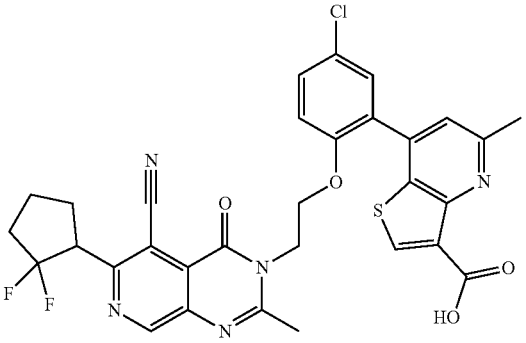 [SMILES: Cc1cc(-c2cc(Cl)ccc2OCCn2c(C)nc3cnc(C4CCCC4(F)F)c(C#N)c3c2=O)c2scc(C(=O)O)c2n1] | MS (ESI) m/z 636.20 [M + 1]+; 1H NMR (400 MHz, DMSO-d6) δ 13.20 (bs, 1H), 9.04 (s, 1H), 8.37 (s, 1H), 7.61-7.56 (m, 1H), 7.44-7.38 (m, 2H), 7.34 (d, J = 8.96 Hz, 1H), 4.40-4.36 (m, 2H), 4.27-4.15 (m, 3H), 2.68 (s, 3H), 2.59-2.56 (m, 1H), 2.32-2.17 (m, 3H), 2.07-2.03 (m, 1H), 1.93-1.83 (m, 4H) |
| 930 | 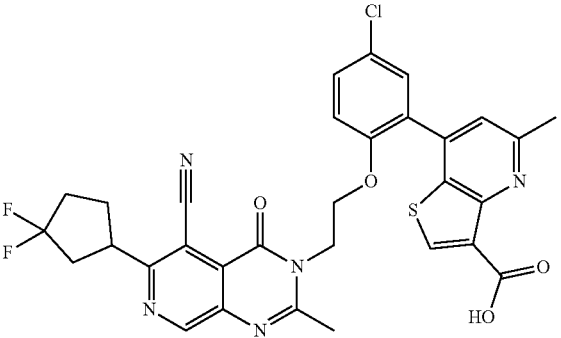 [SMILES: Cc1cc(-c2cc(Cl)ccc2OCCn2c(C)nc3cnc(C4CCC(F)(F)C4)c(C#N)c3c2=O)c2scc(C(=O)O)c2n1] | MS (ESI) m/z 636.20 [M + 1]+; 1H NMR (400 MHz, DMSO-d6) δ 13.50 (bs, 1H), 8.99 (s, 1H), 8.38 (s, 1H), 7.59 (dd, J = 8.88, 2.52 Hz, 1H), 7.40 (s, 2H), 7.35 (d, J = 8.96 Hz, 1H), 4.41-4.36 (m, 2H), 4.31-4.23 (m, 2H), 4.08-4.02 (m, 1H), 2.70 (s, 3H), 2.63-2.57 (m, 2H), 2.38-2.32 (m, 1H), 2.29-2.26 (m, 2H), 2.09-2.05 (m, 1H), 1.91 (s, 3H) |
| 931 | 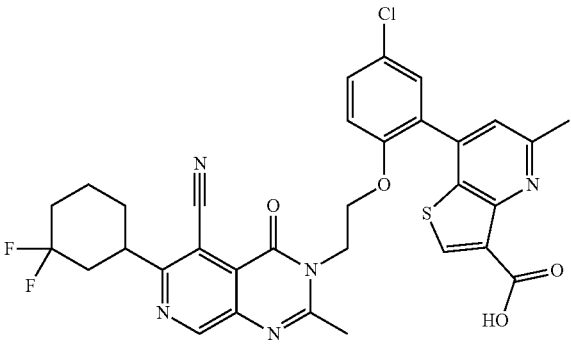 [SMILES: Cc1cc(-c2cc(Cl)ccc2OCCn2c(C)nc3cnc(C4CCCC(F)(F)C4)c(C#N)c3c2=O)c2scc(C(=O)O)c2n1] | MS (ESI) m/z 650.13 [M + 1]+; 1H NMR (400 MHz, DMSO-d6) δ 8.96 (s, 1H), 8.35 (s, 1H), 7.59 (dd, J = 8.88, 2.56 Hz, 1H), 7.44-7.40 (m, 2H), 7.35 (d, J = 8.96 Hz, 1H), 4.40 (t, J = 4.68 Hz, 2H), 4.25 (t, J = 4.68, 2H), 3.60-3.50 (bs, 1H), 2.70 (s, 3H), 2.40-2.21 (m, 2H), 2.20-2.09 (m, 1H), 2.00.1.80 (m, 6H), 1.68-1.63 (m, 2H) |
| 940 | 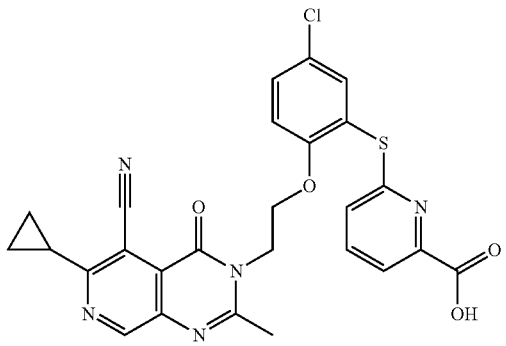 [SMILES: Cc1nc2cnc(C3CC3)c(C#N)c2c(=O)n1CCOc1ccc(Cl)cc1Sc1cccc(C(=O)O)n1] | MS (ESI) m/z 534.16 [M + 1]+;1H NMR (400 MHz, DMSO-d6) δ 13.08 (bs, 1H), 8.82 (s, 1H), 7.61-7.56 (m, 2H), 7.36-7.26 (m, 3H), 6.73 (d, J = 7.88 Hz, 1H), 4.46-4.30 (m, 4H), 2.60-2.59 (m, merged, 1H), 2.57 (s, 3H), 1.28-1.10 (m, 4H) |

TABLE 1-continued

7-Aza-Thienylpyridine and Derivative Compounds

| Compound | | Characterization |
|---|---|---|
| 941 | 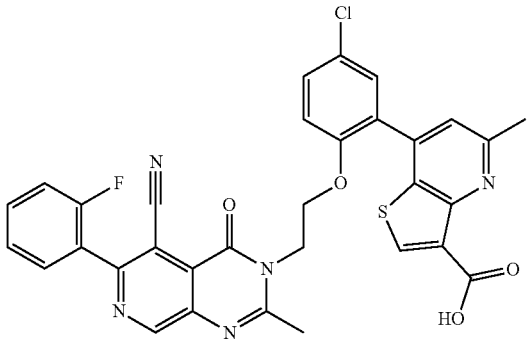 [SMILES: Cc1cc(-c2cc(Cl)ccc2OCCn2c(C)nc3cnc(-c4ccccc4F)c(C#N)c3c2=O)c2scc(C(=O)O)c2n1] | MS (ESI) m/z 626.17 [M + 1]+; 1H NMR (400 MHz, DMSO-d6) δ 13.56 (bs, 1H), 9.09 (s, 1H), 8.48 (s, 1H), 7.74-7.71 (m, 1H), 7.65-7.58 (m, 2H), 7.45-7.34 (m, 4H), 7.35 (d, J = 8.8 Hz, 1H), 4.41 (t, J = 4.60 Hz, 2H), 4.28 (t, J = 4.60 Hz, 2H), 2.70 (s, 3H),1.90 (s, 3H) |
| 942 | 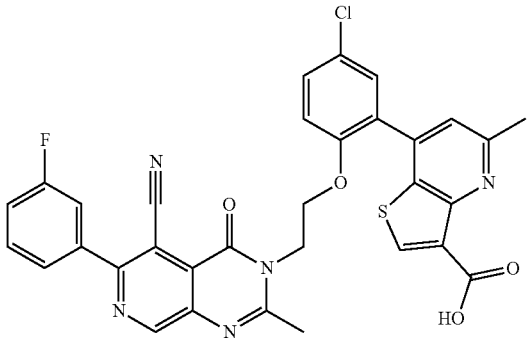 [SMILES: Cc1cc(-c2cc(Cl)ccc2OCCn2c(C)nc3cnc(-c4cccc(F)c4)c(C#N)c3c2=O)c2scc(C(=O)O)c2n1] | MS (ESI) m/z 626.19 [M + 1]+; 1H NMR (400 MHz, DMSO-d6) δ 13.55 (bs, 1H), 9.04 (s, 1H), 8.38 (s, 1H), 7.74 (t, J = 6.92 Hz, 2H), 7.67-7.58 (m, 2H), 7.45-7.41 (m, 3H), 7.36 (d, J = 8.76 Hz, 1H), 4.42 (t, J = 4.68 Hz, 2H), 4.28 (t, J = 4.08, Hz, 2H), 2.66 (s, 3H), 1.98 (s, 3H) |
| 943 | 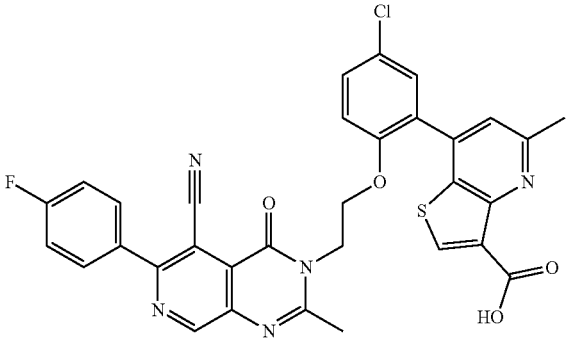 [SMILES: Cc1cc(-c2cc(Cl)ccc2OCCn2c(C)nc3cnc(-c4ccc(F)cc4)c(C#N)c3c2=O)c2scc(C(=O)O)c2n1] | MS (ESI) m/z 626.05 [M + 1]+; 1H NMR (400 MHz, DMSO-d6) δ 13.55 (bs, 1H), 9.03 (s, 1H), 8.41 (s, 1H), 7.99-7.95 (m, 2H), 7.59 (dd, J = 2.56, 8.88 Hz, 1H), 7.45-7.41 (m, 4H), 7.36 (d, J = 8.96 Hz, 1H), 4.42 (t, J = 4.76 Hz, 2H), 4.28 (t, J = 4.52 Hz, 2H), 2.70 (s, 3H), 1.90 (s, 3H) |
| 944 | 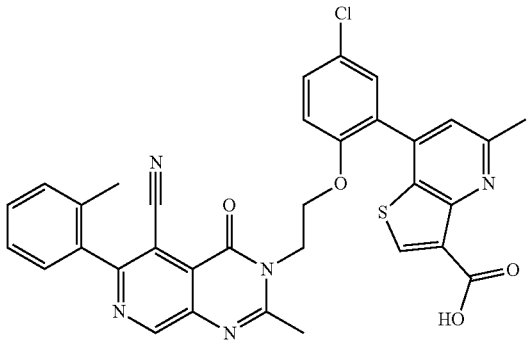 | MS (ESI) m/z 622.08 [M + 1]+; 1H NMR (400 MHz, DMSO-d6) δ 9.03 (s, 1H), 8.43 (s, 1H), 7.60 (dd, J = 8.92 Hz, 2.64 Hz, 1H), 7.47-7.35 (m, 7H), 4.42 (t, J = 5.64 Hz, 2H), 4.27 (t, J = 4.4 Hz, 2H), 2.73 (s, 3H), 2.19 (s, 3H), 1.86 (s, 3H) |

TABLE 1-continued

7-Aza-Thienylpyridine and Derivative Compounds

| Compound | | Characterization |
|---|---|---|
| 945 | 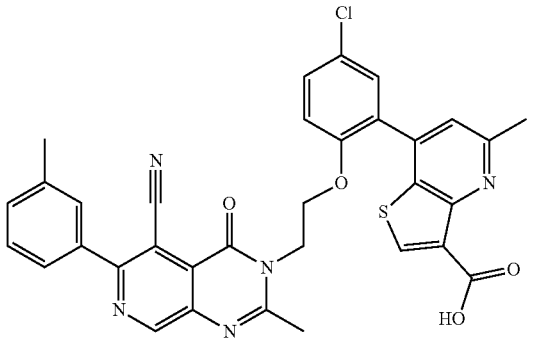 [SMILES: Cc1cccc(-c2ncc3nc(C)n(CCOc4ccc(Cl)cc4-c4cc(C)nc5c(C(=O)O)csc45)c(=O)c3c2C#N)c1] | MS (ESI) m/z 622.05 [M + 1]+; 1H NMR (400 MHz, DMSO-d6) δ 9.02 (s, 1H), 8.41 (s, 1H), 7.90 (s, 1H), 7.68 (s, 1H), 7.58 (dd, J = 8.2, 2.12 Hz, 1H), 7.48-7.35 (m, 5H), 4.42 (t, J = 4.48, 2H), 4.27 (t, J = 5.68, 2H), 2.71 (s, 3H), 2.43 (s, 3H), 1.88 (s, 3H) |
| 946 | 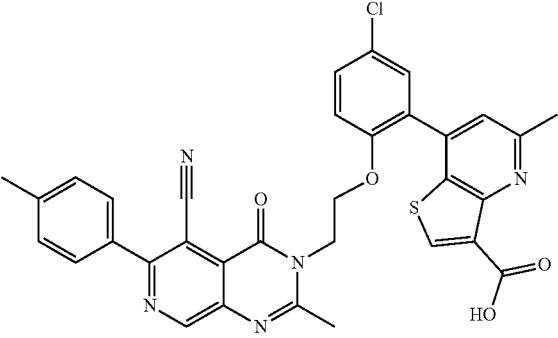 | MS (ESI) m/z 622.08 [M + 1]+; 1H NMR (400 MHz, DMSO-d6) δ 13.5 (s, 1H), 9.027 (s, 1H), 8.40 (s, 1H), 7.80 (d, J = 8.0 Hz, 2H), 7.58 (dd, J = 2.56 Hz, J = 2.52 Hz, 1H), 7.34- 7.42 (m, 5H), 4.40-4.42 (bs, 2H), 4.26- 4.28 (bs, 2H), 2.70 (s, 3H), 2.42 (s, 3H), 1.87 (s, 3H) |
| 947 | 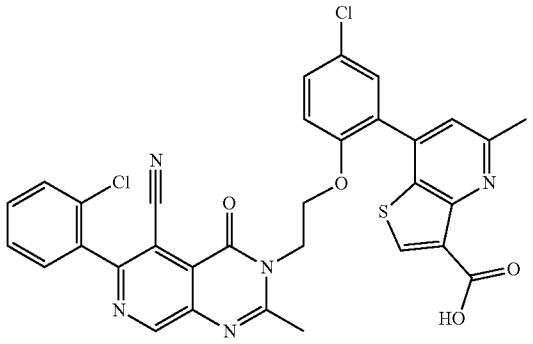 | MS (ESI) m/z 642.01 [M + 1]+; 1H NMR (400 MHz, DMSO-d6) δ 13.54 (bs, 1H), 9.07 (s, 1H), 8.43 (s, 1H), 7.70-7.68 (m, 2H), 7.66-7.54 (m, 3H), 7.43-7.42 (m, 2H), 7.35 (d, J = 9.0 Hz, 1H), 4.41 (t, J = 6.16 Hz, 2H), 4.27 (t, J = 4.48 Hz, 2H), 2.71 (s, 3H), 1.88 (s, 3H) |
| 948 | 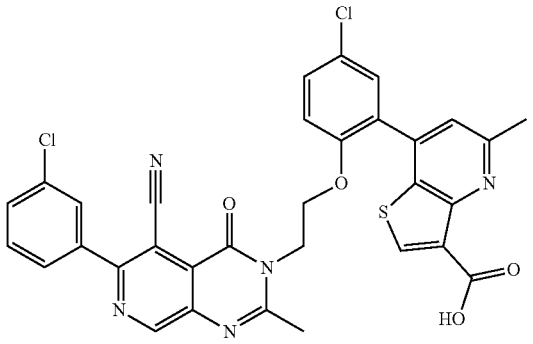 | MS (ESI) m/z 642.06 [M + 1]+; 1H NMR (400 MHz, DMSO-d6) δ 13.50 (bs, 1H), 9.03 (s, 1H), 8.37 (s, 1H), 7.97 (t, J = 2.0 Hz 1H), 7.90-7.84 (m, 1H), 7.67-7.58 (m, 3H), 7.42-7.40 (m, 2H), 7.41 (d, J = 2.6 Hz, 1H), 4.42 (t, J = 5.48 Hz, 2H), 4.28 (t, J = 4.40 Hz, 2H), 2.71 (s, 3H), 1.91 (s, 3H) |

TABLE 1-continued

7-Aza-Thienylpyridine and Derivative Compounds

| Compound | | Characterization |
|---|---|---|
| 949 | 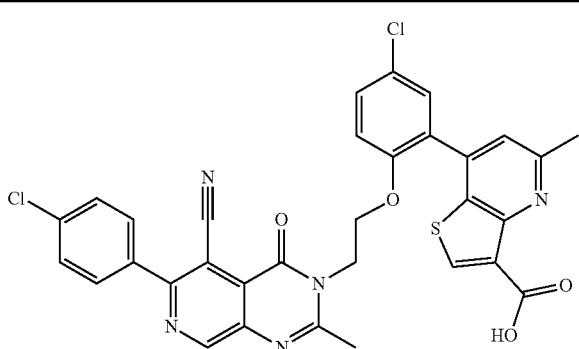 | MS (ESI) m/z 642.01 [M + 1]+; 1H NMR (400 MHz, DMSO-d6) δ 9.04 (s, 1H), 8.40 (s, 1H), 7.94 (d, J = 8.5 Hz, 2H), 7.67 (d, J = 8.5 Hz, 2H), 7.59 (dd, J = 8.9, 2.6 Hz, 1H), 7.45-7.40 (m, 2H), 7.36 (d, J = 8.9 Hz, 1H), 4.42 (t, J = 8.3 Hz, 2H), 4.28 (t, J = 4.4 Hz, 2H), 2.70 (s, 3H), 1.90 (s, 3H) |
| 950 | 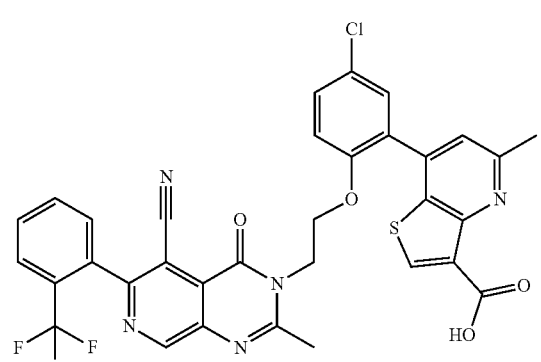 | MS (ESI) m/z 676 [M + 1]+; 1H NMR (400 MHz, DMSO-d6) δ 9.03 (s, 1H), 8.41 (s, 1H), 7.97 (d, J = 7.6 Hz, 1H), 7.91 (t, J = 7.6 Hz, 1H), 7.83 (t, J = 8.0 Hz, 2H), 7.61 (dd, J = 2.8, 8.8 Hz, 1H), 7.44 (s, 1H), 7.36 (d, J = 9.2 Hz) 1H), 4.42 (bs, 1H), 4.27 (bs, 1H), 2.72 (s, 3H), 1.87 (s, 3H) |
| 951 | 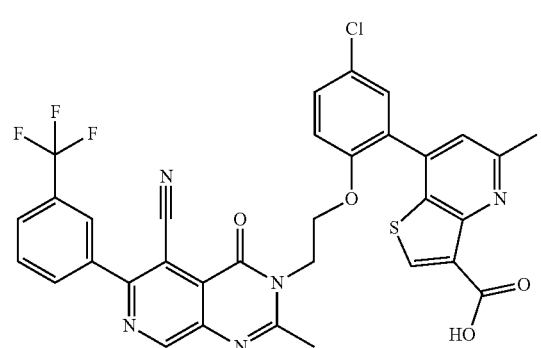 | MS (ESI) m/z 676.10 [M + 1]+; 1H NMR (400 MHz, DMSO-d6) δ 9.06 (s, 1H), 8.37 (s, 1H), 8.27 (s, 1H), 8.22 (d, J = 7.6 Hz ,1H), 7.96 (d, J = 7.4 Hz, 1H), 7.84 (t, J = 7.8 Hz, 1H), 7.60 (dd, J = 2.52, 8.8 Hz, 1H), 7.43 (s, 1H), 7.41 (d, J = 2.5 Hz ,1H), 7.37 (d, J = 8.9 Hz, 1H), 4.43 (t, J = 5.4 Hz, 2H), 4.29 (t, J = 4.96 Hz, 2H), 2.75 (s, 3H), 1.92 (s, 1H) |
| 952 | 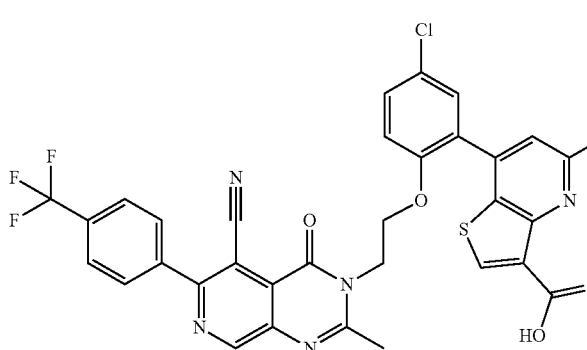 | MS (ESI) m/z 676.01 [M + 1]+; 1H NMR (400 MHz, DMSO-d6) δ 13.49 (bs, 1H), 9.07 (s, 1H), 8.41 (s, 1H), 8.13 (d, J = 8.16 Hz, 2H), 7.98 (d, J = 8.28 Hz, 2H), 7.60 (dd, J = 8.92, 2.60 Hz 1H), 7.43-7.40 (m, 2H), 7.36 (d, J = 8.96 Hz 1H), 4.42 (t, J = 6.48 Hz 2H), 4.29 (t, J = 4.48 Hz 2H), 2.71 (s, 3H), 1.92 (s, 3H) |

TABLE 1-continued

7-Aza-Thienylpyridine and Derivative Compounds

| Compound | | Characterization |
|---|---|---|
| 953 | 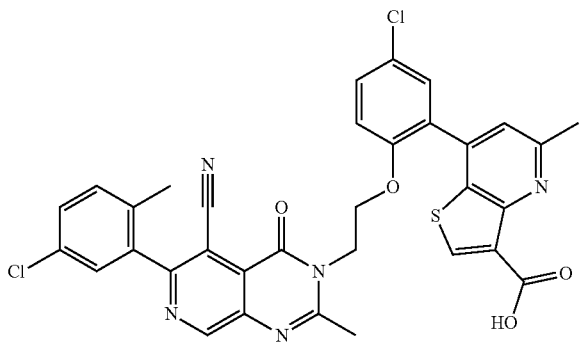 | MS (ESI) m/z 655.99 [M + 1]+; 1H NMR (400 MHz, DMSO-d6) δ, 9.03(s, 1H), 8.33 (s, 1H), 7.62-7.58 ( m, 2H), 7.52 (dd, J = 2.16, 8.24 Hz, 1H), 7.47-7.42 (m, 3H), 7.37 (d, J = 8.92 Hz, 1H), 4.43 (t, J = 4.96 Hz, 2H), 4.29 (t, J = 3.88 Hz, 2H), 2.72 (s, 3H), 2.15 (s, 3H), 1.85 (s, 3H) |
| 954 | 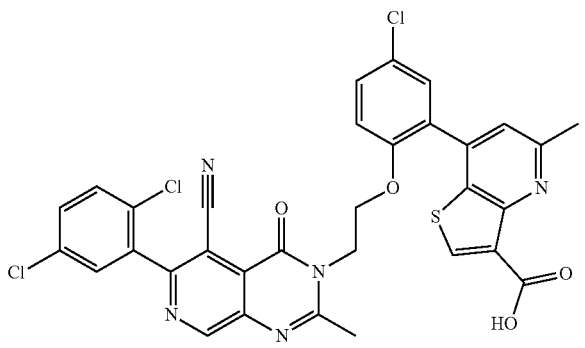 | MS (ESI) m/z 675.95 [M + 1]+; 1H NMR (400 MHz, DMSO-d6) δ 9.06 (s, 1H), 8.36 (s, 1H), 7.90 (s, 1H), 7.74-7.68 (m, 2H), 7.59 (d, J = 6.6 Hz, 1H), 7.42 (s, 2H), 7.35 (d, J = 8.8 Hz, 1H), 4.42 (s, 2H), 4.28 (s, 2H), 2.72 (s, 3H), 1.89 (s, 3H) |
| 970 | 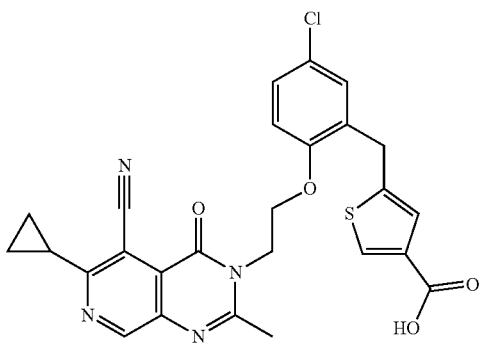 [SMILES: Cc1nc2cnc(C3CC3)c(C#N)c2c(=O)n1CCOc1ccc(Cl)cc1Cc1cc(C(=O)O)cs1] | MS (ESI) m/z 521.01 [M + 1]+; 1H NMR (400 MHz, DMSO-d6) δ 12.47 (bs, 1H), 8.96 (s, 1H), 7.70 (s, 1H), 7.29 (d, J = 8.8 Hz, 1H), 7.17 (s, 1H), 7.10 (d, J = 8.8 Hz, 1H), 6.83 (s, 1H), 4.53 (t, J = 6.4 Hz, 2H), 4.39 (t, J = 4.8 Hz, 2H), 3.99 (s, 2H), 2.65 (s, 3H), 2.57 (bs, 1H), 1.20 (d, J = 7.6 Hz, 2H), 0.93 (d, J = 6.4 Hz, 2H) |
| 971 | 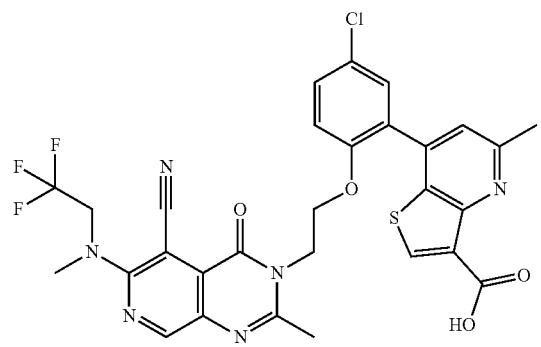 [SMILES: Cc1cc(-c2cc(Cl)ccc2OCCn2c(C)nc3cnc(N(C)CC(F)(F)F)c(C#N)c3c2=O)c2scc(C(=O)O)c2n1] | MS (ESI) m/z 643.13 [M + 1]+; 1H NMR (400 MHz, DMSO-d6) δ 13.38 (bs, 1H), 8.63 (s, 1H), 8.46 (s, 1H), 7.59 (dd, J = 2.5, 8.9 Hz, 1H), 7.42 (d, J = 2.4 Hz, 1H), 7.36 (s, 1H), 7.34 (s, 1H), 4.76-4.69 (m, 2H), 4.38 (t, J = 4.3 Hz, 2H), 4.21 (t, J = 6.2 Hz, 2H), 3.43 (s, 3H), 2.69 (s, 3H), 1.81 (s, 3H) |

TABLE 1-continued

7-Aza-Thienylpyridine and Derivative Compounds

| Compound | | Characterization |
|---|---|---|
| 972 | 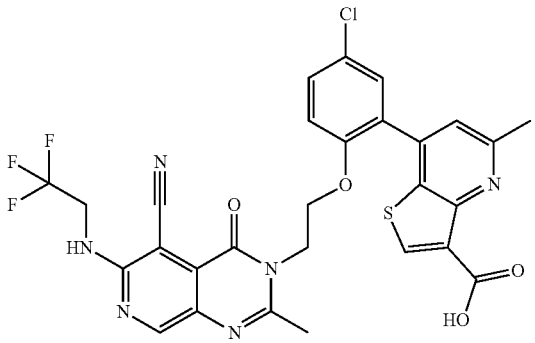 [SMILES: Cc1cc(-c2cc(Cl)ccc2OCCn2c(C)nc3cnc(NCC(F)(F)F)c(C#N)c3c2=O)c2scc(C(=O)O)c2n1] | MS (ESI) m/z 629.09 [M + 1]+; 1H NMR (400 MHz, DMSO-d6) δ 8.65 (s, 1H), 8.43 (s, 1H), 7.77 (t, J = 6.0 Hz, 1H), 7.57 (d, J = 9.0 Hz, 1H), 7.41 (s, 1H), 7.35 (t, J = 5.3 Hz, 2H), 4.37-4.30 (m, 4H), 4.20 (bs, 2H), 2.68 (s, 3H), 1.78 (s, 3H) |
| 973 | 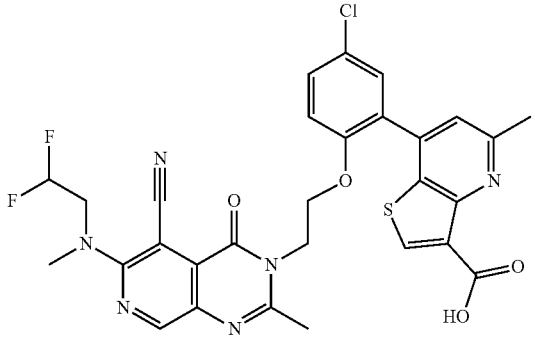 [SMILES: Cc1cc(-c2cc(Cl)ccc2OCCn2c(C)nc3cnc(N(C)CC(F)F)c(C#N)c3c2=O)c2scc(C(=O)O)c2n1] | MS (ESI) m/z 625.11 [M + 1]+; 1H NMR (400 MHz, DMSO-d6) δ 8.59 (s, 1H), 8.44 (s, 1H), 7.59 (dd, J = 2.56, 6.28 Hz, 1H), 7.40 (bs, 2H), 7.35 (d, J = 8.96 Hz, 1H), 6.38 (tt, J = 4.08, 59.88 Hz, 1H), 4.38 (t, J = 6.20 Hz, 2H), 4.21 (t, J = 4.48 Hz, 2H), 4.16-4.12 (m, 2H), 3.39 (s, 3H), 2.71 (s, 3H), 1.84 (s, 3H) |
| 974 | 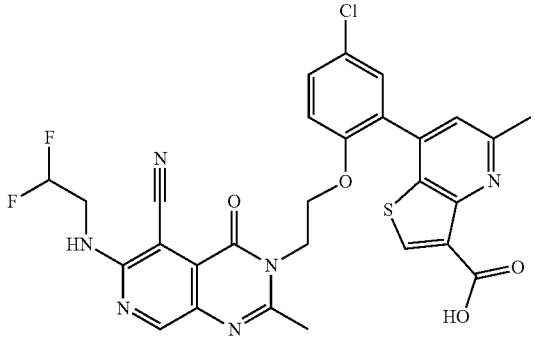 [SMILES: Cc1cc(-c2cc(Cl)ccc2OCCn2c(C)nc3cnc(NCC(F)F)c(C#N)c3c2=O)c2scc(C(=O)O)c2n1] | MS (ESI) m/z 611.18 [M + 1]+; 1H NMR (400 MHz, DMSO-d6) δ 8.60 (s, 1H), 8.47 (s, 1H), 7.60-7.55 (m, 2H), 7.40 (s, 2H), 7.34 (d, J = 8.96 Hz 1H), 6.21 (tt, J = 5.28, 57.68 Hz, 1H), 4.36 (t, J = 4.60 Hz, 2H), 4.20 (t, J = 4.60 Hz, 2H), 3.93-3.86 (m, 2H), 2.70 (s, 3H), 1.80 (s, 3H) |
| 975 | 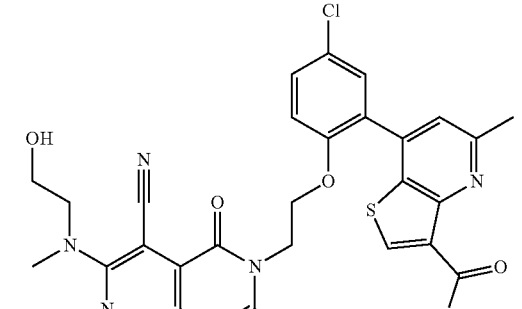 | MS (ESI) m/z 560.11 [M + 1]+; 1H NMR (400 MHz, DMSO-d6) δ 9.14 (s, 1H), 8.61 (s, 1H), 7.62-7.59 (dd, J = 2.4, 8.4 Hz, 1H), 7.46 (s, 1H), 7.42 (d, J = 2.4 Hz, 1H), 7.37 (d, J = 9.2 Hz, 1H), 4.88 (t, J = 9.6 Hz, 2H), 4.40 (t, J = 4.4 Hz, 2H), 4.23 (t, J = 4.8 Hz, 2H), 4.17 (t, J = 9.6 Hz, 2H), 3.52 (s, 1H), 2.66 (s, 3H), 1.86 (s, 3H) |

TABLE 1-continued

7-Aza-Thienylpyridine and Derivative Compounds

| Compound | | Characterization |
|---|---|---|
| 976 | 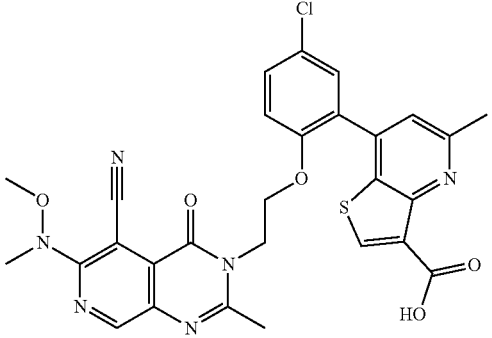 | MS (ESI) m/z 591.19 [M + 1]+; 1H NMR (400 MHz, DMSO-d6) δ 8.75 (s, 1H), 8.23 (bs, 1H), 7.57 (d, J = 8.4 Hz, 1H), 7.38 (s, 1H), 7.33 (m, 2H), 4.37 (t, J = 5.2 Hz, 2H), 4.22 (t, J = 4.0 Hz, 2H), 3.84 (s, 3H), 3.26 (s, 3H), 2.66 (s, 3H), 1.63 (s, 3H) |
| 977 | 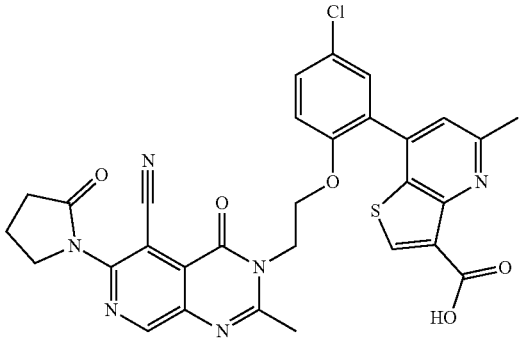 [SMILES: Cc1cc(-c2cc(Cl)ccc2OCCn2c(C)nc3cnc(N4CCCC4=O)c(C#N)c3c2=O)c2scc(C(=O)O)c2n1] | MS (ESI) m/z 615.03 [M + 1]+; 1H NMR (400 MHz, DMSO-d6) δ 8.92 (s, 1H), 8.44 (s, 1H), 7.59 (dd, J1 = 2.5 Hz, J2 = 8.8 Hz, 1H), 7.41-7.40 (m, 2H), 7.35 (d, J = 9.0 Hz, 1H), 4.40 (t, J = 8.8 Hz, 2H), 4.25 (t, J = 9.1 Hz, 2H), 4.08, (t, J = 13.6 Hz, 2H), 2.70 (s, 3H), 2.60-2.58 (m, 2H), 2.20 (t, J = 14.3 Hz, 2H), 1.87 (s, 3H) |
| 978 | 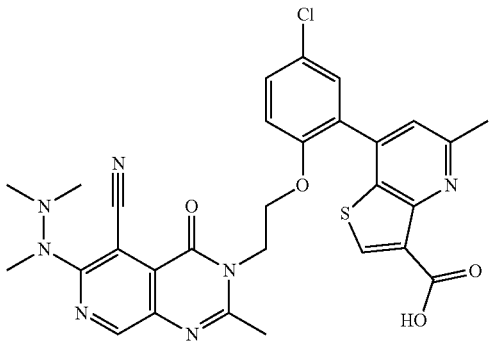 | MS (ESI) m/z 604.24 [M + 1]+; 1H NMR (400 MHz, DMSO-d6) δ 8.54 (s, 1H), 8.48 (s, 1H), 7.59 (dd, J = 8.8 Hz, 2.48 Hz, 1H), 7.42-7.39 (m, 2H), 7.35 (d, J = 8.96 Hz, 1H), 4.37 (d, J = 4.48 Hz, 2H), 4.19 (d, J = 4.8 Hz, 2H), 3.05 (s, 3H), 2.70 (s, 3H), 2.53 (s, 6H), 1.78 (s, 3H) |
| 979 | 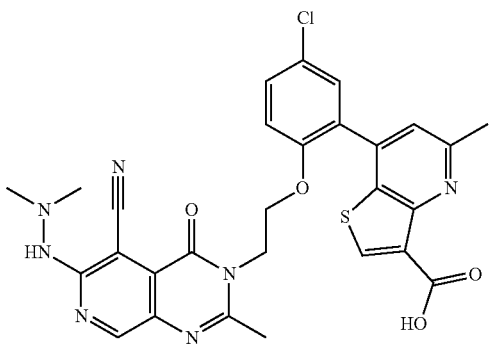 | MS (ESI) m/z 590.16 [M + 1]+; 1H NMR (400 MHz, DMSO-d6) δ 8.69 (bs, 1H), 8.57 (s, 1H), 8.46 (s, 1H), 7.59 (dd, J = 8.88 Hz, 2.44 Hz, 1H), 7.43-7.41 (m, 2H), 7.34 (d, J = 8.96 Hz, 1H), 4.36 (t, J = 4.28 Hz, 2H), 4.18 (t, J = 4.6 Hz, 2H), 2.70 (s, 9H), 1.71 (s, 3H) |

TABLE 1-continued

7-Aza-Thienylpyridine and Derivative Compounds

| Compound | | Characterization |
|---|---|---|
| 980 | | MS (ESI) m/z 716.23 [M + 1]+; 1H-NMR (400 MHz, DMSO-d6) δ 8.76 (d, J = 3.60 Hz, 1H), 8.68 (s, 1H), 8.59 (s, 1H), 7.74 (d, J = 8.40 Hz, 1H), 7.67-7.64 (m, 2H), 7.43 (d, J = 3.60 Hz, 1H), 4.80 (s, 2H), 4.25 (bs, 1H), 3.83 (s, 3H), 3.10 (s, 3H), 3.02 (d, J = 9.6 Hz, 2H), 2.78-2.71 (m, 2H), 2.39-2.34 (m, 2H), 2.03 (s, 3H), 1.93-1.91 (m, 2H), 1.76-1.05 (m, 5H) |
| 981 | | MS (ESI) m/z 554.13 [M + 1]+; 1H NMR (400 MHz, DMSO-d6) δ 9.22 (s, 1H), 9.19 (s, 1H), 8.79 (d, J = 4.8 Hz, 1H), 8.45 (s, 1H), 7.61 (dd, J = 2.64, 8.88, 1H), 7.48 (d, J = 4.8 Hz, 1H), 7.45 (d, J = 2.68 Hz, 1H), 7.37 (d, J = 8.96 Hz, 1H), 6.72-6.46 (t, J = 51.6 Hz, 1H), 4.41 (d, J = 4.64 Hz, 2H), 4.36 (d, J = 4.52 Hz, 2H) |
| 982 | | MS (ESI) m/z 649.06 [M + 1]+; 1H NMR (400 MHz, DMSO-d6) δ 13.60 (s, 1H), 8.69 (s, 1H), 8.47 (s, 1H), 7.60 (dd, J = 2.56 Hz, J = 8.88 Hz, 1H), 7.42-7.35 (m, 4H), 7.29 (d, J = 7.25 Hz, 1H), 7.12 (t, J = 7.52 Hz, 1H), 6.96 (t J = 7.24 Hz, 1H), 4.41 (t, J = 5.04 Hz, 2H), 4.34 (t, J = 8.04 Hz, 2H), 4.24 (t, J = 4.76 Hz, 2H), 3.22 (t, J = 7.88 Hz, 2H), 2.71 (s, 3H), 1.83 (s, 3H) |
| 983 | | MS (ESI) m/z 647.10 [M + 1]+; 1H NMR (400 MHz, DMSO-d6) δ 8.99 (s, 1H), 8.43 (s, 1H), 7.92 (d, J = 3.36 Hz, 1H), 7.74 (d, J = 8.12 Hz 1H), 7.69 (s, J = 7.60 Hz 1H), 7.61 (dd, J = 8.88, 2.48 Hz 1H), 7.45 (s, 1H), 7.43 (d, J = 2.48 Hz, 1H), 7.37 (d, J = 9.0 Hz, 1H), 7.29-7.20 (m, 2H), 6.84 (d, J = 3.28 Hz, 1H), 4.44 (d, J = 4.48 Hz, 2H), 4.29 (d, J = 4.48 Hz, 2H), 2.70 (s, 3H), 1.87 (s, 3H) |

TABLE 1-continued

7-Aza-Thienylpyridine and Derivative Compounds

| Compound | Characterization |
|---|---|
| 984 | MS (ESI) m/z 598.05 [M + 1]+; 1H NMR (400 MHz, DMSO-d6) δ 8.91 (s, 1H), 8.58 (s, 1H), 8.44 (s, 1H), 7.96 (s, 1H), 7.59 (d, J = 8.76 Hz, 1H), 7.42 (s, 2H), 7.35 (d, J = 8.88 Hz, 1H), 6.70 (s, 1H), 4.41 (t, J = 4.12 Hz, 2H), 4.27 (t, J = 4.00 Hz, 2H), 2.71 (s, 3H), 1.83 (s, 3H) |
| 985 | MS (ESI) m/z 561.13 [M + 1]+; 1H NMR (400 MHz, DMSO-d6) δ 13.52 (bs, 1H), 8.59 (s, 1H), 8.47 (s, 1H), 7.58 (dd, J = 8.8, 2.12 Hz, 1H), 7.41 (s, 1H), 7.381H), 7.33 (d, J = 8.96 Hz, 1H), 7.28-7.20 (m, 1H), 4.36 (t, J = 5.68 Hz, 2H), 4.18 (t, J = 6.16 Hz, 2H), 2.97 (d, J = 4.24 Hz, 3H), 2.69 (s, 3H), 1.75 (s, 3H) |
| 986 | MS (ESI) m/z 637.13 [M + 1]+; 1H NMR (400 MHz, DMSO-d6) δ 13.59 (bs, 1H), 8.76 (s, 1H), 8.52 (s, 1H), 7.58 (dd, J = 8.84, 2.48 Hz, 1H), 7.43-7.32 (m, 5H), 7.18 (d, J = 8.00 Hz, 2H), 7.12 (t, J = 7.20 Hz, 1H), 4.35 (t, J = 5.48 Hz, 2H), 4.18 (t, J = 3.64 Hz, 2H), 3.53 (s, 3H), 2.72 (s, 3H), 1.78 (s, 3H) |
| 987 | MS (ESI) m/z 651.29 [M + 1]+; 1H NMR (400 MHz, DMSO-d6) δ 13.45 (bs, 1H), 8.69 (s, 1H), 8.62 (s, 1H), 8.13 (t, J = 3.36 Hz, 2H), 7.58 (dd, J = 2.52, 8.84 Hz, 1H), 7.53-7.51 (m, 3H), 7.42 (d, J = 2.52 Hz, 1H), 7.39-7.36 (m, 2H), 4.41 (t, J = 4.60 Hz, 2H), 4.25 (t, J = 4.4 Hz, 2H), 3.31 (s, 6H), 2.56 (s, 3 H) 1.88 (s, 3H) |

TABLE 1-continued

7-Aza-Thienylpyridine and Derivative Compounds

| Compound | | Characterization |
|---|---|---|
| 988 | 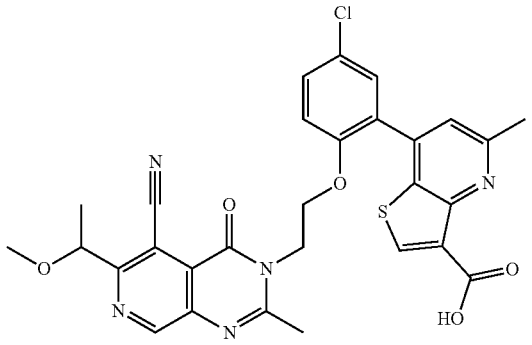 | MS (ESI) m/z 590.2 [M + 1]+; 1H NMR (400 MHz, DMSO-d6) δ 9.01 (s, 1H), 8.40 (s, 1H), 7.60 (dd, J = 8.8 Hz, 2.4 Hz, 1H), 7.43-7.42 (m, 2H), 7.35 (d, J = 8.9 Hz, 1H), 4.95-4.90 (m, 1H), 4.39 (s, 2H), 4.23-4.20 (m, 2H), 3.22 (s, 3H), 2.70 (s, 3H), 1.84 (s, 3H), 1.50 (s, 3H) |
| 989 | 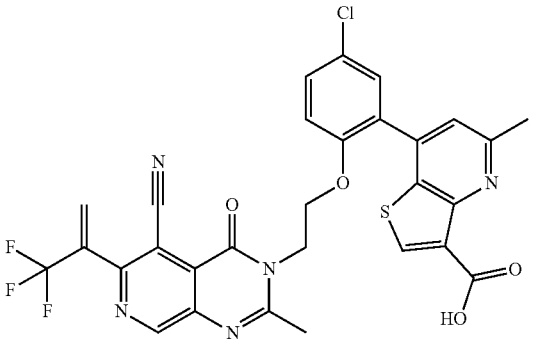 [SMILES: C=C(c1ncc2nc(C)n(CCOc3ccc(Cl)cc3-c3cc(C)nc4c(C(=O)O)csc34)c(=O)c2c1C#N)C(F)(F)F] | MS (ESI) m/z 626.13 [M + 1]+; 1H NMR (400 MHz, DMSO-d6 with D2O) δ 9.14 (s, 1H), 7.79 (s, 1H), 7.50 (dd, J = 8.64 Hz, 1.96 Hz, 1H), 7.31 (d, J = 2.56 Hz, 1H), 7.25 (d, J = 8.68 Hz, 1H), 7.04 (s, 1H), 6.63 (s, 1H), 6.41 (s, 1H), 4.33 (s, 2H), 4.25 (s, 2H), 2.66 (s, 3H), 1.82 (s, 3H) |
| 993 | 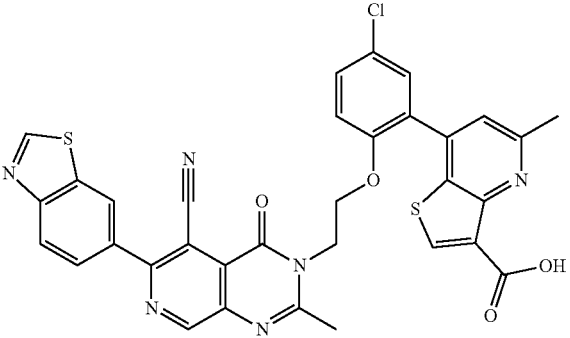 [SMILES: Cc1cc(-c2cc(Cl)ccc2OCCn2c(C)nc3cnc(-c4ccc5ncsc5c4)c(C#N)c3c2=O)c2scc(C(=O)O)c2n1] | MS (ESI) m/z 665.02 [M + 1]+; 1H NMR (400 MHz, DMSO-d6) δ 13.53 (bs, 1H), 9.56 (s, 1H), 9.11 (s, 1H), 8.72 (s, 1H), 8.32 (bs, 1H), 8.28 (d, J = 8.56 Hz, 1H), 8.06 (d, J = 8.48 Hz,1H), 7.59 (dd, J = 8.92Hz, 2.36 Hz, 1H), 7.41 (d, J = 2.28 Hz, 1H), 7.37-7.35 (m, 2H), 4.42 (t, J = 6.24 Hz, 2H), 4.30 (t, J = 4.56 Hz, 2H), 2.70 (s, 3H), 1.90 (s, 3H) |
| 994 | 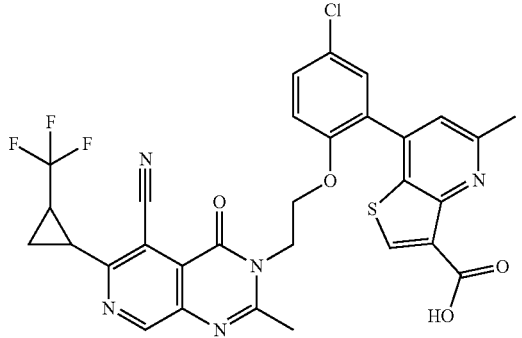 [SMILES: Cc1cc(-c2cc(Cl)ccc2OCCn2c(C)nc3cnc(C4CC4C(F)(F)F)c(C#N)c3c2=O)c2scc(C(=O)O)c2n1] | MS (ESI) m/z 640.13 [M + 1]+; 1H NMR (400 MHz, DMSO-d6) δ 8.88 (s, 1H), 8.39 (s, 1H), 7.59 (dd, J = 8.88, 2.62 Hz, 1H), 7.41 (t, J = 2.8 Hz, 2H), 7.36 (d, J = 8.8 Hz, 1H), 4.40 (t, J 5.2 Hz, 2H), 4.27 (t, J = 5.2 Hz, 2H), 2.94 (d, 4.4 Hz, 1H), 2.70 (s, 3H), 2.66- 2.60 (m, 1H), 1.91 (s, 3H), 1.68 (t, J = 7.2 Hz, 2H) |

TABLE 1-continued

7-Aza-Thienylpyridine and Derivative Compounds

| Compound | | Characterization |
|---|---|---|
| 997 |  | MS (ESI) m/z 673.99 [M + 1]+; 1H NMR (400 MHz, DMSO-d6) δ 13.50 (s, 1H), 8.50 (s, 1H), 7.86 (dd, J = 2.56, 6.08 Hz, 1H), 7.70 (dd, J = 4.60, 8.60 Hz, 1H), 7.58 (dd, J = 2.52, 8.92 Hz, 1H), 7.49 (t, J = 9.28 Hz, 2H), 7.42-7.36 (m, 2H), 4.44 (t, J = 4.40 Hz, 2H), 4.29 (t, J = 4.40 Hz, 2H), 2.79 (s, 3H), 2.70 (s, 3H), 2.00 (s, 3H) |
| 998 |  | MS (ESI) m/z 658.03 [M + 1]+; 1H NMR (400 MHz, DMSO-d6) δ 13.50 (s, 1H), 8.52 (s, 1H), 7.64-7.61 (m, 1H), 7.60 (dd, J = 2.4, 8.92 Hz, 1H), 7.50-7.47 (m, 2H), 7.42 (bs, 1H), 7.40 (d, J = 2.56 Hz, 1H), 7.37 (d, J = 9.00 Hz, 1H), 4.44 (t, J = 4.72 Hz, 2H), 4.29 (t, J = 4.52 Hz, 2H) 2.79 (s, 3H), 2.70 (s, 3H), 2.06 (s, 3H) |
| 999 |  | MS (ESI) m/z 674.0 [M + 1]+; 1H NMR (400 MHz, DMSO-d6) δ 13.50 (bs, 1H), 8.50 (s, 1H), 7.72-7.68 (m, 2H), 7.59 (dd, J = 2.56, 8.92 Hz, 1H), 7.53-7.45 (m, 1H), 7.43-7.41 (m, 2H), 7.34 (d, J = 9.2 Hz, 1H), 4.45 (t, J = 4.96 Hz, 2H), 4.29 (bs, 2H), 2.78 (s, 3H), 2.70 (s, 3H), 1.98 (s, 3H) |
| 1004 |  | MS (ESI) m/z 548.02 [M + 1]+; 1H NMR (400 MHz, DMSO-d6) δ 13.62 (bs, 2H), 8.51 (s, 1H), 8.30 (bs, 1H), 7.59 (dd, J = 8.88, 2.52 Hz, 1H), 7.42 (s, 2H), 7.34 (d, J = 9.00 Hz 1H), 4.35 (t, J = 5.48 Hz, 2H), 4.15 (t, J = 3.64 Hz, 2H), 2.71 (s, 3H), 1.65 (s, 3H) |

TABLE 1-continued

7-Aza-Thienylpyridine and Derivative Compounds

| Compound | | Characterization |
|---|---|---|
| 1008 | 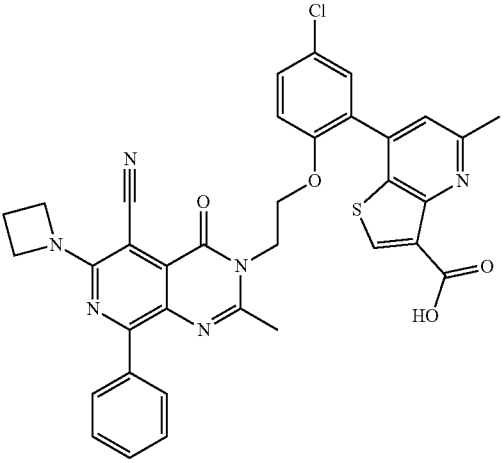 [SMILES: Cc1cc(-c2cc(Cl)ccc2OCCn2c(C)nc3c(-c4ccccc4)nc(N4CCC4)c(C#N)c3c2=O)c2scc(C(=O)O)c2n1] | MS (ESI) m/z 663.13 [M + 1]+; 1H NMR (400 MHz, DMSO-d6) δ 8.68 (s, 1H), 8.10-8.08 (m, 2H), 7.60 (dd, J = 2.4, 6.8 Hz, 2H), 7.51-7.50 (m, 3H), 7.41-7.36 (m, 3H), 4.42 (t, J = 4.8 Hz, 6H), 4.24 (t, J = 4.4 Hz, 2H), 2.57 (s, 3H), 2.42-2.32 (m, 2H), 1.97 (s, 3H) |
| 1010 | 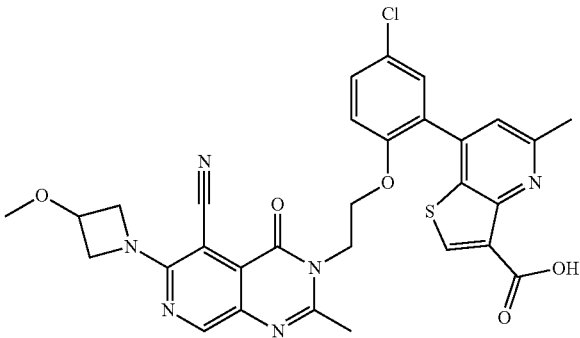 | MS (ESI) m/z 617.14 [M + 1]+; 1H NMR (400 MHz, DMSO-d6) δ 13.59 (s, 1H), 8.55 (s, 1H), 8.47 (s, 1H), 7.58 (d, J = 8.72 Hz ,1H), 7.40-7.38 (m, 2H), 7.34 (d, J = 8.76 Hz, 1H), 4.55 (t, J = 6.76 Hz, 2H), 4.36 (m, 3H), 4.18-4.13 (m, 4H), 3.28 (s, 3H), 2.70 (s, 3H), 1.80 (s, 3H) |
| 1011 | 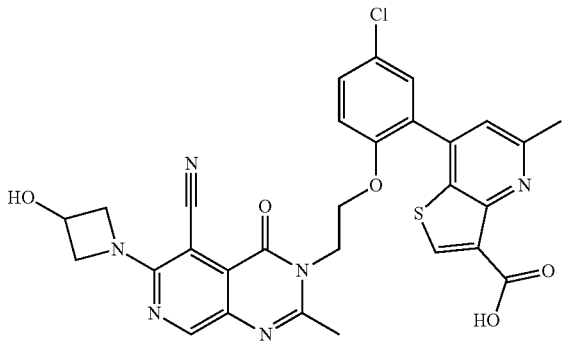 [SMILES: Cc1cc(-c2cc(Cl)ccc2OCCn2c(C)nc3cnc(N4CC(O)C4)c(C#N)c3c2=O)c2scc(C(=O)O)c2n1] | MS (ESI) m/z 603.09 [M + 1]+; 1H NMR (400 MHz, DMSO-d6) δ 8.55 (s, 1H), 8.48 (s, 1H), 7.59 (dd, J = 2.4, 8.8 Hz 1H), 7.41 (d, J = 2.4 Hz, 1H), 7.39 (s, 1H ), 7.35 (d, J = 9.2 Hz 1H), 5.79 (d, J = 5.2 Hz, 1H), 4.58 (m, 3H), 4.36 (bs, 2H), 4.19 (bs, 2H), 4.07 (d, J = 6.8 Hz, 2H), 2.70 (s, 3H), 1.78 (s, 3H) |
| 1015 | 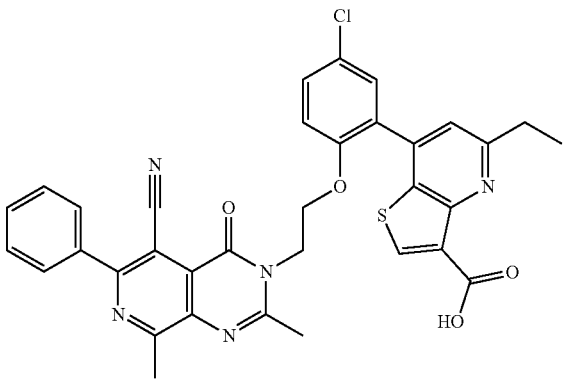 [SMILES: CCc1cc(-c2cc(Cl)ccc2OCCn2c(C)nc3c(C)nc(-c4ccccc4)c(C#N)c3c2=O)c2scc(C(=O)O)c2n1] | MS (ESI) m/z 636.14 [M + 1]+; 1H NMR (400 MHz, DMSO-d6) δ 13.67 (bs, 1H), 8.50 (s, 1H), 7.87 (m, 2H), 7.61-7.55 (m, 4H), 7.46 (s, 1H), 7.42 (d, J = 2.5 Hz, 1H), 7.37 (s, 1H), 4.45 (t, J = 5.3 Hz, 2H), 4.27 (t, J = 4.6 Hz, 2H), 3.04-2.98 (m, 2H), 2.78 (s, 3H), 1.35 (s, 3H), 1.08 (t, J = 7.5 Hz, 3H) |

TABLE 1-continued

7-Aza-Thienylpyridine and Derivative Compounds

| Compound | | Characterization |
|---|---|---|
| 1016 | 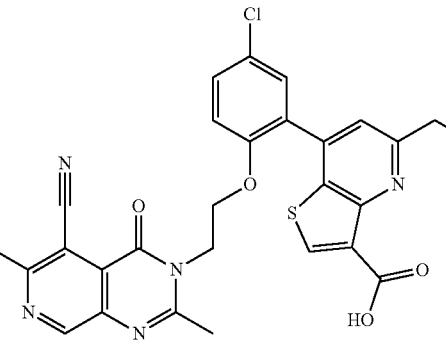 | MS (ESI) m/z 622.14 [M + 1]+; 1H NMR (400 MHz, DMSO-d6) δ 13.73 (bs, 1H), 9.02 (s, 1H), 8.39 (s, 1H) 7.94-7.87 (m, 2H), 7.61-7.58 (m, 4H), 7.46-7.43 (m, 2H), 7.36 (d, J = 8.96 Hz, 1H), 4.42 (t, J = 5.6 Hz, 2H), 4.27 (t, J = 4.32 Hz, 2H), 3.02 (q, J = 7.52 Hz, 2H), 1.83 (s, 3H) 1.35 (t, J = 7.56 Hz, 3H) |
| 1037 | 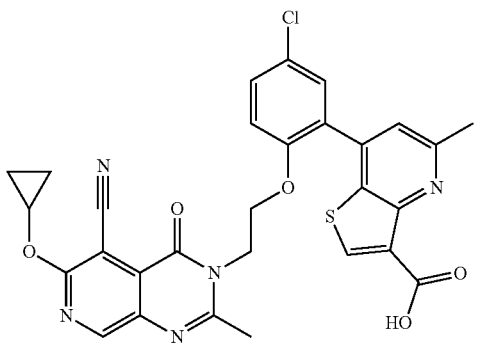 | MS (ESI) m/z 688.18 [M + 1]+; 1H NMR (400 MHz, DMSO-d6) δ 12.86 (bs, 1H), 8.87 (s, 1H), 8.11 (s, 1H), 7.54 (d, J = 8.72 Hz, 1H), 7.36 (s, 1H), 7.30 (d, J = 8.88 Hz, 1H), 7.23 (s, 1H), 4.48 (t, J = 4.4 Hz, 1H), 4.35 (t, J = 4.08 Hz, 2H), 4.22 (t, J = 3.24, 2H), 2.66 (s, 3H), 1.80 (s, 3H), 0.86 (d, J = 5.56 Hz, 2H), 0.81 (s, 2H) |
| 1038 | 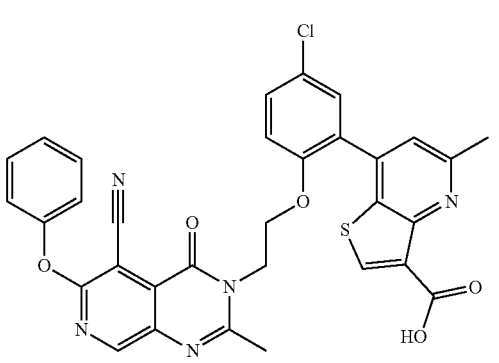 [SMILES: Cc1cc(-c2cc(Cl)ccc2OCCn2c(C)nc3cnc(Oc4ccccc4)c(C#N)c3c2=O)c2scc(C(=O)O)c2n1] | MS (ESI) m/z 624.06 [M + 1]+; 1H NMR (400 MHz, DMSO-d6) δ 13.57 (bs, 1H), 8.62 (s, 1H), 8.44 (s, 1H), 7.60 (dd, J = 8.8 Hz, 2.4 Hz 1H), 7.54-7.46 (m, 2H), 7.45-7.40 (m, 2H), 7.36 (d, J = 8.8 Hz, 1H), 7.35-7.28 m, 3H), 4.41 (t, J = 4.4 Hz, 2H), 4.26 (t, J = 5.2 Hz, 2H), 2.71 (s, 3H), 1.82 (s, 3H) |
| 1039 | 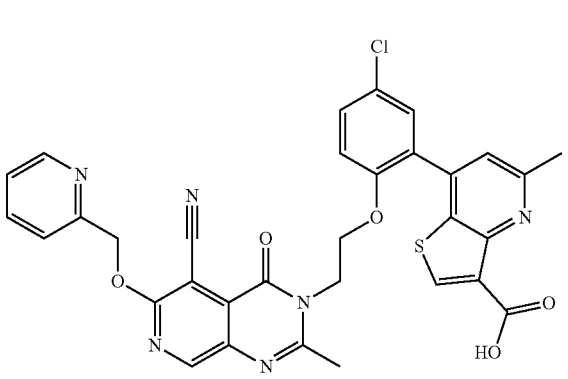 [SMILES: Cc1cc(-c2cc(Cl)ccc2OCCn2c(C)nc3cnc(OCc4ccccn4)c(C#N)c3c2=O)c2scc(C(=O)O)c2n1] | MS (ESI) m/z 639.08 [M + 1]+; 1H NMR (400 MHz, DMSO-d6) δ 13.62 (bs, 1H), 8.71 (s, 1H), 8.59 (d, J = 4 Hz, 1H), 8.43 (s, 1H), 7.89 (t, J = 7.08 Hz, 1H), 7.60-7.57 (m, 2H), 7.40 (s, 2H), 7.39-7.34 (m, 2H), 5.68 (s, 2H), 4.40 (t, J = 5.36 Hz, 2H), 4.24 (t, J = 4.36 Hz,2H), 2.70 (s, 3H), 1.85 (s, 3H) |

TABLE 1-continued

7-Aza-Thienylpyridine and Derivative Compounds

| Compound | Characterization |
|---|---|
| 1041 | MS (ESI) m/z 653.12 [M + 1]+; 1H NMR (400 MHz, DMSO-d6) ) δ 8.58 (s, 1H), 8.46 (s, 1H), 7.58 (dd, J = 2.4, 8.8 Hz, 1H), 7.40 (t, J = 2.4 Hz, 2H), 7.35 (d, J = 8.8 Hz, 1H), 7.03-6.65 (m, 1H), 5.12 (t, J = 3.6 Hz, 1H), 4.72 (m, 2H), 4.38 (t, J = 5.2 Hz, 2H), 4.32 (m, 2H), 4.21 (t, J = 4.4 Hz, 2H), 3.40 (s, 1H), 2.71 (s, 3H), 1.83 (s, 3H) |
| 1042 | MS (ESI) m/z 671.16 [M + 1]-; 1H NMR (400 MHz, DMSO-d6) δ 8.60 (s, 1H), 8.47 (s, 1H), 7.60 (dd, J = 2.8, 8.8 Hz, 1H), 7.41-7.40 (m, 2H), 7.36 (d, J = 8.8 Hz, 1H), 5.36-5.33 (m, 1H), 4.79-4.75 (m, 2H), 4.43 (t, J = 3.2 Hz, 2H), 4.40 (t, J = 7.6 Hz, 2H), 4.21 (d, J = 4.4 Hz, 2H), 2.17 (s, 3H), 1.85 (s, 3H) |
| 1043 | MS (ESI) m/z 667.13 [M + 1]+; 1H NMR (400 MHz, DMSO-d6) δ 8.56 (s, 1H), 8.47 (s, 1H), 7.57 (dd, J = 2.52, 8.8 Hz ,1H), 7.40 (t, J = 2.4 Hz, 2H), 7.34 (d, J = 8.84 Hz, 1H), 6.35-6.06 (m, 1H), 4.59 (t, J = 6.24 Hz, 2H), 4.36 (t, J = 4.8 Hz, 2H), 4.18 (d, J = 6.8 Hz, 4H), 3.84-3.75 (m, 2H), 2.70 (s, 3H), 1.80 (s, 3H) |
| 1044 | MS (ESI) m/z 685.20 [M + 1]+; 1H NMR (400 MHz, DMSO-d6) δ 13.58 (bs, 1H), 8.57 (s, 1H), 8.47 (s, 1H), 7.58 (dd, J = 2.48, 8.88 Hz ,1H), 7.40 (d, J = 2.56 Hz, 1H), 7.39 (s, 1H), 7.34 (d, J = 9.00 Hz, 1H), 4.65-4.58 (m, 3H), 4.37 (t, J = 6.08 Hz, 2H), 4.25-4.19 (m, 6H), 2.70 (s, 3H), 1.81 (s, 3H) |

TABLE 1-continued

7-Aza-Thienylpyridine and Derivative Compounds

| Compound | | Characterization |
|---|---|---|
| 1045 |  | MS (ESI) m/z 659.25 [M + 1]+; 1H NMR (400 MHz, DMSO-d6) δ 13.59 (bs, 1H), 8.55 (s, 1H), 8.47 (s, 1H), 7.59 (dd, J = 2.48, 8.84 Hz, 1H), 7.41 (d, J = 2.52 Hz, 1H), 7.39 (s, 1H), 7.34 (d, J = 8.96 Hz, 1H), 4.68-4.65 (m, 1H), 4.61-4.57 (m, 2H), 4.34 (t, J = 4.68 Hz, 2H), 4.16 (t, J = 3.72 Hz, 2H), 4.06-4.03 (m, 2H), 2.67 (s, 3H), 1.82 (s, 3H), 1.15 (s, 9H) |
| 1051 |  | MS (ESI) m/z 641.11 [M + 1]+; 1H NMR (400 MHz, DMSO-d6) δ 13.52 (s, 1H), 9.06 (s, 1H), 8.67 (d, J = 2.76 Hz, 1H), 8.36 (s, 1H), 8.06 (dd, J = 2.64, 9.0 Hz, 1H), 7.60 (dd, J = 2.52, 8.8 Hz ,1H), 7.43 (s, 2H), 7.36 (d, J = 8.96 Hz, 1H), 4.43 (t, J = 5.0 Hz, 2H), 4.29 (t, J = 5.5 Hz, 2H), 2.72 (s, 3H), 2.36 (s, 3H), 1.91 (s, 3H) |
| 1052 |  | MS (ESI) m/z, 640.13 [M + 1]+; 1H NMR (400 MHz, DMSO-d6) δ 13.51 (bs, 1H), 9.03 (s, 1H), 8.37 (s, 1H), 7.60 (dd, J = 2.40, 8.84 Hz, 1H), 7.43 (bs, 4H), 7.34 (d, J = 8.92 Hz, 1H), 7.32-7.28 (m, 1H), 4.42 (t, J = 4.72 Hz, 2H), 4.27 (t, J = 4.76 Hz, 2H), 2.72 (s, 3H), 2.14 (s, 3H), 1.86 (s, 3H) |
| 1053 |  | MS (ESI) m/z 603.17 [M + 1]+; 1H NMR (400 MHz, DMSO-d6) δ 8.94 (s, 1H), 8.38 (s, 1H), 7.59 (d, J = 8.72 Hz, 1H), 7.42 (s, J = 2.76, 2H), 7.36 (d, J = 8.96 Hz, 1H), 4.41 (s, 2H), 4.26 (s, 2H), 3.34 (s, 3H), 2.71 (s, 3H), 2.00 (bs, 3H), 1.84 (s, 3H) |

TABLE 1-continued

7-Aza-Thienylpyridine and Derivative Compounds

| Compound | | Characterization |
|---|---|---|
| 1056 | | MS (ESI) m/z 617.15 [M + 1]+; 1H NMR (400 MHz, DMSO-d6) δ 8.55 (s, 1H), 8.50 (s, 1H), 7.59 (dd, J = 8.8 Hz, 2.44 Hz, 1H), 7.42-7.40 (m, 2H), 7.35 (d, J = 9 Hz, 1H), 4.38 (bs, 1H), 4.36 (m, 2H), 4.21-4.18 (m, 2H), 3.93-3.87 (m, 3H), 3.78-3.73 (m,1H), 3.56 (d, J = 11.68 Hz, 1H), 2.70 (s, 3H), 2.04-2.02 (m, 1H), 1.94-1.92 (m, 1H), 1.79 (s, 3H) |
| 1057 | | MS (ESI) m/z 617.18 [M + 1]+; 1H NMR (400 MHz, DMSO-d6) δ 13.59 (bs, 1H), 8.56 (s, 1H), 8.47 (s, 1H), 7.58 (d, J = 8.64 Hz, 1H), 7.40 (d, J = 8.84 Hz, 2H), 7.34 (d, J = 8.88 Hz, 1H), 5.70 (bs, 1H) 4.36 (t, J = 6.56 Hz, 2H), 4.20 (m, 6H), 2.70 (s, 3H), 1.77 (s, 3H), 1.47 (s, 3H) |
| 1062 | | MS (ESI) m/z 574.12 [M + 1]+; 1H NMR (400 MHz, DMSO-d6) δ 13.7 (bs, 1H), 8.92 (s, 1H), 8.35 (s, 1H), 7.60 (d, J = 8.4 Hz, 1H), 7.44-7.43 (m, 2H), 7.36 (d, J = 8.8 Hz, 1H), 4.40 (t, J = 4.4 Hz, 2H), 4.25 (t, J = 4.0 Hz, 2H), 3.12-3.07(m, 2H), 3.03-2.97 (m, 2H), 1.83 (s, 3H), 1.36 (t, J = 7.2 Hz, 6H) |
| 1063 | | MS (ESI) m/z 573.12 [M + 1]+; 1H NMR (400 MHz, DMSO-d6) δ 8.86 (s, 1H), 8.30 (s, 1H), 7.55 (dd, J = 8.88 Hz, 2.32 Hz, 1H), 7.35-7.30 (m, 3H), 4.36 (t, J = 6.6 Hz, 2H), 4.22 (t, J = 5.12 Hz, 2H), 3.02 (t, J = 7.36 Hz, 2H), 2.71 (s, 3H), 1.90 (s, 3H), 1.80-1.74 (m, 2H),0.93 (t, J = 14.6Hz, 3H) |

TABLE 1-continued

7-Aza-Thienylpyridine and Derivative Compounds

| Compound | | Characterization |
|---|---|---|
| 1064 | 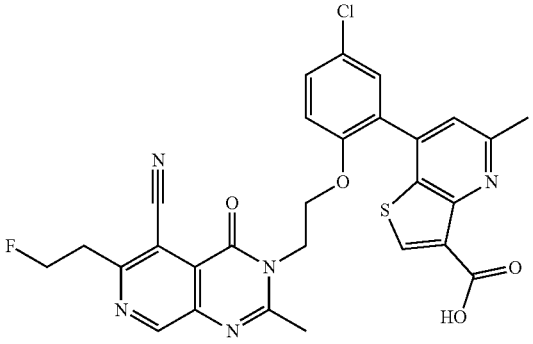 [SMILES: Cc1cc(-c2cc(Cl)ccc2OCCn2c(C)nc3cnc(CCF)c(C#N)c3c2=O)c2scc(C(=O)O)c2n1] | MS (ESI) m/z 578.19 [M + 1]+; 1H NMR (400 MHz, DMSO-d6) δ 8.98 (s, 1H), 8.40 (s, 1H), 7.59 (dd, J = 8.88 Hz, 2.62 Hz, 1H), 7.41 (s, 2H), 7.35 (d, J = 8.89 Hz, 1H), 4.94 (dt, J = 48 Hz, 6.0 Hz, 2H), 4.40 (t, J = 5.2 Hz, 2H), 4.26 (t, J = 4.8 Hz, 2H), 3.49 (dt, J = 25 Hz, 6.0 Hz, 2H), 2.70 (s, 3H), 1.89 (s, 3H) |
| 1065 | 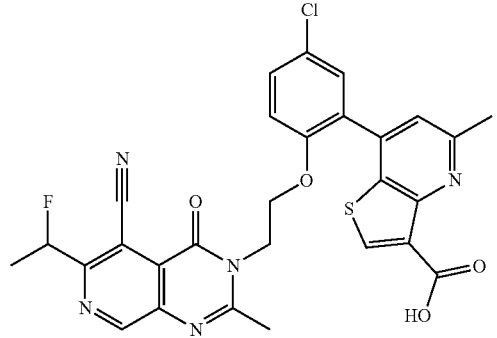 [SMILES: Cc1cc(-c2cc(Cl)ccc2OCCn2c(C)nc3cnc(C(C)F)c(C#N)c3c2=O)c2scc(C(=O)O)c2n1] | MS (ESI) m/z 578.14 [M + 1]+; 1H NMR (400 MHz, DMSO-d6) δ 13.50 (bs, 1H), 9.03 (s, 1H), 8.39 (s, 1H), 7.59 (dd, J = 8.8, 2.2 Hz 1H), 7.45-7.38 (m, 2H), 7.35 (d, J = 8.92 Hz, 1H), 6.24-6.15 (dq, J = 47.20, 6.80 Hz, 1H), 4.47-4.35 (m, 2H), 4.35-4.29 (m, 2H), 2.69 (s, 3H), 1.87 (s, 3H), 1.78 (dd, J = 24.4, 6.32 Hz, 3H) |
| 1066 | 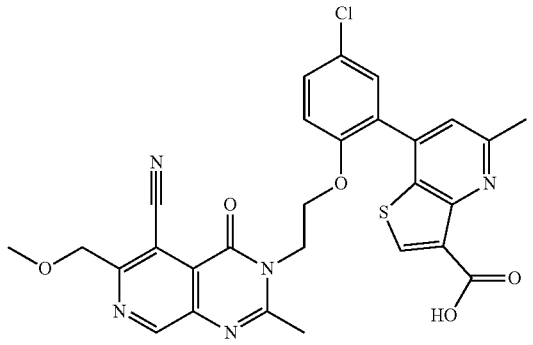 | MS (ESI) m/z 576.18 [M + 1]+; 1H NMR (400 MHz, DMSO-d6) δ 13.58 (s, 1H), 8.98 (s, 1H), 8.35 (s, 1H), 7.58 (s, 1H), 7.41-7.35 (m, 3H), 4.74 (s, 2H), 4.39 (s, 2H), 4.26 (s, 2H), 3.38 (s, 3H) 2.69 (s, 3H), 1.85 (s, 3H) |
| 1067 | 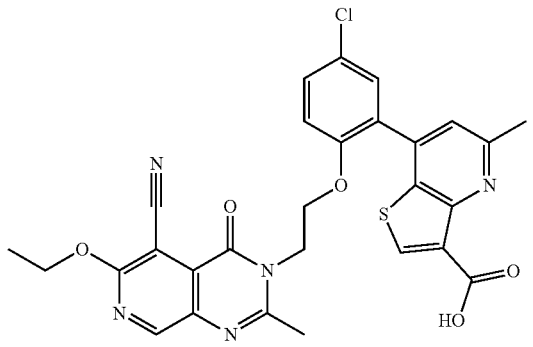 | MS (ESI) m/z 576.14 [M + 1]+; 1H NMR (400 MHz, DMSO-d6) δ 8.69 (s, 1H), 8.42 (s, 1H), 7.57 (dd, J = 2.52, 8.8 Hz, 1H), 7.41 (s, 2H), 7.35 (d, J = 8.92 Hz, 1H), 4.59-4.54 (m, 2H), 4.39 (t, J = 4.4 Hz, 2H), 4.23 (t, J = 4.3 Hz, 2H), 2.71 (s, 3H), 1.84 (s, 3H) |

TABLE 1-continued

7-Aza-Thienylpyridine and Derivative Compounds

| Compound | | Characterization |
|---|---|---|
| 1068 | (structure) | MS (ESI) m/z 602.16 [M + 1]+; 1H NMR (400 MHz, DMSO-d6) δ 13.70 (bs, 1H), 8.69 (s, 1H), 8.37 (s, 1H), 7.59 (dd, J = 8.88, 2.64 Hz, 1H), 7.40 (d, J = 2.60 Hz, 1H), 7.38 (s, 1H), 7.34 (d, J = 8.96 Hz, 1H), 4.41-4.31 (m, 4H), 4.23 (t, J = 4.60 Hz, 2H), 2.70 (s, 3H), 1.83 (s, 3H), 1.40-1.40 (m, 1H), 0.65-0.58 (m, 2H), 0.46-0.39 (m, 2H) |
| 1068 | (structure) | MS (ESI) m/z 561.20 [M + 1]+; 1H NMR (400 MHz, DMSO-d6) δ 13.59 (bs, 1H), 8.55 (s, 1H), 7.58 (d, J = 8.0 Hz, 1H), 7.40-7.34 (m, 3H), 7.03 (s, 2H), 4.38 (t, J = 5.9 Hz, 2H), 4.17 (t, J = 4.0 Hz, 2H), 2.69 (s, 3H), 2.56 (s, 3H), 1.72 (s, 3H) |
| 1070 | (structure) | MS (ESI) m/z 575.20 [M + 1]+; 1H NMR (400 MHz, DMSO-d6) δ 8.56 (s, 1H), 7.60 (dd, J = 2.0, 8.8 Hz, 1H), 7.44 (t, J = 3.6 Hz, 2H), 7.36 (d, J = 9.2 Hz, 1H), 7.03 (bs, 2H), 4.40 (bs, 2H), 4.17 (bs, 2H), 3.03 (m, 2H), 2.55 (s, 3H), 1.69 (s, 3H), 2.96 (t, J = 7.6 Hz, 3H) |
| 1071 | (structure) | MS (ESI) m/z 561.21 [M + 1]+; 1H NMR (400 MHz, DMSO-d6) δ 13.80 (bs, 1H), 8.47 (s, 1H), 8.44 (s, 1H) 7.59 (d, J = 9.20 Hz, 1H), 7.44 (s, 2H), 7.33 (d, J = 9.0 Hz, 1H), 7.21 (bs, 2H), 4.35 (t, J = 5.48 Hz, 2H), 4.16 (t, J = 6.28 Hz, 2H), 3.01 (q, J = 7.52 Hz, 2H), 1.64 (s, 3H), 1.34 (t, J = 7.48 Hz, 3H) |

TABLE 1-continued

7-Aza-Thienylpyridine and Derivative Compounds

| Compound | | Characterization |
|---|---|---|
| 1072 | 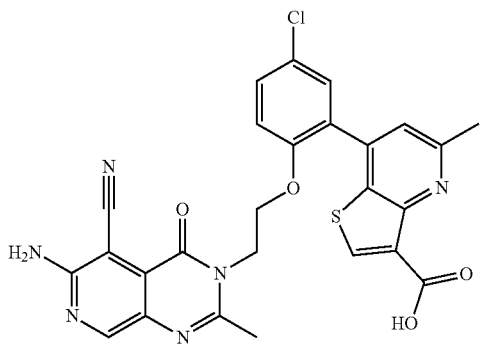 [SMILES: Cc1cc(-c2cc(Cl)ccc2OCCn2c(C)nc3cnc(N)c(C#N)c3c2=O)c2scc(C(=O)O)c2n1] | MS (ESI) m/z 547.10 [M + 1]+; 1H NMR (400 MHz, DMSO-d6) δ 8.49 (s, 1H), 8.47 (s, 1H) 7.59 (dd, J = 8.92, 2.44 Hz, 1H), 7.45-7.39 (m, 2H), 7.33 (d, J = 8.92 Hz 1H), 7.21 (bs, 2H), 4.36 (t, J = 6.0 Hz, 2H), 4.17 (t, J = 6.04 Hz, 2H), 2.70 (s, 3H), 1.68 (s, 3H) |
| 1076 | 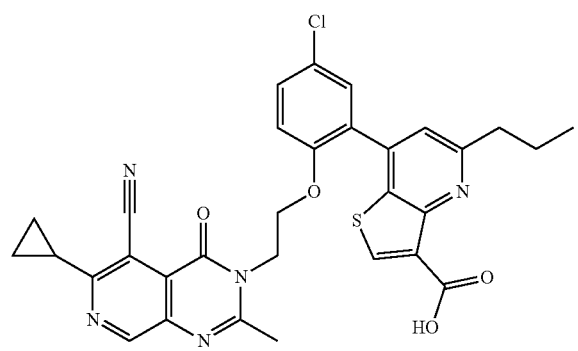 [SMILES: CCCc1cc(-c2cc(Cl)ccc2OCCn2c(C)nc3cnc(C4CC4)c(C#N)c3c2=O)c2scc(C(=O)O)c2n1] | MS (ESI) m/z 600.18 [M + 1]+; 1H NMR (400 MHz, DMSO-d6) δ 13.71 (s, 1H), 8.81 (s, 1H), 8.35 (s, 1H), 7.60 (dd, J = 2.4, 8.8 Hz, 1H), 7.43 (s, 1H), 7.36 (d, J = 9.2 Hz, 1H), 4.41 (t, J = 4.8 Hz, 2H), 4.24 (t, J = 4.4 Hz, 2H), 2.96 (t, J = 7.2 Hz, 2H), 2.66 (m, 1H), 1.85-1.75 (m, 5H), 1.23-1.18 (m, 2H), 1.10-1.06 (m, 2H), 1.00 (t, J = 7.2 Hz, 3H) |
| 1086 | 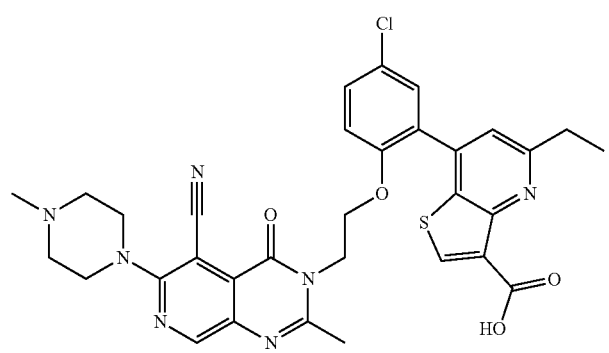 [SMILES: CCc1cc(-c2cc(Cl)ccc2OCCn2c(C)nc3cnc(N4CCN(C)CC4)c(C#N)c3c2=O)c2scc(C(=O)O)c2n1] | MS (ESI) m/z 644.20 [M + 1]+; 1H NMR (400 MHz, DMSO-d6) δ 13.70 (bs, 1H), 9.90 (bs, 1H), 8.66 (s, 1H), 8.38 (s, 1H) 7.60 (dd, J = 8.88, 2.36 Hz, 1H), 7.46 (s, 1H), 7.41 (d, J = 2.36 Hz 1H), 7.37 (d, J = 8.96 Hz, 1H), 4.40 (t, J = 4.88 Hz, 2H), 4.31 (d, J = 13.92 Hz, 2H), 4.22 (t, J = 5.84 Hz, 2H), 3.61 (d, J = 11.36 Hz, 2H), 3.44 (t, J = 11.92 Hz, 2H), 3.30-3.28 (m, 2H), 3.02 (q, J = 7.44 Hz, 2H), 2.91 (s, 3H), 1.84 (s, 3H), 1.37 (t, J = 7.52 Hz, 3H) |
| 1089 | 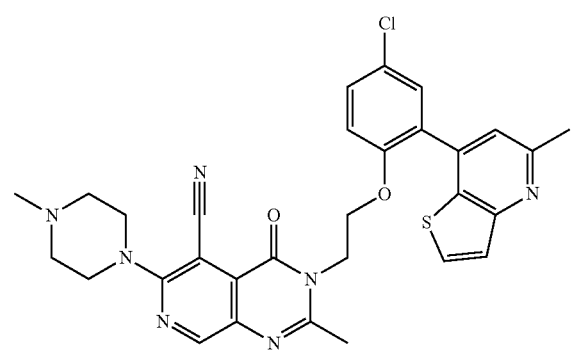 | MS (ESI) m/z 586.27 [M + 1]+; 1H NMR (400 MHz, DMSO-d6) 8.75 (s, 1H), 7.68 (s, 1H), 7.52 (d, J = 7.0 Hz, 1H), 7.34-7.28 (m, 3H), 7.09 (s, 1H), 4.34(5, 2H), 4.20 (s, 2H), 3.65 (s, 4H), 2.58 (s, 4H), 2.49 (s, 3H), 2.24 (s, 3H), 1.8 (s, 3H) |

TABLE 1-continued

7-Aza-Thienylpyridine and Derivative Compounds

| Compound | | Characterization |
|---|---|---|
| 1091 | 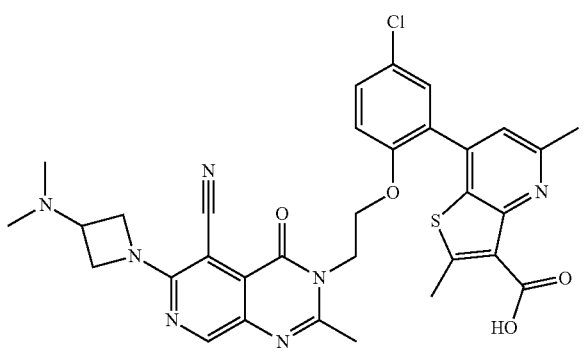 | MS (ESI) m/z 644.27 [M + 1]+; 1H NMR (400 MHz, DMSO-d6) δ 14.39 (bs, 1H), 8.62 (s, 1H), 7.59 (dd, J = 2.48, 8.88 Hz ,1H), 7.40-7.38 (m, 2H), 7.35 (d, J = 8.92 Hz, 1H), 4.63-4.59 (m, 2H), 4.47 (bs, 2H), 4.39 (t, J = 4.64 Hz, 2H), 4.23 (t, J = 4.64 Hz, 3H), 2.82 (bs, 6H), 2.70 (s, 3H), 2.54 (s, 3H), 1.94 (s, 3H) |
| 1092 | 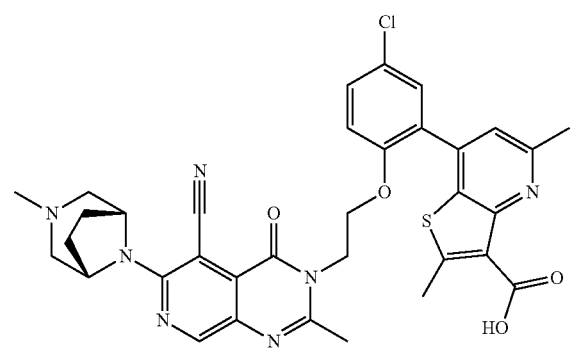 | MS (ESI) m/z 670.20 [M + 1]+; 1H NMR (400 MHz, DMSO-d6) δ 8.58 (s, 1H), 7.55 (d, J = 8.8 Hz, 1H), 7.33-7.30 (m, 3H), 4.88 (s, 2H), 4.35 (s, 2H), 4.22 (s, 2H), 3.53 (d, J = 12 Hz, 2H), 3.31 (d, J = 11.6 Hz, 2H), 2.79 (s, 3H), 2.66 (s, 3H), 2.46 (s, 3H), 2.05 (s, 7H) |
| 1097 | 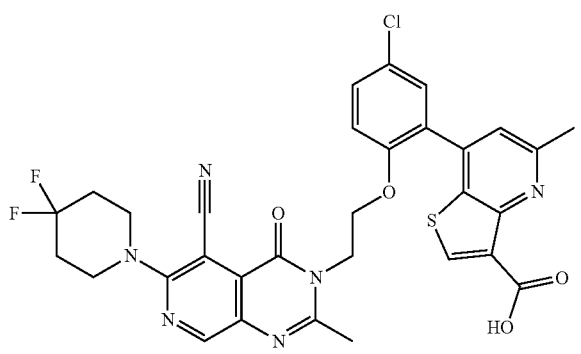 [SMILES: Cc1cc(-c2cc(Cl)ccc2OCCn2c(C)nc3cnc(N4CCC(F)(F)CC4)c(C#N)c3c2=O)c2scc(C(=O)O)c2n1] | MS (ESI) m/z 651.21 [M + 1]+; 1H NMR (400 MHz, DMSO-d6) δ 8.64 (s, 1H), 8.42 (s, 1H), 7.59 (dd, J = 8.8, 2.56 Hz, 1H), 7.41 (s, 2H), 7.36 (d, J = 8.95 Hz, 1H), 4.39 (t, J = 6.9 Hz, 2H), 4.22 (t, J = 4.56 Hz, 2H), 3.87-3.75 (m, 4H), 2.71 (s, 3H), 2.21-2.15 (m, 4H) 1.87 (s, 3H) |
| 1099 | 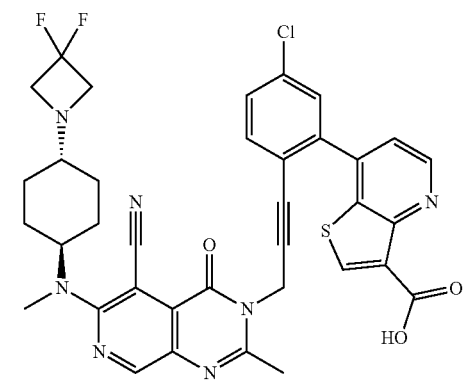 | MS (ESI) m/z 325.5 [M + 1]+; 1H NMR (400 MHz, DMSO-d6) δ 7.39-7.28 (m, 5H), 7.19 (d, J = 7.9 Hz, 1H), 4.99 (s, 2H), 3.50 (t, J = 12.4 Hz, 4H), 3.29-3.17 (m, 1H), 2.04 (t, J = 10.8 Hz, 2H), 1.77 (d, J = 12.4 Hz, 2H), 1.70 (d, J = 12.8 Hz, 2H), 1.15 (dq, J = 12.9, 3.2 Hz, 2H), 0.99 (q, J = 13.3 Hz, 2H) |

TABLE 1-continued

7-Aza-Thienylpyridine and Derivative Compounds

| Compound | | Characterization |
|---|---|---|
| 1100 | 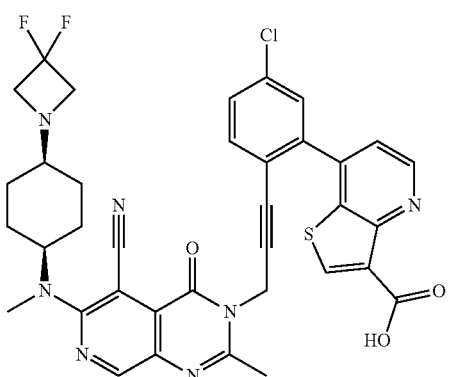 | MS (ESI) m/z 714.6 [M + 1]+; 1H NMR (400 MHz, DMSO-d6) δ 8.76 (d, J = 4.7 Hz, 1H), 8.71 (s, 1H), 8.66 (s, 1H), 7.78-7.74 (m, 1H), 7.69 (dd, J = 6.4, 2.2 Hz, 2H), 7.55 (d, J = 4.8 Hz, 1H), 4.92 (br, 4H), 4.82 (s, 2H), 4.33 (br, 2H), 3.13 (s, 3H), 2.07 (s, 3H), 2.03-1.61 (m, 8H) |
| 1101 | 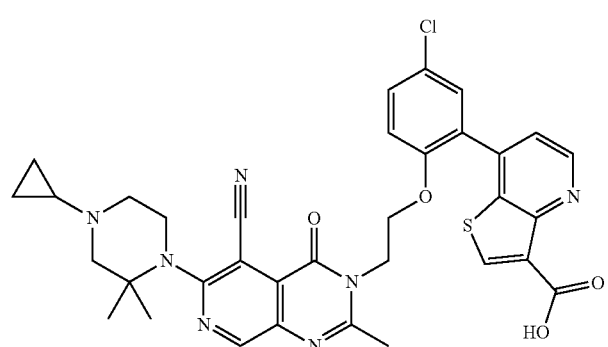 | MS (ESI) m/z 670.4 [M + 1]+; 1H NMR (400 MHz, DMSO-d6) δ 8.83 (d, J = 4.8 Hz, 1H), 8.77 (s, 1H), 8.36 (s, 1H), 7.60 (dd, J = 8.9, 2.7 Hz, 1H), 7.47 (d, J = 4.8 Hz, 1H), 7.44 (d, J = 2.7 Hz, 1H), 7.36 (d, J = 9.0 Hz, 1H), 4.40 (br, 2H), 4.23 (br, 2H), 3.81-3.03 (br, 6H), 1.79 (s, 3H), 1.62 (br, 3H), 1.31 (br, 4H), 0.96-0.75 (m, 4H) |
| 1102 | 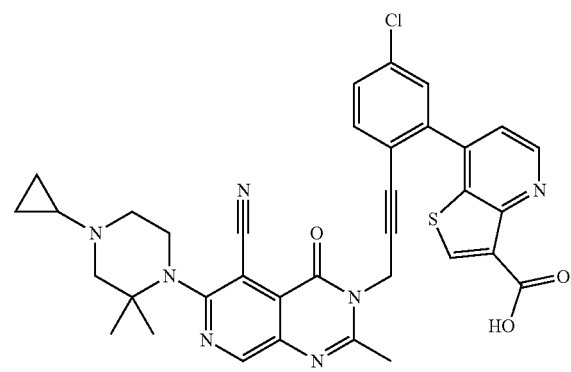 [SMILES: Cc1nc2cnc(N3CCN(C4CC4)CC3(C)C)c(C#N)c2c(=O)n1CC#Cc1ccc(Cl)cc1-c1ccnc2c(C(=O)O)csc12] | MS (ESI) m/z 664.4 [M + 1]+; 1H NMR (400 MHz, DMSO-d6) δ 8.90 (s, 1H), 8.75 (d, J = 4.8 Hz, 1H), 8.63 (s, 1H), 7.78-7.73 (m, 1H), 7.69 (dd, J = 6.6, 2.2 Hz, 2H), 7.55 (d, J = 4.8 Hz, 1H), 4.85 (d, J = 7.1 Hz, 2H), 3.83-2.97 (br, 6H), 2.12 (s, 3H), 1.63 (br 3H), 1.34 (br, 3H), 1.23-0.78 (m, 5H) |
| 1103 | 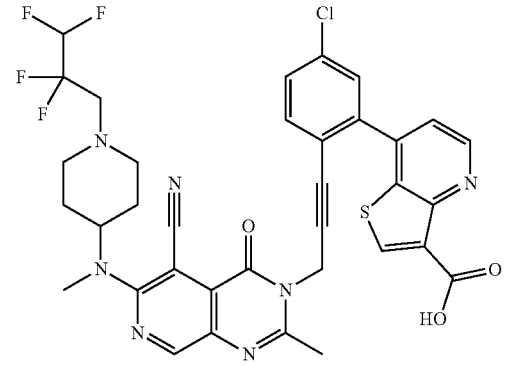 [SMILES: Cc1nc2cnc(N(C)C3CCN(CC(F)(F)C(F)F)CC3)c(C#N)c2c(=O)n1CC#Cc1ccc(Cl)cc1-c1ccnc2c(C(=O)O)csc12] | MS (ESI) m/z 738.3 [M + 1]+; 1H NMR (400 MHz, DMSO-d6) δ 8.77 (d, J = 4.8 Hz, 1H), 8.72 (s, 1H), 8.66 (s, 1H), 7.78-7.73 (m, 1H), 7.71-7.67 (m, 2H), 7.55 (d, J = 4.8 Hz, 1H), 6.79-6.41 (m, 1H), 4.82 (s, 2H), 4.36 (br, 1H), 3.11 (s, 3H), 2.07 (s, 3H), 2.05-1.82 (br, 2H). Protons on piperidine were not seen |

TABLE 1-continued

7-Aza-Thienylpyridine and Derivative Compounds

| Compound | | Characterization |
|---|---|---|
| 1104 | 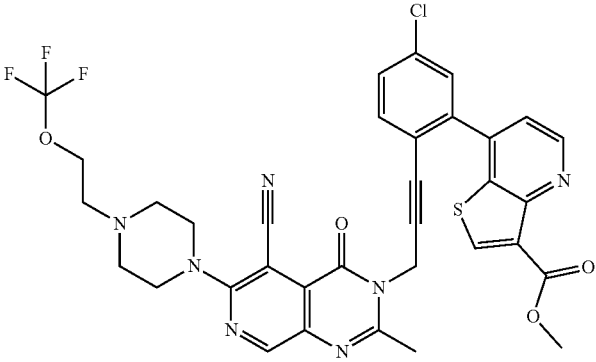 [SMILES: COC(=O)c1csc2c(-c3cc(Cl)ccc3C#CCn3c(C)nc4cnc(N5CCN(CCOC(F)(F)F)CC5)c(C#N)c4c3=O)ccnc12] | MS (ESI) m/z 722.5 [M + 1]+; 1H NMR (400 MHz, DMSO-d6) δ 8.82 (s, 1H), 8.74 (d, J = 4.7 Hz, 1H), 8.62 (s, 1H), 7.74 (d, J = 8.4 Hz, 1H), 7.71-7.61 (m, 2H), 7.43 (d, J = 4.7 Hz, 1H), 4.82 (s, 2H), 4.54 (bs, 2H), 3.86 (s, 3H), 3.68-3.23 (br, 2H), 2.15 (s, 3H). Some aliphatic protons were not seen |
| 1105 | 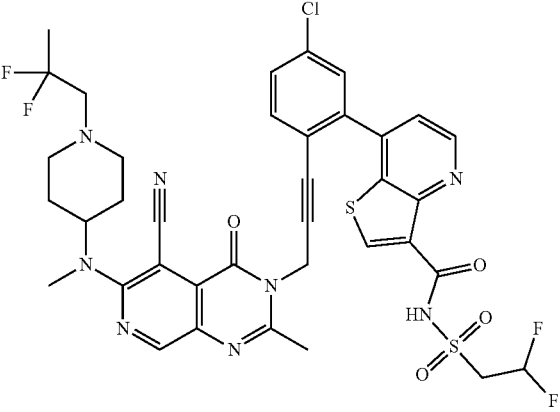 [SMILES: Cc1nc2cnc(N(C)C3CCN(CC(C)(F)F)CC3)c(C#N)c2c(=O)n1CC#Cc1ccc(Cl)cc1-c1ccnc2c(C(=O)NS(=O)(=O)CC(F)F)csc12] | MS (ESI) m/z 829.4 [M + 1]+; 1H NMR (400 MHz, DMSO-d6) δ 8.84 (d, J = 4.9 Hz, 1H), 8.82 (s, 1H), 8.75 (s, 1H), 7.78 (d, J = 9.1 Hz, 1H), 7.71 (dd, J = 6.6, 2.2 Hz, 2H), 7.64 (d, J = 4.9 Hz, 1H), 7.26-6.94 (m, 1H), 6.59 (tt, J = 54.1, 4.3 Hz, 2H), 4.84 (s, 2H), 4.56 (br, 1H), 4.48 (td, J = 14.7, 4.3 Hz, 2H), 3.12 (s, 3H), 2.34-1.97 (br, 8H), 1.95 (s, 3H), 1.76 (t, J = 19.4 Hz, 3H) |
| 1106 | 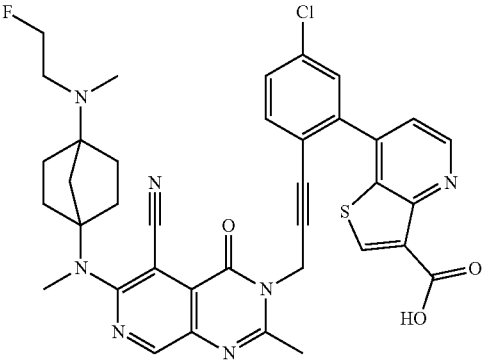 [SMILES: Cc1nc2cnc(N(C)C34CCC(N(C)CCF)(CC3)C4)c(C#N)c2c(=O)n1CC#Cc1ccc(Cl)cc1-c1ccnc2c(C(=O)O)csc12] | MS (ESI) m/z 710.4 [M + 1]+; 1H NMR (400 MHz, DMSO-d6) δ 10.06 (s, 1H), 8.76 (d, J = 4.8 Hz, 1H), 8.73 (s, 1H), 8.66 (s, 1H), 7.76 (d, J = 9.0 Hz, 1H), 7.71-7.66 (m, 2H), 7.55 (d, J = 4.8 Hz, 1H), 5.00-4.86 (m, 1H), 4.83 (s, 2H), 4.81-4.68 (m, 1H), 3.78-3.29 (m, 2H), 3.19 (s, 3H), 2.87 (s, 3H), 2.44-2.11 (m, 5H), 2.08 (s, 3H), 2.06-1.77 (m, 5H) |
| 1107 | 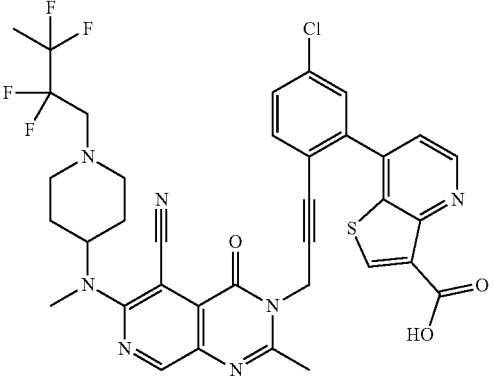 [SMILES: Cc1nc2cnc(N(C)C3CCN(CC(F)(F)C(C)(F)F)CC3)c(C#N)c2c(=O)n1CC#Cc1ccc(Cl)cc1-c1ccnc2c(C(=O)O)csc12] | MS (ESI) m/z 752.3 [M + 1]+; 1H NMR (400 MHz, DMSO-d6) δ 8.77 (d, J = 4.8 Hz, 1H), 8.73 (s, 1H), 8.66 (s, 1H), 7.78-7.74 (m, 1H), 7.71-7.67 (m, 2H), 7.55 (d, J = 4.9 Hz, 1H), 4.82 (s, 2H), 4.38 (br, 1H), 3.11 (s, 3H), 2.08 (s, 3H), 2.07-1.92 (br, 2H), 1.84 (t, J = 20.0 Hz, 3H). Piperidine protons were not seen |

TABLE 1-continued

7-Aza-Thienylpyridine and Derivative Compounds

| Compound | Characterization |
|---|---|
| 1108 | MS (ESI) m/z 791.2 [M + 1]+; 1H NMR (400 MHz, DMSO-d6) δ 12.47 (s, 1H), 8.82-8.78 (m, 2H), 8.76 (s, 1H), 7.77 (dd, J = 8.3, 0.6 Hz, 1H), 7.73-7.66 (m, 2H), 7.62 (d, J = 4.9 Hz, 1H), 4.83 (s, 2H), 4.78 (br, 4H), 4.36-4.22 (m, 2H), 3.54 (s, 3H), 3.09 (s, 3H), 2.12-2.02 (m, 2H), 1.98 (s, 3H), 1.80-1.67 (m, 3H), 1.46-1.32 (m, 3H) |
| 1109 | MS (ESI) m/z 854.4 [M + 1]+; 1H NMR (400 MHz, DMSO-d6) δ 13.01 (s, 1H), 8.89 (d, J = 4.8 Hz, 1H), 8.72 (ddd, J = 4.6, 1.7, 0.9 Hz, 1H), 8.66 (s, 1H), 8.59 (s, 1H), 8.27 (dt, J = 8.0, 1.1 Hz, 1H), 8.25-8.18 (m, 1H), 7.79-7.72 (m, 2H), 7.72-7.68 (m, 2H), 7.66 (d, J = 4.9 Hz, 1H), 4.82 (s, 2H), 4.76 (br, 4H), 4.34-4.23 (m, 1H), 3.24 (br, 1H), 3.07 (s, 3H), 2.13-2.01 (m, 2H), 1.97 (br, 2H), 1.94 (s, 3H), 1.71 (q, J = 12.1 Hz, 2H), 1.38 (q, J = 12.0 Hz, 2H) |
| 1110 | MS (ESI) m/z 854.4 [M + 1]+; 1H NMR (400 MHz, DMSO-d6) δ 9.29 (dd, J = 2.4, 0.8 Hz, 1H), 8.92 (dd, J = 4.8, 1.6 Hz, 1H), 8.83 (d, J = 4.9 Hz, 1H), 8.69 (s, 1H), 8.54 (ddd, J = 8.2, 2.4, 1.6 Hz, 1H), 8.47 (s, 1H), 7.77-7.67 (m, 3H), 7.66 (dd, J = 2.2, 0.5 Hz, 1H), 7.62 (dd, J = 4.8, 0.4 Hz, 1H), 4.84 (br, 4H), 4.80 (s, 2H), 4.39-4.27 (m, 1H), 3.28 (br, 1H), 3.09 (s, 3H), 2.14-2.05 (m, 2H), 2.02-1.94 (m, 2H), 1.91 (s, 3H), 1.74 (q, J = 12.2 Hz, 2H), 1.42 (q, J = 11.9 Hz, 2H) |

TABLE 1-continued

7-Aza-Thienylpyridine and Derivative Compounds

| Compound | | Characterization |
|---|---|---|
| 1111 | 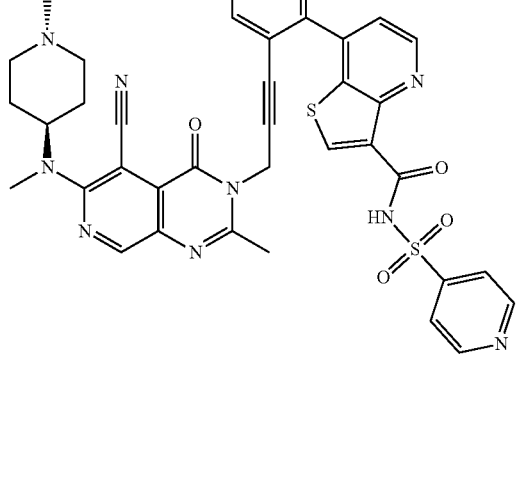 | MS (ESI) m/z 854.4 [M + 1]+; 1H NMR (400 MHz, DMSO-d6) δ 8.98-8.93 (m, 2H), 8.84 (d, J = 4.9 Hz, 1H), 8.70 (s, 1H), 8.48 (s, 1H), 8.11-7.70 (dd, J = 8.4, 2.2 Hz, 1H), 7.66 (dd, J = 2.2, 0.5 Hz, 1H), 7.64 (dd, J = 4.9, 0.4 Hz, 1H), 4.84 (br, 4H), 4.81 (s, 2H), 4.38-4.25 (m, 1H), 3.28 (br, 1H), 3.08 (s, 3H), 2.15-2.06 (m, 2H), 2.01-1.94 (m, 2H), 1.92 (s, 3H), 1.73 (q, J = 12.1 Hz, 2H), 1.41 (q, J = 11.8 Hz, 2H) |
| 1112 | 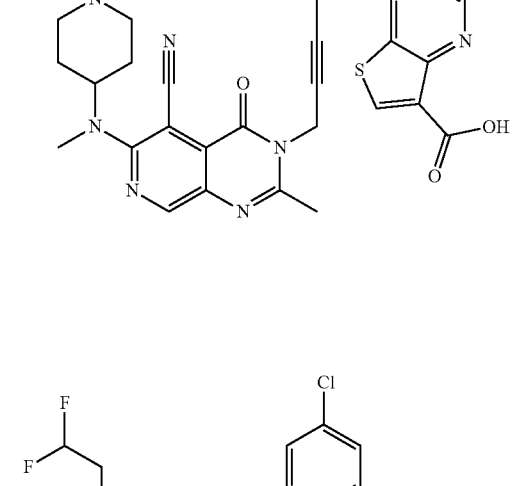 | MS (ESI) m/z 688.1 [M + 1]+; 1H NMR (400 MHz, DMSO-d6) δ 8.76 (d, J = 4.8 Hz, 1H), 8.74 (s, 1H), 8.65 (s, 1H), 7.77-7.74 (m, 1H), 7.71-7.67 (m, 2H), 7.55 (d, J = 4.8 Hz, 1H), 6.52 (t, J = 53.4 Hz, 1H), 4.83 (s, 2H), 4.50 (bs, 1H), 3.11 (s, 3H), 2.25-1.98 (m, 7H) |
| 1113 | 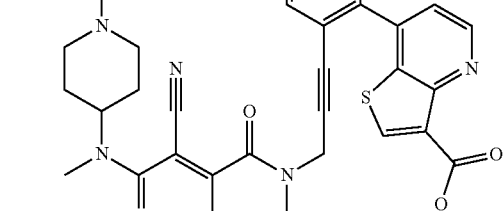 | MS (ESI) m/z 702.1 [M + 1]+; 1H NMR (400 MHz, DMSO-d6) δ 8.77 (d, J = 4.7 Hz, 1H), 8.69 (s, 1H), 8.59 (s, 1H), 7.74 (dd, J = 8.1, 0.8 Hz, 1H), 7.68-7.64 (m, 2H), 7.44 (d, J = 4.7 Hz, 1H), 6.15 (tt, J = 55.8, 4.4 Hz, 1H), 4.81 (s, 2H), 4.26 (ddt, J = 11.6, 7.7, 4.0 Hz, 1H), 3.84 (s, 3H), 3.10 (s, 3H), 3.03 (d, J = 11.2 Hz, 2H), 2.76 (td, J = 15.7, 4.3 Hz, 2H), 2.33 (t, J = 11.5 Hz, 2H), 2.03 (s, 3H), 1.92 (qd, J = 12.1, 3.9 Hz, 2H), 1.79 (d, J = 11.7 Hz, 2H); 19F NMR (377 MHz, DMSO-d6) 6-118.73 (dt, J = 55.8, 15.7 Hz, 2F) |

TABLE 1-continued

7-Aza-Thienylpyridine and Derivative Compounds

| Compound | | Characterization |
|---|---|---|
| 1115 | 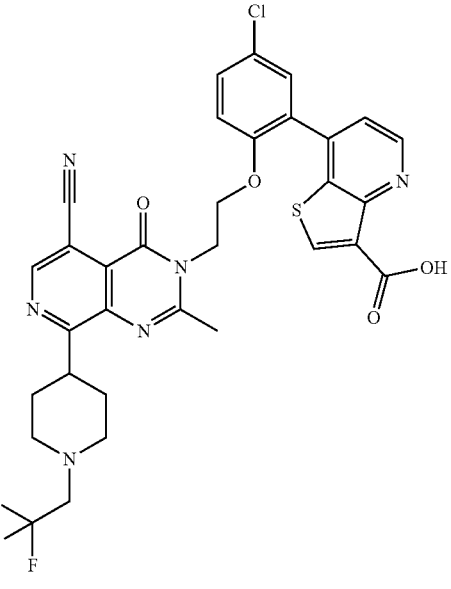 | MS (ESI) m/z 683.3 [M + 1]+; 1H NMR (400 MHz, DMSO-d6) δ 8.94 (s, 1H), 8.79 (d, J = 4.8 Hz, 1H), 8.59 (s, 1H), 7.59 (dd, J = 8.9, 2.7 Hz, 1H), 7.47 (d, J = 4.8 Hz, 1H), 7.45 (d, J = 2.7 Hz, 1H), 7.35 (d, J = 9.0 Hz, 1H), 4.42 (t, J = 4.9 Hz, 2H), 4.25 (t, J = 5.0 Hz, 2H), 3.82-3.70 (m, 1H), 3.20-3.09 (m, 2H), 2.78-2.67 (m, 2H), 1.92-1.79 (m, 7H) |
| 1116 | 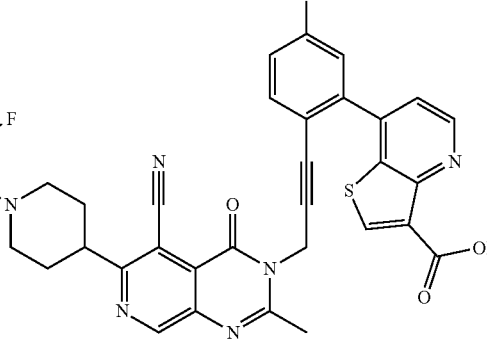 | MS (ESI) m/z 677.1 [M + 1]+; 1H NMR (400 MHz, Chloroform-d) δ 9.16 (s, 1H), 8.78 (d, J = 4.9 Hz, 1H), 8.56 (s, 1H), 7.59 (d, J = 8.4 Hz, 1H), 7.51 (dd, J = 8.4, 2.1 Hz, 1H), 7.46-7.41 (m, 2H), 4.81 (s, 2H), 3.66-3.38 (m, 5H), 3.01 I (t, J = 11.8 Hz, 2H), 2.50-2.31 (m, 5H), 2.13 (d, J = 14.0 Hz, 2H) |
| 1117 | 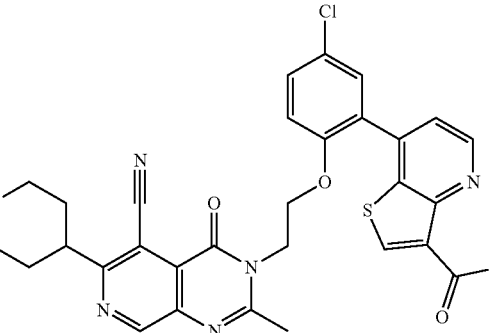 | MS (ESI) m/z 683.3 [M + 1]+; 1H NMR (400 MHz, Chloroform-d) δ 9.12 (s, 1H), 8.78 (d, J = 4.8 Hz, 1H), 8.45 (s, 1H), 7.48 (dd, J = 8.9, 2.6 Hz, 1H), 7.32-7.27 (m, 2H), 7.03 (d, J = 8.9 Hz, 1H), 4.41 (t, J = 4.9 Hz, 2H), 4.29 (t, J = 4.9 Hz, 2H), 3.64-3.48 (m, 6H), 3.13-3.01 (m, 2H), 2.46-2.32 (m, 2H), 1.89 (s, 3H) |

TABLE 1-continued

7-Aza-Thienylpyridine and Derivative Compounds

| Compound | Characterization |
|---|---|
| 1118 | MS (ESI) m/z 694.3 [M + 1]+; 1H NMR (400 MHz, Chloroform-d) δ 8.75 (s, 1H), 8.71 (d, J = 4.8 Hz, 1H), 8.49 (s, 1H), 7.59 (d, J = 8.4 Hz, 1H), 7.52 (dd, J = 8.4, 2.1 Hz, 1H), 7.40 (d, J = 2.1 Hz, 1H), 7.38 (d, J = 4.9 Hz, 1H), 5.36 (d, J = 7.0 Hz, 2H), 4.77-4.64 (m, 3H), 4.34 (d, J = 7.0 Hz, 2H), 3.37 (d, J = 11.5 Hz, 2H), 3.28 (t, J = 12.1 Hz, 2H), 3.19 (s, 3H), 2.84-2.70 (m, 2H), 2.44 (s, 3H), 2.34 (d, J = 13.5 Hz, 2H), 1.85 (s, 3H) |
| 1119 | MS (ESI) m/z 756.2 [M + 1]+; 1H NMR (400 MHz, DMSO-d6) δ 8.77 (d, J = 4.8 Hz, 1H), 8.72 (s, 1H), 8.66 (s, 1H), 7.76 (d, J = 9.0 Hz, 1H), 7.71-7.66 (m, 2H), 7.55 (d, J = 4.8 Hz, 1H), 4.82 (s, 2H), 4.35-4.24 (m, 1H), 3.38-3.22 (m, 2H), 3.12-3.00 (m, 5H), 2.63-2.52 (m, 2H), 2.06 (s, 3H), 2.00-1.86 (m, 2H), 1.85-1.75 (m, 2H) |
| 1120 | MS (ESI) m/z 623.1 [M + 1]+; 1H NMR (400 MHz, DMSO-d6) δ 8.80-8.58 (m, 3H), 7.78-7.63 (m, 3H), 7.53 (d, J = 4.8 Hz, 1H), 4.82 (s, 2H), 4.27 (t, J = 11.8 Hz, 1H), 3.09 (s, 3H), 2.04 (s, 3H), 1.89-1.75 (m, 4H), 1.71-1.56 (m, 3H), 1.38 (q, J = 12.8, 12.2 Hz, 2H), 1.16 (q, J = 13.1 Hz, 1H) |
| 1121 | LCMS (ESI) m/z 677.1 [M + 1]+; 1H NMR (400 MHz, DMSO-d6) δ 9.01 (s, 1H), 8.83 (d, J = 4.8 Hz, 1H), 8.36 (s, 1H), 7.60 (dd, J = 8.9, 2.7 Hz, 1H), 7.48 (d, J = 4.8 Hz, 1H), 7.44 (s, 1H), 7.42 4.41 (t, J = 4.9 Hz, 2H), 4.33-4.09 (m, 4H), 2.08 (d, J = 4.4 Hz, 3H), 1.80 (s, 3H) |

TABLE 1-continued

7-Aza-Thienylpyridine and Derivative Compounds

| Compound | | Characterization |
|---|---|---|
| 1122 | 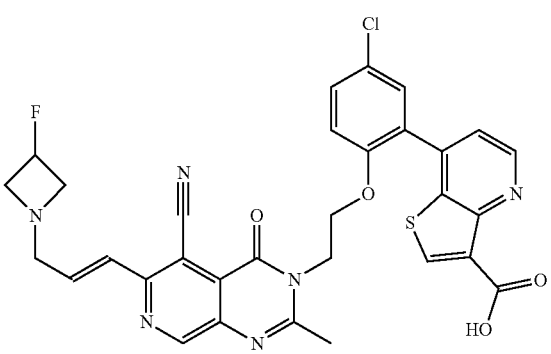 [SMILES: Cc1nc2cnc(/C=C/CN3CC(F)C3)c(C#N)c2c(=O)n1CCOc1ccc(Cl)cc1-c1ccnc2c(C(=O)O)csc12] | LCMS (ESI) m/z 631.1 [M + 1]+; 1H NMR (400 MHz, DMSO-d6) δ 9.00 (s, 1H), 8.83 (d, J = 4.8 Hz, 1H), 8.37 (s, 1H), 7.60 (dd, J = 8.9, 2.7 Hz, 1H), 7.48 (d, J = 4.8 Hz, 1H), 7.44 (d, J = 2.7 Hz, 1H), 7.36 (d, J = 9.0 Hz, 2H), 7.05 (dt, J = 14.5, 6.8 Hz, 1H), 5.46 (d, J = 57.5 Hz, 1H), 4.56 (s, 2H), 4.46-4.32 (m, 4H), 4.26 (t, J = 5.0 Hz, 4H), 1.79 (s, 3H) |
| 1123 | 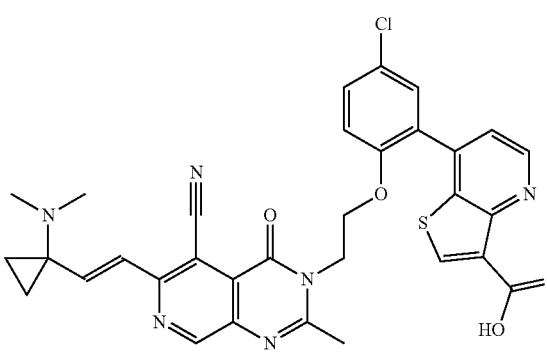 | LCMS (ESI) m/z 627.3 [M + 1]+; 1H NMR (400 MHz, DMSO-d6) δ 9.01 (s, 1H), 8.83 (d, J = 4.8 Hz, 1H), 8.38 (s, 1H), 7.67-7.58 (m, 2H), 7.48 (d, J = 4.8 Hz, 1H), 7.43 (d, J = 2.7 Hz, 1H), 7.37 (d, J = 9.1 Hz, 1H), 7.04 (d, J = 15.0 Hz, 1H), 4.42 (t, J = 5.0 Hz, 2H), 4.28 (t, J = 5.0 Hz, 2H), 2.98 (s, 6H), 1.86 (s, 3H), 1.53 (s, 2H), 1.35 (s, 2H) |
| 1124 | 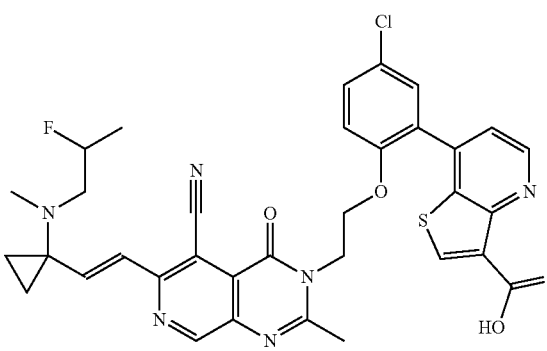 | LCMS (ESI) m/z 677.1 [M + 1]+; 1H NMR (400 MHz, DMSO-d6) δ 8.92 (s, 1H), 8.84 (dd, J = 4.8, 1.4 Hz, 1H), 8.38 (d, J = 2.2 Hz, 1H), 7.60 (ddd, J = 9.0, 2.7, 0.8 Hz, 1H), 7.50 (s, 1H), 7.51-7.41 (m, 1H), 7.35 (d, J = 9.0 Hz, 1H), 7.11 (d, J = 15.4 Hz, 1H), 6.93 (d, J = 15.4 Hz, 1H), 6.06 (tt, J = 56.0, 4.2 Hz, 1H), 4.40 (t, J = 4.9 Hz, 2H), 4.24 (t, J = 4.9 Hz, 2H), 3.19 (td, J = 15.5, 4.2 Hz, 2H), 2.61 (s, 3H), 1.73 (d, J = 1.3 Hz, 3H), 1.16-1.13 (m, 2H), 1.12-1.01 (m, 2H) |
| 1125 | 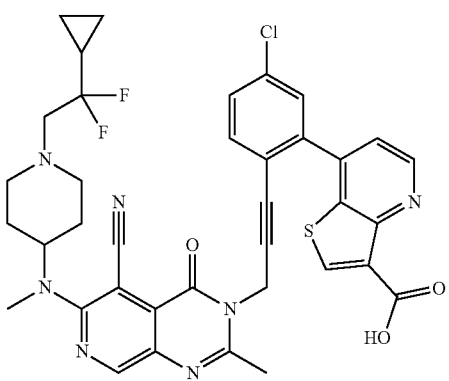 [SMILES: Cc1nc2cnc(N(C)C3CCN(CC(F)(F)C4CC4)CC3)c(C#N)c2c(=O)n1CC#Cc1ccc(Cl)cc1-c1ccnc2c(C(=O)O)csc12] | LCMS (ESI) m/z 728.1 [M + 1]+; 1H NMR (400 MHz, DMSO-d6) δ 8.78-8.71 (m, 2H), 8.64 (s, 1H), 7.75 (dd, J = 7.9, 1.0 Hz, 1H), 7.71-7.64 (m, 2H), 7.54 (d, J = 4.8 Hz, 1H), 4.82 (s, 2H), 2.09 (s, 3H), 0.70 (s, 2H), 0.65 (s, 2H) |

TABLE 1-continued

7-Aza-Thienylpyridine and Derivative Compounds

| Compound | | Characterization |
|---|---|---|
| 1126 |  | LCMS (ESI) m/z 734.1 [M + 1]+; 1H NMR (400 MHz, DMSO-d6) δ 8.79 (d, J = 4.8 Hz, 1H), 8.58 (s, 1H), 8.38 (s, 1H), 7.57 (dd, J = 8.9, 2.7 Hz, 1H), 7.47-7.37 (m, 2H), 7.33 (d, J = 9.0 Hz, 1H), 4.49 (bs, 1H), 4.36 (t, J = 4.9 Hz, 2H), 4.18 (t, J = 4.9 Hz, 2H), 2.99 (s, 3H), 1.73 (s, 3H), 1.51 (ddd, J = 13.2, 8.1, 4.9 Hz, 1H), 0.71-0.60 (m, 4H) |
| 1127 | 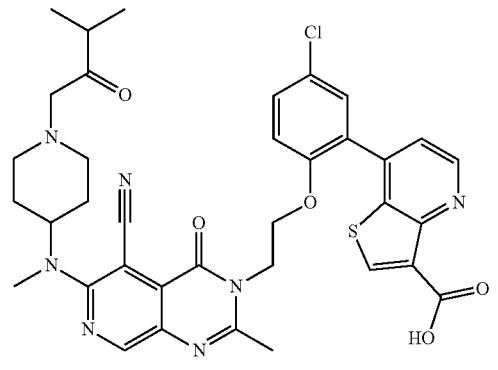 [SMILES: Cc1nc2cnc(N(C)C3CCN(CC(=O)C(C)C)CC3)c(C#N)c2c(=O)n1CCOc1ccc(Cl)cc1-c1ccnc2c(C(=O)O)csc12] | LCMS (ESI) m/z 714.4 [M + 1]+; 1H NMR (400 MHz, DMSO-d6) δ 8.79 (d, J = 4.8 Hz, 1H), 8.54 (s, 1H), 8.34 (s, 1H), 7.57 (dd, J = 8.9, 2.7 Hz, 1H), 7.44 (d, J = 4.8 Hz, 1H), 7.39-7.29 (m, 2H), 4.51 (s, 1H), 4.46-4.30 (m, 4H), 4.19 (t, J = 5.1 Hz, 2H), 3.50 (d, J = 11.8 Hz, 2H), 3.26-3.11 (m, 2H), 3.08 (s, 3H), 2.75-2.66 (m, 1H), 2.25 (d, J = 12.7 Hz, 2H), 2.03 (d, J = 12.8 Hz, 2H), 1.79 (s, 3H), 1.07 (d, J = 6.9 Hz, 6H) |
| 1128 | 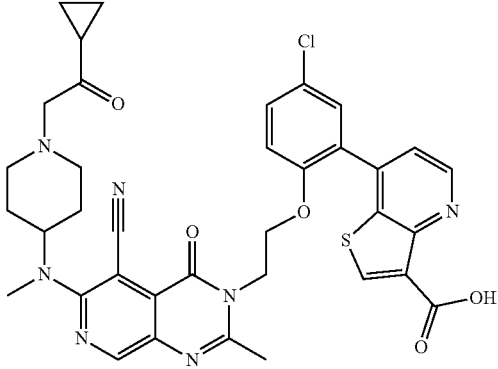 [SMILES: Cc1nc2cnc(N(C)C3CCN(CC(=O)C4CC4)CC3)c(C#N)c2c(=O)n1CCOc1ccc(Cl)cc1-c1ccnc2c(C(=O)O)csc12] | LCMS (ESI) m/z 712.4 [M + 1]+; 1H NMR (400 MHz, DMSO-d6) δ 8.79 (d, J = 4.8 Hz, 1H), 8.53 (s, 1H), 8.33 (s, 1H), 7.57 (dd, J = 8.9, 2.7 Hz, 1H), 7.44 (d, J = 4.9 Hz, 1H), 7.38-7.30 (m, 2H), 4.58-4.43 (m, 3H), 4.36 (t, J = 5.1 Hz, 2H), 4.19 (t, J = 5.0 Hz, 2H), 3.52 (d, J = 11.8 Hz, 3H), 3.18 (t, J = 12.7 Hz, 2H), 3.07 (s, 3H), 2.24 (d, J = 12.7 Hz, 2H), 2.17-1.95 (m, 3H), 1.80 (s, 3H), 1.06 (dd, J = 23.8, 2.3 Hz, 4H) |
| 1129 | 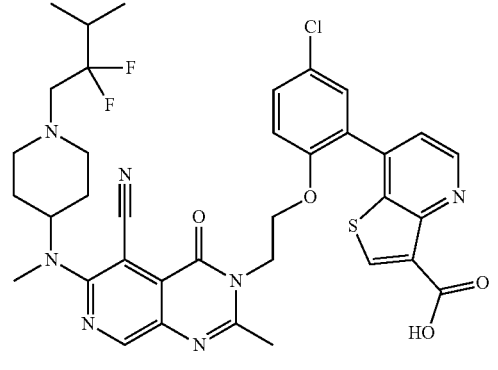 | LCMS (ESI) m/z 730.3 [M + 1]+; 1H NMR (400 MHz, DMSO-d6) δ 8.81-8.71 (m, 2H), 8.65 (s, 1H), 7.76 (dd, J = 7.9, 1.0 Hz, 1H), 7.72-7.66 (m, 2H), 7.55 (d, J = 4.8 Hz, 1H), 4.83 (s, 2H), 3.11 (s, 3H), 2.40-2.18 (m, 2H), 2.11 (s, 4H), 1.03 (d, J = 6.9 Hz, 6H) |

TABLE 1-continued

7-Aza-Thienylpyridine and Derivative Compounds

| Compound | | Characterization |
|---|---|---|
| 1130 | 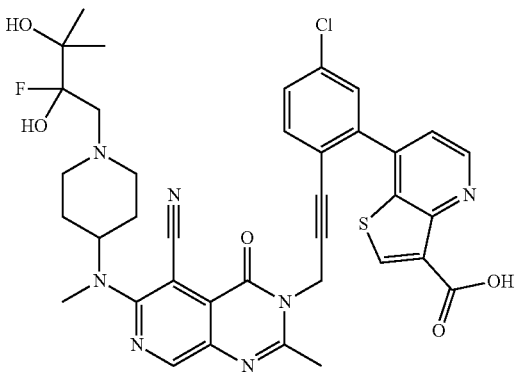 | LCMS (ESI) m/z 469.5 [M + 1]+; 1H NMR (400 MHz, DMSO-d6) δ 8.76-8.69 (m, 4H), 8.62 (s, 2H), 7.76-7.61 (m, 7H), 7.52 (d, J = 4.8 Hz, 2H), 4.79 (s, 5H), 4.51 (s, 1H), 3.71 (s, 1H), 3.34 (s, 1H), 2.07 (s, 8H), 2.01 (s, 1H), 1.22 (s, 14H) |
| 1131 | 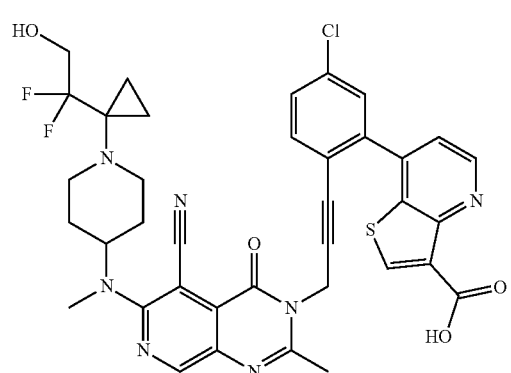 | LCMS (ESI) m/z 744.1 [M + 1]+; 1H NMR (400 MHz, DMSO-d6) δ 8.76 (d, J = 4.8 Hz, 1H), 8.68 (d, J = 14.8 Hz, 2H), 7.76 (d, J = 9.0 Hz, 1H), 7.73-7.66 (m, 2H), 7.55 (d, J = 4.7 Hz, 1H), 4.82 (s, 2H), 4.21 (d, J = 6.9 Hz, 1H), 3.75 (s, 1H), 3.07 (s, 3H), 3.00 (s, 2H), 2.05 (s, 3H), 1.77 (s, 4H), 0.85 (s, 4H) |
| 1132 | 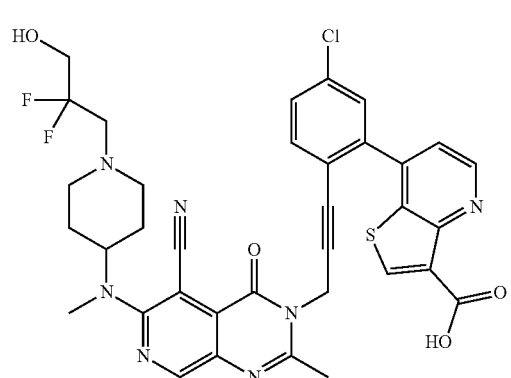 | LCMS (ESI) m/z 718.1 [M + 1]+; 1H NMR (400 MHz, DMSO-d6) δ 8.73 (d, J = 4.8 Hz, 1H), 8.70 (s, 1H), 8.61 (s, 1H), 7.72 (d, J = 8.9 Hz, 1H), 7.68-7.63 (m, 2H), 7.51 (d, J = 4.8 Hz, 1H), 4.79 (s, 2H), 4.50 (s, 1H), 3.71 (t, J = 13.7 Hz, 7H), 3.08 (s, 3H), 2.22 (s, 2H), 2.06 (s, 3H), 2.03-1.91 (m, 2H) |
| 1133 | 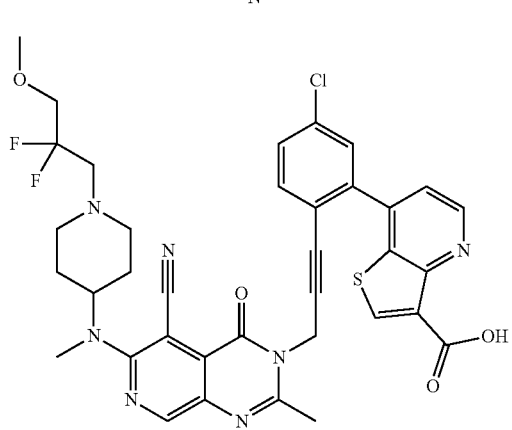 | LCMS (ESI) m/z 732.4 [M + 1]+; 1H NMR (400 MHz, DMSO-d6) δ 8.79-8.71 (m, 2H), 8.65 (s, 1H), 7.79-7.72 (m, 1H), 7.72-7.65 (m, 2H), 7.55 (d, J = 4.8 Hz, 1H), 4.82 (s, 2H), 3.76 (s, 2H), 3.11 (s, 3H), 2.08 (s, 3H) |

TABLE 1-continued

7-Aza-Thienylpyridine and Derivative Compounds

| Compound | | Characterization |
|---|---|---|
| 1134 | 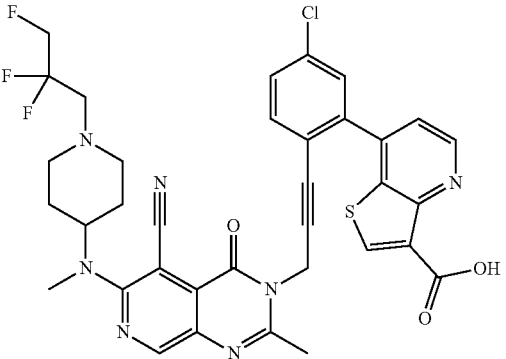 [SMILES: Cc1nc2cnc(N(C)C3CCN(CC(F)(F)CF)CC3)c(C#N)c2c(=O)n1CC#Cc1ccc(Cl)cc1-c1ccnc2c(C(=O)O)csc12] | LCMS (ESI) m/z 720.0 [M + 1]+; 1H NMR (400 MHz, DMSO-d6) δ 8.76-8.68 (m, 2H), 8.62 (s, 1H), 7.76-7.69 (m, 1H), 7.69-7.62 (m, 2H), 7.52 (d, J = 4.8 Hz, 1H), 4.86-4.58 (m, 2H), 4.79 (s, 3H), 4.42 (s, 1H), 2.05 (s, 3H), 1.92 (bs, 3H) |
| 1135 | 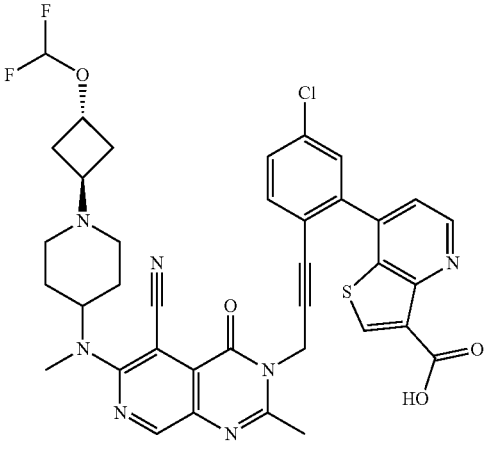 [SMILES: Cc1nc2cnc(N(C)C3CCN([C@H]4C[C@H](OC(F)F)C4)CC3)c(C#N)c2c(=O)n1CC#Cc1ccc(Cl)cc1-c1ccnc2c(C(=O)O)csc12] | LCMS (ESI) m/z 744.0 [M + 1]+; 1H NMR (400 MHz, DMSO-d6) δ 8.75 (d, J = 1.8 Hz, 2H), 8.65 (s, 1H), 7.76 (d, J = 8.2 Hz, 1H), 7.69 (d, J = 8.9 Hz, 2H), 7.55 (d, J = 4.8 Hz, 1H), 6.72 (t, J = 75.2 Hz, 1H), 4.83 (s, 2H), 4.78 (s, 1H), 4.56 (s, 1H), 3.94 (d, J = 8.4 Hz, 1H), 3.57 (d, J = 11.9 Hz, 2H), 3.12 (s, 3H), 3.06 (d, J = 10.5 Hz, 2H), 2.77-2.64 (m, 2H), 2.54 (s, 1H), 2.11 (s, 7H). 19F NMR (377 MHz, DMSO-d6) δ-73.82-82.25 (d, J = 75.1 Hz) |
| 1136 | 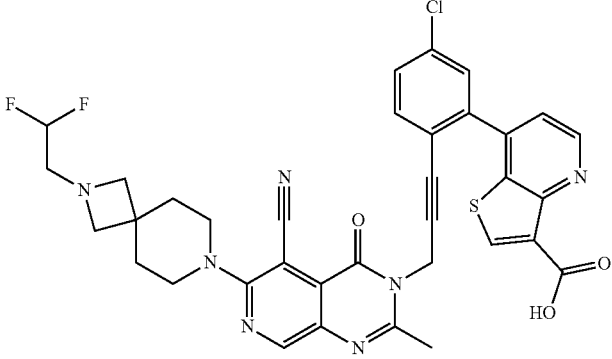 [SMILES: Cc1nc2cnc(N3CCC4(CC3)CN(CC(F)F)C4)c(C#N)c2c(=O)n1CC#Cc1ccc(Cl)cc1-c1ccnc2c(C(=O)O)csc12] | LCMS: 1.77 Min, 700.2. [M + 1]+; 1H NMR (400 MHz, DMSO-d6) δ10.73 (s, 1H), 8.78-8.72 (m, 2H), 8.64 (s, 1H), 7.81-7.73 (m, 1H), 7.72 J = 53.2 Hz, 1H), 4.82 (s, 2H), 4.12 (s, 4H), 3.92 (t, J = 16.0 Hz, 2H), 3.64 (d, J = 31.4 Hz, 4H), 2.06 (s, 3H) |
| 1137 | 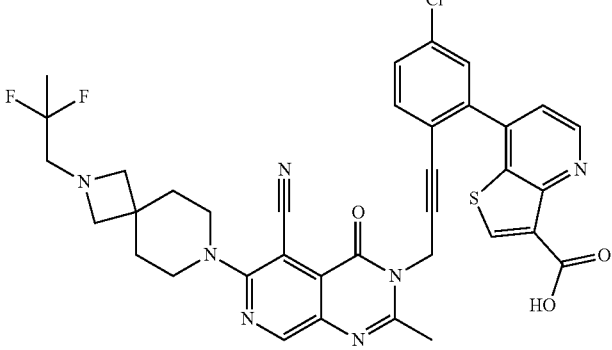 | LCMS: 1.71 Min, 714.5 [M + 1]+; 1H NMR (400 MHz, DMSO-d6) δ 10.61 (s, 1H), 8.81-8.72 (m, 2H), 8.64 (s, 1H), 7.79-7.72 (m, 1H), 7.71 (s, 2H), 4.32-3.89 (m, 6H), 3.64 (m, 4H), 2.07 (d, J = 1.6 Hz, 6H), 2.00 (s, 3H), 1.74 (t, J = 19.6 Hz, 3H) |

TABLE 1-continued

7-Aza-Thienylpyridine and Derivative Compounds

| Compound | Characterization |
|---|---|
| 1139 | MS (ESI) m/z 708.4 [M + 1]+; 1H NMR (400 MHz, DMSO-d6) δ 8.83 (d, J = 4.8 Hz, 1H), 8.61 (s, 1H), 8.41 (s, 1H), 7.60 (dd, J = 8.9, 2.7 Hz, 1H), 7.47 (d, J = 4.8 Hz, 1H), 7.43 (d, J = 2.7 Hz, 1H), 7.36 (d, J = 9.0 Hz, 1H), 4.39 (t, J = 5.0 Hz, 2H), 4.21 (t, J = 5.0 Hz, 2H), 3.75-3.30 (m, 10H), 3.09 (s, 3H), 1.75 (s, 6H) |
| 1140 | MS (ESI) m/z 706.2 [M + 1]+; 1H NMR (400 MHz, DMSO-d6) δ 8.77 (d, J = 4.8 Hz, 1H), 8.69 (d, J = 22.6 Hz, 2H), 7.76 (d, J = 9.0 Hz, 1H), 7.71-7.66 (m, 2H), 7.55 (d, J = 4.8 Hz, 1H), 4.82 (s, 2H), 4.31 (s, 1H), 3.34 (s, 1H), 3.10 (s, 5H), 2.61 (s, 2H), 2.06 (s, 3H), 1.96 (q, J = 11.8 Hz, 2H), 1.82 (d, J = 12.1 Hz, 2H) |
| 1141 | MS (ESI) m/z 702.2 [M + 1]+; 1H NMR (400 MHz, DMSO-d6) δ 8.76 (d, J = 4.8 Hz, 1H), 8.74 (s, 1H), 8.65 (s, 1H), 7.78-7.74 (m, 1H), 7.71-7.67 (m, 2H), 7.55 (d, J = 4.8 Hz, 1H), 4.83 (s, 2H), 3.11 (s, 3H), 2.09 (s, 3H), 1.78 (t, J = 19.5 Hz, 3H) |
| 1142 | MS (ESI) m/z 698.4 [M + 1]+; 1H NMR (400 MHz, DMSO-d6) δ 8.78-8.73 (m, 2H), 8.65 (s, 1H), 7.76 (dd, J = 8.1, 0.8 Hz, 1H), 7.72-7.66 (m, 2H), 7.55 (d, J = 4.8 Hz, 1H), 4.83 (s, 2H), 4.57 (d, J = 12.1 Hz, 1H), 3.67 (d, J = 12.6 Hz, 2H), 3.48 (dd, J = 22.6, 5.0 Hz, 2H), 3.33 (d, J = 11.5 Hz, 1H), 3.12 (s, 3H), 2.40-2.26 (m, 2H), 2.15-1.98 (m, 5H), 1.50 (d, J = 21.4 Hz, 6H) |

TABLE 1-continued

7-Aza-Thienylpyridine and Derivative Compounds

| Compound | | Characterization |
|---|---|---|
| 1143 | | MS (ESI) m/z 842.3 [M + 1]+; 1H NMR (400 MHz, DMSO-d6) δ 1H NMR (400 MHz, DMSO-d6) 613.21 (bs, 1H), 9.97 (s, 1H), 8.97-8.93 (m, 2H), 8.85 (d, J = 4.9 Hz, 1H), 8.69 (s, 1H), 8.50 (s, 1H), 8.10-8.05 (m, 2H), 7.77 (dd, J = 8.4, 0.5 Hz, 1H), 7.70 (dd, J = 8.4, 2.2 Hz, 1H), 7.66 (dd, J = 2.2, 0.5 Hz, 1H), 7.64 (dd, J = 4.9, 0.4 Hz, 1H), 4.82 (s, 2H), 4.57 (s, 1H), 3.96-3.26 (m, 4H), 3.11 (s, 3H), 2.26 (s, 2H), 2.04 (dd, J = 20.6, 10.2 Hz, 2H), 1.92 (s, 3H), 1.78 (t, J = 19.5 Hz, 3H) |
| 1144 | | MS (ESI) m/z 842.4 [M + 1]+; 1H NMR (400 MHz, DMSO-d6) δ 13.12 (s, 1H), 9.28 (d, J = 2.3 Hz, 1H), 8.92 (d, J = 4.6 Hz, 1H), 8.84 (d, J = 4.9 Hz, 1H), 8.67 (s, 1H), 8.56-8.51 (m, 1H), 8.48 (s, 1H), 7.73 (ddd, J = 16.1, 10.9, 8.4 Hz, 3H), 7.66 (d, J = 2.2 Hz, 1H), 7.63 (d, J = 4.9 Hz, 1H), 4.81 (s, 2H), 3.11 (s, 3H), 1.90 (s, 3H) |
| 1145 | | MS (ESI) m/z 630.2 [M + 1]+; 1H NMR (400 MHz, DMSO-d6) δ 9.89 (s, 1H), 8.69 (s, 1H), 8.41 (s, 1H), 7.60 (dd, J = 8.9, 2.7 Hz, 1H), 7.42 (s, 1H), 7.40 (d, J = 2.7 Hz, 1H), 7.37 (d, J = 9.0 Hz, 1H), 4.40 (t, J = 5.1 Hz, 2H), 4.31 (d, J = 14.2 Hz, 2H), 4.24 (t, J = 5.1 Hz, 2H), 3.61 (d, J = 12.0 Hz, 2H), 3.45 (t, J = 13.1 Hz, 2H), 3.24 (q, J = 10.2 Hz, 2H), 2.91 (d, J = 3.4 Hz, 3H), 2.72 (s, 3H), 1.90 (s, 3H) |

TABLE 1-continued

7-Aza-Thienylpyridine and Derivative Compounds

| Compound | | Characterization |
|---|---|---|
| 1146 | 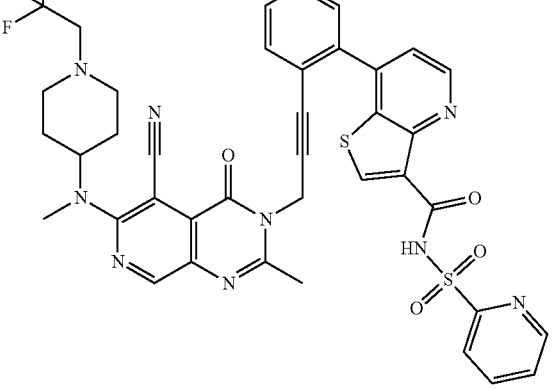 | MS (ESI) m/z 842.4 [M + 1]+; 1H NMR (400 MHz, DMSO-d6) δ 1H NMR (400 MHz, DMSO-d6) δ 13.03 (s, 1H), 8.90 (d, J = 4.9 Hz, 1H), 8.72 (ddd, J = 4.6, 1.7, 0.9 Hz, 1H), 8.65 (s, 1H), 8.60 (s, 1H), 8.30-8.25 (m, 1H), 8.21 (td, J = 7.7, 1.7 Hz, 1H), 7.80-7.72 (m, 2H), 7.72-7.68 (m, 2H), 7.66 (d, J = 4.8 Hz, 1H), 4.83 (s, 2H), 3.09 (s, 3H), 1.94 (s, 3H), 1.77 (t, J = 18.9 Hz, 2H) |
| 1148 | 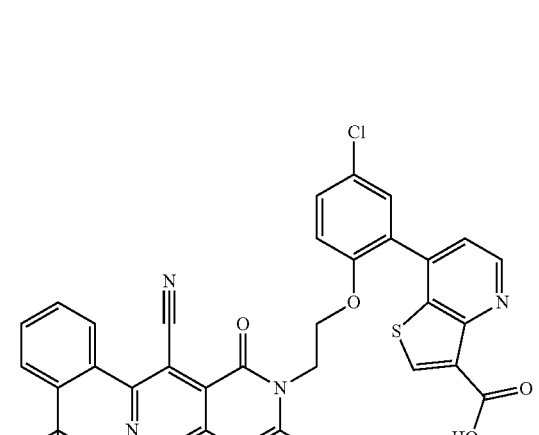 | MS (ESI) m/z 676.21. [M + 1]+; 1H NMR (400 MHz, DMSO-d6) δ 13.22 (bs, 1H), 8.83 (d, J = 4.6 Hz, 1H), 8.49 (s, 1H), 7.94 (d, J = 7.8 Hz, 1H), 7.87 (t, J = 7.4 Hz, 1H), 7.77 (m, 2H), 7.60 (dd, J = 2.4, 8.8 Hz, 1H), 7.47 (d, J = 4.7 Hz, 1H), 7.44 (d, J = 2.4 Hz, 1H), 7.37 (d, J = 8.9 Hz, 1H), 4.44 (s, 2H), 4.27 (s, 2H), 2.77 (s, 3H), 1.85 (s, 3H) |
| 1149 | 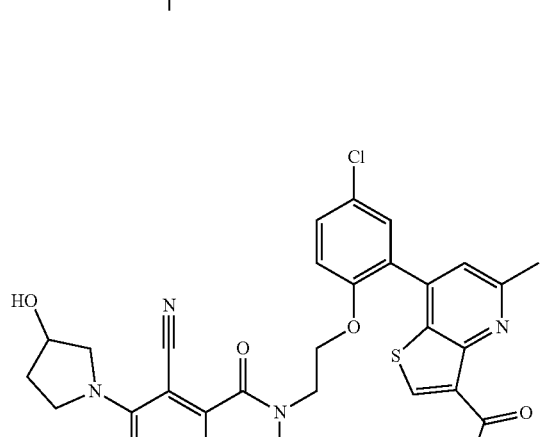 | MS (ESI) m/z 631.26 [M + 1]+; 1H-NMR (400 MHz, DMSO-d6) δ 13.60 (bs, 1H), 8.56 (s, 1H), 7.58 (dd, J = 8.8, 2.4 Hz, 1H), 7.40-7.35 (m, 3H), 5.02 (bs, 1H), 4.39 (s, 2H), 4.19 (s, 2H), 3.90-3.82 (m, 2H), 3.74 (t, J = 8.0 Hz, 1H), 3.54 (d, J = 11.6 Hz 1H), 2.70 (s, 3H), 2.59 (s, 3H), 2.05-1.85 (m, 2H), 1.84 (s, 3H) |

TABLE 1-continued

7-Aza-Thienylpyridine and Derivative Compounds

| Compound | | Characterization |
|---|---|---|
| 1152 | 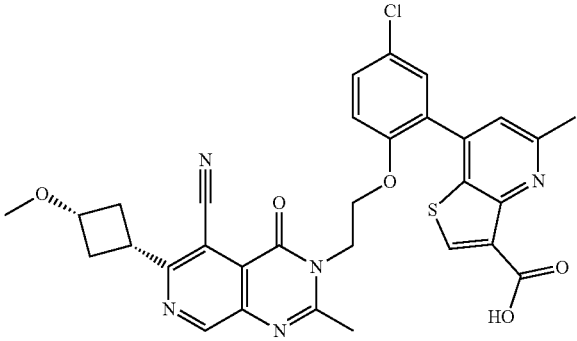 | MS (ESI) m/z 616.24 [M + 1]+; 1H-NMR (400 MHz, DMSO-d6) δ 13.56 (bs, 1H), 9.01 (s, 1H), 8.39 (s, 1H), 7.59 (dd, J = 2.8, 9.2 Hz, 1H), 7.41 (d, J = 2.4 Hz, 1H), 7.39 (s 1H), 7.34 (d, J = 8.8 Hz, 1H), 4.38 (s, 2H) 4.24 (s, 2H), 4.0-3.9 (m, 1H), 3.67-3.61 (m, 1H), 3.19 (s, 3H), 2.69 (bs, 5H), 2.35-2.31 (m, 2H), 1.86 (s, 3H) |
| 1157 | 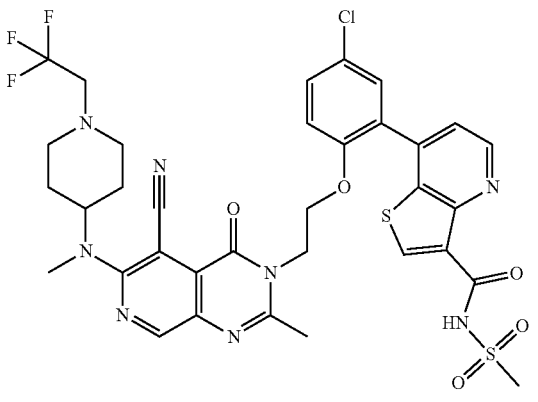 [SMILES: Cc1nc2cnc(N(C)C3CCN(CC(F)(F)F)CC3)c(C#N)c2c(=O)n1CCOc1ccc(Cl)cc1-c1ccnc2c(C(=O)NS(C)(=O)=O)csc12] | MS (ESI) m/z 789.51 [M + 1]+; 1H NMR (400 MHz, DMSO-d6) δ 12.66 (s, 1H), 8.87 (d, J = 4.8 Hz, 1H), 8.60 (m, 1H), 8.58 (s, 1H), 7.60 (dd, J = 8.8, 2.4 Hz, 1H), 7.54 (d, J = 4.8 Hz, 1H), 7.43 (d, J = 2.4 Hz, 1H), 7.38 (d, J = 9.2 Hz, 1H), 4.39 (t, J = 6.0 Hz, 2H), 4.35-4.25 (m, 1H), 4.19 (t, J = 6.0 Hz, 2H), 3.58 (s, 3H), 3.40-3.20 (m, 2H), 3.07 (s, 5H), 2.65-2.55 (m, 2H), 1.99-1.90 (m, 2H), 1.85-1.79 (m, 2H), 1.74 (s, |
| 1160 | 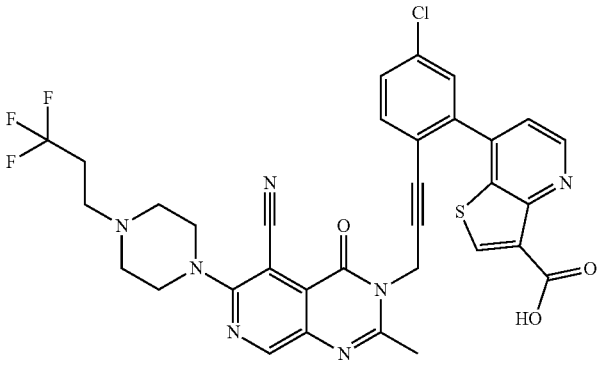 [SMILES: Cc1nc2cnc(N3CCN(CCC(F)(F)F)CC3)c(C#N)c2c(=O)n1CC#Cc1ccc(Cl)cc1-c1ccnc2c(C(=O)O)csc12] | MS (ESI) m/z 692.45 [M + 1]+; 1H-NMR (400 MHz, DMSO-d6) δ 13.05 (bs, 1H), 8.83 (s, 1H), 8.75 (d, J = 4.6 Hz, 1H), 8.64 (s, 1H), 7.75 (d, J = 8.2 Hz, 1H), 7.69 (s, 1H), 7.66 (s, 1H), 7.52 (d, J = 4.5 Hz, 1H), 4.83 (s, 2H), 4.31 (bs, 1H), 3.43 (bs, 7H), 2.85 (s, 4H), 2.11 (s, 3H) |
| 1161 | 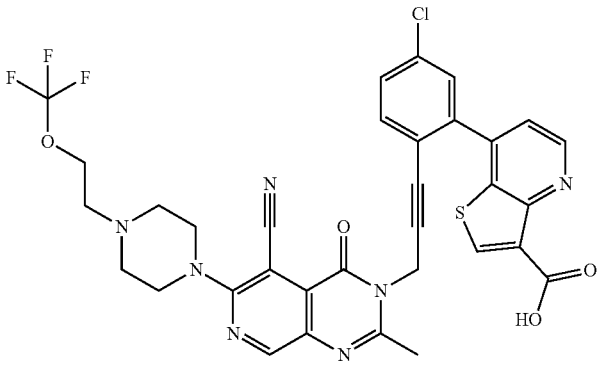 | MS (ESI) m/z 708.3 [M + 1]+; 1H NMR (400 MHz, DMSO-d6) δ 8.84 (s, 1H), 8.76 (d, J = 4.8 Hz, 1H), 8.65 (s, 1H), 7.76 (dd, J = 8.3, 0.5 Hz, 1H), 7.71-7.65 (m, 2H), 7.54 (d, J = 4.8 Hz, 1H), 4.84 (s, 2H), 4.53 (s, 2H), 4.06-2.83 (m, 8H), 2.13 (s, 3H) |

TABLE 1-continued

7-Aza-Thienylpyridine and Derivative Compounds

| Compound | | Characterization |
|---|---|---|
| 1162 | 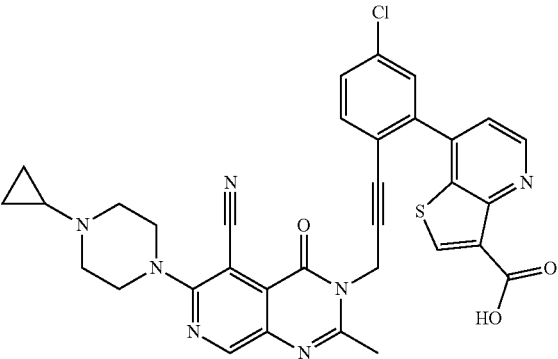 [SMILES: Cc1nc2cnc(N3CCN(C4CC4)CC3)c(C#N)c2c(=O)n1CC#Cc1ccc(Cl)cc1-c1ccnc2c(C(=O)O)csc12] | MS (ESI) m/z 636.25 [M + 1]+; 1H NMR (400 MHz, DMSO-d6) δ 13.18 (bs, 1H), 8.84 (s, 1H), 8.75 (d, J = 4.8 Hz, 1H), 8.65 (s, 1H), 7.75 (d, J = 8.4 Hz, 1H), 7.70-7.65 (m, 2H), 7.53 (d, J = 4.8 Hz, 1H), 4.84 (s, 2H), 4.38 (m, 2H), 3.79 (m, 2H,), 3.49 (m, 4H), 3.03 (m, 1H), 2.14 (s, 3H), 0.93 (m, 4H) |
| 1163 | 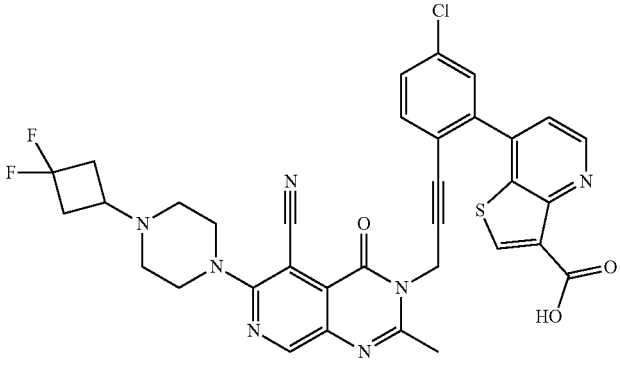 [SMILES: Cc1nc2cnc(N3CCN(C4CC(F)(F)C4)CC3)c(C#N)c2c(=O)n1CC#Cc1ccc(Cl)cc1-c1ccnc2c(C(=O)O)csc12] | MS (ESI) m/z 686.0 [M + 1]+; 1H-NMR (400 MHz, DMSO-d6) δ 13.03 (s, 1H), 8.83 (s, 1H), 8.75 (d, J = 4.8 Hz, 1H), 8.64 (s, 1H), 7.75 (d, J = 8.4 Hz, 1H), 7.70-7.66 (m, 1H), 7.53 (d, J = 4.8 Hz, 1H), 4.72 (s, 2H), 3.80 (bs, 4H), 3.39 (bs, 4H), 3.05-3.02 (m, 5H), 2.16 (s, 3H) |
| 1164 | 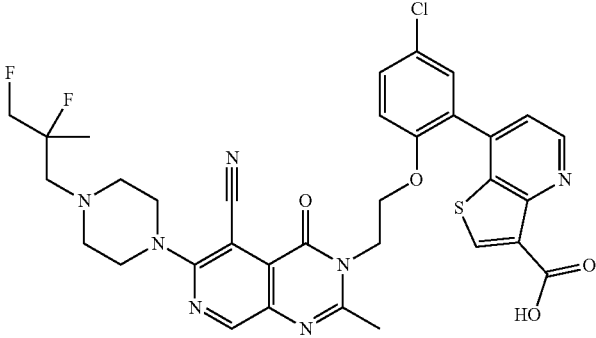 | MS (ESI) m/z 694.52 [M + 1]+; 1H NMR (400 MHz, DMSO-d6) δ 8.82 (d, J = 4.8 Hz, 1H), 8.68 (s, 1H), 8.45 (s, 1H), 7.60 (dd, J = 8.8 Hz, 2.4 Hz, 1H), 7.48 (d, J = 4.8 Hz, 1H), 7.42 (d, J = 2.8 Hz, 1H), 7.36 (d, J = 8.8 Hz, 1H), 4.72-4.54 (m, 2H), 4.39 (bs, 2H), 4.22 (bs, 2H), 3.25-2.78 (m, 10H), 1.81 (s, 3H), 1.45 (bs, 3H) |
| 1165 | 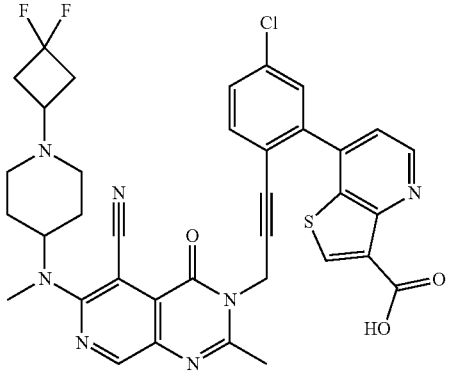 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)O)csc12] | MS (ESI) m/z, 714.50 [M + 1]+; 1H-NMR (400 MHz, DMSO-d6) δ 9.80 (bs, 1H), 8.76 (s, 1H), 8.75 (s, 1H), 8.65 (s, 1H), 7.75 (d, J = 8.4 Hz, 1H), 7.70-7.67 (m, 2H), 7.54 (d, J = 4.8 Hz, 1H), 4.83 (s, 2H), 4.56 (bs, 1H), 3.56 (bs, 4H), 3.11 (bs, 1H), 3.06 (s, 3H), 3.05 (bs, 4H), 2.13 (bs, 4H), 2.11 (s, 3H) |

TABLE 1-continued

7-Aza-Thienylpyridine and Derivative Compounds

| Compound | | Characterization |
|---|---|---|
| 1166 | 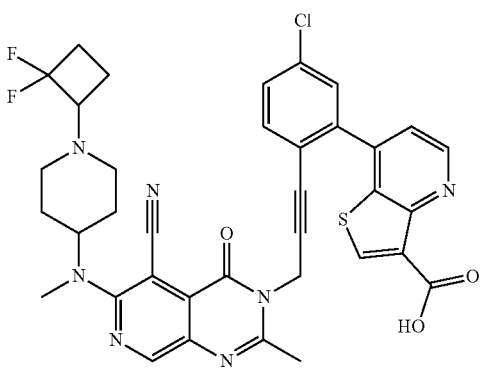 [SMILES: Cc1nc2cnc(N(C)C3CCN(C4CCC4(F)F)CC3)c(C#N)c2c(=O)n1CC#Cc1ccc(Cl)cc1-c1ccnc2c(C(=O)O)csc12] | MS (ESI) m/z 714.58 [M + 1]+; 1H-NMR (400 MHz, DMSO-d6) δ 8.76-8.74 (m, 2H), 8.65 (s, 1H), 7.75 (d, J = 8.0 Hz, 1H), 7.70-7.67 (m, 2H), 7.55 (d, J = 4.8 Hz, 1H), 4.82 (s, 2H), 4.58-4.38 (m, 2H), 3.11 (s, 3H), 2.90-2.88 (m, 2H), 2.50-2.32 (m, 4H), 2.20-2.15 (m, 5H), 2.12-2.10 (m, 2H) |
| 1167 | 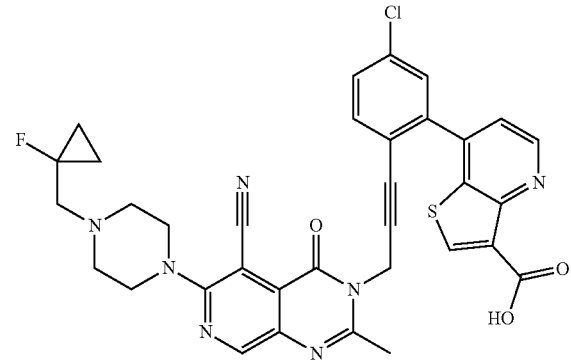 | MS (ESI) m/z 668.42 [M + 1]+; 1H NMR (400 MHz, DMSO-d6) δ 13.08 (bs, 1H), 10.22 (bs, 1H), 8.85 (s, 1H), 8.76 (d, J = 4.8 Hz, 1H), 8.65 (s, 1H), 7.76 (d, J = 8.4 Hz, 1H), 7.69-7.66 (m, 2H), 7.53 (d, J = 4.8 Hz, 1H), 4.83 (s, 2H), 4.39 (d, J = 11.6 Hz, 2H), 3.76 (bs, 6H), 3.43 (bs, 2H), 2.14 (s, 3H), 1.29 (d, J = 18.8 Hz, 2H), 0.99 (d, J = 7.6 Hz, 2H) |
| 1168 | 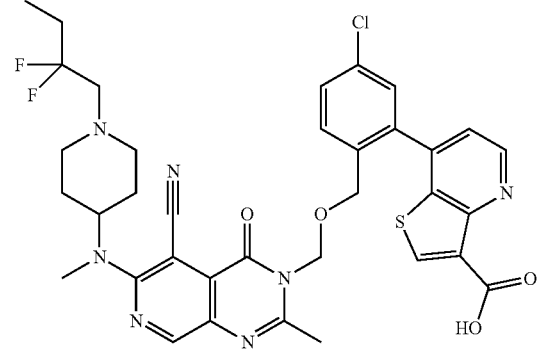 [SMILES: CCC(F)(F)CN1CCC(N(C)c2ncc3nc(C)n(COCc4ccc(Cl)cc4-c4ccnc5c(C(=O)O)csc45)c(=O)c3c2C#N)CC1] | MS (ESI) m/z 722.51 [M + 1]+; 1H NMR (400 MHz, DMSO-d6) δ 8.82 (d, J = 4.8 Hz, 1H), 8.61 (s, 1H), 8.41 (s, 1H), 7.60 (dd, J = 8.8 Hz, 2.4 Hz, 1H), 7.47 (d, J = 4.8 Hz, 1H), 7.43 (d, J = 2.8 Hz, 1H), 7.36 (d, J = 9.2 Hz, 1H), 4.52 (bs, 1H), 4.39 (s, 2H), 4.21 (s, 2H), 3.90-3.82 (m, 1H), 3.36-3.31 (m, 6H), 3.09 (s, 3H), 2.33-2.27 (m, 1H), 2.02-2.07 (m, 4H), 1.79 (s, 3H), 0.99 (t, J = 7.2 Hz, 3H) |
| 1169 | 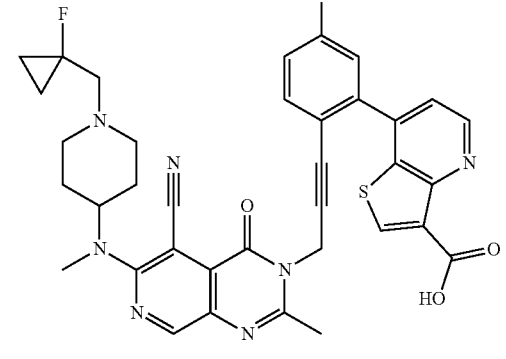 | MS (ESI) m/z 696.24 [M + 1]+; 1H-NMR (400 MHz, DMSO-d6) δ 8.76-8.75 (m, 2H), 8.64 (s, 1H), 7.75 (d, J = 8.4 Hz, 1H), 7.69-7.67 (m, 2H), 7.54 (d, J = 4.8 Hz, 1H), 4.82 (s, 2H), 4.54 (s, 1H), 3.74-3.72 (m, 4H), 3.31-3.29 (m, 2H), 3.12 (s, 3H), 2.28-2.22 (m, 2H), 2.13-2.10 (m, 5H), 1.25 (d, J = 19.6 Hz, 2H), 0.96 (d, J = 8.0 Hz, 2H) |

TABLE 1-continued
7-Aza-Thienylpyridine and Derivative Compounds
| Compound | | Characterization |
|---|---|---|
| 1170 | 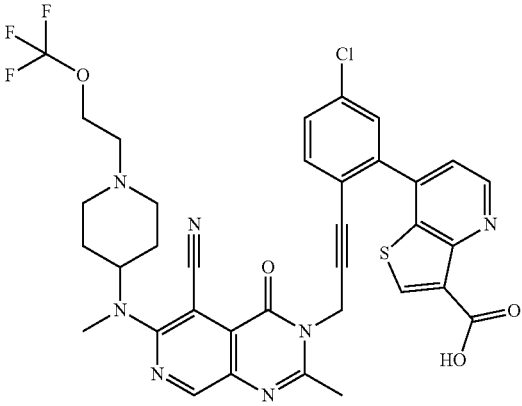 [SMILES: Cc1nc2cnc(N(C)C3CCN(CCOC(F)(F)F)CC3)c(C#N)c2c(=O)n1CC#Cc1ccc(Cl)cc1-c1ccnc2c(C(=O)O)csc12] | MS (ESI) m/z 736.43 [M + 1]+; 1H-NMR (400 MHz, DMSO-d6) δ 8.76-.8.74 (m, 2H), 8.64 (s, 1H), 7.75 (d, J = 8.0 Hz, 1H), 7.70-7.67 (m, 2H), 7.54 (d, J = 4.8 Hz, 1H), 4.82 (s, 2H), 4.56-4.52 (m, 3H), 3.67-3.55 (m, 4H), 3.25-3.19 (m, 2H), 3.11 (s, 3H), 2.23-2.20 (m, 2H), 2.17-2.10 (m, 5H) |
| 1171 | 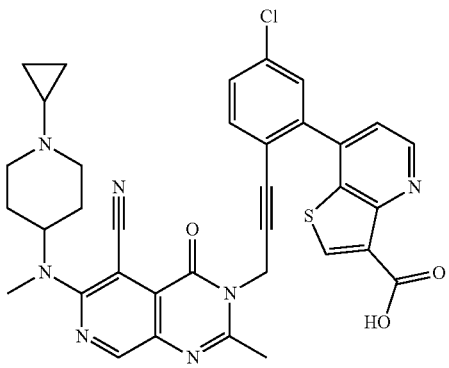 [SMILES: Cc1nc2cnc(N(C)C3CCN(C4CC4)CC3)c(C#N)c2c(=O)n1CC#Cc1ccc(Cl)cc1-c1ccnc2c(C(=O)O)csc12] | MS (ESI) m/z 664.42 [M + 1]+; 1H NMR (400 MHz, DMSO-d6) δ 8.76 (d, J = 6.0 Hz, 2H), 8.65 (s, 1H), 7.76 (d, J = 8.0 Hz, 1H), 7.70-7.67 (m, 2H), 7.55 (d, J = 4.8 Hz, 1H), 4.83 (s, 2H), 4.60-4.59 (m, 1H), 3.66 (d, J = 11.6 Hz, 2H), 3.43-3.22 (m, 2H), 3.09 (s, 3H), 2.85 (bs, 1H), 2.10 (s, 7H), 0.95-0.85 (m, 4H) |
| 1172 | 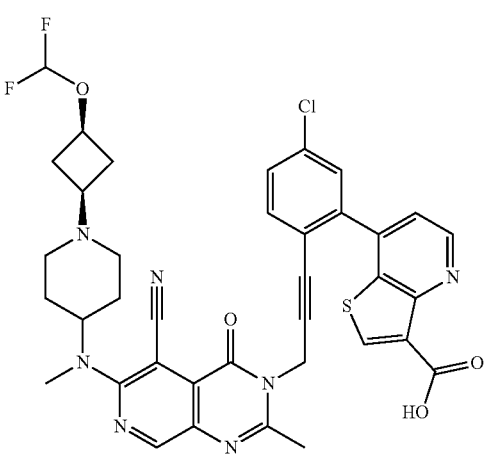 Chiral | MS (ESI) m/z 744.02 [M + 1]+; 1H-NMR (400 MHz, DMSO-d6) δ 8.76-8.74 (m, 2H), 8.64 (s, 1H), 7.75 (d, J = 8.4 Hz, 1H), 7.70-7.67 (m, 2H), 7.54 (d, J = 4.8 Hz, 1H), 6.89-6.52 (m, 1H), 4.82 (s, 2H), 4.58-4.45 (m, 2H), 3.48-3.38 (m, 5H), 3.10 (s, 3H), 3.08-3.06 (m, 2H), 2.40.2.38 (m, 2H), 2.20-2.10 (m, 5H) |

TABLE 1-continued
7-Aza-Thienylpyridine and Derivative Compounds
| Compound | | Characterization |
|---|---|---|
| 1173a | 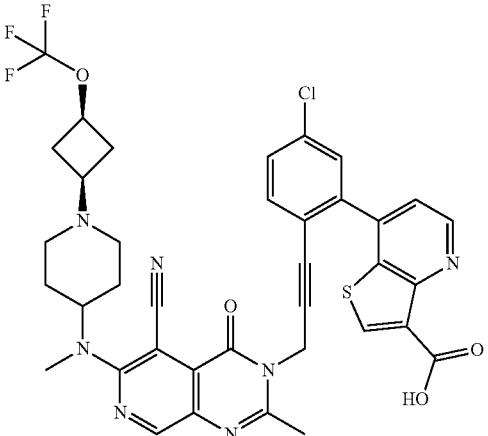<br>Chiral | MS (ESI) m/z 762.47 [M + 1]+; 1H-NMR (400 MHz, DMSO-d6) δ 8.77-8.75 (m, 2H), 8.65 (s, 1H), 7.76 (d, J = 8.0 Hz, 1H), 7.70 (d, J = 2.0 Hz, 1H), 7.68 (s, 1H), 7.56 (d, J = 4.8 Hz, 1H), 4.83 (s, 2H), 4.73 (quin, J = 7.2 Hz, 1H), 4.59 (bs, 1H), 3.62 (bs, 4H), 3.41 (bs, 1H), 3.12 (bs, 5H), 2.89 (bs, 2H), 2.11 (bs, 7H) |
| 1173b | 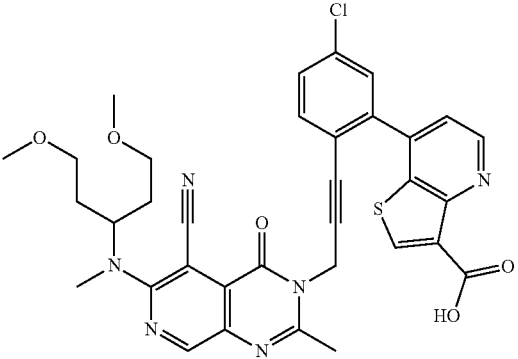 [SMILES: COCCC(CCOC)N(C)c1ncc2nc(C)n(CC#Cc3ccc(Cl)cc3-c3ccnc4c(C(=O)O)csc34)c(=O)c2c1C#N] | MS (ESI) m/z 671.41 [M + 1]+; 1H-NMR (400 MHz, DMSO-d6) δ 8.76 (d, J = 4.8 Hz, 1H), 8.68 (d, J = 1.6 Hz, 2H), 7.75 (d, J = 8.4 Hz, 1H), 7.70-7.67 (m, 2H), 7.55 (d, J = 4.8 Hz, 1H), 4.82 (s, 3H), 3.38-3.28 (m, 4H), 3.11 (s, 9H), 2.02 (s, 3H), 1.97-1.91 (m, 2H), 1.89-1.83 (m, 2H) |
| 1174 | 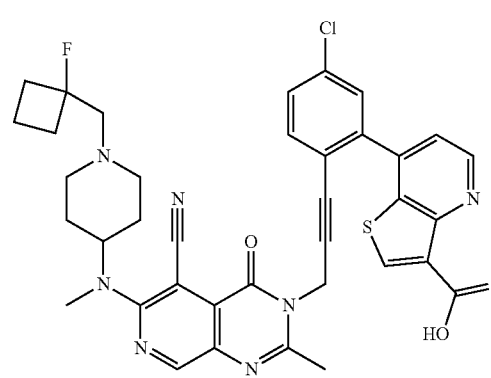 | MS (ESI) m/z 710.42 [M + 1]+; 1H-NMR (400 MHz, DMSO-d6) δ 9.40 (bs, 1H), 8.76-8.74 (m, 2H), 8.64 (s, 1H), 7.75 (d, J = 8.0 Hz, 1H), 7.70-7.67 (m, 2H), 7.55 (d, J = 4.8 Hz, 1H), 4.82 (s, 2H), 4.56-4.53 (m, 1H), 3.94-3.80 (m, 4H), 3.66-3.59 (m, 4H), 3.11 (s, 3H), 2.40-2.34 (m, 3H), 2.27-2.24 (m, 1H), 2.10-2.01 (m, 5H), 1.91-1.88(m, 1H), 1.70-1.63(m, 1H) |

TABLE 1-continued

7-Aza-Thienylpyridine and Derivative Compounds

| Compound | | Characterization |
|---|---|---|
| 1175 | 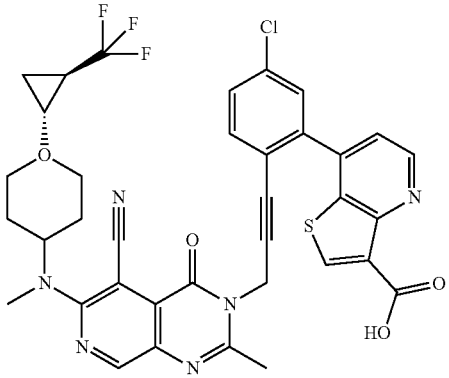 | MS (ESI) m/z 732.40 [M + 1]+; 1H NMR (400 MHz, DMSO-d6) δ 8.77-8.74 (m, 2H), 8.65 (s, 1H), 7.76 (d, J = 8.4 Hz, 1H), 7.69 (d, J = 1.6 Hz, 1H), 7.68 (s, 1H), 7.55 (d, J = 4.8 Hz, 1H), 4.82 (s, 2H), 4.48 (bs, 1H), 3.65 (m, 4H), 3.10 (s, 3H), 2.50-2.39 (m, 2H), 2.09 (s, 3H), 2.04 (bs, 4H), 1.44-1.33 (m, 2H) |
| 1176 | 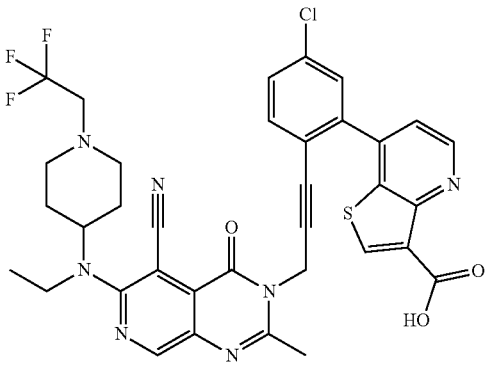 [SMILES: CCN(c1ncc2nc(C)n(CC#Cc3ccc(Cl)cc3-c3ccnc4c(C(=O)O)csc34)c(=O)c2c1C#N)C1CCN(CC(F)(F)F)CC1] | MS (ESI) m/z 720.44 [M + 1]+; 1H NMR (400 MHz, DMSO-d6) δ 8.77 (d, J = 4.4 Hz, 1H), 8.74 (s, 1H), 8.67 (s, 1H), 7.76 (d, J = 8.8 Hz, 1H), 7.69-7.67 (m, 2H), 7.56 (d, J = 4.8 Hz, 1H), 4.82 (s, 2H), 4.18-4.15 (m, 1H), 3.67-3.64 (m, 2H), 3.29 (bs, 2H), 3.07 (d, J = 9.2 Hz, 2H), 2.60-2.55 (m, 2H), 2.06 (s, 3H), 1.96-1.94 (m, 2H), 1.85-1.82 (m, 2H), 1.11 (t, J = 6.8 Hz, 3H) |
| 1177 | 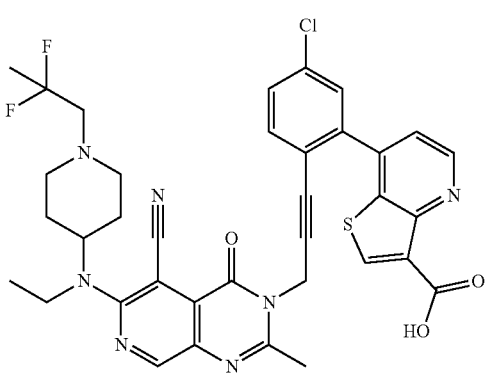 [SMILES: CCN(c1ncc2nc(C)n(CC#Cc3ccc(Cl)cc3-c3ccnc4c(C(=O)O)csc34)c(=O)c2c1C#N)C1CCN(CC(C)(F)F)CC1] | MS (ESI) m/z 716.60 [M + 1]+; 1H NMR (400 MHz, DMSO-d6) δ 13.14 (bs, 1H), 8.77 (d, J = 4.4 Hz, 2H), 8.66 (s, 1H), 7.77-7.74 (m, 1H), 7.69-7.68 (m, 2H), 7.56 (d, J = 4.8 Hz, 1H), 4.82 (s, 2H), 4.39 (bs, 1H), 3.63 (bs, 4H), 3.30 (bs, 4H), 2.34 (bs, 2H), 2.08 (s, 5H), 1.75 (t, J = 18.0 Hz, 3H), 1.13 (t, J = 6.8 Hz, 3H) |
| 1180 | 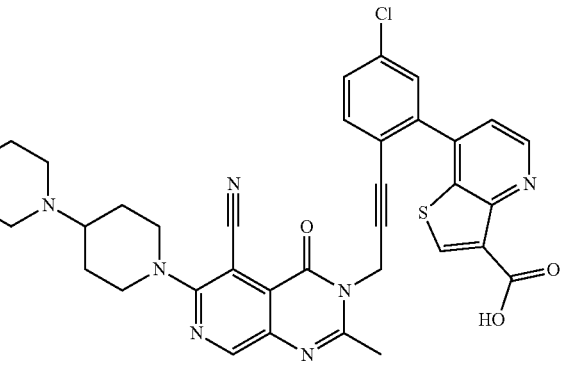 | MS (ESI) m/z 713.37 [M + 1]+; 1H NMR (400 MHz, DMSO-d6) δ 9.62 (bs, 1H), 8.79 (s, 1H), 8.75 (d, J = 4.8 Hz, 1H), 8.65 (s, 1H), 7.75 (d, J = 8.0 Hz, 1H), 7.70-7.68 (m, 2H), 7.54 (d, J = 4.8 Hz, 1H), 4.83 (s, 2H), 4.41-4.39 (d, J = 12.8 Hz, 2H), 3.83-3.69 (m, 4H), 3.23-3.14 (m, 4H), 2.43 (m, 2H), 2.33-2.25 (m, 3H), 2.10 (s, 3H), 1.91-1.88 (m, 2H) |

TABLE 1-continued
7-Aza-Thienylpyridine and Derivative Compounds
| Compound | | Characterization |
|---|---|---|
| 1181 | 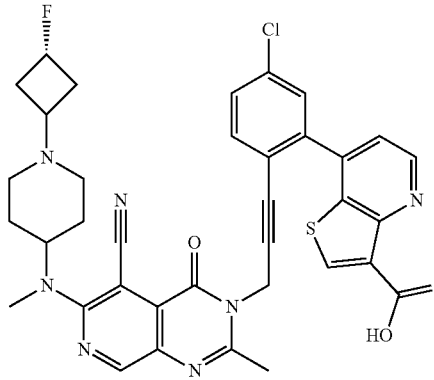 | MS (ESI) m/z 696.32 [M + 1]+; 1H NMR (400 MHz, DMSO-d6) δ 9.74 (bs, 1H), 8.78-8.72 (m, 2H), 8.64 (s, 1H), 7.75 (d, J = 8.1 Hz, 1H), 7.70-7.62 (m, 2H), 7.55 (d, J = 4.8 Hz, 1H), 5.35-5.18 (m, 1H), 4.82 (s, 2H), 4.60-4.52 (m, 1H), 4.04-3.98 (m, 1H), 3.60-3.50 (m, 2H), 3.15-2.95 (m, 5H), 2.80-2.45 (m, 4H), 2.20-2.00 (m, 7H) |
| 1182 | 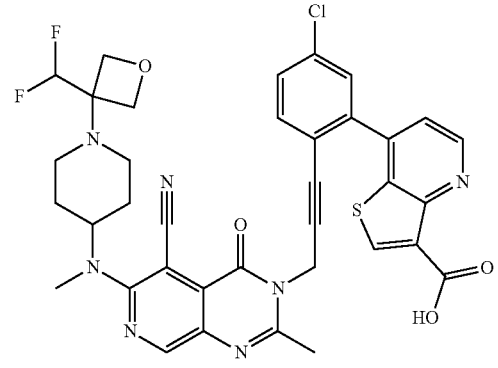 [SMILES: Cc1nc2cnc(N(C)C3CCN(C4(C(F)F)COC4)CC3)c(C#N)c2c(=O)n1CC#Cc1ccc(Cl)cc1-c1ccnc2c(C(=O)O)csc12] | MS (ESI) m/z 730.45 [M + 1]+; 1H NMR (400 MHz, DMSO-d6) δ 8.76 (d, J = 4.8 Hz 1H), 8.71 (s, 1H), 8.65 (s, 1H), 7.76-7.74 (m, 1H), 7.69-7.67 (m, 2H), 7.55 (d, J = 4.8 Hz, 1H), 6.46 (t, J = 54.4 Hz, 1H), 4.81 (s, 2H), 4.50 (d, J = 6.8 Hz, 2H), 4.44 (d, J = 6.4 Hz, 2H), 4.32-4.28 (m, 1H), 3.16 (s, 3H), 2.91-2.89 (m, 2H), 2.59-2.53 (m, 2H), 2.05 (s, 3H), 1.89-1.86 (m, 4H) |
| 1183 | 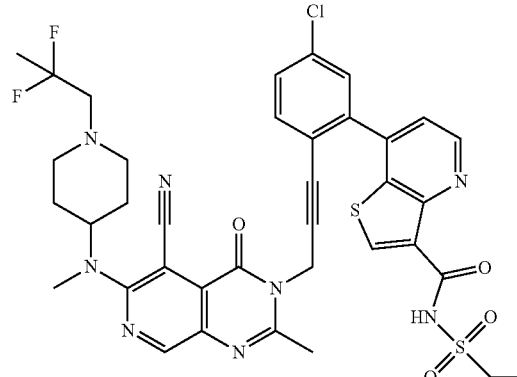 | MS (ESI) m/z 821.52 [M + 1]+; 1H-NMR (400 MHz, DMSO-d6) δ 12.71 (s, 1H), 8.82 (d, J = 4.8 Hz, 1H), 8.75 (d, J = 2.4 Hz, 2H), 7.77 (d, J = 8.8 Hz, 1H), 7.71-7.68 (m, 2H), 7.62 (d, J = 4.8 Hz, 1H), 5.21 (quin, J = 7.6 Hz, 1H), 4.97-4.90 (m, 4H), 4.82 (s, 2H), 4.59 (m, 1H), 3.69-3.49 (m, 4H), 3.11 (bs, 5H), 2.32 (m, 2H), 1.98 (m, 2H), 1.93 (s, 3H), 1.76 (t, J = 19.6 Hz, 3H) |

TABLE 1-continued

7-Aza-Thienylpyridine and Derivative Compounds

| Compound | | Characterization |
|---|---|---|
| 1184 | 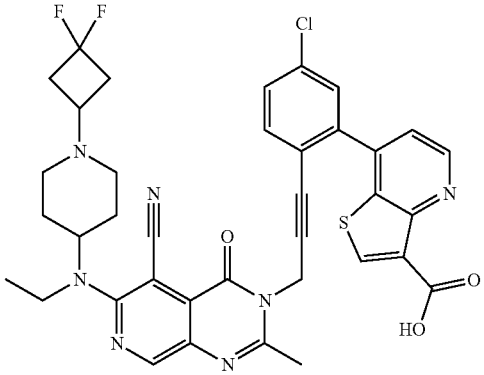 [SMILES: CCN(c1ncc2nc(C)n(CC#Cc3ccc(Cl)cc3-c3ccnc4c(C(=O)O)csc34)c(=O)c2c1C#N)C1CCN(C2CC(F)(F)C2)CC1] | MS (ESI) m/z 728.48 [M + 1]+; 1H-NMR (400 MHz, DMSO-d6) 613.11 (bs, 1H), 8.78-8.76 (m, 2H), 8.65 (s, 1H), 7.76 (d, J = 9.2 Hz, 1H), 7.70-7.68 (m, 2H), 7.56 (d, J = 4.8 Hz, 1H), 4.82 (s, 2H), 4.37 (bs, 1H), 3.75- 3.59 (m, 5H), 3.05 (bs, 6H), 2.15 (bs, 4H), 2.10 (s, 3H), 1.16 (t, J = 6.4 Hz, 3H) |
| 1185 | 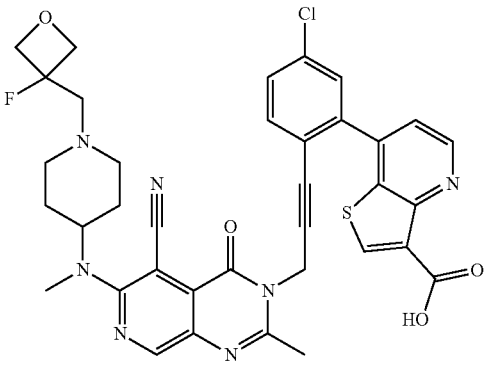 | MS (ESI) m/z 712.32 [M + 1]+; 1H-NMR (400 MHz, DMSO-d6) δ 13.09 (bs, 1H), 8.76-8.74 (m, 2H), 8.64 (s, 1H), 7.75 (d, J = 8.0 Hz, 1H), 7.70-7.67 (m, 2H), 7.54 (d, J = 4.8 Hz, 1H), 4.82-4.75 (m, 6H), 4.55 (bs, 1H), 3.91-3.85 (m, 2H), 3.52-3.35 (m, 4H), 3.10 (s, 3H), 2.32-2.21 (m, 2H), 2.09 (bs, 5H) |
| 1186 | 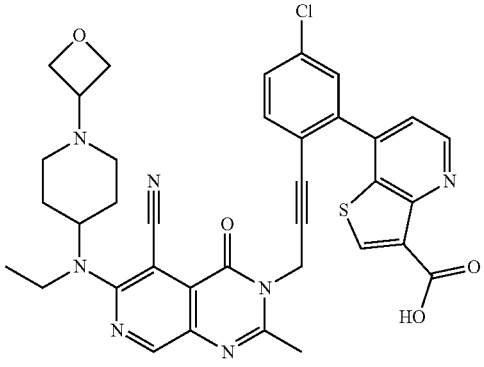 [SMILES: CCN(c1ncc2nc(C)n(CC#Cc3ccc(Cl)cc3-c3ccnc4c(C(=O)O)csc34)c(=O)c2c1C#N)C1CCN(C2COC2)CC1] | MS (ESI) m/z 694.43 [M + 1]+; 1H NMR (400 MHz, DMSO-d6) δ 8.78 (d, J = 2.8 Hz, 1H), 8.76 (s, 1H), 8.65 (s, 1H), 7.76 (d, J = 9.2 Hz, 1H), 7.69 (d, J = 6.8 Hz, 2H), 7.55 (d, J = 4.8 Hz, 1H), 4.82 (s, 2H), 4.75 (bs, 4H), 4.38 (bs, 2H), 3.61 (d, J = 6.8 Hz, 2H), 3.52 (bs, 2H), 3.16 (bs, 2H), 2.16-2.10 (m, 7H), 1.15 (t, J = 6.8 Hz, 3H) |
| 1187 | 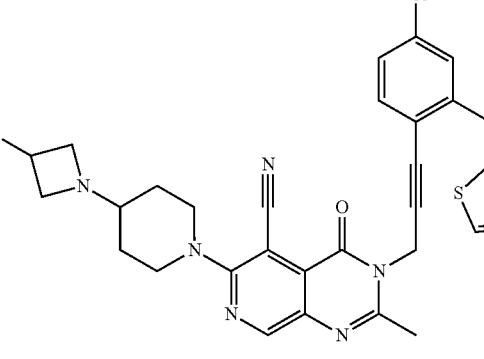 | MS (ESI) m/z 715.47 [M + 1]+; 1H NMR (400 MHz, DMSO-d6) δ 8.75 (d, J = 4.8 Hz, 1H), 8.73 (s, 1H), 8.63 (s, 1H), 7.75 (d, J = 8.8, 1H), 7.68-7.68 (m, 2H), 7.63 (d, J = 4.8 Hz, 1H), 6.69 (t, J = 75.2 Hz, 1H), 4.81 (s, 2H), 4.70 (t, J = 5.6 Hz, 1H), 4.04 (d, J = 13.2 Hz, 2H), 3.60 (t, J = 6.4 Hz, 2H), 3.32-3.27 (m, 2H), 3.00 (t, J = 6.8 Hz, 2H), 2.37 (bs, 1H), 2.05 (s, 3H), 1.80 (d, J = 10.4 Hz, 2H), 1.39-1.32 (m, 2H) |

TABLE 1-continued
7-Aza-Thienylpyridine and Derivative Compounds
| Compound | | Characterization |
|---|---|---|
| 1188 | 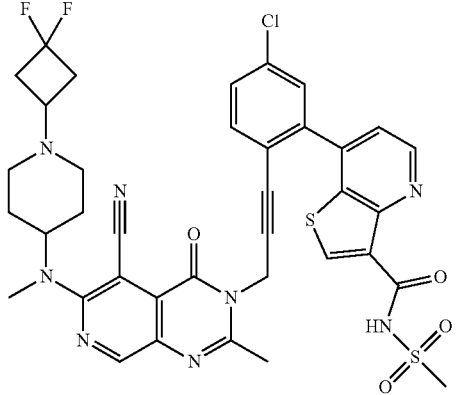 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(C)(=O)=O)csc12] | MS (ESI) m/z 791.62 [M + 1]+; 1H NMR (400 MHz, DMSO-d6) δ 12.47 (s, 1H), 8.81-8.78 (m, 3H), 7.77 (d, J = 8.40 Hz, 1H), 7.71-7.67 (m, 2H), 7.62 (d, J = 4.80 Hz, 1H), 4.83 (s, 2H), 4.59 (bs, 1H), 3.74-3.54 (m, 6H), 3.08 (s, 3H), 2.98-2.88 (m, 6H), 2.11-2.05 (m, 4H), 2.00 (s, 3H) |
| 1189 | 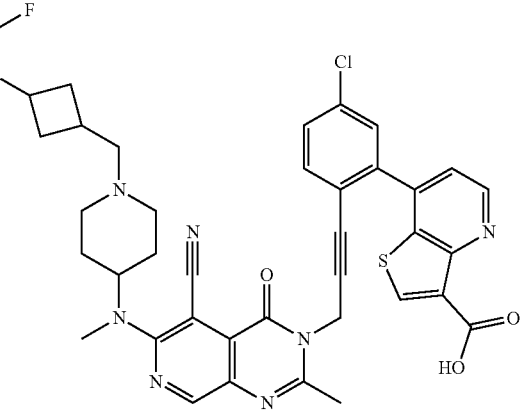 | MS (ESI) m/z 758.56 [M + 1]+; 1H NMR (400 MHz, DMSO-d6) δ 8.76-8.74 (m, 2H), 8.64 (s, 1H), 7.76 (d, J = 8.4 Hz, 1H), 7.70-7.67 (m, 2H), 7.55 (d, J = 4.8 Hz, 1H), 6.65 (t, J = 74.4 Hz, 1H), 4.82 (s, 2H), 4.57-4.47 (m, 2H), 3.53 (d, J = 11.6 Hz, 2H), 3.23-3.10 (m, 7H), 2.54-2.49 (m, 2H), 2.32-2.28 (m, 1H), 2.16-2.09 (m, 7H), 2.06-1.91 (m, 2H) |
| 1190 | 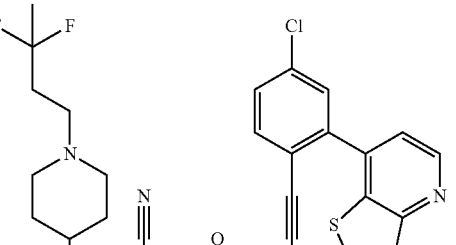 | MS (ESI) m/z 716.53 [M + 1]+; 1H NMR (400 MHz, DMSO-d6) δ 13.09 (bs, 1H), 9.32 (bs, 1H), 8.76-8.74 (m, J = 7.8 Hz, 2H), 8.64 (s, 1H) 7.75 (d, J = 8.2 Hz, 1H), 7.71-7.65 (m, 2H), 7.54 (d, J = 4.8 Hz, 1H), 4.82 (s, 2H), 4.60-4.50 (m, 1H), 3.69 (d, J = 10.4 Hz, 2H), 3.30-311 (m, 4H), 3.10 (s, 3H), 2.50-2.32 (merged, 2H), 2.20-2.05 (m, 7H), 1.70 (t, J = 19.2 Hz, 3H) |

TABLE 1-continued

7-Aza-Thienylpyridine and Derivative Compounds

| Compound | | Characterization |
|---|---|---|
| 1191 | 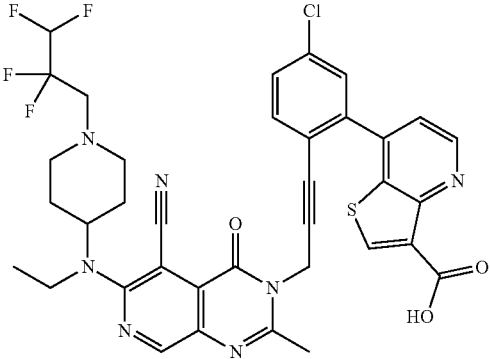 [SMILES: CCN(c1ncc2nc(C)n(CC#Cc3ccc(Cl)cc3-c3ccnc4c(C(=O)O)csc34)c(=O)c2c1C#N)C1CCN(CC(F)(F)C(F)F)CC1] | MS (ESI) m/z 752.52 [M + 1]+; 1H NMR (400 MHz, DMSO-d6) δ 13.15 (s, 1H), 8.77-8.741 (m, 2H), 8.66 (s, 1H), 7.75 (d, J = 9.2 Hz, 1H), 7.68 (d, J = 6.0 Hz, 2H), 7.55 (d, J = 4.8 Hz, 1H), 6.57 (t, J = 52.0 Hz, 1H), 4.81 (s, 2H), 4.29 (bs, 1H), 3.64 (d, J = 6.8 Hz, 2H), 3.03 (bs, 4H), 2.50 (s, 2H), 2.06 (s, 3H), 1.98-1.84 (m, 4H), 1.13-1.08 (m, 3H) |
| 1194 | 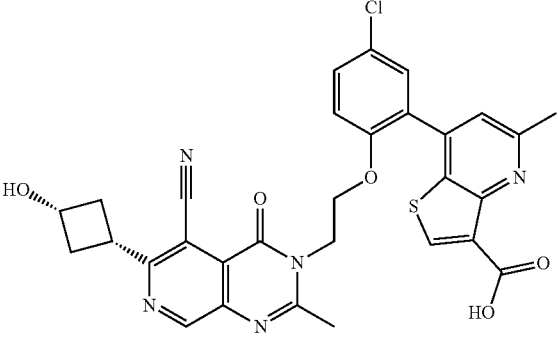 [SMILES: Cc1cc(-c2cc(Cl)ccc2OCCn2c(C)nc3cnc([C@H]4C[C@@H](O)C4)c(C#N)c3c2=O)c2scc(C(=O)O)c2n1] | MS (ESI) m/z 602.22 [M + 1]+; 1H-NMR (400 MHz, DMSO-d6) δ 13.62 (bs, 1H), 9.01 (s, 1H), 8.41 (s, 1H), 7.62-7.57 (m, 2H), 7.41 (d, J = 2.4 Hz, 1H), 7.39 (s, 1H), 7.34 (d, J = 8.0 Hz, 1H), 4.38 (s, 2H), 4.24 (s, 2H), 4.19-4.15 (m, 1H), 3.56 (bs, 1H), 2.68-2.62 (m, 5H), 2.32-2.27 (m, 2H), 1.84 (s, 3H) |
| 1195 | 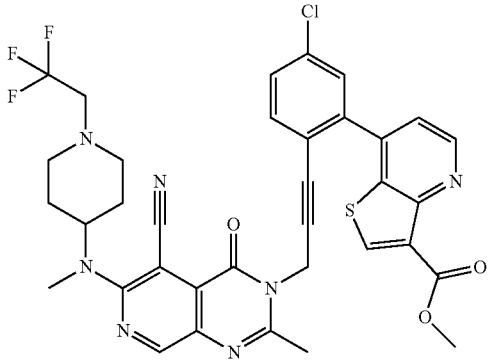 | MS (ESI) m/z 720.41 [M + 1]+; 1H-NMR (400 MHz, DMSO-d6) δ 8.76 (d, J = 4.56 Hz, 1H), 8.68 (s, 1H), 8.59 (s, 1H), 7.74 (d, J = 8.12 Hz, 1H), 7.67-7.64 (m, 2H), 7.43 (d, J = 4.64 Hz, 1H), 4.80 (s, 2H), 4.29-4.23 (m, 1H), 3.83 (s, 3H), 3.21 (q, J = 10.08 Hz, 2H), 3.10 (s, 3H), 3.04 (d, J = 11.4 Hz, 2H), 2.54 (bs, 2H), 2.03 (s, 3H), 1.98-1.89 (m, 2H), 1.78 (d, J = 10.52 Hz, 2H) |
| 1196 | 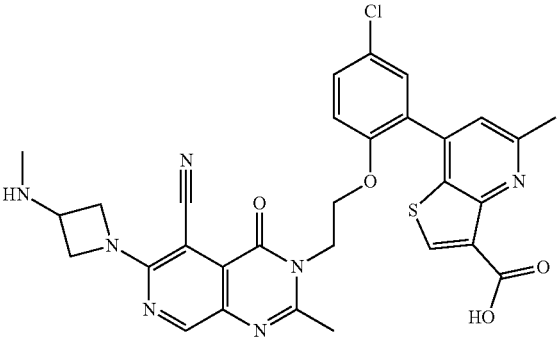 | MS (ESI) m/z 644.27 [M + 1]+; 1H NMR (400 MHz, DMSO-d6) δ 14.39 (bs, 1H), 8.62 (s, 1H), 7.59 (dd, J = 2.48, 8.88 Hz ,1H), 7.40-7.38 (m, 2H), 7.35 (d, J = 8.92 Hz, 1H), 4.63-4.59 (m, 2H), 4.47 (bs, 2H), 4.39 (t, J = 4.64 Hz, 2H), 4.23 (t, J = 4.64 Hz, 3H), 2.82 (bs, 6H), 2.70 (s, 3H), 2.54 (s, 3H), 1.94 (s, 3H) |

TABLE 1-continued

7-Aza-Thienylpyridine and Derivative Compounds

| Compound | | Characterization |
|---|---|---|
| 1198 | 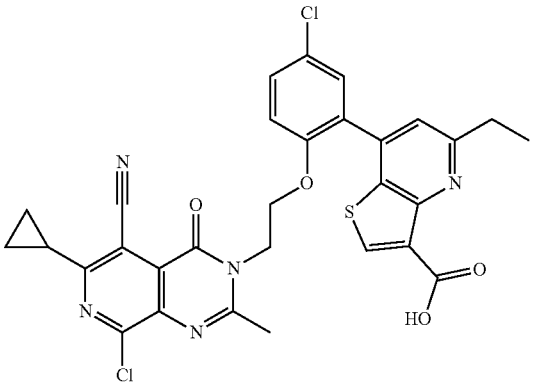 [SMILES: CCc1cc(-c2cc(Cl)ccc2OCCn2c(C)nc3c(Cl)nc(C4CC4)c(C#N)c3c2=O)c2scc(C(=O)O)c2n1] | MS (ESI) m/z 620.15 [M + 1]+; 1H NMR (400 MHz, DMSO-d6) δ 13.63 (bs, 1H) 8.55 (s, 1H), 7.59 (dd, J = 8.88, 2.62 Hz, 1H), 7.42 (t, J = 6.0 Hz, 2H), 7.35 (d, J = 8.8 Hz, 1H), 4.40 (d, J = 4.4 Hz, 2H), 4.26 (s, 2H), 4.26 (t, J = 4.8 Hz, 2H), 2.98- 3.04 (m, 2H), 2.55 (d, J = 4.0 Hz, 1H), 1.93 (s, 3H), 1.13-1.36 (m, 7H) |
| 1199 | 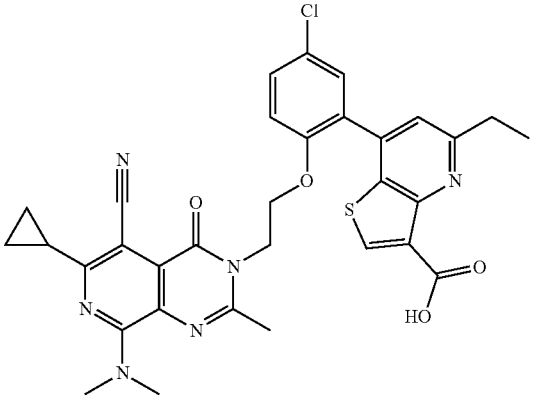 [SMILES: CCc1cc(-c2cc(Cl)ccc2OCCn2c(C)nc3c(N(C)C)nc(C4CC4)c(C#N)c3c2=O)c2scc(C(=O)O)c2n1] | MS (ESI) m/z 629.24 [M + 1]+; 1H NMR (400 MHz, DMSO-d6) δ 13.69 (bs, 1H), 8.49 (s, 1H), 7.59 (dd, J = 8.88, 2.62 Hz, 1H), 7.36- 7.43 (m, 3H), 4.41 (t, J = 6.0 Hz, 2H), 4.20 (t, J = 6.0 Hz, 2H), 4.26 (t, J = 4.8 Hz, 2H), 3.34 (s, 6H), 2.96- 3.01 (m, 2H), 2.40 (d, J = 4.0 Hz, 1H), 1.81 (s, 3H), 1.31 (t, J = 12.8 Hz, 3H), 1.03- 1.12 (m, 4H) |
| 1202 | 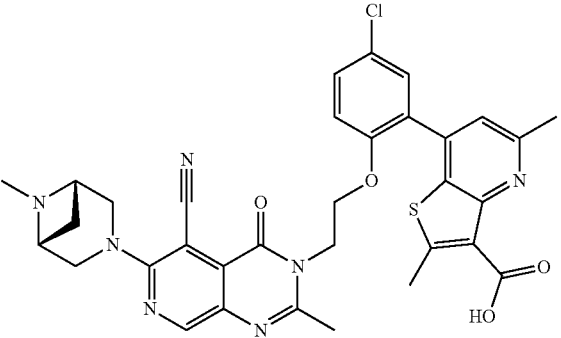 | MS (ESI) m/z 656.33 [M + 1]+; 1H NMR (400 MHz, DMSO-d6) 14.39 (bs, 1H), 10.23 (bs, 1H), 8.68 (s, 1H), 7.59 (d, J = 8.0, 2.4 Hz, 1H), 7.45-7.38 (m, 2H), 7.39 (d, J = 8.8 Hz, 1H), 4.87 (d, J = 4.8 Hz, 2H), 4.39 (bs, 2H), 4.23 (bs, 2H), 3.91-3.82 (m, 2H), 3.60-3.49 (m, 2H), 3.00-2.88 (m, 2H), 2.75 (s, 3H), 2.70 (s, 3H), 2.53 (s, 3H), 1.86 (s, 3H) |
| 1203 | 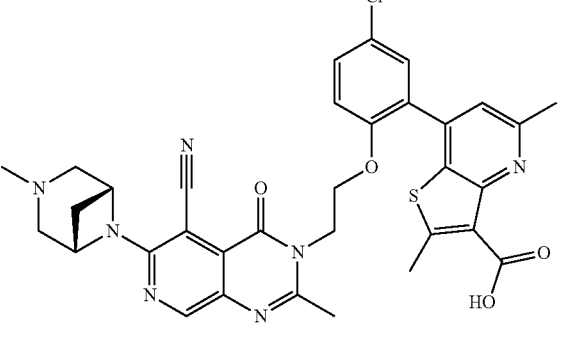 | MS (ESI) m/z 656.33 [M + 1]+; 1H NMR (400 MHz, DMSO-d6) 14.39 (bs, 1H), 10.23 (bs, 1H), 8.68 (s, 1H), 7.59 (d, J = 8.0, 2.4 Hz, 1H), 7.45-7.38 (m, 2H), 7.39 (d, J = 8.8 Hz, 1H), 4.87 (d, J = 4.8 Hz, 2H), 4.39 (bs, 2H), 4.23 (bs, 2H), 3.91-3.82 (m, 2H), 3.60-3.49 (m, 2H), 3.00-2.88 (m, 2H), 2.75 (s, 3H), 2.70 (s, 3H), 2.53 (s, 3H), 1.86 (s, 3H) |

TABLE 1-continued

7-Aza-Thienylpyridine and Derivative Compounds

| Compound | | Characterization |
|---|---|---|
| 1204 | 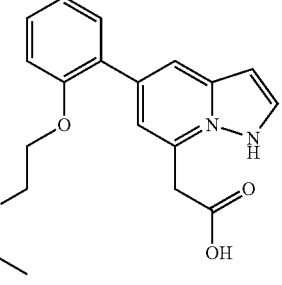 | MS (ESI) m/z 554.23 [M + 1]+; 1H NMR (400 MHz, DMSO-d6) δ 11.14 (s, 1H), 8.99 (s, 1H), 7.37 (s, 1H), 7.31-7.28 (m, 2H), 7.21 (d, J = 2.4 Hz, 1H), 7.14 (d, J = 9.2 Hz, 1H), 6.92 (s, 1H), 6.38 (bs 1H), 4.33 (bs, 2H), 4.30 (bs, 2H), 3.80 (s, 2H), 2.60 (t, J = 3.6 Hz, 1H), 2.18 (s, 3H), 1.21 (d, J = 7.6 Hz, 2H), 1.12 (bs, 2H) |
| 1216 | 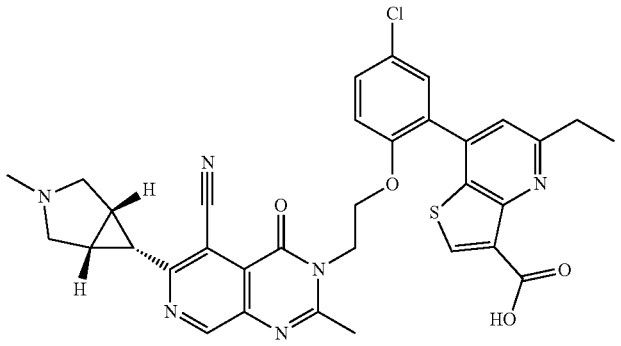 [SMILES: CCc1cc(-c2cc(Cl)ccc2OCCn2c(C)nc3cnc([C@@H]4[C@@H]5CN(C)C[C@@H]54)c(C#N)c3c2=O)c2scc(C(=O)O)c2n1] | MS (ESI) m/z 641.37 [M + 1]+; 1H-NMR (400 MHz, DMSO-d6) δ 13.75 (bs, 1H), 8.84 (s, 1H), 8.31 (s, 1H), 7.60 (dd, J = 2.52, 8.88 Hz, 1H), 7.45 (s, 1H), 7.41 (d, J = 2.48 Hz, 1H), 7.36 (d, J = 8.96 Hz, 1H), 4.39 (t, J = 4.40 Hz, 2H), 4.26 (t, J = 4.44 Hz, 2H), 3.84 (bs, 2H), 3.52 (bs, 2H), 3.31 (s, 3H), 3.01 (q, J = 7.48 Hz, 2H), 2.97 (bs, 1H), 2.91 (bs, 2H), 1.97 (s, 3H), 1.36 (t, J = 7.56 Hz, 3H) |
| 1217 |  | MS (ESI) m/z 706.31 [M + 1]+; 1H-NMR (400 MHz, DMSO-d6) δ 13.43 (bs, 1H), 8.59 (s, 1H), 8.16 (d, J = 3.6 Hz, 2H), 7.59 (dd, J = 2.0, 7.2 Hz, 1H), 7.54 (bs, 3H), 7.41 (bs, 3H), 4.45 (bs, 4H), 4.27 (bs, 2H), 3.60 (bs, 2H), 3.48 (bs, 2H), 3.33 (bs, 2H), 2.90 (s, 3H), 2.66 (bs, 3H), 2.008 (s, 3H) |
| 1219 |  | MS (ESI) m/z 656.26 [M + 1]+; 1H-NMR (400 MHz, DMSO-d6) δ 8.56 (s, 1H), 8.41 (s, 1H), 7.58 (dd, J = 2.48, 8.92 Hz, 1H), 7.42 (m, 2H), 7.35 (d, J = 8.9 Hz, 1H), 4.39-4.37 (m, 2H), 4.20-4.19 (m, 2H), 3.36-3.33 (m, 1H), 3.13-3.07 (m, 1H), 3.01 (q, J 7.5 Hz, 2H), 2.75-2.72 (m, 2H), 2.32 (s, 3 H), 2.20-2.15 (m, 1H), 1.75 (s, 3H), 1.34 (t, J = 7.5 Hz, 3H), 0.70-0.65 (m, 2H), 0.55-0.70 (m, 2H) |

TABLE 1-continued

7-Aza-Thienylpyridine and Derivative Compounds

| Compound | | Characterization |
|---|---|---|
| 1220 | 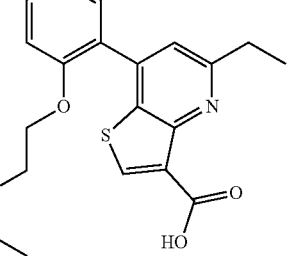 | MS (ESI) m/z 642.25 [M + 1]+; 1H-NMR (400 MHz, DMSO-d6) δ 13.76 (bs, 1H), 9.42 (bs, 2H), 8.62 (s, 1H), 8.41 (s, 1H), 7.60 (dd, J = 2.4, 8.8 Hz, 1H), 7.46 (s, 1H), 7.42 (d, J = 2.4 Hz, 1H), 7.37 (d, J = 8.8 Hz, 1H), 4.44-4.40 (m, 3H), 4.22 (s, 2H), 3.51-3.38 (m, 1H), 3.41-319 (m, 2H), 3.04 (m, 3H), 1.83 (s, 3H), 1.36 (m, 4H), 0.84 (m, 1H) |
| 1227 | 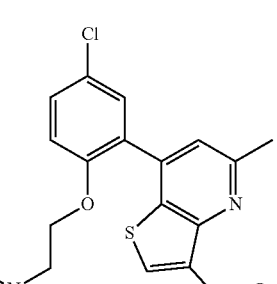 | MS (ESI) m/z 638.14 [M + 1]+; 1H-NMR (400 MHz, DMSO-d6) δ 13.56 (bs, 1H), 9.65 (bs, 1H), 9.01 (s, 1H), 8.45 (s, 1H), 7.59 (dd, J = 2.4, 8.8 Hz, 1H), 7.42 (d, J = 2.4 Hz, 2H), 7.36-7.32 (m, 2H), 7.28-7.23 (m, 2H), 4.41 (bs, 2H), 4.26 (bs, 2H), 2.70 (s, 3H), 2.16 (s, 3H), 1.38 (s, 3H) |
| 1229 | 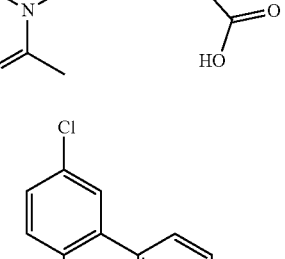 | MS (ESI) m/z 698.43 [M + 1]+; 1H NMR (400 MHz, DMSO-d6) δ 9.59 (bs, 1H), 8.76 (d, J = 4.8 Hz, 1H), 8.72 (s, 1H), 8.65 (s, 1H), 7.75 (d, J = 9.2 Hz, 1H), 7.70-7.65 (m, 2H), 7.55 (d, J = 4.8 Hz, 1H), 4.90-4.79 (m, 4H), 4.40-4.29 (m, 1H), 3.65-3.35 (m, 3H), 3.09 (s, 3H), 2.85-2.80 (m, 3H), 2.18-1.65 (m, 11H) |
| 1231 | 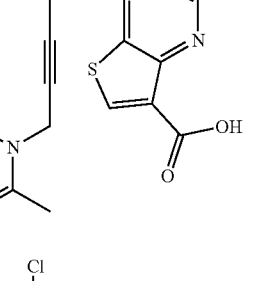 | MS (ESI) m/z 592.13 [M + 1]+; 1H NMR (400 MHz, DMSO-d6) δ 8.79-8.77 (m, 2H), 8.15 (s, 1H), 7.57 (dd, J = 2.60, 8.84 Hz, 1H), 7.34-7.32 (m, 3H), 4.38 (t, J = 4.60 Hz, 2H), 4.26 (t, J = 4.56 Hz, 2H), 1.77 (s, 3H), 1.63 (s, 9H) |

TABLE 1-continued

7-Aza-Thienylpyridine and Derivative Compounds

| Compound | | Characterization |
|---|---|---|
| 1232 | | MS (ESI) m/z 615.03 [M + 1]+; 1H NMR (400 MHz, DMSO-d6) δ 8.96 (s, 1H), 8.34 (s, 1H), 7.60 (dd, J = 8.8 Hz, 2.4 Hz, 1H), 7.47 (s, 1H), 7.44 (d, J = 2.4 Hz, 1H), 7.35 (d, J = 8.8 Hz, 1H), 4.40-3.79 (m, 10H), 3.05-3.00 (m, 2H), 2.95 (s, 3H). 1.83 (s, 3H), 1.38-1.34 (t, J = 7.6 Hz, 3H) |
| 1233 | | MS (ESI) m/z 586.32 [M + 1]+; 1H NMR (400 MHz, DMSO-d6) δ 8.94 (s, 1H), 8.68 (d, J = 4.80 Hz, 1H), 8.51 (s, 1H), 7.74 (d, J = 8.40 Hz, 1H), 7.67-7.63 (m, 3H), 7.40 (d, J = 4.80 Hz, 1H), 4.88 (s, 2H), 2.18 (s, 3H), 1.59 (s, 9H) |
| 1234 | | MS (ESI) m/z 631.23 [M + 1]+; 1H NMR (400 MHz, DMSO-d6) δ 8.56 (s, 1H), 8.49 (s, 1H), 7.59 (dd, J = 8.88, 2.50 Hz, 1H), 7.41 (d, J = 2.60 Hz, 1H), 7.40 (s, 1H), 7.35 (d, J = 8.96 Hz, 1H), 4.37 (t, J = 5.00 Hz, 2H), 4.19 (t, J = 5.00 Hz, 2H), 4.11 (bs, 1H), 3.92-3.70 (m, 4H), 3.29 (s, 3H), 2.70 (s, 3H), 2.11-2.04 (m, 2H), 1.81 (s, 3H) |
| 1235 | | MS (ESI) m/z 631.26 [M + 1]+; 1H NMR (400 MHz, DMSO-d6) δ 13.76 (s, 1H), 8.54 (s, 1H), 8.48 (s, 1H), 7.59 (dd, J = 8.8 Hz, 2.4 Hz, 1H) 7.43 (s, 2H), 7.35 (d, J = 8.8 Hz, 1H), 5.07 (d, J = 2.8 Hz, 1H), 4.41 (bs, 1H), 4.37-4.36 (m, 2H), 4.42 (m, 2H), 3.93-3.87 (m, 2H), 3.79-3.75 (m, 1H), 3.59 (d, J = 11.2 Hz, 1H), 3.01 (q, J = 7.6 Hz, 2H), 2.04-2.01 (m, 1H), 1.93 (bs, 1H), 1.75 (s, 3H),1.35 (t, J = 7.6 Hz, 3H) |

TABLE 1-continued

7-Aza-Thienylpyridine and Derivative Compounds

| Compound | | Characterization |
|---|---|---|
| 1236 | 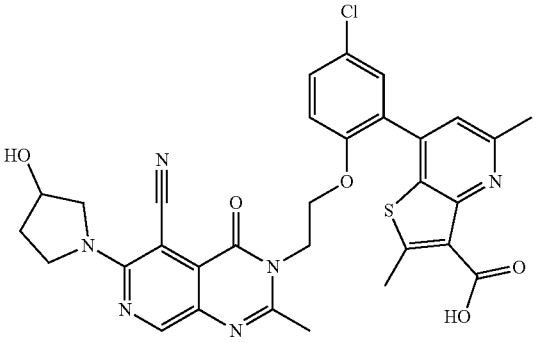 [SMILES: Cc1cc(-c2cc(Cl)ccc2OCCn2c(C)nc3cnc(N4CCC(O)C4)c(C#N)c3c2=O)c2sc(C)c(C(=O)O)c2n1] | MS (ESI) m/z 631.23 [M + 1]+; 1H NMR (400 MHz, DMSO-d6) δ 14.35 (bs, 1H), 8.53 (s, 1H), 7.58 (dd, J = 8.96, 2.36 Hz, 1H), 7.39-7.34 (m, 3H), 4.45-4.36 (m, 3H), 4.21 (t, J = 4.24 Hz, 2H), 3.92-3.86 (m, 2H), 3.78-3.68 (m, 2H), 3.56 (d, J = 12.04 Hz, 1H), 2.70 (s, 3H), 2.53 (s, 3H), 2.22-1.86 (m, 5H) |
| 1257 | 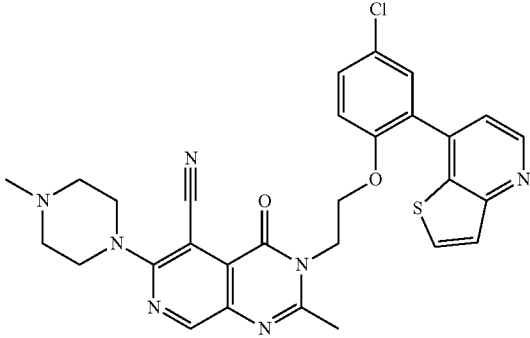 [SMILES: Cc1nc2cnc(N3CCN(C)CC3)c(C#N)c2c(=O)n1CCOc1ccc(Cl)cc1-c1ccnc2ccsc12] | MS (ESI) m/z 572.27 [M + 1]+; 1H NMR (400 MHz, DMSO-d6) δ 8.86 (s, 1H), 8.65 (d, J = 4.8 Hz, 1H), 7.71 (d, J = 5.2 Hz, 1H), 7.55 (dd, J = 8.8, 2.8 Hz, 1H), 7.44 (d, J = 5.2 Hz, 1H), 7.39 (d, J = 2.4 Hz, 1H), 7.31 (d, J = 9.2 Hz, 1H), 7.21 (d, J = 4.4 Hz, 1H), 4.36-4.23 (m, 6H), 3.60 (d, J = 12.0 Hz, 2H), 3.41 (t, J = 11.6 Hz, 2H), 3.29-3.16 (m, 2H), 2.90 (s, 3H), 1.81 (s, 3H) |
| 1258 | 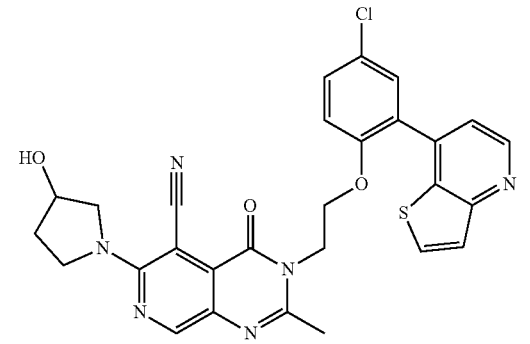 [SMILES: Cc1nc2cnc(N3CCC(O)C3)c(C#N)c2c(=O)n1CCOc1ccc(Cl)cc1-c1ccnc2ccsc12] | MS (ESI) m/z 559.20 [M + 1]+; 1H NMR (400 MHz, DMSO-d6) δ 8.69 (s, 1H), 8.65 (d, J = 3.8, 1H), 7.75 (d, J = 4.76, 1H), 7.55-7.53 (m, 1H), 7.47 (d, J = 5.0 Hz, 1H), 7.39 (s, 1H), 7.31 (d, J = 8.6 Hz, 1H), 7.21 (d, J = 3.6 Hz, 1H), 5.07 (s, 1H), 4.41 (s, 1H), 4.35 (t, J = 3.6 Hz, 2H), 4.19 (t, J = 5.6 Hz, 2H), 3.89 (t, J = 5.9 Hz, 2H), 3.77-3.73 (m, 1H), 3.58 (d, J = 11.4 Hz, 1H), 2.00-1.98 (m, 1H), 1.93 (bs, 1H), 1.74 (s, 3H) |
| 1264 | 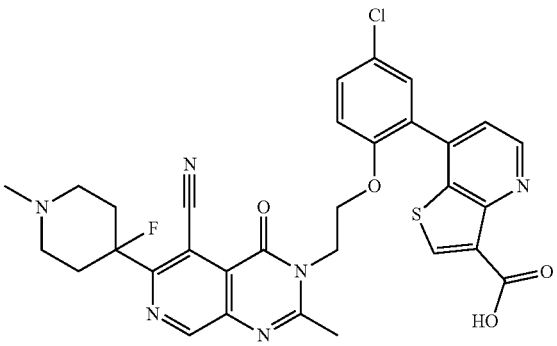 [SMILES: Cc1nc2cnc(C3(F)CCN(C)CC3)c(C#N)c2c(=O)n1CCOc1ccc(Cl)cc1-c1ccnc2c(C(=O)O)csc12] | MS (ESI) m/z 633.24 [M + 1]+; 1H NMR (400 MHz, DMSO-d6) δ 8.99 (s, 1H), 8.83 (d, J = 4.8 Hz, 1H), 8.37 (s, 1H), 7.61 (d, J = 9.2 Hz, 1H), 7.48 (d, J = 4.8 Hz, 1H), 7.44 (s, 1H), 7.36 (d, J = 8.8 Hz, 1H), 4.41 (t, J = 5.2 Hz, 2H), 4.27 (t, J = 4.0 Hz, 2H), 3.52 (bs, 6H), 3.77-3.25 (m, 2H), 2.92 (d, J = 3.2 Hz, 3H), 1.82 (s, 3H) |

TABLE 1-continued

7-Aza-Thienylpyridine and Derivative Compounds

| Compound | | Characterization |
|---|---|---|
| 1265 | 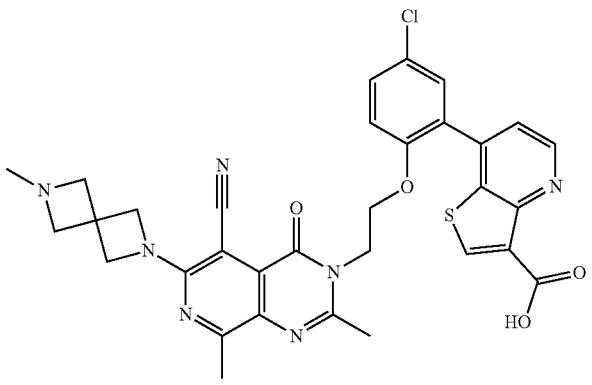 [SMILES: Cc1nc(N2CC3(CN(C)C3)C2)c(C#N)c2c(=O)n(CCOc3ccc(Cl)cc3-c3ccnc4c(C(=O)O)csc34)c(C)nc12] | MS (ESI) m/z 642.16 [M + 1]+; 1H-NMR (400 MHz, DMSO-d6) δ 9.54 (s, 1H), 8.80 (d, J = 4.8 Hz,1H), 8.55 (s, 1H), 7.57 (dd, J = 2.4, 8.8 Hz, 1H), 7.45 (d, J = 4.8 Hz, 1H), 7.40-7.36 (m, 2H), 4.55 (s, 2H), 4.48 (d, J = 14 Hz, 4H), 4.40 (s, 2H), 4.22 (d, J = 14.4 Hz, 4H), 2.85 (d, J = 4 Hz, 3H), 2.60 (s, 3H), 1.86 (s, 3H) |
| 1266 | 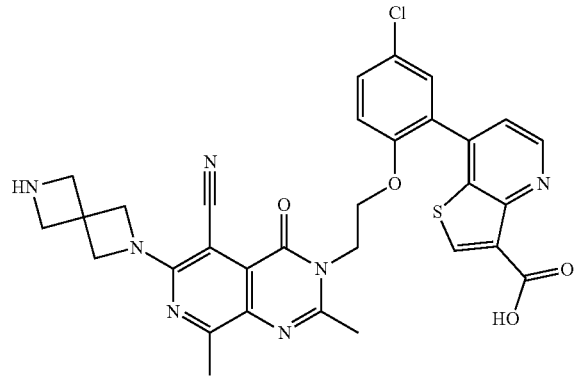 [SMILES: Cc1nc(N2CC3(CNC3)C2)c(C#N)c2c(=O)n(CCOc3ccc(Cl)cc3-c3ccnc4c(C(=O)O)csc34)c(C)nc12] | MS (ESI) m/z 629.0 [M + 1]+; 1H-NMR (400 MHz, DMSO-d6) δ 8.80 (d, J = 4.8 Hz, 1H), 8.55 (s, 1H), 8.49 (bs, 2H), 7.57 (dd, J = 2.4, 8.8 Hz ,1H), 7.45 (d, J = 4.8 Hz, 1H), 7.40-7.36 (m, 2H), 4.52 (s, 4H), 4.39 (d, J = 4.8 Hz, 2H), 4.22 (d, J = 5.2 Hz, 6H), 2.60 (s, 3H), 1.85 (s, 3H) |
| 1268 | 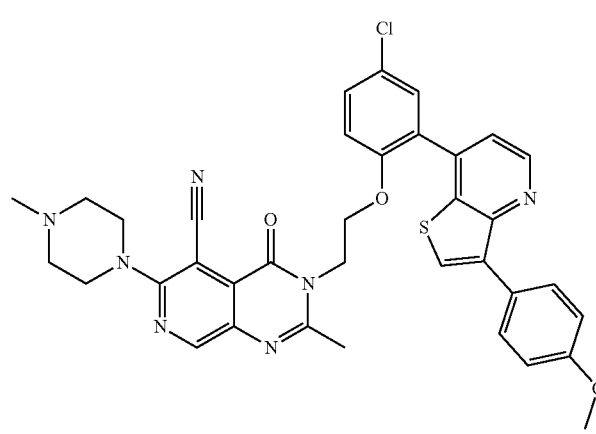 | MS (ESI) m/z 678.28 [M + 1]+; 1H NMR (400 MHz, DMSO-d6) δ 9.82 (bs, 1H), 8.74 (d, J = 4.8 Hz, 1H), 8.48 (s, 1H), 8.05 (d, J = 8.4 Hz, 2H), 7.76 (s, 1H), 7.56 (dd, J = 8.8, 2.4 Hz, 1H), 7.41 (d, J = 2.8 Hz, 1H), 7.34 (d, J = 8.9 Hz, 1H), 7.28 (d, J = 4.4 Hz, 1H), 7.10 (d, J = 8.8 Hz, 2H), 4.43-4.36 (m, 2H), 4.27-4.17 (m, 4H), 3.86 (s, 3H), 3.62-3.53 (m, 2H), 3.41-3.29 (m, 2H), 3.21-3.10 (m, 2H), 2.90 (s, 3H), 1.78 (s, 3H) |

TABLE 1-continued

7-Aza-Thienylpyridine and Derivative Compounds

| Compound | | Characterization |
|---|---|---|
| 1273 | 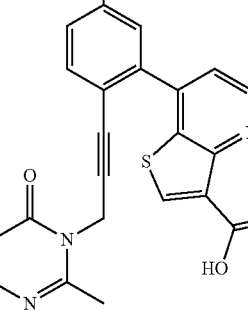 | MS (ESI) m/z 624.30 [M + 1]+; 1H NMR (400 MHz, DMSO-d6) δ 13.00 (bs, 1H), 8.76 (d, J = 4.80 Hz, 1H), 8.66 (s, 1H), 7.76-7.64 (m, 3H), 7.53 (d, J = 4.80 Hz, 1H), 4.82 (s, 2H), 4.38-4.35 (m, 2H), 3.63-3.60 (m, 2H), 3.48-3.25 (m, 4H), 2.91 (s, 3H), 2.73 (s, 3H), 2.14 (s, 3H) |
| 1274 |  | MS (ESI) m/z 680.33 [M + 1]+; 1H NMR (400 MHz, DMSO-d6) δ 8.81 (d, J = 4.72 Hz, 1H), 8.52 (s, 1H), 7.59 (dd, J = 8.88, 2.44 Hz, 1H), 7.44 (d, J = 4.68, 1H), 7.40 (d, J = 2.4 Hz, 1H), 7.36 (d J = 9.0 Hz, 1H), 6.35-6.05 (m, 1H), 4.40 (t, J = 4.48 Hz, 2H), 4.20 (t, J = 4.72 Hz, 2H), 3.64 (s, 4H), 2.87-2.878 (m, 2H), 2.71 (s, 4H), 2.63 (s, 3H), 1.78 (s, 3H) |
| 1279 |  | MS (ESI) m/z 622.22 [M + 1]+; 1H NMR (400 MHz, DMSO-d6) δ 9.01 (s, 1H), 8.82 (d, J = 4.8 Hz, 1H), 8.39 (s, 1H), 7.59 (dd, J = 8.8, 2.4 Hz, 1H), 7.48 (d, J = 4.8 Hz, 1H), 7.42 (d, J = 2.4 Hz, 1H), 7.35 (d, J = 8.8 Hz, 1H), 4.45-4.36 (m, 2H), 4.30-4.20 (m, 2H), 4.15-4.00 (m, 1H), 2.70-2.50 (m, 2H), 2.44-2.20 (m, 3H), 2.14-2.01 (m, 1H), 1.84 (s, 3H) |
| 1281 | 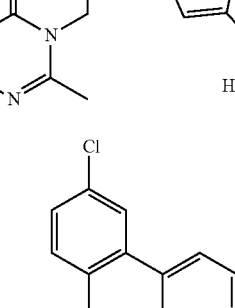 | MS (ESI) m/z 687.47 [M + 1]+; 1H-NMR (400 MHz, DMSO-d6) δ 10.05 (bs, 1H), 8.87 (d, J = 3.2 Hz, 1H), 8.74 (s, 1H), 8.72 (d, J = 4.8 Hz, 1H), 8.47 (s, 1H), 7.75 (d, J = 8.0 Hz, 1H), 7.69 (d, J = 2.0 Hz, 2H), 7.66 (s, 1H), 7.49 (d, J = 4.4 Hz, 1H), 6.53 (tt, J = 5.2, 51.2 Hz, 1H), 4.82 (s, 2H), 4.49 (bs, 1H), 3.64 (bs, 4H), 3.38 (bs, 2H), 3.16 (s, 3H), 2.17 (bs, 2H), 2.04 (bs, 5H) |

TABLE 1-continued

7-Aza-Thienylpyridine and Derivative Compounds

| Compound | | Characterization |
|---|---|---|
| 1282 | | MS (ESI) m/z 630.28 [M + 1]+; 1H NMR (400 MHz, DMSO-d6) δ 14.09 (bs, 1H), 8.77 (d, J = 4.8 Hz, 1H), 8.61 (s, 1H), 7.59 (dd, J = 8.8, 2.4 Hz, 1H), 7.48 (d, J = 4.8 Hz, 1H), 7.40 (d, J = 2.4 Hz, 1H), 7.35 (d, J = 9.2 Hz, 1H), 4.39 (s, 2H), 4.21 (s, 2H), 3.64 (s, 4H), 2.55-2.35 (m, 7H), 2.23 (s, 3H), 1.83 (s, 3H) |
| 1297 | | MS (ESI) m/z 644.30 [M + 1]+; 1 H NMR (400 MHz, DMSO-d6) δ 13.46 (bs, 1H), 8.66 (d, J = 4.8 Hz, 1H), 7.55 (dd, J = 8.8, 2.4 Hz, 1H), 7.37-7.28 (m, 3H), 4.42-4.34 (m, 2H), 4.21 (s, 2H), 3.63 (bs, 4H), 2.64 (s, 3H), 2.49-2.35 (m, 7H), 2.22 (s, 3H), 1.84 (s, 3H) |
| 1301 | | MS (ESI) m/z 628.33 [M + 1]+; 1H NMR (400 MHz, DMSO-d6) δ 10.82 (bs, 1H), 8.83 (d, J = 4.8 Hz, 1H), 8.67 (s, 1H), 8.46 (s, 1H), 7.60 (dd, J = 8.8, 2.4 Hz, 1H), 7.48 (d, J = 4.8 Hz, 1H), 7.43 (d, J = 2.8 Hz, 1H), 7.37 (d, J = 8.8 Hz, 1H), 4.48- 4.40 (m, 3H), 4.29-4.19 (m, 2H), 3.45-3.19 (m, 3H), 3.10-2.89 (m, 5H), 1.80 (s, 3H), 1.48-1.27 (m, 2H) |
| 1302 | | MS (ESI) m/z 648.15 [M + 1]+; 1H NMR (400 MHz, DMSO-d6) δ 10.15 (bs, 1H), 8.83 (d, J = 4.8 Hz, 1H), 8.70 (s, 1H), 8.43 (s, 1H), 7.57 (dd, J = 2.4, 8.8 Hz, 1H), 7.47 (d, J = 4.8 Hz, 1H), 7.41-7.36 (m, 2H), 4.95 (s, 1H), 4.84 (s, 1H), 4.39 (d, J = 4.4 Hz, 2H), 4.30 (d, J = 7.6 Hz, 2H), 4.23 (s, 2H), 3.83-3.59 (m, 4H), 3.53-3.34 (m, 4H), 1.83 (s, 3H) |

TABLE 1-continued

7-Aza-Thienylpyridine and Derivative Compounds

| Compound | | Characterization |
|---|---|---|
| 1303 | 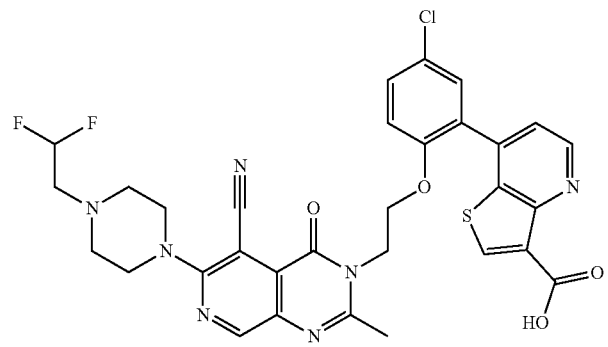 [SMILES: Cc1nc2cnc(N3CCN(CC(F)F)CC3)c(C#N)c2c(=O)n1CCOc1ccc(Cl)cc1-c1ccnc2c(C(=O)O)csc12] | MS (ESI) m/z 666.24 [M + 1]+; 1H NMR (400 MHz, DMSO-d6) δ 8.83 (d, J = 4.8 Hz, 1H), 8.68 (s, 1H), 8.46 (s, 1H), 7.60 (dd, J = 8.8 Hz, 2.4 Hz, 1H), 7.48 (d, J = 4.8 Hz, 1H), 7.42 (d, J = 2.4 Hz, 1H), 7.37-7.35 (m, 1H), 6.46 (t, J = 54.8 Hz, 1H), 4.41-4.38 (m, 2H), 4.28-4.22 (m, 2H), 3.87-3.83 (m, 4H), 3.38-3.32 (m, 2H), 3.24-3.11 (m, 4H), 1.80 (s, 3H) |
| 1304 | 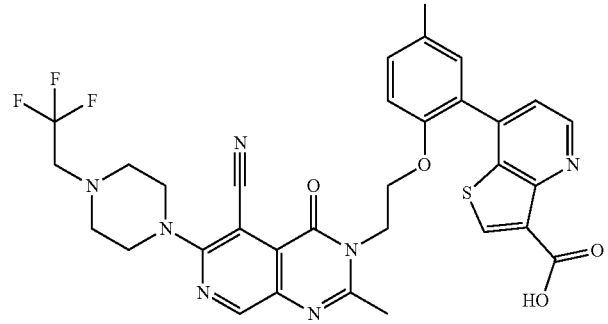 | MS (ESI) m/z 684.26 [M + 1]+; 1H NMR (400 MHz, DMSO-d6) δ 11.77 (bs, 1H), 8.81 (d, J = 4.8 Hz, 1H), 8.66 (s, 1H), 8.40 (s, 1H), 7.58 (dd, J = 9.2, 6.8 Hz, 1H), 7.45-7.40 (m, 2H), 7.34 (d, J = 8.8 Hz, 1H), 4.37 (s, 2H), 4.20 (s, 2H), 3.65 (s, 4H), 3.35-3.20 (m, 2H), 2.81 (s, 4H), 1.75 (s, 3H) |
| 1305 | 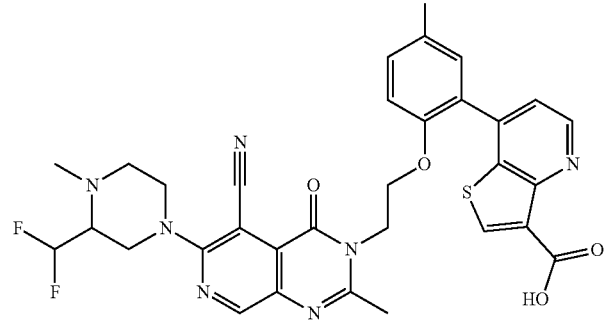 | MS (ESI) m/z 666 [M + 1]+; 1H NMR (400 MHz, DMSO-d6) δ 8.82 (d, J = 4.8 Hz , 1H), 8.70 (s, 1H), 8.43 (s, 1H), 7.61 (dd, J = 2.4, 8.8 Hz, 1H), 7.47 (d, J = 4.8 Hz, 1H), 7.42 (d, J = 2.8 Hz, 1H), 7.37 (d, J = 8.8 Hz, 1H), 6.73-6.46 (m, 1H), 4.39 (s, 2H), 4.34 (s, 1H), 4.23 (s, 2H), 4.18 (s, 1H), 3.56-3.15 (m, 5H), 2.83 (s, 3H), 1.82 (s, 3H) |
| 1306 | 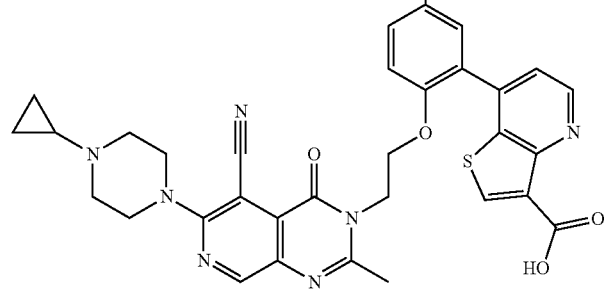 | MS (ESI) m/z 642.35 [M + 1]+; 1H NMR (400 MHz, DMSO-d6) δ 13.43 (bs, 1H), 8.83 (d, J = 4.8 Hz, 1H), 8.70 (s, 1H), 8.44 (s, 1H), 7.61 (dd, J = 8.8 Hz, J = 2.4 Hz, 1H), 7.48 (d, J = 4.8 Hz, 1H), 7.41-7.38 (m, 2H), 4.41-4.40 (m, 4H), 4.31 (t, J = 2.4 Hz, 2H), 3.47 (bs, 6H), 3.01 (bs, 1H), 1.85 (s, 3H), 1.00-0.88 (bs, 2H) |

TABLE 1-continued

7-Aza-Thienylpyridine and Derivative Compounds

| Compound | | Characterization |
|---|---|---|
| 1307 | 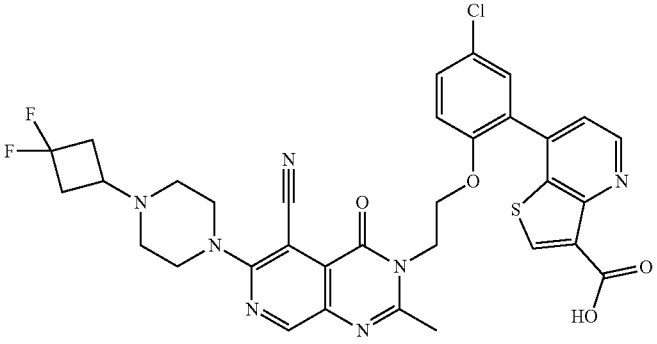 | MS (ESI) m/z 692.28 [M + 1]+; 1H NMR (400 MHz, DMSO-d6) δ 13.31 (bs, 1H), 8.82 (d, J = 4.8 Hz, 1H), 8.68 (s, 1H), 8.43 (s, 1H), 7.59 (dd, J = 2.40, 8.8 Hz, 1H), 7.46 (d, J = 4.4 Hz, 1H), 7.41 (d, J = 2.0 Hz, 1H), 7.36 (d, J = 8.8 Hz, 1H), 4.39 (s, 2H), 4.22 (s, 2H), 3.76 (m, 4H), 3.19-2.93 (m, 8H), 2.32 (m, 1H), 1.80 (s, 3H) |
| 1308 | 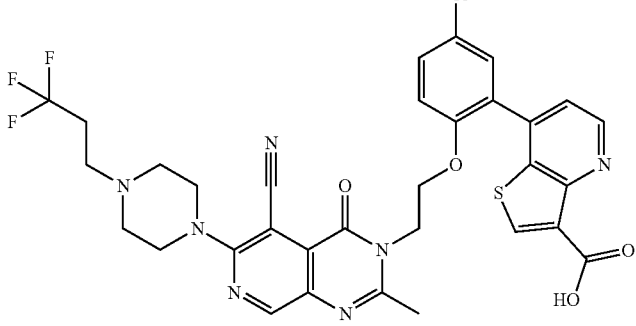 | MS (ESI) m/z 698.28 [M + 1]+; 1H NMR (400 MHz, DMSO-d6) δ 13.33 (bs, 1H), 8.82 (d, J = 4.76 Hz, 1H), 8.69 (s, 1H), 8.43 (s, 1H), 7.59 (dd, J = 2.4, 8.8 Hz, 1H), 7.46 (d, J = 4.7 Hz, 1H), 7.41 (d, J = 2.5 Hz, 1H), 7.35 (d, J = 8.9 Hz, 1H) , 4.39 (t, J = 4.8 Hz, 2H), 4.22 (t, J = 4.4 Hz, 2H), 3.38 (bs, 8H), 2.82 (s, 4H), 1.81 (s, 3H) |
| 1309 | 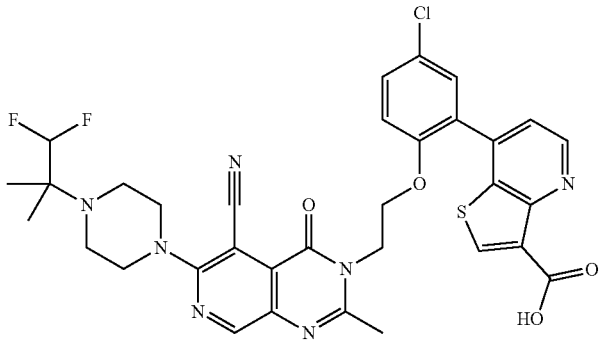 [SMILES: Cc1nc2cnc(N3CCN(C(C)(C)C(F)F)CC3)c(C#N)c2c(=O)n1CCOc1ccc(Cl)cc1-c1ccnc2c(C(=O)O)csc12] | MS (ESI) m/z 694.37 [M + 1]+; 1H NMR (400 MHz, DMSO-d6) δ 8.82 (d, J = 4.8 Hz, 1H), 8.67 (s, 1H), 8.45 (s, 1H), 7.59 (dd, J = 2.4, 8.8 Hz, 1H), 7.47 (d, J = 4.8 Hz, 1H), 7.42 (d, J = 2.0 Hz, 1H), 7.36 (d, J = 9.2 Hz, 1H), 6.22 (m, 1H), 4.39 (s, 2H), 4.21 (s, 2H), 3.72 (m, 4H), 2.96 (s, 4H), 1.79 (s, 3H), 1.23 (s, 6H) |
| 1310 | 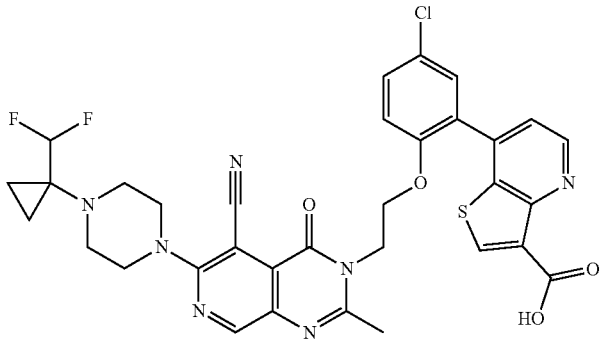 [SMILES: Cc1nc2cnc(N3CCN(C4(C(F)F)CC4)CC3)c(C#N)c2c(=O)n1CCOc1ccc(Cl)cc1-c1ccnc2c(C(=O)O)csc12] | MS (ESI) m/z 692.51 [M + 1]+; 1H NMR (400 MHz, DMSO-d6) δ 8.83 (d, J = 4.8 Hz, 1H), 8.64 (s, 1H), 8.48 (s, 1H), 7.60 (dd, J = 8.8, 2.4 Hz, 1H), 7.49 (d, J = 4.80, 1H), 7.43 (d, J = 2.4 Hz, 1H), 7.35 (d, J = 8.8 Hz, 1H), 6.04 (t, J = 55.6 Hz, 1H), 4.38 (s, 2H), 4.20 (s, 2H), 3.55 (s, 4H), 3.01 (s, 4H), 1.75 (s, 3H), 0.90-078 (m, 4H) |

TABLE 1-continued

7-Aza-Thienylpyridine and Derivative Compounds

| Compound | | Characterization |
|---|---|---|
| 1311 | 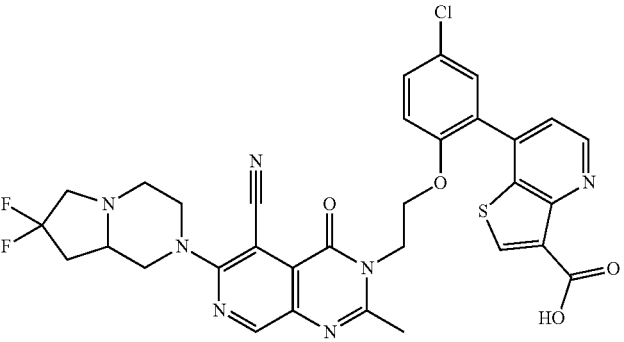 [SMILES: Cc1nc2cnc(N3CCN4CC(F)(F)CC4C3)c(C#N)c2c(=O)n1CCOc1ccc(Cl)cc1-c1ccnc2c(C(=O)O)csc12] | MS (ESI) m/z 678.43 [M + 1]+; 1H NMR (400 MHz, DMSO-d6) δ 8.83 (d, J = 4.8 Hz, 1H), 8.66 (s, 1H), 8.45 (s, 1H) 7.60 (dd, J = 9.2 Hz, 2.8 Hz, 1H), 7.48 (d, J = 4.8 Hz, 1H), 7.42 (d, J = 2.4 Hz, 1H), 7.36 (d, J = 9.2 Hz, 1H), 4.39 (bs, 2H), 4.32 (d, J = 12.8 Hz, 2H), 4.22 (bs, 4H), 3.64 (bs, 1H), 3.38 (bs, 1H), 3.19 (bs, 2H), 2.93 (bs, 2H), 2.15 (bs, 1H), 1.759 (s, 3H) |
| 1312 | 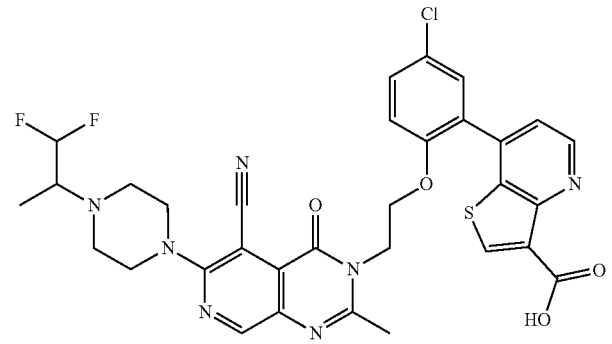 | MS (ESI) m/z 680.29 [M + 1]+; 1H NMR (400 MHz, DMSO-d6) δ 13.22 (bs, 1H), 8.82 (d, J = 4.8 Hz 1H), 8.66 (s, 1H), 8.44 (s, 1H), 7.598 (dd, J = 2.4, 8.8 Hz, 1H), 7.47 (d, J = 4.4 Hz, 1H), 7.42 (d, J = 2.4 Hz, 1H), 7.35 (d, J = 8.8 Hz, 1H), 6.25 (m, 1H), 4.38 (s, 2H), 4.21 (s, 2H), 3.64 (m, 4H), 2.97 (m, 4H), 2.63 (s, 1H), 1.77 (s, 3H), 1.16 (s, 3H) |
| 1313 | 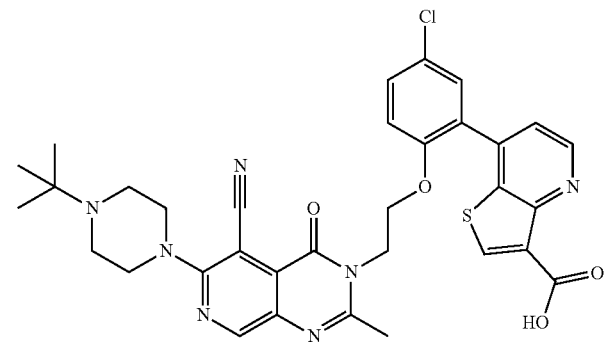 [SMILES: Cc1nc2cnc(N3CCN(C(C)(C)C)CC3)c(C#N)c2c(=O)n1CCOc1ccc(Cl)cc1-c1ccnc2c(C(=O)O)csc12] | MS (ESI) m/z 658.37 [M + 1]+; 1H NMR (400 MHz, DMSO-d6) δ 9.43 (bs, 1H), 8.82 (d, J = 4.8 Hz, 1H), 8.70 (s, 1H), 8.41 (s, 1H), 7.60 (dd, J = 8.8 Hz, 2.4 Hz, 1H), 7.47 (d, J = 4.4 Hz, 1H), 7.41-7.36 (m, 2H), 4.42-4.39 (m, 4H), 4.24 (s, 2H), 3.72 (d, J = 12 Hz, 2H), 3.51 (t, J = 12.4 Hz, 2H), 3.19 (d, J = 9.6 Hz, 2H), 1.86 (s, 3H), 1.39 (s, 9H) |
| 1314 | 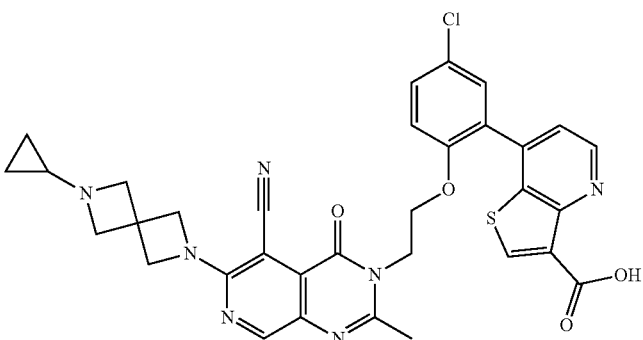 | MS (ESI) m/z 654.34 [M + 1]+; 1H NMR (400 MHz, DMSO-d6) δ 13.22 (bs, 1H), 8.82 (d, J = 4.7 Hz, 1H), 8.57 (s, 1H), 8.46 (s, 1H), 7.59 (dd, J = 8.8, 2.5 Hz, 1H), 7.45 (d, J = 4.7 Hz, 1H), 7.42 (d, J = 2.4 Hz, 1H), 7.34 (d, J = 9.0 Hz, 1H), 4.41 (s, 4H), 4.36 (s, 2H), 4.18 (s, 2H), 3.49 (bs, 4H), 1.90 (bs, 1H), 1.73 (s, 3H), 0.42-0.20 (m, 4H) |

TABLE 1-continued

7-Aza-Thienylpyridine and Derivative Compounds

| Compound | Characterization |
|---|---|
| 1315 | MS (ESI) m/z 698.12 [M + 1]+; 1H NMR (400 MHz, DMSO-d6) δ 8.83 (d, J = 4.4 Hz, 1H), 8.65 (s, 1H), 8.47 (s, 1H), 7.60 (dd, J = 8.8, 2.4 Hz, 1H), 7.49 (d, J = 4.8 Hz, 1H), 7.43 (d, J = 2.4 Hz, 1H), 7.35 (d, J = 8.8 Hz, 1H), 4.42-4.34 (m, 2H), 4.20 (s, 2H), 3.63-3.57 (m, 5H), 2.90-2.80 (m, 4H), 1.76 (s, 3H), 1.21 (d, J = 6.8 Hz, 3H) |
| 1316 | MS (ESI) m/z 712.41 [M + 1]+; 1H NMR (400 MHz, DMSO-d6) δ 8.83 (d, J = 4.8 Hz, 1H), 8.65 (s, 1H), 8.47 (s, 1H), 7.59 (dd, J = 8.8, 2.4 Hz, 1H), 7.48 (d, J = 4.8 Hz, 1H), 7.43 (d, J = 2.4 Hz, 1H), 7.35 (d, J = 8.8 Hz, 1H), 4.41-4.35 (m, 2H), 4.23-4.16 (m, 2H), 3.61 (s, 4H), 2.93 (s, 4H), 1.75 (s, 3H), 1.32 (s, 6H) |
| 1317 | MS (ESI) m/z 676.42 [M + 1]+; 1H NMR (400 MHz, DMSO-d6) δ 13.23 (bs, 1H), 8.82 (d, J = 4.8 Hz, 1H), 8.64 (s, 1H), 8.45 (s, 1H), 7.59-7.57 (m, 1H), 7.45 (d, J = 4.8 Hz, 1H), 7.42 (d, J = 2.0 Hz, 1H), 7.35 (d, J = 8.8 Hz, 1H), 4.38 (s, 2H), 4.20 (s, 2H), 3.65 (s, 4H), 2.67 (s, 4H), 2.60-2.48 (m, 2H), 1.74 (s, 3H), 1.35 (J = 21.6 Hz, 6H) |
| 1318 | MS (ESI) m/z 7694.3 [M + 1]+; 1H NMR (400 MHz, DMSO-d6) δ 8.78 (d, J = 4.8 Hz, 1H), 8.51 (s, 1H), 8.31 (s, 1H), 7.59 (dd, J = 2.4, 8.8 Hz, 1H), 7.45 (d, J = 4.8 Hz, 1H), 7.42 (d, J = 2.4 Hz, 1H), 7.36 (d, J = 9.2 Hz, 1H), 6.54 (t, J = 57.2 Hz, 1H), 4.49 (bs, 2H), 4.39 (bs, 2H), 4.21 (bs, 2H), 3.60 (bs, 4H), 3.08 (t, J = 12.0 Hz, 2H), 3.08 (s, 3H), 2.17 (bs, 1H), 2.03 (bs, 4H) 1.76 (s, 3H) |

TABLE 1-continued

7-Aza-Thienylpyridine and Derivative Compounds

| Compound | | Characterization |
|---|---|---|
| 1319 | 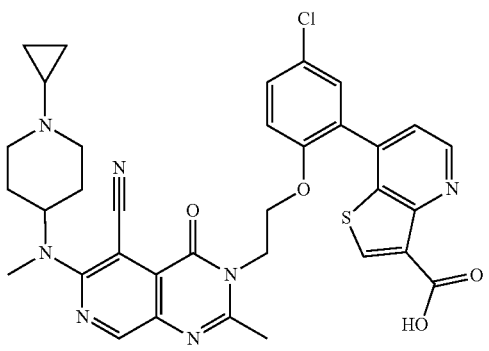 [SMILES: Cc1nc2cnc(N(C)C3CCN(C4CC4)CC3)c(C#N)c2c(=O)n1CCOc1ccc(Cl)cc1-c1ccnc2c(C(=O)O)csc12] | MS (ESI) m/z 670.45 [M + 1]+; 1H NMR (400 MHz, DMSO-d6) δ 8.82 (d, J = 4.76 Hz, 1H), 8.62 (s, 1H), 8.41 (s, 1H), 7.60 (dd, J = 8.9 Hz, 2.4 Hz, 1H), 7.47 (d, J = 4.7 Hz, 1H), 7.42 (d, J = 2.5 Hz, 1H), 7.36 (d, J = 9.0 Hz, 1H), 4.57-4.52 (m, 1H), 4.39 (d, J = 5.6 Hz, 2H), 4.17 (d, J = 5.28, 2H), 3.65 (d, J = 11.44, 2H), 3.95 (bs, 2H), 3.07 (s, 3H), 2.83 (bs, 1H), 2.07 (s, 4H), 1.76 (s, 3H), 0.94-0.85 (m, 4H) |
| 1320 | 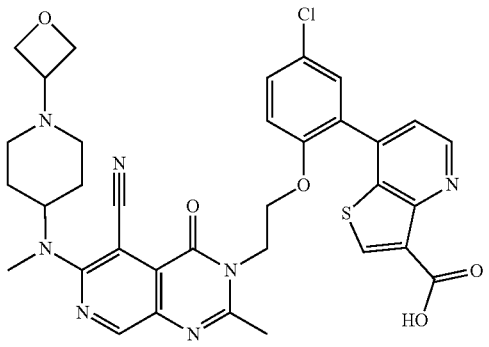 [SMILES: Cc1nc2cnc(N(C)C3CCN(C4COC4)CC3)c(C#N)c2c(=O)n1CCOc1ccc(Cl)cc1-c1ccnc2c(C(=O)O)csc12] | MS (ESI) m/z 686.26 [M + 1]+; 1H NMR (400 MHz, DMSO-d6) δ 13.32 (s, 1H), 8.82 (d, J = 4.8, 1H), 8.61 (s, 1H), 8.40 (s, 1H), 7.59 (dd, J = 2.4, 8.8 Hz, 1H), 7.46 (d, J = 4.8 Hz, 1H), 7.42 (d, J = 2.4 Hz, 1H), 7.36 (d, J = 8.8 Hz, 1H), 4.77-4.76 (m, 4H), 4.55 (bs, 1H), 4.39 (s, 3H), 4.21 (s, 2H), 3.26-3.15 (m, 2H), 3.09-2.97 (m, 5H), 2.21-2.08 (m, 4H), 1.77 (s, 3H) |
| 1321 | 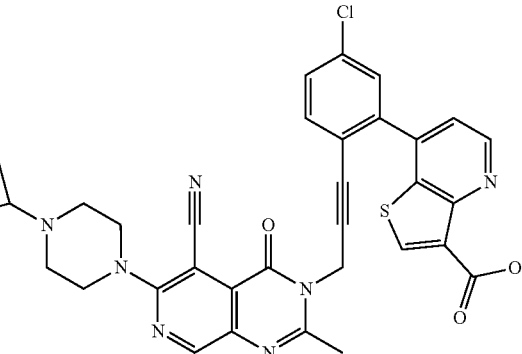 | MS (ESI) m/z 652.12 [M + 1]+; 1H NMR (400 MHz, DMSO-d6) δ 8.83 (s, 1H), 6 8.74 (d, J = 4.8 Hz, 1H), 8.64 (s, 1H), 7.75 (d, J = 8.4 Hz, 1H), 7.69-7.66 (m, 2H), 7.53 (d, J = 4.4 Hz, 1H), 4.83 (s, 2H), 4.76 (s, 4H), 4.37 (bs, 4H), 4.04 (bs, 1H), 3.34-2.82 (m, 4H), 2.12 (s, 3H) |
| 1322 | 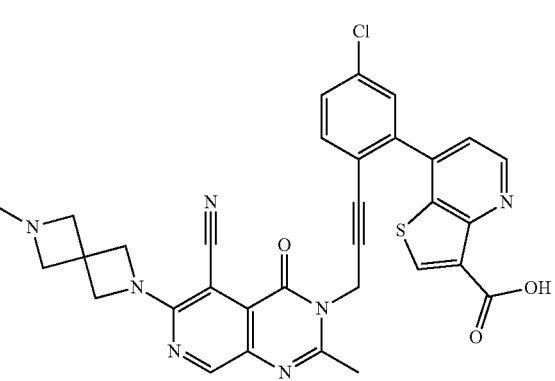 | MS (ESI) m/z 664.45 [M + 1]+; 1H NMR (400 MHz, DMSO-d6) δ 8.74 (d, J = 4.8 Hz, 1H), 8.70 (s, 1H), 8.64 (s, 1H), 7.76-7.73 (m, 1H), 7.69-7.66 (m, 2H), 7.52 (d, J = 4.8 Hz, 1H), 4.80 (s, 2H), 4.54 (t, J = 6.4 Hz, 2H), 4.47 (s, 4H), 4.35 (t, J = 6 Hz, 2H), 3.69 (t, J = 5.6 Hz, 1H), 3.42 (s, 4H), 2.0 (s, 3H) |

TABLE 1-continued

7-Aza-Thienylpyridine and Derivative Compounds

| Compound | | Characterization |
|---|---|---|
| 1323 | 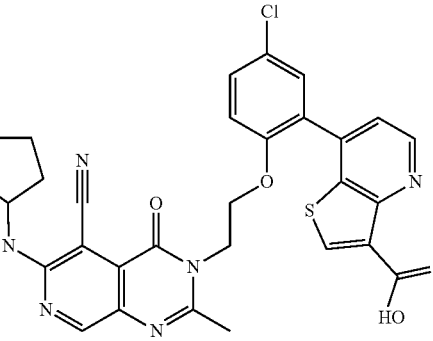 | MS (ESI) m/z 630.32 [M + 1]+; 1H NMR (400 MHz, DMSO-d6) δ 9.62 (s, 1H), 8.80 (d, J = 4.8 Hz, 1H), 8.59 (s, 1H), 8.50 (s, 1H), 7.59 (dd, J = 2.4, 8.8 Hz, 1H), 7.45 (d, J = 4.8 Hz, 1H), 7.40 (d, J = 2.4 Hz, 1H), 7.36 (d, J = 9.2 Hz, 1H), 7.19 (s, 1H), 4.41 (t, J = 4.8 Hz, 2H), 4.24 (t, J = 4.8 Hz, 2H), 3.64 (s, 2H), 2.96 (m, 5H), 2.5 (m, 3H), 2.10 (m, 2H), 1.85 (s, 3H) |
| 1324 | 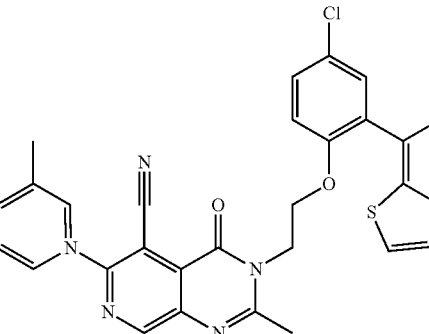 | MS (ESI) m/z 652.29 [M + 1]+; 1H NMR (400 MHz, DMSO-d6) δ 9.17 (s, 1H), 8.85 (d, J = 4.81 Hz, 1H), 8.36 (s, 1H), 7.62-7.59 (m, 2H), 7.47 (d, J = 4.8 Hz, 1H), 7.43 (d, J = 2.8 Hz, 1H), 7.36 (d, J = 8.8 Hz, 1H), 7.06 (bs, 1H), 4.44 (s, 2H), 4.33 (s, 2H), 3.29 (s, 6H), 2.60 (s, 3H), 1.92 (s, 3H) |
| 1325 | 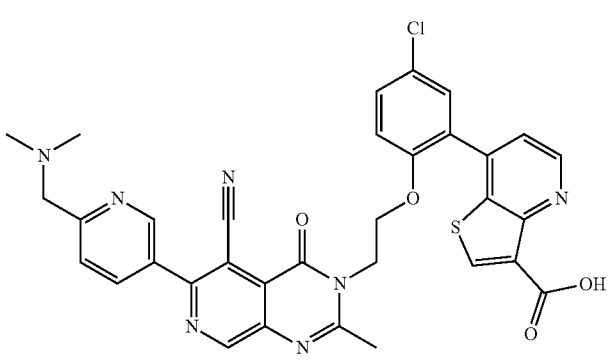 [SMILES: Cc1nc2cnc(-c3ccc(CN(C)C)nc3)c(C#N)c2c(=O)n1CCOc1ccc(Cl)cc1-c1ccnc2c(C(=O)O)csc12] | MS (ESI) m/z 652.36 [M + 1]+; 1H NMR (400 MHz, DMSO-d6) δ 13.23 (bs, 1H), 9.09 (s, 1H), 9.00 (s, 1H), 8.85 (d, J = 4.4 Hz, 1H), 8.38 (s, 1H), 8.31 (d, J = 8.0 Hz, 1H), 7.65 (d, J = 8.0 Hz, 1H), 7.60 (dd, J = 8.8, 2.4 Hz, 1H), 7.47 (d, J = 4.8 Hz, 1H), 7.43 (d, J = 2.4 Hz, 1H), 7.36 (d, J = 8.8 Hz, 1H), 4.42 (s, 2H), 4.28 (s, 2H), 3.66 (s, 2H), 2.26 (s, 6H), 1.83 (s, 3H) |
| 1326 | 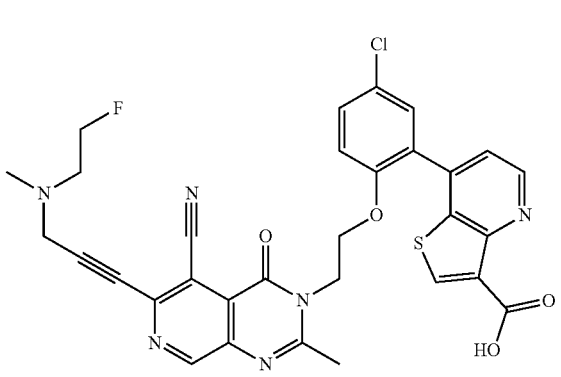 [SMILES: Cc1nc2cnc(C#CCN(C)CCF)c(C#N)c2c(=O)n1CCOc1ccc(Cl)cc1-c1ccnc2c(C(=O)O)csc12] | MS (ESI) m/z 631.39 [M + 1]+; 1H NMR (400 MHz, DMSO-d6) δ 13.23 (bs, 1H), 8.97 (s, 1H), 8.83 (d, J = 4.8 Hz, 1H), 8.36 (s, 1H), 7.60 (dd, J = 9.2, 2.0 Hz, 1H), 7.47 (d, J = 4.8 Hz, 1H), 7.44 (d, J = 2.4 Hz, 1H), 7.35 (d, J = 8.8 Hz, 1H), 4.81 (d, J = 46.4 Hz, 2H), 4.47-4.38 (m, 4H), 4.26 (s, 2H), 3.65-3.30 (m, 2H), 2.86 (s, 3H), 1.77 (s, 3H) |

TABLE 1-continued

7-Aza-Thienylpyridine and Derivative Compounds

| Compound | | Characterization |
|---|---|---|
| 1327 | 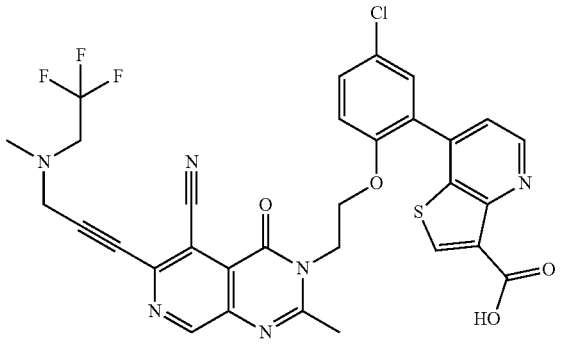 [SMILES: Cc1nc2cnc(C#CCN(C)CC(F)(F)F)c(C#N)c2c(=O)n1CCOc1ccc(Cl)cc1-c1ccnc2c(C(=O)O)csc12] | MS (ESI) m/z 667.38 [M + 1]+; 1H NMR (400 MHz, DMSO-d6) δ 13.16 (bs, 1H), 8.94 (s, 1H), 8.83 (d, J = 4.8 Hz, 1H), 8.38 (s, 1H), 7.59 (dd, J = 9.2, 2.4 Hz, 1H), 7.47 (d, J = 4.8 Hz, 1H), 7.43 (d, J = 2.4 Hz, 1H), 7.34 (d, J = 8.8 Hz, 1H), 4.39 (s, 2H), 4.25 (s, 2H), 3.88 (s, 2H), (q, J = 10.0 Hz, 2H), 2.54 (s, 3H), 1.73 (s, 3H) |
| 1328 | 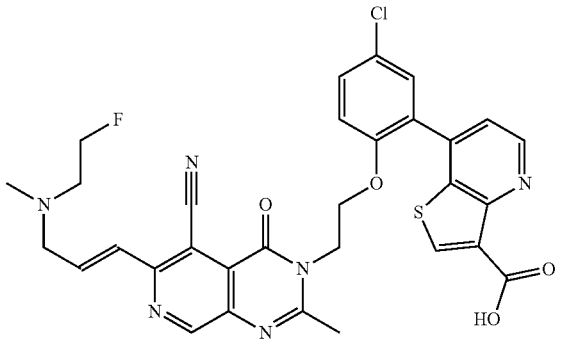 [SMILES: Cc1nc2cnc(/C=C/CN(C)CCF)c(C#N)c2c(=O)n1CCOc1ccc(Cl)cc1-c1ccnc2c(C(=O)O)csc12] | MS (ESI) m/z 633.40 [M + 1]+; 1H NMR (400 MHz, DMSO-d6) δ 13.40 (bs, 1H), 10.08 (bs, 1H), (9.01 (s, 1H), 8.82 (d, J = 4.8 Hz, 1H), 8.36 (s, 1H), 7.60 (dd, J = 8.9, 2.5 Hz, 1H), 7.48 (d, J = 4.7 Hz, 1H), 7.45-7.33 (m, 3H), 7.21-7.18 (m, 1H), 4.88 (d, J = 47.2 Hz, 2H), 4.41 (t, J = 4.9 Hz, 2H), 4.27-4.13 (m, 4H), 3.70-3.55 (m, merged, 2H), 2.90 (s, 3H), 1.81 (s, 3H) |
| 1329 | 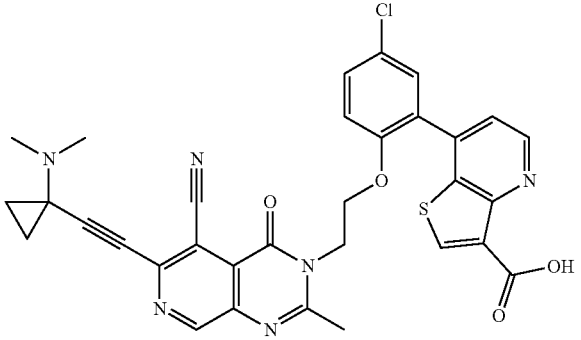 [SMILES: Cc1nc2cnc(C#CC3(N(C)C)CC3)c(C#N)c2c(=O)n1CCOc1ccc(Cl)cc1-c1ccnc2c(C(=O)O)csc12] | MS (ESI) m/z 625.37 [M + 1]+; 1H NMR (400 MHz, DMSO-d6) δ 8.92 (s, 1H), 8.83 (d, J = 4.8 Hz, 1H), 8.34 (s, 1H), 7.59 (dd, J = 8.8, 2.4 Hz, 1H), 7.48 (d, J = 4.4 Hz, 1H), 7.43 (d, J = 2.4 Hz, 1H), 7.35 (d, J = 8.8 Hz, 1H), 4.40 (bs, 2H), 4.25 (bs, 2H), 2.74 (bs, 6H), 1.75 (s, 3H), 1.36 (bs, 4H) |
| 1330 | 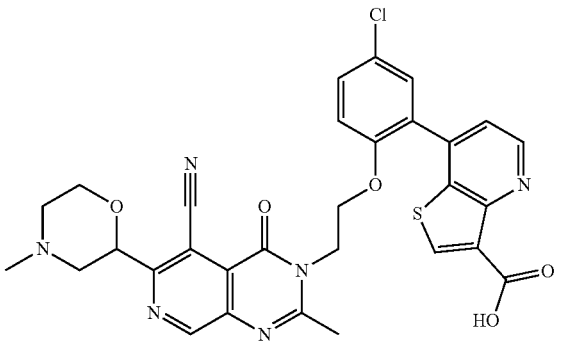 [SMILES: Cc1nc2cnc(C3CN(C)CCO3)c(C#N)c2c(=O)n1CCOc1ccc(Cl)cc1-c1ccnc2c(C(=O)O)csc12] | MS (ESI) m/z 617.43 [M + 1]+; 1H NMR (400 MHz, DMSO-d6) δ 13.38 (bs, 1H), 10.15 (bs, 1H), 9.02 (s, 1H), 8.82 (d, J = 4.8 Hz, 1H), 8.34 (s, 1H), 7.60 (dd, J = 2.4, 8.8 Hz, 1H), 7.46 (d, J = 4.4 Hz, 1H), 7.43 (d, J = 2.8 Hz, 1H), 7.35 (d, J = 9.2 Hz, 1H), 5.27 (d, J = 8.0 Hz, 1H), 4.40 (bs, 2H), 4.32-4.23 (m, 2H), 3.94 (t, J = 12.4 Hz, 1H), 3.78 (bs, 2H), 3.49 (bs, 2H), 3.24 (bs, 1H), 2.99 (s, 3H), 1.81 (s, 3H) |

TABLE 1-continued

7-Aza-Thienylpyridine and Derivative Compounds

| Compound | | Characterization |
|---|---|---|
| 1332 | 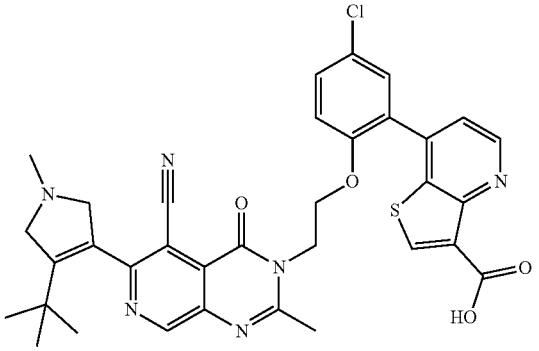 [SMILES: Cc1nc2cnc(C3=C(C(C)(C)C)CN(C)C3)c(C#N)c2c(=O)n1CCOc1ccc(Cl)cc1-c1ccnc2c(C(=O)O)csc12] | MS (ESI) m/z 655.5 [M + 1]+; 1H NMR (400 MHz, DMSO-d6) δ 8.98 (s, 1H), 8.84 (d, J = 4.8 Hz, 1H), 8.23 (s, 1H), 7.61 (dd, J = 9.2, 2.8 Hz, 1H), 7.46 (d, J = 4.8 Hz, 1H), 7.43 (d, J = 2.4 Hz, 1H), 7.37 (d, J = 9.2 Hz, 1H), 4.42 (bs, 2H), 4.30 (bs, 2H), 2.82 (bs, 2H), 2.72 (s, 6H), 2.61 (bs, 2H) 1.30 (s, 9H) |
| 1333 | 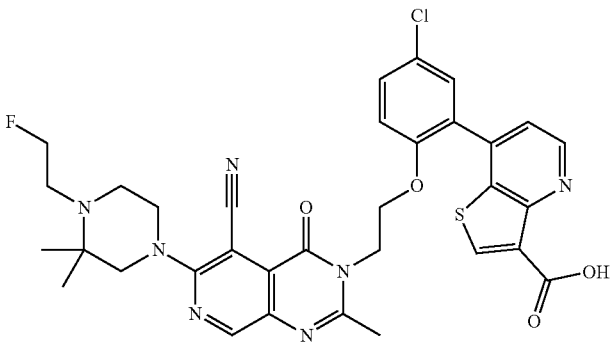 [SMILES: Cc1nc2cnc(N3CCN(CCF)C(C)(C)C3)c(C#N)c2c(=O)n1CCOc1ccc(Cl)cc1-c1ccnc2c(C(=O)O)csc12] | MS (ESI) m/z 676.51 [M + 1]+; 1H NMR (400 MHz, DMSO-d6) δ 13.33 (bs, 1H), 9.75 (bs, 1H), 8.83 (d, J = 4.8 Hz, 1H), 8.71 (s, 1H), 8.38 (s, 1H), 7.61-7.58 (dd, J = 2.8, 9.2 Hz, 1H), 7.47 (d, J = 4.4 Hz, 1H), 7.42 (d, J = 2.4 Hz, 1H), 7.37 (d, J = 9.2 Hz, 1H), 4.97-4.79 (m, 2H), 4.39 (bs, 2H), 4.22 (bs, 2H), 3.88-3.48 (m, 6H), 1.79 (s, 3H), 1.45 (s, 3H), 1.40 (s, 3H) |
| 1334 | 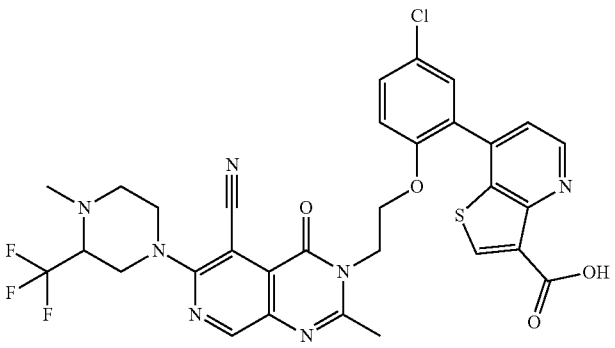 [SMILES: Cc1nc2cnc(N3CCN(C)C(C(F)(F)F)C3)c(C#N)c2c(=O)n1CCOc1ccc(Cl)cc1-c1ccnc2c(C(=O)O)csc12] | MS (ESI) m/z 684.26 [M + 1]+; 1H NMR (400 MHz, DMSO-d6) δ 13.38 (s, 1H), 8.82 (d, J = 4.8 Hz, 1H), 8.67 (s, 1H), 8.43 (s, 1H), 7.59 (d, J = 7.2 Hz, 1H), 7.47 (d, J = 4.4 Hz, 1H), 7.43 (s, 1H), 7.35 (d, J = 9.2 Hz, 1H), 4.38 (s, 2H), 4.21 (s, 2H), 4.08 (d, J = 11.2 Hz, 1H), 3.82-3.05 (m, 5H), 2.67 (s, 1H), 2.50 (s, 3H), 1.76 (s, 3H) |
| 1335 | 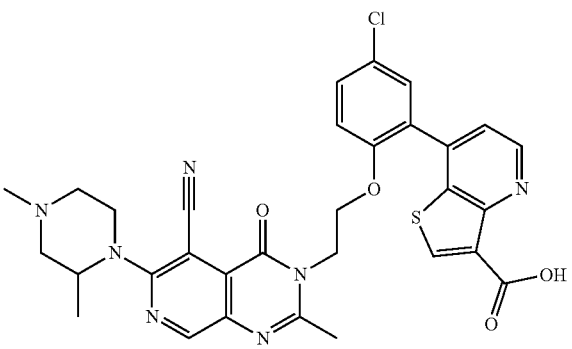 [SMILES: Cc1nc2cnc(N3CCN(C)CC3C)c(C#N)c2c(=O)n1CCOc1ccc(Cl)cc1-c1ccnc2c(C(=O)O)csc12] | MS (ESI) m/z 630.46 [M + 1]+; 1H NMR (400 MHz, DMSO-d6) δ 9.85 (s, 1H), 8.85 (d, J = 8.4 Hz, 1H), 8.67 (s, 1H), 8.40 (s, 1H), 7.61 (d, J = 8.8 Hz, 1H), 7.48 (d, J = 4.8 Hz, 1H), 7.41 (m, 2H), 4.74 (bs, 1H), 4.42 (m, 2H), 4.23 (m, 4H), 3.52 (m, 2H), 3.32 (m, 2H). 2.91 (s, 3H), 1.78 (s, 3H), 1.49 (d, J = 6.8 Hz, 3H), 1.04 (d, J = 5.6 Hz, 1H) |

TABLE 1-continued

7-Aza-Thienylpyridine and Derivative Compounds

| Compound | | Characterization |
|---|---|---|
| 1336 | 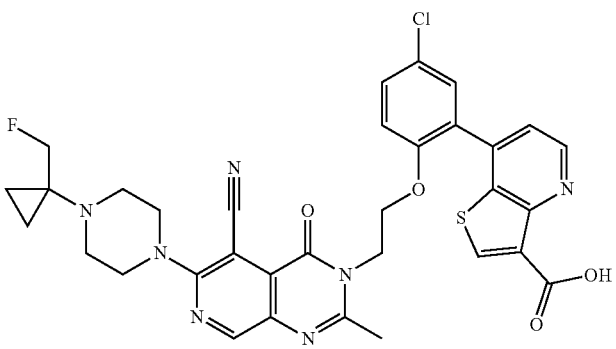 [SMILES: Cc1nc2cnc(N3CCN(C4(CF)CC4)CC3)c(C#N)c2c(=O)n1CCOc1ccc(Cl)cc1-c1ccnc2c(C(=O)O)csc12] | MS (ESI) m/z 674.50 [M + 1]+; 1H NMR (400 MHz, DMSO-d6) δ 8.82 (d, J = 4.8 Hz, 1H), 8.67 (s, 1H), 8.45 (s, 1H), 7.60 (dd, J = 9.2, 2.8 Hz, 1H), 7.47 (d, J = 4.8 Hz, 1H), 7.42 (d, J = 2.4 Hz, 1H), 7.36 (d, J = 8.8 Hz, 1H), 4.62 (d, J = 49.6 Hz, 2H), 4.40-4.35 (m, 2H), 4.25-4.15 (m, 2H), 3.75-3.55 (m, 4H), 3.30-3.00 (m, 4H), 1.79 (s, 3H), 1.15-.0.80 (m, 4H) |
| 1337 | 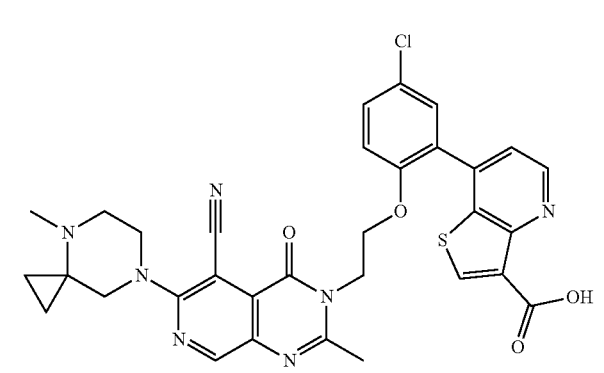 [SMILES: Cc1nc2cnc(N3CCN(C)C4(CC4)C3)c(C#N)c2c(=O)n1CCOc1ccc(Cl)cc1-c1ccnc2c(C(=O)O)csc12] | MS (ESI) m/z 642.53 [M + 1]+; 1H NMR (400 MHz, DMSO-d6) δ 13.37 (bs, 1H), 8.82 (d, J = 4.4 Hz, 1H), 8.70 (s, 1H), 8.38 (s, 1H), 7.60 (t, J = 6.8 Hz, 1H), 7.47-7.21 (m, 3H), 4.39 (s, 2H), 4.23 (s, 2H), 4.05 (bs, 2H), 3.93 (bs, 2H), 3.52 (bs, 2H), 2.99 (s, 3H), 1.79 (s, 3H), 1.26-1.07 (m, 4H) |
| 1338 | 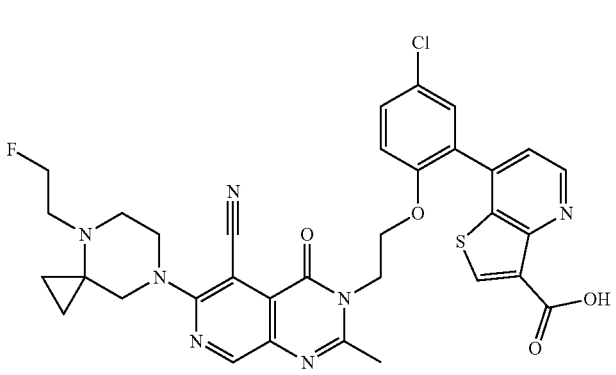 | MS (ESI) m/z 674.53 [M + 1]+; 1H NMR (400 MHz, DMSO-d6) δ 13.21 (bs, 1H), 8.83 (d, J = 4.8 Hz, 1H), 8.68 (s, 1H), 8.39 (s, 1H), 7.60 (dd, J = 8.8, 2.0 Hz, 1H), 7.47 (d, J = 4.8 Hz, 1H), 7.43 (d, J = 2.4 Hz, 1H), 7.36 (d, J = 8.8 Hz, 1H), 4.83-4.72 (m, 2H), 4.39 (s, 2H), 4.23 (s, 2H), 3.98-3.53 (m, 8H), 1.77 (s, 3H), 1.03 (bs, 4H) |
| 1339 | 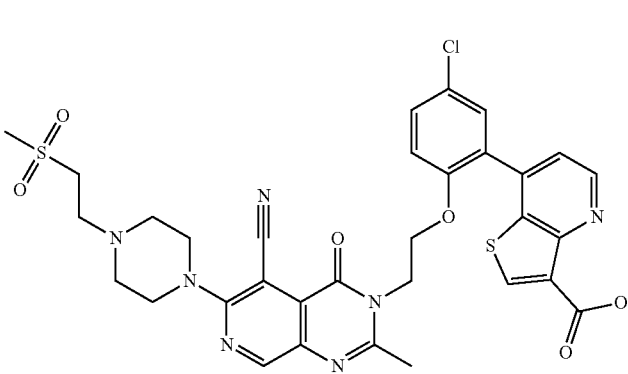 | MS (ESI) m/z 708.26 [M + 1]+; 1H NMR (400 MHz, DMSO-d6) δ 13.27 (bs, 1H), 8.82 (d, J = 8.0 Hz, 1H), 8.67 (s, 1H), 8.43 (s, 1H), 7.59 (d, J = 6.8 Hz, 1H), 7.46 (d, J = 4.4 Hz, 1H), 7.42 (s, 1H), 7.36 (d, J = 9.2 Hz, 1H), 4.39 (s, 2H), 4.22 (s, 2H), 3.59-3.30 (m, 12H), 3.10 (s, 3H), 1.79 (s, 3H) |

TABLE 1-continued

7-Aza-Thienylpyridine and Derivative Compounds

| Compound | | Characterization |
|---|---|---|
| 1340 | 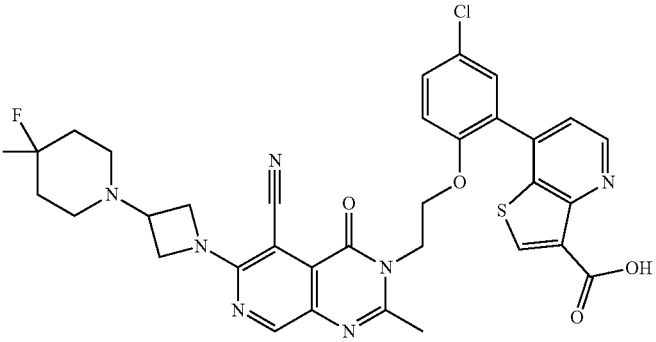 | MS (ESI) m/z 692.45 [M + 1]+; 1H NMR (400 MHz, DMSO-d6) δ 8.83 (d, J = 4.8 Hz, 1H), 8.63 (s, 1H), 8.47 (s, 1H), 7.60 (dd, J = 2.4, 8.8 Hz, 1H), 7.47 (d, J = 4.8 Hz, 1H), 7.43 (d, J = 2.4 Hz, 1H), 7.36 (d, J = 8.8 Hz, 1H), 4.57 (t, J = 8.0 Hz, 2H), 4.38 (bs, 4H), 4.20 (bs, 2H), 3.94 (bs, 1H), 3.07 (bs, 4H), 2.20 (bs, 4H), 1.76 (s, 3H) |
| 1341 | 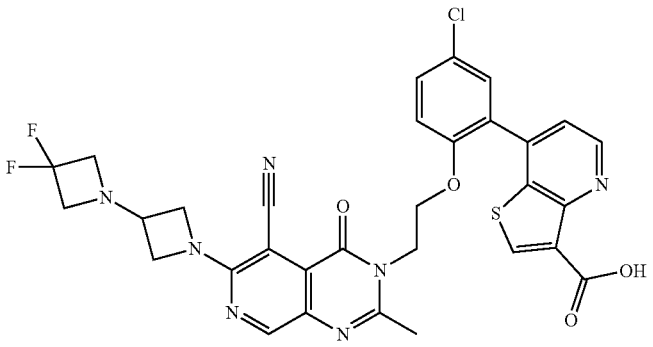 [SMILES: Cc1nc2cnc(N3CC(N4CC(F)(F)C4)C3)c(C#N)c2c(=O)n1CCOc1ccc(Cl)cc1-c1ccnc2c(C(=O)O)csc12] | MS (ESI) m/z 664.51 [M + 1]+; 1H NMR (400 MHz, DMSO-d6) δ 8.83 (d, J = 4.8 Hz, 1H), 8.58 (s, 1H), 8.47 (s, 1H), 8.48 (s, 1H), 7.59 (dd, J = 2.4, 8.8 Hz, 1H), 7.47 (d, J = 4.8 Hz, 1H), 7.35 (d, J = 9.2 Hz, 1H), 4.47-4.42 (m, 2H), 4.37 (bs, 2H), 4.18 (bs, 2H), 4.13-4.10 (m, 2H), 3.95-3.74 (m, 5H), 1.74 (s, 3H) |
| 1342 | 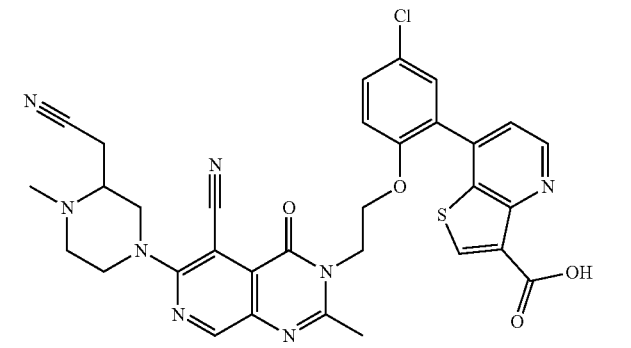 [SMILES: Cc1nc2cnc(N3CCN(C)C(CC#N)C3)c(C#N)c2c(=O)n1CCOc1ccc(Cl)cc1-c1ccnc2c(C(=O)O)csc12] | MS (ESI) m/z 655.35 [M + 1]+; 1H NMR (400 MHz, DMSO-d6) δ 13.27 (bs, 1H), 8.83 (d, J = 4.8 Hz, 1H), 8.67 (s, 1H), 8.43 (s, 1H), 7.60 (dd, J = 8.8, 2.4 Hz, 1H), 7.46 (d, J = 4.0 Hz, 1H), 7.43 (d, J = 2.4 Hz, 1H), 7.35 (d, J = 9.2 Hz, 1H), 4.43-4.35 (m, 2H), 4.25-4.15 (m, 2H), 4.13-4.00 (m, 2H), 3.16-3.10 (m, 1H), 2.97-2.83 (m, 4H), 2.48-2.33 (m, 2H), 2.30 (s, 3H), 1.74 (s, 3H) |
| 1343 | 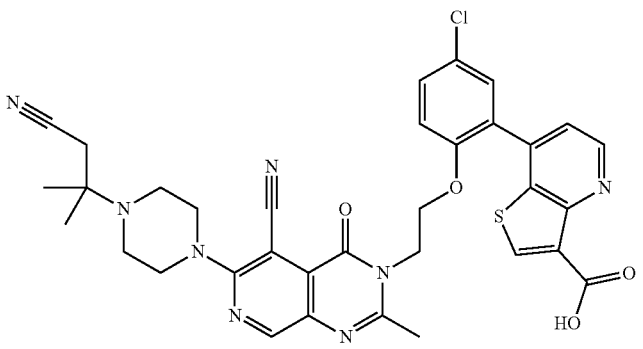 [SMILES: Cc1nc2cnc(N3CCN(C(C)(C)CC#N)CC3)c(C#N)c2c(=O)n1CCOc1ccc(Cl)cc1-c1ccnc2c(C(=O)O)csc12] | MS (ESI) m/z 683.44 [M + 1]+; 1H NMR (400 MHz, DMSO-d6) δ 8.83 (d, J = 4.8 Hz, 1H), 8.69 (s, 1H), 8.43 (s, 1H), 7.60 (dd, J = 8.8, 2.4 Hz, 1H), 7.48 (d, J = 4.8 Hz, 1H), 7.42 (d, J = 2.4 Hz, 1H), 7.37 (d, J = 8.8 Hz, 1H), 4.40 (s, 2H), 4.23 (s, 2H), 3.95 (s, 2H), 3.57-3.40 (m, 4H), 3.30-3.15 (m, 4H), 1.83 (s, 3H), 1.46 (s, 6H) |

TABLE 1-continued

7-Aza-Thienylpyridine and Derivative Compounds

| Compound | | Characterization |
|---|---|---|
| 1344 | 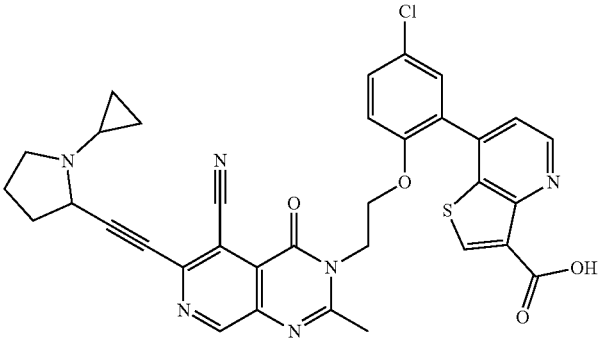 [SMILES: Cc1nc2cnc(C#CC3CCCN3C3CC3)c(C#N)c2c(=O)n1CCOc1ccc(Cl)cc1-c1ccnc2c(C(=O)O)csc12] | MS (ESI) m/z 651.48 [M + 1]+; 1H NMR (400 MHz, DMSO-d6) δ 8.96 (s, 1H), 8.83 (d, J = 4.4 Hz, 1H), 8.36 (s, 1H), 7.60 (dd, J = 8.8, 2.4 Hz, 1H), 7.48 (d, J = 4.4 Hz, 1H), 7.44 (d, J = 2.4 Hz, 1H), 7.35 (d, J = 9.2 Hz, 1H), 4.80-4.60 (m, 1H), 4.40 (s, 2H), 4.25 (s, 2H), 3.55-3.30 (m, merged, 2H), 2.50-2.30 (m, 1H), 2.22-1.91 (m, 4H), 1.75 (s, 3H), 1.04-0.61 (m, 4H) |
| 1345 | 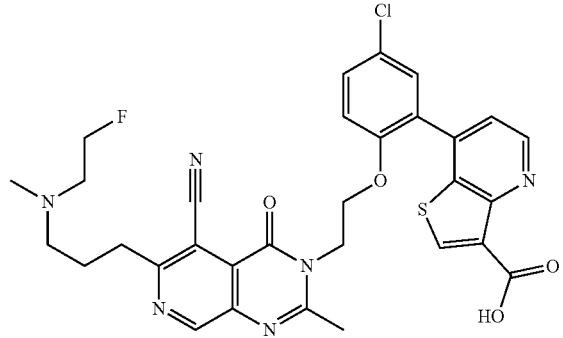 [SMILES: Cc1nc2cnc(CCCN(C)CCF)c(C#N)c2c(=O)n1CCOc1ccc(Cl)cc1-c1ccnc2c(C(=O)O)csc12] | MS (ESI) m/z 635.42 [M + 1]+; 1H NMR (400 MHz, DMSO-d6) δ 13.40 (bs. 1H), 9.67 (bs, 1H), 8.96 (s, 1H), 8.82 (d, J = 4.7 Hz, 1H), 8.32 (s, 1H), 7.60 (dd, J = 8.92, 2.36 Hz, 1H), 7.47 (d, J = 4.7 Hz, 1H), 7.43 (d, J = 2.4 Hz, 1H), 7.36 (d, J = 8.9 Hz, 1H), 4.92-4.76 (m, 1H), 4.40 (t, J = 4.4 Hz, 2H), 4.26 (t, J = 5.0 Hz, 2H), 3.62-3.52 (m, 2H), 3.40-3.20 (m, 2H), 3.18 (t, J = 7.24 Hz, 2H), 2.88 (s, 3H), 2.31-2.17 (m, 2H), 1.82 (s, 3H) |
| 1346 | 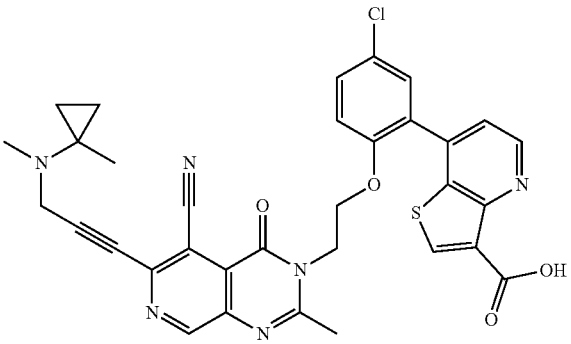 [SMILES: Cc1nc2cnc(C#CCN(C)C3(C)CC3)c(C#N)c2c(=O)n1CCOc1ccc(Cl)cc1-c1ccnc2c(C(=O)O)csc12] | MS (ESI) m/z 639.42 [M + 1]+; 1H NMR (400 MHz, DMSO-d6) δ 8.97 (s, 1H), 8.83 (d, J = 4.7 Hz, 1H), 8.37 (s, 1H), 7.59 (dd, J = 8.9, 2.4 Hz, 1H), 7.47 (d, J = 4.7 Hz, 1H), 7.44 (d, J = 2.4 Hz, 1H ), 7.34 (d, J = 9.0 Hz, 1H), 4.65-4.35 (m, 4H), 4.25 (t, J = 3.8 Hz, 2H), 2.85 (bs, 3H), 1.75 (s, 3H), 1.36 (s, 3H), 1.03 (bs, 2H), 0.72 (bs, 2H) |
| 1347 | 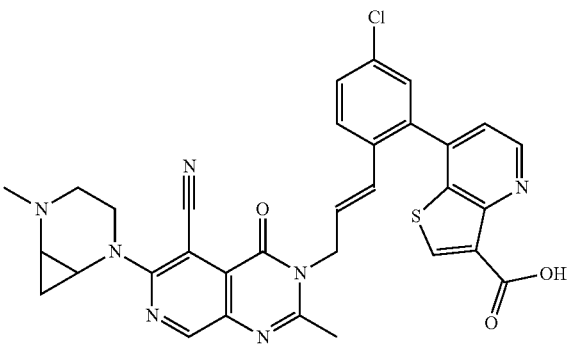 [SMILES: Cc1nc2cnc(N3CCN(C)C4CC43)c(C#N)c2c(=O)n1C/C=C/c1ccc(Cl)cc1-c1ccnc2c(C(=O)O)csc12] | MS (ESI) m/z 624.49 [M + 1]+; 1H NMR (400 MHz, DMSO-d6) δ 13.08 (bs, 1H), 8.86 (s, 1H), 8.79 (d, J = 4.4 Hz, 1H), 8.66 (s, 1H), 7.88 (d, J = 8.4 Hz, 1H), 7.61 (d, J = 8.8 Hz, 1H), 7.52 (s, 1H), 7.42 (d, J = 4.8 Hz, 1H), 6.52-6.38 (m, 1H), 5.89 (d, J = 16.0 Hz, 1H), 4.68 (d, J = 4.0 Hz, 2H), 4.39 (d, J = 13.2 Hz, 1H), 3.11 (t, J = 12.4 Hz, 2H), 2.82-2.65 (m, 1H), 2.40-2.10 (m, 8H), 0.72-0.45 (m, 2H) |

TABLE 1-continued

7-Aza-Thienylpyridine and Derivative Compounds

| Compound | | Characterization |
|---|---|---|
| 1348 | 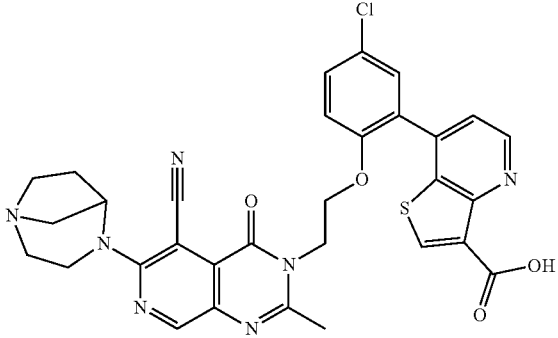 [SMILES: Cc1nc2cnc(N3CCN4CCC3C4)c(C#N)c2c(=O)n1CCOc1ccc(Cl)cc1-c1ccnc2c(C(=O)O)csc12] | MS (ESI) m/z 628.18 [M + 1]+; 1H NMR (400 MHz, DMSO-d6), 68.81 (d, J = 4.8 Hz, 1H), 6 8.62 (s, 1H), 8.43 (s, 1H), 7.59 (dd, J = 8.8 Hz, 2.4 Hz, 1H), 7.45-7.42 (m, 2H), 7.35 (d, J = 8.8 Hz, 1H), 4.78 (bs, 1H), 4.37 (t, J = 5.1 Hz, 2H), 4.27 (t, J = 4.5 Hz, 2H), 3.45-3.43 (m, 2H), 3.32-2.8 (m, 4H), 2.75-2.56 (m, 2H), 1.93-1.90 (m, 2H), 1.74 (s, 3H) |
| 1349 | 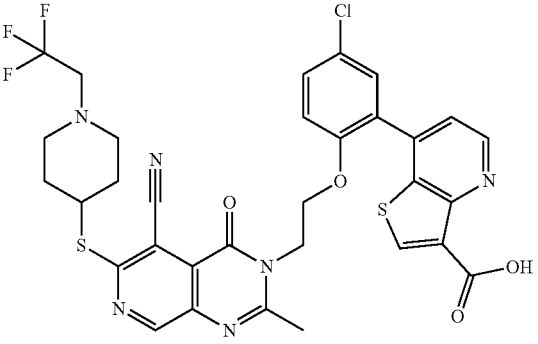 [SMILES: Cc1nc2cnc(SC3CCN(CC(F)(F)F)CC3)c(C#N)c2c(=O)n1CCOc1ccc(Cl)cc1-c1ccnc2c(C(=O)O)csc12] | MS (ESI) m/z 715.66 [M + 1]+; 1H NMR (400 MHz, DMSO-d6) δ 8.89 (s, 1H), 8.82 (d, J = 4.8 Hz, 1H), 8.41 (s, 1H), 7.58 (dd, J = 8.8 Hz, 2.8 Hz, 1H), 7.47 (d, J = 4.8 Hz, 1H), 7.43 (d, J = 2.4 Hz, 1H), 7.34 (d, J = 8.8 Hz, 1H), 4.38 (s, 2H), 4.22 (s, 2H), 4.05 (s, 1H), 3.40-3.32 (m, 2H), 2.93 (s, 2H), 2.66-2.61 (m, 2H), 2.11-2.09 (m, 2H), 1.74 (s, 5H) |
| 1350 | 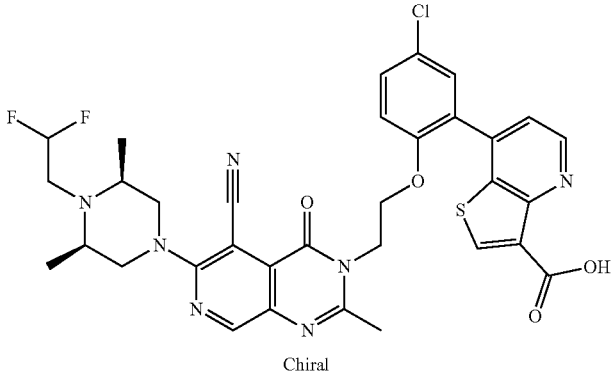 [SMILES: Cc1nc2cnc(N3C[C@@H](C)N(CC(F)F)[C@@H](C)C3)c(C#N)c2c(=O)n1CCOc1ccc(Cl)cc1-c1ccnc2c(C(=O)O)csc12]<br>Chiral | MS (ESI) m/z 694.59 [M + 1]+; 1H NMR (400 MHz, DMSO-d6) δ 8.83 (d, J = 4.8 Hz, 1H), 8.65 (s, 1H), 8.41 (s, 1H), 7.59 (dd, J = 2.0, 8.8 Hz, 1H), 7.48 (d, J = 4.8 Hz, 1H), 7.42 (d, J = 2.0 Hz, 1H), 7.36 (d, J = 8.8 Hz, 1H), 6.15 (bs, 1H), 4.39 (s, 2H), 4.21-4.16 (m, 2H), 4.14 (bs, 2H), 3.01 (bs, 6H), 1.77 (s, 3H), 1.21 (s, 6H) |
| 1351 | 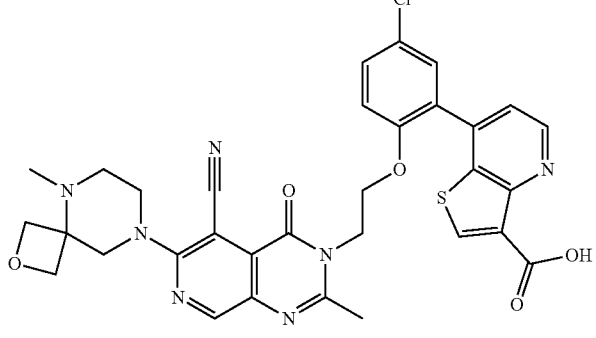 | MS (ESI) m/z 658.47 [M + 1]+; 1H NMR (400 MHz, DMSO-d6) δ 8.83 (d, J = 2.36 Hz, 1H), 8.74 (s, 1H), 8.40 (s, 1H), 7.60 (dd, J = 8.9, 2.5 Hz, 1H), 7.47 (d, J = 4.7 Hz, 1H), 7.42 (d, J = 2.5 Hz, 2H), 7.37 (d, J = 9.0 Hz, 2H), 4.66 (d, J = 7.5 Hz, 2H), 4.40 (s, 2H), 4.24 (s, 2H), 4.14 (bs, 4H), 3.40 (s, 2H), 3.06 (s, 3H), 1.82 (s, 3H) |

TABLE 1-continued

7-Aza-Thienylpyridine and Derivative Compounds

| Compound | | Characterization |
|---|---|---|
| 1352 | 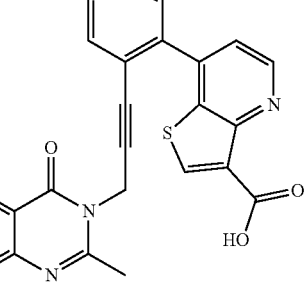 | MS (ESI) m/z 652.12 [M + 1]+; 1H NMR (400 MHz, DMSO-d6) δ 8.83 (s, 1H), 6 8.74 (d, J = 4.8 Hz, 1H), 8.64 (s, 1H), 7.75 (d, J = 8.4 Hz, 1H), 7.69-7.66 (m, 2H), 7.53 (d, J = 4.4 Hz, 1H), 4.83 (s, 2H), 4.76 (s, 4H), 4.37 (bs, 4H), 4.04 (bs, 1H), 3.34-2.82 (m, 4H), 2.12 (s, 3H) |
| 1353 | 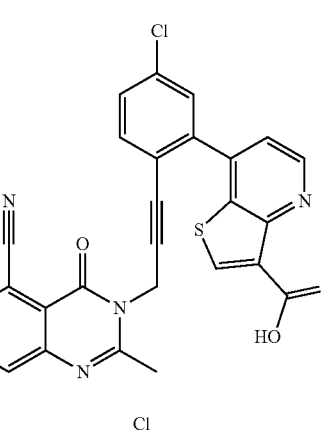 | MS (ESI) m/z 692.45 [M + 1]+; 1H NMR (400 MHz, DMSO-d6) δ 13.05 (bs, 1H), 8.83 (s, 1H), 8.75 (d, J = 4.6 Hz, 1H), 8.64 (s, 1H), 7.75 (d, J = 8.2 Hz, 1H), 7.69 (s, 1H), 7.66 (s, 1H), 7.52 (d, J = 4.6 Hz, 1H), 4.83 (s, 2H), 4.31 (bs, 1H), 3.43 (bs, 7H), 2.85 (s, 4H), 2.11 (s, 3H) |
| 1354 | 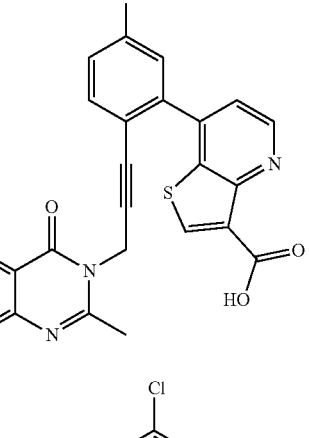 | MS (ESI) m/z 636.25 [M + 1]+; 1H NMR (400 MHz, DMSO-d6) δ 13.18 (bs, 1H), 8.84 (s, 1H), 8.75 (d, J = 4.8 Hz, 1H), 8.65 (s, 1H), 7.75 (d, J = 8.4 Hz, 1H), 7.70-7.65 (m, 2H), 7.53 (d, J = 4.8 Hz, 1H), 4.84 (s, 2H), 4.38 (m, 2H), 3.79 (m, 2H,), 3.49 (m, 4H), 3.03 (m, 1H), 2.14 (s, 3H), 0.93 (m, 4H) |
| 1355 | 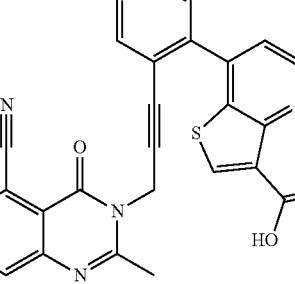 | MS (ESI) m/z 686.0 [M + 1]+; 1H NMR (400 MHz, DMSO-d6) δ 13.03 (s, 1H), 8.83 (s, 1H), 8.75 (d, J = 4.8 Hz, 1H), 8.64 (s, 1H), 7.75 (d, J = 8.4 Hz, 1H), 7.70-7.66 (m, 1H), 7.53 (d, J = 4.8 Hz, 1H), 4.72 (s, 2H), 3.80 (bs, 4H), 3.39 (bs, 4H), 3.05-3.02 (m, 5H), 2.16 (s, 3H) |

TABLE 1-continued

7-Aza-Thienylpyridine and Derivative Compounds

| Compound | | Characterization |
|---|---|---|
| 1356 | 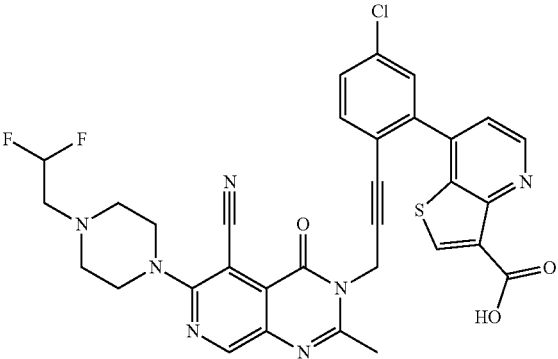 [SMILES: Cc1nc2cnc(N3CCN(CC(F)F)CC3)c(C#N)c2c(=O)n1CC#Cc1ccc(Cl)cc1-c1ccnc2c(C(=O)O)csc12] | MS (ESI) m/z 660.27 [M + 1]+; 1H NMR (400 MHz, DMSO-d6) δ 13.05 (bs, 1H), 8.79 (s, 1H), 8.75 (d, J = 4.6 Hz, 1H), 8.65 (s, 1H), 7.75 (d, J = 8.1 Hz, 1H), 7.68 (m, 2H), 7.53 (d, J = 4.6 Hz, 1H), 6.34 (m, 1H), 4.82 (s, 2H), 3.76-2.66 (m, 10H), 2.09 (s, 1H) |
| 1357 | 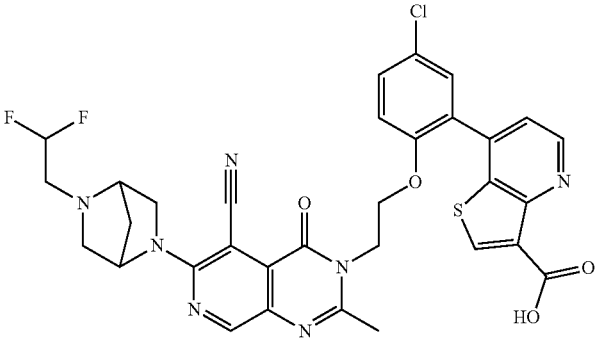 | MS (ESI) m/z 658.37 [M + 1]+; 1H NMR (400 MHz, DMSO-d6) δ 8.83 (d, J = 4.8 Hz, 1H), 8.61 (s, 1H), 8.46 (s, 1H), 7.60 (dd, J = 8.8, 2.4 Hz, 1H), 7.47 (d, J = 4.8 Hz, 1H), 7.43 (d, J = 2.6 Hz, 1H), 7.36 (d, J = 9.0 Hz, 1H), 6.33 (t, J = 53.6 Hz, 1H), 5.09 (s, 1H), 4.38 (t, J = 4.3 Hz, 2H), 4.21 (t, J = 5.7, 2H), 4.15-3.80 (m, 7H), 2.21 (bs, 2H), 1.76 (s, 3H) |
| 1358 | 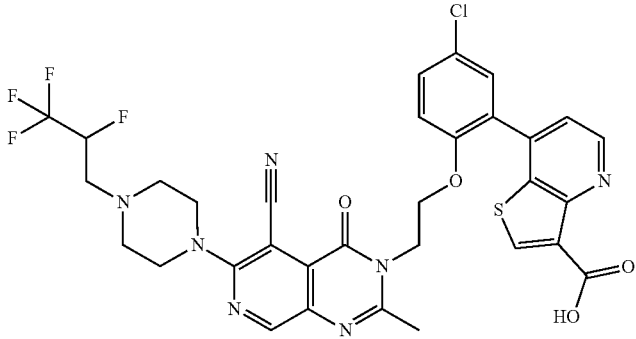 [SMILES: Cc1nc2cnc(N3CCN(CC(F)C(F)(F)F)CC3)c(C#N)c2c(=O)n1CCOc1ccc(Cl)cc1-c1ccnc2c(C(=O)O)csc12] | MS (ESI) m/z 716.50 [M + 1]+; 1H NMR (400 MHz, DMSO-d6) δ 8.83 (d, J = 4.8 Hz, 1H), 8.68 (s, 1H), 8.45 (s, 1H), 7.60 (dd, J = 8.8 Hz, 2.4 Hz, 1H), 7.48 (d, J = 4.8 Hz, 1H), 7.37-7.33 (m, 2H), 5.77 (d, J = 46 Hz, 1H), 4.39 (s, 2H), 4.22 (s, 2H), 3.24 (bs, 2H), 3.29-3.15 (m, 8H), 1.79 (s, 3H) |
| 1359 | 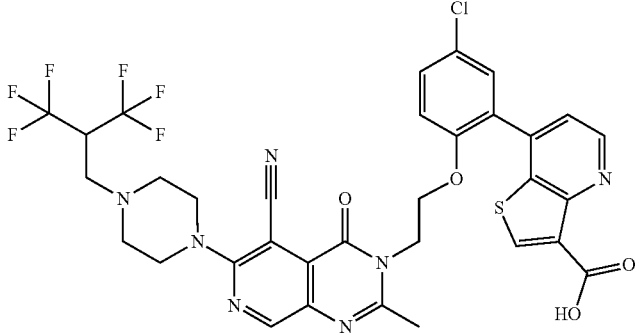 [SMILES: Cc1nc2cnc(N3CCN(CC(C(F)(F)F)C(F)(F)F)CC3)c(C#N)c2c(=O)n1CCOc1ccc(Cl)cc1-c1ccnc2c(C(=O)O)csc12] | MS (ESI) m/z 766.56 [M + 1]+; 1H NMR (400 MHz, DMSO-d6) δ 8.83 (d, J = 4 Hz, 1H), 8.66 (s, 1H), 8.46 (s, 1H), 7.60 (dd, J = 2.4, 8.8 Hz, 1H), 7.48 (d, J = 4.8 Hz, 1H), 7.43 (d, J = 2.4 Hz, 1H), 7.36 (d, J = 8.8 Hz, 1H), 4.39 (bs, 2H), 4.21 (bs, 2H), 3.68 (bs, 4H), 2.96 (bs, 2H), 2.78 (bs, 4H), 2.46 (s, 1H) 1.77 (s, 3H) |

TABLE 1-continued

7-Aza-Thienylpyridine and Derivative Compounds

| Compound | | Characterization |
|---|---|---|
| 1360 | 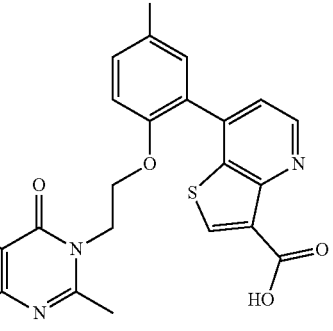 | MS (ESI) m/z 726.51 [M + 1]+; 1H NMR (400 MHz, DMSO-d6) δ 9.53 (bs, 1H), 8.83 (d, J = 4.8 Hz, 1H), 8.61 (s, 1H), 8.40 (s, 1H), 7.59 (dd, J = 8.8 Hz, 2.4 Hz, 1H), 7.47 (d, J = 4.4 Hz, 1H), 7.42 (d, J = 2.4 Hz, 1H), 7.36 (d, J = 8.8 Hz, 1H), 4.49 (bs, 1H), 4.52 (bs, 1H), 4.21 (bs, 2H), 3.69 (d, J = 10.4 Hz, 2H), 3.50 (bs, 2H), 3.40 (bs, 2H), 3.21 (s, 3H), 2.89-2.85 (m, 2H), 2.11 (bs, 4H), 1.78 (s, 3H) |
| 1361 | 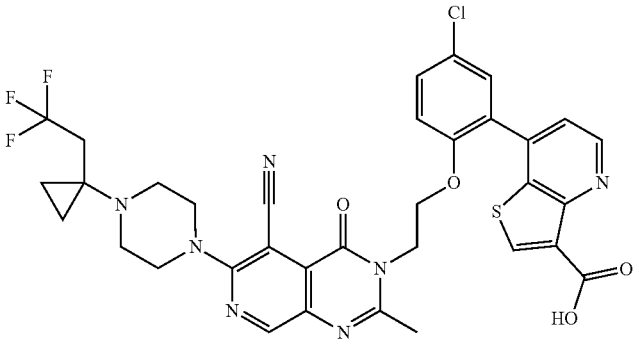 [SMILES: Cc1nc2cnc(N3CCN(C4(CC(F)(F)F)CC4)CC3)c(C#N)c2c(=O)n1CCOc1ccc(Cl)cc1-c1ccnc2c(C(=O)O)csc12] | MS (ESI) m/z 724.51 [M + 1]+; 1H NMR (400 MHz, DMSO-d6) δ 8.82 (d, J = 4.8 Hz, 1H), 8.64 (s, 1H), 8.46 (s, 1H), 7.60 (dd, J = 8.8, 2.8 Hz, 1H), 7.48 (d, J = 4.8 Hz, 1H), 7.42 (d, J = 2.4 Hz, 1H), 7.35 (d, J = 8.8 Hz, 1H), 4.37 (s, 2H), 4.20 (s, 2H), 3.63 (bs, 4H), 2.84 (bs, 4H), 2.70-2.50 (m, 2H), 1.77 (s, 3H), 0.84-0.74 (m, 4H) |
| 1362 |  | MS (ESI) m/z 755.45 [M + 1]+; 1H NMR (400 MHz, DMSO- d6) δ 12.44 (s, 1H), 8.83-8.79 (m, 3H), 7.76 (d, J = 8.4 Hz, 1H), 7.71- 7.67 (m, 2H), 7.61 (d, J = 4.8 Hz, 1H), 4.82 (s, 2H), 3.75-3.60 (m, 4H), 3.56 (s, 3H), 3.31 (q, J = 10.0 Hz, 2H), 2.90-2.80 (m, 4H), 2.00 (s, 3H) |
| 1363 | 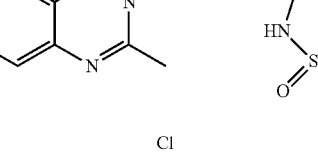 | MS (ESI) m/z 668.48 [M + 1]+; 1H NMR (400 MHz, DMSO-d6) δ 13.21 (bs, 1H), 9.37 (bs, 1H), 8.82 (d, J = 4.8 Hz, 1H), 8.67 (s, 1H), 8.37 (s, 1H), 7.59 (dd, J = 8.8, 2.4 Hz, 1H), 7.47 (d, J = 4.8 Hz, 1H), 7.41 (d, J = 2.0 Hz, 1H), 7.36 (d, J = 9.2 Hz, 1H), 4.38 (s, 2H), 4.21 (s, 2H), 3.80-3.50 (m, 2H), 3.20-2.90 (m, 2H), 2.61 (s, 3H), 1.78 (s, 3H), 1.40-0.80 (m, 8H) |

TABLE 1-continued

7-Aza-Thienylpyridine and Derivative Compounds

| Compound | | Characterization |
|---|---|---|
| 1364 | 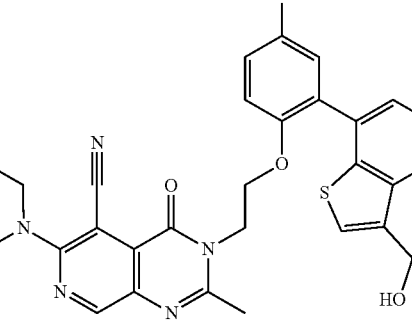 | MS (ESI) m/z 642.35 [M + 1]+; 1H NMR (400 MHz, DMSO-d6) δ 8.83 (d, J = 4.8 Hz, 1H), 8.68 (s, 1H), 8.45 (s, 1H), 7.60 (dd, J = 8.8, 2.4 Hz, 1H), 7.47 (d, J = 4.8 Hz, 1H), 7.42 (d, J = 2.4 Hz, 1H), 7.36 (d, J = 8.8 Hz, 1H), 4.87-4.75 (m, 4H), 4.39 (bs, 2H), 4.22 (bs, 2H), 3.56-3.14 (m, 8H), 2.41 (s, 1H), 1.78 (s, 3H) |
| 1365 | 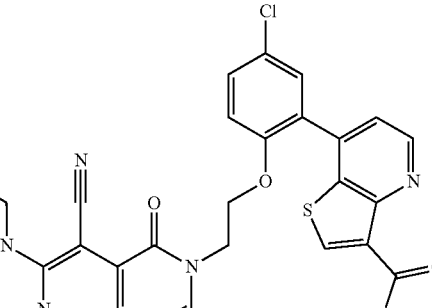 | MS (ESI) m/z 656.52 [M + 1]+; 1H NMR (400 MHz, DMSO-d6) δ 9.30 (bs, 1H), 8.83 (d, J = 4.8 Hz, 1H), 8.69 (s, 1H), 8.41 (s, 1H), 7.62-7.59 (dd, J = 2.4, 8.8 Hz, 1H), 7.48 (d, J = 4.8 Hz, 1H), 7.41-7.36 (m, 2H), 4.40 (bs, 4H), 4.24 (bs, 2H), 3.48 (bs, 6H), 1.85 (s, 3H), 1.39 (s, 3H), 1.19 (bs, 2H), 0.82 (bs, 2H) |
| 1366 | 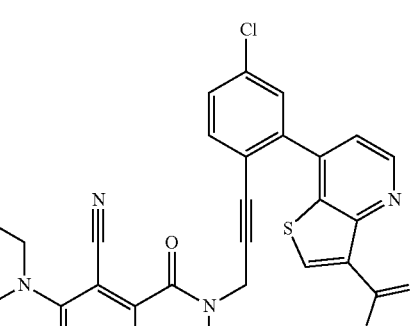 | MS (ESI) m/z 686.46 [M + 1]+; 1H NMR (400 MHz, DMSO-d6) δ 8.79-8.73 (m, 2H), 8.66 (s, 1H), 7.75 (d, J = 9.2 Hz, 1H), 7.72-7.66 (m, 2H), 7.55 (d, J = 4.8 Hz, 1H), 6.04 (t, J = 55.6 Hz, 1H), 4.82 (s, 2H), 3.59 (s, 4H), 3.02 (s, 4H), 2.06 (s, 3H), 0.90-0.78 (m, 4H) |
| 1367 | 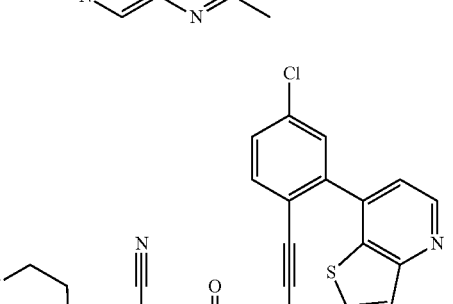 | MS (ESI) m/z 677.49 [M + 1]+; 1H NMR (400 MHz, DMSO-d6) δ 13.05 (bs, 1H), 9.99 (bs, 1H), 8.82 (s, 1H), 8.75 (d, J = 4.8 Hz, 1H), 8.65 (s, 1H), 7.75 (d, J = 8.4 Hz, 1H), 7.71-7.66 (m, 2H), 7.54 (d, J = 4.8 Hz, 1H), 4.83 (s, 2H), 4.45 (bs, 2H), 3.62 (bs, 4H), 3.27 (bs, 4H), 2.13 (s, 3H), 1.46 (bs, 6H) |

TABLE 1-continued

7-Aza-Thienylpyridine and Derivative Compounds

| Compound | | Characterization |
|---|---|---|
| 1368 | 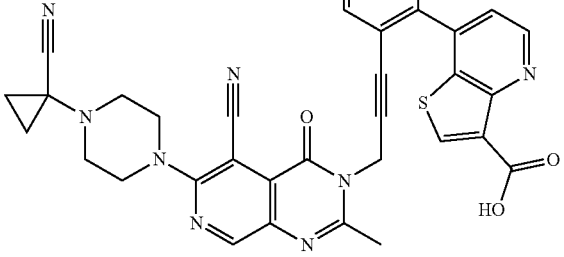 | MS (ESI) m/z 661.35 [M + 1]+; 1H NMR (400 MHz, DMSO-d6) δ 8.78 (s, 1H), 8.77 (d, J = 3.2 Hz, 1H), 8.67 (s, 1H), 7.76 (d, J = 8.8 Hz, 1H), 7.71-7.65 (m, 2H), 7.55 (d, J = 4.8 Hz, 1H), 4.82 (s, 2H), 3.67 (s, 4H), 2.82 (s, 4H) 2.07 (s, 3H), 1.32-1.27 (m, 2H), 1.17-1.09 (m, 2H) |
| 1369 | 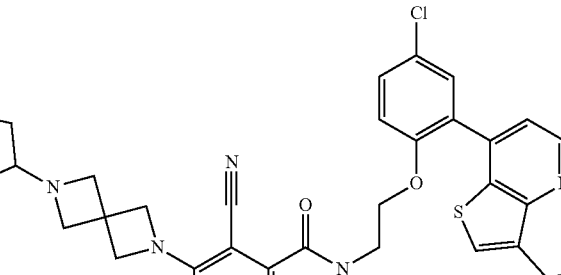 | MS (ESI) m/z 682.51 [M + 1]+; 1H NMR (400 MHz, DMSO-d6) δ 8.81 (d, J = 4.4 Hz, 1H), 8.60 (s, 1H), 8.47 (s, 1H), 7.60 (dd, J = 9.2, 2.4 Hz, 1H), 7.46 (d, J = 4.4 Hz, 1H), 7.42 (d, J = 2.4 Hz, 1H), 7.35 (d, J = 9.2 Hz, 1H), 4.60 (s, 2H), 4.52 (s, 2H), 4.43-4.38 (m, 4H), 4.33-4.28 (m, 2H), 4.20 (bs, 2H), 3.79 (bs, 1H), 1.89 (t, J = 6.8 Hz, 2H), 1.80 (s, 3H), 1.67-1.58 (m, 4H), 1.47 (t, J = 6.4 Hz, 2H) |
| 1370 | 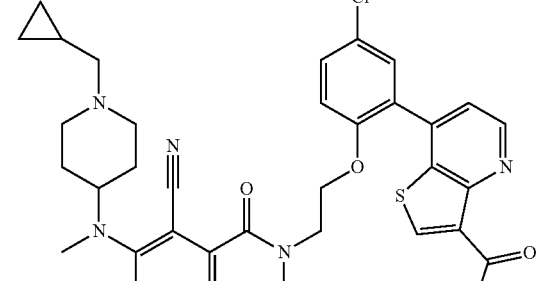 | MS (ESI) m/z 684.53 [M + 1]+; 1H NMR (400 MHz, DMSO-d6) δ 8.83 (d, J = 4.9 Hz, 1H), 8.61 (s, 1H), 8.40 (s, 1H), 7.60 (dd, J = 2.4, 8.8 Hz, 1H), 7.46 (d, J = 4.8 Hz, 1H), 7.42 (d, J = 2.4 Hz, 1H), 7.36 (d, J = 8.8 Hz, 1H), 4.51 (bs, 1H), 4.39 (s, 2H), 4.21 (s, 2H), 3.68 (d, J = 10.4 Hz, 2H), 3.21-3.16 (m, 2H), 3.09 (s, 3H), 3.01 (t, J = 5.6 Hz, 2H), 2.21-2.15 (m, 2H), 2.12-2.06 (m, 2H), 1.77 (s, 3H), 1.10 (bs, 1H), 0.67 (d, J = 7.2 Hz , 2H), 0.44-0.38 (m, 2H) |
| 1371 |  | MS (ESI) m/z 654.44 [M + 1]+; 1H NMR (400 MHz, DMSO-d6) δ 10.48 (bs, 1H), 8.82 (d, J = 4.8 Hz, 1H), 8.64 (s, 1H), 8.44 (s, 1H), 7.60 (dd, J = 9.2, 2.4 Hz, 1H), 7.47 (d, J = 4.8 Hz, 1H), 7.42 (d, J = 2.4 Hz, 1H), 7.36 (d, J = 8.8 Hz, 1H), 5.25-4.89 (m, 2H), 4.63 (d, J = 10.4 Hz, 2H), 4.38 (s, 2H), 4.21 (s, 2H), 3.98 (bs, 2H), 3.18 (bs, 1H), 2.75 (bs, 2H), 1.78 (s, 3H), 0.86 (bs, 4H) |

TABLE 1-continued
7-Aza-Thienylpyridine and Derivative Compounds
| Compound | | Characterization |
|---|---|---|
| 1378 | 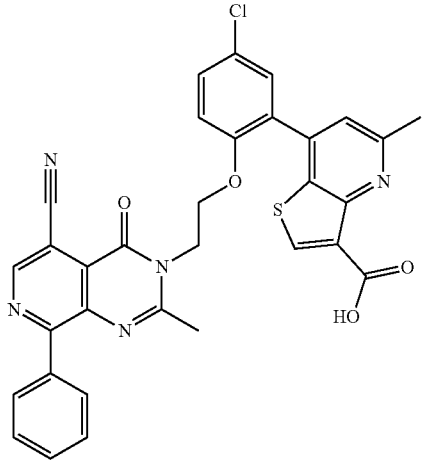 [SMILES: Cc1cc(-c2cc(Cl)ccc2OCCn2c(C)nc3c(-c4ccccc4)ncc(C#N)c3c2=O)c2scc(C(=O)O)c2n1] | MS (ESI) m/z 608.1 |
| 1382 | 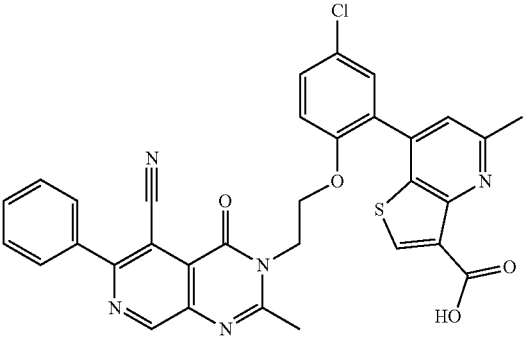 [SMILES: Cc1cc(-c2cc(Cl)ccc2OCCn2c(C)nc3cnc(-c4ccccc4)c(C#N)c3c2=O)c2scc(C(=O)O)c2n1] | MS (ESI) m/z 608.0 [M + 1]+; 1H NMR (400 MHz, DMSO-d6) δ 1H NMR (400 MHz, DMSO-d6) δ 9.05 (s, 1H), 8.44 (s, 1H), 7.94-7.86 (m, 2H), 7.64-7.54 (m, 4H), 7.46-7.40 (m, 2H), 7.37 (d, J = 9.0 Hz, 1H), 4.42 (d, J = 4.9 Hz, 2H), 4.29 (d, J = 4.9 Hz, 2H), 2.71 (s, 3H), 1.89 (s, 3H) |
| 1390 | 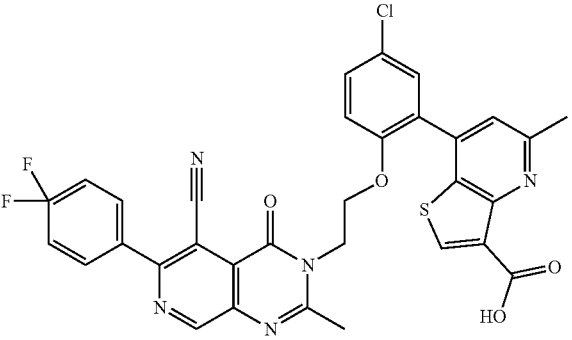 | MS (ESI) m/z 650.1 [M + 1]+; 1H NMR (400 MHz, DMSO-d6) δ 8.93 (s, 1H), 8.39 (s, 1H), 7.59 (dd, J = 8.9, 2.7 Hz, 1H), 7.42 (d, J = 2.8 Hz, 2H), 7.35 (d, J = 9.0 Hz, 1H), 6.29 (s, 1H), 4.39 (d, J = 5.0 Hz, 2H), 4.26 (d, J = 4.9 Hz, 2H), 2.91-2.78 (m, 4H), 2.71 (s, 3H), 2.35-2.15 (m, 2H), 1.85 (s, 3H) |

TABLE 1-continued

7-Aza-Thienylpyridine and Derivative Compounds

| Compound | Characterization |
|---|---|
| 1395 | MS (ESI) m/z 714.2 [M + 1]+; 1H NMR (400 MHz, DMSO-d6) δ 8.81 (d, J = 4.8 Hz, 1H), 8.54 (s, 1H), 8.48 (s, 1H), 7.61 (dd, J = 8.9, 2.7 Hz, 1H), 7.48 (d, J = 4.8 Hz, 1H), 7.43 (d, J = 2.7 Hz, 1H), 7.39 (d, J = 9.0 Hz, 1H), 4.54 (s, 2H), 4.43 (t, J = 5.1 Hz, 2H), 4.24 (t, J = 5.1 Hz, 2H), 3.82-3.40 (m, 10H), 1.83 (s, 3H) |
| 1396 | MS (ESI) m/z 708.3 [M + 1]+; 1H NMR (400 MHz, DMSO-d6) δ 8.84 (s, 1H), 8.76 (d, J = 4.8 Hz, 1H), 8.65 (s, 1H), 7.76 (dd, J = 8.3, 0.5 Hz, 1H), 7.71-7.65 (m, 2H), 7.54 (d, J = 4.8 Hz, 1H), 4.84 (s, 2H), 4.53 (s, 2H), 4.06-2.83 (m, 8H), 2.13 (s, 3H) |
| 1397 | MS (ESI) m/z 708.4 [M + 1]+; 1H NMR (400 MHz, DMSO-d6) δ 8.82 (d, J = 4.8 Hz, 1H), 8.60 (s, 1H), 8.40 (s, 1H), 7.60 (dd, J = 8.9, 2.7 Hz, 1H), 7.51-7.47 (m, 1H), 7.44 (d, J = 2.7 Hz, 1H), 7.36 (d, J = 9.0 Hz, 1H), 6.46 (t, J = 54.6 Hz, 1H), 4.54 (s, 4H), 4.41 (t, J = 4.9 Hz, 2H), 4.21 (t, J = 4.8 Hz, 2H), 4.10 (s, 4H), 2.75 (t, J = 4.7 Hz, 4H), 1.75 (s, 3H) |

TABLE 1-continued

7-Aza-Thienylpyridine and Derivative Compounds

| Compound | | Characterization |
|---|---|---|
| 1398 | 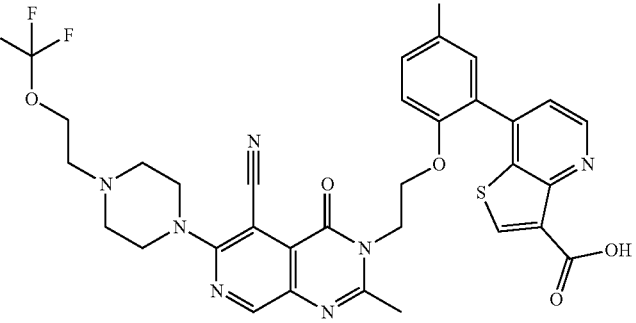 | MS (ESI) m/z 650.1 [M + 1]+; 1H NMR (400 MHz, DMSO-d6) δ 8.93 (s, 1H), 8.39 (s, 1H), 7.59 (dd, J = 8.9, 2.7 Hz, 1H), 7.42 (d, J = 2.8 Hz, 2H), 7.35 (d, J = 9.0 Hz, 1H), 6.29 (s, 1H), 4.39 (d, J = 5.0 Hz, 2H), 4.26 (d, J = 4.9 Hz, 2H), 2.91-2.78 (m, 4H), 2.71 (s, 3H), 2.35-2.15 (m, 2H), 1.85 (s, 3H) |
| 1399 | 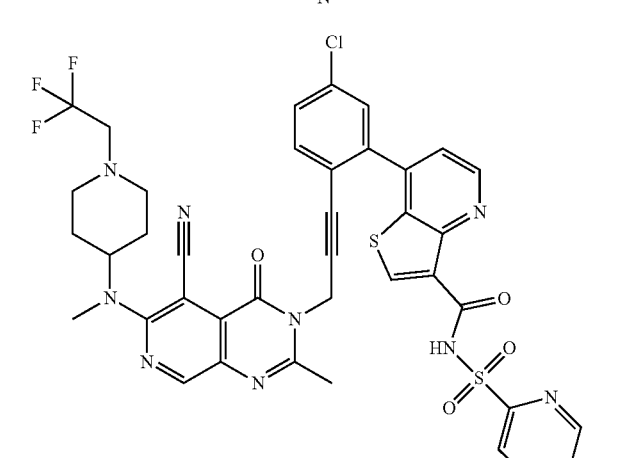 | MS (ESI) m/z 842.4 [M + 1]+; 1H NMR (400 MHz, DMSO-d6) δ 13.03 (s, 1H), 8.90 (d, J = 4.9 Hz, 1H), 8.72 (ddd, J = 4.6, 1.7, 0.9 Hz, 1H), 8.65 (s, 1H), 8.60 (s, 1H), 8.30-8.25 (m, 1H), 8.21 (td, J = 7.7, 1.7 Hz, 1H), 7.80-7.72 (m, 2H), 7.72-7.68 (m, 2H), 7.66 (d, J = 4.8 Hz, 1H), 4.83 (s, 2H), 3.09 (s, 3H), 1.94 (s, 3H), 1.77 (t, J = 18.9 Hz, 2H) |
| 1400 | 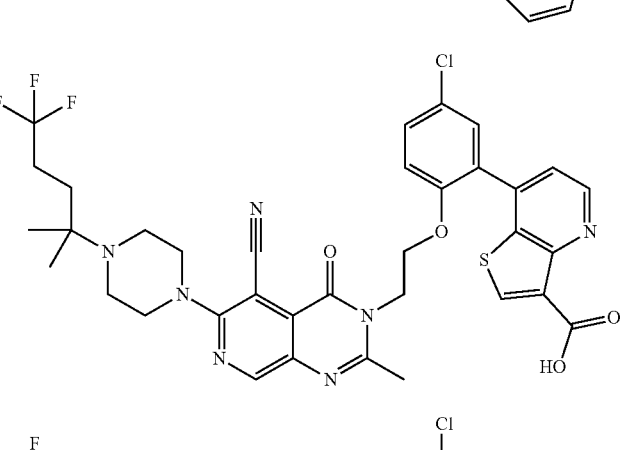 | MS (ESI) m/z = 740.3 [M + 1]+; 1H NMR (400 MHz, d6-DMSO) δ 9.59-9.49 (b, 1H), 8.83 (d, J = 4.6 Hz, 1H), 8.70 (s, 1H), 8.42 (s, 1H), 7.61 (dd, J = 8.9, 2.7 Hz, 1H), 7.49 (d, J = 4.8 Hz, 1H), 7.42 (d, J = 2.7 Hz, 1H), 7.38 (d, J = 8.9 Hz, 1H), 4.43-4.36 (m, 2H), 4.24 (t, J = 4.8 Hz, 2H), 3.61-3.49 (m, 2H), 3.34-3.20 (m, 2H), 2.49-2.39 (m, 2H), 2.00-1.92 (m, 2H), 1.85 (s, 3H), 1.39 (s, 6H). Remaining protons partially obscured by water peak |
| 1401 |  | MS (ESI) m/z = 738.3 [M + 1]+; 1H NMR (400 MHz, d6-DMSO) δ 8.83 (d, J = 4.9 Hz, 1H), 8.67 (s, 1H), 8.42 (s, 1H), 7.60 (dd, J = 8.9, 2.7 Hz, 1H), 7.48 (d, J = 4.7 Hz, 1H), 7.42 (d, J = 2.7 Hz, 1H), 7.37 (d, J = 8.9 Hz, 1H), 4.40 (t, J = 4.9 Hz, 2H), 4.23 (t, J = 4.9 Hz, 2H), 2.39-2.25 (m, 2H), 1.82 (s, 3H), 1.40-0.45 (b, 4H). Remaining protons appear as very broad signals and/or are partially obscured by water peak |

TABLE 1-continued

7-Aza-Thienylpyridine and Derivative Compounds

| Compound | | Characterization |
|---|---|---|
| 1402 | 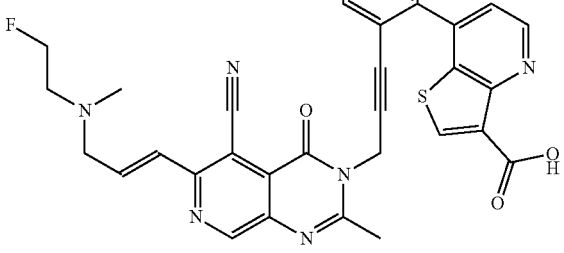 | MS (ESI) m/z = 627.3 [M + 1]+; 1H NMR (400 MHz, d6-DMSO) δ 10.20-10.10 ppm (b, 1H), 9.15 (s, 1H), 8.74 (d, J = 4.8 Hz, 1H), 8.61 (s, 1H), 7.78-7.75 (m, 1H), 7.71-7.68 (m, 2H), 7.54 (d, J = 4.8 Hz, 1H), 7.42 (d, J = 15 Hz, 1H), 7.19 (dt, J = 7.3, 15 Hz, 1H), 4.97-4.79 (m, 2H), 4.88 (s, 2H), 4.35-4.13 (m, 2H), 3.75-3.53 (m, 2H), 2.91 (s, 3H), 2.15 (s, 3H) |
| 1403 | 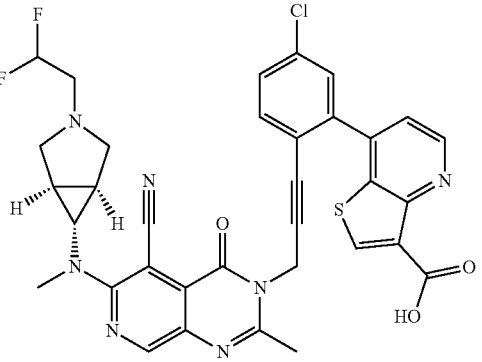 | MS (ESI) m/z = 686.2 [M + 1]+; 1H NMR (400 MHz, d6-DMSO) δ 8.77 (d, J = 4.8 Hz, 1H), 8.71 (s, 1H), 8.65 (s, 1H), 7.77-7.73 (m, 1H), 7.71-7.66 (m, 2H), 7.53 (d, J = 4.8 Hz, 1H), 6.37 (bt, J = 55 Hz, 1H), 4.81 (s, 2H), 3.25 (s, 3H), 2.37-2.18 (b, 2H), 2.11 (s, 3H). Remaining protons are (partially) obscured by water peak |
| 1404 | 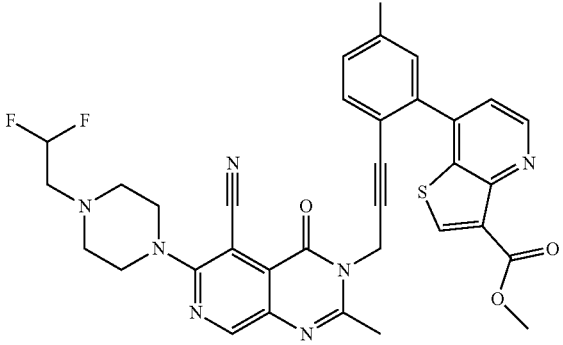 | MS (ESI) m/z = 674.4 [M + 1]+; 1H NMR (400 MHz, d6-DMSO) δ 8.75 (s, 1H), 8.75 (d, J = 4.7 Hz, 1H), 8.59 (s, 1H), 7.74 (dd, J = 8.1, 0.5 Hz, 1H), 7.69-7.64 (m, 2H), 7.43 (dd, J = 4.7, 0.3 Hz, 1H), 6.22 (tt, J = 55.7, 4.4 Hz, 1H), 4.81 (s, 2H), 3.85 (s, 3H), 3.71-3.67 (m, 4H), 2.84 (dt, J = 15.7, 4.2 Hz, 2H), 2.78-2.72 (m, 4H), 2.06 (s, 3H) |
| 1405 | 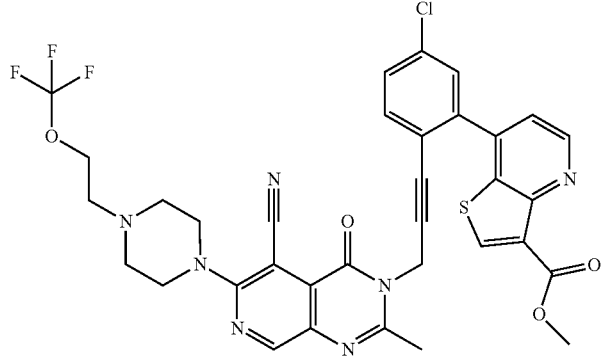 [SMILES: COC(=O)c1csc2c(-c3cc(Cl)ccc3C#CCn3c(C)nc4cnc(N5CCN(CCOC(F)(F)F)CC5)c(C#N)c4c3=O)ccnc12] | MS (ESI) m/z = 722.5 [M + 1]+; 1H NMR (400 MHz, d6-DMSO) δ 8.82 (s, 1H), 8.74 (d, J = 4.7 Hz, 1H), 8.62 (s, 1H), 7.73 (d, J = 8.4 Hz, 1H), 7.67 (dd, J = 8.4, 2.2 Hz, 1H), 7.61 (dd, J = 2.2, 0.4, 1H), 7.43 (d, J = 4.7 Hz, 1H), 4.82 (s, 2H), 4.59-4.53 (m, 2H), 3.86 (s, 3H), 3.69-3.62 (m, 2H), 2.16 (s, 3H). Remaining protons appear as very broad signals and/or are partially obscured by water peak |

TABLE 1-continued

7-Aza-Thienylpyridine and Derivative Compounds

| Compound | | Characterization |
|---|---|---|
| 1406 | 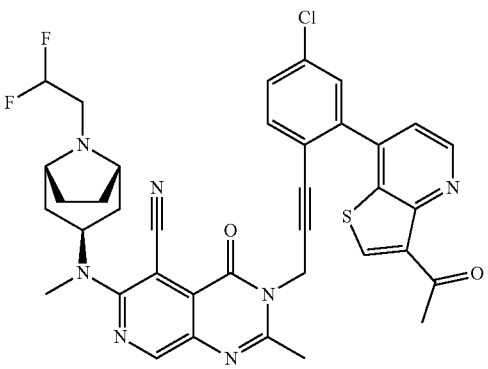 [SMILES: CC(=O)c1csc2c(-c3cc(Cl)ccc3C#CCn3c(C)nc4cnc(N(C)[C@H]5C[C@H]6CC[C@@H](C5)N6CC(F)F)c(C#N)c4c3=O)ccnc12] | MS (ESI) m/z = 714.5 [M + 1]+; 1H NMR (400 MHz, d6-DMSO) δ 10.38-10.18 (b, 1H), 8.76 (d, J = 4.7 Hz, 1H), 8.75 (s, 1H), 8.66 (s, 1H), 7.78-7.66 (m, 3H), 7.55 (d, J = 4.7 Hz, 1H), 6.59 (t, J = 52.6 Hz, 1H), 4.82 (s, 2H), 4.78-4.68 (m, 1H), 4.24-4.14 (m, overlapping with water peak), 3.76-3.58 (m, overlapping with water peak), 3.12 (s, 3H), 2.47-2.37 (m, 2H), 2.37-2.26 (m, 2H), 2.21-2.13 (m, 2H), 2.10-2.01 (m, 2H) |
| 1407 | 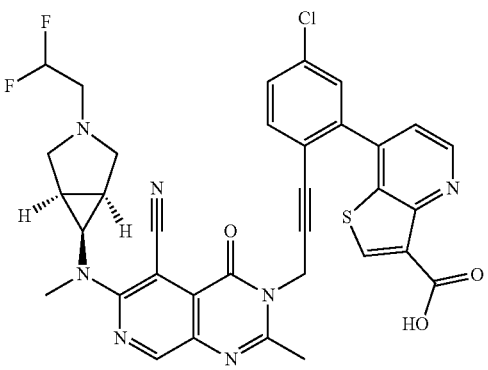 [SMILES: Cc1nc2cnc(N(C)[C@@H]3[C@@H]4CN(CC(F)F)C[C@@H]43)c(C#N)c2c(=O)n1CC#Cc1ccc(Cl)cc1-c1ccnc2c(C(=O)O)csc12] | MS (ESI) m/z = 686.1 [M + 1]+; 1H NMR (400 MHz, d6-DMSO) δ8.79 (b, 1H), 8.77 (d, J = 4.7 Hz, 1H), 8.67 (s, 1H), 7.79-7.74 (m, 1H), 7.71-7.67 (m, 2H), 7.54 (d, J = 4.7 Hz, 1H), 6.58-5.69 (b, 1H), 4.84 (s, 2H), 3.33 (t, J = 6.6 Hz, 1H), 3.28 (s, 3H), 2.08 (s, 3H). Remaining protons appear as broad signals and/or are (partially) obscured by water peak |
| 1408 | 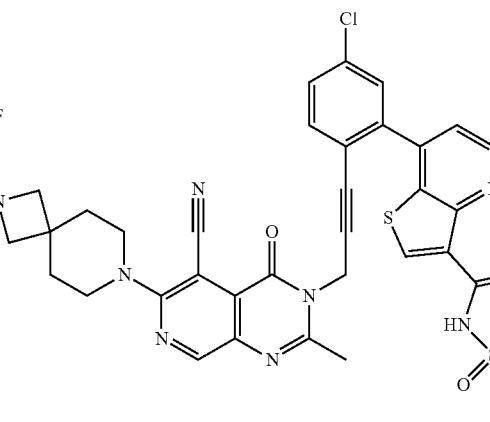 | MS (ESI) m/z = 819.2 [M + 1]+; 1H NMR (400 MHz, d6-DMSO) δ 12.98 (bs, 1H), 10.80-10.54 (b, 1H), 8.81 (d, J = 4.8 Hz, 1H), 8.79 (s, 1H), 8.75 (s, 1H), 7.77 (dd, J = 8.3, 0.5 Hz, 1H), 7.72-7.66 (m, 2H), 7.63 (d, J = 4.8 Hz, 1H), 6.40 (tt, J = 53.6, 2.8 Hz, 1H), 5.27-5.17 (m, 1H), 5.00-4.90 (m, 4H), 4.82 (s, 2H), 4.12 (bs, 2H), 3.99-3.85 (m, 2H), 3.76-3.55 (m, 4H), 2.11-1.93 (m, 4H), 1.96 (s, 3H) |

TABLE 1-continued

7-Aza-Thienylpyridine and Derivative Compounds

| Compound | Characterization |
|---|---|
| 1409 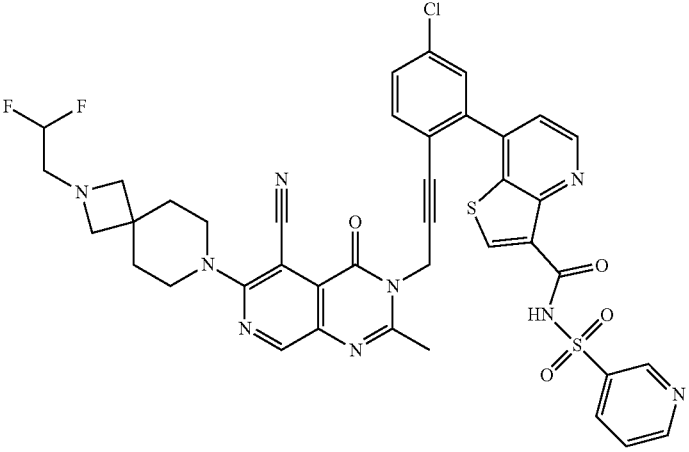 [SMILES: Cc1nc2cnc(N3CCC4(CC3)CN(CC(F)F)C4)c(C#N)c2c(=O)n1CC#Cc1ccc(Cl)cc1-c1ccnc2c(C(=O)NS(=O)(=O)c3cccnc3)csc12] | MS (ESI) m/z = 840.5 [M + 1]+; 1H NMR (400 MHz, d6-DMSO) δ 13.15-12.95 (b, 1H), 10.75-10.55 (b, 1H), 9.26 (dd, J = 2.4, 0.7 Hz, 1H), 8.89 (dd, J = 4.8, 1.6 Hz, 1H), 8.81 (d, J = 4.8 Hz, 1H), 8.61 (s, 1H), 8.52 (ddd, J = 8.1, 2.4, 1.6 Hz, 1H), 8.46 (s, 1H), 7.74-7.64 (m, 3H), 7.62 (dd, J = 2.2, 0.5 Hz, 1H), 7.59 (d, J = 4.8 Hz, 1H), 6.37 (tt, J = 53.7, 3.1 Hz, 1H), 4.77 (s, 2H), 4.10 (bs, 4H), 3.97-3.82 (m, 2H), 3.72-3.50 (m, 4H), 2.07-1.94 (m, 4H), 1.87 (s, 3H) |
| 1410 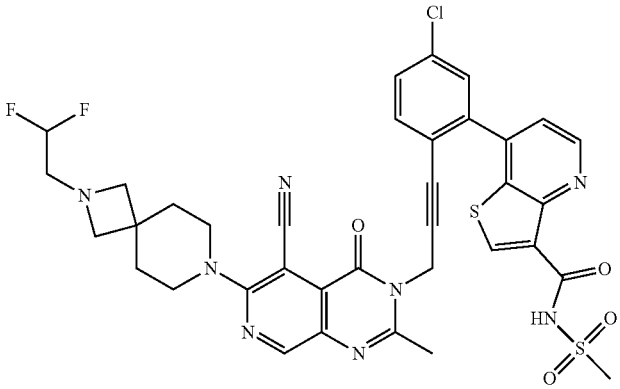 | MS (ESI) m/z = 791.4 [M + 1]+; 1H NMR (400 MHz, d6-DMSO) δ 12.44 (s, 1H), 10.60-10.50 (b, 1H), 8.80 (s, 1H), 8.80 (d, J = 4.8 Hz, 1H), 8.78 (s, 1H), 7.77 (dd, J = 8.3, 0.5 Hz, 1H), 7.70 (dd, J = 8.3, 2.1 Hz, 1H), 7.67 (dd, J = 2.1, 0.5 Hz, 1H), 7.62 (d, J = 4.8 Hz, 1H), 4.83 (s, 2H), 4.27-3.90 (m, 6H), 3.79-3.56 (m, 4H expected; partially obscured by water peak), 3.55 (s, 3H expected; partially obscured by water peak), 2.12-1.95 (m, 4H), 2.00 (s, 3H), 1.73 (t, J = 19 Hz, 3H) |
| 1411 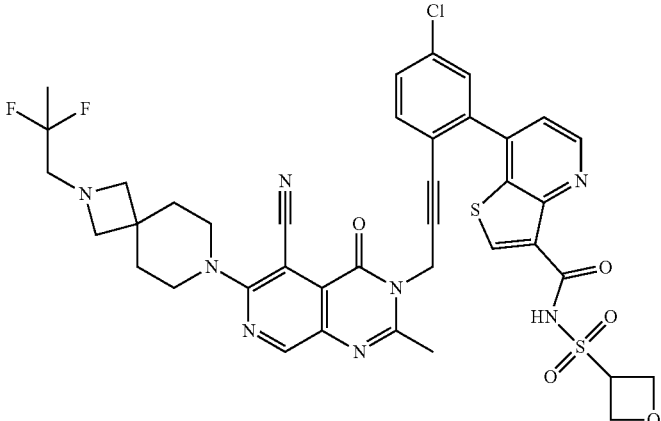 | MS (ESI) m/z = 833.3 [M + 1]+; 1H NMR (400 MHz, d6-DMSO) δ 12.65 (bs, 1H), 10.59 (bs, 1H), 8.78 (d, J = 4.8 Hz, 1H), 8.75 (s, 1H), 8.71 (s, 1H), 7.74 (dd, J = 8.3, 0.5 Hz, 1H), 7.67 (dd, J = 8.3, 2.1, 1H), 7.64 (dd, J = 2.1, 0.5 Hz, 1H), 7.59 (d, J = 4.8 Hz, 1H), 5.24-5.15 (m, 1H), 4.98-4.85 (m, 4H), 4.79 (s, 2H), 4.21-3.87 (m, 4H), 3.74-3.54 (m, 4H), 2.10-1.91 (m, 4H), 1.92 (s, 3H), 1.70 (t, J = 19.3 Hz, 3H) |

TABLE 1-continued

7-Aza-Thienylpyridine and Derivative Compounds

| Compound | | Characterization |
|---|---|---|
| 1412 | 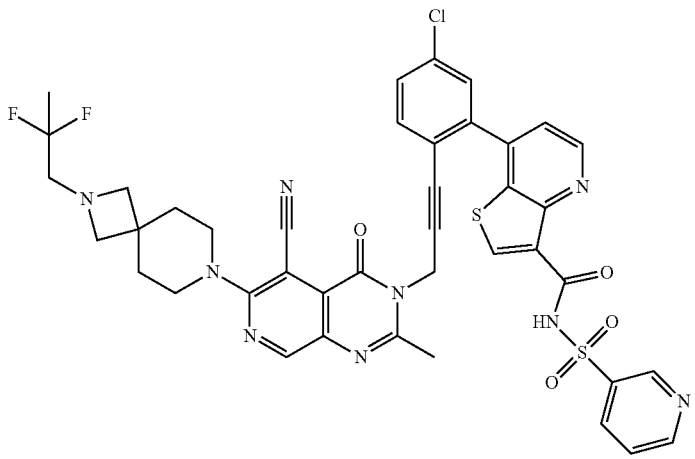 [SMILES: Cc1nc2cnc(N3CCC4(CC3)CN(CC(C)(F)F)C4)c(C#N)c2c(=O)n1CC#Cc1ccc(Cl)cc1-c1ccnc2c(C(=O)NS(=O)(=O)c3cccnc3)csc12] | MS (ESI) m/z = 854.4 [M + 1]+; 1H NMR (400 MHz, d6-DMSO) d/ppm = 13.13-13.93 (b, 1H), 10.65-10.49 (b, 1H), 9.26 (dd, J = 2.4, 0.8 Hz, 1H), 8.89 (dd, J = 4.9, 1.6 Hz, 1H), 8.81 (d, J = 4.8 Hz, 1H), 8.61 (s, 1H), 8.52 (ddd, J = 8.1, 2.4, 1.6 Hz, 1H), 8.46 (s, 1H), 7.73 (dd, J = 8.4, 0.4 Hz, 1H), 7.69 (ddd, J = 8.1, 3.3, 0.8 Hz, 1H), 7.66 (dd, J = 8.4, 2.2 Hz, 1H), 7.62 (dd, J = 2.2, 0.4 Hz, 1H), 7.59 (d, J = 4.8 Hz, 1H), 4.77 (s, 2H), 4.24-3.90 (m, 6H expected, overlapping with water peak), 3.71-3.51 (m, 4H), 2.08-1.93 (m, 4H), 1.87 (s, 3H), 1.70 (t, J = 19.4 Hz, 3H) |
| 1413 | 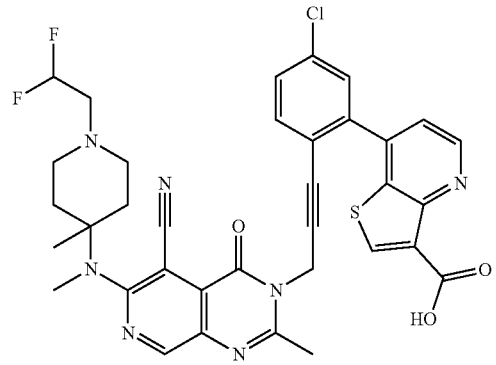 [SMILES: Cc1nc2cnc(N(C)C3(C)CCN(CC(F)F)CC3)c(C#N)c2c(=O)n1CC#Cc1ccc(Cl)cc1-c1ccnc2c(C(=O)O)csc12] | MS (ESI) m/z 702.5 [M + 1]+; 1H NMR (400 MHz, DMSO-d6) δ 10.61 (s, 1H), 8.81-8.72 (m, 2H), 8.64 (s, 1H), 7.79-7.72 (m, 1H), 7.71 –7.64 (m, 2H), 7.54 (d, J = 4.8 Hz, 1H), 4.82 (s, 2H), 4.32-3.89 (m, 6H), 3.64 (m, 4H), 2.07 (d, J = 1.6 Hz, 6H), 2.00 (s, 3H), 1.74 (t, J = 19.6 Hz, 3H) |
| 1414 | | LCMS (ESI) m/z 702.5 [M + 1]+ |
| 1415 | 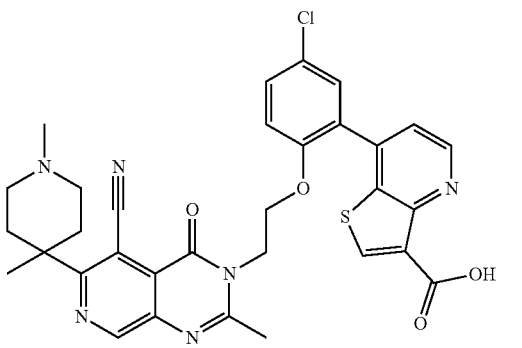 [SMILES: Cc1nc2cnc(C3(C)CCN(C)CC3)c(C#N)c2c(=O)n1CCOc1ccc(Cl)cc1-c1ccnc2c(C(=O)O)csc12] | MS (ESI) m/z 629.1 [M + 1]+; 1H NMR (400 MHz, DMSO-d6) δ 9.23 (d, J = 22.2 Hz, 1H), 8.78 (m, 1H), 8.44 (d, J = 17.1 Hz, 1H), 8.11 (d, J = 57.3 Hz, 1H), 7.57 (m, 1H), 7.48-7.40 (m, 2H), 7.34 (dd, J = 12.2, 9.0 Hz, 1H), 4.39 (m, 2H), 4.26 (d, J = 5.4 Hz, 2H), 3.47-3.31 (m, 2H), 3.25 (dd, J = 13.1, 9.7 Hz, 1H), 2.29 (m, 1H), 2.22-2.11 (m, 1H), 2.11-2.01 (m, 1H), 1.99 (d, J = 2.0 Hz, 3H), 1.82 (d, J = 14.3 Hz, 1H), 1.46 (s, 1H), 1.26 (s, 3H) |

TABLE 1-continued

7-Aza-Thienylpyridine and Derivative Compounds

| Compound | | Characterization |
|---|---|---|
| 1418 |  | MS (ESI) m/z 644.0 [M + 1]+; 1H NMR (400 MHz, DMSO-d6) δ 9.86 (s, 1H), 8.71 (s, 1H), 7.60 (dd, J = 8.9, 2.7 Hz, 1H), 7.40 (s, 1H), 7.39 (d, J = 2.7 Hz, 1H), 7.36 (d, J = 9.0 Hz, 1H), 4.40 (t, J = 5.1 Hz, 2H), 4.31-4.22 (m, 4H), 3.62 (d, J = 12.1 Hz, 2H), 3.40 (t, J = 13.0 Hz, 2H), 3.20 (q, J = 11.4 Hz, 2H), 2.90 (s, 3H), 2.70 (s, 3H), 2.53 (s, 3H), 2.00 (s, 3H) |
| 1419 |  | MS (ESI) m/z 588.1 [M + 1]+; 1H NMR (400 MHz, DMSO-d6) δ 8.90 (s, 1H), 8.63 (s, 1H), 7.59 (dd, J = 8.9, 2.7 Hz, 1H), 7.43 (d, J = 2.7 Hz, 1H), 7.41 (s, 1H), 7.36 (d, J = 9.0 Hz, 1H), 6.33 (q, J = 1.6 Hz, 1H), 5.97 (q, J = 1.9 Hz, 1H), 4.54-4.48 (m, 2H), 4.42 (t, J = 5.0 Hz, 2H), 4.28 (t, J = 5.1 Hz, 2H), 2.67 (s, 3H), 1.99 (s, 3H) |
| 1421 |  | MS (ESI) m/z 619.45 [M + 1]+; 1H NMR (400 MHz, DMSO-d6) δ 9.17 (bs, 1H), 7.92 (bs, 1H), 7.52 (d, J = 5.2 Hz, 1H), 7.34-7.27 (m, 2H), 7.14 (bs, 1H), 4.35 (bs, 2H), 4.26 (bs, 2H), 4.04-3.97 (m, 2H), 3.74-3.67 (m, 2H), 2.34 (s, 3H), 1.82 (s, 3H), 1.78 (s, 3H) |
| 1422 |  | MS (ESI) m/z 676.42 [M + 1]+; 1H NMR (400 MHz, DMSO-d6) δ 13.23 (bs, 1H), 8.82 (d, J = 4.8 Hz, 1H), 8.64 (s, 1H), 8.45 (s, 1H), 7.59-7.57 (m, 1H), 7.45 (d, J = 4.80, 1H), 7.42 (d, J = 2.0 Hz, 1H), 7.35 (d, J = 8.8 Hz, 1H), 4.38 (s, 2H), 4.20 (s, 2H), 3.65 (s, 4H), 2.67 (s, 4H), 2.60-2.48 (m, 2H), 1.74 (s, 3H), 1.35 (J = 21.6 Hz, 6H) |

TABLE 1-continued

7-Aza-Thienylpyridine and Derivative Compounds

| Compound | | Characterization |
|---|---|---|
| 1423 | 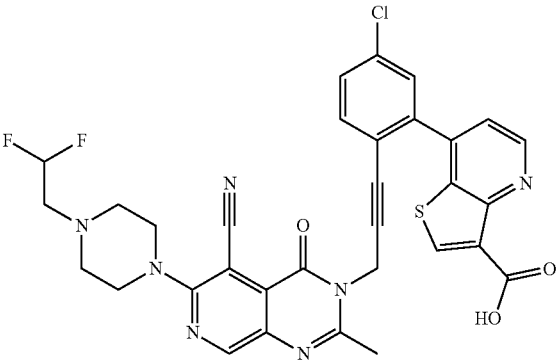 [SMILES: Cc1nc2cnc(N3CCN(CC(F)F)CC3)c(C#N)c2c(=O)n1CC#Cc1ccc(Cl)cc1-c1ccnc2c(C(=O)O)csc12] | MS (ESI) m/z 660.27 [M + 1]+; 1H NMR (400 MHz, DMSO-d6) δ 13.05 (bs, 1H), 8.79 (s, 1H), 8.75 (d, J = 4.64 Hz, 1H), 8.65 (s, 1H), 7.75 (d, J = 8.12 Hz, 1H), 7.68 (m, 2H), 7.53 (d, J = 4.64 Hz, 1H), 6.34 (m, 1H), 4.82 (s, 2H), 3.76-2.66 (m, 10H), 2.09 (s, 1H) |
| 1424 | 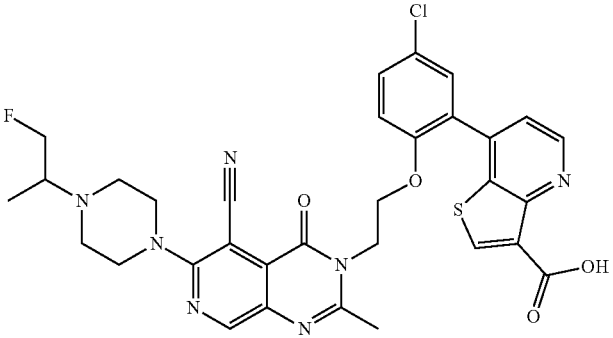 [SMILES: Cc1nc2cnc(N3CCN(C(C)CF)CC3)c(C#N)c2c(=O)n1CCOc1ccc(Cl)cc1-c1ccnc2c(C(=O)O)csc12] | MS (ESI) m/z 662.41 [M + 1]+; 1H NMR (400 MHz, DMSO-d6) δ 8.84 (d, J = 4.8 Hz, 1H), 8.70 (s, 1H), 8.42 (s, 1H), 7.61 (dd, J = 8.8 Hz, 2.8 Hz, 1H), 7.47 (d, J = 4.4 Hz, 1H), 7.41 (d, J = 2.8 Hz, 1H), 7.37 (d, J = 9.2 Hz, 1H), 4.96-4.67 (m, 2H), 4.40-4.21 (m, 5H), 3.57-3.36 (m, 8H), 1.84 (s, 3H), 1.37 (d, J = 6.0 Hz, 3H) |
| 1425 | 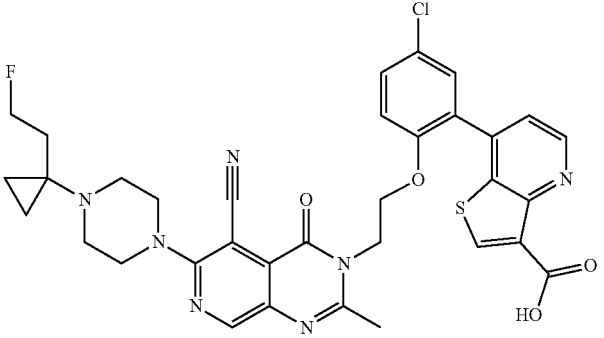 [SMILES: Cc1nc2cnc(N3CCN(C4(CCF)CC4)CC3)c(C#N)c2c(=O)n1CCOc1ccc(Cl)cc1-c1ccnc2c(C(=O)O)csc12] | MS (ESI) m/z 688.50 [M + 1]+; 1H NMR (400 MHz, DMSO-d6) δ 8.82 (d, J = 4.8 Hz,1H), 8.67 (s, 1H), 8.44 (s, 1H), 7.60 (dd, J = 2.8, 8.8 Hz, 1H), 7.47 (d, J = 4.8 Hz, 1H), 7.41 (d, J = 2.8 Hz, 1H), 7.37 (d, J = 8.8 Hz, 1H), 4.58-4.48 (m, 1H), 4.44-4.41 (m, 2H), 4.39-4.36 (m, 2H), 3.56-3.53 (m, 4H), 3.30-3.28 (m, 1H), 3.17-2.95 (m, 4H), 2.22-2.19 (m, 2H), 1.84 (s, 3H), 1.14-0.77 (m, 4H) |
| 1427 | 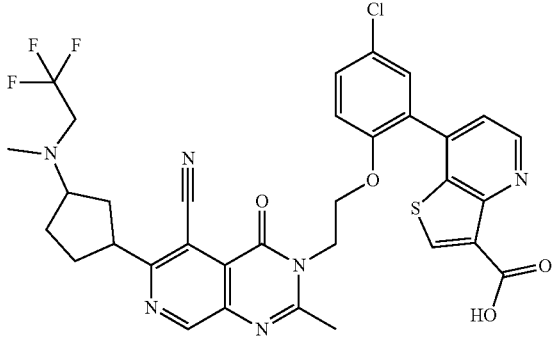 [SMILES: Cc1nc2cnc(C3CCC(N(C)CC(F)(F)F)C3)c(C#N)c2c(=O)n1CCOc1ccc(Cl)cc1-c1ccnc2c(C(=O)O)csc12] | MS (ESI) m/z 697.51 [M + 1]+; 1H NMR (400 MHz, DMSO-d6) δ 9.01 (s, 1H), 8.82 (d, J = 4.4 Hz, 1H), 8.41 (s, 1H), 7.59 (dd, J = 8.8, 2.8 Hz, 1H), 7.46 (d, J = 4.8 Hz, 1H), 7.43 (d, J = 2.4 Hz, 1H), 7.35 (d, J = 8.8 Hz, 1H), 4.39 (t, J = 4.4 Hz, 2H), 4.24 (t, J = 4.4 Hz, 2H), 3.81-3.75 (m, 1H), 3.31 (bs, 3H), 2.45 (s, 3H), 2.32-2.23 (m, 1H), 2.11-1.93 (m, 3H), 1.92-1.66 (m, 5H) |

TABLE 1-continued

7-Aza-Thienylpyridine and Derivative Compounds

| Compound | | Characterization |
|---|---|---|
| 1428 | 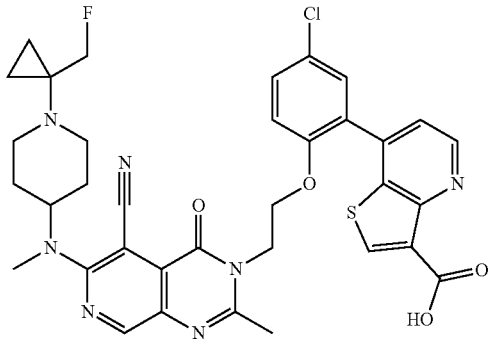 [SMILES: Cc1nc2cnc(N(C)C3CCN(C4(CF)CC4)CC3)c(C#N)c2c(=O)n1CCOc1ccc(Cl)cc1-c1ccnc2c(C(=O)O)csc12] | MS (ESI) m/z 702.53 [M + 1]+; 1H NMR (400 MHz, DMSO-d6) δ 8.83 (d, J = 4.8 Hz, 1H), 8.59 (s, 1H), 8.42 (s, 1H), 7.59 (dd, J = 2.4, 8.8 Hz, 1H), 7.46 (d, J = 4.8 Hz, 1H), 7.43 (d, J = 2.8 Hz, 1H) 7.36 (d, J = 9.2 Hz, 1H), 4.52 (s, 2H), 4.37-4.40 (m, 2H), 4.23-4.26 (m, 1H), 4.18-4.21 (m, 2H), 3.03 (s, 3H), 2.94-2.97 (m, 2H), 2.66-2.72 (m, 2H), 1.71-1.75 (m, 7H), 0.64-0.68 (m, 4H) |
| 1426 | 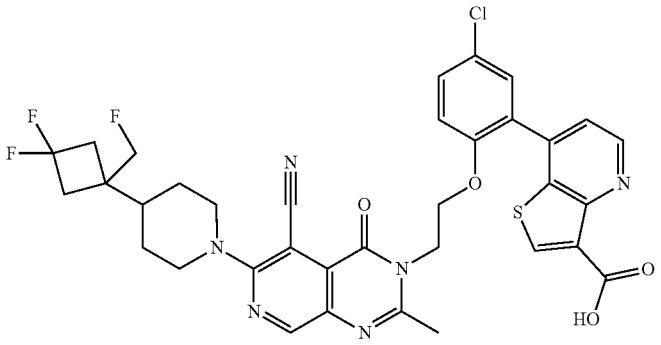 [SMILES: Cc1nc2cnc(N3CCC(C4(CF)CC(F)(F)C4)CC3)c(C#N)c2c(=O)n1CCOc1ccc(Cl)cc1-c1ccnc2c(C(=O)O)csc12] | MS (ESI) m/z 724.56 [M + 1]+; 1H NMR (400 MHz, DMSO-d6) δ 8.83 (d, J = 4.8 Hz, 1H), 8.66 (s, 1H), 8.47 (s, 1H), 7.60 (dd, J = 2.4, 8.8 Hz, 1H), 7.49 (d, J = 4.8 Hz, 1H), 7.41 (d, J = 2.8 Hz, 1H), 7.35 (d, J = 9.2 Hz, 1H), 4.74 (s, 1H), 4.63 (s, 1H), 4.39 (t, J = 4.4 Hz, 2H), 4.21 (t, J = 4.4 Hz, 2H), 3.69 (bs, 4H), 2.88 (bs, 4H), 2.72 (bs, 4H), 1.7(s, 3H) |
| 1430 | 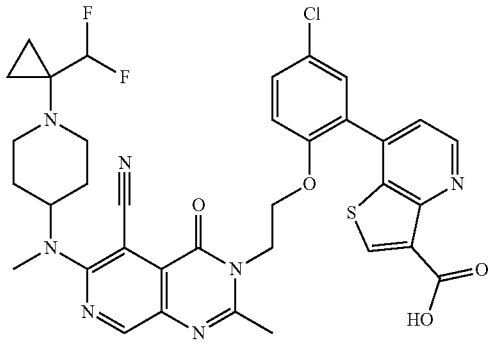 [SMILES: Cc1nc2cnc(N(C)C3CCN(C4(C(F)F)CC4)CC3)c(C#N)c2c(=O)n1CCOc1ccc(Cl)cc1-c1ccnc2c(C(=O)O)csc12] | MS (ESI) m/z 720.50 [M + 1]+; 1H NMR (400 MHz, DMSO-d6) δ 8.84 (d, J = 4.8 Hz, 1H), 8.59 (s, 1H), 8.44 (s, 1H), 7.60 (dd, J = 2.4, 6.4 Hz, 1H), 7.49 (d, J = 4.8 Hz, 1H), 7.44 (d, J = 2.8 Hz, 1H), 7.37 (d, J = 8.8 Hz, 1H), 6.08 (t, J = 55.6 Hz, 1H), 4.38 (d, J = 4.4 Hz, 2H), 4.25 (bs, 1H), 4.19 (bs, 2H), 3.08 (bs, 2H), 3.03 (s, 3H), 2.92 (bs, 2H), 1.77 (bs, 7H), 0.48-0.78 (m, 4H) |
| 1431 | 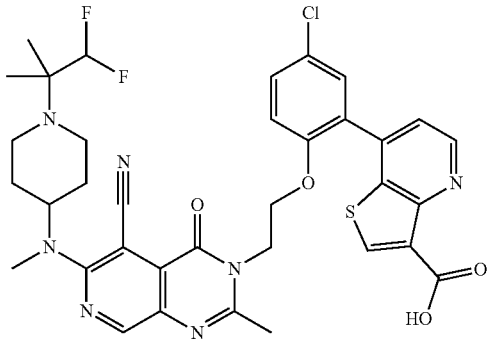 [SMILES: Cc1nc2cnc(N(C)C3CCN(C(C)(C)C(F)F)CC3)c(C#N)c2c(=O)n1CCOc1ccc(Cl)cc1-c1ccnc2c(C(=O)O)csc12] | MS (ESI) m/z 722.55 [M + 1]+; 1H NMR (400 MHz, DMSO-d6) δ 8.83 (d, J = 4.8 Hz, 1H), 8.61 (s, 1H), 8.39 (s, 1H) 7.61 (dd, J = 2.4, 9.2 Hz, 1H), 7.48 (d, J = 4.8 Hz, 1H), 7.42-7.35 (m, 2H), 6.52 (t, J = 52 Hz, 1H), 4.62-4.56 (m, 1H), 4.39 (bs, 2H), 4.21 (bs, 2H,), 3.38-3.34 (m, 4H), 3.09 (s, 3H), 2.32-2.26 (m, 2H), 2.12-2.09 (m, 2H), 1.76 (s, 3H), 1.44 (s, 6H) |

TABLE 1-continued

7-Aza-Thienylpyridine and Derivative Compounds

| Compound | Characterization |
|---|---|
| 1429 | MS (ESI) m/z 704.54 [M − F1]; 1H NMR (400 MHz, DMSO-d6) 613.2 (bs, 1H), 9.11 (bs, 1H), 8.83 (d, J = 4.8 Hz, 1H), 8.61 (s, 1H), 8.38 (s, 1H), 7.60 (dd, J = 2.8, 8.8 Hz, 1H), 7.47 (d, J = 4.8 Hz, 1H), 7.42 (d, J = 2.8 Hz, 1H) 7.36 (d, J = 8.8 Hz, 1H), 4.74-4.62 (d, J = 46.8 Hz, 2H), 4.60-4.57 (m, 1H), 4.39 (bs, 2H), 4.21 (bs, 2H), 3.66-3.58 (m, 2H), 3.30-3.24 (m, 2H), 3.09 (s, 3H), 2.26-2.20 (m, 2H), 2.11-2.08 (m, 2H), 1.76 (s, 3H), 1.38 (s, 6H) |
| 1433 | MS (ESI) m/z 708.50 [M + 1]+; 1H NMR (400 MHz, DMSO-d6) δ 8.82 (d, J = 4.2 Hz, 1H), 8.65 (s, 1H), 8.41 (s, 1H), 7.59 (d, J = 8.6 Hz, 1H), 7.47-7.43 (m, 2H), 7.35 (d, J = 8.8 Hz, 1H), 6.51 (t, J = 53.4 Hz, 1H), 4.38 (s, 4H), 4.21 (s, 2H), 3.07 (bs, 5H), 2.52 (s, 2H), 2.17 (bs, 2H), 2.02 (bs, 2H), 1.75 (s, 3H), 1.11 (t, J = 6.3 Hz, 3H) |
| 1434 | MS (ESI) m/z 667.18 [M + 1]+; 1H NMR (400 MHz, DMSO-d6) δ 13.32 (bs, 1H), 8.81 (d, J = 4.8 Hz, 1H), 8.60 (s, 1H), 8.46 (s, 1H), 7.60 (dd, J = 9.2, 2.8 Hz, 1H), 7.44 (dd, J = 15.6 Hz, 2H), 7.35 (d, J = 9.2 Hz, 1H), 4.59 (s, 2H), 4.53 (s, 2H), 4.38 (bs, 4H), 4.24- 4.20 (m, 4H), 3.91-3.88 (m, 1H), 2.17 (bs, 2H), 2.01 (t, J = 9.6 Hz, 2H), 1.82 (s, 3H), 1.78-1.71 (m, 2H) |
| 1432 | MS (ESI) m/z 708.2 [M + 1]+; 1H NMR (400 MHz, DMSO-d6) δ 8.83 (dd, J = 4.8 Hz, 2 Hz, 1H), 8.61 (d, J = 2 Hz, 1H), 8.40 (s, 1H), 7.61 (d, J = 8.8 Hz, 1H), 7.46 (dd, J = 4.8 Hz, 2 Hz, 1H), 7.43 (d, J = 4.0 Hz, 1H), 7.36 (d, J = 7.2 Hz, 1H), 4.99 (bs, 4H), 4.58 (bs, 1H), 4.39 (s, 2H), 4.21 (s, 2H), 4.0 (bs, 2H), 3.70 (bs, 2H), 3.28 (bs, 1H), 3.09 (s, 3H), 2.33-2.00 (m, 4H), 1.76 (s, 3H) |

TABLE 1-continued

7-Aza-Thienylpyridine and Derivative Compounds

| Compound | | Characterization |
|---|---|---|
| 1436 | 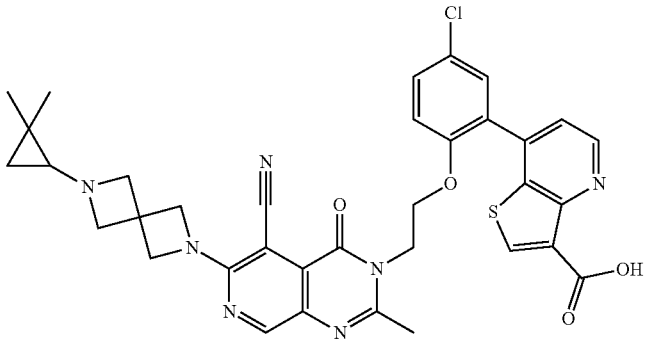 [SMILES: Cc1nc2cnc(N3CC4(C3)CN(C3CC3(C)C)C4)c(C#N)c2c(=O)n1CCOc1ccc(Cl)cc1-c1ccnc2c(C(=O)O)csc12] | MS (ESI) m/z 682.52 [M + 1]+; 1H NMR (400 MHz, DMSO-d6) δ 13.5 (bs, 1H), 9.66 (bs, 1H), 8.80 (d, J = 4.8 Hz, 1H), 8.61 (s, 1H), 8.47 (s, 1H), 7.60 (dd, J = 9.2, 2.8 Hz, 1H), 7.46 (d, J = 4.8 Hz, 1H), 7.42 (d, J = 2.4 Hz, 1H), 7.36 (d, J = 8.8 Hz, 1H), 4.65-4.45 (m, 8H), 4.40-4.35 (m, 2H), 4.25-4.15 (m, 2H), 2.91 (bs, 1H), 1.80 (s, 3H), 1.17 (s, 3H), 1.06 (s, 3H), 0.85-0.55 (m, 2H) |
| 1437 | 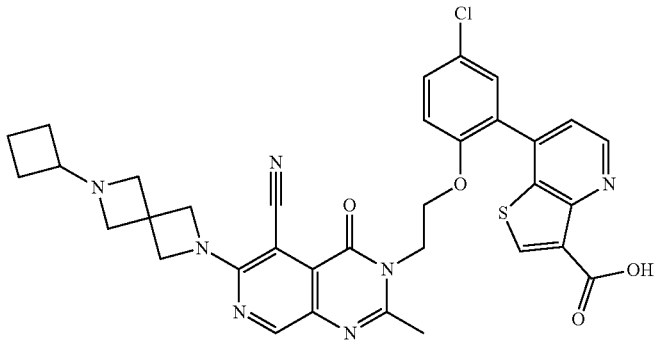 | MS (ESI) m/z 667.18 [M + 1]+; 1H NMR (400 MHz, DMSO-d6) δ 13.32 (bs, 1H), 8.81 (d, J = 4.8 Hz, 1H), 8.60 (s, 1H), 8.46 (s, 1H), 7.60 (dd, J = 9.2, 2.8 Hz, 1H), 7.44 (dd, J = 15.6 Hz, 2H), 7.35 (d, J = 9.2 Hz, 1H), 4.59 (s, 2H), 4.53 (s, 2H), 4.38 (bs, 4H), 4.24- 4.20 (m, 4H), 3.91-3.88 (m, 1H), 2.17 (bs, 2H), 2.01 (t, J = 9.6 Hz, 2H), 1.82 (s, 3H), 1.78-1.71 (m, 2H) |
| 1435 | 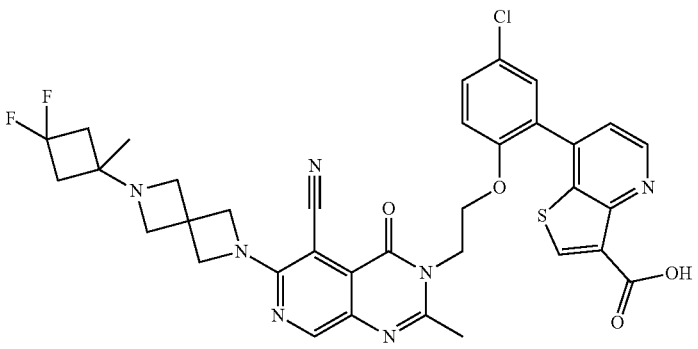 | MS (ESI) m/z 718.48 [M + 1]+; 1H NMR (400 MHz, DMSO-d6) δ 8.82 (d, J = 4.8 Hz, 1H), 8.61 (s, 1H), 8.47 (s, 1H), 7.60 (dd, J = 9.2, 2.8 Hz, 1H), 7.46 (d, J = 4.8 Hz, 1H), 7.42 (d, J = 2.8 Hz, 1H), 7.36 (d, J = 8.8 Hz, 1H), 4.78-4.59 (m, 4H), 4.40-4.30 (m, 6H), 4.23-4.18 (m, 2H), 3.35-3.15 (m, 2H), 2.80-2.65 (m, 2H), 1.80 (s, 3H), 1.47 (s, 3H) |
| 1439 | 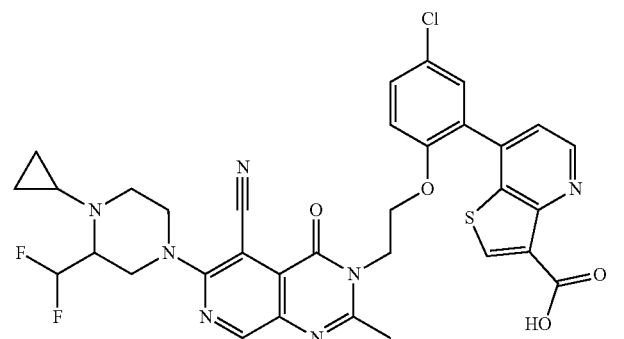 | MS (ESI) m/z 692.45 [M + 1]+; 1H NMR (400 MHz, DMSO-d6) δ 8.83 (d, J = 4.8 Hz, 1H), 8.67 (s, 1H), 8.44 (s, 1H), 7.59 (dd, J = 8.8, 2.4 Hz, 1H), 7.47 (d, J = 4.8 Hz, 1H), 7.43 (d, J = 2.4 Hz, 1H), 7.36 (d, J = 8.8 Hz, 1H), 6.54 (t, J = 54.8 Hz, 1H), 4.38 (d, J = 4.8 Hz, 2H), 4.22 (d, J = 4.8 Hz, 2H), 4.10 (d, J = 12 Hz, 1H), 3.93 (d, J = 12.4 Hz, 1H), 3.41-3.32 (m, 2H), 3.16-3.13 (m, 3H), 2.02 (bs, 1H), 1.76 (s, 3H), 0.53-0.41 (m, 4H) |

TABLE 1-continued

7-Aza-Thienylpyridine and Derivative Compounds

| Compound | Characterization |
|---|---|
| 1440 | MS (ESI) m/z 693.42 [M + 1]+; 1H NMR (400 MHz, DMSO-d6) δ 9.03 (s, 1H), 8.84 (d, J = 4.8 Hz, 1H), 8.33 (s, 1H), 7.65-7.58 (m, 1H), 7.48 (d, J = 4.8 Hz, 1H), 7.42 (d, J = 2.4 Hz, 1H), 7.36 (d, J = 8.8 Hz, 1H), 6.40 (t, J = 62.4 Hz, 1H), 4.41 (s, 2H), 4.28 (d, J = 5.2 Hz, 2H), 3.51-3.05 (m, 8H), 2.50 (bs, 2H), 1.82 (s, 3H), 1.77 (s, 1H) |
| 1438 | MS (ESI) m/z 710.17 [M + 1]+; 1H NMR (400 MHz, DMSO-d6) δ 8.83 (d, J = 4.8 Hz, 1H), 8.67 (s, 1H), 8.46 (s, 1H), 7.60 (dd, J = 8.8 Hz, 2.4 Hz, 1H), 7.49 (d, J = 4.8 Hz, 1H), 7.43 (d, J = 2.8 Hz, 1H), 7.36 (d, J = 8.8 Hz, 1H), 4.39 (d, J = 4.8 Hz, 2H), 4.29 (bs, 2H), 3.96 (dd, J = 14, 5.2 Hz, 1H), 3.87 (bs, 2H), 3.71 (bs, 1H), 3.59 (t, J = 9.2 Hz, 1H), 3.27 (bs, 1H), 2.90 (d, J = 12.8 Hz, 1H), 2.26 (bs, 1H), 1.76 (s, 3H), 0.58 (d, J = 6.4 Hz, 2H), 0.46 (s, 2H) |
| 1443 | MS (ESI) m/z 656.45 [M + 1]+; 1H NMR (400 MHz, DMSO-d6) δ 13.07 (s, 1H), 8.75 (d, J = 4.8, 2H), 8.65 (s, 1H), 7.75 (d, J = 8.8 Hz, 1H), 7.68 (d, J = 6.8 Hz, 2H), 7.53 (d, J = 4.8 Hz, 1H), 4.82 (s, 2H), 4.47 (d, J = 44 Hz, 2H), 3.66 (bs, 4H), 2.96 (bs, 1H), 2.74 (s, 3H), 2.07-2.08 (m, 4H), 1.23 (s, 3H) |
| 1444 | MS (ESI) m/z 650.47 [M + 1]+; 1H NMR (400 MHz, DMSO-d6) δ 9.29 (bs, 1H), 8.83 (s, 1H), 8.76 (d, J = 4.8 Hz, 1H), 8.65 (s, 1H), 7.76 (d, J = 8.4 Hz, 1H), 7.70-7.65 (m, 2H), 7.54 (d, J = 4.8 Hz, 1H), 4.83 (s, 2H), 4.46 (bs, 2H), 3.53 (bs, 6H), 2.14 (s, 3H), 1.39 (s, 3H), 1.20 (bs, 2H), 0.83 (bs, 2H) |

TABLE 1-continued

7-Aza-Thienylpyridine and Derivative Compounds

| Compound | Characterization |
|---|---|
| 1441 | MS (ESI) m/z 728.40 [M + 1]+; 1H NMR (400 MHz, DMSO-d6) δ 8.83 (d, J = 4.8 Hz, 1H), 8.59 (s, 1H), 8.44 (s, 1H), 7.60-7.58 (dd, J = 2.4, 8.8 Hz, 1H), 7.48 (d, J = 4.8 Hz, 1H), 7.43 (d, J = 2.4 Hz, 1H), 7.36 (d, J = 8.8 Hz, 1H), 4.38 (bs, 2H), 4.25-4.19 (m, 3H), 3.35-3.30 (m, 2H), 3.07(s, 5H), 2.66-2.59 (m, 2H), 1.92 (d, J = 9.2 Hz, 2H), 1.78-1.72 (m, 5H) |
| 1446 | MS (ESI) m/z 682.44 [M + 1]+; 1H NMR (400 MHz, DMSO-d6) δ 8.81 (s, 1H), 8.75 (d, J = 4.8 Hz, 1H), 8.66 (s, 1H), 7.75 (d, J = 8.4 Hz, 1H), 7.70-7.67 (m, 2H), 7.54 (d, J = 4.8 Hz, 1H), 4.83 (s, 2H), 4.56-4.41 (m, 2H), 3.77-3.06 (m, 8H), 2.23 (s, 3H), 1.23-0.72 (m, 6H) |
| 1447 | MS (ESI) m/z 664.45 [M + 1]+; 1H NMR (400 MHz, DMSO-d6) δ 12.99 (bs, 1H), 9.00 (bs, 1H), 8.83 (bs, 1H), 8.75 (d, J = 4.8 Hz, 1H), 8.65 (s, 1H), 7.75 (d, J = 8.4 Hz, 1H), 7.70-7.64 (m, 2H), 7.54 (d, J = 4.8 Hz, 1H), 4.83 (s, 2H), 4.37 (bs, 2H), 3.85-3.40 (m, 6H), 2.90-2.80 (m, 1H), 2.13 (s, 3H), 1.38 (s, 3H), 1.07 (s, 3H), 0.95-0.75 (m, 2H) |
| 1445 | MS (ESI) m/z 668.45 [M + 1]+; 1H NMR (400 MHz, DMSO-d6) δ 8.79 (s, 1H), 8.76 (d, J = 4.8 Hz, 1H), 8.66 (s, 1H), 7.75 (d, J = 8.4 Hz, 1H), 7.69-7.67 (m, 2H), 7.54 (d, J = 4.8 Hz, 1H), 4.83 (s, 2H), 4.60 (d, J = 48.4 Hz, 2H), 3.80-3.50 (m, 4H), 3.30-2.80 (m, 4H), 2.09 (s, 3H), 1.20-0.80 (m, 4H) |

TABLE 1-continued

7-Aza-Thienylpyridine and Derivative Compounds

| Compound | | Characterization |
|---|---|---|
| 1449 | 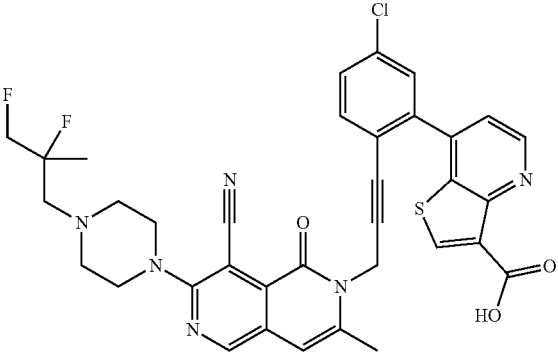 [SMILES: Cc1cc2cnc(N3CCN(CC(C)(F)CF)CC3)c(C#N)c2c(=O)n1CC#Cc1ccc(Cl)cc1-c1ccnc2c(C(=O)O)csc12] | MS (ESI) m/z 688.47 [M + 1]+; 1H NMR (400 MHz, DMSO-d6) δ 8.81 (s, 1H), 8.75 (d, J = 4.8 Hz, 1H), 8.65 (s, 1H), 7.75 (d, J = 8.4 Hz, 1H), 7.69-7.67 (m, 2H), 7.54 (d, J = 4.8 Hz, 1H), 4.83 (s, 2H), 4.72-4.54 (m, 2H), 4.32 (bs, 2H), 3.14-2.67 (m, 8H), 2.10 (s, 3H), 1.48-1.45 (m, 3H) |
| 1450 | 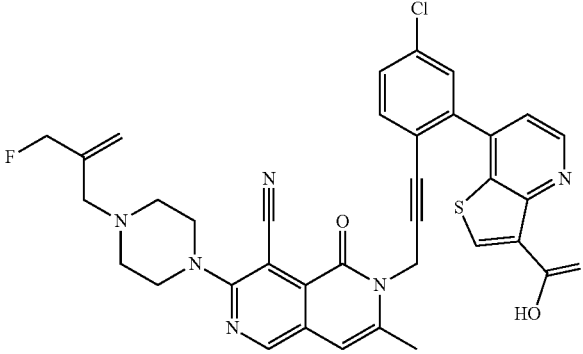 | MS (ESI) m/z 668.42 [M + 1]+; 1H NMR (400 MHz, DMSO-d6) δ 9.74 (bs, 1H), 8.46 (s, 1H), 8.75 (d, J = 4.8 Hz, 1H), 8.65 (s, 1H), 7.76 (d, J = 8.4 Hz, 1H), 7.69-7.66 (m, 2H), 7.54 (d, J = 4.8 Hz, 1H), 5.74 (d, J = 34.0 Hz, 2H), 5.10 (s, 1H), 4.98 (s, 1H), 4.83 (s, 2H), 4.40 (d, J = 20.8 Hz, 2H), 3.96 (bs, 2H), 3.65 (m, 2H), 3.54 (m, 2H), 3.29 (bs, 2H), 2.14 (s, 3H) |
| 1448 | 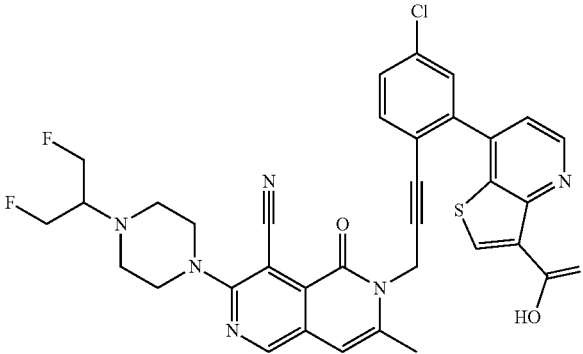 | MS (ESI) m/z 674.2 [M + 1]+; 1H NMR (400 MHz, DMSO-d6) δ 8.81 (s, 1H), 8.75 (d, J = 4.4 Hz, 1H), 8.65 (s, 1H), 7.75 (d, J = 8.0 Hz, 1H), 7.69-7.67 (m, 2H), 7.54 (d, J = 4.8 Hz, 1H), 4.91-4.83 (m, 6H), 4.12 (bs, 1H), 3.79 (bs, 4H), 3.27 (bs, 4H), 2.10 (s, 3H) |
| 1452 | 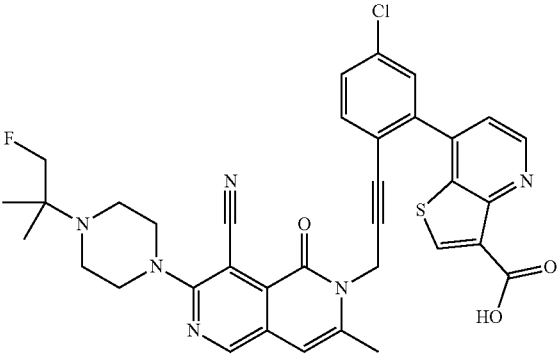 [SMILES: Cc1cc2cnc(N3CCN(C(C)(C)CF)CC3)c(C#N)c2c(=O)n1CC#Cc1ccc(Cl)cc1-c1ccnc2c(C(=O)O)csc12] | MS (ESI) m/z 670.50 [M + 1]+; 1H NMR (400 MHz, DMSO-d6) δ 9.76 (bs, 1H), 8.84 (s, 1H), 8.76 (d, J = 4.4 Hz, 1H), 8.65 (s, 1H), 7.75 (d, J = 8.4 Hz, 1H), 7.70-7.66 (m, 2H), 7.54 (d, J = 4.8 Hz, 2H), 4.83 (s, 2H), 4.72 (d, J = 46.8 Hz, 2H), 4.46 (d, J = 14.0 Hz, 2H), 3.85-3.50 (m, 4H), 3.40-3.30 (m, 2H), 2.15 (s, 3H), 1.40 (s, 6H) |

TABLE 1-continued

7-Aza-Thienylpyridine and Derivative Compounds

| Compound | | Characterization |
|---|---|---|
| 1453 | | MS (ESI) m/z 670.13 [M + 1]+; 1H NMR (400 MHz, DMSO-d6) δ 9.78 (bs, 1H), 8.83 (s, 1H), 8.75 (d, J = 4.8 Hz, 1H), 8.65 (s, 1H), 7.75 (d, J = 8.4 Hz, 1H), 7.71-7.64 (m, 2H), 7.53 (d, J = 4.8 Hz, 1H), 4.83 (s, 2H), 4.32 (bs, 2H), 3.85-3.30 (m, 8H), 2.13 (s, 3H), 1.50 (d, J = 21.2 Hz, 6H) |
| 1451 | | MS (ESI) m/z 664.24 [M + 1]+; 1H NMR (400 MHz, DMSO-d6) δ 8.84 (s, 1H), 8.75 (d, J = 4.8 Hz, 1H), 8.65 (s, 1H), 7.75 (d, J = 8.4 Hz, 1H), 7.70-7.66 (m, 2H), 7.53 (d, J = 4.8 Hz, 1H), 4.83 (s, 2H), 4.36 (m, 2H), 3.71-3.57 (m, 4H), 3.30-3.18 (m, 4H), 2.15 (s, 3H), 2.21 (s, 3H), 0.60-0.51 (m, 4H) |
| 1455 | | MS (ESI) m/z 688.32 [M + 1]+; 1H NMR (400 MHz, DMSO-d6) δ 8.80 (s, 1H), 8.75 (d, J = 4.8 Hz, 1H), 8.66 (s, 1H), 7.75 (d, J = 8.4 Hz, 1H), 7.69-7.67 (m, 2H), 7.54 (d, J = 4.8 Hz, 1H), 6.45-6.14 (m, 1H), 4.82 (s, 2H), 3.98-3.69 (m, 4H), 3.17 (m, 4H), 2.11 (s, 3H), 1.29 (s, 6H) |
| 1456 | | MS (ESI) m/z 674.18 [M + 1]+; 1H NMR (400 MHz, DMSO-d6) δ 13.16 (bs, 1H), 8.84 (s, 1H), 8.75 (d, J = 4.8 Hz, 1H), 8.64 (s, 1H), 7.75 (d, J = 8.4 Hz, 1H), 7.67 (t, J = 8.4 Hz, 2H), 7.53 (d, J = 4.8 Hz, 1H), 6.26 (t, J = 56 Hz, 1H), 4.83 (s, 2H), 4.36 (bs, 2H), 3.73 (bs, 2H), 3.37 (bs, 6H), 2.40 (bs, 2H), 2.13 (s, 3H) |

TABLE 1-continued

7-Aza-Thienylpyridine and Derivative Compounds

| Compound | | Characterization |
|---|---|---|
| 1454 | 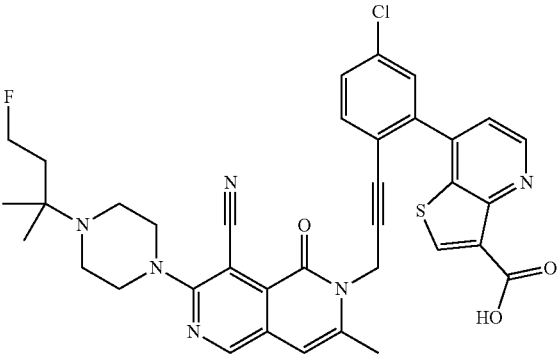 [SMILES: Cc1cc2cnc(N3CCN(C(C)(C)CCF)CC3)c(C#N)c2c(=O)n1CC#Cc1ccc(Cl)cc1-c1ccnc2c(C(=O)O)csc12] | MS (ESI) m/z 684.48 [M + 1]+; 1H NMR (400 MHz, DMSO-d6) δ 8.84 (s, 1H), 8.75 (d, J = 4.8 Hz, 1H), 8.65 (s, 1H), 7.75 (d, J = 8 Hz, 1H), 7.70-7.66 (m, 2H), 7.54 (d, J = 4.8 Hz, 1H), 4.83 (s, 2H), 4.74-4.60 (m, 2H), 4.47 (d, J = 13.6 Hz, 2H), 3.75 (d, J = 11.2 Hz, 2H), 3.60-3.53 (m, 2H), 3.31-3.28 (m, 2H), 2.21-2.15 (m, 5H) 1.42 (s, 6H) |
| 1458 | 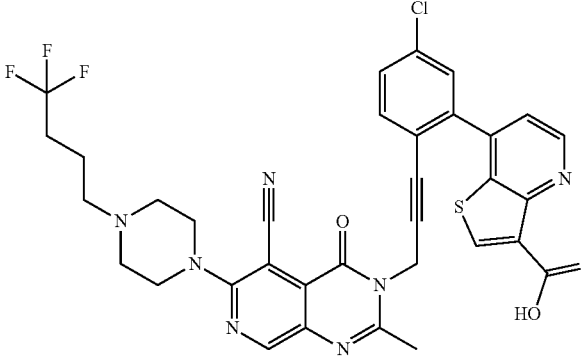 | MS (ESI) m/z 706.49 [M + 1]+; 1H NMR (400 MHz, DMSO-d6) δ 12.96 (bs, 1H), 8.84 (s, 1H), 8.76 (d, J = 4.8 Hz, 1H), 8.64 (s, 1H), 7.76 (d, J = 8.4 Hz, 1H), 7.69 (dd, J = 8.4, 2.0 Hz, 1H), 7.65 (d, J = 2.0 Hz, 1H), 7.53 (d, J = 4.8 Hz, 1H), 4.84 (s, 2H), 4.40-4.36 (m, 2H), 3.74-3.72 (m, 2H), 3.29 (bs, 6H), 2.45-2.38 (m, 2H), 2.14 (s, 3H), 1.98-1.93 (m, 2H) |
| 1459 | 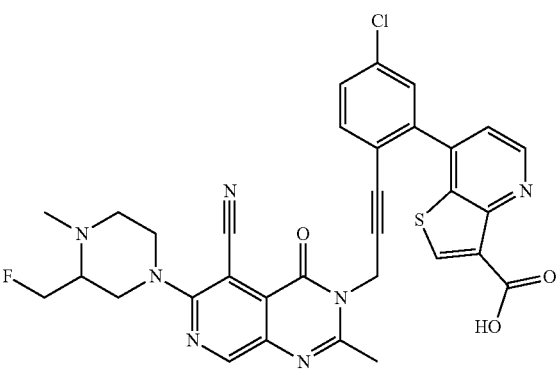 [SMILES: Cc1nc2cnc(N3CCN(C)C(CF)C3)c(C#N)c2c(=O)n1CC#Cc1ccc(Cl)cc1-c1ccnc2c(C(=O)O)csc12] | MS (ESI) m/z 642.17 [M + 1]+; 1H NMR (400 MHz, DMSO-d6) δ 8.85 (s, 1H), 8.76 (d, J = 4.8 Hz, 1H), 8.65 (s, 1H), 7.75 (d, J = 8.0 Hz, 1H), 7.69 (dd, J = 8.4 Hz, 2.0 Hz, 1H), 7.65 (s, 1H), 7.53 (d, J = 4.8 Hz, 1H), 5.12-4.93 (m, 2H), 4.84 (s, 2H), 4.44 (dd, J = 42.4 Hz, 14.4 Hz, 1H), 3.54-3.51 (m, 4H), 3.00 (s, 3H), 2.50-2.43 (m, 1H), 2.14 (s, 3H) |
| 1457 | 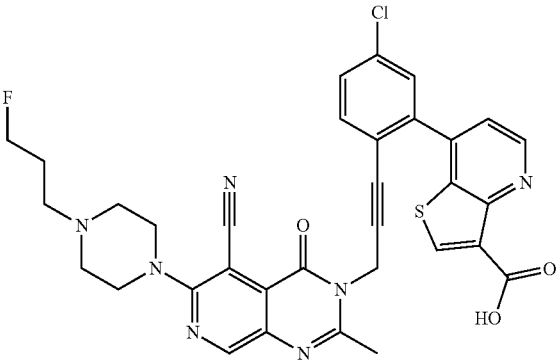 | MS (ESI) m/z 656.39 [M + 1]+; 1H NMR (400 MHz, DMSO-d6) δ 8.84 (s, 2H), 8.75 (d, J = 4.8 Hz, 1H), 8.64 (s, 1H), 7.75 (d, J = 8.4 Hz, 1H), 7.70-7.65 (m, 2H), 7.53 (d, J = 4.8 Hz, 1H), 4.83 (s, 2H), 4.65-4.50 (m, 2H), 4.38 (d, J = 13.6 Hz, 2H), 3.46 (bs, 4H), 3.32 (bs, 4H), 2.19-2.06 (m, 5H) |

TABLE 1-continued

7-Aza-Thienylpyridine and Derivative Compounds

| Compound | Characterization |
|---|---|
| 1461 | MS (ESI) m/z 633.40 [M + 1]+; 1H NMR (400 MHz, DMSO-d6) δ 13.05 (bs, 1H), 9.51 (bs, 1H), 9.12 (s, 1H), 8.74 (d, J = 4.8 Hz, 1H), 8.61 (s, 1H), 7.76 (d, J = 9.1 Hz, 1H), 7.81-7.67 (m, 2H), 7.55 (d, J = 4.8 Hz, 1H), 6.56 (s, 1H), 4.87 (s, 2H), 4.30-4.10 (m, 2H), 3.80 (bs, 1H), 3.01 (bs, 4H), 2.19 (s, 3H), 1.10-0.84 (m, 4H) |
| 1462 | MS (ESI) m/z 639.37 [M + 1]+; 1H NMR (400 MHz, DMSO-d6) δ 13.07 (bs, 1H), 10.26 (bs, 1H), 9.12 (s, 1H), 8.75 (d, J = 4.8 Hz, 1H), 8.61 (s, 1H), 7.76 (d, J = 8.8 Hz, 1H), 7.71-7.66 (m, 2H), 7.55 (d, J = 4.8 Hz, 1H), 6.57 (s, 1H), 5.00-4.85 (m, 4H), 4.29-3.95 (m, 2H), 3.90-3.80 (m, 2H), 3.60-3.45 (m, 2H), 3.10-2.90 (m, 2H), 2.18 (s, 3H) |
| 1460 | MS (ESI) m/z 708.44 [M + 1]+; 1H NMR (400 MHz, DMSO-d6) δ 8.85 (s, 1H), 8.76 (d, J = 4.8 Hz, 1H), 8.65 (s, 1H), 7.75 (d, J = 8.0 Hz, 1H), 7.70-7.66 (m, 2H), 7.53 (d, J = 4.8 Hz, 1H), 4.84 (s, 2H), 4.66-4.36 (m, 5H), 3.91-3.78 (m, 4H), 2.95 (bs, 3H), 2.13 (s, 3H) |
| 1464 | MS (ESI) m/z 690.43 [M + 1]+; 1H NMR (400 MHz, DMSO-d6) δ 13.04 (bs, 1H), 8.81-8.75 (m, 2H), 8.65 (s, 1H), 7.75 (d, J = 8.4 Hz, 1H), 7.68 (d, J = 10.0 Hz, 1H), 7.53 (d, J = 4.4 Hz, 1H), 4.83 (s, 2H), 4.36-4.02 (m, 4H), 3.69-3.59 (m, 4H), 3.36-2.9 (m, 4H), 2.11 (s, 3H) |

TABLE 1-continued

7-Aza-Thienylpyridine and Derivative Compounds

| Compound | | Characterization |
|---|---|---|
| 1465 | 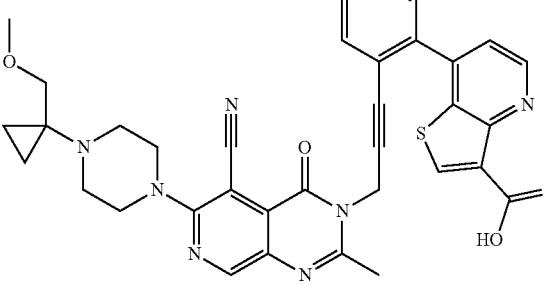 | MS (ESI) m/z 680.51 [M + 1]+; 1H NMR (400 MHz, DMSO-d6) δ 8.83 (s,1H), 8.76 (d, J = 4.8 Hz, 1H), 8.65 (s, 1H), 7.75 (d, J = 8.0 Hz, 1H), 7.70-7.67 (m, 2H), 7.55 (d, J = 4.8 Hz, 1H), 4.83 (s, 2H), 4.49-4.43 (m, 2H), 3.76-3.46 (m, 8H), 3.26 (s, 3H), 2.49 (s, 1H), 2.12 (s, 3H), 1.25 (bs, 2H), 0.97 (bs, 2H) |
| 1463 | 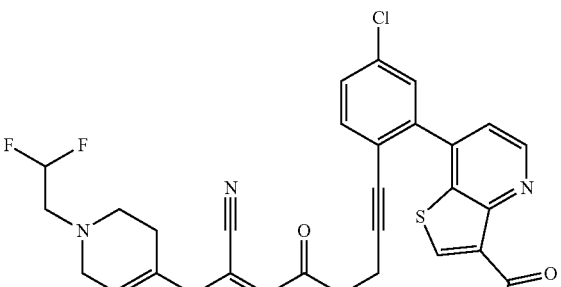 | MS (ESI) m/z 657.40 [M + 1]+; 1H NMR (400 MHz, DMSO-d6) δ 9.10 (s, 1H), 8.75 (d, J = 4.8 Hz, 1H), 8.62 (s, 1H), 7.76 (d, J = 9.2 Hz, 1H), 7.70-7.68 (m, 2H), 7.54 (d, J = 4.8 Hz, 1H), 6.62-6.34 (m, 2H), 4.86 (s, 2H), 3.41-3.24 (m, 4H), 3.15-2.95 (m, 2H), 2.87 (bs, 2H), 2.16 (s, 3H) |
| 1467 | 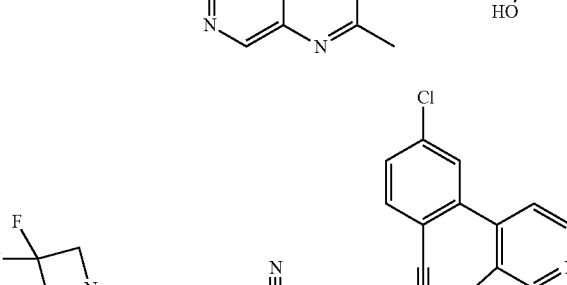 | MS (ESI) m/z 686.19 [M + 1]+; 1H NMR (400 MHz, DMSO-d6) δ 8.77-8.74 (m, 2H), 8.64 (s, 1H), 7.75 (d, J = 9.2 Hz, 1H), 7.69-7.67 (m, 2H), 7.54 (d, J = 4.8 Hz, 1H), 4.82 (s, 2H), 4.57-4.55 (m, 4H), 4.24 (d, 2H), 3.21-3.15 (m, 2H), 2.41 (s, 1H), 2.08-2.04 (m, 5H), 1.55 (s, 2H) |
| 1468 | 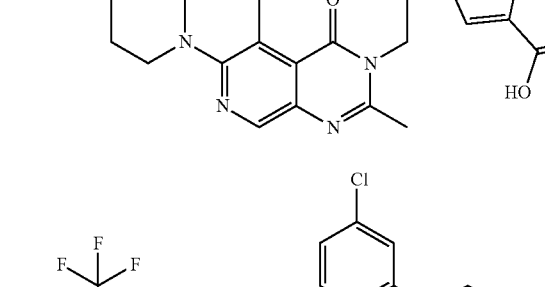 | MS (ESI) m/z 661.37 [M + 1]+; 1H NMR (400 MHz, DMSO-d6) δ 13.02 (bs, 1H), 9.07 (s, 1H), 8.76 (s, 1H), 8.61 (s, 1H), 7.76 (d, J = 8.0 Hz, 1H), 7.69 (s, 2H), 7.53 (s, 1H), 4.87 (s, 2H), 3.90 (s, 2H), 3.50-3.30 (m, merged, 2H), 2.55 (s, 3H), 2.09 (s, 3H) |

TABLE 1-continued

7-Aza-Thienylpyridine and Derivative Compounds

| Compound | Characterization |
|---|---|
| 1466 | MS (ESI) m/z 674.47 [M + 1]+; 1; H NMR (400 MHz, DMSO-d6) δ 8.80 (s, 1H), 8.75 (d, J = 4.8 Hz, 1H), 8.65 (s, 1H), 7.75 (d, J = 8.4 Hz, 1H), 7.69 (bs, 1H), 7.67 (s, 1H), 7.53 (d, J = 4.4 Hz, 1H), 6.31 (t, J = 53.2 Hz, 1H), 4.82 (s, 2H), 3.79 (bs, 4H), 3.11 (bs, 4H), 2.64-2.59 (m, 1H), 2.09 (s, 3H), 1.21 (bs, 3H) |
| 1470 | MS (ESI) m/z 674.44 [M + 1]+; 1H NMR (400 MHz, DMSO-d6) δ 9.74 (bs, 1H), 8.83 (d, J = 4.8 Hz, 1H), 8.70 (s, 1H), 8.44 (s, 1H), 7.61-7.58 (dd, J = 2.4, 8.8 Hz, 1H), 7.47 (d, J = 4.8 Hz, 1H), 7.41 (d, J = 2.4 Hz, 1H), 7.38 (d, J = 8.8 Hz, 1H), 5.73 (d, J = 30.4 Hz, 2H), 5.09 (s, 1H), 4.98 (s, 1H), 4.40 (d, J = 4.8 Hz, 2H), 4.31 (bs, 2H), 4.24 (d, J = 4.8 Hz, 2H), 3.96 (bs, 2H), 3.63 (m, 2H), 3.32-3.18 (m, 4H), 1.84 (s, 3H) |
| 1471 | MS (ESI) m/z 724.09 [M + 1]+; 1H NMR (400 MHz, DMSO-d6) δ 8.82 (d, J = 4.8 Hz, 1H), 8.70 (s, 1H), 8.45 (s, 1H), 7.60 (dd, J = 2.4, 8.8 Hz, 1H), 7.46 (d, J = 4.8 Hz, 1H), 7.41 (d, J = 2.4 Hz, 1H), 7.36 (d, J = 8.8 Hz, 1H), 4.39 (s, 2H), 4.32-4.23 (m, 4H), 3.28-2.86 (m, 4H), 1.83 (s, 3H), 1.30-1.21 (m, 4H) |
| 1469 | MS (ESI) m/z 704.21 [M + 1]+; 1H NMR (400 MHz, DMSO-d6) δ 8.83 (d, J = 4.9 Hz, 1H), 8.70 (s, 1H), 8.40 (s, 1H), 7.55 (dd, J = 2.4, 8.8 Hz, 1H), 7.50 (d, J = 4.9 Hz, 1H), 7.31 (d, J = 2.8 Hz, 2H), 4.46 (t, J = 4.9 Hz, 2H), 4.34 (t, J = 4.9 Hz, 2H), 4.10 (bs, 4H), 3.72 (bs, 4H), 3.61 (s, 2H), 2.11 (s, 3H), 1.99-1.80 (m, 4H), 1.03 (t, J = 7.4 Hz, 6H) |

TABLE 1-continued

7-Aza-Thienylpyridine and Derivative Compounds

| Compound | | Characterization |
|---|---|---|
| 1473 | 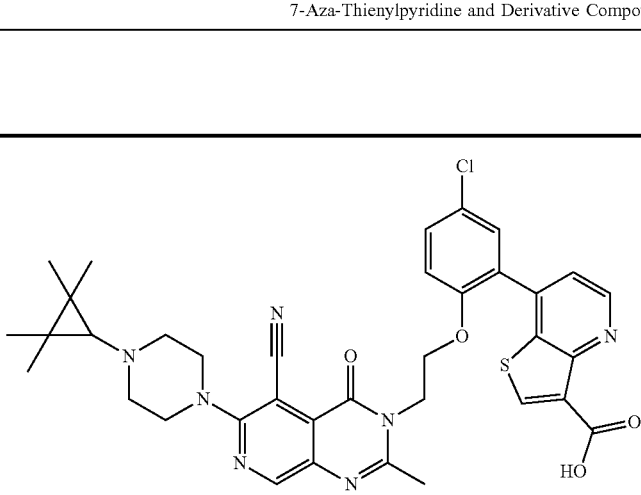 | MS (ESI) m/z 698.22 [M + 1]+; 1H NMR (400 MHz, DMSO-d6) δ 8.82 (d, J = 4.8 Hz, 1H), 8.69 (bs, 1H), 8.45 (s, 1H), 7.59 (dd, J = 2.4, 9.2 Hz, 1H), 7.45 (d, J = 4.8 Hz, 1H), 7.42 (d, J = 2.4 Hz, 1H), 7.36 (d, J = 9.2 Hz, 1H), 4.39 (s, 2H), 4.22 (s, 4H), 3.54 (bs, 6H), 1.98-1.64 (m, 2H), 1.18 (d, J = 7.2 Hz, 2H), 1.10-1.05 (m, 12H) |
| 1474 | 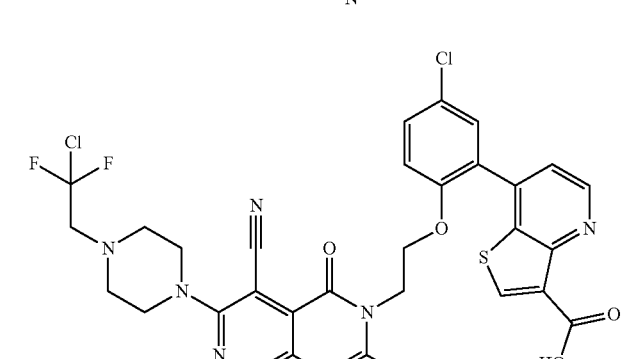 | MS (ESI) m/z 700.44 [M + 1]+; 1H NMR (400 MHz, DMSO-d6) δ 8.82 (d, J = 5.2 Hz, 1H), 8.60 (s, 1H), 8.43 (s, 1H), 7.59-7.57 (dd, J = 2.4, 10.8 Hz, 1H), 7.49 (d, J = 4.8 Hz, 1H), 7.39 (d, J = 2.4 Hz, 1H), 7.35 (d, J = 9.2 Hz, 1H), 4.36 (s, 2H), 4.19 (s, 2H), 3.65 (m, 4H), 4.44-3.38 (m, 2H), 2.87 (bs, 4H), 1.77 (s, 3H) |
| 1472 | 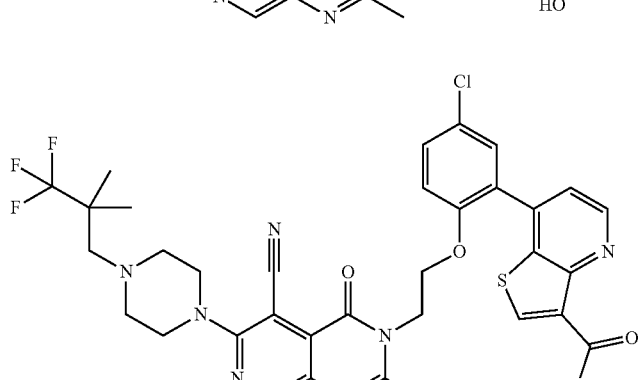 | MS (ESI) m/z 726.18 [M + 1]+; 1H NMR (400 MHz, DMSO-d6) δ 8.82 (d, J = 4.8 Hz, 1H), 8.66 (bs, 1H), 8.45 (s, 1H), 7.59 (dd, J = 2.4, 9.2 Hz, 1H), 7.47 (d, J = 4.8 Hz, 1H), 7.42 (d, J = 2.4 Hz, 1H), 7.36 (d, J = 9.2 Hz, 1H), 4.38 (s, 2H), 4.21 (s, 2H), 3.75 (bs, 8H), 2.71 (s, 2H), 1.76 (s, 3H), 1.15 (s, 6H) |
| 1476 | 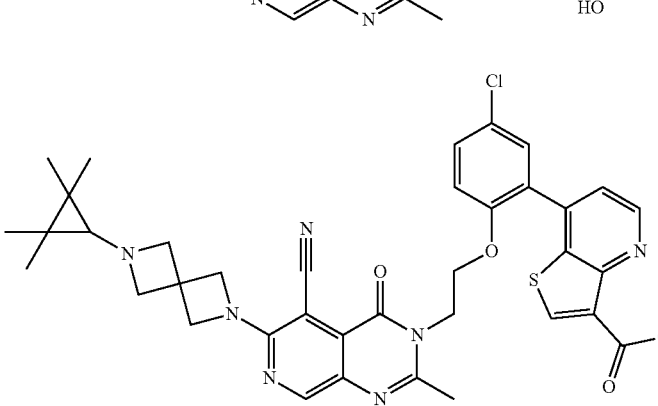 | MS (ESI) m/z 710.49 [M + 1]+; 1H NMR (400 MHz, DMSO-d6) δ 8.90 (bs, 1H), 8.81 (d, J = 5.2 Hz, 1H), 8.61 (s, H), 8.47 (s, 1H), 7.60 (dd, J = 8.8, 2.4 Hz, 1H), 7.46 (d, J = 4.8 Hz, 1H), 7.43 (d, J = 2.8 Hz, 1H), 7.36 (d, J = 8.8 Hz, 1H), 4.63 (s, 2H), 4.59-4.47 (m, 6H), 4.38 (t, J = 4.4 Hz, 2H), 4.21 (d, J = 4.8 Hz, 2H), 2.70 (s, 1H), 1.81 (s, 3H), 1.09 (s, 6H), 1.07 (s, 6H) |

TABLE 1-continued

7-Aza-Thienylpyridine and Derivative Compounds

| Compound | | Characterization |
|---|---|---|
| 1477 | 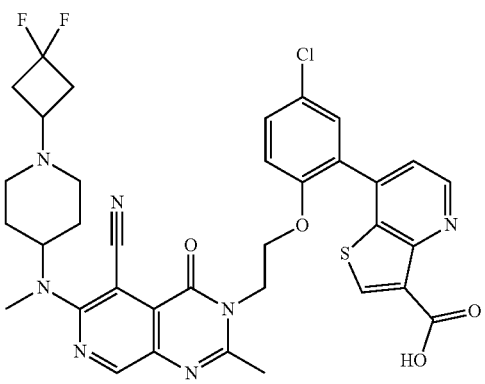 [SMILES: Cc1nc2cnc(N(C)C3CCN(C4CC(F)(F)C4)CC3)c(C#N)c2c(=O)n1CCOc1ccc(Cl)cc1-c1ccnc2c(C(=O)O)csc12] | MS (ESI) m/z 720.50 [M + 1]+; 1H NMR (400 MHz, DMSO-d6) δ 13.35 (bs, 1H), 8.82 (d, J = 4.8 Hz, 1H), 8.61 (s, 1H), 8.40 (s, 1H), 7.59 (dd, J = 2.40, 8.8 Hz, 1H), 7.47 (d, J = 4.4 Hz, 1H), 7.42 (d, J = 2.8 Hz, 1H), 7.36 (d, J = 8.8 Hz, 1H), 4.53 (bs, 1H), 4.39 (bs, 2H), 4.21 (bs, 2H), 3.74 (bs, 1H), 3.58 (bs, 2H), 3.09 (bs, 9H), 2.10 (bs, 4H), 1.77 (s, 3H) |
| 1475 | 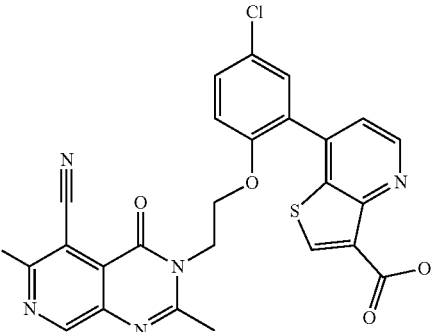 | MS (ESI) m/z 704.47 [M + 1]+; 1H NMR (400 MHz, DMSO-d6) δ 8.81 (d, J = 4.8 Hz, 1H), 8.60 (s, 1H), 8.47 (s, 1H), 7.59 (dd, J = 9.2, 2.8 Hz, 1H), 7.46 (d, J = 4.8 Hz, 1H), 7.42 (d, J = 2.4 Hz, 1H), 7.35 (d, J = 9.2 Hz, 1H), 4.53 (bs, 4H), 4.45-4.35 (m, 2H), 4.25-4.15 (m, 2H), 3.60-3.45 (m, 1H), 3.20-2.70 (m, 4H), 2.60-2.40 (m, merged, 4H), 1.81 (s, 3H) |
| 1479 | 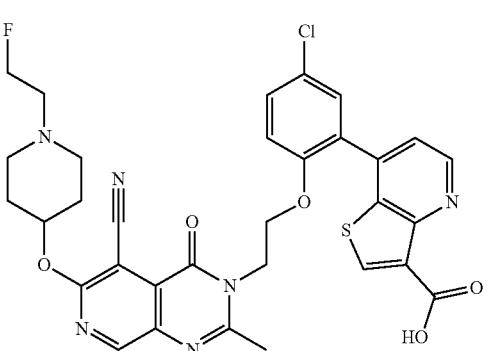 | MS (ESI) m/z 663.41 [M + 1]+; 1H NMR (400 MHz, DMSO-d6) δ 8.83 (d, J = 4.8 Hz, 1H), 8.72 (s, 1H), 8.37 (s, 1H), 7.60 (d, J = 8.4 Hz, 1H), 7.47 (d, J = 4.4 Hz, 1H), 7.42 (bs, 1H), 7.36 (d, J = 8.8 Hz, 1H), 5.47 (d, J = 48.4 Hz, 1H), 4.93 (bs, 1H), 4.82 (bs, 1H), 4.39 (bs, 2H), 4.24 (bs, 2H), 3.68 (bs, 4H), 3.37-3.27 (m, 4H), 2.29-2.10 (m, 1H), 2.01-1.98 (m, 1H), 1.82-1.77 (m, 3H) |
| 1480 | 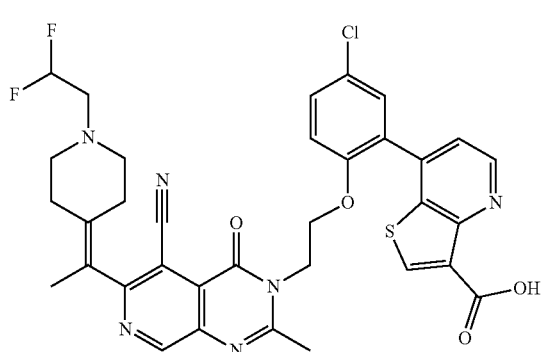 | MS (ESI) m/z 691.44 [M + 1]+; 1H NMR (400 MHz, DMSO-d6) δ 9.00 (s, 1H), 8.84 (d, J = 4.8 Hz, 1H), 8.39 (s, 1H), 7.61-7.58 (dd, J = 2.8, 8.8 Hz, 1H), 7.48-7.45 (dd, J = 10.8, 8.8 Hz, 2H), 7.37 (d, J = 9.2 Hz, 1H), 6.46 (m, 1H), 4.40 (t, 2H), 4.25 (bs, 2H), 3.07-2.97 (m, 8H), 2.22 (m, 2H), 2.06 (s, 3H), 1.79 (s, 3H) |

… TABLE 1-continued

7-Aza-Thienylpyridine and Derivative Compounds

| Compound | | Characterization |
|---|---|---|
| 1478 | 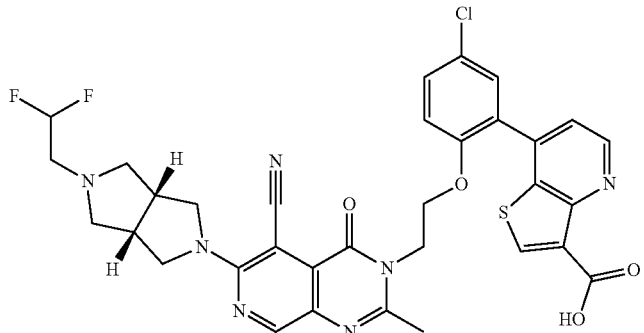 | MS (ESI) m/z 692.2 [M + 1]+; 1H NMR (400 MHz, DMSO-d6) δ 8.81 (d, J = 4.8 Hz, 1H), 8.62 (s, 1H), 8.47 (s, 1H), 7.60 (dd, J = 9.2, 2.8 Hz, 1H), 7.45 (d, J = 4.8 Hz, 1H), 7.43 (d, J = 2.4 Hz, 1H), 7.36 (d, J = 9.2 Hz, 1H), 6.41 (t, J = 53.6 Hz, 1H), 4.38-4.37 (m, 2H), 4.21 (s, 2H), 3.91 (bs, 6H), 3.17 (s, 4H), 3.03-2.81 (m, 2H), 1.79 (s, 3H) |
| 1482 | 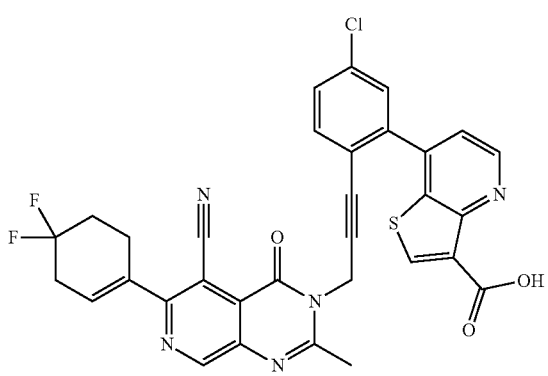 [SMILES: Cc1nc2cnc(C3=CCC(F)(F)CC3)c(C#N)c2c(=O)n1CC#Cc1ccc(Cl)cc1-c1ccnc2c(C(=O)O)csc12] | MS (ESI) m/z 628.33 [M + 1]+; 1H NMR (400 MHz, DMSO-d6) δ 13.04 (bs, 1H), 9.07 (s, 1H), 8.76 (d, J = 4.8 Hz, 1H), 8.61 (s, 1H), 7.77 (d, J = 9.2 Hz, 1H), 7.69 (t, J = 3.2 Hz, 1H), 7.54 (d, J = 4.4 Hz, 1H), 6.33 (s, 1H), 4.86 (s, 2H), 2.89-2.84 (m, 4H), 2.29-2.22 (m, 2H), 2.14 (s, 3H) |
| 1483 | 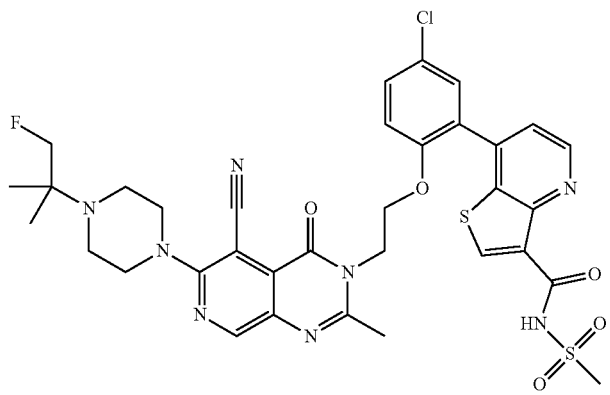 [SMILES: Cc1nc2cnc(N3CCN(C(C)(C)CF)CC3)c(C#N)c2c(=O)n1CCOc1ccc(Cl)cc1-c1ccnc2c(C(=O)NS(C)(=O)=O)csc12] | MS (ESI) m/z 753.43 [M + 1]+; 1H NMR (400 MHz, DMSO-d6) δ 12.65 (s, 1H), 9.87 (bs, 1H), 8.90 (d, J = 4.8 Hz, 1H), 8.76 (s, H), 8.55 (s, 1H), 7.63 (dd, J = 8.8, 2.4 Hz, 1H), 7.57 (d, J = 4.8 Hz, 1H), 7.44-7.37 (m, 2H), 4.73 (d, J = 46.0 Hz, 2H), 4.50-4.35 (m, 4H), 4.23 (s, 2H), 3.80-3.50 (m, 7H), 3.45-3.22 (m, 2H), 1.85 (s, 3H), 1.42 (s, 6H) |
| 1481 | 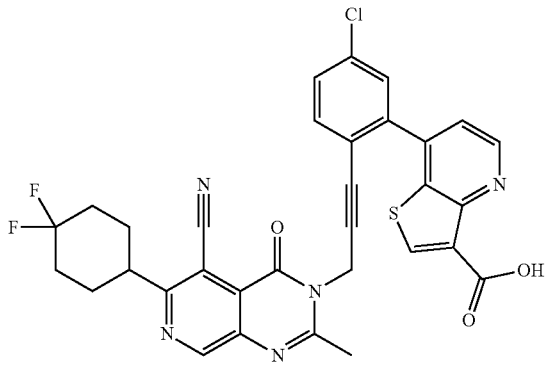 [SMILES: Cc1nc2cnc(C3CCC(F)(F)CC3)c(C#N)c2c(=O)n1CC#Cc1ccc(Cl)cc1-c1ccnc2c(C(=O)O)csc12] | MS (ESI) m/z 630.38 [M + 1]+; 1H NMR (400 MHz, DMSO-d6) δ 9.11 (s, 1H), 8.57 (d, J = 4.8 Hz, 1H), 8.61 (s, 1H), 7.77-7.75 (m, 1H), 7.69 (dd, J = 2.0, 6.8 Hz, 2H), 7.54 (d, J = 4.8 Hz, 1H), 4.86 (s, 2H), 2.53 (s, 1H), 2.17-2.15 (m, 3H), 2.08-2.06 (m, 2H), 2.01 (d, J = 5.6 Hz, 6H) |

TABLE 1-continued

7-Aza-Thienylpyridine and Derivative Compounds

| Compound | | Characterization |
|---|---|---|
| 1485 | 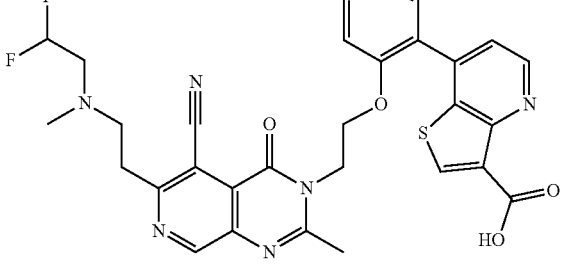 | MS (ESI) m/z 639.38 [M + 1]+; 1H NMR (400 MHz, DMSO-d6) δ 8.96 (s, 1H), 8.82 (d, J = 4.4 Hz, 1H), 8.34 (s, 1H), 7.60 (dd, J = 9.2, 2.8 Hz, 1H), 7.47 (d, J = 4.8 Hz, 1H), 7.43 (d, J = 2.8 Hz, 1H), 7.36 (d, J = 9.2, 1H), 6.36 (t, J = 49.2 Hz, 1H), 4.40 (t, J = 4.8 Hz, 2H), 4.27-4.26 (m, 2H), 3.43 (bs, 4H), 2.73 (bs, 2H), 1.82 (s, 3H) |
| 1486 | 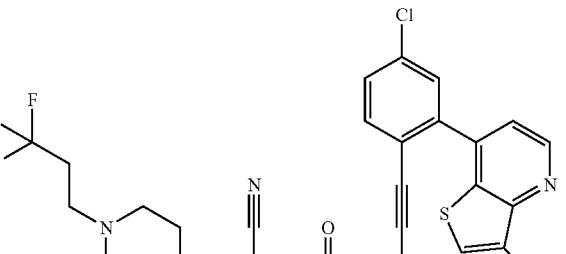 | MS (ESI) m/z 769.56 [M + 1]+ |
| 1484 | 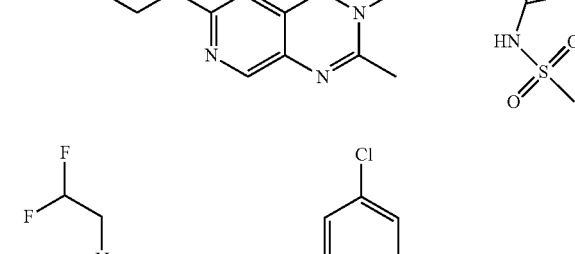 | MS (ESI) m/z 679.16 [M + 1]+; 1H NMR (400 MHz, DMSO-d6) δ 9.85 (bs, 1H), 8.96 (s, 1H), 8.82 (d, J = 4.8 Hz ,1H), 8.33 (s, 1H), 7.60 (dd, J = 2.4, 8.8 Hz, 2H), 7.47-7.43 (m, 1H), 7.36 (d, J = 8.8 Hz ,1H), 6.66-6.39 (m, 1H), 4.39 (t, J = 4.4 Hz ,2H), 4.25 (bs, 2H), 3.66-3.51 (m, 4H), 3.05 (d, J = 5.6 Hz, 4H), 2.19 (bs, 1H), 1.80 (s, 6H), 1.63-1.60 (m, 2H) |
| 1488 | 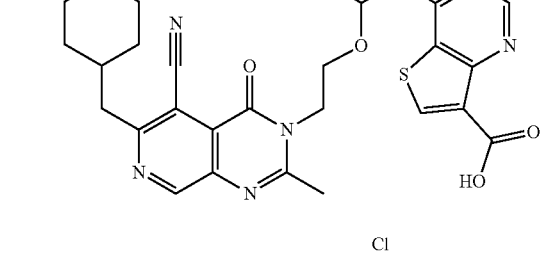 | MS (ESI) m/z 719.44 [M + 1]+; 1H NMR (400 MHz, DMSO-d6) δ 12.45 (s, 1H), 10.12 (bs, 1H), 8.89 (s, 1H), 8.82 (d, J = 4.8 Hz, 1H), 8.79 (s, 1H), 7.77 (d, J = 8.4 Hz, 1H), 7.72-7.69 (m, 1H), 7.66 (d, J = 1.6 Hz, 1H), 7.62 (d, J = 4.8 Hz, 1H), 5.00-4.80 (m, 2H), 4.35 (bs, 2H), 3.82-3.60 (m, 4H), 3.55 (s, 3H), 3.50-3.22 (m, 4H), 2.03 (s, 3H) |

TABLE 1-continued

7-Aza-Thienylpyridine and Derivative Compounds

| Compound | | Characterization |
|---|---|---|
| 1489 | 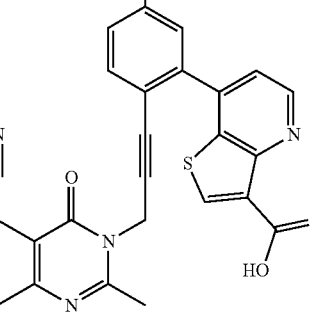 | MS (ESI) m/z 698.22 [M + 1]+; 1H NMR (400 MHz, DMSO-d6) δ 8.80 (s, 1H), 8.75 (d, J = 4.8 Hz, 1H), 8.65 (s, 1H), 7.75 (d, J = 8.4 Hz, 1H), 7.68 (d, J = 9.2 Hz, 2H), 7.53 (d, J = 4.4 Hz, 1H), 4.83 (s, 2H), 3.59 (bs, 2H), 3.09 (bs, 8H), 5.19 (s, 5H), 1.82 (bs, 1H) |
| 1487 | 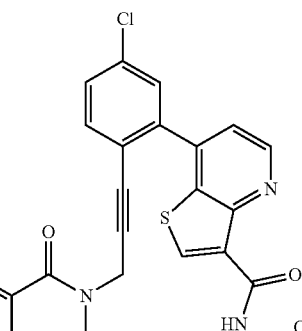 | MS (ESI) m/z 737.44 [M + 1]+; 1H NMR (400 MHz, DMSO-d6) δ 12.44 (bs, 1H), 8.84-8.80 (m, 3H), 7.77 (d, J = 8.4 Hz, 1H), 7.71-7.66 (m, 2H), 7.61 (d, J = 4.8 Hz, 1H), 6.32 (t, J = 52.0 Hz, 1H), 4.83 (s, 2H), 3.75 (bs, 4H), 3.56 (bs, 3H), 2.95 (bs, 6H), 2.01 (s, 3H) |
| 1491 | 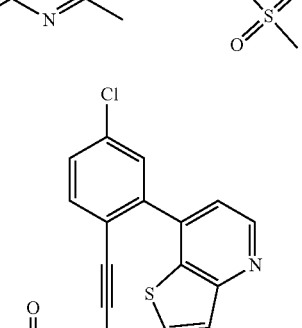 | MS (ESI) m/z 680.42 [M + 1]+; 1H NMR (400 MHz, DMSO-d6) d 8.76 (d, J = 4.8 Hz, 1H), 8.68 (d, J = 8.8 Hz, 2H), 7.75 (d, J = 8.8 Hz, 1H), 7.68 (d, J = 6.4 Hz, 2H), 7.55 (d, J = 4.8 Hz, 1H), 4.81 (s, 2H), 3.82 (t, J = 6.8 Hz, 2H), 3.33-3.25 (m, 5H), 2.92 (t, J = 6.8 Hz, 2H), 2.45 (s, 3H), 2.04 (s, 3H) |
| 1492 | 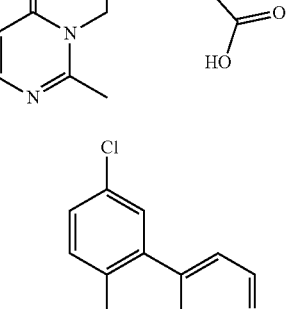 | MS (ESI) m/z 633.31 [M + 1]+; 1H NMR (400 MHz, DMSO-d6) δ 9.11 (s, 1H), 8.73 (d, J = 4.8 Hz 1H), 8.59 (s, 1H), 7.76 (d, J = 8.4 Hz, 1H), 7.70-7.67 (m, 2H), 7.54 (d, J = 4.8 Hz, 1H), 6.40 (t, J = 50.8 Hz, 1H), 4.87 (s, 2H), 3.49 (bs, 4H), 3.12-2.77 (m, 5H), 2.17 (s, 3H) |

TABLE 1-continued

7-Aza-Thienylpyridine and Derivative Compounds

| Compound | | Characterization |
|---|---|---|
| 1490 | 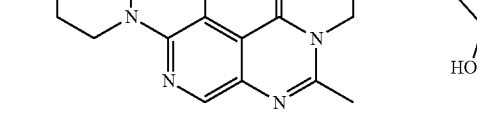 | MS (ESI) m/z 700.41 [M + 1]+; 1H NMR (400 MHz, DMSO-d6) δ 10.35 (s, 1H), 8.78 (s, 1H), 8.75 (d, J = 4.4 Hz, 1H), 8.64 (s, 1H), 7.76 (d, J = 8.0 Hz, 1H), 7.69 (d, J = 9.6 Hz, 2H), 7.54 (d, J = 4.8 Hz, 1H), 6.39 (bs, 1H), 4.83 (s, 2H), 4.37-4.08 (m, 4H), 3.87 (bs, 4H), 3.26 (bs, 2H), 2.18 (bs, 4H), 2.10 (s, 3H) |
| 1494 | 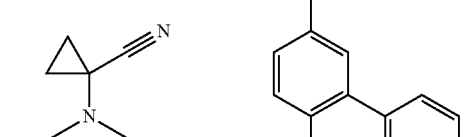 | MS (ESI) m/z 689.42 [M + 1]+; 1H NMR (400 MHz, DMSO-d6) δ 8.77 (d, J = 4.8 Hz, 1H), 8.73 (s, 1H), 8.66 (s, 1H), 7.76 (d, J = 9.2 Hz, 1H), 7.69-7.68 (m, 2H), 7.55 (d, J = 4.4 Hz, 1H), 4.82 (s, 2H), 4.30 (s, 1H), 3.06-3.01 (m, 7H), 2.06 (s, 3H), 1.86-1.83 (m, 4H), 1.25 (dd, J = 8.0 Hz, 5.6 Hz, 2H), 1.05 (dd, J = 7.2, 4.8 Hz, 2H) |
| 1495 | 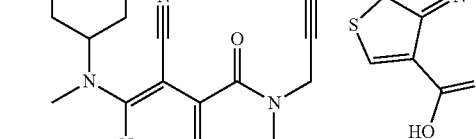 | MS (ESI) m/z 638.41 [M + 1]+; 1H NMR (400 MHz, DMSO-d6) δ 8.79-8.74 (m, 2H), 8.65 (s, 1H), 7.78 (d, J = 8.0 Hz, 1H), 7.70-7.68 (m, 2H), 7.55 (d, J = 4.8 Hz, 1H), 4.83 (s, 2H), 4.54-4.53 (m, 1H), 3.58-3.55 (m, 2H), 3.20 (bs, 2H), 3.01 (s, 3H), 2.83-2.82 (m, 3H), 2.10 (bs, 7H) |
| 1493 | 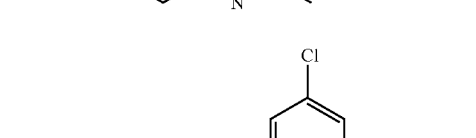 | MS (ESI) m/z 700.47 [M + 1]+; 1H NMR (400 MHz, DMSO-d6) δ 8.82 (s, 1H), 8.75 (d, J = 4.8 Hz, 1H), 8.65 (s, 1H), 7.75 (d, J = 8.0 Hz, 1H), 7.70-7.67 (m, 2H), 7.54 (d, J = 4.8 Hz, 1H), 4.83 (s, 2H), 4.43-3.90 (m, 4H), 3.22-2.87 (m, 8H), 2.13 (s, 3H), 1.46 (s, 3H) |

TABLE 1-continued

7-Aza-Thienylpyridine and Derivative Compounds

| Compound | | Characterization |
|---|---|---|
| 1497 | 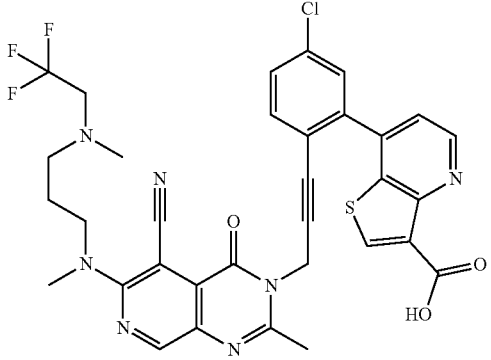 [SMILES: Cc1nc2cnc(N(C)CCCN(C)CC(F)(F)F)c(C#N)c2c(=O)n1CC#Cc1ccc(Cl)cc1-c1ccnc2c(C(=O)O)csc12] | MS (ESI) m/z 694.46 [M + 1]+; 1H NMR (400 MHz, DMSO-d6) δ 8.76 (d, J = 4.8 Hz, 1H), 8.69 (d, J = 6.8 Hz, 1H), 7.76-7.43 (m, 1H), 7.68 (dd, J = 2.0, 4.0 Hz, 1H), 7.54 (d, J = 4.8 Hz, 1H), 4.81 (s, 2H), 3.73-3.70 (m, 2H), 3.27 (bs, 5H), 2.68-2.64 (m, 2H), 2.41 (s, 3H), 2.05 (s, 3H), 1.90 (t, J = 13.6 Hz, 2H) |
| 1498 | 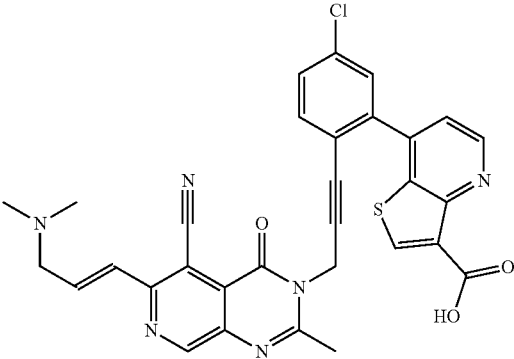 [SMILES: Cc1nc2cnc(/C=C/CN(C)C)c(C#N)c2c(=O)n1CC#Cc1ccc(Cl)cc1-c1ccnc2c(C(=O)O)csc12] | MS (ESI) m/z 595.39 [M + 1]+; 1H NMR (400 MHz, DMSO-d6) δ 13.11 (bs, 1H), 9.73 (bs, 1H), 9.14 (s, 1H), 8.73 (d, J = 4.8 Hz, 1H), 8.60 (s, 1H), 7.76 (d, J = 9.2 Hz, 1H), 7.71-7.67 (m, 2H), 7.54 (d, J = 4.8 Hz, 1H), 7.39 (d, J = 15.2 Hz, 1H), 7.20-7.10 (m, 1H), 4.88 (s, 2H), 4.16-4.08 (m, 2H), 2.87 (s, 6H), 2.15 (s, 3H) |
| 1496 | 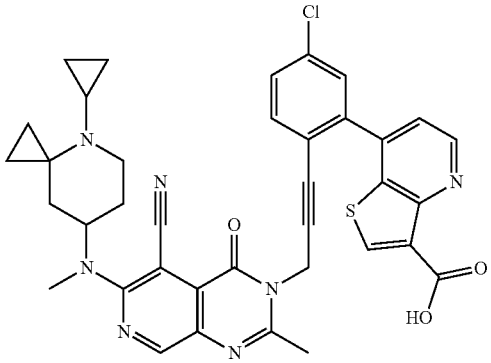 [SMILES: Cc1nc2cnc(N(C)C3CCN(C4CC4)C4(CC4)C3)c(C#N)c2c(=O)n1CC#Cc1ccc(Cl)cc1-c1ccnc2c(C(=O)O)csc12] | MS (ESI) m/z 690.46 [M + 1]+; 1H NMR (400 MHz, DMSO-d6) δ 8.75 (d, J = 4.7 Hz 1H), 8.72 (s, 1H), 8.69 (s, 1H), 7.74 (d, J = 8.2 Hz, 1H), 7.66-7.64 (m, 2H), 7.53 (d, J = 4.6 Hz, 1H), 4.83 (s, 2H), 4.60-4.58 (m, 1H), 3.18 (s, 3H), 3.10-3.00 (m, 1H), 2.27 (s, 3H), 1.60-1.57 (m, 1H), 1.30-1.24 (m, 5H), 0.87-0.67 (m, 8H) |
| 1500 | 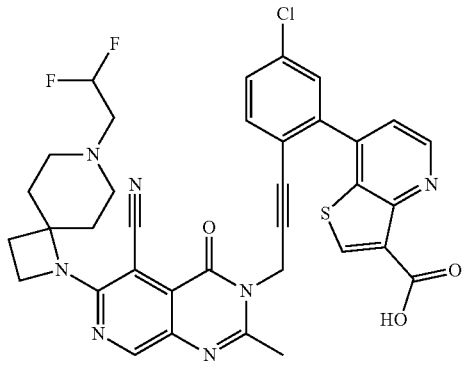 [SMILES: Cc1nc2cnc(N3CCC34CCN(CC(F)F)CC4)c(C#N)c2c(=O)n1CC#Cc1ccc(Cl)cc1-c1ccnc2c(C(=O)O)csc12] | MS (ESI) m/z 700.47 [M + 1]+; 1H NMR (400 MHz, DMSO-d6) δ 8.74 (d, J = 4.8 Hz, 1H), 8.63 (s, 1H), 8.60 (s, 1H), 7.75 (d, J = 8 Hz, 1H), 7.68-7.66 (m, 2H), 7.51 (d, J = 4.8 Hz, 1H), 6.15 (tt, J = 4.0, 55.6 Hz, 1H), 4.79 (s, 2H), 4.53 (t, J = 7.2 Hz, 2H), 2.89 (d, J = 11.2 Hz, 2H), 2.77-2.67 (m, 4H), 2.21-2.16 (m, 4H), 2.03 (s, 3H), 1.81 (d, J = 11.6 Hz, 2H) |

TABLE 1-continued
7-Aza-Thienylpyridine and Derivative Compounds
| Compound | | Characterization |
|---|---|---|
| 1501 | 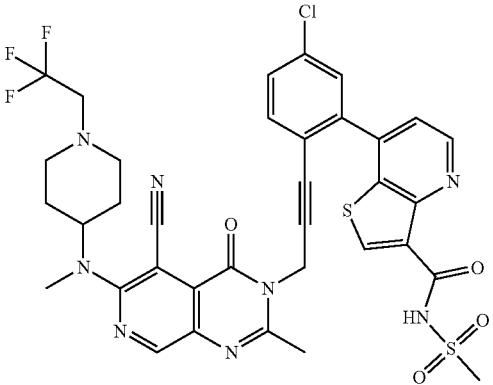 [SMILES: Cc1nc2cnc(N(C)C3CCN(CC(F)(F)F)CC3)c(C#N)c2c(=O)n1CC#Cc1ccc(Cl)cc1-c1ccnc2c(C(=O)NS(C)(=O)=O)csc12] | MS (ESI) m/z 783.47 [M + 1]+; 1H NMR (400 MHz, DMSO-d6) δ 12.47 (s, 1H), 8.81 (d, J = 5.6 Hz, 2H), 8.75 (s, 1H), 7.78 (d, J = 8.4 Hz, 1H), 7.71-7.68 (dd, J = 2.0, 10.4 Hz, 2H), 7.62 (d, J = 4.4 Hz, 1H), 4.82 (s, 2H), 4.32 (bs, 1H), 3.55 (s, 3H), 3.31 (bs, 2H), 3.10 (bs, 5H), 2.51 (bs, 2H), 1.97 (bs, 5H), 1.82-1.79 (m, 2H) |
| 1499 | 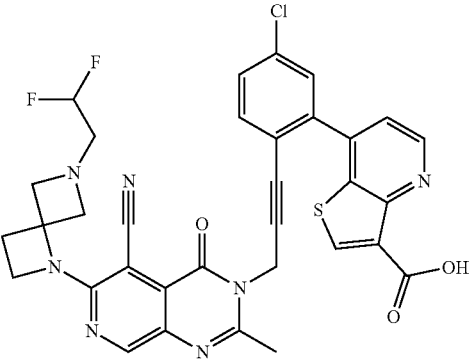 [SMILES: Cc1nc2cnc(N3CCC34CN(CC(F)F)C4)c(C#N)c2c(=O)n1CC#Cc1ccc(Cl)cc1-c1ccnc2c(C(=O)O)csc12] | MS (ESI) m/z 672.39 [M + 1]+; 1H NMR (400 MHz, DMSO-d6) δ 13.26 (bs, 1H), 9.90 (bs, 1H), 8.89 (s, 1H), 8.75 (d, J = 4.8 Hz, 1H), 8.69 (s, 1H), 7.76 (d, J = 8.4 Hz, 1H), 7.71-7.66 (m, 2H), 7.55 (d, J = 4.8 Hz, 1H), 6.48 (t, J = 53.2 Hz, 1H), 5.21-5.02 (m, 2H), 4.82 (s, 2H), 4.53 (bs, 4H), 4.20-3.80 (m, 2H), 2.78-2.63 (m, 2H), 2.18 (s, 3H) |
| 1503 | 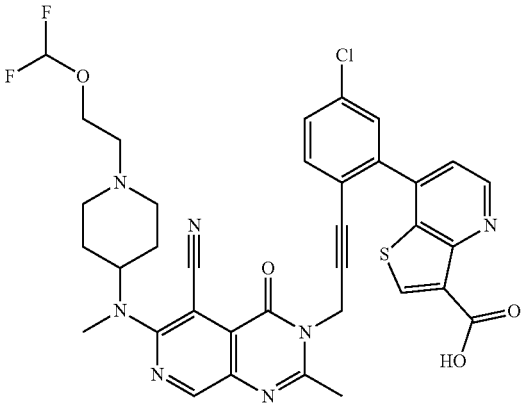 [SMILES: Cc1nc2cnc(N(C)C3CCN(CCOC(F)F)CC3)c(C#N)c2c(=O)n1CC#Cc1ccc(Cl)cc1-c1ccnc2c(C(=O)O)csc12] | MS (ESI) m/z 718.42 [M + 1]+; 1H NMR (400 MHz, DMSO-d6) δ 13.08 (bs, 1H), 8.76-8.74 (m, 2H), 8.65 (s, 1H), 7.75 (d, J = 8.0 Hz, 1H), 7.69-7.67 (m, 2H), 7.54 (d, J = 4.8 Hz, 1H), 6.79 (t, J = 74.8 Hz, 1H), 4.82 (s, 2H), 4.56 (bs, 1H), 4.23 (s, 2H), 3.65 (bs, 2H), 3.46 (bs, 2H), 3.26-3.19 (m, 2H), 3.11 (s, 3H), 2.26-2.08 (m, 2H), 2.04 (s, 5H) |

TABLE 1-continued

7-Aza-Thienylpyridine and Derivative Compounds

| Compound | | Characterization |
|---|---|---|
| 1504 | 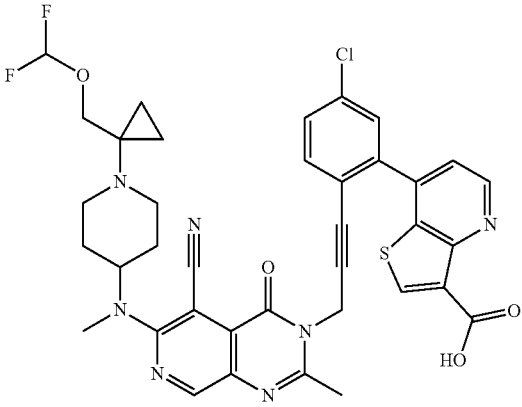 [SMILES: Cc1nc2cnc(N(C)C3CCN(C4(COC(F)F)CC4)CC3)c(C#N)c2c(=O)n1CC#Cc1ccc(Cl)cc1-c1ccnc2c(C(=O)O)csc12] | MS (ESI) m/z 744.4 [M + 1]+; 1H NMR (400 MHz, DMSO-d6) δ 8.75 (d, J = 4.8 Hz, 2H), 8.65 (s, 1H), 7.75 (d, J = 8.0 Hz, 1H), 7.70 (d, J = 2.0 Hz, 2H), 7.55 (d, J = 4.8 Hz, 1H), 6.73 (t, J = 75 Hz, 1H), 4.82 (s, 2H), 4.65 (bs, 1H), 4.21 (bs, 2H), 3.09 (s, 3H), 2.70-2.50 (m, 4H), 2.09 (bs, 7H), 1.33 (bs, 2H), 1.12 (bs, 2H) |
| 1502 | 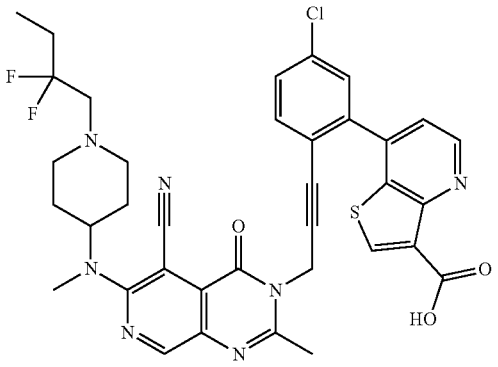 [SMILES: CCC(F)(F)CN1CCC(N(C)c2ncc3nc(C)n(CC#Cc4ccc(Cl)cc4-c4ccnc5c(C(=O)O)csc45)c(=O)c3c2C#N)CC1] | MS (ESI) m/z 716.50 [M + 1]+; 1H NMR (400 MHz, DMSO-d6) δ 8.75 (d, J = 4.8 Hz, 1H), 8.72 (s, 1H), 8.57 (s, 1H), 7.75 (d, J = 9.2 Hz, 1H), 7.68-7.66 (m, 2H), 7.50 (d, J = 4.8 Hz, 1H), 4.82 (s, 2H), 4.28-4.22 (m, 1H), 3.09 (s, 3H), 3.01 (d, J = 11.2 Hz, 2H), 2.75 (t, J = 14.4 Hz, 2H), 2.38-2.32 (m, 2H), 2.05 (s, 3H), 2.01-1.85 (m, 4H), 1.77 (d, J = 11.6 Hz, 2H), 0.96 (t, J = 7.2 Hz, 3H) |
| 1506 | 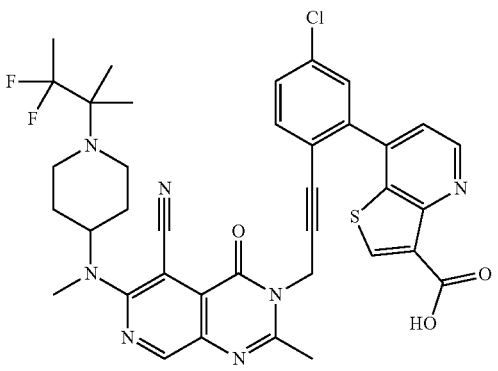 [SMILES: Cc1nc2cnc(N(C)C3CCN(C(C)(C)C(C)(F)F)CC3)c(C#N)c2c(=O)n1CC#Cc1ccc(Cl)cc1-c1ccnc2c(C(=O)O)csc12] | MS (ESI) m/z 730.26 [M + 1]+; 1H NMR (400 MHz, DMSO-d6) δ 8.76-8.74 (m, 2H), 8.65 (s, 1H), 7.75 (d, J = 6.0 Hz, 1H), 7.70-7.67 (m, 2H), 7.55 (d, J = 4.8 Hz, 1H), 4.82 (s, 2H), 4.65-4.60 (m, 1H), 3.91-3.78 (m, 2H), 3.41-3.39 (m, 2H), 3.22 (s, 3H), 2.32-2.26 (m, 2H), 2.24-2.08 (m, 5H), 1.84-1.79 (m, 3H), 1.51 (s, 6H) |
| 1507 | 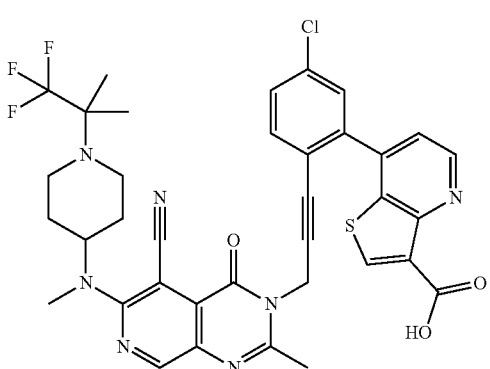 | MS (ESI) m/z 734.30 [M + 1]+; 1H NMR (400 MHz, DMSO-d6) δ 8.76 (d, J = 4.8 Hz, 1H), 8.71 (s, 1H), 8.66 (s, 1H), 7.76 (d, J = 5.2 Hz, 1H), 7.70-7.67 (m, 2H), 7.55 (d, J = 4.8 Hz, H), 4.81 (s, 2H), 4.30-4.06 (m, 2H), 3.53-3.37 (m, 2H), 3.08 (s, 3H), 2.05 (s, 3H), 1.90-1.86 (m, 4H), 1.33 (s, 6H) |

TABLE 1-continued

7-Aza-Thienylpyridine and Derivative Compounds

| Compound | | Characterization |
|---|---|---|
| 1505 | 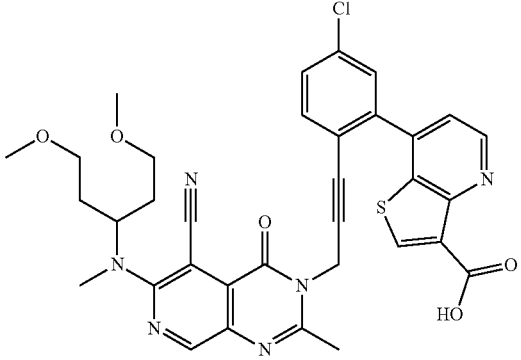 [SMILES: COCCC(CCOC)N(C)c1ncc2nc(C)n(CC#Cc3ccc(Cl)cc3-c3ccnc4c(C(=O)O)csc34)c(=O)c2c1C#N] | MS (ESI) m/z 671.41 [M + 1]+; 1H NMR (400 MHz, DMSO-d6) δ 8.76 (d, J = 4.8 Hz, 1H), 8.68 (d, J = 1.6 Hz, 2H), 7.75 (d, J = 8.4 Hz, 1H), 7.70-7.67 (m, 2H), 7.55 (d, J = 4.8 Hz, 1H), 4.82 (s, 3H), 3.38-3.28 (m, 4H), 3.11 (s, 9H), 2.02 (s, 3H), 1.97-1.91 (m, 2H), 1.89-1.83 (m, 2H) |
| 1509 | 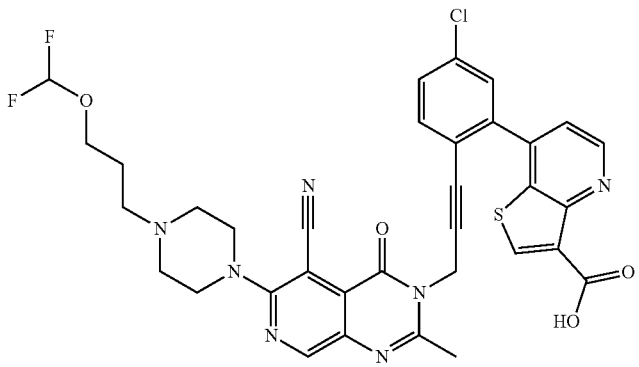 [SMILES: Cc1nc2cnc(N3CCN(CCCOC(F)F)CC3)c(C#N)c2c(=O)n1CC#Cc1ccc(Cl)cc1-c1ccnc2c(C(=O)O)csc12] | MS (ESI) m/z 704.38 [M + 1]+; 1H NMR (400 MHz, DMSO-d6) δ 13.06 (bs, 1H), 9.76 (bs, 1H), 8.84 (s,1H), 8.75 (d, J = 4.8 Hz, 1H), 8.64 (s, 1H), 7.75 (d, J = 8.4 Hz, 1H), 7.70-7.65 (m, 2H), 7.53 (d, J = 4.8 Hz, 1H), 6.71 (t, J = 75.6 Hz, 1H), 4.83 (s, 2H), 4.40-4.36 (m, 2H), 3.94 (t, J = 6.0 Hz, 2H), 3.74-3.71 (m, 2H), 3.60-3.20 (m, 6H), 2.14 (s, 3H), 2.10-2.05 (m, 2H) |
| 1510 | 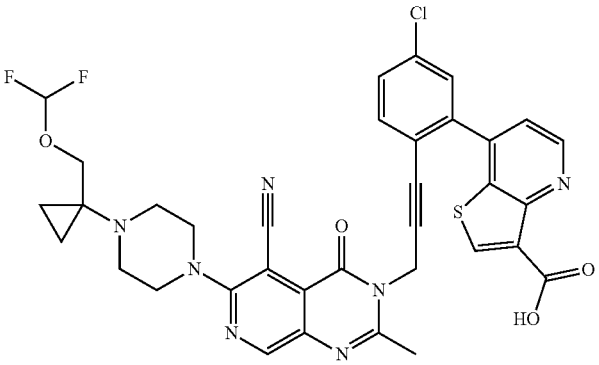 [SMILES: Cc1nc2cnc(N3CCN(C4(COC(F)F)CC4)CC3)c(C#N)c2c(=O)n1CC#Cc1ccc(Cl)cc1-c1ccnc2c(C(=O)O)csc12] | MS (ESI) m/z 716.40 [M + 1]+; 1H NMR (400 MHz, DMSO-d6) δ 13.15 (bs, 1H), 8.79 (s, 1H), 8.75 (d, J = 4.8 Hz, 1H), 8.66 (s, 1H), 7.75 (d, J = 9.1 Hz, 1H), 7.69-7.67 (m, 2H), 7.54 (d, J = 4.8 Hz, 1H), 6.68 (t, J = 75.9 Hz, 1H), 4.82 (s, 2H), 4.01 (bs, 2H), 3.40-2.80 (m, 8H), 2.08 (s, 3H), 1.05-0.65 (m, 4H) |
| 1508 | 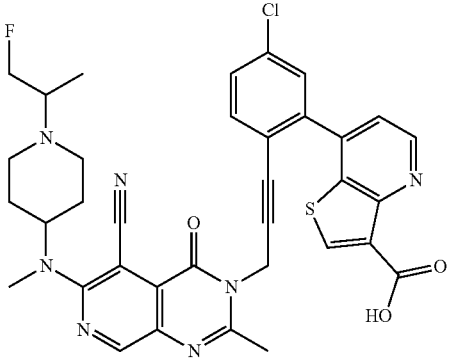

Chiral | MS (ESI) m/z, 684.48 [M + 1]+; 1H NMR (400 MHz, DMSO-d6) δ 8.76 (d, J = 4.8 Hz, 1H), 8.74 (s, 1H), 8.65 (s, 1H), 7.75 (d, J = 8.4 Hz, 1H), 7.69 (d, J = 2.0 Hz, 1H), 7.67 (s, 1H), 7.55 (d, J = 4.8 Hz, 1H), 4.82 (bs, 4H), 4.68-4.62 (m, 2H), 3.60 (bs, 2H), 3.33 (bs, 2H), 3.11 (s, 3H), 2.24 (bs, 2H), 2.13 (bs, 2H), 2.09 (s, 3H), 1.33 (d, J = 6.8 Hz, 3H) |

TABLE 1-continued

7-Aza-Thienylpyridine and Derivative Compounds

| Compound | | Characterization |
|---|---|---|
| 1512 | 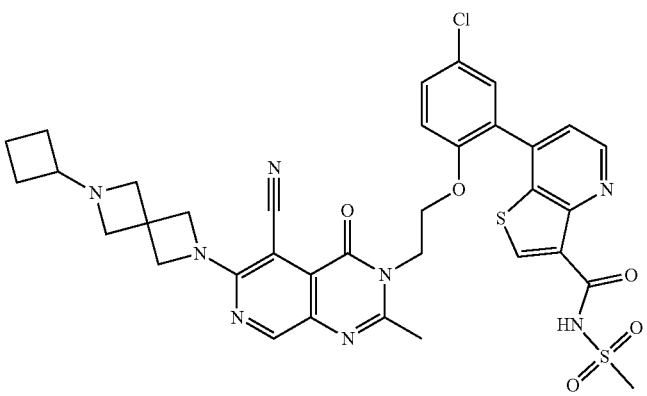 [SMILES: Cc1nc2cnc(N3CC4(C3)CN(C3CCC3)C4)c(C#N)c2c(=O)n1CCOc1ccc(Cl)cc1-c1ccnc2c(C(=O)NS(C)(=O)=O)csc12] | MS (ESI) m/z 745.4 [M + 1]+; 1H NMR (400 MHz, DMSO-d6) δ 12.65 (s, 1H), 10.01 (bs, 1H), 8.87 (d, J = 4.8 Hz, 1H ), 8.62 (s, 1H ), 8.60 (s, 1H ), 7.61 (dd, J = 8.8, 4.8 Hz, 1H), 7.54 (d, J = 4.8 Hz, 1H), 7.43 (d, J = 2.5 Hz, 1H), 7.38 (d, J = 9.0 Hz, 1H), 4.60 (s, 2H), 4.54 (s, 2H), 4.44-4.37 (m, 4H), 4.28-4.16 (m, 4H), 4.00-3.80 (m, 1H), 3.49 (s, 3H), 2.23-2.14 (m, 2H), 2.09-1.95 (m, 2H), 1.85-1.70 (m, 5H) |
| 1513 | 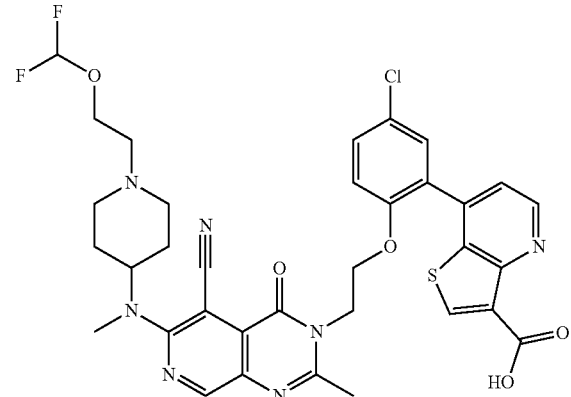 | MS (ESI) m/z 724.49 [M + 1]+; 1H NMR (400 MHz, DMSO-d6) δ 8.82 (d, J = 4.8 Hz, 1H), 8.61 (s, 1H), 8.40 (s, 1H), 7.60 (dd, J = 8.8, 2.4 Hz, 1H), 7.46 (d, J = 4.8 Hz, 1H), 7.42 (d, J = 2.4 Hz, 1H), 7.36 (d, J = 9.2 Hz, 1H), 6.79 (t, J = 75.2 Hz, 1H), 4.54-4.51 (m, 1H), 4.38 (d, J = 4.4 Hz, 2H), 4.28 (d, J = 4.4 Hz, 4H), 3.67-3.63 (m, 2H), 3.45 (bs, 2H), 3.25-3.22 (m, 2H), 3.09 (s, 3H), 2.21-2.15 (m, 2H), 2.08-2.05 (m, 2H), 1.71 (s, 3H) |
| 1511 | 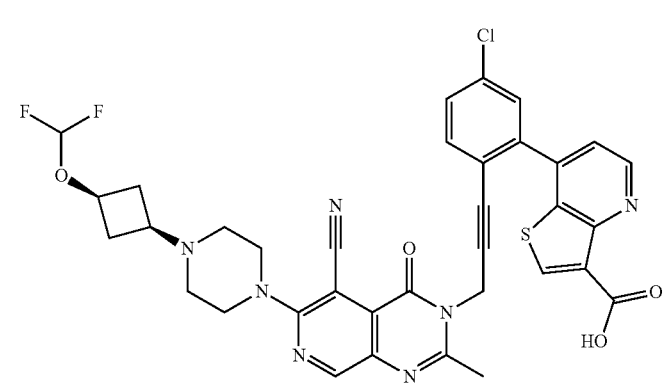 Chiral | MS (ESI) m/z 716.44 [M + 1]+; 1H NMR (400 MHz, DMSO-d6) δ 13.01 (bs, 1H), 10.04 (bs, 1H), 8.84 (s, 1H), 8.75 (d, J = 4.8 Hz,1H), 8.64 (s,1H), 7.75 (d, J = 8.4 Hz, 1H), 7.70-7.60 (m, 2H), 7.52 (d, J = 4.4 Hz,1H), 6.71 (t, J = 75.2 Hz, 1H), 4.83 (s, 2H), 4.55-4.36 (m, 3H), 3.70-3.40 (m, 5H), 3.16 (bs, 2H), 2.77 (bs, 2H), 2.50-2.35 (m, 2H), 2.14 (s, 3H) |

TABLE 1-continued

7-Aza-Thienylpyridine and Derivative Compounds

| Compound | Characterization |
|---|---|
| 1515 | MS (ESI) m/z 744.51 [M + 1]+; 1H NMR (400 MHz, DMSO-d6) δ 8.83 (d, J = 4.8 Hz, 1H), 8.60 (s, 1H), 7.85 (dd, J = 8.8 Hz, 2.4 Hz, 1H), 7.48 (d, J = 4.8 Hz, 1H), 7.43 (d, J = 2.8 Hz, 1H), 7.36 (d, J = 9.2 Hz, 1H), 6.57 (t, J = 52 Hz, 1H), 4.38 (d, J = 4.8 Hz, 2H), 4.30-4.02 (m, 3H), 3.30-2.89 (m, 9H), 1.99 (bs, 2H), 1.82 (bs, 2H), 1.74 (s, 3H) |
| 1516 | MS (ESI) m/z 753.18 [M + 1]+; 1H NMR (400 MHz, DMSO-d6) δ 12.66 (s, 1H), 9.81 (bs, 1H), 8.89 (d, J = 4.4 Hz, 1H), 8.75 (s, 1H), 8.57 (s, 1H), 7.59 (dd, J = 2.8, 9.2 Hz, 1H), 7.56 (d, J = 4.8 Hz, 1H), 7.40 (d, J = 8.4 Hz, 2H), 2.26 (s, 2H), 4.23 (s, 4H), 3.80 (bs, 6H), 3.61 (s, 3 H), 3.42 (bs, 2H), 1.81 (s, 3H), 1.53-1.48 (m, 6H) |
| 1514 | MS (ESI) m/z 740.49 [M + 1]+; 1H NMR (400 MHz, DMSO-d6) δ 8.82 (d, J = 4.8 Hz, 1H), 8.59 (s, 1H), 8.43 (s, 1H), 7.60 (dd, J = 9.2, 2.8 Hz, 1H), 7.48 (d, J = 4.8 Hz, 1H), 7.43 (d, J = 2.4 Hz, 1H), 7.35 (d, J = 8.8 Hz, 1H), 4.38-4.37 (m, 2H), 4.26 (bs, 2H), 4.19 (s,2H), 3.36 (bs, 2H), 3.05 (s, 3H), 1.83 (bs, 4H), 1.73 (s, 4H), 1.33 (s, 6H) |
| 1519 | MS (ESI) m/z 680.45 [M + 1]+; 1H NMR (400 MHz, DMSO-d6) δ 13.08 (bs, 1H), 8.75 (d, J = 4.8 Hz, 2H), 8.64 (s, 1H), 7.75 (d, J = 8.4 Hz, 1H), 7.69 (d, J = 2 Hz, 2H), 7.5 (d, J = 4.8 Hz, 1H), 4.82 (s, 2H), 4.57 (bs, 2H), 4.34 (bs, 2H), 3.23 (d, J = 11.6 Hz, 2H), 3.19 (s, 1H), 3.11 (s, 3H), 2.31 (m, 2H), 2.21 (s, 3H), 2.10-2.03 (m, 5H) |

US 11,286,268 B1

TABLE 1-continued

7-Aza-Thienylpyridine and Derivative Compounds

| Compound | | Characterization |
|---|---|---|
| 1520 | 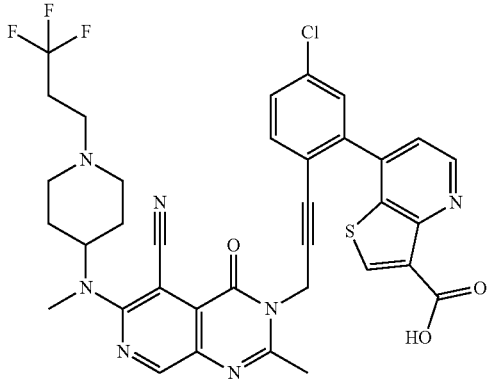 [SMILES: Cc1nc2cnc(N(C)C3CCN(CCC(F)(F)F)CC3)c(C#N)c2c(=O)n1CC#Cc1ccc(Cl)cc1-c1ccnc2c(C(=O)O)csc12] | MS (ESI) m/z 720.44 [M + 1]+; 1H NMR (400 MHz, DMSO-d6) δ 13.09 (bs, 1H), 8.77-8.75 (m, 2H), 8.65 (s, 1H), 7.76 (d, J = 8.0 Hz, 1H), 7.68 (d, J = 9.2 Hz, 2H), 7.55 (d, J = 4.4 Hz, 1H), 4.83 (s, 2H), 4.55 (bs, 1H), 3.70 (bs, 2H), 3.24 (bs, 4H), 3.11 (bs, 3H), 2.89 (bs, 2H), 2.15-2.11 (m, 7H) |
| 1518 | 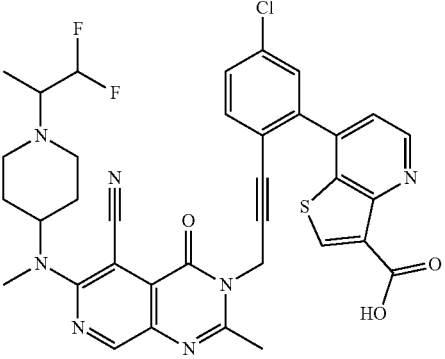 [SMILES: Cc1nc2cnc(N(C)C3CCN(C(C)C(F)F)CC3)c(C#N)c2c(=O)n1CC#Cc1ccc(Cl)cc1-c1ccnc2c(C(=O)O)csc12] | MS (ESI) m/z 702.43 [M + 1]+; 1H NMR (400 MHz, DMSO-d6) δ 8.75 (d, J = 4.8 Hz, 1H), 8.74 (s, 1H), 8.65 (s, 1H), 7.75 (d, J = 8.4 Hz, 1H), 7.69 (s, 1H), 7.67 (s, 1H), 7.55 (d, J = 4.8 Hz, 1H), 6.53 (t, J = 50.0 Hz, 1H), 4.82 (bs, 2H), 4.57 (d, J = 2.4 Hz, 1H), 3.58 (bs, 2H), 3.36 (bs, 2H), 3.16 (s, 3H), 2.98 (bs, 1H), 2.24 (bs, 2H), 2.08 (bs, 5H), 1.35 (s, 3H) |
| 1522 | 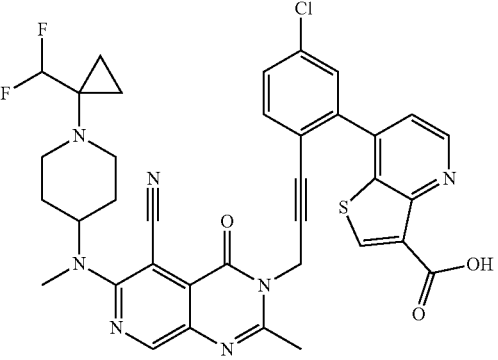 [SMILES: Cc1nc2cnc(N(C)C3CCN(C4(C(F)F)CC4)CC3)c(C#N)c2c(=O)n1CC#Cc1ccc(Cl)cc1-c1ccnc2c(C(=O)O)csc12] | MS (ESI) m/z 714.42 [M + 1]+; 1H NMR (400 MHz, DMSO-d6) δ 8.76 (d, J = 4.8 Hz, 1H), 8.71 (s, 1H), 7.66 (s, 1H), 7.75 (d, J = 9.2 Hz, 1H), 7.68 (t, J = 2.8 Hz, 2H), 7.55 (d, J = 4.8 Hz, 1H), 6.08 (t, J = 56.4 Hz, 1H), 4.81 (s, 2H), 4.09 (bs, 1H), 3.05 (bs, 5H), 2.92 (bs, 2H), 2.05 (s, 3H), 1.79-1.73 (m, 4H), 0.85-0.78 (m, 4H) |
| 1523 | 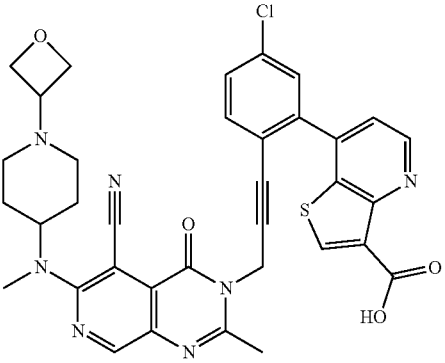 [SMILES: Cc1nc2cnc(N(C)C3CCN(C4COC4)CC3)c(C#N)c2c(=O)n1CC#Cc1ccc(Cl)cc1-c1ccnc2c(C(=O)O)csc12] | MS (ESI) m/z 680.48 [M + 1]+; 1H NMR (400 MHz, DMSO-d6) δ 8.76 (d, J = 6.4 Hz, 2H), 8.64 (s, 1H), 7.75 (d, J = 8.4 Hz, 1H), 7.70-7.67 (m, 2H), 7.55 (d, J = 4.4 Hz, 1H), 4.82 (s, 2H), 4.80-4.76 (m, 4H), 4.58 (bs, 1H), 4.37 (bs, 1H), 3.55 (d, J = 8.8 Hz, 2H), 3.12 (bs, 5H), 2.15-2.10 (m, 5H), remainder of protons are merged in moisture peak |

TABLE 1-continued

7-Aza-Thienylpyridine and Derivative Compounds

| Compound | | Characterization |
|---|---|---|
| 1521 | 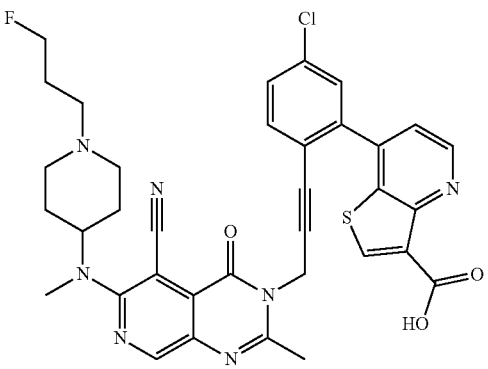 | MS (ESI) m/z 784.45 [M + 1]+; 1H NMR (400 MHz, DMSO-d6) δ 8.76-8.75 (m, 2H), 8.65 (s, 1H), 7.75 (d, J = 8.4 Hz, 1H), 7.70-7.67 (m, 2H), 7.54 (d, J = 4.8 Hz, 1H), 4.82 (s, 2H), 4.56 (dt, J = 47.2, 5.6 Hz, 2H), 4.59-4.57 (m, 1H), 3.68-3.55 (m, 2H), 3.21-3.19 (m, 4H), 3.11 (s, 3H), 2.21-2.05 (m, 9H) |
| 1525 | 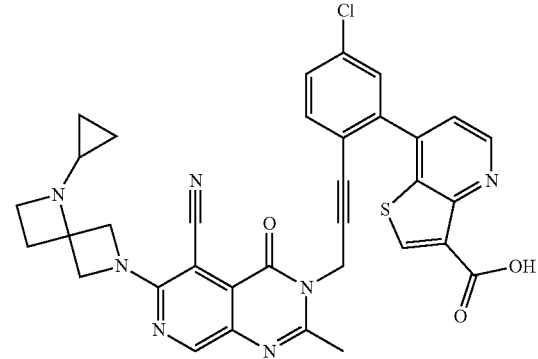 [SMILES: Cc1nc2cnc(N3CC4(CCN4C4CC4)C3)c(C#N)c2c(=O)n1CC#Cc1ccc(Cl)cc1-c1ccnc2c(C(=O)O)csc12] | MS (ESI) m/z 648.39 [M + 1]; 1H NMR (400 MHz, DMSO-d6) δ 8.78 (s, 1H), 8.76 (d, J = 4.4 Hz, 1H), 8.65 (s, 1H), 7.75 (d, J = 8.4 Hz, 1H), 7.70-7.67 (m, 1H), 7.55 (d, J = 4.8 Hz, 1H), 5.13 (bs, 1H), 4.81-4.67 (m, 6H), 3.97 (bs, 2H), 2.77 (bs, 2H), 2.10 (s, 3H), 0.85 (bs, 4H) |
| 1526 | 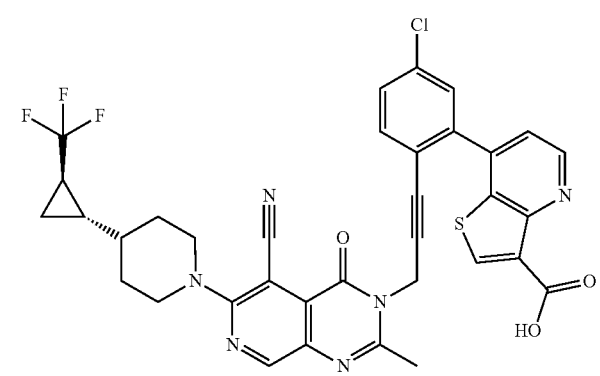 [SMILES: Cc1nc2cnc(N3CCC([C@@H]4C[C@H]4C(F)(F)F)CC3)c(C#N)c2c(=O)n1CC#Cc1ccc(Cl)cc1-c1ccnc2c(C(=O)O)csc12] | MS (ESI) m/z 704.41 [M + 1]+; 1H NMR (400 MHz, DMSO-d6) δ 13.16 (bs, 1H), 8.79 (s, 1H), 8.75 (d, J = 4.8 Hz, 1H), 8.65 (s, 1H), 7.75 (d, J = 8.3 Hz, 1H), 7.69-7.67 (m, 2H), 7.54 (d, J = 4.8 Hz, 1H), 4.82 (s, 2H), 3.73 bs, 4H), 3.00 (bs, 4H), 2.70-2.50 (m, merged, 1H), 2.20-2.07 (m, 1H), 2.08 (s, 3H), 1.03-1.08 (m, 2H) |
| 1524 | 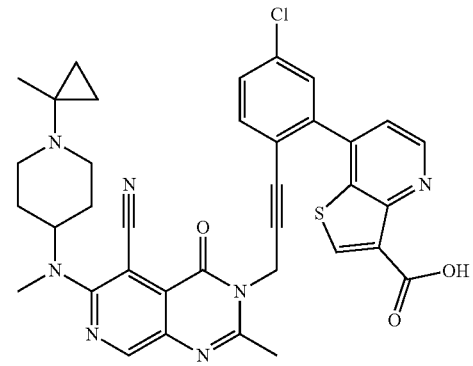 [SMILES: Cc1nc2cnc(N(C)C3CCN(C4(C)CC4)CC3)c(C#N)c2c(=O)n1CC#Cc1ccc(Cl)cc1-c1ccnc2c(C(=O)O)csc12] | MS (ESI) m/z 678.20 [M + 1]+; 1H NMR (400 MHz, DMSO-d6) δ 13.06 (bs, 1H), 8.75.-8.74 (m, 2H), 8.65 (s, 1H), 7.75 (d, J = 8.4 Hz ,1H), 7.68 (d, J = 8.8 Hz ,2H), 7.54 (d, J = 4.8 Hz, 1H), 4.82 (s, 2H), 4.64 (t, J = 8.4 Hz, 1H), 3.49 (s, 4H), 3.10 (s, 3H), 2.21-2.08 (m, 7H), 1.39 (s, 3H), 1.14 (bs, 2H), 0.81 (bs, 2H) |

TABLE 1-continued

7-Aza-Thienylpyridine and Derivative Compounds

| Compound | | Characterization |
|---|---|---|
| 1528 | 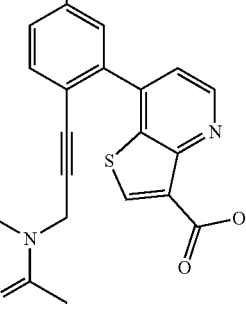 | MS (ESI) m/z 625.37 [M + 1]+; 1H NMR (400 MHz, DMSO-d6) δ 8.77 (d, J = 4.8 Hz, 1H), 8.72 (s, 1H), 8.66 (s, 1H), 7.75 (d, J = 8.8 Hz, 1H), 7.70-7.65 (m, 2H), 7.55 (d, J = 4.8 Hz, 1H), 4.81 (s, 2H), 4.60-4.45 (m, 1H), 4.05-3.95 (m, 2H), 3.65-3.40 (m, 2H), 3.11 (s, 3H), 2.06 (s, 3H), 2.00-1.85 (m, 2H), 1.78 (d, J = 10.8 Hz, 2H) |
| 1529 | 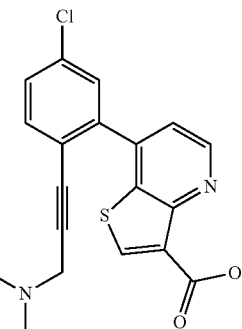 | MS (ESI) m/z 696.48 [M + 1]+; 1H NMR (400 MHz, DMSO-d6) δ 9.00 (bs, 1H), 8.76-8.74 (m, 2H), 8.65 (s, 1H), 7.76 (d, J = 8.0 Hz, 1H), 7.70-7.67 (m, 2H), 7.75 (d, J = 4.8 Hz, 1H), 4.83 (s, 2H), 4.72-4.66 (m, 2H), 3.65 (bs, 4H), 3.09 (s, 3H), 2.71 (s, 1H), 2.12-2.08 (m, 7H), 1.35 (bs, 2H), 1.16 (bs, 2H) |
| 1527 | 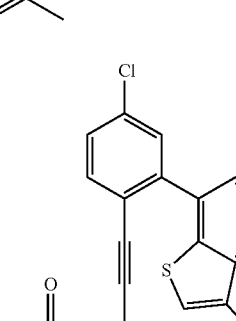 | MS (ESI) m/z 664.45 [M + 1]+; 1H NMR (400 MHz, DMSO-d6) δ 9.05 (bs, 1H), 8.79 (s, 1H), 8.75 (d, J = 4.8 Hz, 1H), 8.65 (s, 1H), 7.75 (d, J = 8.0 Hz, 1H), 7.71-7.65 (m, 2H), 7.54 (d, J = 4.8 Hz, 1H), 4.83 (s, 2H), 4.39 (d, J = 12.4 Hz, 2H), 3.19 (t, J = 12.0 Hz, 2H), 2.95-2.90 (m, 5H), 2.32-2.28 (m, 2H), 2.10 (s, 3H), 2.00-1.80 (m, 2H), 1.02-0.91 (m, 2H), 0.90-0.81 (m, 2H) |
| 1531 | 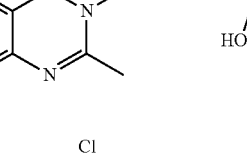 | MS (ESI) m/z 714.45 [M + 1]+; 1H NMR (400 MHz, DMSO-d6) δ 13.06 (bs, 1H), 10.53 (bs, 1H), 8.77-8.70 (m, 2H), 8.65 (s, 1H), 7.75 (d, J = 4.4 Hz, 1H), 7.69-7.67 (m, 2H), 7.55 (d, J = 4.8 Hz, 1H), 6.49 (t, J = 56.4 Hz, 1H), 4.82 (s, 2H), 4.57 (bs, 2H), 3.80-3.48 (m, 3H), 3.40-3.20 (m, 2H), 3.16 (s, 4H), 3.01-2.70 (m, 2H), 2.02-2.15 (m, 2H), 2.06 (s, 3H), 1.80-1.65 (m, 2H) |

TABLE 1-continued

7-Aza-Thienylpyridine and Derivative Compounds

| Compound | | Characterization |
|---|---|---|
| 1532 | | MS (ESI) m/z 670.30 [M + 1]+; 1H NMR (400 MHz, DMSO-d6) δ 10.05 (bs, 1H), 8.76-8.70 (m, 2H), 8.65 (s, 1H), 7.75 (d, J = 8.8 Hz, 1H), 7.70-7.68 (m, 2H), 7.55 (d, J = 4.8 Hz, 1H), 4.96- 4.68 (m, 4H), 4.01-3.95 (m, 1H), 3.65-3.28 (m, 3H), 3.22 (s, 3H), 2.82 (s, 3H), 2.80-2.55 (m, 4H), 2.08 (s, 3H) |
| 1530 | | MS (ESI) m/z 732.40 [M + 1]+; 1H NMR (400 MHz, DMSO- d6) δ 8.76 (d, J = 4.8, 1H), 8.70 (s, 1H), 8.65 (s, 1H), 7.79-7.73 (m, 1H), 7.71-7.65 (m, 2H), 7.55 (d, J = 4.8 Hz, 1H), 4.81 (s, 2H), 4.32-4.20 (m, 1H), 3.12-3.10 (m, 5H), 2.81 (t, J = 11.2 Hz, 2H), 2.05 (s, 3H), 1.85-1.65 (m, 4H), 1.06-0.90 (m, 4H) |
| 1534 | | MS (ESI) m/z 597.28 [M + 1]+; 1H NMR (400 MHz, DMSO-d6) δ 9.35 (s, 1H), 8.79-8.75 (m, 2H), 7.75 (d, J = 8.0 Hz, 1H), 7.71-7.66 (m, 2H), 7.54 (d, J = 4.4 Hz, 1H), 5.00-4.97 (m, 1H), 4.88 (d, J = 18.4 Hz, 1H), 4.77-4.73 (m, 2H), 4.44 (bs, 1H), 3.89 (d, J = 12.0 Hz, 1H), 3.64 (d, J = 12.0 Hz, 1H), 3.57 (s, 3H), 2.13 (s, 3H) |
| 1535 | | MS (ESI) m/z 702.43 [M + 1]+; 1H NMR (400 MHz, DMSO-d6) δ 8.77 (d, J = 4.4 Hz, 2H), 8.66 (s, 1H), 7.75 (d, J = 9.2 Hz, 1H), 7.70-7.68 (m, 2H), 7.55 (d, J = 4.8 Hz, 1H), 6.51 (bs, 1H), 4.82 (s, 2H), 4.35 (bs, 1H), 3.66-3.51 (m, 6H), 3.06-2.97 (m, 2H), 2.16-2.02 (m, 7H), 1.13 (t, J = 6.8 Hz, 3H) |

TABLE 1-continued
7-Aza-Thienylpyridine and Derivative Compounds
| Compound | Characterization |
|---|---|
| 1533 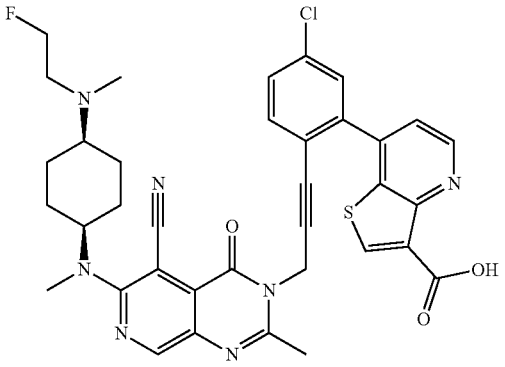 | MS (ESI) m/z 698.43 [M + 1]+; 1H NMR (400 MHz, DMSO-d6) δ 9.19 (bs, 1H), 8.76-8.75 (m, 2H), 8.65 (s, 1H), 7.75 (d, J = 8.8 Hz, 1H), 7.70-7.68 (m, 2H), 7.55 (d, J = 8.8 Hz, 1H), 4.95-4.82 (m, 4H), 4.35-4.25 (m, 1H), 3.60-3.40 (m, 3H), 3.12 (s, 3H), 2.95-2.90 (m, 3H), 2.13-1.72(m, 11H) |
| 1537 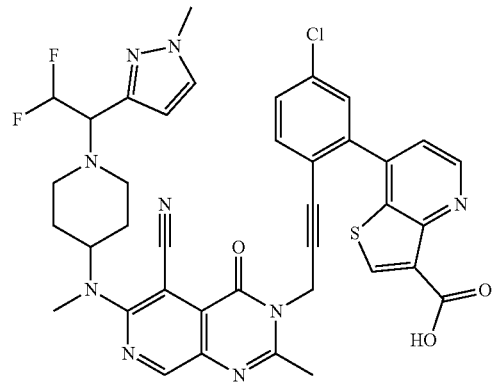 [SMILES: Cc1nc2cnc(N(C)C3CCN(C(c4ccn(C)n4)C(F)F)CC3)c(C#N)c2c(=O)n1CC#Cc1ccc(Cl)cc1-c1ccnc2c(C(=O)O)csc12] | MS (ESI) m/z 768.43 [M + 1]+; 1H NMR (400 MHz, DMSO-d6) δ 8.74 (d, J = 5.2 Hz, 1H), 8.70 (s, 1H), 8.63 (s, 1H), 7.83 (bs, 1H), 7.75 (d, J = 8.4 Hz, 1H), 7.70-7.69 (m, 2H), 7.54 (d, J = 4.8 Hz, 1H), 6.74-6.60 (m, 1H), 6.48 (bs, 1H), 4.81 (s, 2H), 4.5-4.25 (m, 2H), 4.15-4.05 (bs, 2H), 3.90 (s, 3H), 3.45-3.3 (bs, 2H), 3.09 (s, 3H), 2.2-2.13 (bs, 2H), 2.06 (s, 3H), 2.05-1.9 (bs, 2H) |
| 1538 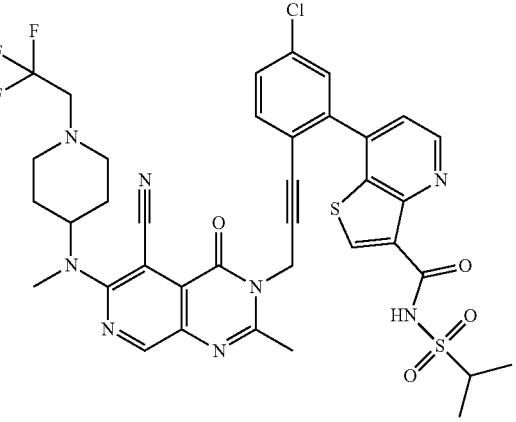 | MS (ESI) m/z 811.19 [M + 1]+; 1H NMR (400 MHz, DMSO-d6) δ 12.45 (s, 1H), 8.85 (d, J = 4.8 Hz 1H), 8.70 (s, 2H), 8.69 (s, 1H), 7.78-7.69 (m, 3H), 7.63 (d, J = 4.8 Hz, 1H), 4.82 (s, 2H), 4.32 (t, J = 11.6 Hz, 1H), 3.94-3.87 (m, 2H), 3.31 (bs, 2H), 3.10-3.07 (m, 5H), 2.59 (m, 1H), 1.96 (d, J = 9.3 Hz, 2H), 1.90-1.77 (m, 5H), 1.44 (s, 6H) |

TABLE 1-continued

7-Aza-Thienylpyridine and Derivative Compounds

| Compound | | Characterization |
|---|---|---|
| 1536 | 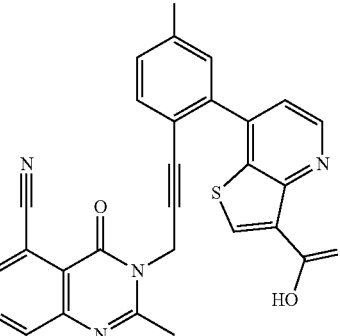 | MS (ESI) m/z 768.45 [M + 1]+; 1H NMR (400 MHz, DMSO-d6) δ 8.76 (d, J = 4.8 Hz, 1H), 8.74 (s, 1H), 8.65 (s, 1H), 7.90 (bs, 1H), 7.76 (d, J = 8.0 Hz, 1H), 7.70 (d, J = 2.0 Hz, 1H), 7.67 (s, 1H), 7.55 (d, J = 4.8 Hz, 1H), 6.61 (bs, 1H), 4.82 (s, 2H), 4.53-4.24 (m, 5H), 3.92 (s, 3H), 3.53 (m, 2H), 3.09 (s, 5H), 2.00 (s, 5H) |
| 1540 | 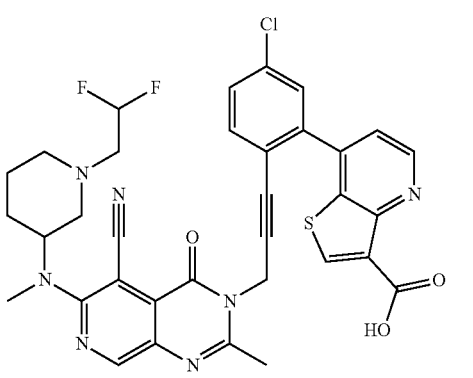 [SMILES: Cc1nc2cnc(N(C)C3CCCN(CC(F)F)C3)c(C#N)c2c(=O)n1CC#Cc1ccc(Cl)cc1-c1ccnc2c(C(=O)O)csc12] | MS (ESI) m/z 688.42 [M + 1]+; 1H NMR (400 MHz, DMSO-d6) δ 8.80-8.74 (m, 2H), 8.65 (s, 1H), 7.75 (d, J = 8.8 Hz, 1H), 7.70-7.66 (m, 1H), 7.55 (d, J = 4.8 Hz, 1H), 6.47 (t, J = 58.0 Hz, 1H), 4.83 (s, 2H), 4.68 (bs, 1H), 3.70-3.40 (m, 4H), 3.16 (s, 3H), 3.08-2.75 (m, 2H), 2.08 (s, 3H), 2.05-1.75 (m, 4H) |
| 1541 |  | MS (ESI) m/z 701.18 [M + 1]+; 1H NMR (400 MHz, DMSO-d6) δ 9.92 (bs, 1H), 8.76 (d, J = 4.8 Hz, 1H), 8.69-8.66 (m, 2H), 7.76 (d, J = 8.8 Hz, 1H), 7.68 (t, J = 3.6 Hz, 2H), 7.55 (d, J = 4.4 Hz, 1H), 6.59 (bs, 1H), 4.81 (s, 2H), 3.72 (d, J = 6.0 Hz, 2H), 3.40 (bs, 4H), 3.33 (s, 3H), 3.11-2.99 (m, 2H), 2.06 (s, 3H), 1.79 (bs, 4H), 1.47 (bs, 1H) |
| 1539 | 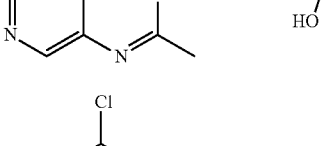 | MS (ESI) m/z 833.16 [M + 1]+; 1H NMR (400 MHz, DMSO-d6) δ 12.88 (bs, 1H), 8.84-8.83 (m, 2H), 8.73 (s, 1H), 7.77 (d, J = 4.4 Hz, 1H), 7.76-7.69 (m, 2H), 7.63 (d, J = 4.8 Hz, 1H), 6.73-6.46 (tt, J = 54.4, 4.4 Hz, 1H), 4.82 (s, 2H), 4.49 (dt, J = 14.8, 4.0 Hz, 2H), 4.36-4.30 (m, 1H), 3.36 (bs, 2H), 3.10 (s, 5H), 2.66-2.63 (m, 2H), 2.05-1.77 (m, 7H) |

TABLE 1-continued
7-Aza-Thienylpyridine and Derivative Compounds
| Compound | | Characterization |
|---|---|---|
| 1543 | 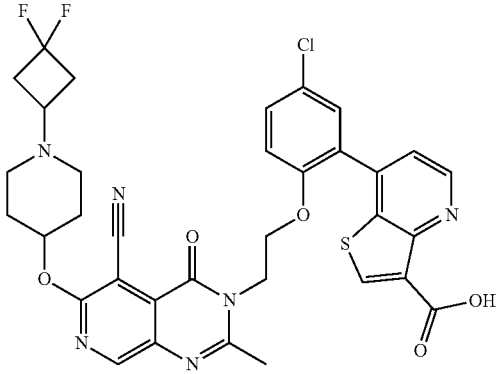 [SMILES: Cc1nc2cnc(OC3CCN(C4CC(F)(F)C4)CC3)c(C#N)c2c(=O)n1CCOc1ccc(Cl)cc1-c1ccnc2c(C(=O)O)csc12] | MS (ESI) m/z 707.43 [M + 1]+; 1H NMR (400 MHz, DMSO-d6) δ 13.35 (bs, 1H), 8.38 (d, J = 4.8 Hz, 1H), 8.72 (s, 1H), 8.36 (s, 1H), 7.61 (dd, J = 2.4, 8.8 Hz, 1H), 7.59 (d, J = 2.4 Hz, 1H), 7.48 (d, J = 4.8 Hz, 1H), 7.37 (d, J = 8.8 Hz, 1H), 5.46-5.45 (m, 1H), 4.39 (bs, 2H), 4.24 (bs, 2H), 3.92 (m, 1H), 3.60-3.58 (m, 2H), 3.08-3.05 (m, 8H), 2.14-1.90 (m, 2H), 1.79-1.77 (m, 3H) |
| 1544 | 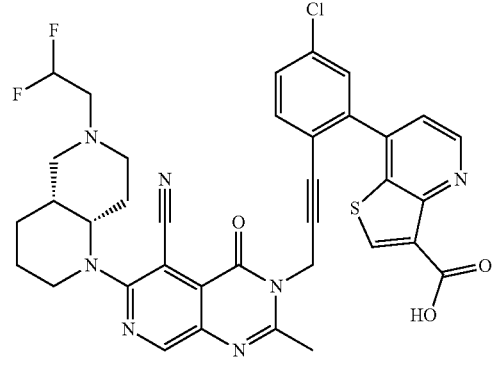 [SMILES: Cc1nc2cnc(N3CCC[C@@H]4CN(CC(F)F)CC[C@@H]43)c(C#N)c2c(=O)n1CC#Cc1ccc(Cl)cc1-c1ccnc2c(C(=O)O)csc12] | MS (ESI) m/z 714.18 [M + 1]+; 1H NMR (400 MHz, DMSO-d6) δ 8.76 (d, J = 4.8 Hz, 2H), 8.64 (s, 1H), 7.75 (d, J = 9.2 Hz, 1H), 7.69 (t, J = 8.8 Hz, 2H), 7.54 (d, J = 4.8 Hz, 1H), 6.49 (bs, 1H), 4.82 (s, 2H), 4.49 (s, 1H), 3.75 (bs, 8H), 2.97 (s, 2H), 2.08 (bs, 5H), 1.81 (s, 1H), 1.68 (d, J = 12.8 Hz, 2H) |
| 1542 | 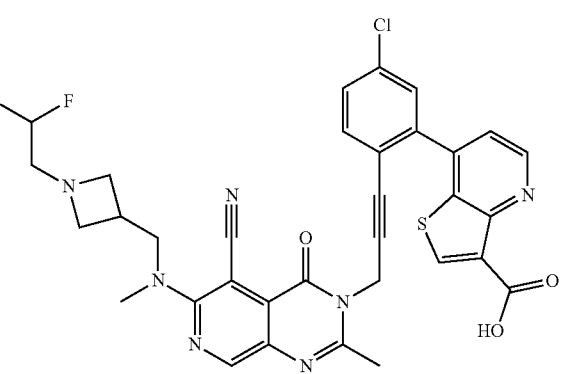 | MS (ESI) m/z 674.40 [M + 1]+; 1H NMR (400 MHz, DMSO-d6) δ 9.26 (s, 1H), 8.81 (d, J = 4.8 Hz, 1H), 8.73 (s, 1H), 7.77 (d, J = 8.4 Hz, 1H), 7.72-7.69 (m, 2H), 7.57 (d, J = 4.4 Hz, 1H), 6.42-6.15 (m, 1H), 4.90-4.80 (m, 3H), 4.51-4.46 (m, 1H), 3.87-3.84 (m, 2H), 3.68-3.61 (m, 3H), 3.58-3.37 (m, 2H), 3.25-3.17 (m, 2H), 2.87 (bs, 2H), 2.17 (s, 3H) |

TABLE 1-continued

7-Aza-Thienylpyridine and Derivative Compounds

| Compound | | Characterization |
|---|---|---|
| 1546 | 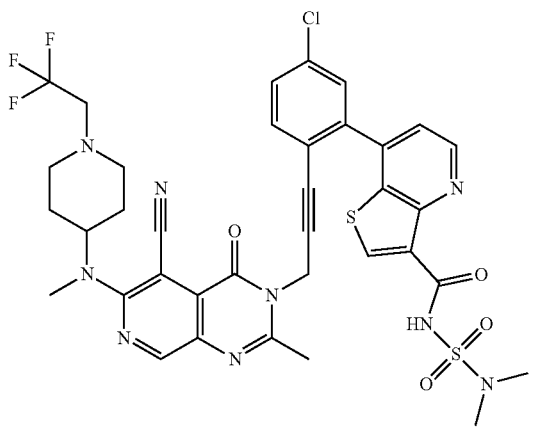 | MS (ESI) m/z 811.16 [M + 1]+; 1H NMR (400 MHz, DMSO-d6) δ 12.43 (s, 1H), 8.82 (d, J = 4.8 Hz, 1H), 8.74 (d, J = 8.0 Hz, 2H), 7.78 (d, J = 8.8 Hz, 1H), 7.70 (d, J = 2.0 Hz, 1H), 7.68 (s, 1H), 7.61 (d, J = 4.8 Hz, 1H), 4.82 (s, 2H), 4.29 (t, J = 23.2 Hz, 1H), 3.22 (q, J = 10.0 Hz, 2H), 3.09 (s, 3H), 3.04 (d, J = 19.2 Hz, 10H), 1.92 (d, J = 8.0 Hz, 5H), 1.78 (d, J = 9.6 Hz, 2H) |
| 1547 | 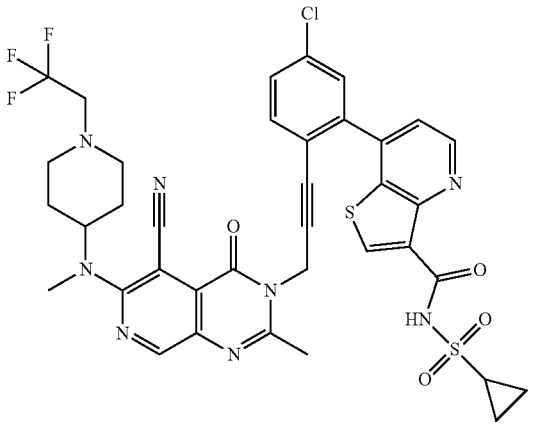 [SMILES: Cc1nc2cnc(N(C)C3CCN(CC(F)(F)F)CC3)c(C#N)c2c(=O)n1CC#Cc1ccc(Cl)cc1-c1ccnc2c(C(=O)NS(=O)(=O)C3CC3)csc12] | MS (ESI) m/z 809.16 [M + 1]+; 1H NMR (400 MHz, DMSO-d6) δ 12.52 (s, 1H), 8.79 (t, J = 8.0 Hz, 2H), 8.73 (s, 1H), 7.75 (d, J = 8.4 Hz, 1H), 7.70 (d, J = 2 Hz, 2H), 7.60 (d, J = 4.8 Hz, 1H), 4.82 (s, 2H), 4.31 (t, J = 21.2 Hz, 1H), 3.29-3.22 (m, 4H), 3.10 (bs, 5H), 2.50 (s, 1H), 1.94 (d, J = 11.7 Hz, 5H), 1.78 (s, 2H), 1.29 (d, J = 3.8 Hz, 2H), 1.26-1.14 (m, 2H) |
| 1545 | 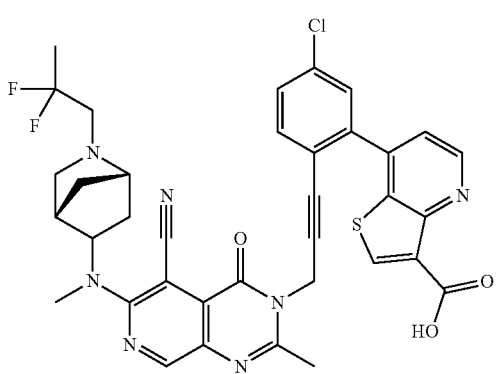 [SMILES: Cc1nc2cnc(N(C)C3C[C@@H]4C[C@H]3CN4CC(C)(F)F)c(C#N)c2c(=O)n1CC#Cc1ccc(Cl)cc1-c1ccnc2c(C(=O)O)csc12] | MS (ESI) m/z 714.45 [M + 1]+; 1H NMR (400 MHz, DMSO-d6 at 353.1 K) 68.15 (s, 1H), 8.77 (d, J = 4.8 Hz, 1H), 8.68 (s, 1H), 7.75 (d, J = 8.4 Hz, 1H), 7.67-7.64 (m, 2H), 7.53 (d, J = 4.8 Hz, 1H), 4.86-4.80 (m, 2H), 4.08-4.05 (m, 1H), 3.09 (s, 3H), 2.98 (m, 3H), 2.18 (s, 3H), 2.06-2.01 (m, 1H), 1.67 (t, J = 18.4 Hz, 3H), 1.38-1.26 (m, 4H) |

TABLE 1-continued

7-Aza-Thienylpyridine and Derivative Compounds

| Compound | | Characterization |
|---|---|---|
| 1549 | | MS (ESI) m/z 859.42 [M + 1]+; 1H NMR (400 MHz, DMSO-d6) δ 13.05 (bs, 1H), 8.93 (d, J = 4.8 Hz, 1H), 8.56 (s, 1H), 8.25 (s, 1H), 8.17 (d, J = 7.6 Hz, 1H), 7.77-7.55 (m, 1H), 7.70-7.63 (m, 4H), 7.55-7.51 (m, 1H), 7.45 (d, J = 7.6 Hz, 1H) 4.82 (s, 2H), 4.29 (bs, 1H), 3.31 (bs, 2H), 3.08 (bs, 5H), 2.67 (s, 3H), 2.63-2.58 (m, 2H), 1.94-1.88 (m, 2H). 1.83 (s, 3H), 1.79-1.76 (m, 2H) |
| 1550 | | MS (ESI) m/z 881.42 [M + 1]+; 1H NMR (400 MHz, DMSO-d6) δ 13.28 (bs, 1H), 8.94 (d, J = 5.2 Hz, 1H), 8.58 (s, 1H), 8.28 (s, 1H), 8.24-8.19 (m, 1H), 7.77-7.75 (m, 1H), 7.70-7.68 (m, 2H), 7.66 (d, J = 4.8 Hz, 1H), 7.61-7.56 (m, 1H), 7.48-7.40 (m, 1H), 4.80 (s, 2H), 4.37-4.26 (m, 1H), 3.37 (bs, 2H), 3.12-3.10 (m, 2H), 3.07 (s, 3H), 2.66-2.63 (m, 2H), 1.99-1.88 (m, 2H), 1.85-1.74 (m, 5H) |
| 1548 | | MS (ESI) m/z 845.44 [M + 1]+; 1H NMR (400 MHz, DMSO-d6) δ 12.09 (bs, 1H), 8.83 (d, J = 4.8 Hz, 1H), 8.67 (s, 1H), 8.45 (s, 1H), 8.15 (d, J = 7.2 Hz, 2H), 7.78-7.74 (m, 2H), 7.69-7.66 (m, 4H), 7.61 (d, J = 4.8 Hz, 1H), 4.80 (s, 2H), 4.31 (bs, 1H), 3.28 (bs, 2H), 3.09-3.06 (m, 5H), 2.58-2.50 (m, 2H), 1.94 (d, J = 11.2 Hz, 2H), 1.87 (s, 3H), 1.79 (d, 10.4 Hz, 2H) |

TABLE 1-continued
7-Aza-Thienylpyridine and Derivative Compounds
| Compound | | Characterization |
|---|---|---|
| 1553 | 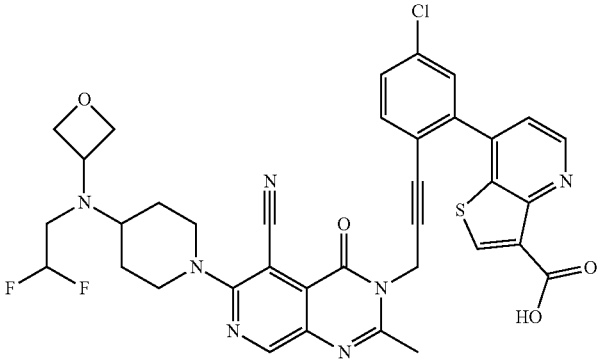 [SMILES: Cc1nc2cnc(N3CCC(N(CC(F)F)C4COC4)CC3)c(C#N)c2c(=O)n1CC#Cc1ccc(Cl)cc1-c1ccnc2c(C(=O)O)csc12] | MS (ESI) m/z 730.17 [M + 1]+; 1H NMR (400 MHz, DMSO-d6) δ 8.74 (s, 1H), 8.56 (s, 1H), 7.60-7.73 (m, 1H), 7.67-7.66 (m, 2H), 7.51 (d, J = 4.8 Hz, 1H), 6.14-5.56 (m, 1H), 4.82 (s, 2H), 4.59-4.55 (m, 2H), 4.48 (t, J = 6.4 Hz, 2H), 4.34-4.31 (m, 2H), 4.26-4.21 (m, 1H), 3.14-3.03 (m, 4H), 2.87 (t, J = 12.4 Hz, 1H), 2.07 (s, 3H), 1.76 (d, J = 12.0 Hz, 2H), 1.56-1.48 (m, 2H) |
| 1554 | 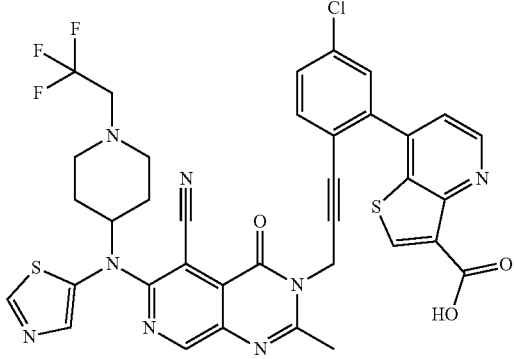 [SMILES: Cc1nc2cnc(N(c3cncs3)C3CCN(CC(F)(F)F)CC3)c(C#N)c2c(=O)n1CC#Cc1ccc(Cl)cc1-c1ccnc2c(C(=O)O)csc12] | MS (ESI) m/z 757.34 [M + 1]+; 1H NMR (400 MHz, DMSO-d6) δ 8.89 (s, 1H), 8.79 (d, J = 4.8 7.71 (d, J = 2.0 Hz, 1H), 7.68 (bs, 1H), 7.58 (d, J = 4.4 Hz, 1H), 6.29 (t, J = 61.2 Hz, 1H), 4.86 (s, 2H), 4.44 (bs, 2H), 4.04 (bs, 4H), 3.25 (bs, 2H), 2.16 (bs, 4H), 2.10 (bs, 3H) |
| 1551 | 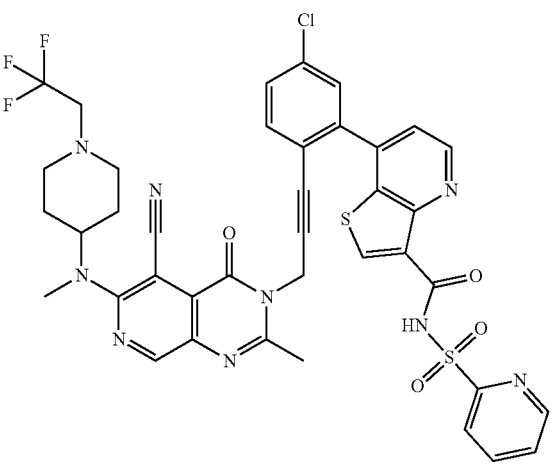 | MS (ESI) m/z 859.42 [M + 1]+; 1H NMR (400 MHz, DMSO-d6) δ 13.05 (bs, 1H), 8.93 (d, J = 4.8 Hz, 1H), 8.56 (s, 1H), 8.25 (s, 1H), 8.17 (d, J = 7.6 Hz, 1H), 7.77-7.55 (m, 1H), 7.70-7.63 (m, 4H), 7.55-7.51 (m, 1H), 7.45 (d, J = 7.6 Hz, 1H) 4.82 (s, 2H), 4.29 (bs, 1H), 3.31 (bs, 2H), 3.08 (bs, 5H), 2.67 (s, 3H), 2.63-2.58 (m, 2H), 1.94-1.88 (m, 2H). 1.83 (s, 3H), 1.79-1.76 (m, 2H) |

TABLE 1-continued

7-Aza-Thienylpyridine and Derivative Compounds

| Compound | Characterization |
|---|---|
| 1556 | MS (ESI) m/z 700.34 [M + 1]+; 1H NMR (400 MHz, DMSO-d6) δ 10.04 (s, 1H), 8.77-8.74 (m 2H), 8.65 (s, 1H), 7.76 (d, J = 8.4 Hz, 1H), 7.70-7.66 (dd, J = 2.0, 10.4 Hz, 2H), 7.55 (d, J = 4.4 Hz, 1H), 6.54 (bs, 1H), 4.82 (s, 2H), 4.42 (s, 1H), 4.19 (bs, 1H), 3.86-3.59 (bs, 4H), 3.16-2.74 (s, 4H), 2.11 (s, 5H), 1.97-1.78 (bs, 2H) |
| 1557 | MS (ESI) m/z 702.35 [M + 1]+; 1H NMR (400 MHz, DMSO-d6) δ 13.00 (bs, 1H), 10.03 (bs, Hz, 1H), 8.59 (s, 1H), 7.77 (s, 1H), 7.75 (s, 1H), Cl 1H), 8.80-8.68 (m, 3H), 7.74-7.63 (m, 3H), 7.59 (d, J = 5.2 Hz, 1H), 6.53 (t, J = 54.4 Hz, 1H), 5.90-5.40 (m, 1H), 4.48 (bs, 1H), 3.81-3.41 (m, 4H), 3.38-3.10 (m, 2H), 3.09 (s, 3H), 2.40-1.95 (m, 7H), 1.47 (t, J = 6.8 Hz, 3H) |
| 1555 | MS (ESI) m/z 764.14 [M + 1]+; 1H NMR (400 MHz, DMSO-d6) δ 10.13 (bs, 1H), 8.77 (s, 1H), 8.75 (d, J = 7.2 Hz, 1H), 8.65 (s, 1H), 7.76 (s, 1H), 7.70 (d, J = 2.0 Hz, 2H), 7.67-7.54 (m, 6H), 4.82 (s, 2H), 4.56-4.22 (m, 5H), 3.01 (s, 5H), 2.97-2.87 (m, 2H), 2.09 (s, 5H) |
| 1559 | MS (ESI) m/z 695.2 [M + 1]+; 1H NMR (400 MHz, DMSO-d6) δ 9.22 (bs, 1H), 8.78 (d, J = 4.7 Hz, 1H), 8.65 (s, 1H), 8.00-7.99 (m, 2H), 7.77 (d, J = 9.0 Hz, 1H), 7.70-7.66 (m, 4H), 7.56 (d, J = 4.7 Hz, 1H), 6.43 (t, J = 53.4 Hz, 1H), 4.90 (s, 2H), 4.23 (bs, 2H), 3.41 (bs, 2H), 2.66 (bs, 3H), 2.19 (s, 3H) |

TABLE 1-continued

7-Aza-Thienylpyridine and Derivative Compounds

| Compound | Characterization |
|---|---|
| 1560 | MS (ESI) m/z 703.32 [M + 1]+; 1H NMR (400 MHz, DMSO-d6) δ 11.40 (s, 1H), 9.44 (bs, 1H), 8.73 (s, 1H), 8.68 (d, J = 4.8 Hz, 1H), 8.48 (s, 1H), 7.74-7.72 (m, 1H), 7.66-7.64 (m, 2H), 7.48 (d, J = 4.8 Hz, 1H), 6.45 (b, 1H), 4.80 (s, 2H), 4.49 (bs, 1H), 3.35 (s, 4H), 3.08 (s, 3H), 2.50-2.47 (m, 2H), 2.08 (bs, 2H), 1.99 (s, 5H) |
| 1558 | MS (ESI) m/z 707.32 [M + 1]+; 1H NMR (400 MHz, DMSO-d6) δ 9.18 (s, 1H), 8.79 (d, J = 4.8 Hz, 1H), 8.64 (s, 1H), 7.77 (d, J = 8.8 Hz, 1H), 7.70-7.68 (m, 2H), 7.56 (d, J = 4.8 Hz, 1H), 7.49-7.44 (m, 2H), 7.36 (bs, 1H), 6.42 (tt, J = 52.4, 7.4 Hz, 1H), 4.90 (s, 2H), 4.38 (bs, 2H), 3.48 (bs, 2H), 3.24 (bs, 2H), 2.86 (bs, 2H), 2.16 (s, 3H) |
| 1562 | MS (ESI) m/z 722.38 [M + 1]+; 1H NMR (400 MHz, DMSO-d6) δ 9.86 (bs, 1H), 8.81 (d, J = 4.8 Hz, 1H), 8.46 (s, 1H), 7.61-7.58 (m, 1H), 7.46 (d, J = 4.8 Hz, 1H), 7.41-7.36 (m, 2H), 4.50 (m, 1H), 4.41 (bs, 2H), 4.21 (bs, 2H), 3.65-3.37 (m, 4H), 3.06 (s, 3H), 2.62 (s, 3H), 2.25 (m, 2H), 2.00 (m, 2H), 1.79-1.69 (m, 8H) |
| 1563 | MS (ESI) m/z 722.45 [M + 1]+; 1H NMR (400 MHz, DMSO-d6) δ 8.59 (s, 1H), 8.41 (bs, 1H), 7.59 (dd, J = 2.4, 8.8 Hz, 1H), 7.42-7.40 (m, 2H), 7.36 (d, J = 9.2 Hz, 1H), 4.53 (bs, 1H), 4.38 (bs, 2H), 4.21 (bs, 2H), 3.84 (bs, 4H), 3.08 (s, 3H), 3.54 (bs, 2H), 2.70 (s, 3H)), 1.99 (bs, 2H), 1.82 (bs, 5H), 1.76 (bs, 3H) |

TABLE 1-continued
7-Aza-Thienylpyridine and Derivative Compounds
| Compound | | Characterization |
|---|---|---|
| 1561 | 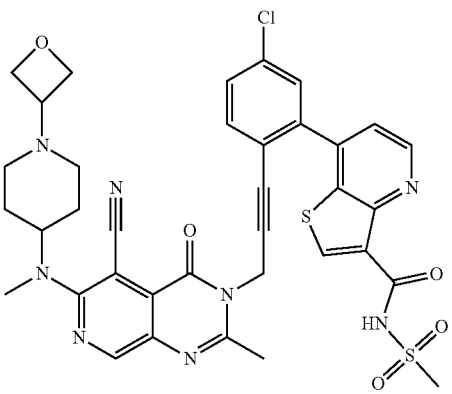 [SMILES: Cc1nc2cnc(N(C)C3CCN(C4COC4)CC3)c(C#N)c2c(=O)n1CC#Cc1ccc(Cl)cc1-c1ccnc2c(C(=O)NS(C)(=O)=O)csc12] | MS (ESI) m/z 757.43 [M + 1]+; 1H NMR (400 MHz, DMSO-d6) δ 12.47 (s, 1H), 8.81-8.78 (m, 3H), 7.77 (d, J = 8.4, 1H), 7.72-7.67 (m, 2H), 7.62 (d, J = 4.8 Hz, 1H), 4.83 (s, 2H), 4.78 (t, J = 6.8 Hz, 4H), 4.60 (bs, 1H), 4.36 (bs, 1H), 3.58 (bs, 2H), 3.53 (s, 3H), 3.12 (s, 3H), 3.05 (d, J = 14.0 Hz, 2H), 2.14 (bs, 4H), 1.99 (s, 3H) |
| 1565 | 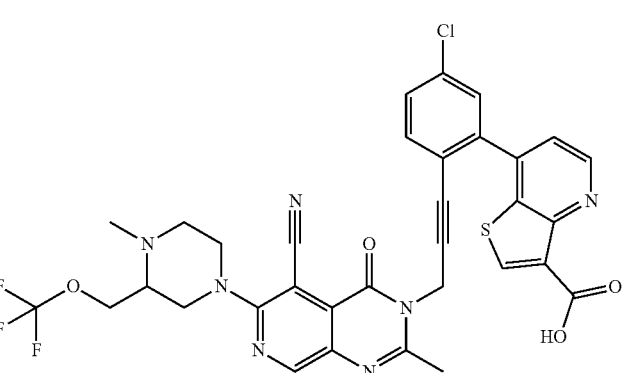 | MS (ESI) m/z 708.44 [M + 1]+; 1H NMR (400 MHz, DMSO-d6) δ 8.85 (s, 1H), 8.76 (d, J = 4.8 Hz, 1H), 8.65 (s, 1H), 7.75 (d, J = 8.0 Hz, 1H), 7.70-7.66 (m, 2H), 7.53 (d, J = 4.8 Hz, 1H), 4.84 (s, 2H), 4.66-4.36 (m, 5H), 3.91-3.78 (m, 4H), 2.95 (bs, 3H), 2.13 (s, 3H) |
| 1566 | 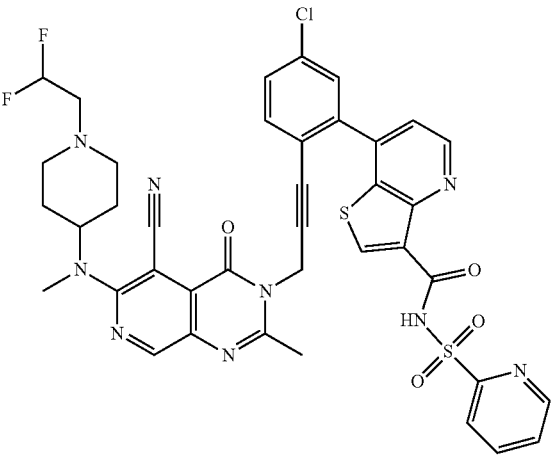 [SMILES: Cc1nc2cnc(N(C)C3CCN(CC(F)F)CC3)c(C#N)c2c(=O)n1CC#Cc1ccc(Cl)cc1-c1ccnc2c(C(=O)NS(=O)(=O)c3ccccn3)csc12] | MS (ESI) m/z 828.47 [M + 1]+; 1H NMR (400 MHz, DMSO-d6) δ 13.02 (s, 1H), 8.90 (d, J = 4.8 Hz, 1H), 8.71 (d, J = 4.4 Hz, 1H), 8.65 (s, 1H), 8.60 (s, 1H), 8.27-8.18 (m, 2H), 7.77-7.53 (m, 4H), 7.49 (d, J = 5.6 Hz, 1H), 6.66-6.29 (m, 1H), 4.82 (s, 2H), 4.60-4.45 (m, 1H), 3.50-3.15 (m, 6H), 3.09 (s, 3H), 2.30-1.80 (m, 7H) |

TABLE 1-continued

7-Aza-Thienylpyridine and Derivative Compounds

| Compound | | Characterization |
|---|---|---|
| 1564 | 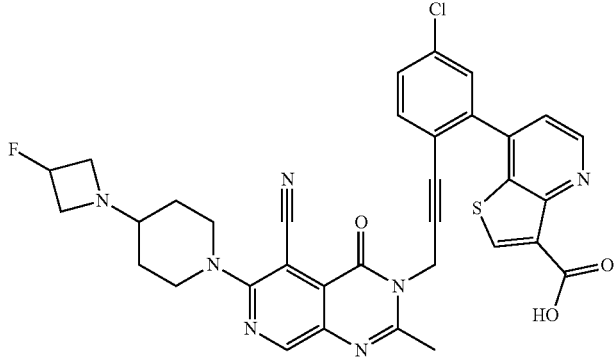 [SMILES: Cc1nc2cnc(N3CCC(N4CC(F)C4)CC3)c(C#N)c2c(=O)n1CC#Cc1ccc(Cl)cc1-c1ccnc2c(C(=O)O)csc12] | MS (ESI) m/z 668.2 [M + 1]+; 1H NMR (400 MHz, DMSO-d6) δ 8.78 (s, 1H), 8.75 (d, J = 4.8 Hz, 1H), 8.64 (s, 1H), 7.75 (d, J = 9.2 Hz, 1H), 7.67-7.70 (m, 2H), 7.54 (d, J = 4.8 Hz, 1H), 5.45 (d, J = 56.8 Hz, 1H), 4.83 (s, 2H), 4.54-4.29 (m, 5H), 3.52 (bs, 2H), 3.15-3.09 (m, 2H), 2.19-2.09 (m, 5H), 1.60-1.52 (m, 2H) |
| 1569 | 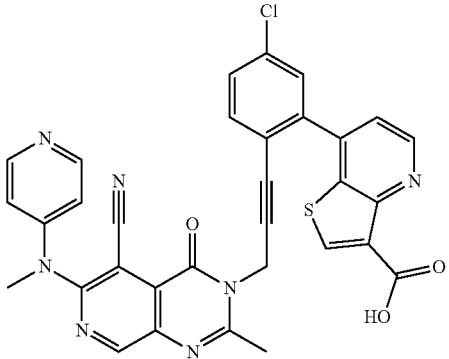 [SMILES: Cc1nc2cnc(N(C)c3ccncc3)c(C#N)c2c(=O)n1CC#Cc1ccc(Cl)cc1-c1ccnc2c(C(=O)O)csc12] | MS (ESI) m/z 618.28 [M + 1]+; 1H NMR (400 MHz, DMSO-d6) 614.24 (bs, 1H), 13.11 (bs, 1H), 9.17 (s, 1H), 8.79 (d, J = 4.80 Hz, 1H), 8.67 (s, 1H), 8.52 (d, J = 7.20 Hz, 2H), 7.76 (d, J = 8.00 Hz, 1H), 7.71-7.68 (m, 2H), 7.53 (d, J = 4.80 Hz, 1H), 7.38 (d, J = 7.20 Hz, 2H), 4.89 (s, 2H), 3.69 (s, 3H), 2.23 (s, 3H) |
| 1571 | 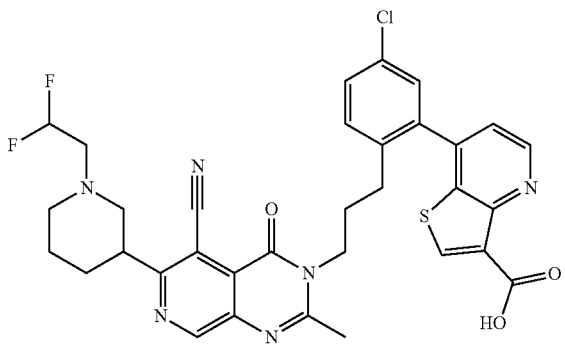 [SMILES: Cc1nc2cnc(C3CCCN(CC(F)F)C3)c(C#N)c2c(=O)n1CCCc1ccc(Cl)cc1-c1ccnc2c(C(=O)O)csc12] | MS (ESI) m/z 665.43 [M + 1]+; 1H NMR (400 MHz, DMSO-d6) δ 9.00 (s, 1H), 8.82 (d, J = 4.4 Hz, 1H), 8.35 (s, 1H), 7.60 (dd, J = 8.8 Hz, 2.4 Hz, 1H), 7.47 (d, J = 4.8 Hz, 1H), 7.43 (d, J = 2.4 Hz, 1H), 7.36 (d, J = 8.8 Hz, 1H), 6.55 (t, J = 53.2 Hz, 1H), 4.40 (d, J = 4.4 Hz, 2H), 4.26 (s, 2H), 3.87 (bs, 1H), 3.47-3.24 (m, 4H), 2.00-1.89 (m, 4H), 1.78 (s, 3H), 1.74-1.67 (m, 2H) |
| 1568 | 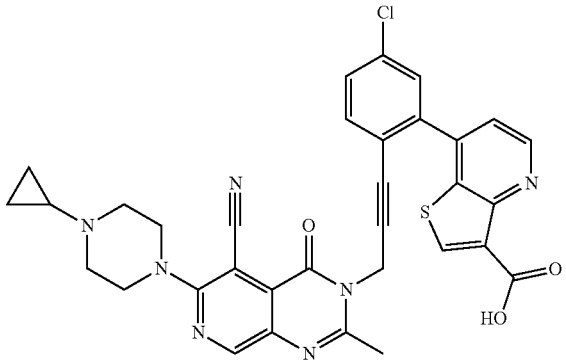 [SMILES: Cc1nc2cnc(N3CCN(C4CC4)CC3)c(C#N)c2c(=O)n1CC#Cc1ccc(Cl)cc1-c1ccnc2c(C(=O)O)csc12] | MS (ESI) m/z 636.25 [M + 1]+; 1H NMR (400 MHz, DMSO-d6) δ 13.18 (bs, 1H), 8.84 (s, 1H), 8.75 (d, J = 4.8 Hz,1H), 8.65 (s, 1H), 7.75 (d, J = 8.4 Hz, 1H), 7.70-7.65 (m, 2H), 7.53 (d, J = 4.8 Hz, 1H), 4.84 (s, 2H), 4.38 (m, 2H), 3.79 (m, 2H,), 3.49 (m, 4H), 3.03 (m, 1H), 2.14 (s, 3H), 0.93 (m, 4H) |

TABLE 1-continued

7-Aza-Thienylpyridine and Derivative Compounds

| Compound | Characterization |
|---|---|
| 1573 | MS (ESI) m/z 685.39 [M + 1]+; 1H NMR (400 MHz, DMSO-d6) δ 9.06 (s, 1H), 8.75 (d, J = 4.8 Hz, 1H), 8.61 (s, 1H), 7.77-7.75 (m, 1H), 7.70-7.68 (m, 2H), 7.55 (d, J = 4.4 Hz, 1H), 6.60 (bs, 1H), 6.41 (s, 1H), 4.86 (s, 2H), 3.99-3.58 (m, 2H), 3.03-2.76 (m, 4H), 2.54 (s, 3H), 2.29-2.14 (m, 5H), 1.77-1.75 (m, 1H) |
| 1574 | MS (ESI) m/z 659.38 [M + 1]+; 1H NMR (400 MHz, DMSO-d6) δ 9.14 (s, 1H), 8.77 (d, J = 4.8 Hz, 1H), 8.60 (s, 1H), 7.76 (d, J = 18.4 Hz, 1H), 7.70 (d, J = 2.0 Hz, 1H), 7.55 (d, J = 4.8 Hz, 2H), 6.55 (t, J = 54.4 Hz, 1H), 4.87 (s, 2H), 3.60-2.87 (m, 7H), 2.17 (s, 3H), 2.04-1.73 (m, 4H) |
| 1572 | MS (ESI) m/z 709.45 [M + 1]+; 1H NMR (400 MHz, DMSO-d6) δ 9.18 (s, 1H), 8.77 (d, J = 4.8 Hz, 1H), 8.63 (s, 1H), 7.76 (d, J = 9.2 Hz, 1H), 7.70 (dd, J = 6.4 Hz, 2.0 Hz, 2H), 7.55 (d, J = 4.8 Hz, 1H), 4.89 (s, 2H), 3.78-3.56 (m, 3H), II s, 3.28-3.19 (m, 2H), 3.00-2.79 (m, 2H), 2.08 (s, 3H), 1.98-1.85 (m, 4H) |
| 1576 | MS (ESI) m/z 714.55 [M + 1]+; 1H-NMR (400 MHz, DMSO-d6) δ 8.80 (s, 1H), 8.76 (d, J = 4.8 Hz, 1H), 8.64 (s, 1H), 7.75 (d, J = 8.8 Hz, 1H), 7.68-7.67 (m, 2H), 7.54 (d, J = 4.8 Hz, 1H), 4.82 (s, 2H), 3.81-3.38 (m, 5H), 3.08 (s, 3H), 2.82-2.70 (m, 2H), 2.43-2.33 (m, 2H), 2.06 (s, 3H), 1.68-1.53 (m, 7H) |

TABLE 1-continued
7-Aza-Thienylpyridine and Derivative Compounds
| Compound | | Characterization |
|---|---|---|
| 1577 | 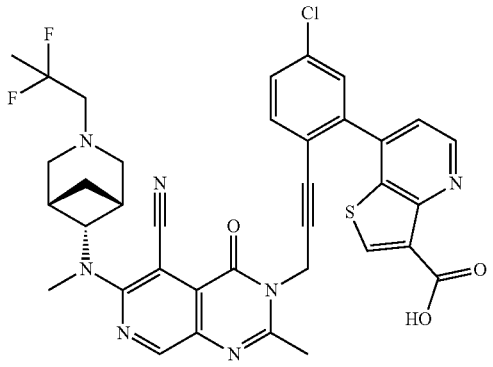 | MS (ESI) m/z 714.49 [M + 1]+; 1H-NMR (400 MHz, DMSO-d6) δ 8.80 (s, 1H), 8.76 (d, J = 4.8 Hz, 1H), 8.64 (s, 1H), 7.75 (d, J = 8.8 Hz, 1H), 7.68-7.67 (m, 2H), 7.54 (d, J = 4.8 Hz, 1H), 4.82 (s, 2H), 3.81-3.38 (m, 5H), 3.08 (s, 3H), 2.82-2.70 (m, 2H), 2.43-2.33 (m, 2H), 2.06 (s, 3H), 1.68-1.53 (m, 7H) |
| 1575 | 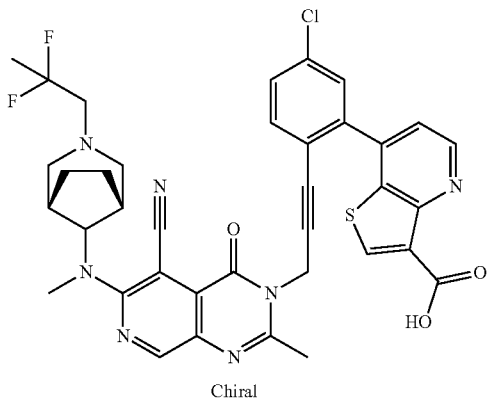 [SMILES: Cc1nc2cnc(N(C)C3[C@@H]4CC[C@H]3CN(CC(C)(F)F)C4)c(C#N)c2c(=O)n1CC#Cc1ccc(Cl)cc1-c1ccnc2c(C(=O)O)csc12] | MS (ESI) m/z 728.08 [M + 1]+; 1H-NMR (400 MHz, DMSO-d6) δ 8.80 (s, 1H), 8.76 (d, J = 4.8 Hz, 1H), 8.64 (s, 1H), 7.75 (d, J = 8.8 Hz, 1H), 7.68-7.67 (m, 2H), 7.54 (d, J = 4.8 Hz, 1H), 4.82 (s, 2H), 3.81-3.38 (m, 5H), 3.08 (s, 3H), 2.82-2.70 (m, 2H), 2.43-2.33 (m, 2H), 2.06 (s, 3H), 1.68-1.53 (m, 7H) |
| 1579 | 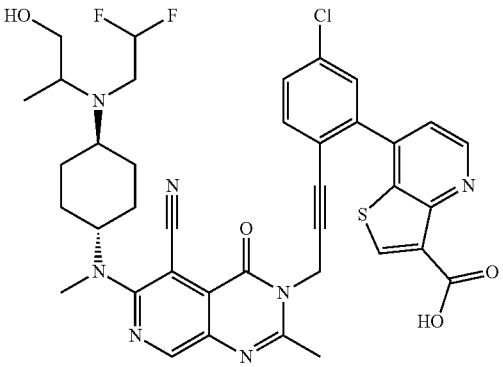 | MS (ESI) m/z 760.64 [M + 1]+; 1H NMR (400 MHz, DMSO-d6) δ 8.76 (d, J = 4.8 Hz, 1H), 8.17 (s, 1H), 8.66 (s, 1H), 7.76-7.74 (m, 1H), 7.70-7.68 (m, 2H), 7.56 (d, J = 4.8 Hz, 1H), 6.43-4.15 (m, 1H), 4.81 (s, 2H), 4.30 (bs, 1H), 3.54 (bs, 4H), 3.08 (s, 3H), 2.05 (bs, 7H), 1.83-1.67 (m, 6H), 1.17 (bs, 3H) |

TABLE 1-continued

7-Aza-Thienylpyridine and Derivative Compounds

| Compound | | Characterization |
|---|---|---|
| 1581 | 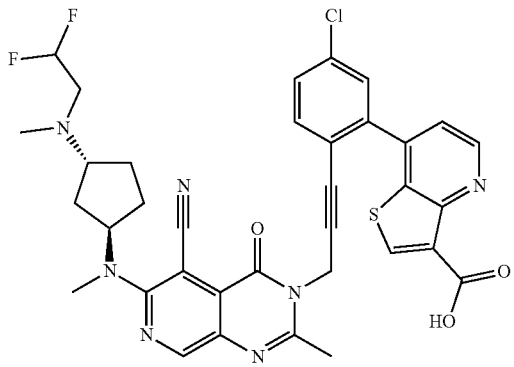 Chiral | MS (ESI) m/z 702.52 [M + 1]+; 1H NMR (400 MHz, DMSO-d6) δ 8.74-8.70 (m, 2H), 8.37 (s, 1H), 7.74 (d, J = 8.4 Hz, 1H), 7.67-7.64 (m, 2H), 7.44 (d, J = 4.4 Hz, 1H), 6.16 (t, J = 55.6 Hz, 1H), 4.89-4.84 (m, 3H), 3.081 (bs, 4H), 2.80-2.72 (m, 2H), 2.33 (bs, 3H), 2.07-1.98 (m, 4H), 1.90 (bs, 3H), 1.75-1.71 (m, 1H), 1.41 (t, J = 7.2 Hz, 1H) |
| 1578 | 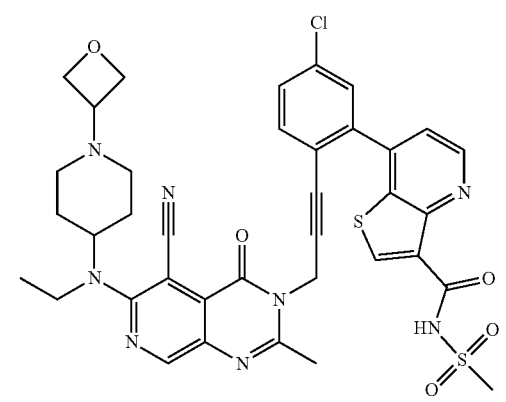 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN(C2COC2)CC1] | MS (ESI) m/z 771.57 [M + 1]+; 1H NMR (400 MHz, DMSO-d6) δ 12.48 (s, 1H), 8.82 (d, J = 4.4 Hz, 2H), 8.78 (s, 1H), 7.75 (d, J = 8.4 Hz, 1H), 7.72-7.67 (m, 2H), 7.63 (d, J = 4.8 Hz, 1H), 4.83 (s, 2H), 4.77-4.75 (m, 4H), 4.44-4.35 (m, 2H), 3.76-3.59 (m, 3H), 3.54 (s, 3H), 3.28-3.19 (m, 1H), 3.02 (bs, 2H), 2.15 (s, 4H), 1.99 (s, 3H), 1.15 (t, J = 6.8 Hz, 3H) |
| 1583 | 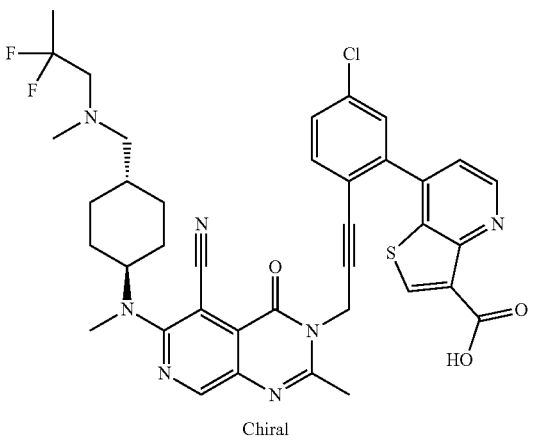 [SMILES: Cc1nc2cnc(N(C)[C@H]3CC[C@H](CN(C)CC(C)(F)F)CC3)c(C#N)c2c(=O)n1CC#Cc1ccc(Cl)cc1-c1ccnc2c(C(=O)O)csc12] Chiral | MS (ESI) m/z 744.52 [M + 1]+; 1H NMR (400 MHz, DMSO-d6) δ 8.76 (d, J = 4.8 Hz, 1H), 8.70 (s, 1H), 8.66 (s, 1H), 7.75 (d, J = 9.2 Hz, 1H), 7.69-7.68 (m, 2H), 7.55 (d, J = 4.8 Hz, 1H), 4.81 (s, 2H), 4.26-4.23 (m, 1H), 3.12-3.09 (m, 4H), 2.93 (bs, 3H), 2.57-2.52 (m, 2H), 2.06 (s, 3H), 1.89 (bs, 4H), 1.75-1.72 (m, 7H), 1.22 (bs, 2H) |

TABLE 1-continued

7-Aza-Thienylpyridine and Derivative Compounds

| Compound | | Characterization |
|---|---|---|
| 1584 | 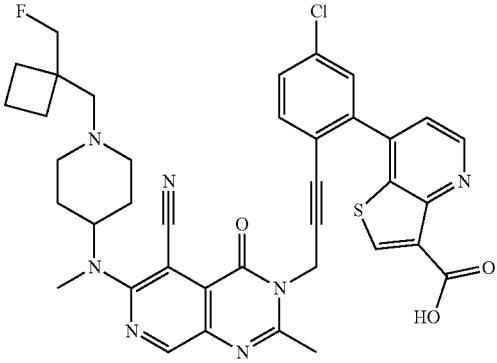 [SMILES: Cc1nc2cnc(N(C)C3CCN(CC4(CF)CCC4)CC3)c(C#N)c2c(=O)n1CC#Cc1ccc(Cl)cc1-c1ccnc2c(C(=O)O)csc12] | MS (ESI) m/z 724.3 [M + 1]+; 1H NMR (400 MHz, DMSO-d6) δ 13.01 (bs, 1H), 8.76-8.74 (m, 2H), 8.64 (s, 1H), 7.75 (d, J = 8.4 Hz, 1H), 7.70-7.67 (m, 2H), 7.55 (d, J = 4.8 Hz, 1H), 4.82 (s, 2H), 4.74-7.56 (m, 3H), 3.52-3.49 (m, 2H), 3.32-3.26 (m, 4H), 3.11 (s, 3H), 2.26-2.21 (m, 2H), 2.10 (s, 3H), 2.03-1.91 (m, 8H) |
| 1582 | 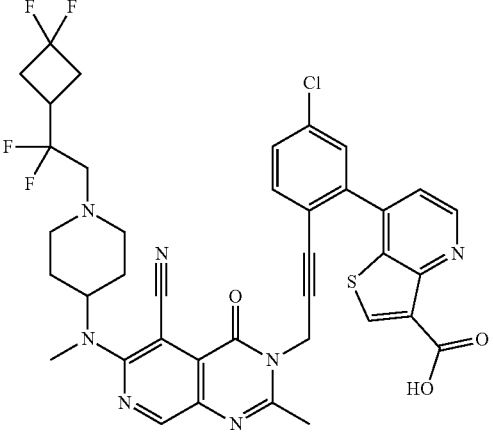 [SMILES: Cc1nc2cnc(N(C)C3CCN(CC(F)(F)C4CC(F)(F)C4)CC3)c(C#N)c2c(=O)n1CC#Cc1ccc(Cl)cc1-c1ccnc2c(C(=O)O)csc12] | MS (ESI) m/z 778.66 [M + 1]+; 1H NMR (400 MHz, DMSO-d6) δ 8.76 (d, J = 4.8 Hz, 1H), 8.73 (s, 1H), 8.65 (s, 1H), 7.75 (d, J = 8.8 Hz, 1H), 7.70-7.67 (m, 2H), 7.55 (d, J = 4.8 Hz, 1H), 4.82 (s, 2H), 4.58 (bs, 2H), 4.24 (bs, 2H), 3.11 (s, 3H), 2.94-2.67 (m, 6H), 2.32-2.08 (m, 9H) |
| 1586 | 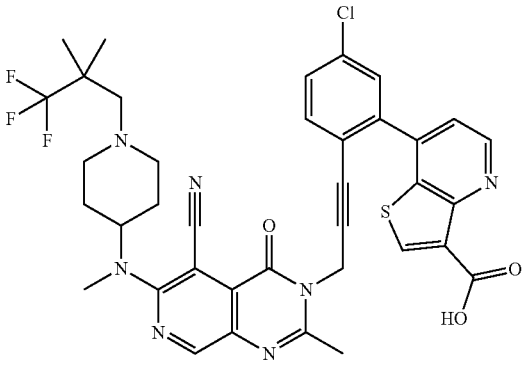 [SMILES: Cc1nc2cnc(N(C)C3CCN(CC(C)(C)C(F)(F)F)CC3)c(C#N)c2c(=O)n1CC#Cc1ccc(Cl)cc1-c1ccnc2c(C(=O)O)csc12] | MS (ESI) m/z 748.52 [M + 1]+; 1H NMR (400 MHz, DMSO-d6) δ 8.76 (d, J = 4.8 Hz, 1H), 8.72 (s, 1H), 8.70 (s, 1H), 7.74 (d, J = 8.0 Hz, 1H), 7.70-7.62 (m, 2H), 7.53 (d, J = 4.8 Hz, 1H), 4.84 (s, 2H), 4.48-4.30 (m, 1H), 3.40-2.85 (m, 9H), 2.20-1.75 (m, 7H), 1.20 (s, 6H) |
| 1587 | 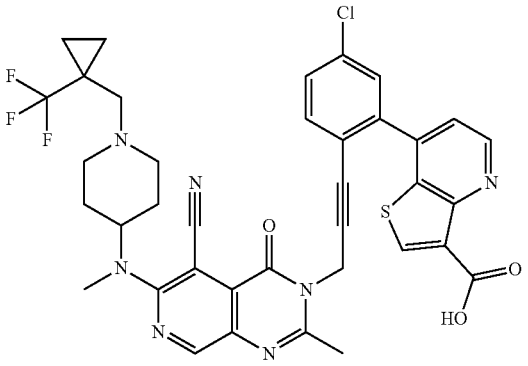 [SMILES: Cc1nc2cnc(N(C)C3CCN(CC4(C(F)(F)F)CC4)CC3)c(C#N)c2c(=O)n1CC#Cc1ccc(Cl)cc1-c1ccnc2c(C(=O)O)csc12] | MS (ESI) m/z 746.54 [M + 1]+; 1H NMR (400 MHz, DMSO-d6) δ 13.13 (bs, 1H), 8.75 (d, J = 4.8 Hz, 1H), 8.70 (s, 1H), 8.65 (s, 1H), 7.75 (d, J = 9.2 Hz, 1H), 7.68-7.67 (m, 2H), 7.54 (d, J = 4.8 Hz, 1H), 4.81 (s, 2H), 4.26 (bs, 1H), 3.09 (s, 3H), 3.04 (d, J = 10.8 Hz, 2H), 2.70-2.50 (merged, 2H), 2.10-2.00 (m, 5H), 1.88-1.81 (m, 4H), 0.97 (s, 2H), 0.74 (s, 2H) |

TABLE 1-continued

7-Aza-Thienylpyridine and Derivative Compounds

| Compound | | Characterization |
|---|---|---|
| 1585 | 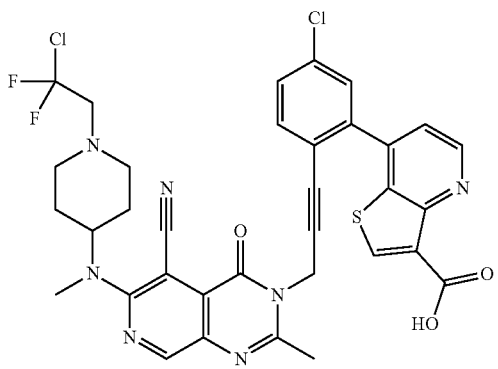 [SMILES: Cc1nc2cnc(N(C)C3CCN(CC(F)(F)Cl)CC3)c(C#N)c2c(=O)n1CC#Cc1ccc(Cl)cc1-c1ccnc2c(C(=O)O)csc12] | MS (ESI) m/z 722.42 [M + 1]+; 1H NMR (400 MHz, DMSO-d6) δ 8.77 (d, J = 4.8 Hz, 1H), 8.71 (s, 1H), 8.66 (s, 1H), 7.76-7.74 (m, 1H), 7.69-7.68 (m, 2H), 7.55 (d, J = 4.8 Hz, 1H), 4.81 (s, 2H), 4.29-4.27 (m, 1H), 3.44 (bs, 2H), 3.17-3.09 (m, 5H), 2.66 (bs, 2H), 2.05 (s, 3H), 1.94 (d, J = 10.4 Hz, 2H), 1.80 (d, J = 10.8 Hz, 2H) |
| 1589 | 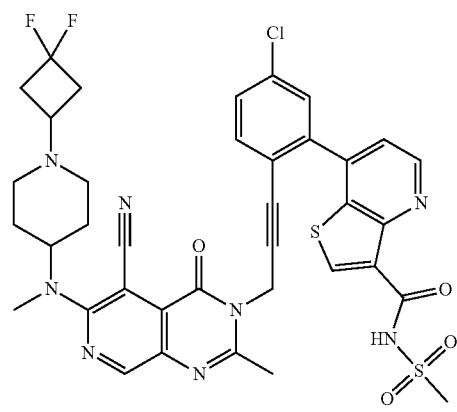 | MS (ESI) m/z 791.49 [M + 1]+; 1H NMR (400 MHz, DMSO-d6) δ 12.47 (s, 1H), 9.72 (bs, 1H), 8.81-8.78 (m, 3H), 7.77 (d, J = 8.4 Hz, 1H), 7.72-7.67 (m, 2H), 7.62 (d, J = 4.8 Hz, 1H), 4.83 (s, 2H), 4.59 (bs, 1H), 3.82-3.45 (m, 6H), 3.30-2.95 (m, 9H), 2.20-2.14 (m, 4H), 1.99 (s, 3H) |
| 1590 | 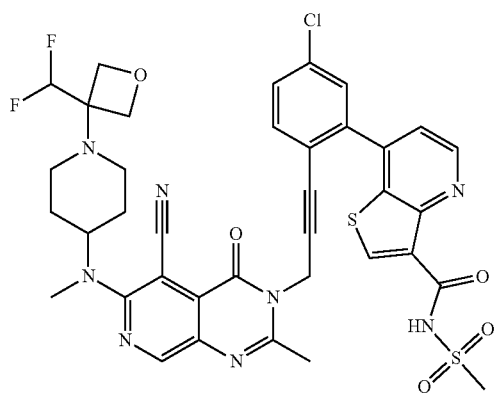 [SMILES: Cc1nc2cnc(N(C)C3CCN(C4(C(F)F)COC4)CC3)c(C#N)c2c(=O)n1CC#Cc1ccc(Cl)cc1-c1ccnc2c(C(=O)NS(C)(=O)=O)csc12] | MS (ESI) m/z 807.10 [M + 1]+; 1H NMR (400 MHz, DMSO-d6) δ 12.47 (s, 1H), 8.80 (d, J = 5.2 Hz 1H), 8.78 (s, 1H), 8.75 (s, 1H), 7.77 (d, J = 8.4 Hz, 1H), 7.70 (dd, J = 10.4 Hz, 2 Hz, 2H), 7.62 (d, J = 4.8 Hz, 1H), 6.45 (t, J = 54.8 Hz, 1H), 4.82 (s, 2H), 4.50 (d, J = 6.8 Hz, 2H), 4.45 (d, J = 6.8 Hz, 2H), 4.34-4.29 (m, 1H), 3.55 (s, 3H), 3.11 (s, 3H), 2.91 (d, J = 10.8 Hz, 2H), 2.60-2.53 (m, 2H), 1.96-1.85 (m, 7H) |
| 1588 | 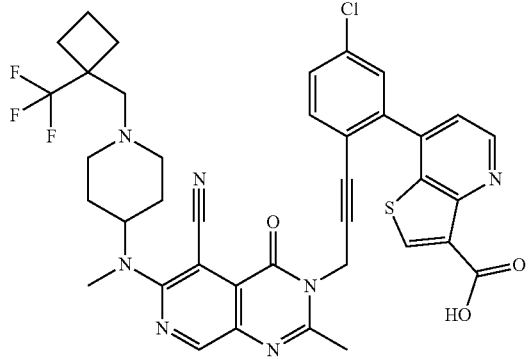 [SMILES: Cc1nc2cnc(N(C)C3CCN(CC4(C(F)(F)F)CCC4)CC3)c(C#N)c2c(=O)n1CC#Cc1ccc(Cl)cc1-c1ccnc2c(C(=O)O)csc12] | MS (ESI) m/z 760.61 [M + 1]+; 1H NMR (400 MHz, DMSO-d6) δ 13.05 (bs, 1H), 9.09 (bs, 1H), 8.80-8.70 (m, 2H), 8.65 (s, 1H), 7.75 (d, J = 8.40 Hz, 1H), 7.71-7.63 (m, 2H), 7.54 (d, J = 4.00 Hz, 1H), 4.82 (s, 2H), 4.56 (bs, 1H), 3.70-3.50 (m, 4H), 3.20-3.20 (merged, 2H), 3.11 (s, 3H), 2.41-2.20 (m, 6H), 2.18-1.94 (m, 7H) |

TABLE 1-continued

7-Aza-Thienylpyridine and Derivative Compounds

| Compound | Characterization |
|---|---|
| 1592 | MS (ESI) m/z 714.10 [M + 1]+; 1H-NMR (400 MHz, DMSO-d6) δ 13.09 (bs, 1H), 8.75-8.74 (m, 2H), 8.64 (s, 1H), 7.75 (d, J = 8.4 Hz, 1H), 7.69-7.67 (m, 2H), 7.53 (d, J = 4.8 Hz, 1H), 4.82 (s, 2H), 4.39 (bs, 2H), 4.01 (bs, 1H), 3.66 (bs, 1H), 3.20-2.95 (m, 5H), 2.72-2.66 (m, 2H), 2.08 (bs, 5H), 1.90-1.60 (m, 4H) |
| 1593 | MS (ESI) m/z 851.58 [M + 1]+; 1H-NMR (400 MHz, DMSO-d6) δ 13.03 (bs, 1H), 8.87 (d, J = 4.80 Hz, 1H), 8.84 (s, 1H), 8.73 (s, 1H), 7.77 (d, J = 9.20 Hz, 1H), 7.71-7.69 (m, 2H), 7.65 (d, J = 4.80 Hz, 1H), 5.06 (q, J = 9.60 Hz, 2H), 4.82 (s, 2H), 4.32-4.29 (m, 1H), 3.33 (bs, 2H), 3.09 (bs, 5H), 2.58 (bs, 2H), 1.96 (bs, 2H), 1.92 (s, 3H), 1.80 (d, J = 11.2 Hz, 2H) |
| 1591 | MS (ESI) m/z 857.53 [M + 1]+; 1H NMR (400 MHz, DMSO-d6) δ 8.85 (d, J = 5.2 Hz, 1H), 8.81 (s, 1H), 8.75 (s, 1H), 7.78 (d, J = 8.8 Hz, 1H), 7.71-7.69 (m, 2H), 7.64 (d, J = 4.8 Hz, 1H), 6.73-6.58 (m, 1H), 6.15-5.87 (m, 1H), 4.82 (s, 2H), 4.59-4.55 (m, 2H), 4.52-4.47 (m, 4H), 4.35-4.22 (m, 4H), 3.16-3.04 (m, 3H), 2.86 (m, 1H), 1.92 (s, 3H), 1.76 (d, J = 11.2 Hz, 2H), 1.56-1.48 (m, 2H) |

TABLE 1-continued

7-Aza-Thienylpyridine and Derivative Compounds

| Compound | | Characterization |
|---|---|---|
| 1595 | [structure] | MS (ESI) m/z 847.0 [M + 1]+; 1H-NMR (400 MHz, DMSO-d6) δ 13.06 (bs, 1H), 8.85 (d, J = 4.8 Hz, 1H), 8.83 (s, 1H), 8.75 (s, 1H), 7.78 (d, J = 8.80 Hz, 1H), 7.71 (bs, 2H), 7.65 (d, J = 4.80 Hz, 1H), 5.04 (q, J = 9.60 Hz, 2H), 4.83 (s, 2H), 4.59 (bs, 1H), 3.77 (bs, 4H), 3.37 (bs, 2H), 3.11 (s, 3H), 2.26 (bs, 2H), 2.02 (bs, 2H), 1.95 (s, 3H), 1.76 (t, J = 17.6 Hz, 3H) |
| 1596 | [structure] | MS (ESI) m/z 701.0 [M + 1]+; 1H-NMR (400 MHz, DMSO-d6 with D2O) 6 8.68 (s, 1H), 8.67 (s, 1H), 8.39 (s, 1H), 7.71 (d, J = 8.4 Hz, 1H), 7.65-7.63 (m, 1H), 7.57 (d, J = 1.6 Hz, 1H), 7.41 (d, J = 4.8 Hz, 1H), 4.73 (s 2H), 4.55-4.49 (m, 1H), 3.80-3.72 (m, 2H), 3.62-3.57 (m, 2H), 3.28 (t, J = 11.6 Hz, 2H), 3.09 (s, 1H), 2.53 (bs, 1H), 2.32-2.20 (m, 2H), 2.06 (bs, 6H), 1.74 (t, J = 19.6 Hz, 3H) |
| 1594 | [structure] | MS (ESI) m/z 705.48 [M + 1]+; 1H-NMR (400 MHz, DMSO-d6) δ 8.68 (s, 1H), 8.67 (s, 1H), 8.45 (s, 1H), 7.72 (d, J = 8.00 Hz, 1H), 7.65 (d, J = 8.40 Hz, 1H), 7.61 (bs, 1H), 7.44 (d, J = 2.40 Hz, 1H), 4.76 (s, 2H), 4.32 (t, J = 12.00 Hz, 1H), 3.49 (d, J = 8.80 Hz, 2H), 3.18 (d, J = 10.80 Hz, 2H), 3.07 (s, 3H), 2.73 (t, J = 11.2 Hz, 2H), 2.02 (s, 3H), 1.96 (d, J = 13.2 Hz, 2H), 1.85 (d, J = 10.8 Hz, 2H) |
| 1598 | [structure] | MS (ESI) m/z 758.69 [M + 1]+; 1H NMR (400 MHz, DMSO-d6) δ 9.94 (bs, 1H), 8.77 (d, J = 4.8 Hz, 1H), 8.64 (s, 1H), 7.76 (d, J = 8.0 Hz, 1H), 7.69-7.67 (m, 2H), 7.55 (d, J = 4.4 Hz, 1H), 6.43 (bs, 1H), 4.82 (s, 2H), 4.53 (bs, 1H), 3.79 (bs, 4H), 3.39-3.35 (m, 2H), 3.11 (s, 3H), 2.41 (bs, 2H), 2.32-2.26 (m, 2H), 2.09 (s, 7H), 1.86-1.82 (m, 1H), 1.65-1.60 (m, 1H) |

TABLE 1-continued
7-Aza-Thienylpyridine and Derivative Compounds
| Compound | | Characterization |
|---|---|---|
| 1599 | 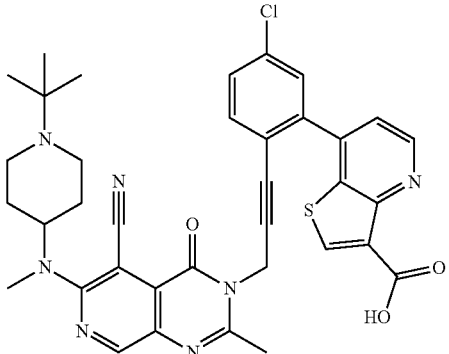 | MS (ESI) m/z 638.41 [M + 1]+; 1H NMR (400 MHz, DMSO-d6) δ 8.79-8.74 (m, 2H), 8.65 (s, 1H), 7.78 (d, J = 8.0 Hz, 1H), 7.70-7.68 (m, 2H), 7.55 (d, J = 4.8 Hz, 1H), 4.83 (s, 2H), 4.54-4.53 (m, 1H), 3.58-3.55 (m, 2H), 3.20 (bs, 2H), 3.01 (s, 3H), 2.83-2.82 (m, 3H), 2.10 (bs, 7H) |
| 1597 | 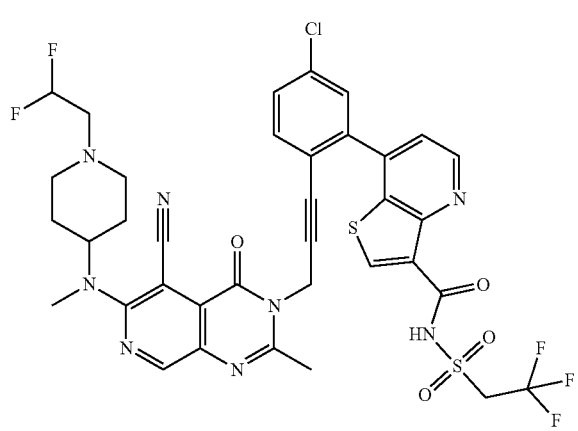 [SMILES: Cc1nc2cnc(N(C)C3CCN(CC(F)F)CC3)c(C#N)c2c(=O)n1CC#Cc1ccc(Cl)cc1-c1ccnc2c(C(=O)NS(=O)(=O)CC(F)(F)F)csc12] | MS (ESI) m/z 833.52 [M + 1]+; 1H-NMR (400 MHz, DMSO-d6) δ 13.08 (bs, 1H), 8.86-8.84 (m, 2H), 7.79-7.769 (m, 1H), 7.71 (t, J = 2.0 Hz, 2H), 7.66 (d, J = 5.2 Hz, 1H), 6.51 (bs, 1H), 5.08-5.01 (m, 2H), 4.83 (s, 2H), 4.52 (bs, 1H), 3.94 (bs, 2H), 3.41 (bs, 4H), 3.21 (s, 3H), 2.15 (bs, 2H), 2.07 (s, 5H) |
| 1601 | 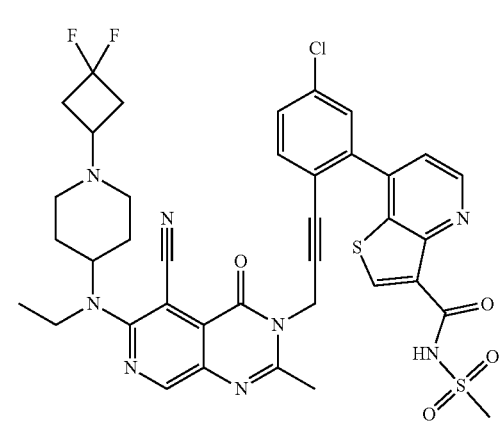 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN(C2CC(F)(F)C2)CC1] | MS (ESI) m/z 805.69 [M + 1]+; 1H-NMR (400 MHz, DMSO-d6) δ 12.47 (bs, 1H), 8.81 (d, J = 4.8 Hz, 1H), 8.78 (bs, 2H), 7.79 (d, J = 11.6 Hz, 1H), 7.70 (bs, 1H), 7.68 (bs, 1H), 7.63 (d, J = 4.80 Hz, 1H), 4.82 (s, 2H), 4.20 (bs, 1H), 3.65 (g, J = 6.80 Hz, 2H), 3.54 (s, 3H), 2.93-2.90 (m, 2H), 2.69-2.66 (m, 4H), 2.42-2.32 (m, 3H), 1.94 (s, 3H), 1.92-1.89 (m, 4H) 1.11 (t, J = 6.8 Hz, 3H) |

TABLE 1-continued

7-Aza-Thienylpyridine and Derivative Compounds

| Compound | | Characterization |
|---|---|---|
| 1602 | 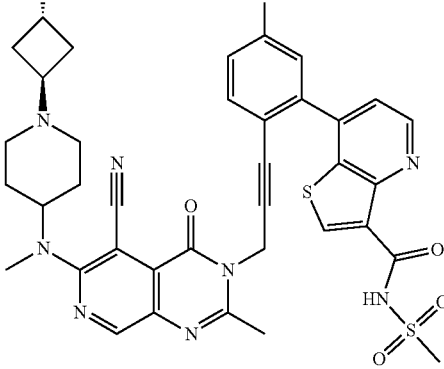<br>Chiral | MS (ESI) m/z 773.67 [M + 1]+; 1H NMR (400 MHz, DMSO-d6) δ 12.47 (s, 1H), 9.72 (bs, 1H), 8.81-8.78 (m, 3H), 7.77 (d, J = 8.36 Hz, 1H), 7.72-7.67 (m, 2H), 7.62 (d, J = 4.80 Hz, 1H), 5.33-5.14 (dm, 1H), 4.83 (s, 2H), 4.63-4.55 (m, 1H), 4.03-3.97 (m, 1H), 3.60-3.50 (merged, 3H), 3.11 (s, 3H), 3.09-3.02 (m, 2H), 2.76-2.50 (m, 6H), 2.12-2.07 (m, 4H), 1.99 (s, 3H) |
| 1600 | 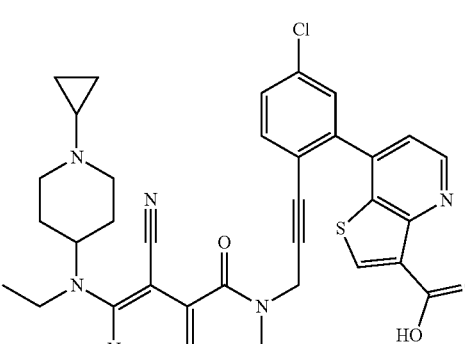 | MS (ESI) m/z 678.56 [M + 1]+; 1H NMR (400 MHz, DMSO-d6) δ 13.12 (bs, 1H), 8.83-8.73 (m, 3H), 8.66 (s, 1H), 7.76 (d, J = 8.8 Hz, 1H), 7.70-7.68 (m, 2H), 7.55 (d, J = 4.8 Hz, 1H), 4.83 (s, 2H), 4.40 (bs, 1H), 3.71-3.57 (m, 4H), 3.40-3.20 (merged, 2H), 2.85 (bs, 1H), 2.18-2.00 (m, 7H), 1.14 (t, J = 6.4 Hz, 3H), 0.98-0.79 (m, 4H) |
| 1604 | 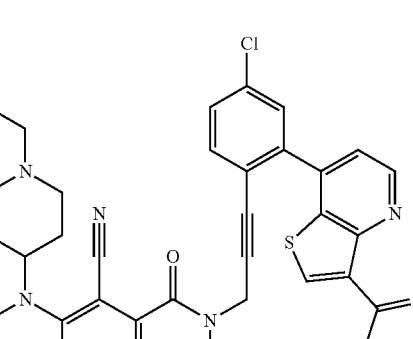 | MS (ESI) m/z 793.67 [M + 1]+; 1H-NMR (400 MHz, DMSO-d6) δ 12.45 (s, 1H), 8.83 (d, J = 4.8 Hz, 1H), 8.73 (bs, 2H), 7.78 (d, J = 8.4 Hz, 1H), 7.71-7.69 (m, 2H), 7.63 (d, J = 4.8 Hz, 1H), 4.83 (s, 2H), 4.61 (bs, 1H), 3.84 (bs, 1H), 3.69-3.65 (m, 2H), 3.11 (s, 3H), 2.02-1.91 (m, 6H), 1.76 (bs, 4H), 1.38 (t, J = 14.4 Hz, 3H) |

TABLE 1-continued

7-Aza-Thienylpyridine and Derivative Compounds

| Compound | | Characterization |
|---|---|---|
| 1605 | 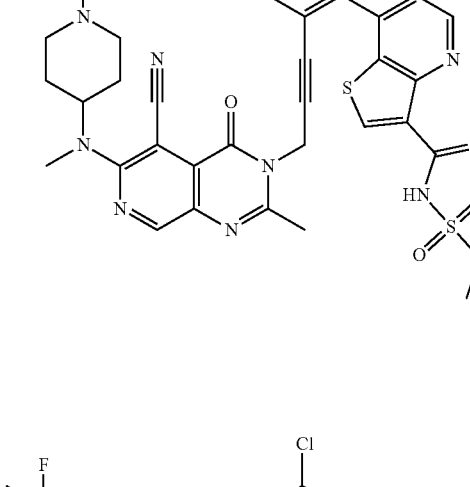 | MS (ESI) m/z 793.67 [M + 1]+; 1H-NMR (400 MHz, DMSO-d6) δ 12.45 (s, 1H), 8.83 (d, J = 4.8 Hz, 1H), 8.73 (bs, 2H), 7.78 (d, J = 8.4 Hz, 1H), 7.71-7.69 (m, 2H), 7.63 (d, J = 4.8 Hz, 1H), 4.83 (s, 2H), 4.61 (bs, 1H), 3.84 (bs, 1H), 3.69-3.65 (m, 2H), 3.11 (s, 3H), 2.02-1.91 (m, 6H), 1.76 (bs, 4H), 1.38 (t, J = 14.4 Hz, 3H) |
| 1603 | 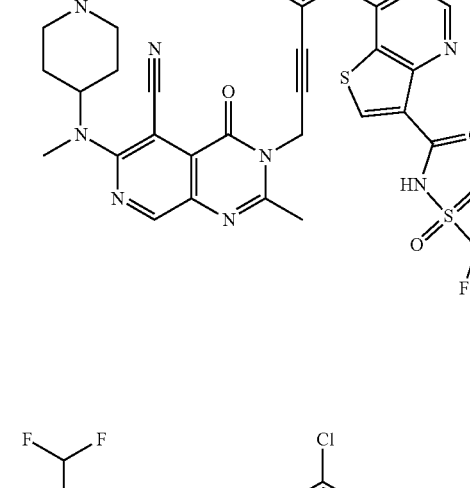 | MS (ESI) m/z 833.74 [M + 1]+; 1H-NMR (400 MHz, DMSO-d6) δ 9.86 (bs, 1H), 8.80-8.78 (d, J = 8.80 Hz, 2H), 8.68 (s, 1H), 7.80-7.67 (m, 4H), 4.88 (s, 2H), 4.54 (bs, 1H), 3.66-3.38 (m, 4H), 3.33-3.27 (m, 2H), 3.09 (s, 3H), 2.40-2.25 (m, 2H), 2.12 (s, 3H), 2.10-1.99 (m, 2H), 1.76 (t, J = 19.2 Hz, 3H) |
| 1607 | 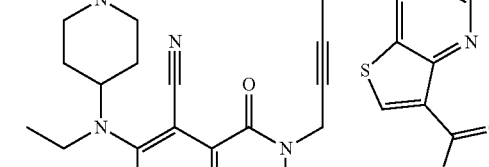 | MS (ESI) m/z 829.71 [M + 1]+; 1H NMR (400 MHz, DMSO-d6) δ 12.49 (s, 1H), 8.81 (d, J = 4.8 Hz, 1H), 8.78 (d, J = 3.0 Hz, 2H), 7.77 (d, J = 8.16 Hz, 1H), 7.70-7.68 (m, 2H), 7.49 (d, J = 6.36 Hz, 1H), 6.56 (tt, J = 4.16 Hz, J = 88.08 Hz, 1H), 4.82 (s, 2H), 4.22-4.16 (m, 1H), 3.65 (d, J = 6.88 Hz, 2H), 3.55 (s, 3H) 3.04-2.94 (m, 4H), 2.49-2.41 (m, 2H), 1.99-1.89 (m, 5H), 1.78 (d, J = 10.68 Hz, 2H), 1.11 (t, J = 6.72 Hz, 3H) |

TABLE 1-continued

7-Aza-Thienylpyridine and Derivative Compounds

| Compound | | Characterization |
|---|---|---|
| 1608 | 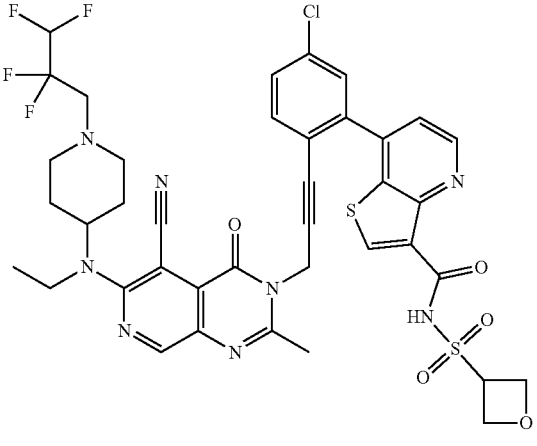 [SMILES: CCN(c1ncc2nc(C)n(CC#Cc3ccc(Cl)cc3-c3ccnc4c(C(=O)NS(=O)(=O)C5COC5)csc34)c(=O)c2c1C#N)C1CCN(CC(F)(F)C(F)F)CC1] | MS (ESI) m/z 871.79 [M + 1]+; 1H NMR (400 MHz, DMSO-d6) δ 12.71 (s, 1H), 8.83 (d, J = 4.8 Hz, 1H), 8.78 (s, 1H), 8.72 (s, 1H), 7.77 (d, J = 8.16 Hz, 1H), 7.71-7.69 (m, 2H), 7.64 (d, J = 4.84 Hz, 1H), 6.58 (tt, J = 52.56 Hz, 5.4 Hz, 1H), 5.25-5.20 (m, 1H), 4.98-4.92 (m, 4H), 4.82 (s, 2H), 4.24 (bs, 1H), 3.95 (bs, 2H), 3.68-3.62 (m, 2H), 3.50-3.10 (m, 4H), 2.01-1.97 (m, 2H), 1.90 (s, 3H), 1.86 (bs, 2H), 1.12 (t, J = 6.8 Hz, 3H) |
| 1606 | 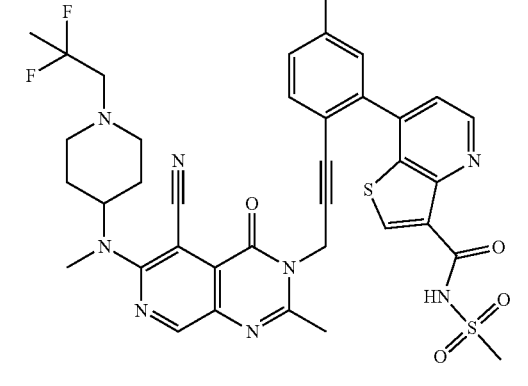 | MS (ESI) m/z 821.52 [M + 1]+; 1H-NMR (400 MHz, DMSO-d6) δ 12.48 (s, 1H), 8.80 (d, J = 4.84 Hz, 1H), 8.78 (d, J = 2.6 Hz, 2H), 7.77 (d, J = 8.31 Hz, 1H), 7.71-7.67 (m, 2H), 7.62 (d, J = 4.80 Hz, 1H), 4.76 (s, 2H), 4.60-4.57 (m, 1H), 3.85-3.58 (m, 4H), 3.49 (s, 3H), 3.32 (t, J = 12 Hz, 2H), 3.10 (s, 3H), 2.32-2.02 (m, 4H), 1.98 (s, 3H), 1.80-1.70 (m, 3H) |
| 1610 | 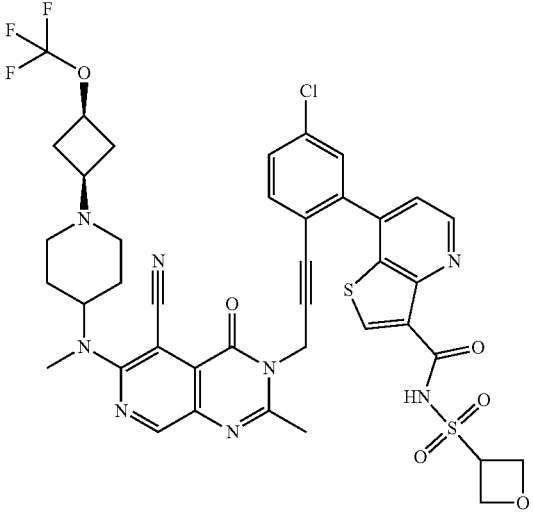<br>Chiral | MS (ESI) m/z 881.27 [M + 1]+; 1H-NMR (400 MHz, DMSO-d6) δ 12.71 (s, 1H), 8.81 (d, J = 4.84 Hz, 1H), 8.77 (s, 1H), 8.76 (s, 1H), 7.77 (d, J = 8.36 Hz, 1H), 7.72-7.67 (m, 2H), 7.62 (d, J = 4.84 Hz, 1H), 5.20-5.16 (m, 1H), 4.97-4.89 (m, 4H), 4.82 (s, 2H), 4.75-4.70 (m, 1H), 4.61-4.57 (m, 1H), 3.54-3.51 (m, 2H), 3.54-3.43 (m, 3H), 3.11 (s, 3H), 3.08-3.06 (m, 2H), 2.87-2.83 (m, 2H), 2.11-2.08 (m, 4H), 1.95 (s, 3H) |

TABLE 1-continued

7-Aza-Thienylpyridine and Derivative Compounds

| Compound | | Characterization |
|---|---|---|
| 1611 | 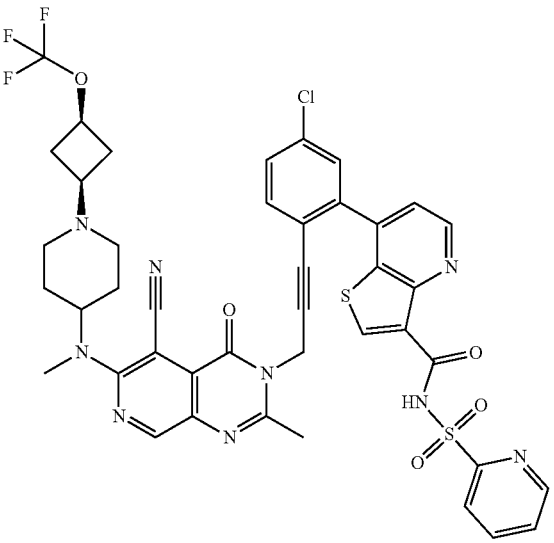<br>Chiral | MS (ESI) m/z 902.74 [M + 1]+; 1H-NMR (400 MHz, DMSO-d6) δ 13.02 (s, 1H), 8.89 (d, J = 4.80 Hz, 1H), 8.72 (d, J = 4.40 Hz, 1H), 8.64 (s, 1H), 8.61 (s, 1H), 8.27-8.25 (m, 1H), 8.22-8.18 (m, 1H), 7.77-7.73 (m, 2H), 7.71-7.69 (m, 2H), 7.65 (d, J = 4.80 Hz, 1H), 4.83 (s, 2H), 4.75-4.70 (m, 1H), 4.58 (bs, 1H), 3.67 (bs, 3H), 3.54 (d, J = 10.80 Hz, 2H), 3.42-3.38 (m, 1H), 2.86-2.84 (m, 2H), 2.85 (bs, 2H), 2.45-2.40 (m, 2H), 2.08 (bs, 4H), 1.95 (s, 3H) |
| 1609 | 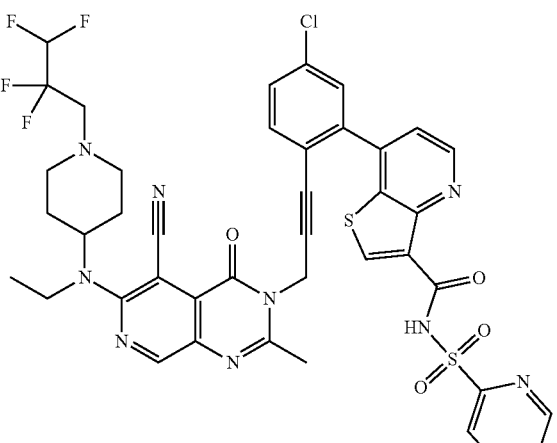 | MS (ESI) m/z 892.75 [M + 1]+; 1H NMR (400 MHz, DMSO-d6) δ 13.05 (s, 1H), 8.91 (d, J = 4.4 Hz, 1H), 8.72 (d, J = 3.6 Hz, 1H), 8.65 (s, 1H), 8.60 (s, 1H), 8.28 (d, J = 8.0 Hz, 1H), 8.21 (t, J = 7.6 Hz, 1H), 7.77-7.75 (m, 2H), 7.70-7.66 (m, 3H), 6.58 (t, J = 52.8 Hz, 1H), 4.82 (s, 2H), 4.23 (bs, 1H), 3.62 (d, J = 7.2 Hz, 2H), 3.16-3.12 (m, 4H), 2.53 (s, 2H), 2.01 (bs, 2H), 1.90-1.84 (m, 5H), 1.09 (t, J = 6.4 Hz, 3H) |
| 1617 | 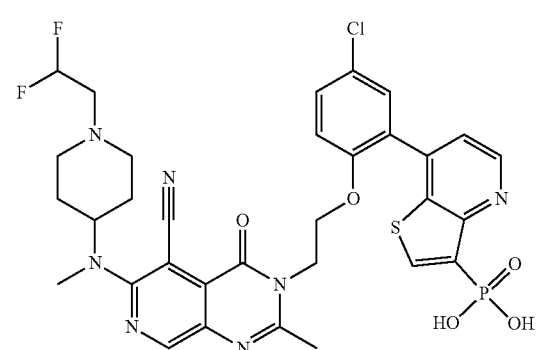 | MS (ESI) m/z 730.46 [M + 1]+; 1H NMR (400 MHz, DMSO-d6 with D2O) δ 8.67 (bs, 2H), 7.95 (d, J = 7.6 Hz, 1H), 7.50 (d, J = 8.4 Hz, 1H), 7.28 (s, 1H), 7.21 (bs, 2H), 6.28 (m, J = 53.6 Hz, 1H), 4.30 (bs, 2H), 4.21-4.00 (m, 3H), 3.29-3.19 (m, 4H), 2.99 (s, 3H), 2.80 (bs, 2H), 2.03 (bs, 2H), 1.86 (bs, 2H), 1.64 (s, 3H) |

TABLE 1-continued

7-Aza-Thienylpyridine and Derivative Compounds

| Compound | | Characterization |
|---|---|---|
| 1618 | 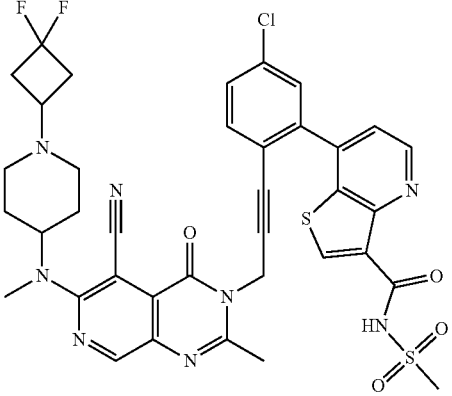 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(C)(=O)=O)csc12] | MS (ESI) m/z 791.49 [M + 1]+; 1H NMR (400 MHz, DMSO-d6) δ 12.47 (s, 1H), 9.72 (bs, 1H), 8.81-8.78 (m, 3H), 7.77 (d, J = 8.4 Hz, 1H), 7.72-7.67 (m, 2H), 7.62 (d, J = 4.8 Hz, 1H), 4.83 (s, 2H), 4.59 (bs, 1H), 3.82-3.45 (m, 6H), 3.30-2.95 (m, 9H), 2.20-2.14 (m, 4H), 1.99 (s, 3H) |
| 1616 | 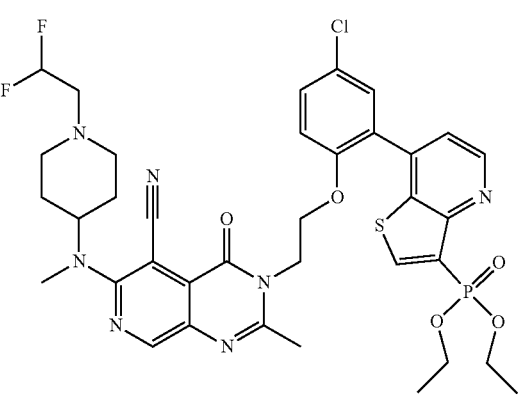 [SMILES: CCOP(=O)(OCC)c1csc2c(-c3cc(Cl)ccc3OCCn3c(C)nc4cnc(N(C)C5CCN(CC(F)F)CC5)c(C#N)c4c3=O)ccnc12] | MS (ESI) m/z 786.58 [M + 1]+; 1H NMR (400 MHz, DMSO-d6 with D2O) δ 8.77 (d, J = 4.40 Hz, 1H), 8.68 (s, 1H), 8.19 (d, J = 9.60 Hz, 1H), 7.52 (dd, J = 2.2, 8.8 Hz, 1H), 7.35-7.26 (m, 3H), 6.24 (t, J = 54.4 Hz, 1H), 4.33-4.17 (m, 10H), 3.21 (bs, 3H), 3.03 (s, 3H), 2.70 (bs, 1H), 2.58 (bs, 1H), 1.97 (bs, 2H), 1.82 (bs, 2H), 1.55 (s, 3H), 1.28 (t, J = 6.8 Hz, 6H) |
| 1621 | 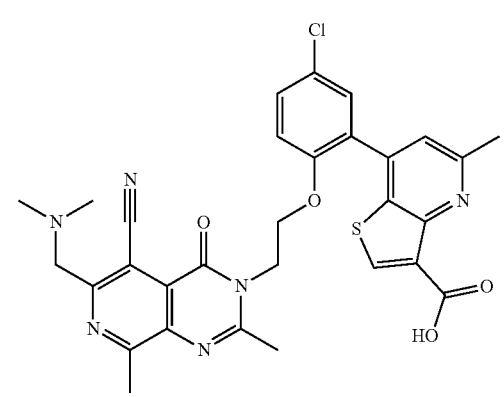 | LCMS: 603.6 [M + H]+; 1H NMR (400 MHz, Methanol-d4) δ 8.31 (s, 1H), 7.54 (dd, J = 8.9, 2.6 Hz, 1H), 7.41 (s, 1H), 7.36-7.25 (m, 2H), 4.46 (t, J = 5.1 Hz, 2H), 4.34 (t, J = 5.1 Hz, 2H), 3.13 (s, 6H), 2.89 (s, 3H), 2.83 (s, 3H), 2.24 (s, 3H) |
| 1622 | 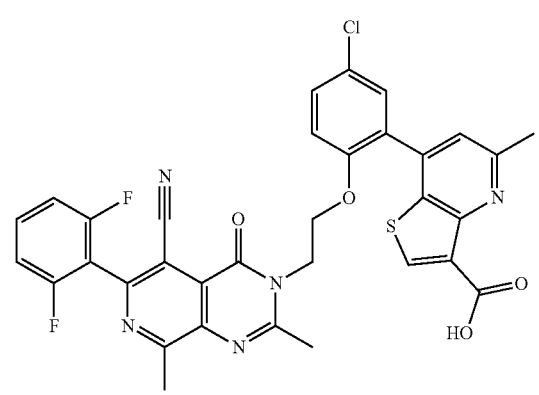 | LCMS (ESI) m/z 658.1 [M + 1]+; 1H NMR (400 MHz, DMSO-d6) δ 8.62 (s, 1H), 7.69 (tt, J = 8.5, 6.6 Hz, 1H), 7.60 (dd, J = 8.9, 2.7 Hz, 1H), 7.48-7.43 (m, 2H), 7.40-7.32 (m, 3H), 4.43 (t, J = 5.0 Hz, 2H), 4.27 (t, J = 4.9 Hz, 2H), 2.81 (s, 3H), 2.69 (s, 3H), 1.88 (s, 3H) |

TABLE 1-continued

7-Aza-Thienylpyridine and Derivative Compounds

| Compound | | Characterization |
|---|---|---|
| 1620 |  | MS (ESI) m/z 726.41 [M + 1]+; 1H-NMR (400 MHz, DMSO-d6) δ 8.81 (d, J = 4.0 Hz, 1H), 8.57 (s, 1H), 8.34 (s, 1H), 7.58 (d, J = 7.2, 1H), 7.39-7.33 (m, 3H), 4.37 (bs, 2H), 4.25 (bs, 3H), 3.91 (s, 3H), 3.3; 2-3.30 (m, 2H), 3.07-2.72 (m, 5H), 2.44-2.32 (m, 2H), 1.93-1.74 (bs, 4H), 1.69 (s, 3H) |
| 1624 | 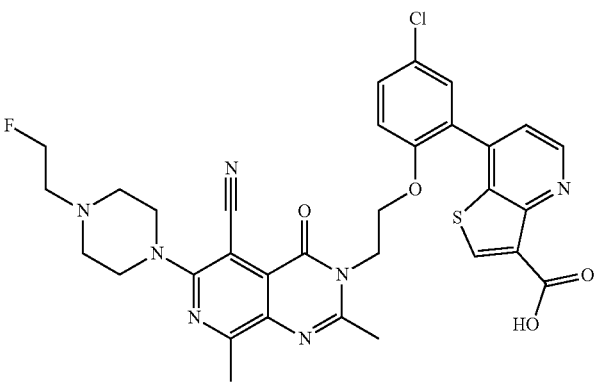 [SMILES: Cc1nc(N2CCN(CCF)CC2)c(C#N)c2c(=O)n(CCOc3ccc(Cl)cc3-c3ccnc4c(C(=O)O)csc34)c(C)nc12] | LCMS (ESI) m/z 662.1 [M + 1]+; 1H NMR (400 MHz, DMSO-d6) δ 8.79 (d, J = 4.8 Hz, 1H), 8.46 (s, 1H), 7.57 (dd, J = 9.0, 2.6 Hz, 1H), 7.44 (d, J = 4.8 Hz, 1H), 7.39-7.32 (m, 2H), 4.98-4.74 (m, 2H), 4.40 (t, J = 5.1 Hz, 2H), 4.29 (s, 1H), 4.21 (t, J = 5.1 Hz, 2H), 3.64 (s, 3H), 3.56 (s, 1H), 3.47 (s, 1H), 3.31 (s, 2H), 2.63 (s, 3H), 1.86 (s, 3H) |
| 1625 | 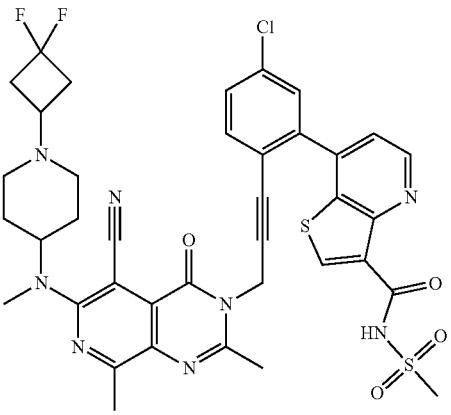 [SMILES: Cc1nc(N(C)C2CCN(C3CC(F)(F)C3)CC2)c(C#N)c2c(=O)n(CC#Cc3ccc(Cl)cc3-c3ccnc4c(C(=O)NS(C)(=O)=O)csc34)c(C)nc12] | MS (ESI) m/z 805.29 [M + 1]+ |
| 1623 | 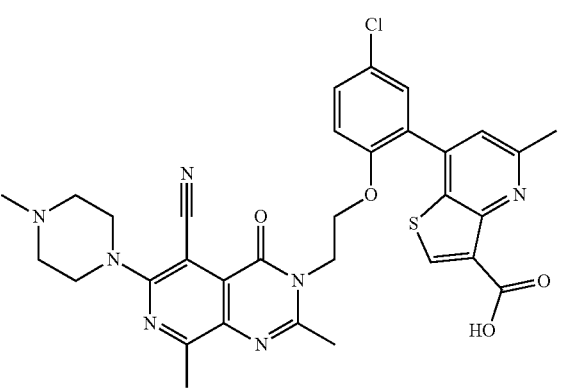 | LCMS (ESI) m/z 644.1 [M + 1]+; 1H NMR (400 MHz, Chloroform-d) δ 8.48 (s, 1H), 7.61 (dd, J = 8.9, 2.7 Hz, 1H), 7.43 (s, 1H), 7.42-7.37 (m, 2H), 4.42 (d, J = 5.3 Hz, 2H), 4.33 (s, 1H), 4.30 (s, 1H), 4.25 (d, J = 5.0 Hz, 2H), 3.61 (d, J = 12.2 Hz, 2H), 3.44 (d, J = 13.6 Hz, 4H), 3.24 (d, J = 11.0 Hz, 1H), 2.92 (d, J = 4.4 Hz, 3H), 2.73 (s, 3H), 2.66 (s, 4H), 1.98 (s, 3H) |

TABLE 1-continued

7-Aza-Thienylpyridine and Derivative Compounds

| Compound | | Characterization |
|---|---|---|
| 1627 | | MS (ESI) m/z 602.29 [M + 1]+ |
| 1628 | | MS (ESI) m/z 608.3 [M + 1]+ |
| 1626 | | LCMS (ESI) m/z 599.2 [M + 1]+ |
| 1630 | | MS (ESI) m/z 618.09 [M + 1]+ |

TABLE 1-continued
7-Aza-Thienylpyridine and Derivative Compounds
| Com-pound | | Characterization |
|---|---|---|
| 1631 | 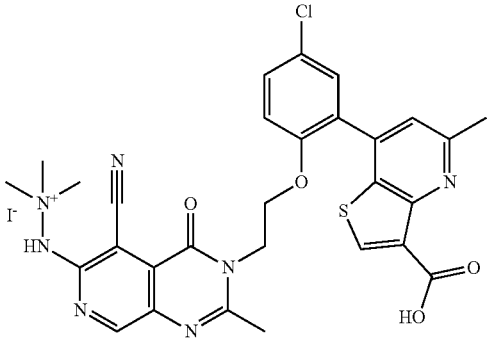 | |
| 1629 | 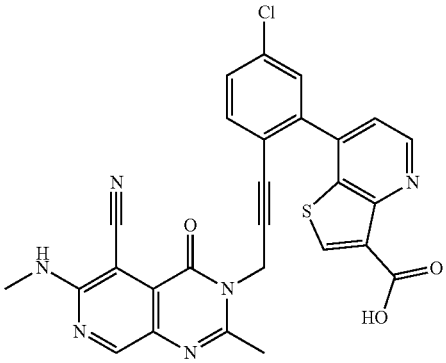 [SMILES: CNc1ncc2nc(C)n(CC#Cc3ccc(Cl)cc3-c3ccnc4c(C(=O)O)csc34)c(=O)c2c1C#N] | |
| 1633 | 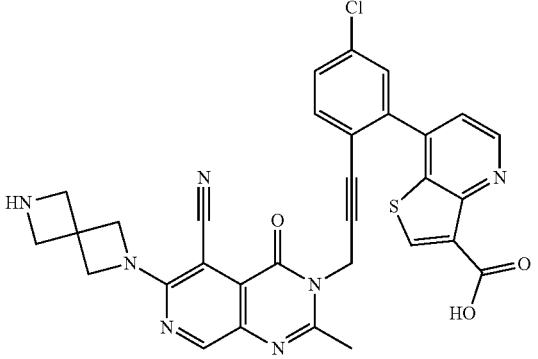 [SMILES: Cc1nc2cnc(N3CC4(CNC4)C3)c(C#N)c2c(=O)n1CC#Cc1ccc(Cl)cc1-c1ccnc2c(C(=O)O)csc12] | LCMS (ESI) m/z 608.2 [M + 1]+; 1H NMR (400 MHz, DMSO-d6) δ 8.70 (d, J = 4.7 Hz, 2H), 8.63 (s, 1H), 8.47 (s, 2H), 7.72 (dd, J = 8.1, 0.8 Hz, 1H), 7.68-7.61 (m, 2H), 7.50 (d, J = 4.8 Hz, 1H), 4.77 (s, 2H), 4.54 (s, 4H), 4.20 (t, J = 6.2 Hz, 4H), 2.06 (s, 3H), 1.20 (s, 1H) |
| 1634 | 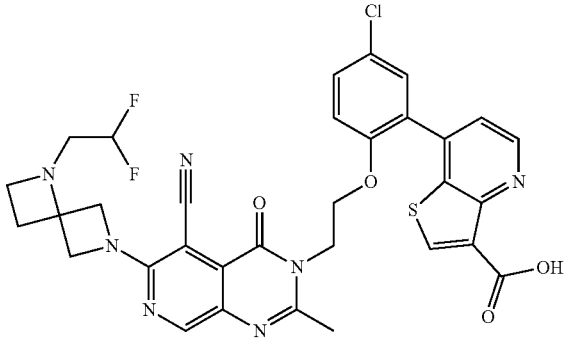 [SMILES: Cc1nc2cnc(N3CC4(CCN4CC(F)F)C3)c(C#N)c2c(=O)n1CCOc1ccc(Cl)cc1-c1ccnc2c(C(=O)O)csc12] | MS (ESI) m/z 678.5 [M + 1]+ |

TABLE 1-continued

7-Aza-Thienylpyridine and Derivative Compounds

| Compound | | Characterization |
|---|---|---|
| 1632 | | LCMS (ESI) m/z 469.5 [M + 1]+; 1H NMR (400 MHz, DMSO-d6) δ 8.77-8.71 (m, 2H), 8.66 (s, 1H), 7.75 (dd, J = 8.1, 0.8 Hz, 1H), 7.72-7.64 (m, 2H), 7.54 (d, J = 4.9 Hz, 1H), 4.81 (s, 2H), 4.63 (s, 2H), 4.53 (s, 2H), 4.44 (s, 2H), 4.39 (s, 2H), 3.36 (s, 4H), 2.73-2.62 (m, 1H), 2.10 (s, 3H) |
| 1636 | | MS (ESI) m/z 619.45 [M + 1]+ |
| 1637 | | MS (ESI) m/z 638.39 [M + 1]+ |
| 1635 | | MS (ESI) m/z 688.48 [M + 1]+ |

TABLE 1-continued

7-Aza-Thienylpyridine and Derivative Compounds

| Compound | | Characterization |
|---|---|---|
| 1639 | | MS (ESI) m/z 706.46 [M + 1]+ |
| 1640 | | |
| 1638 | | MS (ESI) m/z 670.50 [M + 1]+ |
| 1642 | | MS (ESI) m/z 710.46 [M + 1]+ |

TABLE 1-continued

7-Aza-Thienylpyridine and Derivative Compounds

| Compound | | Characterization |
|---|---|---|
| 1643 | | MS (ESI) m/z 706.47 [M + 1]+ |
| 1641 | | MS (ESI) m/z 706.55 [M + 1] |
| 1645 | | MS (ESI) m/z 628.46 [M + 1]+ |
| 1646 | | MS (ESI) m/z 668.45 [M + 1]+ |

TABLE 1-continued
7-Aza-Thienylpyridine and Derivative Compounds
| Compound | | Characterization |
|---|---|---|
| 1644 | 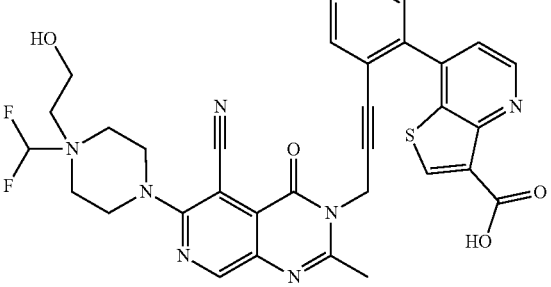 | MS (ESI) m/z 690.47 [M + 1]+ |
| 1648 | 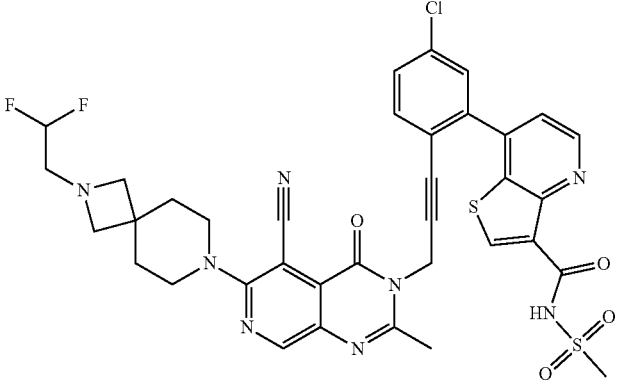 [SMILES: Cc1nc2cnc(N3CCC4(CC3)CN(CC(F)F)C4)c(C#N)c2c(=O)n1CC#Cc1ccc(Cl)cc1-c1ccnc2c(C(=O)NS(C)(=O)=O)csc12] | LCMS: 2.01 Min, 777.3 [M + H]+ |
| 1649 | 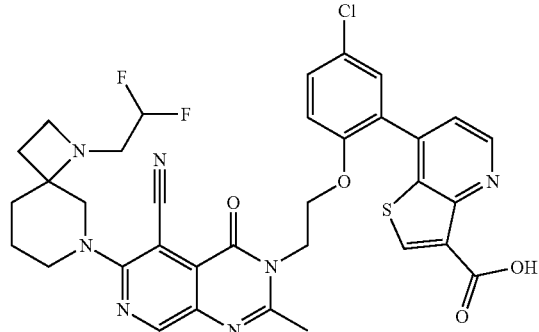 | MS (ESI) m/z = 706.48 [M + 1]+ |
| 1647 | 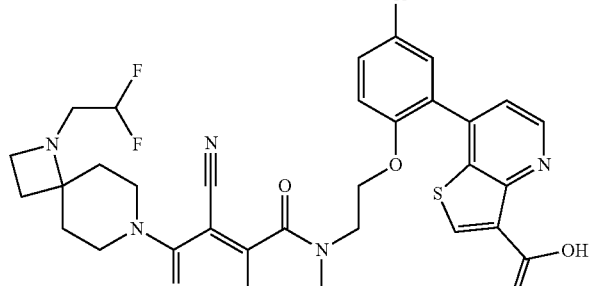 | MS (ESI) m/z 706.46 [M + 1]+ |

TABLE 1-continued

7-Aza-Thienylpyridine and Derivative Compounds

| Compound | | Characterization |
|---|---|---|
| 1651 | | |
| 1652 | | |
| 1650 | | MS (ESI) m/z 720.47 [M + 1]+ |
| 1654 | | MS (ESI) m/z, 690.46 [M + 1]+ |

TABLE 1-continued
7-Aza-Thienylpyridine and Derivative Compounds
| Compound | | Characterization |
|---|---|---|
| 1655 | 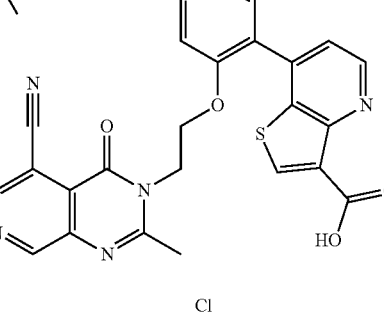 | MS (ESI) m/z 704.57 [M + 1]+ |
| 1653 | 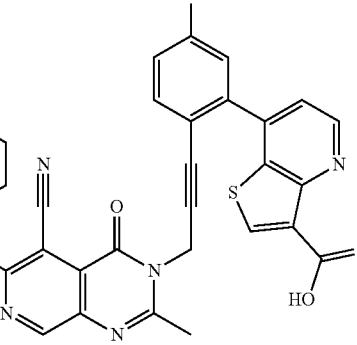 | MS (ESI) m/z 670.43 [M + 1]+ |
| 1657 | 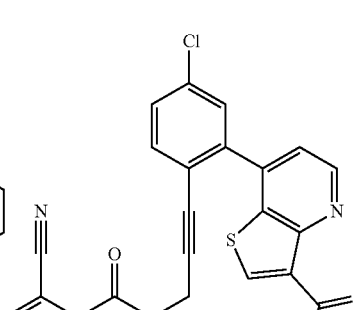 | |
| 1658 | 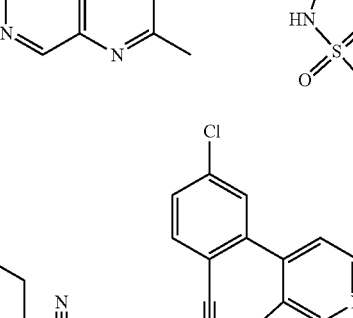 | |

TABLE 1-continued

7-Aza-Thienylpyridine and Derivative Compounds

| Compound | | Characterization |
|---|---|---|
| 1656 | | |
| 1660 | | |
| 1661 | | |
| 1659 | | |

TABLE 1-continued

7-Aza-Thienylpyridine and Derivative Compounds

| Compound | | Characterization |
|---|---|---|
| 1663 | | MS (ESI) m/z 688.2 [M + 1]+; 1H NMR (400 MHz, DMSO-d6) δ 8.72 (d, J = 4.8 Hz, 1H), 8.70 (s, 1H), 8.61 (s, 1H), 7.74-7.71 (m, 1H), 7.67-7.63 (m, 2H), 7.52 (d, J = 4.8 Hz, 1H), 7.03 (d, J = 8.5 Hz, 1H), 6.80 (tt, J = 52.4, 3.5 Hz, 1H), 4.78 (s, 2H), 4.55-4.40 (m, 1H), 4.02 (td, J = 14.3, 3.9 Hz, 2H), 3.69-3.60 (m, 4H), 3.25(s, 3H), 2.32-2.18 (m, 2H), 2.10-2.01 (m, 2H), 2.00 (s, 3H). |
| 1664 | | |
| 1662 | | MS (ESI) m/z 708.54 [M + 1]+ |
| 1666 | | |

TABLE 1-continued

7-Aza-Thienylpyridine and Derivative Compounds

| Compound | | Characterization |
|---|---|---|
| 1672 | | |
| 1676 | | |
| 1665 | | MS (ESI) m/z = 714.5 [M + 1]+ |

TABLE 1-continued

7-Aza-Thienylpyridine and Derivative Compounds

| Compound | Characterization |
|---|---|
| 1669 | |
| 1670 | |
| 1667 | |

TABLE 1-continued

7-Aza-Thienylpyridine and Derivative Compounds

| Compound | Characterization |
|---|---|
| 1668 | |
| 1673 | |
| 1671 | |

TABLE 1-continued

7-Aza-Thienylpyridine and Derivative Compounds

| Compound | Characterization |
|---|---|
| 1675 | |
| 1677 | |
| 1674 | |

TABLE 1-continued

7-Aza-Thienylpyridine and Derivative Compounds

| Compound | Characterization |
|---|---|
| 1678 | |
| 1679 | |
| 1680 | |

TABLE 1-continued

7-Aza-Thienylpyridine and Derivative Compounds

| Compound | Characterization |
|---|---|
| 1681 | |
| 1683 | |
| 1687 | |

TABLE 1-continued

7-Aza-Thienylpyridine and Derivative Compounds

| Compound | | Characterization |
|---|---|---|
| 1684 | | |
| 1686 | | |
| 1690 | | MS (ESI) m/z 728.47 [M + 1]+ |

TABLE 1-continued

7-Aza-Thienylpyridine and Derivative Compounds

| Compound | Characterization |
|---|---|
| 1682 | |
| 1685 | |
| 1688 | MS (ESI) m/z 720.47 [M + 1]+ |

TABLE 1-continued

7-Aza-Thienylpyridine and Derivative Compounds

| Compound | | Characterization |
|---|---|---|
| 1689 | (structure) | MS (ESI) m/z 714.45 [M + 1]+ |
| 1691 | (structure) | MS (ESI) m/z 714.55 [M + 1]+ |
| 1697 | (structure) | |
| 1700 | (structure) | |

TABLE 1-continued

7-Aza-Thienylpyridine and Derivative Compounds

| Compound | Characterization |
|---|---|
| 1693 | |
| 1694 | |
| 1702 | Chiral |
| 1692 | |

TABLE 1-continued

7-Aza-Thienylpyridine and Derivative Compounds

| Compound | Characterization |
|---|---|
| 1696 | |
| 1695 | |
| 1699 | |
| 1701 | |

TABLE 1-continued
7-Aza-Thienylpyridine and Derivative Compounds
| Compound | | Characterization |
|---|---|---|
| 1698 | 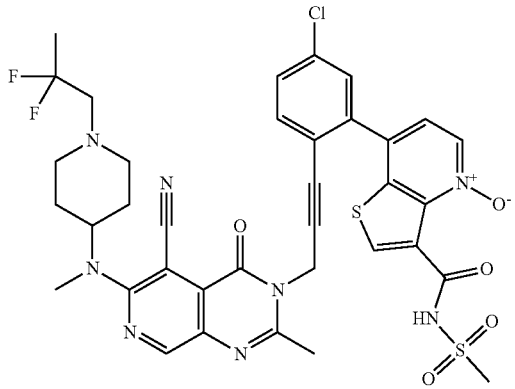 [SMILES: Cc1nc2cnc(N(C)C3CCN(CC(C)(F)F)CC3)c(C#N)c2c(=O)n1CC#Cc1ccc(Cl)cc1-c1cc[n+]([O-])c2c(C(=O)NS(C)(=O)=O)csc12] | |
| 1706 | 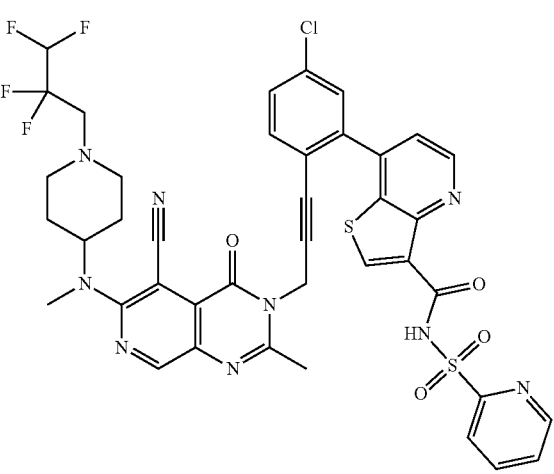 [SMILES: Cc1nc2cnc(N(C)C3CCN(CC(F)(F)C(F)F)CC3)c(C#N)c2c(=O)n1CC#Cc1ccc(Cl)cc1-c1ccnc2c(C(=O)NS(=O)(=O)c3ccccn3)csc12] | MS (ESI) m/z 878.31 [M + 1]+ |
| 1703 | 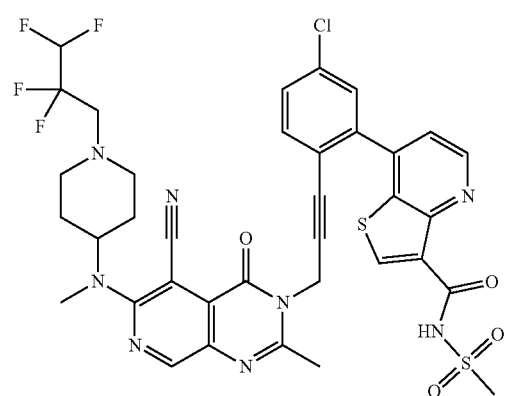 [SMILES: Cc1nc2cnc(N(C)C3CCN(CC(F)(F)C(F)F)CC3)c(C#N)c2c(=O)n1CC#Cc1ccc(Cl)cc1-c1ccnc2c(C(=O)NS(C)(=O)=O)csc12] | MS (ESI) m/z 815.32 [M + 1]+ |

TABLE 1-continued
7-Aza-Thienylpyridine and Derivative Compounds
| Compound | | Characterization |
|---|---|---|
| 1704 | 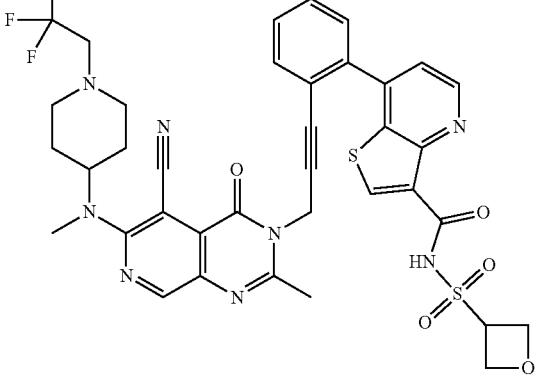 | MS (ESI) m/z 857.25 [M + 1]+ |
| 1705 | 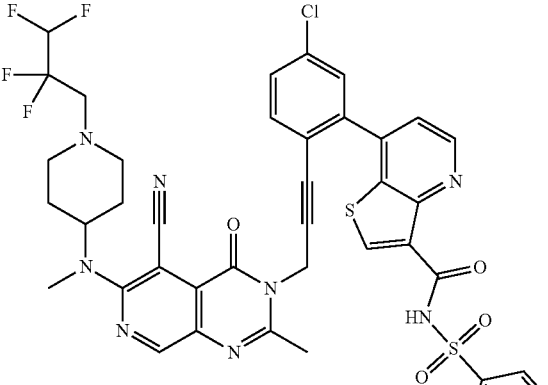 | MS (ESI) m/z 878.28 [M + 1]+ |
| 1707 | 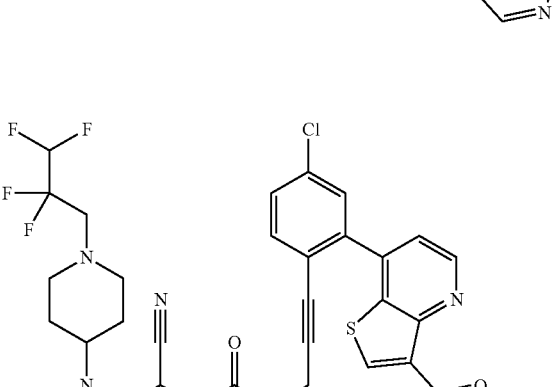 | |

TABLE 1-continued

7-Aza-Thienylpyridine and Derivative Compounds

| Compound | | Characterization |
|---|---|---|
| 1711 | | |
| 1708 | | |
| 1709 | | |

TABLE 1-continued
7-Aza-Thienylpyridine and Derivative Compounds
| Compound | Characterization |
|---|---|
| 1710 | 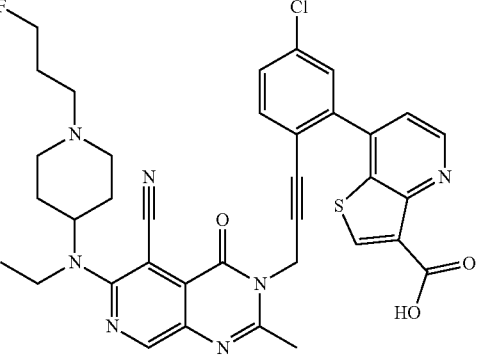 |
| 1714 | 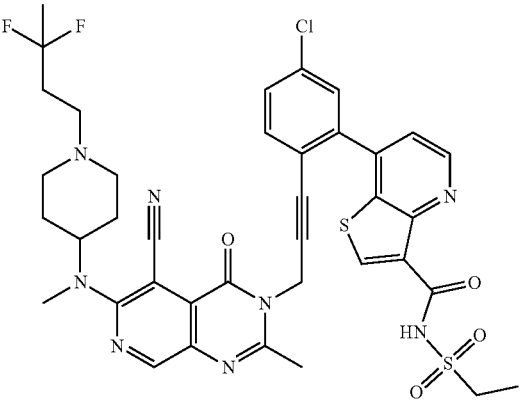 [SMILES: CCS(=O)(=O)NC(=O)c1csc2c(-c3cc(Cl)ccc3C#CCn3c(C)nc4cnc(N(C)C5CCN(CCC(C)(F)F)CC5)c(C#N)c4c3=O)ccnc12] |
| 1712 | 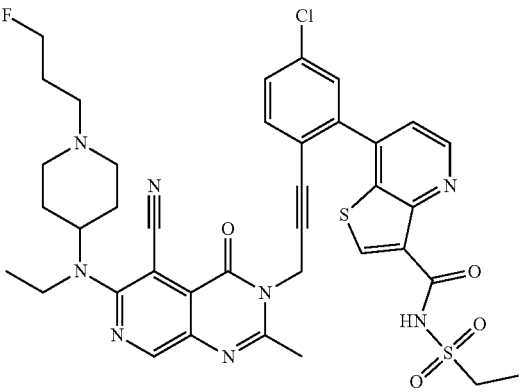 [SMILES: CCN(c1ncc2nc(C)n(CC#Cc3ccc(Cl)cc3-c3ccnc4c(C(=O)NS(=O)(=O)CC)csc34)c(=O)c2c1C#N)C1CCN(CCCF)CC1] |

TABLE 1-continued
7-Aza-Thienylpyridine and Derivative Compounds
| Compound | | Characterization |
|---|---|---|
| 1713 | 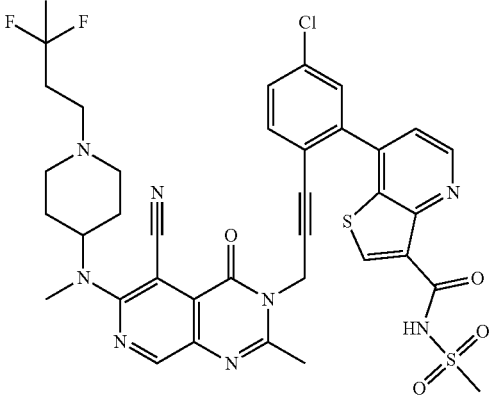 [SMILES: Cc1nc2cnc(N(C)C3CCN(CCC(C)(F)F)CC3)c(C#N)c2c(=O)n1CC#Cc1ccc(Cl)cc1-c1ccnc2c(C(=O)NS(C)(=O)=O)csc12] | |
| 1715 | 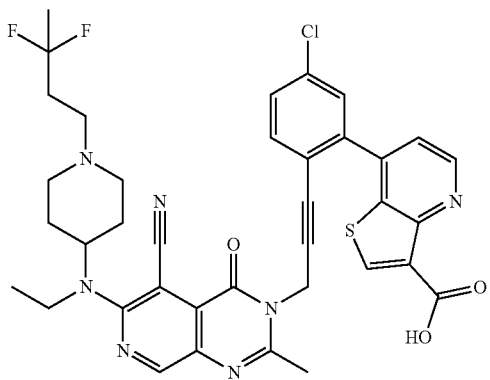 [SMILES: CCN(c1ncc2nc(C)n(CC#Cc3ccc(Cl)cc3-c3ccnc4c(C(=O)O)csc34)c(=O)c2c1C#N)C1CCN(CCC(C)(F)F)CC1] | |
| 1716 | 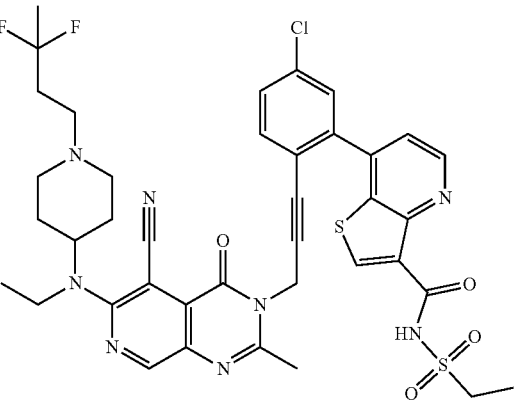 | |

TABLE 1-continued
7-Aza-Thienylpyridine and Derivative Compounds
| Compound | | Characterization |
|---|---|---|
| 1717 | 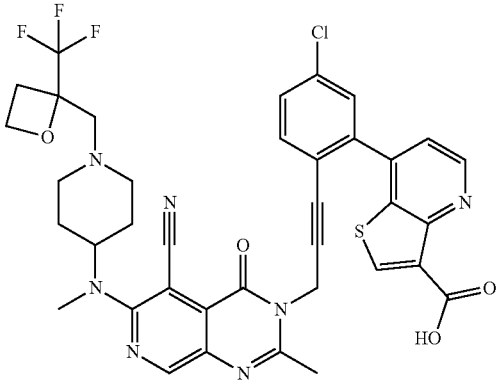 [SMILES: Cc1nc2cnc(N(C)C3CCN(CC4(C(F)(F)F)CCO4)CC3)c(C#N)c2c(=O)n1CC#Cc1ccc(Cl)cc1-c1ccnc2c(C(=O)O)csc12] | MS (ESI) m/z 762.2 [M + 1]+; 1H NMR (400 MHz, DMSO-d6) δ 8.77 (d, J = 4.8 Hz, 1H), 8.75 (s, 1H), 8.65 (s, 1H), 7.76 (d, J = 8.2 Hz, 1H), 7.71-7.66 (m, 2H), 7.55 (d, J = 4.8 Hz, 1H), 7.26 (s, 1H), 4.83 (s, 2H), 4.68-4.55 (m, 1H), 4.22 (d, J = 13.7 Hz, 1H), 3.99-3.71 (m, 7H), 3.20 (s, 3H), 2.70-2.61 (m, 2H), 2.42-2.30 (m, 2H), 2.18-2.00 (m, 5H) |
| 1721 | 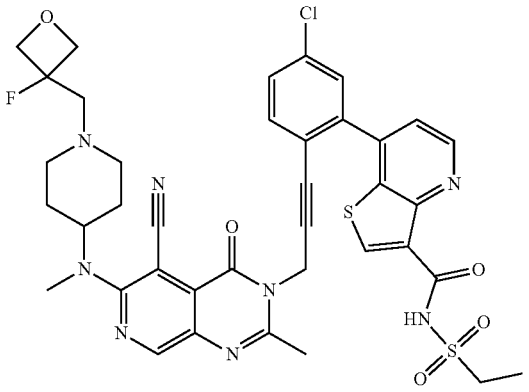 [SMILES: CCS(=O)(=O)NC(=O)c1csc2c(-c3cc(Cl)ccc3C#CCn3c(C)nc4cnc(N(C)C5CCN(CC6(F)COC6)CC5)c(C#N)c4c3=O)ccnc12] | |
| 1719 | 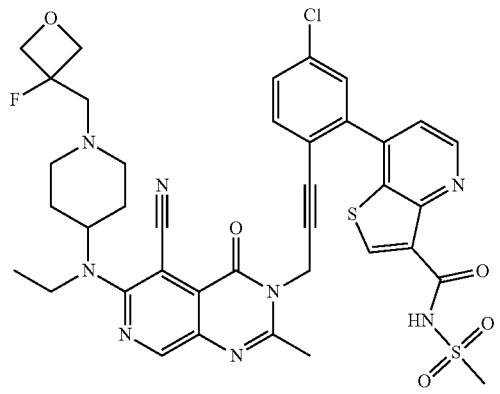 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN(CC2(F)COC2)CC1] | |
| 1723 | 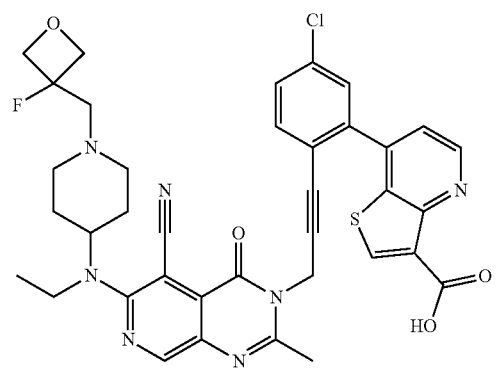 [SMILES: CCN(c1ncc2nc(C)n(CC#Cc3ccc(Cl)cc3-c3ccnc4c(C(=O)O)csc34)c(=O)c2c1C#N)C1CCN(CC2(F)COC2)CC1] | MS (ESI) m/z 726.28 [M + 1]+ |

TABLE 1-continued
7-Aza-Thienylpyridine and Derivative Compounds
| Compound | | Characterization |
|---|---|---|
| 1718 | 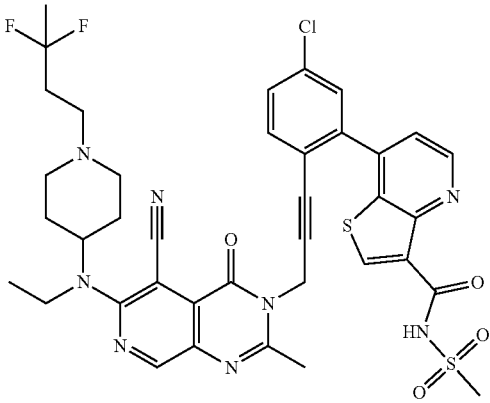 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN(CCC(C)(F)F)CC1] | |
| 1720 | 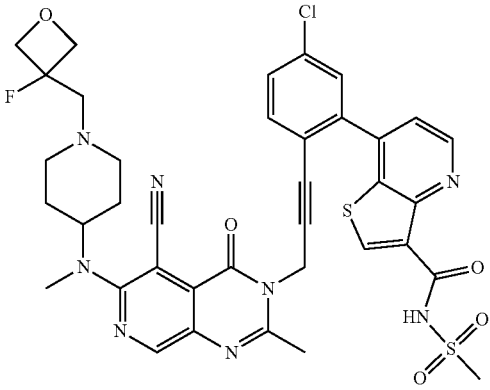 [SMILES: Cc1nc2cnc(N(C)C3CCN(CC4(F)COC4)CC3)c(C#N)c2c(=O)n1CC#Cc1ccc(Cl)cc1-c1ccnc2c(C(=O)NS(C)(=O)=O)csc12] | |
| 1725 | 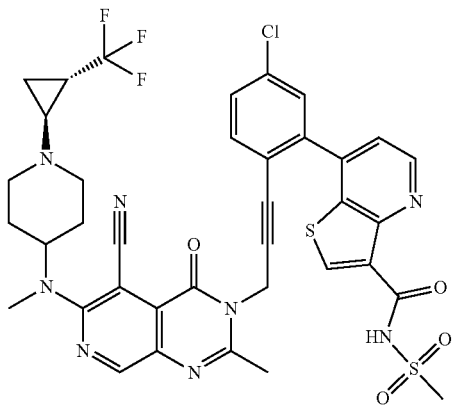<br>Chiral | MS (ESI) m/z 732.19 [M + 1]+ |

TABLE 1-continued
7-Aza-Thienylpyridine and Derivative Compounds
| Compound | | Characterization |
|---|---|---|
| 1722 | 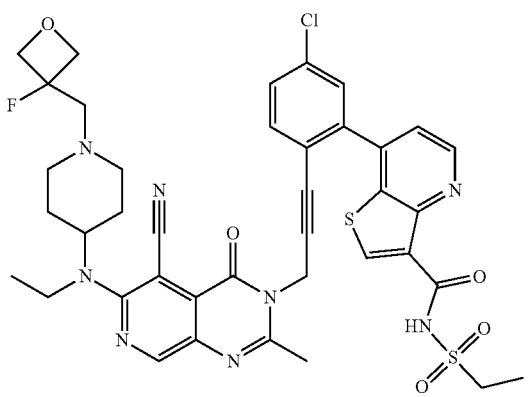 [SMILES: CCN(c1ncc2nc(C)n(CC#Cc3ccc(Cl)cc3-c3ccnc4c(C(=O)NS(=O)(=O)CC)csc34)c(=O)c2c1C#N)C1CCN(CC2(F)COC2)CC1] | MS (ESI) m/z 817.25 [M + 1]+ |
| 1724 | 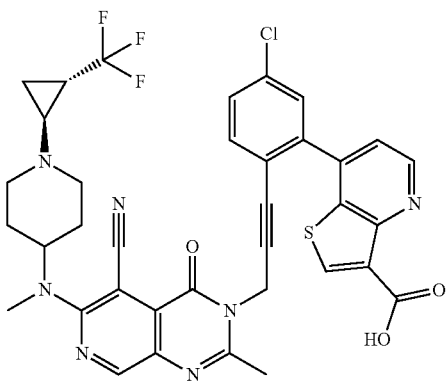<br>Chiral | MS (ESI) m/z 732.18 [M + 1]+ |
| 1728 | 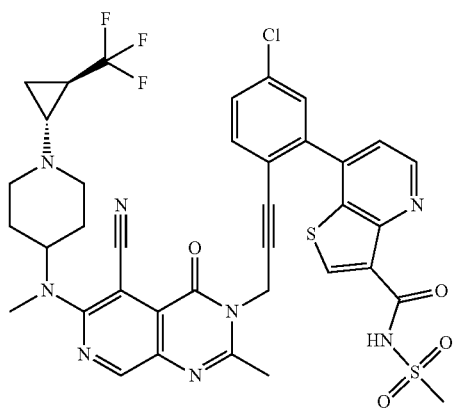<br>Chiral | MS (ESI) m/z 809.32 [M + 1]+ |

TABLE 1-continued
7-Aza-Thienylpyridine and Derivative Compounds
| Compound | | Characterization |
|---|---|---|
| 1726 | 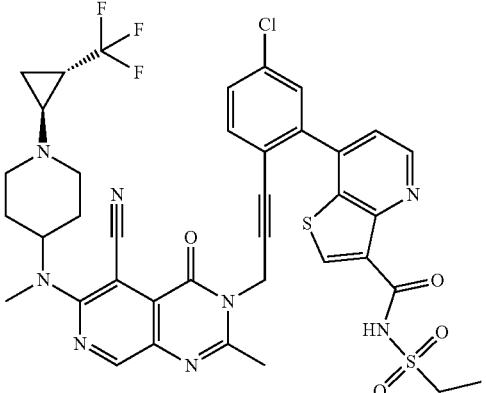 Chiral | MS (ESI) m/z 823.30 [M + 1]+ |
| 1727 | 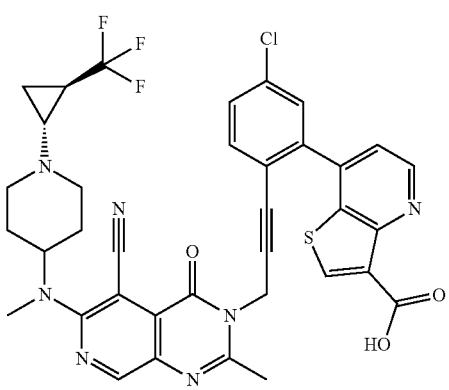 Chiral | MS (ESI) m/z 732.19 [M + 1]+ |
| 1729 | 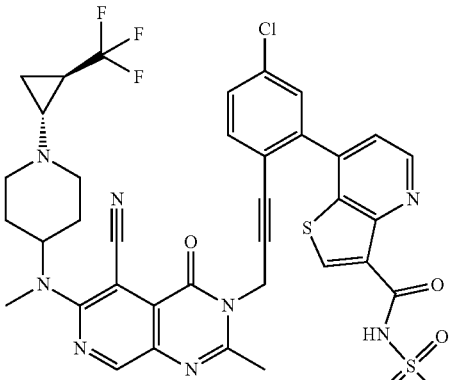 Chiral | MS (ESI) m/z 823.3 [M + 1]+ |

TABLE 1-continued
7-Aza-Thienylpyridine and Derivative Compounds
| Compound | | Characterization |
|---|---|---|
| 1732 | 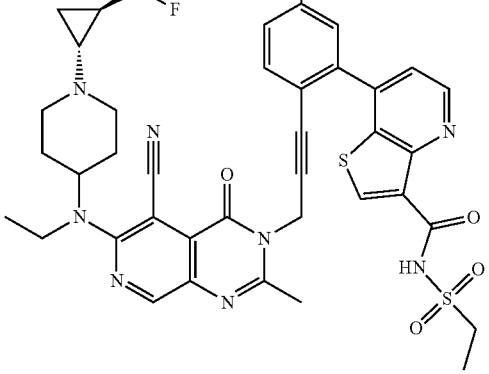<br>Chiral | MS (ESI) m/z 837.31 [M + 1]+ |
| 1730 | 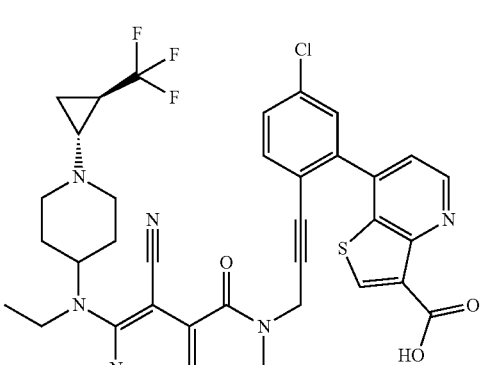<br>Chiral | MS (ESI) m/z 746.28 [M + 1]+ |
| 1731 | 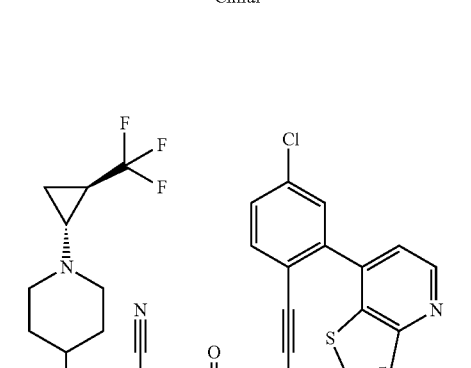<br>Chiral | MS (ESI) m/z 823.27 [M + 1]+ |

TABLE 1-continued

7-Aza-Thienylpyridine and Derivative Compounds

| Compound | | Characterization |
|---|---|---|
| 1735 | | MS (ESI) m/z 796.33 [M + 1]+ |
| 1733 | | MS (ESI) m/z 785.26 [M + 1]+ |
| 1734 | | MS (ESI) m/z 839.26 [M + 1]+ |

TABLE 1-continued
7-Aza-Thienylpyridine and Derivative Compounds
| Compound | | Characterization |
|---|---|---|
| 1738 | 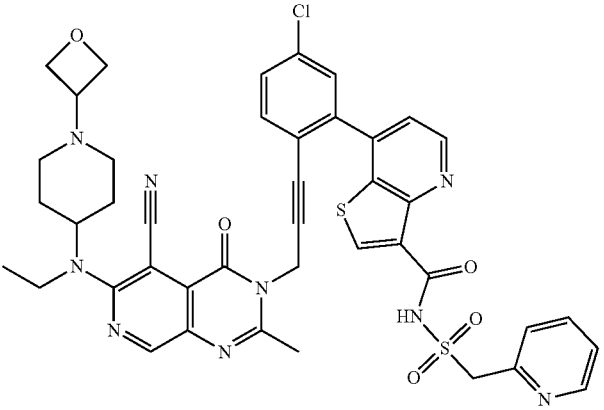 [SMILES: CCN(c1ncc2nc(C)n(CC#Cc3ccc(Cl)cc3-c3ccnc4c(C(=O)NS(=O)(=O)Cc5ccccn5)csc34)c(=O)c2c1C#N)C1CCN(C2COC2)CC1] | MS (ESI) m/z 848.33 [M + 1]+ |
| 1736 | 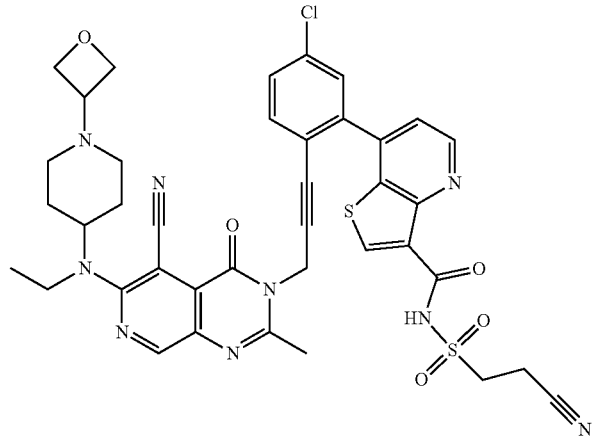 [SMILES: CCN(c1ncc2nc(C)n(CC#Cc3ccc(Cl)cc3-c3ccnc4c(C(=O)NS(=O)(=O)CCC#N)csc34)c(=O)c2c1C#N)C1CCN(C2COC2)CC1] | MS (ESI) m/z 810.23 [M + 1]+ |
| 1737 | 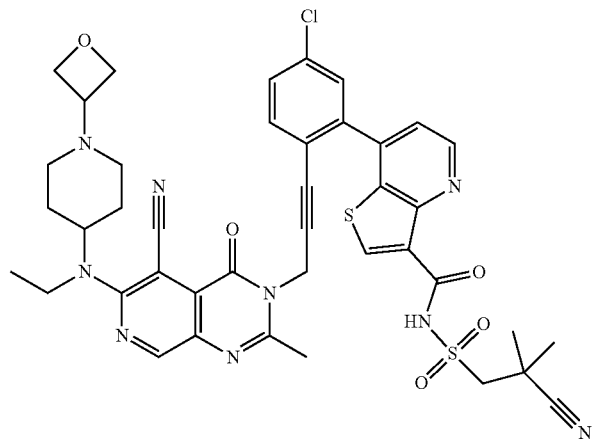 [SMILES: CCN(c1ncc2nc(C)n(CC#Cc3ccc(Cl)cc3-c3ccnc4c(C(=O)NS(=O)(=O)CC(C)(C)C#N)csc34)c(=O)c2c1C#N)C1CCN(C2COC2)CC1] | MS (ESI) m/z 838.32 [M + 1]+ |

TABLE 1-continued

7-Aza-Thienylpyridine and Derivative Compounds

| Compound | | Characterization |
|---|---|---|
| 1741 | | MS (ESI) m/z 834.32 [M + 1]+ |
| 1739 | | MS (ESI) m/z 847.32 [M + 1]+ |
| 1740 | | MS (ESI) m/z 834.36 [M + 1]+ |

TABLE 1-continued
7-Aza-Thienylpyridine and Derivative Compounds
| Compound | | Characterization |
|---|---|---|
| 1744 | 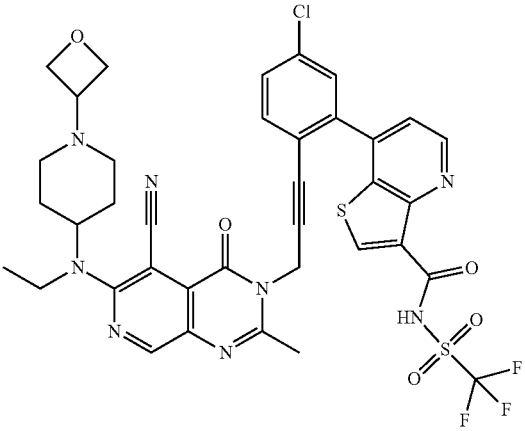 [SMILES: CCN(c1ncc2nc(C)n(CC#Cc3ccc(Cl)cc3-c3ccnc4c(C(=O)NS(=O)(=O)C(F)(F)F)csc34)c(=O)c2c1C#N)C1CCN(C2COC2)CC1] | MS (ESI) m/z 825.21 [M + 1]+ |
| 1742 | 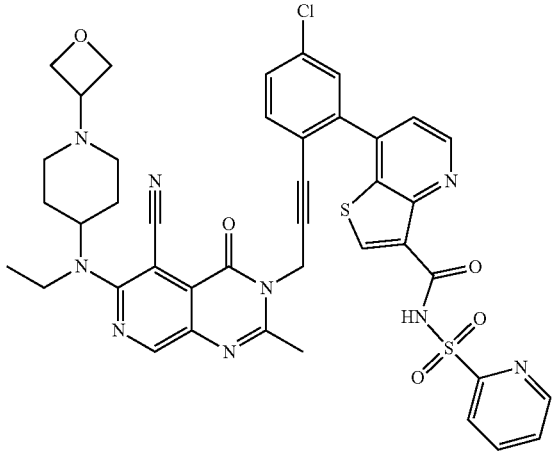 [SMILES: CCN(c1ncc2nc(C)n(CC#Cc3ccc(Cl)cc3-c3ccnc4c(C(=O)NS(=O)(=O)c5ccccn5)csc34)c(=O)c2c1C#N)C1CCN(C2COC2)CC1] | MS (ESI) m/z 834.31 [M + 1]+ |
| 1743 | 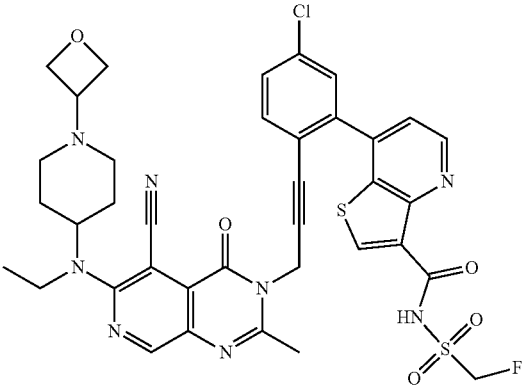 [SMILES: CCN(c1ncc2nc(C)n(CC#Cc3ccc(Cl)cc3-c3ccnc4c(C(=O)NS(=O)(=O)CF)csc34)c(=O)c2c1C#N)C1CCN(C2COC2)CC1] | MS (ESI) m/z 788.18 [M + 1]+ |

TABLE 1-continued

7-Aza-Thienylpyridine and Derivative Compounds

| Compound | Characterization |
|---|---|
| 1747 | MS (ESI) m/z 813.29 [M + 1]+ |
| 1745 | MS (ESI) m/z 821.25 [M + 1]+ |
| 1746 | MS (ESI) m/z 799.24 [M + 1]+ |

TABLE 1-continued
7-Aza-Thienylpyridine and Derivative Compounds
| Compound | | Characterization |
|---|---|---|
| 1750 | 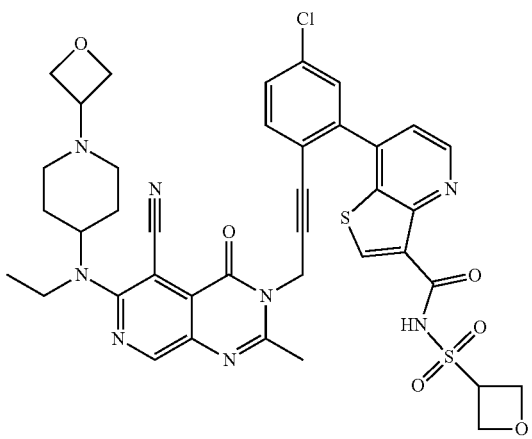 [SMILES: CCN(c1ncc2nc(C)n(CC#Cc3ccc(Cl)cc3-c3ccnc4c(C(=O)NS(=O)(=O)C5COC5)csc34)c(=O)c2c1C#N)C1CCN(C2COC2)CC1] | MS (ESI) m/z 813.22 [M + 1]+ |
| 1748 | 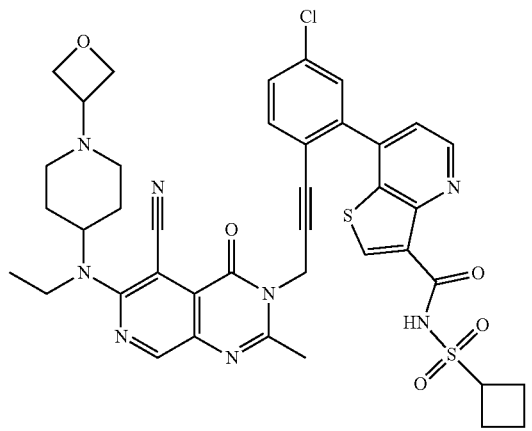 [SMILES: CCN(c1ncc2nc(C)n(CC#Cc3ccc(Cl)cc3-c3ccnc4c(C(=O)NS(=O)(=O)C5CCC5)csc34)c(=O)c2c1C#N)C1CCN(C2COC2)CC1] | MS (ESI) m/z 811.27 [M + 1]+ |
| 1749 | 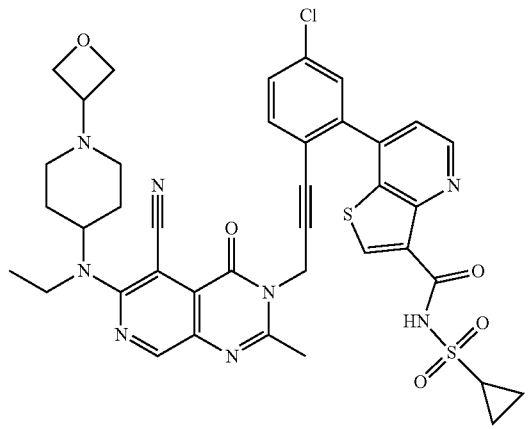 [SMILES: CCN(c1ncc2nc(C)n(CC#Cc3ccc(Cl)cc3-c3ccnc4c(C(=O)NS(=O)(=O)C5CC5)csc34)c(=O)c2c1C#N)C1CCN(C2COC2)CC1] | MS (ESI) m/z 797.29 [M + 1]+ |

TABLE 1-continued
7-Aza-Thienylpyridine and Derivative Compounds
| Compound | | Characterization |
|---|---|---|
| 1753 | 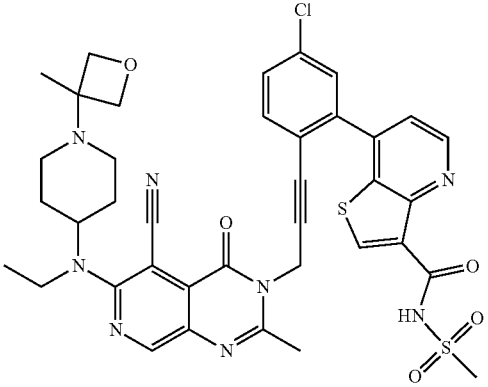 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN(C2(C)COC2)CC1] | MS (ESI) m/z 785.32 [M + 1]+ |
| 1751 | 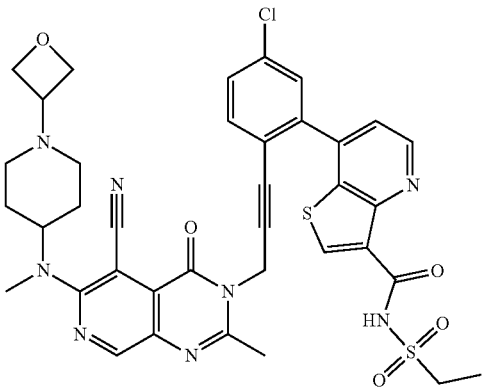 [SMILES: CCS(=O)(=O)NC(=O)c1csc2c(-c3cc(Cl)ccc3C#CCn3c(C)nc4cnc(N(C)C5CCN(C6COC6)CC5)c(C#N)c4c3=O)ccnc12] | MS (ESI) m/z 771.31 [M + 1]+ |
| 1752 | 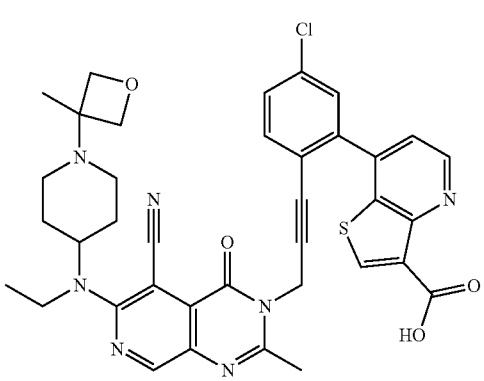 [SMILES: CCN(c1ncc2nc(C)n(CC#Cc3ccc(Cl)cc3-c3ccnc4c(C(=O)O)csc34)c(=O)c2c1C#N)C1CCN(C2(C)COC2)CC1] | MS (ESI) m/z 708.23 [M + 1]+ |

TABLE 1-continued

7-Aza-Thienylpyridine and Derivative Compounds

| Compound | | Characterization |
|---|---|---|
| 1756 | | MS (ESI) m/z 821.28 [M + 1]+ |
| | Chiral | |
| 1754 | | MS (ESI) m/z 799.34 [M + 1]+ |
| 1755 | | MS (ESI) m/z 821.31 [M + 1]+ |

TABLE 1-continued
7-Aza-Thienylpyridine and Derivative Compounds
| Compound | | Characterization |
|---|---|---|
| 1757 | 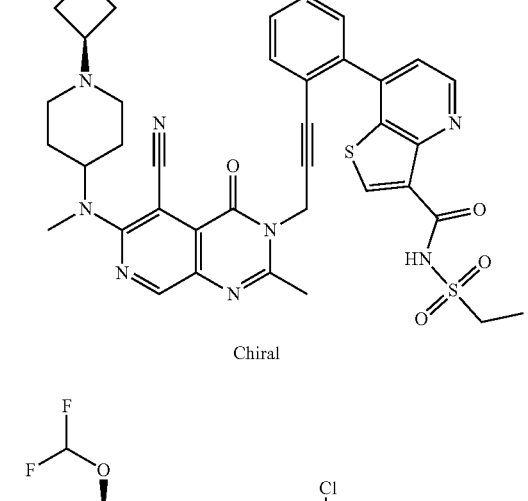<br>Chiral | MS (ESI) m/z 835.45 [M + 1]+ |
| 1758 | 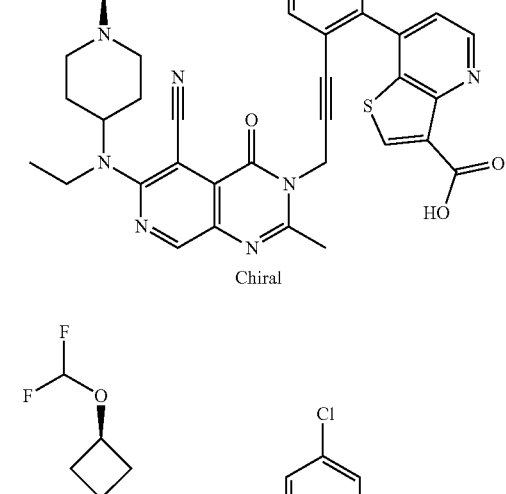<br>Chiral | MS (ESI) m/z 758.28 [M + 1]+ |
| 1759 | 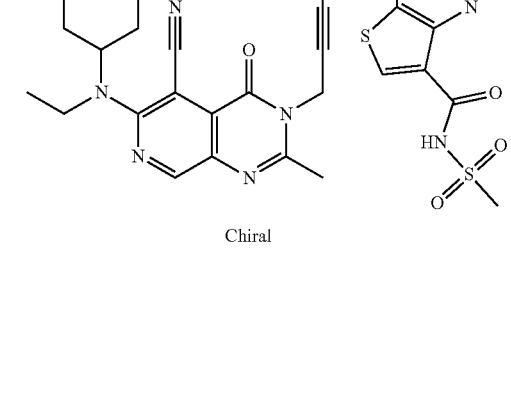<br>Chiral | MS (ESI) m/z 835.26 [M + 1]+ |

TABLE 1-continued
7-Aza-Thienylpyridine and Derivative Compounds
| Compound | | Characterization |
|---|---|---|
| 1760 | 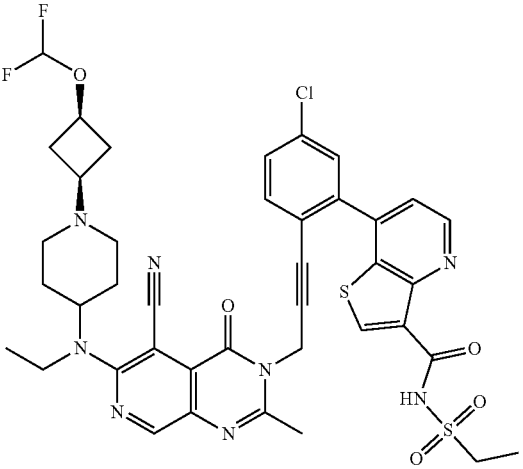 Chiral | MS (ESI) m/z 849.43 [M + 1]+ |
| 1761 | 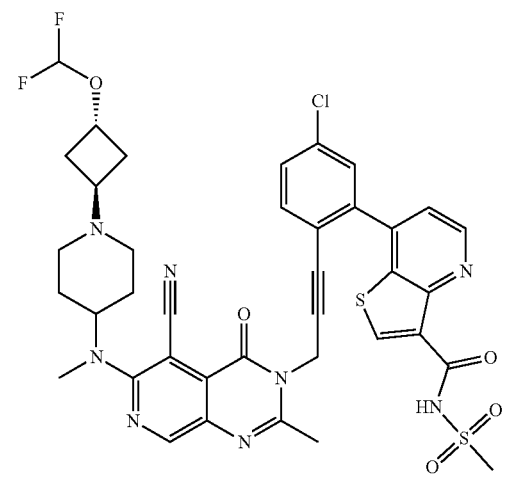 [SMILES: Cc1nc2cnc(N(C)C3CCN([C@H]4C[C@H](OC(F)F)C4)CC3)c(C#N)c2c(=O)n1CC#Cc1ccc(Cl)cc1-c1ccnc2c(C(=O)NS(C)(=O)=O)csc12] | LCMS (ESI) m/z 821.4 [M + 1]+ |
| 1762 | 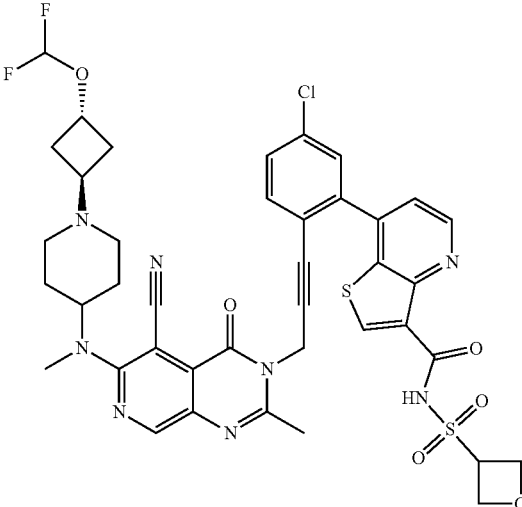 [SMILES: Cc1nc2cnc(N(C)C3CCN([C@H]4C[C@H](OC(F)F)C4)CC3)c(C#N)c2c(=O)n1CC#Cc1ccc(Cl)cc1-c1ccnc2c(C(=O)NS(=O)(=O)C3COC3)csc12] | LCMS (ESI) m/z 863.3 [M + 1]+; 1H NMR (400 MHz, DMSO-d6) δ 12.72 (s, 1H), 9.53 (d, J = 9.3 Hz, 1H), 8.83 (d, J = 4.9 Hz, 1H), 8.78 (d, J = 6.8 Hz, 2H), 7.78 (dd, J = 8.3, 0.5 Hz, 1H), 7.77-7.66 (m, 2H), 7.64 (d, J = 4.9 Hz, 1H), 6.73 (t, J = 21 Hz, 1H), 5.21 (tt, J = 7.8, 6.2 Hz, 1H), 5.00-4.89 (m, 4H), 4.84 (s, 2H), 4.82-4.74 (m, 1H), 4.60 (p, J = 8.0 Hz, 1H), 3.94 (q, J = 7.8 Hz, 1H), 3.58 (d, J = 11.8 Hz, 2H), 3.13 (s, 3H), 3.05 (s, 2H), 2.78-2.68 (m, 1H), 2.72 (s, 1H), 2.17-2.06 (m, 4H), 1.97 (s, 3H) |

TABLE 1-continued
7-Aza-Thienylpyridine and Derivative Compounds
| Compound | | Characterization |
|---|---|---|
| 1763 | 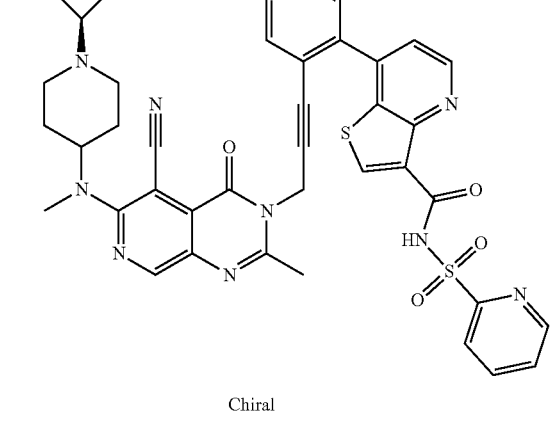 Chiral | LCMS (ESI) m/z 884.5 [M + 1]+; 1H NMR (400 MHz, DMSO-d6) δ 13.02 (s, 1H), 8.90 (d, J = 4.9 Hz, 1H), 8.72 (ddd, J = 4.7, 1.7, 1.0 Hz, 1H), 8.63 (d, J = 13.4 Hz, 2H), 8.27 (dt, J = 7.9, 1.1 Hz, 1H), 8.24-8.16 (m, 1H), 7.80-7.67 (m, 4H), 7.66 (d, J = 4.8 Hz, 1H), 6.72 (t, J = 76 Hz, 1H), 4.83 (s, 2H), 4.78 (dt, J = 7.3, 3.8 Hz, 1H), 4.58 (d, J = 5.8 Hz, 1H), 3.93 (q, J = 7.6 Hz, 1H), 3.56 (d, J = 11.8 Hz, 2H), 3.04 (s, 1H), 2.72 (dd, J = 14.6, 7.1 Hz, 2H), 2.09 (s, 3H), 1.97 (s, 3H) |
| 1764 | 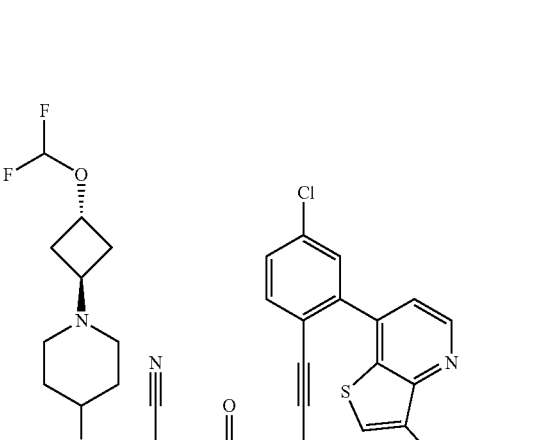 Chiral | LCMS (ESI) m/z 884.5 [M + 1]+; 1H NMR (400 MHz, DMSO-d6) δ 8.95-8.89 (m, 2H), 8.82 (d, J = 4.9 Hz, 1H), 8.65 (s, 1H), 8.47 (s, 1H), 8.07 76 Hz, 1H) 4.81-4.71 (m, 2H), 4.55 (p, J = 8.0 Hz, 1H), 3.93-3.85 (m, 1H), 3.53 (d, J = 11.7 Hz, 2H), 3.01 (s, 1H), 2.77-2.63 (m, 2H), 2.07 (s, 3H), 1.90 (s, 2H), 1.90 (d, J = 16.7 Hz, OH) |

TABLE 1-continued
7-Aza-Thienylpyridine and Derivative Compounds
| Compound | | Characterization |
|---|---|---|
| 1765 | 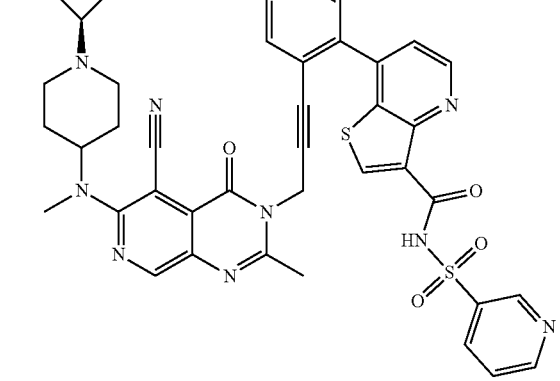<br>Chiral | LCMS (ESI) m/z 884.5 [M + 1]+; 1H NMR (400 MHz, DMSO-d6) δ 9.24 (dd, J = 2.5, 0.8 Hz, 1H), 8.89 (dd, J = 4.8, 1.6 Hz, 1H), 8.81 (d, J = 4.9 Hz, 1H), 8.63 (s, 1H), 8.50 (ddd, J = 8.2, 2.4, 1.6 Hz, 1H), 8.46 (s, 1H), 7.76-7.64 (m, 3H), 7.64-7.57 (m, 2H), 6.69 (t, J = 76 Hz, 1H), 4.76 (d, J = 10.9 Hz, 3H), 4.55 (t, J = 8.0 Hz, 1H), 3.94-3.85 (m, 1H), 3.52 (s, 1H), 3.08 (s, 3H), 3.02 (s, 1H), 2.74-2.64 (m, 2H), 2.08 (s, 4H), 1.88 (s, 3H) |
| 1766 | 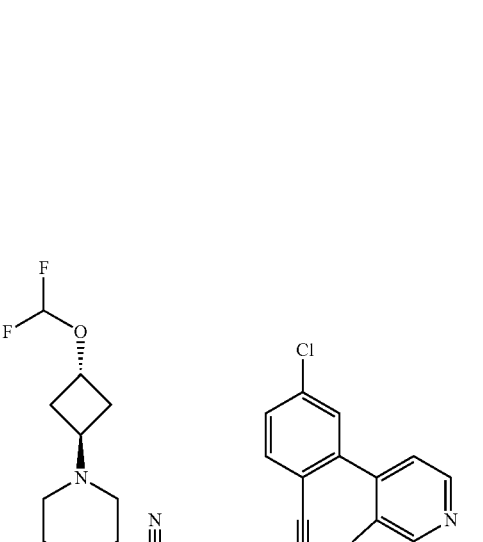<br>Chiral | MS (ESI) m/z 758.34 [M + 1]+ |

TABLE 1-continued
7-Aza-Thienylpyridine and Derivative Compounds
| Compound | | Characterization |
|---|---|---|
| 1767 | 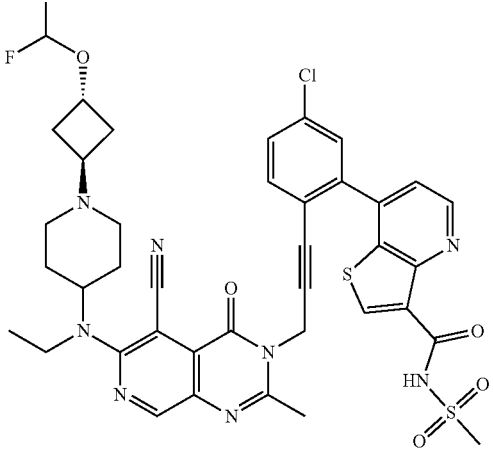 Chiral | MS (ESI) m/z 835.33 [M + 1]+ |
| 1768 | 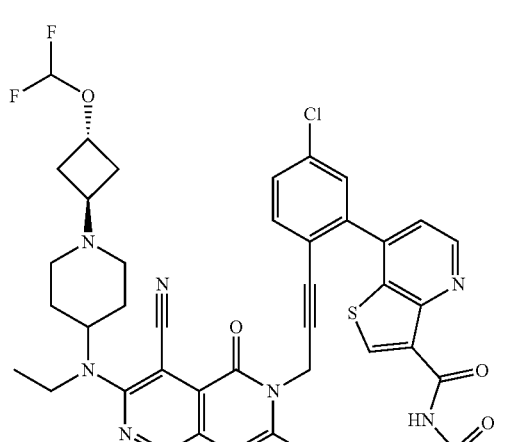 Chiral | MS (ESI) m/z 877.29 [M + 1]+ |

TABLE 1-continued

7-Aza-Thienylpyridine and Derivative Compounds

| Compound | | Characterization |
|---|---|---|
| 1769 | | MS (ESI) m/z 898.4 [M + 1]+ |
| | Chiral | |
| 1770 | | MS (ESI) m/z 898.26 [M + 1]+ |
| | Chiral | |

TABLE 1-continued
7-Aza-Thienylpyridine and Derivative Compounds
| Compound | | Characterization |
|---|---|---|
| 1771 | 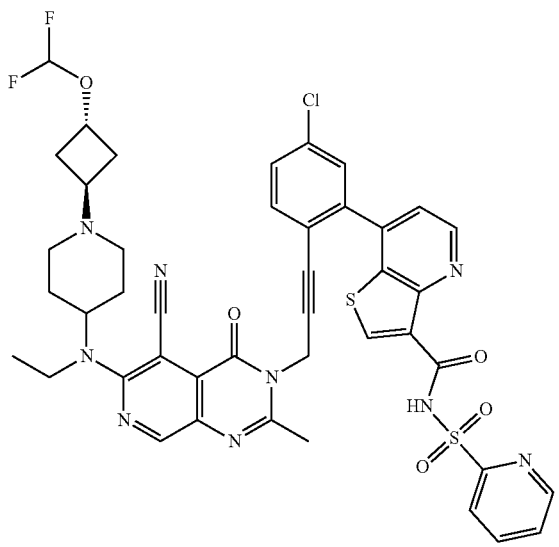<br>Chiral | MS (ESI) m/z 898.29 [M + 1]+ |
| 1772 | 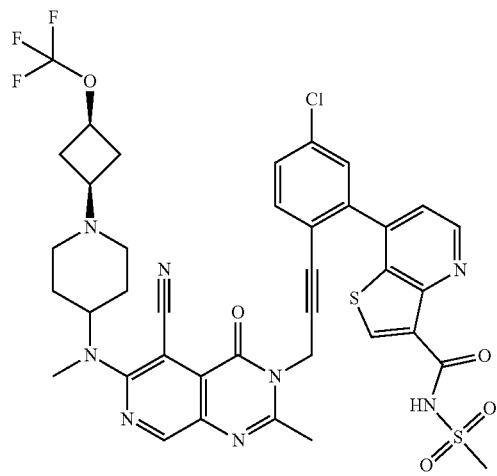<br>Chiral | MS (ESI) m/z 839.28 [M + 1]+ |

TABLE 1-continued
7-Aza-Thienylpyridine and Derivative Compounds
| Compound | | Characterization |
|---|---|---|
| 1773 | 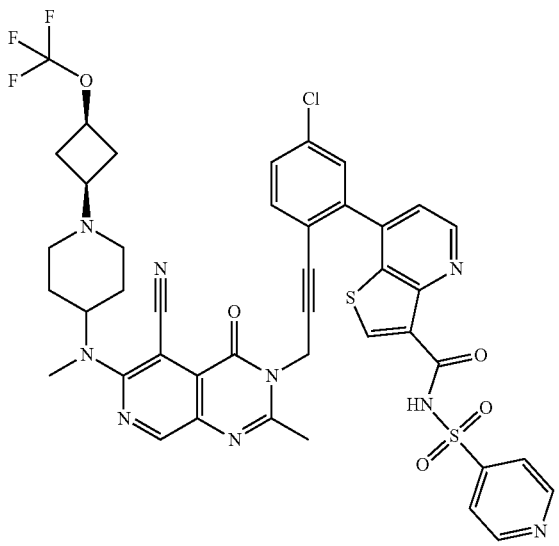<br>Chiral | MS (ESI) m/z 902.19 [M + 1]+ |
| 1774 | 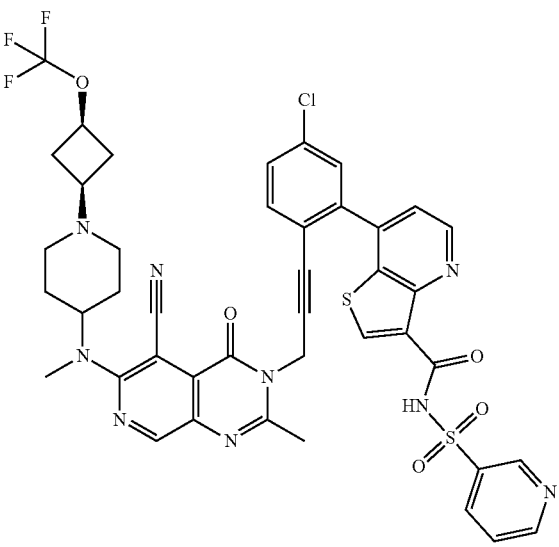<br>Chiral | MS (ESI) m/z 902.23 [M + 1]+ |

TABLE 1-continued
7-Aza-Thienylpyridine and Derivative Compounds
| Compound | | Characterization |
|---|---|---|
| 1775 | 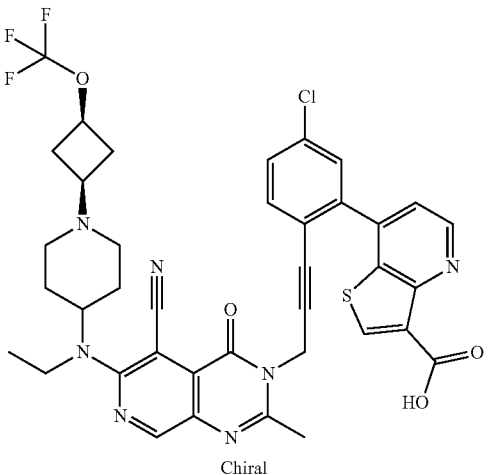 Chiral | MS (ESI) m/z 776.35 [M + 1]+ |
| 1776 | 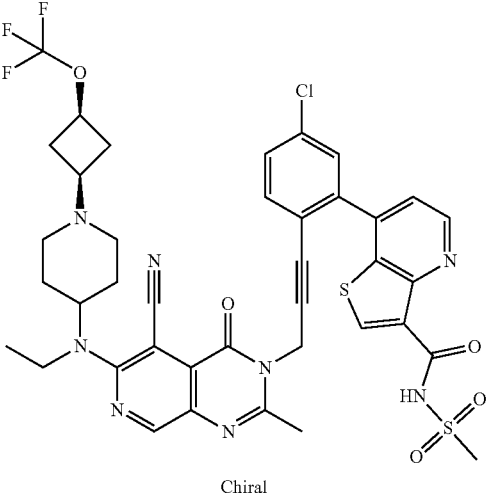 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN([C@H]2C[C@@H](OC(F)(F)F)C2)CC1] Chiral | MS (ESI) m/z 853.3 [M + 1]+ |
| 1777 | 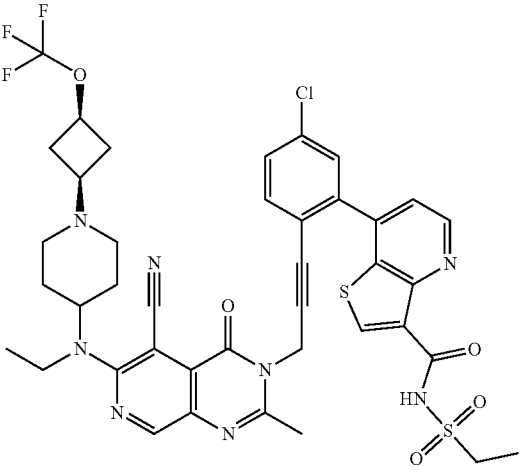 Chiral | MS (ESI) m/z 819.33 [M + 1]+ |

TABLE 1-continued
7-Aza-Thienylpyridine and Derivative Compounds
| Compound | | Characterization |
|---|---|---|
| 1778 | 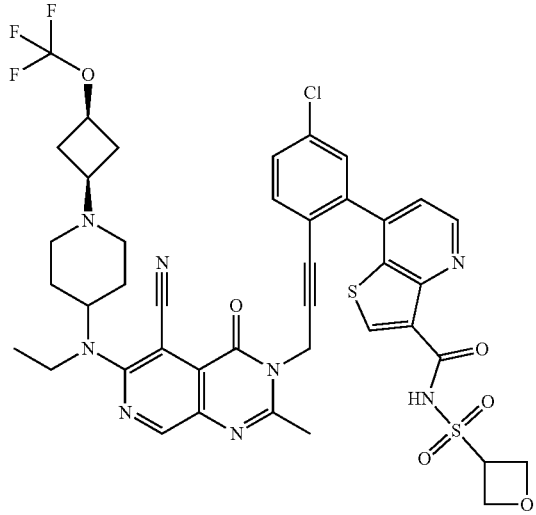 Chiral | MS (ESI) m/z 895.27 [M + 1]+ |
| 1779 | 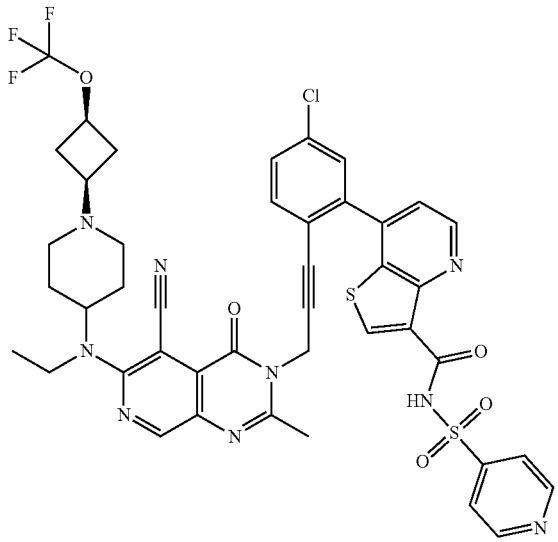 Chiral | MS (ESI) m/z 916.3 [M + 1]+ |

TABLE 1-continued
7-Aza-Thienylpyridine and Derivative Compounds
| Compound | | Characterization |
|---|---|---|
| 1780 | 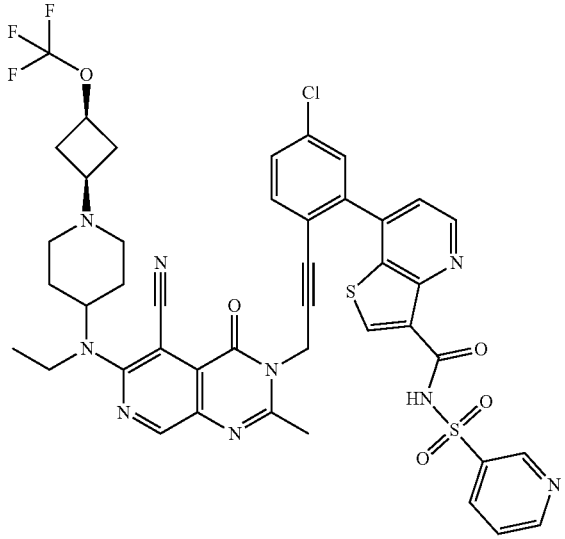<br>Chiral | MS (ESI) m/z 916.27 [M + 1]+ |
| 1781 | 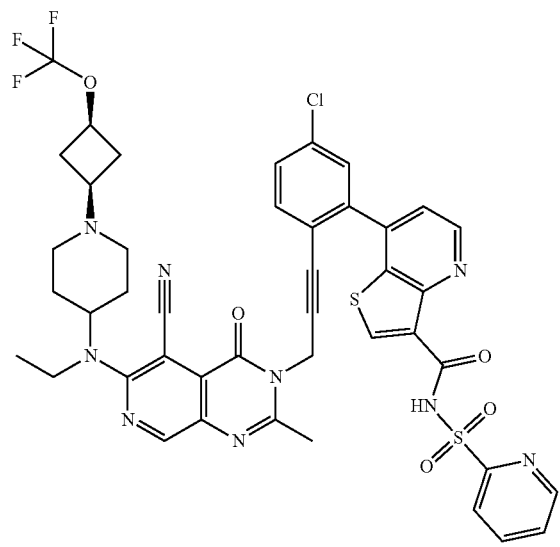<br>Chiral | MS (ESI) m/z 916.27 [M + 1]+ |

TABLE 1-continued
7-Aza-Thienylpyridine and Derivative Compounds
| Compound | | Characterization |
|---|---|---|
| 1782 | 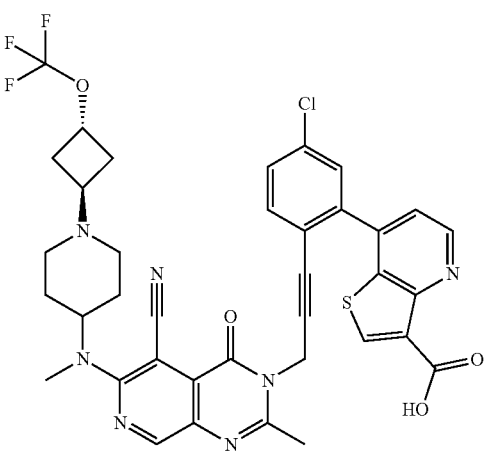 Chiral | MS (ESI) m/z 762.31 [M + 1]+ |
| 1783 | 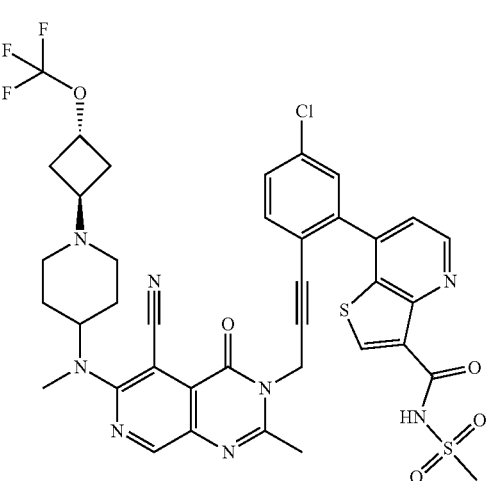 Chiral | MS (ESI) m/z 839.26 [M + 1]+ |
| 1784 | 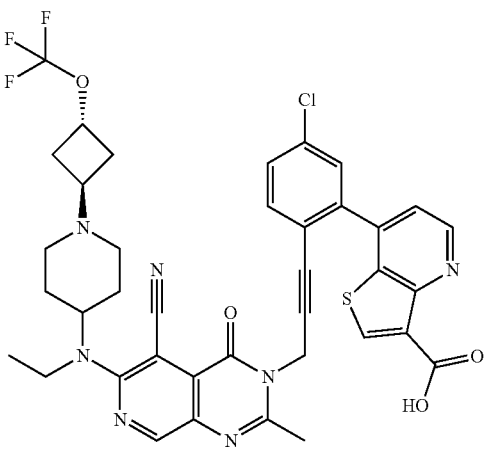 Chiral | MS (ESI) m/z 776.29 [M + 1]+ |

TABLE 1-continued
7-Aza-Thienylpyridine and Derivative Compounds
| Compound | | Characterization |
|---|---|---|
| 1785 | 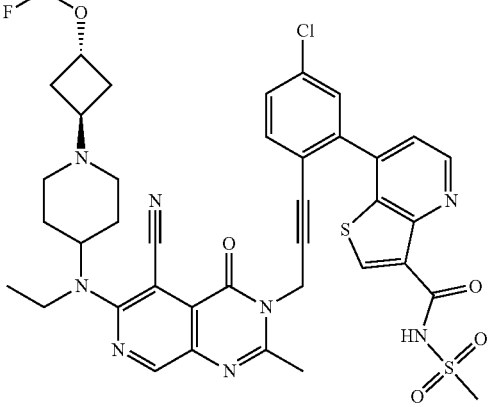<br>Chiral | MS (ESI) m/z 853.37 [M + 1]+ |
| 1786 | 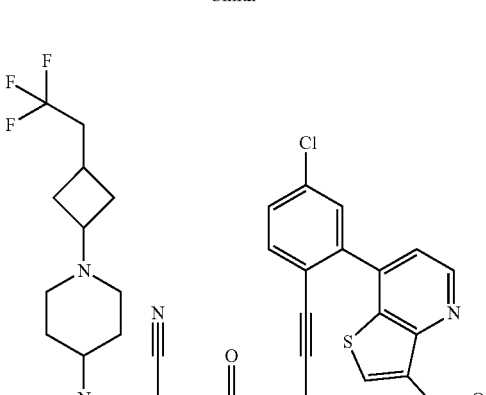 | MS (ESI) m/z 760.31 [M + 1]+ |
| 1787 | 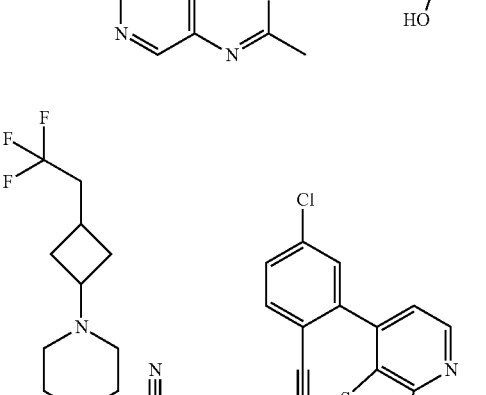 | MS (ESI) m/z 837.35 [M + 1]+ |

TABLE 1-continued

7-Aza-Thienylpyridine and Derivative Compounds

| Compound | | Characterization |
|---|---|---|
| 1788 | | MS (ESI) m/z 851.42 [M + 1]+ |
| 1789 | | MS (ESI) m/z 851.41 [M + 1]+ |
| 1790 | | MS (ESI) m/z 865.46 [M + 1]+ |

561 562
TABLE 1-continued
7-Aza-Thienylpyridine and Derivative Compounds
| Compound | | Characterization |
|---|---|---|
| 1791 | 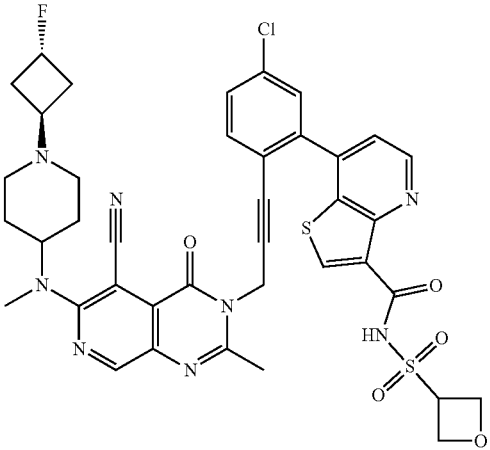<br>Chiral | MS (ESI) m/z 815.24 [M + 1]+ |
| 1792 | 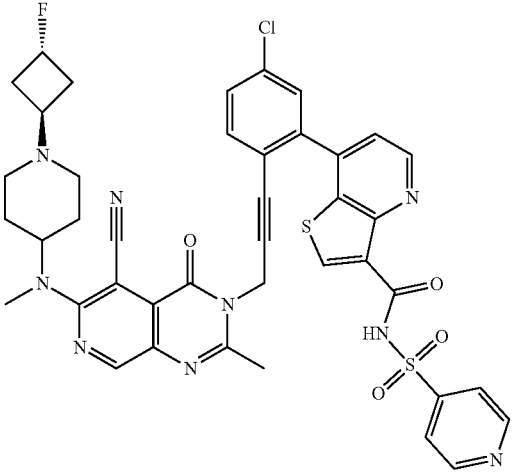<br>Chiral | MS (ESI) m/z 836.27 [M + 1]+ |
| 1793 | 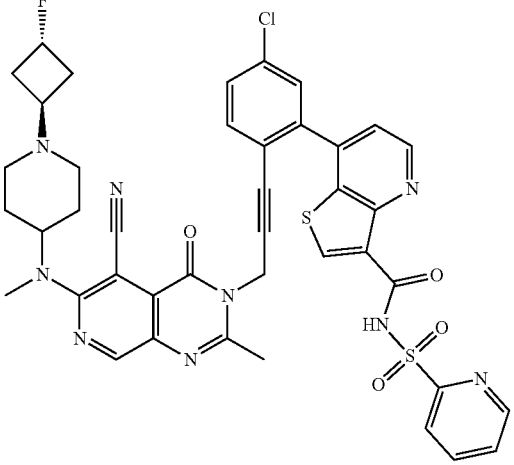<br>Chiral | MS (ESI) m/z 836.3 [M + 1]+ |

TABLE 1-continued
7-Aza-Thienylpyridine and Derivative Compounds
| Compound | | Characterization |
|---|---|---|
| 1794 | 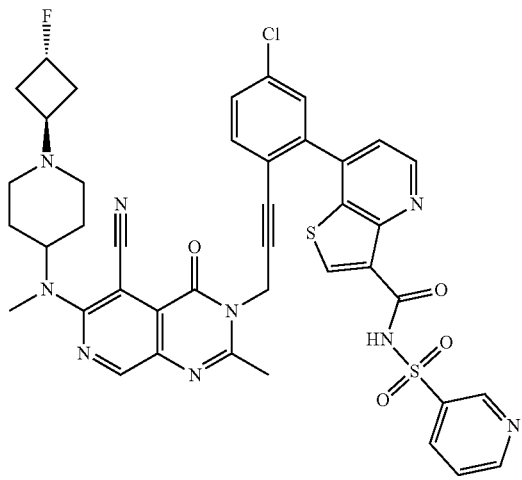<br>Chiral | MS (ESI) m/z 836.33 [M + 1]+ |
| 1795 | 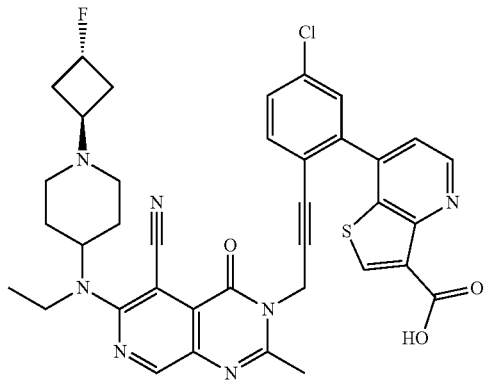<br>Chiral | MS (ESI) m/z 710.25 [M + 1]+ |
| 1796 | 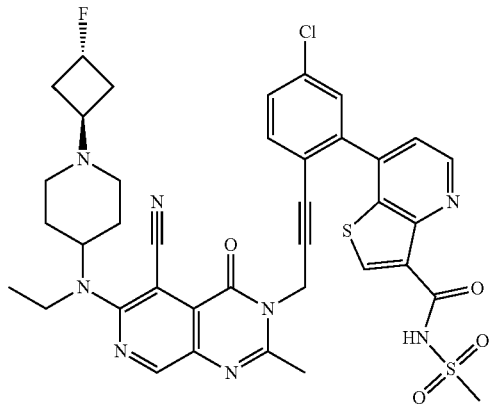<br>Chiral | MS (ESI) m/z 787.34 [M + 1]+ |

TABLE 1-continued

7-Aza-Thienylpyridine and Derivative Compounds

| Compound | Characterization |
|---|---|
| 1797 | MS (ESI) m/z 829.34 [M + 1]+ |
| 1798 | MS (ESI) m/z 850.31 [M + 1]+ |
| 1799 | MS (ESI) m/z 850.34 [M + 1]+ |

TABLE 1-continued
7-Aza-Thienylpyridine and Derivative Compounds
| Compound | | Characterization |
|---|---|---|
| 1800 | 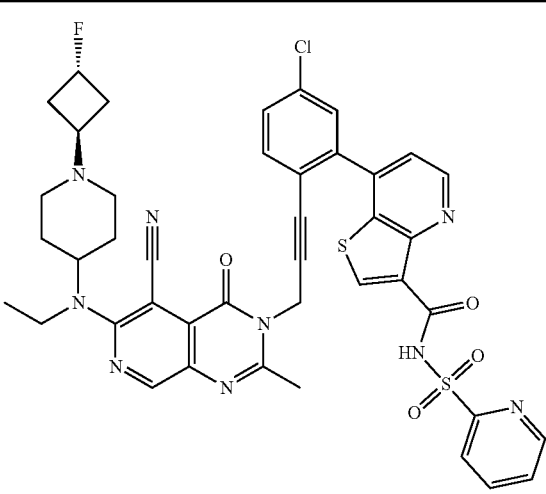 Chiral | MS (ESI) m/z 850.25 [M + 1]+ |
| 1801 | 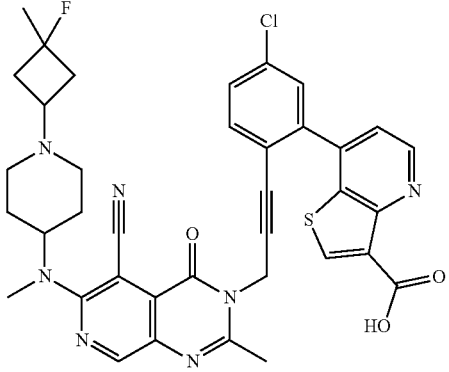 [SMILES: Cc1nc2cnc(N(C)C3CCN(C4CC(C)(F)C4)CC3)c(C#N)c2c(=O)n1CC#Cc1ccc(Cl)cc1-c1ccnc2c(C(=O)O)csc12] | MS (ESI) m/z 710.28 [M + 1]+ |
| 1802 | 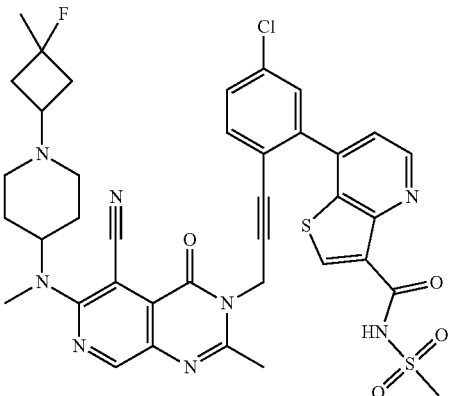 [SMILES: Cc1nc2cnc(N(C)C3CCN(C4CC(C)(F)C4)CC3)c(C#N)c2c(=O)n1CC#Cc1ccc(Cl)cc1-c1ccnc2c(C(=O)NS(C)(=O)=O)csc12] | MS (ESI) m/z 787.28 [M + 1]+ |

TABLE 1-continued
7-Aza-Thienylpyridine and Derivative Compounds
| Compound | | Characterization |
|---|---|---|
| 1803 | 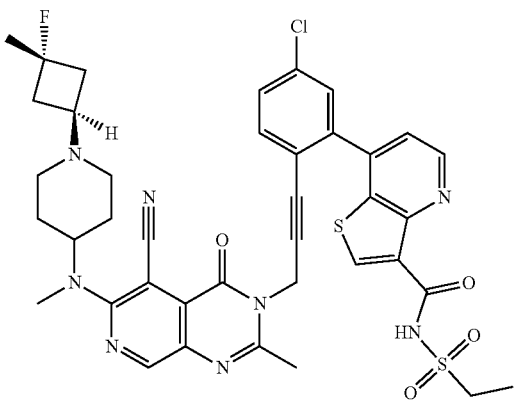 Chiral | MS (ESI) m/z 801.44 [M + 1]+ |
| 1804 | 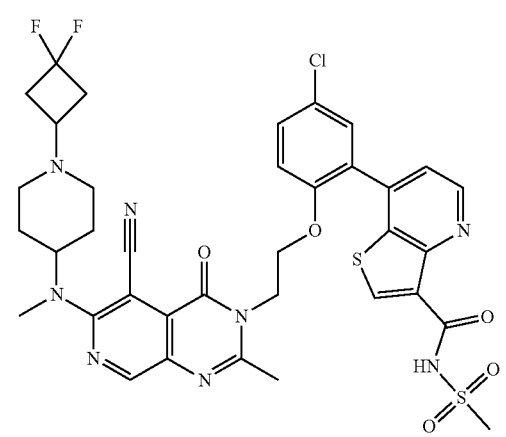 [SMILES: Cc1nc2cnc(N(C)C3CCN(C4CC(F)(F)C4)CC3)c(C#N)c2c(=O)n1CCOc1ccc(Cl)cc1-c1ccnc2c(C(=O)NS(C)(=O)=O)csc12] | MS (ESI) m/z 797.32 [M + 1]+ |
| 1805 | 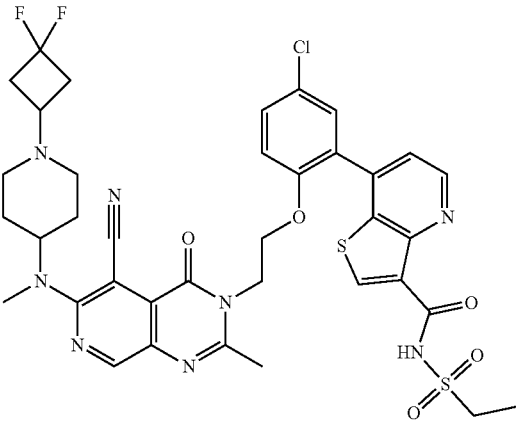 [SMILES: CCS(=O)(=O)NC(=O)c1csc2c(-c3cc(Cl)ccc3OCCn3c(C)nc4cnc(N(C)C5CCN(C6CC(F)(F)C6)CC5)c(C#N)c4c3=O)ccnc12] | MS (ESI) m/z 811.3 [M + 1]+ |

TABLE 1-continued
7-Aza-Thienylpyridine and Derivative Compounds
| Compound | | Characterization |
|---|---|---|
| 1806 | 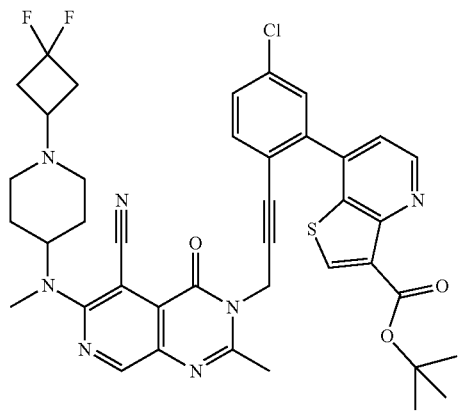 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)OC(C)(C)C)csc12] | MS (ESI) m/z 770.31 [M + 1]+ |
| 1807 | 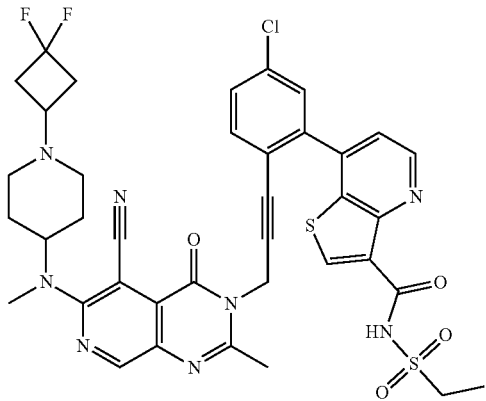 [SMILES: CCS(=O)(=O)NC(=O)c1csc2c(-c3cc(Cl)ccc3C#CCn3c(C)nc4cnc(N(C)C5CCN(C6CC(F)(F)C6)CC5)c(C#N)c4c3=O)ccnc12] | MS (ESI) m/z 805.28 [M + 1]+ |
| 1808 | 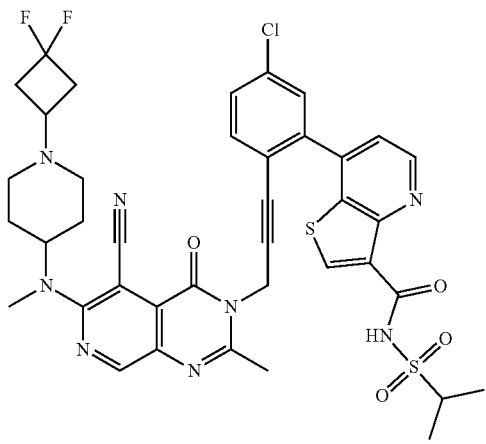 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(=O)(=O)C(C)C)csc12] | MS (ESI) m/z 819.358 [M + 1]+ |

TABLE 1-continued
7-Aza-Thienylpyridine and Derivative Compounds
| Compound | | Characterization |
|---|---|---|
| 1809 | 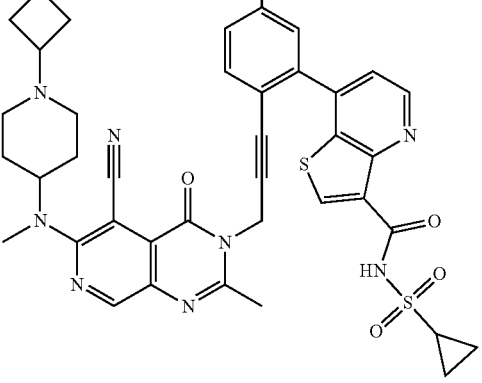 | MS (ESI) m/z 817.27 [M + 1]+ |
| 1810 | 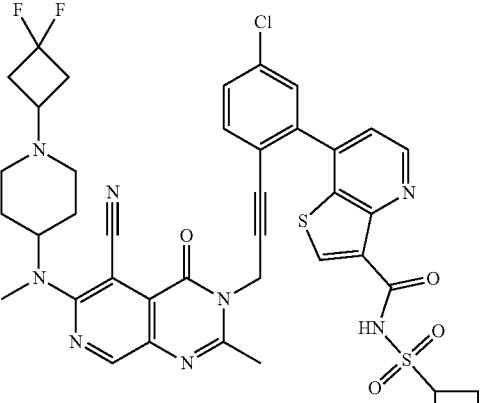 | MS (ESI) m/z 831.26 [M + 1]+ |
| 1811 | 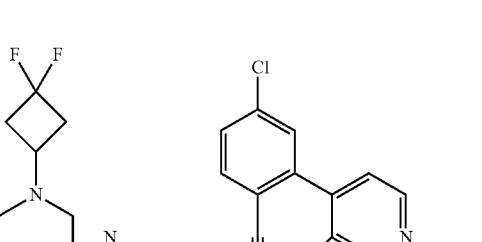 | MS (ESI) m/z 833.22 [M + 1]+ |

TABLE 1-continued

7-Aza-Thienylpyridine and Derivative Compounds

| Compound | | Characterization |
|---|---|---|
| 1812 | | MS (ESI) m/z 833.39 [M + 1]+ |
| 1813 | | MS (ESI) m/z 624.2 [M + 1]+ |
| 1814 | | MS (ESI) m/z 843.32 [M + 1]+ |

TABLE 1-continued

7-Aza-Thienylpyridine and Derivative Compounds

| Compound | Characterization |
|---|---|
| 1815 | MS (ESI) m/z 787.34 [M + 1]+ |
| 1816 | MS (ESI) m/z 850.31 [M + 1]+ |
| 1817 | MS (ESI) m/z 809.22 [M + 1]+ |

TABLE 1-continued
7-Aza-Thienylpyridine and Derivative Compounds
| Compound | | Characterization |
|---|---|---|
| 1818 | 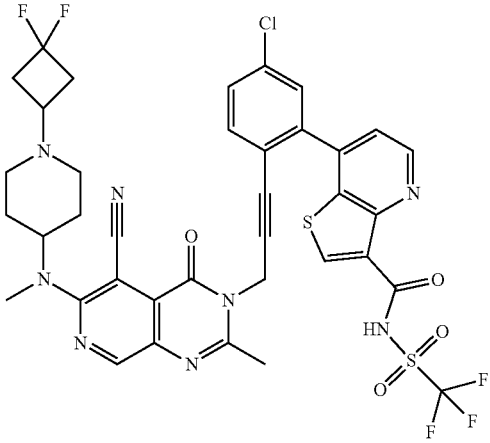 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(=O)(=O)C(F)(F)F)csc12] | MS (ESI) m/z 845.26 [M + 1]+ |
| 1819 | 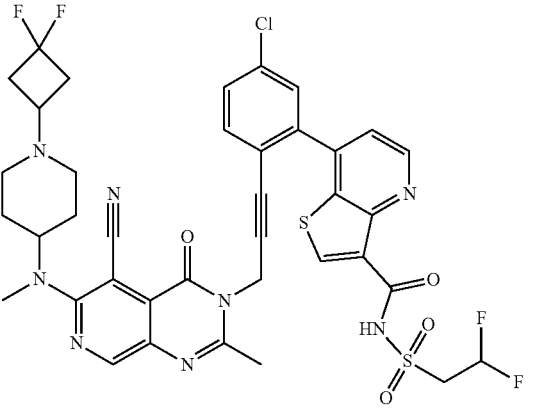 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(=O)(=O)CC(F)F)csc12] | MS (ESI) m/z 841.17 [M + 1]+ |
| 1820 | 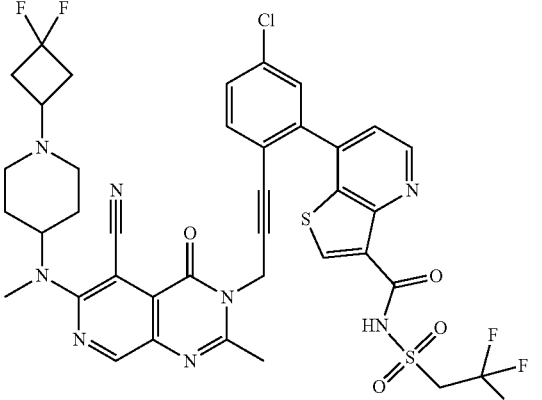 | MS (ESI) m/z 817.25 [M + 1]+ |

TABLE 1-continued
7-Aza-Thienylpyridine and Derivative Compounds
| Compound | | Characterization |
|---|---|---|
| 1821 | 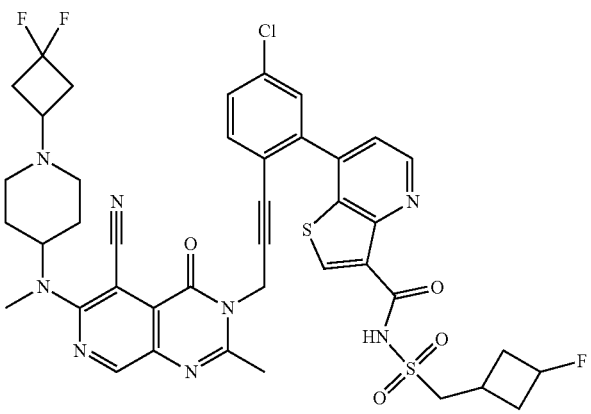 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(=O)(=O)CC3CC(F)C3)csc12] | MS (ESI) m/z 863.33 [M + 1]+ |
| 1822 | 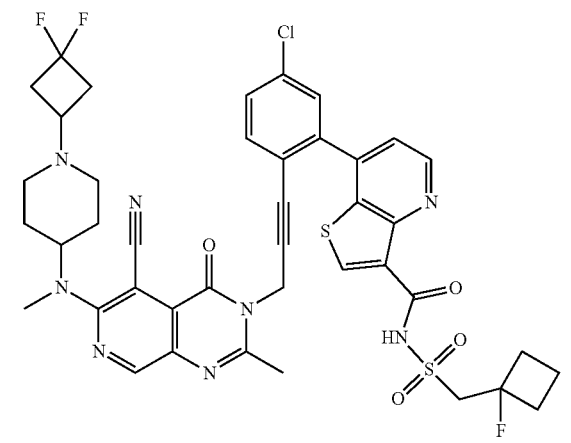 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(=O)(=O)CC3(F)CCC3)csc12] | MS (ESI) m/z 863.38 [M + 1]+ |
| 1823 | 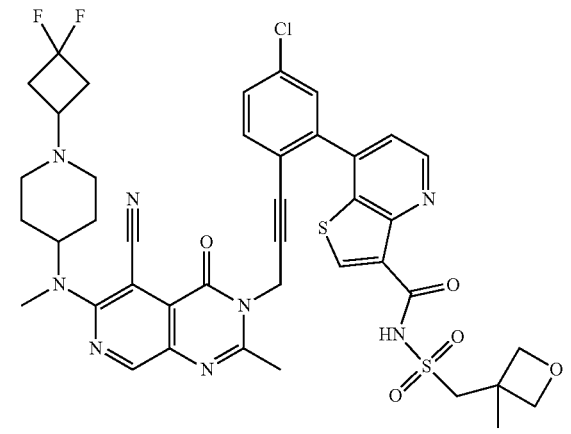 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(=O)(=O)CC3(C)COC3)csc12] | MS (ESI) m/z 861.36 [M + 1]+ |

TABLE 1-continued
7-Aza-Thienylpyridine and Derivative Compounds
| Compound | | Characterization |
|---|---|---|
| 1824 | 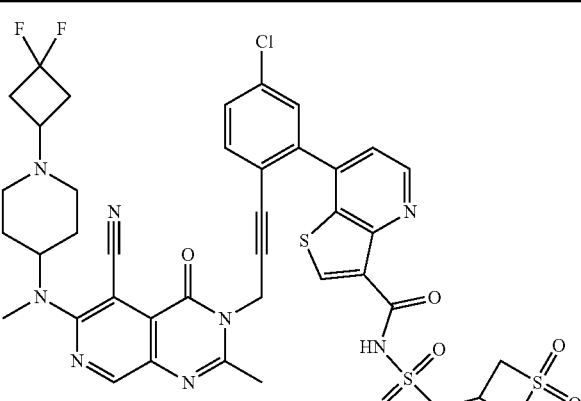 | MS (ESI) m/z 895.39 [M + 1]+ |
| 1825 | 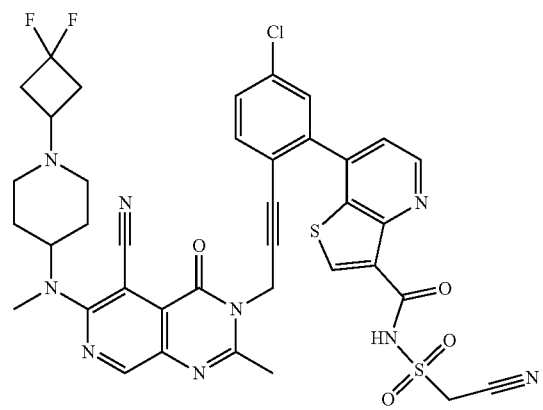 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(=O)(=O)CC#N)csc12] | MS (ESI) m/z 816.24 [M + 1]+ |
| 1826 | 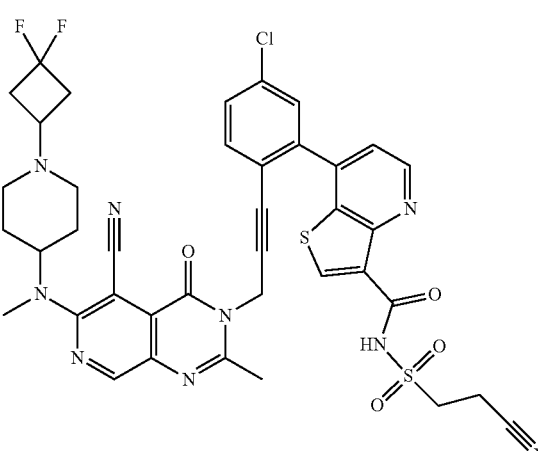 | MS (ESI) m/z 830.3 [M + 1]+ |

TABLE 1-continued

7-Aza-Thienylpyridine and Derivative Compounds

| Compound | | Characterization |
|---|---|---|
| 1827 | | MS (ESI) m/z 858.28 [M + 1]+ |
| 1828 | | MS (ESI) m/z 833.34 [M + 1]+ |
| 1829 | | MS (ESI) m/z 854.26 [M + 1]+ |

TABLE 1-continued

7-Aza-Thienylpyridine and Derivative Compounds

| Compound | | Characterization |
|---|---|---|
| 1830 | | MS (ESI) m/z 854.26 [M + 1]+ |
| 1831 | | MS (ESI) m/z 854.22 [M + 1]+ |
| 1832 | | MS (ESI) m/z 868.26 [M + 1]+ |

TABLE 1-continued

7-Aza-Thienylpyridine and Derivative Compounds

| Compound | | Characterization |
|---|---|---|
| 1833 | | MS (ESI) m/z 867.24 [M + 1]+ |
| 1834 | | MS (ESI) m/z 811.4 [M + 1]+ |
| 1835 | | MS (ESI) m/z 825.41 [M + 1]+ |

TABLE 1-continued
7-Aza-Thienylpyridine and Derivative Compounds
| Compound | | Characterization |
|---|---|---|
| 1836 | 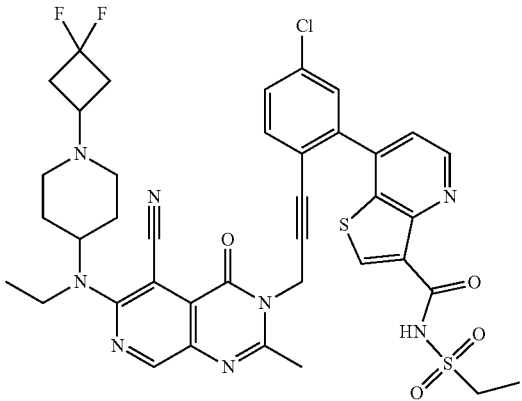 [SMILES: CCN(c1ncc2nc(C)n(CC#Cc3ccc(Cl)cc3-c3ccnc4c(C(=O)NS(=O)(=O)CC)csc34)c(=O)c2c1C#N)C1CCN(C2CC(F)(F)C2)CC1] | MS (ESI) m/z 819.33 [M + 1]+ |
| 1837 | 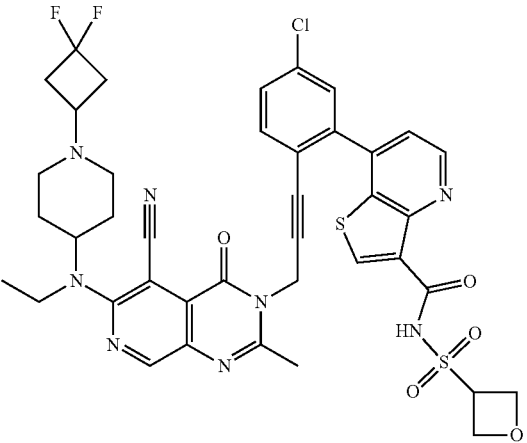 [SMILES: CCN(c1ncc2nc(C)n(CC#Cc3ccc(Cl)cc3-c3ccnc4c(C(=O)NS(=O)(=O)C5COC5)csc34)c(=O)c2c1C#N)C1CCN(C2CC(F)(F)C2)CC1] | MS (ESI) m/z 847.35 [M + 1]+ |
| 1838 | 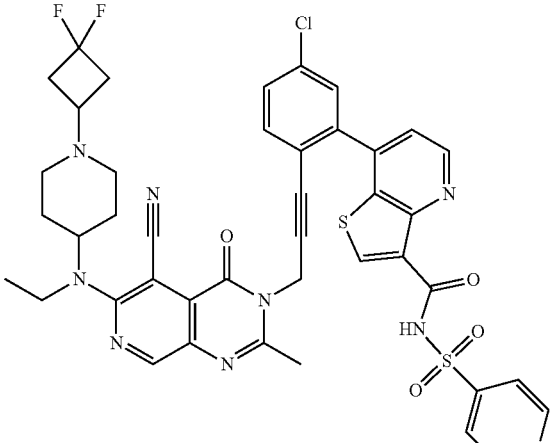 | MS (ESI) m/z 868.26 [M + 1]+ |

TABLE 1-continued
7-Aza-Thienylpyridine and Derivative Compounds
| Compound | | Characterization |
|---|---|---|
| 1839 | 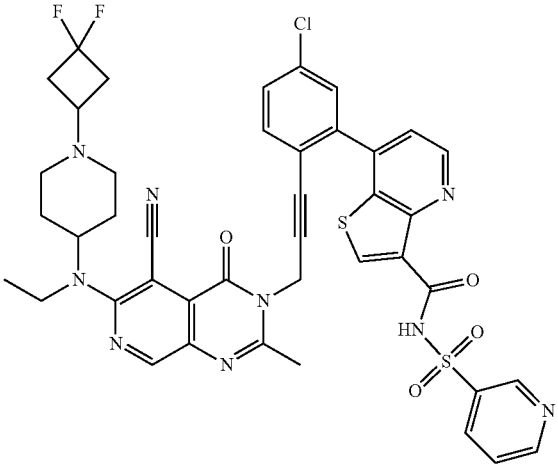 [SMILES: CCN(c1ncc2nc(C)n(CC#Cc3ccc(Cl)cc3-c3ccnc4c(C(=O)NS(=O)(=O)c5cccnc5)csc34)c(=O)c2c1C#N)C1CCN(C2CC(F)(F)C2)CC1] | MS (ESI) m/z 868.26 [M + 1]+ |
| 1840 | 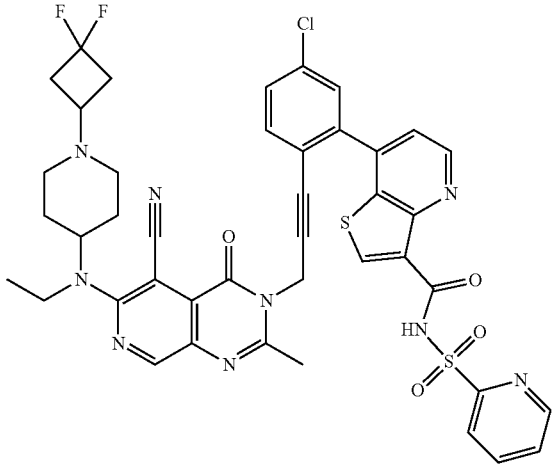 [SMILES: CCN(c1ncc2nc(C)n(CC#Cc3ccc(Cl)cc3-c3ccnc4c(C(=O)NS(=O)(=O)c5ccccn5)csc34)c(=O)c2c1C#N)C1CCN(C2CC(F)(F)C2)CC1] | MS (ESI) m/z 868.29 [M + 1]+ |
| 1840 | 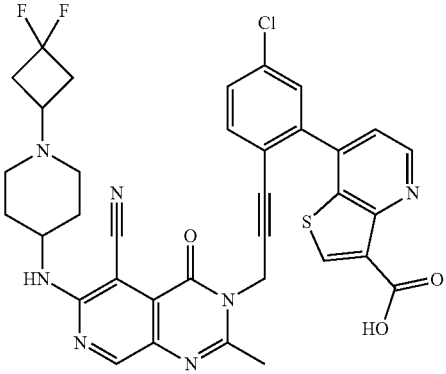 [SMILES: Cc1nc2cnc(NC3CCN(C4CC(F)(F)C4)CC3)c(C#N)c2c(=O)n1CC#Cc1ccc(Cl)cc1-c1ccnc2c(C(=O)O)csc12] | MS (ESI) m/z 700.33 [M + 1]+ |

TABLE 1-continued
7-Aza-Thienylpyridine and Derivative Compounds
| Compound | | Characterization |
|---|---|---|
| 1842 | 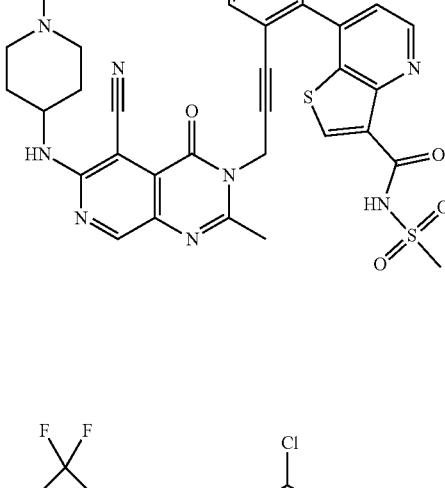 | MS (ESI) m/z 777.26 [M + 1]+ |
| 1843 | 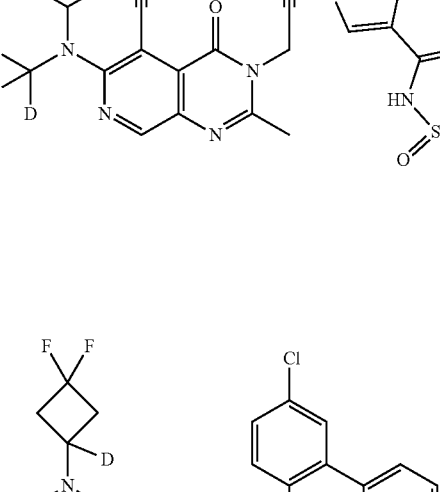 | MS (ESI) m/z 794.33 [M + 1]+ |
| 1844 | 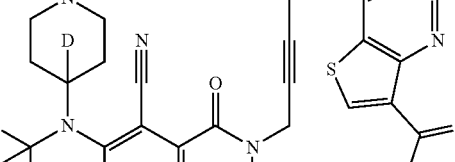 | MS (ESI) m/z 796.44 [M + 1]+ |

TABLE 1-continued
7-Aza-Thienylpyridine and Derivative Compounds
| Compound | | Characterization |
|---|---|---|
| 1845 | 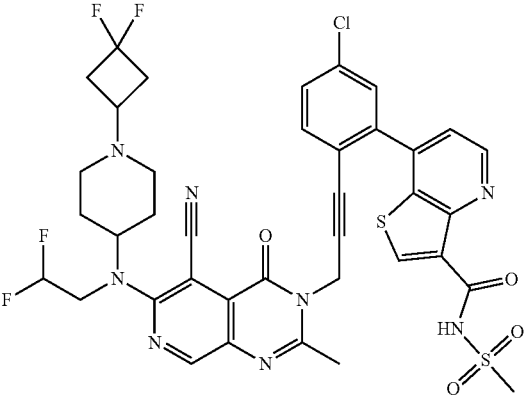 [SMILES: Cc1nc2cnc(N(CC(F)F)C3CCN(C4CC(F)(F)C4)CC3)c(C#N)c2c(=O)n1CC#Cc1ccc(Cl)cc1-c1ccnc2c(C(=O)NS(C)(=O)=O)csc12] | MS (ESI) m/z 841.34 [M + 1]+ |
| 1846 | 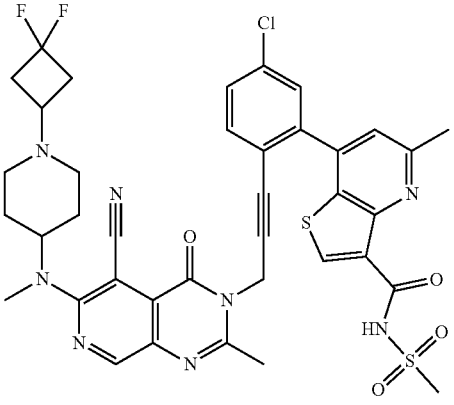 [SMILES: Cc1cc(-c2cc(Cl)ccc2C#CCn2c(C)nc3cnc(N(C)C4CCN(C5CC(F)(F)C5)CC4)c(C#N)c3c2=O)c2scc(C(=O)NS(C)(=O)=O)c2n1] | MS (ESI) m/z 805.38 [M + 1]+ |
| 1847 | 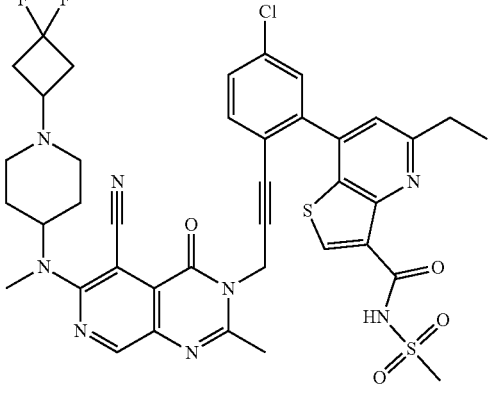 | MS (ESI) m/z 819.34 [M + 1]+ |

TABLE 1-continued

7-Aza-Thienylpyridine and Derivative Compounds

| Compound | | Characterization |
|---|---|---|
| 1848 | | MS (ESI) m/z 823.3 [M + 1]+ |
| 1849 | | MS (ESI) m/z 835.36 [M + 1]+ |
| 1850 | | MS (ESI) m/z 730.34 [M + 1]+ |

TABLE 1-continued
7-Aza-Thienylpyridine and Derivative Compounds
| Compound | | Characterization |
|---|---|---|
| 1851 | 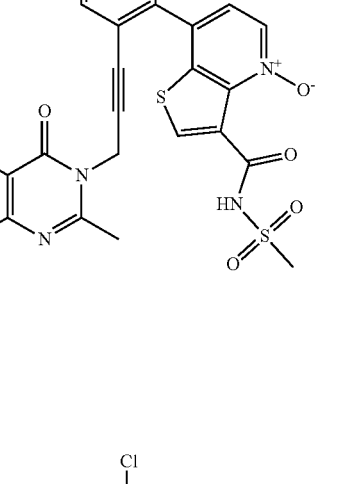 | MS (ESI) m/z 807.33 [M + 1]+ |
| 1852 | 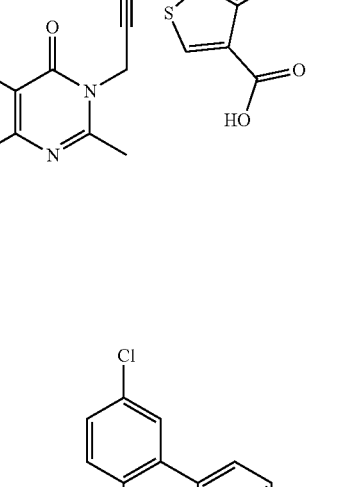 | MS (ESI) m/z 730.36 [M + 1]+ |
| 1853 | 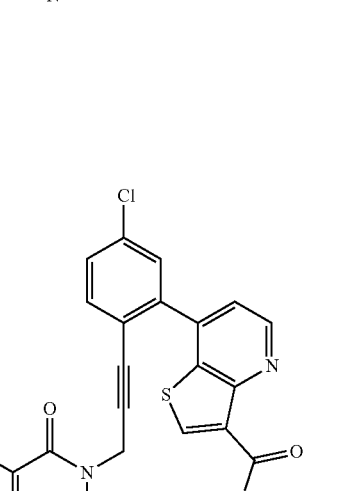 | MS (ESI) m/z 807.18 [M + 1]+ |

TABLE 1-continued

7-Aza-Thienylpyridine and Derivative Compounds

| Compound | | Characterization |
|---|---|---|
| 1854 | | MS (ESI) m/z 746.16 [M + 1]+ |
| 1855 | | MS (ESI) m/z 823.36 [M + 1]+ |
| 1856 | | MS (ESI) m/z 730.37 [M + 1]+ |

TABLE 1-continued
7-Aza-Thienylpyridine and Derivative Compounds
| Compound | | Characterization |
|---|---|---|
| 1857 | 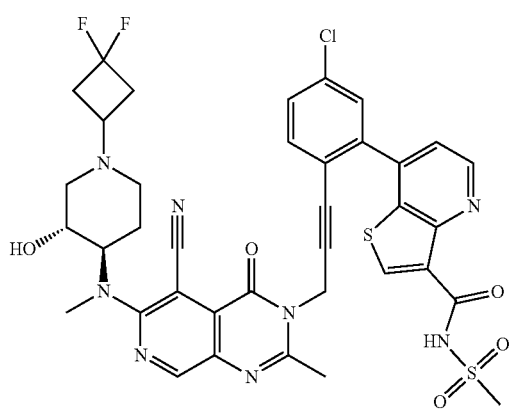<br>Chiral | MS (ESI) m/z 807.4 [M + 1]+ |
| 1858 | 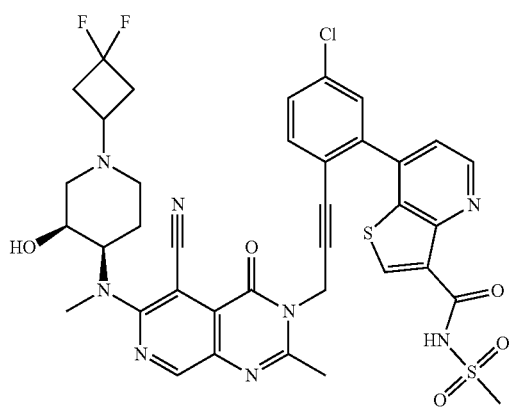<br>Chiral | MS (ESI) m/z 807.3 [M + 1]+ |
| 1589 | 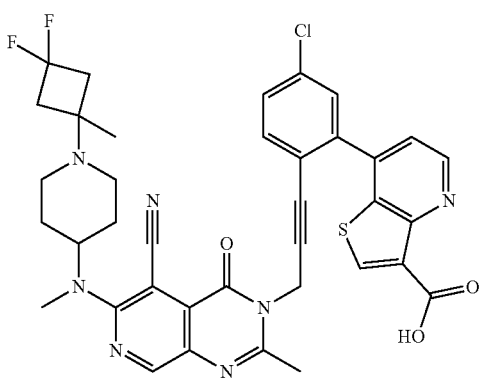 [SMILES: Cc1nc2cnc(N(C)C3CCN(C4(C)CC(F)(F)C4)CC3)c(C#N)c2c(=O)n1CC#Cc1ccc(Cl)cc1-c1ccnc2c(C(=O)O)csc12] | MS (ESI) m/z 728.3 [M + 1]+ |

TABLE 1-continued
7-Aza-Thienylpyridine and Derivative Compounds
| Compound | | Characterization |
|---|---|---|
| 1860 | 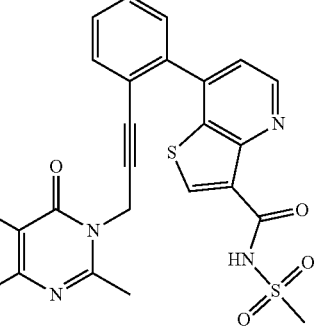 | MS (ESI) m/z 805.32 [M + 1]+ |
| 1861 | 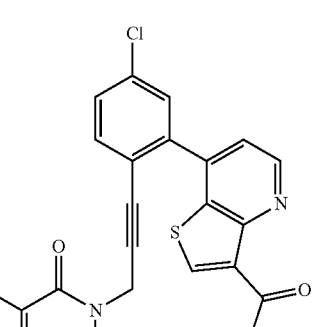 | MS (ESI) m/z 746.31 [M + 1]+ |
| 1862 | 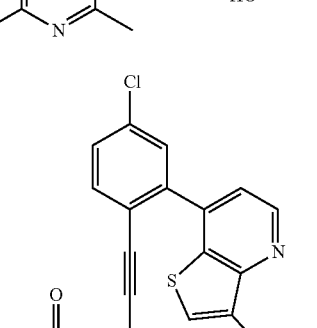 | MS (ESI) m/z 823.39 [M + 1]+ |
| 1863 | 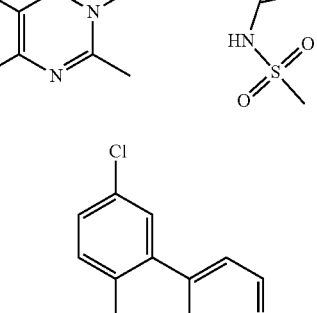 | MS (ESI) m/z 704.27 [M + 1]+ |

TABLE 1-continued
7-Aza-Thienylpyridine and Derivative Compounds
| Compound | | Characterization |
|---|---|---|
| 1864 | 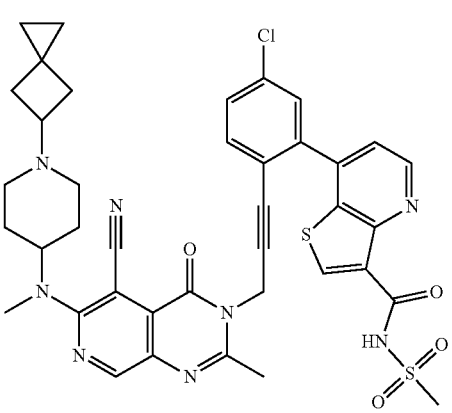 [SMILES: Cc1nc2cnc(N(C)C3CCN(C4CC5(CC5)C4)CC3)c(C#N)c2c(=O)n1CC#Cc1ccc(Cl)cc1-c1ccnc2c(C(=O)NS(C)(=O)=O)csc12] | MS (ESI) m/z 781.26 [M + 1]+ |
| 1865 | 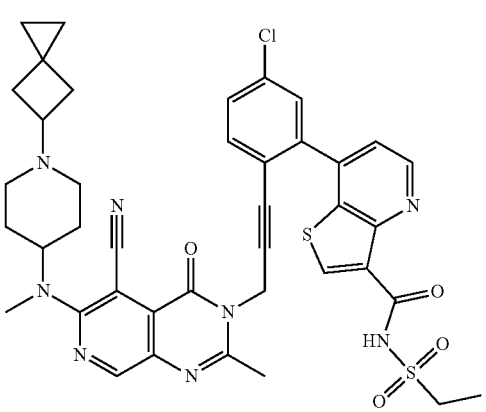 [SMILES: CCS(=O)(=O)NC(=O)c1csc2c(-c3cc(Cl)ccc3C#CCn3c(C)nc4cnc(N(C)C5CCN(C6CC7(CC7)C6)CC5)c(C#N)c4c3=O)ccnc12] | MS (ESI) m/z 795.37 [M + 1]+ |
| 1866 | 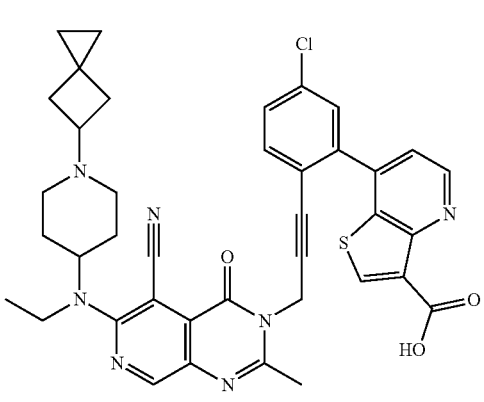 [SMILES: CCN(c1ncc2nc(C)n(CC#Cc3ccc(Cl)cc3-c3ccnc4c(C(=O)O)csc34)c(=O)c2c1C#N)C1CCN(C2CC3(CC3)C2)CC1] | MS (ESI) m/z 718.34 [M + 1]+ |

TABLE 1-continued
7-Aza-Thienylpyridine and Derivative Compounds
| Compound | | Characterization |
|---|---|---|
| 1867 | 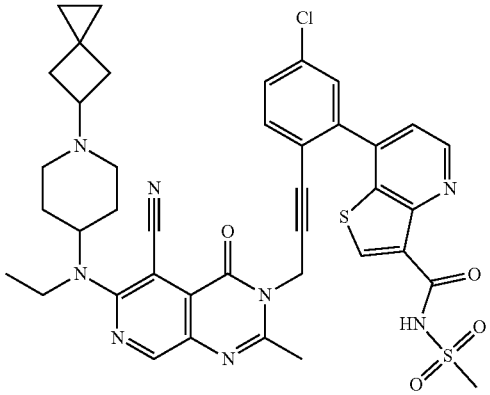 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN(C2CC3(CC3)C2)CC1] | MS (ESI) m/z 795.35 [M + 1]+ |
| 1868 | 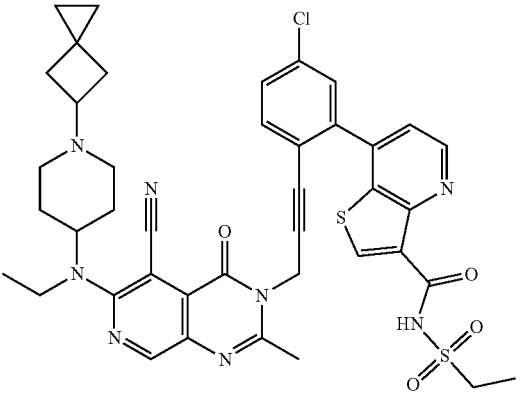 [SMILES: CCN(c1ncc2nc(C)n(CC#Cc3ccc(Cl)cc3-c3ccnc4c(C(=O)NS(=O)(=O)CC)csc34)c(=O)c2c1C#N)C1CCN(C2CC3(CC3)C2)CC1] | MS (ESI) m/z 809.44 [M + 1]+ |
| 1869 | 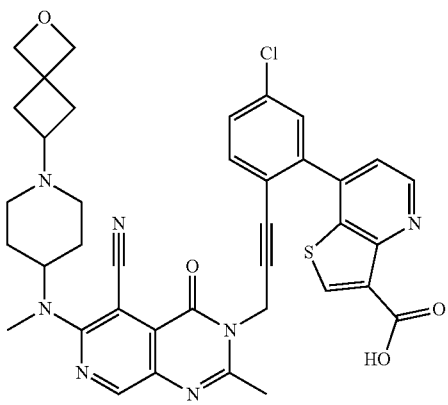 [SMILES: Cc1nc2cnc(N(C)C3CCN(C4CC5(COC5)C4)CC3)c(C#N)c2c(=O)n1CC#Cc1ccc(Cl)cc1-c1ccnc2c(C(=O)O)csc12] | MS (ESI) m/z 720.3 [M + 1]+ |

TABLE 1-continued
7-Aza-Thienylpyridine and Derivative Compounds
| Compound | | Characterization |
|---|---|---|
| 1870 | 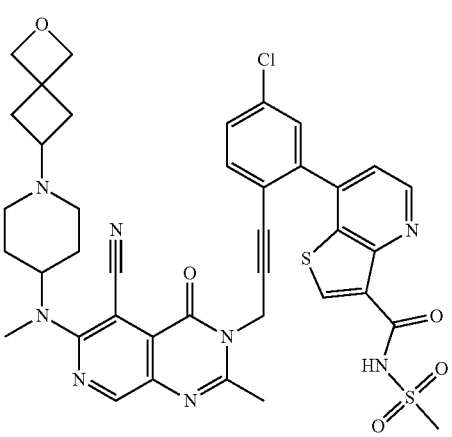 [SMILES: Cc1nc2cnc(N(C)C3CCN(C4CC5(COC5)C4)CC3)c(C#N)c2c(=O)n1CC#Cc1ccc(Cl)cc1-c1ccnc2c(C(=O)NS(C)(=O)=O)csc12] | MS (ESI) m/z 797.35 [M + 1]+ |
| 1871 | 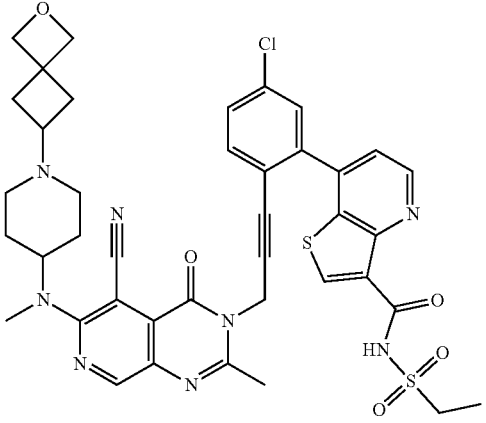 [SMILES: CCS(=O)(=O)NC(=O)c1csc2c(-c3cc(Cl)ccc3C#CCn3c(C)nc4cnc(N(C)C5CCN(C6CC7(COC7)C6)CC5)c(C#N)c4c3=O)ccnc12] | MS (ESI) m/z 811.4 [M + 1]+ |
| 1872 | 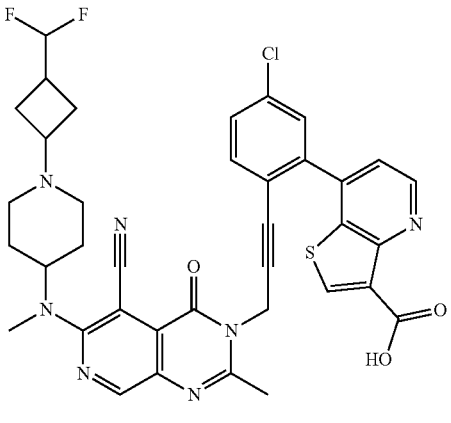 [SMILES: Cc1nc2cnc(N(C)C3CCN(C4CC(C(F)F)C4)CC3)c(C#N)c2c(=O)n1CC#Cc1ccc(Cl)cc1-c1ccnc2c(C(=O)O)csc12] | MS (ESI) m/z 728.26 [M + 1]+ |

TABLE 1-continued
7-Aza-Thienylpyridine and Derivative Compounds
| Compound | | Characterization |
|---|---|---|
| 1873 | 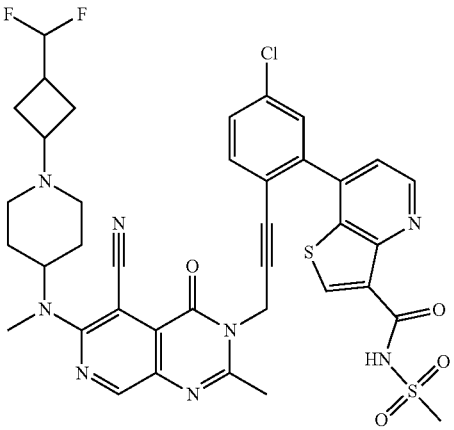 [SMILES: Cc1nc2cnc(N(C)C3CCN(C4CC(C(F)F)C4)CC3)c(C#N)c2c(=O)n1CC#Cc1ccc(Cl)cc1-c1ccnc2c(C(=O)NS(C)(=O)=O)csc12] | MS (ESI) m/z 805.26 [M + 1]+ |
| 1874 | 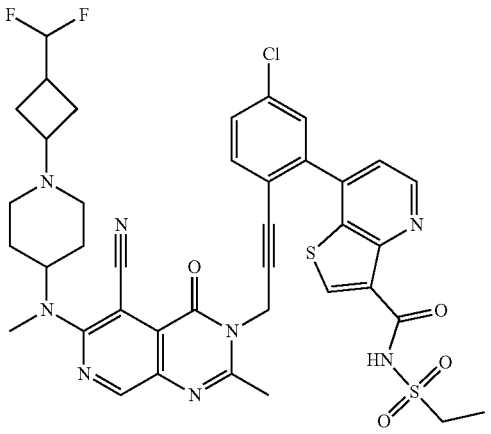 [SMILES: CCS(=O)(=O)NC(=O)c1csc2c(-c3cc(Cl)ccc3C#CCn3c(C)nc4cnc(N(C)C5CCN(C6CC(C(F)F)C6)CC5)c(C#N)c4c3=O)ccnc12] | MS (ESI) m/z 819.46 [M + 1]+ |
| 1875 | 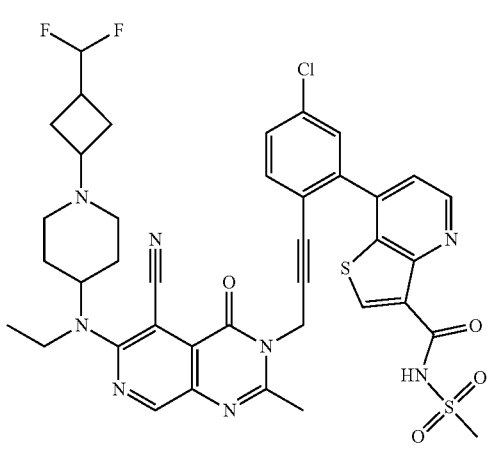 [SMILES: CCN(c1ncc2nc(C)n(CC#Cc3ccc(Cl)cc3-c3ccnc4c(C(=O)NS(C)(=O)=O)csc34)c(=O)c2c1C#N)C1CCN(C2CC(C(F)F)C2)CC1] | MS (ESI) m/z 819.33 [M + 1]+ |

TABLE 1-continued
7-Aza-Thienylpyridine and Derivative Compounds
| Compound | | Characterization |
|---|---|---|
| 1876 | 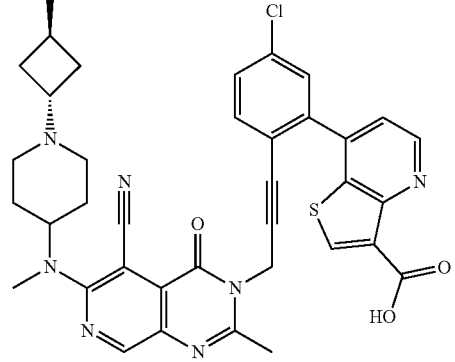 | MS (ESI) m/z 746.28 [M + 1]+ |
| 1877 | 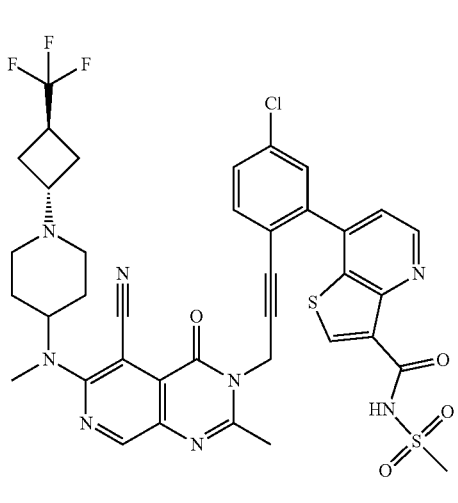 [SMILES: Cc1nc2cnc(N(C)C3CCN([C@H]4C[C@H](C(F)(F)F)C4)CC3)c(C#N)c2c(=O)n1CC#Cc1ccc(Cl)cc1-c1ccnc2c(C(=O)NS(C)(=O)=O)csc12] | MS (ESI) m/z 823.3 [M + 1]+ |
| 1878 | 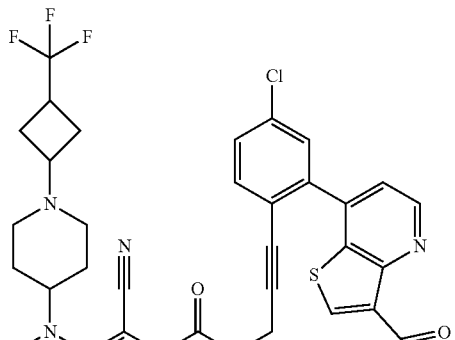 | MS (ESI) m/z 746.34 [M + 1]+ |

TABLE 1-continued
7-Aza-Thienylpyridine and Derivative Compounds
| Compound | | Characterization |
|---|---|---|
| 1879 |  | MS (ESI) m/z 823.33 [M + 1]+ |
| 1880 |  | MS (ESI) m/z 756.29 [M + 1]+ |
| 1881 |  | MS (ESI) m/z 833.32 [M + 1]+ |

TABLE 1-continued
7-Aza-Thienylpyridine and Derivative Compounds
| Compound | | Characterization |
|---|---|---|
| 1882 | 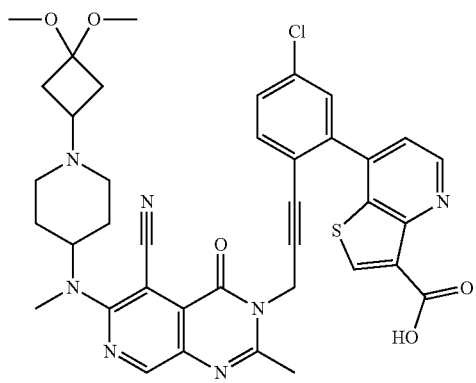 [SMILES: COC1(OC)CC(N2CCC(N(C)c3ncc4nc(C)n(CC#Cc5ccc(Cl)cc5-c5ccnc6c(C(=O)O)csc56)c(=O)c4c3C#N)CC2)C1] | MS (ESI) m/z 738.34 [M + 1]+ |
| 1883 | 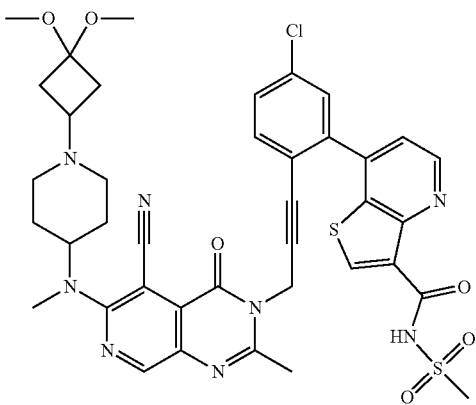 [SMILES: COC1(OC)CC(N2CCC(N(C)c3ncc4nc(C)n(CC#Cc5ccc(Cl)cc5-c5ccnc6c(C(=O)NS(C)(=O)=O)csc56)c(=O)c4c3C#N)CC2)C1] | MS (ESI) m/z 815.4 [M + 1]+ |
| 1884 | 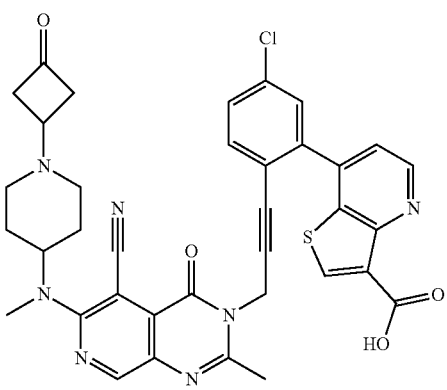 [SMILES: Cc1nc2cnc(N(C)C3CCN(C4CC(=O)C4)CC3)c(C#N)c2c(=O)n1CC#Cc1ccc(Cl)cc1-c1ccnc2c(C(=O)O)csc12] | MS (ESI) m/z 692.31 [M + 1]+ |

TABLE 1-continued
7-Aza-Thienylpyridine and Derivative Compounds
| Compound | | Characterization |
|---|---|---|
| 1885 | 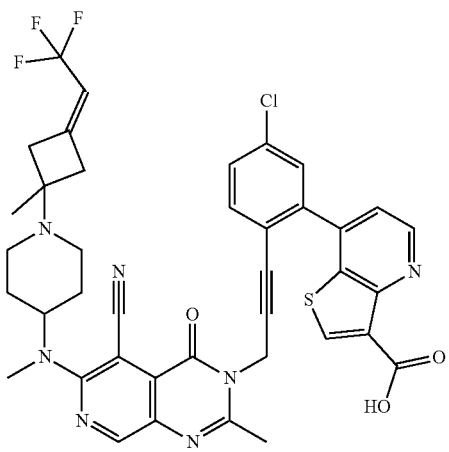 [SMILES: Cc1nc2cnc(N(C)C3CCN(C4(C)CC(=CC(F)(F)F)C4)CC3)c(C#N)c2c(=O)n1CC#Cc1ccc(Cl)cc1-c1ccnc2c(C(=O)O)csc12] | MS (ESI) m/z 772.35 [M + 1]+ |
| 1886 | 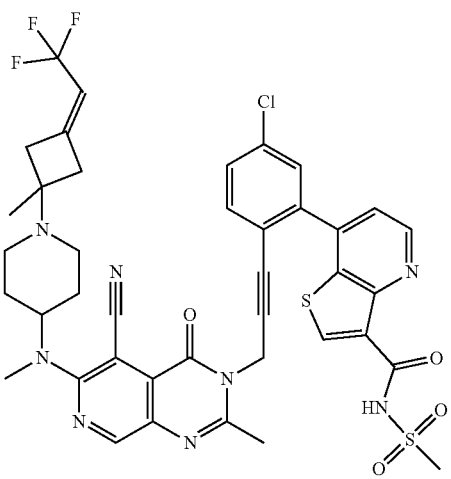 [SMILES: Cc1nc2cnc(N(C)C3CCN(C4(C)CC(=CC(F)(F)F)C4)CC3)c(C#N)c2c(=O)n1CC#Cc1ccc(Cl)cc1-c1ccnc2c(C(=O)NS(C)(=O)=O)csc12] | MS (ESI) m/z 849.4 [M + 1]+ |
| 1887 | 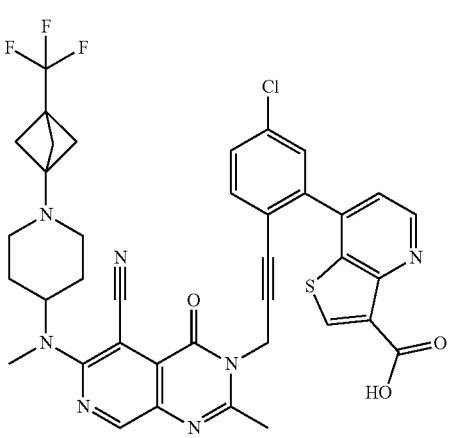 [SMILES: Cc1nc2cnc(N(C)C3CCN(C45CC(C(F)(F)F)(C4)C5)CC3)c(C#N)c2c(=O)n1CC#Cc1ccc(Cl)cc1-c1ccnc2c(C(=O)O)csc12] | MS (ESI) m/z 758.28 [M + 1]+ |

TABLE 1-continued

7-Aza-Thienylpyridine and Derivative Compounds

| Compound | | Characterization |
|---|---|---|
| 1888 | | MS (ESI) m/z 835.26 [M + 1]+ |
| 1889 | | MS (ESI) m/z 754.34 [M + 1]+ |
| 1890 | | MS (ESI) m/z 831.29 [M + 1]+ |

TABLE 1-continued
7-Aza-Thienylpyridine and Derivative Compounds
| Compound | | Characterization |
|---|---|---|
| 1891 | 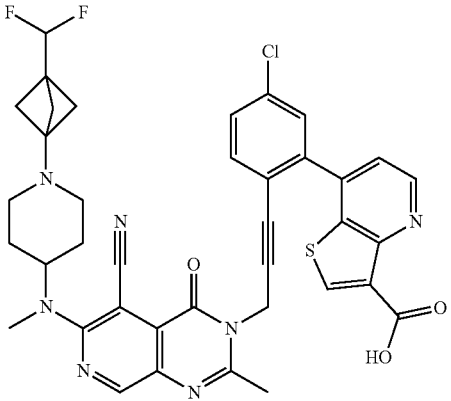 | MS (ESI) m/z 740.33 [M + 1]+ |
| 1892 | 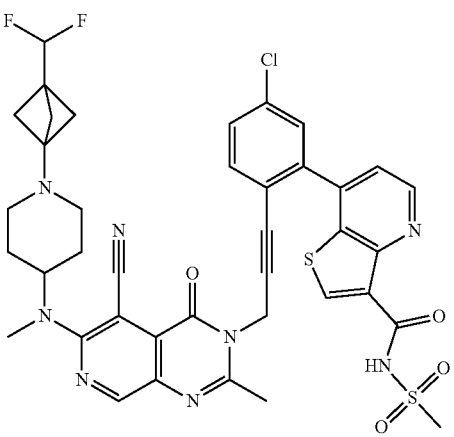 [SMILES: Cc1nc2cnc(N(C)C3CCN(C45CC(C(F)F)(C4)C5)CC3)c(C#N)c2c(=O)n1CC#Cc1ccc(Cl)cc1-c1ccnc2c(C(=O)NS(C)(=O)=O)csc12] | MS (ESI) m/z 817.32 [M + 1]+ |
| 1893 | 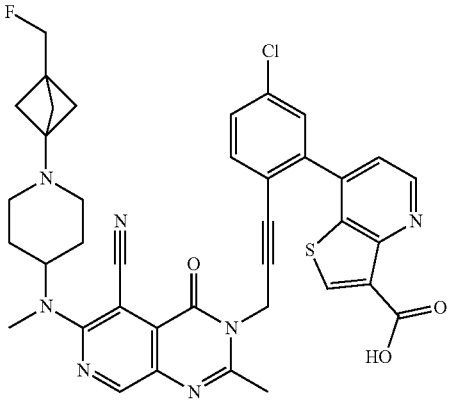 [SMILES: Cc1nc2cnc(N(C)C3CCN(C45CC(CF)(C4)C5)CC3)c(C#N)c2c(=O)n1CC#Cc1ccc(Cl)cc1-c1ccnc2c(C(=O)O)csc12] | MS (ESI) m/z 722.34 [M + 1]+ |

TABLE 1-continued
7-Aza-Thienylpyridine and Derivative Compounds
| Compound | | Characterization |
|---|---|---|
| 1894 | 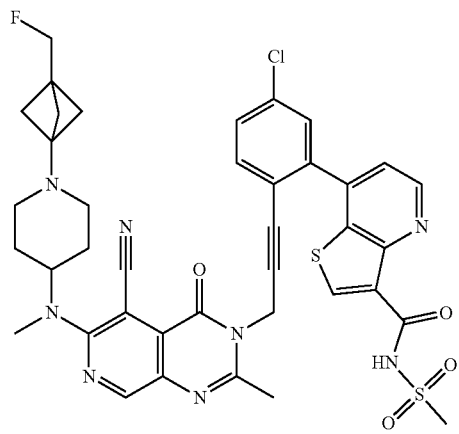 [SMILES: Cc1nc2cnc(N(C)C3CCN(C45CC(CF)(C4)C5)CC3)c(C#N)c2c(=O)n1CC#Cc1ccc(Cl)cc1-c1ccnc2c(C(=O)NS(C)(=O)=O)csc12] | MS (ESI) m/z 799.27 [M + 1]+ |
| 1895 | 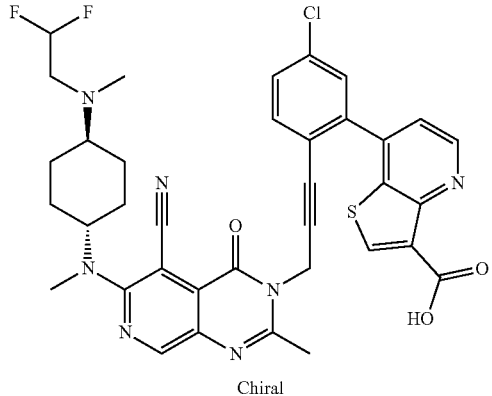 [SMILES: Cc1nc2cnc(N(C)[C@H]3CC[C@H](N(C)CC(F)F)CC3)c(C#N)c2c(=O)n1CC#Cc1ccc(Cl)cc1-c1ccnc2c(C(=O)O)csc12] Chiral | MS (ESI) m/z 716.5 [M + 1]+ |
| 1896 | 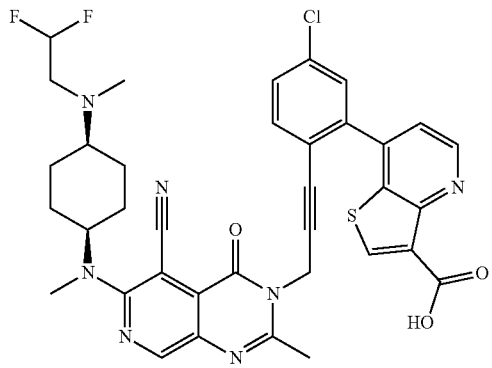 Chiral | MS (ESI) m/z 716.33 [M + 1]+ |

TABLE 1-continued

7-Aza-Thienylpyridine and Derivative Compounds

| Compound | Characterization |
|---|---|
| 1897 | MS (ESI) m/z 702.46 [M + 1]+ |
| 1898 | LCMS 1.90 (ESI) m/z 669.3 [M + 1]+; 1H NMR (400 MHz, DMSO-d6) δ 8.97 (s, 1H), 8.83 (d, J = 4.8 Hz, 1H), 8.40 (s, 1H), 7.59 (dd, J = 8.9, 2.7 Hz, 1H), 7.50- 7.41 (m, 2H), 7.36 (s, 1H), 7.23- 7.09 (m, 2H), 4.40 (t, J = 5.0 Hz, 2H), 4.24 (t, J = 4.9 Hz, 2H), 3.55 (d, J = 4.8 Hz, 2H), 3.38-3.24 (m, 3H), 2.71-2.62 (m, 2H), 2.46 (s, 3H), 2.33 (p, J = 1.9 Hz, 1H), 1.75 (s, 3H) |
| 1982 | MS (ESI) m/z 461.0 [M + 1]+ |
| 1983 | MS (ESI) m/z 497.0 [M + 1]+ |

TABLE 1-continued

7-Aza-Thienylpyridine and Derivative Compounds

| Compound | Characterization |
|---|---|
| 1984 | MS (ESI) m/z 655.19 [M + 1]+ |
| 1985 | MS (ESI) m/z 734.34 [M + 1]+ |
| 2020 | MS (ESI) m/z 627.43 [M + 1]+ |
| 2021 | MS (ESI) m/z 806.23 [M + 1]+ |

TABLE 1-continued

7-Aza-Thienylpyridine and Derivative Compounds

| Compound | Characterization |
|---|---|
| 2022 | MS (ESI) m/z 731.29 [M + 1]+ |
| 2029 | MS (ESI) m/z 746.25 [M + 1]+ |
| 2023 | MS (ESI) m/z 790.3 [M + 1]+ |
| 2024 | MS (ESI) m/z 713.31 [M + 1]+ |

TABLE 1-continued
7-Aza-Thienylpyridine and Derivative Compounds
| Compound | | Characterization |
|---|---|---|
| 2025 | 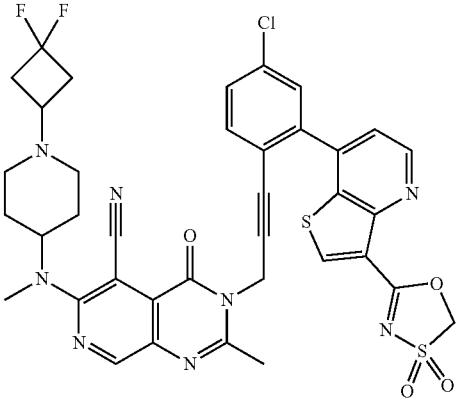 [SMILES: Cc1nc2cnc(N(C)C3CCN(C4CC(F)(F)C4)CC3)c(C#N)c2c(=O)n1CC#Cc1ccc(Cl)cc1-c1ccnc2c(C3=NS(=O)(=O)CO3)csc12] | MS (ESI) m/z 789.36 [M + 1]+ |
| 2032 | 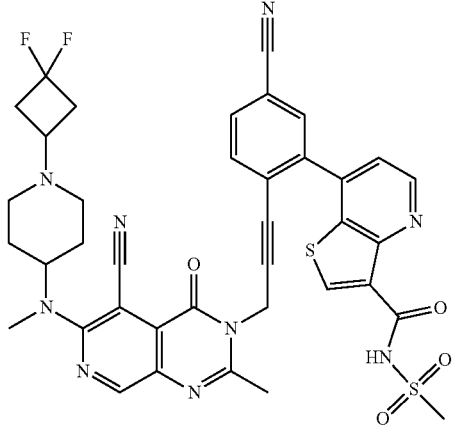 [SMILES: Cc1nc2cnc(N(C)C3CCN(C4CC(F)(F)C4)CC3)c(C#N)c2c(=O)n1CC#Cc1ccc(C#N)cc1-c1ccnc2c(C(=O)NS(C)(=O)=O)csc12] | |
| 2030 | 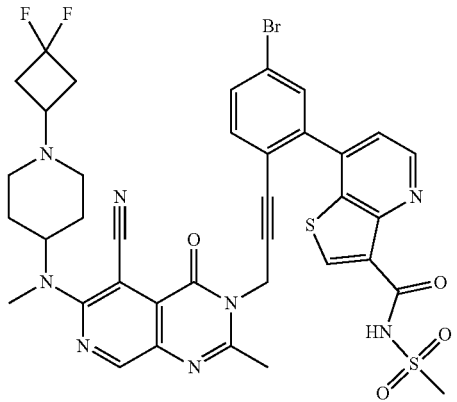 [SMILES: Cc1nc2cnc(N(C)C3CCN(C4CC(F)(F)C4)CC3)c(C#N)c2c(=O)n1CC#Cc1ccc(Br)cc1-c1ccnc2c(C(=O)NS(C)(=O)=O)csc12] | MS (ESI) m/z 837.28 [M + 1]+ |

TABLE 1-continued

7-Aza-Thienylpyridine and Derivative Compounds

| Compound | Characterization |
|---|---|
| 2031 | MS (ESI) m/z 705.34 [M + 1]+ |
| 2041 | MS (ESI) m/z 807.38 [M + 1]+ |
| 2038 | MS (ESI) m/z 718.1 [M + 1]+ |
| 2039 | MS (ESI) m/z 734.37 [M + 1]+ |

TABLE 1-continued

7-Aza-Thienylpyridine and Derivative Compounds

| Compound | | Characterization |
|---|---|---|
| 2042 | 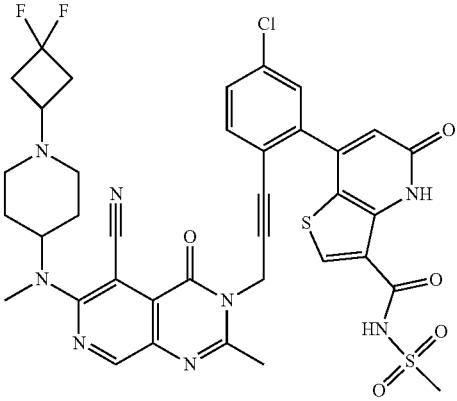 [SMILES: Cc1nc2cnc(N(C)C3CCN(C4CC(F)(F)C4)CC3)c(C#N)c2c(=O)n1CC#Cc1ccc(Cl)cc1-c1cc(=O)[nH]c2c(C(=O)NS(C)(=O)=O)csc12] | MS (ESI) m/z 807.38 [M + 1]+ |

Example 2. General Methods for Synthesizing 7-CF$_3$-Thienylpyridine and Derivative Compounds The 7-CF3-thienylpyridine and derivative compounds in Table 2 can be synthesized using methods described in Example 2. Many of the reactions described in Example 1 were used to synthesize compounds in Table 2. For some compounds, some of the reactions described in Example 3, below, can be used to prepare the compounds.

Example 2A. Methods of Synthesizing the Left-Hand Side

Example 2A.1

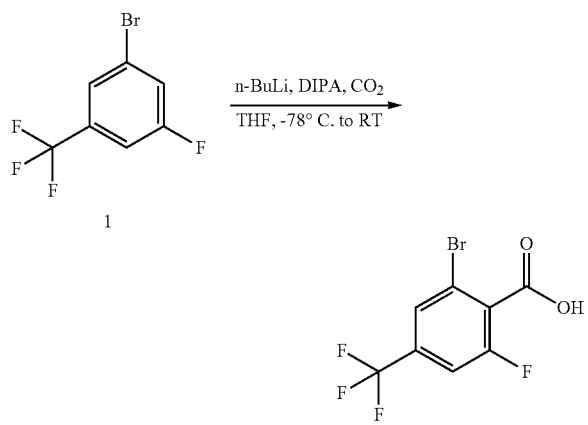

To a solution of diisopropyl amine (17.8 mL, 0.123 mol) in dry tetrahydrofuran (200 mL) is added n-butyllithium (1.6 M, 66.5 mL, 0.113 mol) drop wise at −78° C. under argon atmosphere. The reaction mixture is warmed to −10° C. and stirred for 30 min. A solution of 1-bromo-3-fluoro-5-(trifluoromethyl)benzene (1, 25.0 g, 0.102 mol) in dry tetrahydrofuran (50 mL) is added at −78° C. and mixture stirred for 45 min at −78° C. To this reaction mixture carbon dioxide gas is purged for 15 min and the temperature is gradually increased to room temperature in 2 h. After completion, the reaction mixture is cooled to −78° C. and quenched with ice water. The mixture is basified with 1 N aqueous sodium hydroxide solution and washed with diethyl ether. The aqueous layer is acidified with 2 N hydrochloric acid to pH~1 and extracted with ethyl acetate. The organic layer is separated, dried over anhydrous sodium sulphate, filtered and concentrated to afford 2-bromo-6-fluoro-4-(trifluoromethyl)benzoic acid (2).

Example 2A.2

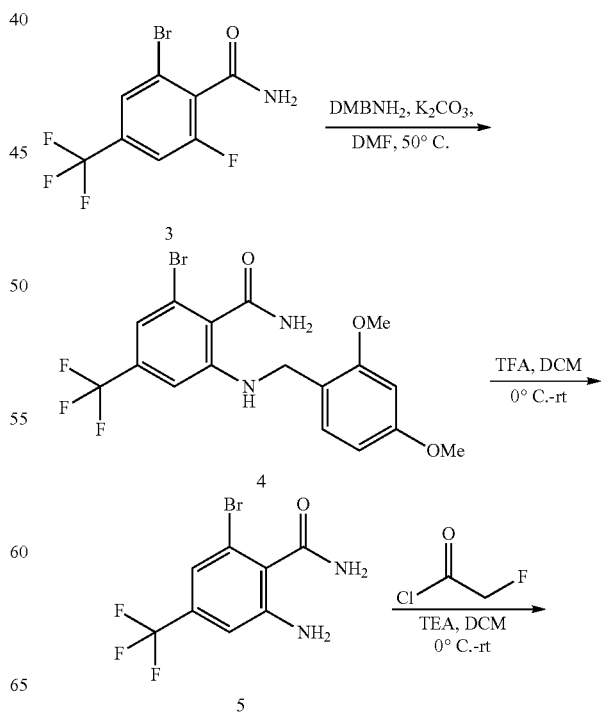

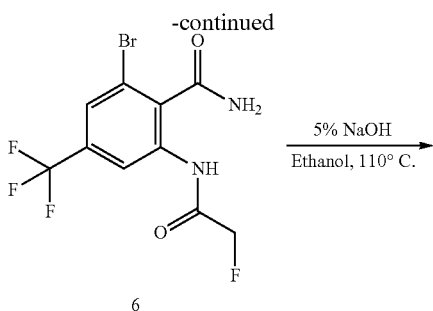

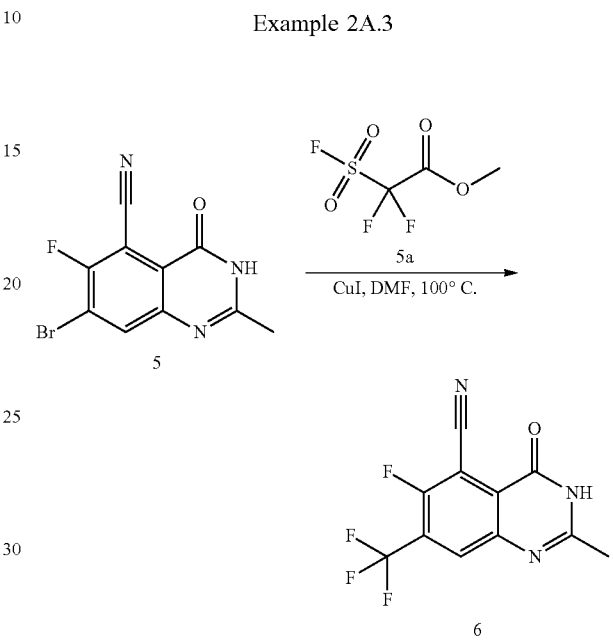

To a solution 2-bromo-6-fluoro-4-(trifluoromethyl)benzamide (3, 4.5 g, crude, 15.7 mmol) in N,N-dimethylformamide (40 mL), potassium carbonate (6.5 g, 47.2 mmol) and (2,4-dimethoxyphenyl)methanamine (3.1 mL, 20.45 mmol) are added at room temperature. The reaction mixture is heated to 50° C. and stirred for 16 h. After completion of reaction, the reaction mixture is poured into ice water and extracted with ethyl acetate The organic layer is washed with brine solution, dried over anhydrous sodium sulphate, filtered, concentrated under reduced pressure to get crude. The crude is purified by column chromatography using 5% methanol in dichloromethane as eluent. The desired fractions are concentrated under reduced pressure to afford 2-bromo-6-((2,4-dimethoxybenzyl)amino)-4-(trifluoromethyl)benzamide (4).

To a solution of 2-bromo-6-((2,4-dimethoxybenzyl)amino)-4-(trifluoromethyl)benzamide (4, 1.0 g, 2.30 mmol) in dichloromethane (10 mL) is added trifluoroacetic acid (1.8 mL, 23.0 mmol), and the mixture is stirred for 30 min. After completion of reaction, the reaction mixture is concentrated, and the resulting crude is diluted with dichloromethane and washed with saturated sodium bicarbonate solution, brine solution, dried over anhydrous sodium sulphate and concentrated under reduced pressure to get crude. The crude is purified by column chromatography using 5% methanol in dichloromethane as eluent. The desired fractions are concentrated under reduced to afford 2-amino-6-bromo-4-(trifluoromethyl)benzamide (5).

To a solution of 2-amino-6-bromo-4-(trifluoromethyl)benzamide (5, 2.0 g, 7.06 mmol) in dichloromethane (20 mL) are added triethylamine (2.93 mL, 21 mmol) and 2-fluoroacetyl chloride (1.0 mL, 14.1 mmol) at 0° C., and the reaction mixture is stirred for 30 min at same temperature. After completion of reaction, the reaction mixture is diluted with ice water and extracted with dichloromethane. The organic layer is washed with saturated brine solution, dried over anhydrous sodium sulphate and concentrated under reduced pressure to afford 2-bromo-6-(2-fluoroacetamido)-4-(trifluoromethyl)benzamide (6).

To a solution of 2-bromo-6-(2-fluoroacetamido)-4-(trifluoromethyl)benzamide (6, 0.600 g, 1.749 mmol) in ethanol (5 mL) is added 5% sodium hydroxide (4.0 mL). The mixture is heated to 110° C. and stirred for 30 min. After completion of reaction, the reaction mixture is neutralized with 1 N hydrochloric acid and extracted with ethyl acetate. The organic layer is washed with saturated brine solution, dried over anhydrous sodium sulphate and concentrated under reduced pressure to get crude product. The crude product is purified by column chromatography using silica gel (100-200 mesh) and 0-5% methanol in dichloromethane as eluent. The desired fractions are concentrated under reduced pressure to afford 5-bromo-2-(fluoromethyl)-7-(trifluoromethyl)quinazolin-4(3H)-one (7).

Example 2A.3

To a solution of 7-bromo-6-fluoro-2-methyl-4-oxo-3,4-dihydroquinazoline-5-carbonitrile (5, 0.200 g, 0.7 mmol) in N,N-dimethylformamide (2 mL), copper(I) iodide (0.159 g, 0.84 mmol) and methyl 2,2-difluoro-2-(fluorosulfonyl)acetate (5a, 0.403 g, 2.1 mmol) are added and reaction mixture is heated at 100° C. for 16 h. After completion, reaction mixture is cooled; water is added to reaction mixture and extracted with ethyl acetate. The organic layer is dried over anhydrous sodium sulphate, filtered and concentrated to afford 6-fluoro-2-methyl-4-oxo-7-(trifluoromethyl)-3,4-dihydroquinazoline-5-carbonitrile (6).

Example 2A.4

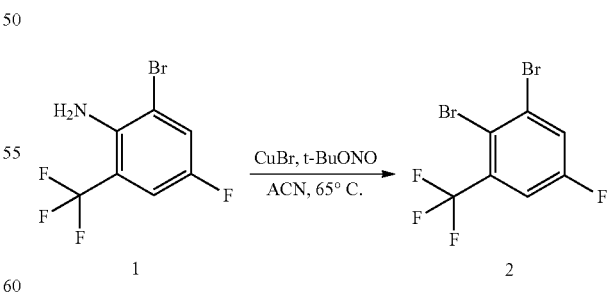

A suspension of copper(I) bromide (89.8 g, 620.1 mmol) and tert-butyl nitrite (63.8 mL, 620.1 mmol) in acetonitrile (2500 mL) is heated at 65° C. for 15 min. A solution of 2-bromo-4-fluoro-6-(trifluoromethyl)aniline (1, 100 g, 387.6 momol) in acetonitrile is added and heated the reaction mixture at 65° C. for 1 h. After completion, the reaction mass is quenched with water and extracted with ethyl acetate. The organic layer is dried over anhydrous sodium sulphate, filtered and concentrated under reduced pressure to get the crude material. The crude compound is purified by column chromatography using 0-5% ethyl acetate in hexanes over silica gel (100-200 mesh) to afford 1,2-dibromo-5-fluoro-3-(trifluoromethyl)benzene (2).

Example 2A.5

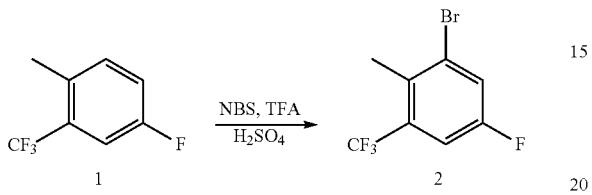

To a stirred solution of 4-fluoro-1-methyl-2-(trifluoromethyl)benzene (1, 1.05 g, 5.89 mmol) in TFA (4 mL) is added sulfuric acid (1.25 mL) and then N-bromosuccinimide (1.05 g, 5.89 mmol). The resulting mixture is capped, covered in aluminum foil to keep light out, and stirred at room temperature overnight. The reaction mixture is poured into vigorously stirred ice water and then extracted with hexanes. The organics are washed with brine, then saturated aqueous sodium bicarbonate. The organics are dried over magnesium sulfate, filtered, concentrated on a rotary evaporator, and purified via silica gel chromatography (100% hexanes) to afford 1-bromo-5-fluoro-2-methyl-3-(trifluoromethyl)benzene (2).

Example 2A.6

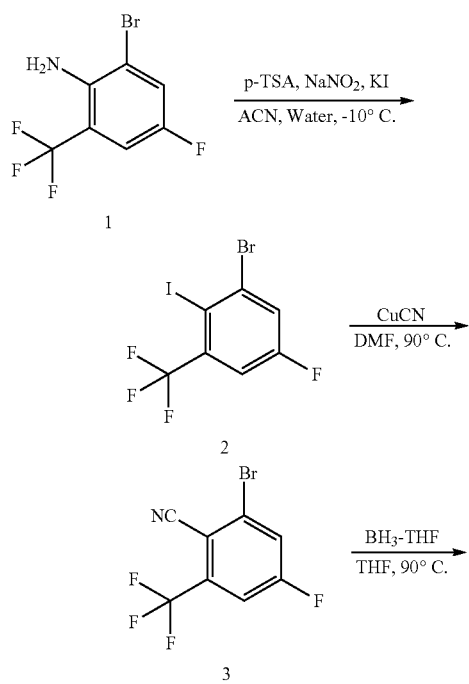

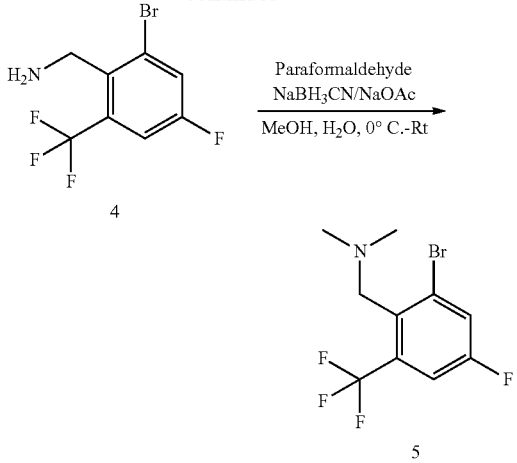

To a solution of 2-bromo-4-fluoro-6-(trifluoromethyl)aniline (1, 100.0 g, 389.2 mmol) in acetonitrile (2500 mL) is added p-toluenesulfonic acid (220.9 g, 1160.1 mmol) portion wise at −10° C. A solution of sodium nitrite (51.68 g, 750 mmol) and potassium iodide (157.7 g, 949.2 mmol) in water (100 mL) is added at −10° C. and the mixture is stirred for 45 min at −10° C. After completion, the reaction mixture is quenched with water & extracted with ethyl acetate (5000 mL). The organic layer is washed with aqueous saturated sodium thiosulphate (500 mL). Organic layer is separated, dried over anhydrous sodium sulphate, filtered and concentrated to afford 1-bromo-5-fluoro-2-iodo-3-(trifluoromethyl) benzene (2).

To a solution of 1-bromo-5-fluoro-2-iodo-3-(trifluoromethyl) benzene (2, 80.0 g, 217.3 mmol) in N,N-dimethylformamide (500 mL), copper(I) cyanide (19.4 g, 217.2 mmol) is added at room temperature. The reaction mixture is stirred at 90° C. for 12 h. After completion, it is cooled to room temperature, poured into ice water and extracted with ethyl acetate (2.0 L). The organic layer is washed with brine solution, dried over anhydrous sodium sulphate and concentrated under reduced pressure to get crude. The crude compound is purified by flash column chromatography using 0-5% ethyl acetate in hexanes to afford 2-bromo-4-fluoro-6-(trifluoromethyl)benzonitrile (3).

To a solution 2-bromo-4-fluoro-6-(trifluoromethyl)benzonitrile (3, 12.0 g, 44.9 mmol) in tetrahydrofuran (200 mL), borane in tetrahydrofuran (1 M, 67 mL, 67.1 mmol) is added drop wise at 0° C. The reaction mixture is allowed to stir at 90° C. for 12 h. After completion, the reaction mixture is poured into chilled methanol and concentrated under reduced pressure. The crude compound is purified by flash column chromatography using 0-15% ethyl acetate in hexanes to afford (2-bromo-4-fluoro-6-(trifluoromethyl) phenyl)methanamine (4).

To a solution of (2-bromo-4-fluoro-6-(trifluoromethyl) phenyl)methanamine (4, 6.0 g, 22.6 mmol) in methanol (100 mL), paraformaldehyde (6.0 g, 200.0 mmol) and solution of sodium acetate (5.4 g, 66.0 mmol) in water (10 mL) are added and stirred at room temperature for 1 h. Sodium cyanoborohydride (4.03 g, 66.1 mmol) is added portion wise at 0° C. The reaction mixture is allowed to stir at room temperature for 12 h. After completion, the reaction mixture is concentrated under reduced pressure. Crude residue is diluted with water and extracted with diethyl ether (100 mL). The crude compound is purified by flash column chromatography using 0-15% ethyl acetate in hexanes to afford 1-(2-bromo-4-fluoro-6-(trifluoromethyl)phenyl)-N,N-dimethylmethanamine (5).

Example 2A.7

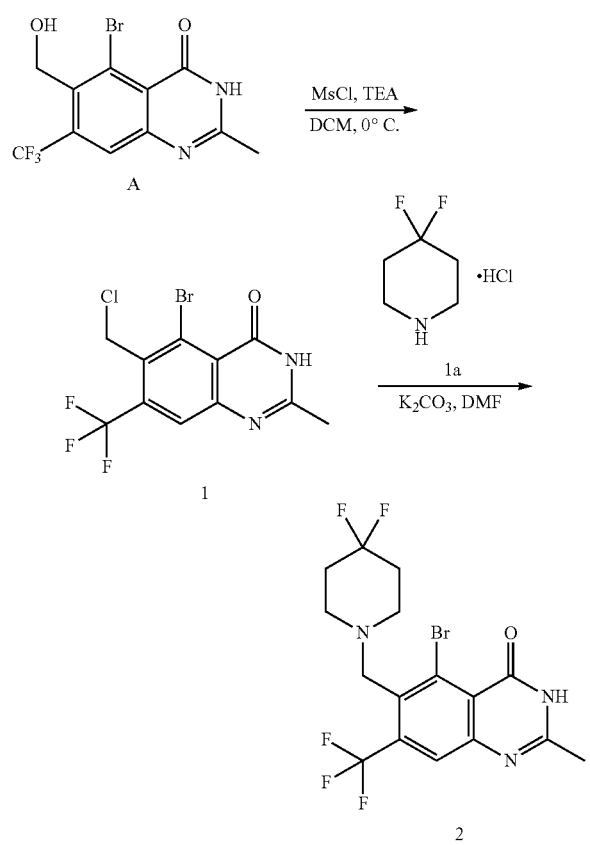

To a solution of 5-bromo-6-(hydroxymethyl)-2-methyl-7-(trifluoromethyl)quinazolin-4(3H)-one (A, 0.32 g, 0.94 mmol) in dichlomethane (6 mL) at 0° C., triethyl amine (0.39 mL, 2.84 mmol) and methanesulfonyl chloride (0.11 mL, 1.42 mmol) are added and stirred at 0° C. for 1 h. After completion, the reaction mixture is diluted with water and extracted with dichloromethane. The organic layer is washed with water, saturated brine, dried over anhydrous sodium sulfate and concentrated under reduced pressure to afford 5-bromo-6-(chloromethyl)-2-methyl-7-(trifluoromethyl) quinazolin-4(3H)-one (1).

To a solution of 4,4-difluoro piperidine (1a, 2.0 g, 12.7 mmol) in N,N-dimethylformamide (10.0 mL) is added potassium carbonate (1.06 g, 7.62 mmol) at room temperature and the mixture is stirred for 20 min. Then 5-bromo-6-(chloromethyl)-2-methyl-7-(trifluoromethyl)quinazolin-4(3H)-one (1, 0.9 g, 2.54 mmol) is added to the reaction mixture at room temperature and stirring is continued for 24 h. After completion, the reaction mixture is diluted with water and extracted with ethyl acetate. The organic layer is washed with water and saturated brine solution, dried over anhydrous sodium sulphate, filtered and concentrated. The crude product is purified by column chromatography using silica gel (100-200 mesh) and 50% ethyl acetate in hexane as eluent. The desired fractions are concentrated under reduced pressure to afford 5-bromo-6-((4,4-difluoropiperidin-1-yl)methyl)-2-methyl-7-(trifluoromethyl)quinazolin-4(3H)-one (2).

Example 2A.8

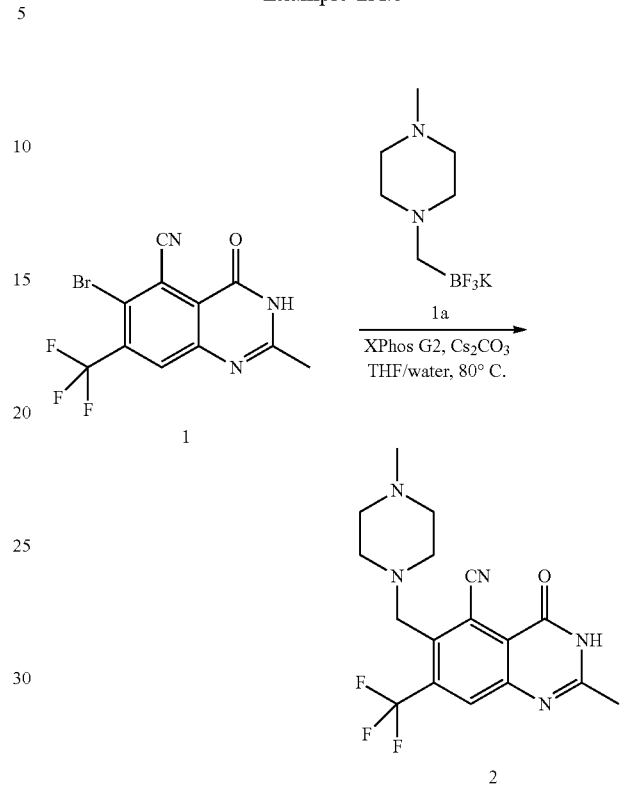

To a solution of 6-bromo-2-methyl-4-oxo-7-(trifluoromethyl)-3,4-dihydroquinazoline-5-carbonitrile (1, 50 mg, 0.151 mmol) in tetrahydrofuran (3 mL) and water (0.75 mL) are added 1-methyl-4-((trifluoro-$\lambda^4$-boranyl)methyl)piperazine, potassium salt (1a, 497 mg, 2.25 mmol), cesium carbonate (196 mg, 0.602 mmol) and XPhos Chloro(2-dicyclohexylphosphino-2',4',6'-triisopropyl-1,1'-biphenyl)[2-(2'-amino-1,1'-biphenyl)]palladium(II) (24 mg, 0.0301 mmol) and the mixture is sparged with argon for 5 min, then it is sealed and heated to 80° C. for 15 h. After completion, the mixture is concentrated under reduced pressure to get crude product. The crude product obtained is purified by prep-HPLC to afford 2-methyl-6-((4-methylpiperazin-1-yl)methyl)-4-oxo-7-(trifluoromethyl)-3,4-dihydroquinazoline-5-carbonitrile (2).

Example 2A.9

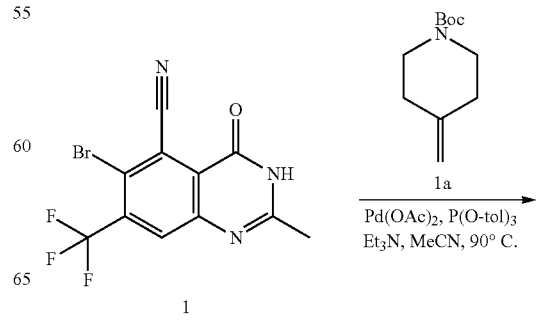

649
-continued

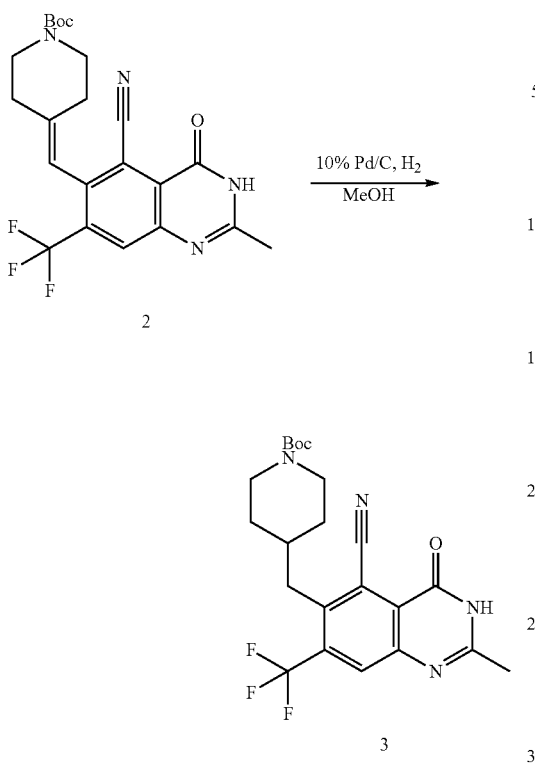

A solution of 6-bromo-2-methyl-4-oxo-7-(trifluoromethyl)-3,4-dihydroquinazoline-5-carbonitrile (1, 1.00 g, 3.02 mmol), tert-butyl 4-methylenepiperidine-1-carboxylate (1a, 5.90 g, 30.1 mmol), triethylamine (1.20 mL, 9.03 mmol), and tri (o-tolyl)phosphine (0.366 g, 1.23 mmol) in acetonitrile (10.0 mL) is degassed with argon for 10 min. Palladium (II) acetate (0.134 g, 0.60 mmol) is then added to the reaction mixture and degassing is continued for 5 min. The reaction mixture is heated at 90° C. for 24 h. After this time, the reaction mixture is cooled to room temperature, diluted with ethyl acetate, and concentrated to dryness under reduced pressure. The crude product is purified by silica gel (100-200 mesh) column chromatography using 30-50% ethyl acetate in hexanes as eluent. The desired fractions are concentrated under reduced pressure to afford tert-butyl 4-((5-cyano-2-methyl-4-oxo-7-(trifluoromethyl)-3,4-dihydroquinazolin-6-yl)methylene)piperidine-1-carboxylate (2).

To a solution of tert-butyl 4-((5-cyano-2-methyl-4-oxo-7-(trifluoromethyl)-3,4-dihydroquinazolin-6-yl)methylene)piperidine-1-carboxylate (2, 0.90 g, 2.0 mmol) in methanol (20 mL) is added 10% palladium on carbon (1.35 g) at room temperature. The reaction mixture is stirred at room temperature for 2 h under hydrogen atmosphere. Then, the reaction mixture is filtered with Celite. The filtrate is washed with ethyl acetate and concentrated to dryness under reduced pressure to obtain a crude product. The crude product is purified by silica gel (100-200 mesh) column chromatography using 3-5% methanol in dichloromethane as eluent. The desired fractions are concentrated under reduced pressure to afford tert-butyl 4-((5-cyano-2-methyl-4-oxo-7-(trifluoromethyl)-3,4-dihydroquinazolin-6-yl)methyl)piperidine-1-carboxylate (3).

650
Example 2A.10

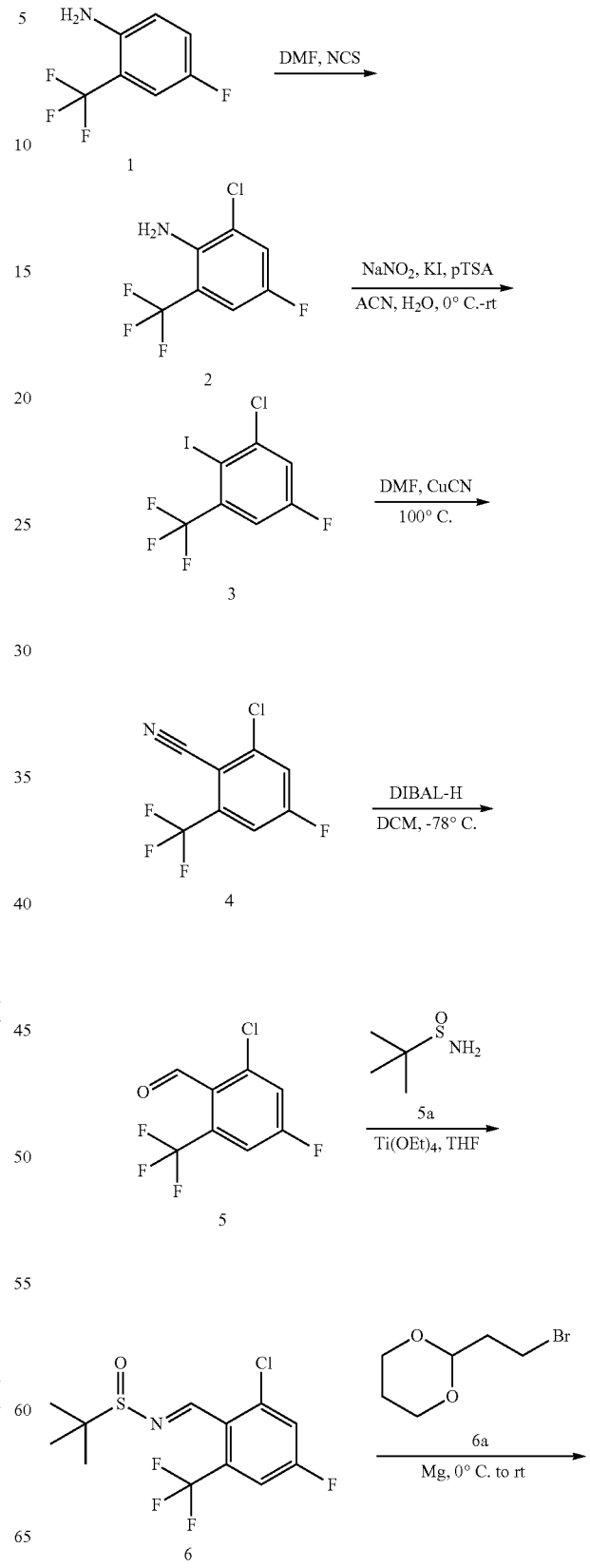

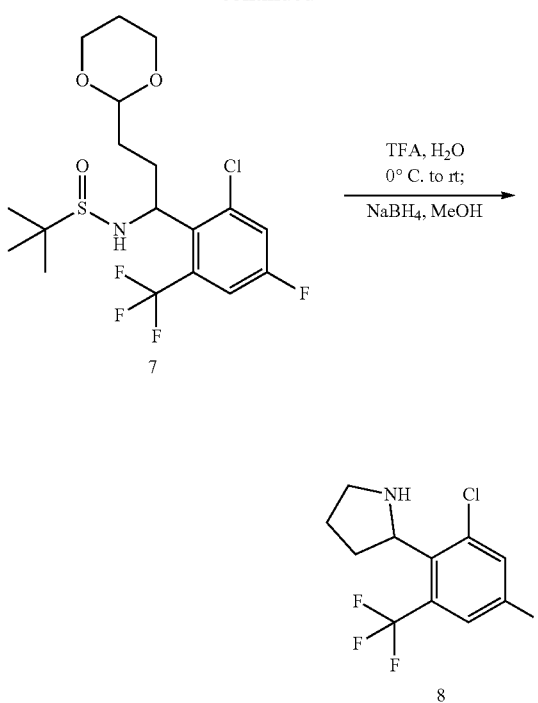

To a solution of 4-fluoro-2-(trifluoromethyl)aniline (1, 100.0 g, 558.66 mmol) in N,N-dimethylformamide (500 mL), N-chlorosuccinamide (78.7 g, 558.66 mmol) is added at room temperature. This reaction mixture is stirred for 16 h. After this time, the mixture is diluted with water and extracted with ethyl acetate. The organic layer is washed with water and then brine, dried over anhydrous sodium sulfate, filtered, and concentrated. The crude product is purified by silica gel (100-200 mesh) column chromatography using hexanes as eluent. The desired fractions are concentrated under reduced pressure to afford 2-chloro-4-fluoro-6-(trifluoromethyl)aniline (2).

To a solution of 2-chloro-4-fluoro-6-(trifluoromethyl)aniline (2, 43.0 g, 201.87 mmol) in acetonitrile (200 mL) at −10° C., p-toluenesulfonic acid monohydrate (115.0 g, 605.63 mmol) is added. This reaction mixture is stirred for 15 min at the same temperature. A solution of sodium nitrite (27.85 g, 403.74 mmol) and potassium iodide (83.77 g, 504.67 mmol) in water (50 mL) is added dropwise to the reaction mixture as it is stirred at −10° C. for 30 min. Next, the reaction mixture is diluted with water and extracted with ethyl acetate. The organic layer is washed with aqueous saturated sodium thiosulfate solution and then brine, dried over anhydrous sodium sulfate, filtered, and concentrated. The crude product is purified by silica gel (100-200 mesh) column chromatography using hexanes as eluent. The desired fractions are concentrated under reduced pressure to afford 1-chloro-5-fluoro-2-iodo-3-(trifluoromethyl)benzene (3).

To a solution of 1-chloro-5-fluoro-2-iodo-3-(trifluoromethyl)benzene (3, 30 g, 92.6 mmol) in N,N-dimethylformamide (200 mL), copper(I) cyanide (12.36 g, 138.88 mmol) is added. This reaction mixture is heated at 100° C. for 16 h. After this time, the mixture is diluted with water and extracted with ethyl acetate. The organic layer is washed with water and brine, dried over anhydrous sodium sulfate, filtered, and concentrated. The crude product is purified by silica gel (100-200 mesh) column chromatography using 3% ethyl acetate in hexanes as eluent. The desired fractions are concentrated under reduced pressure to afford 2-chloro-4-fluoro-6-(trifluoromethyl)benzonitrile (4).

To a solution of 2-chloro-4-fluoro-6-(trifluoromethyl)benzonitrile (4, 15.0 g, 67.26 mmol) in dry dichloromethane (150 mL) at −78° C., diisobutylaluminiumhydride (1.0 M in toluene, 134.52 mL, 134.52 mmol) is added dropwise. The mixture is stirred at same temperature for 30 min. Next, the reaction mixture is quenched with 1 N aqueous hydrochloric acid and extracted with dichloromethane. The organic layer is dried over anhydrous sodium sulfate, filtered, and concentrated to dryness under reduced pressure to afford 2-chloro-4-fluoro-6-(trifluoromethyl)benzaldehyde (5).

To a solution of 2-chloro-4-fluoro-6-(trifluoromethyl)benzaldehyde (5, 17.00 g, 75.22 mmol) in tetrahydrofuran (100 mL), 2-methylpropane-2-sulfinamide (5a, 13.65 g, 112.83 mmol) and titanium ethoxide (34.30 mL, 150.44 mmol) are added dropwise at room temperature. This reaction mixture is stirred at the same temperature for 16 h. After this time, the reaction mixture is quenched with aqueous ammonium chloride solution, filtered with Celite, and washed with ethyl acetate. The filterate is concentrated and the crude residue is purified by Combi-flash (40 g, Redi-Sep column) using 20% ethyl acetate in hexanes as eluent. The desired fractions are concentrated under reduced pressure to afford (E)-N-(2-chloro-4-fluoro-6-(trifluoromethyl)benzylidene)-2-methylpropane-2-sulfinamide (6).

Magnesium turnings (5.0 g) are added to dry tetrahydrofuran (50 mL) followed by iodine (0.002 g) and the mixture is heated to just above room temperature. Then, 2-(2-bromoethyl)-1,3-dioxane (6a, 9.8 mL, 72.94 mmol) is added and the mixture is heated till it became colorless. Then, this mixture is added dropwise to a solution of (E)-N-(2-chloro-4-fluoro-6-(trifluoromethyl)benzylidene)-2-methylpropane-2-sulfinamide (6, 12.00 g, 36.47 mmol) in tetrahydrofuran (50 mL) at room temperature. The resulting mixture is stirred at room temperature for 1 h. Next, the reaction mixture is quenched with aqueous ammonium chloride solution and extracted with ethyl acetate. The organic layer dried over anhydrous sodium sulfate and concentrated. The crude residue is purified by Combi-flash (40 g, Redi-Sep column) using 30% ethyl acetate in hexanes as eluent. The desired fractions are concentrated under reduced pressure to afford N-(1-(2-chloro-4-fluoro-6-(trifluoromethyl)phenyl)-3-(1,3-dioxan-2-yl)propyl)-2-methylpropane-2-sulfinamide (7).

A solution mixture of N-(1-(2-chloro-4-fluoro-6-(trifluoromethyl)phenyl)-3-(1,3-dioxan-2-yl)propyl)-2-methylpropane-2-sulfinamide (7, 12.00 g, 26.96 mmol) in trifluroacetic acid in water (3:1, 180 mL) is stirred at room temperature for 16 h. After this time, the reaction mixture is quenched with aqueous sodium bicarbonate solution and extracted with ethyl acetate. The organic layer is dried over anhydrous sodium sulfate, filtered, and concentrated. The solid residue is dissolved in methanol, after which sodium borohydrate (8.00 g, 269.66 mmol) is added at 0° C. and the mixture is stirred at room temperature for 8 h. After this time, the reaction mixture is quenched with ice-cold water and extracted with ethyl acetate. The organic layer is dried over anhydrous sodium sulfate, filtered, and concentrated to dryness under reduced pressure to afford 2-(2-chloro-4-fluoro-6-(trifluoromethyl)phenyl)pyrrolidine (8).

Example 2A.11

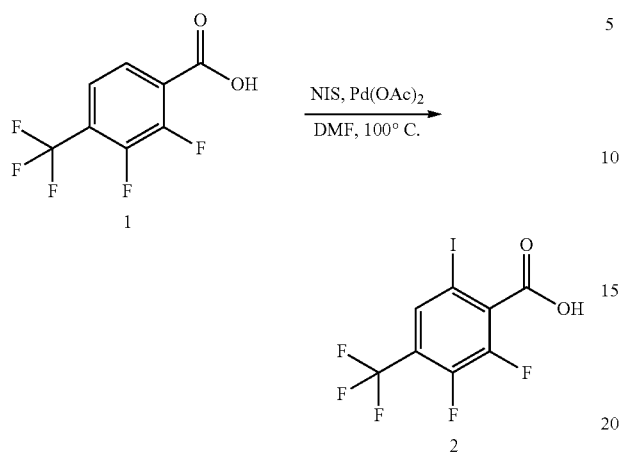

To a solution of 2,3-difluoro-4-(trifluoromethyl)benzoic acid (1, 5 g, 22.123 mmol) in N,N-dimethylformamide (50 mL), N-iodosuccinimide (7.43 g, 33.185 mmol) is added and purged with argon for 20 min. Then, palladium acetate (1.48 g, 6.637 mmol) is added and reaction mixture is heated at 100° C. for 48 h. After completion, the reaction mixture is cooled, diluted with water and extracted with ethyl acetate. The combined organic layer is washed with cold water and brine solution, dried over anhydrous sodium sulphate, filtered and concentrated under reduced pressure to afford 2,3-difluoro-6-iodo-4-(trifluoromethyl)benzoic acid (2).

Example 2B. Methods of Synthesizing the Right-Hand Side

Example 2B.1

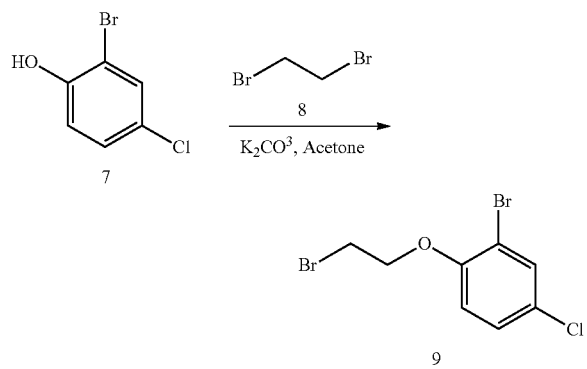

To a solution 2-bromo-4-chlorophenol (7, 50.0 g, 241.0 mmol) in aqueous sodium hydroxide (1 M) (1.0 L), tetra-n-butylammonium bromide (11.64 g, 36.15 mmol) and potassium iodide (6.00 g, 36.15 mmol) are added. 1,2-dibromoethane (8,165.6 g, 891.7 mmol) is added at 85° C. and stirred for 16 h at the same temperature. After completion, the reaction mixture is poured into water and extracted with ethyl acetate. Combined organic layer are washed with water, brine, dried over anhydrous sodium sulfate and concentrated under reduced pressure to get crude; the crude compound is purified by flash column chromatography (using 0-5% ethyl acetate in hexanes) to afford 2-bromo-1-(2-bromoethoxy)-4-chlorobenzene (9).

Example 2B.2

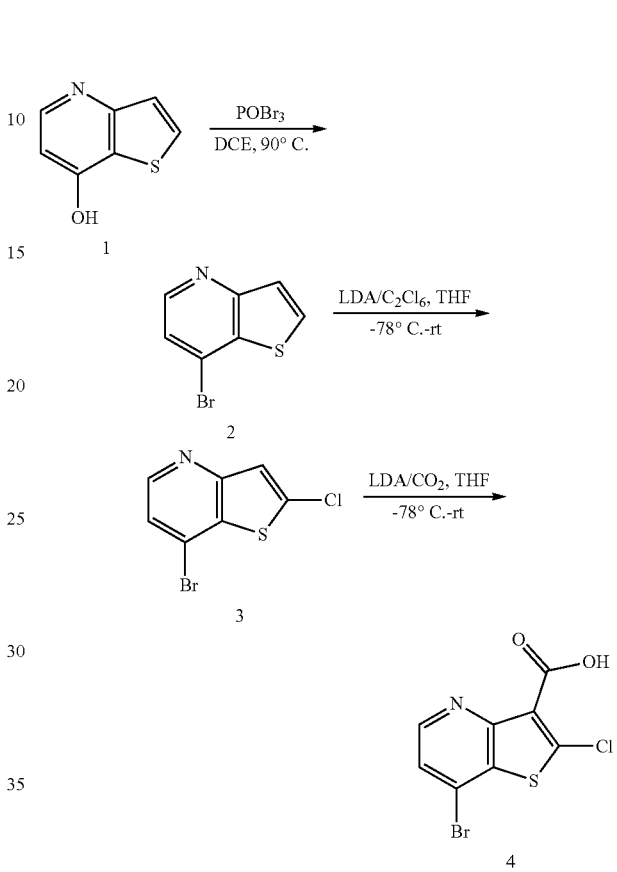

A stirred solution of thieno[3,2-b]pyridin-7-ol (1, 2.0 g, 13.2 mmol) in phosphorous oxybromide (7.5 g, 26.4 mmol) and 1,2-dichloroethane is heated at 90° C. for 12 h. After completion of the reaction, the mixture is cooled to room temperature and quenched with saturated aqueous solution of sodium bicarbonate and extracted with ethyl acetate. The organic layer is washed with brine, dried over anhydrous sodium sulphate, filtered and concentrated to afford 7-bromothieno[3,2-b]pyridine (2).

To a stirred solution of 7-bromothieno[3,2-b]pyridine (2, 1.5 g, 7.04 mmol) in dry tetrahydrofuran (20 mL), freshly prepared lithium diisopropylamide (2.0 M in hexane, 8.75 mL, 17.5 mmol) is added at −78° C. and the mixture is stirred at same temperature for 1 h. Hexachloroethane (2.0 mL, 8.44 mmol) is added drop wise and the reaction mixture is allowed to warm up to room temperature over 3 h. The reaction is quenched with aqueous ammonium chloride solution, diluted with water and extracted with ethyl acetate. The organic layer is washed with water and saturated brine solution, dried over anhydrous sodium sulphate, filtered and concentrated. The crude product is purified over a plug of silica gel eluting the compound with ethyl acetate in hexanes (0-10%). The desired fractions are concentrated under reduced pressure to afford 7-bromo-2-chlorothieno[3,2-b] pyridine (3).

To a solution of 7-bromo-2-chlorothieno[3,2-b]pyridine (3, 0.5 g, 2.02 mmol) in dry tetrahydrofuran (10 mL) and the mixture is cooled to −78° C. Lithium diisopropylamide (2 M, 1.5 mL, 3.03 mmol) is added drop wise and the reaction mixture is stirred at −78° C. for 1 h. Carbon dioxide gas is purged through the reaction mass for 20 min at same temperature and is stirred for 1 h at −78° C. The reaction mixture is slowly warmed to 0° C. and stirred for 30 min. After completion, reaction mixture is quenched with water and washed with ethyl acetate. Ethyl acetate layer is discarded and aqueous layer is acidified with aqueous solution of citric acid. It is then extracted with ethyl acetate. The organic layer is separated, dried over anhydrous sodium sulphate, filtered and concentrated under reduced pressure to afford 7-bromo-2-chlorothieno[3,2-b]pyridine-3-carboxylic acid (4).

Example 2B.3

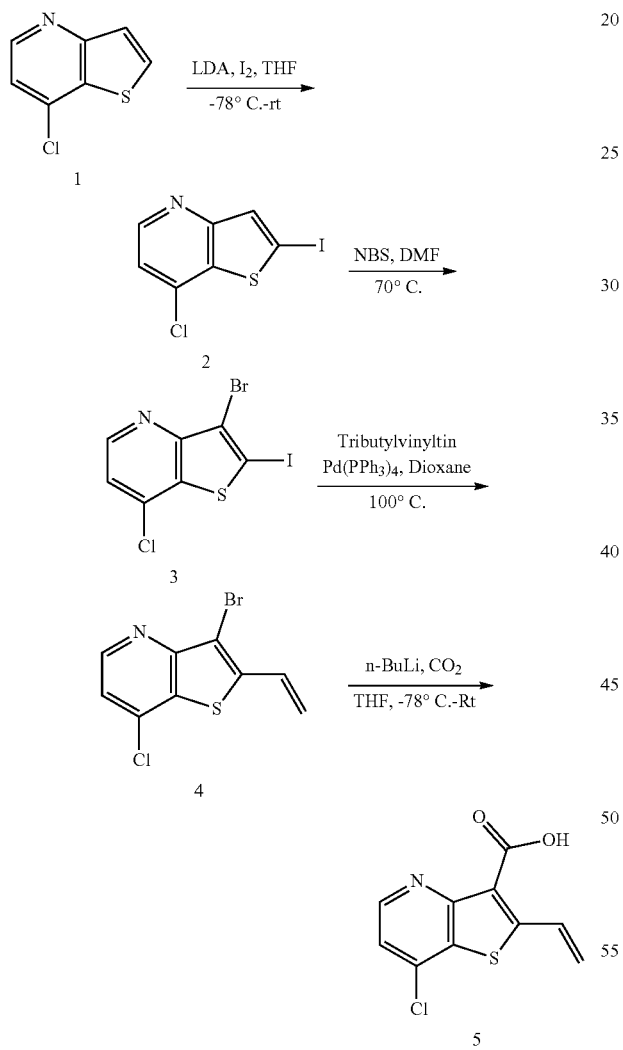

To a stirred solution of 7-chlorothieno[3,2-b]pyridine (1, 1.5 g, 8.9 mmol) in dry tetrahydrofuran (50 mL) is added drop wise lithium diisopropylamide (11.7 mL, 19.5 mmol) at −78° C. and the mixture is stirred at same temperature for 1 h. Iodine (2.25 g, 8.87 mmol dissolved in tetrahydrofuran, 10 mL) is added drop wise and the reaction mixture is allowed to warm up to room temperature over 4 h. It is quenched with aqueous solution of ammonium chloride and extracted with ethyl acetate. The organic layer is washed with water and saturated brine solution, dried over anhydrous sodium sulphate, filtered and concentrated to dryness under reduced pressure. The crude product is purified by Combiflash (12 g, RediSep column) using 5-10% ethyl acetate in hexanes as eluent. The desired fractions are concentrated under reduced pressure to afford 7-chloro-2-iodothieno[3,2-b]pyridine (2).

To a solution of 7-chloro-2-iodothieno[3,2-b]pyridine (2, 1.0 g, 3.4 mmol) in N,N-dimethylformamide (10 mL), N-bromo succinamide is added at room temperature. The reaction mixture is heated and stirred at 70° C. for 12 h. After completion of the reaction, the mixture is diluted with water and extracted with ethyl acetate. The organic layer is washed with water and saturated brine solution, dried over anhydrous sodium sulphate, filtered and concentrated under reduced pressure. The crude product is purified by Combiflash (12 g, RediSep column) using 5-10% ethyl acetate in hexanes as eluent. The desired fractions are concentrated under reduced pressure to afford 3-bromo-7-chloro-2-iodothieno[3,2-b]pyridine (3).

A suspension 3-bromo-7-chloro-2-iodothieno[3,2-b]pyridine (3, 1.0 g, 2.7 mmol) and tributyl vinyl tin (1.01 mL, 3.21 mmol) in 1,4-dioxane (10 mL) is degassed using argon for 10 min. Tetrakis(triphenylphosphine)palladium(0) (0.21 g, 0.19 mmol) is added to the reaction mixture at room temperature and the mixture is heated at 100° C. for 1 h. After completion, the reaction mixture is cooled to room temperature, diluted with water and extracted with ethyl acetate. The ethyl acetate layer is dried over sodium sulfate and concentrated to dryness under reduced pressure. The crude product is purified over a plug of silica gel eluting the compound with ethyl acetate:hexanes (1-10%). The desired fractions are concentrated under reduced pressure to afford 3-bromo-7-chloro-2-vinylthieno[3,2-b]pyridine (4).

To a solution of 3-bromo-7-chloro-2-vinylthieno[3,2-b]pyridine (4, 0.6 g, 2.19 mmol) in dry tetrahydrofuran (20 mL) is added drop wise n-Butyl lithium (1.7 mL 1.3 M in hexanes, 2.19 mmol) at −78° C. and reaction mixture is stirred at the same temperature for 2 h. Carbon dioxide gas is purged through the reaction mixture at −78° C. for 30 min and the reaction mixture is stirred for 1 h at the same temperature. The reaction mixture is slowly warmed to 0° C. and stirred for 30 min. After completion, reaction mixture is quenched with water and washed with ethyl acetate. Ethyl acetate layer is discarded and aqueous layer is acidified with aqueous solution of citric acid and extracted with ethyl acetate. The organic layer is separated, dried over anhydrous sodium sulphate, filtered and concentrated under reduced pressure to afford 7-chloro-2-vinylthieno[3,2-b]pyridine-3-carboxylic acid (5).

Example 2B.4

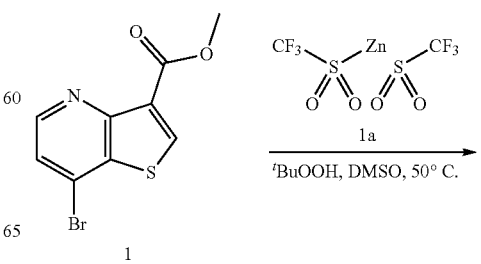

-continued

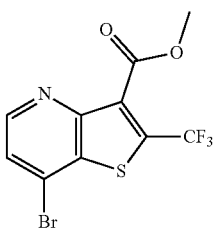

2

Methyl 7-bromothieno[3,2-b]pyridine-3-carboxylate (1, 68.0 mg, 0.25 mmol) and bis(trifluoromethylsulfinyloxy) zinc (1a, 139.8 mg, 0.50 mmol) are dissolved in dimethylsulfoxide (1.71 mL) in an oven-dried screw capped vial equipped with a stir bar. The mixture is stirred vigorously at 0° C. while tert-butyl hydroperoxide (0.09 mL, 0.92 mmol) is added slowly. After completion of addition the ice bath is removed and the reaction mixture is heated to 50° C. in a heating block for 2.5 h before being cooled to room temperature. The reaction mixture is diluted with saturated aqueous sodium bicarbonate and ethyl acetate. The layers are separated and the aqueous phase extracted with ethyl acetate three times. The combined organic material is washed with brine and dried over magnesium sulfate. The solids are filtered and solvent removed in vacuo to afford a crude residue that is purified via silica gel chromatography (5 to 40% ethyl acetate in hexanes), affording methyl 7-bromo-2-(trifluoromethyl)thieno[3,2-b]pyridine-3-carboxylate (2).

Example 2B.5

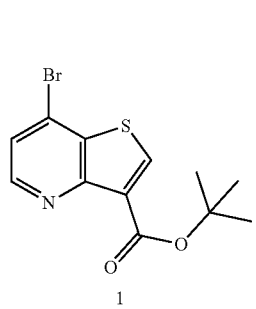

1

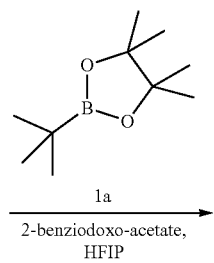

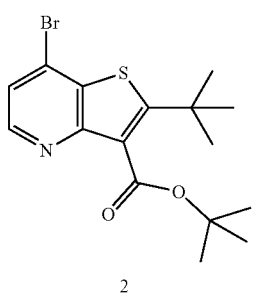

2

A solution of tert-butyl 7-bromothieno[3,2-b]pyridine-3-carboxylate (1, 150.0 mg, 0.480 mmol), (3-oxo-1λ{3},2-benziodoxol-1-yl) acetate (417.5 mg, 0.950 mmol), 2-(tert-butyl)-4,4,5,5-tetramethyl-1,3,2-dioxaborolane (1a, 132.0 mg, 0.720 mmol) and tris(2,2'-bipyridyl)dichloro-ruthenium (II)hexahydrate (35.7 mg, 0.048 mmol) in hexafluoroisopropanol (1.25 mL) is stirred at room temperature and irradiated with a 60 watt household lamp positioned 10 cm away from the vial for 24 h. After completion, reaction mixture is diluted with dichloromethane and silica gel is added. The solvent is evaporated. The crude silica mixture is purified by flash chromatography using silica gel (100-200 mesh) using 0-10% methanol in dichloromethane as eluent. The desired fractions are concentrated under reduced pressure to afford tert-butyl 7-bromo-2-(tert-butyl)thieno[3,2-b]pyridine-3-carboxylate (2).

Example 2B.6

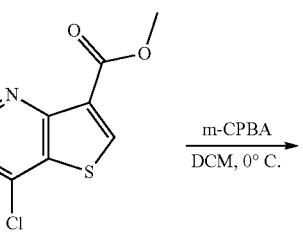

1

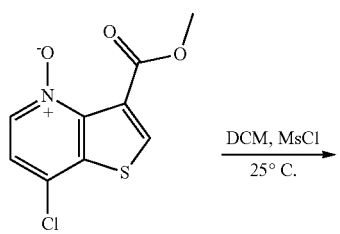

2

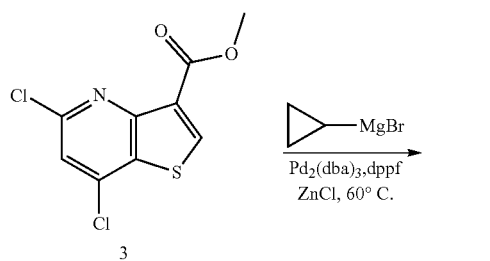

3

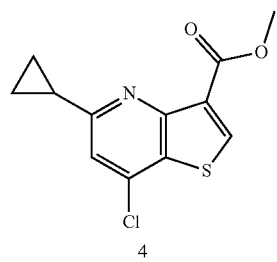

4

Methyl 7-chlorothieno[3,2-b]pyridine-3-carboxylate (1, 0.2 g, 0.88 mmol) is dissolved in dichloromethane (2.2 mL) in an oven-dried screw capped vial equipped with a stir bar. The reaction mixture is stirred at room temperature while 3-chloroperbenzoic acid (0.24 g, 1.41 mmol) is added in 4 portions over 2 min. After 24 h the reaction mixture is poured onto silica gel and purification via silica gel chromatography (50-100% ethyl acetate in hexanes, then 10% methanol in ethyl acetate) afforded 7-chloro-3-(methoxycarbonyl)thieno[3,2-b]pyridine 4-oxide (2).

7-chloro-3-(methoxycarbonyl)thieno[3,2-b]pyridine 4-oxide (2, 0.12 g, 0.47 mmol) is dissolved in dichloromethane (3.3 mL) in an oven-dried screw capped vial equipped with a stir bar. The mixture is stirred at room temperature while methanesulfonyl chloride (0.18 mL, 2.36 mmol) dropwise. After 3 h more methanesulfonyl chloride (0.18 mL, 2.36 mmol) is added dropwise. After 4.5 h the reaction mixture is warmed to 40° C. and stirred an additional 16 h before being cooled to room temperature. The reaction mixture is poured onto silica gel and purification via silica gel chromatography (0-50% ethyl acetate in hexanes) afforded methyl 5,7-dichlorothieno[3,2-b]pyridine-3-carboxylate (3).

Zinc chloride solution (0.5 M, 0.59 mL, 0.29 mmol) is dissolved in tetrahydrofuran (1.0 mL) in an oven-dried screw capped vial equipped with a stir bar. The reaction mixture is stirred at room temperature while bromo(cyclopropyl)magnesium (0.59 mL, 0.29 mmol) solution is added slowly. After 45 min a solution of methyl 5,7-dichlorothieno[3,2-b]pyridine-3-carboxylate (3, 67.0 mg, 0.25 mmol) in tetrahydrofuran (1.5 mL) is added slowly. After 1 min $Pd_2(dba)_3$ (28.4 mg, 0.03 mmol) and dppf (30.4 mg, 0.06 mmol) are added and the reaction mixture subsequently heated to 60° C. for 1 h. The reaction mixture is cooled to room temperature and poured onto saturated aqueous $NH_4Cl$. The aq. phase is extracted with ethyl acetate three times. The combined organic material is washed with brine and dried over magnesium sulfate, filtered and solvent removed in vacuo to provide a brown oil. Purification via silica gel chromatography (8-29% ethyl acetate in hexanes) afforded methyl 7-chloro-5-cyclopropylthieno[3,2-b]pyridine-3-carboxylate (4).

Example 2B.7

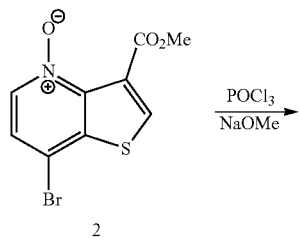

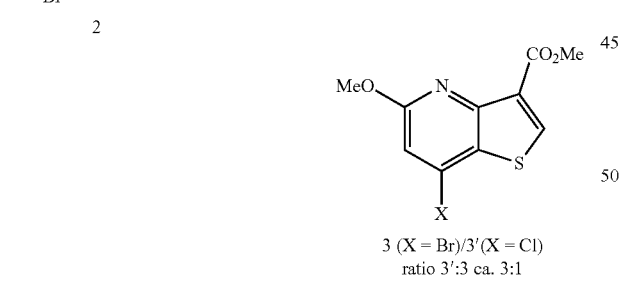

3 (X = Br)/3' (X = Cl)
ratio 3':3 ca. 3:1

7-bromo-3-(methoxycarbonyl)thieno[3,2-b]pyridine 4-oxide (2, 148 mg, 0.514 mmol) is dissolved in chloroform (10 mL) and $POCl_3$ (0.48 mL, 0.79 g, 5.1 mmol) is added. The vial is sealed and the mixture is stirred at 60° C. for 4 h, then over night at room temperature. Then the mixture is concentrated, taken up in DCM, washed with $NaHCO_3$(aq), dried ($Na_2SO_4$), filtered, and concentrated. The crude product (140 mg) is dissolved in THF (9 mL) and sodium methanolate (25% in MeOH, 0.12 mL, 0.12 g, 0.52 mmol) is added. The mixture is stirred at room temperature for 2.75 h, and another 0.13 mL NaOMe sln (25% in MeOH) are added. After 30 min another 0.04 mL NaOMe sln (25% in MeOH) are added. After another 10 min another 0.04 mL NaOMe sln (25% in MeOH) are added. Then the mixture is diluted with DCM and washed with water. The organic phase is dried ($Na_2SO_4$), filtered, concentrated. Purification by column chromatography yielded 23.9 mg of a 3:1 mixture of 3' and 3.

Example 2B.8

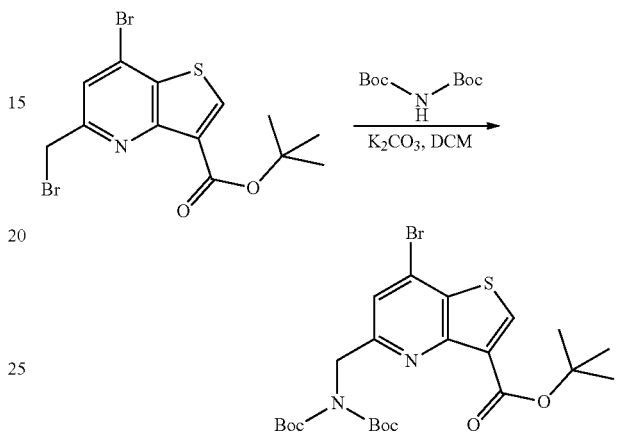

To a solution of tert-butyl 7-bromo-5-(bromomethyl)thieno[3,2-b]pyridine-3-carboxylate (2, 200.0 mg, 0.491 mmol) in N,N-dimethylpyrrolidone (3 mL) is added tert-butyl N-tert-butoxycarbonylcarbamate (160.1 mg, 0.736 mmol) and potassium carbonate (203.6 mg, 1.473 mmol) and the reaction mixture is stirred at room temperature for 24 h. After completion, reaction mixture is diluted with dichloromethane and silica gel is added. The solvent is evaporated. The crude silica mixture is purified by Isco column chromatography using 0-10% methanol in dichloromethane as eluent. The desired fractions are concentrated under reduced pressure to afford tert-butyl 5-[[bis(tert-butoxycarbonyl)amino]methyl]-7-bromo-thieno[3,2-b]pyridine-3-carboxylate (3).

Example 2B.9

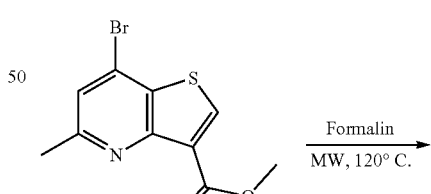

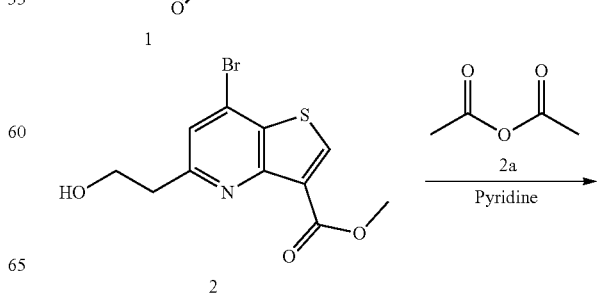

-continued

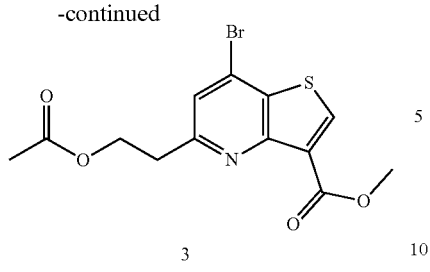

A suspension of methyl 7-bromo-5-methylthieno[3,2-b]pyridine-3-carboxylate (1, 3.50 g, 12.3 mmol) in formalin (37-40%) 10 mL is irradiated in microwave at 120° C. for 1 h. After 1 h, the reaction mass is cooled and extracted with ethyl acetate. The starting material is not consumed in 1 h, reaction is irradiated again after work-up 3 times under microwave. The reaction is monitored by LCMS, still 50% starting material is remaining. The reaction mass is cooled and extracted with ethyl acetate. The organic layer is dried over anhydrous sodium sulfate and concentrated to dryness under reduced pressure. The residue is purified by column chromatography using silica (100-200 mesh) and 0-40% ethyl acetate in hexane to afford methyl 7-bromo-5-(2-hydroxyethyl)thieno[3,2-b]pyridine-3-carboxylate (2).

To a solution of methyl 7-bromo-5-(2-hydroxyethyl)thieno[3,2-b]pyridine-3-carboxylate (2, 0.32 g, 1.01 mmol) in pyridine (10 mL), acetic anhydride (0.115 mL, 1.22 mmol) is added to the reaction mixture. The reaction mixture is stirred at room temperature for 16 h. After completion of reaction as confirmed on thin layer chromatography and LCMS, reaction mixture is diluted with water and extracted with ethyl acetate. The organic layer is dried over anhydrous sodium sulfate and concentrated to dryness under reduced pressure. The crude is purified by combi flash (4 g, Redi Sep column) using 50% ethyl acetate in hexanes as eluent to afford methyl 5-(2-acetoxyethyl)-7-bromothieno[3,2-b]pyridine-3-carboxylate (3).

Example 2B.10

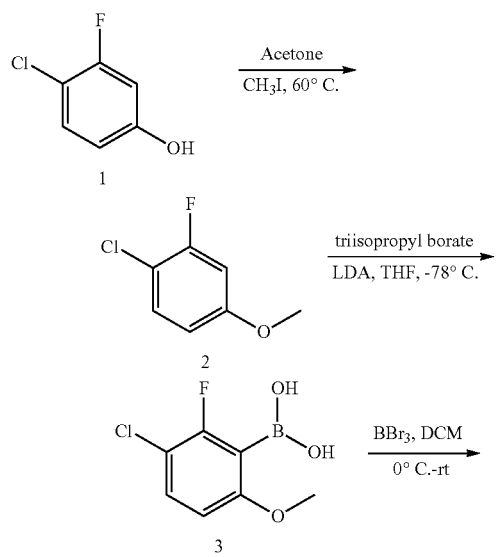

-continued

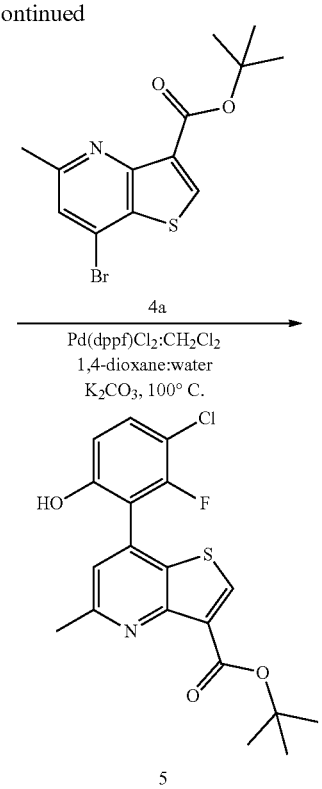

To a solution of 4-chloro-3-fluorophenol (1, 3.0 g, 20.59 mmol) in acetone (30 mL) iodomethane (5.2 mL, 82.00 mmol) and potassium carbonate (5.6 g, 41.00 mmol) are added at room temperature and reaction mixture is stirred at 60° C. for 12 h. After completion of reaction as confirmed on thin layer chromatography, reaction mass is evaporated and reaction mixture is diluted with water and extracted with ethyl acetate. The organic layer is dried over anhydrous sodium sulphate, filtered and concentrated to get afford 1-chloro-2-fluoro-4-methoxybenzene (2).

To a solution of 1-chloro-2-fluoro-4-methoxybenzene (2, 1.9 g, 11.84 mmol) in tetrahydrofuran (20 mL), lithium di-isopropylamide (2 M in tetrahydrofuran) (11.8 mL, 23.75 mmol) is added drop wise at −78° C. and reaction mixture is stirred at same temperature for 1 h. Then Tri-Iso propyl Borate (3.26 mL, 14.16 mmol) is added dropwise at −78° C. The reaction mixture is stirred for 2 h at room temperature. After completion reaction, reaction mixture is quenched with saturated solution of ammonium chloride and extracted with ethyl acetate. The organic layer is dried over anhydrous sodium sulphate, filtered and concentrated to get crude compound. The crude compound obtained is purified by combi flash chromatography using 12 gm redisep column eluting with 80% ethyl acetate in hexane to afford of (3-chloro-2-fluoro-6-methoxyphenyl)boronic acid (3).

To a solution of (3-chloro-2-fluoro-6-methoxyphenyl)boronic acid (3, 0.35 g, 1.71 mmol) in dichloromethane (5 mL) Boron tribromide (0.324 mL, 3.43 mmol) is added drop wise at 0° C. and reaction mixture is stirred at room temperature for 1 h. After completion of reaction as confirmed on thin layer chromatography the reaction mixture is quenched with ice cold water. The solid precipitated is filtered and washed with pentane to afford as (3-chloro-2-fluoro-6-hydroxyphenyl)boronic acid (4).

A suspension of tert-butyl 7-bromo-5-methylthieno[3,2-b]pyridine-3-carboxylate (4a, 0.230 g 0.8 mmol), (3-chloro-2-fluoro-6-hydroxyphenyl)boronic acid (4, 0.30 g, 1.6 mmol) and potassium carbonate (0.334 g, 2.4 mmol) in 1,4-dioxane (2.0 mL) and water (0.5 mL) is degassed with argon gas 10 min. [1,1'-Bis(diphenylphosphino)ferrocene]dichloropalladium(II),complex with dichloromethane (0.03 g, 0.04 mmol) is added to above suspension and reaction mixture is stirred for 3 h at 90° C. The reaction mixture is monitored with LCMS and thin layer chromatography reaction mixture. After completion, the reaction mass is filtered through Celite bed and washed with ethyl acetate. The crude compound obtained is purified through combi flash chromatography using 4 gm redisep column by eluting with 90% ethyl acetate in hexane to afford tert-butyl 7-(3-chloro-2-fluoro-6-hydroxyphenyl)-5-methylthieno[3,2-b]pyridine-3-carboxylate (5).

Example 2B.11

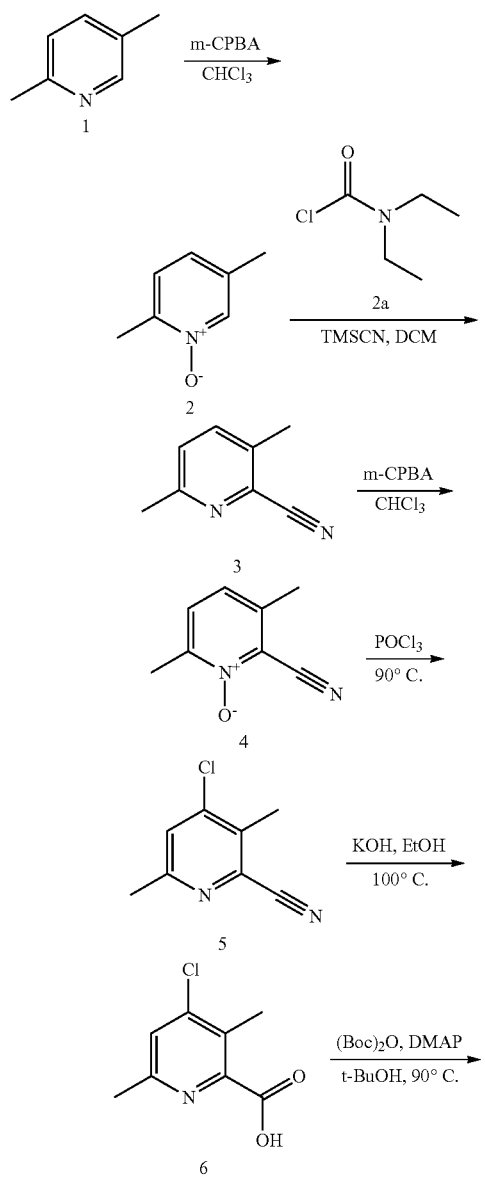

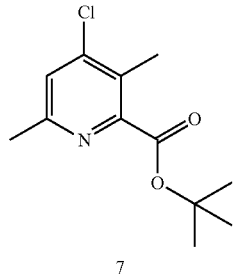

To a solution of 2,5-dimethylpyridine (1, 10.0 g, 93.4 mmol) in Chloroform (100 mL) is added to metachloroperbenzoic acid (19.3 g, 112.1 mmol) at 0° C. under argon atmosphere and mixture is stirred at room temperature for 16 h. After completion, the reaction mixture is diluted with 10% calcium hydroxide solution and the solution is filtered through celite, filtrate is concentrated and dried to afford 2,5-dimethylpyridine 1-oxide (2).

To a solution of 2,5-dimethylpyridine 1-oxide (2, 10.0 g, 81.3 mmol) in dichloromethane (100 ml) is added to Trimethylsilylcyanide (11.2 g, 89.4 mmol) at 0° C. under argon atmosphere and stirred at room temperature for 30 minute, diethylcarbamic chloride (2a, 11.3 mL, 89.4 mmol) is added and stirring continued at room temperature for 24 h. After completion, the reaction mixture is quenched with 10% potassium carbonate solution and extracted with ethyl acetate. Organic layer is dried over anhydrous sodium sulfate and concentrated to dryness under reduced pressure. The crude product is purified by column chromatography using silica (100-200 mesh) using 30-40% ethyl acetate in hexanes as eluent. The desired fractions are concentrated under reduced pressure to afford 3,6-dimethylpicolinonitrile (3).

To a solution of 3,6-dimethylpicolinonitrile (3, 7.00 g, 46.9 mmol) in Chloroform (70 mL) is added to metachloroperbenzoic acid (8.75 g, 56.6 mmol) at 0° C. under argon atmosphere and stirring continued at room temperature for 16 h. After completion, the reaction mixture is diluted with 10% calcium hydroxide solution and filtered through celite, filtrate is concentrated and dried to afford 2-cyano-3,6-dimethylpyridine 1-oxide (4).

A solution of 2-cyano-3,6-dimethylpyridine 1-oxide (4, 7.0 g, 46.9 mmol) in phosphoryl chloride (50 mL) is stirred at 90° C. for 4 h. After completion, the reaction mixture is concentrated and purified by column chromatography using silica (100-200 mesh) using 20-30% ethyl acetate in hexanes as eluent. The desired fractions are concentrated under reduced pressure to afford 4-chloro-3,6-dimethylpicolinonitrile (5).

A solution of 4-chloro-3,6-dimethylpicolinonitrile (5, 4.0 g, 24.0 mmol) in ethanol (20 mL) and 10% Potassium hydroxide solution (20 mL) is stirred at 100° C. for 16 h. After completion, the reaction mixture is cooled and acidified with 2M hydrochloric acid solution up to pH 5 and extracted with ethyl acetate. Organic layer is dried over anhydrous sodium sulfate, filtered and concentrated to dryness under reduced pressure. To afford 4-chloro-3,6-dimethylpicolinic acid (6).

To a solution of 4-chloro-3,6-dimethylpicolinic acid (6, 1.50 g, 8.10 mmol) in tert-butyl alcohol (9.0 ml) is added di-tert-butyl dicarbanate (0.75 mL, 3.56 mmol) and 4-dimethylamino pyridine (1.48 g, 12.1 mmol) at 0° C. under argon atmosphere and stirred at 90° C. for 4 h. After completion, the reaction mixture is concentrated under reduced pressure. The crude compound is purified by flash column chromatography using 20-30% ethyl acetate in hexane to afford tert-butyl 4-chloro-3,6-dimethylpicolinate (7).

Example 2B.12

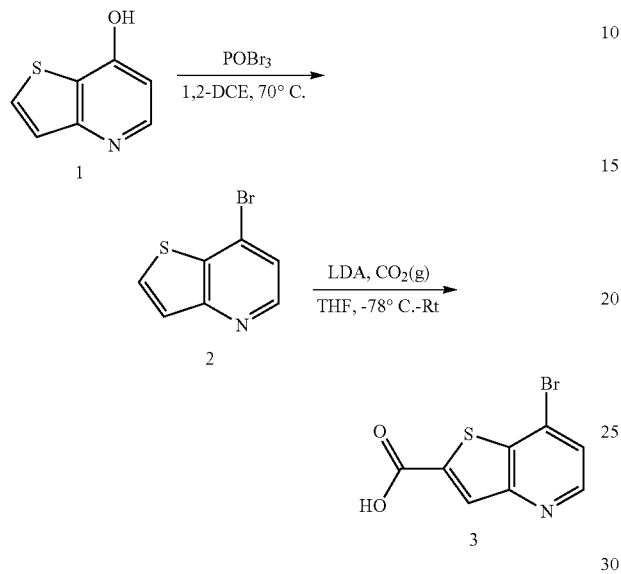

To a stirred solution of thieno [3,2-b]pyridin-7-ol (1, 5.0 g, 33.07 mmol) in 1,2-dichloroethane (50 mL) is added phosphorous oxybromide (143.21 g, 496.09 mmol) portion-wise at room temperature and the mixture is stirred at 70° C. for 10 h. The reaction mixture is cooled at 0° C., basified with 10% aqueous solution of sodium hydroxide and extracted with dichloromethane. The organic layer is washed with brine, dried over anhydrous sodium sulfate, filtered and concentrated to dryness under reduced pressure to afford 7-bromothieno[3,2-b]pyridine (2).

To a stirred solution of 7-bromothieno[3,2-b]pyridine (2, 4.0 g, 18.78 mmol) in dry tetrahydrofuran (40 mL) is added lithium diisopropylamide solution (2.0 M in hexanes, 26.30 mL, 53.60 mmol) drop wise at −78° C. and the mixture is stirred at same temperature for 1 h. Carbon dioxide gas is purged through the reaction mass for 15 min and the reaction mixture is allowed to warm up to room temperature over 4 h. The reaction is quenched with aqueous ammonium chloride solution, diluted with water and extracted with ethyl acetate. The organic layer is washed with saturated brine, dried over anhydrous sodium sulphate, filtered and concentrated to afford 7-bromothieno[3,2-b]pyridine-2-carboxylic acid (3).

Example 2B.12

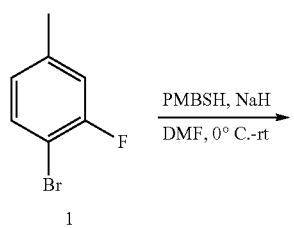

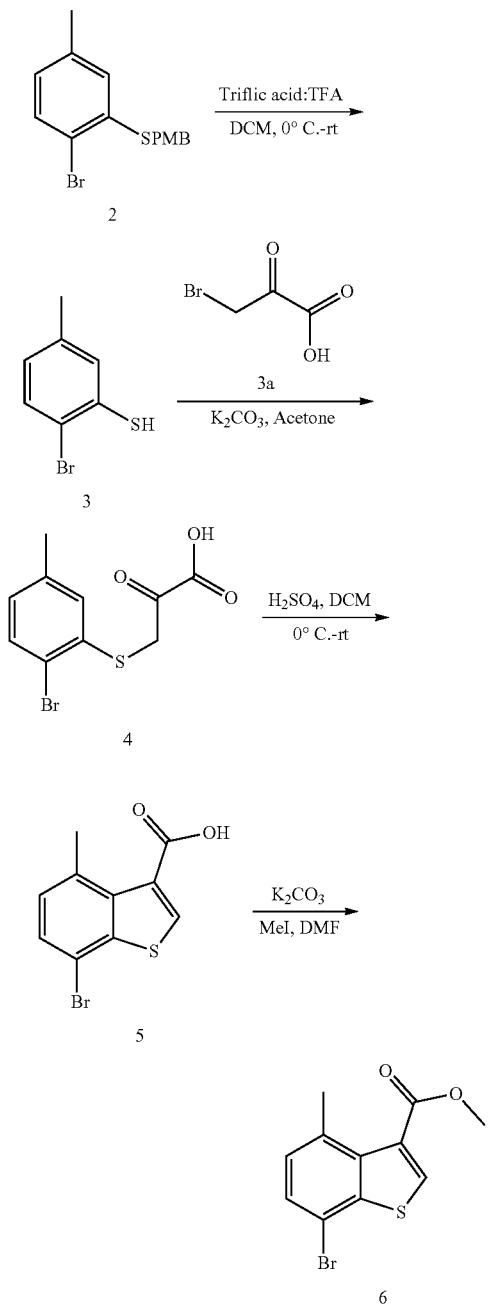

To a stirred solution of (4-methoxyphenyl)methanethiol (12.3 g, 87.77 mmol) in N,N-dimethylformamide (150 mL) is added sodium hydride (4.60 g, 119.69 mmol) portion wise at 0° C. After 10 min, 1-bromo-2-fluoro-4-methylbenzene (1, 15.0 g, 79.79 mmol) is added and the reaction is stirred at room temperature for 2 h. After completion, the reaction is poured into ice water and extracted with ethyl acetate. The organic layer is washed with water, brine, dried over anhydrous sodium sulfate and concentrated under reduced pressure to get the crude. The crude product is purified by Combiflash (40 g, RediSep column) using 0-5% ethyl acetate in hexanes as eluent. The desired fractions are concentrated under reduced pressure to afford (2-bromo-5-methylphenyl)(4-methoxybenzyl)sulfane          (2).-

To a solution of (2-bromo-5-methylphenyl)(4-methoxybenzyl)sulfane (2, 18.0 g, 55.90 mmol) in dichloromethane (140 mL) is added a mixture of trifluoroacetic acid (20 mL) and triflic acid (5 mL) in dichloromethane (40 mL) at 0° C. drop wise and the reaction mixture is stirred at room temperature for 2 h. After completion, the reaction is poured into ice-water and extracted with dichloromethane. The organic layer is washed with water, brine, dried over anhydrous sodium sulfate and concentrated under reduced pressure to get the crude product 2-bromo-5-methylbenzenethiol (3).

To a solution 2-bromo-5-methylbenzenethiol (3, 4.7 g, 23.27 mmol) in acetone (47.0 mL) is added potassium carbonate (16.0 g, 116.35 mmol) at room temperature and the mixture is stirred for 10 min. 3-Bromo-2-oxopropanoic acid (3a, 11.6 g, 69.80 mmol) is added to the reaction mixture and stirred for 5 h at room temperature. After completion, the acetone is evaporated under reduced pressure; the residue is diluted with water and extracted with ethyl acetate. The organic layer is washed with water, brine, dried over anhydrous sodium sulfate and concentrated under reduced pressure to get 3-((2-bromo-5-methylphenyl)thio)-2-oxopropanoic acid (4).

To a solution of 3-((2-bromo-5-methylphenyl)thio)-2-oxopropanoic acid (4, 4.0 g, 13.89 mmol) in dichloromethane (40.0 mL) is added sulfuric acid (10.0 mL) and the reaction mixture is stirred at room temperature for 5 h. After completion, the reaction mixture is poured into ice water, extracted with dichloromethane. The organic layer is washed with water, brine, dried over anhydrous sodium sulfate and concentrated under reduced pressure to get 7-bromo-4-methylbenzo[b]thiophene-3-carboxylic acid (5).

To a solution 7-bromo-4-methylbenzo[b]thiophene-3-carboxylic acid (5, 3.0 g, 11.11 mmol) in N,N-dimethylformamide (30.0 mL) is added potassium carbonate (4.6 g, 33.33 mmol) and iodomethane (1.4 mL, 22.22 mmol) at 0° C. and the reaction mixture is stirred at room temperature for 4 h. After completion, the reaction mass is poured into water and extracted with ethyl acetate. The organic layer is washed with water, brine, dried over anhydrous sodium sulfate and concentrated under reduced pressure; the crude product is purified by flash column chromatography using 5% ethyl acetate in hexanes as eluent. The desired fractions are concentrated under reduced pressure to afford methyl 7-bromo-4-methylbenzo[b]thiophene-3-carboxylate (6).

Example 2B.13

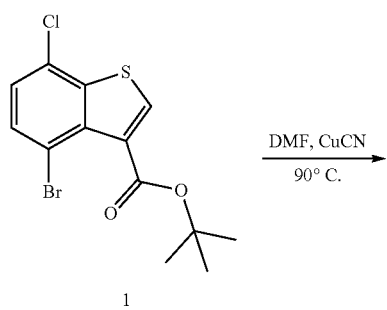

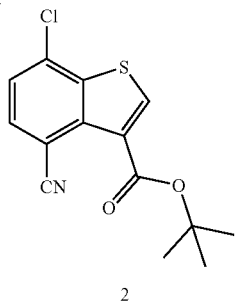

To a solution of tert-butyl 4-bromo-7-chlorobenzo[b]thiophene-3-carboxylate (1, 0.7 g, 2.01 mmol) in N,N-dimethylformamide (2 mL), copper(I) cyanide (0.180 g, 2.01 mmol) is added. This reaction mixture is heated at 90° C. for 2 h. After this time, the reaction mixture is filtered with Celite and washed with ethyl acetate. The filtrate is washed with water and then brine solution, dried over anhydrous sodium sulfate, and concentrated under reduced pressure to obtain the crude product. This is purified by column chromatography using silica gel (100-200 mesh) and 30-50% ethyl acetate in hexane as eluent. The desired fractions are concentrated under reduced pressure to afford tert-butyl 7-chloro-4-cyanobenzo[b]thiophene-3-carboxylate (2).

Example 2B.14

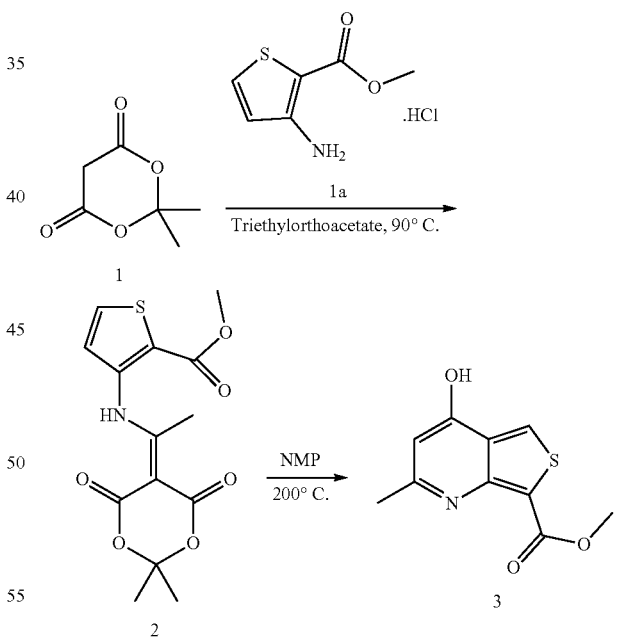

A solution of 2,2-dimethyl-1,3-dioxane-4,6-dione (1, 0.41 g, 2.84 mmol) and diethoxymethoxyethane (50.0 mL) is stirred and heated at 90° C. for 2 h in a closed vessel. Methyl 3-aminothiophene-2-carboxylate hydrochloride (1a, 0.5 g, 2.58 mmol) is added portion wise at 90° C. under argon atmosphere and continued heating at 90° C. for 12 h. After completion, the reaction mass is cooled to room temperature, added water and extracted with ethyl acetate. The organic layer is dried over anhydrous sodium sulfate, filtered and concentrated under vacuo to get crude. The crude is triturated with diethyl ether to afford methyl 3-((1-(2,2-dimethyl-4,6-dioxo-1,3-dioxan-5-ylidene)ethyl)amino)thiophene-2-carboxylate (2).

A solution of methyl 3-((1-(2,2-dimethyl-4,6-dioxo-1,3-dioxan-5-ylidene)ethyl)amino)thiophene-2-carboxylate (2, 0.200 g, 0.61 mmol) in N-methyl pyrrolidone (15 mL) is heated in microwave at 200° C. for 30 min. After completion, the reaction mass is cooled to room temperature, filtered and the crude solid is purified by prep-HPLC to afford methyl 4-hydroxy-2-methylthieno[3,4-b]pyridine-7-carboxylate (3).

Example 2B.15

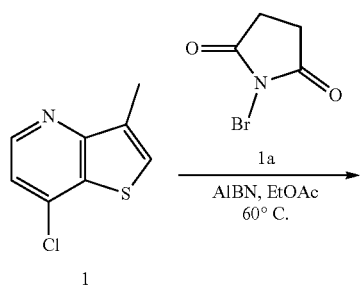

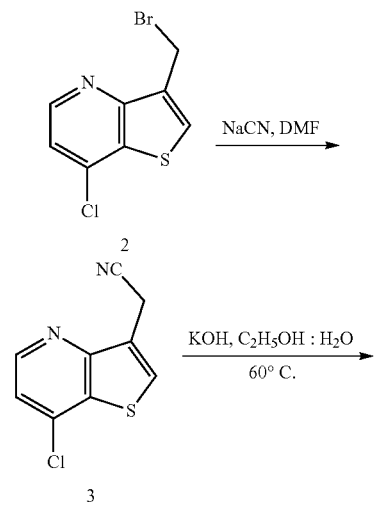

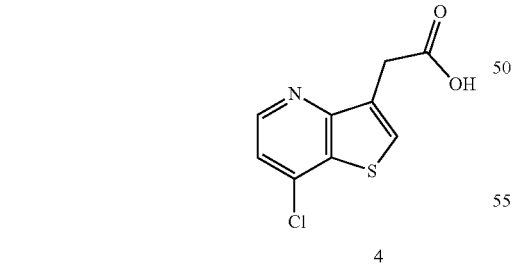

To a stirred solution of 7-chloro-3-methylthieno[3,2-b]pyridine (1, 1.0 g, 5.44 mmol) in ethylacetate (10 mL) are added 1-bromopyrrolidine-2,5-dione (1a, 1.93 g, 10.8 mmol) and azobisisobutyronitrile (0.088 g, 0.540 mmol) at room temperature. The reaction is stirred at 60° C. for 4 h. After completion, the reaction mixture is quenched with water and extracted with ethyl acetate. The organic layer is washed with brine solution, dried over anhydrous sodium sulfate, filtered and concentrated to dryness under reduced pressure. The crude product is purified by Combiflash (12 g, RediSep column) using 1-5% ethylacetate in hexanes as eluent to afford 3-(bromomethyl)-7-chlorothieno[3,2-b]pyridine (2).

To a solution of 3-(bromomethyl)-7-chlorothieno[3,2-b]pyridine (2, 1.50 g, 5.70 mmol) in N,N-dimethylformamide (15 mL) is added sodium cyanide (0.561 g, 11.40 mmol) and the mixture is stirred at room temperature for 3 h. After completion, the reaction is quenched with ice cold water and extracted with ethyl acetate. The organic layer is washed with cold water, dried over anhydrous sodium sulfate, filtered and concentrated to dryness under reduced pressure to afford 2-(7-chlorothieno[3,2-b]pyridin-3-yl)acetonitrile (3).

To a solution of 2-(7-chlorothieno[3,2-b]pyridin-3-yl)acetonitrile (3, 1.10 g, 5.20 mmol) in a mixture of ethanol and water (1:1, (20 mL) is added potassium hydroxide (2.96 g, 52.8 mmol) and the mixture is stirred at 60° C. for 10 h. After completion, the reaction mixture is concentrated and extracted with diethyl ether. The aqueous layer is acidified with 1 N aqueous hydrochloric acid solution, and extracted with ethyl acetate. The organic layer is washed with saturated brine solution, dried over anhydrous sodium sulphate, filtered and concentrated to afford 2-(7-chlorothieno[3,2-b]pyridin-3-yl)acetic acid (4).

Example 2B.16

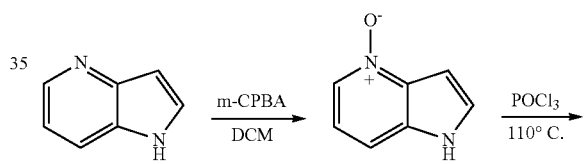

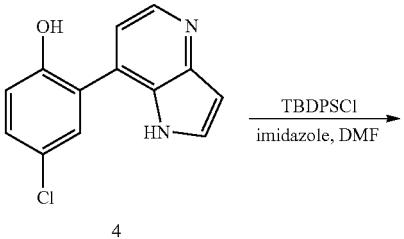

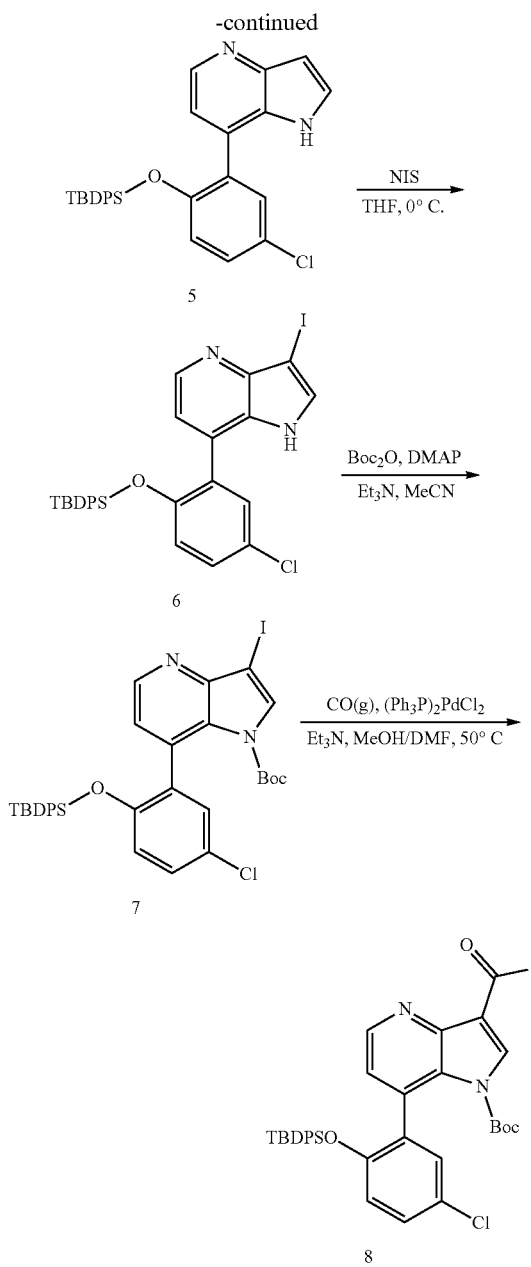

To a solution of 1H-pyrrolo[3,2-b]pyridine (1, 2.5 g, 21 mmol) in DCM (75 mL) at 0° C. is slowly added m-CPBA (5.69 g, 25.4 mmol). The mixture is stirred from 0° C. to rt. After 16 h the reaction is complete as judged by TLC (SiO2, 10% MeOH/DCM). The mixture is concentrated and the residue purified by column chromatography (SiO₂, 0-20% MeOH/DCM). The product is isolated as a mixture with m-CBA (ratio ca. 1:0.7 by ¹H-NMR). The so-obtained material 1H-pyrrolo[3,2-b]pyridine 4-oxide (2).

1H-pyrrolo[3,2-b]pyridine 4-oxide (2, 3.64 g) in POCl₃ (30 mL, 50 g, 0.32 mol) are refluxed overnight under argon (oil-bath, 130° C.). Then the mixture is carefully transferred into an Erlenmeyer flask with crushed ice with stirring. The mixture is then basified with NaOH (aq, 12.5%) to pH ca. 8, and the precipitated material is collected by filtration. The aq. phase is extracted (3×EtOAc), and the combined organic phases are dried (Na₂SO₄), filtered and concentrated. The precipitated and extracted material are combined, dissolved in DCM and washed with NaHCO₃(aq). The organic phase is dried (Na₂SO₄), filtered and concentrated to afford 7-chloro-1H-pyrrolo[3,2-b]pyridine (3).

The reaction is run in two batches (0.80 g of (3) per batch), and the two batches are combined for purification purposes. To a solution of 7-chloro-1H-pyrrolo[3,2-b]pyridine (3, 0.80 g, 5.2 mmol) in 1,4-dioxane (14 mL) and water (3.5 mL) are added (5-chloro-2-hydroxyphenyl)boronic acid (3a, 1.4 g, 8.1 mmol) and potassium carbonate (2.2 g, 16 mmol) and the mixture is degassed by bubbling argon through it for 5 min. Pd(PPh₃)₄ (0.61 g, 0.53 mmol) is added, and the mixture is degassed for another 5 min, then placed in a preheated heating block (100° C.) and stirred for 20 h. Then the mixture is cooled down to room temperature. The two batches are combined, diluted with water, extracted with EtOAc. The organic phase is dried (Na₂SO₄), filtered, and concentrated. Purification by column chromatography (SiO₂, 0-20% MeOH/DCM) to afford 4-chloro-2-(1H-pyrrolo[3,2-b]pyridin-7-yl)phenol (4).

To a solution of 4-chloro-2-(1H-pyrrolo[3,2-b]pyridin-7-yl)phenol (4, 37 mg, 0.15 mmol) in DMF (0.7 mL) at 0° C. are added imidazole (23 mg, 0.34 mmol) and tert-butyl-chloro-diphenyl-silane (0.05 mL, 0.05 g, 0.2 mmol), and the mixture is stirred at rt. After 3 h the mixture is diluted with water and EtOAc, and the aq. phase is extracted (3×EtOAc). The combined organic phases are dried (Na₂SO₄), filtered and concentrated. Purification by column chromatography (SiO₂, 0-40% EtOAc/hexane) to afford 7-(2-((tert-butyldiphenylsilyl)oxy)-5-chlorophenyl)-1H-pyrrolo[3,2-b]pyridine (5).

To a solution of 7-(2-((tert-butyldiphenylsilyl)oxy)-5-chlorophenyl)-1H-pyrrolo[3,2-b]pyridine (5; 1.08 g, 2.24 mmol) in THF (20 mL) at 0° C. is added N-Iodosuccinimide (503 mg, 2.24 mmol) and the mixture is stirred for 10 min. Then the reaction is diluted with EtOAc, quenched with Na₂S₂O₃(aq) and water, and extracted (2×EtOAc). The combined organic phases are dried, filtered and concentrated. Purification by column chromatography (SiO₂, 0-40% EtOAc/hexane) afforded to afford 7-(2-((tert-butyldiphenylsilyl)oxy)-5-chlorophenyl)-3-iodo-1H-pyrrolo[3,2-b]pyridine (6).

To a solution of 7-(2-((tert-butyldiphenylsilyl)oxy)-5-chlorophenyl)-3-iodo-1H-pyrrolo[3,2-b]pyridine (6, 990 mg, 1.63 mmol) in MeCN (11 mL) at 0° C. are added triethylamine (0.45 mL, 0.33 g, 3.2 mmol), di-tert-butyl dicarbonate (531 mg, 2.43 mmol) in 2 mL MeCN and 4-dimethylaminopyridine (40 mg, 0.33 mmol) and the mixture is stirred at rt. After 1 h water is added, and the mixture is extracted with DCM (3×). The combined organic phases are dried (Na₂SO₄), filtered and concentrated. Purification by column chromatography (SiO₂, 0-20% EtOAc/hexane) to afford tert-butyl 7-(2-((tert-butyldiphenylsilyl)oxy)-5-chlorophenyl)-3-iodo-1H-pyrrolo[3,2-b]pyridine-1-carboxylate (7).

To a solution of tert-butyl 7-(2-((tert-butyldiphenylsilyl)oxy)-5-chlorophenyl)-3-iodo-1H-pyrrolo[3,2-b]pyridine-1-carboxylate (7, 1.06 g, 1.49 mmol) in methanol (11 mL) and DMF (4 mL) are added triethylamine (0.43 mL, 0.31 g, 3.1 mmol) and (Ph₃P)₂PdCl₂ (105 mg, 0.149 mmol). Then the mixture is stirred at 50° C. under a CO atmosphere. After 18 h the mixture is concentrated and purified by column chromatography (SiO₂, 0-50% EtOAc/hexane) to afford 1-(tert-butyl) 3-methyl 7-(2-((tert-butyldiphenylsilyl)oxy)-5-chlorophenyl)-1H-pyrrolo[3,2-b]pyridine-1,3-dicarboxylate (8).

Example 2B.17

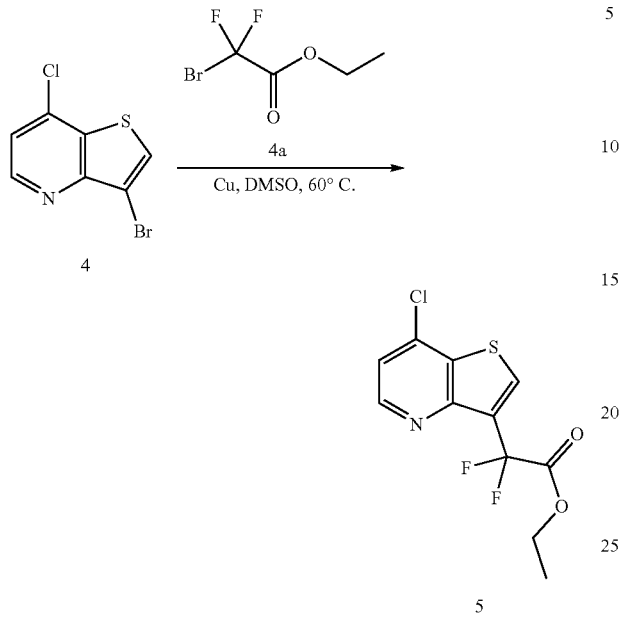

To a solution of 3-bromo-7-chlorothieno[3,2-b]pyridine (4, 0.30 g, 1.21 mmol), and ethyl 2-bromo-2,2-difluoroacetate (4a, 0.73 g, 3.62 mmol) in dimethylsulfoxide (12.0 mL), cupper powder (0.11 g, 1.81 mmol) is added at room temperature and the mixture is heated at 60° C. for 16 h. After completion, reaction mass is diluted with ethyl acetate and filtered through Celite. The filterate is washed with water and brine solution, dried over sodium sulfate filtered and concentrated. The crude is purified by flash column chromatography using silica gel (100-200 mesh) and 20-30% ethyl acetate in hexane as eluent. The desired fractions are concentrated under reduced pressure to afford ethyl 2-(7-chlorothieno[3,2-b]pyridin-3-yl)-2,2-difluoroacetate (5).

Example 2B.18

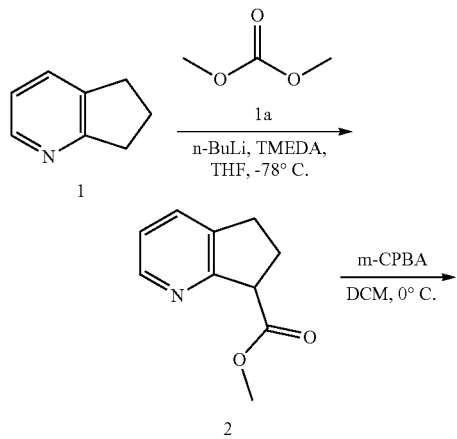

To a solution of N,N,N',N'-tetramethylethylenediamine (11.69 g, 100.42 mmol) in tetrahydrofuran (100 mL), n-butyllithium (1.3 M in hexane, 71.1 mL, 92.43 mmol) is added at −78° C., then 6,7-dihydro-5H-cyclopenta[b]pyridine (1, 10.0 g, 84.03 mmol) is added dropwise and the mixture is stirred at −78° C. for 45 min. Then, a solution of dimethyl carbonate (1a, 8.31 g, 92.43 mmol) in tetrahydrofuran (10 mL) is added drop wise and the mixture is allowed to room temperature over an 1 h. The reaction mixture is quenched with saturated ammonium chloride solution and extracted with ethyl acetate. The combined organic layer is dried over anhydrous sodium sulphate, filtered and concentrated. The crude is purified by column chromatography using silica gel (100-200 mesh) and 0-25% ethyl acetate in hexane as eluent to afford methyl 6,7-dihydro-5H-cyclopenta[b]pyridine-7-carboxylate (2).

To a solution of methyl 6,7-dihydro-5H-cyclopenta[b]pyridine-7-carboxylate (2, 2.5 g, 14.12 mmol) in dichloromethane (30 mL), 3-chloroperbenzoic acid (4.85 g, 28.24 mL) is added at 0° C. and the mixture is stirred at the same temperature for 30 min. After completion, the reaction mixture is quenched with saturated sodium bicarbonate solution (10 mL) and extracted with dichloromethane. The combined organic layer is washed brine, dried over anhydrous sodium sulphate, filtered and concentrated. The crude is purified by column chromatography using silica gel (100-200 mesh) and 0-10% methanol in dichloromethane as eluent. The desired fractions are concentrated under reduced pressure to afford 7-(methoxycarbonyl)-6,7-dihydro-5H-cyclopenta[b]pyridine 1-oxide (3).

To a solution of 7-(methoxycarbonyl)-6,7-dihydro-5H-cyclopenta[b]pyridine 1-oxide (3, 1.5 g, 7.77 mmol) in acetonitrile (25 mL), lithium bromide (0.67 g, 7.77 mmol) and phosphorus bromide (22.3 g, 77.72 mmol) are added and the reaction mixture is heated at 80° C. for 24 h. After completion, the reaction mixture is cooled to 0° C., quenched with saturated sodium bicarbonate solution (50 mL) and extracted with ethyl acetate. The combined organic layer is dried over anhydrous sodium sulphate, filtered and concentrated. The crude is purified by column chromatography using silica gel (100-200 mesh) and 0-25% ethyl acetate in hexane to afford methyl 4-bromo-6,7-dihydro-5H-cyclopenta[b]pyridine-7-carboxylate (4).

Example 2B.19

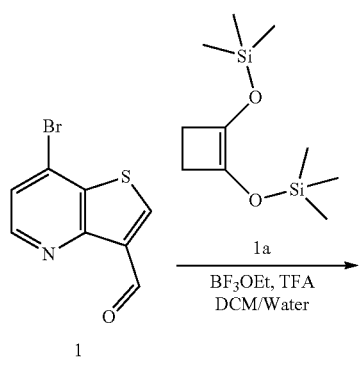

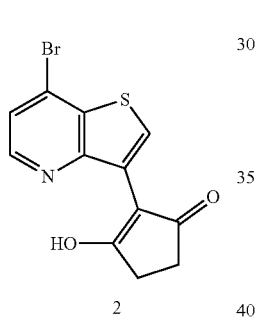

To a solution of 7-bromothieno[3,2-b]pyridine-3-carbaldehyde (1, 36 mg, 0.148 mmol) in DCM (1 mL) in an oven-dried screw capped vial is equipped with a stir bar. To the mixture is added ethoxyethane trifluoroborane (0.02 mL, 0.163 mmol) with constant stirring at room tem added slowly. Then 1,2-bis((trimethylsilyl)oxy)cyclobut-1-ene (1a, 0.06 mL, 0.222 mmol) is added dropwise and the clear yellow mixture continued to stir at room temperature for 40 min. Water (0.030 mL) is added followed by ethoxyethane; trifluoroborane (0.27 mL, 2.22 mmol) and the reaction is allowed to stir at room temperature overnight. No conversion to pinacol rearrangement product observed so water and DCM added and the aqueous phase extracted with dichloromethane three times. The combined organic material is washed with brine and dried over magnesium sulfate. The solids are filtered and solvent removed in vacuo to afford a crude yellow residue. Aqueous layer is concentrated in vacuum. Both aqueous and organic layer combined and is taken up in TFA (3.5 mL, 0.1480 mmol) and placed in a vial that is sealed and stirred in a heating block at 70° C. for 3 h. The reaction is cooled to room temperature and solvent removed in vacuo. Preparatory HPLC (water with 0.1% TFA) afforded the product 2-(7-bromothieno[3,2-b]pyridin-3-yl)-3-hydroxycyclopent-2-en-1-one (2).

Example 2B.20

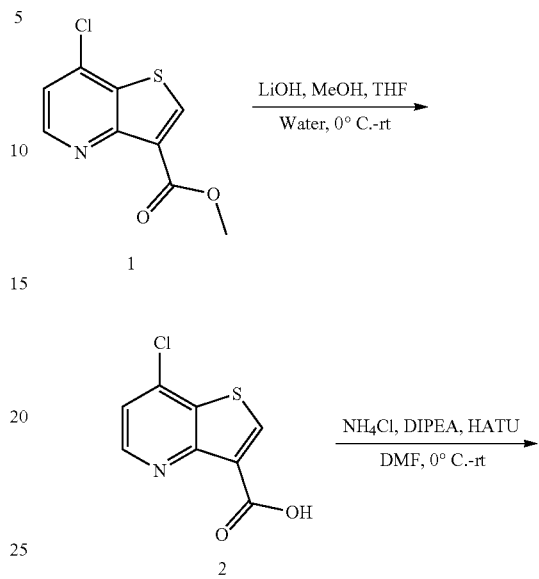

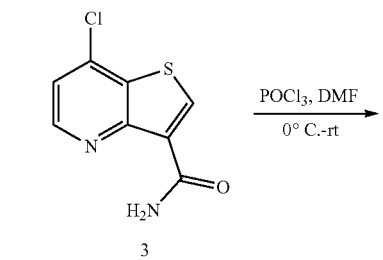

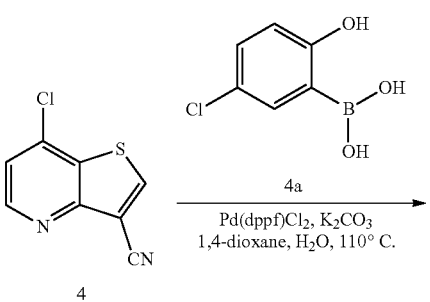

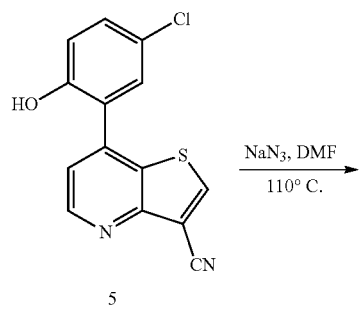

-continued

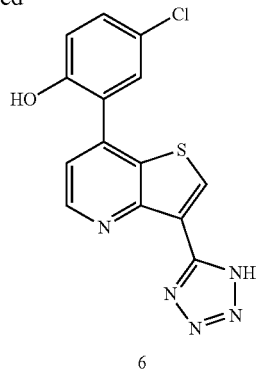

6

To a stirred solution of methyl 7-chlorothieno[3,2-b]pyridine-3-carboxylate (1, 15.0 g, 65.88 mmol) in methanol, tetrahydrofuran and water (2:1:1, 225 mL) is added lithium hydroxide (13.82 g, 329.43 mmol) at 0° C. and reaction mixture is stirred at room temperature for 16 h. After completion, the solvents are concentrated under reduced pressure and the aqueous layer is acidified with 1 N aqueous hydrochloric acid solution up to pH-3. Solid precipitate obtained is filtered and washed with n-pentane to afford 7-chlorothieno[3,2-b]pyridine-3-carboxylic acid (2).

To a solution of 7-chlorothieno[3,2-b]pyridine-3-carboxylic acid (2, 12.20 g, 57.10 mmol) in N,N-dimethylformamide (50 mL) is added 1-[bis(dimethylamino)methylene]-1H-1,2,3-triazolo[4,5-b]pyridinium 3-oxide hexafluorophosphate (32.5 g, 85.65 mmol) and reaction mixture is stirred for 10 min. The reaction mixture is then cooled to 0° C. and N,N-diisopropylethylamine (29.841 mL, 171.316 mmol) and ammonium chloride (15.2 g, 285.52 mmol) are added and reaction mixture is allowed to warm to room temperature and stirred for 16 h. After completion, the reaction is quenched with ice cold water and extracted with ethyl acetate. The organic layer is washed with cold water, dried over anhydrous sodium sulfate, filtered and concentrated to dryness under reduced pressure. The crude product is triturated with pentane and dried to afford 7-chlorothieno[3,2-b]pyridine-3-carboxamide (3).

To a solution of 7-chlorothieno[3,2-b]pyridine-3-carboxamide (3, 10.0 g, 51.37 mmol) in N,N-dimethylformamide (100 mL) at 0° C. is added phosphorus oxytrichloride (48.0 mL, 513.76 mmol). The reaction is allowed to warm up to room temperature and stirred for 16 h. After completion, reaction mixture concentrated to dryness under reduced pressure. The reaction mixture is basified with saturated sodium bicarbonate solution up to pH-8 and extracted with ethyl acetate. The organic layer is washed with brine solution, dried over anhydrous sodium sulfate, filtered and concentrated to dryness under reduced pressure. The crude product is purified by Combiflash (40 g, RediSep column) using 0-20% ethyl acetate in hexanes as eluent. The desired fractions are concentrated under reduced pressure to afford 7-chlorothieno[3,2-b]pyridine-3-carbonitrile (4).

To a solution of 7-chlorothieno[3,2-b]pyridine-3-carbonitrile (4, 8.0 g, 41.10 mmol), and (5-chloro-2-hydroxyphenyl) boronic acid (4a, 14.1 g, 82.20 mmol) in 1,4-dioxane (120.0 mL) is added 2 M solution of potassium carbonate (14.2 g, 102.7 mmol) reaction mixture is degassed with argon gas for 10 min. [1,1'-Bis(diphenylphosphino)ferrocene]palladium (II) dichloride (3.0 g, 4.11 mmol) is then added to reaction mixture and reaction mixture is stirred at 110° C. for 2 h. After completion, reaction mixture is cooled to room temperature, diluted with water and extracted with ethyl acetate. The organic layer is washed with brine solution, dried over anhydrous sodium sulfate, filtered and concentrated to dryness under reduced pressure. The crude product is purified by column chromatography using silica gel (100-200 mesh) and 0-50% ethyl acetate in hexanes as eluent. The desired fractions are concentrated under reduced pressure to afford 7-(5-chloro-2-hydroxyphenyl)thieno[3,2-b]pyridine-3-carbonitrile (5).

To a solution of 7-(5-chloro-2-hydroxyphenyl)thieno[3,2-b]pyridine-3-carbonitrile (5, 5.1 g, 17.78 mmol) in N,N-dimethylformamide (50.0 mL) is added sodium azide (5.8 g, 88.93 mmol) at room temperature and the reaction mixture is heated to 110° C. for 36 h. After completion, reaction mixture is concentrated to dryness under reduced pressure. The crude product obtained is triturated with n-pentane to afford 2-(3-(1H-tetrazol-5-yl)thieno[3,2-b]pyridin-7-yl)-4-chlorophenol (6).

Example 2C. General Coupling Methods

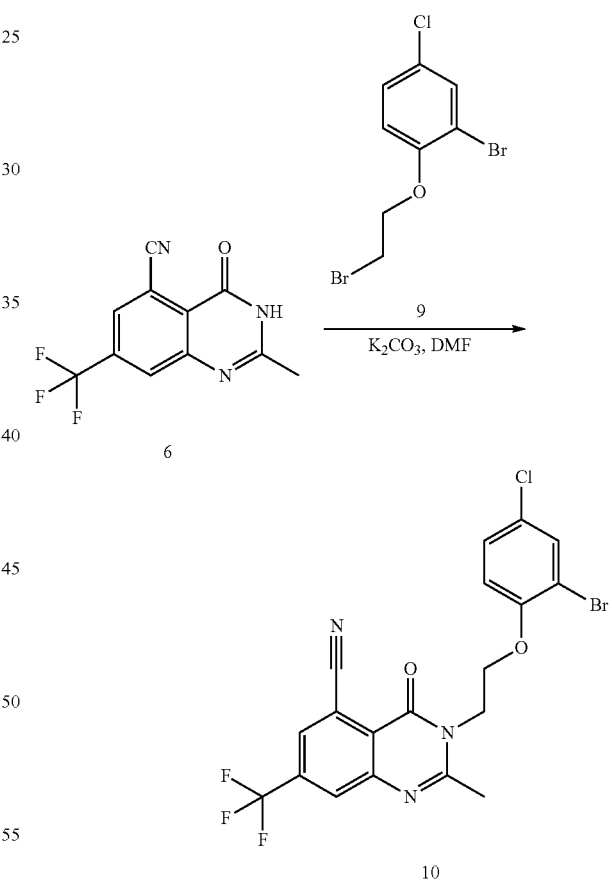

To a solution 2-methyl-4-oxo-7-(trifluoromethyl)-3,4-dihydroquinazoline-5-carbonitrile (6, 0.20 g, 0.79 mmol) in N,N-dimethylformamide (5 mL), potassium carbonate (0.33 g, 2.37 mmol) is added at room temperature. After 10 min, 2-bromo-1-(2-bromoethoxy)-4-chlorobenzene (9, 0.25 g, 0.79 mmol) is added and stirred for 16 h at room temperature. After completion, the reaction mixture is poured into water and extracted with ethyl acetate. Combined organic layer is washed with water, brine, dried over anhydrous sodium sulfate and concentrated under reduced pressure to get crude; the crude compound is purified by flash column chromatography (using 10-70% ethyl acetate in hexanes) to afford 3-(2-(2-bromo-4-chloro-phenoxy)ethyl)-2-methyl-4-oxo-7-(trifluoromethyl)-3,4-dihydroquinazoline-5-carbonitrile (10).

Example 2D. Post Coupling Modification Methods

Example 2D.1

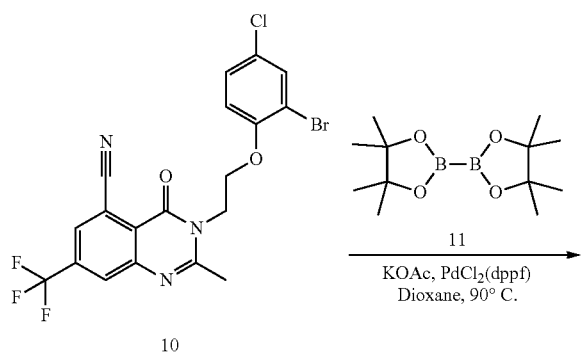

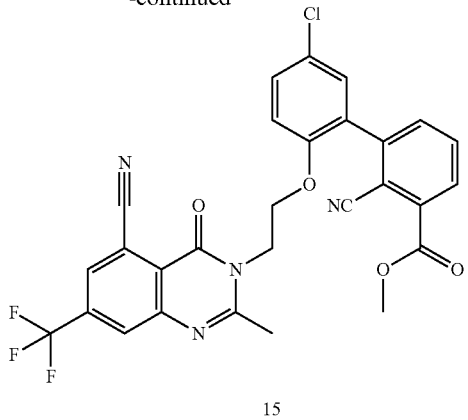

A solution of 3-(2-(2-bromo-4-chlorophenoxy)ethyl)-2-methyl-4-oxo-7-(trifluoromethyl)-3,4-dihydroquinazoline-5-carbonitrile (10, 1.8 g, 3.71 mmol), 4,4,4',4',5,5,5',5'-octamethyl-2,2'-bi(1,3,2-dioxaborolane) (11, 1.13 g, 4.45 mmol) and potassium acetate (0.73 g, 7.42 mmol) in 1,4-dioxane (35 mL) is degassed using argon gas for 10 min. 1,1'-Bis(diphenylphosphino)ferrocene-palladium(II)dichloride (0.217 g, 0.296 mmol) is added and the reaction mixture is degassed for another 10 min. The reaction mixture is heated and stirred at 90° C. for 6 h. After completion, the reaction mixture is diluted with water and extracted with ethyl acetate. The organic layer is dried over anhydrous sodium sulfate, filtered and concentrated to dryness under reduced pressure. The crude compound is purified by flash column chromatography 40% ethyl acetate in hexanes as eluent to afford 3-(2-(4-chloro-2-(4,4,5,5-tetramethyl-1,3,2-dioxaborolan-2-yl)phenoxy)ethyl)-2-methyl-4-oxo-7-(trifluoromethyl)-3,4-dihydroquinazoline-5-carbonitrile (12).

To a solution methyl 3-bromo-2-iodobenzoate (13, 2.0 g, 5.88 mmol) N,N-dimethylformamide (20 mL), copper(I) cyanide (0.58 g, 6.47 mmol) is added and heated at 60° C. for 4 h. After completion, the reaction mass is diluted with water (100 mL) and extracted with ethyl acetate. Combined organic layer are washed with water, brine, dried over anhydrous sodium sulfate and concentrated under reduced pressure to get crude. The crude compound is purified by flash column chromatography (using 0-10% ethyl acetate in hexane) to afford methyl 3-bromo-2-cyanobenzoate (14).

To a solution of 3-(2-(4-chloro-2-(4,4,5,5-tetramethyl-1,3,2-dioxaborolan-2-yl)phenoxy)ethyl)-2-methyl-4-oxo-7-(trifluoromethyl)-3,4-dihydroquinazoline-5-carbonitrile (12, 0.40 g, 0.75 mmol) and methyl 3-bromo-2-cyanobenzoate (14, 0.215 g, 0.90 mmol) in 1,4-dioxane (8 mL) and water (2 mL), potassium carbonate (0.313 g, 2.25 mmol) is added at room temperature. The reaction mass is degassed by purging argon gas through the reaction mass for 10 min. 1,1'-Bis(diphenylphosphino)ferrocene-palladium(II)dichloride (0.055 g, 0.075 mmol) is added under argon atmosphere, heated and stirred the reaction mixture at 90° C. for 3 h. After completion, the reaction mass is diluted with water, extracted with ethyl acetate; combined organic layer is washed with water, brine and dried over anhydrous sodium sulfate and concentrated under reduced pressure to get crude. The crude compound is purified by flash column chromatography (using 0-50% ethyl acetate in hexane) to afford methyl 5'-chloro-2-cyano-2'-(2-(5-cyano-2-methyl-4-oxo-7-(trifluoromethyl)quinazolin-3(4H)-yl)ethoxy)-[1,1'-biphenyl]-3-carboxylate (15).

Example 2D.2

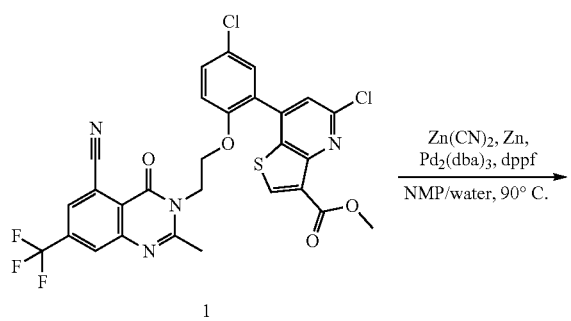

To a stirred solution of methyl 5-chloro-7-[5-chloro-2-[2-[5-cyano-2-methyl-4-oxo-7-(trifluoromethyl)quinazolin-3-yl]ethoxy]phenyl]thieno[3,2-b]pyridine-3-carboxylate (0.050 g, 0.079 mmol) in N-methyl-2-pyrrolidone and water (9:1, 2 mL) in a microwave vial, zinc cyanide (0.011 g, 0.095 mmol) and zinc dust (0.030 mg, 0.034 mmol) are added and the mixture is degassed with argon for 30 min. After adding 1,1'-bis(diphenylphosphino)ferrocene (0.0131 g, 0.023 mmol) and tris(dibenzylideneacetone)dipalladium (0) (10.8 mg, 0.012 mmol), the vial is sealed and then placed in a preheated heating block at 80° C. for 30 min. After completion of the reaction, the reaction mixture loaded on the Isco silica column. Purification by column chromatography eluting with 0 to 5% methanol/dichloromethane to afford methyl 7-(5-chloro-2-(2-(5-cyano-2-methyl-4-oxo-7-(trifluoromethyl)quinazolin-3(4H)-yl)ethoxy)phenyl)-5-cyanothieno[3,2-b]pyridine-3-carboxylate (2).

To a solution of methyl 7-(5-chloro-2-(2-(5-cyano-2-methyl-4-oxo-7-(trifluoromethyl)quinazolin-3(4H)-yl)ethoxy)phenyl)-5-cyanothieno[3,2-b]pyridine-3-carboxylate (2, 25.0 mg, 0.040 mmol) in 1,2-dichloroethane (2 mL), trimethyltin hydroxide (0.029 g, 0.160 mmol) is added at room temperature. The reaction mixture is heated at 90° C. for 16 h. After completion of the reaction, the organic solvent is evaporated and the crude is diluted with 50% dimethyl sulfoxide/methanol. The crude product is purified by prep-HPLC to afford 5-carbamoyl-7-(5-chloro-2-(2-(5-cyano-2-methyl-4-oxo-7-(trifluoromethyl)quinazolin-3(4H)-yl)ethoxy)phenyl)thieno[3,2-b]pyridine-3-carboxylic acid (Cpd. No. 445F).

Example 2D.3

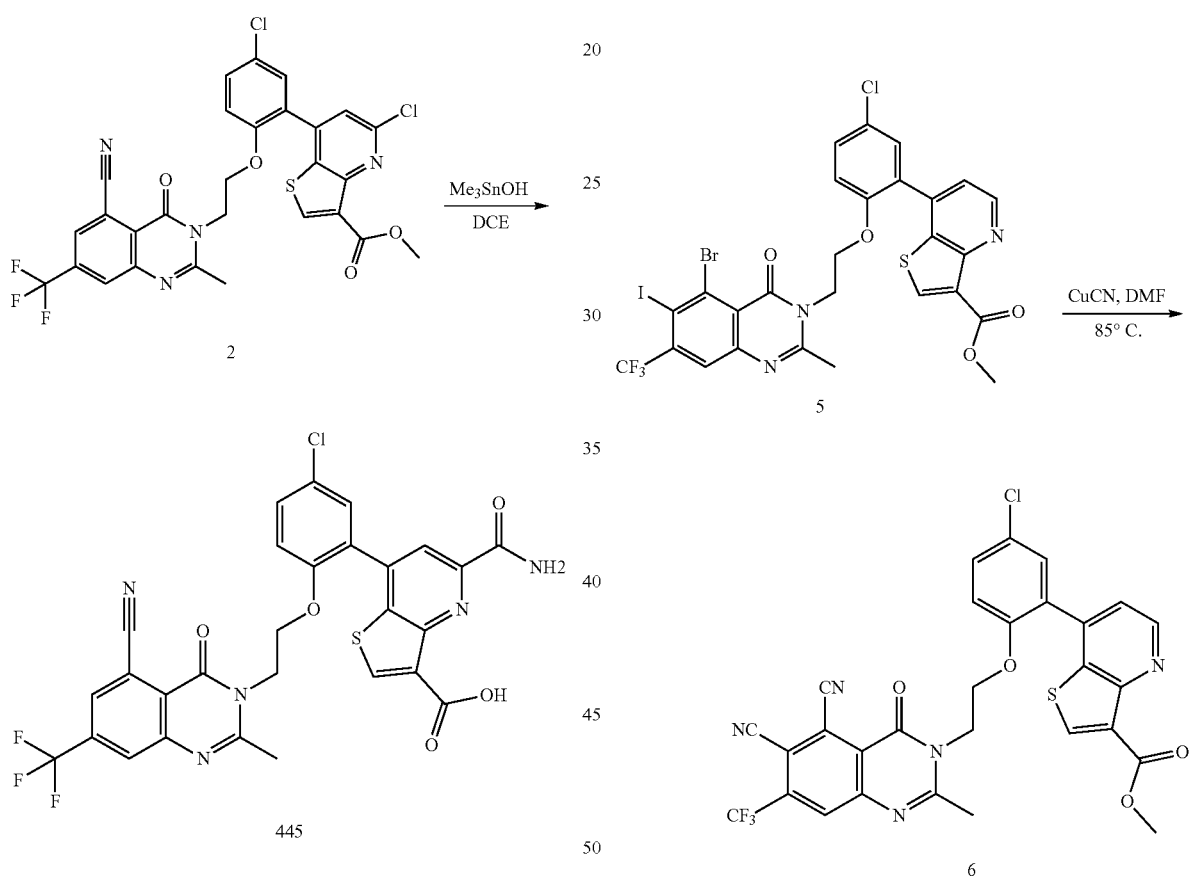

To a solution of methyl 7-(2-(2-(5-bromo-6-iodo-2-methyl-4-oxo-7-(trifluoromethyl)quinazolin-3(4H)-yl)ethoxy)-5-chlorophenyl)thieno[3,2-b]pyridine-3-carboxylate (5, 0.20 g, 0.256 mmol) in N,N-dimethylformamide is added copper(I) cyanide (0.069 g, 0.770 mmol) and stirred at 85° C. for 2 h. After completion, the reaction mixture is cooled to room temperature and poured into ice-water. The precipitate formed is collected by filtration and dried. The solid is dissolved in 10% methanol in dichloromethane and passed through Celite bed. The filtrate is concentrated under reduced pressure to afford methyl 7-(5-chloro-2-(2-(5, 6-dicyano-2-methyl-4-oxo-7-(trifluoromethyl)quinazolin-3(4H)-yl)ethoxy)phenyl)thieno[3,2-b]pyridine-3-carboxylate (6).

Example 2D.3

Example 2D.4

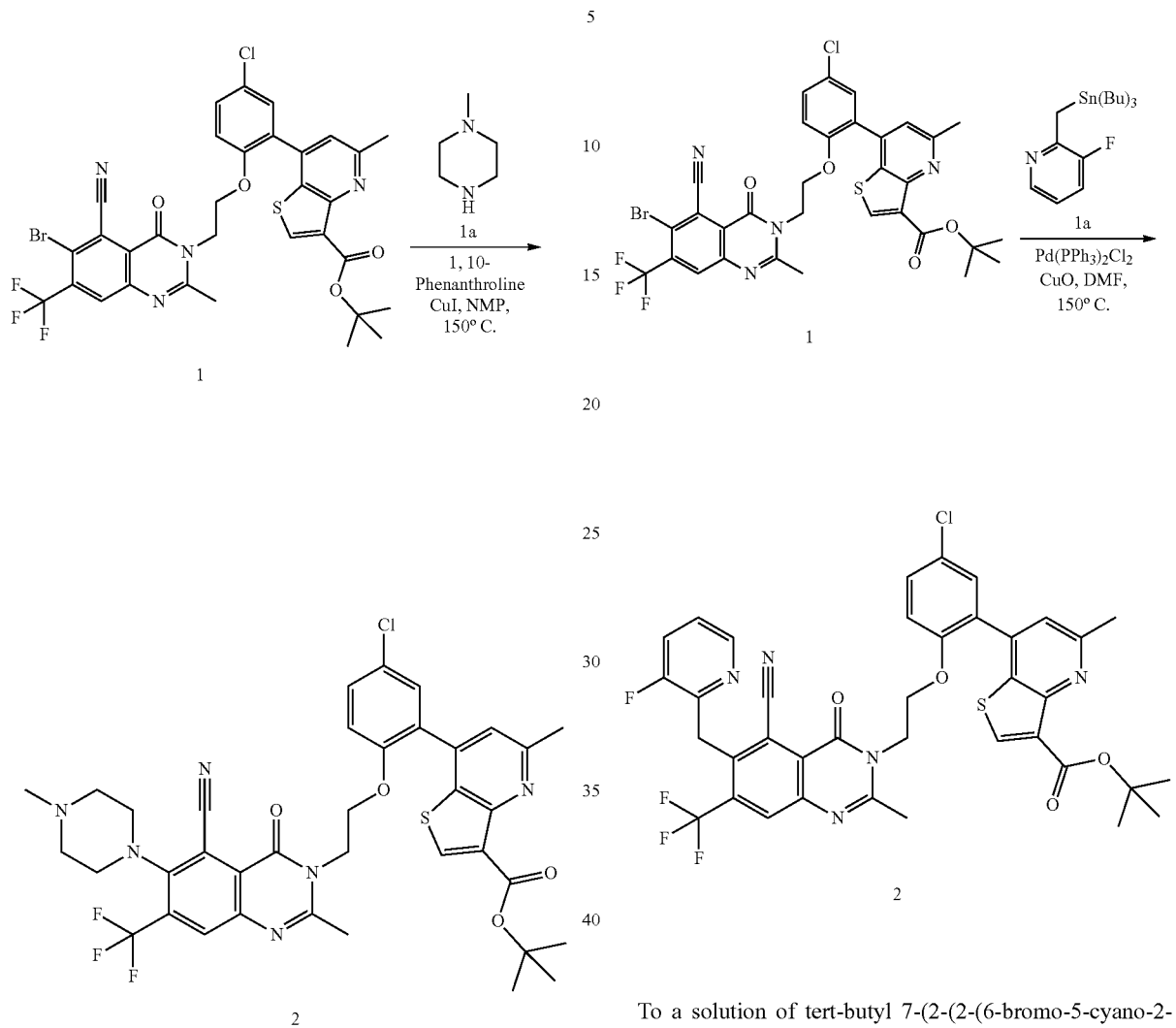

To a solution of tert-butyl 7-(2-(2-(6-bromo-5-cyano-2-methyl-4-oxo-7-(trifluoromethyl)quinazolin-3(4H)-yl)ethoxy)-5-chlorophenyl)-5-methylthieno[3,2-b]pyridine-3-carboxylate (1, 0.20 g, 0.273 mmol) in N-Methyl-2-pyrrolidone (5.0 mL) is added 1-methylpiperazine (1a, 0.06 mL, 0.546 mmol) and the reaction mixture is degassed by argon for 10 min. Then copper(I) iodide (0.005 g, 0.027 mmol) and 1,10-phenanthroline (0.009 g, 0.054 mmol) is added and reaction mixture is heated at 150° C. for 6 h. After completion reaction mixture is diluted with water and extracted with ethyl acetate. The organic layer is dried over anhydrous sodium sulphate, filtered and concentrated to get crude compound. Crude compound obtained is purified by column chromatography using silica gel (100-200 mesh) and 3-4% methanol in dichloromethane to afford tert-butyl 7-(5-chloro-2-(2-(5-cyano-2-methyl-6-(4-methylpiperazin-1-yl)-4-oxo-7-(trifluoromethyl)quinazolin-3(4H)-yl)ethoxy)phenyl)-5-methylthieno[3,2-b]pyridine-3-carboxylate (2).

To a solution of tert-butyl 7-(2-(2-(6-bromo-5-cyano-2-methyl-4-oxo-7-(trifluoromethyl)quinazolin-3(4H)-yl)ethoxy)-5-chlorophenyl)-5-methylthieno[3,2-b]pyridine-3-carboxylate (1, 50 mg, 0.0681 mmol) and 3-fluoro-2-((tributylstannyl)methyl)pyridine (1 a, 190 mg, 0.476 mmol) in N,N-dimethylformamide (2 mL), is added copper(II) oxide (11 mg, 0.136 mmol) at room temperature. The reaction mixture is purged with argon gas for 5 min, added bis(triphenylphosphine)palladium(II) dichloride (9.6 mg, 0.0136 mmol) and the vessel is then sealed, microwaved for 1 h at 150° C. After completion, the reaction mixture is then directly loaded on an Isco loading column. Purified by column chromatography using 5 to 80% ethyl acetate in hexane as eluent and product eluted around 60% ethylacetate/hexane. The desired fractions are concentrated under reduced pressure to afford tert-butyl 7-(5-chloro-2-(2-(5-cyano-6-((3-fluoropyridin-2-yl)methyl)-2-methyl-4-oxo-7-(trifluoromethyl)quinazolin-3(4H)-yl)ethoxy)phenyl)-5-methylthieno[3,2-b]pyridine-3-carboxylate (2).

Compounds made using one or more of the general methods described above are shown in Table 2. Where provided, characterization data is to the right of the compounds.

TABLE 2
7-CF3-Thienylpyridine and Derivative Compounds
| Compound | | Characterization |
|---|---|---|
| 51 | 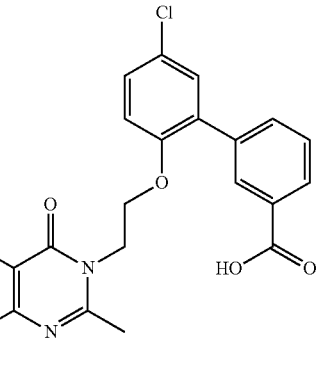 | MS (ESI) m/z 528.44 [M + 1]+; 1H NMR (400 MHz, DMSO-d6) δ 12.931 (s, 1H), 8.359 (s, 1H), 8.194 (s, 1H), 7.8409 (d, J = 11.6 Hz, 2H), 7.528 (d, J = 7.6 Hz, 1H), 7.412 (m, 2H), 7.278 (d, J = 2.6 Hz, 1H), 7.212 (d, J = 8.8 Hz, 1H), 4.359 (s, 4H), 2.208 (s, 3H) |
| 58 | 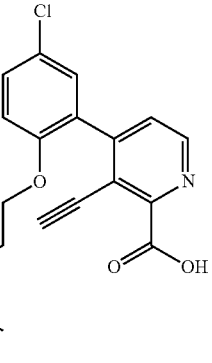 | MS (ESI) m/z 553.34 [M + 1]+; UPLC: 98.94%; 1H NMR (400 MHz, DMSO-d6) δ 8.44 (d, J = 3.96, 1H), 8.36 (s, 1H), 8.22 (s, 1H), 7.43 (dd, J = 2.48, 8.88 Hz, 1H), 7.23-7.18 (m, 3H), 4.33 (m, 4H), 4.03 (s, 1H), 2.09 (s, 3H) |
| 59 | 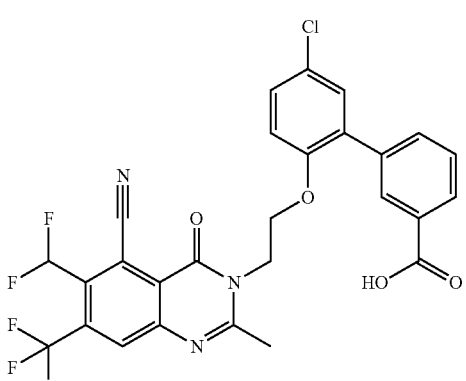 | MS (ESI) m/z 578.08 [M + 1]+; 1H NMR (400 MHz, DMSO-d6) δ 12.91 (s, 1H), 8.28 (s, 1H), 7.84-7.81 (m, 2H), 7.6-7.2 (m, 6H), 4.37 (s, 4H), 2.21 (s, 3H) |
| 60 | 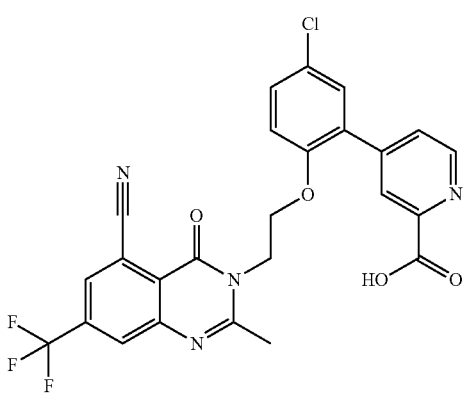 [SMILES: Cc1nc2cc(C(F)(F)F)cc(C#N)c2c(=O)n1CCOc1ccc(Cl)cc1-c1ccnc(C(=O)O)c1] | MS (ESI) m/z 527.02 [M + 1]−. 1H NMR (400 MHz, DMSO-d6) δ 8.63 (bs, 1H), 8.37 (s, 1H), 8.19 (s, 1H), 7.98 (bs, 1H), 7.61 (bs, 1H), 7.48 (d, J = 8.68 Hz, 1H), 7.42 (s, 1H), 7.26 (d, J = 8.92 Hz, 1H), 4.39 (s, 4H), 2.20 (s, 3H) |

TABLE 2-continued

7-CF3-Thienylpyridine and Derivative Compounds

| Compound | Characterization |
|---|---|
| 61 | MS (ESI) m/z 585.13 [M + 1]+; 1H NMR (400 MHz, DMSO-d6) δ 13.27 (s, 1H), 8.84 (d, J = 4.76, 1H), 8.37 (d, J = 0.96 Hz, 1H), 8.26 (s, 1H), 8.00 (s, 1H), 7.59 (dd, J = 2.64, 8.92 Hz, 1H), 7.48 (d, J = 4.76 Hz, 1H), 7.43 (d, J = 2.6 Hz, 1H), 7.36 (d, J = 8.96, 1H), 4.42-4.23 (m, 4H), 1.74 (s, 3H) |
| 65 | MS (ESI) m/z 621.17 [M + 1]+; 1H NMR (400 MHz, DMSO-d6) δ 8.7935 (d, J = 4.8 Hz, 1H), 8.568 (s, 1H), 8.338 (s, 1H), 8.236 (s, 1H), 7.610 (dd, J = 8.8 Hz, 1H), 7.487 (d, J = 4.8 Hz, 1H), 7.441 (d, J = 2.8 Hz, 1H), 7.372 (d, J = 9 Hz, 1H), 6.687-6.429 (m, 1H), 4.431-4.355 (m, 4H) |
| 120 | MS (ESI) m/z 579.15 [M + 1]+; 1H NMR (400 MHz, DMSO-d6) δ 8.75 (d, J = 4.48 Hz, 1H), 8.59 (s, 1H), 8.41 (s, 1H), 8.14 (s, 1H), 7.76 (d, J = 8.8 Hz, 1H), 7.69 (d, J = 6.04 Hz, 2H), 7.56 (d, J = 4.48 Hz, 1H), 4.88 (s, 2H), 2.10 (s, 3H) |
| 121 | MS (ESI) m/z 599.14 [M + 1]+; 1H NMR (400 MHz, DMSO-d6) δ 13.55 (s, 1H), 8.36 (s, 1H), 8.27 (s, 1H), 7.97 (s, 1H), 7.60-7.57 (dd, J = 2.52 Hz, 1H), 7.41 (s, 2H), 7.35 (d, J = 8.96 Hz, 1H), 4.40 (t, J = 4.6 Hz, J = 4.48 Hz, 2H), 4.25 (t, J = 4.04 Hz, J = 5.0 Hz, 2H), 2.69 (s, 3H), 1.81 (s, 3H) |

TABLE 2-continued

7-CF3-Thienylpyridine and Derivative Compounds

| Compound | Characterization |
|---|---|
| 122 | MS (ESI) m/z 601.98 [M + 1]+; 1H NMR (400 MHz, DMSO-d6) δ 12.93 (bs, 1H), 8.35 (s, 1H), 8.06 (s, 1H), 7.77 (s, 1H), 7.51 (dd, J = 8.88, 2.6 Hz, 1H), 7.29-7.22 (m, 4H), 4.35 (t, J = 4.4 Hz, 2H), 4.24 (t, J = 4.84 Hz, 2H), 1.77 (s, 3H) |
| 145 | MS (ESI) m/z 524.41 [M + 1]+; 1H NMR (400 MHz, DMSO-d6) δ 13.05 (s, 1H), 8.37 (s, 1H), 8.19 (s, 1H), 7.8480-7.726 (m, 3H), 7.4848-7.454 (m, 3H), 7.36 (s, 1H), 6.43 (d, J = 15.68 Hz, 1H), 6.15 (d, J = 15.68 Hz, 1H), 4.83 (d, J = 3.4 Hz, 2H), 2.56 (s, 3H) |
| 146 | MS (ESI) m/z 526.46 [M + 1]+; 1H NMR (400 MHz, DMSO-d6) δ 12.98 (bs, 1H), 8.35 (d, J = 1.36 Hz, 1H), 8.177 (s, 1H), 7.767 (s, 1H), 7.744 (s, 1H), 7.58-7.557 (m, 1H), 7.467-7.382 (m, 3H), 7.229 (d, J = 6.4 Hz, 1H), 3.933 (t, J = 7.04 Hz, 2H), 2.611 (t, J = 8.44 Hz, 2H), 2.447 (s, 3H), 1.768 (m, 2H) |
| 156 | MS (ESI) m/z 552.22 [M + 1]+; 1H NMR (400 MHz, DMSO-d6) δ 12.92 (bs, 1H), 8.34 (s, 1H), 8.18 (s, 1H), 7.83 (dd, J = 7.64, 1.0 Hz, 1H), 7.44-7.34 (m, 3H), 7.16-7.14 (m, 2H), 4.31 (bs, 4H), 3.73 (s, 1H), 1.98 (s, 3H) |

TABLE 2-continued

7-CF3-Thienylpyridine and Derivative Compounds

| Compound | Characterization |
|---|---|
| 158 | MS (ESI) m/z 572.49 [M + 1]+; 1H NMR (400 MHz, DMSO-d6) δ 13.15 (bs, 1H), 8.36 (s, 1H), 8.21 (s, 1H), 7.63 (s, 1H), 7.58 (d, J = 8 Hz, 1H), 7.51 (d, J = 7.6 Hz, 1H), 7.429-7.401 (dd, J = 2.4 Hz, J' = 8.72 Hz, 1H), 7.33 (d, J = 2.4 Hz, 1H), 7.21 (d, J = 8.8 Hz, 1H), 4.37 (s, 4H), 2.25 (s, 3H) |
| 159 | MS (ESI) m/z 538 [M + 1]+. 1H NMR (400 MHz, DMSO-d6) δ 8.43 (s, 1H), 8.29 (s, 1H), 8.01 (s, 1H), 7.59 (bs, 1H), 7.38-7.36 (m, 1H), 7.32-7.30 (m, 1H), 7.20 (d, J = 2.56 Hz, 2H), 7.16 (d, J = 8.76 Hz, 1H), 4.26 (s, 4H), 3.8 (s, 1H) |
| 162 | MS (ESI) m/z 515.10 [M + 1]+; 1H NMR (400 MHz, DMSO-d6) δ 8.63 (d, J = 5.04 Hz, 1H), 8.43 (d, J = 1.08 Hz, 1H), 8.27 (s, 1H), 8.23 (s, 1H), 8.03 (s, 1H), 7.67-7.65 (dd, J = 1.52, 4.96 Hz, 1H), 7.49 (d, J = 2.72 Hz, 1H), 7.47 (s, 1H), 7.25 (d, J = 9.28 Hz, 1H), 4.40-4.37 (m, 4H) |
| 164 | MS (ESI) m/z 571 [M + 1]; 1H NMR (400 MHz, DMSO-d6) δ 8.79 (s, 1H), 8.43 (d, J = 16.6 Hz, 2H), 8.11 (s, 1H), 7.79 (bs, 1H), 7.60 (s, 1H), 7.46 (m, 2H), 7.35 (m, 1H), 4.40 (s, 2H), 4.20 (s, 2H), 3.89 (s, 1H) |

TABLE 2-continued

7-CF3-Thienylpyridine and Derivative Compounds

| Compound | Characterization |
|---|---|
| 168 | MS (ESI) m/z 553.20 [M + 1]+. UPLC: 98.95%; 1H NMR (400 MHz, DMSO-d6) δ 13.65 (s, 1H), 8.37 (s, 1H), 8.19 (s, 1H), 8.08 (d, J = 7.68 1H), 7.78-7.76 (t, J = 7.76 Hz, 1H), 7.61 (d, J = 7.24 Hz, 1H), 7.49 (dd, J = 2.4, 8.84 Hz, 1H), 7.28 (d, J = 2.52 Hz, 1H), 7.25 (d, J = 8.92 Hz 1H), 4.32 (m, 4H), 1.95 (s, 3H) |
| 169 | MS (ESI) m/z 554.24 [M + 1]+; 1H NMR (400 MHz, DMSO-d6) δ 12.77 (bs, 1H), 8.36 (s, 1H), 8.17 (s, 1H), 7.71 (d, J = 7.32 Hz, 1H), 7.36-7.28 (m, 2H), 7.23 (d, J = 7.8 Hz, 1H), 7.10 (d, J = 9.56 Hz, 2H), 6.57-6.50 (q, J = 6.32, 11.64 Hz, 1H), 4.88 (d, J = 11.32 Hz, 1H), 4.64 (d, J = 17.52 Hz, 1H), 4.30 (s, 4H), 2.02 (s, 3H) |
| 181 | MS (ESI) m/z 603.04 [M + 1]+; 1H-NMR (400 MHz, DMSO-d6) δ 8.83 (s, 1H), 8.50 (s, 1H), 8.33 (s, 1H), 8.15 (s, 1H), 7.60-7.36 (m, 4H), 4.72 (d, J = 44 Hz, 2H), 4.39 (bs, 2H), 4.12 (bs, 2H) |
| 182 | MS (ESI) m/z 546.08 [M + 1]+; 1H NMR (400 MHz, DMSO-d6) δ 8.40 (s, 1H), 8.30 (s, 1H), 7.87-7.83 (m, 2H), 7.55 (d, J = 7.50 Hz, 1H), 7.45-7.39 (m, 2H), 7.30 (d, J = 2.48 Hz, 1H), 7.20 (d, J = 8.0 Hz, 1H), 5.10 (d, J = 45 Hz, 2H), 4.39 (bs, 4H) |

TABLE 2-continued

7-CF3-Thienylpyridine and Derivative Compounds

| Compound | | Characterization |
|---|---|---|
| 185 | 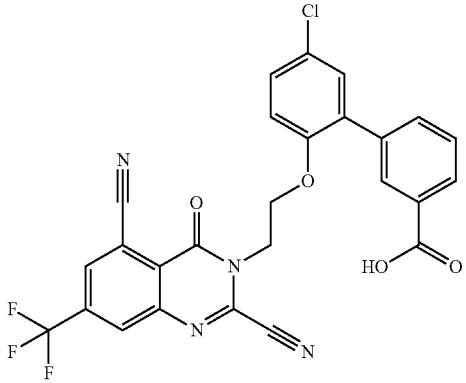 [SMILES: N#Cc1cc(C(F)(F)F)cc2nc(C#N)n(CCOc3ccc(Cl)cc3-c3cccc(C(=O)O)c3)c(=O)c12] | MS (ESI) m/z 539.07 [M + 1]+; 1H NMR (400 MHz, DMSO-d6) δ 12.82 (s, 1H), 8.60 (s, 1H), 8.50 (s, 1H), 7.87-7.71 (m, 2H), 7.53-7.51 (d, J = 8 Hz, 1H), 7.43-7.37 (m, 2H), 7.35-7.20 (m, 2H), 4.53 (t, J = 4 Hz, 2H), 4.39 (t, J = 4 Hz, 2H) |
| 186 | 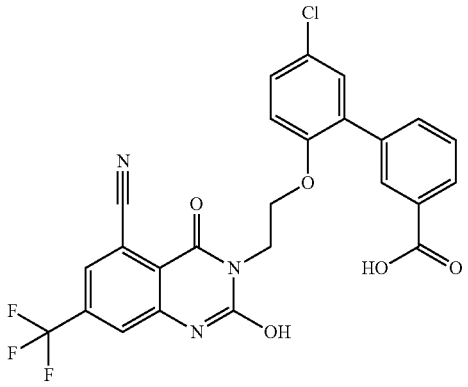 [SMILES: N#Cc1cc(C(F)(F)F)cc2nc(Cl)n(CCOc3ccc(Cl)cc3-c3cccc(C(=O)O)c3)c(=O)c12] | MS (ESI) m/z 530.11 [M + 1]+; 1H NMR (400 MHz, DMSO-d6) δ 12.43 (s, 1H), 8.08 (s, 1H), 7.88 (s, 1H), 7.73 (d, J = 7.2 Hz, 1H), 7.65 (s, 2H), 7.41-7.33 (m, 3H), 7.22 (d, J = 8.72, 1H), 4.30-4.27 (t, J = 6 Hz, 2H), 4.22-4.20 (t, J = 5.54 Hz, 2H) |
| 187 | 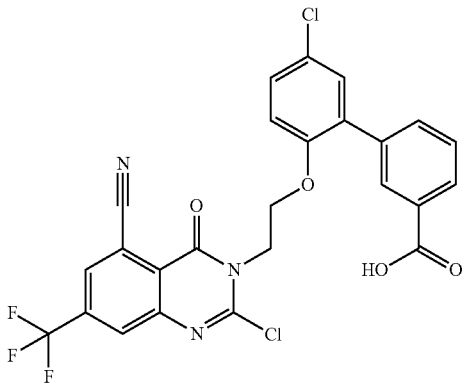 | MS (ESI) m/z 548.03 [M + 1]+; 1H NMR (400 MHz, DMSO-d6) δ 12.91 (s, 1H), 8.47 (s, 1H), 8.29 (s, 1H), 7.88 (s, 1H), 7.77 (d, J = 7.50 Hz, 1H), 7.59 (d, J = 7.90 Hz, 1H), 7.42-7.38 (m, 2H), 7.31 (d, J = 2.48 Hz, 1H), 7.22 (d, J = 9.0 Hz, 1H), 4.52 (d, J = 4.72 Hz, 2H), 4.38 (d, J = 4.8 Hz, 2H) |
| 199 | 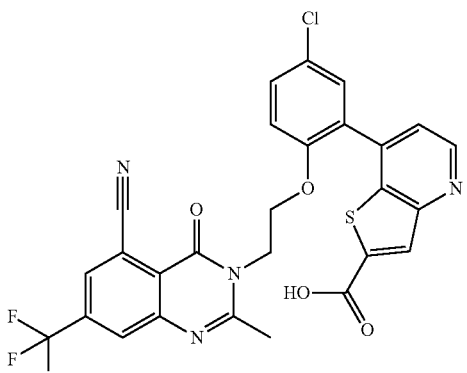 | MS (ESI) m/z 584.69 [M + 1]+; 1H NMR (400 MHz, DMSO-d6) δ 13.50 (s, 1H), 8.72 (d, 4.08 Hz, 1H), 8.29 (s, 1H), 8.08 (s, 1H), 7.70 (s, 1H), 7.58 (dd, J = 2.32, 8.52 Hz, 1H), 7.40 (d, J = 2.36 Hz, 1H), 7.35 (d, J = 8.96 Hz, 2H), 4.42 (s, 2H), 4.26 (s, 2H), 1.81 (s, 3H) |

TABLE 2-continued

7-CF3-Thienylpyridine and Derivative Compounds

| Compound | | Characterization |
|---|---|---|
| 201 | 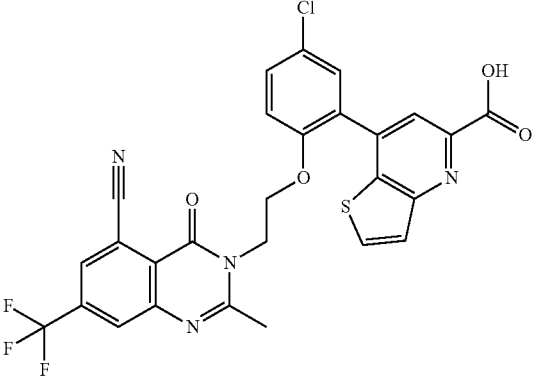 [SMILES: Cc1nc2cc(C(F)(F)F)cc(C#N)c2c(=O)n1CCOc1ccc(Cl)cc1-c1cc(C(=O)O)nc2ccsc12] | MS (ESI) m/z 585.16 [M + 1]+; 1H NMR (400 MHz, DMSO-d6) δ 14.04 (b, 1H), 8.30 (s, 1H), 8.25 (d, J = 5.56 Hz, 1H), 7.96 (d, J = 6.4 Hz, 2H), 7.60-7.58 (m, 2H), 7.50 (dd, J = 8.8 Hz, 1H), 7.30 (d, J = 8.84 Hz, 1H), 4.45 (t, J = 4.72 Hz, 2H), 4.36 (t, J = 4.6 Hz, 2H), 2.18 (s, 1H) |
| 202 | 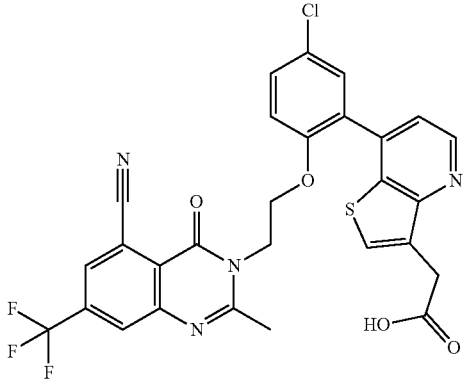 [SMILES: Cc1nc2cc(C(F)(F)F)cc(C#N)c2c(=O)n1CCOc1ccc(Cl)cc1-c1ccnc2c(CC(=O)O)csc12] | MS (ESI) m/z 599.18 [M + 1]+; 1H NMR (400 MHz, DMSO-d6) δ 12.41 (s, 1H), 8.66 (d, 4.56 Hz, 1H), 8.37 (s, 1H), 8.17 (s, 1H), 7.56 (m, 2H), 7.40 (d, J = 2.44 Hz, 1H), 7.33 (d, J = 9.04 Hz, 1H), 7.26 (d, J = 4.6 Hz, 1H), 4.38 (s, 2H), 4.25 (s, 2H), 3.84 (s, 2H), 1.78 (s, 3H) |
| 203 | 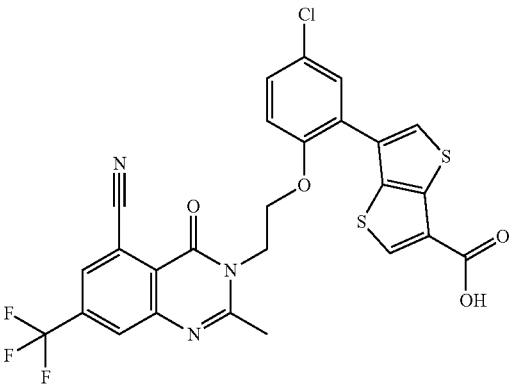 [SMILES: Cc1nc2cc(C(F)(F)F)cc(C#N)c2c(=O)n1CCOc1ccc(Cl)cc1-c1csc2c(C(=O)O)csc12] | MS (ESI) m/z 589.91 [M + 1]+; 1H NMR (400 MHz, DMSO-d6) δ 12.88 (s, 1H), 8.29 (s, 1H), 8.04 (s, 1H), 8.01 (s, 1H), 7.92 (s, 1H), 7.48-7.44 (m, 2H), 7.29 (d, J = 8.8 Hz, 1H), 4.50 (m, 2H), 4.25 (s, 2H), 2.08 (s, 3H) |
| 205 | 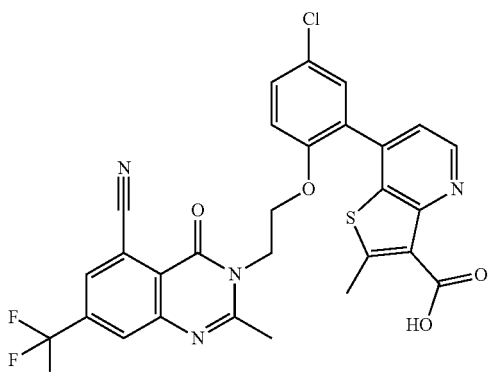 | MS (ESI) m/z 599.18 [M + 1]+; 1H NMR (400 MHz, DMSO-d6) δ 8.79 (d, J = 4.96 Hz, 1H), 8.38 (s, 1H), 7.98 (s, 1H), 7.60 (dd, J = 8.88, 2.6 Hz, 1H), 7.53 (d, J = 4.88 Hz, 1H), 7.43 (d, J = 2.56 Hz, 1H), 7.36 (d, J = 8.96 Hz, 1H), 4.43 (s, 2H), 4.27 (s, 2H), 2.34 (s, 3H), 1.85 (s, 3H) |

TABLE 2-continued
7-CF3-Thienylpyridine and Derivative Compounds
| Compound | Characterization |
|---|---|
| 206 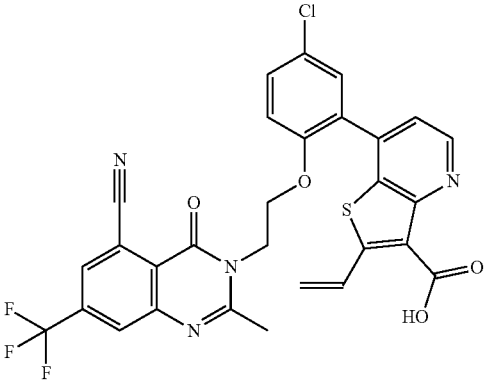 | MS (ESI) m/z 619.24 [M + 1]+; 1H NMR (400 MHz, DMSO-d6) δ 8.82 (d, J = 4.64 Hz, 1H), 8.36 (s, 1H), 8.07 (s, 1H), 7.60 (d, J = 8.84 Hz, 1H), 7.52 (d, J = 4.4 Hz, 1H), 7.41 (s, 1H), 7.34 (d, J = 8.92 Hz, 1H), 4.44 (s, 2H), 4.28 (s, 2H), 1.81 (s, 3H) |
| 210 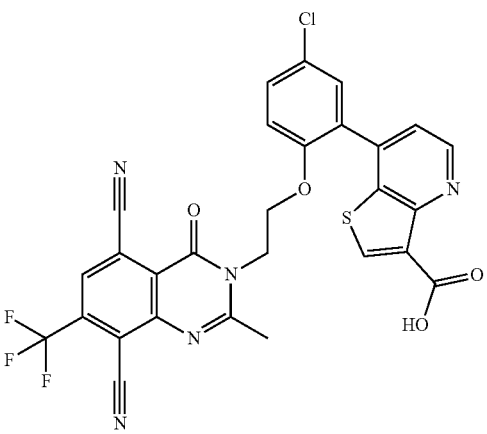 [SMILES: Cc1nc2c(C#N)c(C(F)(F)F)cc(C#N)c2c(=O)n1CCOc1ccc(Cl)cc1-c1ccnc2c(C(=O)O)csc12] | MS (ESI) m/z 610.15 [M + 1]+; 1H NMR (400 MHz, DMSO-d6) δ 13.16 (s, 1H), 8.82 (d, J = 4.64 Hz, 1H), 8.41 (d, J = 9.8 Hz, 2H), 7.6 (dd, J = 8.92, 2.48 Hz, 1H), 7.45 (dd, J = 9.68, 4.72 Hz, 2H), 7.37 (d, J = 8.88 Hz, 1H), 4.42 (t, J = 5.04 Hz , 2H), 4.27 (t, J = 5.2 Hz, 2H), 1.96 (s, 3H) |
| 214 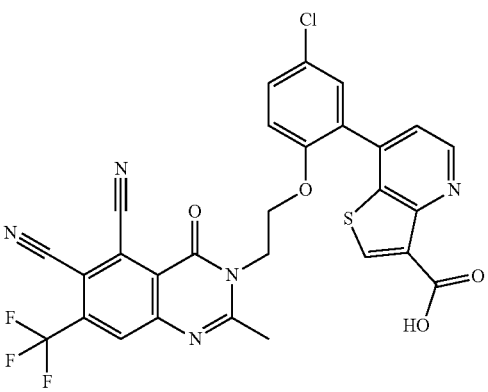 [SMILES: Cc1nc2cc(C(F)(F)F)c(C#N)c(C#N)c2c(=O)n1CCOc1ccc(Cl)cc1-c1ccnc2c(C(=O)O)csc12] | MS (ESI) m/z 609.05 [M + 1]+; 1H NMR (400 MHz, DMSO-d6) δ 13.16 (bs, 1H), 8.86 (d, J = 4.6 Hz, 1H), 8.16 (s, 1H), 8.11 (s, 1H), 7.60 (d, J = 8.96 Hz, 1H), 7.49 (d, J = 4.44 Hz, 1H), 7.42 (s, 1H), 7.36 (d, J = 9.04 Hz, 1H), 4.42 (bs, 2H), 4.28 (bs, 2H), 1.74 (s, 3H) |

TABLE 2-continued

7-CF3-Thienylpyridine and Derivative Compounds

| Compound | Characterization |
|---|---|
| 215 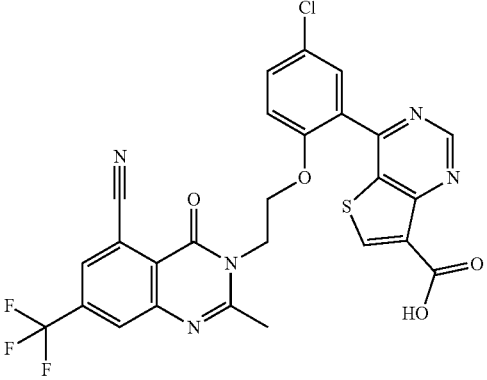 [SMILES: Cc1nc2cc(C(F)(F)F)cc(C#N)c2c(=O)n1CCOc1ccc(Cl)cc1-c1ncnc2c(C(=O)O)csc12] | MS (ESI) m/z 585 [M + 1]+; 1H NMR (400 MHz, DMSO-d6) δ 13.10 (bs, 1H), 9.33 (s, 1H), 8.38 (s, 2H), 7.98 (s, 1H), 7.64 (dd, J = 8.8, 2.4 Hz, 1H), 7.45 (d, J = 2.4 Hz, 1H), 7.38 (d, J = 9.2 Hz, 1H), 4.45 (s, 2H), 4.27 (s, 2H), 1.77 (s, 3H) |
| 225 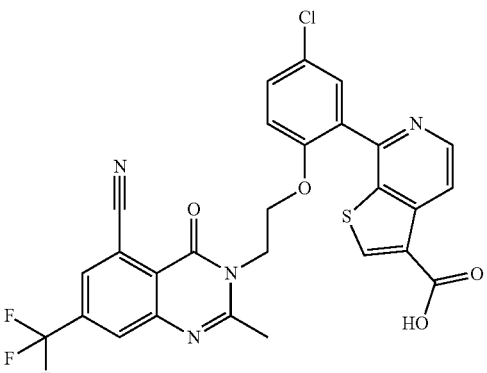 | MS (ESI) m/z 585.16 [M + 1]+; 1H NMR (400 MHz, DMSO-d6) δ 13.19 (s, 1H), 8.59 (d, J = 5.56 Hz, 1H), 8.35-8.32 (m, 2H), 8.05 (s, 1H), 7.93 (s, 1H), 7.55 (dd, J = 9.0, 2.56 Hz, 1H), 7.33-7.30 (m, 1H), 4.38 (s, 2H), 4.22 (s, 2H), 1.69 (s, 3H) |
| 226 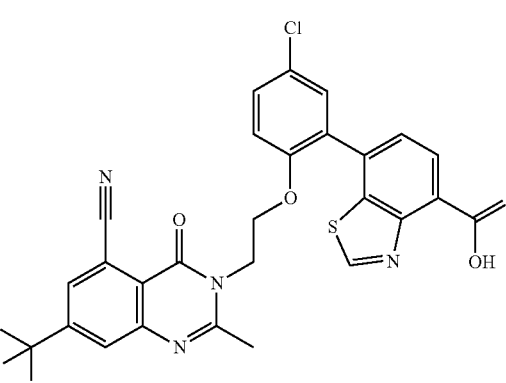 | MS (ESI) m/z 585.39 [M + 1]+; 1H NMR (400 MHz, DMSO-d6) δ 13.54 (s, 1H), 8.38 (s, 1H), 8.18 (s, 1H), 7.97 (t, J = 6.30 Hz, 2H), 7.55-7.52 (dd, J = 2.24, 2.32 Hz, 1H), 7.46 (d, J = 7.8 Hz, 1H), 7.30-7.25 (m, 2H), 4.45-4.29 (m, 4H), 1.98 (s, 3H) |
| 227 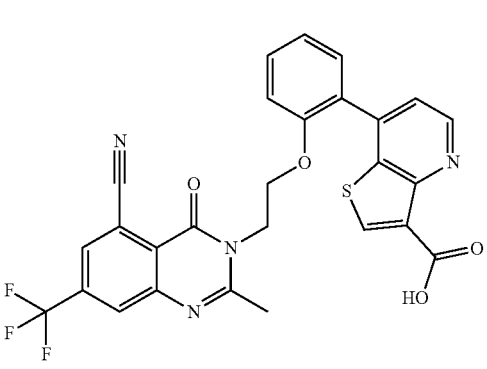 [SMILES: Cc1nc2cc(C(F)(F)F)cc(C#N)c2c(=O)n1CCOc1ccccc1-c1ccnc2c(C(=O)O)csc12] | MS (ESI) m/z 551.14 [M + 1]+; 1H NMR (400 MHz, DMSO-d6) δ 8.83 (d, J = 4.96 Hz, 1H), 8.38 (s, 1H), 8.32 (s, 1H), 8.01 (s, 1H), 7.55 (t, J = 7.16 Hz, 1H), 7.50 (d, J = 4.48 Hz, 1H), 7.34 (t, J = 5.6 Hz, 2H), 7.16 (t, J = 7.40 Hz, 1H), 4.41 (s, 2H), 4.27 (s, 2H), 1.80 (s, 3H) |

TABLE 2-continued

7-CF3-Thienylpyridine and Derivative Compounds

| Compound | Characterization |
|---|---|
| 246 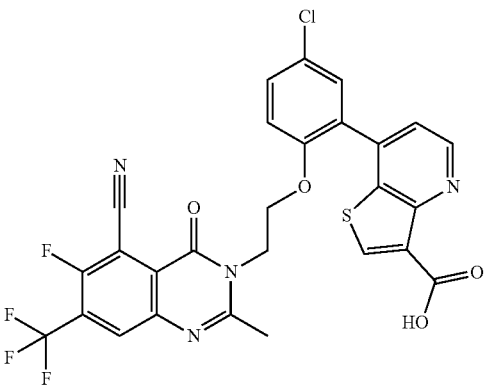 [SMILES: Cc1nc2cc(C(F)(F)F)c(F)c(C#N)c2c(=O)n1CCOc1ccc(Cl)cc1-c1ccnc2c(C(=O)O)csc12] | MS (ESI) m/z 603.15 [M + 1]+; 1H NMR (400 MHz, DMSO-d6) δ 8.77 (d, J = 4.84 Hz, 1H), 8.64 (s, 1H), 8.40 (d, J = 9.16 Hz, 1H), 7.60 (dd, J = 8.92 Hz, 2.6 Hz, 1H), 7.49 (d, J = 4.84 Hz, 1H), 7.45 (d, J = 2.6 Hz, 1H), 7.37 (d, J = 8.96 Hz, 1H), 4.44 (t, J = 4.8 Hz, 2H), 4.29 (t, J = 4.64 Hz, 2H), 1.99 (s, 3H) |
| 255 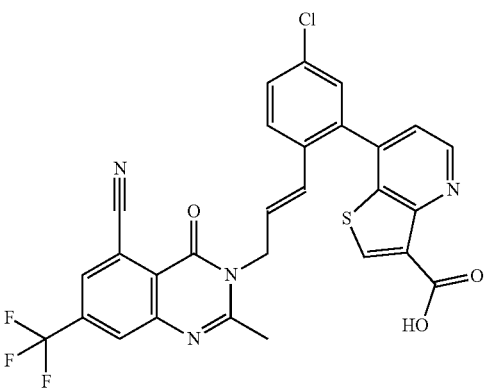 [SMILES: Cc1nc2cc(C(F)(F)F)cc(C#N)c2c(=O)n1C/C=C/c1ccc(Cl)cc1-c1ccnc2c(C(=O)O)csc12] | MS (ESI) m/z 581.20 [M + 1]+; 1H NMR (400 MHz, DMSO-d6) δ 13.16 (bs, 1H), 8.83 (s, 1H), 7.77 (d, J = 4.4 Hz, 1H), 8.35 (s, 1H), 8.14 (s, 1H), 7.87 (d, J = 8.8 Hz, 1H), 7.61 (d, J = 8.4 Hz, 1H), 7.53 (s, 1H), 7.42 (d, J = 4.4 Hz, 1H), 6.50-6.44 (m, 1H), 5.98 (d, J = 16.0, 1H), 4.73 (d, J = 4.0, 2H), 2.38 (s, 3H) |
| 259 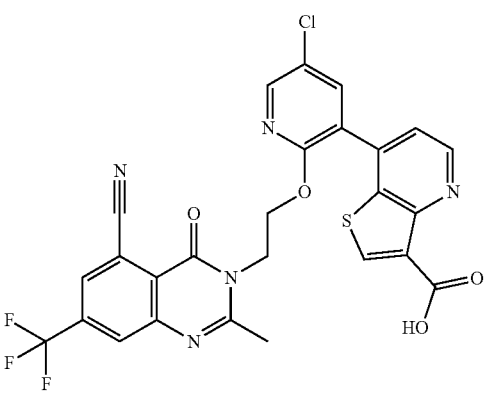 [SMILES: Cc1nc2cc(C(F)(F)F)cc(C#N)c2c(=O)n1CCOc1ncc(Cl)cc1-c1ccnc2c(C(=O)O)csc12] | MS (ESI) m/z 586.14 [M + 1]+; 1H NMR (400 MHz, DMSO-d6) δ 8.91 (s, 1H), 8.80 (d, J = 4.92 Hz, 1H), 8.39 (d, J = 1.12 Hz, 1H), 8.35 (d, J = 2.80 Hz, 1H), 8.25 (s, 1H), 7.98 (d, J = 2.80 Hz, 1H), 7.49 (d, J = 4.88 Hz, 1H), 4.53 (t, J = 5.4 Hz, 2H), 4.41 (t, J = 5.2 Hz, 2H), 2.62 (s, 3H) |
| 261 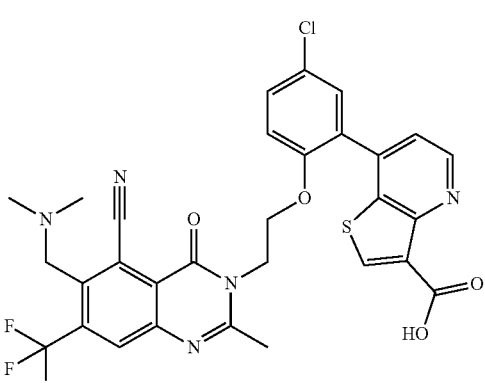 | MS (ESI) m/z 644.23 [M + 1]+; 1H NMR (400 MHz, DMSO-d6) δ 8.83-8.79 (m, 3H), 8.29 (s, 1H), 8.22 (s, 1H), 7.93 (s, 1H), 7.84 (d, J = 5.68 Hz, 2H), 7.59 (dd, J = 2.56, J = 8.84 Hz, 1H), 7.51 (d, J = 4.8 Hz, 1H), 7.44 (d, J = 2.60 Hz, 1H), 7.34 (d, J = 8.96 Hz, 1H) 4.38 (t, J = 5.76 Hz, 2H), 4.22 (t, J = 4.60 Hz, 2H), 1.69 (s, 3H) |

TABLE 2-continued

7-CF3-Thienylpyridine and Derivative Compounds

| | Compound | Characterization |
|---|---|---|
| 265 | | MS (ESI) m/z 591.15 [M + 1]+; 1H NMR (400 MHz, DMSO-d6) δ 12.98 (bs, 1H), 8.9 (s, 1H), 8.28 (s, 1H), 8.16 (s, 1H), 7.68 (d, J = 2.4 Hz, 1H), 7.6 (dd, J = 8.8, 2.3 Hz, 1H), 7.5 (d, J = 9.0 Hz, 1H), 4.76 (t, J = 5.2 Hz, 2H), 4.57 (t, J = 3.6 Hz, 2H), 2.56 (s, 3H) |
| 266 | | MS (ESI) m/z 619.24 [M + 1]+; 1H NMR (400 MHz, DMSO-d6) δ 8.82 (d, J = 4.64 Hz, 1H), 8.36 (s, 1H), 8.07 (s, 1H), 7.60 (d, J = 8.84 Hz, 1H), 7.52 (d, J = 4.4 Hz, 1H), 7.41 (s, 1H), 7.34 (d, J = 8.92 Hz, 1H), 4.44 (s, 2H), 4.28 (s, 2H), 1.81 (s, 3H) |
| 267 | | MS (ESI) m/z 609.20 [M + 1]+; 1H NMR (400 MHz, DMSO-d6) δ 13.04 (bs, 1H), 8.88 (d, J = 4.8 Hz, 1H), 8.30 (d, J = 1.2 Hz, 1H), 8.03 (d, J = 1.4 Hz, 1H), 7.61-7.56 (m, 2H), 7.42 (d, J = 2.8 Hz, 1H), 7.35 (d, J = 8.8 Hz, 1H), 4.91 (s, 1H), 4.44 (t, J = 4.4 Hz, 2H), 4.26 (d, J = 4.4 Hz, 2H), 1.73 (s, 3H) |
| 27 | | MS (ESI) m/z 586.17 [M + 1]+. 1H NMR (400 MHz, DMSO-d6) δ 13.95 (bs, 1H), 8.98 (d, J = 4.4 Hz, 1H), 8.38 (s, 1H), 8.11 (s, 1H), 7.66 (d, J = 4.0 Hz, 1H), 7.60 (d, J = 9.6 Hz, 1H) 7.49 (s, 1H), 7.36 (d, J = 9.2 Hz, 1H), 4.45 (s, 2H), 4.28 (s, 2H), 1.74 (s, 3H) |

TABLE 2-continued
7-CF3-Thienylpyridine and Derivative Compounds
| Compound | Characterization |
|---|---|
| 275 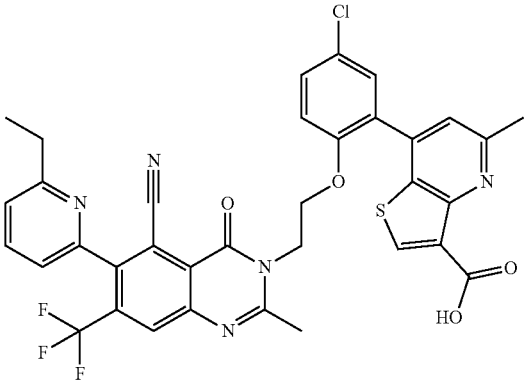 | MS (ESI) m/z 601.13 [M + 1]+; 1H NMR (400 MHz, DMSO-d6) 8.85 (d, J = 4.80 Hz, 1H), 8.39 (s, 1H), 7.89 (s, 1H), 7.60 (dd, J = 8.88, 2.36 Hz, 1H), 7.50 (d, J = 4.80 Hz, 1H), 7.42 (d, J = 2.44 Hz, 1H), 7.35 (d, J = 8.96 Hz, 1H), 4.40 (t, J = 5.28 Hz, 2H). 4.23 (t, J = 4.40 Hz, 2H), 1.71 (s, 3H) |
| 285 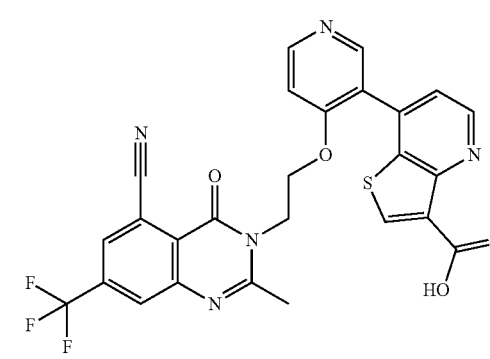 | MS (ESI) m/z 552.20 [M + 1]+; 1H NMR (400 MHz, DMSO-d6) δ 8.91 (d, J = 4.8 Hz, 1H), 8.79 (d, J = 6.2 Hz, 1H), 8.64 (s, 1H), 8.40 (s, 1H), 8.34 (s, 1H), 8.05 (s, 1H), 7.61 (d, J = 3.1 Hz, 1H), 7.55 (d, J = 4.7 Hz, 1H), 4.62 (t, J = 4.2 Hz, 2H), 4.31 (t, J = 4.7 Hz, 2H), 1.75 (s, 3H) |
| 287 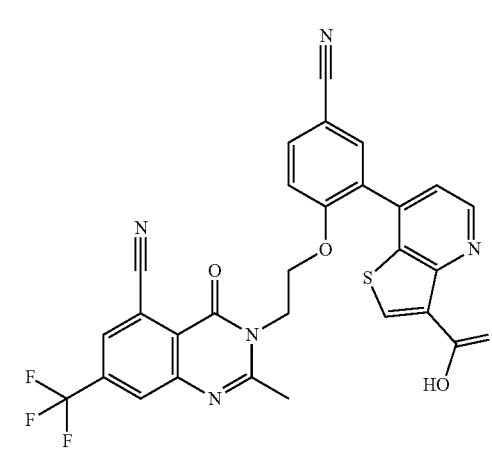 | MS (ESI) m/z 576.26 [M + 1]+; 1H NMR (400 MHz, DMSO-d6) δ 13.28 (bs, 1H), 8.84 (d, J = 4.8 Hz, 1H), 8.38 (s, 1H), 8.26 (s, 1H), 8.05 (dd, J = 8.6, 2.0 Hz, 1H), 8.01 (s, 1H), 7.89 (d, J = 2.0 Hz, 1H), 7.52 (d, J = 3.4 Hz, 1H), 7.5 (s, 1H), 4.51 (t, J = 4.8 Hz, 2H), 4.26 (t, J = 5.9 Hz, 2H), 1.7 (s, 3H) |

TABLE 2-continued
7-CF3-Thienylpyridine and Derivative Compounds
| Compound | Characterization |
| --- | --- |
| 289 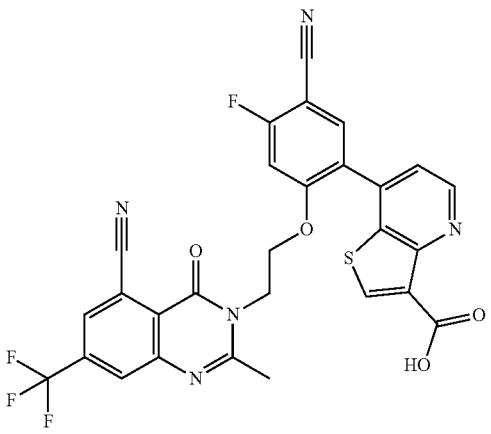 [SMILES: Cc1nc2cc(C(F)(F)F)cc(C#N)c2c(=O)n1CCOc1cc(F)c(C#N)cc1-c1ccnc2c(C(=O)O)csc12] | MS (ESI) m/z 594.14 [M + 1]+; 1H NMR (400 MHz, DMSO-d6) δ 8.85 ( d, J = 4.5 1H), 8.39 (s, 1H), 8.28 (s, 1H), 8.00 (d, J = 8.52, 2H), 7.63 (d, J = 11.4 Hz, 1H), 7.49 (d, J = 4.28 Hz, 1H), 4.527 (s, 2H), 4.26 (s, 2H), 1.683 (s, 3H) |
| 291 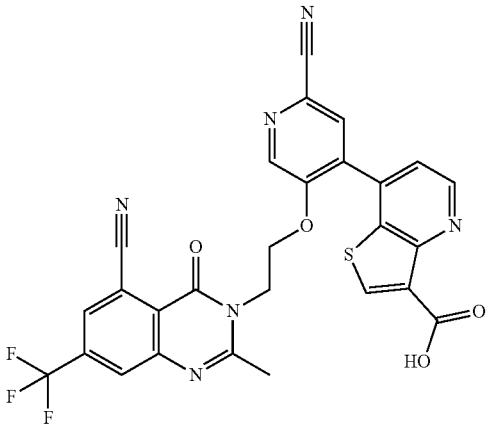 [SMILES: Cc1nc2cc(C(F)(F)F)cc(C#N)c2c(=O)n1CCOc1cnc(C#N)cc1-c1ccnc2c(C(=O)O)csc12] | MS (ESI) m/z 577.06 [M + 1]+; 1H NMR (400 MHz, DMSO-d6) δ 13.15 (s, 1H), 8.91 (d, J = 4.72 Hz, 1H), 8.87 (s, 1H), 8.39 (s, 1H), 8.35 (s, 1H), 8.17 (s, 1H), 8.05 (s, 1H), 7.54 (d, J = 4.72 Hz, 1H), 4.66 (s, 2H), 4.27 (s, 2H), 1.79 (s, 3H) |
| 292 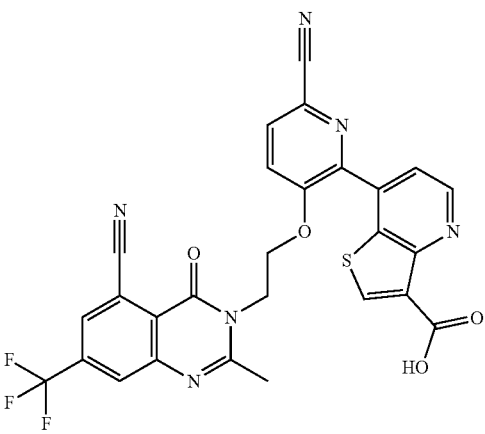 [SMILES: Cc1nc2cc(C(F)(F)F)cc(C#N)c2c(=O)n1CCOc1ccc(C#N)nc1-c1ccnc2c(C(=O)O)csc12] | MS (ESI) m/z 577.0 [M + 1]+; 1H NMR (400 MHz, DMSO-d6) δ 8.88 (s, 1H), 8.87 (s, 1H), 8.38 (s, 1H), 8.27 (d, J = 8.7 Hz, 1H), 8.22 (s, 1H), 8.1 (d, J = 4.9 Hz, 1H), 8.04 (d, J = 8.7 Hz, 1H), 4.68 (t, J = 4.2 Hz, 2H), 4.55 (t, J = 4.4 Hz, 2H), 2.37 (s, 3H) |

TABLE 2-continued

7-CF3-Thienylpyridine and Derivative Compounds

| Compound | Characterization |
|---|---|
| 294 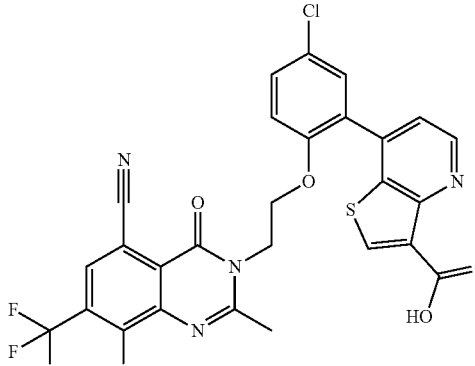 | MS (ESI) m/z 603.17 [M + 1]+; 1H NMR (400 MHz, DMSO-d6) δ 8.82 (d, J = 4.84 Hz, 1H), 8.45 (s, 1H), 8.37 (d, J = 5.28 Hz, 1H), 7.60 (dd, J = 8.56, 6.72, Hz, 1H), 7.49 (d, J = 4.56 Hz 1H), 7.43 (d, J = 2.04 Hz, 1H), 7.37 (d, J = 8.88 Hz, 1H), 4.42 (t, J = 4.90, 2H), 4.27 (t, J = 4.40 Hz, 2H), 1.86 (s, 3H) |
| 295 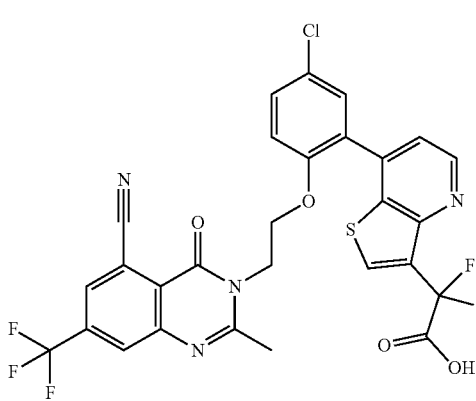 | MS (ESI) m/z 634.99 [M + 1]+; 1H NMR (400 MHz, DMSO-d6), 68.76 (d, J = 2.68 Hz 1H), 8.35 (s, 1H), 8.10 (s, 1H), 7.74 (s, 1H), 7.58 (dd, J = 9.24, 2.81 Hz, 1H), 7.42 (d, J = 2.80 Hz, 1H), 7.40 (d, J = 4.40 Hz, 1H), 7.34 (d, J = 8.96 Hz, 1H), 4.45-4.37 (m, 2H), 4.30-4.22 (m, 2H), 1.82 (s, 3H) |
| 296 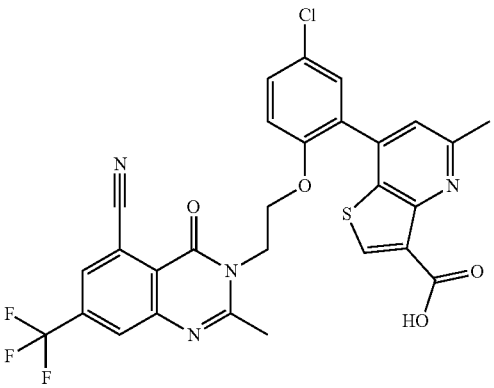 [SMILES: Cc1cc(-c2cc(Cl)ccc2OCCn2c(C)nc3cc(C(F)(F)F)cc(C#N)c3c2=O)c2scc(C(=O)O)c2n1] | MS (ESI) m/z 599.14 [M + 1]+; 1H NMR (400 MHz, DMSO-d6) δ 13.55 (s, 1H), 8.36 (s, 1H), 8.27 (s, 1H), 7.97 (s, 1H), 7.60-7.57 (dd, J = 2.52, 8.8 Hz, 1H), 7.41 (m, 2H), 7.35 (d, J = 8.96 Hz, 1H), 4.40 (t, J = 5 Hz, 2H), 4.25 (t, J = 5.0 Hz, 2H), 2.69 (s, 3H), 1.82 (s, 3H) |
| 299 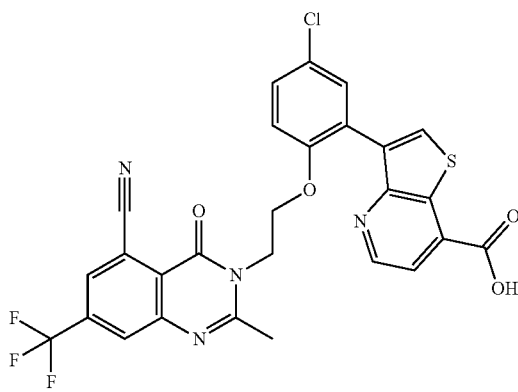 [SMILES: Cc1nc2cc(C(F)(F)F)cc(C#N)c2c(=O)n1CCOc1ccc(Cl)cc1-c1csc2c(C(=O)O)ccnc12] | MS (ESI) m/z 585.17 [M + 1]+. 1H NMR (400 MHz, DMSO-d6) δ 14.22 (bs, 1H), 8.37 (s, 1H), 8.34 (d, J = 4.8 Hz, 1H), 8.18 (s, 1H), 7.98 (s, 1H), 7.47-7.44 (m, 2H), 7.38 (d, J = 2.4 Hz, 1H), 7.25 (d, J = 9.2 Hz, 1H), 4.34 (t, 4.8 Hz, 2H), 4.25 (t, J = 4.4 Hz, 2H), 1.97 (s, 3H) |

TABLE 2-continued

7-CF3-Thienylpyridine and Derivative Compounds

| Compound | | Characterization |
|---|---|---|
| 300 | 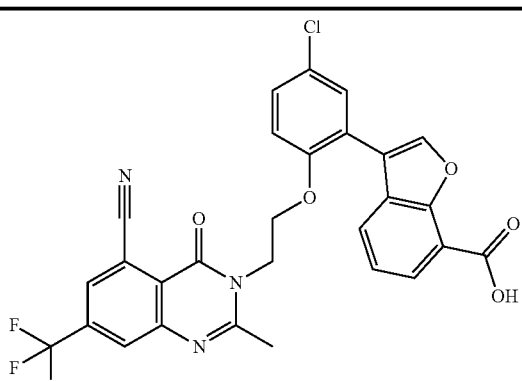 | MS (ESI) m/z 568.19 [M + 1]+; 1H NMR (400 MHz, DMSO-d6) δ 13.19 (s, 1H), 8.33 (s,1H), 8.20 (s, 1H), 8.06 (s, 1H), 7.61 (d, J = 7.28 Hz, 1H), 7.51 (d, J = 7.56 Hz, 1H), 7.47 (d, J = 2.32 Hz, 1H), 7.43 (d, J = 2.2 Hz, 1H), 7.28 (d, J = 8.8 Hz, 1H), 6.97 (t, J = 7.56 Hz, 1H,), 4.43 (s, 2H), 4.32 (s,2H), 2.10 (s, 3H) |
| 301 | 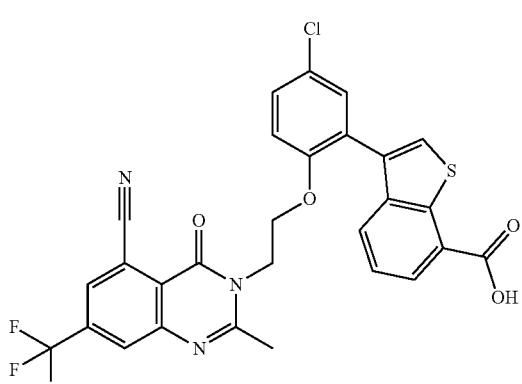 | MS (ESI) m/z 583.99 [M + 1]+; 1H NMR (400 MHz, DMSO-d6) δ 13.46 (bs, 1H), 8.35 (s, 1H), 7.94 (s, 1H), 7.79 (s, 1H), 7.55 (d, J = 7.32 Hz, 1H), 7.49 (dd, J = 8.80, 2.68 Hz, 1H), 7.32-7.27 (m, 3H), 6.89 (t, J = 7.64 Hz, 1H), 4.30 (t, J = 5.08 Hz, 2H), 4.16 (t, J = 5.12 Hz, 2H), 1.92 (s, 3H) |
| 314 | 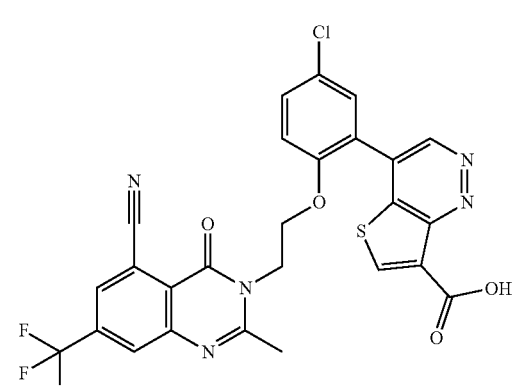 | MS (ESI) m/z 585.94 [M + 1]+; 1H NMR (400 MHz, DMSO-d6) δ 13.25 (s, 1H), 9.18 (s, 1H), 8.33 (s, 1H), 8.24 (s, 1H), 7.97 ( s, 1H), 7.62 (dd, J = 8.8, 2.7 Hz, 1H), 7.49 (d, J = 2.32 Hz, 1H), 7.36 (d, J = 9.0 Hz, 1H), 4.44 (t, J = 4.96 Hz, 2H), 4.27 (t, J = 4.96 Hz, 2H), 1.71 (s, 3H) |
| 315 | 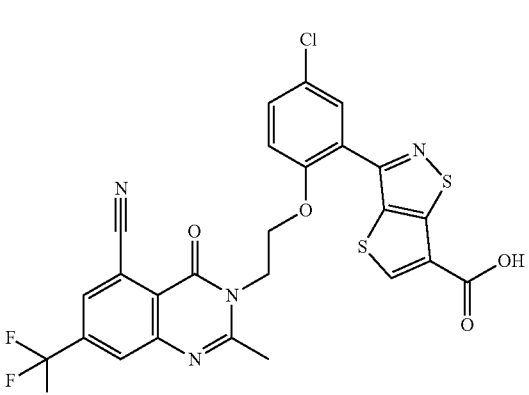 | MS (ESI) m/z 591.15 [M + 1]+; 1H NMR (400 MHz, DMSO-d6) δ 13.54 ( s, 1H), 8.33 (s, 1H), 8.11 (s, 1H), 8.01 (s, 1H), 7.67 (d, J = 2.64 Hz, 1H), 7.59 (dd, J = 8.92, 2.68 Hz, 1H), 7.38 (d, J = 9 Hz, 1H), 4.60 (t, J = 5.24 Hz, 2H), 4.37 (t, J = 5.36 Hz, 2H), 2.14 (s, 3H) |

TABLE 2-continued

7-CF3-Thienylpyridine and Derivative Compounds

| Compound | | Characterization |
|---|---|---|
| 319 | 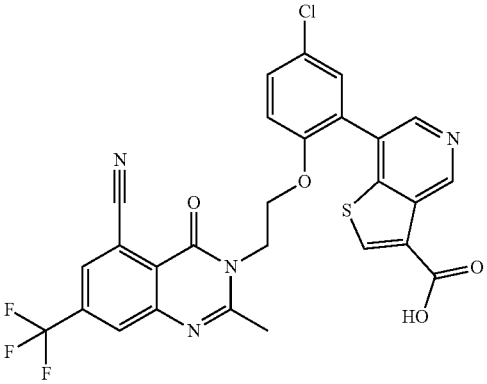 | MS (ESI) m/z 585.2 [M + 1]+; 1H-NMR (400 MHz, d6-DMSO)/ppm = 13.31 (bs, 1H), 9.59 (s, 1H), 8.37 (s, 1H), 8.34 (d, J = 1.9 Hz, 1H), 7.95-7.94 (m, 1H), 7.91 (s, 1H), 7.54 (dd, J = 8.9, 2.6 Hz, 1H), 7.38 (d, J = 2.6 Hz, 1H), 7.30 (d, J = 8.9 Hz, 1H), 4.36 (t, J = 4.7 Hz, 2H), 4.21 (t, J = 4.7 Hz, 2H), 1.70 (s, 3H) |
| 320 | 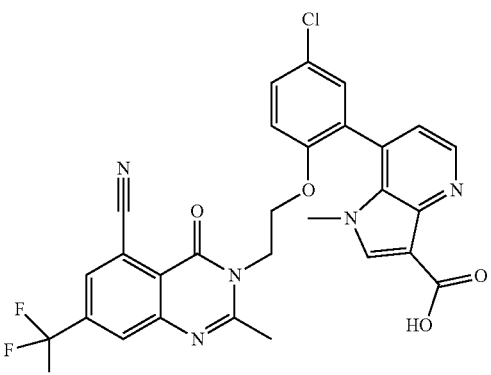 | MS (ESI) m/z 582.1 [M + 1]+; 1H-NMR (400 MHz, d6-DMSO) / ppm = 8.49 (d, J = 5.1 Hz, 1H), 8.39 (d, J = 1.5 Hz, 1H), 8.15-8.02 (m, 2H), 7.60 (dd, J = 9.1, 2.6 Hz, 1H), 7.41 (d, J = 2.6 Hz, 1H), 7.30 (d, J = 9.1 Hz, 1H), 7.34-7.20 (m, 1H), 4.46-4.33 (m, 2H), 4.28-4.20 (m, 2H), 3.16 (s, 3H), 1.66 (s, 3H) |
| 321 | 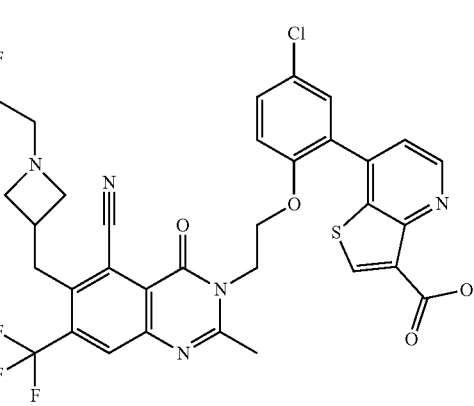 | MS (ESI) m/z 700.1 [M + 1]+; 1H NMR (400 MHz, DMSO-d6) δ 10.16 (s, 1H), 8.87-8.81 (m, 1H), 8.24-8.17 (m, 1H), 7.98 (s, 1H), 7.61 (dd, J = 8.9, 2.7 Hz, 1H), 7.49 (dd, J = 4.9, 2.0 Hz, 1H), 7.43 (d, J = 2.6 Hz, 1H), 7.37 (d, J = 9.0 Hz, 1H), 4.77-4.71 (m, 1H), 4.66-4.59 (m, 1H), 4.42 (t, J = 5.0 Hz, 2H), 4.32-4.11 (m, 6H), 3.70-3.53 (m, 2H), 3.23-3.11 (m, 2H), 1.81 (s, 3H) |
| 322 | 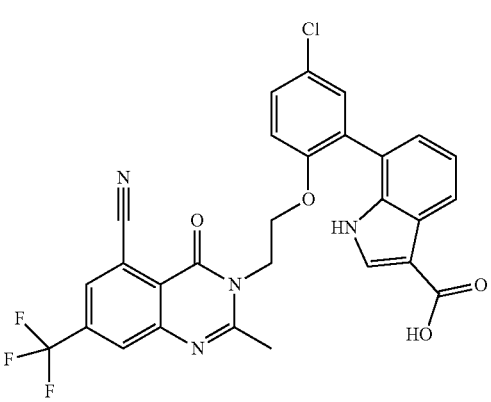 [SMILES: Cc1nc2cc(C(F)(F)F)cc(C#N)c2c(=O)n1CCOc1ccc(Cl)cc1-c1cccc2c(C(=O)O)c[nH]c12] | [0503] MS (ESI) m/z 567.2 [M + 1]+; 1H NMR (400 MHz, d6-DMSO) δ/ppm = 11.04 (d, J = 3.2 Hz, 1H), 8.38-8.37 (m, 1H), 8.10-8.08 (m, 1H), 8.02 (d, J = 8.1 Hz, 1H), 7.45 (dd, J = 8.9 Hz, 2.8 Hz, 1H), 7.25-7.15 (m, 4H), 7.02 (dd, J = 7.2, 1.2 Hz, 1H), 4.40-4.35 (m, 2H), 4.22-4.18 (m, 2H), 1.61 (s, 3H) |

TABLE 2-continued
7-CF3-Thienylpyridine and Derivative Compounds
| | Compound | Characterization |
|---|---|---|
| 323 | 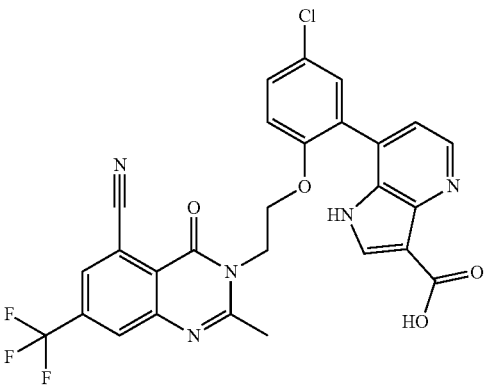 [SMILES: Cc1nc2cc(C(F)(F)F)cc(C#N)c2c(=O)n1CCOc1ccc(Cl)cc1-c1ccnc2c(C(=O)O)c[nH]c12] | MS (ESI) m/z 568.0 [M + 1]+; 1H-NMR (400 MHz, d6-DMSO) δ/ppm = 13.49 (b, 1H), 8.59 (d, J = 5.6 Hz, 1H), 8.40-8.39 (m, 1H), 8.07-8.05 (m, 1H), 7.87-7.77 (m, 1H), 7.62 (dd, J = 8.9, 2.6 Hz, 1H), 7.60-7.49 (m, 1H), 7.42 (d, J = 2.6 Hz, 1H), 7.34 (d, J = 8.9 Hz, 1H), 4.45 (t, J = 4.6 Hz, 2H), 4.25 (t, J = 4.6 Hz, 2H), 1.76 (s, 3H) |
| 324 | 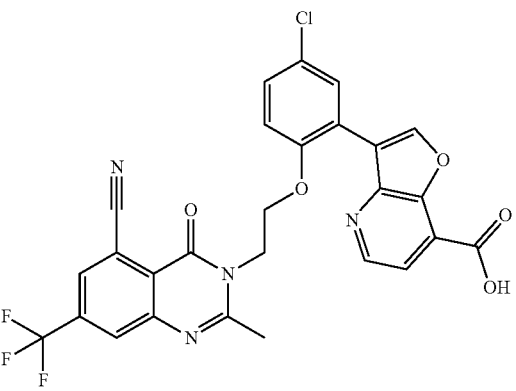 [SMILES: Cc1nc2cc(C(F)(F)F)cc(C#N)c2c(=O)n1CCOc1ccc(Cl)cc1-c1coc2c(C(=O)O)ccnc12] | MS (ESI) m/z 569.0 [M + 1]+; 1H-NMR (400 MHz, d6-DMSO) δ/ppm = 8.80 (s, 1H), 8.65 (d, J = 4.9 Hz, 1H), 8.53 (d, J = 2.7 Hz, 1H), 8.33 (bd, J = 1.7 Hz, 1H), 8.15-8.14 (m, 1H), 7.69 (d, J = 4.9 Hz, 1H), 7.43 (dd, J = 8.9, 2.7 Hz, 1H), 7.30 (d, J = 8.9 Hz, 1H), 4.55-4.52 (m, 4H), 2.45 (s, 3H) |
| 325 | 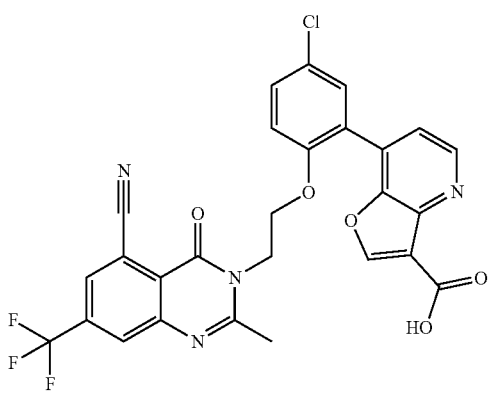 [SMILES: Cc1nc2cc(C(F)(F)F)cc(C#N)c2c(=O)n1CCOc1ccc(Cl)cc1-c1ccnc2c(C(=O)O)coc12] | MS (ESI) m/z 569.0 [M + 1]+; 1H-NMR (400 MHz, d6-DMSO) δ/ppm = 8.98-8.90 (m, 1H), 8.54-8.45 (m, 1H), 8.36-8.31 (m, 1H), 8.23-8.18 (m, 1H), 7.64-7.51 (m, 3H), 7.34-7.27 (m, 1H), 4.43-4.34 (m, 2H), 4.34-4.23 (m, 2H), 1.77 (s, 3H) |
| 326 | 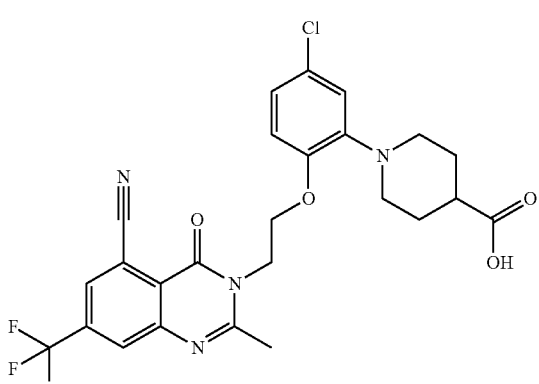 | [0506] MS (ESI) m/z 535.1 [M + 1]+ |

TABLE 2-continued

7-CF3-Thienylpyridine and Derivative Compounds

| Compound | | Characterization |
|---|---|---|
| 327 | 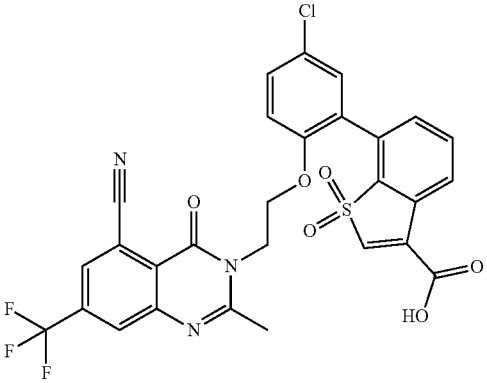 [SMILES: Cc1nc2cc(C(F)(F)F)cc(C#N)c2c(=O)n1CCOc1ccc(Cl)cc1-c1cccc2c1S(=O)(=O)C=C2C(=O)O] | MS (ESI) m/z 616.4 [M + 1]+; 1H-NMR (400 MHz, d6-DMSO) δ/ppm = 8.33 (bd, J = 1.7 Hz, 1H), 8.24 (dd, J = 7.8, 0.9 Hz, 1H), 7.95 (s, 1H), 7.76 (dd, J = 7.8, 7.8 Hz, 1H), 7.50 (dd, J = 8.9, 2.6 Hz, 1H), 7.45 (bd, J = 7.8 Hz, 1H), 7.23-7.20 (m, 2H), 7.14 (s, 1H), 4.36-4.21 (m, 4H), 1.84 (s, 3H) |
| 328 | 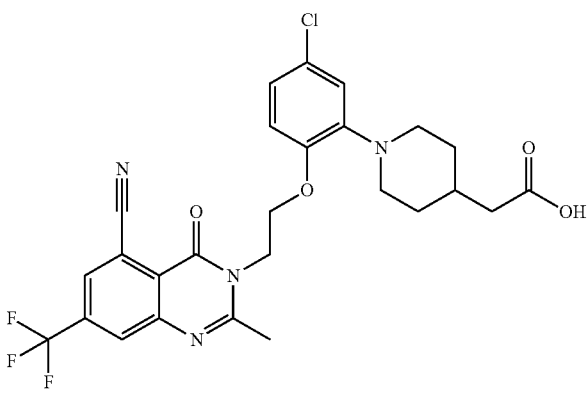 [SMILES: Cc1nc2cc(C(F)(F)F)cc(C#N)c2c(=O)n1CCOc1ccc(Cl)cc1N1CCC(CC(=O)O)CC1] | MS (ESI) m/z 549.3 [M + 1]+; 1H-NMR (400 MHz, d6-DMSO) δ/ppm = 8.39 (bd, J = 1.7 Hz, 1H), 8.24-8.22 (m, 1H), 7.01-6.87 (m, 3H), 4.52 (t, J = 4.8 Hz, 2H), 4.35 (t, J = 4.8 Hz, 2H), 3.22-3.16 (m, 2H), 2.80 (s, 3H), 2.50-2.43 (m, 2H), 2.13-2.09 (m, 2H), 1.74-1.57 (m, 3H), 1.27-1.11 (m, 2H) |
| 329 | 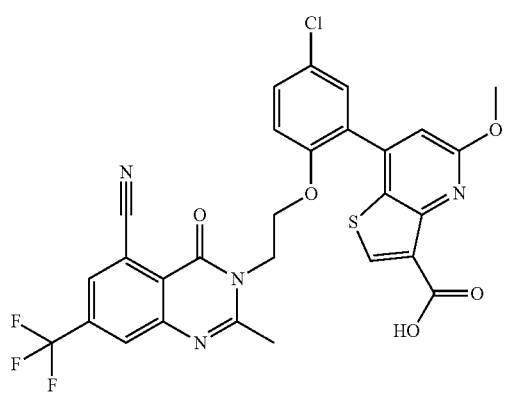 [SMILES: COc1cc(-c2cc(Cl)ccc2OCCn2c(C)nc3cc(C(F)(F)F)cc(C#N)c3c2=O)c2scc(C(=O)O)c2n1] | MS (ESI) m/z 615.0 [M + 1]+; 1H-NMR (400 MHz, d6-DMSO) δ/ppm = 8.36 (bd, J = 1.6 Hz, 1H), 8.12 (s, 1H), 8.01-8.00 (m, 1H), 7.57 (dd, J = 8.9, 2.7 Hz, 1H), 7.39 (d, J = 2.7 Hz, 1H), 7.33 (d, J = 8.9 Hz, 1H), 6.90 (d, J = 0.3 Hz, 1H), 4.40 (t, J = 5.0 Hz, 2H), 4.26 (t, J = 5.0 Hz, 1H), 4.03 (s, 3H), 1.87 (s, 3H) |
| 330 | 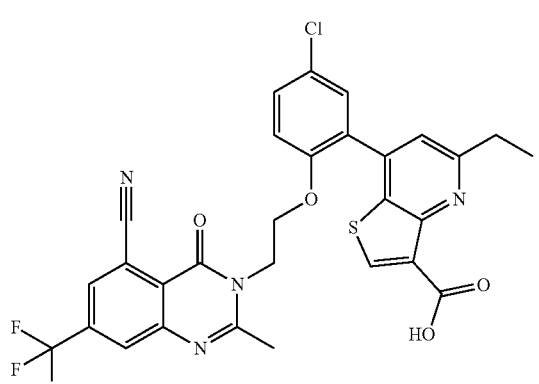 | MS (ESI) m/z 613.1 [M + 1]+; 1H-NMR (400 MHz, d6-DMSO) δ/ppm = 8.37 (bs, 1H), 8.24 (s, 1H), 7.95 (bs, 1H), 7.60 (dd, J = 8.8, 2.6, 1H), 7.47 (s, 1H), 7.43 (d, J = 2.6 Hz, 1H), 7.35 (d, J = 8.8 Hz, 1H), 4.41 (bt, 2H), 4.25 (bt, 2H), 3.01 (q, J = 7.6 Hz, 2H), 1.78 (s, 3H), 1.34 (t, J = 7.6 Hz, 3H) |

TABLE 2-continued

7-CF3-Thienylpyridine and Derivative Compounds

| Compound | Characterization |
|---|---|
| 331 | MS (ESI) m/z 601.6 [M + 1]+; 1H-NMR (400 MHz, d6-DMSO) δ/ppm = 10.48 (s, 1H), 8.37-8.36 (m, 1H), 7.95 (bs, 1H), 7.78 (bs, 1H), 7.56 (dd, J = 8.7, 2.6, 1H), 7.38 (d, J = 2.6 Hz, 1H), 7.31 (d, J = 8.7 Hz, 1H), 6.36 (bs, 1H), 4.41 (bt, 2H), 4.32 (bt, 2H), 2.15 (s, 3H) |
| 332 | MS (ESI) m/z 615.1 [M + 1]+; 1H-NMR (400 MHz, d6-DMSO) δ/ppm = 13.35 (b, 1H), 8.32 (d, J = 1.2 Hz, 1H), 8.06-8.04 (m, 1H), 7.68 (s, 1H), 7.51 (dd, J = 8.8, 2.7 Hz, 1H), 7.32 (d, J = 2.7 Hz, 1H), 7.26 (d, J = 8.8 Hz, 1H), 6.35 (s, 1H), 4.35 (bt, 1H), 4.28 (bt, 1H), 3.65 (s, 3H), 2.06 (s, 3H) |
| 333 | MS (ESI) m/z 616.2 [M + 1]+; 1H-NMR (400 MHz, d6-DMSO) δ/ppm = 12.89 (b, 1H), 8.35 (d, J = 1.5 Hz, 1H), 8.07 (bs, 1H), 7.77 (bs, 1H), 7.50 (dd, J = 8.9, 2.7 Hz, 1H), 7.30-7.26 (m, 2H), 7.19 (d, J = 6.0 Hz, 1H), 4.35 (bt, 2H), 4.25 (bt, 2H), 2.33 (s, 3H), 1.83 (s, 3H) |
| 341 | MS (ESI) m/z 690.1 [M + 1]+; 1H-NMR (400 MHz, d6-DMSO) δ/ppm = 8.75 (d, J = 5.3 Hz, 1H), 8.28 (s, 1H), 8.06 (s, 1H), 7.60 (dd, J = 8.9, 2.8 Hz, 1H), 7.59 (s, 1H), 7.52 (bd, J = 5.3 Hz, 1H), 7.45 (s, 1H), 7.42 (d, J = 2.8 Hz, 1H), 7.37 (d, J = 8.9 Hz, 1H), 4.42 (t, J = 5.2 Hz, 2H), 4.28 (t, J = 5.2 Hz, 2H), 2.73 (s, 3H), 2.64 (s, 3H), 1.87 (s, 3H) |

TABLE 2-continued

7-CF3-Thienylpyridine and Derivative Compounds

| Compound | Characterization |
|---|---|
| 342 | MS (ESI) m/z 694.2 [M + 1]+; 1H-NMR (400 MHz, d6-DMSO) δ/ppm = 8.82 (d, J = 2.8 Hz, 1H), 8.60-8.59 (m, 1H), 8.28 (s, 1H), 8.11-8.06 (m, 1H), 8.07 (s, 1H), 7.60 (dd, J = 8.9, 2.7 Hz, 1H), 7.45 (s, 1H), 7.42 (d, J = 2.7 Hz, 1H), 7.37 (d, J = 8.9 Hz, 1H), 4.43 (t, J = 4.9 Hz, 2H), 4.29 (t, J = 4.9 Hz, 2H), 2.73 (s, 3H), 1.89 (s, 3H) |
| 343 | MS (ESI) m/z 694.5 [M + 1]+; 1H-NMR (400 MHz, d6-DMSO) δ/ppm = 8.85 (dd, J = 7.5, 5.8 Hz, 1H), 8.79 (d, J = 9.9 Hz, 1H), 8.35 (s, 1H), 8.12 (s 1H), 7.64 (dd, J = 9.8, 5.8 Hz 1H), 7.60 (dd, J = 8.9, 2.7 Hz, 1H), 7.47 (s, 1H), 7.43 (d, J = 2.7 Hz, 1H), 7.37 (d, J = 8.9 Hz, 1H), 4.49-4.19 (m, 4H), 2.73 (s, 3H), 1.87 (s, 3H) |
| 344 | MS (ESI) m/z 694.2 [M + 1]+; 1H-NMR (400 MHz, d6-DMSO) δ/ppm = 8.87 (s, 1H), 8.71 (d, J = 4.7 Hz, 1H), 8.34 (s, 1H), 8.14 (s, 1H), 7.74-7.70 (m, 1H), 7.60 (dd, J = 8.9, 2.7 Hz, 1H), 7.45 (s, 1H), 7.43 (d, J = 2.7 Hz, 1H), 7.36 (d, J = 8.9 Hz, 1H), 4.48-4.20 (m, 4H), 2.72 (s, 3H), 1.87 (s, 3H) |
| 347 | MS (ESI) m/z 682.5 [M + 1]+; 1H-NMR (400 MHz, d6-DMSO) δ/ppm = 9.32 (s, 1H), 8.71 (s, 1H), 8.30 (s, 1H), 8.05 (s, 1H), 7.60 (dd, J = 8.9, 2.7 Hz, 1H), 7.44 (s, 1H), 7.42 (d, J = 2.7 Hz, 1H), 7.37 (d, J = 8.9 Hz, 1H), 4.42 (t, J = 4.7 Hz, 2H), 4.28 (t, J = 4.7 Hz, 2H), 2.72 (s, 3H), 1.88 (s, 3H) |

TABLE 2-continued

7-CF3-Thienylpyridine and Derivative Compounds

| Compound | Characterization |
|---|---|
| 348 | MS (ESI) m/z 682.4 [M + 1]+; 1H-NMR (400 MHz, d6-DMSO) δ/ppm = 8.74 (d, J = 1.7 Hz, 1H), 8.31 (s, 1H), 8.06 (s, 1H), 7.67 (d, J = 1.7 Hz, 1H), 7.60 (dd, J = 8.9, 2.7 Hz, 1H), 7.47 (s, 1H), 7.43 (d, J = 2.7 Hz, 1H), 7.36 (d, J = 8.6 Hz, 1H), 4.42 (t, J = 4.9 Hz, 2H), 4.28 (t, J = 4.9 Hz, 2H), 2.74 (s, 3H), 1.86 (s, 3H) |
| 349 | MS (ESI) m/z 704.3 [M + 1]+; 1H-NMR (400 MHz, d6-DMSO) δ/ppm = 8.28 (s, 1H), 8.08 (s, 1H), 7.83-7.77 (m, 1H), 7.60 (dd, J = 9.0, 2.8 Hz, 1H), 7.46 (s, 1H), 7.44 (d, J = 2.8 Hz, 1H), 7.43-7.38 (m, 1H), 7.37 (d, J = 9.0 Hz, 1H), 4.47-4.38 (m, 2H), 4.33-4.19 (m, 2H), 2.73 (s, 3H), 2.59 (s, 3H), 2.22 (s, 3H), 1.84 (s, 3H) |
| 350 | MS (ESI) m/z 704.5 [M + 1]+; 1H-NMR (400 MHz, d6-DMSO) ☐/ppm = 8.47-8.37 (m, 1H), 8.29 (s, 1H), 8.08 (s, 1H), 7.60 (dd, J = 8.9, 2.7 Hz, 1H), 7.46 (s, 1H), 7.44 (d, J = 2.7 Hz, 1H), 7.43-7.39 (m, 1H), 7.37 (d, J = 8.9 Hz, 1H), 4.47-4.43 (m, 2H), 4.34-4.18 (m, 2H), 2.73 (s, 3H), 2.57 (s, 3H), 2.06 (s, 3H), 1.84 (s, 3H) |
| 352 | MS (ESI) m/z 599.2 [M + 1]+; 1H NMR (400 MHz, DMSO-d6) δ 8.68 (d, J = 4.7 Hz, 1H), 8.38 (dd, J = 1.8, 0.6 Hz, 1H), 8.22 (dt, J = 1.8, 0.8 Hz, 1H), 7.53 (dd, J = 8.9, 2.7 Hz, 1H), 7.42 (s, 1H), 7.39 (d, J = 2.7 Hz, 1H), 7.29 (d, J = 9.0 Hz, 1H), 7.21 (d, J = 4.7 Hz, 1H), 5.43 (s, 1H), 4.37 (t, J = 4.9 Hz, 2H), 4.24 (t, J = 4.9 Hz, 2H), 1.75 (s, 6H), 1.65 (s, 3H) |

TABLE 2-continued

7-CF3-Thienylpyridine and Derivative Compounds

| | Compound | Characterization |
|---|---|---|
| 354 | 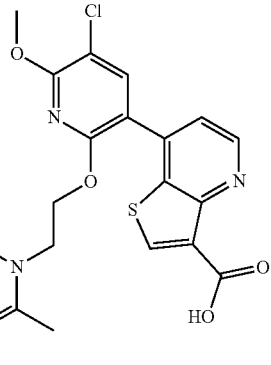 | MS (ESI) m/z 615.0 [M + 1]+; 1H NMR (400 MHz, DMSO-d6) δ 8.87-8.84 (m, 2H), 7.61-7.57 (m, 2H), 7.53-7.51 (m, 2H), 7.38 (d, J = 9.0 Hz, 1H), 7.35 (s, 1H), 4.23 (t, J = 5.5 Hz, 2H), 3.74 (t, J = 5.4 Hz, 2H), 2.75 (s, 3H), 1.07 (s, 6H) |
| 356 | 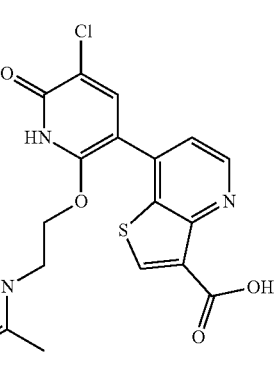 | MS (ESI) m/z 602.3 [M + 1]+; 1H NMR (400 MHz, DMSO-d6) δ 12.34 (s, 1H), 8.82 (d, J = 4.9 Hz, 1H), 8.45 (s, 1H), 8.37-8.36 (m, 1H), 8.05-8.04 (m, 1H), 7.95 (s, 1H), 7.52 (d, J = 4.9 Hz, 1H), 4.63 (t, J = 5.0 Hz, 2H), 4.31 (t, J = 5.0 Hz, 2H), 1.90 (s, 3H) |
| 363 | 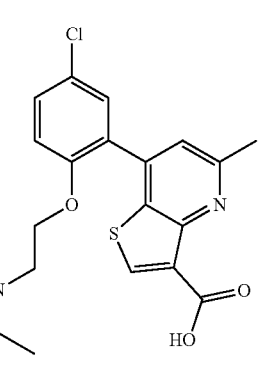 | MS (ESI) m/z 613.2 [M + 1]+; 1H NMR (400 MHz, DMSO-d6) δ 8.25 (s, 1H), 7.92 (s, 1H), 7.60 (dd, J = 8.9, 2.7 Hz, 1H), 7.43 (s, 1H), 7.41 (d, J = 2.7 Hz, 1H), 7.36 (d, J = 9.0 Hz, 1H), 4.41 (t, J = 5.0 Hz, 2H), 4.25 (t, J = 5.0 Hz, 2H), 2.71 (s, 3H), 2.70 (s, 3H), 1.85 (s, 3H) |
| 364 | 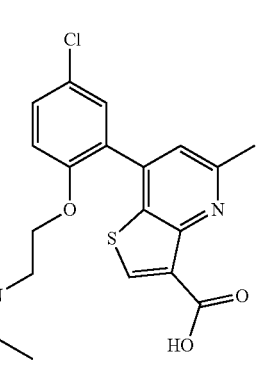 | MS (ESI) m/z 613.1 [M + 1]+; 1H NMR (400 MHz, DMSO-d6) δ 8.41 (s, 1H), 8.16 (s, 1H), 7.60 (dd, J = 8.9, 2.7 Hz, 1H), 7.43 (s, 1H), 7.41 (d, J = 2.7 Hz, 1H), 7.38 (d, J = 9.0 Hz, 1H), 4.44 (t, J = 5.0 Hz, 2H), 4.26 (t, J = 5.0 Hz, 2H), 2.68 (s, 3H), 2.69-2.63 (m, 3H), 1.93 (s, 3H) |

TABLE 2-continued

7-CF3-Thienylpyridine and Derivative Compounds

| Compound | Characterization |
|---|---|
| 373 | MS (ESI) m/z 694.2 [M + 1]+; 1H NMR (400 MHz, DMSO-d6) δ 10.09 (s, 1H), 8.25 (d, J = 5.1 Hz, 1H), 7.98 (d, J = 5.3 Hz, 1H), 7.60 (dd, J = 8.9, 2.6 Hz, 1H), 7.44 (s, 1H), 7.42 (d, J = 2.6 Hz, 1H), 7.37 (d, J = 9.0 Hz, 1H), 5.95 (s, 1H), 4.41 (t, J = 5.4 Hz, 2H), 4.26 (t, J = 5.1 Hz, 2H), 4.13 (d, J = 17.4 Hz, 1H), 3.84 (d, J = 17.8 Hz, 1H), 3.02-2.88 (m, 5H), 2.73-2.66 (m, 5H), 1.87 (s, 3H) |
| 374 | MS (ESI) m/z 626.2 [M + 1]+; 1H NMR (400 MHz, DMSO-d6) δ 9.74 (s, 1H), 8.15 (s, 1H), 7.83 (dt, J = 7.7, 1.5 Hz, 1H), 7.80 (t, J = 1.8 Hz, 1H), 7.50 (dt, J = 7.7, 1.6 Hz, 1H), 7.45-7.38 (m, 2H), 7.28 (d, J = 2.7 Hz, 1H), 7.21 (d, J = 8.9 Hz, 1H), 3.85 (t, J = 12.3 Hz, 2H), 3.54 (d, J = 11.7 Hz, 2H), 3.19 (d, J = 12.8 Hz, 2H), 3.12-2.99 (m, 2H), 2.89 (s, 3H), 2.21 (s, 3H) |
| 375 | MS (ESI) m/z 619.4 [M + 1]+; 1H NMR (400 MHz, DMSO-d6) δ 8.25 (s, 1H), 7.92-7.85 (m, 2H), 7.84 (t, J = 1.8 Hz, 1H), 7.54 (dt, J = 7.8, 1.6 Hz, 1H), 7.45 (d, J = 7.6 Hz, 1H), 7.43-7.37 (m, 3H), 7.29 (d, J = 2.6 Hz, 1H), 7.21 (d, J = 8.9 Hz, 1H), 4.40-4.33 (m, 4H), 2.52 (s, 3H), 2.24 (s, 3H) |
| 376 | MS (ESI) m/z 717.9 [M + 1]+; 1H NMR (400 MHz, DMSO-d6) δ 8.84 (d, J = 4.8 Hz, 1H), 8.22 (s, 1H), 7.98 (s, 1H), 7.61 (dd, J = 8.9, 2.7 Hz, 1H), 7.49 (d, J = 4.8 Hz, 1H), 7.43 (d, J = 2.6 Hz, 1H), 7.37 (d, J = 9.0 Hz, 1H), 6.38 (tt, J = 53.3, 3.0 Hz, 1H), 4.42 (t, J = 5.1 Hz, 2H), 4.31-4.25 (m, 6H), 3.87 (td, J = 16.3, 3.0 Hz, 2H), 3.41 (s, 2H), 3.24 (s, 1H), 1.81 (s, 3H) |

TABLE 2-continued

7-CF3-Thienylpyridine and Derivative Compounds

| Compound | Characterization |
|---|---|
| 377 | MS (ESI) m/z 676.3 [M + 1]+; 1H NMR (400 MHz, DMSO-d6) δ 8.13 (s, 1H), 7.85-7.78 (m, 2H), 7.51 (dt, J = 7.7, 1.5 Hz, 1H), 7.44-7.37 (m, 2H), 7.28 (d, J = 2.7 Hz, 1H), 7.21 (d, J = 8.9 Hz, 1H), 6.38 (t, J = 54.0 Hz, 1H), 2.20 (s, 3H). Note: some aliphatic signals were very broad and could not be integrated |
| 378 | MS (ESI) m/z 654.1 [M + 1]+; 1H NMR (400 MHz, DMSO-d6) δ 8.12 (s, 1H), 7.85-7.79 (m, 2H), 7.51 (dt, J = 7.7, 1.6 Hz, 1H), 7.44-7.37 (m, 2H), 7.27 (d, J = 2.6 Hz, 1H), 7.21 (d, J = 8.9 Hz, 1H), 4.34 (s, 4H), 3.06-2.76 (m, 2H), 2.20 (s, 3H), 2.06 (s, 3H) Note: some aliphatic signals were very broad and could not be integrated |
| 379 | MS (ESI) m/z 689.2 [M + 1]+; 1H NMR (400 MHz, DMSO-d6) δ 8.15 (s, 1H), 8.11 (dd, J = 5.6, 1.9 Hz, 1H), 7.87-7.79 (m, 3H), 7.51 (dt, J = 7.7, 1.6 Hz, 1H), 7.45-7.38 (m, 2H), 7.28 (d, J = 2.7 Hz, 1H), 7.21 (d, J = 8.9 Hz, 2H), 6.85 (t, J = 6.3 Hz, 1H), 4.35 (s, 4H), 2.20 (s, 3H). Note: some aliphatic signals were very broad and could not be integrated |
| 380 | MS (ESI) m/z 689.2 [M + 1]+; 1H NMR (400 MHz, DMSO-d6) δ 8.51 (d, J = 2.9 Hz, 1H), 8.22 (d, J = 5.3 Hz, 1H), 8.15 (s, 1H), 8.08 (dd, J = 8.8, 2.8 Hz, 1H), 7.85 (dt, J = 7.7, 1.5 Hz, 1H), 7.83-7.78 (m, 2H), 7.51 (dt, J = 7.7, 1.6 Hz, 1H), 7.45-7.38 (m, 2H), 7.28 (d, J = 2.7 Hz, 1H), 7.21 (d, J = 8.9 Hz, 1H), 4.35 (s, 4H), 2.20 (s, 3H). Note: some aliphatic signals were very broad and could not be integrated |

TABLE 2-continued

7-CF3-Thienylpyridine and Derivative Compounds

| Compound | Characterization |
|---|---|
| 381 | MS (ESI) m/z 640.1 [M + 1]+; 1H NMR (400 MHz, DMSO-d6) δ 8.13 (s, 1H), 7.84 (dt, J = 7.7, 1.5 Hz, 1H), 7.80 (t, J = 1.8 Hz, 1H), 7.51 (dt, J = 7.7, 1.5 Hz, 1H), 7.45-7.38 (m, 2H), 7.27 (d, J = 2.6 Hz, 1H), 7.21 (d, J = 8.9 Hz, 1H), 4.35 (s, 4H), 2.92 (s, 3H), 2.19 (s, 3H). Note: some aliphatic signals were very broad and could not be integrated |
| 382 | MS (ESI) m/z 688.2 [M + 1]+; 1H NMR (400 MHz, DMSO-d6) δ 8.13 (s, 1H), 7.87-7.80 (m, 2H), 7.52 (dt, J = 7.7, 1.5 Hz, 1H), 7.45-7.37 (m, 2H), 7.30-7.19 (m, 4H), 7.05-6.99 (m, 2H), 6.83 (t, J = 7.3 Hz, 1H), 4.35 (s, 4H), 2.20 (s, 3H). Note: some aliphatic signals were very broad and could not be integrated |
| 383 | MS (ESI) m/z 711.0 [M + 1]+; 1H NMR (400 MHz, DMSO-d6) δ 8.26 (s, 1H), 7.92 (s, 1H), 7.60 (dd, J = 8.9, 2.7 Hz, 1H), 7.43 (s, 1H), 7.42 (d, J = 2.6 Hz, 1H), 7.36 (d, J = 9.0 Hz, 1H), 4.40 (t, J = 5.1 Hz, 2H), 4.24 (t, J = 5.0 Hz, 2H), 2.94 (s, 3H), 2.72 (s, 3H), 1.82 (s, 3H). Note: some aliphatic signals were very broad and could not be integrated |
| 386 | MS (ESI) m/z 605.1 [M + 1]+; 1H NMR (400 MHz, DMSO-d6) δ 8.80 (d, J = 5.1 Hz, 2H), 8.29 (s, 1H), 7.86 (dt, J = 7.6, 1.6 Hz, 1H), 7.82 (t, J = 1.8 Hz, 1H), 7.55-7.50 (m, 3H), 7.47-7.39 (m, 2H), 7.28 (d, J = 2.7 Hz, 1H), 7.22 (d, J = 8.9 Hz, 1H), 4.43-4.31 (m, 4H), 2.24 (s, 3H) |

TABLE 2-continued

7-CF3-Thienylpyridine and Derivative Compounds

| Compound | Characterization |
|---|---|
| 387 | MS (ESI) m/z 689.2 [M + 1]+; 1H NMR (400 MHz, DMSO-d6) δ 8.24 (d, J = 7.4 Hz, 2H), 7.88 (s, 1H), 7.45-7.34 (m, 5H), 7.26 (d, J = 2.7 Hz, 1H), 7.19 (d, J = 8.9 Hz, 1H), 7.13 (d, J = 7.1 Hz, 2H), 4.31 (s, 4H), 3.85-3.49 (m, 8H), 2.20 (s, 3H) |
| 388 | MS (ESI) m/z 605.2 [M + 1]+; 1H NMR (400 MHz, DMSO-d6) δ 8.75 (dd, J = 4.9, 1.6 Hz, 1H), 8.62 (s, 1H), 8.28 (s, 1H), 7.91 (dt, J = 7.9, 1.9 Hz, 1H), 7.86 (dt, J = 7.6, 1.5 Hz, 1H), 7.82 (t, J = 1.8 Hz, 1H), 7.62 (dd, J = 7.8, 4.8 Hz, 1H), 7.53 (dt, J = 7.7, 1.5 Hz, 1H), 7.48-7.38 (m, 2H), 7.28 (d, J = 2.6 Hz, 1H), 7.22 (d, J = 8.9 Hz, 1H), 4.42-4.32 (m, J = 2.5 Hz, 4H), 2.24 (s, 3H) |
| 389 | MS (ESI) m/z 703.9 [M + 1]+;; 1H NMR (400 MHz, DMSO-d6) δ 8.58 (s, 1H), 8.27 (s, 1H), 8.06 (s, 1H), 8.00 (s, 1H), 7.60 (dd, J = 8.9, 2.7 Hz, 1H), 7.46 (s, 1H), 7.42 (d, J = 2.7 Hz, 1H), 7.37 (d, J = 9.0 Hz, 1H), 4.43 (t, J = 5.0 Hz, 2H), 4.28 (t, J = 4.9 Hz, 2H), 2.73 (s, 3H), 2.64 (s, 3H), 2.42 (s, 3H), 1.88 (s, 3H) |
| 398 | MS (ESI) m/z 656.0 [M + 1]+; 1H NMR (400 MHz, DMSO-d6) δ 10.16 (t, J = 5.4 Hz, 1H), 8.34 (d, J = 1.7 Hz, 1H), 8.14 (s, 1H), 8.05 (dd, J = 1.8, 0.8 Hz, 1H), 7.58 (dd, J = 8.9, 2.7 Hz, 1H), 7.39 (d, J = 2.7 Hz, 1H), 7.34 (d, J = 9.0 Hz, 1H), 7.33 (s, 1H), 4.40 (t, J = 5.0 Hz, 2H), 4.26 (t, J = 5.0 Hz, 2H), 4.21 (d, J = 5.4 Hz, 2H), 2.69 (s, 3H), 1.84 (s, 3H) |

TABLE 2-continued

7-CF3-Thienylpyridine and Derivative Compounds

| Compound | | Characterization |
|---|---|---|
| 401 | 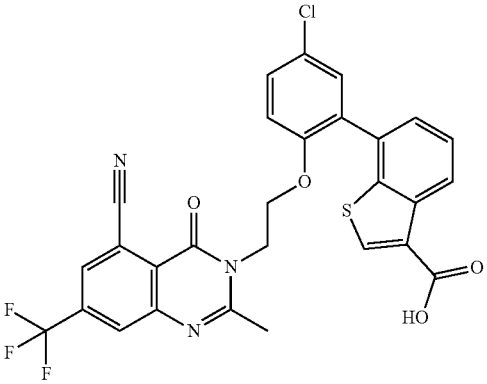 | MS (ESI) m/z 568.2 [M + H]+; 1H NMR (400 MHz, CD3OD) δ 8.16-8.13 (m, 1H), 8.05-8.02 (m, 1H), 7.97 (s, 1H), 7.90 (dd, J = 7.9, 1.3 Hz, 1H), 7.41 (dd, J = 8.8, 2.7 Hz, 1H), 7.31 (t, J = 7.6 Hz, 1H), 7.23 (d, J = 2.7 Hz, 1H), 7.20 (dd, J = 7.4, 1.3 Hz, 1H), 7.19 (d, J = 8.9 Hz, 1H), 4.40-4.30 (m, 4H), 1.98 (s, 3H) |
| 402 | 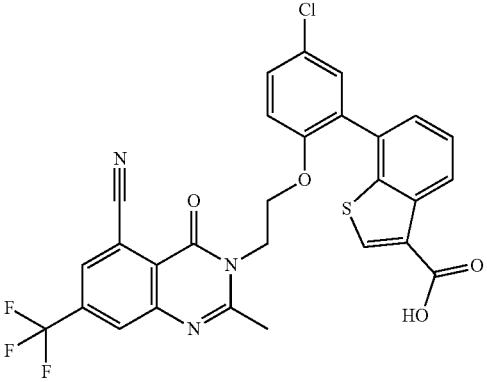 [SMILES: Cc1nc2cc(C(F)(F)F)cc(C#N)c2c(=O)n1CCOc1ccc(Cl)cc1-c1cccc2c(C(=O)O)csc12] | MS (ESI) m/z 584.3 [M + H]+; 1H NMR (400 MHz, Methanol-d4) δ 8.52 (dd, J = 8.3, 1.1 Hz, 1H), 8.15 (dd, J = 1.8, 0.6 Hz, 1H), 8.01 (dd, J = 1.7, 0.8 Hz, 1H), 7.77 (s, 1H), 7.51 (dd, J = 8.2, 7.2 Hz, 1H), 7.45 (dd, J = 8.9, 2.7 Hz, 1H), 7.30-7.25 (m, 1H), 7.22 (s, 1H), 7.21-7.16 (m, 1H), 4.40 (t, J = 4.8 Hz, 2H), 4.31 (t, J = 4.8 Hz, 2H), 1.82 (s, 3H) |
| 410 | 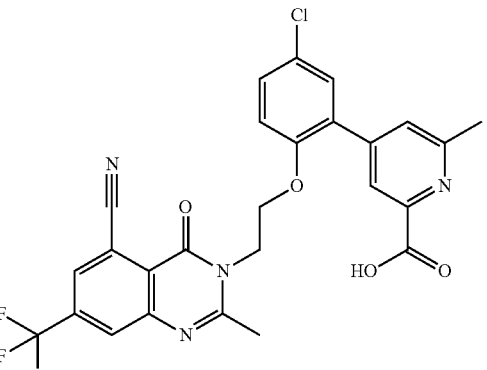 | MS (ESI) m/z 543.2 [M + 1]+; 1H NMR (400 MHz, DMSO-d6) δ 8.37 (d, J = 1.7 Hz, 1H), 8.17 (bs, 1H), 7.77 (bd, J = 1.6 Hz, 1H), 7.48 (bd, J = 1.4 Hz, 1H), 7.47 (dd, J = 8.9, 2.7 Hz, 1H), 7.36 (d, J = 2.7 Hz, 1H), 7.25 (d, J = 8.9 Hz, 1H), 4.39 (bs, 4H), 2.51 (s, 3H), 2.24 (s, 3H) |
| 411 | 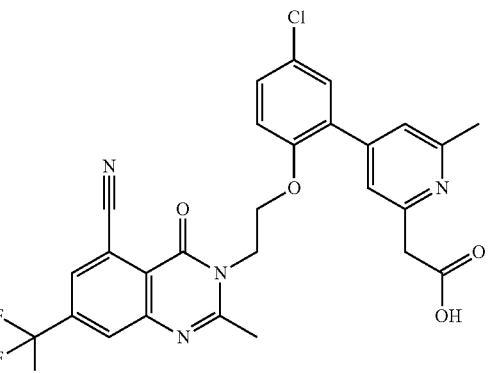 | MS (ESI) m/z 557.6 [M + 1]+; 1H NMR (400 MHz, DMSO-d6) δ 8.40 (d, J = 1.7 Hz, 1H), 8.20 (d, J = 1.7 Hz, 1H), 7.49 (dd, J = 8.9, 2.7 Hz, 1H), 7.46-7.40 (br, 2H), 7.37 (d, J = 2.7 Hz, 1H), 7.26 (d, J = 8.9 Hz, 1H), 4.49-4.35 (m, 4H), 3.86 (s, 2H), 2.53 (s, 3H), 2.31 (s, 3H) |

TABLE 2-continued

7-CF3-Thienylpyridine and Derivative Compounds

| Compound | Characterization |
| --- | --- |
| 414 | MS (ESI) m/z 583.1 [M + 1]+; 1H NMR (400 MHz, DMSO-d6) δ 8.38 (d, J = 1.8 Hz, 1H), 8.10 (br, 1H), 7.97 (s, 1H), 7.62 (dd, J = 8.9, 2.7 Hz, 1H), 7.53 (d, J = 2.7 Hz, 1H), 7.32 (d, J = 9.0 Hz, 1H), 7.15 (s, 1H), 4.37 (t, J = 4.9 Hz, 2H), 4.25 (t, J = 4.9 Hz, 2H), 2.59 (s, 3H), 1.85 (s, 3H) |
| 415 | MS (ESI) m/z 599.0 [M + 1]+; 1H NMR (400 MHz, DMSO-d6) δ 8.83 (bs, 1H), 8.24 (s, 1H), 7.95 (s, 1H), 7.61 (d, J = 8.8 Hz, 1H), 7.50 (bs, 1H), 7.42 (bs, 1H), 7.36 (d, J = 7.8 Hz), 4.40 (bs, 2H), 4.25 (bs, 2H), 2.72 (s, 3H), 1.76 (s, 3H) |
| 416 | MS (ESI) m/z 599.0 [M + 1]+; 1H NMR (400 MHz, DMSO-d6) δ 8.81 (d, J = 4.6 Hz, 1H), 8.42 (s, 1H), 8.17 (s, 1H), 7.60 (dd, J = 9.4, 2.6 Hz, 1H), 7.49 (d, J = 4.8 Hz, 1H), 7.42 (d, J = 2.7 Hz, 1H), 7.37 (d, J = 9.0 Hz, 1H), 4.44 (t, J = 4.8 Hz, 2H), 4.26 (t, J = 4.8 Hz, 2H), 2.67 (s, 3H), 1.84 (s, 3H) |
| 417 | MS (ESI) m/z 725.2 [M + 1]+; 1H NMR (400 MHz, DMSO-d6) δ 7.94 (s, 1H), 7.60 (dd, J = 8.8, 2.6 Hz, 1H), 7.44 (s, 1H), 7.42 (d, J = 2.7 Hz, 1H), 7.36 (d, J = 9.0 Hz, 1H), 4.42 (t, J = 5.0 Hz, 2H), 4.27 (t, J = 5.0 Hz, 2H), 3.94 (s, 2H), 3.43-3.29 (m, 4H), 2.99-2.82 (m, 4H), 2.78 (d, J = 4.3 Hz, 3H), 2.70 (s, 3H), 2.31 (s, 3H), 1.91 (s, 3H) |

TABLE 2-continued

7-CF3-Thienylpyridine and Derivative Compounds

| Compound | | Characterization |
|---|---|---|
| 421 | 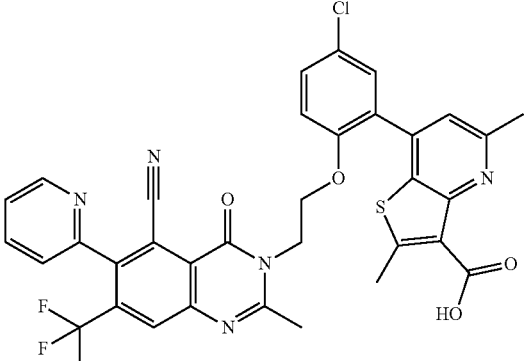 | MS (ESI) m/z 690.7 [M + 1]+; 1H NMR (400 MHz, DMSO-d6) δ 8.75 (dt, J = 4.8, 1.4 Hz, 1H), 8.08-7.99 (m, 2H), 7.65-7.53 (m, 3H), 7.45 (s, 1H), 7.42 (d, J = 2.6 Hz, 1H), 7.36 (d, J = 9.0 Hz, 1H), 4.42 (t, J = 4.9 Hz, 2H), 4.28 (br, 2H), 2.72 (s, 3H), 2.48 (s, 3H), 1.94 (s, 3H) |
| 422 | 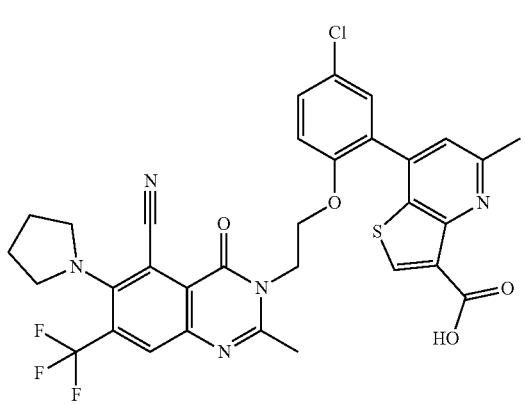 [SMILES: Cc1cc(-c2cc(Cl)ccc2OCCn2c(C)nc3cc(C(F)(F)F)c(N4CCCC4)c(C#N)c3c2=O)c2scc(C(=O)O)c2n1] | MS (ESI) m/z 668.4 [M + 1]+; 1H NMR (400 MHz, DMSO-d6) δ 8.35 (s, 1H), 7.92 (s, 1H), 7.60 (dd, J = 8.9, 2.7 Hz, 1H), 7.43 (dd, J = 4.3, 1.8 Hz, 2H), 7.36 (d, J = 9.0 Hz, 1H), 4.40 (t, J = 5.0 Hz, 2H), 4.24 (t, J = 5.0 Hz, 2H), 3.37-3.28 (m, 4H), 2.70 (s, 3H), 2.10-1.99 (m, 4H), 1.82 (s, 3H) |
| 423 | 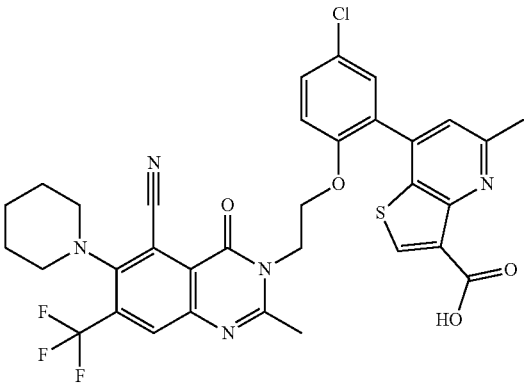 [SMILES: Cc1cc(-c2cc(Cl)ccc2OCCn2c(C)nc3cc(C(F)(F)F)c(N4CCCCC4)c(C#N)c3c2=O)c2scc(C(=O)O)c2n1] | MS (ESI) m/z 682.6 [M + 1]+; 1H NMR (400 MHz, DMSO-d6) δ 8.32 (s, 1H), 7.89 (s, 1H), 7.60 (dd, J = 8.9, 2.7 Hz, 1H), 7.44 (s, 1H), 7.42 (d, J = 2.6 Hz, 1H), 7.36 (d, J = 9.0 Hz, 1H), 5.04 (br, 6H), 4.39 (t, J = 5.0 Hz, 2H), 4.23 (t, J = 5.0 Hz, 2H), 3.21 (br, 4H), 2.71 (s, 3H), 1.80 (s, 3H) |
| 424 | 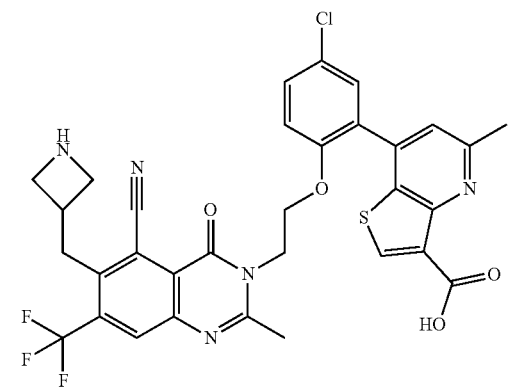 [SMILES: Cc1cc(-c2cc(Cl)ccc2OCCn2c(C)nc3cc(C(F)(F)F)c(CC4CNC4)c(C#N)c3c2=O)c2scc(C(=O)O)c2n1] | MS (ESI) m/z 668.3 [M + 1]+; 1H NMR (400 MHz, DMSO-d6) δ 8.18 (s, 1H), 7.95 (s, 1H), 7.60 (dd, J = 8.9, 2.7 Hz, 1H), 7.43 (s, 1H), 7.42 (d, J = 2.7 Hz, 1H), 7.37 (d, J = 9.0 Hz, 1H), 4.41 (t, J = 5.0 Hz, 2H), 4.26 (t, J = 5.0 Hz, 2H), 4.11-3.92 (m, 4H), 3.39 (br, 2H), 3.35-3.21 (m, 1H), 2.71 (s, 3H), 1.85 (s, 3H) |

TABLE 2-continued

7-CF3-Thienylpyridine and Derivative Compounds

| Compound | Characterization |
|---|---|
| 425 | MS (ESI) m/z 682.5 [M + 1]+; 1H NMR (400 MHz, CDCl3) δ 8.35 (s, 1H), 8.12 (s, 1H), 7.47 (dd, J = 8.9, 2.6 Hz, 1H), 7.26 (s, 1H), 7.18 (s, 1H), 7.03 (d, J = 8.9 Hz, 1H), 4.56 (t, J = 9.0 Hz, 2H), 4.40 (t, J = 4.8 Hz, 2H), 4.29 (t, J = 4.9 Hz, 2H), 3.84 (t, J = 9.6 Hz, 2H), 3.49 (d, J = 6.6 Hz, 2H), 3.45-3.29 (m, 1H), 2.89 (s, 3H), 2.80 (s, 3H), 1.89 (s, 3H) |
| 428 | MS (ESI) m/z 747.7 [M + 1]+; 1H NMR (400 MHz, DMSO-d6) δ 8.27 (s, 1H), 7.91 (s, 1H), 7.60 (dd, J = 8.9, 2.7 Hz, 1H), 7.43 (s, 1H), 7.42 (d, J = 2.7 Hz, 1H), 7.36 (d, J = 9.0 Hz, 1H), 6.38 (br, 1H), 4.40 (t, J = 5.0 Hz, 2H), 4.24 (t, J = 5.0 Hz, 3H), 4.06-2.83 (br, 10H), 2.71 (s, 3H), 1.83 (s, 3H) |
| 429 | MS (ESI) m/z 681.7 [M + 1]+; 1H NMR (400 MHz, DMSO-d6) δ 8.31 (s, 1H), 7.96 (s, 1H), 7.60 (dd, J = 8.9, 2.7 Hz, 1H), 7.43 (dd, J = 7.3, 2.1 Hz, 2H), 7.36 (d, J = 9.0 Hz, 1H), 5.92 (s, 1H), 4.41 (t, J = 5.0 Hz, 2H), 4.29-4.15 (m, 4H), 3.86 (m, 4H), 2.71 (s, 3H), 1.85 (s, 3H) |
| 430 | MS (ESI) m/z 729.5 [M + 1]+; 1H NMR (400 MHz, DMSO-d6) δ 8.25 (s, 1H), 7.93 (s, 1H), 7.61 (dd, J = 8.9, 2.7 Hz, 1H), 7.43 (s, 1H), 7.42 (d, J = 2.7 Hz, 1H), 7.37 (d, J = 9.0 Hz, 1H), 4.95 (t, J = 4.4 Hz, 1H), 4.82 (d, J = 4.6 Hz, 1H), 4.41 (t, J = 5.0 Hz, 2H), 4.25 (t, J = 5.0 Hz, 2H), 3.65-3.03 (br, 10H), 2.72 (s, 3H), 1.85 (s, 3H) |

TABLE 2-continued

7-CF3-Thienylpyridine and Derivative Compounds

| Compound | Characterization |
|---|---|
| 431 | MS (ESI) m/z 683.4 [M + 1]+; 1H NMR (400 MHz, DMSO-d6) δ 8.57 (s, 1H), 8.50 (s, 1H), 7.59 (dd, J = 8.9, 2.7 Hz, 1H), 7.44 (d, J = 2.6 Hz, 1H), 7.40 (s, 1H), 7.37 (d, J = 9.0 Hz, 1H), 4.35 (t, J = 5.1 Hz, 2H), 4.26 (t, J = 5.1 Hz, 2H), 3.98 (dd, J = 11.3, 4.0 Hz, 2H), 3.43 (t, J = 11.3 Hz, 2H), 3.22 (m, 1H), 2.72 (s, 3H), 2.08 (s, 3H), 2.03-1.88 (m, 2H), 1.59 (d, J = 12.6 Hz, 2H) |
| 433 | MS (ESI) m/z 712.4 [M + 1]+; 1H NMR (400 MHz, DMSO-d6) δ 8.80 (d, J = 2.4 Hz, 1H), 8.42 (s, 1H), 8.33 (td, J = 9.1, 2.4 Hz, 1H), 8.17 (s, 1H), 7.59 (dd, J = 8.9, 2.7 Hz, 1H), 7.45 (d, J = 2.4 Hz, 1H), 7.44 (s, 1H), 7.35 (d, J = 9.0 Hz, 1H), 4.40 (t, J = 5.0 Hz, 2H), 4.27 (t, J = 5.1 Hz, 2H), 2.70 (s, 3H), 1.84 (s, 3H) |
| 434 | MS (ESI) m/z 708.6 [M + 1]+; 1H NMR (400 MHz, DMSO-d6) δ 8.46 (s, 1H), 8.15 (s, 1H), 7.89 (t, J = 8.9 Hz, 1H), 7.62-7.53 (m, 2H), 7.45 (s, 1H), 7.44 (d, J = 2.6, 0.9 Hz, 1H), 7.35 (d, J = 9.0 Hz, 1H), 4.40 (t, J = 5.0 Hz, 2H), 4.28 (d, J = 5.0 Hz, 2H), 2.71 (s, 3H), 2.52 (s, 3H), 1.82 (s, 3H) |
| 437 | MS (ESI) m/z 705.0 [M + 1]+; 1H NMR (400 MHz, DMSO-d6) δ 8.67 (s, 1H), 8.27 (s, 1H), 8.10 (s, 1H), 7.60 (dd, J = 8.9, 2.7 Hz, 1H), 7.46 (s, 1H), 7.43 (d, J = 2.7 Hz, 1H), 7.37 (d, J = 9.0 Hz, 1H), 4.43 (t, J = 5.1 Hz, 2H), 4.28 (tt, J = 9.5, 5.0 Hz, 2H), 2.74 (s, 3H), 2.71 (s, 3H), 2.23 (s, 3H), 1.85 (s, 3H) |

TABLE 2-continued

7-CF3-Thienylpyridine and Derivative Compounds

| Compound | Characterization |
|---|---|
| 442 | MS (ESI) m/z 691.3 [M + 1]+; 1H NMR (400 MHz, DMSO-d6) δ 9.27 (d, J = 2.1 Hz, 1H), 8.26 (s, 1H), 8.08 (s, 1H), 7.85 (d, J = 2.1 Hz, 1H), 7.60 (dd, J = 8.9, 2.6 Hz, 1H), 7.45 (s, 1H), 7.42 (d, J = 2.7 Hz, 1H), 7.37 (d, J = 9.0 Hz, 1H), 4.43 (t, J = 5.0 Hz, 2H), 4.29 (t, J = 5.0 Hz, 2H), 2.77 (s, 3H), 2.73 (s, 3H), 1.89 (s, 3H) |
| 443 | MS (ESI) m/z 604.2 [M + 1]+; 1H NMR (400 MHz, DMSO-d6) δ 8.58 (d, J = 4.8 Hz, 1H), 8.36-8.32 (m, 1H), 8.15-8.11 (m, 1H), 7.52 (dd, J = 8.9, 2.7 Hz, 1H), 7.38 (d, J = 2.7 Hz, 1H), 7.29 (d, J = 9.0 Hz, 1H), 7.23 (d, J = 4.8 Hz, 1H), 4.36 (t, J = 5.0 Hz, 2H), 4.25 (d, J = 5.0 Hz, 2H), 1.88 (s, 3H), 1.33 (s, 9H) |
| 444 | MS (ESI) m/z 619.2 [M + 1]+; 1H NMR (400 MHz, DMSO-d6) δ 8.34 (d, J = 1.9 Hz, 1H), 8.22 (s, 1H), 7.97 (dd, J = 1.9, 0.8 Hz, 1H), 7.56 (dd, J = 8.9, 2.7 Hz, 1H), 7.48 (s, 1H), 7.42 (d, J = 2.7 Hz, 1H), 7.31 (d, J = 9.0 Hz, 1H), 4.37 (t, J = 5.0 Hz, 2H), 4.23 (t, J = 5.0 Hz, 2H), 1.79 (s, 3H) |
| 445 | MS (ESI) m/z 628.7 [M + 1]+; 1H NMR (400 MHz, DMSO-d6) δ 8.32 (d, J = 1.8 Hz, 1H), 8.25 (s, 1H), 8.01 (d, J = 3.1 Hz, 1H), 7.94 (dd, J = 1.8, 0.9 Hz, 1H), 7.89 (s, 2H), 7.57 (dd, J = 8.9, 2.7 Hz, 1H), 7.43 (d, J = 2.6 Hz, 1H), 7.32 (d, J = 9.0 Hz, 1H), 4.37 (t, J = 5.0 Hz, 2H), 4.20 (t, J = 5.0 Hz, 2H), 1.65 (s, 3H) |

TABLE 2-continued

7-CF3-Thienylpyridine and Derivative Compounds

| Compound | | Characterization |
|---|---|---|
| 446 |  | MS (ESI) m/z 610.7 [M + 1]+; 1H NMR (400 MHz, DMSO-d6) δ 8.41 (d, J = 1.1 Hz, 1H), 8.35 (d, J = 1.7 Hz, 1H), 8.01-7.97 (m, 2H), 7.58 (ddd, J = 9.1, 2.7, 1.0 Hz, 1H), 7.44 (dd, J = 2.6, 1.0 Hz, 1H), 7.33 (d, J = 9.0 Hz, 1H), 4.38 (t, J = 5.0 Hz, 2H), 4.23 (t, J = 5.0 Hz, 2H), 1.71 (s, 3H) |
| 447 |  | MS (ESI) m/z 599.14 [M + 1]+; 1H NMR (400 MHz, DMSO-d6) δ 8.37-8.31 (m, 1H), 7.97 (d, J = 1.3 Hz, 1H), 7.95 (dt, J = 1.8, 0.8 Hz, 1H), 7.55 (dd, J = 8.9, 2.7 Hz, 1H), 7.35-7.28 (m, 2H), 7.17 (d, J = 0.9 Hz, 1H), 4.36 (t, J = 5.0 Hz, 2H), 4.20 (t, J = 5.0 Hz, 2H), 2.65 (d, J = 0.7 Hz, 3H), 1.86 (s, 3H) |
| 452 |  | MS (ESI) m/z 614.5 [M + 1]+; 1H NMR (400 MHz, DMSO-d6) δ 12.86 (s, 1H), 8.50-8.37 (m, 4H), 8.30 (s, 1H), 8.01 (s, 1H), 7.62 (dd, J = 8.9, 2.7 Hz, 1H), 7.57 (s, 1H), 7.40-7.35 (m, 2H), 4.44 (q, J = 6.1 Hz, 4H), 4.27 (t, J = 5.2 Hz, 2H), 1.77 (s, 3H) |
| 453 |  | MS (ESI) m/z 552.9 [M + 1]+; 1H NMR (400 MHz, DMSO-d6) δ 9.18 (dd, J = 6.2, 0.7 Hz, H), 8.89-8.84 (m, 2H), 8.37-8.33 (m, 1H), 8.20 (dt, J = 1.8, 0.8 Hz, 1H), 8.07-8.03 (m, 1H), 7.66 (dd, J = 6.2, 0.8 Hz, 1H), 4.63 (t, J = 5.0 Hz, 2H), 4.53 (t, J = 5.0 Hz, 2H), 3.88 (s, 1H), 2.33 (s, 3H) |

TABLE 2-continued
7-CF3-Thienylpyridine and Derivative Compounds
| Compound | Characterization |
|---|---|
| 454 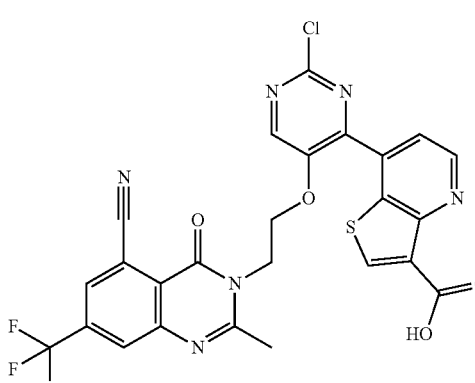 | MS (ESI) m/z 587.2 [M + 1]+; 1H NMR (400 MHz, DMSO-d6) δ 8.99 (s, 1H), 8.96 (s, 1H), 8.93 (d, J = 5.0 Hz, 1H), 8.39-8.37 (m, 1H), 8.26 (d, J = 5.0 Hz, 1H), 8.24 (dd, J = 1.7, 0.8 Hz, 1H), 4.77 (t, J = 5.1 Hz, 2H), 4.62 (t, J = 5.1 Hz, 2H), 2.53 (s, 3H) |
| 455 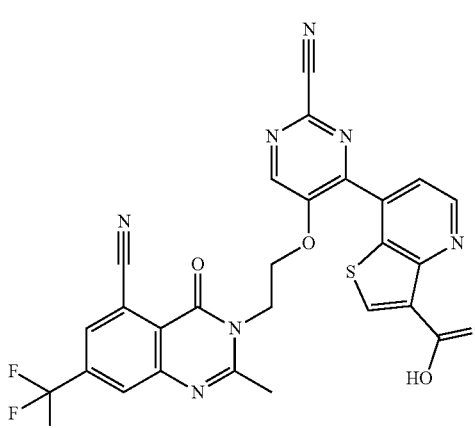 | MS (ESI) m/z 578.3 [M + 1]+; 1H NMR (400 MHz, DMSO-d6) δ 9.15 (s, 1H), 8.92 (s, 2H), 8.35 (s, 1H), 8.20 (d, J = 4.9 Hz, 2H), 4.83 (s, 2H), 4.60 (s, 2H), 2.56 (2, 3H) |
| 465 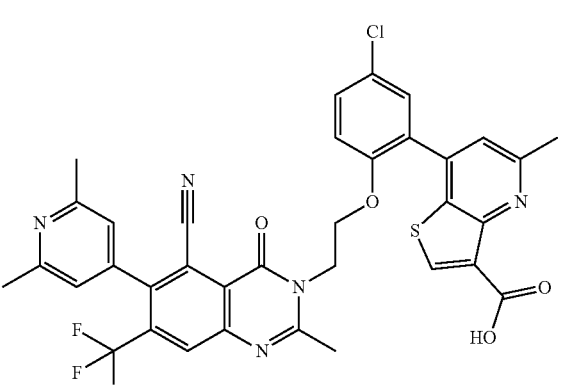 | LCMS: 704.5 [M + H]+; 1H NMR (400 MHz, DMSO-d6) δ 8.25 (s, 1H), 8.05 (s, 1H), 7.61 (dd, J = 8.9, 2.7 Hz, 1H), 7.50-7.33 (m, 4H), 4.42 (t, J = 5.0 Hz, 2H), 4.28 (t, J = 5.0 Hz, 2H), 2.73 (s, 3H), 2.62 (s, 6H), 1.87 (s, 3H) |

TABLE 2-continued

7-CF3-Thienylpyridine and Derivative Compounds

| Compound | | Characterization |
|---|---|---|
| 466 | 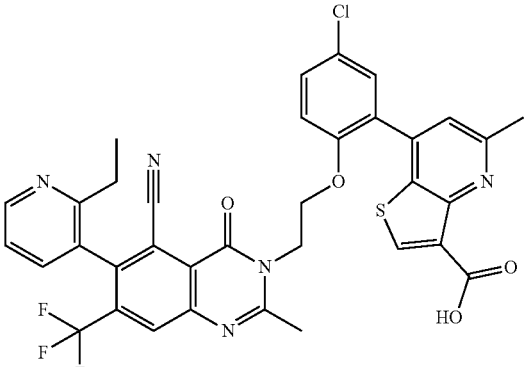 | LCMS: 704.5 [M + H]+; 1H NMR (400 MHz, DMSO-d6) δ 8.74-8.65 (m, 1H), 8.32 (s, 1H), 8.09 (s, 1H), 7.80 (d, J = 7.8 Hz, 1H), 7.60 (dd, J = 8.9, 2.7 Hz, 1H), 7.49-7.41 (m, 3H), 7.37 (d, J = 9.0 Hz, 1H), 4.52-4.10 (m, 2H), 2.73 (s, 3H), 2.45-2.35 (m, 2H), 1.85 (s, 3H), 1.15 (t, J = 7.5 Hz, 3H) |
| 468 | 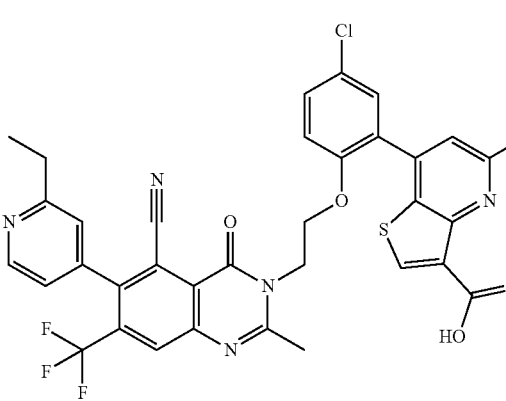 | LCMS: 704.5 [M + H]+; 1H NMR (400 MHz, DMSO-d6) δ 8.75 (d, J = 5.2 Hz, 1H), 8.29 (s, 1H), 8.06 (s, 1H), 7.60 (dd, J = 8.9, 2.7 Hz, 1H), 7.57 (s, 1H), 7.52-7.47 (m, 1H), 7.45 (s, 1H), 7.42 (d, J = 2.6 Hz, 1H), 7.37 (d, J = 9.0 Hz, 1H), 4.42 (t, J = 5.1 Hz, 2H), 4.29 (d, J = 5.2 Hz, 2H), 2.91 (q, J = 7.5 Hz, 2H), 2.73 (s, 3H), 1.87 (s, 3H), 1.29 (t, J = 7.6 Hz, 3H) |
| 469 | 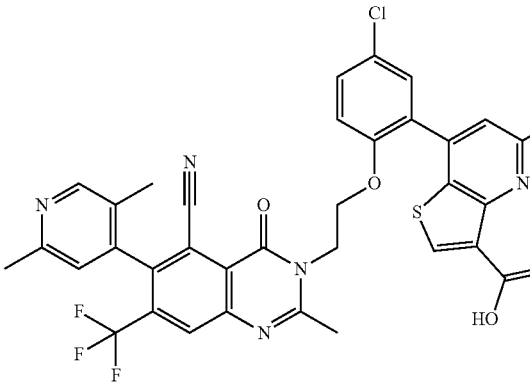 | LCMS: 704.5 [M + H]+; 1H NMR (400 MHz, DMSO-d6) δ 8.72 (s, 1H), 8.25 (s, 1H), 8.11 (s, 1H), 7.63-7.58 (m, 2H), 7.47 (s, 1H), 7.44 (d, J = 2.6 Hz, 1H), 7.37 (d, J = 9.0 Hz, 1H), 4.43 (h, J = 5.9 Hz, 2H), 4.27 (dd, J = 11.3, 5.7 Hz, 1H), 2.74 (s, 3H), 2.64 (s, 3H), 2.08 (s, 3H), 1.84 (s, 3H) |
| 470 | 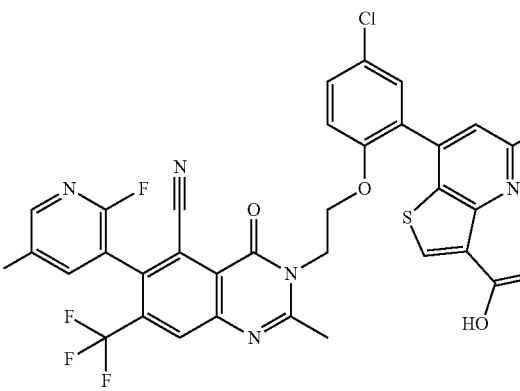 | LCMS: 708.5 [M + H]+; 1H NMR (400 MHz, DMSO-d6) δ 8.70-8.65 (m, 1H), 8.27 (d, J = 0.9 Hz, 1H), 8.10 (s, 1H), 7.91 (dd, J = 9.0, 2.9 Hz, 1H), 7.60 (ddd, J = 8.9, 2.6, 1.0 Hz, 1H), 7.47-7.41 (m, 2H), 7.37 (d, J = 8.9 Hz, 1H), 4.43 (d, J = 4.8 Hz, 2H), 4.37-4.17 (m, 2H), 2.74 (d, J = 0.9 Hz, 3H), 2.21 (s, 3H), 1.86 (s, 3H) |

TABLE 2-continued
7-CF3-Thienylpyridine and Derivative Compounds
| Compound | Characterization |
|---|---|
| 471 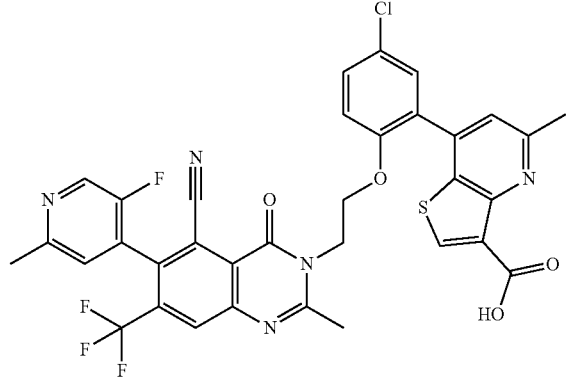 | LCMS: 708.6 [M + H]+; 1H NMR (400 MHz, DMSO-d6); 1H NMR (400 MHz, DMSO-d6) δ 8.69 (d, J = 0.8 Hz, 1H), 8.30 (s, 1H), 8.11 (s, 1H), 7.61-7.57 (m, 1H), 7.55 (d, J = 5.6 Hz, 1H), 7.45-7.42 (m, 2H), 7.36 (d, J = 9.0 Hz, 1H), 4.54-4.10 (m, 1H), 2.72 (s, 3H), 2.58 (d, J = 1.0 Hz, 3H), 1.86 (s, 3H) |
| 472 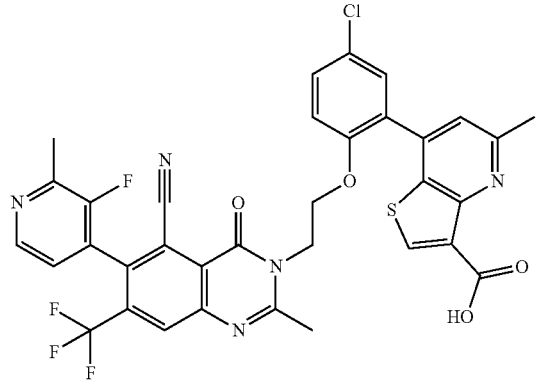 [SMILES: Cc1cc(-c2cc(Cl)ccc2OCCn2c(C)nc3cc(C(F)(F)F)c(-c4ccnc(C)c4F)c(C#N)c3c2=O)c2scc(C(=O)O)c2n1] | LCMS: 708.6 [M + H]+; 1H NMR (400 MHz, DMSO-d6) δ 8.54 (d, J = 4.8 Hz, 1H), 8.33 (s, 1H), 8.12 (s, 1H), 7.60 (dd, J = 8.9, 2.7 Hz, 1H), 7.51 (t, J = 5.1 Hz, 1H), 7.46-7.41 (m, 2H), 7.36 (d, J = 9.0 Hz, 1H), 4.57-4.15 (m, 2H), 2.72 (s, 3H), 2.56 (d, J = 3.0 Hz, 3H), 1.87 (s, 3H) |
| 473 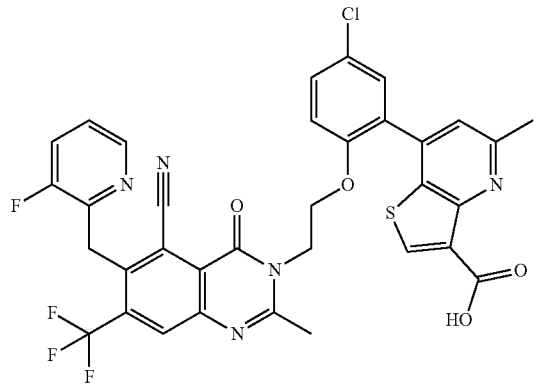 [SMILES: Cc1cc(-c2cc(Cl)ccc2OCCn2c(C)nc3cc(C(F)(F)F)c(Cc4ncccc4F)c(C#N)c3c2=O)c2scc(C(=O)O)c2n1] | LCMS: 708.6 [M + H]+; 1H NMR (400 MHz, DMSO-d6) δ 8.27 (s, 1H), 8.17 (dt, J = 4.7, 1.4 Hz, 1H), 7.99 (s, 1H), 7.77 (ddd, J = 9.8, 8.3, 1.3 Hz, 1H), 7.59 (dd, J = 8.9, 2.7 Hz, 1H), 7.45-7.40 (m, 2H), 7.36 (dt, J = 8.4, 1.9 Hz, 2H), 4.66 (s, 2H), 4.42 (t, J = 5.0 Hz, 2H), 4.26 (t, J = 5.1 Hz, 2H), 2.70 (s, 3H), 1.86 (s, 3H) |

TABLE 2-continued
7-CF3-Thienylpyridine and Derivative Compounds
| Compound | Characterization |
|---|---|
| 483 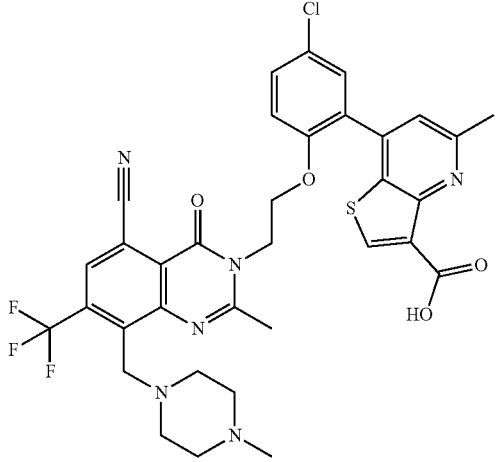 [SMILES: Cc1cc(-c2cc(Cl)ccc2OCCn2c(C)nc3c(CN4CCN(C)CC4)c(C(F)(F)F)cc(C#N)c3c2=O)c2scc(C(=O)O)c2n1] | MS (ESI) m/z 711.6 [M + 1]+; 1H NMR (400 MHz, DMSO-d6) δ 9.36 (s, 1H), 8.38 (s, 1H), 8.27 (s, 1H), 7.60 (dd, J = 8.9, 2.7 Hz, 1H), 7.46-7.34 (m, 3H), 4.43 (d, J = 5.3 Hz, 2H), 4.27 (s, 2H), 4.14 (s, 2H), 3.30 (d, J = 11.8 Hz, 2H), 2.77 (d, J = 20.8 Hz, 7H), 2.68 (s, 3H), 1.88 (s, 3H) |
| 484 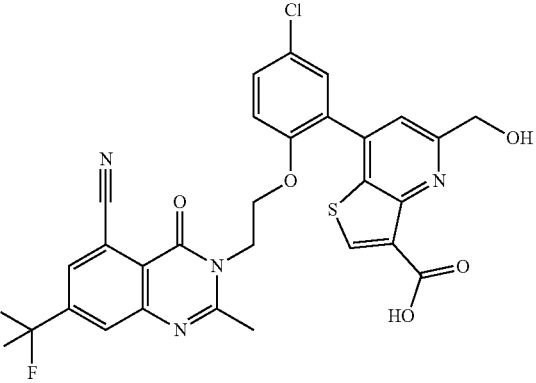 | MS (ESI) m/z 615.6 [M + 1]+; 1H NMR (400 MHz, DMSO-d6) δ 8.37 (d, J = 1.7 Hz, 1H), 8.24 (s, 1H), 7.98-7.94 (m, 1H), 7.60 (dd, J = 8.9, 2.7 Hz, 1H), 7.53 (s, 1H), 7.41 (d, J = 2.6 Hz, 1H), 7.36 (d, J = 9.0 Hz, 1H), 4.81 (s, 2H), 4.41 (t, J = 5.1 Hz, 2H), 4.25 (t, J = 5.1 Hz, 2H), 1.77 (s, 3H) |
| 485 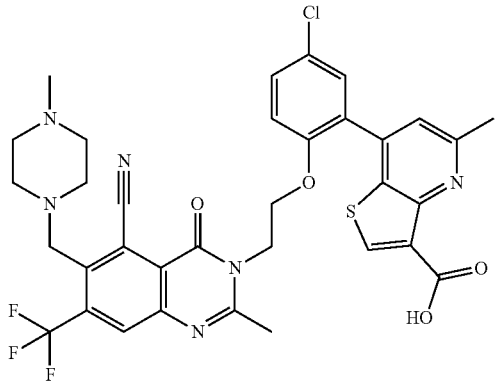 [SMILES: Cc1cc(-c2cc(Cl)ccc2OCCn2c(C)nc3cc(C(F)(F)F)c(CN4CCN(C)CC4)c(C#N)c3c2=O)c2scc(C(=O)O)c2n1] | MS (ESI) m/z 711.6 [M + 1]+; 1H NMR (400 MHz, DMSO-d6) δ 9.48 (s, 1H), 8.22 (s, 1H), 7.96 (s, 1H), 7.60 (dd, J = 8.9, 2.7 Hz, 1H), 7.43 (d, J = 2.5 Hz, 2H), 7.36 (d, J = 9.0 Hz, 1H), 4.41 (t, J = 5.1 Hz, 2H), 4.26 (d, J = 5.0 Hz, 2H), 3.95 (s, 2H), 3.38 (d, J = 11.4 Hz, 2H), 2.92 (d, J = 11.8 Hz, 4H), 2.78 (d, J = 4.5 Hz, 3H), 2.70 (s, 3H), 1.85 (s, 3H) |

TABLE 2-continued

7-CF3-Thienylpyridine and Derivative Compounds

| | Compound | Characterization |
|---|---|---|
| 486 | | MS (ESI) m/z 711.6 [M + 1]+; 1H NMR (400 MHz, DMSO-d6) δ 8.27 (s, 1H), 7.96 (s, 1H), 7.60 (dd, J = 8.9, 2.7 Hz, 1H), 7.43 (d, J = 2.5 Hz, 2H), 7.36 (d, J = 9.0 Hz, 1H), 4.41 (t, J = 5.0 Hz, 2H), 4.25 (t, J = 5.0 Hz, 2H), 3.89 (s, 2H), 3.53 (s, 4H), 2.70 (s, 3H), 1.83 (s, 3H) |
| 487 | | MS (ESI) m/z 791.5 [M + 1]+; 1H NMR (400 MHz, DMSO-d6) δ 8.75 (d, J = 5.0 Hz, 1H), 8.50 (s, 1H), 8.33 (d, J = 1.8 Hz, 1H), 7.96-7.93 (m, 1H), 7.60 (dd, J = 8.9, 2.7 Hz, 1H), 7.49 (d, J = 5.0 Hz, 1H), 7.44 (d, J = 2.6 Hz, 1H), 7.36 (d, J = 9.0 Hz, 1H), 4.42 (t, J = 5.0 Hz, 2H), 4.26 (t, J = 5.1 Hz, 2H), 2.61 (s, 4H), 1.86 (s, 3H) |
| 489 | | MS (ESI) m/z 741.8 [M + 1]+; 1H NMR (400 MHz, DMSO-d6) δ 9.47 (s, 1H), 8.21 (s, 1H), 7.97 (s, 1H), 7.60 (dd, J = 8.9, 2.7 Hz, 1H), 7.48-7.41 (m, 2H), 7.36 (d, J = 9.0 Hz, 1H), 4.74 (s, 2H), 4.41 (t, J = 5.0 Hz, 2H), 4.25 (t, J = 5.0 Hz, 2H), 3.94 (s, 2H), 2.92 (d, J = 12.0 Hz, 5H), 2.78 (d, J = 4.2 Hz, 3H), 1.77 (s, 3H) |
| 494 | | MS (ESI) m/z 735.9 [M + 1]+; 1H NMR (400 MHz, DMSO-d6) δ 8.85 (d, J = 4.8 Hz, 1H), 8.23 (s, 1H), 7.98 (s, 1H), 7.61 (dd, J = 8.9, 2.7 Hz, 1H), 7.51 (d, J = 4.8 Hz, 1H), 7.43 (d, J = 2.6 Hz, 1H), 7.37 (d, J = 9.0 Hz, 1H), 4.42 (t, J = 4.9 Hz, 2H), 4.26 (t, J = 5.0 Hz, 2H), 4.08-3.82 (m, 4H), 3.38 (d, J = 6.2 Hz, 2H), 3.16-3.02 (m, 1H), 1.79 (s, 3H) |

TABLE 2-continued

7-CF3-Thienylpyridine and Derivative Compounds

| Compound | Characterization |
|---|---|
| 495 | MS (ESI) m/z: 599.01; 1H-NMR (400 MHz, DMSO-d6) δ 8.70 (s, 1H), 8.36 (s, 1H), 8.22 (s, 1H), 8.01 (s, 1H), 7.59-7.56 (m, 1H), 7.37-7.35 (m, 2H), 4.48-4.44 (m, 1H), 4.27-4.20 (m, 3H), 2.08 (s, 3H), 1.17 (s, 3H) |
| 496 | MS (ESI) m/z 569.23 [M + 1]+; 1H NMR (400 MHz, DMSO-d6) δ 8.39 (s, 1H), 8.34 (d, J = 4.28 Hz, 1H), 8.23 (s, 1H), 7.44 (dd, J = 8.80, 2.40 Hz, 1H), 7.25 (d, J = 2.16 Hz, 1H), 7.21 (d, J = 8.84 Hz, 1H), 7.10 (s, 1H), 4.41-4.29 (m, 4H), 4.08 (t, J = 8.48, 1H), 2.12-2.10 (m, 4H), 2.03 (s, 3H) |
| 501 | MS (ESI) m/z 684.11 [M + 1]+; 1H NMR (400 MHz, DMSO-d6) δ 8.84 (d, J = 4.8 Hz, 1H), 8.28 (s, 1H), 7.99 (s, 1H), 7.61 (dd, J = 8.92, 2.6 Hz, 1H), 7.51 (d, J = 4.76 Hz, 1H), 7.44 (d, J = 2.6 Hz, 1H), 7.37 (d, J = 9.00 Hz, 1H), 4.42 (t, J = 5.76 Hz, 2H), 4.26 (t, J = 4.36 Hz, 2H), 3.95 (bs, 2H), 3.55 (bs, 4H), 2.56 (bs, 4H), 1.76 (s, 3H) |
| 502 | MS (ESI) m/z 697.15 [M + 1]+; 1H NMR (400 MHz, DMSO-d6) δ 8.84 (d, J = 4.76 Hz, 1H), 8.23 (s, 1H), 7.98 (s, 1H), 7.61 (dd, J = 8.84, 2.56 Hz, 1H), 7.48 (d, J = 4.76 Hz, 1H), 7.44 (d, J = 2.6 Hz, 1H), 7.37 (d, J = 9.00 Hz, 1H), 4.42 (t, J = 3.8 Hz, 2H), 4.26 (t, J = 5.8, 2H), 3.94 (bs, 2H), 3.40 (d, J = 10.68 Hz, 2H), 2.94 (d, J = 10.68 Hz, 4H), 2.79 (d, J = 3.4 Hz, 3H), 2.50 (m, 2H), 1.77 (s, 3H) |

TABLE 2-continued

7-CF3-Thienylpyridine and Derivative Compounds

| Compound | Characterization |
|---|---|
| 503 | MS (ESI) m/z 660.1 [M + 1]+; 1H NMR (400 MHz, DMSO-d6) δ 8.86 (d, J = 4.68 Hz, 1H), 8.11 (s, 1H), 8.07 (s,1H), 7.63 (d, J = 8.36, 1H), 7.57 (d, J = 11.32 Hz, 1H), 7.49 (d, J = 4.72 Hz, 1H), 4.63 (bs, 2H), 4.46 (t, J = 4.64 Hz, 2H), 4.28 (t, J = 4.72 Hz, 2H), 2.89 (bs, 6H), 1.75 (s, 3H) |
| 505 | MS (ESI) m/z 637.1 [M + 1]+; 1H NMR (400 MHz, DMSO-d6) δ 8.86 (d, J = 4.76 Hz, 1H), 8.25 (s, 1H), 8.08 (s, 1H), 7.63 (d, J = 8.32 Hz, 1H), 7.55 (d, J = 11.2 Hz, 1H), 7.50 (d, J = 4.68 Hz, 1H), 4.43 (t, J = 5.00 Hz, 2H), 4.26 (t, J = 4.44 Hz, 2H), 1.68 (s, 3H) |
| 519 | MS (ESI) m/z 696.3 [M + 1]+; 1H NMR (400 MHz, DMSO-d6) δ 12.69 (s, 1H), 8.92 (d, J = 4.44 Hz, 1H), 8.34 (s, 1H), 8.09 (s, 1H), 7.65-7.54 (m, 2H), 7.45 (d, J = 1.84 Hz, 1H), 7.36 (d, J = 8.84 Hz, 1H), 4.42 (t, J = 4.68 Hz, 2H), 4.24 (t, J = 5.24 Hz, 2H), 3.56 (s, 3H), 1.65 (s, 3H) |
| 521 | MS (ESI) m/z 648.07 [M + 1]+. 1H NMR (400 MHz, DMSO-d6) δ 12.10 (s, 1H), 8.84 (d, J = 4.80 Hz, 1H), 8.12 (s, 1H), 8.09 (S, 1H), 7.59 (dd, J = 8.88, 2.80 1H), 7.46 (d, J = 4.76 Hz, 1H), 7.41 (d, J = 2.60 Hz,1H), 7.34 (d, J = 9.04 Hz, 1H), 4.42-4.38 (m, 2H), 4.28-4.21 (m, 2H), 3.88 (s, 3H), 1.66 (s, 3H) |

TABLE 2-continued

7-CF3-Thienylpyridine and Derivative Compounds

| | Compound | Characterization |
|---|---|---|
| 522 | | MS (ESI) m/z 718.18 [M + 1]+; 1H NMR (400 MHz, DMSO-d6) δ 8.84 (d, J = 4.16 Hz, 1H), 8.27 (s, 1H), 8.98 (s, 1H), 7.59 (d, J = 8.52 Hz, 1H), 7.50 (d, J = 4.4 Hz, 1H), 7.43 (s, 1H), 7.36 (d, J = 9.08 Hz, 1H), 4.41 (bs, 2H), 4.24 (bs, 2H), 3.94 (s, 2H), 2.61 (s, 4H), 1.92 (s, 4H), 1.76 (s, 3H) |
| 523 | | MS (ESI) m/z 710.21 [M + 1]+; 1H-NMR (400 MHz, DMSO-d6) δ 13.23 (bs, 1H), 8.82 (d, J = 3.2 Hz, 1H), 8.27 (s, 1H), 7.99 (s, 1H), 7.59 (d, J = 8.88 Hz, 1H), 7.50-7.42 (m, 1H), 7.43 (s, 1H) 7.35 (d, J = 8.24 Hz, 1H), 4.41 (s, 2H), 4.24 (s, 2H), 3.84 (s, 1H), 3.50-3.30 (m, 4H), 3.07 (s, 2H), 2.02 (s, 2H), 1.85-1.70 (m, 5H) |
| 524 | | MS (ESI) m/z 616.13 [M + 1]+; 1H-NMR (400 MHz, DMSO-d6) δ 13.27 (bs, 1H), 8.82 (s, J = 4.72 Hz, 1H), 8.17 (s, 1H), 8.00 (s, 1H), 7.58 (dd, J = 8.80, 2.44 Hz, 1H ), 7.46 (d, J = 4.76 Hz, 1H), 7.40 (d, J = 2.52 Hz, 1H), 7.35 (d, J = 8.8 Hz, 1H), 5.52 (s, 2H), 4.40 (t, J = 4.28 Hz, 2H), 4.23 (t, J = 5.2 Hz, 2H), 1.73 (s, 3H) |
| 525 | | MS (ESI) m/z 692.27 [M + 1]+; 1H NMR (400 MHz, DMSO-d6) δ 8.83 (s, 1H), 8.23 (s, 1H), 7.97 (s, 1H), 7.65-7.26 (m, 4H), 6.16 (t, J = 56.26 Hz, 1H), 4.40 (s, 2H), 4.24 (s, 2H), 4.04 (s, 2H), 2.94 (t, J = 14.2 Hz, 2H), 2.28 (s, 3H), 1.75 (s, 3H) |

TABLE 2-continued

7-CF3-Thienylpyridine and Derivative Compounds

| | Compound | Characterization |
|---|---|---|
| 526 | | MS (ESI) m/z 668.20 [M + 1]+; 1H-NMR (400 MHz, CD3OD) δ 8.80 (d ,J = 4.84 Hz, 1H), 8.27 (s, 1H), 8.19 (s, 1H), 7.57 (dd, J = 2.96, 9.76 Hz, 1H), 7.49 (d, J = 4.84 Hz, 1H), 7.36 (d, J = 2.36 Hz, 1H), 7.31 (d, J = 8.88 Hz, 1H), 4.98 (s, 2H), 4.46 (t, J = 2.36, 2H), 4.37 (t, J = 4.6 Hz, 2H),.3.74 (s, 4H), 2.20 (s, 4H), 2.03 (s, 3H) |
| 527 | | MS (ESI) m/z 670.40 [M + 1]+; 1H-NMR (400 MHz CD3OD) δ 8.78 (d, J = 4.88 Hz, 1H), 8.27 (s, 1H), 8.20 (s, 1H), 7.57 (dd, J = 2.56, 8.92 Hz, 1H), 7.49 (d, J = 4.92 Hz, 1H), 7.36 (d, J = 2.48 Hz, 1H), 7.32 (d, J = 8.84 Hz, 1H), 4.98 (s, 2H), 4.46 (t, J = 4.76, 2H), 4.37 (t, J = 4.5 Hz, 2H),.3.52-3.47 (m, 4H), 2.03 (s, 3H), 1.48-1.29 (m, 6H) |
| 528 | | MS (ESI) m/z 682.19 [M + 1]+; 1H NMR (400 MHz, DMSO-d6 + D20) δ 8.83 (d, J = 4.80 Hz, 1H), 8.21 (s, 1H), 8.06 (s, 1H), 7.61-7.57 (dd, J = 2.48, 8.80 Hz, 1H), 7.48 (d, J = 4.68 Hz, 1H), 7.44 (d, J = 2.48 Hz, 1H), 7.36 (d, J = 8.92 Hz, 1H), 4.58 (m, 2H), 4.40 (t, J = 6.36 Hz, 2H), 4.26 (t, J = 4.52 Hz, 2H)., 3.29 (m, 4H), 1.75 (m, 7H), 1.54 (m, 2H) |
| 535 | | MS (ESI) m/z 537.11 [M +1]+. 1H NMR (400 MHz, DMSO-d6) δ 12.77 (bs, 1H), 8.39 (s, 1H), 7.23 (s, 1H), 7.03 (d, J = 8.9 Hz), 6.92 (s, 1H), 4.51 (m, 2H), 4.38 (t, J = 4.8 Hz, 3H), 4.19-4.16 (m, 2H), 3.95 (d, J = 11.2 Hz, 1H), 3.63-3.59 (m, 1H), 3.27 (d, J = 9.6 Hz, 1H), 2.94-2.79 (m, 5H) |

TABLE 2-continued
7-CF3-Thienylpyridine and Derivative Compounds
| | Compound | Characterization |
|---|---|---|
| 549 | 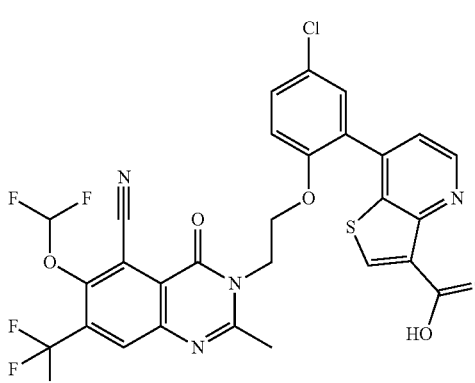 | MS (ESI) m/z 651.08 [M + 1]+; 1H NMR (400 MHz, DMSO-d6) δ 8.84 (d, J = 4.72 Hz, 1H), 8.22 (s, 1H), 8.07 (s, 1H), 7.61-7.23 (m, 5H), 4.41 (t, J = 4.2 Hz, 2H), 4.26 (t, J = 4.2 Hz, 2H), 1.72 (s, 3H) |
| 553 | 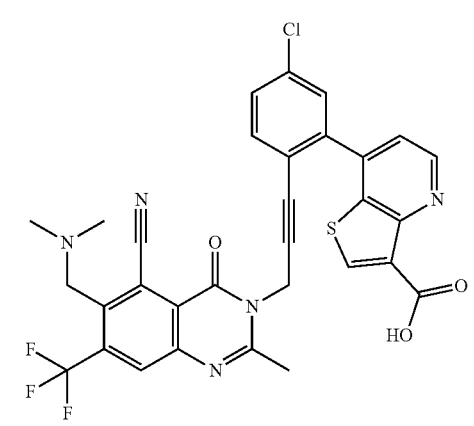 [SMILES: Cc1nc2cc(C(F)(F)F)c(CN(C)C)c(C#N)c2c(=O)n1CC#Cc1ccc(Cl)cc1-c1ccnc2c(C(=O)O)csc12] | MS (ESI) m/z 636.0 [M + 1]+;; 1H NMR (400 MHz, DMSO-d6) δ 8.74 (d, J = 4.7 Hz, 1H), 8.53 (s, 1H), 8.21 (s, 1H), 7.77 (d, J = 8.1 Hz, 1H), 7.7 (d, J = 2.0 Hz, 1H), 7.68 (s, 1H), 7.54 (d, J = 4.7 Hz, 1H), 4.91 (s, 2H), 4.63 (bs, 2H), 2.87 (bs, 6H), 2.11 (s, 3H) |
| 554 | 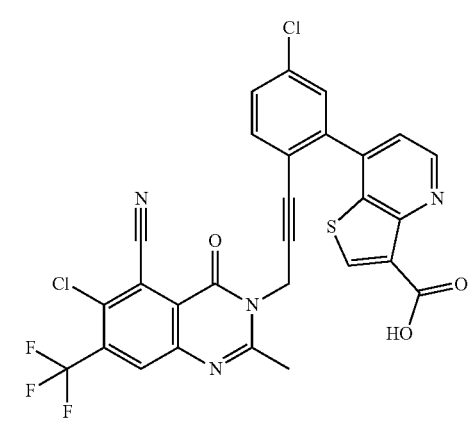 [SMILES: Cc1nc2cc(C(F)(F)F)c(Cl)c(C#N)c2c(=O)n1CC#Cc1ccc(Cl)cc1-c1ccnc2c(C(=O)O)csc12] | MS (ESI) m/z 613.04 [M + 1]+; 1H NMR (400 MHz, DMSO-d6) δ 8.77 (d, J = 4.8 Hz, 1H), 8.55 (s, 1H), 8.22 (s, 1H), 7.76 (d, J = 8.2 Hz, 1H), 7.7 (d, J = 2.0 Hz, 1H), 7.67 (s, 1H), 7.55 (d, J = 4.7 Hz, 1H), 4.88 (s, 2H), 2.07 (s, 3H) |

TABLE 2-continued

7-CF3-Thienylpyridine and Derivative Compounds

| | Compound | Characterization |
|---|---|---|
| 555 | | MS (ESI) m/z 633. [M + 1]+; 1H NMR (400 MHz, DMSO-d6) δ 8.78 (d, J = 4.88, 1H), 8.089 (s, 1H), 7.615 (dd, J = 8.92, 8.96, 1H), 7.519 (d, J = 4.88 Hz, 1H), 7.414 (d, J = 2.6, 1H), 7.37 (d, J = 8.96 Hz, 1H), 4.43 (bs, 2H), 4.29 (bs, 2H), 2.41 (s, 3H), 1.89 (s, 3H) |
| 556 | | MS (ESI) m/z 656.21 [M + 1]+; 1H NMR (400 MHz, DMSO-d6) δ 8.79 (d, J = 4.76, 1H), 8.088 (s,1H), 7.618 (dd, J = 8.84, 8.72, 1H), 7.517 (d, J = 4.84 Hz, 1H), 7.44 (d, J = 2.16, 1H), 7.36 (d, J = 8.88 Hz, 1H), 4.602 (bs, 2H), 4.419 (bs, 2H), 4.28 (bs, 2H), 2.84 (bs, 6H), 2.34 (s, 3H), 1.83 (s, 3H) |
| 558 | | MS (ESI) m/z 633.10 [M + 1]+; 1H-NMR (400 MHz, DMSO-d6) δ 8.24 (s ,1H), 8.03 (s, 1H), 7.61-7.58 (dd, J = 2.52,J = 8.84 Hz, 1H), 7.44 (s, 1H),-7.41 (d, J = 2.52, 1H),7.37 (d, J = 8.92 Hz, 1H), 4.42 (t, J = 5.46 Hz, 2H), 4.27 (t, J = 4.32 Hz, 2H), 2.71 (s, 3H),1.79 (s, 3H) |
| 559 | | MS (ESI) m/z 656.15 [M + 1]+; 1H NMR (400 MHz, DMSO-d6) δ 13.48 (s, 1H), 8.06 (bs, 1H), 8.03 (s, 1H), 7.62 (dd, J = 8.92 Hz, 2.52 Hz, 1 H), 7.45-7.34 (m, 2 H), 7.36 (d, J = 8.32 Hz, 1H), 4.75 (s, 2 H), 4.44 (t, J = 3.6 Hz, 2H), 4.29 (t, J = 5.6 Hz, 2 H), 2.99 (s, 6H), 2.72 (s, 3H), 1.82 (s, 3 H) |

TABLE 2-continued
7-CF3-Thienylpyridine and Derivative Compounds
| Compound | Characterization |
|---|---|
| 560 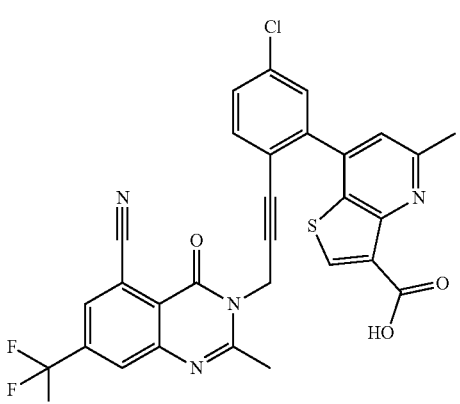 | MS (ESI) m/z: 593 [M + 1]+; 1H-NMR (400 MHz, DMSO-d6) δ 13.24 (s, 1H), 8.59 (s, 1H), 8.42 (s, 1H), 8.12 (s, 1H), 7.75 (d, J = 8.24 Hz, 1H), 7.68-7.64 (m, 2H), 7.46 (s, 1H), 4.87 (s, 2H), 2.59 (s, 3H), 2.14 (s, 3H) |
| 561 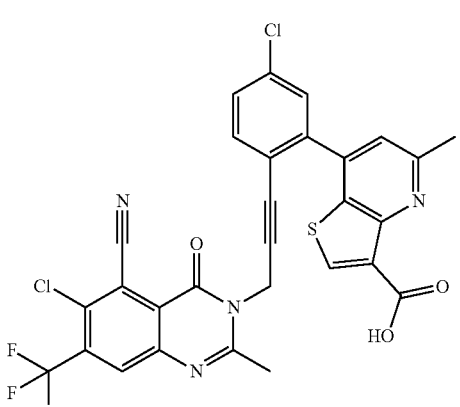 | MS (ESI) m/z 627.06 [M + 1]+; 1H-NMR (400 MHz, DMSO-d6) 13.23 (bs, 1H), 8.54 (s, 1H), 8.20 (s, 1H), 7.75 (d, J = 8.32 Hz, 1H), 7.69 (dd, J = 8.24, 1.96 Hz, 1H), 7.64 (s, 1H), 7.47 (s, 1H), 4.87 (s, 2H). 2.64 (s, 3H), 2.14 (s 3H) |
| 562 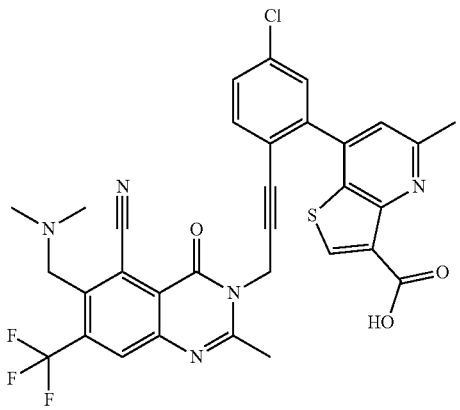 [SMILES: Cc1cc(-c2cc(Cl)ccc2C#CCn2c(C)nc3cc(C(F)(F)F)c(CN(C)C)c(C#N)c3c2=O)c2scc(C(=O)O)c2n1] | MS (ESI) m/z 650.17 [M + 1]+; 1H NMR (400 MHz, DMSO-d6) δ 13.34 (bs, 1H), 8.73 (d, J = 4.7 Hz, 1H), 8.66 (s, 1H), 8.13 (d, J = 9.7 Hz, 1H), 7.76 (d, J = 9.0 Hz, 1H), 7.68 (m, 1H), 7.53 (d, J = 4.7 Hz, 1H), 7.37 (t, J = 53.7 Hz, 1H), 4.88 (s, 2H), 2.22 (s, 3H) |

TABLE 2-continued

7-CF3-Thienylpyridine and Derivative Compounds

| Compound | | Characterization |
|---|---|---|
| 563 | | MS (ESI) m/z 635.09 [M + 1]+; 1H NMR (400 MHz, DMSO-d6) δ 12.98 (bs, 1H), 8.37 (s, 1H), 8.28 (s, 1H), 8.00 (s, 1H), 7.67 (s, 1H), 7.60 (dd, J = 1.68, 8.56 Hz, 1H), 7.45 (bs, 1H), 7.35 (d, J = 8.88 Hz, 1H), 7.18 (t, J = 54.84 Hz, 1H), 4.39-4.35 (m, 2H), 4.23-4.20 (m, 2H), 1.67 (s, 3H) |
| 564 | | MS (ESI) m/z 655.21 [M + 1]+; 1H NMR (400 MHz, DMSO-d6) δ 13.06 (s, 1H), 9.45 (s, 1H), 8.18 (s, 1H), 7.50 (dd, J = 2.52 Hz, J = 9.12 Hz, 2H), 7.28-7.25 (m, 2H), 7.15 (d, J = 7.28 Hz, 1H), 4.75 (s, 2H), 4.36 (bs, 2H), 4.24 (bs, 2H), 2.98 (s, 6H), 2.68 (s, 3H), 1.72 (s, 3H) |
| 565 | | MS (ESI) m/z 676.11 [M + 1]+; 1H NMR (400 MHz, DMSO-d6) δ 13.02 (bs, 1H), 8.38 (s, 1H), 8.35 (s, 1H), 7.60 (dd, J = 8.80, 2.40 Hz, 1H), 7.47 (s, 1H), 7.42 (d, J = 2.48 Hz, 1H), 7.35 (d, J = 8.16 Hz, 1H), 4.41 (t, J = 5.0 Hz, 2H), 4.24 (t, J = 4.72 Hz, 2H), 3.56 (s, 3H), 2.68 (s, 3H), 1.78 (s, 3H) |
| 568 | | MS (ESI) m/z 733.16 [M + 1]+; 1H NMR (400 MHz, DMSO-d6) δ 13.02 (s, 1H), 8.32 (s, 1H), 7.97 (s, 1H), 7.61-7.59 (m, 1H), 7.48 (s, 1H), 7.43 (s, 1H), 7.36 (d, J = 8.8 Hz, 1H), 4.41 (s, 2H), 4.23 (bs, 2H), 3.77 (bs, 2H), 3.55 (s, 3H), 2.69 (s, 3H), 2.22 (s, 6H), 1.75 (s, 3H) |

TABLE 2-continued

7-CF3-Thienylpyridine and Derivative Compounds

| Compound | Characterization |
|---|---|
| 569  | MS (ESI) m/z 662.07 [M + 1]+; 1H NMR (400 MHz, DMSO-d6) δ 12.70 (s, 1H), 8.89 (d, J = 4.76 Hz, 1H), 8.39 (s, 2H), 8.02 (s, 1H), 7.63-7.60 (dd, J = 2.56, 2.44 Hz 1H), 7.56 (d, J = 4.72 Hz, 1H), 7.46 (d, J = 2.44 Hz, 1H), 7.36 (d, J = 9.0 Hz, 1H), 4.41 (t, J = 4.4 Hz, 2H), 4.24 (t, J = 3.86 Hz, 2H), 3.56 (s, 3H), 1.73 (s, 3H) |
| 571  | MS (ESI) m/z 617.11 [M + 1]+; 1H NMR (400 MHz, MeOD) δ 8.31 (s, 1H), 8.16 (s, 1H), 8.00 (s, 1H), 7.56 (s, 1H), 7.51 (d, J = 8.08 Hz, 1H), 7.34 (d, J = 10.84 Hz, 1H), 4.50 (t, J = 4.80 Hz, 2H), 4.38 (t, J = 5.20 Hz, 2H), 2.96 (s, 3H), 2.03 (s, 3H) |
| 589  | MS (ESI) m/z 617.11 [M + 1]+; 1H-NMR (400 MHz, DMSO-d6) δ 8.46 (s, 1H), 8.36 (d, J = 5.64 Hz, 1H), 7.60 (dd, J = 8.88, 2.64 Hz, 1H), 7.43-7.39 (m, 2H), 7.36 (d, J = 9.00 Hz, 1H), 4.42 (t, J = 4.52 Hz, 2H), 4.28 (t, J = 4.76 Hz, 2H), 2.69 (s, 3H), 1.94 (s, 3H) |
| 590  | MS (ESI) m/z 615.23 [M + 1]+; 1H NMR (400 MHz, DMSO-d6) δ 8.35 (s, 1H), 7.95-7.93 (m, 3H), 7.57 (dd, J = 2.56, 8.92 Hz, 1H), 7.39 (d, J = 2.52 Hz, 1H), 7.33 (d, J = 9.04 Hz, 1H), 4.39 (t, J = 4.48 Hz, 2H), 4.30 (t, J = 4.36 Hz, 2H), 3.69 (s, 3H), 2.10 (s, 3H) |

TABLE 2-continued

7-CF3-Thienylpyridine and Derivative Compounds

| Compound | Characterization |
|---|---|
| 591 | MS (ESI) m/z 612.91 [M + 1]+; 1H-NMR (400 MHz, DMSO-d6) δ 14.09 (bs, 1H), 68.77 (d, J = 4.56 Hz, 1H), 8.37 (s, 1H), 7.97 (s, 1H), 7.59 (d, J = 8.48 Hz, 1H), 7.50 (d, J = 4.56 Hz, 1H), 7.42 (bs, 1H), 7.35 (d, J = 8.84 Hz, 1H), 4.42 (t, J = 4.32 Hz, 2H), 4.26 (t, J = 3.20 Hz, 2H), 2.85-2.79 (m, 2H), 1.85 (s, 3H), 0.97 (t, J = 7.24 Hz, 3H) |
| 595 | MS (ESI) m/z 629.10 [M + 1]+; 1H NMR (400 MHz, DMSO-d6) δ 8.37-8.28 (m, 2H), 7.61 (s, 1H), 7.48-7.43 (m, 1H), 7.31-7.26 (m, 2H), 7.05 (bs, 1H), 4.33 (bs, 2H), 4.24 (bs, 2H), 3.81 (s, 2H), 3.01 (s, 2H), 1.80 (s, 3H) |
| 605 | MS (ESI) m/z 615.09 [M + 1]+; 1H NMR (400 MHz, DMSO-d6) δ 8.34 (s, 1H), 8.16 (s, 1H), 7.52 (d, J = 7.44, 1H), 7.36 (s, 1H), 7.29 (d, J = 9.04 Hz, 1H), 6.54 (s, 1H), 6.30 (s, 1H), 4.88 (s, 2H), 4.38 (s, 2H), 4.31 (s, 2H), 2.32 (s, 3H) |
| 610 | MS (ESI) m/z 670.01 [M + 1]+; 1H NMR (400 MHz, DMSO-d6) δ 8.22 (s, 1H), 7.93 (s, 1H), 7.59 (dd, J = 8.68, 2.16 Hz, 1H), 7.41-7.34 (m, 3H), 4.40 (t, J = 4.76 Hz, 2H), 4.24 (t, J = 4.68 Hz, 2H), 3.20 (d, J = 7.48 Hz, 2H), 2.69 (s, 3H), 2.57 (d, J = 10.48 Hz, 2H), 2.28 (s, 6H), 1.83 (s, 3H) |

TABLE 2-continued
7-CF3-Thienylpyridine and Derivative Compounds
| Compound | Characterization |
|---|---|
| 614 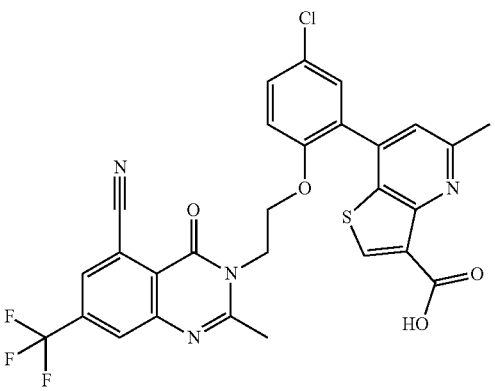 | MS (ESI) m/z 617.06 [M + 1]+; 1H-NMR (400 MHz, DMSO-d6) δ 8.38 (s, 1H), 8.14 (bs, 2H), 7.74 (t, J = 8.56 Hz, 1H), 7.29 (bs, 1H), 7.20 (d, J = 9.08 Hz, 1H), 4.41 (bs, 1H), 4.36 (bs, 1H), 4.23 (s, 2H), 2.66 (s, 3H), 1.70 (s, 3H) |
| 615 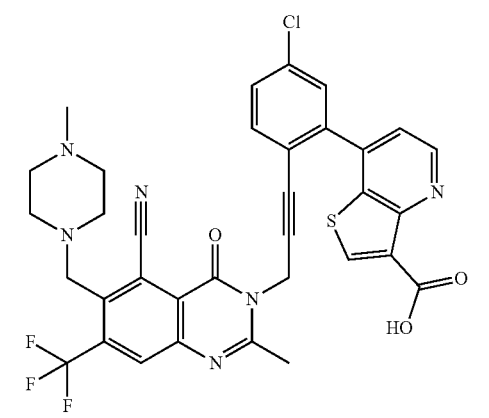 [SMILES: Cc1nc2cc(C(F)(F)F)c(CN3CCN(C)CC3)c(C#N)c2c(=O)n1CC#Cc1ccc(Cl)cc1-c1ccnc2c(C(=O)O)csc12] | MS (ESI) m/z 691.19 [M + 1]+; ; 1H NMR (400 MHz, DMSO-d6) δ 8.69 (d, J = 4.72 Hz, 1H), 8.48 (s, 1H), 8.06 (s, 1H), 7.73 (d, J = 8.4 Hz, 1H), 7.66 (d, J = 7.1 Hz, 1H), 7.57 (s, 1H), 7.47 (d, J = 4.64, 1H), 4.78 (s, 2H), 3.95 (s, 2H), 3.37 (d, J = 12.5 Hz, 2H), 2.97 (d, J = 10.68 Hz, 4H), 2.75 (s, 3H), 2.58-2.56 (m, 2H), 2.1 (s, 3H) |
| 616 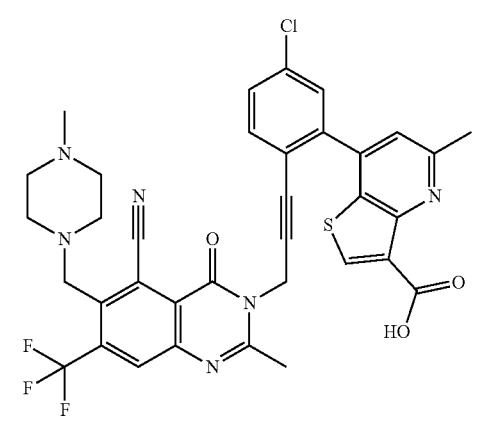 [SMILES: Cc1cc(-c2cc(Cl)ccc2C#CCn2c(C)nc3cc(C(F)(F)F)c(CN4CCN(C)CC4)c(C#N)c3c2=O)c2scc(C(=O)O)c2n1] | MS (ESI) m/z 705.23 [M + 1]+; 1H NMR (400 MHz, DMSO-d6) δ 13.31 (s, 1H), 9.43 (s, 1H), 8.54 (s, 1H), 8.11 (s, 1H), 7.75 (d, J = 8.32 Hz, 1H), 7.69 (dd, J = 8.36, 6.2 Hz, 1H), 7.65 (d, J = 1.96 Hz, 1H), 7.47 (s, 1H), 4.87 (s, 2H), 3.97 (s, 2H), 2.95 (d, J = 10.08 Hz, 4H), 2.80 (s, 3H), 2.66 (s, 3H), 2.62 (s, 4H), 2.17 (s, 3H) |

TABLE 2-continued

7-CF3-Thienylpyridine and Derivative Compounds

| Compound | | Characterization |
|---|---|---|
| 617 | 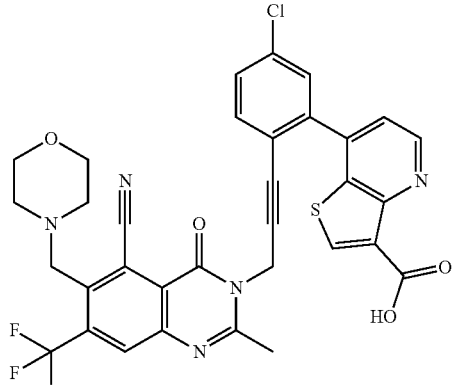 | MS (ESI) m/z 678.16 [M + 1]+; ; 1H NMR (400 MHz, DMSO-d6) δ 8.73 (d, J = 4.76 Hz, 1H), 8.6 (s, 1H), 8.1 (s, 1H), 7.76 (d, J = 8.0 Hz, 1H), 7.69 (d, J = 2.0 Hz, 1H), 7.67 (s, 1H), 7.55 (d, J = 4.76 Hz, 1H), 4.88 (s, 2H), 3.97 (s, 2H), 3.56 (s, 4H), 2.58 (s, 4H), 2.13 (s, 3H) |
| 629 | 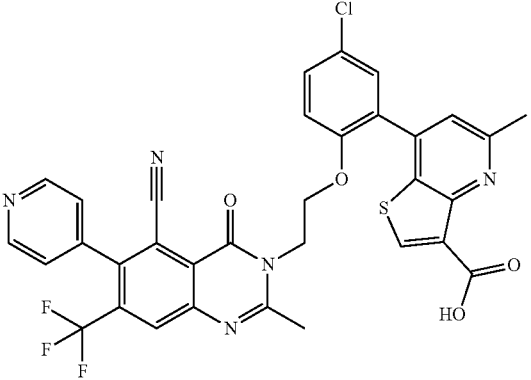 [SMILES: Cc1cc(-c2cc(Cl)ccc2OCCn2c(C)nc3cc(C(F)(F)F)c(-c4ccncc4)c(C#N)c3c2=O)c2scc(C(=O)O)c2n1] | MS (ESI) m/z 676.18 [M + 1]+; ; 1H NMR (400 MHz, DMSO-d6) δ 8.78 (d, J = 5.56 Hz, 2H), 8.25 (s, 1H), 8.09 (s, 1H), 7.59 (dd, J = 7.56 Hz, 2.64 Hz, 1H), 7.53 (d, J = 4.88 Hz, 2H), 7.42-7.40 (m, 2H), 7.36 (d, J = 8.92 Hz, 1H), 4.41 (t, J = 4.76 Hz ,2H), 4.28 (t, J = 4.36 Hz, 2H), 2.72 (s, 3H), 1.86 (s, 3H) |
| 630 | 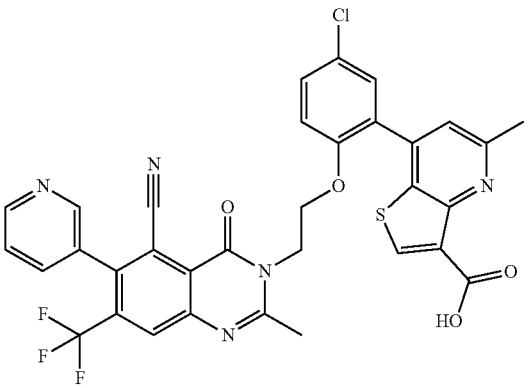 [SMILES: Cc1cc(-c2cc(Cl)ccc2OCCn2c(C)nc3cc(C(F)(F)F)c(-c4cccnc4)c(C#N)c3c2=O)c2scc(C(=O)O)c2n1] | MS (ESI) m/z 676.18 [M + 1]+; 1H NMR (400 MHz, DMSO-d6) δ 8.76 (d, J = 3.7, 1H), 8.69 (s, 1H), 8.31 (s, 1H), 8.05 (s,1H), 7.99 (d, J = 7.8 Hz, 1H), 7.66-7.58 (m, 2H), 7.45 (s, 1H), 7.424 (d, J = 2.56 Hz, 1H), 7.36 (d, J = 8.9, 1H), 4.42 (t, J = 9.2 Hz, 2H), 4.28 (t, J = 9.6 Hz, 2H), 2.73 (s, 3H), 1.87 (s, 3H) |
| 631 | 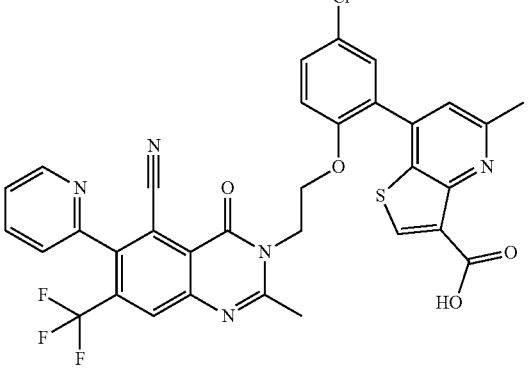 | MS (ESI) m/z 676.18 [M + 1]+; 1H NMR (400 MHz, DMSO-d6) δ 8.74 (d, J = 4.7 Hz, 1H), 8.37 (s, 1H), 8.07 (s, 1H), 8.03 (t, J = 7.8 Hz, 1H), 7.68 (d, J = 7.6 Hz, 1H), 7.61-7.52 (m, 2H), 7.43 (s, 2H), 7.36 (d, J = 8.9 Hz, 1H), 4.40 (s, 2H), 4.26 (s, 2H), 2.72 (s, 3H), 1.83 (s, 3H) |

TABLE 2-continued

7-CF3-Thienylpyridine and Derivative Compounds

| Compound | Characterization |
|---|---|
| 632 | MS (ESI) m/z 665.30 [M + 1]+; 1H-NMR (400 MHz, DMSO-d6), 13.51 (bs, 1H), 8.26 (s ,1H), 8.09 (s, 1H), 7.98 (s, 1H), 7.60 (dd, J = 2.36, 8.88 Hz, 1H), 7.52 (s, 1H), 7.44 (s, 1H),7.42 (d, J = 2.52 Hz, 1H), 7.37 (d, J = 8.88 Hz, 1H), 7.19 (s, 1H), 4.42 (t, J = 5.28 Hz, 2H), 4.28 (t, J = 4.24 Hz, 2H), 2.73 (s, 3H), 1.87 (s, 3H) |
| 633 | MS (ESI) m/z 665.23 [M + 1]+; 1H-NMR (400 MHz, DMSO-d6) 8.35 (s ,1H), 8.19 (d, J = 2.08 Hz,1H), 8.11 (s, 1H), 7.87 (d, J = 1.52 Hz, 1H), 7.61-7.58 (dd, J = 2.64, 8.88 Hz, 1H), 7.44-7.42 (m, 2H), 7.37 (d, J = 8.88 Hz, 1H), 6.63 (t, J = 2.24 Hz, 1H), 4.41 (t, J = 4.52 Hz, 2H), 4.28 (t, J = 4.12 Hz, 2H), 2.72 (s, 3H), 1.84 (s, 3H) |
| 634 | MS (ESI) m/z 697.13 [M + 1]+; 1H-NMR (400 MHz, DMSO-d6) δ 13.51 (bs, 1H), 9.75 (bs, 1H), 8.23 (s, 1H), 7.92 (s, 1H), 7.61-7.58 (t, J = 6.5 Hz, 1H), 7.42-7.41 (t, J = 6.5 Hz, 2H), 7.37 (d, J = 8.9 Hz, 1H), 4.40 (t, J = 6.2 Hz, 2H), 4.24 (t, J = 6.1 Hz, 2H), 3.83 (m, 2H), 3.49 (m, 2H), 3.24 (m, 2H), 3.03 (m, 2H), 2.28 (s, 3H), 2.71 (s, 3H), 1.82 (s, 3H) |
| 636 | MS (ESI) m/z 642.20 [M + 1]+; 1H NMR (400 MHz, DMSO-d6) δ 12.87 (bs, 1H), 9.92 (s, 1H), 8.39 (s, 1H), 8.29 (s, 1H), 8.03 (s, 1H), 7.62 (dd, J = 2.40, 8.8 Hz, 1H), 7.57 (s, 1H), 7.42 (d, J = 3.28 Hz, 1H), 7.37 (d, J = 8.92 Hz, 1H), 4.63 (bs, 2H), 4.43 (t, J = 4.84 Hz, 2H), 4.26 (t, J = 4.64 Hz, 2H), 2.96 (s, 6H), 1.76 (s, 3H) |

TABLE 2-continued

7-CF3-Thienylpyridine and Derivative Compounds

| Compound | | Characterization |
|---|---|---|
| 637 | 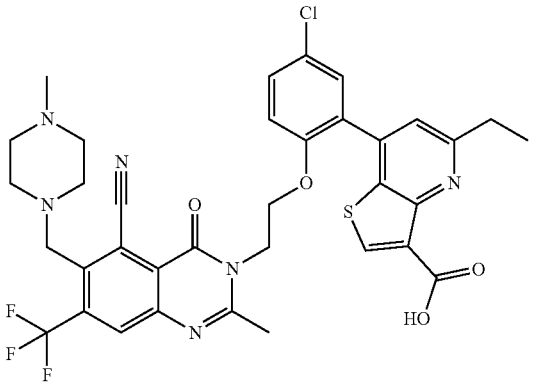 [SMILES: CCc1cc(-c2cc(Cl)ccc2OCCn2c(C)nc3cc(C(F)(F)F)c(CN4CCN(C)CC4)c(C#N)c3c2=O)c2scc(C(=O)O)c2n1] | MS (ESI) m/z 725.09 [M + 1]+; 1H-NMR (400 MHz, DMSO-d6) δ 8.18 (s,1H), 7.94 (s, 1H), 7.61-7.59 (dd, J = 8.8, 2.4 Hz, 1H), 7.46 (s, 1H), 7.44 (d, J = 2.48 Hz, 1H), 7.36 (d, J = 8.96 Hz, 1H), 4.41 (t, J = 5.2 Hz, 2H), 4.24 (t, J = 5.2 Hz, 2H), 3.94 (s, 2H), 3.40-3.37 (m, 2H), 3.04-2.98 (m, 2H), 2.92 (m, 4H), 2.78 (d, J = 3.52 Hz, 3H), 2.54 (m, 2H), 1.80 (s, 3H), 1.35 (t, J = 7.2 Hz, 3H) |
| 638 | 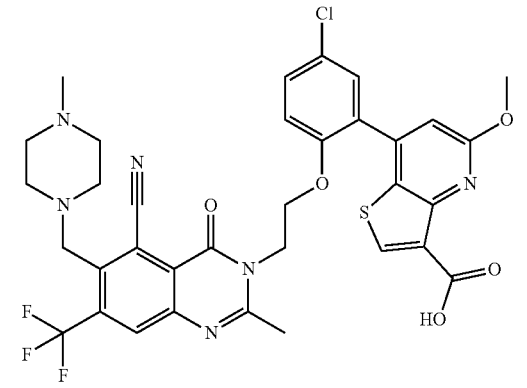 [SMILES: COc1cc(-c2cc(Cl)ccc2OCCn2c(C)nc3cc(C(F)(F)F)c(CN4CCN(C)CC4)c(C#N)c3c2=O)c2scc(C(=O)O)c2n1] | MS (ESI) m/z 727.07 [M + 1]+; ; 1H NMR (400 MHz, DMSO-d6) δ 12.7 (bs, 1H), 8.09 (s, 1H), 7.98 (s, 1H), 7.59-7.56 (dd, J = 2.8, 9.2 Hz, 1H), 7.40 (d, J = 2.4 Hz, 1H), 7.34 (d, J = 8.8 Hz, 1H), 6.90 (s, 1H), 4.41 (t, J = 6.4 Hz, 2H), 4.28 (t, J = 5.6 Hz, 2H), 4.07 (s, 3H), 3.94 (s, 2H), 3.39 (d, J = 11.2 Hz, 2H), 2.91 (d, J = 11.2 Hz, 4H), 2.78 (d, J = 3.2 Hz, 2H), 2.56 (d, J = 7.6 Hz, 2H), 1.88 (s, 3H) |
| 640 | 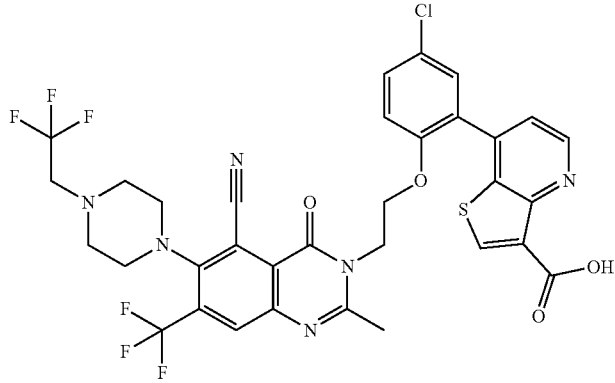 [SMILES: Cc1nc2cc(C(F)(F)F)c(N3CCN(CC(F)(F)F)CC3)c(C#N)c2c(=O)n1CCOc1ccc(Cl)cc1-c1ccnc2c(C(=O)O)csc12] | MS (ESI) m/z 751.1 [M + 1]+; 1H NMR (400 MHz, DMSO-d6) δ 8.85 (d, J = 4.9 Hz, 1H), 8.32 (s, 1H), 7.93 (s, 1H), 7.61 (dd, J = 8.9, 2.7 Hz, 1H), 7.53 (d, J = 4.9 Hz, 1H), 7.43 (d, J = 2.6 Hz, 1H), 7.37 (d, J = 9.0 Hz, 1H), 4.41 (t, J = 4.9 Hz, 2H), 4.24 (t, J = 5.0 Hz, 2H), 3.31 (q, J = 10.1 Hz, 2H), 3.07-2.58 (m, 6H), 1.75 (s, 3H). Note: piperazine protons were very broad and could not be properly integrated |
| 641 | 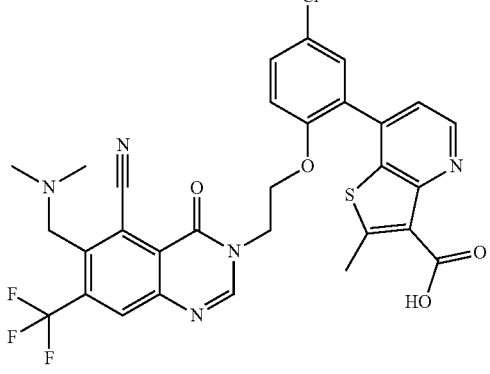 | MS (ESI) m/z 642.08 [M + 1]+; 1H NMR (400 MHz, DMSO-d6) δ 8.74 (d, J = 4.92 Hz, 1H), 8.15 (s, 1H), 7.86 (s, 1H), 7.61 (dd, J = 8.6, 2.4 Hz, 1H), 7.47 (m, 2H), 7.37 (d, J = 9 Hz, 1H), 4.67 (s, 2H), 4.41 (t, J = 5.28 Hz, 2H), 4.25 (t, J = 4.28 Hz, 2H), 2.88 (s, 6H), 2.53 (s, 3H) |

TABLE 2-continued

7-CF3-Thienylpyridine and Derivative Compounds

| Compound | Characterization |
|---|---|
| 642 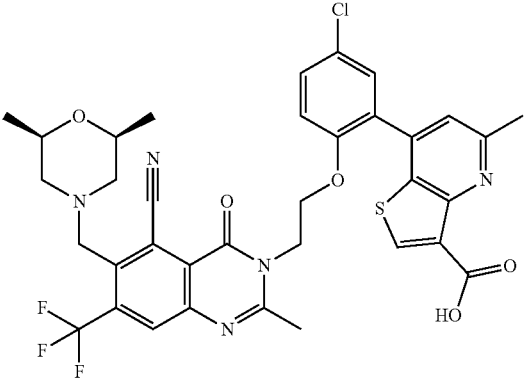 | MS (ESI) m/z 726.20 [M + 1]+; 1H NMR (400 MHz, DMSO-d6) δ 13.44 (bs, 1H), 8.27 (s, 1H), 7.95 (s, 1H), 7.59 (dd, J = 8.8, 2.5 Hz, 1H), 7.42-7.41 (m, 2H), 7.35 (d, J = 8.9 Hz, 1H), 4.4 (t, J = 5.9 Hz, 2H), 4.24 (t, J = 5.6 Hz, 2H), 3.83 (s, 2H), 3.47-3.43 (m, 2H), 2.68 (s, 3H), 2.62 (d, J = 10.5 Hz, 2H), 1.89 (d, J = 6.2 Hz, 2H), 1.86 (s, 3H), 1.01 (d, J = 6.2 Hz, 6H) |
| 643 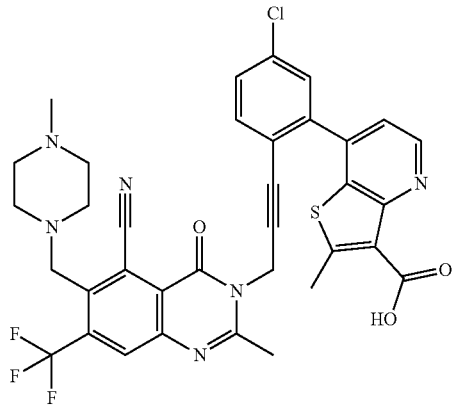 [SMILES: Cc1sc2c(-c3cc(Cl)ccc3C#CCn3c(C)nc4cc(C(F)(F)F)c(CN5CCN(C)CC5)c(C#N)c4c3=O)ccnc2c1C(=O)O] | MS (ESI) m/z 705.27 [M + 1]+; 1H NMR (400 MHz, DMSO-d6) δ 8.72 (d, J = 4.84 Hz, 1H), 8.05 (s, 1H), 7.75 (d, J = 8.20 Hz, 1H), 7.69 (d, J = 8.48 Hz, 1H), 7.65 (s, 1H), 7.57 (d, J = 4.76 Hz, 1H), 4.88 (s, 2H), 3.86 (s, 2H), 2.50-2.32 (m, 8H, merged with moisture peak in DMSO), 2.17 (s, 3H), 2.10 (s, 3H), 1.23 (s, 3H) |
| 644 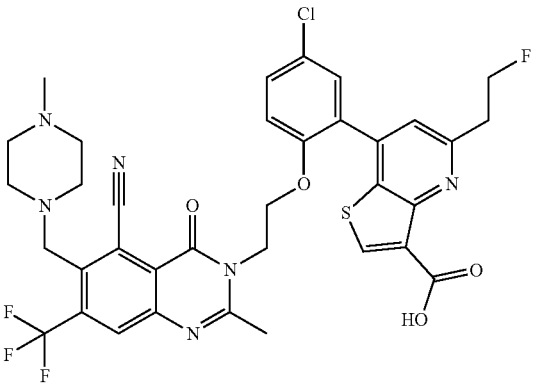 [SMILES: Cc1nc2cc(C(F)(F)F)c(CN3CCN(C)CC3)c(C#N)c2c(=O)n1CCOc1ccc(Cl)cc1-c1cc(CCF)nc2c(C(=O)O)csc12] | MS (ESI) m/z 743.07 [M + 1]+.;; 1H NMR (400 MHz, DMSO-d6) δ 13.2 (bs, 1H), 8.16 (s, 1H), 7.96 (s, 1H), 7.62-7.59 (dd, J = 2.4, 8.8 Hz, 1H), 7.59 (s, 1H), 7.43 (d, J = 2.4 Hz, 1H ), 7.37 (d, J = 8.8 Hz, 1H), 4.99 (t, J = 6.0 Hz, 1H), 4.87 (t, J = 6.0 Hz, 1H), 4.42 (t, J = 6.4 Hz, 2H), 4.26 (t, J = 6.8 Hz, 2H), 3.94 (s, 2H), 3.45 (t, J = 6.0 Hz, 2H), 2.93 (m, 4H), 2.78 (s, 3H), 2.50 (m, 2H), 1.76 (s, 3H) |

TABLE 2-continued

7-CF3-Thienylpyridine and Derivative Compounds

| Compound | Characterization |
|---|---|
| 645 | MS (ESI) m/z 729.05 [M + 1]+; 1H NMR (400 MHz, DMSO-d6) δ 13.04 (bs, 1H), 9.40 (s, 1H), 8.26 (s, 1H), 7.99 (s, 1H), 7.60 (dd, J = 2.28, 8.72 Hz, 1H), 7.53 (bs, 1H), 7.44 (d, J = 2.32 Hz, 1H), 7.36 (d, J = 8.92 Hz, 1H), 5.76-5.65 (d, J = 46.8 Hz, 2H), 4.41 (t, J = 5.16 Hz, 2H), 4.25 (t, J = 5.72 Hz, 2H), 3.94 (s, 2H), 3.40-3.37 (m, 2H), 2.93-2.90 (m, 4H), 2.79 (d, J = 3.32 Hz, 3H), 2.56-2.54 (m, 2H), 1.77 (s, 3H) |
| 649 | MS (ESI) m/z 697.18 [M + 1]+; 1H NMR (400 MHz, DMSO-d6) δ 8.52 (bs, 2H), 8.22 (s, 1H), 7.59 (s, 1H), 7.61 (dd, J = 2.76, 8.64 Hz, 1H), 7.42 (s, 2H), 7.37 (d, J = 9.0, 1H), 4.42 (t, J = 4.44 Hz, 2H), 4.26 (t, J = 4.96 Hz, 2H), 3.93 (s, 2H), 3.07 (s, 4H), 2.70 (m, 6H ), 1.84 (s , 3H) |
| 652 | MS (ESI) m/z 667.97 [M + 1]+; 1H NMR (400 MHz, DMSO-d6) δ 8.29 (s, 1H), 7.93 (s, 1H), 7.61 (dd, J = 2.56 Hz, 8.8 Hz, 1H), 7.41 (s, 2H), 7.37 (d, J = 9.0 Hz, 1H ), 4.39 (m, 2H), 4.26 (m, 3H), 3.96 (bs, 2H), 3.55 (bs, 2H), 2.70 (s, 3H), 2.35 (s, 3H), 1.85 (s, 3H) |
| 655 | MS (ESI) m/z 715.3 [M + 1]+; 1H NMR (400 MHz, DMSO-d6) δ 8.84 (d, J = 4.8 Hz, 1H), 8.25 (s, 1H), 7.96 (s, 1H), 7.61 (dd, J = 8.9, 2.7 Hz, 1H), 7.48 (d, J = 4.8 Hz, 1H), 7.43 (d, J = 2.6 Hz, 1H), 7.37 (d, J = 9.0 Hz, 1H), 4.89 (dt, J = 47.3, 4.5 Hz, 2H), 4.41 (t, J = 5.0 Hz, 2H), 4.25 (t, J = 5.0 Hz, 2H), 4.03-3.88 (m, 2H), 3.74-3.09 (m, 8H), 1.77 (s, 3H) |

TABLE 2-continued

7-CF3-Thienylpyridine and Derivative Compounds

| Compound | Characterization |
|---|---|
| 660 | LCMS (ESI) m/z 553.1 [M + 1]+; 1H NMR (400 MHz, DMSO-d6) δ 9.14 (d, J = 2.1 Hz, 1H), 8.71 (d, J = 2.1 Hz, 1H), 8.31 (dd, J = 1.8, 0.7 Hz, 1H), 8.23 (t, J = 2.1 Hz, 1H), 7.80 (dd, J = 1.7, 0.8 Hz, 1H), 7.50-7.39 (m, 2H), 7.26 (d, J = 8.9 Hz, 1H), 4.43-4.31 (m, 4H), 2.11 (s, 3H) |
| 661 | LCMS (ESI) m/z 569.1 [M + 1+9-; 1H NMR (400 MHz, DMSO-d6) δ 8.75 (d, J = 4.3 Hz, 1H), 8.37-8.31 (m, 1H), 8.07 (dt, J = 1.7, 0.8 Hz, 1H), 7.98 (s, 1H), 7.64-7.47 (m, 3H), 7.29 (d, J = 9.0 Hz, 1H), 7.22 (d, J = 4.2 Hz, 1H), 4.35 (t, J = 5.0 Hz, 2H), 4.21 (t, J = 4.9 Hz, 2H), 1.79 (s, 3H) |
| 662 | LCMS (ESI) m/z 553.0 [M + 1]+; 1H NMR (400 MHz, DMSO-d6) δ 8.71 (dd, J = 5.0, 0.8 Hz, 1H), 8.34-8.28 (m, 1H), 8.05 (dd, J = 1.7, 0.8 Hz, 1H), 7.88 (dd, J = 1.8, 0.8 Hz, 1H), 7.57 (dd, J = 5.0, 1.7 Hz, 1H), 7.52-7.40 (m, 2H), 7.26 (d, J = 8.9 Hz, 1H), 4.44-4.31 (m, 4H), 2.96 (s, 3H), 2.13 (s, 3H).5 (t, J = 4.7 Hz, 2H), 1.69 (s, 3H) |
| 663 | LCMS (ESI) m/z 557.0 [M + 1]+1H NMR (400 MHz, DMSO-d6) δ 8.60 (d, J = 4.7 Hz, 1H), 8.32 (s, 1H), 8.11 (s, 1H), 7.51 (dd, J = 8.9, 2.7 Hz, 1H), 7.33 (d, J = 2.6 Hz, 1H), 7.28 (d, J = 9.0 Hz, 1H), 7.22 (d, J = 4.4 Hz, 1H), 6.32 (d, J = 1.6 Hz, 1H), 4.34 (s, 2H), 4.23 (s, 2H), 1.81 (s, 3H) |

TABLE 2-continued

7-CF3-Thienylpyridine and Derivative Compounds

| Compound | | Characterization |
|---|---|---|
| 664 | 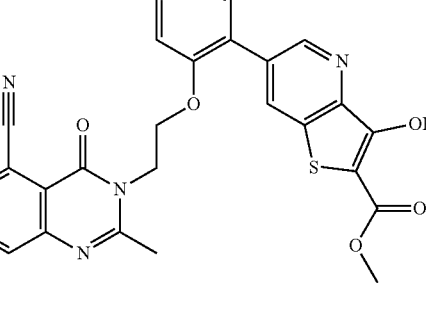 | LCMS (ESI) m/z 615.0 [M + 1]+1H NMR (400 MHz, DMSO-d6) δ 8.65 (d, J = 1.9 Hz, 1H), 8.35 (d, J = 1.9 Hz, 1H), 8.32-8.28 (m, 1H), 8.01 (dd, J = 1.7, 0.8 Hz, 1H), 7.49-7.40 (m, 2H), 7.25 (dd, J = 8.6, 0.6 Hz, 1H), 4.36 (dd, J = 11.4, 4.4 Hz, 4H), 3.85 (s, 3H), 2.19 (s, 3H) |
| 666 | 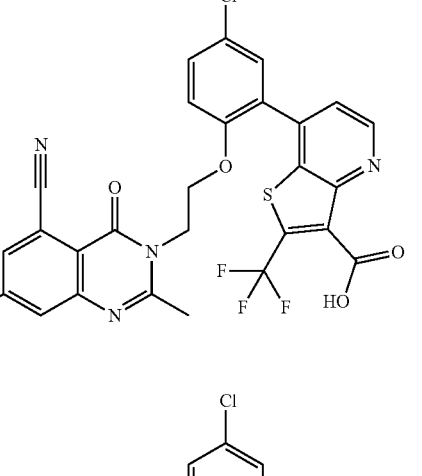 | LCMS (ESI) m/z 653.1 [M + 1]+; 1H NMR (400 MHz, DMSO-d6) δ 8.88 (d, J = 4.7 Hz, 1H), 8.38-8.32 (m, 1H), 8.17-8.05 (m, 1H), 7.61-7.51 (m, 2H), 7.42 (d, J = 2.6 Hz, 1H), 7.32 |
| 667 | 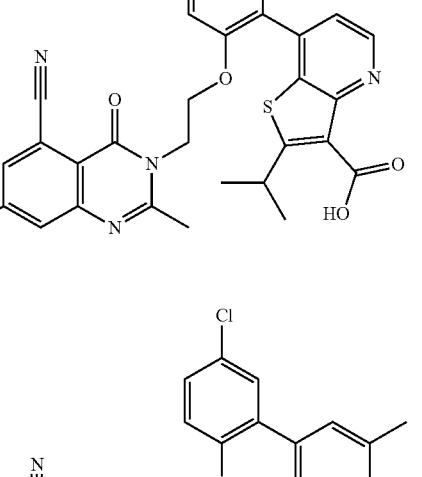 | LCMS (ESI) m/z 627.3 [M + 1]+; 1H NMR (400 MHz, DMSO-d6) δ 8.75 (d, J = 5.0 Hz, 1H), 8.35 (dd, J = 1.7, 0.6 Hz, 1H), 7.97 (dt, J = 1.7, 0.8 Hz, 1H), 7.57 (dd, J = 8.9, 2.7 Hz, 1H), 7.49 (d, J = 5.0 Hz, 1H), 7.42 (d, J = 2.6 Hz, 1H), 7.32 (d, J = 9.0 Hz, 1H), 4.37 (t, J = 5.0 Hz, 1H), 4.23 (t, J = 5.1 Hz, 1H), 3.85 (q, J = 6.8 Hz, OH), 1.83 (s, 2H), 0.99 (d, J = 6.8 Hz, 3H) |
| 668 | 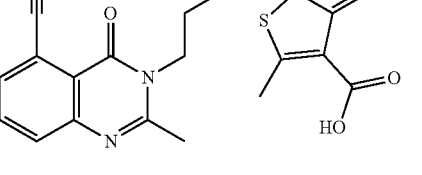 | LCMS (ESI) m/z 613.3 [M + 1+9-; 1H NMR (400 MHz, DMSO-d6) δ 8.33 (d, J = 1.7 Hz, 1H), 7.93 (dt, J = 1.7, 0.8 Hz, 1H), 7.56 (dd, J = 8.9, 2.7 Hz, 1H), 7.42-7.29 (m, 2H), 4.39 (t, J = 5.0 Hz, 1H), 4.24 (t, J = 5.0 Hz, 1H), 2.66 (s, 2H), 2.35 (s, 2H), 1.92 (s, 2H) |

TABLE 2-continued

7-CF3-Thienylpyridine and Derivative Compounds

| Compound | Characterization |
|---|---|
| 670 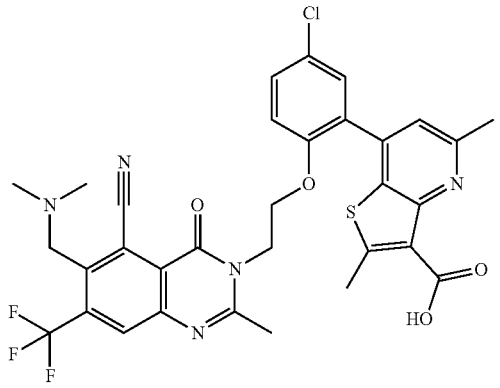 [SMILES: Cc1cc(-c2cc(Cl)ccc2OCCn2c(C)nc3cc(C(F)(F)F)c(CN(C)C)c(C#N)c3c2=O)c2sc(C)c(C(=O)O)c2n1] | LCMS (ESI) m/z 670.2 [M + 1+9-; 1H NMR (400 MHz, DMSO-d6) δ 7.57 (dd, J = 8.9, 2.7 Hz, 1H), 7.43-7.36 (m, 2H), 7.32 (d, J = 9.0 Hz, 1H), 4.38 (t, J = 4.9 Hz, 2H), 2.67 (s, 4H), 2.32 (s, 3H), 1.87 (s, 3H) |
| 672 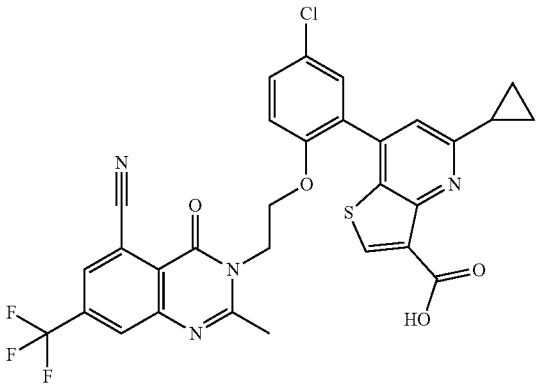 [SMILES: Cc1nc2cc(C(F)(F)F)cc(C#N)c2c(=O)n1CCOc1ccc(Cl)cc1-c1cc(C2CC2)nc2c(C(=O)O)csc12] | LCMS (ESI) m/z 625.9 [M + 1+9-; 1H NMR (400 MHz, DMSO-d6) δ 8.33 (d, J = 1.7 Hz, 1H), 8.17 (s, 1H), 7.92 (d, J = 1.7 Hz, 1H), 7.56 (dd, J = 8.9, 2.7 Hz, 1H), 7.44-7.38 (m, 2H), 7.32 (d, J = 9.0 Hz, 1H), 4.36 (t, J = 5.1 Hz, 2H), 4.23 t, J = 5.1 Hz, 2H), 1.78 (s, 3H) |
| 675 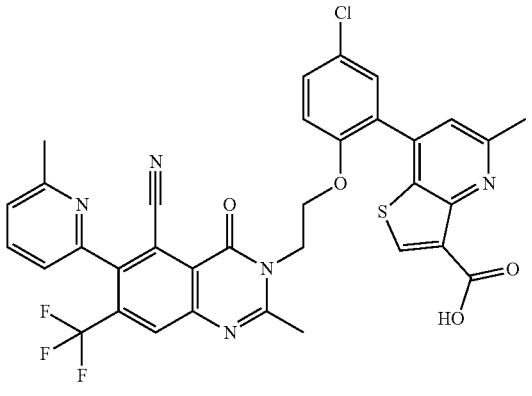 [SMILES: Cc1cccc(-c2c(C(F)(F)F)cc3nc(C)n(CCOc4ccc(Cl)cc4-c4cc(C)nc5c(C(=O)O)csc45)c(=O)c3c2C#N)n1] | LCMS (ESI) m/z 690.1 [M + 1]+; 1H NMR (400 MHz, DMSO-d6) δ 8.36 (s, 1H), 8.03 (s, 1H), 7.87 (t, J = 7.8 Hz, 1H), 7.56 (dd, J = 8.9, 2.7 Hz, 1H), 7.46-7.36 (m, 5H), 7.33 (d, J = 9.0 Hz, 1H), 4.37 (s, 2H), 4.24 (s, 2H), 2.69 (s, 3H), 2.50 (s, 4H), 1.80 (s, 3H) |
| 684 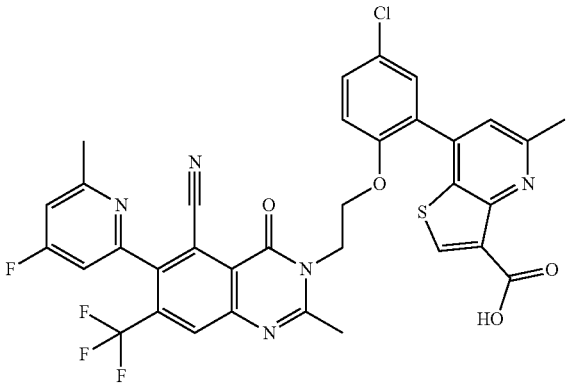 [SMILES: Cc1cc(F)cc(-c2c(C(F)(F)F)cc3nc(C)n(CCOc4ccc(Cl)cc4-c4cc(C)nc5c(C(=O)O)csc45)c(=O)c3c2C#N)n1] | LCMS (ESI) m/z 708.1 [M + 1]+; 1H NMR (400 MHz, DMSO-d6) δ 8.36 (s, 1H), 8.06 (s, 1H), 7.60 (dd, J = 8.9, 2.7 Hz, 1H), 7.56 (dd, J = 9.3, 2.3 Hz, 1H), 7.43 (dd, J = 6.7, 4.0 Hz, 3H), 7.36 (d, J = 9.0 Hz, 1H), 4.41 (bs, 2H), 4.28 (bs, 2H), 2.73 (s, 3H), 2.56 (s, 3H), 1.85 (s, 3H) |

TABLE 2-continued

7-CF3-Thienylpyridine and Derivative Compounds

| Compound | Characterization |
|---|---|
| 686 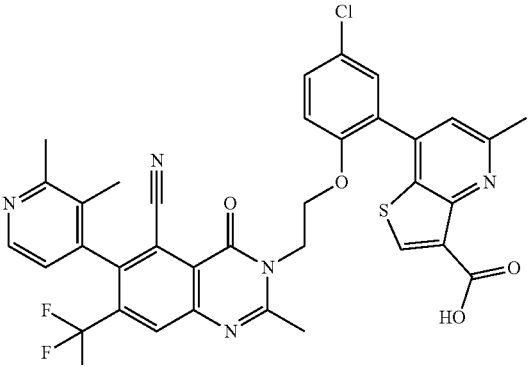 | LCMS (ESI) m/z 704.0 [M + 1]+; 1H NMR (400 MHz, DMSO-d6) δ 8.57 (d, J = 5.4 Hz, 1H), 8.27 (s, 1H), 8.08 (s, 1H), 7.57 (dd, J = 8.9, 2.7 Hz, 1H), 7.50-7.38 (m, 3H), 7.33 (d, J = 9.0 Hz, 1H), 4.39 (m, 2H), 4.25 (m 2H), 2.70 (s, 3H), 2.61 (s, 3H), 2.00 (s, 3H), 1.81 (s, 3H) |
| 687 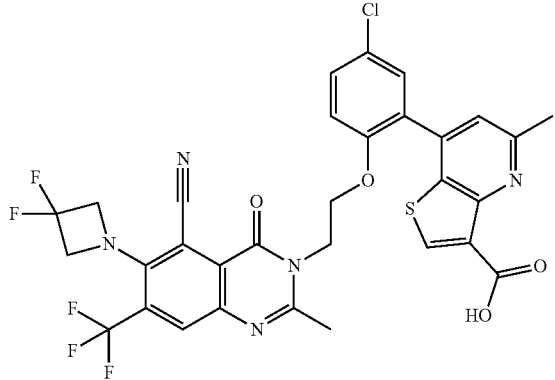 [SMILES: Cc1cc(-c2cc(Cl)ccc2OCCn2c(C)nc3cc(C(F)(F)F)c(N4CC(F)(F)C4)c(C#N)c3c2=O)c2scc(C(=O)O)c2n1] | LCMS (ESI) m/z 690.2 [M + 1+9-; 1H NMR (400 MHz, DMSO-d6) δ 8.34 (s, 1H), 7.85 (s, 1H), 7.60 (dd, J = 8.9, 2.7 Hz, 1H), 7.43 (s, 1H), 7.41 (d, J = 2.7 Hz, 1H), 7.36 (d, J = 9.0 Hz, 1H), 4.86 (t, J = 12.5 Hz, 4H), 4.39 (t, J = 5.0 Hz, 2H), 4.22 (t, J = 5.0 Hz, 2H), 2.72 (s, 3H), 1.79 (s, 3H) |
| 705 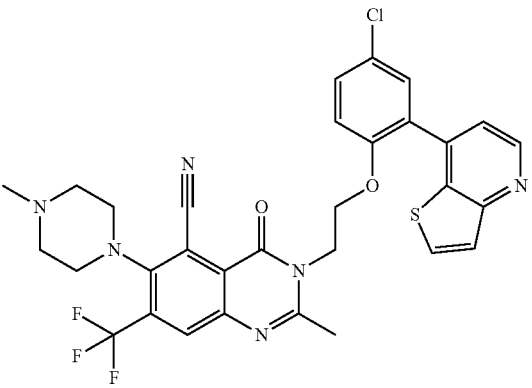 [SMILES: Cc1nc2cc(C(F)(F)F)c(N3CCN(C)CC3)c(C#N)c2c(=O)n1CCOc1ccc(Cl)cc1-c1ccnc2ccsc12] | MS (ESI) m/z 639.0 [M + 1]+; 1H-NMR (400 MHz, d6-DMSO) δ/ppm = 9.81-9.70 (b, 1H), 8.63 (d, J = 4.7 Hz, 1H), 8.09 (s, 1H), 7.72 (d, J = 5.4 Hz, 1H), 7.56 (dd, J = 8.9, 2.6 Hz, 1H), 7.38 (d, J = 2.6 Hz, 1H), 7.37 (d, J = 5.4 Hz, 1H), 7.33 (d, J = 8.9 Hz, 1H), 7.22 (d, J = 4.7 Hz, 1H), 4.38 (t, J = 4.9 Hz, 2H), 4.27 (t, J = 4.9 Hz, 2H), 3.92-3.82 (m, 2H), 3.59-3.50 (m, 2H), 3.30-3.20 (m, 2H), 3.14-3.01 (m, 2H), 2.91 (bs, 3H), 1.90 (s, 3H) |
| 706 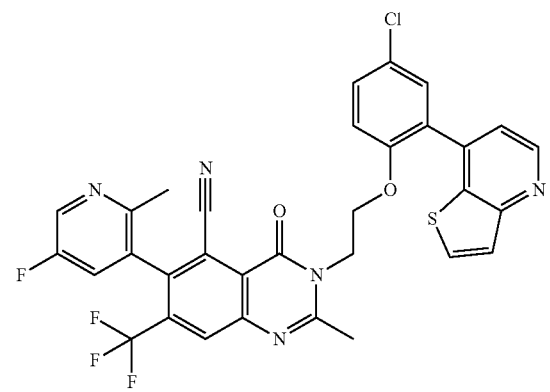 [SMILES: Cc1ncc(F)cc1-c1c(C(F)(F)F)cc2nc(C)n(CCOc3ccc(Cl)cc3-c3ccnc4ccsc34)c(=O)c2c1C#N] | MS (ESI) m/z 650.8 [M + 1]+; 1H NMR (400 MHz, DMSO-d6) δ 8.71-8.64 (m, 2H), 8.29 (d, J = 0.6 Hz, 1H), 7.90 (dd, J = 9.2, 3.0 Hz, 1H), 7.78 (d, J = 5.6 Hz, 1H), 7.56 (dd, J = 8.9, 2.7 Hz, 1H), 7.48 (d, J = 5.5 Hz, 1H), 7.41 (d, J = 2.7 Hz, 1H), 7.33 (d, J = 8.9 Hz, 1H), 7.26 (d, J = 4.7 Hz, 1H), 4.43-4.35 (m, 2H), 4.34-4.15 (m, 1H), 2.19 (d, J = 1.0 Hz, 3H), 1.88 (s, 3H) |

TABLE 2-continued

7-CF3-Thienylpyridine and Derivative Compounds

| Compound | Characterization |
|---|---|
| 708 | MS (ESI) m/z 682.0 [M + 1]+; 1H NMR (400 MHz, DMSO-d6) δ 8.28 (s, 1H), 7.90 (s, 1H), 7.63-7.56 (m, 1H), 7.46-7.38 (m, 2H), 7.35 (d, J = 8.96 Hz, 1H), 4.49-4.32 (m, 2H), 4.31-4.18 (m, 2H), 3.70-3.66 (m, 1H), 3.26-3.22 (m, 2H), 2.69 (s, 3H), 2.32-2.22 (m, 2H), 2.22-2.09 (m, 2H), 2.07 (s, 3H), 1.80 (s, 3H) |
| 709 | MS (ESI) m/z 684.07 [M + 1+9-; 1H NMR (400 MHz, DMSO-d6) 8.23 (s, 1H), 7.94 (s, 1H), 7.60 (dd, J = 8.80, 2.40 Hz, 1H), 7.44-7.38 (m, 2H), 7.36 (d, J = 8.96 Hz, 1H), 4.40 (t, J = 4.76 Hz, 2H), 4.25 (t, J = 4.24 Hz, 2H), 3.05-3.01 (m, 4H), 2.69 (s, 3H), 2.50-2.30 (m, 6H), 1.91-1.78 (m, 5H) |
| 711 | MS (ESI) m/z 670.05 [M + 1+9-; 1H NMR (400 MHz, DMSO-d6) δ 8.28 (s, 1H), 7.89 (s, 1H), 7.59 (dd, J = 8.80, 2.40 Hz, 1H), 7.45-7.40 (m, 2H), 7.35 (d, J = 8.84 Hz, 1H), 4.39 (t, J = 5.40 Hz, 2H),), 4.30-4.22 (m, 2H) 3.72-3.67 (m, 1H), 2.70 (s, 3H), 2.16 (s, 6H), 1.80 (s, 3H), 1.55 (d, J = 6.68 Hz, 3H) |
| 713 | MS (ESI) m/z 710.17 [M + 1+9-; 1H NMR (400 MHz, DMSO-d6-FD20) δ 9.18 (bs, 1H), 8.20 (s, 1H), 7.97 (s, 1H), 7.61-7.58 (dd, J = 2.4, 8.8 Hz, 1H), 7.43 (s, 1H), 7.37 (d, J = 9.2 Hz, 1H), 4.42 (t, J = 5.6 Hz, 2H), 4.26 (t, J = 3.6 Hz, 2H), 3.43 (bs, 3H), 3.06 (d, J = 6.8 Hz, 2H), 2.92-2.86 (m, 2H), 2.73-2.70 (m, 3H), 2.02 (bs, 1H), 1.83-1.78 (m, 5H), 1.63-1.54 (m, 2H) |

TABLE 2-continued

7-CF3-Thienylpyridine and Derivative Compounds

| Compound | Characterization |
|---|---|
| 714 | MS (ESI) m/z 696.11 [M + 1+9-; 1H NMR (400 MHz, DMSO-d6) δ 8.50 (bs, 1H), 8.19-8.15 (m, 2H), 7.97 (s, 1H), 7.61-7.58 (dd, J = 2.8, 9.2 Hz, 1H), 7.43-7.42 (m, 2H), 7.37 (d, J = 8.8 Hz, 1H), 4.42 (t, J = 4.8 Hz, 2H), 4.26 (t, J = 4.4 Hz, 2H), 3.29 (d, J = 11.2 Hz, 2H), 3.06 (d, J = 11.2 Hz, 2H), 2.83-2.78 (m, 2H), 2.70 (s, 3H), 2.11-2.01 (m, 1H), 1.82 (s, 3H), 1.75 (d, J = 12.4 Hz, 2H), 1.59-1.50 (m, 2H) |
| 717 | MS (ESI) m/z 621.98 [M + 1+9-; 1H NMR (400 MHz, DMSO-d6) δ 8.69 (d, J = 4.76 Hz, 1H), 8.65 (s, 1H), 8.30 (bs, 2H), 7.75 (d, J = 8.32, 1H), 7.69 (m, 2H), 7.54 (d, J = 4.72 Hz, 1H), 4.85 (s, 2H), 4.48 (s, 2H), 2.77 (s, 6H) |
| 719 | MS (ESI) m/z 710.06 [M + 1]+; 1H NMR (400 MHz, DMSO-d6) δ 12.99 (s, 1H), 8.10 (s, 1H), 7.65 (s, 1H), 7.49 (dd, J = 8.76, 2.48 Hz, 1H), 7.28-7.24 (m, 3H), 7.13 (d, J = 7.32 Hz, 1H), 4.34 (t, J = 5.16 Hz, 2H), 4.22 (t, J = 5.12 Hz, 2H), 3.93 (s, 2H), 3.37 (d, J = 11.32, 2H,), 3.33-3.29 (m, 2H, merged with moisture peak in DMSO), 2.90-2.88 (m, 4H), 2.78 (s, 3H), 2.67 (s, 3H), 1.72 (s, 3H) |
| 735 | MS (ESI) m/z 690.35 [M + 1]+; 1H NMR (400 MHz, DMSO-d6) δ 8.67 (d, J = 3.72 Hz, 1H), 8.29 (s, 1H), 8.09 (s, 1H), 7.86 (d, J = 7.76 Hz, 1H), 7.60 (dd, J = 2.52, 8.84 Hz, 1H), 7.50 (d, J = 4.96 Hz, 1H), 7.48 (s, 1H), 7.44 (d, J = 2.6 Hz, 1H), 7.38 (d, J = 8.92 Hz, 1H), 4.43 (t, J = 6.12 Hz, 2H), 4.27 (t, J = 5.32, 2H), 2.73 (s, 3H), 2.24 (s, 3H), 1.84 (s, 3H) |

TABLE 2-continued

7-CF3-Thienylpyridine and Derivative Compounds

| Compound | | Characterization |
|---|---|---|
| 736 | 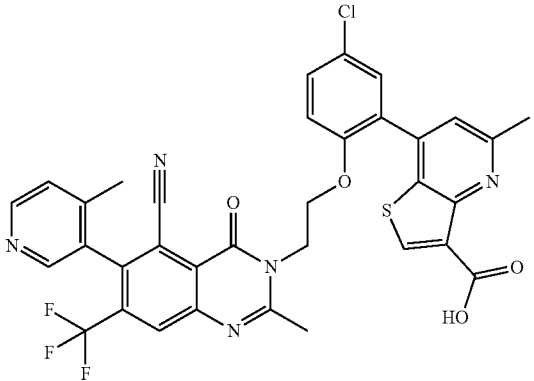 [SMILES: Cc1cc(-c2cc(Cl)ccc2OCCn2c(C)nc3cc(C(F)(F)F)c(-c4cnccc4C)c(C#N)c3c2=O)c2scc(C(=O)O)c2n1] | MS (ESI) m/z 690.04 [M + 1]+; 1H NMR (400 MHz, DMSO-d6) δ 8.65 (d, J = 4.0 Hz, 1H), 8.56 (s, 1H), 8.29 (s, 1H), 8.09 (s, 1H), 7.60 (dd, J = 8.8, 2.5 Hz, 1H), 7.56 (d, J = 5 Hz, 1H), 7.46 (s, 1H), 7.45 (d, J = 2.5 Hz, 1H), 7.37 (d, J = 8.9 Hz, 1H), 4.43 (bs, 2H), 4.28-4.26 (m, 2H), 2.73 (s, 3H), 2.11 (s, 3H), 1.84 (s, 3H) |
| 738 | 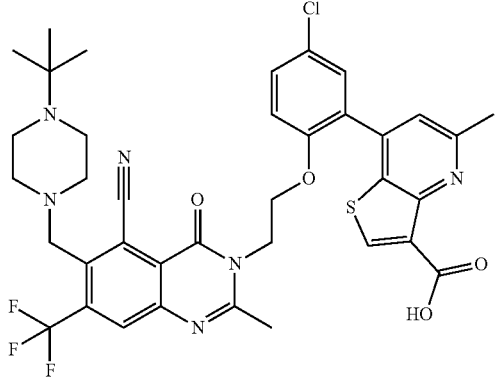 [SMILES: Cc1cc(-c2cc(Cl)ccc2OCCn2c(C)nc3cc(C(F)(F)F)c(CN4CCN(C(C)(C)C)CC4)c(C#N)c3c2=O)c2scc(C(=O)O)c2n1] | MS (ESI) m/z 753.46 [M + 1]+.; 1H-NMR (400 MHz, CD3OD) δ 13.50 (bs, 1H), 8.94 (t, J = 8.44 Hz, 1H), 8.21 (s, 1H), 7.96 (s, 1H), 7.57 (dd, J = 2.25, 8.88 Hz, 1H),7.42 (s, 1H), 7.36 (d, J = 8.80 Hz, 1H), 4.41 (t, J = 4.32 Hz, 2H), 4.25 (t, J = 3.24 Hz, 2H), 3.96 (s, 2H),.3.50 (d, J = 10.48 Hz, 2H), 2.95 (d, J = 11.64 Hz, 2H), 2.82 (d, J = 10.52 Hz, 2H), 2.70 (s, 3H), 2.65 (d, J = 11.68 Hz, 2H), 1.85 (s, 3H), 1.30 (s, 9H) |
| 739 | 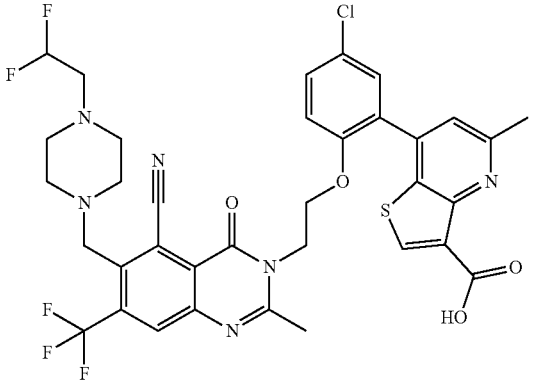 [SMILES: Cc1cc(-c2cc(Cl)ccc2OCCn2c(C)nc3cc(C(F)(F)F)c(CN4CCN(CC(F)F)CC4)c(C#N)c3c2=O)c2scc(C(=O)O)c2n1] | MS (ESI) m/z 761.12 [M + 1]+; 1H NMR (400 MHz, DMSO-d6) δ 8.22 (s, 1H), 7.96 (s, 1H), 7.60 (dd, J = 2.44, 8.88 Hz, 1H), 7.43 (s, 1H), 7.42 (s, 1H), 7.36 (d, J = 8.96 Hz, 1H), 6.58-6.31 (m, 1H), 4.41 (t, J = 4.56 Hz, 2H), 4.25 (t, J = 4.64 Hz, 2H), 3.95 (bs, 2H), 3.60-3.45 (m, 2H), 3.32-3.11 (m, 4H), 2.77-2.72 (m, 4H), 2.70 (s, 3H), 1.83 (s, 3H) |
| 740 | 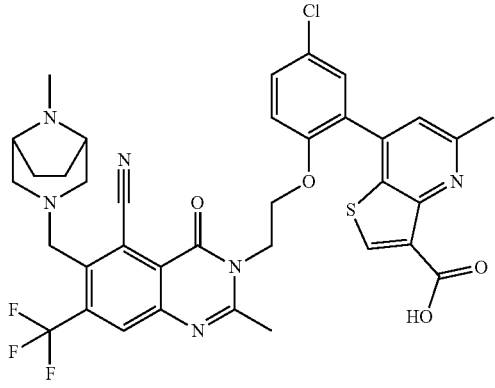 [SMILES: Cc1cc(-c2cc(Cl)ccc2OCCn2c(C)nc3cc(C(F)(F)F)c(CN4CC5CCC(C4)N5C)c(C#N)c3c2=O)c2scc(C(=O)O)c2n1] | MS (ESI) m/z 737.12 [M + 1]+; 1H NMR (400 MHz, DMSO-d6) δ 13.61 (bs, 1H), 9.01 (bs, 1H), 8.23 (s, 1H), 7.96 (s, 1H), 7.59 (dd, J = 8.88, 2.56 Hz, 1H), 7.42 (s, 2H), 7.37 (d, J = 8.96 Hz, 1H), 4.41 (t, J = 4.16 Hz, 2H), 4.25 (t, J = 4.96 Hz, 2H), 3.93 (s, 2H), 3.43 (s, 2H), 3.32-3.29 (m, 2H), 2.98-2.88 (m, 2H), 2.72 (d, J = 3.60 Hz, 3H), 2.69 (s, 3H), 2.18-2.16 (m, 2H), 1.91 (d, J = 8.2 Hz, 2H), 1.84 (s, 3H) |

TABLE 2-continued

7-CF3-Thienylpyridine and Derivative Compounds

| Compound | Characterization |
|---|---|
| 747 | MS (ESI) m/z 690.06 [M + 1]+; 1H NMR (400 MHz, DMSO-d6) δ 8.73 (s, 1H), 8.30 (d, J = 10.6 Hz, 1H), 8.07 (t, J = 9.7 Hz, 2H), 7.66 (bs, 1H), 7.57 (s, 2H), 7.44 (bs, 2H), 7.36-7.29 (m, 1H), 4.39 (bs, 2H), 4.26 (bs, 2H), 3.02 (bs, 2H), 1.77 (d, J = 11.0 Hz, 3H), 1.35 (s, 3H) |
| 751 | MS (ESI) m/z 693.99 [M + 1]+; 1H NMR (400 MHz, DMSO-d6) δ 8.86 (s, 1H), 8.71 (d, J = 4.6 Hz, 1H), 8.33 (s, 1H), 8.13 (s, 1H), 7.72 (t, J = 10.4 Hz, 1H), 7.60 (dd, J = 8.84, 2.28 Hz, 1H), 7.45-7.35 (m, 2H), 7.36 (d, J = 8.9 Hz, 1H), 4.44-4.24 (m, 4H), 2.72 (s, 3H), 1.87 (s, 3H) |
| 753 | MS (ESI) m/z 629.08 [M + 1]+; 1H NMR (400 MHz, DMSO-d6) δ 16.55 (s, 1H), 8.00-7.83 (m, 3H), 7.60-7.52 (m, 1H), 7.40-7.28 (m, 2H), 4.49-4.23 (m, 4H), 3.70 (s, 3H), 2.69 (s, 3H), 2.16 (s, 3H) |
| 754 | MS (ESI) m/z 622.96 [M + 1]+; 1H NMR (400 MHz, DMSO-d6) δ 16.04 (s, 1H), 8.18 (s, 1H), 8.02 (s, 1H), 8.01 (s, 1H), 7.71 (d, J = 8.36 Hz, 1H), 7.65 (dd, J = 8.36, 1.88 Hz, 1H), 7.58 (d, J = 1.72 Hz, 1H), 4.90 (s, 2H) 3.64 (s, 3H), 2.73 (s, 3H), 2.36 (s, 3H) |

TABLE 2-continued

7-CF3-Thienylpyridine and Derivative Compounds

| Compound | Characterization |
|---|---|
| 774 | MS (ESI) m/z 703.98 [M + 1]+; 1H NMR (400 MHz, DMSO-d6) δ 8.59 (s, 1H), 8.32 (s, 1H), 8.05 (s, 1H), 7.92 (d, J = 7.2 Hz, 1H), 7.60 (dd, J = 2.56, 8.88 Hz, 1H), 7.54 (d, J = 8.04 Hz, 1H), 7.45 (s, 1H), 7.42 (d, J = 2.60 Hz, 1H), 7.36 (d, J = 8.96 Hz, 1H) 4.42 (t, J = 4.64 Hz, 2H), 4.27 (t, J = 4.20 Hz, 2H), 2.90 (q, J = 7.52 Hz, 2H), 2.73 (s, 3H), 1.87 (s, 3H), 1.32 ( t, J = 7.60 Hz, 3H) |
| 775 | MS (ESI) m/z 690.05 [M + 1]+; 1H NMR (400 MHz, DMSO-d6) δ 8.64 (s, 1H), 8.52 (s, 1H), 8.29 (s, 1H), 8.04 (s, 1H), 7.86 (s, 1H), 7.59 (dd, J = 8.84, 2.52 Hz, 1H), 7.45 (s, 1H), 7.41 (d, J = 2.56 Hz, 1H), 7.36 (d, J = 8.96 Hz, 1H), 4.42 (t, J = 5.76 Hz, 2H), 4.28 (t, J = 4.24 Hz, 2H), 2.73 (s, 3H), 2.43 (s, 3H), 1.87 (s, 3H) |
| 776 | MS (ESI) m/z 704.04 [M + 1]+; 1H NMR (400 MHz, DMSO-d6) δ 8.42 (s, 1H), 8.06 (s, 1H), 7.92 (t, J = 7.80 Hz, 1H), 7.59 (dd, J = 8.80, 2.40 Hz, 1H), 7.50-7.39 (m, 4H), 7.36 (d, J = 8.88 Hz, 1H), 4.40 (s, 2H), 4.27 (s, 2H), 2.80 (q, J = 7.44 Hz, 2H), 2.72 (s, 3H), 1.84 (s, 3H), 1.22 (q, J = 7.44 Hz, 3H) |
| 777 | MS (ESI) m/z 693.96 [M + 1]+; 1H NMR (400 MHz, DMSO-d6) δ 8.85 (dd, J = 5.88, 7.96 Hz, 1H), 8.79 (d, J = 10.04 Hz, 1H), 8.34 (s, 1H), 8.12 (s, 1H), 7.65-7.58 (m, 2H), 7.45 (s, 1H), 7.43 (d, J = 2.56 Hz, 1H), 7.37 (d, J = 8.96 Hz, 1H), 4.45-4.26 (m, 4H), 2.72 (s, 3H), 1.87 (s, 3H) |

TABLE 2-continued

7-CF3-Thienylpyridine and Derivative Compounds

| Compound | | Characterization |
|---|---|---|
| 779 | 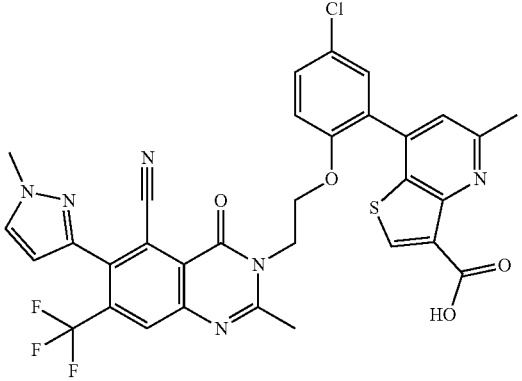 [SMILES: Cc1cc(-c2cc(Cl)ccc2OCCn2c(C)nc3cc(C(F)(F)F)c(-c4ccn(C)n4)c(C#N)c3c2=O)c2scc(C(=O)O)c2n1] | MS (ESI) m/z 679.00 [M + 1]+; 1H NMR (400 MHz, DMSO-d6) δ 8.37 (s, 1H), 8.02 (s, 1H), 7.87 (d, J = 1.92 Hz, 1H), 7.59 (dd, J = 8.88, 2.62 Hz, 1H), 7.42 (d, J = 3.0 Hz, 2H), 7.35 (d, J = 8.96 Hz, 1H), 6.48 (s, 1H), 4.40 (t, J = 6.04 Hz, 2H), 4.25 (t, J = 5.2 Hz, 2H), 3.93 (s, 3H), 2.70 (s, 3H), 1.82 (s, 3H) |
| 789 | 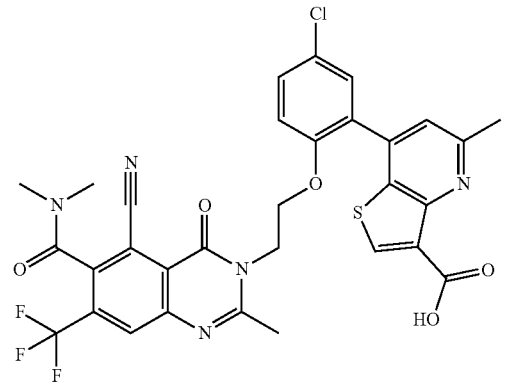 [SMILES: Cc1cc(-c2cc(Cl)ccc2OCCn2c(C)nc3cc(C(F)(F)F)c(C(=O)N(C)C)c(C#N)c3c2=O)c2scc(C(=O)O)c2n1] | MS (ESI) m/z 670.09 [M + 1]+; 1H NMR (400 MHz, DMSO-d6 with D2O) δ 8.24 (s, 1H), 7.97 (s, 1H), 7.56 (dd, J = 8.88, 2.52 Hz, 1H), 7.39-7.37 (m, 2H), 7.31 (d, J = 8.96 Hz, 1H), 4.39-4.34 (m, 2H), 4.22 (bs, 2H), 3.05 (s, 3H), 2.84 (s, 3H), 2.69 (s, 3H), 1.75 (s, 3H) |
| 790 | 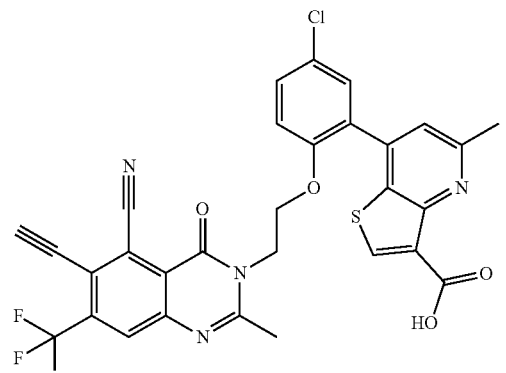 | MS (ESI) m/z 622.9 [M + 1]+; 1H NMR (400 MHz, DMSO-d6) δ 8.28 (s, 1H), 7.95 (s, 1H), 7.59 (dd, J = 8.84, 2.52 Hz, 1H), 7.42 (s, 1H), 7.41 (d, J = 2.56 Hz, 1H), 7.35 (d, J = 8.96 Hz, 1H), 5.25 (s, 1H), 4.40 (t, J = 4.52 Hz, 2H), 4.25 (t, J = 2.44 Hz, 2H), 2.70 (s, 3H), 1.79 (s, 3H) |
| 808 | 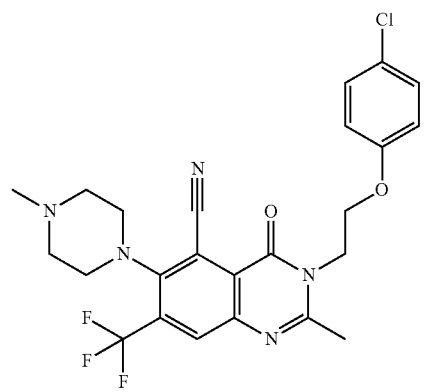 [SMILES: Cc1nc2cc(C(F)(F)F)c(N3CCN(C)CC3)c(C#N)c2c(=O)n1CCOc1ccc(Cl)cc1] | MS (ESI) m/z 506.4 [M + 1]+; 1H NMR (400 MHz, DMSO-d6) δ 8.18 (s, 1H), 7.34-7.24 (m, 2H), 6.98-6.93 (m, 2H), 4.49 (t, J = 5.2 Hz, 2H), 4.31 (t, J = 5.2 Hz, 2H), 3.85 (t, J = 12.3 Hz, 2H), 3.53 (d, J = 11.8 Hz, 2H), 3.17 (d, J = 12.9 Hz, 2H), 3.05 (d, J = 11.6 Hz, 2H), 2.88 (s, 3H), 2.77 (s, 3H) |

US 11,286,268 B1

TABLE 2-continued

7-CF3-Thienylpyridine and Derivative Compounds

| Compound | | Characterization |
|---|---|---|
| 832 | 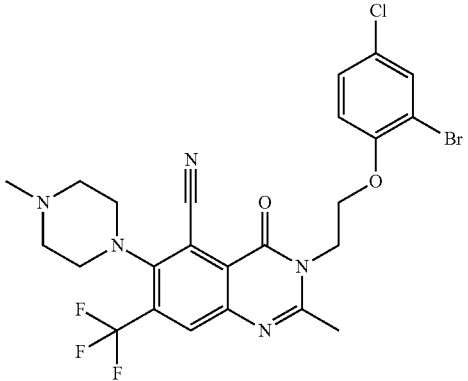 [SMILES: Cc1nc2cc(C(F)(F)F)c(N3CCN(C)CC3)c(C#N)c2c(=O)n1CCOc1ccc(Cl)cc1Br] | MS (ESI) m/z = 584.1 [M + 1]+; 1H-NMR (400 MHz, d6-DMSO) δ/ppm = 9.85-9.70 (b, 1H), 8.20 (s, 1H), 7.67 (d, J = 2.6 Hz, 1H), 7.40 (dd, J = 8.9, 2.6 Hz, 1H), 7.17 (d, J = 8.9 Hz, 1H), 4.55 (t, J = 4.5 Hz, 2H), 4.39 (t, J = 4.5 Hz, 2H), 3.84 (bt, J = 12.0 Hz, 2H), 3.53 (bd, J = 12.0 Hz, 2H), 3.17 (d, J = 12.5 Hz, 2H), 3.12-2.97 (m, 2H), 2.92-2.84 (m, 6H) |
| 833 | 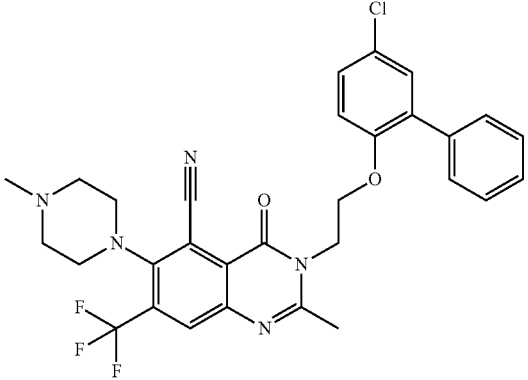 [SMILES: Cc1nc2cc(C(F)(F)F)c(N3CCN(C)CC3)c(C#N)c2c(=O)n1CCOc1ccc(Cl)cc1-c1ccccc1] | MS (ESI) m/z = 582.1 [M + 1]+; 1H-NMR (400 MHz, d6-DMSO) δ/ppm = 9.84-9.70 (b, 1H), 8.22 (s, 1H), 7.37 (dd, J = 8.8, 2.7, 1H), 7.34-7.24 (m, 5H), 7.23 (d, J = 2.7 Hz, 1H), 7.17 (d, J = 8.8 Hz, 1H), 4.41-4.30 (m, 4H), 3.86 (bt, J = 12.6 Hz, 2H), 3.54 (bd, J = 11.5 Hz, 2H), 3.18 (d, J = 12.5 Hz, 2H), 3.12-2.99 (m, 2H), 2.89 (bs, 3H), 2.23 (s, 3H) |
| 834 | 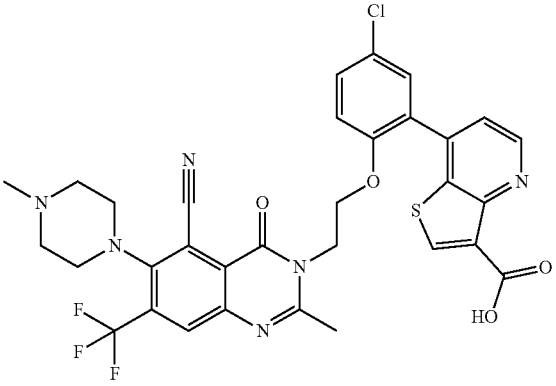 [SMILES: Cc1nc2cc(C(F)(F)F)c(N3CCN(C)CC3)c(C#N)c2c(=O)n1CCOc1ccc(Cl)cc1-c1ccnc2c(C(=O)O)csc12] | MS (ESI) m/z = 683.3 [M + 1]+; 1H-NMR (400 MHz, d6-DMSO) δ/ppm = 9.81-9.69 (b, 1H), 8.84 (d, J = 4.7 Hz, 1H), 8.23 (s, 1H), 7.96 (s, 1H), 7.61 (dd, J = 8.9, 2.7 Hz, 1H), 7.48 (d, J = 4.7 Hz, 1H), 7.43 (d, J = 2.7 Hz, 1H), 7.37 (d, J = 8.9 Hz, 1H), 4.41 (t, J = 5.1 Hz, 2H), 4.25 (t, J = 5.1 Hz, 2H), 3.92-3.82 (m, 2H), 3.57 (bd, J = 11.2 Hz, 2H), 3.26 (bd, J = 13.3 Hz, 2H), 3.15-3.02 (m, 2H), 2.92 (bs, 3H), 1.77 (s, 3H) |
| 835 | 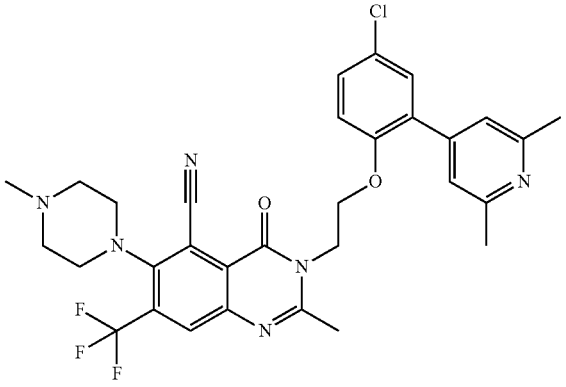 | MS (ESI) m/z = 611.3 [M + 1]+; 1H-NMR (400 MHz, d6-DMSO) δ/ppm = 9.98-9.85 (b, 1H), 8.15 (s, 1H), 7.73-7.64 (bs, 2H), 7.55 (dd, J = 8.9, 2.8 Hz, 1H), 7.46 (d, J = 2.8 Hz, 1H), 7.31 (d, J = 8.9 Hz, 1H), 4.43 (bs, 4H), 3.85 (bt, J = 11.1 Hz, 2H), 3.54 (bd, J = 11.4 Hz, 2H), 3.17 (bd, J = 12.8 Hz, 2H), 3.12-2.99 (m, 2H), 2.89 (s, 3H), 2.62 (s, 6H), 2.37 (s, 3H) |

TABLE 2-continued

7-CF3-Thienylpyridine and Derivative Compounds

| Compound | Characterization |
|---|---|
| 836 | MS (ESI) m/z = 653.0 [M + 1]+; 1H-NMR (400 MHz, d6-DMSO) δ/ppm = 9.85-9.74 (b, 1H), 8.06 (s, 1H), 7.70 (d, J = 5.4 Hz, 1H), 7.55 (dd, J = 8.9, 2.6 Hz, 1H), 7.36 (d, J = 2.6 Hz, 1H), 7.32 (d, J = 8.9 Hz, 1H), 7.25 (d, J = 5.4 Hz, 1H), 7.18 (s, 1H), 4.38 (t, J = 4.7 Hz, 2H), 4.28 (t, J = 4.7 Hz, 2H), 3.87 (bt, J = 13 Hz, 2H), 3.56 (bd, J = 11.7 Hz, 2H), 3.25 (bd, J = 13 Hz, 2H), 3.15-3.01 (m, 2H), 2.91 (bs, 3H), 2.62 (s, 3H), 1.96 (s, 3H) |
| 847 | LCMS: 694.4.5 [M + H]+; 1H NMR (400 MHz, DMSO-d6) δ 8.88 (d, J = 4.8 Hz, 1H), 8.67 (d, J = 2.9 Hz, 1H), 8.29 (s, 1H), 8.13 (s, 1H), 7.89 (dd, J = 9.0, 2.8 Hz, 1H), 7.61 (dd, J = 8.9, 2.7 Hz, 1H), 7.53 (d, J = 4.8 Hz, 1H), 7.44 (d, J = 2.7 Hz, 1H), 7.37 (d, J = 9.0 Hz, 1H), 4.43 (q, J = 4.9 Hz, 2H), 4.28 (q, J = 6.6, 5.9 Hz, 2H), 2.22 (s, 3H), 1.79 (s, 3H) |
| 852 | LCMS: 669.6 [M + H]+; 1H NMR (400 MHz, DMSO-d6) δ 9.70 (s, 1H), 8.59 (d, J = 4.7 Hz, 1H), 8.05 (s, 1H), 7.68 (d, J = 5.5 Hz, 1H), 7.52 (dd, J = 8.9, 2.7 Hz, 1H), 7.38-7.26 (m, 3H), 7.18 (d, J = 4.7 Hz, 1H), 4.35 (t, J = 5.2 Hz, 2H), 4.24 (t, J = 4.9 Hz, 2H), 3.92 (d, J = 12.8 Hz, 2H), 3.76 (t, J = 5.2 Hz, 2H), 3.60 (d, J = 12.0 Hz, 2H), 3.23 (dd, J = 26.4, 8.6 Hz, 4H), 3.09 (s, 3H), 1.86 (s, 3H) |
| 853 | LCMS: 669.6 [M + H]+; 1H NMR (400 MHz, DMSO-d6) δ 8.61 (d, J = 4.7 Hz, 1H), 8.08 (s, 1H), 7.70 (d, J = 5.5 Hz, 1H), 7.52 (dd, J = 8.9, 2.7 Hz, 1H), 7.42-7.34 (m, 2H), 7.29 (d, J = 9.0 Hz, 1H), 7.19 (d, J = 4.7 Hz, 1H), 4.43 (t, J = 5.4 Hz, 2H), 4.35 (t, J = 5.0 Hz, 2H), 4.23 (t, J = 5.0 Hz, 2H), 3.14 (s, 5H), 3.01 (s, 2H), 2.83 (s, 5H), 1.83 (s, 3H) |

TABLE 2-continued

7-CF3-Thienylpyridine and Derivative Compounds

| Compound | Characterization |
|---|---|
| 855 | MS (ESI) m/z 625.1 [M + 1]+; 1H NMR (400 MHz, DMSO-d6) δ 8.79 (d, J = 27.2 Hz, 2H), 8.62 (d, J = 4.7 Hz, 1H), 8.08 (s, 1H), 7.72 (d, J = 5.5 Hz, 1H), 7.55 (dd, J = 8.9, 2.7 Hz, 1H), 7.44-7.26 (m, 3H), 7.21 (d, J = 4.7 Hz, 1H), 4.38 (t, J = 5.0 Hz, 2H), 4.27 (t, J = 5.0 Hz, 2H), 3.38 (s, 2H), 3.23 (s, 1H), 3.04 (s, 2H), 1.89 (s, 3H) |
| 856 | LCMS: 720.9 [M + H]+; 1H NMR (400 MHz, DMSO-d6) δ 9.81 (d, J = 9.6 Hz, 1H), 8.59 (s, 1H), 8.09 (s, 1H), 7.79-7.63 (m, 3H), 7.50 (s, 1H), 4.85 (s, 2H), 4.07-3.92 (m, 2H), 3.87-3.74 (m, 2H), 3.66 (d, J = 11.7 Hz, 2H), 3.29 (d, J = 18.2 Hz, 4H), 3.14 (d, J = 11.5 Hz, 2H), 2.67 (s, 3H), 2.23 (s, 3H) |
| 859 | LCMS: 707.4 [M + H; ]+. 1H NMR (400 MHz, DMSO-d6) δ 9.79 (s, 1H), 8.77 (d, J = 4.8 Hz, 1H), 8.59 (s, 1H), 8.11 (s, 1H), 7.76 (d, J = 8.3 Hz, 1H), 7.72-7.66 (m, 2H), 7.57 (d, J = 4.8 Hz, 1H), 4.87 (s, 2H), 3.98 (d, J = 12.8 Hz, 2H), 3.80 (t, J = 5.2 Hz, 2H), 3.72-3.53 (m, 2H), 3.39-3.21 (m, 4H), 3.21-3.03 (m, 1H), 2.16 (s, 3H) |

TABLE 2-continued

7-CF3-Thienylpyridine and Derivative Compounds

| Compound | Characterization |
|---|---|
| 867  | MS (ESI) m/z 732.2 [M + 1]+; 1H NMR (400 MHz, DMSO-d6) δ 8.22 (s, 1H), 7.91 (s, 1H), 7.60 (dd, J = 8.9, 2.7 Hz, 1H), 7.43 (s, 1H), 7.42 (d, J = 2.7 Hz, 1H), 7.36 (d, J = 9.0 Hz, 1H), 4.40 (t, J = 4.9 Hz, 2H), 4.24 (t, J = 5.0 Hz, 2H), 3.98 (t, J = 11.9 Hz, 2H), 3.50 (d, J = 13.5 Hz, 2H), 3.34 (d, J = 13.5 Hz, 2H), 3.18 (d, J = 12.0 Hz, 2H), 2.72 (s, 3H), 1.81 (s, 3H) |
| 870  | MS (ESI) m/z 650.8 [M + 1]+; 1H NMR (400 MHz, DMSO-d6) δ 8.71-8.64 (m, 2H), 8.29 (d, J = 0.6 Hz, 1H), 7.90 (dd, J = 9.2, 3.0 Hz, 1H), 7.78 (d, J = 5.6 Hz, 1H), 7.56 (dd, J = 8.9, 2.7 Hz, 1H), 7.48 (d, J = 5.5 Hz, 1H), 7.41 (d, J = 2.7 Hz, 1H), 7.33 (d, J = 8.9 Hz, 1H), 7.26 (d, J = 4.7 Hz, 1H), 4.43-4.35 (m, 2H), 4.34-4.15 (m, 1H), 2.19 (d, J = 1.0 Hz, 3H), 1.88 (s, 3H) |
| 876  | LCMS (ESI) m/z 678.8 [M + 1]+; 1H NMR (400 MHz, DMSO-d6) δ 8.24 (s, 1H), 7.96 (s, 1H), 7.57 (dd, J = 8.9, 2.7 Hz, 1H), 7.43-7.36 (m, 2H), 7.33 (d, J = 9.0 Hz, 1H), 4.38 (t, J = 4.9 Hz, 2H), 4.23 (t, J = 4.9 Hz, 2H), 2.68 (s, 3H), 1.76 (s, 3H) |
| 879  | LCMS (ESI) m/z 697.1 [M + 1]+; 1H NMR (400 MHz, DMSO-d6) δ 8.94 (s, 1H), 8.81 (s, 1H), 7.93 (s, 1H), 7.61 (dd, J = 8.9, 2.7 Hz, 1H), 7.49-7.34 (m, 3H), 4.41 (s, 2H), 4.26 (s, 2H), 3.79 (s, 7H), 3.40 (d, J = 12.1 Hz, 2H), 3.18 (d, J = 12.2 Hz, 2H), 3.05 (s, 2H), 2.72 (s, 3H), 2.42 (s, 3H), 1.97 (s, 3H) |

TABLE 2-continued

7-CF3-Thienylpyridine and Derivative Compounds

| Compound | Characterization |
|---|---|
| 887 | LCMS (ESI) m/z 682.2 [M + 1]+; 1H NMR (400 MHz, DMSO-d6) δ 8.83 (d, J = 11.8 Hz, 1H), 8.76 (d, J = 4.9 Hz, 1H), 8.41 (d, J = 11.5 Hz, 1H), 7.94 (s, 1H), 7.58 (dd, J = 8.9, 2.7 Hz, 1H), 7.49 (d, J = 4.9 Hz, 1H), 7.39 (d, J = 2.7 Hz, 1H), 7.34 (d, J = 9.0 Hz, 1H), 4.40 (t, J = 5.1 Hz, 2H), 4.22 (t, J = 5.0 Hz, 2H), 3.66 (s, 2H), 3.58 (s, 1H), 3.45 (d, J = 12.3 Hz, 2H), 3.35 (s, 1H), 3.15-3.08 (m, 1H), 3.05 (d, J = 12.2 Hz, 1H), 2.75 (d, J = 13.4 Hz, 2H), 2.30 (s, 3H), 1.85 (d, J = 17.3 Hz, 1H), 1.84 (s, 3H |
| 899 | MS (ESI) m/z 643.06 [M + 1]+; 1H NMR (400 MHz, DMSO-d6) δ 7.92 (s, 1H), 7.90 (s, 1H), 7.57 (dd, J = 8.80, 2.56 Hz, 1H), 7.31-7.30 (m, 2H), 4.41 (t, J = 4.80 Hz, 2H), 4.33 (t, J = 4.80 Hz, 2H), 3.69 (s, 3H), 2.64 (s, 3H), 2.31 (s, 3H), 2.27 (s, 3H) |
| 901 | MS (ESI) m/z 690.05 [M + 1]+; 1H NMR (400 MHz, DMSO-d6) δ 8.71 (s, 1H), 8.65 (d, J = 4.60 Hz, 1H), 8.29 (s, 1H), 8.10 (s, 1H), 7.60 (d, J = 8.88, 2.44 Hz, 1H), 7.48 (bs, 1H), 7.46 (s, 1H), 7.44 (d, J = 2.48 Hz, 1H), 7.36 (d, J = 8.96 Hz, 1H) 4.42 (t, J = 6.20 Hz, 2H), 4.32-4.22 (m, 2H), 2.73 (s, 3H), 2.07 (s, 3H), 1.84 (s, 3H) |
| 902 | MS (ESI) m/z 704.06 [M + 1]+; 1H NMR (400 MHz, DMSO-d6) δ 13.41 (bs, 1H), 8.45 (s, 1H), 8.25 (s, 1H), 8.08 (s, 1H), 7.63-7.57 (m, 2H), 7.46-7.40 (m, 2H), 7.36 (d, J = 8.80 Hz, 1H), 4.45-4.35 (m, 2H), 4.35-4.23 (m, 2H), 2.72 (s, 3H), 2.35 (s, 3H), 2.15 (s, 3H), 1.83 (s, 3H) |

TABLE 2-continued

7-CF3-Thienylpyridine and Derivative Compounds

| Compound | | Characterization |
|---|---|---|
| 903 | 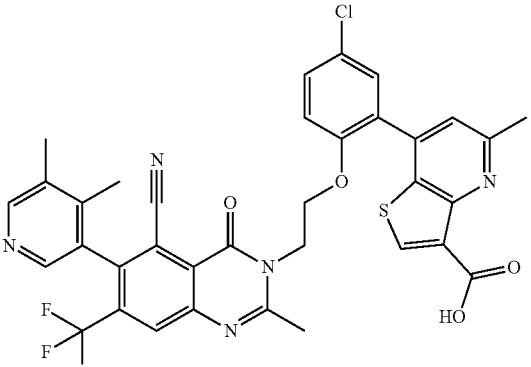 | MS (ESI) m/z 704.16 [M +1]+; 1H NMR (400 MHz, DMSO-d6) 8.46 (s, 1H), 8.30 (s, 1H), 8.24 (s, 1H), 7.84 (bs, 1H), 7.58-7.49 (m, 1H), 7.37 (s, 1H), 7.29 (d, J = 8.8 Hz, 1H), 7.16 (s, 1H), 4.37 (t, J = 4.68 Hz, 2H), 4.27 (t, J = 4.2 Hz, 2H), 2.64 (s, 3H), 2.31 (s, 3H), 1.95 (s, 3H), 1.85 (s, 3H) |
| 904 | 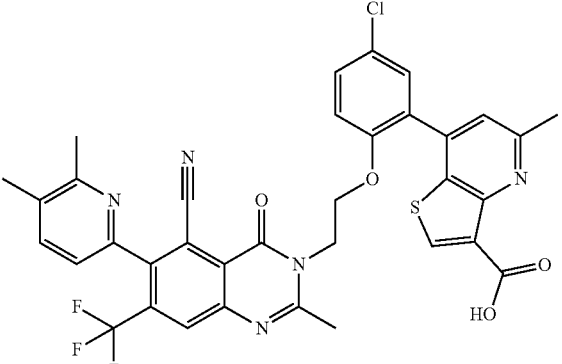 | MS (ESI) m/z 704.22 [M + 1]+;; 1H NMR (400 MHz, DMSO-d6) δ 8.38 (s, 1H), 8.04 (s, 1H), 7.73 (d, J = 8.0 Hz, 1H), 7.57 (dd, J = 8.88 Hz, 2.4 Hz, 1H), 7.43 (s, 2H), 7.40-7.34 (m, 2H), 4.40 (t, J = 4.48 Hz, 2H), 4.22 (t, J = 5.2 Hz, 2H), 2.72 (s, 3H), 2.50 (s, 3H), 2.36 (s, 3H), 1.82 (s, 3H) |
| 905 | 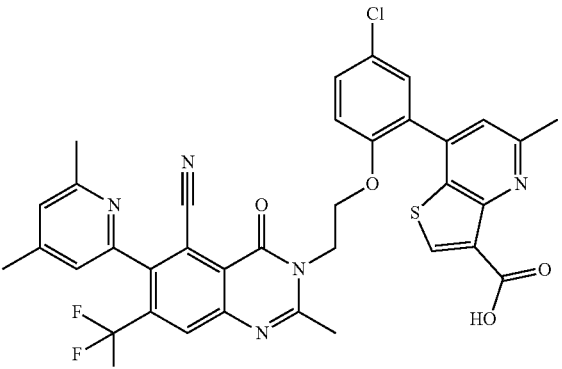 | MS (ESI) m/z 704.03 [M + 1]+; 1H NMR (400 MHz, DMSO-d6) δ 8.36 (s, 1H), 8.04 (s, 1H), 7.59 (dd, J = 8.84 Hz, 2.60 Hz, 1H), 7.43 (s, 2H), 7.36 (d, J = 8.96 Hz, 1H), 7.30 (s, 1H), 7.25 (s, 1H), 4.40 (s, 2H), 4.27 (s, 2H), 2.72 (s, 3H), 2.50 (s, 3H), 2.39 (s, 3H), 1.82 (s, 3H) |
| 906 | 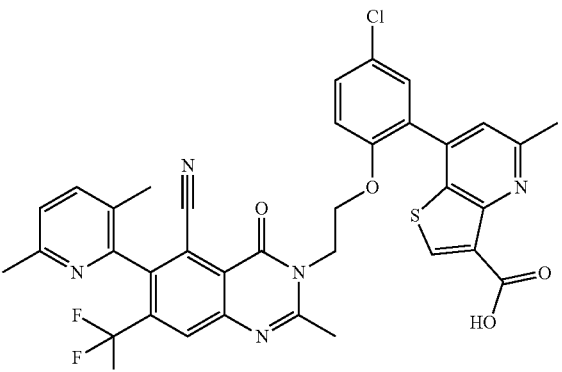 | MS (ESI) m/z 704.03 [M + 1]+; 1H NMR (400 MHz, DMSO-d6) δ 13.52 (bs, 1H), 8.37 (s, 1H), 8.11 (s, 1H), 7.72 (d, J = 7.88 Hz, 1H), 7.59 (dd, J = 8.88, 2.4 Hz, 1H), 7.45-7.43 (m, 2H), 7.36-7.31 (m, 2H), 4.43 (t, J = 4.36 Hz, 2H), 4.26 (t, J = 5.88 Hz, 2H), 2.72 (s, 3H), 2.46 (s, 3H), 2.04 (s, 3H), 1.80 (s, 3H) MS (ESI) m/z 679.00 [M + 1]+; 1H NMR (400 MHz, |

TABLE 2-continued

7-CF3-Thienylpyridine and Derivative Compounds

| Compound | | Characterization |
|---|---|---|
| 907 | 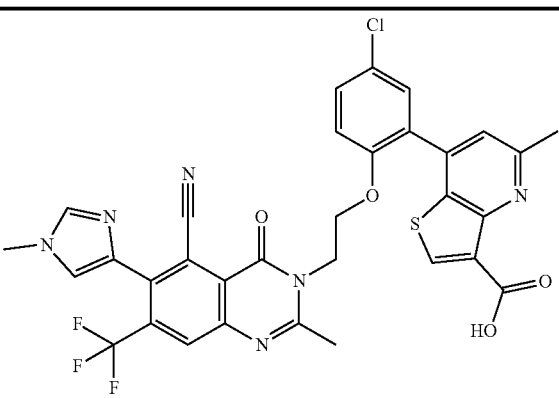 | DMSO-d6) δ 13.56 (bs, 1H), 8.40 (s, 1H), 7.99 (s, 1H), 7.77 (s, 1H), 7.58 (d, J = 7.20 Hz, 1H), 7.42-7.34 (m, 4H), 4.39 (s, 2H), 4.25 (s, 2H), 3.77 (s, 3H), 2.69 (s, 3H), 1.82 (s, 3H) |
| 908 | 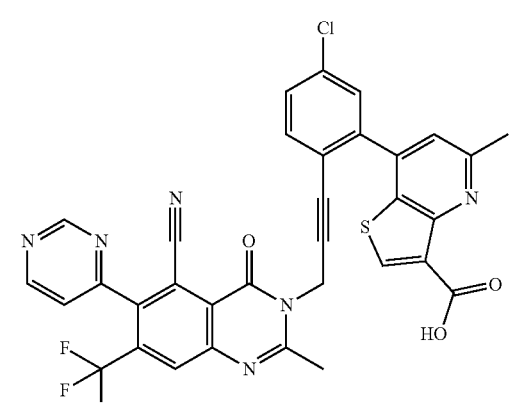 | MS (ESI) m/z 670.97 [M + 1]+; 1H NMR (400 MHz, DMSO-d6) δ 9.44 (s, 1H) 9.15 (d, J = 5.08 Hz, 1H), 8.64 (s, 1H), 8.27 (s, 1H), 7.97 (d, J = 5 Hz, 1H), 7.75 (d, J = 8.4 Hz, 1H), 7.70-7.67 (m, 1H), 7.65 (d, J = 0.84 Hz, 1H), 7.49 (s, 1H), 4.89 (s, 2H), 2.64 (s, 3H), 2.22 (s, 3H) |
| 909 | 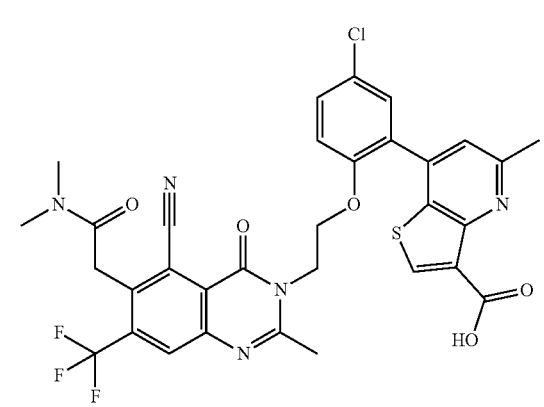 | MS (ESI) m/z 684.20 [M + 1]+; 1H NMR (400 MHz, DMSO-d6) δ 13.57 (bs, 1H), 8.23 (s, 1H), 7.93 (s, 1H), 7.59 (dd, J = 2.44, 8.84 Hz, 1H), 7.41 (d, J = 2.76 Hz, 2H), 7.35 (d, J = 8.96 Hz, 1H), 4.40 (t, J = 4.20 Hz, 2H), 4.25 (t, J = 5.88 Hz, 2H), 4.16 (s, 2H), 3.17 (s, 3H), 2.86 (s, 3H), 2.69 (s, 3H), 1.82 (s, 3H) |
| 934 | 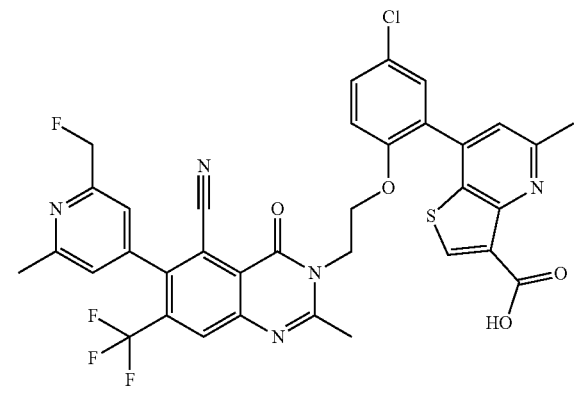 | MS (ESI) m/z 722.05 [M + 1]+; 1H NMR (400 MHz, DMSO-d6) δ 13.5 (bs,1H), 8.24 (s, 1H), 8.05 (s, 1H), 7.59 (dd, J = 8.88, 2.4 Hz, 1H), 7.43-7.40 (m, 4H), 7.36 (d, J = 9.2 Hz,1H), 5.55 (d, J = 44 Hz, 2H), 4.41 (t, J = 5.2 Hz, 2H), 4.27 (t, J = 5.2 Hz, 2H), 2.72 (s, 3H), 2.58 (s, 3H), 1.84 (s, 3H) |

TABLE 2-continued

7-CF3-Thienylpyridine and Derivative Compounds

| Compound | Characterization |
|---|---|
| 937  | MS (ESI) m/z 688.11 [M + 1]+; 1H NMR (400 MHz, DMSO-d6) δ 8.28 (s, 1H), 8.06 (s, 1H), 7.41-7.35 (m, 2H), 7.25 (dd, J = 8.56, 2.84 Hz, 1H), 4.38 (t, J = 4.48 Hz, 2H), 4.27 (t, J = 4.32 Hz, 2H), 2.72 (s, 3H), 2.63 (s, 6H), 1.90 (s, 3H) |
| 963  | MS (ESI) m/z 705.26 [M + 1]+; 1H NMR (400 MHz, DMSO-d6) δ 13.54 (bs, 1H), 8.33 (s, 1H), 8.07 (s, 1H), 7.60 (dd, J = 2.48, 8.90 Hz, 1H), 7.55 (s, 1H), 7.43-7.42 (m, 2H), 7.36 (d, J = 8.92 Hz, 1H), 4.41 (bs, 2H), 4.27 (bs, 2H), 2.72 (s, 3H), 2.65 (s, 1H), 2.56 (s, 1H), 1.84 (s, 3H) |
| 964  | MS (ESI) m/z 709.07 [M + 1]+; 1H NMR (400 MHz, DMSO-d6) δ 13.57 (bs, 1H), 9.14 (s, 1H), 8.41 (s, 1H), 8.19 (s, 1H), 7.60 (dd, J = 2.56, 8.92 Hz, 1H), 7.44-7.43 (m, 2H), 7.36 (d, J = 8.96 Hz, 1H), 4.42 (t, J = 5.20 Hz, 2H), 4.27 (t, J = 4.52 Hz, 2H), 2.73 (s, 3H), 2.70 (s, 3H), 1.82 (s, 3H) |
| 965  | MS (ESI) m/z 705.10 [M + 1]+; 1H NMR (400 MHz, DMSO-d6) δ 8.41 (s, 1H), 8.11 (s, 1H), 7.58 (d, J = 8.84 Hz, 1H), 7.46-7.39 (m, 3H), 7.34 (d, J = 8.88 Hz, 1H), 4.39 (t, J = 4.76 Hz, 2H), 4.26 (t, J = 4.44, Hz, 2H), 2.70 (s, 3H), 2.49 (s, merged, 6H), 1.77 (s, 3H) |

TABLE 2-continued

7-CF3-Thienylpyridine and Derivative Compounds

| Compound | Characterization |
|---|---|
| 966  | MS (ESI) m/z 695.07 [M + 1]+; 1H NMR (400 MHz, DMSO-d6) δ 13.43 (s, 1H) 9.22 (s, 2H), 8.35 (s, 1H), 8.17 (s, 1H), 7.57 (t, J = 6.56 Hz, 1H), 7.42 (d, J = 2.24 Hz, 1H), 7.38 (s, 1H), 7.34 (d, J = 8.88 Hz, 1H), 4.39 (t, J = 2.96 Hz, 2H), 4.27 (t, J = 3.88 Hz, 2H), 2.69 (s, 3H), 1.82 (s, 3H) |
| 967  | MS (ESI) m/z 691.19 [M + 1]+; 1H NMR (400 MHz, DMSO-d6) δ 8.29 (bs, 1H), 8.16 (bs, 1H), 7.94 (bs, 1H), 7.86-7.83 (m, 1H), 7.59 (d, J = 7.16 Hz, 1H), 7.41-7.28 (m, 3H), 4.41 (bs, 2H), 4.30 (bs, 2H), 2.76 (s, 3H), 2.50 (bs, 3H), 1.86 (bs, 3H) |
| 968  | MS (ESI) m/z 705.13 [M + 1]+; 1H NMR (400 MHz, DMSO-d6 ) 8.63 (s, 1H), 8.37 (s, 1H), 8.14 (s, 1H), 7.60 (dd, J = 8.88, 2.52 Hz, 1H), 7.48-7.43 (m, 2H), 7.36 (d, J = 8.96 Hz, 1H), 4.48-4.35 (m, 2H), 4.30-4.24 (m, 2H), 2.73 (m, 3H), 2.52 (m, 3H), 2.29 (m, 3H), 1.80 (s, 3H) |
| 969  | MS (ESI) m/z 705.12 [M + 1]+; 1H NMR (400 MHz, DMSO-d6) δ 8.61 (s, 1H), 8.36 (s, 1H), 8.08 (s, 1H), 7.60 (dd, J = 8.80, 2.48 Hz,1H), 7.45-7.42 (m, 2H), 7.36 (d, J = 8.92 Hz, 1H), 4.44-4.38 (m, 2H), 4.31-4.23 (m, 2H), 2.72 (s, 3H), 2.66 (s, 3H), 2.57 (s, 3H), 1.84 (s, 3H) |

TABLE 2-continued

7-CF3-Thienylpyridine and Derivative Compounds

| Compound | | Characterization |
|---|---|---|
| 991 | 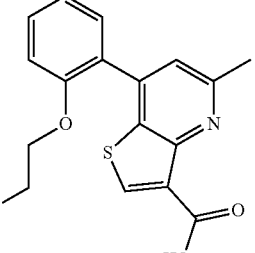 | MS (ESI) m/z 714.06 [M − 1]−; 1H NMR (400 MHz, DMSO-d6) δ 8.29 (s, 1H), 7.90 (s, 1H), 7.59 (dd, J = 8.84, 2.40 Hz, 1H), 7.46-7.40 (m, 2H), 7.36 (d, J = 9.00, 1H), 4.39 (t, J = 4.48 Hz, 2H), 4.23 (t, J = 4.08 Hz, 3H), 3.60-3.40 (m, 2H), 3.20-3.02 (m, 2H), 3.01-2.80 (m, 1H), 2.70 (s, 3H), 2.30-2.10 (m, 2H), 2.00-2.82 (m, 2H), 1.81 (s, 3H) |
| 992 | 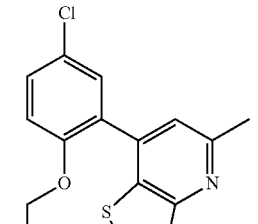 | MS (ESI) m/z 700.13 [M + 1]+; 1H NMR (400 MHz, DMSO-d6) 8.26 (s, 1H), 7.89 (s, 1H), 7.63-7.58 (m, 1H), 7.44-7.39 (m, 2H), 7.36 (d, J = 8.8 Hz, 1H), 4.39 (s, 2H), 4.23 (s, 2H), 3.71-3.50 (m, merged, 2H), 3.31-3.20 (m, 2H), 2.87-.73 (m, 2H), 2.71 (s, 3H), 2.69-2.60 (m. 2H), 1.80 (s, 3H) |
| 995 | 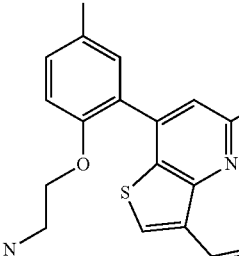 | MS (ESI) m/z 744.09 [M + 1]+; 1H NMR (400 MHz, DMSO-d6) δ 12.20 (bs, 1H), 8.35 (s, 1H), 8.29-8.25 (m, 1H), 8.22 (s, 1H), 8.09-8.06 (m, 1H), 7.57 (d, J = 9.24 Hz, 1H), 7.43-7.33 (m, 3H), 7.07 (t, J = 54.36 Hz, 1H), 4.39 (bs, 2H), 4.27 (bs, 2H), 2.69 (s, 3H), 1.83 (s, 3H) |
| 996 | 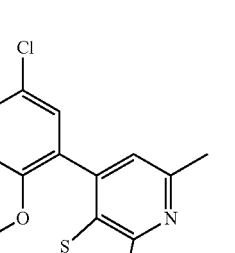 | MS (ESI) m/z 642.01 [M + 1]+; 1H NMR (400 MHz, DMSO-d6) δ 8.33 (s, 1H), 7.89 (s, 1H), 7.59 (dd, J = 2.60, 8.88 Hz, 1H), 7.43 (s, 1H), 7.42 (d, J = 2.64 Hz, 1H), 7.36 (d, J = 8.96 Hz, 1H), 4.39 (t, J = 4.68 Hz, 2H), 4.23 (t, J = 4.64 Hz, 2H), 2.94 (s, 6H), 2.70 (s, 3H), 1.81 (s, 3H) |

TABLE 2-continued

7-CF3-Thienylpyridine and Derivative Compounds

| Compound | | Characterization |
|---|---|---|
| 1009 | 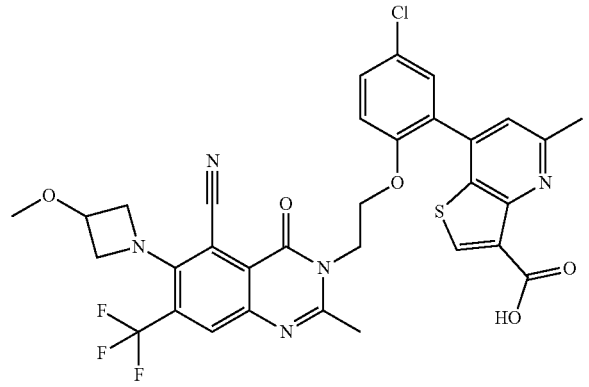 | MS (ESI) m/z 684.15 [M + 1]+; 1H NMR (400 MHz, DMSO-d6) δ 13.56 (s, 1H), 8.39 (s, 1H), 7.77 (s, 1H), 7.58 (dd, J = 2.44, 8.84 Hz, 1H), 7.41-7.39 (m, 2H), 7.35 (d, J = 8.96 Hz, 1H), 4.65-4.62 (m, 2H), 4.37 (bs, 2H), 4.32-4.27 (m, 3H), 4.18 (bs, 2H), 3.37 (s, 3H), 2.70 (s, 3H), 1.74 (s, 3H) |
| 1012 | 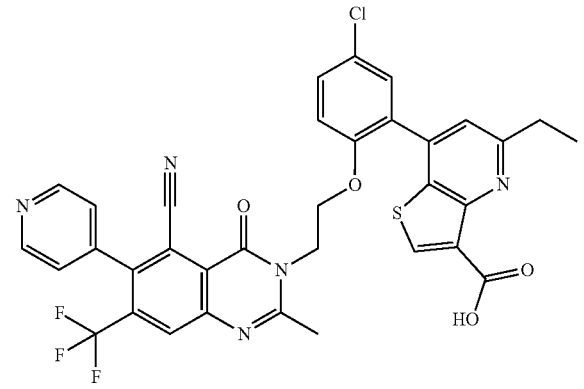 [SMILES: CCc1cc(-c2cc(Cl)ccc2OCCn2c(C)nc3cc(C(F)(F)F)c(-c4ccncc4)c(C#N)c3c2=O)c2scc(C(=O)O)c2n1] | MS (ESI) m/z 690.14 [M + 1]+; ; 1H NMR (400 MHz, DMSO-d6): δ 13.74 (s, 1H), 8.71 (d, J = 5.0 Hz, 2H), 8.26 (s,1H), 8.041 (s, 1H), 7.61 (dd, J = 7.2.24, J = 2.20 Hz,1H), 7.54 (d, J = 4.64 Hz, 2H), 7.48 (s, 1H), 7.44 (d, J = 2.24 Hz, 1H), 7.38 (d, J = 8.88 Hz, 1H), 4.43 (t, J = 4.52 Hz, 2H), 4.27 (t, J = 4.44 Hz, 2H), 3.06 (m, 2H), 1.80 (s, 3H), 1.39 (t, J = 7.52 Hz, 3H) |
| 1013 | 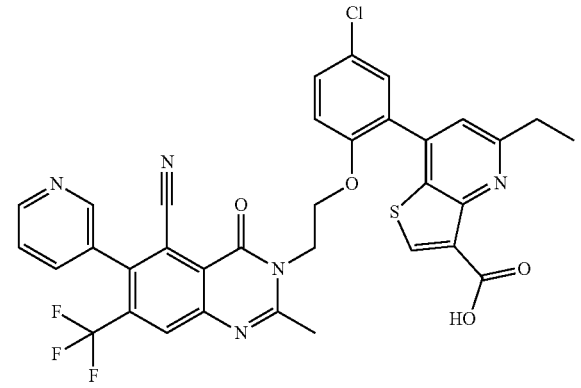 [SMILES: CCc1cc(-c2cc(Cl)ccc2OCCn2c(C)nc3cc(C(F)(F)F)c(-c4cccnc4)c(C#N)c3c2=O)c2scc(C(=O)O)c2n1] | MS (ESI) m/z 690.14 [M + 1]+; 1H NMR (400 MHz, DMSO-d6) δ 8.76 (d, J = 4.12 Hz, 1H), 8.69 (s, 1H), 8.26 (s, 1H), 8.04 (s, 1H), 7.98 (d, J = 7.68 Hz, 1H), 7.65-7.59 (m, 2H), 7.49 (s, 1H), 7.44 (d, J = 2.48 Hz, 1H), 7.38 (d, J = 8.96 Hz, 1H), 4.43 (t, J = 4.52 Hz, 2H), 4.27 (t, J = 4.44 Hz, 2H), 3.06 (m, 2H), 1.80 (s, 3H), 1.39 (t, J = 7.52 Hz, 3H) |
| 1014 | 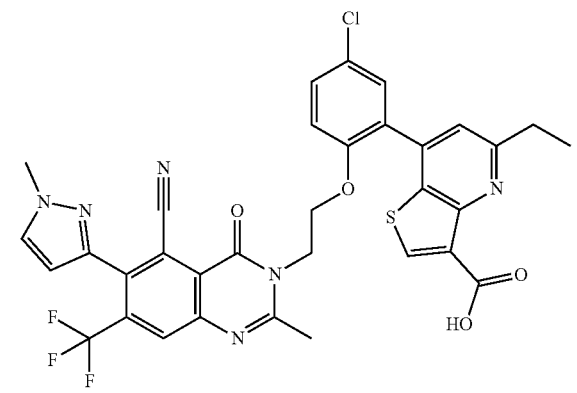 [SMILES: CCc1cc(-c2cc(Cl)ccc2OCCn2c(C)nc3cc(C(F)(F)F)c(-c4ccn(C)n4)c(C#N)c3c2=O)c2scc(C(=O)O)c2n1] | MS (ESI) m/z 693.16 [M + 1]+; 1H NMR (400 MHz, DMSO-d6) δ 8.32 (s, 1H), 8.00 (s, 1H), 7.87 (d, J = 2.56 Hz, 1H), 7.60 (dd, J = 2.56, 8.88 Hz, 1H), 7.46 (s, 1H), 7.44 (d, J = 2.44 Hz, 1H), 7.35 (d, J = 9.00 Hz, 1H), 6.48 (s, 1H), 4.40 (t, J = 4.56 Hz, 2H), 4.24 (t, J = 4.72 Hz, 2H), 3.93 (s, 3H), 3.02 (q, J = 7.36 Hz, 2H), 1.76 (s, 3H), 1.35 (t, J = 7.52 Hz, 3H) |

TABLE 2-continued

7-CF3-Thienylpyridine and Derivative Compounds

| Compound | Characterization |
|---|---|
| 1017 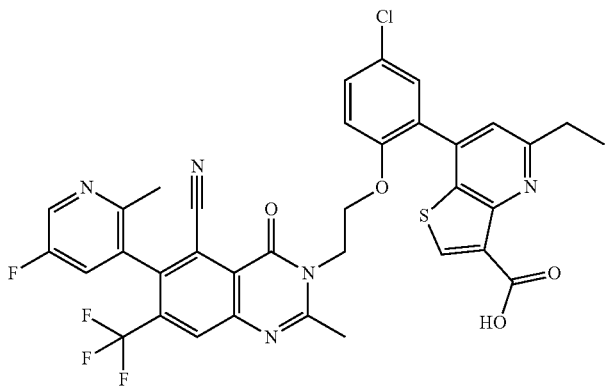 [SMILES: CCc1cc(-c2cc(Cl)ccc2OCCn2c(C)nc3cc(C(F)(F)F)c(-c4cc(F)cnc4C)c(C#N)c3c2=O)c2scc(C(=O)O)c2n1] | MS (ESI) m/z 722.14 [M + 1]+; 1H NMR (400 MHz, DMSO-d6) δ 13.72 (bs, 1H), 8.67 (d, J = 2.68 Hz, 1H), 8.22 (s, 1H), 8.08 (s, 1H), 7.90 (d, J = 6.68 Hz, 1H), 7.59 (dd, J = 2.48, 8.92 Hz, 1H), 7.49 (s, 1H), 7.44 (d, J = 2.48 Hz, 1H), 7.36 (d, J = 9.0 Hz, 1H), 4.41 (t, J = 3.88 Hz, 2H), 4.28 (bs, 2H), 3.04 (q, J = 7.2 Hz, 2H), 2.21 (s, 3H), 1.79 (s, 3H), 1.39 (t, J = 7.2 Hz, 3H) |
| 1025 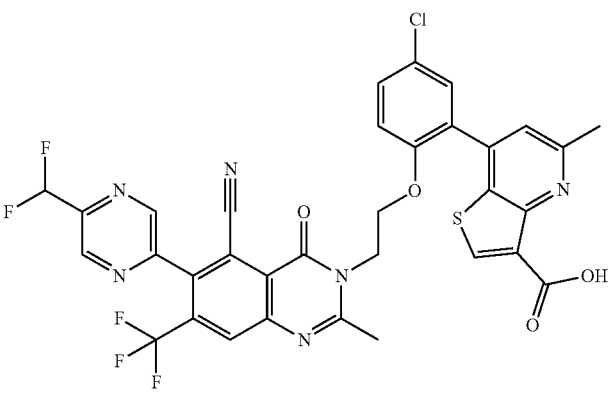 [SMILES: Cc1cc(-c2cc(Cl)ccc2OCCn2c(C)nc3cc(C(F)(F)F)c(-c4cnc(C(F)F)cn4)c(C#N)c3c2=O)c2scc(C(=O)O)c2n1] | MS (ESI) m/z 727.10 [M + 1]+; 1H NMR (400 MHz, DMSO-d6) δ 13.54 (bs, 1H), 9.24 (s, 1H), 9.22 (s, 1H), 8.34 (s, 1H), 8.14 (s, 1H), 7.60 (dd, J = 2.52, 8.84 Hz, 1H), 7.43-7.17 (m, 4H), 4.42 (bs, 2H), 4.28 (bs, 2H), 2.72 (s, 3H), 1.87 (s, 3H) |
| 1026 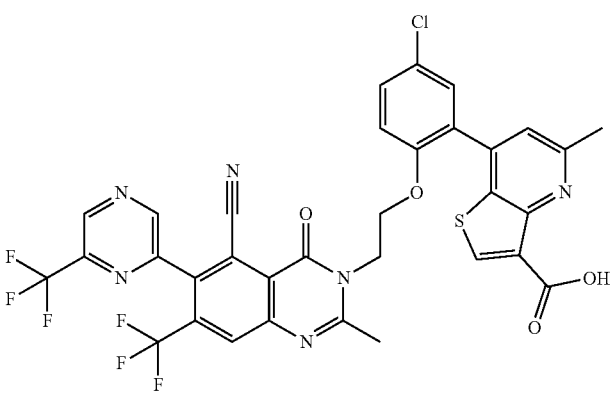 [SMILES: Cc1cc(-c2cc(Cl)ccc2OCCn2c(C)nc3cc(C(F)(F)F)c(-c4cncc(C(F)(F)F)n4)c(C#N)c3c2=O)c2scc(C(=O)O)c2n1] | MS (ESI) m/z 745.11 [M + 1]+; 1H NMR (400 MHz, DMSO-d6) δ 9.51 (s, 1H), 9.49 (s, 1H), 8.36 (s, 1H), 8.15 (s, 1H), 7.61 (dd, J = 2.48, 8.8 Hz, 1H), 7.44-7.42 (m, 2H), 7.37 (d, J = 8.8 Hz, 1H), 4.42 (bs, 2H), 4.30 (bs, 2H), 2.72 (s, 3H), 1.89 (s, 3H) |
| 1027 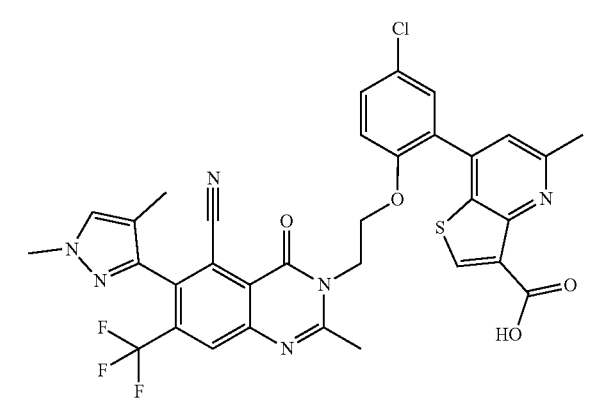 | MS (ESI) m/z 693.14 [M + 1]+; 1H NMR (400 MHz, DMSO-d6) δ 8.37 (s, 1H), 8.04 (s, 1H), 7.65 (s, 1H), 7.59 (dd, J = 8.92 Hz, 1.48 Hz, 1H), 7.44 (s, 2H), 7.36 (s, 1H), 4.41 (s, 2H), 4.25 (s, 2H), 3.86 (s, 3H), 2.71 (s, 3H), 1.86 (s, 3H), 1.79 (s, 3H) |

TABLE 2-continued

7-CF3-Thienylpyridine and Derivative Compounds

| Compound | Characterization |
|---|---|
| 1028 | MS (ESI) m/z 693.16 [M + 1]+; 1H NMR (400 MHz, DMSO-d6) δ 13.57 (s, 1H), 8.32 (s, 1H), 8.07 (s, 1H), 7.61 (dd, J = 2.56 Hz, J = 8.88 Hz, 1H), 7.45-7.43 (m, 2H), 7.37 (d, J = 9.00 Hz, 1H), 6.27 (s, 1H), 4.41 (bs, 3H), 4.27 (bs, 2H), 3.55 (s, 3H), 2.72 (s, 3H), 2.23 (s, 3H), 1.84 (s, 3H) |
| 1029 | MS (ESI) m/z 693.00 [M + 1]+; 1H NMR (400 MHz, DMSO-d6) δ 13.55 (bs, 1H), 8.34 (s, 1H), 8.01 (s, 1H), 7.59 (dd, J = 8.88, 2.4 Hz, 1H), 7.43-7.41 (m, 3H), 7.35 (d, J = 8.8 Hz, 1H), 4.40 (t, J = 6.04 Hz, 2H), 4.25 (t, J = 5.2 Hz, 2H), 3.83 (s, 3H), 2.70 (s, 3H), 2.10 (s, 3H), 1.83 (s, 3H) |
| 1030 | MS (ESI) m/z 693.12 [M + 1]+; 1H NMR (400 MHz, DMSO-d6) δ 13.55 (bs, 1H), 8.26 (s, 1H), 8.10 (s, 1H), 7.61 (dd, J1 = 6.48, J2 = 2.28 Hz 1H), 7.45-7.43 (m, 3H), 7.38 (d, J = 8.88 Hz, 1H), 4.42 (bs, 2H), 4.26 (bs, 2H), 3.57 (s, 3H), 2.72 (s, 3H), 1.82 (s, 6H) |
| 1031 | MS (ESI) m/z 693.13 [M + 1]+; 1H NMR (400 MHz, DMSO-d6) δ 13.56 (bs, 1H), 8.34 (s, 1H), 8.00 (s, 1H), 7.77 (s, 1H), 7.59 (dd, J = 8.84, 2.40 Hz, 1H), 7.43 (s, 2H), 7.36 (d, J = 8.96 Hz, 1H), 4.48-4.36 (m, 2H), 4.35-4.19 (m, 2H), 3.86 (s, 3H), 2.70 (s, 3H), 1.97 (s, 3H), 1.84 (s, 3H) |

TABLE 2-continued

7-CF3-Thienylpyridine and Derivative Compounds

| Compound | Characterization |
|---|---|
| 1032 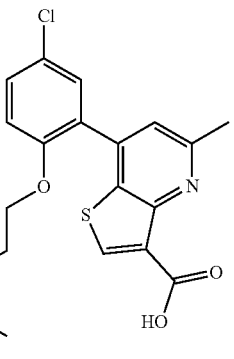 | MS (ESI) m/z 693.10 [M + 1]+; 1H NMR (400 MHz, DMSO-d6) δ 8.33 (s, 1H), 8.01 (s, 1H), 7.60 (dd, J = 9.92, 3.32 Hz, 1H), 7.45-7.39 (m, 3H), 7.36 (d, J = 8.88 Hz, 1H), 4.46-4.45 (m, 2H), 4.30-4.20 (m, 2H), 3.83 (s, 3H), 2.70 (s, 3H), 2.10 (s, 3H), 1.83 (s, 3H) |
| 1033 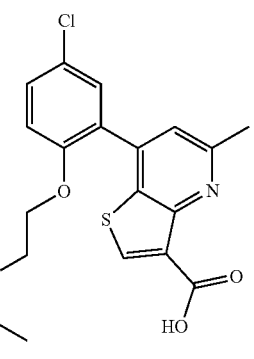 | MS (ESI) m/z 706.14 [M + 1]+; 1H NMR (400 MHz, DMSO-d6) δ 8.60 (d, J = 4.4 Hz, 1H), 8.28 (s, 1H), 8.00-7.95 (m, 2H), 7.72 (d, J = 7.72 Hz, 1H), 7.60 (dd, J = 8.88, 2.56 Hz, 1H), 7.46-7.39 (m, 3H), 7.37 (d, J = 8.96 Hz, 1H), 5.45 (s, 2H), 4.42 (t, J = 3.8 Hz, 2H), 4.25 (t, J = 4.3 Hz, 2H), 2.72 (s, 3H), 1.80 (s, 3H) |
| 1034 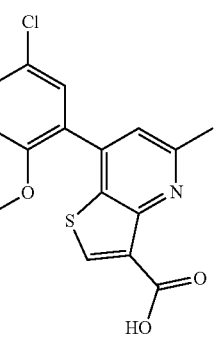 | MS (ESI) m/z 655.18 [M + 1]+; 1H NMR (400 MHz, DMSO-d6) δ 13.54 (bs, 1H), 8.29 (s, 1H), 7.90 (s, 1H), 7.59 (dd, J = 8.92, 2.32 Hz, 1H), 7.42 (s, 2H), 7.36 (d, J = 8.92 Hz, 1H), 4.77-4.70 (m, 1H), 4.40 (t, J = 6.64 Hz, 2H), 4.23 (t, J = 5.12 Hz, 2H), 2.70 (s, 3H), 1.76 (s, 3H), 0.92-0.75 (m, 4H) |
| 1035 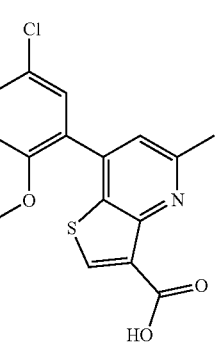 | MS (ESI) m/z 792.25 [M + 1]+; 1H NMR (400 MHz, DMSO-d6) δ 13.45 (bs, 1H), 8.44 (d, J = 2.52 Hz, 1H), 8.38 (d, J = 3.32 Hz, 1H), 8.34 (s, 1H), 8.11 (s, 1H), 7.60 (dd, J = 2.55, 8.88 Hz, 1H), 7.49-7.42 (m, 4H), 7.35 (d, J = 8.90 Hz, 1H), 4.41 (t, J = 5.24 Hz, 2H), 4.05 (t, J = 4.0 Hz, 2H), 2.72 (s, 3H), 1.77 (s, 3H) |

TABLE 2-continued

7-CF3-Thienylpyridine and Derivative Compounds

| Compound | Characterization |
|---|---|
| 1036 | MS (ESI) m/z 629.11 [M + 1]+; 1H NMR (400 MHz, DMSO-d6) δ 8.27 (s, 1H), 7.91 (s, 1H), 7.60 (dd, J = 8.92, 2.56 Hz, 1H), 7.43 (s, 1H)-7.42, (d, J = 2.80 Hz, 1H), 7.36 (d, J = 8.96 Hz, 1H), 4.40 (t, J = 4.72 Hz, 2H), 4.24 (t, J = 4.48 Hz, 2H), 4.13 (s, 3H), 2.71 (s, 3H), 1.78 (s, 3H) |
| 1046 | MS (ESI) m/z 639.16 [M + 1]+; 1H NMR (400 MHz, DMSO-d6) δ 8.27 (s, 1H), 7.90 (s, 1H), 7.59 (dd, J = 8.84, 2.40 Hz, 1H), 7.44-7.39 (m, 2H), 7.35 (d, J = 8.92 Hz, 1H), 4.38 (t, J = 5.56 Hz, 2H), 4.24 (t, J = 6.04 Hz, 2H), 2.69 (s, 3H), 2.30-2.18 (m, 1H) 1.83 (s, 3H), 1.26-1.12 (m, 2 h), 1.00-0.90 (m, 2H) |
| 1049 | MS (ESI) m/z 639.16 [M + 1]+; 1H NMR (400 MHz, DMSO-d6) δ 8.27 (s, 1H), 7.90 (s, 1H), 7.59 (dd, J = 8.84, 2.40 Hz, 1H), 7.44-7.39 (m, 2H), 7.35 (d, J = 8.92 Hz, 1H), 4.38 (t, J = 5.56 Hz, 2H), 4.24 (t, J = 6.04 Hz, 2H), 2.69 (s, 3H), 2.30-2.18 (m, 1H) 1.83 (s, 3H), 1.26-1.12 (m, 2 h), 1.00-0.90 (m, 2H) |
| 1055 | MS (ESI) m/z 684.16 [M + 1]+; 1H NMR (400 MHz, DMSO-d6) δ 13.55 (s, 1H), 8.40 (s, 1H), 7.77 (s, 1H), 7.59 (dd, J = 2.28 Hz, J = 8.84 Hz, 1H), 7.42 (d, J = 2.40 Hz, 1H), 7.40 (s, 1H), 7.35 (d, J = 8.88, 1H), 5.72 (s, 1H), 4.39-4.30 (m, 6H), 4.18 (t, J = 6.68, 2H), 2.70 (s, 3H), 1.73 (s, 3H), 1.45 (s, 3H) |

TABLE 2-continued

7-CF3-Thienylpyridine and Derivative Compounds

| Compound | | Characterization |
|---|---|---|
| 1058 | 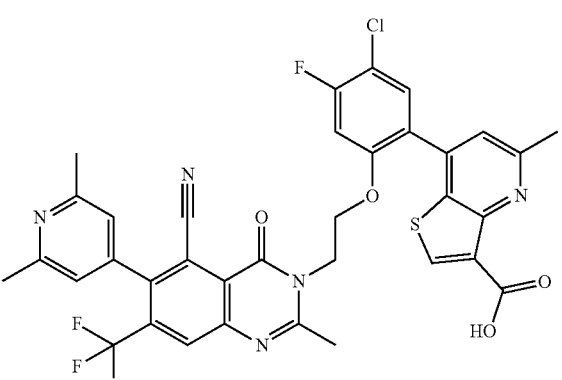 | MS (ESI) m/z 706.19 [M + 1]+; 1H NMR (400 MHz, DMSO-d6) δ 13.49 (bs, 1H), 8.27 (s, 1H), 8.05 (s, 1H), 7.56-7.48 (m, 2H), 7.39 (s, 1H), 4.41 (t, J = 5.52 Hz, 2H), 4.27 (t, J = 5.04 Hz), 2.72 (s, 3H), 2.61 (s, 6H), 1.86 (s, 3H) |
| 1059 | 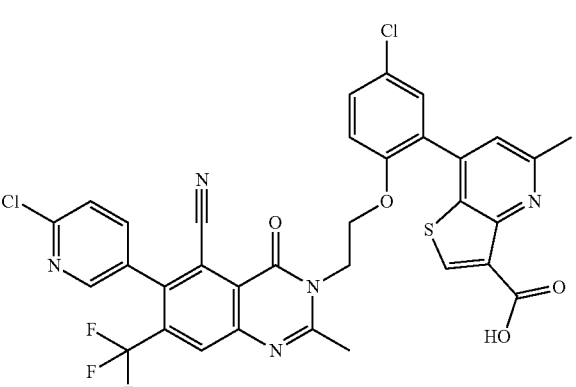 | MS (ESI) m/z 710.5 [M + 1]+; 1H NMR (400 MHz, DMSO-d6) 8.57 (d, J = 1.6 Hz, 1H), 8.27 (s, 1H), 8.10-8.03 (m, 2H), 7.79 (d, J = 8.2 Hz,1H), 7.60 (dd, J = 8.8, 2.6 Hz, 1H), 7.45 (s, 1H), 7.42 (d, J = 2.6 Hz, 1H), 7.36 (d, J = 8.9 Hz, 1H), 4.42 (t, J = 4.24 Hz, 2H), 4.28 (t, J = 5.4 Hz, 2H), 2.73 (s, 3H), 1.87 (s, 3H) |
| 1030 | 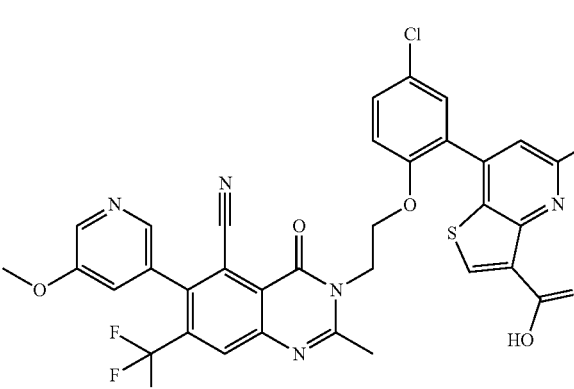 | MS (ESI) m/z 667.06 [M + 1]+; 1H NMR (400 MHz, DMSO-d6) δ 13.53 (bs, 1H), 8.35 (d, J = 2.68 Hz, 1H), 8.29 (s, 1H), 8.08 (s, 1H), 7.60 (dd, J = 8.84, 2.36 Hz, 1H), 7.46-7.40 (m, 3H), 7.36 (d, J = 8.96 Hz, 1H), 4.50-4.20 (m, 4H), 3.86 (s, 3H), 2.72 (s, 3H), 2.12 (s, 3H), 1.86 (s, 3H) |
| 1073 | 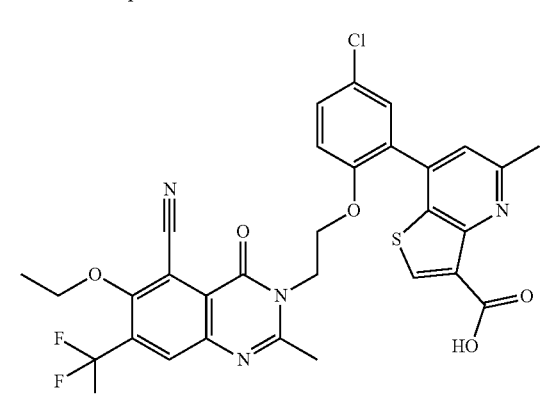 | MS (ESI) m/z 643.20 [M + 1]+; 1H NMR (400 MHz, DMSO-d6) δ 8.27 (s, 1H), 7.91 (s, 1H), 7.59 (dd, J = 8.84 Hz, 2.56 Hz, 1H), 7.43-7.41 (m, 2H), 7.36 (d, J = 8.96 Hz, 1H), 4.40-4.35 (m, 4H), 4.23 (t, J = 4.16 Hz, 2H), 2.70 (s, 3H), 1.78 (s, 3H), 1.46 (t, J = 6.96 Hz, 3H) |

TABLE 2-continued

7-CF3-Thienylpyridine and Derivative Compounds

| Compound | | Characterization |
|---|---|---|
| 1074 | 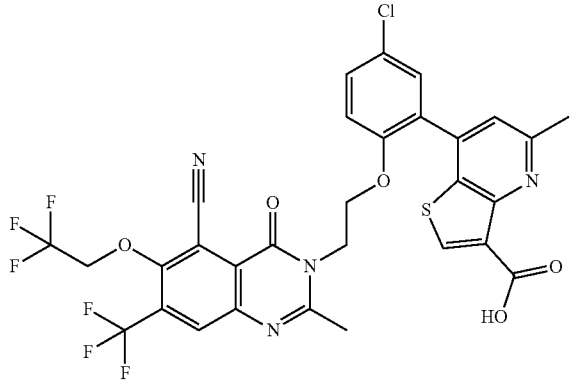 [SMILES: Cc1cc(-c2cc(Cl)ccc2OCCn2c(C)nc3cc(C(F)(F)F)c(OCC(F)(F)F)c(C#N)c3c2=O)c2scc(C(=O)O)c2n1] | MS (ESI) m/z 697.14 [M + 1]+; 1H NMR (400 MHz, DMSO-d6 ) 8.21 (s, 1H), 7.96 (s, 1H), 7.59 (d, J = 8.96 Hz, 1H), 7.43 (s, 1H), 7.41 (s, 1H), 7.36 (d, J = 8.96 Hz, 1H), 5.00 (q, J = 8.40 Hz, 2H), 4.41 (t, J = 5.24 Hz, 2H), 4.25 (t, J = 4.8 Hz, 2H), 2.72 (s, 3H), 1.79 (s, 3H) |
| 1075 | 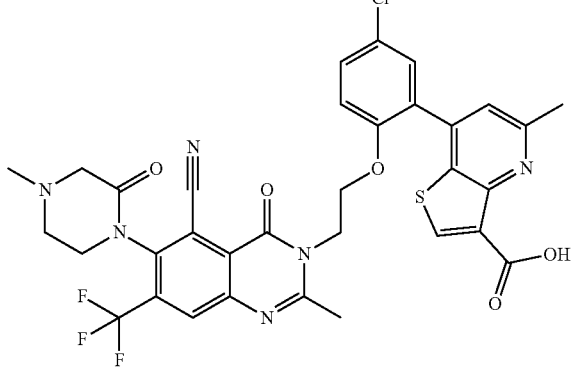 | MS (ESI) m/z 711.15 [M + 1]+; 1H NMR (400 MHz, DMSO-d6) δ 8.24 (s, 1H), 8.06 (s, 1H), 7.59 (d, J = 8.84 Hz, 1H), 7.43 (d, J = 5.5 Hz, 2H), 7.36 (d, J = 8.9 Hz, 1H), 4.46-3.64 (m, 10H), 2.82 (s, 3H), 2.71 (s, 3H), 1.85 (s, 3H) |
| 1079 | 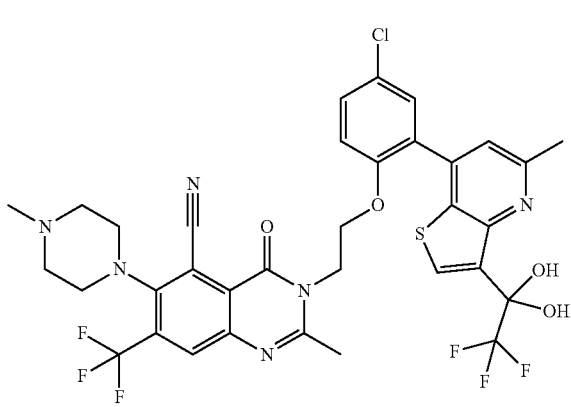 | MS (ESI) m/z 767.24 [M + 1]+; 1H NMR (400 MHz, DMSO-d6 with D2O) δ 8.00 (d, J = 6.4 Hz, 2H), 7.53 (d, J = 7.2 Hz, 1H), 7.33 (s, 1H), 7.27 (d, J = 8.4 Hz, 1H), 7.19 (s, 1H), 4.33 (bs, 2H), 4.20 (bs, 2H), 2.54 (s, 3H), 2.19 (s, 3H), 1.67 (s, 3H) |
| 1080 | 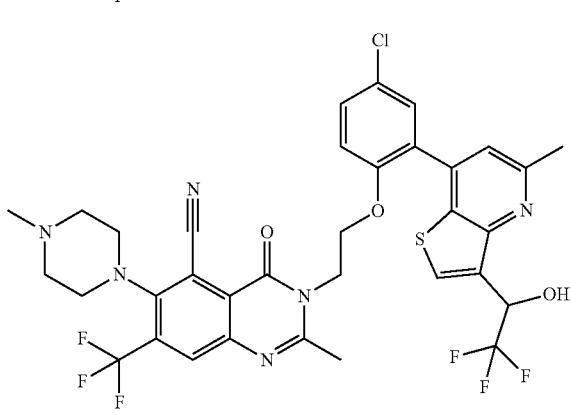 | MS (ESI) m/z 751.17 [M + 1]+; 1H NMR (400 MHz, DMSO-d6) δ 8.06 (s, 1H), 7.94 (s, 1H), 7.53 (dd, J = 8.76, 2.16 Hz, 1H), 7.40 (d, J = 2.16 Hz, 1H), 7.29 (d, J = 8.92 Hz, 1H), 7.19 (s, 1H), 7.00 (d, J = 6.52, Hz, 1H), 5.76-5.68 (m, 1H), 4.40-4.30 (m, 2H), 4.30-4.15 (m, 2H), 3.70-3.45 (m, 2H), 3.10-2.70 (m, 2H), 2.60 (s, 3H), 2.35-1.90 (m, 7H), 1.69 (s, 3H) |

TABLE 2-continued

7-CF3-Thienylpyridine and Derivative Compounds

| Compound | Characterization |
|---|---|
| 1081 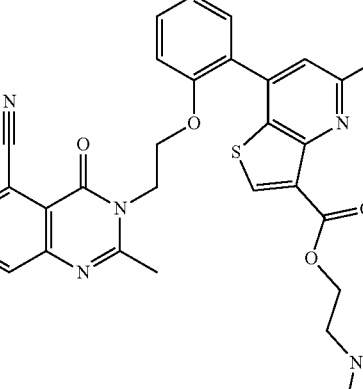 | MS (ESI) m/z 805.02 [M + 1]+; 1H NMR (400 MHz, DMSO-d6) δ 8.67 (d, J = 2.76 Hz, 1H), 8.26 (s, 1H), 8.12 (s, 1H), 7.97 (d, J = 6.76 Hz, 1H), 7.57 (dd, J = 2.56, 8.8 Hz, 1H), 7.36 (t, J = 2.56 Hz, 2H), 7.28 (s, 1H), 4.41-4.21 (m, 6H), 2.82 (bs, 2H), 2.64 (s, 3H), 2.50 (s, 4H), 2.19 (s, 3H), 1.91 (s, 3H), 1.69 (s, 4H) |
| 1082 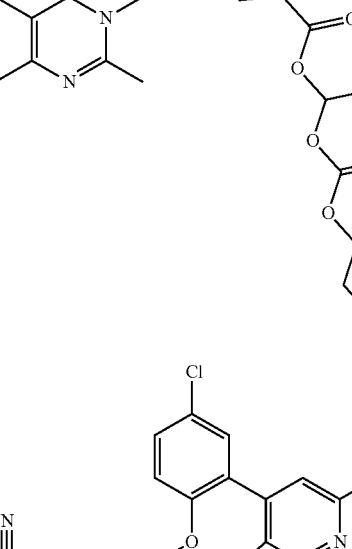 | MS (ESI) m/z, 867.35 [M + 1]+; 1H NMR (400 MHz, DMSO-d6) δ 8.42 (s, 1H), 7.96 (s, 1H), 7.57 (dd, J = 2.52, 8.88 Hz, 1H), 7.36 (d, J = 2.52 Hz, 1H), 7.32 (d, J = 9.0 Hz, 1H), 7.27 (s, 1H), 6.94-6.90 (m, 1H), 4.61-4.56 (m, 1H), 4.37 (bs, 2H), 4.23 (bs, 2H), 3.60 (bs, 2H), 2.95 (bs, 2H), 2.63 (s, 3H), 2.24 (s, 4H), 1.84 (bs, 2H), 1.75 (s, 3H), 1.63 (d, J = 5.36 Hz, 6H), 1.44-1.39 (m, 4H), 1.33-1.20 (m, 4H) |
| 1085 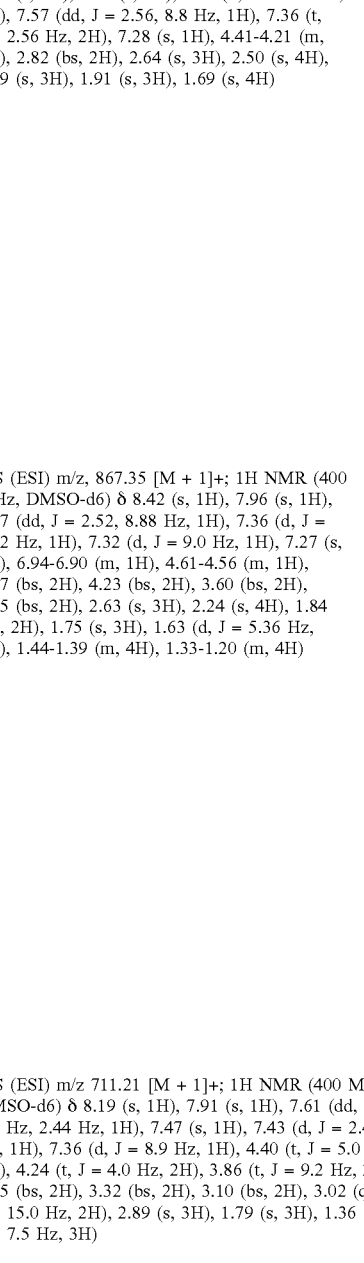 | MS (ESI) m/z 711.21 [M + 1]+; 1H NMR (400 MHz, DMSO-d6) δ 8.19 (s, 1H), 7.91 (s, 1H), 7.61 (dd, J = 8.9 Hz, 2.44 Hz, 1H), 7.47 (s, 1H), 7.43 (d, J = 2.4 Hz, 1H), 7.36 (d, J = 8.9 Hz, 1H), 4.40 (t, J = 5.0 Hz, 2H), 4.24 (t, J = 4.0 Hz, 2H), 3.86 (t, J = 9.2 Hz, 2H), 3.55 (bs, 2H), 3.32 (bs, 2H), 3.10 (bs, 2H), 3.02 (q, J = 15.0 Hz, 2H), 2.89 (s, 3H), 1.79 (s, 3H), 1.36 (t, J = 7.5 Hz, 3H) |

TABLE 2-continued

7-CF3-Thienylpyridine and Derivative Compounds

| Compound | Characterization |
|---|---|
| 1087 | MS (ESI) m/z 725.29 [M + 1]+; 1H NMR (400 MHz, DMSO-d6) δ 14.50 (bs, 1H), 7.92 (s, 1H), 7.60 (dd, J = 2.52, 9.28 Hz, 1H), 7.47 (s, 1H), 7.43 (d, J = 2.28 Hz, 1H), 7.36 (d, J = 8.88 Hz, 2H), 4.40 (t, J = 5.56 Hz, 2H), 4.24 (t, J = 5.76 Hz, 2H), 3.86 (t, J = 11.28 Hz, 2H), 3.56 (d, J = 11.44 Hz, 2H), 3.21-3.18 (m, 2H), 3.08 (d, J = 10.4 Hz, 2H), 3.01 (q, J = 7.6 Hz, 2H), 2.90 (bs, 3H), 2.37 (s, 3H), 1.90 (s, 3H), 1.36 (t, J = 7.6 Hz, 3H) |
| 1088 | MS (ESI) m/z 708.25 [M + 1]+; 1H NMR (400 MHz, DMSO-d6) δ 13.60 (s, 1H), 10.02 (bs,1H), 8.21 (d, J = 5.4 Hz, 1H), 7.97 (d, J = 5.48 Hz, 1H), 7.62 (d, J = 2.28 Hz, 1H), 7.47 (s, 1H), 7.43 (d, J = 2.24 Hz, 1H), 7.37 (d, J = 8.96 Hz, 1H), 5.95 (s, 1H), 4.42 (bs, 2H), 4.39 (bs, 2H), 4.26 (d, J = 4.55 Hz, 1H), 3.85-3.65 (m, 2H), 3.4-3.33 (m, 1H), 3.04-2.99 (m, 6H), 2.67 (bs, 1H), 1.86 (s, 3H), 1.36 (t, J = 7.52, 3H) |
| 1093 | MS (ESI) m/z 697.18 [M + 1]+; 1H NMR (400 MHz, DMSO-d6) δ 8.79 (d, J = 4.9 Hz, 1H), 7.95 (s, 1H), 7.61 (dd, J = 2.5, 8.8 Hz, 1H), 7.52 (d, J = 4.8 Hz, 1H), 7.37 (d, J = 2.5 Hz, 1H), 7.37 (d, J = 9.0 Hz, 1H), 4.42 (t, J = 4.8 Hz, 2H), 4.26 (t, J = 4.3 Hz, 2H), 3.90-3.83 (m, 2H), 3.57-3.54 (m, 2H), 3.21-3.18 (m, 2H), 3.10-3.08 (m, 2H), 2.91 (s, 3H), 2.39 (s, 3H), 1.85 (s, 3H) |
| 1151 | MS (ESI) m/z 760.31 [M + 1]+; 1H NMR (400 MHz, DMSO-d6) δ 12.56 (bs, 1H), 8.89 (d, J = 4.8 Hz, 1H), 8.36 (s, 1H), 7.97 (s, 1H), 7.60 (dd, J = 8.8, 2.4 Hz, 1H), 7.53 (d, J = 4.8 Hz, 1H), 7.45 (d, J = 2.8 Hz, 1H), 7.36 (d, J = 9.2 Hz, 1H), 4.45-4.38 (m, 2H), 4.26-4.19 (m, 2H), 3.80-3.40 (m, 5H), 3.20-2.75 (m, 4H), 2.65-2.50 (s, 2H), 2.27 (s, 3H), 1.68 (s, 3H) |

TABLE 2-continued

7-CF3-Thienylpyridine and Derivative Compounds

| Compound | Characterization |
|---|---|
| 1153 | MS (ESI) m/z 683.16 [M + 1]+; 1H NMR (400 MHz, DMSO-d6) 13.12 (bs, 1H), 8.85 (d, J = 4.8 Hz, 1H), 8.23 (s, 1H), 7.99 (s, 1H), 7.60 (d, J = 9.2, 2.4 Hz, 1H), 7.49 (d, J = 4.8 Hz, 1H), 7.42 (d, J = 2.4 Hz, 1H), 7.36 (d, J = 9.2 Hz, 1H), 5.00 (q, J = 8.4 Hz, 2H), 4.41 (s, 2H), 4.25 (s, 2H), 1.73 (s, 3H) |
| 1154 | MS (ESI) m/z 620.27 [M + 1]+; 1H NMR (400 MHz, DMSO-d6) δ 12.79 (bs, 1H), 8.17 (s, 1H), 7.91 (s, 1H), 7.67-7.62 (m, 3H), 7.51 (bs, 2H), 7.37 (bs, 1H), 5.02 (s, 2H), 3.87-3.45 (m, 4H), 3.21-2.91 (m, 4H), 3.02 (bs, 3H), 2.85 (bs, 3H) |
| 1156 | MS (ESI) m/z 765.30 [M + 1]+; 1H NMR (400 MHz, DMSO-d6) δ 13.26 (bs, 1H), 8.82 (d, J = 4.8 Hz, 1H), 8.28 (s, 1H), 7.93 (s, 1H), 7.59 (d, J = 8.8 Hz, 1H), 7.46 (d, J = 4.4 Hz, 1H), 7.42 (s, 1H), 7.35 (d, J = 10.8 Hz, 1H), 4.39 (bs, 2H), 4.23 (bs, 2H), 3.63 (bs, 2H), 3.31 (bs, 2H), 2.95 (m, 4H), 2.60 (t, J = 7.2 Hz, 4H), 1.71 (s, 3H) |
| 1158 | MS (ESI) m/z 721.16 [M + 1]+; 1H-NMR (400 MHz, DMSO-d6) δ 8.84 (d, J = 4.8 Hz, 1H), 8.41 (s, 1H), 7.83 (s, 1H), 7.60 (dd, J = 2.4, 8.4 Hz, 1H), 7.44 (d, J = 2.4 Hz, 1H), 7.36 (d, J = 8.8 Hz, 1H), 4.71 (s, 2H), 4.63 (s, 2H), 4.40-4.20 (m, 8H), 3.05 (bs, 1H), 1.73 (s, 3H), 0.79-0.77 (m, 4H) |

TABLE 2-continued
7-CF3-Thienylpyridine and Derivative Compounds
| Compound | Characterization |
|---|---|
| 1159  | MS (ESI) m/z 709.12 [M + 1]+; 1H NMR (400 MHz, DMSO-d6) δ 8.83 (d, J = 4.4 Hz, 1H), 8.23 (s, 1H), 7.96 (s, 1H), 7.60 (dd, J = 6.4 Hz, 2.4 Hz, 1H), 7.48 (d, J = 4.8 Hz, 1H), 7.42 (d, J = 2.4 Hz, 1H), 7.36 (d, J = 8.8 Hz, 1H), 4.40 (s, 2H), 4.24 (s, 2H), 3.85 (s, 4H), 3.29 (bs, 4H), 3.12 (bs, 1H), 1.76 (s, 3H), 1.01 (s, 2H), 0.85 (s, 2H) |
| 1178 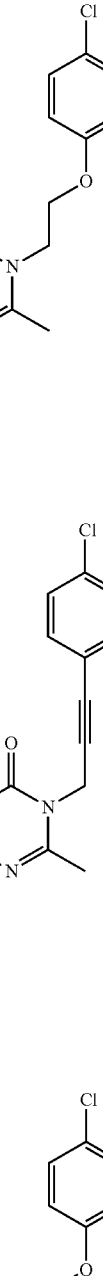 | MS (ESI) m/z 715.47 [M + 1]+; 1H-NMR (400 MHz, DMSO-d6) δ 8.77 (d, J = 5.2 Hz, 1H), 8.66 (s, 1H), 7.93 (s, 1H), 7.75 (d, J = 8.4 Hz, 1H), 7.70-7.66 (m, 2H), 7.56 (d, J = 4.4 Hz, 1H), 4.82 (s, 2H), 4.73-4.41 (m, 8H), 3.05 (bs, 1H), 2.11 (s, 3H), 0.77 (bs, 4H) |
| 1179 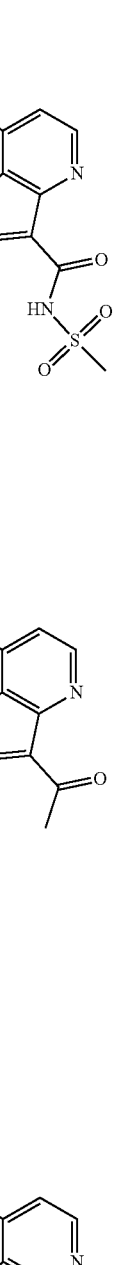 | MS (ESI) m/z 786.04 [M + 1]+. 1H-NMR (400 MHz, DMSO-d6) δ 12.70 (s, 1H), 8.94 (d, J = 4.8 Hz, 1H), 8.31 (s, 1H), 7.97 (s, 1H), 7.63-7.58 (m, 2H), 7.45 (d, J = 2.40 Hz, 1H), 7.37 (d, J = 9.20 Hz, 1H), 4.42 (bs, 2H), 4.22 (bs, 2H), 3.86-3.66 (m, 4H), 3.57 (s, 3H), 3.28-3.122 (m, 5H), 1.67 (s, 3H), 2.01-0.84 (m, 4H) |

TABLE 2-continued

7-CF3-Thienylpyridine and Derivative Compounds

| Compound | | Characterization |
|---|---|---|
| 1192 | | MS (ESI) m/z 717.23 [M + 1]+; 1H NMR (400 MHz, DMSO) δ 13.50 (bs, 1H), 8.27 (s, 1H), 8.05 (s, 1H), 7.81 (d, J = 8.0 Hz, 1H), 7.59 (dd, J = 8.0, 4.0 Hz, 1H), 7.43 (s, 2H), 7.36 (d, J = 8.0 Hz, 1H), 6.66 (s, 1H), 6.42 (d, J = 4.0 Hz, 1H), 4.41 (s, 2H), 4.26 (s, 2H), 3.46 (t, J = 8.0 Hz, 2H), 2.83-2.60 (m, 5H), 1.84 (s, 3H) |
| 1197 | | MS (ESI) m/z 679.22 [M + 1]+; 1H NMR (400 MHz, DMSO-d6) δ 13.46 (bs, 1H), 8.23 (s, 1H), 7.94 (s, 1H), 7.59 (d, J = 8.0 Hz, 1H), 7.42 (s, 1H), 7.41 (d, J = 2.4 Hz, 1H), 7.35 (d, J = 8.0 Hz, 1H), 6.46 (t, J = 52.0 Hz, 1H), 4.70-4.60 (m, 2H), 4.41 (s, 2H), 4.24 (s, 2H), 2.71 (s, 3H), 1.79 (s, 3H) |
| 1200 | | MS (ESI) m/z 684.22 [M + 1]+; 1H NMR (400 MHz, DMSO-d6) δ 14.29 (bs, 1H), δ 10.03 (bs, 1H), δ 7.98 (s, 1H), δ 7.61 (dd, J = 9.0 Hz, 2.46 Hz, 1H), 7.43 (s, 1H), 7.42 (s, 1H), 7.35 (d, J = 9.2 Hz, 1H), 4.41 (t, J = 5.1 Hz, 2H), 4.28 (t, J = 4.5 Hz, 2H), 3.42 (bs, 2H), 3.32 (bs, 2H), 2.93 (s, 6H), 2.70 (s, 3H), 2.34 (s, 3H), 1.96 (s, 3H) |
| 1206 | | MS (ESI) m/z 723.34 [M + 1]+; 1H-NMR (400 MHz, DMSO-d6) δ 8.82 (d, J = 4.6 Hz, 1H), 8.19 (s, 1H), 7.90 (s ,1H), 7.58 (dd, J = 2.48, 8.92 Hz, 1H), 7.38 (d, J = 3.16 Hz, 1H), 7.33 (d, J = 8.96 Hz, 1H), 4.39 (t, J = 5.4 Hz, 2H), 4.22 (t, J = 5.2 Hz, 2H), 3.89 (s, 3H), 3.80-3.40 (m, 4H), 3.10-2.90 (m, 4H), 1.69 (s, 3H), 0.47-0.35 (m, 4H) |

TABLE 2-continued
7-CF3-Thienylpyridine and Derivative Compounds
| Compound | Characterization |
|---|---|
| 1207 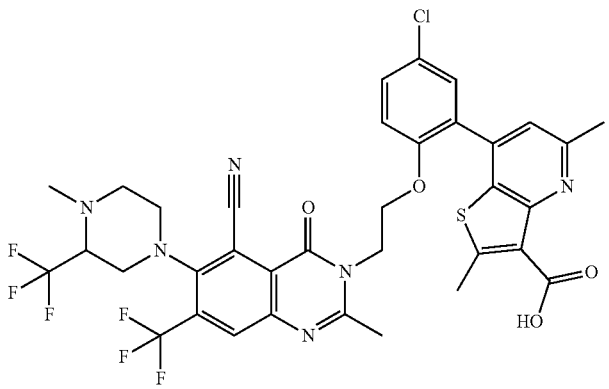 [SMILES: Cc1cc(-c2cc(Cl)ccc2OCCn2c(C)nc3cc(C(F)(F)F)c(N4CCN(C)C(C(F)(F)F)C4)c(C#N)c3c2=O)c2sc(C)c(C(=O)O)c2n1] | MS (ESI) m/z 779.28 [M + 1]+; 1H NMR (400 MHz, DMSO-d6) δ 14.32 (bs, 1H), 7.90 (s, 1H), 7.60 (dd, J = 2.6, 8.9 Hz, 1H), 7.41 (m, 2H), 7.36 (d, J = 8.9 Hz, 1H), 4.40 (s, 2H), 4.26 (s, 2H), 3.66 (m, 2H), 3.20 (m, 2H), 2.97 (m, 2H), 2.70 (s, 3H), 2.66 (m, 1H), 2.49 (s, 3H), 2.44 (s, 3H), 1.97 (s, 3H) |
| 1212 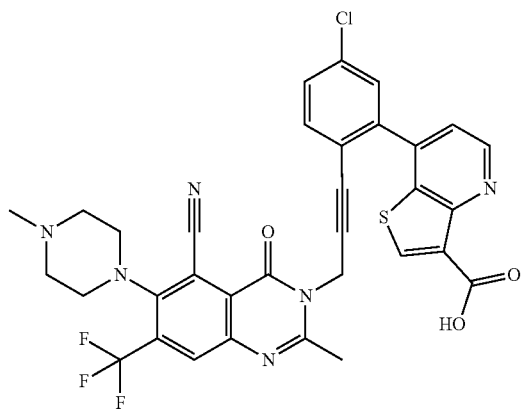 [SMILES: Cc1nc2cc(C(F)(F)F)c(N3CCN(C)CC3)c(C#N)c2c(=O)n1CC#Cc1ccc(Cl)cc1-c1ccnc2c(C(=O)O)csc12] | MS (ESI) m/z 677.23 [M + 1]+; 1H NMR (400 MHz, DMSO-d6) δ 13.11 (bs, 1H), 8.77 (d, J = 4.8 Hz, 1H), 8.59 (s, 1H), 8.11 (s, 1H), 7.76 (d, J = 8.4 Hz, 1H), 7.71-7.67 (m, 2H), 7.56 (d, J = 4.8 Hz, 1H), 4.86 (s, 2H), 3.89-3.86 (m, 2H), 3.59-3.56 (m, 2H), 3.29 (d, J = 11.6 Hz, 2H), 3.11 (bs, 2H), 2.92 (s, 3H), 2.17 (s, 3H) |
| 1213 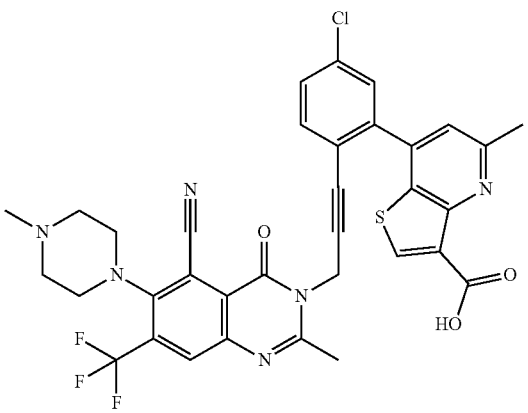 | MS (ESI) m/z 691.29 [M + 1]+; 1H NMR (400 MHz, DMSO-d6) δ 13.31 (s, 1H), 9.77 (s, 1H), 8.58 (s, 1H), 8.09 (s, 1H), 7.76-7.64 (m, 3H), 7.50 (s, 1H), 4.84 (s, 2H), 3.93-3.88 (m, 2H), 3.61-3.58 (m, 2H), 3.32-3.29 (m, 2H), 3.12 (bs, 2H), 2.92 (s, 3H), 2.67 (s, 3H), 2.23 (s, 3H) |

TABLE 2-continued

7-CF3-Thienylpyridine and Derivative Compounds

| | Compound | Characterization |
|---|---|---|
| 1214 | 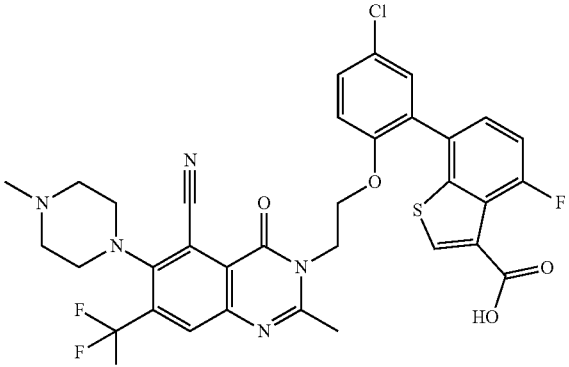 | MS (ESI) m/z 700.25 [M + 1]+; 1H NMR (400 MHz, DMSO-d6) δ 12.83 (bs, 1H), 8.01 (s, 1H), 7.79 (s, 1H), 7.52-7.50 (m, 1H), 7.29-7.20 (m, 4H), 4.34 (bs, 2H), 4.22 (bs, 2H), 3.60-3.38 (m, 2H), 3.25 (bs, 2H), 3.19-2.98 (m, 4H), 2.24 (s, 3H), 1.79 (s, 3H) |
| 1215 | 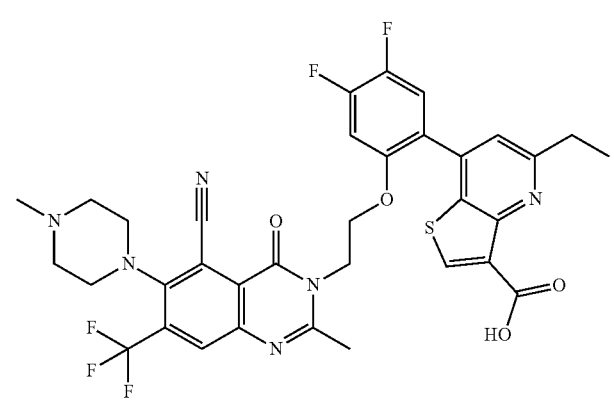 [SMILES: CCc1cc(-c2cc(F)c(F)cc2OCCn2c(C)nc3cc(C(F)(F)F)c(N4CCN(C)CC4)c(C#N)c3c2=O)c2scc(C(=O)O)c2n1] | MS (ESI) m/z 713.31 [M + 1]+; 1H NMR (400 MHz, DMSO-d6) δ 13.66 (bs, 1H), 9.74 (bs, 1H), 8.22 (s, 1H), 7.92 (s, 1H), 7.60-7.54 (m, 2H), 7.44 (s, 1H), 4.39 (bs, 2H), 4.23 (bs, 2 H), 3.86 (m, 2H), 3.58 (m, 2H), 3.26-2.98 (m, 6H), 2.89 (s, 3H), 1.79 (s, 3H), 1.35 (t, J = 7.6 Hz, 3H) |
| 1218 | 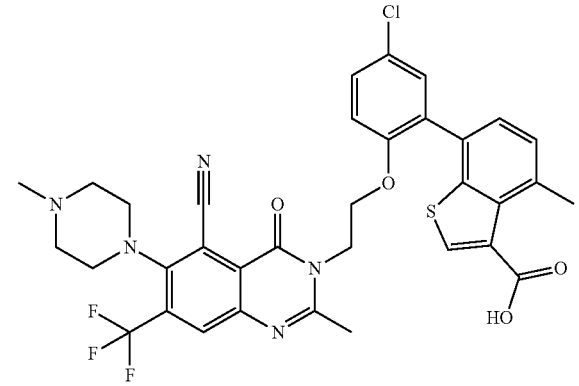 | MS (ESI) m/z 696.26 [M + 1]+; 1H NMR (400 MHz, DMSO-d6) δ 12.98 (s, 1H), 8.02 (s, 1H), 7.66 (s, 1H), 7.50 (dd, J = 2.4 Hz, J = 8.8 Hz, 1H), 7.27-7.25 (m, 3H), 7.13 (d, J = 7.6 Hz, 1H), 4.34 (t, J = 4.8 Hz, 2H), 4.22 (t, J = 4.8 Hz, 2H), 3.86 (t, J = 10.8, 2H), 3.55-3.53 (m, 2H), 3.24-3.21 (m, 2H), 3.07 (bs, 2H), 2.89 (s, 3H), 2.68 (s, 3H), 1.7 (s, 3H) |
| 1221 | 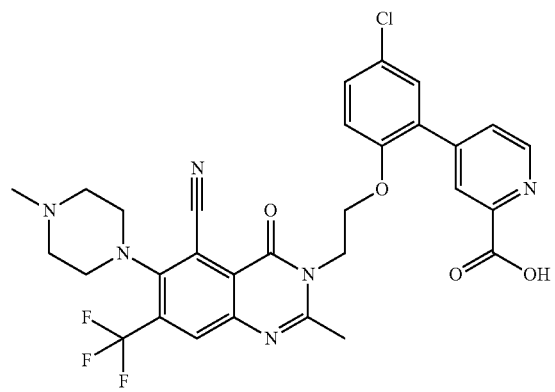 [SMILES: Cc1nc2cc(C(F)(F)F)c(N3CCN(C)CC3)c(C#N)c2c(=O)n1CCOc1ccc(Cl)cc1-c1ccnc(C(=O)O)c1] | MS (ESI) m/z 627.19 [M + 1]+; 1H NMR (400 MHz, DMSO-d6) δ 13.02 (bs, 1H), 9.72 (bs, 1H), 8.58 (d, J = 4.4 Hz, 1H), 8.15 (s, 1H), 7.90 (s, 1H), 7.54 (d, J = 4.2 Hz, 1H), 7.48 (dd, J = 8.8, 2.5 Hz, 1H), 7.40 (d, J = 2.4 Hz, 1H), 7.25 (d, J = 9.6 Hz, 1H), 4.39 (s, 4H), 3.85 (t, J = 11.3 Hz, 2H), 3.52 (t, J = 11.2 Hz, 2H), 3.21 (d, J = 11.8 Hz, 2H), 3.07 (bs, 2H), 2.89 (s, 3H), 2.24 (s, 3H) |

TABLE 2-continued

7-CF3-Thienylpyridine and Derivative Compounds

| Compound | | Characterization |
|---|---|---|
| 1222 | 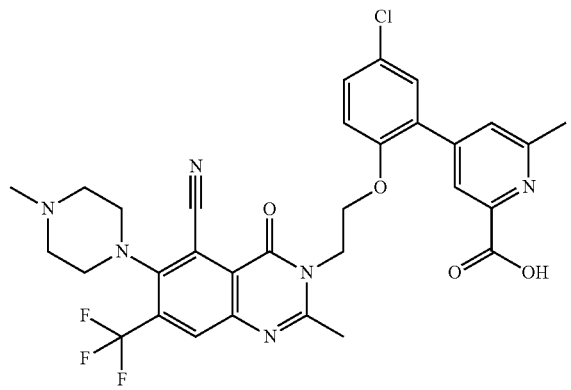 | MS (ESI) m/z 641.28 [M + 1]+; 1H NMR (400 MHz, DMSO-d6) δ 9.73 (bs, 1H), 8.10 (s, 1H), 7.70 (s, 1H), 7.50-7.40 (m, 2H), 7.35 (d, J = 2.8 Hz, 1H), 7.25 (d, J = 9.2 Hz, 1H), 4.38 (s, 4H), 3.85 (t, J = 22.8 Hz, 2H), 3.54 (d, J = 11.2 Hz, 2H), 3.21 (d, J = 11.6 Hz, 2H), 3.13-2.98 (m, 2H), 2.89 (s, 3H), 2.26 (s, 3H) |
| 1223 | 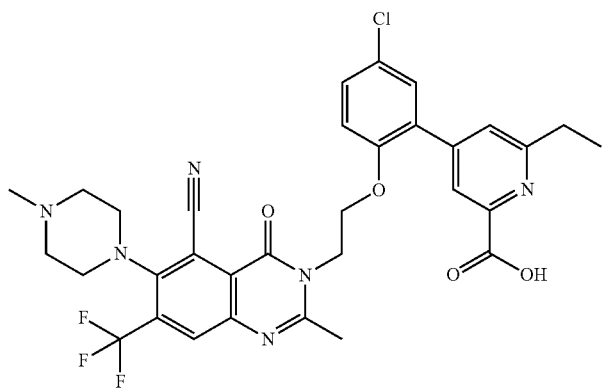 [SMILES: CCc1cc(-c2cc(Cl)ccc2OCCn2c(C)nc3cc(C(F)(F)F)c(N4CCN(C)CC4)c(C#N)c3c2=O)cc(C(=O)O)n1] | MS (ESI) m/z 655.38 [M + 1]+; 1H NMR (400 MHz, DMSO-d6) δ 12.89 (bs, 1H), 9.74 (bs, 1H), 8.10 (s, 1H), 7.72 (s, 1H), 7.48-7.44 (m, 2H), 7.36 (d, J = 2.4 Hz, 1H), 7.24 (d, J = 9.2 Hz, 1H), 4.37 (s, 4H), 4.02-4.00 (m, 2H), 3.91-3.75 (m, 2H), 3.54 (d, J = 10.4 Hz, 2H), 3.19 (d, J = 12.0 Hz, 2H), 3.15-2.98 (m, 2H), 2.89 (s, 3H), 2.80 (q, J = 8.0 Hz, 2H), 2.29 (s, 3H), 1.22 (t, J = 7.6 Hz, 3H) |
| 1224 | 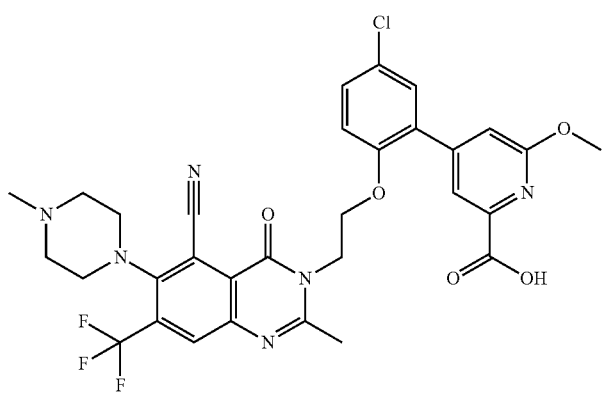 | MS (ESI) m/z 656.30 [M +1]+; 1H NMR (400 MHz, DMSO-d6) δ 12.93 (bs, 1H), 8.05 (s, 1H), 7.52 (s, 1H), 7.46 (dd, J = 8.8, 2.4 Hz, 1H), 7.34 (d, J = 2.4 Hz, 1H), 7.23 (d, J = 8.8 Hz, 1H), 6.95 (s, 1H), 4.36 (bs, 4H), 3.91 (s, 3H), 3.75-3.50 (m, 2H), 3.20-2.70 (m, 6H), 2.26 (s, 3H), 2.24 (s, 3H) |
| 1225 | 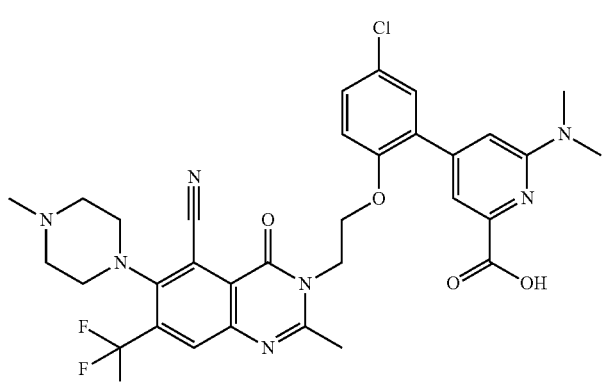 | MS (ESI) m/z 670.31 [M +1]+; 1H NMR (400 MHz, DMSO-d6) δ 12.39 (bs, 1H), 8.04 (s, 1H), 7.42 (dd, J = 8.0, 4.0 Hz, 1H), 7.28 (d, J = 4.0 Hz, 1H), 7.20 (d, J = 8.0 Hz, 1H), 7.09 (s, 1H), 6.63 (s, 1H), 4.34 (s, 4H), 3.82-3.35 (m, 4H), 2.99 (s, 6H), 2.95-2.69 (m, 4H), 2.24 (s, 3H), 2.22 (s, 3H) |

TABLE 2-continued

7-CF3-Thienylpyridine and Derivative Compounds

| Compound | Characterization |
|---|---|
| 1226 | MS (ESI) m/z 655.29 [M + 1]+; 1H NMR (400 MHz, DMSO-d6) δ 12.93 (bs, 1H), 8.09 (s, 1H), 7.46-7.44 (dd, J = 2.0, 8.8 Hz, 1H), 7.21-7.16 (m, 2H), 7.08 (s, 1H), 4.30 (bs, 4H), 3.78 (bs, 2H), 3.14 (m, 4H), 2.91 (bs, 2H), 2.74 (s, 3H), 2.45 (s, 3H), 2.02 (s, 3H), 1.88 (s, 3H) |
| 1228 | MS (ESI) m/z 707.30 [M + 1]+; 1H NMR (400 MHz, DMSO-d6) δ 8.87 (d, J = 4 Hz, 1H), 8.19 (s, 1H), 7.68 (s, 1H), 7.60-7.58 (dd, J = 2.4, 8.8 Hz, 1H), 7.45 (t, J = 4 Hz, 2H), 7.37 (d, J = 8.8 Hz, 1H), 4.41 (bs, 2H), 4.23 (bs, 2H), 3.86-2.64 (m, 8H), 2.32 (s, 3H), 1.74 (s, 3H) |
| 1237 | MS (ESI) m/z 729.25 [M + 1]+; 1H NMR (400 MHz, DMSO-d6) 13.62 (bs, 1H), 7.96 (s, 1H), 7.63-7.60 (dd, J = 2.4, 8.8 Hz, 1H), 7.52 (s, 1H), 7.43 (d, J = 2.4 Hz, 1H), 7.37 (d, J = 8.8 Hz, 1H), 5.79 (d, J = 46.4 Hz, 2H), 4.41 (bs, 2H), 4.26 (bs, 2H), 3.89 (t, J = 12.4 Hz, 2H), 3.56 (t, J = 10.4 Hz, 2H), 3.20 (t, J = 12.8 Hz, 2H), 3.09 (bs, 2H), 2.90 (s, 3H), 2.39 (s, 3H), 1.88 (s, 3H) |
| 1238 | MS (ESI) m/z 741.31 [M + 1]+; 1H NMR (400 MHz, DMSO-d6) 13.98 (bs, 1H), 7.93 (s, 1H), 7.62-7.60 (m, 1H), 7.48 (s, 1H), 7.43 (bs, 1H), 7.37 (d, J = 8.8 Hz, 1H), 4.75 (s, 2H), 4.41 (bs, 2H), 4.25 (bs, 2H), 3.57 (t, J = 12.0 Hz, 2H), 3.44 (bs, 2H), 3.40 (s, 3H), 3.21 (t, J = 10.8 Hz, 2H), 3.10 (bs, 2H), 2.90 (s, 3H), 2.39 (s, 3H), 1.89 (s, 3H) |

TABLE 2-continued

7-CF3-Thienylpyridine and Derivative Compounds

| Compound | Characterization |
|---|---|
| 1239 | MS (ESI) m/z 733.30 [M + 1]+; 1H NMR (400 MHz, DMSO-d6) δ 13.02 (bs, 1H), 8.83 (d, J = 4.8 Hz, 1H), 8.27 (s, 1H), 7.94 (s, 1H), 7.60 (dd, J = 8.8, 2.8 Hz 1H), 7.48 (d, J = 4.8 Hz, 1H), 7.42 (d, J = 2.8 Hz, 1H), 7.36 (d, J = 8.8 Hz, 1H), 6.47-6.19 (m, 1H), 4.40 (s, 2H), 4.24 (s, 2H), 3.70-3.50 (merged, 2H), 3.30-2.80 (m, 8H), 1.75 (s, 3H) |
| 1241 | MS (ESI) m/z 725.25 [M + 1]+; 1H NMR (400 MHz, DMSO-d6) δ 13.77 (bs, 1H), 8.83 (d, J = 4.64 Hz, 1H), 8.24 (s, 1H), 7.96 (s, 1H), 7.11 (dd, J = 8.9 Hz, 2.16 Hz, 1H), 7.48 (d, J = 4.6 Hz, 1H), 7.43 (s, 1H), 7.36 (d, J = 9.0 Hz, 1H), 4.74 (bs, 4H), 4.59 (bs, 1H), 4.41 (s, 2H), 4.25 (s, 2H), 4.07 (bs, 2H), 3.54 (bs, 2H), 3.30 (bs, 2H), 2.93 (bs, 2H), 1.76 (s, 3H) |
| 1242 | MS (ESI) m/z 739.32 [M + 1]+; 1H NMR (400 MHz, DMSO-d6) δ 13.46 (s, 1H), 8.24 (s, 1H), 7.92 (s, 1H), 7.60 (d, J = 8.8 Hz, 1H), 7.42 (d, J = 6 Hz, 2H), 7.36 (d, J = 8.8 Hz, 1H), 4.78-4.73 (m, 4H), 4.59 (bs, 1H), 4.40 (s, 2H), 4.25- (s, 2H), 3.91 (bs, 4H), 3.29 (bs, 2H), 2.92 (bs, 2H), 2.72 (s, 3H), 1.84 (s, 3H) |
| 1243 | MS (ESI) m/z 727.33 [M + 1]+; 1H NMR (400 MHz, DMSO-d6) δ 9.81 (s, 1H), 8.84 (d, J = 4.8 Hz, 1H), 8.26 (s, 1H), 7.96 (s, 1H), 7.62 (dd, J = 2.4, 9.2 Hz, 1H), 7.47 (d, J = 4.8 Hz, 1H), 7.43 (d, J = 2.4 Hz, 1H), 7.37 (d, J = 8.8 Hz, 1H), 4.42 (t, J = 4.8 Hz, 2H), 4.26 (t, J = 4.8 Hz, 2H), 3.95 (bs, 2H), 3.71 (m, 2H), 3.58 (m, 2H), 3.44 (m, 2H), 3.35 (s, 3H), 3.12 (d, J = 10 Hz, 2H), 3.12 (t, J = 10 Hz, 2H), 1.77 (s, 3H) |

TABLE 2-continued

7-CF3-Thienylpyridine and Derivative Compounds

| Compound | Characterization |
|---|---|
| 1244 | MS (ESI) m/z 663.27 [M + 1]+; 1H NMR (400 MHz, DMSO-d6) δ 9.71 (bs, 1H), 8.73 (d, J = 4.4 Hz, 1H), 8.12 (s, 1H), 7.62 (s, 1H), 7.56 (dd, J = 8.8, 2.4 Hz, 1H), 7.38-7.31 (m, 3H), 4.68 (s, 1H), 4.40 (s, 2H), 4.26 (s, 2H), 3.86 (t, J = 12.0 Hz, 2H), 3.54 (d, J = 11.6 Hz, 2H), 3.22 (d, J = 12.8 Hz, 2H), 3.15-3.00 (m, 2H), 2.91 (s, 3H), 1.82 (s, 3H) |
| 1245 | MS (ESI) m/z 664.29 [M + 1]+; 1H NMR (400 MHz, DMSO-d6) δ 8.90 (d, J = 4.4 Hz, 1H), 8.41 (s, 1H), 8.10 (s, 1H), 7.60 (dd, J = 8.8, 2.4 Hz, 1H), 7.56 (d, J = 4.8 Hz, 1H), 7.43 (d, J = 2.4 Hz, 1H), 7.35 (d, J = 8.8 Hz, 1H), 4.43-4.43 (m, 2H), 4.24 (s, 2H), 3.65-3.49 (m, 2H), 2.99-2.89 (m, 4H), 2.74 (s, 2H), 2.24 (s, 3H), 1.69 (s, 3H) |
| 1246 | MS (ESI) m/z 673.24 [M + 1]+; 1H NMR (400 MHz, DMSO-d6) δ 8.68 (s, 1H), 8.08 (s, 1H), 7.56 (d, J = 7.84, 1H), 7.45 (s, 1H), 7.37-7.31 (m, 3H), 4.40 (s, 2H), 4.27 (s, 2H), 3.72-3.51 (m, 2H), 2.90 (bs, 4H), 2.25 (s, 5H), 1.83 (s, 3H) |
| 1247 | MS (ESI) m/z 673.19 [M + 1]+; 1H NMR (400 MHz, DMSO-d6) δ 8.77 (d, J = 4.8 Hz, 1H), 8.01 (s, 1H), 7.58 (dd, J = 2.8, 8.8 Hz, 1H), 7.51 (s, 1H), 7.41 (d, J = 4.8 Hz, 1H), 7.37 (d, J = 2.4 Hz, 1H), 7.34 (d, J = 6.8 Hz, 1H), 4.39 (t, J = 4.8 Hz, 2H), 4.24 (t, J = 4.0 Hz, 2H), 3.62 (bs, 2H), 2.81 (bs, 6H), 2.24 (s, 3H), |

TABLE 2-continued

7-CF3-Thienylpyridine and Derivative Compounds

| Compound | Characterization |
|---|---|
| 1248 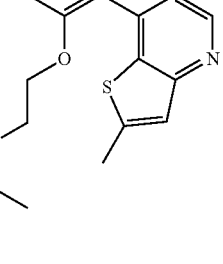 | MS (ESI) m/z 653.30 [M + 1]+; 1H NMR (400 MHz, DMSO-d6) δ 8.54 (s, 1H), 8.06 (s, 1H), 7.52 (s, 1H), 7.31 (t, J = 9.9 Hz, 2H), 7.13 (s, 1H), 7.06 (s, 1H), 4.36 (s, 2H), 4.26 (s, 2H), 3.91-3.42 (m, 2H), 3.22-2.71 (m, 4H), 2.63-2.21 (m, 5H), 2.12 (s, 3H), 1.86 (s, 3H) |
| 1249 | MS (ESI) m/z 653.31 [M + 1]+; 1H NMR (400 MHz, DMSO-d6) δ 9.73 (bs, 1H), 8.66 (d, J = 4.8 Hz, 1H), 8.05 (s, 1H), 7.55 (dd, J = 8.8, 2.4 Hz, 1H), 7.34-7.31 (m, 2H), 7.24 (d, J = 4.8 Hz, 1H), 7.13 (s, 1H), 4.41-4.34 (m, 2H), 4.30-4.20 (m, 2H), 3.87 (t, J = 11.6 Hz, 2H), 3.56 (d, J = 11.6 Hz, 2H), 3.26 (d, J = 12.0 Hz, 2H), 3.15-3.00 (m, 2H), 2.91 (s, 3H), 2.36 (s, 3H), 1.81 (s, 3H) |
| 1250 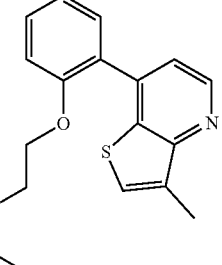 | MS (ESI) m/z 640.24 [M + 1]+; 1H NMR (400 MHz, DMSO-d6) δ 9.74 (bs, 1H), 9.16 (s, 1H), 8.07 (s, 1H), 8.01 (d, J = 5.32 Hz, 1H), 7.62 (dd, J = 8.9, 2.6 Hz, 1H), 7.46 (d, J = 2.6 Hz, 1H) 7.42 (d, J = 5.4 Hz, 1H) 7.36 (d, J = 9.0 Hz, 1H), 4.43 (t, J = 4.9 Hz, 2H), 4.29 (t, J = 4.32 Hz, 2H), 3.87 (t, J = 11.2 Hz, 2H), 3.55 (d, J = 11.6 Hz, 2H), 3.25 (d, 12.36 Hz, 2H), 3.15-3.00 (m, 2H), 2.90 (s, 3H), 1.93 (s, 3H) |
| 1251 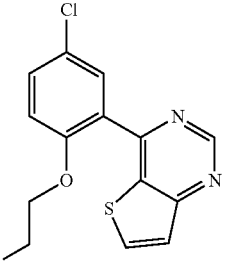 | MS (ESI) m/z 640.27 [M + 1]+; 1H NMR (400 MHz, DMSO-d6) δ 9.10 (s, 1H), 8.84 (d, J = 4.5 Hz, 1H), 8.05 (s, 1H), 7.58 (dd, J = 9.0 Hz, 2.5 Hz, 1H), 7.55 (d, J = 4.5 Hz, 1H), 7.47 (d, J = 2.5 Hz, 1H), 7.35 (d, J = 8.9 Hz, 1H), 4.43 (t, J = 4.16 Hz, 2H), 4.27 (t, J = 4.36 Hz, 2H), 3.61 (bs, 4H), 2.96 (bs, 4H), 2.24 (s, 3H), 1.88 (s, 3H) |

TABLE 2-continued

7-CF3-Thienylpyridine and Derivative Compounds

| Compound | | Characterization |
|---|---|---|
| 1252 | 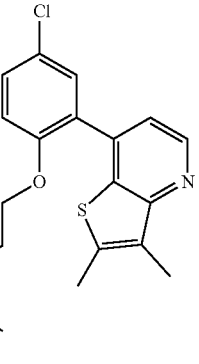 | MS (ESI) m/z 667.36 [M + 1]+; 1H NMR (400 MHz, DMSO-d6) δ 8.60 (d, J = 4.7 Hz, 1H),), 8.01 (s, 1H), 7.54-7.51 (dd, J = 8.8, J = 2.5 Hz, 1H), 7.30 (m, 2H), 7.18 (d, J = 4.6 Hz, 1H), 4.37 (t, J = 12.7 Hz, 2H), 4.23 (t, J = 3.4 Hz, 2H), 3.64 (m, 4H), 2.89 (m, 4H), 2.23 (s, 6H), 1.97 (s, 3H), 1.79 (s, 3H) |
| 1253 |  | MS (ESI) m/z 671.22 [M +1]+; 1H NMR (400 MHz, DMSO-d6) δ 8.01 (s, 1H), 7.78 (d, J = 5.6 Hz, 1H), 7.57 (dd, J = 2.80, 8.8 Hz, 1H), 7.39 (d, J = 2.8 Hz, 1H), 7.37 (d, J = 9.6 Hz, 1H), 7.34-7.31 (m, 2H), 5.59 (d, J = 46.8 Hz, 2H), 4.36 (t, J = 4.4 Hz, 2H), 4.25 (t, J = 4.0 Hz, 2H), 3.61 (bs, 2H), 2.93 (bs, 2H), 2.50 (bs, 2H), 2.25 (bs, 5H), 1.85 (s, 3H) |
| 1254 |  | MS (ESI) m/z 664.26 [M + 1]+; 1H NMR (400 MHz, DMSO-d6) δ 8.83 (d, J = 4.8 Hz, 1H), 8.48 (s, 1H), 8.03 (s, 1H), 7.61 (dd, J = 2.4, 11.2 Hz, 1H), 7.50 (d, J = 4.8 Hz, 1H), 7.43 (d, J = 2.4 Hz, 1H), 7.37 (d, J = 8.8 Hz, 1H), 4.40 (bs, 2H), 4.26 (bs, 2H), 3.57 (m, 2H), 3.02 (m, 4H), 2.60 (m, 2H), 2.24 (s, 3H), 1.76 (s, 3H) |
| 1255 | 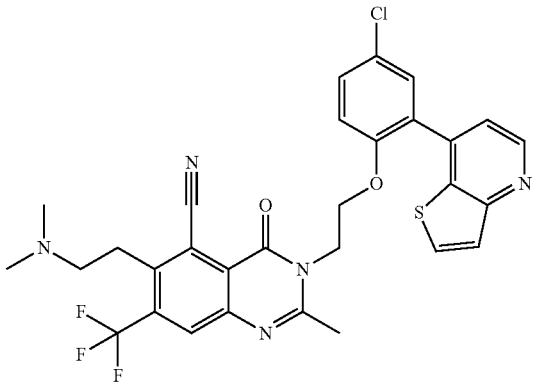 [SMILES: Cc1nc2cc(C(F)(F)F)c(CCN(C)C)c(C#N)c2c(=O)n1CCOc1ccc(Cl)cc1-c1ccnc2ccsc12] | MS (ESI) m/z 612.23 [M + 1]+; 1H NMR (400 MHz, DMSO-d6) δ 9.99 (bs, 1H), 68.63 (d, J = 4.8 Hz, 1H), 68.10 (s, 1H), 7.66 (d, J = 5.6 Hz, 1H), 7.54 (dd, J = 8.7 Hz, 2.5 Hz, 1H), 7.37 (d, J = 2.4 Hz, 1H), 7.33-31 (m, 2H), 7.21 (d, J = 4.4 Hz, 1H), 4.37 (t, J = 5.1 Hz, 2H), 4.27 (t, J = 4.5 Hz, 2H), 3.45-3.43 (m, 2H), 3.32 (bs, 2H), 2.95 (s, 6H), 1.96 (s, 3H) |

TABLE 2-continued

7-CF3-Thienylpyridine and Derivative Compounds

| Compound | Characterization |
|---|---|
| 1256 | MS (ESI) m/z 653.27 [M + 1]+; 1H NMR (400 MHz, DMSO-d6) δ 8.63 (d, J = 4.8 Hz, 1H), 8.05 (s, 1H), 7.72 (d, J = 5.6 Hz, 1H), 7.55 (dd, J = 2.4, 8.8 Hz, 1H), 7.42 (d, J = 5.6, Hz, 1H), 7.39 (d, J = 2.4 Hz, 1H), 7.32 (d, J = 8.8 Hz, 1H), 7.22 (d, J = 4.4 Hz, 1H), 4.38 (t, J = 4.4 Hz, 2H), 4.25 (t, J = 5.2 Hz, 2H), 3.85 (s, 2H), 2.47 (m, 4H), 2.27 (m, 4H), 1.83 (s, 3H), 1.23 (s, 3H) |
| 1259 | MS (ESI) m/z 666.25 [M + 1]+; 1H NMR (400 MHz, DMSO-d6) δ 8.38 (d, J = 4.0 Hz 1H), 8.20 (s, 1H), 8.02 (s, 1H), 7.58 (d, J = 6.4 Hz, 1H), 7.42 (d, J = 9.2 Hz, 2H), 7.33 (d, J = 8.8 Hz 1H), 4.39 (s, 2H), 4.23 (s, 2H), 3.67 (s, 2H), 2.32 (s, 6H), 1.68 (s, 3H) |
| 1260 | MS (ESI) m/z 638.08 [M + 1]+; 1H NMR (400 MHz, DMSO-d6) δ 13.28 (s, 1H), 8.84 (d, J = 4.8 Hz, 1H), 8.47 (bs, 3H), 8.31 (s, 1H), 8.04 (s, 1H), 7.61 (dd, J = 8.8, 2.4 Hz, 1H), 7.49 (d, J = 4.4 Hz, 1H), 7.44 (d, J = 2.8 Hz, 1H), 7.37 (d, J = 9.2 Hz, 1H), 4.41 (bs, 2H), 4.27 (bs, 4H), 1.74 (s, 3H) |
| 1261 | MS (ESI) m/z 713. 27 [M + 1]+; 1H NMR (400 MHz, DMSO-d6) δ 13.25 (bs, 1H), 9.60 (bs, 1H), 8.84 (d, J = 4.8 Hz, 1H), 8.21 (s, 1H), 7.95 (s, 1H), 7.61 (dd, J = 2.4, 8.8 Hz, 1H), 7.48 (d, J = 4.8 Hz, 1H), 7.42 (d, J = 2.4 Hz, 1H), 7.36 (d, J = 9.2 Hz, 1H), 5.69 (bs, 1H), 4.41 (s, 2H), 4.24 (s, 2H), 3.95-3.89 (m, 3H), 3.63-3.58 (m, 2H), 3.22-3.30 (m, 6H), 2.96-2.89 (m, 4H), 1.75 (s, 3H) |

TABLE 2-continued

7-CF3-Thienylpyridine and Derivative Compounds

| Compound | Characterization |
|---|---|
| 1262 | MS (ESI) m/z 749.29 [M + 1]+; 1H NMR (400 MHz, DMSO-d6) δ 13.37 (bs, 1H), 8.84 (d, J = 4.8 Hz, 1H), 8.24 (s, 1H), 7.94 (s, 1H), 7.59 (dd, J = 2.4, 8.8 Hz, 1H), 7.48 (d, J = 4.8 Hz, 1H), 7.42 (d, J = 2.4 Hz, 1H), 7.36 (d, J = 9.2 Hz, 1H), 4.40 (s, 2H), 4.23 (s, 2H), 3.96 (m, 2H), 3.48 (m, 4H), 3.24 (m, 1H), 2.96 (s, 3H), 1.72 (s, 3H) |
| 1263 | MS (ESI) m/z 682.0 [M + 1]+; ; 1H NMR (400 MHz, DMSO-d6) δ 8.28 (s, 1H), 7.90 (s, 1H), 7.63-7.56 (m, 1H), 7.46-7.38 (m, 2H), 7.35 (d, J = 8.96 Hz, 1H), 4.49-4.32 (m, 2H), 4.31-4.18 (m, 2H), 3.70-3.66 (m, 1H), 3.26-3.22 (m, 2H), 2.69 (s, 3H), 2.32-2.22 (m, 2H), 2.22-2.09 (m, 2H), 2.07 (s, 3H), 1.80 (s, 3H) |
| 1269 | MS (ESI) m/z 699.27 [M + 1]+; 1H NMR (400 MHz, DMSO-d6) δ 13.12 (bs, 1H), 8.94 (s, 1H), 8.91 (d, J = 4.8 Hz, 1H), 8.15 (s, 1H), 7.75 (d, J = 9.2 Hz, 1H), 7.57 (d, J = 4.4 Hz, 1H), 7.49 (bs, 2H), 4.18 (t, J = 6.0 Hz, 2H), 3.87 (bs, 2H), 3.54 (d, J = 12.4 Hz, 2H), 3.33 (bs, 2H), 3.22 (d, J = 11.6 Hz, 2H), 3.08 (bs, 2H), 2.90 (s, 3H), 2.52 (s, 3H) |
| 1270 | MS (ESI) m/z 691.31 [M + 1]+; 1H NMR (400 MHz, DMSO-d6) δ 13.11 (bs, 1H), 8.7 (d, J = 4.7 Hz, 1H), 8.62 (s, 1H), 8.26 (s, 1H), 7.76 (d, J = 8.1 Hz, 1H), 7.72-7.66 (m, 2H), 7.25 (d, J = 4.7 Hz, 1H), 5.01-4.45 (m, 2H), 4.20-3.82 (m, 4H), 3.70-3.45 (m, 2H), 2.88 (s, 3H), 2.16 (s, 3H) |

TABLE 2-continued

7-CF3-Thienylpyridine and Derivative Compounds

| Compound | Characterization |
| --- | --- |
| 1271 | MS (ESI) m/z 691.28 [M + 1]+; ; 1H NMR (400 MHz, DMSO-d6) δ 13.75 (bs, 1H), 9.75 (bs, 1H), 8.74 (d, J = 4.8 Hz, 1H), 8.11 (s, 1H), 7.76-7.69 (m, 2H), 7.65 (s, 1H), 7.58 (d, J = 4.8 Hz, 1H), 4.86 (s, 2H), 3.89 (t, J = 22.4 Hz, 2H), 3.59 (d, J = 11.2 Hz, 2H), 3.30 (d, J = 11.2 Hz, 2H), 3.11 (d, J = 8 Hz, 2H), 2.92 (bs, 3H), 2.64 (s, 3H), 2.22 (s, 3H) |
| 1272 | MS (ESI) m/z 711.31 [M + 1]+; 1H NMR (400 MHz, DMSO-d6) δ 8.8 (d, J = 4.8 Hz, 1H), 8.09 (s, 1H), 7.60 (dd, J = 8.8 Hz, 2.4 Hz, 1H), 7.50 (d, J = 4.8 Hz, 1H), 7.44 (d, J = 2.4 Hz, 1H), 7.35 (d, J = 8.8 Hz 1H), 4.42 (bs, 2H), 4.28 (bs, 2H), 4.08-3.55 (m, 6H), 2.87 (s, 3H), 2.37 (s, 3H), 1.82 (s, 3H) |
| 1275 | MS (ESI) m/z 724.28 [M + 1]+; 1H NMR (400 MHz, DMSO-d6) 13.73 (bs, 1H), 8.17 (s, 1H), 7.96 (s, 1H), 7.62-7.59 (dd, J = 2.8, 9.2 Hz, 1H), 7.47-7.44 (m, 2H), 7.37 (d, J = 8.8 Hz, 1H), 4.41 (bs, 2H), 4.24 (bs, 2H), 3.43-3.40 (m, 2H), 3.23-2.86 (m, 6H), 2.73 (s, 3H), 2.02 (bs, 1H), 1.79 (bs, 5H), 1.64-1.55 (m, 2H), 1.37 (t, J = 7.6 Hz, 3H) |

TABLE 2-continued

7-CF3-Thienylpyridine and Derivative Compounds

| Compound | Characterization |
|---|---|
| 1276 | MS (ESI) m/z 710.27 [M + 1]+; ; 1H NMR (400 MHz, DMSO-d6) δ 13.70 (bs, 1H), 8.45 (bs, 1H), 8.17 (s, 1H), 7.96 (s, 1H), 7.61-7.59 (dd, J = 6.8, 8.8 Hz, 1H), 7.46-7.43 (m, 2H), 7.37 (d, J = 8.8 Hz, 1H), 4.41 (bs, 2H), 4.24 (bs, 2H), 3.30 (m, 2H), 3.06-2.98 (m, 4H), 2.84 (m, 2H), 2.08 (bs, 1H), 1.79 (s, 3H), 1.75 (d, J = 13.6 Hz, 2H), 1.60 (t, J = 10.0 Hz, 2H), 1.37 (t, J = 7.6 Hz, 3H) |
| 1283 | MS (ESI) m/z 682.22 [M + 1]+; 1H NMR (400 MHz, DMSO-d6) δ 14.06 (bs, 1H), 8.79 (d, J = 5.2 Hz, 1H), 7.97 (d, J = 5.2 Hz, 1H), 7.61 (dd, J = 2.8, 9.2 Hz, 1H), 7.52 (d, J = 4.8 Hz, 1H), 7.9 (d, J = 2.4 Hz, 1H), 7.38 (d, J = 9.2 Hz, 1H), 4.42 (bs, 2H), 4.27 (bs, 2H), 4.20 (d, J = 6.0 Hz, 2H), 4.02 (d, J = 8.0 Hz, 2H), 3.95 (bs, 1H), 3.38 (d, J = 5.6 Hz, 2H), 2.85 (d, J = 4.8 Hz, 3H), 2.33 (s, 3H), 1.88 (s, 3H) |
| 1286 | MS (ESI) m/z 714.39 [M + 1]+; 1H NMR (400 MHz, DMSO-d6) δ 13.23 (bs, 1H), 8.14 (s, 1H), 7.52 (dd, J = 8.8 Hz, 2.5 Hz, 1H), 7.27-7.25 (m, 2H), 7.23-7.21 (m, 2H), 4.34-4.33 (m, 2H), 4.27-4.25 (m, 2H), 3.87 (t, J = 12.3 Hz, 2H), 3.55-3.53 (m, 2H), 3.18-3.15 (m, 2H), 3.08-3.06 (m, 2H), 2.89 (s, 3H), 2.04 (s, 3H), 1.83 (s, 3H) |
| 1287 | MS (ESI) m/z 704.27 [M + 1]+; 1H NMR (400 MHz, DMSO-d6) δ 8.83 (d, J = 4.8 Hz, 1H), 8.20 (s, 1H), 7.98 (s, 1H), 7.60 (dd, J = 8.8 Hz, 2.4 Hz, 1H), 7.49 (d, J = 4.4 Hz, 1H), 7.42-7.36 (m, 2H), 4.41 (bs, 6H), 4.24 (s, 2H), 3.31 (d, J = 6.4 Hz, 2H), 3.21 (d, J = 4.8 Hz, 2H), 1.81 (s, 3H) |

TABLE 2-continued

7-CF3-Thienylpyridine and Derivative Compounds

| Compound | | Characterization |
|---|---|---|
| 1288 | 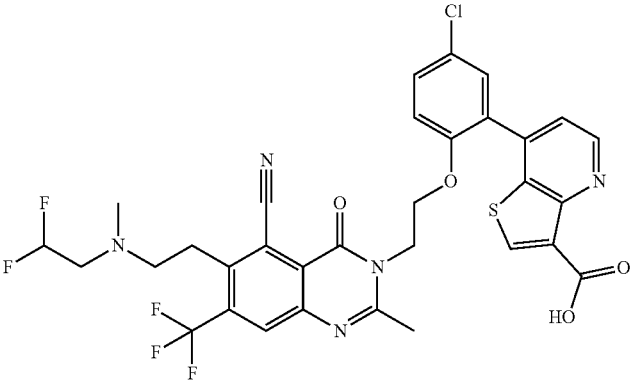 [SMILES: Cc1nc2cc(C(F)(F)F)c(CCN(C)CC(F)F)c(C#N)c2c(=O)n1CCOc1ccc(Cl)cc1-c1ccnc2c(C(=O)O)csc12] | MS (ESI) m/z 706.37 [M + 1]+; 1H NMR (400 MHz, DMSO-d6) δ 8.83 (d, J = 4.4 Hz 1H), 8.21 (s, 1H), 7.98 (s, 1H) 7.59 (dd, J = 8.9, 2.6 Hz, 1H), 7.49 (d, J = 4.8 Hz 1H), 7.42 (d, J = 2.8 Hz, 1H), 7.36 (d, J = 8.8 Hz, 1H), 6.18-6.46 (m, 1H), 4.41 (t, J = 6.02 Hz, 2H), 4.25 (t, J = 8.0 Hz, 2H), 3.39 (s, 4H), 3.09 (s, 2H), 2.73 (s, 3H), 1.77 (s, 3H) |
| 1259 | 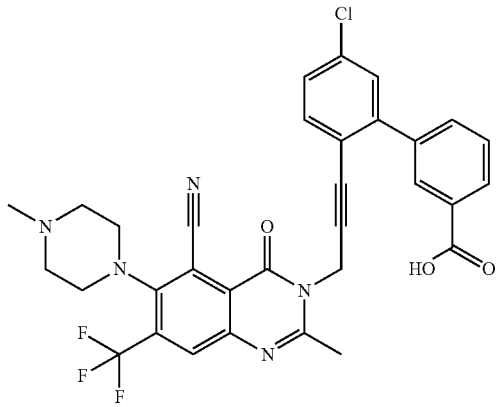 [SMILES: Cc1nc2cc(C(F)(F)F)c(N3CCN(C)CC3)c(C#N)c2c(=O)n1CC#Cc1ccc(Cl)cc1-c1cccc(C(=O)O)c1] | MS (ESI) m/z 620.27 [M + 1]+; 1H NMR (400 MHz, DMSO-d6) δ 12.79 (bs, 1H), 8.17 (s, 1H), 7.91 (s, 1H), 7.67-7.62 (m, 3H), 7.51 (bs, 2H), 7.37 (bs, 1H), 5.02 (s, 2H), 3.87-3.45 (m, 4H), 3.21-2.91 (m, 4H), 3.02 (bs, 3H), 2.85 (bs, 3H) |
| 1291 | 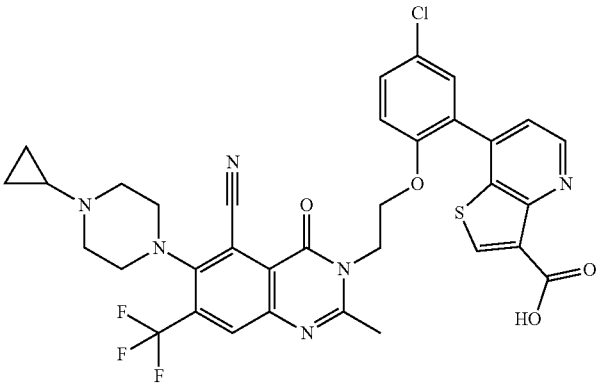 [SMILES: Cc1nc2cc(C(F)(F)F)c(N3CCN(C4CC4)CC3)c(C#N)c2c(=O)n1CCOc1ccc(Cl)cc1-c1ccnc2c(C(=O)O)csc12] | MS (ESI) m/z 709.12 [M + 1]+; 1H NMR (400 MHz, DMSO-d6) δ 8.83 (d, J = 4.4 Hz, 1H), 8.23 (s, 1H), 7.96 (s, 1H), 7.60 (dd, J = 6.4 Hz, 2.4 Hz, 1H), 7.48 (d, J = 4.8 Hz, 1H), 7.42 (d, J = 2.4 Hz, 1H), 7.36 (d, J = 8.8 Hz, 1H), 4.40 (s, 2H), 4.24 (s, 2H), 3.85 (s, 4H), 3.29 (bs, 4H), 3.12 (bs, 1H), 1.76 (s, 3H), 1.01 (s, 2H), 0.85 (s, 2H) |
| 1292 | 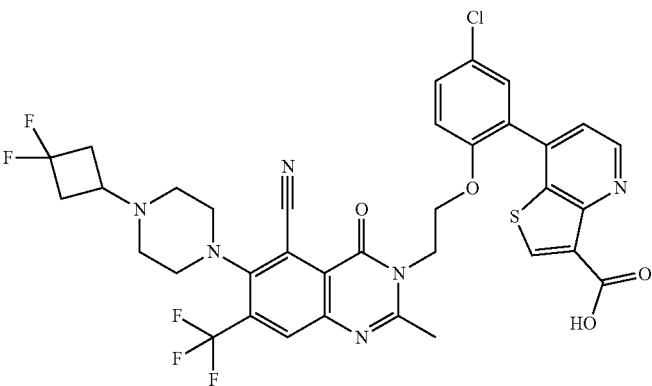 [SMILES: Cc1nc2cc(C(F)(F)F)c(N3CCN(C4CC(F)(F)C4)CC3)c(C#N)c2c(=O)n1CCOc1ccc(Cl)cc1-c1ccnc2c(C(=O)O)csc12] | MS (ESI) m/z 759.38 [M + 1]+; 1H NMR (400 MHz, DMSO-d6) δ 13.30 (bs, 1H), 8.83 (d, J = 4.8 Hz, 1H), 8.25 (s, 1H), 7.96 (s, 1H), 7.60 (dd, J = 6.4, 9.2 Hz, 1H), 7.47 (d, J = 4.8 Hz, 1H), 7.42 (d, J = 2.4 Hz, 1H), 7.36 (d, J = 8.8 Hz, 1H), 4.40 (s, 2H), 4.24 (s, 2H), 3.85-3.52 (m, 5H), 3.02 (m, 8H), 1.75 (m, 3H) |

TABLE 2-continued

7-CF3-Thienylpyridine and Derivative Compounds

| Compound | Characterization |
|---|---|
| 1293 | MS (ESI) m/z 765.30 [M + 1]+; 1H NMR (400 MHz, DMSO-d6) δ 13.26 (bs, 1H), 8.82 (d, J = 4.8 Hz, 1H), 8.28 (s, 1H), 7.93 (s, 1H), 7.59 (d, J = 8.8 Hz, 1H), 7.46 (d, J = 4.4 Hz, 1H), 7.42 (s, 1H), 7.35 (d, J = 10.8 Hz, 1H), 4.39 (bs, 2H), 4.23 (bs, 2H), 3.63 (bs, 2H), 3.31 (bs, 2H), 2.95 (m, 4H), 2.60 (t, J = 7.2 Hz, 4H), 1.71 (s, 3H) |
| 1298 | MS (ESI) m/z 650.26 [M + 1]+; 1H NMR (400 MHz, DMSO-d6) δ 13.06 (bs, 1H), 8.75 (d, J = 4.8 Hz, 1H), 8.57 (s, 1H), 8.14 (s, 1H), 7.77 (d, J = 8.0 Hz, 1H), 7.70-7.66 (m, 2H), 7.55 (d, J = 4.8 Hz, 1H), 4.88 (s, 2H), 3.38-3.23 (m, 4H), 3.18-3.08 (m, 2H), 2.78 (s, 6H), 2.16 (s, 3H) |
| 1372 | MS (ESI) m/z 606.1 [M + 1]+; 1H NMR (400 MHz, DMSO-d6) δ 8.63 (dd, J = 5.0, 0.8 Hz, 1H), 8.38 (d, J = 1.7 Hz, 1H), 8.26 (dd, J = 1.7, 0.8 Hz, 1H), 8.03 (dd, J = 1.7, 0.8 Hz, 1H), 7.70 (dd, J = 5.0, 1.8 Hz, 1H), 7.57-7.39 (m, 2H), 7.27 (d, J = 8.9 Hz, 1H), 4.40 (s, 4H), 3.39 (s, 3H), 2.23 (s, 3H) |

TABLE 2-continued

7-CF3-Thienylpyridine and Derivative Compounds

| Compound | Characterization |
|---|---|
| 1374 | MS (ESI) m/z 628.2 [M + 1]+; 1H NMR (400 MHz, DMSO-d6) δ 8.36 (d, J = 1.7 Hz, 1H), 8.25 (s, 3H), 7.99 (d, J = 1.7 Hz, 1H), 7.60 (dd, J = 8.9, 2.7 Hz, 1H), 7.45 (s, 1H), 7.39-7.34 (m, 2H), 4.41 (d, J = 5.1 Hz, 2H), 4.27 (t, J = 5.1 Hz, 2H), 3.41 (d, J = 6.0 Hz, 2H), 3.28 (t, J = 6.5 Hz, 2H), 1.83 (s, 3H) |
| 1375 | MS (ESI) m/z 624.0 [M + 1]+; 1H NMR (400 MHz, DMSO-d6) δ 11.41 (s, 1H), 8.83 (d, J = 4.7 Hz, 1H), 8.34 (d, J = 1.6 Hz, 1H), 7.95 (s, 1H), 7.81 (d, J = 1.6 Hz, 1H), 7.59 (dd, J = 8.9, 2.7 Hz, 1H), 7.45-7.39 (m, 2H), 7.35 (d, J = 9.0 Hz, 1H), 6.92 (s, 1H), 4.40 (d, J = 5.0 Hz, 2H), 4.25 (t, J = 4.9 Hz, 2H), 1.74 (s, 3H) |
| 1376 | MS (ESI) m/z 714.3 [M + 1]+; 1H NMR (400 MHz, DMSO-d6) δ 8.27 (s, 1H), 7.95 (s, 1H), 7.60 (dd, J = 8.9, 2.7 Hz, 1H), 7.46-7.40 (m, 2H), 7.36 (d, J = 9.0 Hz, 1H), 4.40 (d, J = 5.0 Hz, 2H), 4.25 (s, 2H), 3.91 (s, 2H), 2.70 (s, 5H), 2.58 (s, 2H), 1.83 (s, 3H) |
| 1377 | MS (ESI) m/z 746.4 [M + 1]+; 1H NMR (400 MHz, DMSO-d6) δ 8.31 (s, 1H), 8.16 (s, 1H), 7.60 (dd, J = 8.9, 2.7 Hz, 1H), 7.45-7.34 (m, 3H), 5.49 (d, J = 22.9 Hz, 2H), 4.58 (t, J = 13.1 Hz, 2H), 4.42 (s, 2H), 4.29 (s, 2H), 3.82 (s, 2H), 2.72 (s, 3H), 1.84 (s, 3H) |

TABLE 2-continued

7-CF3-Thienylpyridine and Derivative Compounds

| | Compound | Characterization |
|---|---|---|
| 1380 | 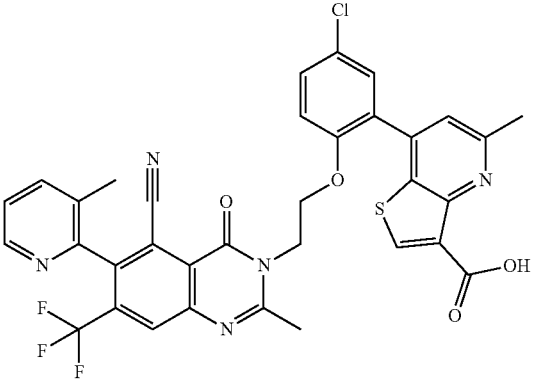 [SMILES: Cc1cc(-c2cc(Cl)ccc2OCCn2c(C)nc3cc(C(F)(F)F)c(-c4ncccc4C)c(C#N)c3c2=O)c2scc(C(=O)O)c2n1] | MS (ESI) m/z 690.1 [M + 1]+; 1H NMR (400 MHz, DMSO-d6) δ 8.60-8.48 (m, 1H), 8.37 (s, 1H), 8.12 (s, 1H), 7.86 (d, J = 7.8 Hz, 1H), 7.60 (dd, J = 8.9, 2.8 Hz, 1H), 7.52-7.42 (m, 3H), 7.36 (d, J = 9.0 Hz, 1H), 4.50-4.34 (m, 2H), 4.27 (d, J = 5.4 Hz, 2H), 2.72 (s, 3H), 2.10 (s, 3H), 1.81 (s, 3H) |
| 1381 | 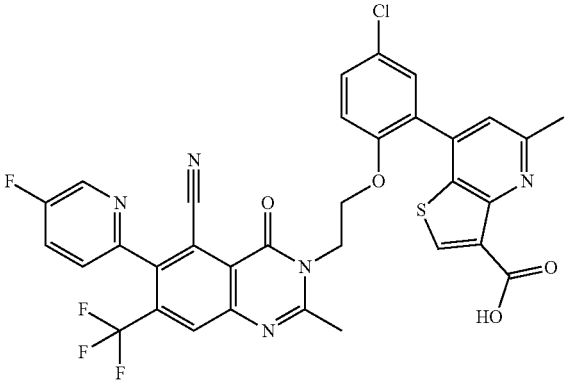 [SMILES: Cc1cc(-c2cc(Cl)ccc2OCCn2c(C)nc3cc(C(F)(F)F)c(-c4ccc(F)cn4)c(C#N)c3c2=O)c2scc(C(=O)O)c2n1] | MS (ESI) m/z 694.0 [M + 1]+; 1H NMR (400 MHz, DMSO-d6) δ 8.87 (s, 1H), 8.76-8.65 (m, 1H), 8.34 (s, 1H), 8.14 (s, 1H), 7.73 (t, J = 5.5 Hz, 1H), 7.60 (dd, J = 8.9, 2.6 Hz, 1H), 7.49-7.40 (m, 2H), 7.37 (d, J = 9.0 Hz, 1H), 4.50-4.18 (m, 4H), 2.72 (s, 3H), 1.87 (s, 3H) |
| 1383 | 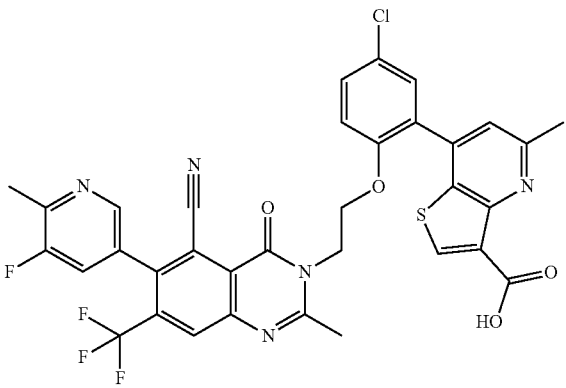 | MS (ESI) m/z 708.2 [M + 1]+; 1H NMR (400 MHz, DMSO-d6) δ 8.42 (s, 1H), 8.28 (s, 1H), 8.05 (s, 1H), 7.98-7.90 (m, 1H), 7.60 (dd, J = 8.9, 2.7 Hz, 1H), 7.47-7.40 (m, 2H), 7.37 (d, J = 9.0 Hz, 1H), 4.42 (t, J = 5.0 Hz, 2H), 4.29 (d, J = 4.9 Hz, 2H), 2.73 (s, 3H), 2.58 (d, J = 2.9 Hz, 3H), 1.88 (s, 3H) |
| 1384 | 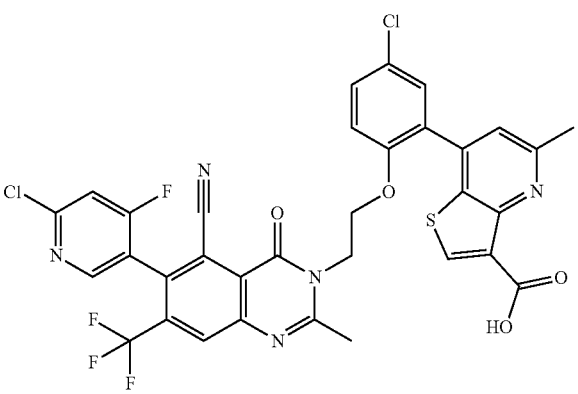 [SMILES: Cc1cc(-c2cc(Cl)ccc2OCCn2c(C)nc3cc(C(F)(F)F)c(-c4cnc(Cl)cc4F)c(C#N)c3c2=O)c2scc(C(=O)O)c2n1] | MS (ESI) m/z 728.0 [M + 1]+; 1H NMR (400 MHz, DMSO-d6) δ 8.72 (d, J = 9.9 Hz, 1H), 8.31 (s, 1H), 8.13 (s, 1H), 8.03 (d, J = 9.1 Hz, 1H), 7.60 (dd, J = 8.9, 2.7 Hz, 1H), 7.45 (s, 1H), 7.43 (d, J = 2.7 Hz, 1H), 7.36 (d, J = 9.0 Hz, 1H), 4.53-4.20 (m, 4H), 2.72 (s, 3H), 1.88 (s, 3H) |

TABLE 2-continued

7-CF3-Thienylpyridine and Derivative Compounds

| Compound | Characterization |
|---|---|
| 1388 | MS (ESI) m/z 708.1 [M + 1]+; 1H NMR (400 MHz, DMSO-d6) δ 8.63-8.59 (m, 1H), 8.33 (s, 1H), 8.11 (s, 1H), 7.60 (dd, J = 8.9, 2.7 Hz, 1H), 7.50 (d, J = 10.7 Hz, 1H), 7.45 (s, 1H), 7.43 (d, J = 2.7 Hz, 1H), 7.36 (d, J = 9.0 Hz, 1H), 4.53-4.02 (m, 4H), 2.72 (s, 3H), 2.62 (s, 3H), 1.85 (s, 3H) |
| 1389 | MS (ESI) m/z 706.2 [M + 1]+; 1H NMR (400 MHz, DMSO-d6) δ 10.03 (s, 1H), 9.47 (s, 1H), 9.18 (s, 1H), 8.23 (s, 1H), 7.60 (dd, J = 8.9, 2.7 Hz, 1H), 7.49 (s, 1H), 7.41 (d, J = 9.0 Hz, 1H), 7.30 (d, J = 2.7 Hz, 1H), 7.19 (s, 1H), 4.53 (t, J = 5.2 Hz, 2H), 4.15 (t, J = 5.2 Hz, 2H), 2.67 (d, J = 0.7 Hz, 3H), 2.33 (s, 3H), 2.29 (s, 3H) |
| 1391 | MS (ESI) m/z 711.0 [M + 1]+; 1H NMR (400 MHz, DMSO-d6) δ 8.13 (s, 1H), 7.93 (s, 1H), 7.58 (dd, J = 8.9, 2.7 Hz, 1H), 7.39-7.31 (m, 2H), 7.28 (s, 1H), 4.40 (s, 2H), 4.26 (s, 2H), 3.87 (s, 5H), 3.57 (d, J = 11.7 Hz, 2H), 3.27 (d, J = 12.9 Hz, 2H), 3.09 (d, J = 10.7 Hz, 2H), 2.91 (d, J = 4.2 Hz, 3H), 2.66 (s, 3H), 1.83 (s, 3H) |
| 1392 | MS (ESI) m/z 740.9 [M + 1]+; 1H NMR (400 MHz, DMSO-d6) δ 9.79 (s, 1H), 7.93 (s, 1H), 7.61 (dd, J = 8.9, 2.7 Hz, 1H), 7.44 (s, 1H), 7.41 (d, J = 2.7 Hz, 1H), 7.37 (d, J = 9.0 Hz, 1H), 5.35 (s, 1H), 4.41 (t, J = 5.0 Hz, 2H), 4.26 (t, J = 5.0 Hz, 2H), 3.97 (t, J = 12.1 Hz, 2H), 3.79 (t, J = 5.2 Hz, 2H), 3.64 (d, J = 11.8 Hz, 2H), 3.15 (dd, J = 29.0, 12.1 Hz, 4H), 2.71 (s, 3H), 2.43 (s, 3H), 1.97 (s, 3H) |

TABLE 2-continued

7-CF3-Thienylpyridine and Derivative Compounds

| Compound | Characterization |
|---|---|
| 1393 | [01858] MS (ESI) m/z 741.0 [M + 1]+; 1H NMR (400 MHz, DMSO-d6) δ 8.59 (s, 2H), 7.93 (s, 1H), 7.60 (dd, J = 8.9, 2.7 Hz, 1H), 7.43 (s, 1H), 7.41 (d, J = 2.7 Hz, 1H), 7.36 (d, J = 9.0 Hz, 1H), 4.42 (t, J = 5.6 Hz, 4H), 4.26 (t, J = 5.0 Hz, 2H), 3.16 (s, 4H), 3.00 (s, 2H), 2.82 (s, 4H), 2.70 (s, 3H), 2.40 (s, 3H), 1.92 (s, 3H) |
| 1394 | MS (ESI) m/z 696.4 [M + 1]+; 1H NMR (400 MHz, DMSO-d6) δ 9.77 (s, 1H), 9.59 (s, 1H), 8.15 (d, J = 5.8 Hz, 1H), 7.94 (d, J = 2.2 Hz, 1H), 7.61 (dd, J = 8.9, 2.7 Hz, 1H), 7.47 (s, 1H), 7.44 (d, J = 2.6 Hz, 1H), 7.37 (d, J = 9.0 Hz, 1H), 4.42 (t, J = 5.0 Hz, 2H), 4.35-4.18 (m, 3H), 4.01 (dt, J = 22.5, 10.9 Hz, 2H), 3.11 (d, J = 8.1 Hz, 1H), 3.01 (q, J = 7.5 Hz, 2H), 2.86 (dd, J = 11.5, 5.1 Hz, 2H), 1.81 (s, 3H), 1.36 (t, J = 7.5 Hz, 3H) |
| 1416 | MS (ESI) m/z 711.0 [M + 1]+; 1H NMR (400 MHz, DMSO-d6) δ 9.75 (s, 1H), 7.93 (s, 1H), 7.61 (dd, J = 8.9, 2.7 Hz, 1H), 7.44 (s, 1H), 7.41 (d, J = 2.7 Hz, 1H), 7.37 (d, J = 9.0 Hz, 1H), 4.40 (t, J = 4.9 Hz, 2H), 4.26 (t, J = 5.0 Hz, 2H), 3.86 (t, J = 12.3 Hz, 2H), 3.56 (d, J = 11.4 Hz, 3H), 3.20 (d, J = 12.6 Hz, 2H), 3.09 (q, J = 11.2 Hz, 2H), 2.95-2.87 (m, 3H), 2.71 (s, 3H), 2.42 (s, 3H), 1.96 (s, 3H) |
| 1417 | MS (ESI) m/z 708.1 [M + 1]+; 1H NMR (400 MHz, DMSO-d6) δ 10.05 (s, 1H), 8.04-7.95 (m, 1H), 7.61 (dd, J = 8.9, 2.7 Hz, 1H), 7.45 (s, 1H), 7.41 (d, J = 2.7 Hz, 1H), 7.37 (d, J = 9.0 Hz, 1H), 6.54 (s, 1H), 5.91 (s, 1H), 4.42 (t, J = 5.1 Hz, 2H), 4.34-4.21 (m, 2H), 4.13 (d, J = 17.4 Hz, 1H), 3.84 (d, J = 16.9 Hz, 1H), 3.70-3.57 (m, 1H), 3.40-3.27 (m, 1H), 3.02-2.89 (m, 3H), 2.71 (s, 3H), 2.64 (s, 1H), 2.41 (s, 3H), 1.98 (s, 3H) |

TABLE 2-continued

7-CF3-Thienylpyridine and Derivative Compounds

| Compound | Characterization |
|---|---|
| 1420 | MS (ESI) m/z 723.2 [M + 1]+; 1H NMR (400 MHz, DMSO-d6) δ 9.37 (s, 1H), 7.78 (s, 1H), 7.60 (dd, J = 8.9, 2.7 Hz, 1H), 7.42-7.40 (m, 2H), 7.36 (d, J = 8.9 Hz, 1H), 4.70 (s, 2H), 4.61 (s, 2H), 4.49-4.39 (m, 2H), 4.38 (t, J = 5.0 Hz, 2H), 4.27-4.17 (m, 4H), 2.82 (d, J = 5.2 Hz, 3H), 2.70 (s, 3H), 1.92 (s, 3H) |
| 1570 | MS (ESI) m/z 715.47 [M + 1]+; 1H-NMR (400 MHz, DMSO-d6) δ 8.77 (d, J = 5.2 Hz, 1H), 8.66 (s, 1H), 7.93 (s, 1H), 7.75 (d, J = 8.4 Hz, 1H), 7.70-7.66 (m, 2H), 7.56 (d, J = 4.4 Hz, 1H), 4.82 (s, 2H), 4.73-4.41 (m, 8H), 3.05 (bs, 1H), 2.11 (s, 3H), 0.77 (bs, 4H) |
| 1612 | MS (ESI) m/z 775.53 [M + 1]+; 1H NMR (400 MHz, DMSO-d6 with D20) δ 8.75 (d, J = 4.68 Hz 1H), 8.10 (d, J = 9.44 Hz, 1H), 8.03 (s, 1H), 7.53 (dd, J = 2.56, 8.92 Hz, 1H), 7.34 (d, J = 2.60 Hz, 1H), 7.31 (d, J = 4.68 Hz, 1H), 7.27 (d, J = 9.0 Hz, 1H), 4.35 (bs, 2H), 4.25-4.20 (m, 6H), 3.55 (bs, 2H), 2.93 (bs, 2H), 2.50 (bs, 2H), 2.20 (s, 5H), 1.58 (s, 3H), 1.27 (t, J = 7.04 Hz, 6H) |
| 1613 | MS (ESI) m/z 719.52 [M + 1]+; 1H NMR (400 MHz, DMSO-d6 with D20) δ 8.60 (d, J = 4.00 Hz 1H), 8.14 (s, 1H), 7.97 (d, J = 8.80 Hz, 1H), 7.49 (dd, J = 2.40, 8.80 Hz, 1H), 7.34 (d, J = 2.00 Hz, 1H), 7.24 (d, J = 9.20 Hz, 1H), 7.13 (d, J = 4.80 Hz, 1H), 4.32 (bs, 2H), 4.21 (bs, 2H), 3.67 (bs, 2H), 3.11 (bs, 4H), 2.76 (bs, 2H), 2.59 (s, 3H), 1.74 (s, 3H) |

TABLE 2-continued

7-CF3-Thienylpyridine and Derivative Compounds

| Compound | Characterization |
|---|---|
| 1614 | MS (ESI) m/z 801.60 [M + 1]+; 1H NMR (400 MHz, DMSO-d6 with D20) δ 8.75 (d, J = 4.80 Hz, 1H), 8.09 (d, J = 9.60 Hz, 1H), 8.03 (s, 1H), 7.53 (dd, J = 2.40, 8.80 Hz, 1H), 7.33-7.30 (m, 2H), 7.26 (d, J = 8.80 Hz, 1H), 4.34 (s, 2H), 4.23-4.19 (m, 6H), 3.50 (bs, 2H), 2.79 (bs, 5H), 1.67 (bs, 2H), 1.58 (s, 3H), 1.27 (t, J = 6.80 Hz, 6H), 0.43 (bs, 2H), 0.35 (bs, 2H) |
| 1615 | MS (ESI) m/z 745.50 [M + 1]+; 1H NMR (400 MHz, DMSO-d6 with D20) δ 8.63 (d, J = 4.80 Hz, 1H), 8.12 (s, 1H), 7.98 (d, J = 8.80 Hz, 1H), 7.49 (dd, J = 2.40, 8.80 Hz, 1H), 7.32 (d, J = 2.40 Hz, 1H), 7.23 (d, J = 9.20 Hz, 1H), 7.14 (d, J = 4.4 Hz, 1H), 4.31 (s, 2H), 4.20 (s, 2H), 3.49 (bs, 3H), 2.84 (bs, 4H), 1.75 (bs, 2H), 1.70 (s, 3H), 0.44 (d, J = 6.00 Hz, 2H), 0.38 (bs, 2H) |
| 1619 | MS (ESI) m/z 642.01[M + 1]+; 1H NMR (400 MHz, DMSO-d6) δ 8.33 (s, 1H), 7.89 (s, 1H), 7.59 (dd, J = 2.60, 8.88 Hz, 1H), 7.43 (s, 1H), 7.42 (d, J = 2.64 Hz, 1H), 7.36 (d, J = 8.96 Hz, 1H), 4.39 (t, J = 4.68 Hz, 2H), 4.23 (t, J = 4.64 Hz, 2H), 2.94 (s, 6H), 2.70 (s, 3H), 1.81 (s, 3H) |
| 1899 | MS (ESI) m/z 571 [M + 1]; 1H NMR (400 MHz, DMSO-d6) δ 8.79 (s, 1H), 8.43 (d, J = 16.6 Hz, 2H), 8.11 (s, 1H), 7.79 (bs, 1H), 7.60 (s, 1H), 7.46 (m, 2H), 7.35 (m, 1H), 4.40 (s, 2H), 4.20 (s, 2H), 3.89 (s, 1H) |

TABLE 2-continued

7-CF3-Thienylpyridine and Derivative Compounds

| Compound | Characterization |
|---|---|
| 1900 | MS (ESI) m/z 599.1 [M + 1] |
| 1901 | MS (ESI) m/z 579.15 [M + 1]+; 1H NMR (400 MHz, DMSO-d6) δ 8.75 (d, J = 4.48 Hz, 1H), 8.59 (s, 1H), 8.41 (s, 1H), 8.14 (s, 1H), 7.76 (d, J = 8.8 Hz, 1H), 7.69 (d, J = 6.04 Hz, 2H), 7.56 (d, J = 4.48 Hz, 1H), 4.88 (s, 2H), 2.10 (s, 3H) |
| 1902 | MS (ESI) m/z 627.8 [M + 1]+ |

TABLE 2-continued

7-CF3-Thienylpyridine and Derivative Compounds

| Compound | Characterization |
|---|---|
| 1903 | MS (ESI) m/z 603.21 [M + 1]+; 1H NMR (400 MHz, DMSO-d6) δ 8.84 (d, J = 4.8 Hz, 1H), 8.38 (bs, 1H), 8.28 (s, 1H), 8.01 (bs, 1H), 7.63 (d, J = 8.4 Hz, 1H), 7.54 (d, J = 11.4 Hz, 1H), 7.49 (d, J = 4.8 Hz, 1H), 4.43 (t, J = 4.4 Hz, 2H), 4.25 (t, J = 4.4 Hz, 2H), 1.73 (s, 3H) |
| 1904 | MS (ESI) m/z 619.07 [M + 1]+; 1H NMR (400 MHz, DMSO-d6) δ 8.86 (d, J = 4.4 Hz, 1H), 8.24 (s, 1H), 8.08 (s, 1H), 7.60 (dd, J = 8.8, 2.6 Hz, 1H), 7.51 (d, J = 4.8 Hz, 1H), 7.43 (d, J = 2.6 Hz, 1H), 7.36 (d, J = 8.8 Hz, 1H), 4.41 (t, J = 4.7 Hz, 2H), 4.25 (t, J = 4.7 Hz, 2H), 1.69 (s, 3H) |
| 1905 | MS (ESI) m/z 633.04 [M + 1]+ |
| 1906 | |

TABLE 2-continued

7-CF3-Thienylpyridine and Derivative Compounds

| Compound | Characterization |
|---|---|
| 1907 | MS (ESI) m/z 656.15 [M + 1] |
| 1908 | MS (ESI) m/z 724.6 [M + 1]+ |
| 1909 | MS (ESI) m/z 708.1 [M + 1]+ |
| 1910 | MS (ESI) m/z 690.3 [M + 1]+ |

TABLE 2-continued

7-CF3-Thienylpyridine and Derivative Compounds

| Compound | Characterization |
|---|---|
| 1911 | MS (ESI) m/z 722.0 [M + 1]+ |
| 1912 | MS (ESI) m/z 773.3 [M + 1]+ |
| 1913 | MS (ESI) m/z 850.3 [M + 1]+ |

TABLE 2-continued
7-CF3-Thienylpyridine and Derivative Compounds
| Compound | Characterization |
|---|---|
| 1914 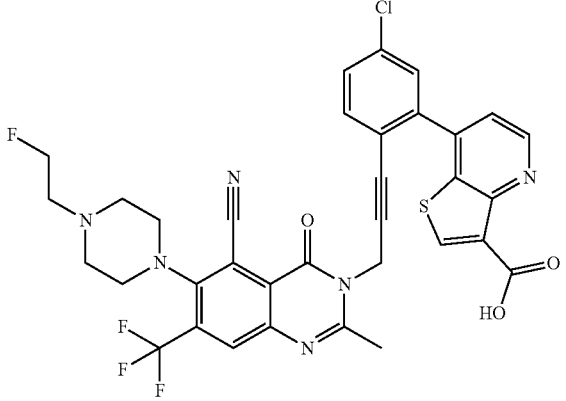 [SMILES: Cc1nc2cc(C(F)(F)F)c(N3CCN(CCF)CC3)c(C#N)c2c(=O)n1CC#Cc1ccc(Cl)cc1-c1ccnc2c(C(=O)O)csc12] | |
| 1915 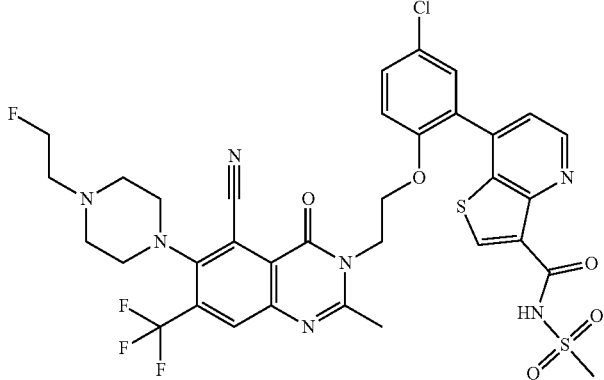 [SMILES: Cc1nc2cc(C(F)(F)F)c(N3CCN(CCF)CC3)c(C#N)c2c(=O)n1CCOc1ccc(Cl)cc1-c1ccnc2c(C(=O)NS(C)(=O)=O)csc12] | |
| 1916 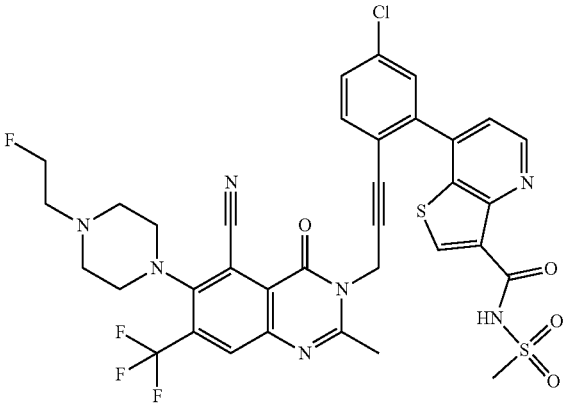 [SMILES: Cc1nc2cc(C(F)(F)F)c(N3CCN(CCF)CC3)c(C#N)c2c(=O)n1CC#Cc1ccc(Cl)cc1-c1ccnc2c(C(=O)NS(C)(=O)=O)csc12] | |

TABLE 2-continued

7-CF3-Thienylpyridine and Derivative Compounds

| Compound | Characterization |
|---|---|

1917

1918

1919

TABLE 2-continued

7-CF3-Thienylpyridine and Derivative Compounds

| Compound | Characterization |
|---|---|

1920

1921

1922

TABLE 2-continued

7-CF3-Thienylpyridine and Derivative Compounds

| Compound | Characterization |
|---|---|

1923

1924

1925

TABLE 2-continued
7-CF3-Thienylpyridine and Derivative Compounds
| Compound | Characterization |
|---|---|
| 1926 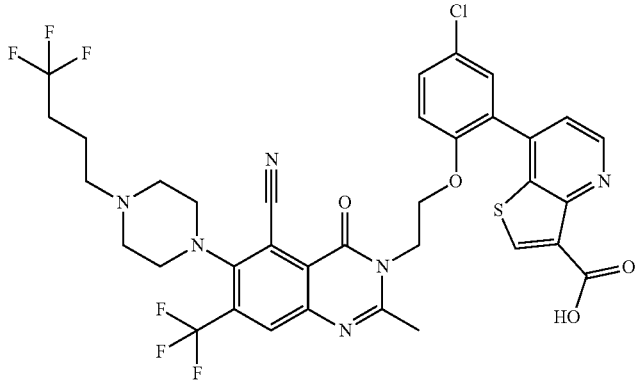 [SMILES: Cc1nc2cc(C(F)(F)F)c(N3CCN(CCCC(F)(F)F)CC3)c(C#N)c2c(=O)n1CCOc1ccc(Cl)cc1-c1ccnc2c(C(=O)O)csc12] | |
| 1927 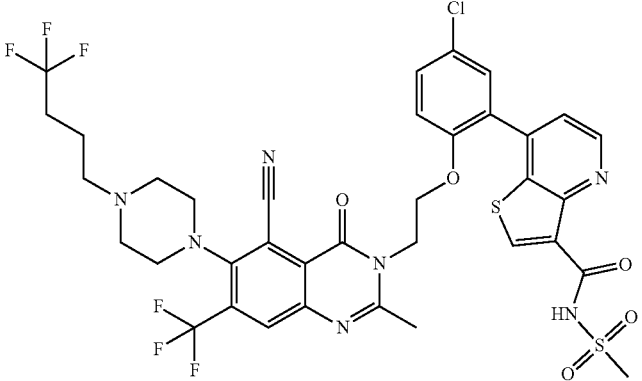 [SMILES: Cc1nc2cc(C(F)(F)F)c(N3CCN(CCCC(F)(F)F)CC3)c(C#N)c2c(=O)n1CCOc1ccc(Cl)cc1-c1ccnc2c(C(=O)NS(C)(=O)=O)csc12] | |
| 1928 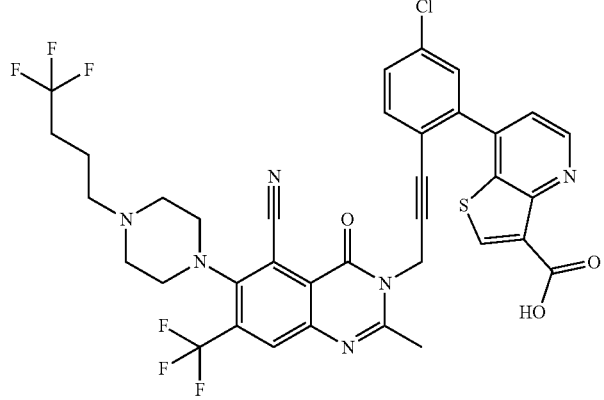 [SMILES: Cc1nc2cc(C(F)(F)F)c(N3CCN(CCCC(F)(F)F)CC3)c(C#N)c2c(=O)n1CC#Cc1ccc(Cl)cc1-c1ccnc2c(C(=O)O)csc12] | |

TABLE 2-continued
7-CF3-Thienylpyridine and Derivative Compounds
| Compound | Characterization |
|---|---|
| 1929 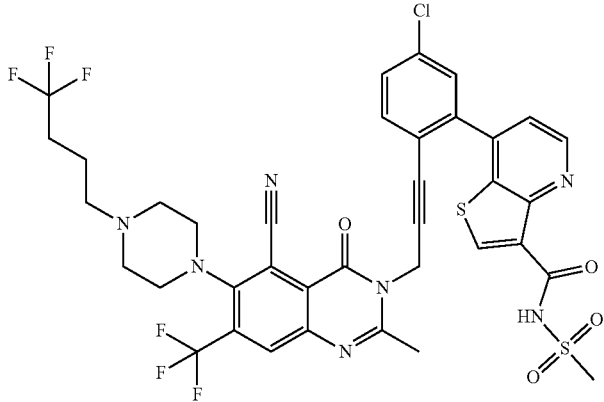 [SMILES: Cc1nc2cc(C(F)(F)F)c(N3CCN(CCCC(F)(F)F)CC3)c(C#N)c2c(=O)n1CC#Cc1ccc(Cl)cc1-c1ccnc2c(C(=O)NS(C)(=O)=O)csc12] | |
| 1930 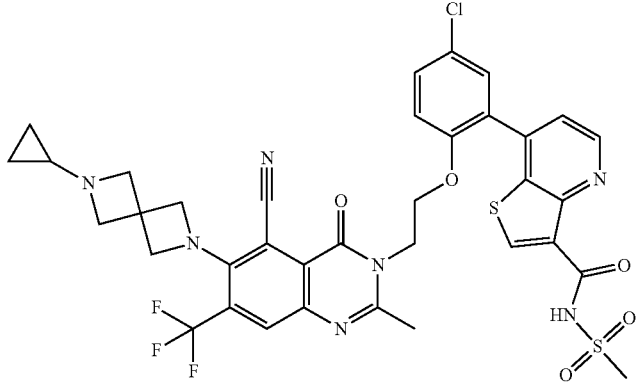 [SMILES: Cc1nc2cc(C(F)(F)F)c(N3CC4(C3)CN(C3CC3)C4)c(C#N)c2c(=O)n1CCOc1ccc(Cl)cc1-c1ccnc2c(C(=O)NS(C)(=O)=O)csc12] | |
| 1931 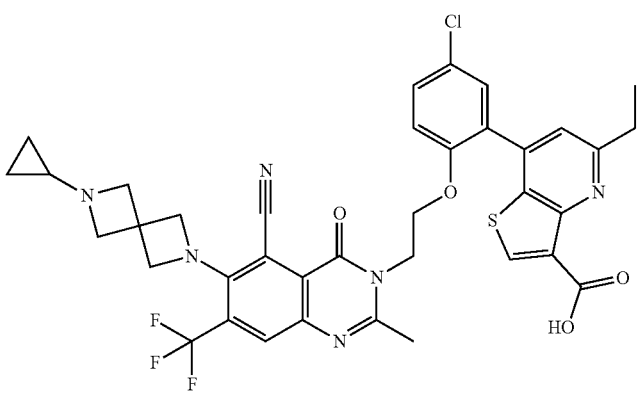 [SMILES: CCc1cc(-c2cc(Cl)ccc2OCCn2c(C)nc3cc(C(F)(F)F)c(N4CC5(C4)CN(C4CC4)C5)c(C#N)c3c2=O)c2scc(C(=O)O)c2n1] | |

TABLE 2-continued

7-CF3-Thienylpyridine and Derivative Compounds

| Compound | Characterization |
|---|---|
| 1932 | |
| 1933 | |
| 1934 | |
| 1994 | |

TABLE 2-continued

7-CF3-Thienylpyridine and Derivative Compounds

| Compound | Characterization |
|---|---|
| 2015 | |
| 2016 | |
| 2018 | |
| 2019 | MS (ESI) m/z 626.05 [M + 1]+ |

TABLE 2-continued

7-CF3-Thienylpyridine and Derivative Compounds

| Compound | Characterization |
|---|---|
| 2028 | MS (ESI) m/z 624.0 [M + 1]+ |
| 2036 | MS (ESI) m/z 747.2 [M + 1]+ |
| 2037 | MS (ESI) m/z 615.1 [M + 1]+ |

Example 3. General Methods for Synthesizing Other Compounds

Compounds in Table 3 can be synthesized using methods described in Example 3. Many of the reactions described in Examples 1 and 2 were also used to synthesize compounds in Table 3.

Example 3A. Methods of Synthesizing the Left-Hand Side

Example 3A.1

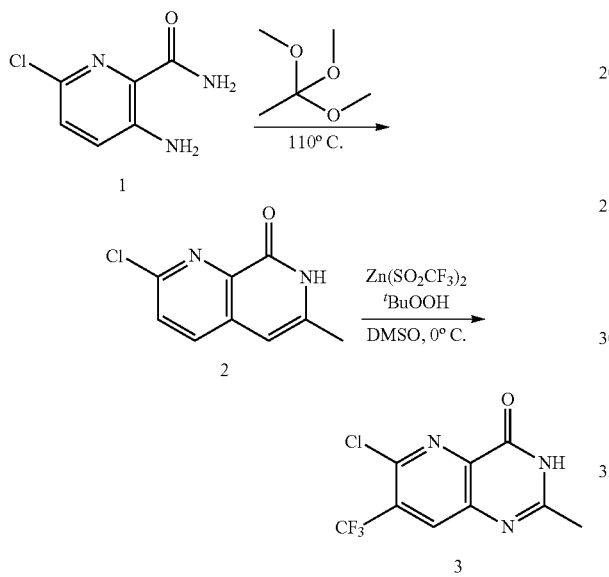

3-amino-6-chloropicolinamide (1, 3.00 g, 16.6 mmol) is dissolved in 1,1,1-triethoxyethane (45 mL, 16.6 mmol) in a flame dried round bottom flask equipped with a stir bar. The reaction mixture heated to 110° C. for 90 min then cooled to 10° C. and diluted with cold ether. The solids are filtered and washed several times with cold ether. Drying the solids in vacuo afforded 6-chloro-2-methylpyrido[3,2-d]pyrimidin-4(3H)-one (2).

6-chloro-2-methylpyrido[3,2-d]pyrimidin-4(3H)-one (2, 1.00 g, 5.1 mmol) is dissolved in DMSO (30 mL) in a round bottomed flask equipped with a stir bar. The reaction mixture is stirred at 10° C. while bis(trifluoromethylsulfonyl)zinc (4.23 g, 12.8 mmol) is added in 1 portion. tert-Butyl hydroperoxide (3.53 mL, 19.2 mmol) is then added dropwise via addition funnel. After 5 min the reaction mixture is warmed to room temperature and after an additional 5 min it is warmed to 50° C. for 6.5 h. The reaction mixture is cooled to room temperature and then the reaction mixture is diluted with saturated sodium bicarbonate and ethyl acetate. The layers are separated and the aqueous phase extracted with ethyl acetate three times. The combined organic material is washed with brine and dried over magnesium sulfate. The solids are filtered and solvent removed in vacuo to afford 6-chloro-2-methyl-7-(trifluoromethyl)pyrido[3,2-d]pyrimidin-4(3H)-one (3).

Example 3A.2

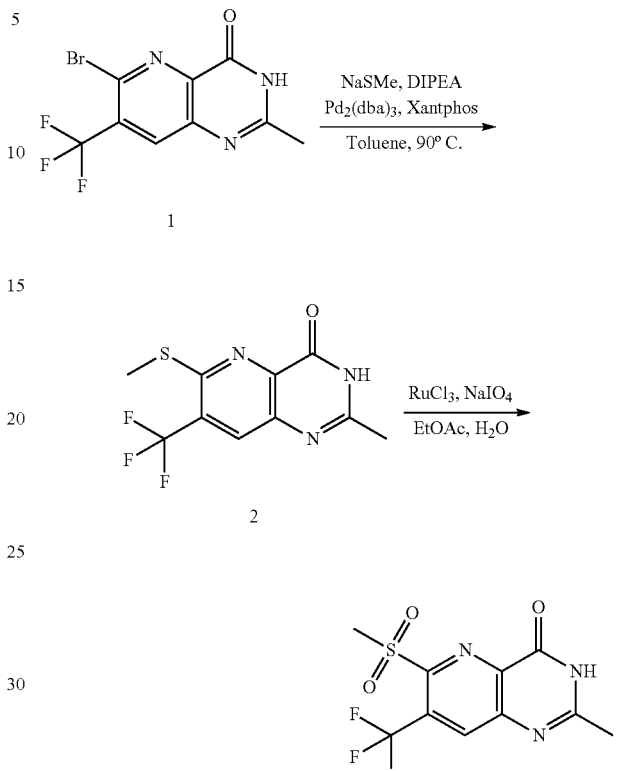

A solution of 6-bromo-2-methyl-7-(trifluoromethyl)pyrido[3,2-d]pyrimidin-4(3H)-one (1, 0.3 g, 0.977 mmol), sodium thiomethoxide (0.102 g, 1.46 mmol), N,N-diisopropylethylamine (0.378 g, 2.93 mmol), and Xantphos (0.056 g, 0.097 mmol) in toluene (3 mL) is degassed for 10 min using argon. Then, tris(dibenzylideneacetone)dipalladium(0) (0.042 g, 0.048 mmol) is added and the mixture is degassed again with argon for 5 min. The reaction mixture is stirred at 90° C. for 2 h. After this time, the reaction mixture is diluted with water and extracted with ethyl acetate. The organic layer is dried over anhydrous sodium sulfate, filtered, and concentrated to dryness under reduced pressure to obtain the crude product. This is purified by flash column chromatography using silica gel (100-200 mesh) and 60-80% ethyl acetate in hexanes as eluent to afford 2-methyl-6-(methylthio)-7-(trifluoromethyl)pyrido[3,2-d]pyrimidin-4(3H)-one (2).

To a solution of 2-methyl-6-(methylthio)-7-(trifluoromethyl)pyrido[3,2-d]pyrimidin-4(3H)-one (2, 0.2 g, 0.727 mmol) in ethyl acetate (4.0 mL) and water (1.0 mL) is added ruthenium(III) chloride (0.007 g, 0.0363 mmol) followed by sodium periodate (0.929 g, 4.36 mmol). The reaction mixture is stirred at room temperature for 30 min. After this time, the reaction mixture is filtered and the filtrate is concentrated under reduced pressure to obtain the crude product. This is purified by pentane wash to afford 2-methyl-6-(methylsulfonyl)-7-(trifluoromethyl)pyrido[3,2-d]pyrimidin-4(3H)-one (3).

Example 3A.3

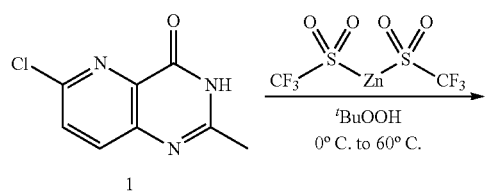

6-chloro-2-methylpyrido[3,2-d]pyrimidin-4(3H)-one (1, 1.00 g, 5.1 mmol) is dissolved in dimethyl sulfoxide (30 mL) in a round bottomed flask equipped with a stir bar. The reaction mixture is stirred at 10° C. while bis(trifluoromethylsulfonyl)zinc (4.23 g, 12.8 mmol) is added in 1 portion. tert-Butyl hydroperoxide (3.53 mL, 19.2 mmol) is then added dropwise via addition funnel. After 5 min the reaction mixture is warmed to room temperature and after an additional 5 min it is warmed to 50° C. for 6.5 h. The reaction mixture is cooled to room temperature and then diluted with saturated aqueous sodium bicarbonate and ethyl acetate. The layers are separated and the aqueous phase extracted with ethyl acetate three times. The combined organic material is washed with brine and dried over magnesium sulfate. The solids are filtered and solvent removed in vacuo to afford a mixture of 6-chloro-2-methyl-8-(trifluoromethyl)pyrido[3,2-d]pyrimidin-4(3H)-one (2).

Example 3A.4

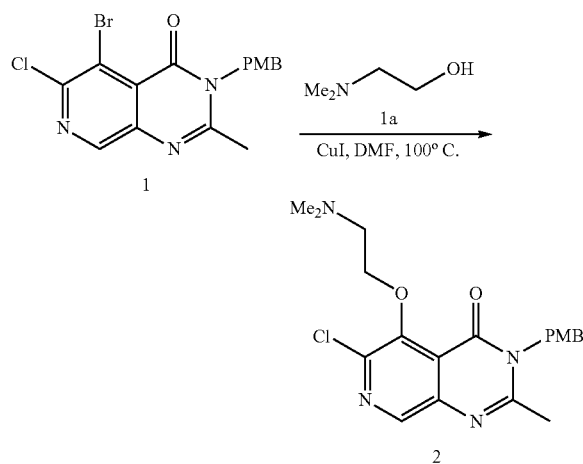

5-bromo-6-chloro-3-(4-methoxybenzyl)-2-methylpyrido[3,4-d]pyrimidin-4(3H)-one (1, 50 mg, 0.13 mmol) and copper(I) iodide (26.5 mg, 0.139 mmol) are combined in a sealable vessel with a stirbar and suspended in 1 mL 2-(dimethylamino)ethan-1-ol (1a). The resulting mixture is sparged with argon for 3 min and then sealed, vigorously stirred, and heated at 100° C. After 10 min LCMS shows complete consumption of the starting material. The mixture is cooled to room temperature and concentrated. The residue is taken up in MeCN/DMSO and purified by prep-HPLC (MeCN/water+0.1% TFA) to afford 6-chloro-5-(2-(dimethylamino)ethoxy)-3-(4-methoxybenzyl)-2-methylpyrido[3,4-d]pyrimidin-4(3H)-one (2).

Example 3A.5

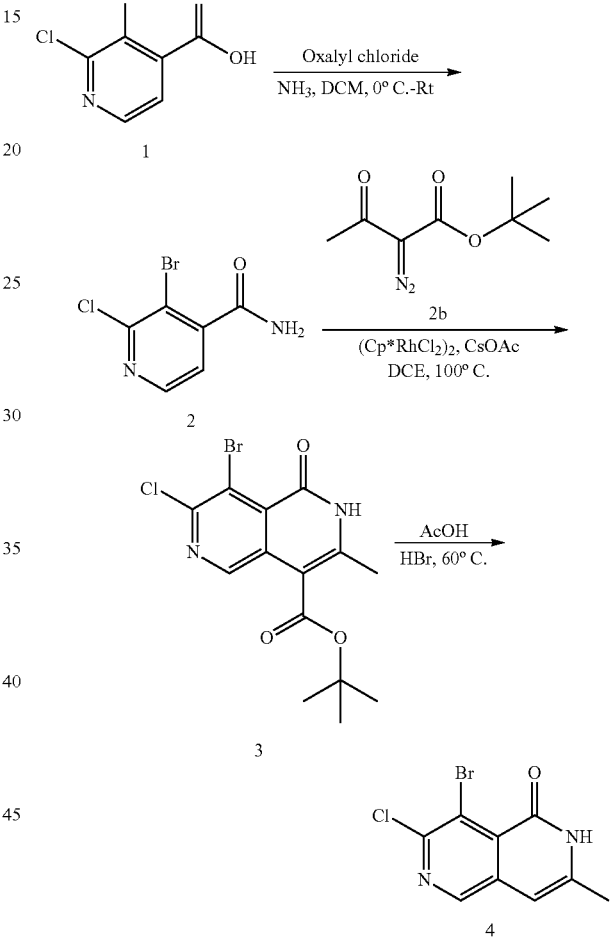

To a solution of 3-bromo-2-chloroisonicotinic acid (1, 3.0 g, 12.76 mmol) in dichloromethane (20 mL) is added N,N-dimethylformamide (0.09 mL, 1.27 mmol) at 0° C. followed by oxalyl chloride (1.7 mL, 19.14 mmol). Then the reaction mixture is stirred at −25° C. for 2 h. After completion, the reaction mixture is evaporated to dryness under reduced pressure. Crude reaction mixture is diluted with dichloromethane (10 mL) and poured into ice cold aqueous ammonia in a drop wise manner. Precipitated solid is filtered through sintered funnel and dried under vacuum to afford 3-bromo-2-chloroisonicotinamide (2).

To a solution of 3-bromo-2-chloroisonicotinamide (2, 2.5 g, 10.68 mmol), pentamethylcyclopentadienylrhodium(III) chloride dimer (0.33 g, 0.53 mmol) and cesium acetate (1.02 g, 5.34 mmol) in 1,2-dichloroethane (25 mL) is added tert-butyl 2-diazo-3-oxobutanoate (2b, 2.96 g, 16.00 mmol)

to the reaction mixture at room temperature under nitrogen atmosphere. Reaction mixture is heated to 100° C. for 16 h. After completion, the reaction mixture is cooled to room temperature, concentrated to dryness under reduced pressure followed by washing with ether and pentane to afford tert-butyl 8-bromo-7-chloro-3-methyl-1-oxo-1,2-dihydro-2,6-naphthyridine-4-carboxylate (3).

To tert-butyl 8-bromo-7-chloro-3-methyl-1-oxo-1,2-dihydro-2,6-naphthyridine-4-carboxylate (3, 3.0 g, 8.00 mmol) 30% hydrobromic acid in acetic acid (30 mL) is added and the reaction mixture is stirred at 80° C. for 16 h. After completion, the reaction is quenched with ice cold water and extracted with ethyl acetate. The organic layer is washed with cold water, dried over anhydrous sodium sulfate, filtered and concentrated to dryness under reduced pressure to afford crude 8-bromo-7-chloro-3-methyl-2,6-naphthyridin-1(2H)-one (4).

Example 3A.6

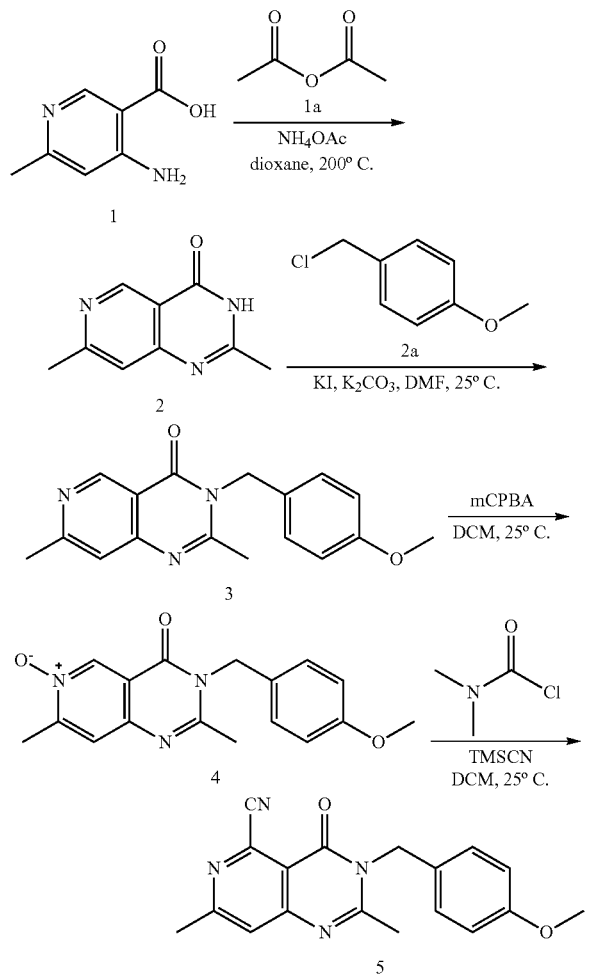

4-Amino-6-methylnicotinic acid (1, 700 mg, 4.6 mmol) and ammonium acetate (1.58 g, 20.6 mmol) are dissolved in 1,4-dioxane (8 mL) and acetic anhydride (1a, 1.74 mL, 18.4 mmol) in an oven-dried microwave vial equipped with a stir bar. The reaction mixture is stirred at 200° C. in a microwave reactor for 24 h. Solvent is removed in vacuo. Ethyl acetate is added and the precipitate is filtered and washed once with ethyl acetate. Solids are dried under vacuum to afford 2,7-dimethylpyrido[4,3-d]pyrimidin-4(3H)-one (2).

2,7-Dimethylpyrido[4,3-d]pyrimidin-4(3H)-one (2, 92 mg, 0.50 mmol) and 1-(chloromethyl)-4-methoxybenzene (2a, 0.08 mL, 0.60 mmol) are dissolved in N,N dimethylformamide (2.5 mL) in an oven-dried screw capped vial equipped with a stir bar. The reaction mixture is stirred at room temperature while potassium carbonate (137.9 mg, 1 mmol) and potassium iodide (16.5 mg, 0.10 mmol) are added sequentially. After 20 h the reaction mixture is diluted with ethyl acetate and then washed with a 50:50 water:brine solution and then twice more with 100% brine. The organic material is then dried over magnesium sulfate, filtered and solvent removed in vacuo. Purification via silica gel chromatography (25-100% ethyl acetate in hexanes) afforded the 3-(4-methoxybenzyl)-2,7-dimethylpyrido[4,3-d]pyrimidin-4(3H)-one (3).

3-(4-Methoxybenzyl)-2,7-dimethylpyrido[4,3-d]pyrimidin-4(3H)-one (3, 109 mg, 0.37 mmol) is dissolved in dichloromethane (2 mL) in an oven-dried screw capped vial equipped with a stir bar. The reaction mixture is stirred at 0° C. while is 3-chlorobenzenecarboperoxoic acid (84 mg, 0.49 mmol) added slowly. After 5 min the reaction mixture is warmed to room temperature. After 3 h the reaction mixture is diluted with saturated aqueous sodium bicarbonate and dichloromethane. The layers are separated and the aqueous phase extracted with dichloromethane once. The combined organic material is washed with brine and dried over magnesium sulfate. The solids are filtered and solvent removed in vacuo to afford 3-(4-methoxybenzyl)-2,7-dimethyl-4-oxo-3,4-dihydropyrido[4,3-d]pyrimidine 6-oxide (4).

3-(4-Methoxybenzyl)-2,7-dimethyl-4-oxo-3,4-dihydropyrido[4,3-d]pyrimidine 6-oxide (4, 25 mg, 0.06 mmol) is dissolved in dichloromethane (1 mL) in an oven-dried screw capped vial equipped with a stir bar. The reaction mixture is stirred at 25° C. and then trimethylsilyl cyanide (0.04 mL, 0.32 mmol) and N,N-dimethylcarbamoyl chloride (0.03 mL, 0.32 mmol) are added sequentially. After 45 min the reaction mixture is warmed to 45° C. After 14 h the reaction mixture is cooled to room temperature and solvent is removed in vacuo. Purification via silica gel chromatography (25-80% ethyl acetate in dichloromethane) afforded 3-(4-methoxybenzyl)-2,7-dimethyl-4-oxo-3,4-dihydropyrido[4,3-d]pyrimidine-5-carbonitrile (5).

Example 3A.7

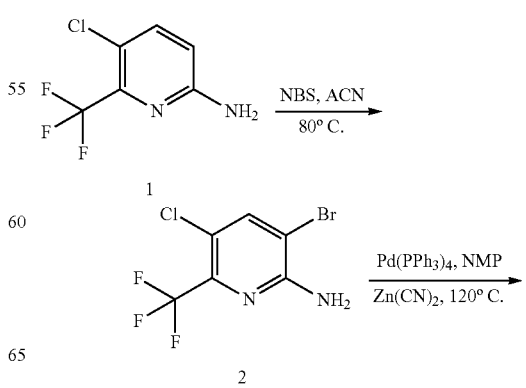

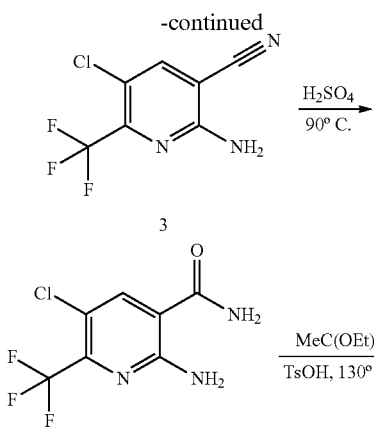

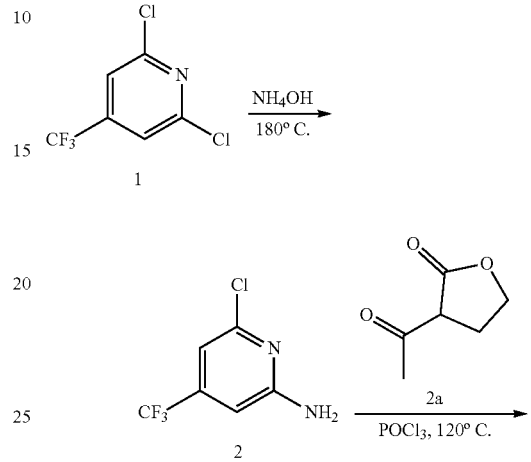

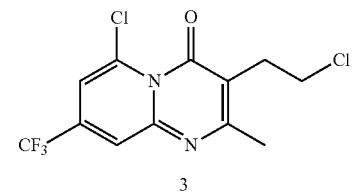

A solution of 5-chloro-6-(trifluoromethyl)pyridin-2-amine (1, 100 mg, 0.51 mmol) and N-Bromosuccinimide (91 mg, 0.51 mmol) in MeCN (4 mL) heated at 80° C. for 1 hr. After this time, the reaction mixture is concentrated, diluted with water and extracted with ethyl acetate. The combined organic layer is washed with water and brine solution, dried over sodium sulfate and concentrated. The crude material then directly loaded on an Isco loading column. Purified by column chromatography using 5 to 40% ethyl acetate in hexane as eluent and product eluted around 20% ethylacetate/hexane. The desired fractions are concentrated under reduced pressure to afford 3-bromo-5-chloro-6-(trifluoromethyl)pyridin-2-amine (2).

A solution of 3-bromo-5-chloro-6-(trifluoromethyl)pyridin-2-amine (2, 50 mg, 0.18 mmol) and dicyanozinc (24 mg, 0.19 mmol) in NMP (3 mL) is purged with argon-gas for 5-min, then Pd(PPh3)4 (21 mg, 0.018 mmol) is added. The mixture is heated at 120° C. for 30 min in microwave. After completion, the reaction mixture is directly loaded on the silica column. Purified by column chromatography using 0 to 20% methanol in dichloromethane as eluent and product eluted around 10% methanol/dicholomethane. The desired fractions are concentrated under reduced pressure to afford 2-amino-5-chloro-6-(trifluoromethyl)nicotinonitrile (3).

2-amino-5-chloro-6-(trifluoromethyl)nicotinonitrile (3, 550 mg, 2.5 mmol) is dissolved in concentrated sulfuric acid (1 mL) in a round bottom flask, and the mixture is stirred at 90° C. for 15 min. After this time, the reaction stopped and the mixture is cooled to room temperature. The reaction mixture is poured into ice-water and adjusted to pH 8 with saturated sodium hydrogen carbonate solution. The precipitate is collected by filtration and washed with cold water and dried in high vacuum to afford 2-amino-5-chloro-6-(trifluoromethyl)nicotinamide (4).

A solution of 2-amino-5-chloro-6-(trifluoromethyl)nicotinamide (4, 65 mg, 0.27 mmol), 1,1,1-triethoxyethane (0.13 mL, 1.09 mmol) and ethanol (2 mL) in a vial is heated to 120° C. in oil bath for 3 h. After this time, the reaction mixture is diluted with 50% DMSO/MeOH, filtered and the crude is purified by HPLC (C18, prep column, 5-35% MeCN/water+0.1% TFA) to afford 6-chloro-2-methyl-7-(trifluoromethyl)pyrido[2,3-d]pyrimidin-4(3H)-one (5).

Example 3A.8

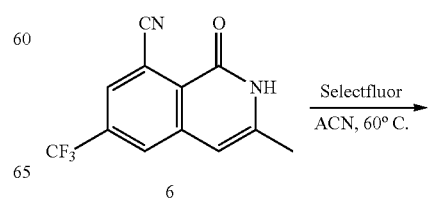

A solution of 2,6-dichloro-4-(trifluoromethyl)pyridine (1, 10.0 g, 4.6 mmol), ammonium hydroxide (50 mL) is heated at 180° C. for 4 h. After completion, the reaction mixture is filtered, washed with water & dried to afford 6-chloro-4-(trifluoromethyl)pyridin-2-amine (2).

To a mixture of 6-chloro-4-(trifluoromethyl)pyridin-2-amine (2, 2.2 g, 1.0 mmol) in phosphorous oxychloride (5 mL), 3-acetyldihydrofuran-2(3H)-one (2a, 0.256 g, 2.0 mmol) is added at room temperature followed by heating and stirring at 20° C. for 1.5 h. After completion, the reaction mixture is poured into crushed ice & extracted with ethyl acetate. Organic layer is dried over anhydrous sodium sulfate and concentrated to dryness under reduced pressure to afford 6-chloro-3-(2-chloroethyl)-2-methyl-8-(trifluoromethyl)-4H-pyrido[1,2-a]pyrimidin-4-one (3).

Example 3A.9

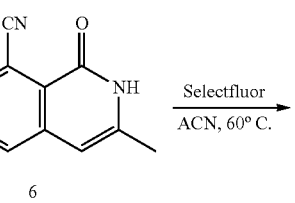

-continued

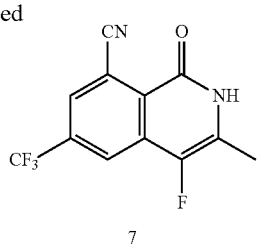

7

To a solution of 3-methyl-1-oxo-6-(trifluoromethyl)-1,2-dihydroisoquinoline-8-carbonitrile (6, 0.2 g, 0.793 mmol) in acetonitrile (2 mL), 1-chloromethyl-4-fluoro-1,4-diazoniabicyclo[2.2.2]octane bis(tetrafluoroborate) or selectfluor (0.42 g, 1.190 mmol) and catalytic amount of acetic acid are added and the reaction mixture is stirred at 60° C. for 8 h. After completion, the reaction mixture is quenched with water and extracted with ethyl acetate. The organic layer is washed with brine solution, dried over anhydrous sodium sulphate, filtered and concentrated under reduced pressure. The crude is purified by column chromatography using silica gel (100-200 mesh) and 0-40% ethyl acetate in hexane as eluent. The desired fractions are concentrated under reduced pressure to afford 4-fluoro-3-methyl-1-oxo-6-(trifluoromethyl)-1,2-dihydroisoquinoline-8-carbonitrile (7).

Example 3A.10

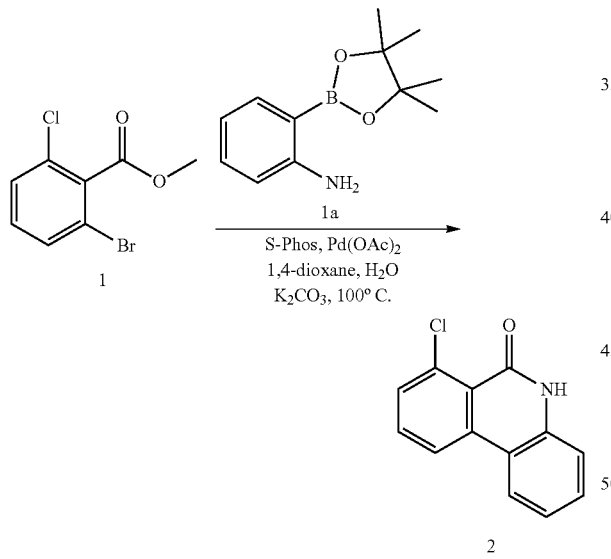

A bottle of 1,4-dioxane is sparged with argon gas for 10 min. Methyl 2-bromo-6-chlorobenzoate (1, 257.7 mg, 1.0 mmol), SPhos (37.0 mg, 0.09 mmol), palladium(II) acetate (6.7 mg, 0.03 mmol), potassium carbonate (276.9 mg, 2.0 mmol) and 2-(4,4,5,5-tetramethyl-1,3,2-dioxaborolan-2-yl)aniline (1a, 257.7 mg, 1.0 mmol) are dissolved in 1,4-dioxane (2 mL) and water (0.20 mL) in an oven-dried screw cap vial equipped with a stir bar. The vial is sealed and the reaction mixture sparged with argon gas for 5 min. The reaction mixture is stirred vigorously at 100° C. for 13 h. The reaction mixture is then cooled to room temperature and diluted with water (20 mL). The solids are filtered to afford a thick yellow semisolid that is taken up in dichloromethane (20 mL) and filtered again. The white solids that remained are collected and dried, affording 7-chlorophenanthridin-6(5H)-one (2).

Example 3A.11

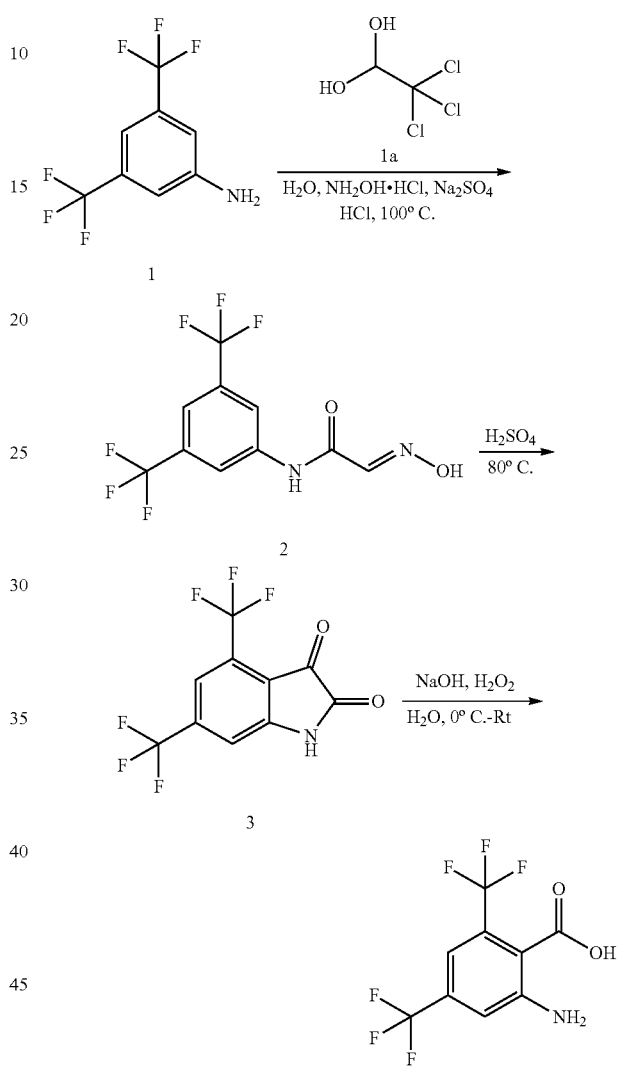

To a stirred solution of 3,5-bis(trifluoromethyl)aniline (1, 10 g, 43.64 mmol) and 402f (1a, 8.66 g, 52.37 mmol) in water (90 mL) is added hydroxyl amine hydrochloride (10.91 g, 157.11 mmol), followed by sodium sulphate (13.63 g, 96.01 mmol) at room temperature and the mixture is stirred at same temperature for 10 min. Concentrated hydrochloric acid (10.0 mL) is added slowly. The reaction mixture is heated to reflux for 16 h and allowed to cool to room temperature. The solid precipitate formed is filtered and washed with diethyl ether and dried under vacuum to afford (E)-N-(3,5-bis(trifluoromethyl)phenyl)-2-(hydroxyimino)acetamide (2).

A solution of (E)-N-(3,5-bis(trifluoromethyl)phenyl)-2-(hydroxyimino)acetamide (2, 8.0 g, 26.65 mmol) in concentrated sulfuric acid (60.0 mL) is heated to 85° C. and stirred for 4 h. After completion, the reaction is quenched with ice cold water. Solid is obtained, filtered, washed with water and dry under vacuum to afford 4, 6-bis (trifluoromethyl) indoline-2, 3-dione (3).

To a stirred solution of 4, 6-bis (trifluoromethyl) indoline-2, 3-dione (3, 6.5 g, 22.96 mmol) in 1 N sodium hydroxide solution (120.0 mL) is added hydrogen peroxide solution (30% in water, 9.10 mL, 80.36 mmol) drop wise at 0° C. The reaction is allowed to warm up to room temperature and stirred for 4 h. After completion, the reaction mixture is quenched with 1 N hydrochloric acid and extracted with ethyl acetate. The organic layer is washed with brine, dried over anhydrous sodium sulfate, filtered and concentrated to dryness under reduced pressure to afford 2-amino-4,6-bis (trifluoromethyl)benzoic acid (4).

Example 3A.12

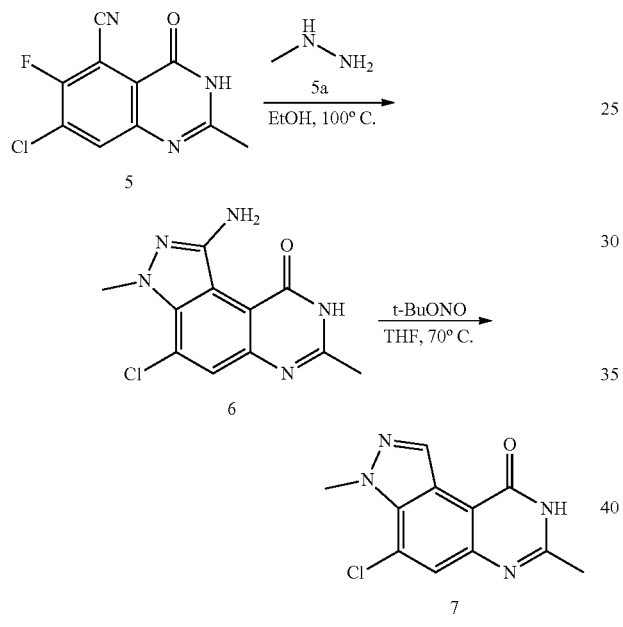

To a solution of 7-chloro-6-fluoro-2-methyl-4-oxo-3,4-dihydroquinazoline-5-carbonitrile (5, 0.280 g, 1.17 mmol) in ethanol (3 mL), methylhydrazine (7, 0.33 mL, 5.85 mmol) is added. This mixture is heated at 100° C. for 16 h. The reaction mixture is cooled and the resulting precipitate is collected by filtration and dried to afford 1-amino-4-chloro-3,7-dimethyl-3,8-dihydro-9H-pyrazolo[4,3-f]quinazolin-9-one (6).

To a solution of 1-amino-4-chloro-3,7-dimethyl-3,8-dihydro-9H-pyrazolo[4,3-f]quinazolin-9-one (6, 0.100 g, 0.37 mmol) in tetrahydrofuran (2 mL), tert-butyl nitrite (0.14 mL, 1.1 mmol) is added. This mixture is heated at 70° C. for 16 h. The reaction mixture is cooled, diluted with water, and extracted with 10% methanol in dichloromethane. The organic layer is dried over anhydrous sodium sulfate, filtered, and concentrated. The crude product is purified by silica gel (100-200 mesh) column chromatography using 0-70% ethyl acetate in hexanes as eluent to afford 4-chloro-3,7-dimethyl-3,8-dihydro-9H-pyrazolo[4,3-f]quinazolin-9-one (7).

Example 3A.13

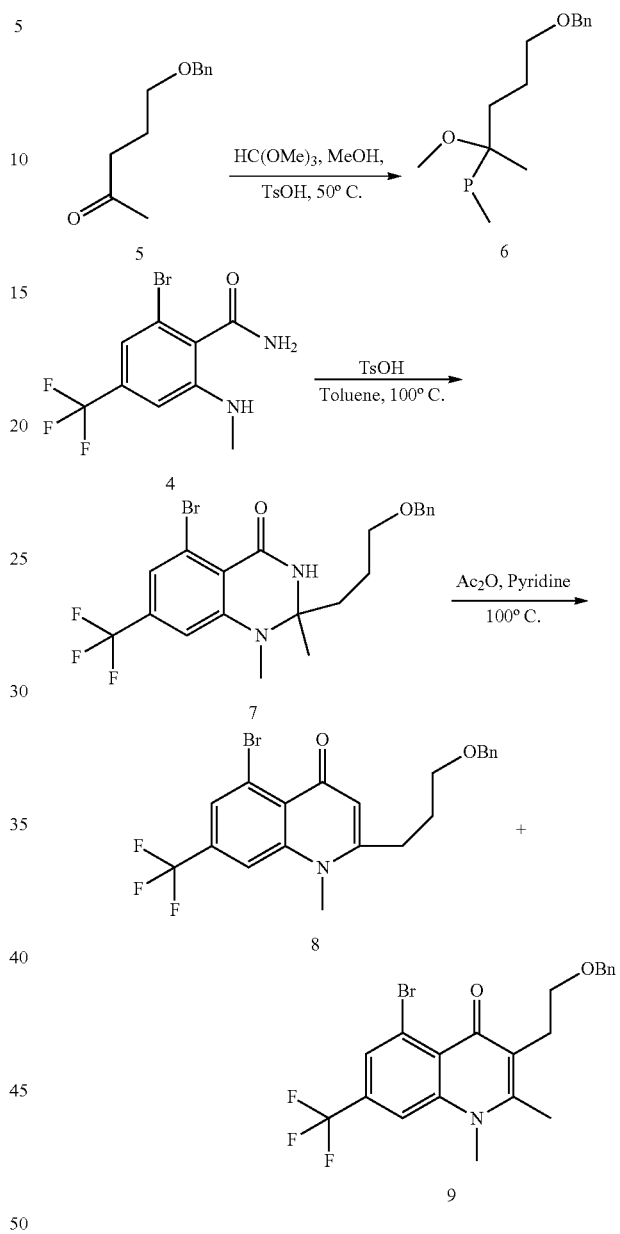

p-Toluenesulfonic acid monohydrate (74.7 mg, 0.39 mmol) is added to a stirred solution of 5-benzyloxypentan-2-one (5, 3.02 g, 15.7 mmol) in methanol (15 mL) and trimethyl orthoformate (3.44 mL, 31.4 mmol) at room temperature under a reflux condenser under argon. The resulting reaction mixture is heated at 50° C. under a reflux condenser under argon for 1.5 h. After cooling to room temperature, sodium methoxide (25 wt. % in methanol) (0.18 mL, 0.78 mmol) is added and then most of the solvent is removed on a rotary evaporator. The residue is partitioned between ethyl acetate and brine with a little 0.1 N NaOH in it. The organics are washed with brine, dried over magnesium sulfate, filtered, concentrated on a rotary evaporator, and dried under high vacuum to afford crude (((4,4-dimethoxypentyl)oxy)methyl)benzene (6).

2-Bromo-6-(methylamino)-4-(trifluoromethyl)benzamide (4, 1.11 g, 3.7 mmol), (((4,4-dimethoxypentyl)oxy)methyl)

benzene (6, 1.33 g, 5.6 mmol), p-toluenesulfonic acid monohydrate (35.5 mg, 0.19 mmol) and toluene (20 mL) are combined in a 100 mL round bottom flask with a stirbar, stirred vigorously, and heated at 100° C. under argon for 40 min. Most of the volatiles are removed on a rotary evaporator. The residue is purified via silica gel chromatography (10-80% ethyl acetate in hexanes) to afford 2-(3-(benzyloxy)propyl)-5-bromo-1,2-dimethyl-7-(trifluoromethyl)-2,3-dihydroquinazolin-4(1H)-one (7).

2-(3-(benzyloxy)propyl)-5-bromo-1,2-dimethyl-7-(trifluoromethyl)-2,3-dihydroquinazolin-4(1H)-one (7, 1.64 g, 3.48 mmol), acetic anhydride (11.1 mL, 118 mmol), and pyridine (1.12 mL, 13.9 mmol) are combined in a sealable vessel with a stirbar, sealed, stirred, and heated at 110° C. with a block heater for 16 h. Most of the volatiles are removed on a rotary evaporator. The residue is taken up in ethyl acetate and purified via silica gel chromatography (30-90% ethyl acetate in hexanes) to afford 2-(3-(benzyloxy)propyl)-5-bromo-1-methyl-7-(trifluoromethyl)quinolin-4(1H)-one (8) and 3-(2-(benzyloxy)ethyl)-5-bromo-1,2-dimethyl-7-(trifluoromethyl)quinolin-4(1H)-one (9).

Example 3A.14

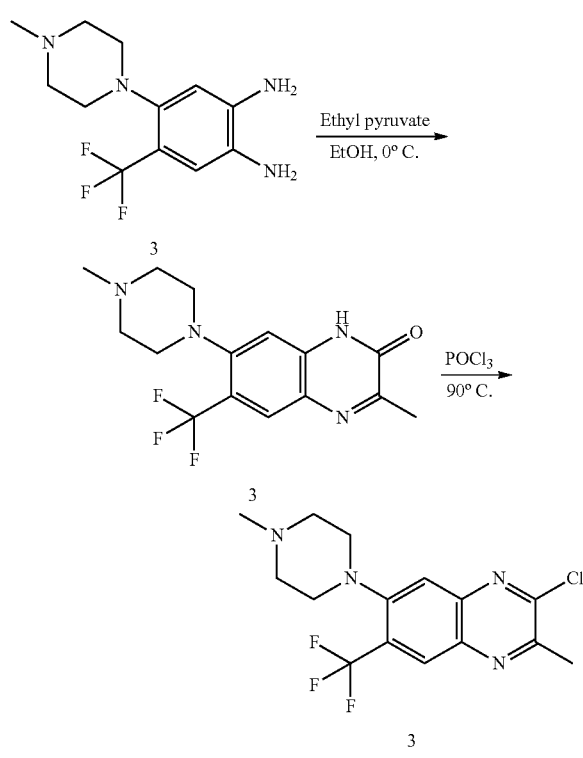

To a solution of 4-(4-methylpiperazin-1-yl)-5-(trifluoromethyl)benzene-1,2-diamine (3, 12.0 g, 43.7 mmol) in ethanol (120 mL) at 0° C. is added ethyl pyruvate (10.0 g, 87.5 mmol) and the reaction mixture is stirred for 3 h at room temperature. After completion, the reaction mixture is cooled to 0° C., filtered and washed with diethyl ether which is dried under reduced pressure to afford 3-methyl-7-(4-methylpiperazin-1-yl)-6-(trifluoromethyl)quinoxalin-2(1H)-one (4).

To a solution of 3-methyl-7-(4-methylpiperazin-1-yl)-6-(trifluoromethyl)quinoxalin-2(1H)-one (4, 4.3 g, 13.1 mmol) is added phosphoryl chloride (43 mL) at room temperature. Then the reaction mixture is stirred for 6 h at 90° C. After completion, the reaction mixture is quenched with icec-cold water, adjusted the pH 8 with 1 N aqueous hydrochloric acid solution and extracted with ethyl acetate, dried over anhydrous sodium sulfate, filtered and concentrated under reduced pressure to get the crude mass. The crude compound is purified by Combi flash (12 g, Redi Sep column) using 4% methanol in dichloromethane as eluent. The desired fractions are concentrated under reduced pressure to afford 2-chloro-3-methyl-7-(4-methylpiperazin-1-yl)-6-(trifluoromethyl)quinoxaline (5).

Example 3A.15

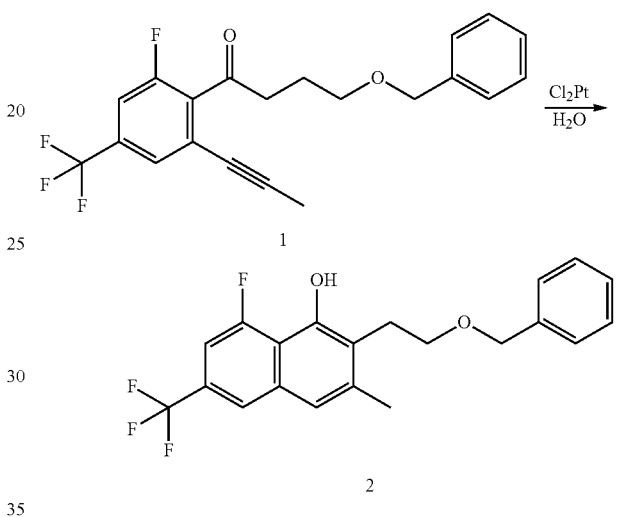

To 4-benzyloxy-1-[2-fluoro-6-prop-1-ynyl-4-(trifluoromethyl)phenyl]butan-1-one (1, 50 mg, 0.13200 mmol) in 1,4-Dioxane (1 mL) and water (0.01 mL, 0.79000 mmol) is added dichloroplatinum (3.52 mg, 0.01320 mmol) and CO (29.6 mg, 1.06 mmol) is bubbled through the reaction mixture for 5 mins. The mixture is stirred at 25° C. for 30 min followed by heating to 100 for 12 hr to afford 2-(2-(benzyloxy)ethyl)-8-fluoro-3-methyl-6-(trifluoromethyl)naphthalen-1-ol (2) after workup.

Example 3A.16

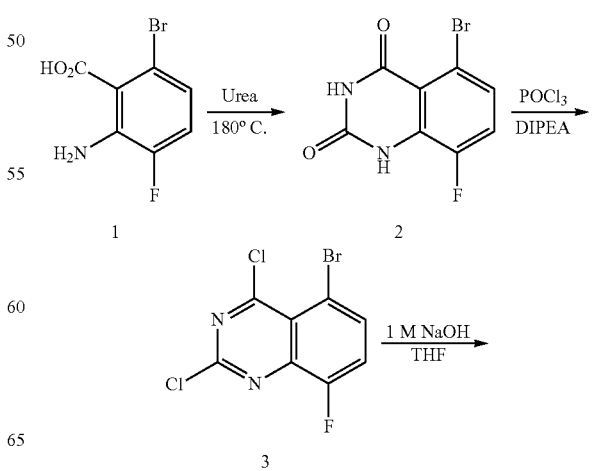

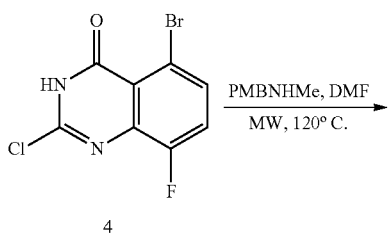

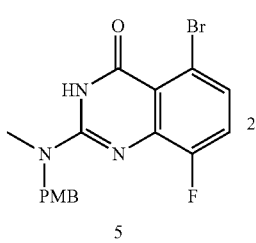

A mixture of 2-amino-6-bromo-3-fluorobenzoic acid (2.00 g, 8.55 mmol) and urea (4.00 g, 66.60 mmol) is heated at 180° C. for 3 h, then cooled to 80° C. Water (7-10 mL) is added. The reaction is stirred at reflux for 10 m. The resulting mixture is cooled to room temperature and filtered. The dark brown solid is washed with water and ethyl ether, and dried under vacuum to afford 5-bromo-8-fluoroquinazoline-2,4(1H,3H)-dione (2).

To a solution of 5-bromo-8-fluoroquinazoline-2,4(1H,3H)-dione (2, 445 mg, 1.72 mmol) in phosphorus oxychloride (6.2 mL) is added N,N-diisopropylethylamine (1.20 mL, 6.89 mmol) dropwise. The reaction is stirred at 120° C. overnight. The resulting mixture is cooled to room temperature and azeptroped with toluene. The crude is diluted with ethyl acetate and washed with water. The combined organics are dried over sodium sulfate, decanted and concentrated. The crude is purified via column chromatography (silica, ethyl acetate/hexanes=0-10%) to afford 5-bromo-2,4-dichloro-8-fluoroquinazoline (3).

To a solution of 5-bromo-2,4-dichloro-8-fluoroquinazoline (3, 395 mg, 1.33 mmol) in tetrahydrofuran (2 mL) is added 1 M sodium hydroxide solution (6.70 mL, 6.70 mmol). The reaction is stirred at room temperature for 1 h 45 min. The resulting mixture is acidified to ~pH 4 with acetic acid. The precipitate is filtered, washed with ethyl ether and dried under vacuum to afford 5-bromo-2-chloro-8-fluoroquinazolin-4(3H)-one (4).

To a solution of 5-bromo-2-chloro-8-fluoroquinazolin-4(3H)-one (4, 100 mg, 0.36 mmol) in N,N-dimethylformamide (2 mL) is added 1-(4-methoxyphenyl)-N-methylmethanamine (68 uL, 0.45 mmol). The reaction is microwaved at 120° C. for 10 m. The resulting mixture is cooled to room temperature and sit for 90 min. The precipitate is filtered and washed with ethyl ether. The filtrate is concentrated and triturated with ethyl acetate. The combined solids are dried under vacuum to afford 5-bromo-8-fluoro-2-((4-methoxybenzyl)(methyl)amino)quinazolin-4(3H)-one (5).

Example 3A.17

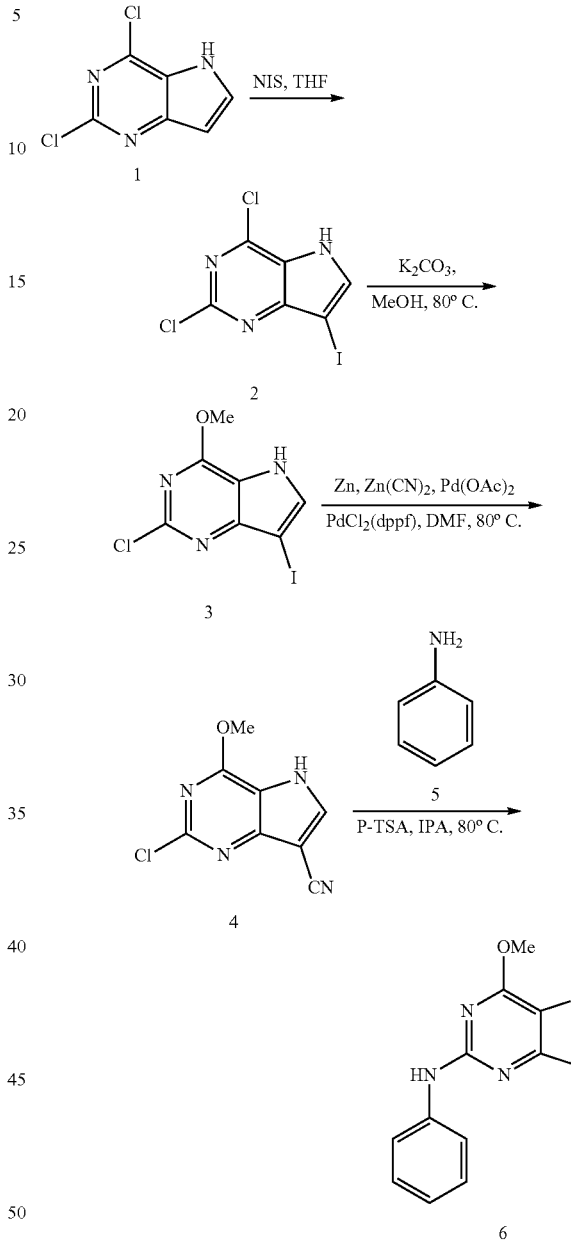

To a solution of 2,4-dichloro-5H-pyrrolo[3,2-d]pyrimidine (1, 25.0 g, 132.9 mmol) in tetrahydrofuran (250 mL), N-iodosuccinimide (35.89 g, 159.5 mmol) is added portion wise over a period of 10 min and the reaction mixture is allowed to stir at room temperature for 30 h. After completion, the reaction mixture is quenched with water and extracted with ethyl acetate. The organic layer is washed with water, separated, dried over anhydrous sodium sulphate and concentrated under reduced pressure to afford 2,4-dichloro-7-iodo-5H-pyrrolo[3,2-d]pyrimidine (2).

To a solution of 2,4-dichloro-7-iodo-5H-pyrrolo[3,2-d]pyrimidine (2, 30.0 g, 95.5 mmol) in methanol (600 mL), potassium carbonate (39.62 g, 286.7 mmol) is added portion wise over a period of 10 min and the reaction mixture is allowed to stir at 80° C. for 24 h. After completion, the reaction mixture is concentrated, diluted with water and extracted with ethyl acetate. The organic layer is washed with water, separated, dried over anhydrous sodium sulphate and concentrated under reduced pressure to get crude. The crude is triturated with diethyl ether to afford 2-chloro-7-iodo-4-methoxy-5H-pyrrolo[3,2-d]pyrimidine (3).

To a solution of 2-chloro-7-iodo-4-methoxy-5H-pyrrolo [3,2-d]pyrimidine (3, 24.0 g, 77.54 mmol) in N,N-dimethylformamide (240 mL), zinc cyanide (9.11 g, 77.54 mmol), zinc acetate (14.22 g, 77.54 mmol) and zinc dust (2.02 g, 31.01 mmol) are added at room temperature. The reaction mixture is degassed with argon for 15 min. [1,1'-Bis(diphenylphosphino)ferrocene]palladium(II) (5.67 g, 7.75 mmol) and palladium acetate (0.87 g, 3.87 mmol) are added and mixture is heated at 80° C. for 1 h. After completion, the reaction mass is diluted with ethyl acetate and washed with cold water. The organic layer is separated, dried over anhydrous sodium sulphate, filtered and concentrated to get crude. The crude is purified by column chromatography over silica gel (100-200 mesh) using 0-50% ethyl acetate in hexanes as eluent. The desired fractions are concentrated in vacuo to afford 2-chloro-4-methoxy-5H-pyrrolo[3,2-d]pyrimidine-7-carbonitrile (4).

To a solution of 2-chloro-4-methoxy-5H-pyrrolo[3,2-d] pyrimidine-7-carbonitrile (4, 10.0 g, 47.9 mmol) in isopropanol (100 mL), aniline (5, 43.76 mL, 479.3 mmol) and p-toluene sulfonic acid monohydrate (10.93 g, 57.48 mmol) are added. The reaction mixture is allowed to stir at 80° C. for 16 h. After completion, the reaction mixture is quenched with water and extracted with ethyl acetate. The organic layer is washed with water, brine, dried over anhydrous sodium sulphate and concentrated under reduced pressure to get crude. The crude is triturated with n-pentane, diethyl ether and dried under high vacuo to afford 4-methoxy-2-(phenylamino)-5H-pyrrolo[3,2-d]pyrimidine-7-carbonitrile (6).

Example 3B. Methods of Synthesizing the Right-Hand Side

Example 3B.1

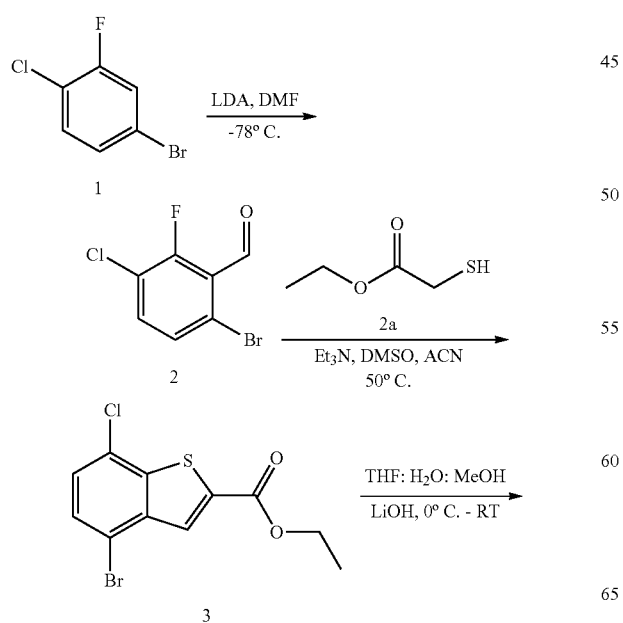

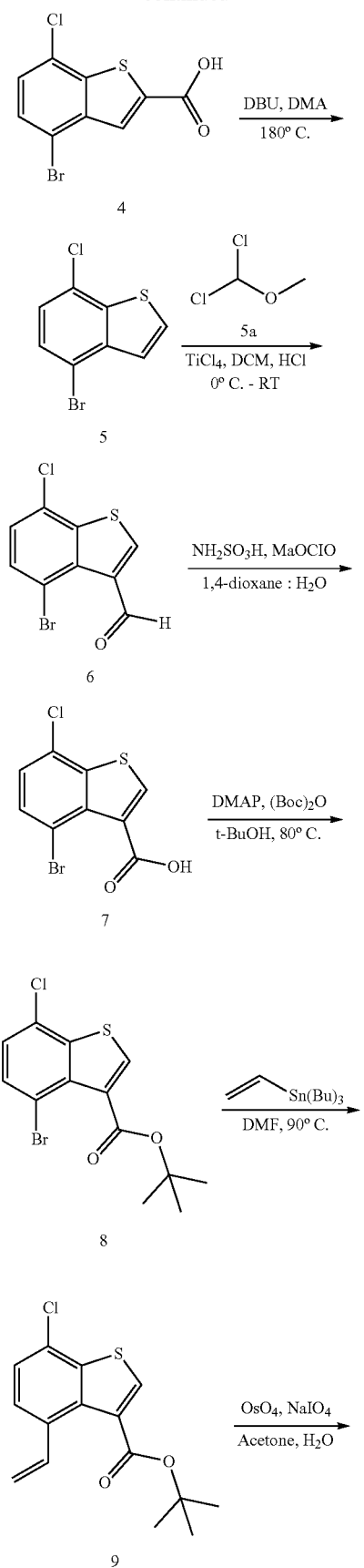

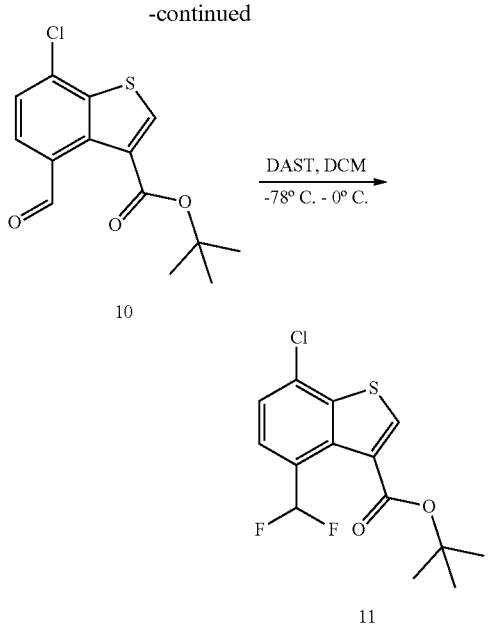

A solution of 4-bromo-1-chloro-2-fluorobenzene (1, 20.0 g, 95.69 mmol) in tetrahydrofuran (200 mL) is cooled at −78° C., then lithium di-isopropyl amide (2 M in tetrahydrofuran) (57.2 mL, 114.83 mmol) is added dropwise to the mixture and reaction mixture is stirred at −78° C. for 1 h. Then, N,N-dimethylformamide (20.0 mL) is added drop wise for 15 min at −78° C. and reaction mixture is stirred for 30 min. After completion reaction mixture is quenched with ammonium chloride solution, diluted with water, and extracted with diethyl ether. The organic layer is dried over anhydrous sodium sulphate, filtered and concentrated to get crude compound. Crude compound obtained is washed with pentane to afford 6-bromo-3-chloro-2-fluorobenzaldehyde (2).

To a solution of 6-bromo-3-chloro-2-fluorobenzaldehyde (2, 18.0 g, 75.94 mmol), in acetonitrile (180.0 mL) and dimethylsulphoxide (48.0 mL), triethyl amine (31.96 mL, 227.84 mmol) is added at 0° C. followed by ethyl 2-mercaptoacetate (2a, 18.2 g, 151.89 mmol) and continued stirring at 50° C. for 4 h. After completion, reaction mixture is diluted with water and extracted with ethyl acetate, washed with 1 N hydrochloric acid, water and brine solution. Organic layer is dried over sodium sulfate and concentrated to dryness under reduced pressure. Triturated with ethanol, filtered and dried to afford ethyl 4-bromo-7-chlorobenzo[b]thiophene-2-carboxylate (3).

To a solution of ethyl ethyl 4-bromo-7-chlorobenzo[b]thiophene-2-carboxylate (3, 18.0 g, 56.42 mmol) and in tetrahydrofuran:water:methanol (90.0 mL: 45 mL: 45 mL), lithium hydroxide (13.54 g, 564.26 mmol) is added, and the reaction mixture is continued stirring for 2 h. After completion, reaction mixture is poured on chilled 1 N aqueous hydrochloric acid, and extracted with ethyl acetate, washed with water and brine solution. Organic layer is dried over anhydrous sodium sulfate and concentrated to dryness under reduced pressure. Triturated with ether, filtered and dried to afford 4-bromo-7-chlorobenzo[b]thiophene-2-carboxylic acid (4).

To a solution of 4-bromo-7-chlorobenzo[b]thiophene-2-carboxylic acid (4, 15.0 g, 51.90 mmol), in N,N-dimethyl acetamide (150.0 mL), 1, 8-diazabicyclo (5.4.0) undec-7-ene (39.55 g, 259.51 mmol) is added and mixture is heated at 180° C. for 4 h. After completion, reaction mixture is cooled to room temperature diluted with water and acidified by 1 N hydrochloric acid and extracted with ethyl acetate, washed with, water and brine solution. Organic layer is dried over anhydrous sodium sulfate and concentrated to dryness under reduced pressure to afford 4-bromo-7-chlorobenzo[b]thiophene (5).

To a solution of 4-bromo-7-chlorobenzo[b]thiophene (5, 4.00 g, 16.19 mmol) in dichloromethane (100.0 mL), dichloro(methoxy)methane (5a, 4.59 g, 24.29 mmol) is added at 0° C. followed by titanium tetrachloride (2.79 g, 24.29 mmol) at same temperature and the reaction mixture is continued stirring for 16 h at room temperature. After completion, reaction mixture is quenched with 1 N aqueous hydrochloric acid and continued stirring for 2 h, diluted with water and extracted with dichloromethane, washed with water and brine solution. Organic layer is dried over anhydrous sodium sulfate and concentrated to dryness under reduced pressure. The crude product is purified by flash chromatography using silica (100-200 mesh) using 0-10% ethyl acetate in hexanes as eluent. The desired fractions are concentrated under reduced pressure to afford 4-bromo-7-chlorobenzo[b]thiophene-3-carbaldehyde (6).

To a solution of 4-bromo-7-chlorobenzo[b]thiophene-3-carbaldehyde (6, 2.50 g, 9.12 mmol) in 1,4-dioxane (24.0 mL) and water (8.0 mL), (3:1 ratio) is added sodium chlorite (1.24 g, 13.68 mmol), followed by sulfamic acid (5.30 g, 54.74 mmol) at room temperature and the mixture is continued stirring for 16 h. After completion, reaction mixture is concentrated under reduced pressure; residue is acidified to pH-2 by 2 N hydrochloric acid and extracted with ethyl acetate, washed with water and brine solution. Organic layer is dried over anhydrous sodium sulfate and concentrated to dryness under reduced pressure. The residue is triturated with n-pentane, filtered and dried to afford 4-bromo-7-chlorobenzo[b]thiophene-3-carboxylic acid (7).

To a solution of 4-bromo-7-chlorobenzo[b]thiophene-3-carboxylic acid (7, 1.40 g, 4.81 mmol) in t-butanol (15.0 mL), di-tert-butyl dicarbonate (2.0 g, 9.62 mmol) followed by dimethylaminopyridine (0.586 g, 4.81 mmol) is added at room temperature. The solution is heated at 90° C. and continued stirring for 16 h. After completion, reaction mixture is concentrated under reduced pressure; diluted with water and extracted with ethyl acetate, washed with water and brine solution. Organic layer is dried over sodium sulfate and concentrated to dryness under reduced pressure. The crude is purified by flash chromatography using silica (100-200 mesh) by eluting with gradient of 5-10% ethyl acetate in hexanes. The desired fractions are concentrated under reduced pressure to afford tert-butyl 4-bromo-7-chlorobenzo[b]thiophene-3-carboxylate (8).

A solution of tert-butyl 4-bromo-7-chlorobenzo[b]thiophene-3-carboxylate (8, 1.10 g, 3.17 mmol) and tributyl (vinyl)stannane (1.20 g, 3.80 mmol) in N,N-dimethylformamide (11 mL) is degassed using argon for 15 min. Bis (triphenylphosphine)palladium dichloride (0.222 g, 0.3170 mmol) is added to the reaction mixture and heated at 90° C. for 2 h. The reaction mixture is cooled to room temperature, diluted with ethyl acetate and water. The organic layer is separated, washed with brine, dried over anhydrous sodium sulphate, filtered and concentrated under reduced pressure to get the crude. The crude is purified by column chromatography using silica (100-200 mesh) and 2.0-5.0% ethyl acetate in hexanes as eluent. The desired fractions are concentrated under reduced pressure to afford tert-butyl 7-chloro-4-vinylbenzo[b]thiophene-3-carboxylate (9).

A solution of tert-butyl 7-chloro-4-vinylbenzo[b]thiophene-3-carboxylate (9, 0.6 g, (2.04 mmol) in acetone (10 mL) and water (2 mL) is cooled to 0° C. and osmium tetraoxide (4% solution in water)(1.3 mL, 0.2040 mmol) followed by sodium periodate (1.3 g, 6.12 mmol) is added. The mixture is stirred at room temperature for 1 h. After completion, the reaction mixture is filtered and filtrate is concentrated under reduced pressure to get the crude product. The crude is purified by pentane wash to afford tert-butyl 7-chloro-4-formylbenzo[b]thiophene-3-carboxylate (10).

To a stirred solution of tert-butyl 7-chloro-4-formylbenzo[b]thiophene-3-carboxylate (10, 0.550 g, 1.85 mmol) in dichloromethane (10 mL), diethylaminosulfur trifluoride (0.503 g, 2.77 mmol) is added at 0° C. The reaction is allowed to warm at room temperature and stirred for 4 h. After completion, reaction mixture is concentrated under reduced pressure to get crude. The crude is purified by column chromatography using silica (100-200 mesh) and 5.0-10.0% ethyl acetate in hexanes as eluent. The desired fractions are concentrated under reduced pressure to afford tert-butyl 7-chloro-4-(difluoromethyl)benzo[b]thiophene-3-carboxylate (11).

Example 3B.2

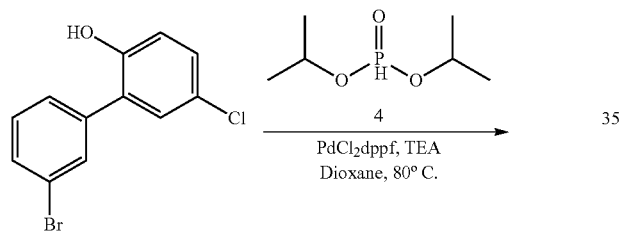

A solution of 3'-bromo-5-chloro-[1,1'-biphenyl]-2-ol (3, 0.5 g, 1.7 mmol), diisopropyl phosphonate (4, 0.585 g, 3.5 mmol), and triethyl amine (0.533 g, 5.2 mmol) in isopropyl alcohol is degassed with argon for 10 min followed by the addition of bis(diphenylphosphino) ferrocene-palladium(II) dichloride.dichloromethane complex The reaction mixture is stirred at 100° C. for 16 h. After completion, the volatiles are removed under reduced pressure. Crude is purified by flash column chromatography using 30% ethyl acetate hexanes to afford diisopropyl (5'-chloro-2'-hydroxy-[1,1'-biphenyl]-3-yl)phosphonate (5).

Example 3B.3

To a solution of 7-bromo-5-methylthieno[3,2-b]pyridine-3-carboxamide (3, 1.50 g, 5.55 mmol) in N,N-dimethylformamide (20 mL), sodium hydride is added at 0° C. and stirred for 10 min. Then, dimethylcarbamic chloride (3a, 0.71 g, 6.66 mmol) is added and the mixture is stirred at room temperature for 2 h. After completion, the reaction mixture is diluted with ethyl acetate, washed with cold water and brine, dried over anhydrous sodium sulphate, filtered and concentrated. The crude product is triturated with diethyl ether and pentane and dried to afford 7-bromo-N-(dimethylcarbamoyl)-5-methylthieno[3,2-b]pyridine-3-carboxamide (4).

Example 3B.4

-continued

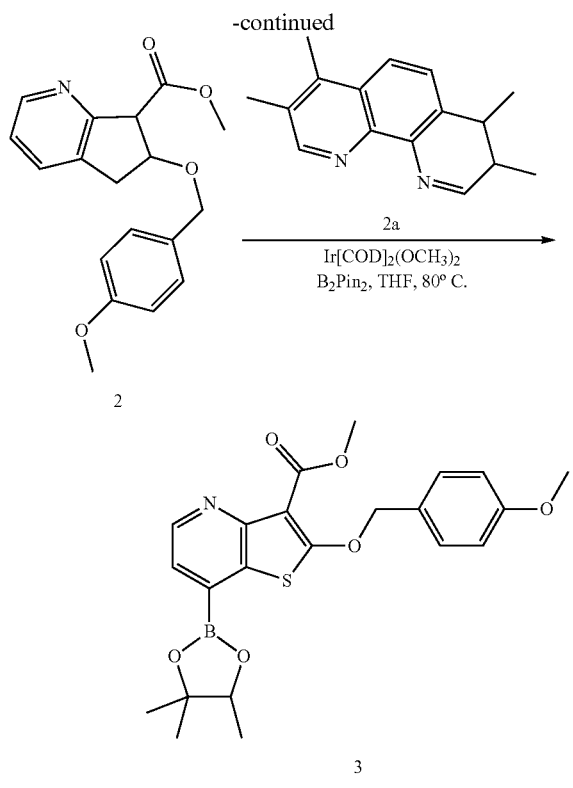

Example 3B.5

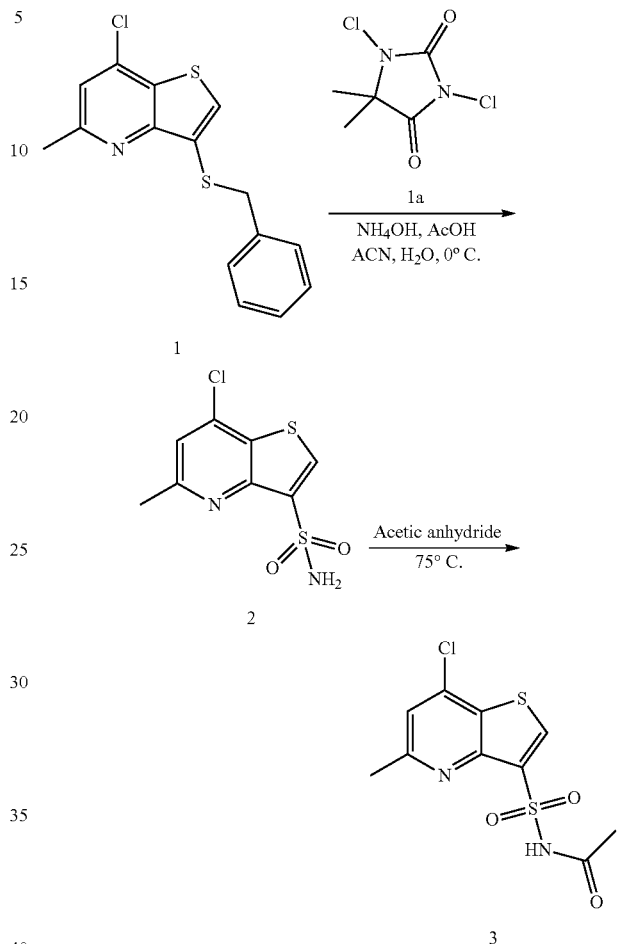

Methyl 2-hydroxythieno[3,2-b]pyridine-3-carboxylate (1, 748 mg, 3.6 mmol) is dissolved in N,N-dimethylformamide (20 mL) in an oven dried screw cap vial equipped with a stir bar. Potassium carbonate (210 mg, 1.52 mmol) is added, followed by the dropwise addition of 1-(chloromethyl)-4-methoxybenzene (1a, 0.42 mL, 4.2 mmol). The vial is sealed and heated to 75° C. After 22 h additional 4-methoxybenzyl chloride (0.42 mL, 4.2 mmol) and potassium carbonate (946.2 mg, 6.8 mmol) are added and the reaction mixture continued to stir at 75° C. After 3 h the reaction mixture is cooled to room temperature and diluted with ethyl acetate and water. The layers are separated and the aqueous phase is extracted with ethyl acetate twice. The combined organic material is washed with brine, dried over magnesium sulfate, filtered, and solvent removed in vacuo to afford a dark brown oil. Purification via silica gel chromatography, eluting with hexanes and ethyl acetate afforded methyl 2-((4-methoxybenzyl)oxy)thieno[3,2-b]pyridine-3-carboxylate (2).

A bottle of tetrahydrofuran is sparged with argon gas for 1 h. An oven dried microwave vial equipped with a stir bar is charged with bis(pinacolato)diboron (308.4 mg, 1.21 mmol), methyl 2-((4-methoxybenzyl)oxy)thieno[3,2-b]pyridine-3-carboxylate (2, 381 mg, 1.16 mmol), 3,4,7,8-tetramethyl-1,10-phenanthroline (2a, 21.8 mg, 0.093 mmol), and (1Z,5Z)-cycloocta-1,5-diene; methoxyiridium (30.6 mg, 0.046 mmol). Tetrahydrofuran (2.3 mL) is added, the vial is sealed and placed under an atmosphere of argon before being stirred in an oil bath at 80° C. After 16 h the reaction mixture is cooled to room temperature and solvent removed in vacuo. The crude residue is used without further purification for the subsequent reaction. Methyl 2-((4-methoxybenzyl)oxy)-7-(4,4,5-trimethyl-1,3,2-dioxaborolan-2-yl)thieno[3,2-b]pyridine-3-carboxylate (3).

To a solution of 3-(benzylthio)-7-chloro-5-methylthieno[3,2-b]pyridine (1, 0.7 g, 2.3 mmol) in a mixture of acetonitrile, acetic acid and water (40:2:1) (10.0 mL) at 0° C. 1,3-Dichloro-5,5-dimethylimidazolidine-2,4-dione (1a, 0.9 g, 4.60 mmol) at 0° C. and the mixture is stirred for 1 h. Ammonium hydroxide (35% in water, 6.0 mL) is added is added to the reaction mixture at 0° C. and stirring is continued for 2 h. After completion, the reaction mixture is diluted with water and extracted with ethyl acetate. The organic layer is washed with water and saturated brine, dried over anhydrous sodium sulfate, filtered and concentrated. The crude product is washed with n-pentanes to afford 7-chloro-5-methylthieno[3,2-b]pyridine-3-sulfonamide (2).

To a solution of methyl 7-chloro-5-methylthieno[3,2-b]pyridine-3-sulfonamide (2, 0.50 g, 1.9 mmol) in acetic anhydride (6.0 mL) is added zinc chloride (0.08 g, 0.57 mmol) at room temperature and the mixture is heated and stirred for 16 h at 75° C. After completion, the reaction mixture is diluted with water and extracted with ethyl acetate. The organic layer is washed with water, saturated brine, dried over anhydrous sodium sulfate, filtered and concentrated. The crude product is purified by washing with diethyl ether and n-pentanes to afford N-((7-chloro-5-methylthieno[3,2-b]pyridin-3-yl)sulfonyl)acetamide (3).

Example 3B.6

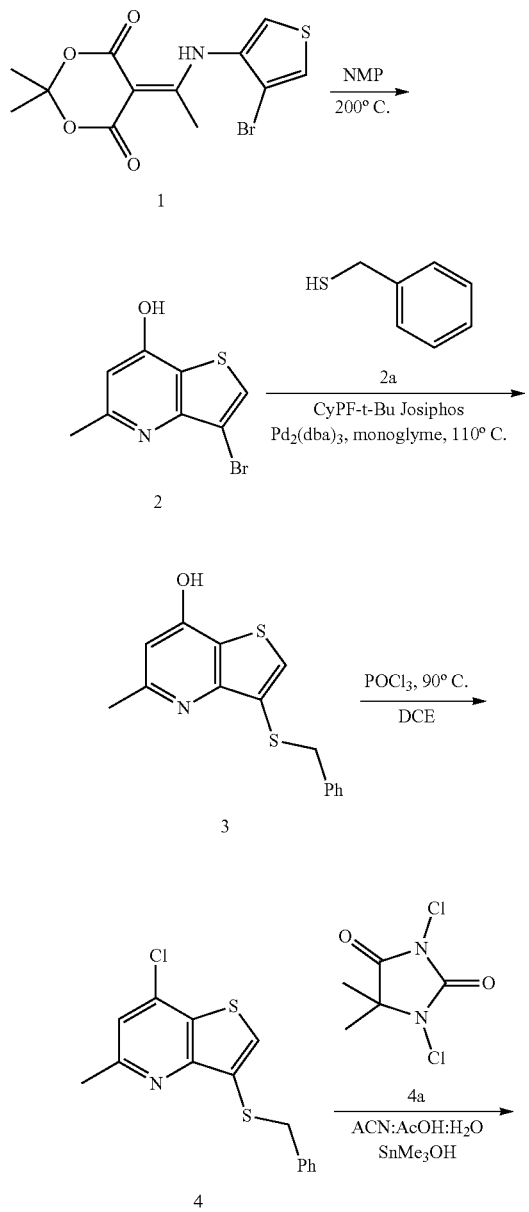

microwave at 200° C. for 30 min. After completion, the reaction mixture is diluted with dichloromethane and then silica gel is added. The solvent is then evaporated and the free flow silica gel is then loaded on the Isco column and purified via silica gel chromatography eluting with methanol/ethylacetate. The desired fractions are concentrated under reduced pressure to afford 3-bromo-5-methylthieno[3,2-b]pyridin-7-ol (2).

To a solution of 3-bromo-5-methylthieno[3,2-b]pyridin-7-ol (2, 177 mg, 0.725 mmol), phenylmethanethiol (2a, 0.361 g, 2.91 mmol) and N,N-diisopropylethylamine (0.379 mL, 2.15 mmol) in monoglyme (4 mL) is added premixed solution of tris(dibenzylideneacetone)dipalladium(0) (132 mg, 0.145 mmol) and (R)-1-[(Sp)-2-(dicyclohexylphosphino)ferrocenyl]ethyldi-tert-butylphosphine (80 mg, 0.145 mmol) in monoglyme (1 mL) at room temperature. The reaction mixture is purged with argon gas for 5 min, and the mixture is heated at 110° C. for 15 h. After completion, the reaction mixture is diluted with dichloromethane and then silica gel is added. The solvent is then evaporated and the free flow silica gel is then loaded on the Isco column and purified via silica gel chromatography eluting with Ethylacetate/hexanes. The desired fractions are concentrated under reduced pressure to afford 3-(benzylthio)-5-methylthieno[3,2-b]pyridin-7-ol (3).

To a solution of 3-(benzylthio)-5-methylthieno[3,2-b]pyridin-7-ol (3, 0.100 g, 0.347 mmol) in 1,2-dichloroethane (3.0 mL), phosphoryl trichloride (0.1 mL, 1.04 mmol) and catalytic amount of N,N-dimethylformamide (0.050 mL) are added at room temperature. The reaction mixture is heated at 90° C. for 2 h. After completion, the reaction mixture is diluted with dichloromethane and then silica gel is added. The solvent is then evaporated and the free flow silica gel is then loaded on the Isco column and purified via silica gel chromatography eluting with methanol/dichloromethane to afford 3-(benzylthio)-7-chloro-5-methylthieno[3,2-b]pyridine (4).

A solution of 3-(benzylthio)-7-chloro-5-methylthieno[3,2-b]pyridine (4, 50 mg, 0.163 mmol) and 1,3-dichloro-5,5-dimethyl-imidazolidine-2,4-dione (4a, 64 mg, 0.329 mmol) in mixture of acetonitrile (3 mL)/water (2 mL)/acetic acid (0.4 mL) is stirred at room temperature for 1 h. To this mixture is then added hydroxyl(trimethylstannane) (295 mg, 1.63 mmol) and then stirred for 15 h at 50° C. The reaction mixture is then concentrated to afford crude 7-chloro-5-methylthieno[3,2-b]pyridine-3-sulfonic acid (5).

Example 3B.7

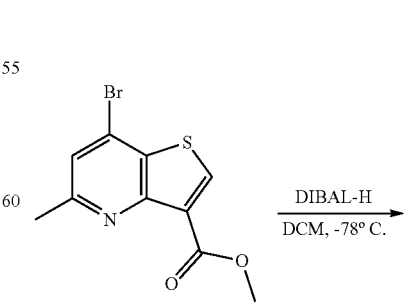

A solution of 5-(1-((4-bromothiophen-3-yl)amino)ethylidene)-2,2-dimethyl-1,3-dioxane-4,6-dione (1, 0.250 g, 0.722 mmol) in N-methyl pyrrolidone (2 mL) is heated in Example 3B.8

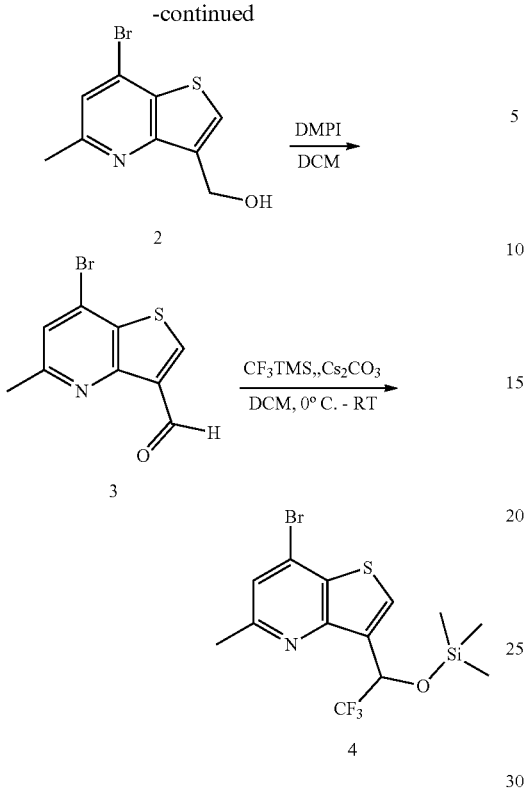

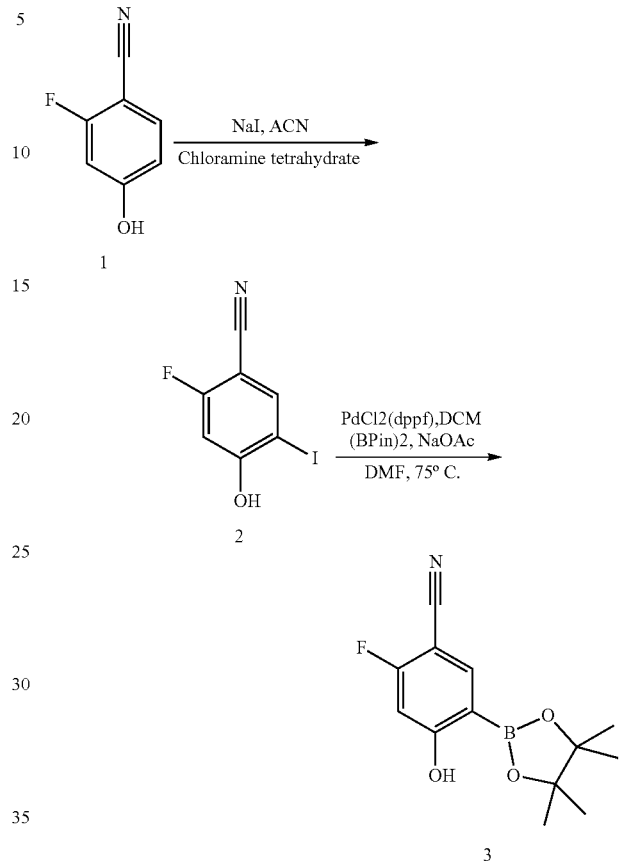

To a solution of methyl 7-bromo-5-methylthieno[3,2-b]pyridine-3-carboxylate (1, 3.00 g, 10.4 mmol) in dichloromethane (30.0 mL) at −78° C., diisobutylaluminium hydride (10.40 mL, 15.7 mmol) is added. The reaction mixture is stirred this temperature for 3 h. After this time, the reaction mixture is diluted with water and extracted with dichloromethane. The organic layer is washed with water and then brine, dried over anhydrous sodium sulfate, and concentrated to dryness under reduced pressure to afford (7-bromo-5-methylthieno[3,2-b]pyridin-3-yl)methanol (2).

To a solution of (7-bromo-5-methylthieno[3,2-b]pyridin-3-yl)methanol (2, 1.70 g, 3.87 mmol) in dichloromethane (20.0 mL) at 0° C., 1,1,1-tris(acetyloxy)-1,1-dihyro-1,2-benziodoxol-3-(1H)-one (3.28 g, 7.75 mmol) is added. The reaction mixture is stirred at room temperature for 3 h. After this time, the reaction mixture is filtered with Celite and washed with dichloromethane. The filtrate is concentrated to dryness under reduced pressure to obtain the crude product. This is purified by silica gel (100-200 mesh) column chromatography using 30-50% ethyl acetate in hexanes as eluent. The desired fractions are concentrated under reduced pressure to afford 7-bromo-5-methylthieno[3,2-b]pyridine-3-carbaldehyde (3).

To a solution of 7-bromo-5-methylthieno[3,2-b]pyridine-3-carbaldehyde (3, 0.50 g, 1.95 mmol) in dichloromethane (5.0 mL) at 0° C., trifluoromethyltrimethylsilane (0.416 g, 2.92 mmol) and cesium carbonate (3.17 g 9.75 mmol) is added. The reaction mixture is stirred at room temperature for 1 h. Then, the reaction mixture is diluted with water and extracted with dichloromethane. The organic layer is washed with water and then brine solution, dried over anhydrous sodium sulfate, and concentrated to dryness under reduced pressure to afford 7-bromo-5-methyl-3-(2,2,2-trifluoro-1-((trimethylsilyl)oxy)ethyl)thieno[3,2-b]pyridine (4).

To a stirred solution of 2-fluoro-4-hydroxybenzonitrile (1, 20 g, 145.0 mmol) in acetonitrile (80 mL) are added sodium iodide (24 g, 160.0 mmol) and chloramine tetrahydrate (45 g, 160.0 mmol) and stirred at room temperature for 16 h. The reaction mixture is diluted with water and extracted with ethyl acetate. The organic layer is washed with water and saturated brine, dried over anhydrous sodium sulphate, filtered and concentrated. The crude product is purified by column chromatography using silica gel (100-200 mesh) and 10% ethyl acetate in hexanes as eluent. The desired fractions are concentrated under reduced pressure to afford 2-fluoro-4-hydroxy-5-iodobenzonitrile (2).

To a solution of 2-fluoro-4-hydroxy-5-iodobenzonitrile (2, 7.0 g, 26.6 mmol) in 1,4-dioxane (70 mL), sodium acetate (4.36 g, 53.23 mmol) and bis pinacolato diboron (20.26 g, 79.8 mmol) are added at room temperature and the mixture is degassed with argon for 10 min. [1,1'-Bis(diphenylphosphino)ferrocene]dichloropalladium dichloromethane complex (1.9 g, 2.66 mmol), is added to the reaction mixture and degassed for another 15 min. The reaction mixture is heated at 75° C. for 16 h. After completion, the reaction mass is diluted with water and extracted with ethyl acetate. The organic layer is washed with brine, dried over anhydrous sodium sulfate, filtered and concentrated to dryness under reduced pressure. The crude product is purified by Combiflash (12 g, RediSep column) using 20% ethyl acetate in hexanes as eluent. The desired fractions are concentrated under reduced pressure to afford 2-fluoro-4-hydroxy-5-(4,4,5,5-tetramethyl-1,3,2-dioxaborolan-2-yl)benzonitrile (3).

Example 3B.9

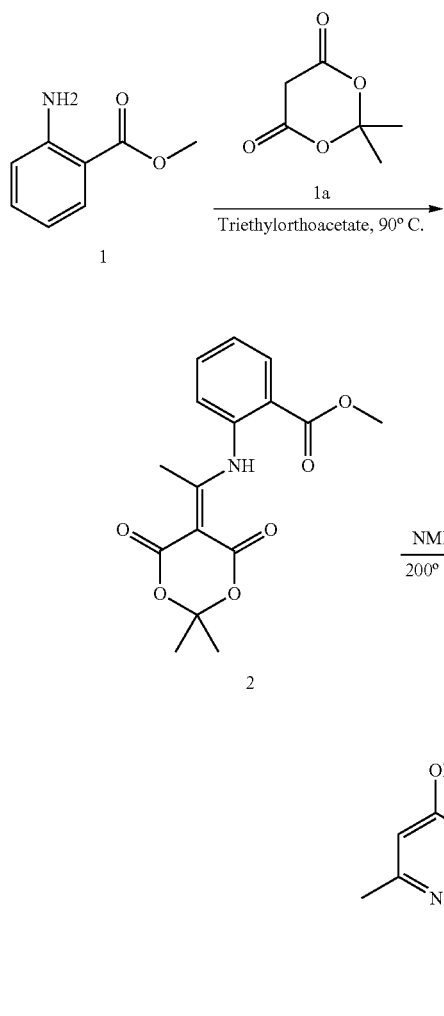

A solution of 2,2-dimethyl-1,3-dioxane-4,6-dione (1a, 1.048 g, 7.27 mmol) and 1,1,1-triethoxyethane (10.0 mL) is stirred and heated at 90° C. for 2 h in a closed vessel. Methyl 2-aminobenzoate (1, 1 g, 6.62 mmol) is added portion wise at 90° C. under argon atmosphere and continued heating at 90° C. for 6 h. After completion, the reaction mass is cooled to room temperature, added water and extracted with ethyl acetate. The organic layer is dried over anhydrous sodium sulfate, filtered and concentrated under vacuo to get crude. The crude methyl 2-((1-(2,2-dimethyl-4,6-dioxo-1,3-dioxan-5-ylidene)ethyl)amino)benzoate (2).

A solution of methyl 2-((1-(2,2-dimethyl-4,6-dioxo-1,3-dioxan-5-ylidene)ethyl)amino)benzoate (2, 0.900 g, 2.82 mmol) in N-methyl pyrrolidone (1 mL) is heated in microwave at 200° C. for 30 min. After completion, the reaction mixture is diluted with dichloromethane and then silica gel is added. The solvent is then evaporated and the free flow silica gel is then loaded on the Isco column and purified via silica gel chromatography eluting with methanol/ethylacetate. The desired fractions are concentrated under reduced pressure to afford methyl 4-hydroxy-2-methylquinoline-8-carboxylate (3).

Example 3B.10

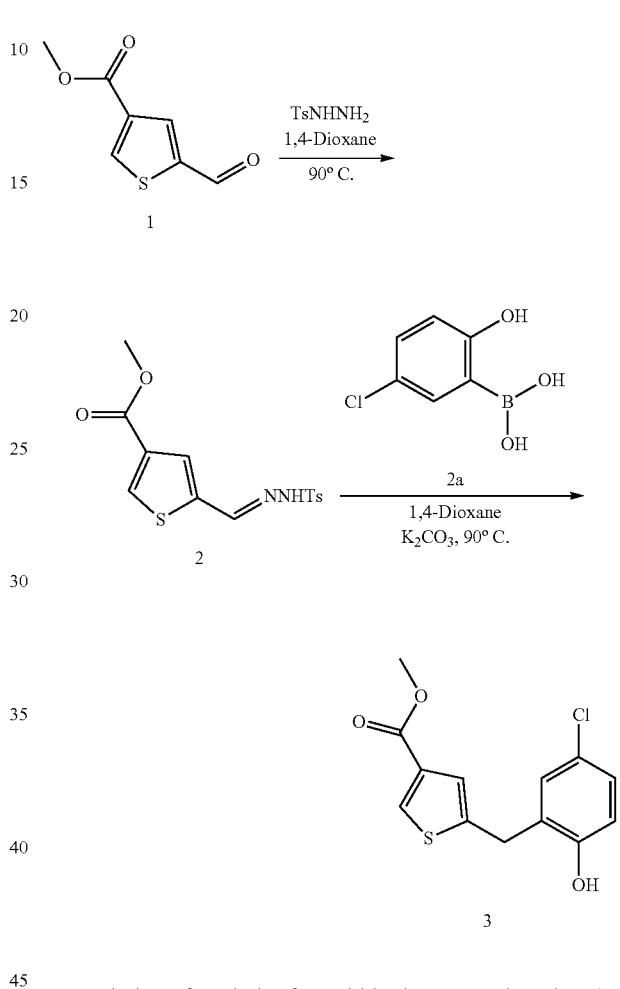

A solution of methyl 5-formylthiophene-3-carboxylate (1, 2.00 g, 11.7 mmol) and 4-methylbenzenesulfonohydrazide (2.19 g, 11.7 mmol) in 1,4-dioxane (20 mL) is heated at 90° C. for 16 h. The reaction mixture is cooled at room temperature, concentrated under reduced pressure to get the crude. The crude is washed with diethyl ether and dried under vacuum to afford methyl (Z)-5-((2-tosylhydrazineylidene)methyl)thiophene-3-carboxylate (2).

To a solution of methyl (Z)-5-((2-tosylhydrazineylidene)methyl)thiophene-3-carboxylate (2, 0.50 g, 1.47 mmol), (5-chloro-2-hydroxyphenyl)boronic acid (2a, 0.307 g, 1.77 mmol) and potassium carbonate (0.40 g, 2.94 mmol) in 1,4-dioxane:water (4:1, 5 mL) is added and reaction mixture is stirred at 90° C. for 16 h. After completion, the reaction mixture is diluted with water and extracted with ethyl acetate. The organic layer is dried over anhydrous sodium sulfate, filtered and concentrated to dryness under reduced pressure to get crude. The crude is purified by flash column chromatography using silica (100-200 mesh) and 10-20% ethyl acetate in hexanes as eluent to afford methyl 5-(5-chloro-2-hydroxybenzyl)thiophene-3-carboxylate (3).

Example 3B.11

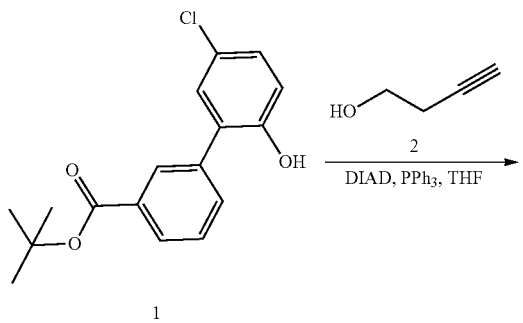

To a cooled solution of tert-butyl 5'-chloro-2'-hydroxy-[1,1'-biphenyl]-3-carboxylate (1, 2.65 g, 8.7 mmol), but-3-yn-1-ol (2, 0.66 mL, 8.7 mmol) and triphenylphosphine (2.28 g, 8.7 mmol) in tetrahydrofuran (14 mL) at 5° C. is added diisopropyl azodicarboxylate (1.71 mL, 8.7 mmol) via syringe over ca. 2 min. This is warmed to room temperature after 15 min and stirred for an additional 18 h. The solvent is removed in vacuo and residue purified via automated flash chromatography, eluting with hexanes and ethyl acetate to afford tert-butyl 2'-(but-3-yn-1-yloxy)-5'-chloro-[1,1'-biphenyl]-3-carboxylate (3).

A flame-dried round bottom flask is charged with ethyl 2,2,2-trifluoroacetate (4, 0.26 mL, 2.18 mmol) and tetrahydrofuran (13 mL). It is cooled to −78° C. and boron trifluoride diethyl etherate (0.29 mL, 2.32 mmol) is added dropwise. After 50 min tert-butyl 2'-(but-3-yn-1-yloxy)-5'-chloro-[1,1'-biphenyl]-3-carboxylate (3, 460 mg, 1.29 mmol) is added slowly followed by slow addition of n-butyl-lithium solution (2.5 M in hexanes, 0.62 mL, 1.55 mmol). After 1 h the reaction is quenched at −78° C. with the slow addition of saturated aqueous ammonium chloride solution. The solution is warmed to room temperature and ethyl acetate is added. The layers are separated, and the aqueous phase is extracted with ethyl acetate twice. The combined organic material is washed with brine, dried over magnesium sulfate, filtered, and concentrated. Purification via automated flash chromatography, eluting with hexanes and ethyl acetate, afforded tert-butyl 5'-chloro-2'-((6,6,6-trifluoro-5-oxohex-3-yn-1-yl)oxy)-[1,1'-biphenyl]-3-carboxylate (5)

Example 3C. General Coupling Methods

Example 3C.1

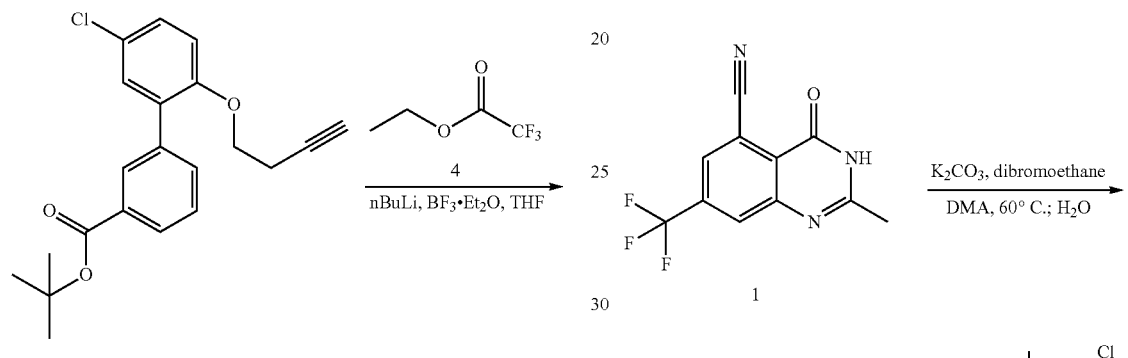

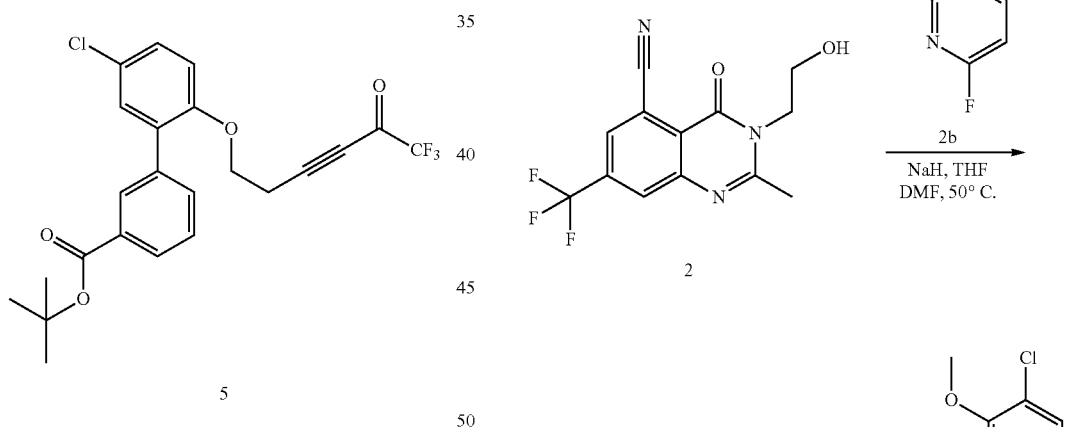

Sodium methoxide (25 wt. % in methanol) (3.16 mL, 13.8 mmol) is added to a stirred solution of 3-chloro-2,6-difluoro-pyridine (2a, 2.01 g, 13.4 mmol) in Methanol (5 mL)

at 0° C. The cold bath is removed and the resulting cloudy mixture is stirred at room temperature under argon for 35 min. The reaction mixture is poured into water (100 mL). Solids are collected by vacuum filtration, washed thoroughly with water, and air dried using vacuum suction for 30 min. The solids are dried under high vacuum to afford 3-chloro-6-fluoro-2-methoxypyridine (2b).

Potassium carbonate (1.82 g, 13.2 mmol) is added to a stirred solution of 2-methyl-4-oxo-7-(trifluoromethyl)-3,4-dihydroquinazoline-5-carbonitrile (1, 835 mg, 3.30 mmol) and 1,2-dibromoethane (2.84 mL, 33.0 mmol) in DMA (15 mL) at room temperature under argon. The resulting mixture is heated at 60° C. under argon for 3 h. Water (0.59 mL, 33.0 mmol) is added. The resulting mixture is heated at 60° C. under argon for 1 h 15 min. After cooling to room temperature the reaction mixture is partitioned between ethyl acetate and water. The organics are washed three times with brine, dried over magnesium sulfate, filtered, concentrated on a rotary evaporator, and purified via silica gel chromatography (20-90% ethyl acetate in hexanes) to afford 3-(2-hydroxyethyl)-2-methyl-4-oxo-7-(trifluoromethyl)-3,4-dihydroquinazoline-5-carbonitrile (2).

3-(2-Hydroxyethyl)-2-methyl-4-oxo-7-(trifluoromethyl)-3,4-dihydroquinazoline-5-carbonitrile (2, 390 mg, 1.31 mmol) is dissolved in DMF (4 mL) with stirring under argon. THF (6 mL) is added and the resulting solution is cooled to −78° C. Sodium hydride (34.6 mg, 1.44 mmol) is added and the resulting cloudy mixture is stirred at −78° C. under argon for 10 min. 3-Chloro-6-fluoro-2-methoxypyridine (2b, 254 mg, 1.57 mmol) is added and the cold bath is removed. The resulting mixture is stirred at room temperature under argon for 20 min and then heated at 50° C. under a reflux condenser under argon for 2.5 h. After cooling to room temperature the resulting mixture is partitioned between ethyl acetate and a mixture of brine and saturated aqueous ammonium chloride. The organics are washed twice more with brine, concentrated on a rotary evaporator with silica gel, and purified via silica gel chromatography (0-100% ethyl acetate in hexanes) to afford impure 3-(2-((5-chloro-6-methoxypyridin-2-yl)oxy)ethyl)-2-methyl-4-oxo-7-(trifluoromethyl)-3,4-dihydroquinazoline-5-carbonitrile (3).

Example 3C.2

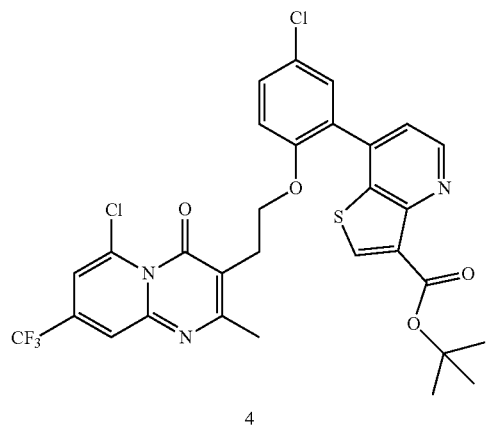

4

To a solution of tert-butyl 7-(5-chloro-2-hydroxyphenyl) thieno[3,2-b]pyridine-3-carboxylate (3a, 2.0 g, 5.5 mmol) in tetrahydrofuran (15 mL), sodium hydride (0.276 g, 6.9 mmol) is added at 0° C. and the mixture is stirred for 0.5 h. 6-Chloro-3-(2-chloroethyl)-2-methyl-8-(trifluoromethyl)-4H-pyrido[1,2-a]pyrimidin-4-one (3, 1.5 g, 4.6 mmol) in tetrahydrofuran is added to the reaction mixture and stirred for 16 h. After completion, the reaction mixture is poured into crushed ice and extracted with ethyl acetate. Organic layer is dried over anhydrous sodium sulfate and concentrated to dryness under reduced pressure. The crude compound obtained is purified through column chromatography using 0-50% ethyl acetate in hexanes as eluent; the fractions containing desired product is distilled off under reduced pressure to afford tert-butyl 7-(5-chloro-2-(2-(6-chloro-2-methyl-4-oxo-8-(trifluoromethyl)-4H-pyrido[1,2-a]pyrimidin-3-yl)ethoxy)phenyl)thieno[3,2-b]pyridine-3-carboxylate (4).

Example 3C.3

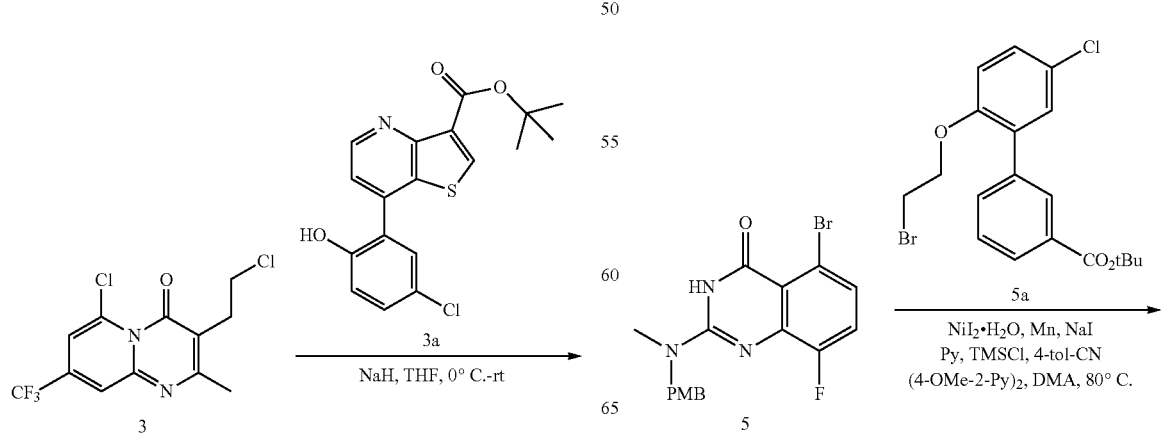

-continued

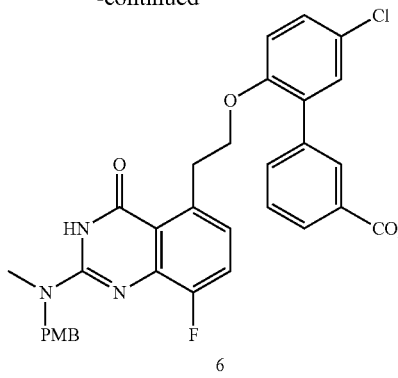

6

To a mixture of 5-bromo-8-fluoro-2-((4-methoxybenzyl)(methyl)amino)quinazolin-4(3H)-one (5, 95 mg, 0.23 mmol), tert-butyl 2'-(2-bromoethoxy)-5'-chloro-[1,1'-biphenyl]-3-carboxylate (5a, 99 mg, 0.24 mmol), nickel(II) iodide hydrate (30 mg, 0.08 mmol), sodium iodide (17 mg, 0.12 mmol), p-tolunitrile (11 mg, 0.09 mmol), 4,4'-dimethoxy-2,2'-bipyridine (20 mg, 0.09 mmol) in freshly sparged N,N-dimethylacetamide (1.2 mL) are added chlorotrimethylsilane (1 drop), pyridine (1 drop) and manganese (25 mg, 0.46 mmol). The reaction is stirred at 80° C. overnight. The resulting mixture is cooled to room temperature and filtered through a pad of Celite. The filtrate is extracted with ethyl acetate and water. The combined organics are dried over sodium sulfate, decanted and concentrated. The crude is purified via column chromatography (silica, ethyl acetate/hexanes=0-40%) to afford 5'-chloro-2'-(2-(8-fluoro-2-((4-methoxybenzyl)(methyl)amino)-4-oxo-3,4-dihydroquinazolin-5-yl)ethoxy)-[1,1'-biphenyl]-3-carboxylic acid (6).

Example 3C.4

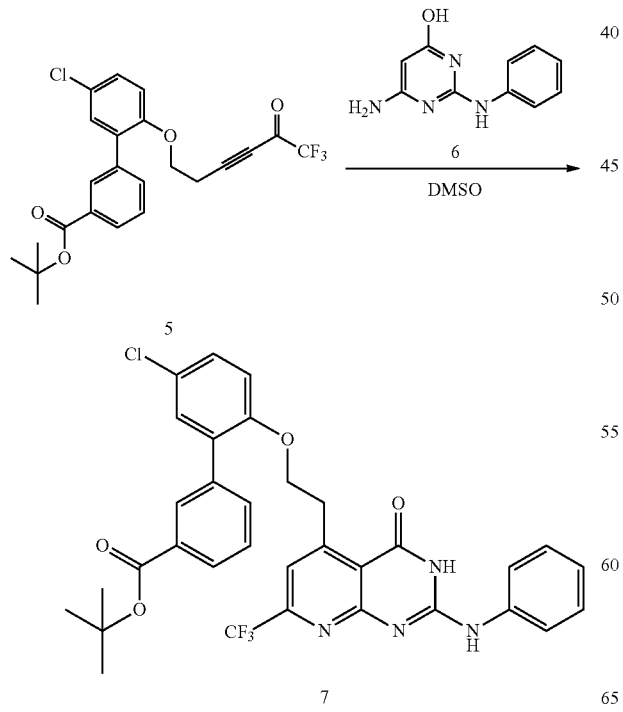

6-Amino-2-(phenylamino)pyrimidin-4-ol (6, 114 mg, 0.45 mmol) is dissolved in dimethylsulfoxide (1.1 mL) and tert-butyl 5'-chloro-2'-((6,6,6-trifluoro-5-oxohex-3-yn-1-yl)oxy)-[1,1'-biphenyl]-3-carboxylate (5, 203 mg, 0.45 mmol) is added in 1 portion. The neon solution is stirred at room temperature for 19 h. The reaction mixture is diluted with water and filtered. The solid is dried in a vacuum oven for 2 h to afford tert-butyl 5'-chloro-2'-(2-(4-oxo-2-(phenylamino)-7-(trifluoromethyl)-3,4-dihydropyrido[2,3-d]pyrimidin-5-yl)ethoxy)-[1,1'-biphenyl]-3-carboxylate (7)

Example 3D. Post Coupling Modification Methods

Example 3D.1

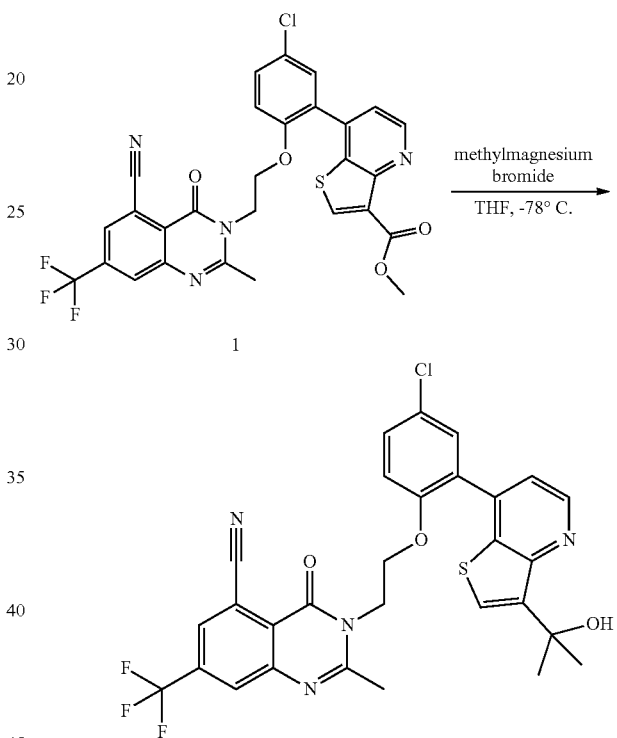

Methylmagnesium bromide (3 M in diethyl ether) (0.051 mL, 0.152 mmol) is added to a stirred solution of methyl 7-(5-chloro-2-(2-(5-cyano-2-methyl-4-oxo-7-(trifluoromethyl)quinazolin-3(4H)-yl)ethoxy)phenyl)thieno[3,2-b]pyridine-3-carboxylate (1, 30.3 mg, 0.051 mmol) in THF (2.5 mL) at −78° C. under argon. The reaction mixture quickly became dark yellow colored. After 20 min the reaction mixture is quenched with saturated aqueous ammonium chloride (0.5 mL), diluted with water (0.5 mL), and partitioned between ethyl acetate and brine. The organics are dried over magnesium sulfate, filtered, concentrated on a rotary evaporator, and dried under high vacuum at 40° C. for 45 min to afford an orange residue. This is dissolved in THF (2.5 mL) with stirring and cooled to −78° C. under argon. Methylmagnesium bromide (3 M in diethyl ether) (0.051 mL, 0.152 mmol) is added and the reaction mixture is stirred at −78° C. under argon for 20 min. The reaction mixture is quenched with saturated aqueous ammonium chloride (0.5 mL), diluted with water (0.5 mL), and partitioned between ethyl acetate and brine. The organics are dried over magnesium sulfate, filtered, concentrated on a rotary evaporator, and purified via preparatory HPLC (15-57% acetonitrile in water with 0.1% TFA). Fractions containing desired product are combined and neutralized with saturated aqueous sodium bicarbonate. The acetonitrile is removed on a rotary evaporator. The residual aqueous phase is extracted three times with dichloromethane. The combined organics are dried over sodium sulfate, filtered, and concentrated on a rotary evaporator. The residue is taken up in acetonitrile and water and lyophilized to dryness to afford 3-(2-(4-chloro-2-(3-(2-hydroxypropan-2-yl)thieno[3,2-b]pyridin-7-yl)phenoxy)ethyl)-2-methyl-4-oxo-7-(trifluoromethyl)-3,4-dihydroquinazoline-5-carbonitrile (Cpd. No. 352F).

Example 3D.2

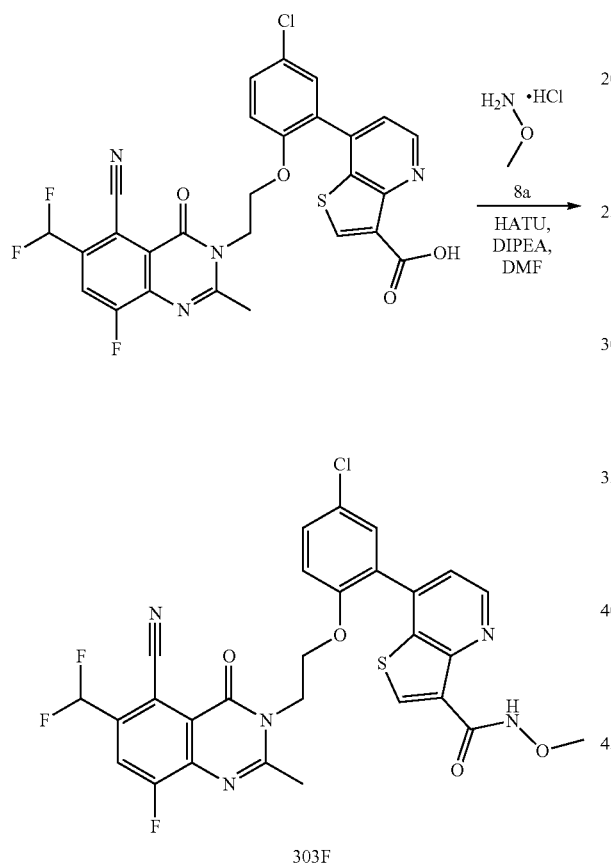

303F

To a solution 7-(5-chloro-2-(2-(5-cyano-6-(difluoromethyl)-8-fluoro-2-methyl-4-oxoquinazolin-3(4H)-yl)ethoxy)phenyl)thieno[3,2-b]pyridine-3-carboxylic acid (8, 0.10 g, 0.171 mmol) in N,N-dimethylformamide (2.0 mL), 1-[bis(dimethylamino)methylene]-1H-1,2,3-triazolo[4,5-b]pyridinium 3-oxide hexafluorophosphate (0.098 g, 0.256 mmol) is added and mixture is stirred at room temperature for 15 min. The reaction mixture is cooled to 0° C., N,N-diisopropylethylamine (0.12 mL, 0.684 mmol) and O-methylhydroxylamine hydrochloride (8a, 0.017 g, 0.205 mmol) are added and the mixture is stirred at room temperature for 1.5 h. After completion, the reaction mixture is diluted with ethyl acetate and washed with cold water and brine solution, dried over anhydrous sodium sulphate and concentrated under reduced pressure. The crude is purified by prep-HPLC to afford 7-(5-chloro-2-(2-(5-cyano-6-(difluoromethyl)-8-fluoro-2-methyl-4-oxoquinazolin-3(4H)-yl)ethoxy)phenyl)-N-methoxythieno[3,2-b]pyridine-3-carboxamide (Cpd. No. 303F).

Example 3D.3

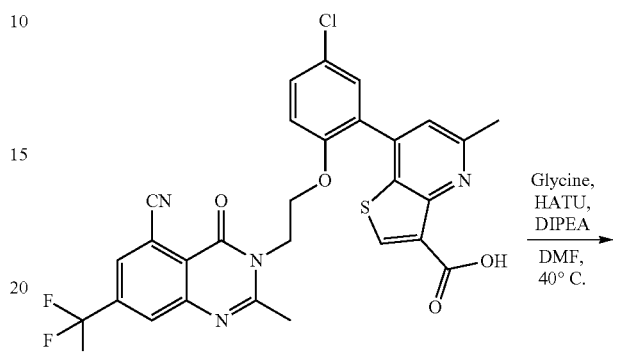

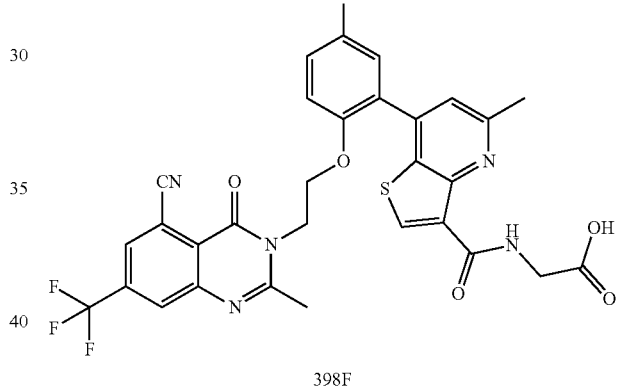

398F

N,N-diisopropylethylamine (0.028 mL, 0.163 mmol) is added to a stirred mixture of 7-(5-chloro-2-(2-(5-cyano-2-methyl-4-oxo-7-(trifluoromethyl)quinazolin-3(4H)-yl)ethoxy)phenyl)-5-methylthieno[3,2-b]pyridine-3-carboxylic acid (1, 32.5 mg, 0.054 mmol) and HATU (22.7 mg, 0.060 mmol) in DMF (0.3 mL) at room temperature under argon. All solids dissolved within 5 min and then shortly thereafter a lot of solids precipitated. After 20 min glycine (6.1 mg, 0.081 mmol) is added followed by more DMF (0.2 mL). The resulting mixture is sealed and stirred vigorously at room temperature for 20 min. More glycine (18.0 mg, 0.240 mmol) is added. The resulting mixture is sealed, stirred vigorously, and heated at 40° C. with a heating block for 14 h. The reaction mixture is diluted with methanol, filtered, and purified via preparatory HPLC (20-70% acetonitrile in water with 0.1% TFA). Fractions containing the desired product are combined and lyophilized to dryness to afford (7-(5-chloro-2-(2-(5-cyano-2-methyl-4-oxo-7-(trifluoromethyl)quinazolin-3(4H)-yl)ethoxy)phenyl)-5-methylthieno[3,2-b]pyridine-3-carbonyl)glycine (Cpd. No. 398F).

961
Example 3D.4

962
Example 3D.5

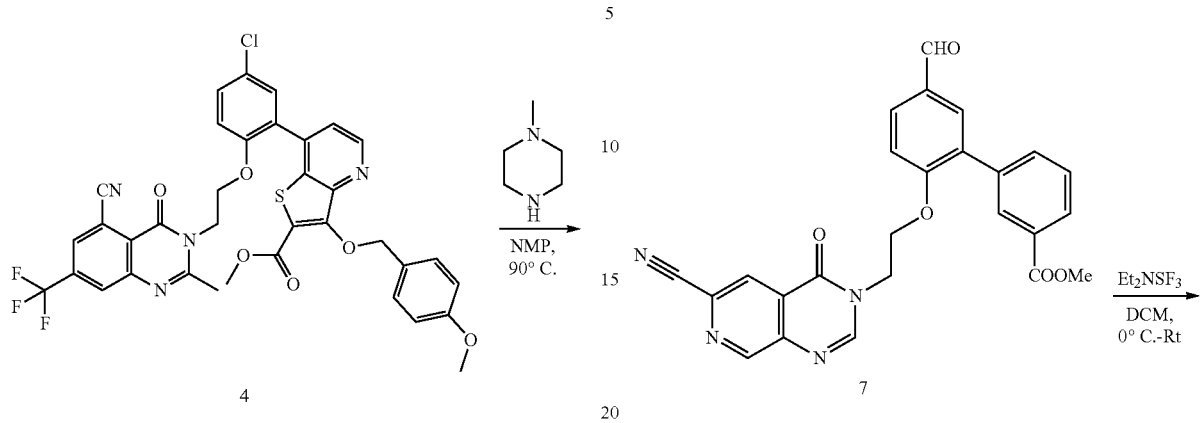

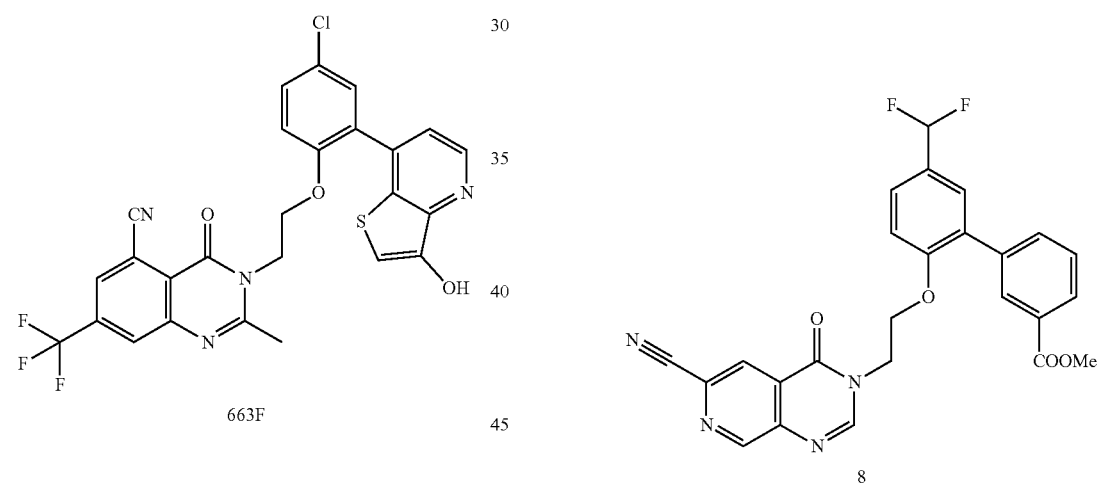

1-Methylpiperazine (0.05 mL, 0.73 mmol) and methyl 7-(5-chloro-2-(2-(5-cyano-2-methyl-4-oxo-7-(trifluoromethyl)quinazolin-3(4H)-yl)ethoxy)phenyl)-3-((4-methoxybenzyl)oxy)thieno[3,2-b]pyridine-2-carboxylate (4, 82 mg, 0.11 mmol) are dissolved in N-methyl pyrrolidinone (1.8 mL) in a screw capped vial equipped with a stir bar. The vial is sealed and heated in a heating block at 145° C. for 4.5 h. The reaction mixture is cooled to room temperature. The reaction mixture is diluted with ethyl acetate and filtered through Celite and volatile solvent removed in vacuo. The residual material is diluted with dimethylsulfoxide and purified via RP-HPLC to afford 3-(2-(4-chloro-2-(3-hydroxythieno[3,2-b]pyridin-7-yl)phenoxy)ethyl)-2-methyl-4-oxo-7-(trifluoromethyl)-3,4-dihydroquinazoline-5-carbonitrile (Cpd. No. 663F).

To a solution of methyl 2'-(2-(6-cyano-4-oxopyrido[3,4-d]pyrimidin-3(4H)-yl)ethoxy)-5'-formyl-[1,1'-biphenyl]-3-carboxylate (7, 0.10 g, 0.22 mmol) in dichloromethane (8 mL), diethylaminosulfur trifluoride (0.052 g, 0.33 mmol) is added at 0° C. The reaction mixture is stirred at room temperature for 16 h. After completion, the reaction mixture is quenched with 10% aqueous sodium hydroxide solution at 0° C. to pH ~7 and extracted with dichloromethane (50 mL). The organic layer is washed with water (50 mL), brine (20 mL), dried over anhydrous sodium sulfate and concentrated under reduced pressure to get crude. The crude is purified by combiflash column (4 g, Redisep) using 10-50% ethyl acetate in hexanes to afford methyl 2'-(2-(6-cyano-4-oxopyrido[3,4-d]pyrimidin-3(4H)-yl)ethoxy)-5'-(difluoromethyl)-[1,1'-biphenyl]-3-carboxylate (8).

Example 3D.6

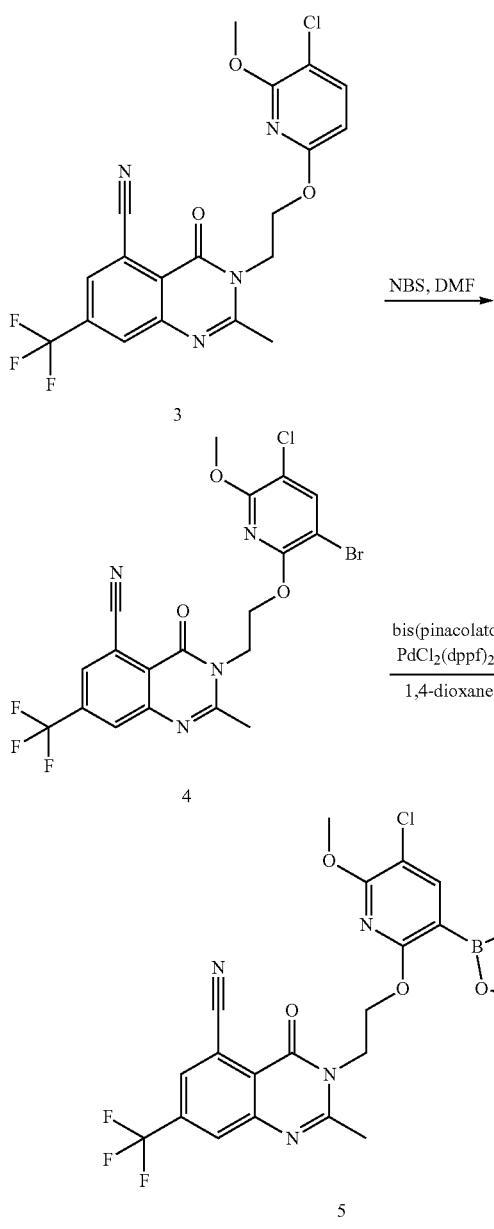

N-bromosuccinimide (39.2 mg, 0.22 mmol) is added to a stirred solution of 3-(2-((5-chloro-6-methoxypyridin-2-yl)oxy)ethyl)-2-methyl-4-oxo-7-(trifluoromethyl)-3,4-dihydroquinazoline-5-carbonitrile (3, 92 mg, 0.21 mmol) in DMF (1 mL) at room temperature. The resulting clear yellow reaction mixture is capped and stirred at room temperature for 3.5 h. More N-bromosuccinimide (19.0 mg, 0.11 mmol) is added and the reaction mixture is capped and stirred at room temperature for 2 h. The reaction mixture is diluted with ethyl acetate and washed three times with brine. The organics are dried over magnesium sulfate, filtered, concentrated on a rotary evaporator, and purified via silica gel chromatography (0-100% ethyl acetate in hexanes) to afford 3-(2-((3-bromo-5-chloro-6-methoxypyridin-2-yl)oxy)ethyl)-2-methyl-4-oxo-7-(trifluoromethyl)-3,4-dihydroquinazoline-5-carbonitrile (4).

3-(2-((3-Bromo-5-chloro-6-methoxypyridin-2-yl)oxy)ethyl)-2-methyl-4-oxo-7-(trifluoromethyl)-3,4-dihydroquinazoline-5-carbonitrile (4, 76.3 mg, 0.147 mmol), potassium acetate (43.4 mg, 0.44 mmol), bis(pinacolato)diboron (44.9 mg, 0.177 mmol), PdCl$_2$(dppf).CH$_2$Cl$_2$ (12 mg, 0.015 mmol), and 1,4-dioxane (0.5 mL) are combined in a 1 dram vial with a stirbar and sparged with argon gas for 1 min. The resulting mixture is sealed, stirred vigorously, and heated at 90° C. with a heating block for 3 h. The reaction mixture is loaded directly onto a silica gel loading column and purified via silica gel chromatography (0-80% ethyl acetate in hexanes) to afford impure 3-(2-((5-chloro-6-methoxy-3-(4,4,5,5-tetramethyl-1,3,2-dioxaborolan-2-yl)pyridin-2-yl)oxy)ethyl)-2-methyl-4-oxo-7-(trifluoromethyl)-3,4-dihydroquinazoline-5-carbonitrile (5)

Example 3D.7

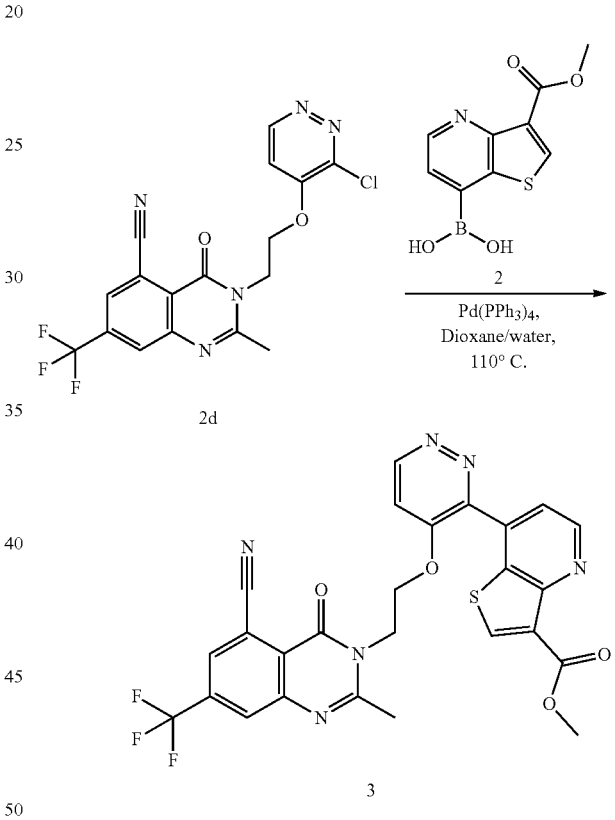

To a solution of 3-(2-((3-chloropyridazin-4-yl)oxy)ethyl)-2-methyl-4-oxo-7-(trifluoromethyl)-3,4-dihydroquinazoline-5-carbonitrile (2d, 20.0 mg, 0.049 mmol), methyl (3-(methoxycarbonyl)thieno[3,2-b]pyridin-7-yl)boronic acid (2, 15.58 mg, 0.049 mmol), Potassium Carbonate (0.15 mL, 0.150 mmol) in 1,4-dioxane (1.5 mL) is added tetrakis (triphenylphosphine)palladium(0) (5.64 mg, 0.0049 mmol) at room temperature and the mixture is degassed by bubbling argon through it for 5 min. The reaction mixture is heated to 90° C. for 16 h. After completion of the reaction, the reaction is diluted with water and extracted with ethyl acetate. The organic layer is washed with water and saturated brine solution, dried over anhydrous sodium sulphate, filtered, and concentrated to dryness under reduced pressure. The crude product is purified by Combiflash (12 g, RediSep column) using 1-5% methanol in dichloromethane as eluent to afford methyl 7-(4-(2-(5-cyano-2-methyl-4-oxo-7-(trifluoromethyl)quinazolin-3(4H)-yl)ethoxy)pyridazin-3-yl)thieno[3,2-b]pyridine-3-carboxylate (3).

Example 3D.8

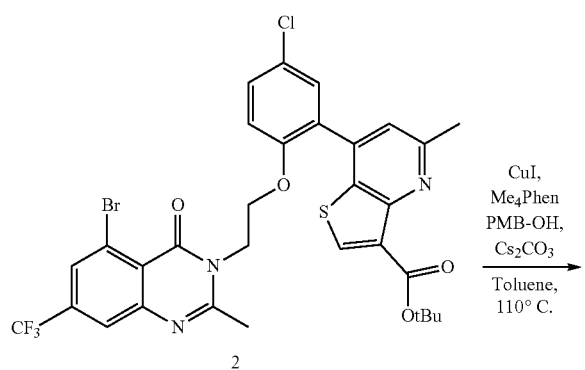

A flame-dried vial is charged with tert-butyl 7-(2-(2-(5-bromo-2-methyl-4-oxo-7-(trifluoromethyl)quinazolin-3(4H)-yl)ethoxy)-5-chlorophenyl)-5-methylthieno[3,2-b]pyridine-3-carboxylate (2, 106 mg, 0.150 mmol), 3,4,7,8-tetramethyl-1,10-phenanthroline (10.8 mg, 0.0457 mmol), copper(I) iodide (6.2 mg, 0.033 mmol), and cesium carbonate (94 mg, 0.290 mmol). The vial is evacuated and backfilled with argon twice. Toluene (1.4 mL) and (4-methoxyphenyl)methanol (29 uL, 33 mg, 0.24 mmol) are added, and the mixture is degassed for 5 min, then stirred at 110° C. After 4 h, the mixture is allowed to cool down to room temperature and stir an additional 14 h, then diluted with EtOAc, then washed with water. The aq. phase is extracted (3×EtOAc), and the combined organic phases are dried (Na$_2$SO$_4$), filtered, and concentrated. Purification by column chromatography (SiO$_2$, 0-50% EtOAc/hexane) provided 61 mg of a ca. 1:1 mixture of products tert-butyl 7-(5-chloro-2-(2-(5-((4-methoxybenzyl)oxy)-2-methyl-4-oxo-7-(trifluoromethyl)quinazolin-3(4H)-yl)ethoxy)phenyl)-5-methylthieno[3,2-b]pyridine-3-carboxylate (3) and tert-butyl 7-(5-chloro-2-(2-(2-methyl-4-oxo-7-(trifluoromethyl)quinazolin-3(4H)-yl)ethoxy)phenyl)-5-methylthieno[3,2-b]pyridine-3-carboxylate (4).

Compounds made using one or more of the general methods described above are shown in Table 3. Where provided, characterization data is to the right of the compounds.

Example 4. Specific Examples

Example 4A. Synthesis of Compound 1188, 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide

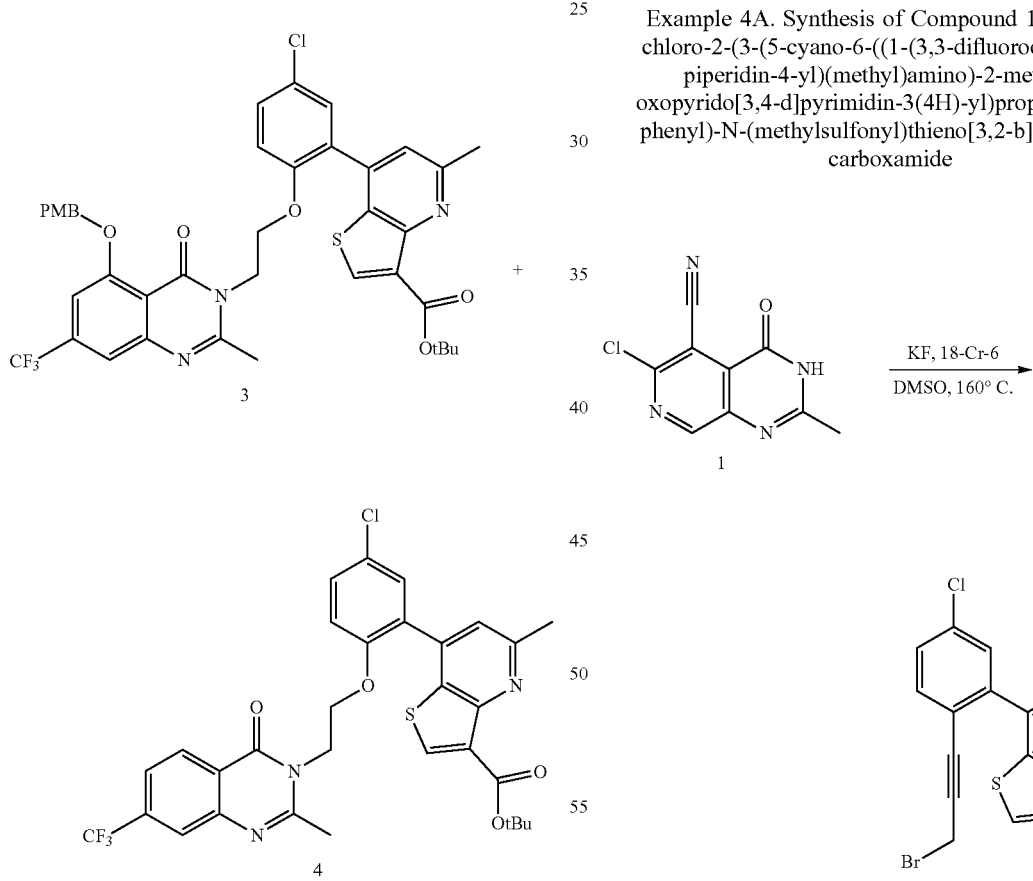

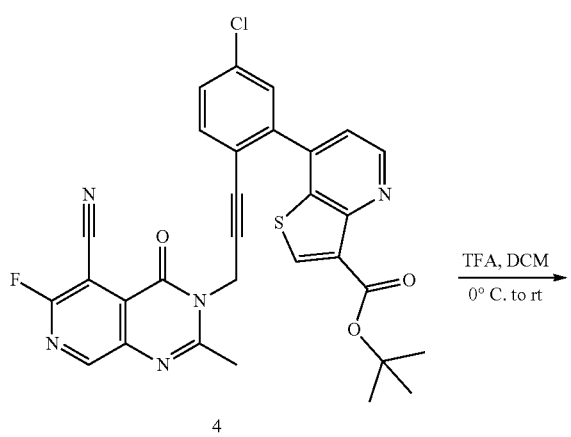

4

TFA, DCM
0° C. to rt

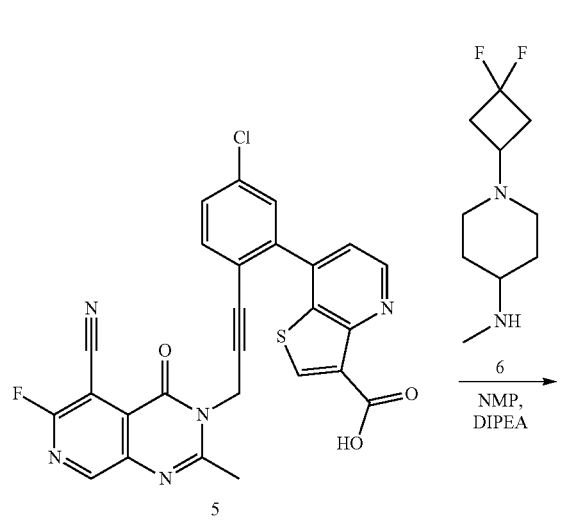

5

NMP, DIPEA

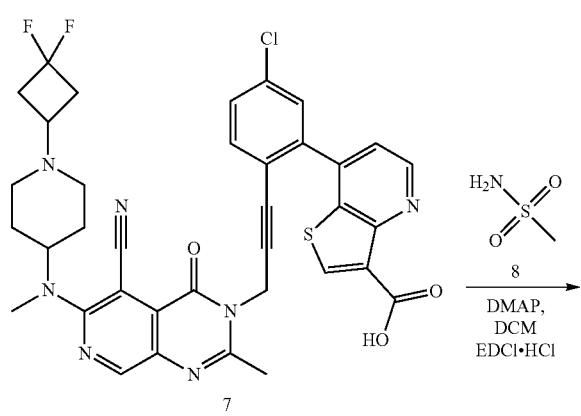

7

DMAP, DCM
EDCI·HCl

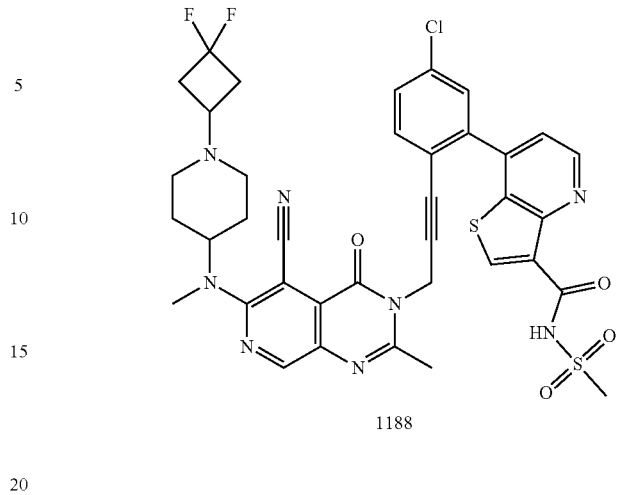

1188

A solution of 6-chloro-2-methyl-4-oxo-3,4-dihydropyrido[3,4-d]pyrimidine-5-carbonitrile (1, 10.0 g, 45.45 mmol) in Dimethyl sulfoxide (200 mL) was purged with argon gas for 10 minutes. 18-crown-6 ether (17.99 g, 68.18 mmol), and Potassium fluoride (13.2 g, 227.25 mmol) were added to reaction mixture and purging continued for 5 minutes. Reaction mixture was then stirred in preheated oil bath at 160° C. for 2 h. Reaction mixture cooled down, poured on to ice cold water and extracted with ethyl acetate. Ethyl acetate layer was washed with brine solution, dried over anhydrous sodium sulphate and concentrated under reduced pressure to get crude product. The crude product obtained was triturated with diethyl ether and dried to get pure 6-fluoro-2-methyl-4-oxo-3,4-dihydropyrido[3,4-d]pyrimidine-5-carbonitrile (2) as light brown solid. Yield: 7.3 g, 78%; MS (ESI) m/z 205.14 [M+1]+.

To a solution of 6-fluoro-2-methyl-4-oxo-3,4-dihydropyrido[3,4-d]pyrimidine-5-carbonitrile (2, 3.70 g, 18.13 mmol) and Potassium carbonate (4.96 g, 36.27 mmol) in N,N-Dimethylformamide (74.0 mL), tert-butyl 7-(2-(3-bromoprop-1-yn-1-yl)-5-chlorophenyl)thieno[3,2-b]pyridine-3-carboxylate (3, 5.85 g, 12.69 mmol) was added at 0° C. and reaction mixture was allowed to come at room temperature over a period of 1 h. After completion, the reaction mixture was poured onto ice cold water. Solid precipitated out was filtered, and dried to get crude product. The crude product was purified by column chromatography using silica gel (100-200 mesh) and 80 to 90% Ethyl acetate in hexanes as eluents. The desired fractions were concentrated under reduced pressure to get solid. Solid obtained was triturated with methanol and dried to afford tert-butyl 7-(5-chloro-2-(3-(5-cyano-6-fluoro-2-methyl-4-oxopyrido[3,4-d]pyrimidin-3(4H)-yl)prop-1-yn-1-yl)phenyl)thieno[3,2-b]pyridine-3-carboxylate (4) as pale yellow solid. Yield: 4.25 g, 40%; MS (ESI) m/z 586.32 [M+1]+. 1H NMR (400 MHz, DMSO-d6) δ 8.94 (s, 1H), 8.68 (d, J=4.80 Hz, 1H), 8.51 (s, 1H), 7.74 (d, J=8.40 Hz, 1H), 7.67-7.63 (m, 3H), 7.40 (d, J=4.80 Hz, 1H), 4.88 (s, 2H), 2.18 (s, 3H), 1.59 (s, 9H).

To a solution of tert-butyl 7-(5-chloro-2-(3-(5-cyano-6-fluoro-2-methyl-4-oxopyrido[3,4-d]pyrimidin-3(4H)-yl) prop-1-yn-1-yl)phenyl)thieno[3,2-b]pyridine-3-carboxylate (4, 0.13 g, 0.22 mmol) in dichloromethane (1.0 mL), 2,2,2-trifluoroacetic acid (1.0 mL) was added at 0° C., and reaction mixture was stirred at room temperature for 6 h. After completion, reaction mixture concentrated under reduced pressure to get solid. The solid obtained was triturated with diethyl ether and dried to 7-(5-chloro-2-(3-(5-cyano-6-fluoro-2-methyl-4-oxopyrido[3,4-d]pyrimidin-3(4H)-yl)prop-1-yn-1-yl)phenyl)thieno[3,2-b]pyridine-3-carboxylic acid (5) as off white solid. Yield: 0.090 g, 81%; MS (ESI) m/z 530.12 [M+1]+. 1H-NMR (400 MHz, DMSO-d6) δ 8.92 (s, 1H), 8.75 (d, J=5.44 Hz, 1H), 8.59 (s, 1H), 7.76 (d, J=8.44 Hz, 1H), 7.69-7.68 (m, 2H), 7.52 (d, J=4.36 Hz, 1H), 4.87 (s, 2H), 2.13 (s, 3H).

To a solution of 7-(5-chloro-2-(3-(5-cyano-6-fluoro-2-methyl-4-oxopyrido[3,4-d]pyrimidin-3(4H)-yl)prop-1-yn-1-yl)phenyl)thieno[3,2-b]pyridine-3-carboxylic acid (5, 0.10 g, 0.189 mmol) and 1-(3,3-difluorocyclobutyl)-N-methylpiperidin-4-amine (6, 0.077 g, 0.37 mmol) in N-methyl-2-pyrrolidone (1.5 mL) was added N,N-diisopropylethylamine (0.064 mL, 0.37 mmol). The reaction mixture was stirred at room temperature for 72 h. After completion, reaction mixture was directly purified by preparative HPLC to afford 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylic acid (7) as a yellow solid. Yield: 0.050 g, 44%; MS (ESI) m/z, 714.50 [M+1]+; 1H-NMR (400 MHz, DMSO-d6) δ 9.80 (bs, 1H), 8.76 (s, 1H), 8.75 (s, 1H), 8.65 (s, 1H), 7.75 (d, J=8.4 Hz, 1H), 7.70-7.67 (m, 2H), 7.54 (d, J=4.8 Hz, 1H), 4.83 (s, 2H), 4.56 (bs, 1H), 3.56 (bs, 4H), 3.11 (bs, 1H), 3.06 (s, 3H), 3.05 (bs, 4H), 2.13 (bs, 4H), 2.11 (s, 3H).

To a solution of 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylic acid (7, 1.70 g, 2.377 mmol) and methanesulfonamide (8, 0.564 g, 5.94 mmol) in dichloromethane (17.0 mL) were added 1-ethyl-3-(3-dimethylaminopropyl) carbodiimide hydrochloride (0.737 g, 4.754 mmol) and 4-(dimethylamino) pyridine (0.725 g, 5.94 mmol) at 0° C. The reaction mixture was stirred at room temperature for 14 h. After completion, the reaction mixture was diluted with water and extracted with dichloromethane. The organic layer was dried over anhydrous sodium sulphate, filtered and concentrated to get crude compound. The crude compound was purified by preparative HPLC to afford 7-(5-chloro-2-(3-(5-cyano-6-((1-(3,3-difluorocyclobutyl)piperidin-4-yl)(methyl)amino)-2-methyl-4-oxopyrido[3,4-d]pyrimidin-3(4H)-yl)prop-1-yn-1-yl)phenyl)-N-(methylsulfonyl)thieno[3,2-b]pyridine-3-carboxamide (Cpd. No. 1188) as a yellow solid. Yield: 1.20 g, 63%; MS (ESI) m/z 791.62 [M+1]+; 1H-NMR (400 MHz, DMSO-d6) δ 12.47 (s, 1H), 8.81-8.78 (m, 3H), 7.77 (d, J=8.40 Hz, 1H), 7.71-7.67 (m, 2H), 7.62 (d, J=4.80 Hz, 1H), 4.83 (s, 2H), 4.59 (bs, 1H), 3.74-3.54 (m, 6H), 3.08 (s, 3H), 2.98-2.88 (m, 6H), 2.11-2.05 (m, 4H), 2.00 (s, 3H).

Example 4B. Synthesis of Compound 1141, 7-(5-chloro-2-(3-(5-cyano-6-((1-(2,2-difluoropropyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylic acid

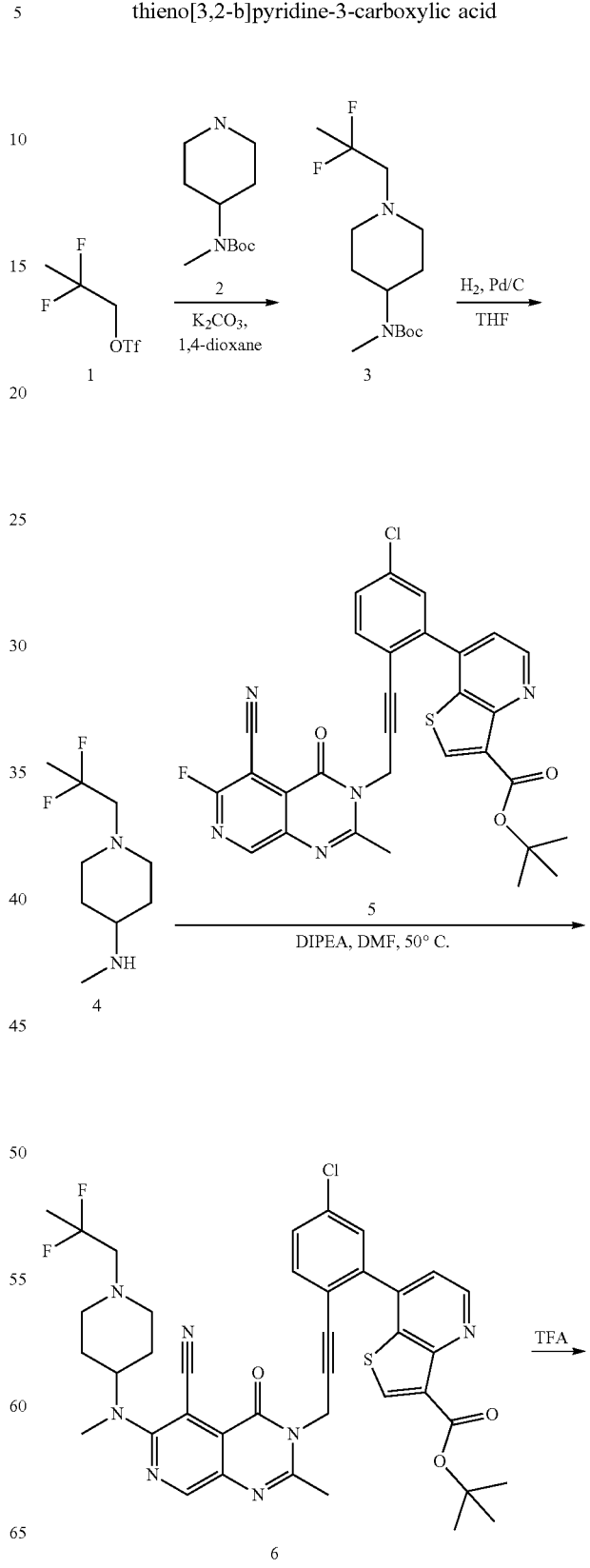

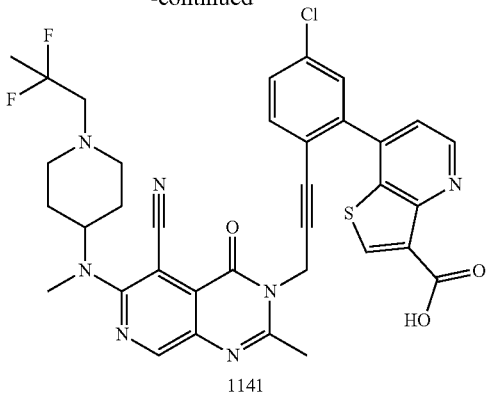

1141

Benzyl methyl(piperidin-4-yl)carbamate (2, 0.990 g, 3.99 mmol), 2,2-difluoropropyl trifluoromethanesulfonate (1, 1.09 g, 4.78 mmol), potassium carbonate (1.10 g, 7.97 mmol), and 1,4-dioxane (15 mL) were combined in a 100 mL round bottom flask with a stirbar under argon. The resulting mixture was stirred vigorously at room temperature under argon for 17 h. The reaction mixture was filtered through Celite and the filter cake was washed thoroughly with ethyl acetate. The filtrate was concentrated on a rotary evaporator. The residue was taken up in dichloromethane and purified via silica gel chromatography (5-60% ethyl acetate in hexanes) to afford benzyl (1-(2,2-difluoropropyl) piperidin-4-yl)(methyl)carbamate (3) as a colorless oil. Yield: 958 mg, 74%; MS (ESI) m/z 327.3 [M+1]+; $^1$H NMR (400 MHz, Chloroform-d) δ 7.40-7.27 (m, 5H), 5.14 (s, 2H), 4.12-3.81 (m, 1H), 2.99 (d, J=11.2 Hz, 2H), 2.82 (s, 3H), 2.66 (t, J=13.7 Hz, 2H), 2.32 (bs, 2H), 1.86-1.68 (m, 2H), 1.70-1.50 (m, 5H).

Benzyl (1-(2,2-difluoropropyl)piperidin-4-yl)(methyl) carbamate (3, 255 mg, 0.781 mmol) was dissolved with stirring in THF (15 mL) in a 100 mL round bottom flask. A combination vacuum/argon/hydrogen manifold was attached and the atmosphere in the flask was removed and replaced with argon twice. 10% palladium on carbon (41.6 mg, 0.039 mmol) was added and the atmosphere in the flask was removed and replaced with hydrogen twice. The resulting mixture was stirred vigorously under hydrogen at room temperature for 45 min. The reaction mixture was filtered through Celite and the filter cake washed thoroughly with diethyl ether. The filtrate was concentrated on a rotary evaporator at room temperature to afford 1-(2,2-difluoropropyl)-N-methylpiperidin-4-amine (4) as a colorless oil with some black carbon impurities. Yield: 150 mg, quantitative yield; MS (ESI) m/z 193.2 [M+1]+; $^1$H NMR (400 MHz, Chloroform-d) δ 2.94-2.86 (m, 2H), 2.65 (t, J=13.6 Hz, 2H), 2.42 (s, 3H), 2.38-2.21 (m, 3H), 1.88-1.79 (m, 2H), 1.62 (t, J=18.7 Hz, 3H), 1.42-1.30 (m, 2H); $^{19}$F NMR (377 MHz, Chloroform-d) 6-91.92 (qt, J=19.0, 13.6 Hz, 2F).

A mixture of tert-butyl 7-(5-chloro-2-(3-(5-cyano-6-fluoro-2-methyl-4-oxopyrido[3,4-d]pyrimidin-3(4H)-yl) prop-1-yn-1-yl)phenyl)thieno[3,2-b]pyridine-3-carboxylate (5, 100 mg, 0.17 mmol), 1-(2,2-difluoropropyl)-N-methylpiperidin-4-amine (4, 98 mg, 0.51 mmol) and N,N-diisopropylethylamine (0.3 mL, 1.71 mmol) in N,N-dimethylformamide (2 mL) was stirred at 50° C. over the weekend. The resulting mixture was concentrated and purified via column chromatography (silica, ethyl acetate/dichloromethane=0-40%) to afford tert-butyl 7-(5-chloro-2-(3-(5-cyano-6-((1-(2,2-difluoropropyl)piperidin-4-yl)(methyl)amino)-2- methyl-4-oxopyrido[3,4-d]pyrimidin-3(4H)-yl)prop-1-yn-1-yl)phenyl)thieno[3,2-b]pyridine-3-carboxylate (6) as a yellow solid. Yield: 98 mg, 76%; MS (ESI) m z 758.2 [M+1]+.

tert-Butyl 7-(5-chloro-2-(3-(5-cyano-6-((1-(2,2-difluoropropyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylate (6, 97 mg, 0.13 mmol) was dissolved in trifluoroacetic acid (3 mL). The reaction was stirred at room temperature for 5 h. The resulting mixture was concentrated. The crude was purified via reversed-phase HPLC (C$_{18}$, acetonitrile/water=15-45%) to afford 7-(5-chloro-2-(3-(5-cyano-6-((1-(2,2-difluoropropyl)piperidin-4-yl)(methyl)amino)-2-methyl-4-oxopyrido[3,4-d]pyrimidin-3(4H)-yl)prop-1-yn-1-yl)phenyl)thieno[3,2-b]pyridine-3-carboxylic acid (1141) as a yellow solid. Yield: 68 mg, 75%; MS (ESI) m z 702.2 [M+1]*; $^1$H NMR (400 MHz, DMSO-d6) δ 8.76 (d, J=4.8 Hz, 1H), 8.74 (s, 1H), 8.65 (s, 1H), 7.78-7.74 (m, 1H), 7.71-7.67 (m, 2H), 7.55 (d, J=4.8 Hz, 1H), 4.83 (s, 2H), 3.11 (s, 3H), 2.09 (s, 3H), 1.78 (t, J=19.5 Hz, 3H).

Example 4C. Synthesis of Compound 634, 7-(5-chloro-2-(2-(5-cyano-2-methyl-6-(4-methylpiperazin-1-yl)-4-oxo-7-(trifluoromethyl)quinazolin-3(4H)-yl)ethoxy)phenyl)-5-methylthieno[3,2-b]pyridine-3-carboxylic acid

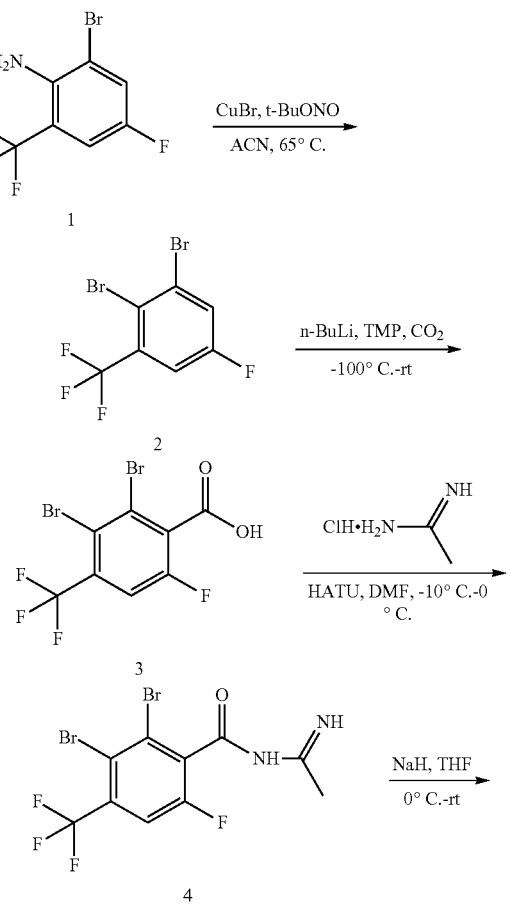

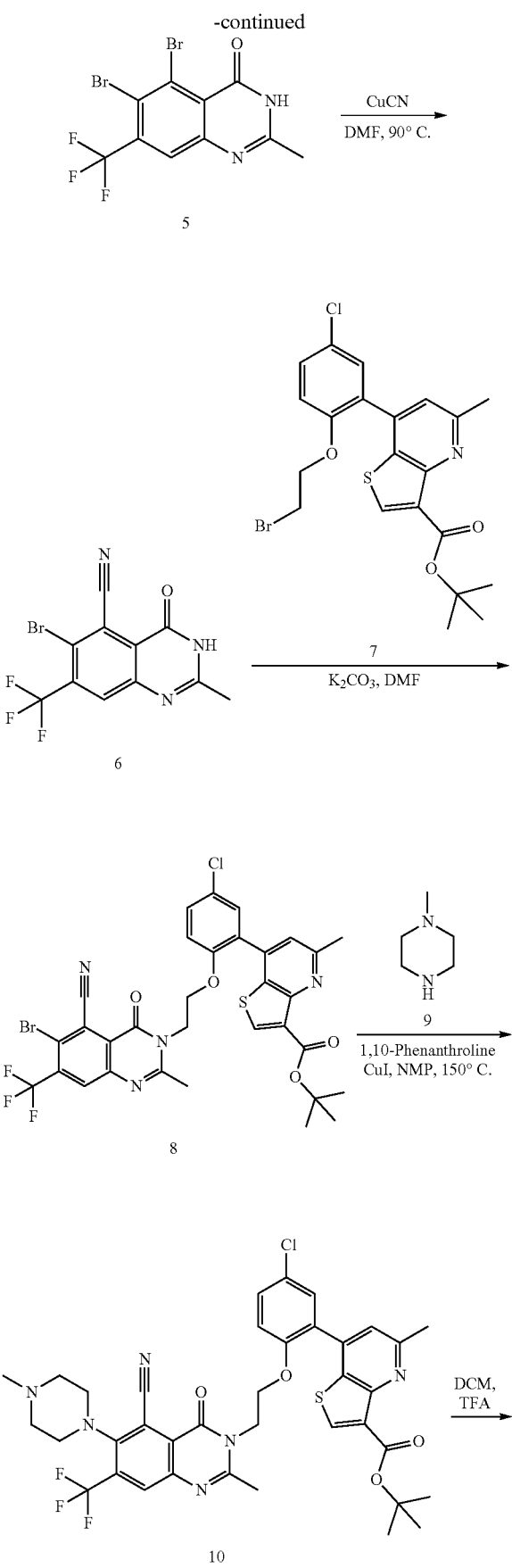

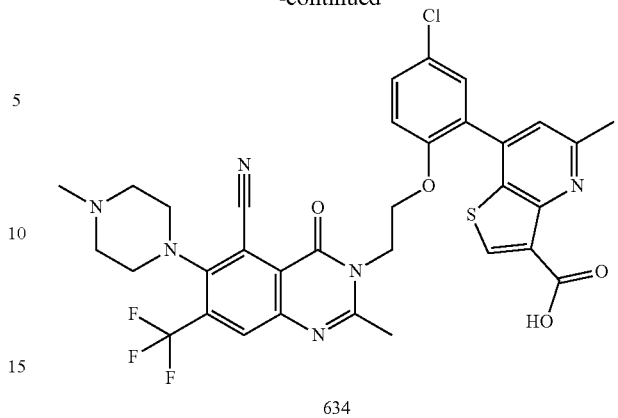

A suspension of copper(I) bromide (89.8 g, 620.1 mmol) and tert-butyl nitrite (63.8 mL, 620.1 mmol) in acetonitrile (2500 mL) was heated at 65° C. for 15 min. A solution of 2-bromo-4-fluoro-6-(trifluoromethyl)aniline (1, 100 g, 387.6 momol) in acetonitrile was added and heated the reaction mixture at 65° C. for 1 h. After completion, the reaction mass was quenched with water and extracted with ethyl acetate. The organic layer was dried over anhydrous sodium sulphate, filtered and concentrated under reduced pressure to get the crude material. The crude compound was purified by column chromatography using 0-5% ethyl acetate in hexanes over silica gel (100-200 mesh) to afford 1,2-dibromo-5-fluoro-3-(trifluoromethyl)benzene (2) as off white solid. Yield: 70.0 g, 55%; no ionization in LCMS; $^1$H NMR (400 MHz, CDCl$_3$) δ 7.60 (dd, J=7.32, 2.84, 1H), 7.43 (dd, J=8.24, 2.80, 1H).

To a solution of 2,2,6,6-tetramethylpiperidine (7.09 mL, 43.61 mmol) in dry tetrahydrofuran (100 mL) was added n-butyllithium (1.2 M, 27.25 mL, 32.71 mmol) drop wise at −78° C. under argon atmosphere. The reaction mixture was warmed to 0° C. and stirred for 30 min It was again cooled to −78° C. and a solution of 1,2-dibromo-5-fluoro-3-(trifluoromethyl)benzene (2, 10.0 g, 31.15 mol) in dry tetrahydrofuran (70 mL) was added at −100° C. and the reaction mixture was stirred for 45 min at −100° C. Carbon dioxide gas was bubbled through the reaction mass at this temperature for 15 min and it was gradually warmed to room temperature in 2 h. After completion, the reaction mixture was quenched with water and washed with diethyl ether. The aqueous layer was acidified to pH ~3-2 with 6 N aqueous hydrogen chloride, extracted with ethyl acetate, washed the organic layer, dried over anhydrous sodium sulfate, filtered and concentrated under reduced pressure to afford 2,3-dibromo-6-fluoro-4-(trifluoromethyl)benzoic acid (3) as brown solid. Yield: 10.0 g, crude, 87%; MS (ESI) m/z 362.9 [M−1]$^-$.

To a solution of 2,3-dibromo-6-fluoro-4-(trifluoromethyl)benzoic acid (3, 27.0 g, 75.8 mmol) and acetamidine hydrochloride (4, 9.31 g, 98.5 mmol) in N,N-dimethylformamide (180 mL), 0-(7-azabenzotriazol-1-yl)-N,N,N',N'-tetramethyluronium hexafluorophosphate (36.5 g, 98.5 mmol) and N,N-diisopropylethyl amine (32.25 mL, 221.9 mmol) were added at −10° C. and stirred for 3 h at 0° C. After completion, the reaction mass was quenched with ice-water and extracted with ethyl acetate. The organic layer was dried over anhydrous sodium sulfate and concentrated to dryness under reduced pressure. The residue was washed with pentanes to afford 2,3-dibromo-6-fluoro-N-(1-iminoethyl)-4-

(trifluoromethyl)benzamide (4) as a brown gum. Yield: 30 g (crude); MS (ESI)) m/z 404.8 [M+1]+.

To a solution of 2,3-dibromo-6-fluoro-N-(1-iminoethyl)-4-(trifluoromethyl)benzamide (4, 30.0 g, 74.4 mmol) in tetrahydrofuran (250 mL), sodium hydride (60%) (5.9 g, 148.8 mmol) was added at 0° C., warmed to room temperature and continued to stir at room temperature for 16 h. After completion, the reaction mixture was quenched with water and extracted with ethyl acetate. The organic layer was dried over anhydrous sodium sulfate and concentrated to dryness under reduced pressure. The residue was washed with diethyl ether to afford 5,6-dibromo-2-methyl-7-(trifluoromethyl)quinazolin-4(3H)-one (5) as white solid. Yield: 9.95 g, 35%; MS (ESI) m/z 383.01 [M−1]−.

To a stirred solution of 5,6-dibromo-2-methyl-7-(trifluoromethyl)quinazolin-4(3H)-one (5, 6.0 g, 15.62 mmol) in dimethylformamide (90 mL), copper(I) cyanide (1.53 g, 17.18 mmol) was added at room temperature and the reaction mixture was heated and stirred at 90° C. for 2 h. After completion, the reaction mass was cooled to room temperature, diluted with ethyl acetate and washed with water and 1 N aqueous hydrogen chloride. The organic layer was separated, dried over sodium sulphate and concentrated under reduced pressure. The crude compound was purified by Combi flash (40 g, Redi Sep column) using 70% ethyl acetate in hexanes as eluent. The desired fractions were concentrated under reduced pressure to afford 6-bromo-2-methyl-4-oxo-7-(trifluoromethyl)-3,4-dihydroquinazoline-5-carbonitrile (6) as yellow solid. Yield: 3.2 g, 62.7%; MS (ESI) m/z 330.06 [M−1]−.

To a stirred solution of 6-bromo-2-methyl-4-oxo-7-(trifluoromethyl)-3,4-dihydroquinazoline-5-carbonitrile (6, 2.0 g, 6.0 mmol) in N,N-dimethylformamide (25.0 mL) was added potassium carbonate (2.48 g, 18.0 mmol) at room temperature and the mixture was stirred for 20 min. Then tert-butyl 7-(2-(2-bromoethoxy)-5-chlorophenyl)-5-methylthieno[3,2-b]pyridine-3-carboxylate (7, 2.91 g, 6.0 mmol) was added to the reaction mixture at room temperature and stirring was continued for 16 h. After completion, the reaction mixture was diluted with water and extracted with ethyl acetate. The organic layer was washed with water and saturated brine, dried over anhydrous sodium sulphate, filtered and concentrated. The crude product was purified by column chromatography using silica gel (100-200 mesh) and 70% ethyl acetate in hexanes as eluent. The desired fractions were concentrated under reduced pressure to afford tert-butyl 7-(2-(2-(6-bromo-5-cyano-2-methyl-4-oxo-7-(trifluoromethyl)quinazolin-3(4H)-yl)ethoxy)-5-chlorophenyl)-5-methylthieno[3,2-b]pyridine-3-carboxylate (8) as a white solid. Yield: 1.7 g, 70%; MS (ESI) m/z 731.14 [M−1].

To a solution of tert-butyl 7-(2-(2-(6-bromo-5-cyano-2-methyl-4-oxo-7-(trifluoromethyl)quinazolin-3(4H)-yl)ethoxy)-5-chlorophenyl)-5-methylthieno[3,2-b]pyridine-3-carboxylate (8, 0.20 g, 0.273 mmol) in N-Methyl-2-pyrrolidone (5.0 mL) was added 1-methylpiperazine (9, 0.06 mL, 0.546 mmol) and the reaction mixture was degassed by argon for 10 min. Then copper(I) iodide (0.005 g, 0.027 mmol) and 1,10-phenanthroline (0.009 g, 0.054 mmol) was added and reaction mixture was heated at 150° C. for 6 h. After completion reaction mixture was diluted with water, and extracted with ethyl acetate. The organic layer was dried over anhydrous sodium sulphate, filtered and concentrated to get crude compound. Crude compound obtained was purified by column chromatography using silica gel (100-200 mesh) and 3-4% methanol in dichloromethane to afford tert-butyl 7-(5-chloro-2-(2-(5-cyano-2-methyl-6-(4-methylpiperazin-1-yl)-4-oxo-7-(trifluoromethyl)quinazolin-3(4H)-yl)ethoxy)phenyl)-5-methylthieno[3,2-b]pyridine-3-carboxylate (10) as white solid. Yield: 0.08 g, 39%; MS (ESI) m/z, 751.23 [M−1]−.

To a solution tert-butyl 7-(5-chloro-2-(2-(5-cyano-2-methyl-6-(4-methylpiperazin-1-yl)-4-oxo-7-(trifluoromethyl)quinazolin-3(4H)-yl)ethoxy)phenyl)-5-methylthieno[3,2-b]pyridine-3-carboxylate (10, 0.10 g, 0.132 mmol) in dichloromethane (1.5 mL), 2,2,2-trifluoroacetic acid (0.5 mL) was added at 0° C., and reaction mixture was stirred for 12 h at room temperature. After completion, reaction mixture concentrated under reduced pressure to get the crude compound. The crude compound was purified by preparative HPLC to afford 7-(5-chloro-2-(2-(5-cyano-2-methyl-6-(4-methylpiperazin-1-yl)-4-oxo-7-(trifluoromethyl)quinazolin-3(4H)-yl)ethoxy)phenyl)-5-methylthieno[3,2-b]pyridine-3-carboxylic acid (634) as white solid. Yield: 0.020 g, 21%; MS (ESI) m/z 697.13 [M+1]+. $^1$H-NMR (400 MHz, DMSO-d6) δ 13.51 (bs, 1H), 9.75 (bs, 1H), 8.23 (s, 1H), 7.92 (s, 1H), 7.61-7.58 (t, J=6.5 Hz, 1H), 7.42-7.41 (t, J=6.5 Hz, 2H), 7.37 (d, J=8.92 Hz, 1H), 4.40 (t, J=6.16 Hz, 2H), 4.24 (t, J=6.12, 2H), 3.83 (m, 2H), 3.49 (m, 2H), 3.24 (m, 2H), 3.03 (m, 2H), 2.28 (s, 3H), 2.71 (s, 3H), 1.82 (s, 3H)

TABLE 3

Other Compounds

| Compound | | Characterization |
|---|---|---|
| 1 | 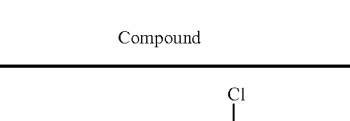 | MS (ESI) m/z 436.26 [M + 1]+; UPLC: 99.88%; 1H NMR (400 MHz, DMSO-d6) δ 12.94 (s, 1H), 8.95 (s, 1H), 8.59 (d, J = 5.2 Hz, 1H), 7.89-7.86 (m, 2H), 7.82 (s, 1H), 7.50 (d, J = 7.6 Hz, 1H), 7.43-7.38 (m, 2H), 7.27 (d, J = 2.6 Hz, 1H), 7.19 (d, J = 8.92 Hz, 1H), 4.34 (s, 4H), 2.23 (s, 3H) |

TABLE 3-continued

| | Other Compounds | |
|---|---|---|
| | Compound | Characterization |
| 2 | 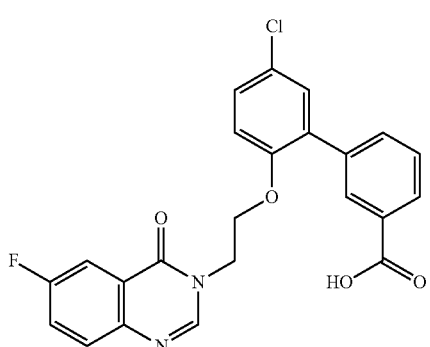 | MS (ESI) m/z 437.16 [M + 1]+; UPLC: 97.10%; 1H NMR (400 MHz, DMSO-d6) δ 12.97 (s, 1H), 7.99 (s, 1H), 7.93 (s, 1H), 7.87 (d, J = 7.7 Hz, 1H), 7.77-7.75 (m, 1H), 7.71-7.68 (m, 2H), 7.57 (d, J = 7.7 Hz, 1H), 7.41-7.38 (m, 2H), 7.34 (d, J = 3.7 Hz, 1H), 7.20 (d, J = 8.8 Hz, 1H), 4.32 (s, 4H) |
| 3 | 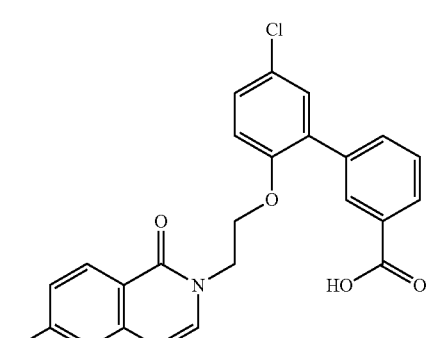 | MS (ESI) m/z 439.25 [M + 1]+; UPLC: 99.82%; 1H NMR (400 MHz, DMSO-d6) δ 12.85 (bs, 1H), 8.17-8.14 (m, 1H), 8.03 (s, 1H), 7.93 (s, 1H), 7.88 (d, J = 7.8 Hz, 1H), 7.58 (d, J = 7.6 Hz, 1H), 7.42-7.36 (m, 4H), 7.34 (d, J = 2.5 Hz, 1H), 7.20 (d, J = 7.7 Hz, 1H), 4.32-4.30 (m, 4H) |
| 4 | 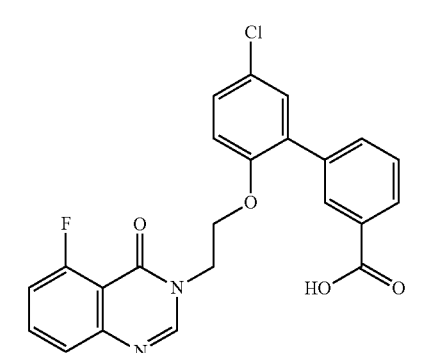 | MS (ESI) m/z 439.2 [M + 1]+; UPLC: 96.95%; 1H NMR (400 MHz, DMSO-d6) δ 13.07 (bs, 1H), 8.00 (s, 1H), 7.95 (s, 1H), 7.87 (d, J = 7.8 Hz, 1H), 7.80-7.75 (m, 1H), 7.60 (d, J = 7.8 Hz, 1H), 7.45 (s, 1H), 7.43-7.38 (m, 2H), 7.35 (d, J = 2.6 Hz, 1H), 7.29-7.24 (m, 1H), 7.20 (d, J = 8.8 Hz, 1H), 4.29 (dd, J = 14.0, 4.44 Hz, 4H) |
| 5 | 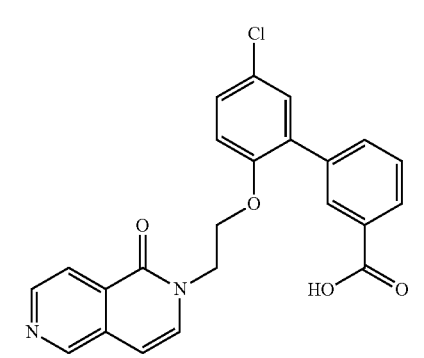 [SMILES: O=C(O)c1cccc(-c2cc(Cl)ccc2OCCn2ccc3cnccc3c2=O)c1] | MS (ESI) m/z 421.21 [M + 1]+; UPLC: 97.35%; 1H NMR (400 MHz, DMSO-d6) δ 13.05 (s, 1H), 9.01 (s, 1H), 8.62 (d, J = 5.3 Hz, 1H), 7.97-7.96 (m, 2H), 7.90 (d, J = 7.8 Hz, 1H), 7.60 (d, J = 7.8 Hz, 1H), 7.45-7.39 (m, 2H), 7.34 (d, J = 2.6 Hz, 1H), 7.27 (d, J = 7.4 Hz, 1H), 7.20 (d, J = 8.92 Hz, 1H), 6.50 (d, J = 7.32 Hz, 1H), 4.32-4.30 (m, 4H) |

TABLE 3-continued

| | Other Compounds | |
|---|---|---|
| | Compound | Characterization |
| 6 | 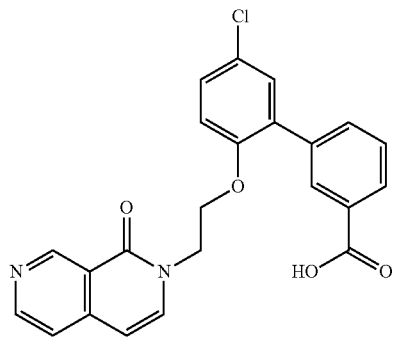 [SMILES: O=C(O)c1cccc(-c2cc(Cl)ccc2OCCn2ccc3ccncc3c2=O)c1] | MS (ESI) m/z 421.21 [M + 1]+; UPLC: 97.08%; 1H NMR (400 MHz, DMSO-d6) δ 13.04 (s, 1H), 9.31 (s, 1H), 8.69 (d, J = 4.72 Hz, 1H), 7.95 (s, 1H), 7.89 (d, J = 7.56 Hz, 1H), 7.61-7.57 (m, 1H), 7.42-7.38 (m, 2H), 7.34 (s, 1H), 7.20 (d, J = 8.76 Hz, 1H), 6.40 (d, J = 7.2 Hz, 1H), 4.31 (s, 4H) |
| 7 | 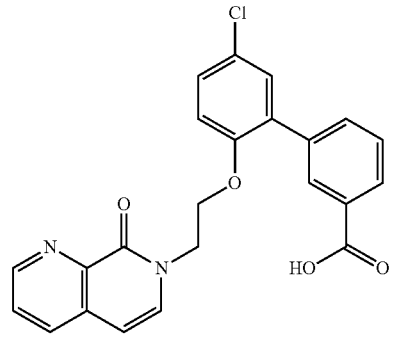 | MS (ESI) m/z 421.18 [M + H]+; UPLC: 99.14%; 1H NMR (400 MHz, DMSO-d6) δ 13.03 (s, 1H), 8.76 (s, 1H), 8.07 (d, J = 8.04 Hz, 1H), 7.98 (s, 1H), 7.91 (d, J = 7.8 Hz, 1H), 7.69-7.66 (m, 1H), 7.62 (d, J = 7.76 Hz, 1H), 7.44 (t, J = 7.72 Hz, 1H), 7.40-7.34 (m, 2H), 7.23-7.19 (m, 2H), 6.37 (d, J = 7.2 Hz, 1H), 4.32 (s, 4H) |
| 8 | 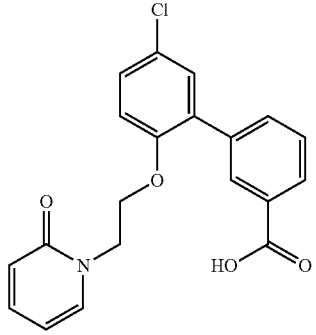 [SMILES: O=C(O)c1cccc(-c2cc(Cl)ccc2OCCn2ccccc2=O)c1] | MS (ESI) m/z 583.31 [M + 1]+; 1H NMR (400 MHz, DMSO-d6) δ 12.46 (bs, 1H), 8.84 (d, J = 4.4 Hz, 1H), 8.47 (s, 1H), 7.85 (s, 1H), 7.71-7.22 (m, 6H), 4.39-4.37 (m, 2H), 4.23-4.20 (m, 2H), 1.73 (s, 3H) |
| 9 | 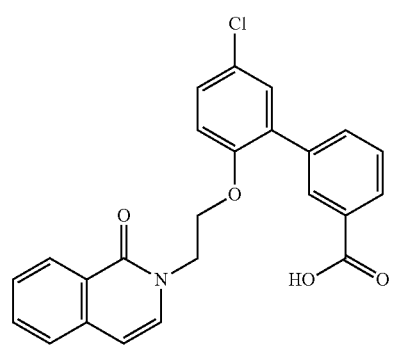 [SMILES: O=C(O)c1cccc(-c2cc(Cl)ccc2OCCn2ccc3ccccc3c2=O)c1] | MS (ESI) m/z 420.37 [M + H]+; UPLC: 99.10%; 1H NMR (400 MHz, DMSO-d6) δ 13.07 (s, 1H), 8.18 (d, J = 8.04 Hz, 1H), 8.00 (s, 1H), 7.92 (d, J = 7.7 Hz, 1H), 7.68 (t, J = 7.0 Hz, 1H), 7.63-7.58 (m, 2H), 7.50-7.42 (m, 2H), 7.40-7.34 (m, 2H), 7.20 (d, J = 8.7 Hz, 1H), 7.13 (d, J = 7.3 Hz, 1H), 6.37 (d, J = 7.36 Hz, 1H), 4.31-4.27 (m, 4H). |

TABLE 3-continued

| Other Compounds | |
|---|---|
| Compound | Characterization |

10

MS (ESI) m/z 421.21 [M + 1]+; UPLC: 99.17%; 1H NMR (400 MHz, DMSO-d6) δ 8.89-8.87 (m, 1H), 8.48 (dd, J = 8.0, 1.5 Hz, 1H), 7.99 (s, 1H), 7.90 (d, J = 7.7 Hz, 1H), 7.55 (d, J = 7.7 Hz, 1H), 7.49-7.33 (m, 5H), 7.19 (d, J = 8.7 Hz, 1H), 6.43 (d, J = 7.56 Hz, 1H), 4.30 (s, 4H)

11

MS (ESI) m/z 421.21 [M + 1]+; UPLC: 98.51%; 1H NMR (400 MHz, DMSO-d6) δ 12.98 (bs, 1H), 8.11 (dd, J = 8.0, 1.2 Hz, 1H), 8.10 (s, 1H), 7.94 (s, 1H), 7.89 (d, J = 7.6 Hz, 1H), 7.83-7.78 (m, 1H), 7.63 (d, J = 8.0 Hz, 1H), 7.54-7.50 (m, 2H), 7.41-7.37 (m, 2H), 7.35 (d, J = 2.6 Hz, 1H), 7.20 (d, J = 8.8 Hz, 1H), 4.32 (s, 4H)

12

MS (ESI) m/z 422.22 [M + 1]+; UPLC: 97.46%; 1H NMR (400 MHz, DMSO-d6) δ 13.02 (bs, 1H), 8.94 (d, J = 2.72 Hz, 1H), 8.49 (dd, J = 7.84, 1.6 Hz, 1H), 8.25 (s, 1H), 7.96 (s, 1H), 7.87 (d, J = 7.68 Hz, 1H), 7.60-7.53 (m, 2H), 7.48-7.34 (m, 3H), 7.20 (d, J = 8.72 Hz, 1H), 4.33 (s, 4H)

13

MS (ESI) m/z 422.18 [M + 1]+; UPLC: 98.27%; 1H NMR (400 MHz, DMSO-d6) δ 12.94 (bs, 1H), 9.26 (s, 1H), 8.82 (d, J = 5.6 Hz, 1H), 8.19 (s, 1H), 7.92 (s, 1H), 7.86 (d, J = 7.7 Hz, 1H), 7.59-7.54 (m, 2H), 7.41-7.37 (m, 2H), 7.33 (d, J = 2.6 Hz, 1H), 7.20 (d, J = 8.8 Hz, 1H), 4.33 (s, 4H)

TABLE 3-continued

| | Other Compounds | |
|---|---|---|
| | Compound | Characterization |
| 14 | | MS (ESI) m/z 422.24 [M + 1]+; UPLC: 93.73%; 1H NMR (400 MHz, DMSO-d6) δ 9.39 (s, 1H), 9.30 (s, 1H), 7.94 (s, 1H), 7.87 (d, J = 7.9 Hz, 1H), 7.66 (d, J = 7.6 Hz, 1H), 7.58 (d, J = 7.4 Hz, 1H), 7.44-7.38 (m, 2H), 7.32 (s, 1H), 7.20 (d, J = 8.8 Hz, 1H), 6.38 (d, J = 7.5 Hz, 1H), 4.32 (s, 4H) |
| 15 | | MS (ESI) m/z 422.18 [M + 1]+; UPLC: 96.38%; 1H NMR (400 MHz, DMSO-d6) δ 13.03 (bs, 1H), 9.43 (d, J = 5.4 Hz, 1H), 8.19 (d, J = 5.0 Hz, 1H), 7.95 (s, 1H), 7.88 (d, J = 6.6 Hz, 1H), 7.60 (d, J = 7.7 Hz, 1H), 7.50 (d, J = 7.6 Hz, 1H), 7.45-7.33 (m, 3H), 7.20 (d, J = 8.8 Hz, 1H), 6.76 (d, J = 7.4 Hz, 1H), 4.34-4.31 (m, 4H) |
| 16 | | MS (ESI) m/z 642.21 [M + 1]+; 1H NMR (400 MHz, DMSO-d6) δ 8.86 (d, J = 4.7 Hz, 1H), 8.11 (s, 1H), 8.07 (s, 1H), 7.63 (dd, J = 8.8, 2.3 Hz, 1H), 7.51 (d, J = 4.8 Hz, 1H), 7.43 (d, J = 2.5 Hz, 1H), 7.39 (d, J = 9.1 Hz, 1H), 4.67 (bs, 2H), 4.45 (t, J = 5.2 Hz 2H), 4.29 (t, J = 3.9 Hz 2H), 2.93 (s, 6H), 1.78 (s, 3H) |
| 17 | | MS (ESI) m/z 423.23 [M + 1]+; UPLC: 92.07%; 1H NMR (400 MHz, DMSO-d6) δ 9.43 (s, 1H). 9.39 (s, 1H), 8.58 (s, 1H), 7.86 (s, 1H), 7.85 (d, J = 7.7 Hz, 1H), 7.58 (d, J = 7.7 Hz, 1H), 7.41-7.37 (m, 2H), 7.33 (d, J = 2.6 Hz, 1H), 7.20 (d, J = 8.8 Hz, 1H), 4.31 (s, 4H) |

TABLE 3-continued

| | Other Compounds | |
|---|---|---|
| | Compound | Characterization |
| 18 | 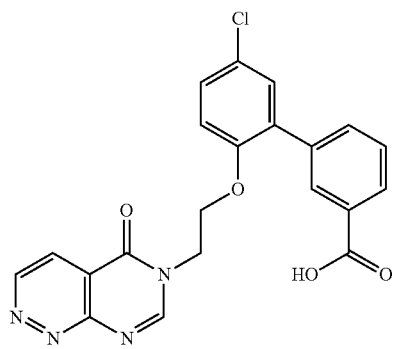 | MS (ESI) m/z 423.23 [M + 1]+; UPLC: 99.81%; 1H NMR (400 MHz, DMSO-d6) δ 13.07 (bs, 1H), 9.48 (d, J = 5.0 Hz, 1H), 8.33 (s, 1H), 8.23 (d, J = 5.1 Hz, 1H), 7.93 (s, 1H), 7.86 (d, J = 7.8 Hz, 1H), 7.62 (d, J = 6.2 Hz, 1H), 7.44-7.34 (m, 3H), 7.20 (d, J = 8.8 Hz, 1H), 4.33 (s, 4H) |
| 19 | 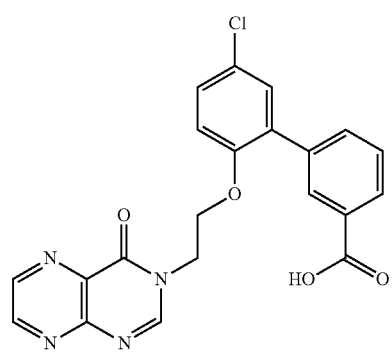 [SMILES: O=C(O)c1cccc(-c2cc(Cl)ccc2OCCn2ccc3ncccc3c2=O)c1] | MS (ESI) m/z 423.23 [M + 1]+; UPLC: 96.78%; 1H NMR (400 MHz, DMSO-d6) δ 8.99 (d, J = 2.0 Hz, 1H), 8.85 (d, J = 2.0 Hz, 1H), 8.32 (s, 1H), 7.95 (s, 1H), 7.86 (d, J = 7.8 Hz, 1H), 7.58 (d, J = 7.7 Hz, 1H), 7.40-7.36 (m, 2H), 7.34 (d, J = 2.7 Hz, 1H), 7.20 (d, J = 8.8 Hz, 1H), 4.36-4.35 (m, 4H) |
| 20 | 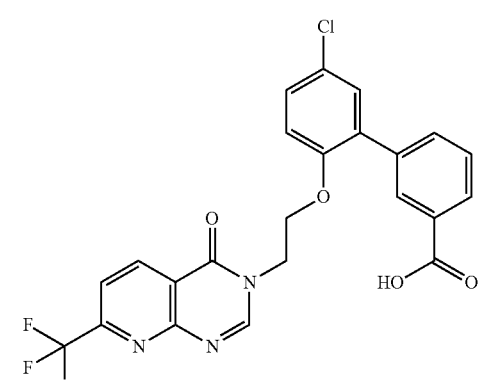 | MS (ESI) m/z 422.22 [M + 1]+; UPLC: 97.46%; 1H NMR (400 MHz, DMSO-d6) δ 12.98 (bs, 1H), 8.74 (d, J = 8.0 Hz, 1H), 8.36 (s, 1H), 7.98 (d, J = 8.1 Hz, 1H), 7.94 (s, 1H), 7.84 (d, J = 7.8 Hz, 1H), 7.62 (d, J = 7.7 Hz, 1H), 7.42-7.38 (m, 2H), 7.35 (d, J = 2.6 Hz, 1H), 7.20 (d, J = 8.8 Hz, 1H), 4.35 (s, 4H) |
| 21 | 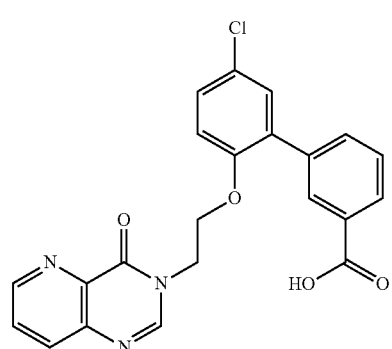 | MS (ESI) m/z 422.18 [M + 1]+; UPLC: 98.77%; 1H NMR (400 MHz, DMSO-d6) δ 12.96 (bs, 1H), 8.79 (dd, J = 4.1, 1.1 Hz, 1H), 8.06-8.04 (m, 2H), 7.93 (s, 1H), 7.88 (d, J = 7.7 Hz, 1H), 7.81-7.78 (m, 1H), 7.60-7.58 (m, 1H), 7.42-7.38 (m, 2H), 7.34 (d, J = 2.6 Hz, 1H), 7.21 (d, J = 8.8 Hz, 1H), 4.34 (s, 4H) |

TABLE 3-continued

| | Other Compounds | |
|---|---|---|
| | Compound | Characterization |
| 22 | | MS (ESI) m/z 585.30 [M + 1]+; 1H NMR (400 MHz, DMSO-d6) δ 8.80 (d, J = 4.8 Hz, 1H), 8.44 (s, 1H), 8.04 (d, J = 9.72 Hz, 1H), 7.61-7.59 (dd, J = 2.56 Hz, J = 2.64 Hz, 1H), 7.50-7.36 (m, 4H), 4.42 (t, J = 4.56 Hz, 2H), 4.28 (t, J = 4.64 Hz, 2H), 1.87 (s, 3H) |
| 23 | | MS (ESI) m/z 438.28 [M + 1]+; 1H NMR (400 MHz, DMSO-d6) δ 9.10 (s, 1H), 8.53 (s, 1H), 8.29 (s, 1H), 7.93 (s, 1H), 7.89 (d, J = 7.6 Hz, 1H), 7.83 (dd, J = 2.12, 8.44 Hz, 1H), 7.77 (d, J = 1.96 Hz, 1H), 7.56 (d, J = 7.72 Hz, 1H), 7.43 (t, J = 15.5 Hz, 1H), 7.33 (d, J = 8.64 Hz, 1H), 4.44 (d, J = 4.84 Hz, 2H), 4.40 (d, J = 4.68 Hz, 2H) |
| 24 | | MS (ESI) m/z 485.37 [M + 1]+; 1H NMR (400 MHz, DMSO-d6) δ 12.74 (s, 1H), 9.11 (s, 1H), 8.56 (s, 1H), 8.01 (s, 1H), 7.74-7.77 (m, 1H), 7.32-7.40 (m, 3H), 7.13-7.16 (m, 2H), 4.29 (s, 4H), 1.55 (s, 3H) |
| 25 | | MS (ESI) m/z 457.23 [M + 1]+; 1H NMR (400 MHz, DMSO-d6) δ 13.05 (s, 1H), 9.19 (s, 1H), 8.86 (s, 1H), 8.62 (s, 1H), 8.34 (s, 1H), 7.99-8.07 (m, 2H), 7.72 (s, 1H), 7.58-7.63 (m, 2H), 7.04 (s, 1H), 5.48 (s, 2H) |

TABLE 3-continued
| Other Compounds | |
|---|---|
| Compound | Characterization |
| 26 | 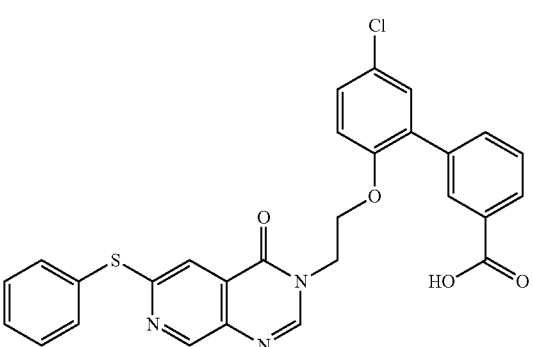 | MS (ESI) m/z 530.0 [M + 1]+; 1H NMR (400 MHz, DMSO-d6) δ 13.01 (s, 1H), 8.88 (s, 1H), 8.02 (s, 1H), 7.58-7.90 (m, 2H), 7.64 (s, 2H), 7.54 (s, 4H), 7.30-7.36 (m, 4H), 7.16 (s, 1H), 4.26 (s, 4H) |
| 27 | 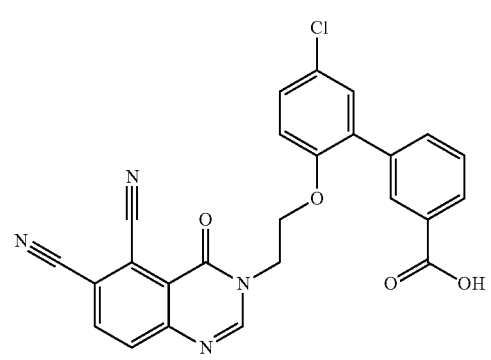 [SMILES: N#Cc1ccc2ncn(CCOc3ccc(Cl)cc3-c3cccc(C(=O)O)c3)c(=O)c2c1C#N] | MS (ESI) m/z 471.32 [M + 1]+; 1H NMR (400 MHz, DMSO-d6) δ 13.06 (s, 1H), 8.38 (s, 1H), 8.20 (s, 1H), 8.039 (d, J = 8.56 1H), 7.87-7.86 (m, 1H), 7.82-7.81 (m, 1H), 7.62-7.58 (m, 1H), 7.43-7.39 (m, 2H), 7.33 (d, J = 2.64 Hz, 1H), 7.21 (d, J = 8.84 Hz, 1H), 4.35 (s, 4H) |
| 28 | 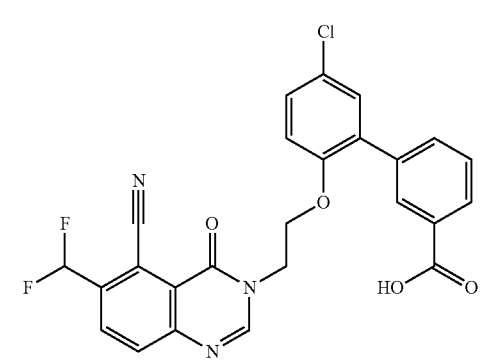 | MS (ESI) m/z 496.36 [M + 1]+UPLC: 99.32%; 1H NMR (400 MHz, DMSO-d6) δ 12.97 (s, 1H), 8.17-8.15 (m, 2H), 8.04 (d, J = 8.56 Hz, 1H), 7.90-7.89 (m, 1H), 7.84-7.82 (m, 1H), 7.61-7.58 (m, 1H), 7.52-7.25 (m, 4H), 7.21 (d, J = 8.88 Hz, 1H), 4.35 (s, 4H) |
| 29 | 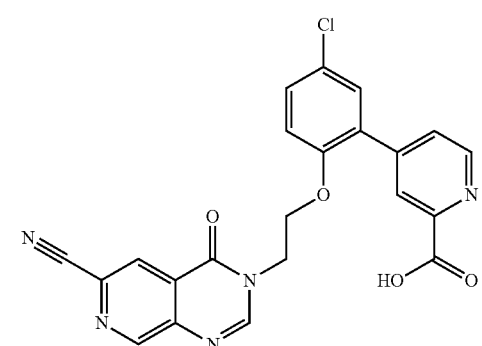 | MS (ESI) m/z 448.31 [M + 1]+; 1H NMR (400 MHz, DMSO-d6) δ 9.09 (s, 1H), 8.63(d, J = 4.47 Hz, 1H), 8.53 (s, 1H), 8.31 (s, 1H), 7.99 (s, 1H), 7.63 (d, J = 3.64 Hz, 1H), 7.49-7.45 (m, 2H), 7.25 (d, J = 8.68 Hz, 1H), 4.38 (m, 4H) |

TABLE 3-continued

Other Compounds

| Compound | Characterization |
|---|---|
| 30 | MS (ESI) m/z 504.39 [M + 1]+. UPLC: 99.59%; 1H NMR (400 MHz, DMSO-d6) δ 8.96 (s, 1H), 8.81(d, J = 4.88 Hz, 1H), 8.55 (s, 1H), 8.45 (s, 1H), 7.91 (s, 1H), 7.61-7.59 (dd, J = 2.60, 8.88 Hz, 1H), 7.49-7.46 (m, 2H), 7.35 (d, J = 8.96 Hz, 1H), 4.40-4.38 (t, J = 5.00 Hz, 2H), 4.25-4.23 (t, J = 4.84 Hz, 2H) |
| 31 | MS (ESI) m/z 457.36 [M + 1]+; 1H NMR (400 MHz, DMSO-d6) δ 12.92 (s, 1H), 8.92 (s, 1H), 8.42 (s, 1H), 7.86 (s, 1H), 7.81 (d, J = 11.08 Hz, 1H), 7.57 (d, J = 7.8 Hz, 1H), 7.42-7.37 (m, 2H), 7.30 (d, J = 2.72 Hz, 1H), 7.21 (d, J = 8.88 Hz, 1H), 4.61 (t, J = 5.12 Hz, 2H), 4.42 (t, J = 10.08 Hz, 2H), 2.11-2.05 (m, 1H), 1.03-0.99 (m, 2H), 0.77-0.72 (m, 2H). |
| 32 | MS (ESI) m/z 515.33 [M + 1]+; 1H NMR (400 MHz, DMSO-d6) δ 13.03 (s, 1H), 9.13 (s, 1H), 8.32 (s, 1H), 8.23 (s, 1H), 7.92 (s, 1H), 7.86 (t, J = 5.76 Hz, 2H), 7.61 (d, J = 7.72 Hz, 1H), 7.43-7.39 (m, 2H), 7.34 (d, J = 2.44 Hz, 1H), 7.2 (d, J = 8.84 Hz, 1H), 4.35 (m, 4H), 2.59 (s, 3H) |
| 33 | MS (ESI) m/z 511.34 [M + 1]+; 1H NMR (400 MHz, DMSO-d6) δ 8.66 (s, 1H), 7.84 (d, J = 7.6 Hz, 2H), 7.74-7.47 (t, J = 5.6 Hz, 1H), 7.43-7.36 (m, 3H), 7.25 (d, J = 2.4 Hz, 1H), 7.17 (d, J = 8.8 Hz, 1H), 4.37 (d, J = 4.4 Hz, 2H), 4.33 (d, J = 3.6 Hz, 2H), 2.89 (s, 3H) |

TABLE 3-continued

Other Compounds

| Compound | Characterization |
|---|---|
| 37 | MS (ESI) m/z 510.40 [M + 1]+; 1H NMR (400 MHz, DMSO-d6) δ 12.95 (s, 1H), 8.13 (d, J = 8.0 Hz, 1H), 8.06 (d, J = 7.6 Hz, 1H), 7.83-7.84 (m, 2H), 7.36-7.72 (m, 4H), 7.27-7.28 (m, 1H), 7.21 (d, J = 8.8 Hz, 1H), 4.35 (s, 4H), 2.22 (s, 3H) |
| 40 | MS (ESI) m/z 603.21 [M + 1]+; 1H NMR (400 MHz, DMSO-d6) δ 8.84 (d, J = 4.8 Hz, 1H), 8.38 (bs, 1H), 8.28 (s, 1H), 8.01 (bs, 1H), 7.63 (d, J = 8.4 Hz, 1H), 7.54 (d, J = 11.4 Hz, 1H), 7.49 (d, J = 4.8 Hz, 1H), 4.43 (t, J = 4.4 Hz, 2H), 4.25 (t, J = 4.4 Hz, 2H), 1.73 (s, 3H) |
| 41 | MS (ESI) m/z 441.24 [M − 1]−; 1H NMR (400 MHz, DMSO-d6) δ 13.06 (s, 1H), 9.1 (s, 1H), 8.6 (s, 1H), 8.57 (s, 1H), 7.84 (d, J = 5.6 Hz, 1H), 7.75 (s, 1H), 7.69 (d, J = 8.3 Hz, 1H), 7.50-7.44 (m, 3H), 7.36 (d, J = 1.76 Hz, 1H), 6.46-6.39 (m, 1H), 6.27 (d, J = 16.09 Hz, 1H), 4.73 (d, J = 5.12 Hz, 2H) |
| 42 | MS (ESI) m/z 445.39 [M + 1]+UPLC: 99.76%; 1H NMR (400 MHz, DMSO-d6) δ 13.01 (s, 1H), 9.12 (s, 1H), 8.51 (s, 1H), 8.47 (s, 1H), 7.69 (s, 1H), 7.64-7.62 (m, 1H), 7.48 (d, J = 7.72 Hz, 1H), 7.41-7.34 (m, 3H), 7.19 (s, 1H), 3.90-3.87 (m, 2H), 2.55-2.50 (m, 2H), 1.80-1.74 (m, 2H) |

TABLE 3-continued

| | Other Compounds | |
|---|---|---|
| | Compound | Characterization |
| 43 | | MS (ESI) m/z 457.36 [M + 1]+; 1H NMR (400 MHz, DMSO-d6) δ 13.08 (b, 1H), 9.14 (s, 1H), 8.56 (d, J = 4.52 Hz, 2H), 7.92 (d, J = 7.44 Hz, 1H), 7.88 (s, 1H), 7.62-7.54 (m, 2H), 7.34 (dd, J = 8.44 Hz, 1H), 7.23 (d, J = 2.2 Hz, 1H), 7.03 (d, J = 8.48 Hz, 1H), 4.02-3.97 (m, 1H), 3.79-3.74 (m, 1H), 1.94 (q, J = 6.68 Hz, 1H), 1.61 (q, J = 6.76 Hz, 1H), 1.07 (t, J = 7.04 Hz, 2H) |
| 46 | | MS (ESI) m/z 638.09 [M + 1]+; 1H NMR (400 MHz, DMSO-d6) δ 13.16 (s, 1H), 8.82 (d, J = 4.84 Hz, 1H), 8.57 (s, 1H), 8.21 (s, 1H), 8.13 (s, 1H), 7.62-7.59 (dd, J = 2.48 Hz, J = 2.44 Hz, 1H), 7.53 (d, J = 4.8 Hz, 1H), 7.40-7.30 (m, 2H), 4.51-4.46 (m, 4H) |
| 47 | | MS (ESI) m/z 558.95 [M + 1]+; 1H NMR (400 MHz, DMSO-d6) δ 13.36 (s, 1H), 8.85 (d, J = 4.68 Hz, 1H), 8.57 (d, J = 1.16 Hz, 1H), 8.23 (d, J = 1.23 Hz, 1H), 8.17 (s, 1H), 7.61-7.58 (dd, J = 2.72 Hz, J = 2.68 Hz, 1H), 7.49 (d, J = 4.72 Hz, 1H), 7.40 (d, J = 2.72 Hz, 1H), 7.36 (d, J = 8.96 Hz, 1H), 4.40 (t, J = 4.40 Hz, J = 4.76 Hz, 2H), 4.18 (t, J = 4.44 Hz, J = 4.28 Hz, 2H), 1.48 (d, J = 3.52 Hz, 3H) |
| 52 | | MS (ESI) m/z 454.33 [M + 1]+. 1H NMR (400 MHz, DMSO-d6) δ 9.12 (s, 1H), 8.69 (s, 1H), 8.56 (s, 1H), 8.20 (d, J = 2.64 Hz, 1H), 8.06 (s, 1H), 7.51 (dd, J = 8.88 Hz, 1H), 7.37 (d, J = 9 Hz, 1H), 4.68 (t, J = 5.52 Hz, 2H), 4.54 (t, J = 5.48 Hz, 2H) |

TABLE 3-continued
| | Other Compounds | |
|---|---|---|
| | Compound | Characterization |
| 53 | 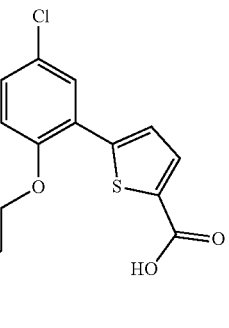 | MS (ESI) m/z 453.31 [M + 1]+; 1H NMR (400 MHz, DMSO-d6) δ 12.99 (b, 1H), 9.09 (s, 1H), 8.60 (s, 1H), 8.53 (s, 1H), 7.83 (d, J = 2.52 Hz, 1H), 7.62 (d, J = 4.04 Hz, 1H), 7.55 (d, J = 4 Hz, 1H), 7.42-7.40 (m, 1H), 7.31 (d, J = 8.96 Hz, 1H), 4.61 (t, J = 5.36 Hz, 2H), 4.58 (t, J = 5.28 Hz, 2H) |
| 54 | 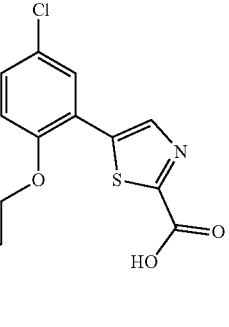 | MS (ESI) m/z 454.36 [M + 1]+. 1H NMR (400 MHz, DMSO-d6) δ 9.13 (s, 1H), 8.63 (s, 1H), 8.57 (s, 1H), 8.25 (bs, 1H), 7.79 (s, 1H), 7.38 (dd, J = 8.72 Hz, 1H), 7.24 (d, J = 8.8 Hz, 1H), 4.50 (t, J = 2.96 Hz, 4H). |
| 55 | 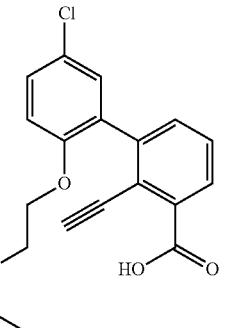 | MS (ESI) m/z 534.37 [M + 1]+; 1H NMR (400 MHz, DMSO-d6) δ 12.94 (s, 1H), 8.11 (d, J = 8.56 Hz, 1H), 7.96 (d, J = 8.52 Hz, 1H), 7.82 (d, J = 7.68 Hz, 1H), 7.48-7.21 (m, 4H), 7.15 (d, J = 9.48 Hz, 2H), 4.30 (s, 4H), 3.75 (s, 1H), 1.98 (s, 3H) |
| 56 | 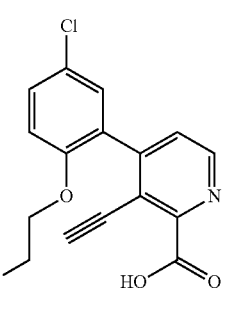 | MS (ESI) m/z 510.73 [M + 1]+; UPLC: 99.83%; 1H NMR (400 MHz, DMSO-d6) δ 12.91 (s, 1H), 8.61 (d, J = 4.56 Hz, 1H), 8.14 (d, J = 8.60 Hz, 1H), 7.98 (d, J = 8.44 Hz, 2H), 7.59-7.58 (m, 1H), 7.51-7.23 (m, 4H), 4.39 (s, 4H), 2.22 (s, 3H) |

TABLE 3-continued
Other Compounds
| Compound | Characterization |
|---|---|
| 57 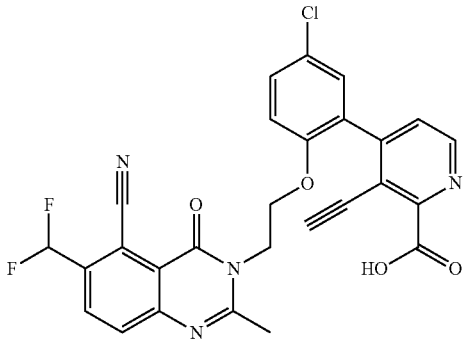 [SMILES: C#Cc1c(-c2cc(Cl)ccc2OCCn2c(C)nc3ccc(C(F)F)c(C#N)c3c2=O)ccnc1C(=O)O] | MS (ESI) m/z 535.17 [M + 1]+; 1H NMR (400 MHz, DMSO-d6) δ 8.41 (s, 1H), 8.13(d, J = 8.72 Hz, 1H), 7.99 (d, J = 8.6 Hz, 1H), 7.49-7.19 (m, 5H), 4.32 (s, 4H), 4.06 (s, 1H), 2.08 (s, 3H) |
| 62 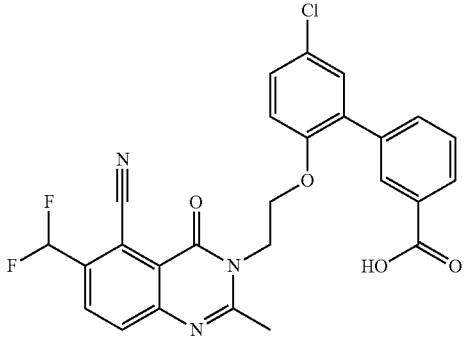 [SMILES: Cc1nc2ccc(C(F)F)c(C#N)c2c(=O)n1CCOc1ccc(Cl)cc1-c1cccc(C(=O)O)c1] | MS (ESI) m/z 508.04 [M − 1]−. UPLC: 98.04%; 1H NMR (400 MHz, DMSO-d6) δ 12.92 (s, 1H), 8.13 (d, J = 8.64 Hz, 1H), 7.97 (d, J = 8.56 Hz, 1H), 7.86 (d, J = 7.84 Hz, 1H), 7.83 (s, 1H), 7.53-7.20 (m, 6H), 4.35 (s, 4H), 2.20 (s, 3H) |
| 63 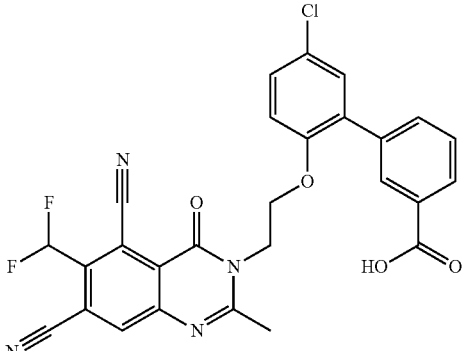 | MS (ESI) m/z 535.26 [M + 1]+; 1H NMR (400 MHz, DMSO-d6) δ 8.57 (s, 1H), 7.84-7.79 (m, 2H), 7.61-7.36 (m, 4H), 7.24 (s, 1H), 7.18 (d, J = 8.88 Hz, 1H), 4.34 (s, 4H), 2.17 (s, 3H) |
| 64 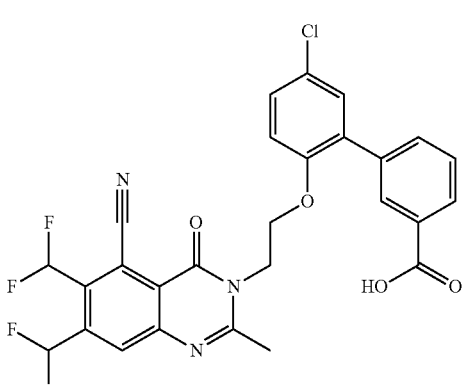 | MS (ESI) m/z 560.18 [M + 1]+. 1H NMR (400 MHz, DMSO-d6) δ 12.93 (bs, 1H), 8.12 (s, 1H), 7.85-7.83 (m, 2H), 7.63-7.19 (m, 7H), 4.35 (s, 4H), 2.21 (s, 3H) |

TABLE 3-continued

Other Compounds

| Compound | Characterization |
|---|---|
| 66 | MS (ESI) m/z 445.13 [M − 1]−; UPLC: 93.91%; 1H NMR (400 MHz, DMSO-d6) δ 12.94 (s, 1H), 9.09 (s, 1H), 8.52 (s, 1H), 8.26 (s, 1H), 7.85-7.83 (m, 2H), 7.58 (d, J = 7.84 Hz, 1H), 7.44-7.39 (m, 2H), 7.32 (d, J = 2.60 Hz, 1H), 7.20 (d, J = 8.88 Hz, 1H) 4.35 (s, 4H) |
| 67 | MS (ESI) m/z 423.16 [M + 1]+; UPLC: 97.88%; 1H NMR (400 MHz, DMSO-d6) δ 12.98 (bs, 1H), 8.02 (s, 1H), 7.92-7.91 (m, 3H), 7.56-7.55 (m, 1H), 7.44 (t, J = 8.0 Hz, 1H), 7.39 (dd, J = 8.8, 2.8 Hz, 1H), 7.33 (d, J = 2.4 Hz, 1H), 7.2 (d, J = 8.8 Hz, 1H), 4.32-4.29 (m, 4H), 3.69 (s, 3H) |
| 68 | MS (ESI) m/z 424.24 [M + 1]+; UPLC: 97.94%; 1H NMR (400 MHz, DMSO-d6) δ 12.98 (bs, 1H), 7.95-7.91 (m, 2H), 7.78 (s, 1H), 7.58-7.55 (m, 1H), 7.44 (t, J = 7.6 Hz, 1H), 7.38 (dd, J = 8.8, 2.4 Hz, 1H), 7.34 (d, J = 2.4 Hz, 1H), 7.19 (d, J = 8.8 Hz, 1H), 7.09 (d, J = 3.2 Hz, 1H), 6.43 (d, J = 3.2 Hz, 1H), 4.27 (s, 4H), 3.66 (s, 3H) |
| 69 | MS (ESI) m/z 424.27 [M + 1]+; UPLC: 98.50%; 1H NMR (400 MHz, DMSO-d6) δ 8.00 (s, 1H), 7.89 (d, J = 7.6 Hz, 1H), 7.78 (s, 1H), 7.51 (d, J = 7.6 Hz, 1H), 7.42-7.34 (m, 4H), 7.18 (d, J = 8.8 Hz, 1H), 6.28 (d, J = 2.8 Hz, 1H), 4.28 (s, 4H), 3.97 (s, 3H) |

TABLE 3-continued

Other Compounds

| Compound | Characterization |
|---|---|
| 70 | MS (ESI) m/z 450.27 [M + 1]+; UPLC: 96.87%; 1H NMR (400 MHz, DMSO-d6) δ 12.98 (bs, 1H), 8.97 (s, 1H), 8.60 (d, J = 5.2 Hz, 1H), 7.89-7.87 (m, 3H), 7.54-7.52 (m, 1H), 7.43-7.37 (m, 2H), 7.28 (d, J = 2.8 Hz, 1H), 7.18 (d, J = 8.8 Hz, 1H), 4.37-4.24 (m, 4H), 2.60-2.49 (m, 2H), 0.97 (t, J = 7.2 Hz, 3H) |
| 71 | MS (ESI) m/z 450.27 [M + 1]+; UPLC: 96.87%; 1H NMR (400 MHz, DMSO-d6) δ 12.98 (bs, 1H), 8.97 (s, 1H), 8.60 (d, J = 5.2 Hz, 1H), 7.89-7.87 (m, 3H), 7.54-7.52 (m, 1H), 7.43-7.37 (m, 2H), 7.28 (d, J = 2.8 Hz, 1H), 7.18 (d, J = 8.8 Hz, 1H), 4.37-4.24 (m, 4H), 2.60-2.49 (m, 2H), 0.97 (t, J = 7.2 Hz, 3H) |
| 72 | MS (ESI) m/z 435.22 [M + 1]+; UPLC: 95.85%; 1H NMR (400 MHz, DMSO-d6) δ 12.98 (bs, 1H), 8.05 (d, J = 8.0 Hz, 1H), 7.91-7.89 (m, 2H), 7.78 (t, J = 7.2 Hz, 1H), 7.56 (d, J = 8.0 Hz, 1H), 7.52-7.37 (m, 4H), 7.29 (d, J = 2.4 Hz, 1H), 7.19 (d, J = 8.8 Hz, 1H), 4.33 (s, 4H), 2.22 (s, 3H) |
| 73 | LCMS Purity: 96.35%, MS: m/z 444.18 [M − 1]−; 1H NMR (DMSO-d6, 400 mHz) δ 12.96 (bs, 1H), 8.09 (s, 1H), 8.02 (m, 1H), 7.92 (m, 3H), 7.85 (d, J = 7.8 Hz, 1H), 7.60 (d, J = 7.8 Hz, 1H), 7.41-7.39 (m, 2H), 7.33 (d, J = 2.7 Hz, 1H), 7.21 (d, J = 8.8 Hz, 1H), 4.33 (m, 4H) |

TABLE 3-continued

Other Compounds

| Compound | Characterization |
|---|---|
| 74 | MS (ESI) m/z 446.22 [M + 1]+; UPLC: 97.68%; 1H NMR (400 MHz, DMSO-d6) δ 12.95 (bs, 1H), 8.21 (d, J = 8.2 Hz, 1H), 8.15 (s, 1H), 8.09 (s, 1H), 7.89-7.84 (m, 3H), 7.57 (d, J = 7.7 Hz, 1H), 7.41-7.38 (m, 2H), 7.33 (d, J = 2.5 Hz, 1H), 7.20 (d, J = 8.8 Hz, 1H), 4.39-4.32 (m, 4H) |
| 75 | MS (ESI) m/z 446.25 [M + 1]+; UPLC: 97.45%; 1H NMR (400 MHz, DMSO-d6) δ 12.96 (s, 1H), 8.36-8.31 (m, 2H), 8.24 (s, 1H), 7.90 (s, 1H), 7.83 (d, J = 7.8 Hz, 1H), 7.65 (t, J = 7.8 Hz, 1H), 7.55 (d, J = 7.8 Hz, 1H), 7.41-7.33 (m, 3H), 7.21 (d, J = 8.8 Hz, 1H), 4.34 (s, 4H) |
| 76 | MS (ESI) m/z 439.21 [M + 1]+; UPLC: 99.71%; 1H NMR (400 MHz, DMSO-d6) δ 8.08 (s, 1H), 7.94-7.85 (m, 3H), 7.70-7.68 (m, 1H), 7.58 (d, J = 7.86 Hz, 1H), 7.53-7.48 (m, 1H), 7.40-7.29 (m, 3H), 7.20 (d, J = 8.8 Hz, 1H), 4.33 (s, 4H) |
| 77 | MS (ESI) m/z 457.25 [M + 1]+; UPLC: 95.49%; 1H NMR (400 MHz, DMSO-d6) δ 12.95 (bs, 1H), 8.07-7.96 (m, 2H), 7.89-7.85 (m, 2H), 7.72-7.67 (m, 1H), 7.57 (d, J = 7.8 Hz, 1H), 7.43-7.38 (m, 2H), 7.32 (d, J = 2.6 Hz, 1H), 7.20 (d, J = 8.8 Hz, 1H), 4.33-4.30 (m, 4H) |

TABLE 3-continued
| | Other Compounds | |
|---|---|---|
| | Compound | Characterization |
| 78 | 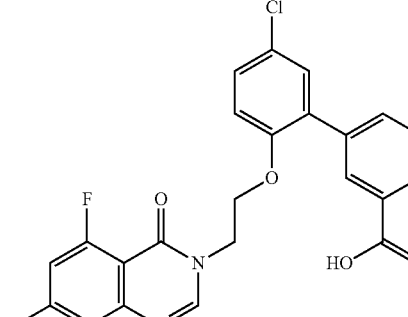 | MS (ESI) m/z 457.21 [M + 1]+; UPLC: 95.45%; 1H NMR (400 MHz, DMSO-d6) δ 12.96 (bs, 1H), 8.01 (s, 1H), 7.92 (s, 1H), 7.87 (d, J = 7.8 Hz, 1H), 7.60 (d, J = 7.8 Hz, 1H), 7.44-7.7.33 (m, 4H), 7.28-7.25 (m, 1H), 7.20 (d, J = 9.6 Hz, 1H), 4.31-4.25 (m, 4H) |
| 79 | 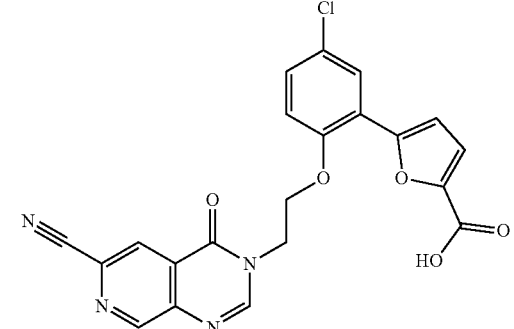 | MS (ESI) m/z 437.2 [M + 1]+; 1H NMR (400 MHz, DMSO-d6) δ 9.13 (s, 1H), 8.74 (s, 1H), 8.60 (s, 1H), 7.69 (d, J = 2.6 Hz, 1H), 7.40 (dd, J = 8.84 Hz, 2.64 Hz, 1H), 7.24 (d, J = 8.96 Hz, 1H), 7.15 (bs, 1H), 7.03 (d, J = 3.32 Hz, 1H), 4.53 (s, 4H) |
| 80 | 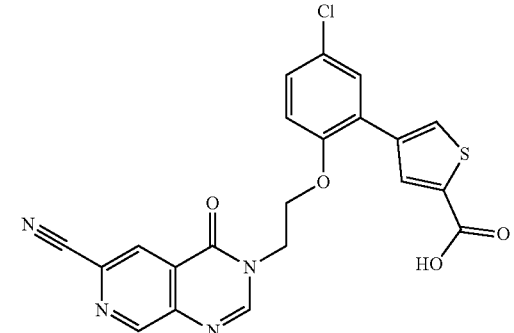 | MS (ESI) m/z 453.20 [M + 1]+; 1H NMR (400 MHz, DMSO-d6) δ 9.13 (s, 1H), 8.56 (s, 2H), 7.87 (s, 1H), 7.72 (s, 1H), 7.51 (d, J = 2.56 Hz, 1H), 7.31 (dd, J = 8.8 Hz, 2.56 Hz, 1H), 7.15 (d, J = 8.92 Hz, 1H), 4.45 (t, J = 4.76 Hz, 2H), 4.41 (t, J = 4.72 Hz, 2H) |
| 81 | 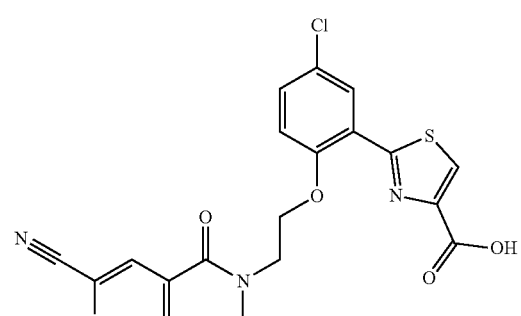 | MS (ESI) m/z 454.29 [M + 1]+; 1H NMR (400 MHz, DMSO-d6) δ 13.17 (bs, 1H), 9.14 (s, 1H), 8.75 (s, 1H), 8.59 (s, 1H), 8.20 (bs, 2H), 7.51 (d, J = 8.00 Hz, 1H), 7.35 (d, J = 8.96 Hz, 1H), 4.66 (bs, 2H), 4.55 (bs, 2H) |

TABLE 3-continued
| Other Compounds | |
|---|---|
| Compound | Characterization |
| 82 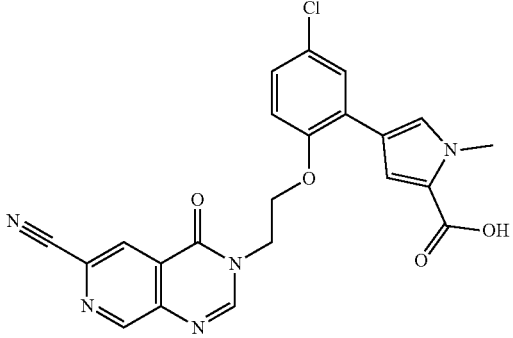 [SMILES: Cn1cc(-c2cc(Cl)ccc2OCCn2cnc3cnc(C#N)cc3c2=O)cc1C(=O)O] | MS (ESI) m/z 450.29 [M + 1]+; 1H NMR (400 MHz, DMSO-d6) δ 12.23 (bs, 1H), 9.13 (s, 1H), 8.67 (s, 1H), 8.57 (s, 1H), 7.49 (d, J = 2.44 Hz, 1H), 7.41 (bs, 1H), 7.17-7.14 (m, 1H), 7.09 (d, J = 8.2 Hz, 1H), 7.04 (bs, 1H), 4.49 (t, J = 4.32 Hz, 2H), 4.46 (t, J = 4.56 Hz, 2H), 3.84 (s, 3H) |
| 83 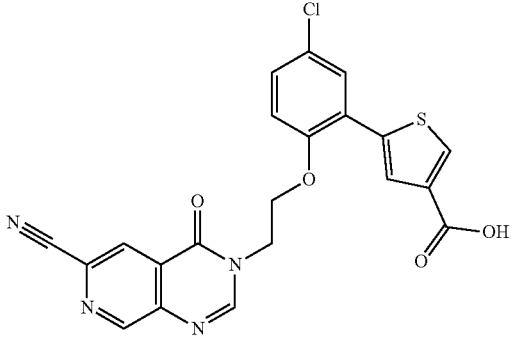 [SMILES: N#Cc1cc2c(=O)n(CCOc3ccc(Cl)cc3-c3cc(C(=O)O)cs3)cnc2cn1] | MS (ESI) m/z 453.31 [M + 1]+; 1H NMR (400 MHz, DMSO-d6) δ 12.74 (s, 1H), 9.12 (s, 1H), 8.63 (s, 1H), 8.56 (s, 1H), 8.09 (bs, 1H), 7.77 (d, J = 2.68 Hz, 2H), 7.36 (dd, J = 8.8 Hz, 2.4 Hz, 1H), 7.25 (d, J = 8.8 Hz, 1H), 4.55 (t, J = 4.8 Hz, 2H), 4.48 (t, J = 5.2 Hz, 2H) |
| 84 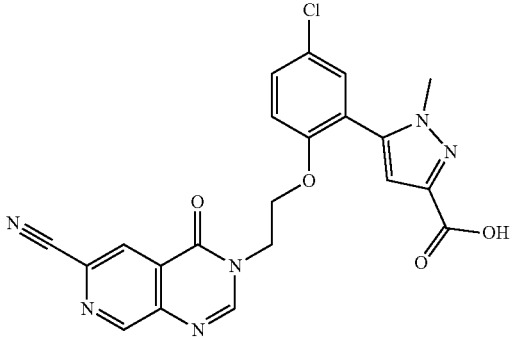 [SMILES: Cn1nc(C(=O)O)cc1-c1cc(Cl)ccc1OCCn1cnc2cnc(C#N)cc2c1=O] | MS (ESI) m/z 451.30 [M + 1]+; 1H NMR (400 MHz, DMSO-d6) δ 12.60 (bs, 1H), 9.09 (s, 1H), 8.52 (s, 1H), 8.25 (s, 1H), 7.52 (dd, J = 8.76 Hz, 2.6 Hz, 1H), 7.34 (d, J = 2.64 Hz, 1H), 7.24 (d, J = 8.92 Hz, 1H), 6.52 (s, 1H), 4.36 (s, 4H), 3.56 (s, 3H) |
| 85 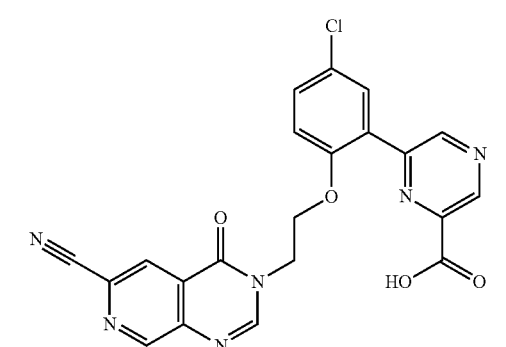 | MS (ESI) m/z 449.36 [M + 1]+; 1H NMR (400 MHz, DMSO-d6) δ 9.09 (s, 1H), 8.98 (bs, 2H), 8.54 (s, 1H), 8.43 (bs, 1H), 7.67 (bs, 1H), 7.51 (d, J = 8.8 Hz, 1H), 7.26 (d, J = 7.84 Hz, 1H), 4.44 (s, 4H) |

TABLE 3-continued

Other Compounds

| Compound | Characterization |
|---|---|
| 86 | MS (ESI) m/z 483.24 [M + 1]+; 1H NMR (400 MHz, DMSO-d6) δ 13.27 (s, 1H), 9.10 (s, 1H), 8.52 (s, 1H), 8.22 (s, 1H), 7.64 (t, J = 8.32 Hz, 1H), 7.46 (dd, J = 8.8 Hz, 2.56 Hz, 1H), 7.31 (d, J = 2.52 Hz, 1H), 7.21-7.18 (m, 2H), 4.32 (s, 4H) |
| 87 | MS (ESI) m/z 478.30 [M + 1]+; 1H NMR (400 MHz, DMSO-d6) δ 9.08 (s, 1H), 9.08 (s, 1H), 8.51 (s, 1H), 8.37 (s, 1H), 7.57 (s, 1H), 7.45 (dd, J = 8.76 Hz, 2.6 Hz, 1H), 7.38 (d, J = 2.72 Hz, 1H), 7.23 (d, J = 8.88 Hz, 1H), 6.87 (bs, 1H), 4.38 (bs, 4H), 3.88 (s, 3H) |
| 88 | MS (ESI) m/z 478.30 [M + 1]+; 1H NMR (400 mHz, DMSO-d6) δ 13.10 (s, 1H), 9.06 (s, 1H), 8.57 (s, 1H), 8.53 (s, 1H), 8.47 (s, 1H), 8.11-8.08 (m, 1H), 7.73 (d, J = 2.68 Hz, 1H), 7.37 (dd, J = 8.76 Hz, 2.68Hz, 1H), 7.21 (d, J = 8.88 Hz, 1H), 4.44 (s, 4H), 2.95 (d, J = 4.24 Hz, 3H) |
| 89 | MS (ESI) m/z 483.24 [M + 1]+; 1H NMR (400 MHz, DMSO-d6) δ 13.31 (s, 1H), 9.08 (s, 1H), 8.51 (s, 1H), 8.22 (s, 1H), 7.81-7.77 (m, 1H), 7.51-7.48 (m, 2H), 7.35 (d, J = 2.6 Hz, 1H), 7.23 (d, J = 8.92 Hz, 1H), 4.36-4.33 (m, 4H) |

TABLE 3-continued

| | Other Compounds | |
|---|---|---|
| | Compound | Characterization |
| 90 | | MS (ESI) m/z 479.35 [M + 1]+; 1H NMR (400 MHz, DMSO-d6) δ 9.12 (s, 1H), 8.58 (s, 1H), 8.56 (s, 1H), 8.41 (bs, 1H), 7.63 (bs, 1H), 7.41 (dd, J = 8.8 Hz, 2.4 Hz, 1H), 7.21 (d, J = 9.2 Hz, 1H), 4.47-4.43 (m, 4H), 3.90 (s, 3H) |
| 91 | | MS (ESI) m/z 483.22 [M + 1]+; 1H NMR (400 MHz, DMSO-d6) δ 13.83 (bs, 1H), 9.11 (s, 1H), 8.54 (s, 1H), 8.23 (s, 1H), 7.46-7.43 (m, 1H), 7.35 (bs, 1H), 7.28 (d, J = 2.56 Hz, 1H), 7.20 (d, J = 8.96 Hz, 1H), 7.07 (t, J = 9.12 Hz, 1H), 4.32 (s, 4H) |
| 92 | | MS (ESI) m/z 487.31 [M + 1]+; 1H NMR (400 MHz, DMSO-d6) δ 12.41 (bs, 1H), 9.07 (s, 1H), 8.47 (s, 1H), 7.96 (s, 1H), 7.65 (dd, J = 8.12 Hz, 1.72 Hz, 1H), 7.43-7.40 (m, 2H), 7.19-7.17 (m, 2H), 6.79 (d, J = 8.2 Hz, 1H), 4.26 (s, 4H), 1.44-1.38 (m, 1H), 0.70-0.47 (m, 4H) |
| 93 | | MS (ESI) m/z 472.23 [M + 1]+; 1H NMR (400 MHz, DMSO-d6) δ 13.50 (bs, 1H), 9.05 (s, 1H), 8.49 (s, 1H), 8.20 (s, 1H), 8.16 (s, 1H), 8.07 (t, J = 1.48 Hz, 1H), 8.01 (t, J = 1.48 Hz, 1H), 7.45 (dd, J = 8.8 Hz, 2.68 Hz, 1H), 7.41 (d, J = 2.6 Hz, 1H), 7.24 (d, J = 8.8 Hz, 1H), 4.38-4.33 (m, 4H) |

TABLE 3-continued

Other Compounds

| Compound | Characterization |
|---|---|
| 94 | MS (ESI) m/z 472.37 [M + 1]+; 1H NMR (400 MHz, DMSO-d6) δ 13.87 (bs, 1H), 9.10 (s, 1H), 8.54 (s, 1H), 8.31 (bs, 1H), 7.98 (bs, 1H), 7.72 (bs, 1H), 7.62 (bs, 1H), 7.45 (dd, J = 8.4, 2.0 Hz, 1H), 7.39 (d, J = 2.4 Hz, 1H), 7.22 (d, J = 8.8 Hz, 1H), 4.35 (s, 4H) |
| 95 | MS (ESI) m/z 493.24 [M + 1]+; 1H NMR (400 MHz, DMSO-d6) δ 13.04 (bs, 1H), 9.04 (s, 1H), 8.47 (s, 1H), 8.24 (s, 1H), 7.56 (bs, 2H), 7.41 (dd, J = 8.8 Hz, 2.52 Hz, 1H), 7.34-7.32 (m, 2H), 7.22 (d, J = 8.84 Hz, 1H), 4.37-4.33 (m, 4H), 2.45 (s, 3H) |
| 96 | MS (ESI) m/z 491.20 [M + 1]+; 1H NMR (400 MHz, DMSO-d6) δ 12.97 b(s, 1H), 9.09 (s, 1H), 8.52 (s, 1H), 8.31 (s, 1H), 7.36 (dd, J = 8.72, 2.56 Hz, 1H), 7.24 (d, J = 2.64 Hz, 1H), 7.17 (d, J = 8.88 Hz, 1H), 7.13 (d, J = 1.64 Hz, 1H), 7.01 (d, J = 1.64 Hz, 1H), 6.16 (s, 2H), 4.35 (s, 4H) |
| 97 | MS (ESI) m/z 495.31 [M + 1]+; 1H NMR (400 MHz, DMSO-d6) 69.08 (s, 1H), 8.50 (s, 1H), 8.13 (s, 1H), 7.41-7.35 (m, 2H), 7.14-7.12 (m, 2H), 6.78 (d, J = 12.88 Hz, 1H), 4.27 (t, J = 4.2 Hz, 2H), 4.25 (t, J = 4.08 Hz, 2H), 3.62 (s, 3H) |

TABLE 3-continued

Other Compounds

| Compound | Characterization |
|---|---|
| 98 | MS (ESI) m/z 495.31 [M + 1]+; 1H NMR (400 MHz, DMSO-d6) δ 13.56 (bs, 1H), 9.07 (d, J = 0.68 Hz, 1H), 8.91 (s, 1H), 8.53 (s, 1H), 8.48 (s, 1H), 7.74 (d, J = 2.8 Hz, 1H), 7.49 (dd, J = 8.92 Hz, 2.72 Hz, 1H), 7.28 (d, J = 9.0 Hz, 1H), 4.48-4.44 (m, 4H), 2.41 (s, 3H) |
| 99 | MS (ESI) m/z 498.33 [M + 1]+; 1H NMR (400 MHz, DMSO-d6) δ 13.78 (bs, 1H), 8.83 (s, 1H), 8.73 (d, J = 7.84 Hz, 1H), 8.33 (s, 2H), 8.19 (s, 1H), 8.07 (d, J = 7.8 Hz, 1H), 7.85-7.81 (m, 1H), 7.76-7.72 (m, 2H), 7.52 (dd, J = 8.76, 2.64 Hz, 1H), 7.32 (d, J = 8.92 Hz, 1H), 4.49 (t, J = 4.92 Hz, 2H), 4.37 (t, J = 4.88 Hz, 2H) |
| 100 | MS (ESI) m/z 498.33 [M + 1]+; 1H NMR (400 MHz, DMSO-d6) δ 9.15 (d, J = 3.12 Hz, 1H), 8.78 (s, 1H), 8.65 (d, J = 7.24 Hz, 1H), 8.47 (d, J = 1.76 Hz, 1H), 8.30 (bs, 2H), 8.15 (s, 1H), 7.89-7.86 (m, 1H), 7.52-7.49 (m, 2H), 7.30 (d, J = 8.8 Hz, 1H), 4.42 (t, J = 4.88 Hz, 2H), 4.32 (t, J = 4.72 Hz, 2H). |
| 101 | MS (ESI) m/z 501.29 [M + 1]+; 1H NMR (400 mHz, DMSO-d6) δ 9.11 (s, 1H), 8.53 (s, 1H), 8.34 (s, 1H), 7.46 (dd, J = 8.88, 2.6 Hz, 1H), 7.36 (t, J = 6.8 Hz, 1H), 7.27 (d, J = 2.68 Hz, 1H), 7.20 (d, J = 8.92 Hz, 2H), 4.34 (s, 4H) |

TABLE 3-continued

| | Other Compounds | |
|---|---|---|
| | Compound | Characterization |
| 102 | [structure] | MS (ESI) m/z 501.29 [M + 1]+; 1H NMR (400 mHz, DMSO-d6) δ 12.88 (s, 1H), 8.87 (s, 1H), 8.50 (s, 1H), 8.31 (s, 1H), 8.21 (s, 1H), 7.69 (s, 1H), 7.64 (s, 1H), 7.43-7.40 (m, 1H), 7.34 (d, J = 2.16 Hz, 1H), 7.25 (d, J = 8.76 Hz, 1H), 4.40 (t, J = 4.68 Hz, 2H), 4.31 (t, J = 4.52 Hz, 2H), 4.23 (s, 3H) |
| 103 | [structure] | MS (ESI) m/z 504.35 [M + 1]+; 1H NMR (400 MHz, DMSO-d6) δ 13.58 (s, 1H), 11.07 (s, 1H), 9.03 (d, J = 0.68 Hz, 1H), 8.44 (s, 1H), 8.36 (d, J = 8.68 Hz, 1H), 8.32 (s, 1H), 7.84 (d, J = 2.2 Hz, 1H), 7.50 (dd, J = 8.64, 2.12 Hz, 1H), 7.38 (dd, J = 8.88, 2.72 Hz, 1H), 7.27 (d, J = 2.6 Hz, 1H), 7.20 (d, J = 8.84 Hz, 1H), 4.35 (s, 4H), 2.19 (s, 3H) |
| 104 | [structure] | MS (ESI) m/z 489.37 [M + 1]+; 1H NMR (400 MHz, DMSO-d6) δ 12.61 (bs, 1H), 9.09 (s, 1H), 8.52 (s, 1H), 8.37 (s, 1H), 7.48 (bs, 1H), 7.37 (bs, 1H), 7.33 (dd, J = 8.80, 2.60 Hz, 1H), 7.23 (d, J = 2.60 Hz, 1H), 7.15 (d, J = 8.80 Hz, 1H), 4.66 (t, J = 8.72 Hz, 2H), 4.35 (bs, 4H), 3.22 (t, J = 8.68 Hz, 2H) |
| 105 | [structure] | MS (ESI) m/z 503.38 [M + 1]+; 1H NMR (400 mHz, DMSO-d6) δ 9.03 (s, 1H), 8.49 (s, 1H), 8.26 (bs, 1H), 7.85 (s, 1H), 7.74 (bs, 1H), 7.53 (s, 1H), 7.38 (d, J = 8.6 Hz, 1H), 7.31 (d, J = 2.4 Hz, 1H), 7.19 (d, J = 9.16 Hz, 1H), 4.33 (s, 4H), 1.27 (s, 9H) |

TABLE 3-continued

Other Compounds

| Compound | Characterization |
|---|---|
| 106 | MS (ESI) m/z 491.31 [M + 1]+; 1H NMR (400 MHz, DMSO-d6) δ 9.06 (s, 1H), 8.51 (s, 1H), 8.30 (s, 1H), 7.73 (bs, 1H), 7.68 (bs, 1H), 7.39-7.36 (m, 2H), 7.29 (d, J = 2.6 Hz, 1H), 7.18 (d, J = 8.88 Hz, 1H), 4.64 (t, J = 5.12 Hz, 1H), 4.34 (s, 4H), 3.62 (t, J = 5.92 Hz, 2H), 2.76 (t, J = 6.64 Hz, 2H) |
| 107 | MS (ESI) m/z 507.29 [M + 1]+; 1H NMR (400 MHz, DMSO-d6) δ 12.79 (s, 1H), 9.05 (s, 1H), 8.50 (s, 1H), 8.28 (s, 1H), 7.38-7.35 (m, 1H 7.31 (d, J = 2.6 Hz, 1H), 7.18-7.16 (m, 2H), 7.10 (d, J = 1.8 Hz, 1H), 4.34 (bs, 4H), 3.80 (s, 3H) ), 3.76 (s, 3H) |
| 108 | MS (ESI) m/z 511.18 [M + 1]+; 1H NMR (400 MHz, DMSO-d6) δ 9.06 (s, 1H), 8.52(s, 1H), 8.36 (s, 1H), 7.57 (d, J = 2.12 Hz, 1H), 7.54 (bs, 1H), 7.38 (dd J = 8.88 Hz, 2.72 Hz, 1H), 7.33 (d, J = 2.60 Hz, 2H), 7.18 (d, J = 8.8 Hz, 1H), 4.36 (s, 4H), 3.89 (s, 3H) |
| 109 | MS (ESI) m/z 498.25 [M + 1]+; 1H NMR (400 MHz, DMSO-d6) δ 13.98 (bs, 1H), 9.05 (s, 1H), 8.71 (s, 1H), 8.51 (s, 1H), 8.40 (s, 1H), 8.28 (s, 1H), 7.77 (t, J = 54.52 Hz, 1H), 7.49-7.45 (m, 2H), 7.23 (d, J = 8.76 Hz, 1H), 4.38 (s, 4H). |

TABLE 3-continued

Other Compounds

| Compound | | Characterization |
|---|---|---|
| 110 | (structure) | MS (ESI) m/z 514.40 [M + 1]+; 1H NMR (400 MHz, DMSO-d6) 13.11 (bs, 1H), 9.03 (s, 1H), 8.48 (s, 1H), 8.17 (s, 1H), 7.97 (t, J = 1.68 Hz, 1H), 7.82 (t, J = 1.36 Hz, 1H), 7.71 (t, J = 1.60 Hz, 2H), 7.43 (dd, J = 8.88, 2.76 Hz, 1H), 7.23 (d, J = 8.92 Hz, 1H), 4.36-4.32 (m, 4H), 1.72 (s, 6H) |
| 111 | (structure) | MS (ESI) m/z 513.32 [M + 1]+; 1H NMR (400 MHz, DMSO-d6) δ 13.20 (bs, 1H), 9.08 (d, J = 0.6 Hz, 1H), 8.54 (d, J = 0.64 Hz, 1H), 8.30 (s, 1H), 7.78 (d, J = 2.24 Hz, 1H), 7.59 (dd, J = 8.44, 2.28 Hz, 1H), 7.41-7.38 (m, 1H), 7.34 (d, J = 2.6 Hz, 1H), 7.21-7.19 (m, 2H), 7.18 (t, J = 67.48 Hz, 1H), 4.35 (s, 4H). |
| 112 | (structure) | MS (ESI) m/z 525.31 [M + 1]+; 1H NMR (400 mHz, DMSO-d6) δ 13.50 (s, 1H), 9.02 (s, 1H), 8.47 (s, 1H), 8.30 (t, J = 1.6 Hz, 1H), 8.18 (s, 1H), 8.13 (s, 2H), 7.50-7.48 (m, 1H), 7.46 (s, 1H), 7.26 (d, J = 8.8 Hz, 1H), 4.39-4.38 (m, 2H), 4.33-4.32 (m, 2H), 3.32 (s, 3H) |
| 113 | (structure) | MS (ESI) m/z 531.29 [M + 1]+; 1H NMR (400 MHz, DMSO-d6) δ 9.10 (s, 1H), 8.57 (s, 1H), 8.54 (bs, 1H), 7.74 (bs, 1H), 7.37-7.32 (m, 2H), 7.30 (d, J = 2.52 Hz, 1H), 7.16 (d, J = 8.88 Hz, 1H), 7.09 (d, J = 8.04 Hz, 1H), 4.39 (t, J = 4.76 Hz, 2H), 4.34 (t, J = 4.68 Hz, 2H) |

TABLE 3-continued

| | Other Compounds | |
|---|---|---|
| | Compound | Characterization |
| 114 | (structure) | MS (ESI) m/z 492.36 [M + 1]+; 1H NMR (400 MHz, DMSO-d6) δ 12.58 (bs, 1H), 9.07 (s, 1H), 8.55 (s, 1H), 8.35 (s, 1H), 7.32 (d, J = 7.16 Hz, 1H), 7.22 (s, 1H), 7.12 (d, J = 8.88 Hz, 1H), 6.92 (s, 1H), 6.87 (s, 1H), 5.10 (bs, 2H), 4.38 (bs, 2H), 4.30 (bs, 2H), 3.76 (s, 3H) |
| 115 | (structure) | MS (ESI) m/z 462.35 [M + 1]+; 1H NMR (400 MHz, DMSO-d6) δ 9.11 (s, 1H), 8.56 (s, 1H), 8.19 (d, J = 3.72 Hz, 1H), 8.12 (s, 1H), 7.41 (dd, J = 8.8, 2.8 Hz, 1H), 7.23 (bs, 1H), 7.16-7.14 (m, 2H), 4.28 (bs, 4H), 2.03 (s, 3H) |
| 116 | (structure) | MS (ESI) m/z 487.39 [M + 1]+; 1H NMR (400 MHz, DMSO-d6) δ 9.10 (s, 1H), 8.54 (s, 1H), 8.11 (s, 1H), 7.68 (bs, 1H), 7.51 (dd, J = 8.8, 2.4 Hz, 1H), 7.31 (d, J = 2.8 Hz, 1H), 7.22 (d, J = 8.8 Hz, 1H), 4.33 (s, 4H), 2.50 (s, 3H) |
| 117 | (structure) | MS (ESI) m/z 487.31 [M + 1]+; 1H NMR (400 MHz, DMSO-d6) δ 13.27 (bs, 1H), 11.92 (s, 1H), 8.91 (s, 1H), 8.40 (bs, 1H), 8.37 (s, 1H), 7.99 (s, 1H), 7.74 (d, J = 2.64 Hz, 1H), 7.68 (t, J = 2.84 Hz, 1H), 7.42 (dd, J = 8.88, 2.8 Hz, 1H), 7.26 (d, J = 8.76 Hz, 1H), 6.84 (t, J = 1.96 Hz, 1H), 4.47 (t, J = 4.72 Hz, 2H), 4.38 (t, J = 4.64 Hz, 2H) |

TABLE 3-continued

| | Other Compounds | |
|---|---|---|
| | Compound | Characterization |
| 118 | | MS (ESI) m/z 498.41 [M + 1]+; 1H NMR (400 MHz, DMSO-d6) δ 8.97 (s, 1H), 8.56 (d, J = 8.56 Hz, 1H), 8.40 (s, 1H), 8.02 (d, J = 5.72 Hz, 1H), 7.70 (t, J = 7.08 Hz, 1H), 7.62-7.60 (m, 2H), 7.54 (dd, J = 8.76, 2.64 Hz, 1H), 7.29-7.26 (m, 2H), 7.18 (d, J = 5.64 Hz, 1H), 4.33-4.23 (m, 2H), 4.17-4.09 (m, 2H) |
| 119 | | MS (ESI) m/z 601.13 [M + 1]+; 1H NMR (400 MHz, DMSO-d6) δ 12.92 (bs, 1H), 8.83 (d, J = 4.64 Hz, 1H), 8.38 (s, 1H), 7.87 (s, 1H), 7.59 (dd, J = 8.76, 2.24 Hz, 1H), 7.51 (t, J = 52.0 Hz, 1H), 7.49 (d, J = 4.68 Hz, 1H), 7.43 (d, J = 2.28 Hz, 1H), 7.35 (d, J = 8.96 Hz, 1H), 4.39 (t, J = 5.56 Hz, 2H). 4.23 (t, J = 4.92 Hz, 2H), 1.73 (s, 3H) |
| 123 | | MS (ESI) m/z 599.53 [M + 1]+; 1H NMR (400 MHz, DMSO-d6) δ 8.77 (d, J = 4.92 Hz, 1H), 8.08 (d, J = 9.72 Hz, 1H), 7.60 (dd, J = 8.88, 2.64 Hz, 1H), 7.53 (d, J = 4.96 Hz, 1H), 7.41 (d, J = 2.56 Hz, 1H), 7.38 (t, J = 64.56 Hz, 1H), 7.35 (d, J = 1.72 Hz, 1H), 4.44 (t, J = 5.40 Hz, 2H), 4.23 (t, J = 4.84 Hz, 2H), 2.49 (s, 3H), 1.96 (s, 3H) |
| 124 | | UPLC: MS (ESI) m/z 443.28 [M + 1]+; 1H NMR (400 MHz, DMSO-d6) δ 9.10 (s, 1H), 8.51 (s, 1H), 8.41 (s, 1H), 7.94 (s, 1H), 7.73 (d, J = 7.52 Hz, 1H), 7.41 (d, J = 7.68 Hz, 1H), 7.25 (t, J = 7.52 Hz, 1H), 7.06 (d, J = 8.76 Hz, 1H), 6.88-6.85(dd, J = 2.84 Hz, J = 2.72 Hz, 1H), 6.82 (d, J = 2.92 Hz, 1H), 4.34 (t, J = 4.6 Hz, J = 4.88 Hz 2H), 4.23 (d, J = 4.48 Hz), 3.72 (s, 3H) |

TABLE 3-continued

| | Other Compounds | |
|---|---|---|
| | Compound | Characterization |
| 125 | 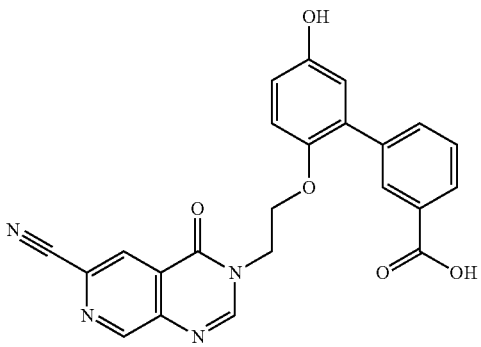 [SMILES: N#Cc1cc2c(=O)n(CCOc3ccc(O)cc3-c3cccc(C(=O)O)c3)cnc2cn1] | UPLC: MS (ESI) m/z 429.28 [M + 1]+; 1H NMR (400 MHz, DMSO-d6) δ 9.20 (bs, 1H), 9.10 (s, 1H), 8.51 (s, 1H), 8.37 (s, 1H), 7.87 (s, 1H), 7.69 (d, J = 7.68 Hz, 1H), 7.42 (d, J = 7.76 Hz, 1H), 7.25 (t, J = 7.64 Hz, 1H), 6.96 (d, J = 8.68 Hz, 1H), 6.71-6.68 (dd, J = 2.96 Hz, J = 2.92 Hz, 1H), 6.65 (d, J = 2.8 Hz, 1H), 4.30 (t, J = 4.8 Hz, 2H), 4.17 (t, J = 4.88 Hz, 2H) |
| 126 | 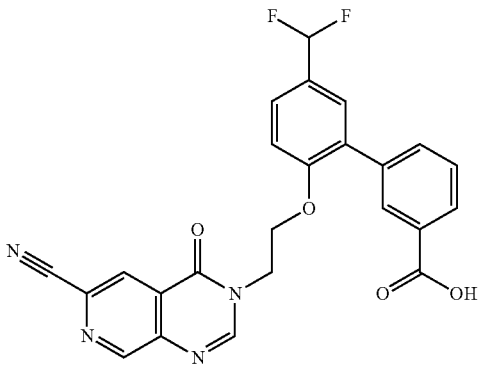 [SMILES: N#Cc1cc2c(=O)n(CCOc3ccc(C(F)F)cc3-c3cccc(C(=O)O)c3)cnc2cn1] | MS (ESI) m/z 463.36 [M + 1]+; UPLC: 99.75%; 1H NMR (400 MHz, DMSO-d6) δ 13.01 (s, 1H), 9.10 (s, 1H), 8.53 (s, 1H), 8.29 (s, 1H), 7.89 (s, 1H), 7.86 (d, J = 7.76 Hz, 1H), 7.58 (t, J = 8.20 Hz, 2H), 7.48 (s, 1H), 7.44 (t, J = 7.68 Hz, 1H) 7.30 (d, J = 8.60 Hz, 1H), 7.14-6.86 (m, 1H), 4.42-4.38 (m, 4H) |
| 127 | 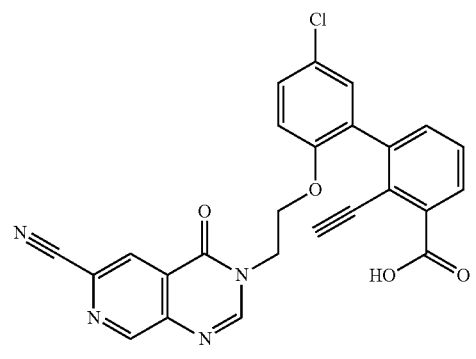 [SMILES: C#Cc1c(C(=O)O)cccc1-c1cc(Cl)ccc1OCCn1cnc2cnc(C#N)cc2c1=O] | MS (ESI) m/z 471.32 [M + 1]+; 1H NMR (400 MHz, DMSO-d6) δ 12.94 (bs, 1H), 9.10 (s, 1H), 8.51 (s, 1H), 7.99 (s, 1H), 7.78 (dd, J = 7.56, 11.2 Hz, 1H), 7.43-7.34 (m, 3H), 7.17-7.15 (m, 2H), 4.28 (s, 4H), 3.80 (s, 1H) |
| 128 | 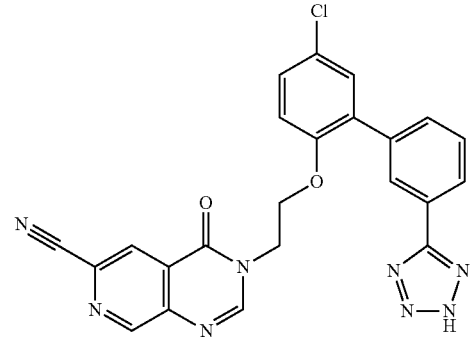 [SMILES: N#Cc1cc2c(=O)n(CCOc3ccc(Cl)cc3-c3cccc(-c4nn[nH]n4)c3)cnc2cn1] | MS (ESI) m/z 471.29 [M + 1]+; 1H NMR (400 MHz, DMSO-d6) δ 16.5 (bs, 1H), 8.92 (s, 1H), 8.47(s, 1H), 8.23 (s, 1H), 7.97 (d, J = 1.48 Hz, 2H),7.55-7.51 (m, 2H), 7.43 (dd, J = 2.56 Hz, J = 2.68 Hz 1H), 7.39 (d, J = 2.6 Hz, 1H), 7.23 (d, J = 8.76 Hz, 1H), 4.36 (s, 4H) |

TABLE 3-continued

| | Other Compounds | |
|---|---|---|
| | Compound | Characterization |
| 129 | | MS (ESI) m/z 461.21 [M + 1]+. UPLC: 99.41%; 1H NMR (400 MHz, DMSO-d6) δ 12.88 (s, 1H), 9.02 (s, 1H), 8.45 (s, 1H), 8.40 (s, 1H), 7.75 (s, 1H), 7.57 (d, J = 7.76 Hz, 1H), 7.44-7.38 (m, 2H), 7.29 (d, J = 2.60 Hz, 1H), 7.23 (d, J = 8.88 Hz, 1H) 7.16 (t, J = 7.72 Hz, 1H), 5.14-5.09 (m, 1H), 4.53-4.49 (m, 1H), 4.42-4.37 (m, 1H), 1.43 (d, J = 6.96 Hz, 3H) |
| 130 | | MS (ESI) m/z 439.10 [M − 1]−; 1H NMR (400 MHz, DMSO-d6) δ 12.83 (bs, 1H), 9.17 (s, 1H), 8.56 (d, J = 8.44 Hz, 2H), 7.96 (s, 1H), 7.71-7.68 (m, 2H), 7.62 (d, J = 8.36 Hz, 1H), 7.53 (d, J = 2.04 Hz, 1H), 7.51-7.58 (dd, J = 2.08 Hz, J = 2.20 Hz, 1H), 7.37 (t, J = 7.68 Hz, 1H), 4.91 (s, 2H) |
| 131 | | MS (ESI) m/z 479.32 [M + 1]+; 1H NMR (400 MHz, DMSO-d6) δ 13.03 (bs, 1H), 10.82 (s, 1H), 8.79 (s, 1H), 8.62 (s, 1H), 7.98 (s, 1H), 7.95 (s, 1H), 7.87 (d, J = 7.76 Hz, 1H), 7.58 (d, J = 7.56 Hz, 1H), 7.42-7.38 (m, 2H), 7.34 (d, J = 2.76 Hz, 1H), 7.19 (d, J = 8.92 Hz, 1H), 4.32 (s, 4H), 2.13 (s, 3H) |
| 132 | | MS (ESI) m/z 479.35 [M + 1]+; 1H NMR (400 MHz, DMSO-d6) δ 9.01 (s, 1H), 8.90 (d, J = 4.8 Hz, 1H), 8.49 (s, 1H), 8.17 (s, 1H), 7.92 (s, 1H), 7.86 (d, J = 7.6 Hz, 1H), 7.61 (d, J = 8.0 Hz, 1H), 7.43-7.38 (m, 2H), 7.34 (d, J = 2.4 Hz, 1H), 7.21 (d, J = 8.8 Hz, 1H), 4.35 (s, 4H), 2.93 (s, 3H) |

TABLE 3-continued

| | Other Compounds | |
|---|---|---|
| | Compound | Characterization |
| 133 | | MS (ESI) m/z 514 [M + 1]+; 1H NMR (400 MHz, DMSO-d6) δ 12.9 (s, 1H), 8.29 (d, J = 8.72 Hz, 1H), 8.19 (s, 1H), 8.07 (d, J = 8.64 Hz, 1H), 7.88 (s, 1H), 7.83 (d, J = 7.76 Hz ,1H), 7.60 (d, J = 7.76 Hz ,1H), 7.38-7.42 (m, J = 8.32 Hz, 2H), 7.33 (d, J = 2.68 Hz, 1H), 7.22 (d, J = 8.8 Hz, 1H), 4.3 (s, 4H) |
| 134 | | MS (ESI) m/z 462 [M + 1]+; 1H NMR (400 MHz, DMSO-d6) δ 12.9 (b, 1H), 9.04 (s, 1H), 8.63 (d, J = 4.96 Hz, 1H), 8.48 (s, 1H), 7.915 (s, 1H), 7.56 (dd, J = 1.52 Hz, J = 4.96Hz, 1H), 7.484 (dd, J = 1.68, 8.92 Hz, 1H), 7.40 (d, J = 2.6 Hz, 1H), 7.24 (d, J = 8.92 Hz, 1H), 4.385 (s, 4H), 2.278 (s, 3H) |
| 135 | | UPLC: MS (ESI) m/z 518.43 [M + 1]+; 1H NMR (400 MHz, DMSO-d6) δ 8.86 (s, 1H), 8.84 (d, J = 4.8 Hz, 1H), 8.43 (s, 1H), 8.36 (s, 1H), 7.60-7.57 (dd, J = 2.6 Hz, J = 2.6 Hz, 1H), 7.47 (d, J = 4.76 Hz, 1H), 7.43 (d, J = 2.6 Hz, 1H), 7.33 (d, J = 8.96 Hz, 1H), 4.38 (t, J = 4.8 Hz, 2H), 4.25 (t, J = 4.76, 5.0 Hz, 2H), 1.81 (s, 3H) |
| 136 | | MS (ESI) m/z 488.32 [M + 1]+; 1H NMR (400 MHz, DMSO-d6) δ 12.96 (bs, 1H), 8.93 (s, 1H), 8.67 (s, 1H), 8.32 (s, 1H), 8.06 (s, 1H), 7.928-7.86 (m, 3H), 7.61 (d, J = 7.2 Hz, 1H), 7.45-7.39 (m, 2H), 7.341 (s, 1H), 7.21 (d, J = 8.4 Hz, 1H), 6.62 (s, 1H), 4.35 (s, 4H) |

TABLE 3-continued
| | Other Compounds | |
|---|---|---|
| | Compound | Characterization |
| 137 | 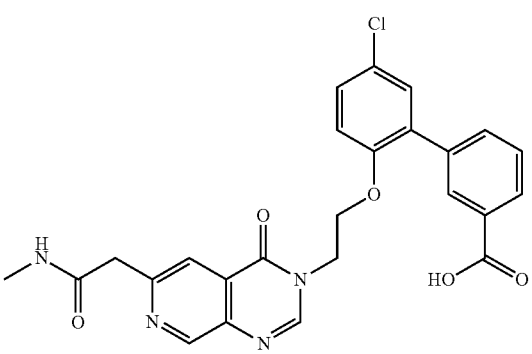 [SMILES: CNC(=O)Cc1cc2c(=O)n(CCOc3ccc(Cl)cc3-c3cccc(C(=O)O)c3)cnc2cn1] | MS (ESI) m/z 493.44 [M + 1]+; 1H NMR (400 MHz, DMSO-d6) δ 12.96 (s, 1H), 8.92 (s, 1H), 8.08 (s, 1H), 8.04 (d, J = 4.32 Hz, 1H), 7.93 (s, 1H), 7.89 (s, 1H), 7.86 (s, 1H), 7.56 (d, J = 6.88 Hz, 1H), 7.40-7.36 (m, 2H), 7.33 (d, J = 2.56 Hz, 1H), 7.20 (d, J = 8.84 Hz, 1H), 4.328 (s, 4H), 3.75 (s, 2H), 2.59 (d, J = 4.6 Hz, 3H) |
| 138 | 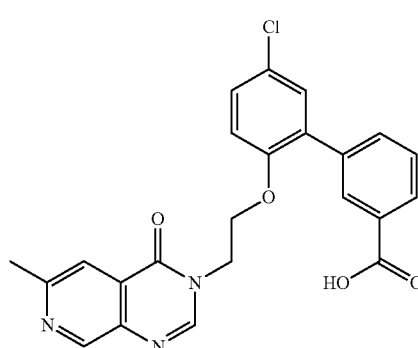 | MS (ESI) m/z 436.10 [M + 1]+; 1H NMR (400 MHz, DMSO-d6) δ 12.97 (s,1H), 8.89 (s, 1H), 8.04 (s, 1H), 7.90 (s, 1H), 7.86 (d, J = 7.72 Hz, 1H), 7.76 (s, 1H),7.57 (d, J = 1.28 Hz, 1H), 7.409-7.37 (m, 2H), 7.333-7.326 (m, 2H), 7.20 (d, J = 8.88 Hz, 1H), 4.34 (s, 4H), 2.607 (s, 3H). |
| 139 | 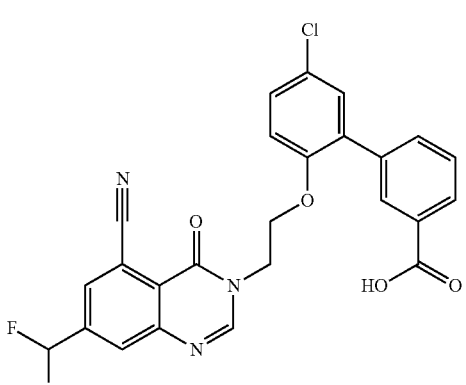 | MS (ESI) m/z 496.35 [M + 1]+; 1H NMR (400 MHz, DMSO-d6) δ 12.927 (bs, 1H), 8.187 (s, 1H), 8.158 (s, 1H), 8.079 (s, 1H), 7.91 (s, 1H), 7.83 (d, J = 7.8 Hz, 1H), 7.599 (d, J = 7.96 Hz, 1H), 7.419-7.08 (m, 5H), 4.349 (s, 4H) |
| 141 | 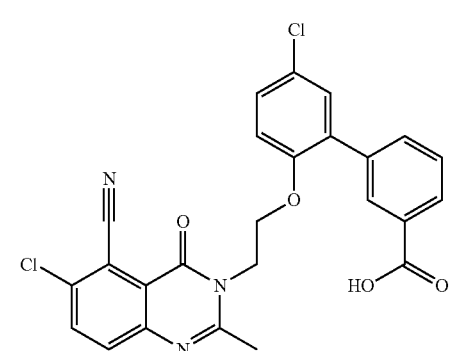 | MS (ESI) m/z 494.34 [M + 1]+; 1H NMR (400 MHz, DMSO-d6) δ 12.931 (bs, 1H), 8.061(d, J = 8.88 Hz, 1H), 7.875-7.82 (m, 3H), 7.517 (d, J = 7.4 Hz, 1H), 7.425-7.386 (m, 2H), 7.276 (d, J = 2.28 Hz, 1H), 7.205 (d, J = 8.8 Hz, 1H), 4.343 (s, 4H), 2.173 (s, 3H) |

TABLE 3-continued

Other Compounds

| Compound | Characterization |
|---|---|
| 142 | MS (ESI) m/z 528.44 [M + 1]+; 1H NMR (400 MHz, DMSO-d6) δ 12.9 (s, 1H), 8.28 (d, J = 7.92 Hz, 1H), 8.08 (d, J = 7.84 Hz, 1H), 7.92 (s, 1H), 7.85 (d, J = 7.76 Hz, 1H), 7.53 (d, J = 7.76 Hz, 1H), 7.33-7.41 (m, 2H), 7.28 (d, J = 4.4 Hz, 1H), 7.21 (d, J = 8.8 Hz, 1H), 4.3 (s, 4H), 2.24 (s, 3H) |
| 143 | MS (ESI) m/z 553.44 [M + 1]+; 1H NMR (400 MHz, DMSO-d6) δ 8.77 (s, 1H), 8.42 (s, 1H), 8.12 (d, J = 6.84 Hz, 1H), 7.99 (t, J = 6.8 Hz, 1H), 7.89 (d, J = 7.28 Hz, 1H), 7.72 (d, J = 4.16 Hz, 1H), 7.47-7.44 (m, 2H), 7.37 (d, J = 8.08 Hz, 1H), 6.59 (t, J = 51.6 Hz, 1 H), 4.41(s, 2H), 4.34 (s, 2H) |
| 144 | MS (ESI) m/z 662.39 [M + 1]+; 1H NMR (400 MHz, DMSO-d6): δ 12.63 (s, 1H), 8.86 (d, J = 4.8 Hz, 1H), 8.54 (s, 1H), 8.06 (d, J = 9.8 Hz, 1H), 7.63-7.60 (dd, J = 2.5, 2.6 Hz, 1H), 7.55 (d, J = 4.8 Hz, 1H), 7.42-7.36 (m, 3H), 4.44 (t, J = 6.1 Hz, 2H), 4.28 (t, J = 5.8 Hz, 2H), 3.53 (s, 3H), 1.90 (s, 3H) |
| 148 | MS (ESI) m/z 540.47 [M + 1]+; 1H NMR (400 MHz, DMSO-d6) δ 13.10 (bs, 1H), 8.15-8.13 (m, 1H), 8.07-8.00 (m, 2H), 7.70 (d, J = 1.3 Hz, 1H), 7.63-7.58 (m, 2H), 7.44-7.42 (dd, J = 2.6, 8.7 Hz, 1H), 7.39 (d, J = 2.6 Hz, 1H), 7.2 (d, J = 8.9 Hz, 1H), 7.08-6.82 (t, J = 51.9 Hz, 1H), 4.43 (t, J = 6.1 Hz, 2H), 4.34 (t, J = 5.5 Hz, 2H) |

TABLE 3-continued

| | Compound | Characterization |
|---|---|---|
| 153 | (structure) | MS (ESI) m/z 510.40 [M + 1]+; 1H NMR (400 MHz, DMSO-d6) δ 12.94 (bs, 1H), 8.12 (s, 1H), 8.00 (s, 1H), 7.89-7.84 (m, 2H), 7.53 (d, J = 7.6 Hz, 1H), 7.41-7.20 (m, 5H), 4.35 (m, 4H), 2.20 (s, 3H) |
| 154 | (structure) | MS (ESI) m/z 528.08 [M + 1]+; 1H NMR (400 MHz, DMSO-d6) δ 8.37 (s, 1H), 7.87 (d, J = 7.72 Hz, 1H), 7.81 (s, 1H), 7.54 (d, J = 7.88 Hz, 1H), 7.45 (m, 2H), 7.27 (d, J = 4 Hz, 1H), 7.27 (d, J = 8 Hz, 1H), 4.39 (m, 4H), 2.21 (s, 3H) |
| 160 | (structure) | MS (ESI) m/z 567.16 [M + 1]+; 1H NMR (400 MHz, DMSO-d6) δ 8.82 (d, J = 4.76 Hz, 1H), 8.40 (s, 1H), 8.12 (d, J = 8.6 Hz, 1H), 7.82 (d, J = 8.52 Hz, 1H), 7.59 (dd, J = 2.4, 8.92 Hz, 1H), 7.50-7.23 (m, 4H), 4.42-4.23 (m, 4H), 1.79 (s, 3H) |
| 161 | (structure) | MS (ESI) m/z 497.87 [M + 1]+; 1H NMR (400 MHz, DMSO-d6) δ 8.64 (d, J = 4.92 Hz, 1H), 8.20 (s, 1H), 8.163 (d, J = 8.6, 1H), 8.0474 (t, J = 8.4 Hz 2H), 7.67 (dd, J = 1.4, 6.4 Hz, 1H), 7.65 (m, 4H), 4.39 (m, 4H) |

TABLE 3-continued

Other Compounds

| Compound | Characterization |
|---|---|
| 163 | MS (ESI) m/z 521.15 [M + 1]+; 1H NMR (400 MHz, DMSO-d6) δ 13.40 (b, 1H), 8.49 (d, J = 4.84 Hz, 1H), 8.14 (d, J = 6.28 Hz, 1H), 8.07-8.02 (m, 2H), 7.49 (m, 1H), 7.43 (d, J = 4.88 Hz, 1H), 7.28 (d, J = 2.2 Hz, 1H), 7.23 (d, J = 8.92 Hz, 1H), 6.71 (t, J = 52.2 Hz, 1H) 4.38-4.33 (m, 4H), 4.19 (s, 1H) |
| 165 | MS (ESI) m/z 520.17 [M + 1]+. 1H NMR (400 MHz, DMSO-d6) δ 12.91 (bs, 1H), 8.12 (d, J = 6.68 Hz, 1H), 8.04-7.98 (m, 2H), 7.78-7.76 (m, 1H), 7.42-7.37 (m, 3H), 7.20-7.07 (m, 2H), 6.68-6.42 (t, J = 52.32 Hz, 1H), 4.36-4.30 (m, 4H), 3.90 (s, 1H) |
| 166 | MS (ESI) m/z 497.15 [M + 1]+; 1H NMR (400 MHz, DMSO-d6) δ 8.59 (s, 1H), 8.15 (d, J = 5.56 Hz, 1H), 8.07-7.99 (m, 3H), 7.645 (s, 1H), 7.51-7.46 (m, 2H), 7.23 (d, J = 8.92 Hz, 1H), 7.04-6.78 (m, 2H), 4.44-4.38 (m, 4H) |
| 167 | MS (ESI) m/z 478.15 [M + 1]+; 1H NMR (400 MHz, DMSO-d6) δ 12.912 (bs, 1H), 8.028 (d, J = 8.84 Hz, 1H), 7.879 (d, J = 7.72 Hz, 2H), 7.813 (s, 1H), 7.696 (d, J = 9.36 Hz, 1H), 7.52 (d, J = 7.48 Hz, 1H), 7.449-7.394 (m, 2H), 7.283 (s, 1H), 7.2079 (d, J = 8.8 Hz, 1H), 4.334 (m, 4H), 2.163 (s, 3H) |

TABLE 3-continued

| | Other Compounds | |
|---|---|---|
| | Compound | Characterization |
| 170 | (structure) | MS (ESI) m/z 421.2 [M + 1]+; 1H NMR (500 MHz, DMSO-d6) δ 13.01 (bs, 1H), 12.21 (bs, 1H), 8.13 (s, 1H), 8.03 (s, 1H), 7.94 (d, J = 7.5 Hz, 1H), 7.62-7.61 (m, 1H), 7.55-7.50 (m, 3H), 7.35-7.34 (m, 2H), 7.20-7.17 (m, 2H), 4.27 (t, J = 6.5 Hz, 2H), 3.62 (t, J = 6.5 Hz, 2H) |
| 171 | (structure) | MS (ESI) m/z 468.2 [M + 1]+; 1H NMR (300 MHz, DMSO-d6) δ 8.03 (s, 1H), 7.93 (d, J = 7.5 Hz, 1H), 7.64 (d, J = 7.5 Hz, 1H), 7.54-7.49 (m, 1H), 7.37-7.34 (m, 2H), 7.27-7.16 (m, 2H), 6.78-6.73 (m, 1H), 4.20 (t, J = 6.5 Hz, 2H), 3.47 (t, J = 6.5 Hz, 2H), 2.87 (d, J = 3.3 Hz, 3H) |
| 172 | (structure) | MS (ESI) m/z 486.2 [M + 1]+. 1H NMR (300 MHz, DMSO-d6) δ 13.00 (bs, 1H), 11.10 (bs, 1H), 8.04 (s, 1H), 7.93 (d, J = 7.5 Hz, 1H), 7.63 (d, J = 7.8 Hz, 1H), 7.51-7.46 (m, 1H), 7.38-7.34 (m, 2H), 7.18 (d, J = 8.4 Hz, 2H), 6.75-6.68 (m, 1H), 6.43 (bs, 1H), 4.24-4.20 (m, 2H), 3.49-3.46 (m, 2H), 2.84 (d, J = 4.8 Hz, 3H) |
| 173 | (structure) | MS (ESI) m/z 563.4 [M + 1]+; 1H NMR (300 MHz, DMSO-d6) δ 12.16 (bs, 1H), 10.34 (bs, 1H), 8.13 (s, 1H), 7.31 (s, 1H), 7.21 (s, 1H), 7.19 (d, J = 7.5 Hz, 1H), 6.87 (d, J = 7.5 Hz, 2H), 6.76-6.75 (m, 1H), 6.68-6.54 (m, 5H), 6.37 (d, J = 8.1 Hz, 1H), 6.29-6.24 (m, 1H), 3.48 (t, J = 6.6 Hz, 2H), 2.74 (t, J = 6.3 Hz, 2H) |

TABLE 3-continued

Other Compounds

| Compound | Characterization |
|---|---|
| 174 | MS (ESI) m/z 555.31 [M + 1]+; UPLC: 97.62%; 1H NMR (400 MHz, DMSO-d6) δ 13.00 (bs, 1H), 10.97 (bs, 1H), 9.04 (s, 1H), 8.01 (s, 1H), 7.92 (d, J = 7.76 Hz, 1H), 7.82 (d, J = 7.92 Hz, 2H), 7.60 (d, J = 7.60 Hz, 1H), 7.45 (t, J = 7.68 Hz, 1H), 7.39-7.33 (m, 4H), 7.18 (d, J = 8.84 Hz, 1H), 7.12-7.07 (m, 1H), 6.86 (d, J = 10.32 Hz, 1H), 4.30 (t, J = 5.96 Hz, 2H), 3.59 (t, J = 5.84 Hz, 2H |
| 175 | MS (ESI) m/z 583.21 [M + 1]+; 1H NMR (400 MHz, DMSO-d6) δ 10.68 (bs, 1H), 8.90 (s, 1H), 8.79 (d, J = 4.96 Hz, 1H), 8.57 (s, 1H), 7.66 (d, J = 7.72 Hz, 2H), 7.57-7.60 (dd, J = 2.68 Hz, J = 2.56 Hz, 1H), 7.52 (d, J = 2.56 Hz, 1H), 7.43 (s, 1H), 7.37-7.32 (m, 4H), 7.01-7.07 (m 1H), 4.51 (d, J = 4.72 Hz, 2H), 4.23 (t, J = 4.56 Hz, 2H) |
| 176 | MS (ESI) m/z 513.32 [M + 1]+; 1H NMR (400 MHz, DMSO-d6) δ 13.0 (bs, 1H), 11.02 (bs, 1H), 8.91 (s, 1H), 8.38 (s, 1H), 8.02 (s, 1H), 7.93 (d, J = 7.6 Hz, 1H), 7.74 (d, J = 7.16 Hz, 2H), 7.60 (d, J = 7.44 Hz, 1H), 7.50 (t, J = 7.56 Hz, 1H), 7.38-7.34 (m, 4H), 7.19 (d, J = 8.80 Hz, 1H), 7.07 (t, J = 7.32 Hz, 1H), 6.88 (s, 1H), 4.30 (t, J = 6.0 Hz, 2H), 3.56 (d, J = 5.72 Hz, 2H) |
| 177 | MS (ESI m/z 544.12 [M + 1]+; 1H NMR (400 MHz, DMSO-d6) δ 12.99 (s, 1H), 11.73 (s, 1H), 8.07 (s, 1H), 7.999-7.995 (t, J = 1.64 Hz, 1H), 7.94-7.91 (td, J = 9.08, J = 1.36 Hz, 1H), 7.56-7.53 (td, J = 7.80, J = 1.64 Hz, 1H), 7.47-7.44 (t, J = 7.68 Hz, 1H), 7.39-7.34 (m, 3H), 7.16 (d, J = 8.88 Hz, 1H), 4.33-4.24 (m, 4H), 3.56-3.53 (t, J = 6.0, 2H) |

TABLE 3-continued

Other Compounds

| Compound | Characterization |
|---|---|
| 178 | LCMS (ESI) m/z 581.2 [M + 1]+; 1H NMR (400 MHz, DMSO-d6) δ 12.94 (bs, 1H), 11.10 (bs, 1H), 8.91 (s, 1H), 8.06 (s, 1H), 7.90 (d, J = 6.0 Hz, 1H), 7.71 (d, J = 5.7 Hz, 2H), 7.63 (d, J = 8.0 Hz, 1H), 7.45 (t, J = 6.0 Hz, 1H), 7.41-7.34 (m, 5H) 7.26 (s, 1H), 7.19 (d. J = 6.8 Hz, 1H), 7.11 (t, J = 6.0 Hz, 1H), 4.35 (m, 2H), 3.68 (m, 2 H) |
| 179 | MS (ESI) m/z 538.4 [M + 1]+; 1H NMR (400 MHz, DMSO-d6) δ 12.99 (b, 1H), 11.20 (s, 1H), 9.09 (s, 1H), 8.11 (s, 1H), 8.00-8.01 (m, 1H), 7.94-7.91 (m, 1H), 7.84 (d, J = 8 Hz, 2H), 7.58-7.55 (m, 1H), 7.48 (t, J = 8 Hz, 1H), 7.40-7.34 (m, 4H), 7.18 (d, J = 9 Hz, 1H), 7.13-7.09 (m, 1H), 4.31 (t, J = 6 Hz, 2H), 3.57 (t, J = 6 Hz, 2H) |
| 180 | MS (ESI) m/z 598.1 [M + 1]+; 1H NMR (400 MHz, DMSO-d6) δ 8.83 (d, J = 4.8 Hz, 1H), 8.51 (s, 1H), 8.27-8.26 (m, 1H), 8.16 (dd, J = 1.5, 0.6 Hz, 1H), 7.56 (dd, J = 8.9, 2.7 Hz, 1H), 7.49 (d, J = 4.8 Hz, 1H), 7.41 (d, J = 2.7 Hz, 1H), 7.37 (d, J = 9.0 Hz, 1H), 4.23 (t, J = 6.1 Hz, 2H), 3.62 (s, 3H), 2.89 (t, J = 6.1 Hz, 2H), 1.85 (s, 3H) |
| 188 | MS (ESI) m/z 603.15 [M + 1]+; 1H NMR (400 MHz, DMSO-d6) δ 8.80-8.74 (m, 1H), 8.44-8.42 (m, 1H), 8.22 (d, J = 8.8, 1H), 8.02 (d, J = 8.8 HZ, 1H), 7.65-7.58 (m, 1H), 7.55-7.28 (m, 4H), 6.73-6.42 (m, 1H), 4.42(s, 2H), 4.34 (s, 2H) |

TABLE 3-continued

Other Compounds

| Compound | Characterization |
|---|---|
| 189 | MS (ESI) m/z 553.14 [M + 1]+; UPLC: 98.14%; 1H NMR (400 MHz, DMSO-d6) δ 13.149 (s, 1H), 8.54 (d, J = 5.48, 1H), 8.21 (d, J = 5.2 Hz, 1H), 8.174 (s, 1H), 8.13 (d, J = 7.32 Hz, 1H), 7.96-8.00 (t, J = 7.64 Hz, 1H), 7.91 (d, J = 8.12 Hz, 1H), 7.59-7.56 (dd, J = 2.6, 8.84 Hz, 1H), 7.36-7.33 (m, 2H), 6.63-6.37 (t, J = 52.08 Hz, 1H), 4.40 (d, J = 4.68, 2H), 4.32 (d, J = 4.68, 2H) |
| 190 | MS (ESI) m/z 553.14 [M + 1]+; 1H NMR (400 MHz, DMSO-d6) δ 13.61 (m, 1H), 9.29 (s, 1H), 8.11-8.07 (t, J = 7.48 Hz, 2H), 8.04-8.00 (t, J = 7.52 Hz, 1H), 7.93 (d, J = 8.2 Hz, 1H), 7.60-7.55 (m, 2H), 7.41 (d, J = 2.52 Hz, 1H), 7.54 (d, J = 8.96 Hz, 1H), 6.68-6.43 (t, J = 51.88 Hz, 1H), 4.40 (d, J = 4.76, 2H), 4.33 (d, J = 4.64, 2H) |
| 191 | MS (ESI) m/z 550.33 [M − 1]−; 1H NMR (400 MHz, DMSO-d6) δ 13.07 (s, 1H), 8.10 (d, J = 7.56 Hz, 1H), 8.005 (t, J = 8.38 Hz, 2H), 7.93 (t, J = 4.28 Hz, 2H), 7.55-7.52 (m, 1H), 7.49 (d, J = 5.6 Hz, 1H), 7.34 (t, J = 3.96 Hz, 1H), 7.30 (d, J = 5.52 Hz, 1H), 7.27 (s, 1H), 6.44 (t, J = 5.2 Hz, 1H), 4.35 (t, J = 5.52 Hz, 2H), 4.28 (t, J = 4.42 Hz, 2H) |
| 192 | MS (ESI) m/z 542.2 [M − 1]−; 1H NMR (400 MHz, DMSO-d6) δ 8.60 (s, 1H), 8.16-8.14 (m, 1H), 8.09-8.03 (m, 2H), 7.76 (s, 1H), 7.39-7.36 (dd, J = 2.60, 2.64 Hz, 1H), 7.13 (d, J = 8.84 Hz ,1H), 7.06 (d, J = 2.6 Hz, 1H), 6.91 (s, 1H), 4.72-4.64 (m, 2H), 4.39 (s, 2H), 4.29 (s, 2H) |

TABLE 3-continued

Other Compounds

| Compound | Characterization |
|---|---|
| 193 | MS (ESI) m/z 542.2 [M − 1]−; 1H NMR (400 MHz, DMSO-d6) δ 8.60 (s, 1H), 8.16-8.14 (m, 1H), 8.09-8.03 (m, 2H), 7.76 (s, 1H), 7.39-7.36 (dd, J = 2.60, 2.64 Hz, 1H), 7.13 (d, J = 8.84 Hz ,1H), 7.06 (d, J = 2.6 Hz, 1H), 6.91 (s, 1H), 4.72-4.64 (m, 2H), 4.39 (s, 2H), 4.29 (s, 2H) |
| 194 | MS (ESI) m/z 595.18 [M + 1]+; 1H NMR (400 MHz, DMSO-d6) δ 8.83 (d, J = 4.5 Hz, 1H), 8.39 (s, 1H), 8.31 (s, 1H), 8.12 (s, 1H), 7.59 (d, J = 8.8 Hz, 1H), 7.48 (d, J = 4.7 Hz, 1H), 7.43 (s, 1H), 7.35 (d, J = 9.1 Hz, 1H), 4.41 (t, J = 4.0 Hz, 2H), 4.24 (t, J = 5.5 Hz, 2H), 1.74 (s, 3H) |
| 195 | MS (ESI) m/z 595.27 [M + 1]+; 1H NMR (400 MHz, DMSO-d6) δ 8.83 (d, J = 4.7 Hz, 1H), 8.417 (s, 1H), 8.35 (d, J = 8.72 Hz, 1H), 7.87 (d, J = 8.76 Hz, 1H), 7.60 (dd, J = 8.8 Hz 2.44 Hz, 1H), 7.48 (d, J = 4.68 Hz, 1H), 7.43 (d, J = 2.44 Hz, 1H), 7.36 (d, J = 9.0 Hz, 1H), 4.405 (d, J = 4.1 Hz, 2H), 4.269 (s, 2H), 3.539 (s, 3H), 1.83 (s, 3H) |
| 196 | MS (ESI) m/z 624.18 [M + 1]+; 1H NMR (400 MHz, DMSO-d6) δ 8.84 (d, J = 4.8 Hz, 1H), 8.43 (s, 1H), 8.26 (d, J = 8.76 Hz, 1H), 7.82 (d, J = 8.76 Hz, 1H), 7.60 (dd, J = 8.8 Hz, 2.64 Hz, 1H), 7.52 (d, J = 4.8 Hz, 1H), 7.46 (d, J = 2.6 Hz, 1H), 7.36 (d, J = 8.96 Hz, 1H), 4.41(t, J = 4.48 Hz, 2H), 4.25 (t, J = 4.68 Hz, 2H), 2.85 (s, 6H). 1.76 (s, 3H) |

TABLE 3-continued

| | Other Compounds | |
|---|---|---|
| | Compound | Characterization |
| 197 | | MS (ESI) m/z 592.22 [M + 1]+; 1H NMR (400 MHz, DMSO-d6) δ 8.81 (d, J = 4.76 Hz, 1H), 8.67 (s, 1H), 8.55 (s, 1H), 7.61 (dd, J = 2.44, 8.96 Hz, 1H), 7.51-7.24 (m, 4H), 4.43 (s, 2H), 4.31 (s, 2H), 1.98 (s, 3H) |
| 198 | | MS (ESI) m/z 592.01 [M − 1]−; 1H NMR (400 MHz, DMSO-d6) δ 8.85 (d, J = 4.84 Hz, 1H), 8.39 (s, 1H), 7.78 (s, 1H), 7.66 (s, 1H), 7.61-7.58 (dd, J = 2.52 Hz, 6.36 Hz, 1H), 7.53 (d, J = 4.80 Hz, 1H), 7.44 (d, J = 2.56 Hz, 1H), 7.354 (d, J = 9.00 Hz, 1H), 4.38-4.36 (m, 2H), 4.20-4.18 (m, 2H), 1.74 (s, 3H) |
| 200 | | MS (ESI) m/z 551.26 [M + 1]+; 1H NMR (400 MHz, DMSO-d6) δ 8.83 (d, J = 4.76 Hz, 1H), 8.38 (s, 1H), 8.11 (s, 1H), 7.73 (d, J = 1.6 Hz, 1H), 7.59 (dd, J = 8.8, 2.3 Hz, 1H), 7.49 (d, J = 4.7 Hz, 1H), 7.43 (d, J = 2.3 Hz, 1H), 7.35 (d, J = 9.0 Hz, 1H), 4.39 (t, J = 4.4 Hz, 2H), 4.22 (t, J = 5.7 Hz, 2H), 1.74 (s, 3H) |

TABLE 3-continued

Other Compounds

| Compound | | Characterization |
|---|---|---|
| 204 | | MS (ESI) m/z 595.21 [M + 1]+; UPLC: 99.31%; 1H NMR (400 MHz, DMSO-d6) δ 9.25 (s, 1H), 9.10 (s, 2H), 8.75 (d, J = 4.8 Hz, 1H), 8.55 (s, 1H), 8.10-8.03 (q, 2H), 7.61-7.58 (dd, J = 2.6 Hz, 2.6 Hz 1H), 7.49 (d, J = 4.76 Hz, 1H), 7.44 (d, J = 8.12, 1H), 7.38 (d, J = 8.92 Hz, 1H), 4.46 (t, J = 4.84 Hz, 2H), 4.28 (t, J = 6.44 Hz, 2H), 1.93 (s, 3H) |
| 207 | | MS (ESI) m/z 585.08 [M + 1]+; 1H NMR (400 MHz, DMSO-d6) δ 13.31 (bs, 1H), 8.83 (d, J = 4.7 Hz, 1H), 8.36 (s, 1H), 7.92 (s, 1H), 7.59 (dd, J = 8.8, 2.5 Hz, 1H), 7.47 (d, J = 4.7 Hz, 1H), 7.42 (d, J = 2.5 Hz, 1H), 7.35 (d, J = 8.8 Hz, 1H), 4.39 (t, J = 5.6 Hz, 2H), 4.23 (t, J = 4.8 Hz, 2H), 1.72 (s, 3H) |
| 208 | | MS (ESI) m/z 594.02 [M + 1]+; 1H NMR (400 MHz, DMSO-d6) δ 13.33 (bs, 1H), 8.83 (d, J = 4.6 Hz, 1H), 8.44 (s, 1H), 7.61-7.57 (m, 2H), 7.47-7.42 (m, 2H), 7.33 (d, J = 8.5 Hz, 1H), 4.35 (bs, 2H), 4.17 (bs, 2H), 1.71 (s, 3H) |
| 209 | | MS (ESI) m/z 585.06 [M + 1]+; UPLC: 99.28%; 1H NMR (400 MHz, DMSO-d6) δ 13.20 (s, 1H), 8.80 (d, J = 4.72 Hz, 1H), 8.54 (s, 1H), 8.39 (s, 1H), 7.60-7.58 (dd, J = 2.32, 2.24 Hz, 1H), 7.45-7.42 (dd, J = 4.76, 2.64 Hz, 2H), 7.36 (d, J = 8.92 Hz, 1H), 4.38 (s, 2H), 4.23 (s, 2H), 1.86 (s, 3H). |

TABLE 3-continued

Other Compounds

| Compound | Characterization |
|---|---|
| 211 | MS (ESI) m/z 541.16 [M + 1]+; UPLC: 99.9%; 1H NMR (400 MHz, DMSO-d6) δ 8.81 (d, J = 4.80 Hz, 1H), 8.65 (s, 1H), 8.05 (d, J = 7.76 1H), 7.89 (d, J = 7.72, 1H), 7.60 (d, J = 2.4 Hz, 1H), 7.46 (d, J = 2.44 Hz, 2H), 7.36 (d, J = 9 Hz, 1H), 4.75 (s, 1H), 4.40 (s, 2H), 4.26 (s, 2H), 1.93 (s, 3H) |
| 212 | MS (ESI) m/z 542.12 [M + 1]+; UPLC: 99.61%; 1H NMR (400 MHz, DMSO-d6) δ 13.34 (bs, 1H), 8.83 (d, J = 4.56 Hz, 1H), 8.47(s, 1H), 8.32 (s, 1H), 8.15 (s,1H), 7.60-7.57 (dd, J = 3.52, 1.72 Hz, 1H), 7.46 (d, J = 4.60 Hz, 1H), 7.42 (d, J = 2.32 Hz, 1H), 7.34 (d, J = 8.96 Hz, 1H), 4.41-4.39 (t, J = 5.28 Hz, 2H), 4.25-4.22 (t, J = 5.04 Hz, 2H), 1.77 (s, 3H) |
| 213 | MS (ESI) m/z 541.16 [M + 1]+; UPLC: 99.87%; 1H NMR (400 MHz, DMSO-d6) δ 13.34 (bs, 1H), 8.83 (d, J = 4.84 Hz, 1H), 8.38 (s, 1H), 8.02 (s, 1H), 7.74 (s, 1H), 7.60-7.57 (dd, J = 8.84, 2.36 Hz, 1H), 7.47-7.43 (dd, J = 11.20, 4.8 Hz, 2H), 7.34 (d, J = 8.92 Hz, 1H), 4.71 (s, 1H), 4.38 (s, 2H), 4.21 (s, 2H), 1.72 (s, 3H) |

TABLE 3-continued
| | Other Compounds | |
|---|---|---|
| | Compound | Characterization |
| 216 | 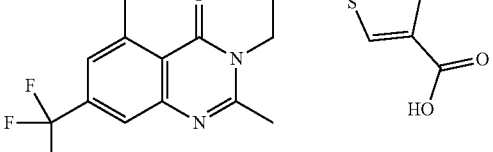 | MS (ESI) m/z 644.23 [M + 1]+; 1H NMR (400 MHz, DMSO-d6) δ 8.83-8.79 (m, 3H), 8.29 (s, 1H), 8.22 (s, 1H), 7.93 (s, 1H), 7.84 (d, J = 5.68 Hz, 2H), 7.59 (dd, J = 2.56, J = 8.84 Hz, 1H), 7.51 (d, J = 4.8 Hz, 1H), 7.44 (d, J = 2.60 Hz, 1H), 7.34 (d, J = 8.96 Hz, 1H) 4.38 (t, J = 5.76 Hz, 2H), 4.22 (t, J = 4.60 Hz, 2H), 1.69 (s, 3H) |
| 217 | 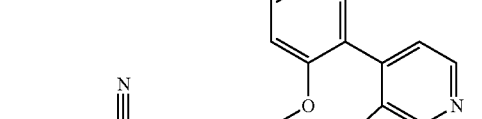 | MS (ESI) m/z 581.08 [M + 1]+. 1H NMR (400 MHz, DMSO-d6) δ 13.39 (bs, 1H), 8.84 (d, J = 4.4 Hz, 1H), 8.26 (s, 1H), 8.13 (s, 1H), 7.81 (s, 1H), 7.59 (dd, J = 8.8, 2.4 Hz, 1H), 7.49 (d, J = 7.2 Hz, 1H), 7.43 (d, J = 2.4 Hz, 1H), 7.35 (d, J = 8.8 Hz, 1H), 4.40 (t, J = 5.9 Hz, 2H), 4.23 (t, J = 4.8 Hz, 2H), 2.14 (t, J = 19.6 Hz, 3H), 1.72 (s, 3H) |
| 218 | 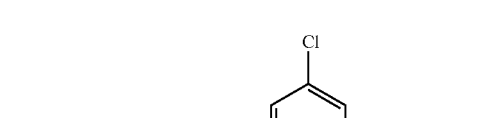 | MS (ESI) m/z 618.02 [M + 1]+. 1H NMR (400 MHz, DMSO-d6) δ 13.2 (s, 1H), 8.85-8.84 (d, J = 4.0 Hz, 1H), 8.47 (s, 1H), 8.21 (s, 1H), 8.01 (s, 1H), 7.59-7.58 (d, J = 4.0 Hz, 1H), 7.51-7.50 (d, J = 4.0 Hz, 1H), 7.39-7.38 (m, 2H), 4.46-4. (bs, 2H), 4.31 (bs, 2H), 1.76 (s, 3H) |

TABLE 3-continued

Other Compounds

| Compound | Characterization |
|---|---|
| 219 | MS (ESI) m/z 628.23 [M + 1]+; 1H NMR (400 MHz, DMSO-d6) δ 12.65 (bs, 1H), 8.83 (d, J = 4.76 Hz, 1H), 8.31 (s, 1H), 8.03 (d, J = 3.84 Hz, 2H), 7.60-7.57 (dd, J = 2.4 Hz 6.36 Hz, 1H), 7.48 (d, J = 4.72 Hz, 1H), 7.43 (d, J = 2.44 Hz, 1H), 7.35 (d, J = 8.96 Hz, 1H), 4.38-4.35 (m, 2H), 4.25-4.22 (m, 2H), 1.77 (s, 3H) |
| 220 | MS (ESI) m/z 610.05 [M + 1]+. 1H NMR (400 MHz, DMSO-d6) δ 13.2 (s, 1H), 8.83-8.82 (d, J = 4, 1H), 8.20 (s, 1H), 7.93-7.87 (m, 2H), 7.60-7.57 (m, 1H), 7.46-7.42 (m, 2H), 7.35-7.33 (d, J = 8 Hz, 1H), 4.36-4.38 (t, J = 4 Hz, 2H), 4.25-4.24 (t, J = 4 Hz, 2H), 1.78 (s, 3H) |
| 221 | MS (ESI) m/z 592.03 [M + 1]+. 1H NMR (400 MHz, DMSO-d6) δ 8.83 (d, J = 4.8 Hz, 1H), 8.41 (s, 1H), 7.81 (s, 1H), 7.60-7.57 (dd, J = 8.0, 2.52 Hz, 1H), 7.49 (d, J = 4.7 Hz, 1H), 7.44 (d, J = 2.52 Hz, 1H), 7.37-7.33 (m, 2H), 5.90 (s, 1H), 4.36-4.34 (t, J = 7.52 Hz, 2H), 4.18-4.15 (t, J = 7.96 Hz, 2H), 1.7 (s, 3H) |
| 222 | MS (ESI) m/z 607.03 [M + 1]+; 1H NMR (400 MHz, DMSO-d6) δ 8.82 (d, J = 4.84 Hz, 1H), 8.39 (s, 1H), 7.60-7.57 (m, 1H), 7.49 (d, J = 4.84 Hz, 1H), 7.43 (d, J = 2.6 Hz, 1H), 7.39 (s, 1H), 7.35 (s, 1H), 7.25 (s, 1H), 4.35-4.34 (t, J = 4.72 Hz, 2H), 4.20-4.18 (t, J = 4.32 Hz, 2H), 2.46 (s, 3H), 1.75 (s, 3H) |

TABLE 3-continued

Other Compounds

| Compound | | Characterization |
|---|---|---|
| 223 | 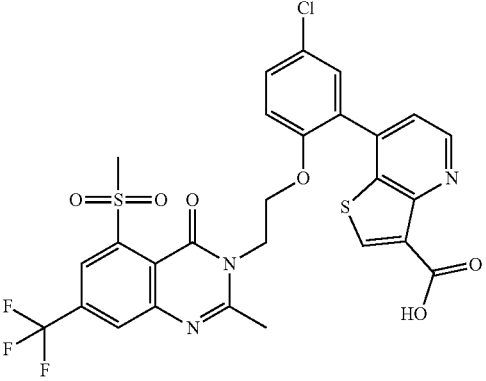 [SMILES: Cc1nc2cc(C(F)(F)F)cc(S(C)(=O)=O)c2c(=O)n1CCOc1ccc(Cl)cc1-c1ccnc2c(C(=O)O)csc12] | MS (ESI) m/z 638.04 [M + 1]. 1H NMR (400 MHz, DMSO-d6) δ 13.2 (s, 1H), 8.83 (s, 1H), 8.32 (s, 1H), 8.23 (s, 1H), 8.09 (s, 1H), 7.59-7.57 (d, J = 8 Hz, 1H), 7.43 (d, J = 12 Hz, 2H), 7.34 (d, J = 8 Hz, 1H), 4.43-4.41 (t, J = 4.0 Hz, 2H), 4.31-4.29(t, J = 4.0 Hz, 2H), 3.61(s, 3H), 1.93 (s, 3H) |
| 224 | 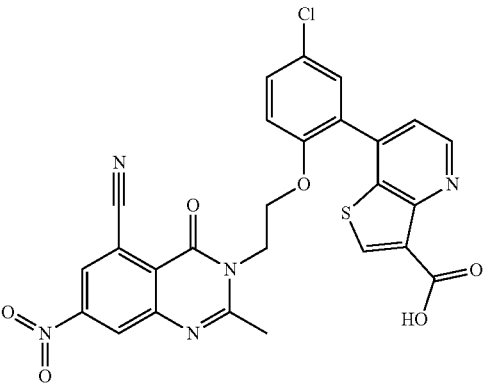 | MS (ESI) m/z 599.14 [M + 1]+; 1H NMR (400 MHz, DMSO-d6) δ 13.3 (s, 1H), 8.83 (d, J = 4 Hz, 1H), 8.66 (s, 1H), 8.36 (s, 1H), 8.32 (s, 1H), 7.60-7.58 (d, J = 8.0 Hz, 1H), 7.46 (d, J = 4.0 Hz, 1H), 7.40 (s, 1H), 7.35 (d, J = 12 Hz, 1H), 4.42-4.40 (t, J = 4.0 Hz, 2H), 4.28-4.26 (t, J = 5.6 Hz, 2H), 1.82 (s, 3H) |
| 228 | 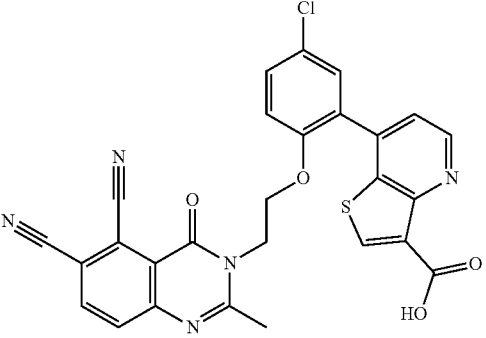 [SMILES: Cc1nc2ccc(C#N)c(C#N)c2c(=O)n1CCOc1ccc(Cl)cc1-c1ccnc2c(C(=O)O)csc12] | MS (ESI) m/z 540.16 [M − 1]−; 1H NMR (400 MHz, DMSO-d6) δ 8.83 (d, J = 4.8 Hz, 1H), 8.35 (t, J = 4.18 Hz, 2H), 7.78 (d, J = 8.6 Hz, 1H), 7.61-7.58 (dd, J = 2.56, 2.56 Hz, 1H), 7.49 (d, J = 4.72 Hz, 1H), 7.42 (d, J = 2.56 Hz, 1H), 7.36 (d, J = 8.96 Hz, 1H), 4.40 (d, J = 4.64 Hz, 2H), 4.26 (d, J = 4.32 Hz, 2H), 1.79 (s, 3H) |
| 229 | 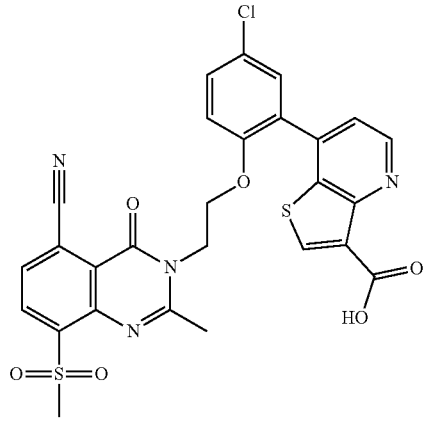 [SMILES: Cc1nc2c(S(C)(=O)=O)ccc(C#N)c2c(=O)n1CCOc1ccc(Cl)cc1-c1ccnc2c(C(=O)O)csc12] | MS (ESI) m/z 595.18 [M + 1]+; UPLC: 99.8%; 1H NMR (400 MHz, DMSO-d6) δ 8.83 (d, J = 4.80 Hz, 1H), 8.76 (s, 1H), 8.37 (d, J = 7.92, 1H), 8.10 (d, J = 7.88, 1H), 7.59 (dd, J = 2.04, 3.76 Hz, 1H), 7.44-7.47 (m, 2H), 7.37 (d, J = 8.92 Hz, 1H), 4.34 (s, 2H), 4.29 (s, 2H), 3.62 (s, 3H), 2.061 (s, 3H) |

TABLE 3-continued

| | Other Compounds | |
|---|---|---|
| | Compound | Characterization |
| 230 | | MS (ESI) m/z 585.05 [M + 1]+; 1H NMR (400 MHz, DMSO-d6) δ 13.19 (bs, 1H), 8.83 (d, J = 4.8 Hz, 1H), 8.40 (s, 1H), 7.64-7.54 (m, 2H), 7.48-7.28 (m, 4H), 4.40 (t, J = 5.7 Hz, 2H), 4.24 (t, J = 5.2 Hz, 2H), 1.76 (s, 3H) |
| 231 | | MS (ESI) m/z 503.25 [M + 1]+; 1H NMR (400 MHz, DMSO-d6) δ 8.57 (s, 1H), 8.54 (s, 1H), 7.88 (d, J = 7.24 Hz, 1H), 7.81 (s, 1H), 7.48 (d, J = 7.16 Hz, 1H), 7.39 (m, 2H), 7.26 (s, 1H), 5.08 (d, J = 45.84 Hz, 2H), 4.31 (s, 4H) |
| 232 | | MS (ESI) m/z 527.16 [M + 1]+; 1H NMR (400 MHz, DMSO-d6) δ 12.96 (s, 1H), 8.58 (d, J = 0.68, 1H), 8.46 (s, 1H), 7.88 (d, J = 7.56 Hz, 1H), 7.47 (t, J = 7.72, 1H), 7.41-7.38 (m, 2H), 7.16 (d, J = 8.92, 1H), 7.13 (d, J = 2.52, 1H), 5.02 (d, J = 46.24 Hz, 2H), 4.28 (s, 4H), 3.73(s, 1H) |
| 233 | | MS (ESI) m/z 556.20 [M + 1]+; 1H NMR (400 MHz, DMSO-d6) δ 13.10 (s,1H), 8.49 (s, 1H), 8.40 (s, 1H), 7.87 (s, 1H), 7.83 (s, 1H), 7.55 (d, J = 7.6 Hz, 1H), 7.44-7.39 (m, 2H), 7.28 (d, J = 2.4 Hz, 1H), 7.20 (d, J = 8.84, 1H), 5.13 (d, J = 45.76 Hz, 2H), 4.33-4.31 (m, 4H), 3.46 (s, 3H) |

TABLE 3-continued

Other Compounds

| Compound | Characterization |
|---|---|
| 234 | MS (ESI) m/z 541.29 [M + 1]+; 1H NMR (400 MHz, DMSO-d6) δ 8.83 (d, J = 4.76 Hz, 1H), 8.36 (d, J = 3.88 Hz, 2H), 8.19 (d, J = 1.08 Hz, 1H), 7.5996-7.5708 (m, 1H), 7.45 (d, J = 4.76 Hz, 1H), 7.41 (d, J = 2.6 Hz, 1H), 7.35 (d, J = 8.96 Hz, 1H), 6.02 (s, 1H), 4.39 (d, J = 4.76 Hz, 2H), 4.2060 (s, 2H), 1.63 (s, 3H) |
| 235 | MS (ESI) m/z 594.36 [M + 1]+; 1H NMR (400 MHz, DMSO-d6) δ 13.3202 (bs, 1H), 8.84 (d, J = 4.76 Hz, 1H), 8.34 (s, 1H), 8.31 (d, J = 1.4 Hz, 1H), 8.22 (d, J = 1.36 Hz, 1H), 7.6002-7.5717 (m, 1H), 7.46 (d, J = 4.76 Hz, 1H), 7.44 (d, J = 2.52 Hz, 1H), 7.36 (d, J = 8.96 Hz, 1H), 6.18 (s, 1H), 4.4153 (t, J = 5.32 Hz, 2H), 4.2160 (t, J = 5.4 Hz, 2H), 3.4635 (s, 3H), 1.6167 (s, 3H) |
| 236 | MS (ESI) m/z 583.31 [M + 1]+; 1H NMR (400 MHz, DMSO-d6) δ 13.4 (bs, 1H), 8.82 (d, J = 4.8 Hz, 1H), 8.40 (s, 1H), 7.86 (d, J = 9.2 Hz, 1H), 7.77 (d, J = 9.2 Hz, 1H), 7.69-7.32 (m, 5H), 4.40-4.38 (m, 2H), 4.24-4.21 (m, 2H), 1.74 (s, 3H) |
| 237 | MS (ESI) m/z 624.32 [M + 1]+; 1H NMR (400 MHz, DMSO-d6) δ 8.87 (s, 1H), 8.85 (d, J = 4.48 Hz, 1H), 8.34 (d, J = 7.72 Hz, 1H), 8.03 (d, J = 7.92 Hz, 1H), 7.59 (d, J = 8.8 Hz , 1H), 7.51 (d, J = 1.96 Hz, 1H), 7.48 (d, J = 4.56 Hz, 1H), 7.35 (d, J = 9 Hz, 1H), 4.41(t, J = 4 Hz, 2H), 4.29 (t, J = 4.28 Hz , 2H), 2.84 (s, 6H). 1.99 (s, 3H) |

TABLE 3-continued

Other Compounds

| Compound | Characterization |
| --- | --- |
| 238 | MS (ESI) m/z 610.19 [M + 1]+; 1H NMR (400 MHz, DMSO-d6) δ 8.85 (m, 2H), 8.30 (d, J = 7.76Hz, 1H), 8.03 (d, J = 7.72 Hz, 1H), 7.58 (d, J = 8.8Hz, 1H), 7.52 (d, J = 1.76 Hz, 1H), 7.45 (d, J = 4.44 Hz, 1H), 7.35 (d, J = 8.84 Hz, 1H), 4.41 (t, J = 4.6 Hz, 2H), 4.29 (t, J = 4.96 Hz, 2H), 2.54 (d, J = 5.92 Hz, 3H). 2.11 (s, 3H) |
| 239 | MS (ESI) m/z 576.04 [M + 1]+; 1H-NMR (400 MHz, DMSO-d6) 8.82 (d, J = 4.8, 1H), 8.75 (s, 1H), 8.55 (s, 1H), 7.61 (dd, J = 2.48 Hz, 8.8 Hz, 1H), 7.48 (d, J = 4.8 Hz, 1H), 7.44 (d, J = 2.36 Hz, 1H), 7.38 (d, J = 8.92, 1H), 4.42 (t, J = 4.64 Hz, 2H), 4.29 (t, J = 4.32 Hz, 2H), 1.95 (s, 3H) |
| 240 | MS (ESI) m/z 560.21 [M + 1]+; 1H NMR (400 MHz, DMSO-d6) δ 13.24 (bs, 1H), 8.80 (d, J = 4.60 Hz, 1H), 8.68 (d, J = 8.84 Hz, 1H), 8.51 (s, 1H), 7.59 (dd, J = 6.64 Hz, 2.8 Hz, 1H), 7.45 (d, J = 4.76 Hz, 1H), 7.43 (d, J = 2.28 Hz, 1H), 7.37 (d, J = 8.84 Hz, 1H), 4.42 (t, J = 4.96 Hz, 2H), 4.28 (t, J = 5.04 Hz, 2H), 1.95 (s, 3H) |
| 241 | MS (ESI) m/z 553.18 [M + 1]+; 1H NMR (400 MHz, DMSO-d6) 8.83 (d, J = 4.76 Hz, 1H), 8.47 (s, 1H), 8.09 (t, J = 9.48 Hz, 1H), 7.60 (dd, J = 2.16, 8.8 Hz, 1H), 7.51 (d, J = 4.64 Hz, 1H), 7.41 (d, J = 2.16 Hz, 1H), 7.37 (d, J = 8.92 Hz, 1H), 4.42 (bs, 2H). 4.26 (bs, 2H), 1.84 (s, 3H) |

TABLE 3-continued

| | Other Compounds | |
|---|---|---|
| | Compound | Characterization |
| 242 | 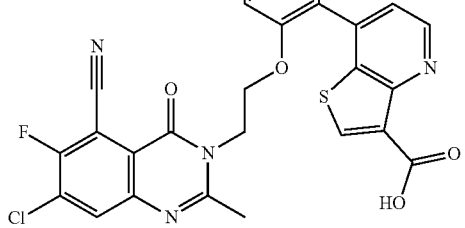 | MS (ESI) m/z 569.11 [M + 1]+; 1H NMR (400 MHz, DMSO-d6) δ 8.84 (d, J = 4.68 Hz, 1H), 8.36 (s, 1H), 7.91 (d, J = 6.84 Hz, 1H), 7.60 (dd, J = 2.28 Hz, 8.84 Hz, 1H), 7.48 (d, J = 4.68 Hz, 1H), 7.42 (d, J = 2.32 Hz, 1H), 7.35 (d, J = 8.96 Hz, 1H), 4.39 (t, J = 5.64 Hz, 2H), 4.22 (t, J = 5.64 Hz, 2H), 1.73 (s, 3H) |
| 243 | 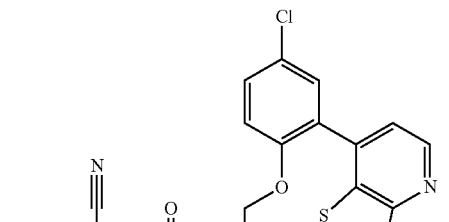 | MS (ESI) m/z 581.08 [M + 1]+. 1H NMR (400 MHz, DMSO-d6) δ 12.35 (bs, 1H), 8.84 (d, J = 4.8 Hz, 1H), 8.40 (s, 1H), 7.65 (d, J = 9.6 Hz, 1H), 7.60 (dd, J = 8.8, 2.4 Hz, 1H), 7.49 (d, J = 4.8 Hz, 1H), 7.42 (d, J = 2.8 Hz, 1H), 7.36 (d, J = 8.8 Hz, 1H), 4.40-4.38 (m, 2H), 4.24-4.22 (m, 2H), 1.75 (s, 3H) |
| 244 | 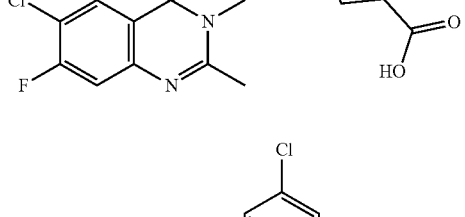 | MS (ESI) m/z 551.16 [M + 1]+; 1H NMR (400 MHz, DMSO-d6) δ 8.83 (d, J = 4.76 Hz, 1H), 8.39 (s, 1H), 8.06 (d, J = 8.88, 1H), 7.68 (d, J = 8.8, 1H), 7.58-7.61 (m, 1H), 7.50 (d, J = 4.56 Hz, 1H), 7.43 (d, J = 2.52 Hz, 1H), 7.39 (d, J = 9.0 Hz, 1H), 4.40 (s, 2H), 4.23 (s, 2H), 1.74 (s, 3H) |
| 245 | 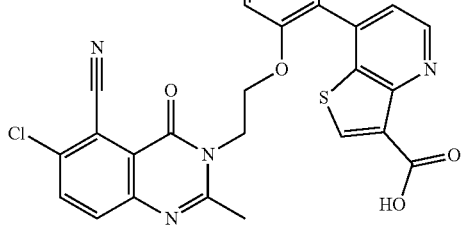 | MS (ESI) m/z 535.14 [M + 1]+; 1H NMR (400 MHz, DMSO-d6) δ 13.33 (bs, 1H), 8.83 (d, J = 4.8 Hz, 1H), 8.4 (s, 1H), 7.93 (t, J = 9.0 Hz, 1H), 7.76 (dd, J = 9.0, 5.0 Hz, 1H), 7.59 (dd, J = 8.8, 2.5 Hz, 1H), 7.51 (d, J = 4.8 Hz, 1H), 7.43 (d, J = 2.5 Hz, 1H), 7.36 (d, J = 8.9 Hz, 1H), 4.4 (t, J = 4.8 Hz, 2H), 4.23 (t, J = 4.7 Hz, 2H), 1.73 (s, 3H) |

TABLE 3-continued

Other Compounds

| Compound | Characterization |
|---|---|
| 247 | MS (ESI) m/z 658.02 [M + 1]+; 1H NMR (400 MHz, DMSO-d6) δ 8.85 (d, J = 4.84 Hz, 1H), 8.42 (s, 1H), 7.88 (s, 1H), 7.60 (dd, J = 2.4, 8.88 Hz, 1H), 7.52 (d, J = 4.8 Hz, 1H), 7.45 (d, J = 2.4 Hz, 1H), 7.36 (d, J = 9.2 Hz, 1H), 4.41 (t, J = 4.72 Hz, 2H), 4.23 (t, J = 4.44 Hz, 2H), 2.96 (s, 6H), 1.71 (s, 3H) |
| 248 | MS (ESI) m/z 636.23 [M + 1]+; 1H NMR (400 MHz, DMSO-d6) δ 8.84 (d, J = 4.76 Hz, 1H), 8.43 (s, 1H), 8.26 (d, J = 8.72 Hz, 1H), 7.84 (d, J = 8.72 Hz, 1H), 7.61 (dd, J = 8.92, 2.6 Hz, 1H), 7.51 (d, J = 4.76 Hz, 1H), 7.46 (d, J = 2.6 Hz, 1H), 7.37 (d, J = 9.0 Hz, 1H), 4.41 (t, J = 5.6 Hz, 2H), 4.25 (t, J = 5.52 Hz, 2H), 3.96 (t, J = 7.52 Hz, 4H), 2.19-2.11 (m, 2H), 1.76 (s, 3H) |
| 249 | MS (ESI) m/z 650.15 [M + 1]+; 1H NMR (400 MHz, DMSO-d6) δ 8.83 (d, J = 4.8 Hz, 1H), 8.40 (s, 1H), 8.28 (d, J = 8.72 Hz, 1H), 7.82 (d, J = 8.76 Hz, 1H), 7.60 (dd, J = 8.92, 2.56 Hz, 1H), 7.50 (d, J = 4.76 Hz, 1H), 7.45 (d, J = 2.6 Hz, 1H), 7.36 (d, J = 9.0 Hz, 1H), 4.40 (t, J = 5.24 Hz, 2H), 4.25 (t, J = 1.96 Hz, 2H), 3.36 (t, J = 6.48 Hz, 4H), 1.83 (t, J = 6.52 Hz, 4H), 1.75 (s, 3H) |
| 250 | MS (ESI) m/z 652.16 [M + 1]+; 1H NMR (400 MHz, DMSO-d6) δ 8.84 (d, J = 4.84 Hz, 1H), 8.43 (s, 1H), 8.31 (d, J = 8.76 Hz, 1H), 7.81 (d, J = 8.8 Hz, 1H), 7.61 (dd, J = 2.72, 8.92 Hz, 1H), 7.52 (d, J = 4.84 Hz, 1H), 7.46 (d, J = 2.72 Hz, 1H), 7.36 (d, J = 9.04 Hz, 1H), 4.41 (t, J = 4.56 Hz, 2H), 4.24 (t, J = 4.5 Hz, 2H), 3.41 (d, J = 7.04 Hz, 4H), 1.74 (s, 3H), 1.10 (t, J = 7.04 Hz, 6H) |

TABLE 3-continued

Other Compounds

| Compound | Characterization |
|---|---|
| 251 | MS (ESI) m/z 663.32 [M + 1]+; 1H NMR (400 MHz, DMSO-d6) δ 8.84 (d, J = 4.76 Hz, 1H), 8.41 (s, 1H), 8.26 (d, J = 8.76 Hz, 1H), 7.82 (d, J = 8.72 Hz, 1H), 7.60 (dd, J = 8.8, 2.52 Hz, 1H), 7.50 (d, J = 4.76 Hz, 1H), 7.46 (d, J = 2.45 Hz, 1H), 7.36 (d, J = 8.96 Hz, 1H), 4.40 (bs, 2H), 4.23 (bs, 2H), 3.20 (d, J = 5.2 Hz, 4H), 1.75 (s, 3H), 1.55 (s, 4H), 1.46 (d, J = 3.64 Hz, 2H) |
| 252 | MS (ESI) m/z 686.21 [M + 1]+; 1H NMR (400 MHz, DMSO-d6) δ 8.83 (d, J = 4.8 Hz, 1H), 8.72 (t, J = 6.1, 1H), 8.4 (s, 1H ) 8.20 (d, J = 8.7, 1H), 7.73 (d, J = 8.7 Hz, 1H), 7.60 (dd, J = 2.1, 8.92 Hz, 1H), 7.46 (m, 2H), 7.37 (d, J = 9 Hz, 1H), 7.1 (m, 4H), 7.07 (t, J = 7.1 Hz, 1H), 4.39 (d, J = 4.56, 2H), 4.24 (m, 4H), 1.72 (s, 3H) |
| 253 | MS (ESI) m/z 714.20 [M + 1]+; 1H NMR (400 MHz, DMSO-d6) δ 8.84 (d, J = 4.8 Hz, 1H), 8.41 (s, 1H), 8.33 (d, J = 8.76 Hz, 1H), 7.80 (d, J = 8.76 Hz, 1H), 7.62 (dd, J = 2.68, 8.90 Hz, 1H), 7.51 (d, J = 4.80 Hz, 1H), 7.44 (d, J = 2.60 Hz, 1H), 7.38 (d, J = 9.00 Hz, 1H), 7.35-7.28 (m, 4H), 7.15-7.20 (m, 1H), 4.59 (s, 2H), 4.40 (t, J = 4.64 Hz, 2H), 4.25 (t, J = 4.36 Hz, 2H), 3.30 (q, J = 6.92 Hz, 2H), 1.75 (s, 3H), 0.91 (t, J = 7.12 Hz, 3H). |
| 254 | MS (ESI) m/z 517.17 [M + 1]+; UPLC: 98.39%; 1H NMR (400 MHz, DMSO-d6) δ 13.42 (s, 1H), 8.82 (d, J = 4.72 Hz, 1H), 8.37 (s, 1H), 7.95 (d, J = 6.52 Hz, 1H), 7.91-7.87 (t, 1H), 7.70 (d, J = 8.16, Hz 1H), 7.60-7.57 (dd, J = 2.48 Hz, 1H), 7.47 (d, J = 4.76 Hz, 1H), 7.43 (d, J = 2.52 Hz, 1H), 7.35 (d, J = 8.96 Hz, 1H), 4.41-4.22 (m, 4H), 1.77 (s, 3H) |

TABLE 3-continued

| | Other Compounds | |
|---|---|---|
| | Compound | Characterization |
| 256 | (structure) | MS (ESI) m/z 581.07 [M + 1]+; 1H NMR (400 MHz, DMSO-d6) δ 13.22 (bs, 1H), 8.83 (s, 1H), 8.80 (d, J = 4.8 Hz, 1H), 8.10 (s, 1H), 7.87 (d, J = 8.4 Hz, 1H), 7.62 (dd, J = 8.4, 2.0 Hz, 1H), 7.52 (d, J = 2.0 Hz, 1H), 7.43 (d, J = 4.8 Hz, 1H), 6.48-6.41 (m, 1H), 5.97 (d, J = 16.0 Hz, 1H), 4.70 (d, J = 4.4 Hz, 2H), 2.36 (s, 3H) |
| 257 | (structure) | MS (ESI) m/z 579.06 [M + 1]+; 1H NMR (400 MHz, DMSO-d6) δ 8.76 (d, J = 4.7 Hz, 1H), 8.62 (s, 1H), 8.09 (s, 1H), 7.76 (d, J = 8.4 Hz, 1H), 7.69 (d, J = 2.0 Hz, 1H), 7.67 (s, 1H), 7.55 (d, J = 4.8 Hz, 1H), 4.85 (s, 2H), 2.09 (s, 3H) |
| 258 | (structure) | MS (ESI) m/z 536.11 [M + 1]+; 1H NMR (400 MHz, DMSO-d6) δ 8.74 (d, J = 4.7 Hz, 1H), 8.6 (s, 1H), 8.51 (d, J = 1.4 Hz, 1H), 8.32 (d, J = 1.4 Hz, 1H), 7.76 (d, J = 9.1 Hz, 1H), 7.68 (m, 2H), 7.53 (d, J = 4.7 Hz, 1H), 4.86 (s, 2H), 2.13 (s, 3H). |
| 262 | (structure) | MS (ESI) m/z 601.02 [M + 1]+; 1H NMR (400 MHz, DMSO-d6) δ 12.53 (bs, 1H), 8.86 (d, J = 4.8 Hz, 1H), 8.46 (s, 1H), 8.06 (d, J = 4.6 Hz, 2H), 7.60 (dd, J = 8.8, 2.6 Hz, 1H), 7.52 (d, J = 4.7 Hz, 1H), 7.40 (d, J = 2.5 Hz, 1H), 7.36 (d, J = 8.9 Hz, 1H), 4.41 (m, 2H), 4.19 (m, 2H), 1.46 (d, J = 3.3 Hz, 3H) |

TABLE 3-continued
| Other Compounds | |
|---|---|
| Compound | Characterization |
263 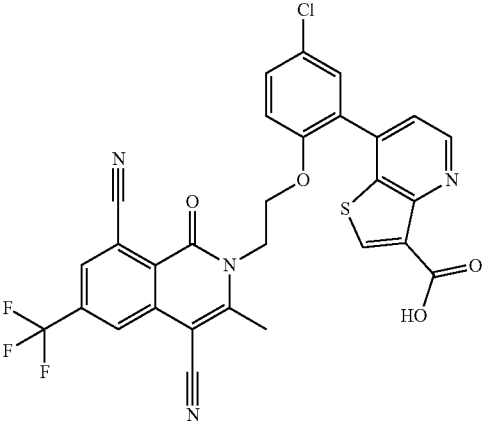 [SMILES: Cc1c(C#N)c2cc(C(F)(F)F)cc(C#N)c2c(=O)n1CCOc1ccc(Cl)cc1-c1ccnc2c(C(=O)O)csc12]
MS (ESI) m/z 608.02 [M + 1]+; 1H NMR (400 MHz, DMSO-d6) δ 13.21 (bs, 1H), 8.87 (d, J = 4.7 Hz, 1H), 8.56 (s, 1H), 8.11 (s, 1H), 8.01 (s, 1H), 7.61 (dd, J = 8.8, 2.8 Hz, 1H), 7.52 (d, J = 4.8 Hz, 1H), 7.39-7.37 (m, 2H), 4.45 (m, 2H), 4.33 (m, 2H), 1.92 (s, 3H)
264 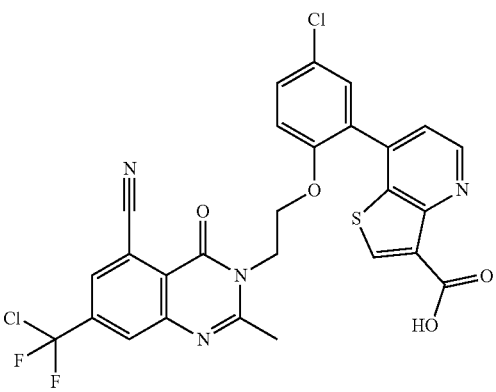 [SMILES: Cc1nc2cc(C(F)(F)Cl)cc(C#N)c2c(=O)n1CCOc1ccc(Cl)cc1-c1ccnc2c(C(=O)O)csc12]
MS (ESI) m/z 601.15 [M + 1]+. 1H NMR (400 MHz, DMSO-d6) δ 8.84 (d, J = 4.8 Hz, 1H), 8.33 (d, J = 1.6 Hz, 1H), 8.30 (s, 1H), 7.96 (d, J = 1.2 Hz 1H), 7.60 (dd, J = 8.8, 2.4 Hz, 1H), 7.50 (d, J = 4.8 Hz, 1H), 7.43 (d, J = 2.4 Hz, 1H), 7.35 (d, J = 8.8 Hz, 1H), 4.40 (t, J = 4.8 Hz, 2H), 4.24 (t, J = 4.8 Hz, 2H), 1.73 (s, 3H)
268 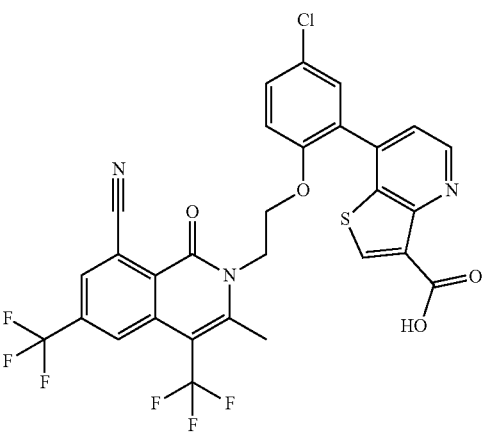 [SMILES: Cc1c(C(F)(F)F)c2cc(C(F)(F)F)cc(C#N)c2c(=O)n1CCOc1ccc(Cl)cc1-c1ccnc2c(C(=O)O)csc12]
MS (ESI) m/z 652.05 [M + 1]+; 1H NMR (400 MHz, DMSO-d6) δ 8.81 (d, J = 4.80 Hz, 1H), 8.50 (s, 1H), 8.24 (s, 1H), 8.08 (s, 1H), 7.60 (dd, J = 2.60, 2.64 Hz, 1H), 7.52 (d, J = 4.76 Hz, 1H), 7.42-7.38 (m, 2H), 4.47 (bs, 2H), 4.39 (bs, 2H), 1.89 (s, 3H)

TABLE 3-continued
| Compound | Characterization |
|---|---|
| 269 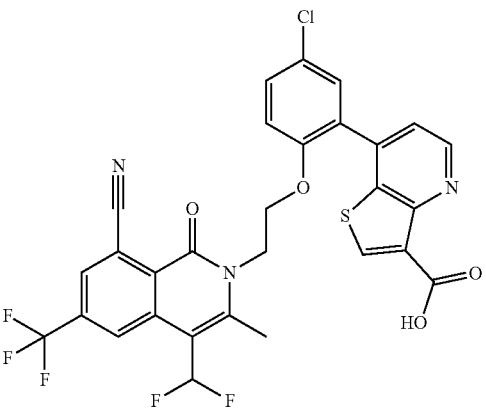 [SMILES: Cc1c(C(F)F)c2cc(C(F)(F)F)cc(C#N)c2c(=O)n1CCOc1ccc(Cl)cc1-c1ccnc2c(C(=O)O)csc12] | MS (ESI) m/z 634.05 [M + 1]+; 1H NMR (400 MHz, DMSO-d6) δ 13.21 (bs, 1H), 8.77 (d, J = 4.84 Hz, 1H), 8.43 (s, 1H), 8.41 (s, 1H), 8.36 (s, 1H), 7.60-7.58 (m, 1H), 7.48 (d, J = 4.72 Hz, 1H), 7.44-7.17 (m, 3H), 4.45 (t, J = 4.47 Hz, 2H), 4.35 (t, J = 4.35 Hz, 2H), 1.99 (s, 3H) |
| 270 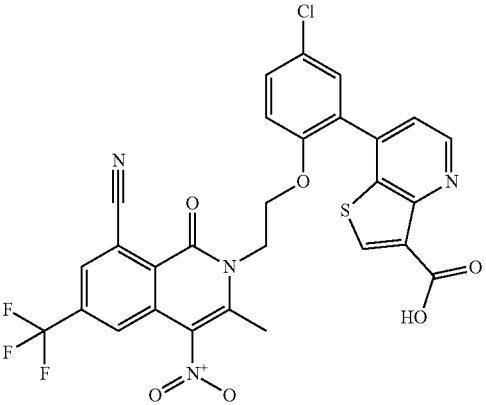 | MS (ESI) m/z 629.04 [M + 1]+; 1H NMR (400 MHz, DMSO-d6) δ 13.21 (bs, 1H), 8.80 (d, J = 4.80 Hz, 1H), 8.54 (s, 1H), 8.33 (s, 1H), 7.94 (s, 1H), 7.62-7.59 (m, 1H), 7.50 (d, J = 4.76 Hz, 1H), 7.42-7.38 (m, 2H), 4.47 (t, J = 4.47 Hz, 2H), 4.36 (t, J = 4.36 Hz, 2H), 1.85 (s, 3H) |
| 271 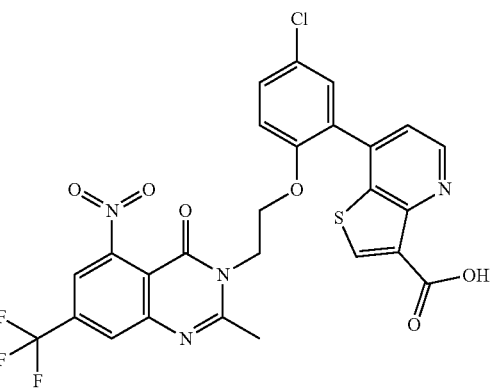 [SMILES: Cc1nc2cc(C(F)(F)F)cc([N+](=O)[O-])c2c(=O)n1CCOc1ccc(Cl)cc1-c1ccnc2c(C(=O)O)csc12] | MS (ESI) m/z 605.04 [M + 1]+; 1H NMR (400 MHz, DMSO-d6) δ 13.30 (bs, 1H), 8.84 (d, J = 4.68 Hz, 1H), 8.36 (s, 1H), 8.35 (d, J = 1.38 Hz, 1H), 7.98 (s, 1H), 7.58 (dd, J = 2.60, 2.60 Hz, 1H), 7.47 (d, J = 4.72 Hz, 1H), 7.43 (d, J = 2.60 Hz, 1H), 7.33 (d, J = 8.96 Hz, 1H), 4.33 (t, J = 4.79 Hz, 2H), 4.20 (t, J = 4.94 Hz, 2H), 1.75 (s, 3H) |

TABLE 3-continued

Other Compounds

| Compound | Characterization |
|---|---|
| 273 | MS (ESI) m/z 558.95 [M + 1]+; 1H NMR (400 MHz, DMSO-d6) δ 8.86-8.85 (d, J = 4.8 Hz, 1H), 8.57 (d, J = 1.2 Hz, 1H), 8.23 (d, J = 1.2 Hz, 1H), 8.17 (s, 1H), 7.61-7.58 (dd, J = 2.8, 8.8 Hz, 1H), 7.50-7.49 (d, J = 4.8 Hz, 1H), 7.40 (d, J = 2.8 Hz, 1H), 7.37-7.35 (d, J = 8.8 Hz, 1H), 4.40 (d, J = 4.4 Hz, 2H), 4.18 (t, J 4.4 Hz, 2H), 1.49 (d, J = 3.6 Hz, 3H) |
| 274 | MS (ESI) m/z 611.97 [M + 1]+. 1H NMR (400 MHz, DMSO-d6) δ 8.87 (d, J = 4.7 Hz, 1H), 8.47 (s, 1H), 8.23 (s, 1H), 8.12 (s, 1H), 7.59 (d, J = 9.3 Hz, 1H), 7.52 (d, J = 4.5 Hz, 1H), 7.41 (s, 1H), 7.37 (d, J = 8.9 Hz, 1H), 4.42 (t, J = 5.2 Hz, 2H), 4.19 (t, J = 5.2 Hz, 2H), 3.52 (s, 3H), 1.46 (s, 3H) |
| 276 | MS (ESI) m/z 559.95 [M + 1]+; 1H NMR (400 MHz, DMSO-d6) δ 12.81 (bs, 1H), 8.85 (d, J = 4.76 Hz, 1H), 8.39 (s, 1H), 7.69 (d, J = 9.60 Hz, 1H), 7.60 (dd, J = 8.84, 2.48 Hz, 1H), 7.50 (d, J = 4.76 Hz, 1H), 7.42 (d, J = 2.56 Hz, 1H), 7.36 (d, J = 8.96 Hz, 1H), 4.40 (t, 4.40 Hz, 2H), 4.25 (t, J = 4.80, 2H), 1.80 (s, 3H) |
| 277 | MS (ESI) m/z 629.53 [M + 1]+; 1H NMR (400 MHz, DMSO-d6) δ 13.35 (bs, 1H), 8.84 (d, J = 4.8 Hz, 1H), 8.32 (s, 1H), 8.21 (s, 1H), 7.60 (dd, J = 8.8, 2.4 Hz, 1H), 7.49 (d, J = 4.8 Hz, 1H), 7.42 (d, J = 2.8 Hz, 1H), 7.37 (d, J = 8.8 Hz, 1H), 4.42 (t, J = 4.4 Hz, 2H), 4.25 (t, J = 5.2 Hz, 2H), 1.71 (s, 3H) |

TABLE 3-continued

Other Compounds

| Compound | Characterization |
|---|---|
| 278 | MS (ESI) m/z 613.09 [M + 1]+; 1H NMR (400 MHz, DMSO-d6) δ 13.21 (bs, 1H), 8.84 (d, J = 3.28 Hz, 1H), 8.26 (s, 1H), 8.07 (d, J = 5.96 Hz, 1H), 7.59 (d, J = 7.96 Hz, 1H), 7.47 (bs, 1H), 7.41 (s, 1H), 7.36 (d, J = 8.68 Hz, 1H), 4.42 (s, 2H), 4.24 (s, 2H), 3.58 (s, 3H), 1.72 (s, 3H) |
| 279 | MS (ESI) m/z 613.19 [M + 1]+; 1H NMR (400 MHz, DMSO-d6) δ 8.85 (d, J = 4.72 Hz, 1H), 8.43 (s, 1H), 7.64 (d, J = 11.36 Hz, 1H), 7.60 (dd, J = 8.88, 2.56 Hz, 1H), 7.48 (d, J = 4.8 Hz, 1H), 7.42 (d, J = 2.6 Hz, 1H), 7.36 (d, J = 9.0 Hz, 1H), 4.40 (t, J = 5.0 Hz, 2H), 4.24 (t, J = 4.64, 2H), 3.58 (s, 3H), 1.78 (s, 3H) |
| 280 | MS (ESI) m/z 642.15 [M + 1]+; 1H NMR (400 MHz, DMSO-d6) δ 8.86 (d, J = 4.84 Hz, 1H), 8.31 (s, 1H), 8.05 (d, J = 6.32 Hz, 1H), 7.59 (dd, J = 8.88, 2.56 Hz, 1H), 7.51 (d, J = 4.84 Hz, 1H), 7.45 (d, J = 2.56 Hz, 1H), 7.35 (d, J = 9.0 Hz, 1H), 4.40 (t, J = 4.60 Hz, 2H), 4.22 (t, J = 4.32 Hz, 2H), 2.94 (s, 6H), 1.62 (s, 3H) |
| 281 | MS (ESI) m/z 641.95 [M + 1]+; 1H NMR (400 MHz, DMSO-d6) δ 8.85 (d, J = 4.76 Hz, 1H), 8.40 (s, 1H), 7.64 (d, J = 11.52 Hz, 1H), 7.60 (dd, J = 2.60, 8.96 Hz, 1H), 7.48 (d, J = 4.76 Hz, 1H), 7.44 (d, J = 2.64 Hz, 1H), 7.36 (d, J = 8.92 Hz, 1H), 4.39 (t, J = 4.4 Hz, 2H), 4.22 (t, J = 4.36 Hz, 2H), 2.92 (s, 6H), 1.77 (s, 3H) |

TABLE 3-continued

Other Compounds

| Compound | Characterization |
|---|---|
| 282 | MS (ESI) m/z 700.01 [M + 1]+; 1H NMR (400 MHz, DMSO-d6) δ 8.84 (d, J = 4.84 Hz, 1H), 8.41 (s, 1H), 8.32 (d, J = 8.76 Hz, 1H), 7.81 (d, J = 8.76, Hz, 1H), 7.61 (dd, J = 2.60, 8.92 Hz, 1H), 7.50 (d, J = 4.80 Hz, 1H), 7.46 (d, J = 2.68 Hz, 1H), 7.36 (d, J = 9.04 Hz, 1H), 4.41 (bs, 2H), 4.24 (bs, 2H), 3.41(m, 4H), 2.14-2.07 (m, 4H), 1.76 (s, 3H) |
| 283 | MS (ESI) m/z 700.22 [M + 1]+; 1H NMR (400 MHz, DMSO-d6) δ 8.85 (d, J = 4.84 Hz, 1H), 8.41 (s, 1H), 8.34 (d, J = 8.8 Hz, 1H), 7.82 (d, J = 8.8, Hz, 1H), 7.61 (dd, J = 2.72, 8.92 Hz, 1H), 7.505 (d, J = 4.84 Hz, 1H), 7.46 (d, J = 2.72 Hz, 1H), 7.36 (m, 6H), 4.48 ( s, 2H), 4.41 (t, J = 4.56 Hz, 2H), 4.24 (t, J = 4.56 Hz, 2H), 2.76 (s, 3H), 1.74 ( s, 3H) |
| 286 | MS (ESI) m/z 538.22 [M + 1]+; 1H NMR (400 MHz, DMSO-d6) δ 8.85 (s, 1H), 8.80 (d, J = 4.8 Hz, 1H), 8.43 (d, J = 0.8 Hz, 1H), 8.33 (d, J = 0.8 Hz, 1H), 7.87 (d, J = 8.8 Hz, 1H ), 7.62 (dd, J = 8.8, 2.0 Hz, 1H), 7.52 (d, J = 2.0 Hz, 1H), 7.45 (d, J = 4.8, 1H), 6.49-6.42 (m,1H), 5.97 (d, J = 16 Hz, 1H), 4.71 (d, J = 4.8 Hz, 1H), 2.39 (s 3H) |
| 288 | MS (ESI) m/z 642.18 [M + 1]+; 1H NMR (400 MHz, DMSO-d6) δ 8.84 (d, J = 4.56 Hz, 1H), 8.45 (s, 1H), 8.11 (d, J = 5.2 Hz, 1H), 7.61 (d, J = 7 Hz, 1H), 7.52 (d, J = 4.52 Hz, 1H), 7.45 (d, J = 2.12 Hz, 1H), 7.37 (d, J = 8.68 Hz, 1H), 4.42 (t, J = 4.6 Hz, 2H), 4.27 (t, J = 6.32 Hz, 2H), 2.89 (s, 6H), 1.83 (s, 3H) |

TABLE 3-continued

Other Compounds

| Compound | Characterization |
|---|---|
| 290 | MS (ESI) m/z 576.13 [M + 1]+; 1H NMR (400 MHz, DMSO-d6) δ 13.26 (bs, 1H), 8.87 (d, J = 4.6 Hz, 1H), 8.37 (s, 1H), 8.05 (dd, J = 8.7, 2.0 Hz, 1H), 7.93 (s, 1H), 7.88 (d, J = 2.0 Hz, 1H), 7.52 (d, J = 3.1 Hz, 1H), 7.5 (s, 1H), 4.5 (t, J = 4.8 Hz, 2H), 4.25 (t, J = 4.6 Hz, 2H), 1.69 (s, 3H) |
| 293 | MS (ESI) m/z 613.15 [M + 1]+; 1H NMR (400 MHz, DMSO-d6) δ 8.81 (d, J = 4.80 Hz, 1H), 8.75 (bs, 1H), 8.30 (d, J = 8.36 Hz, 1H), 7.60 (dd, J = 8.96, 6.52, Hz, 1H), 7.90-7.42 (m, 2H), 7.38 (d, J = 8.88 Hz, 1H), 4.43 (t, J = 5.84 Hz, 2H), 4.30 (t, J = 4.24 Hz, 2H), 3.67 (s, 3H), 2.11 (s, 3H) |
| 297 | MS (ESI) m/z 658.33 [M + 1]+; 1H NMR (400 MHz, DMSO-d6): δ 13.34 (bs, 1H), 8.80 (d, J = 4.7 Hz, 1H), 8.65 (d, J = 4.32 Hz, 1H), 8.61 (d, J = 8.72 Hz, 1H), 8.48 (s, 1H), 8.37 (d, J = 7.88 Hz, 1H), 8.26 (t, J = 7.76 Hz, 1H), 7.96 (d, J = 8.76 Hz, 1H), 7.77-7.74 (m, 1H), 7.58-7.55 (m, 1H), 7.46-7.44 (m, 2H), 7.30 (d, J = 8.96 Hz, 1H), 4.34 (d, J = 4.68 Hz, 2H), 4.20 (d, J = 4.40 Hz, 2H), 1.75 (s, 3H) |
| 298 | MS (ESI) m/z 602.95 [M + 1]+; 1H-NMR (400 MHz, DMSO-d6) δ 13.13 (bs, 1H), 8.82 (d, J = 4.76 Hz ,1H), 8.41 (s, 1H), 7.60 (dd, J = 2.64, 8.92 Hz, 1H), 7.48-7.34 (m, 4H), 4.42 (t, J = 4.6 Hz, 2H), 4.26 (t, J = 4.0 Hz, 2H), 1.85 (s, 3H) |

TABLE 3-continued

Other Compounds

| Compound | Characterization |
|---|---|
| 302 | MS (ESI) m/z 609.60 [M + 1]+; 1H NMR (400 MHz, DMSO-d6) δ 8.90 (d, J = 4.6 Hz, 1H), 8.38 (s, 1H), 7.89 (d, J = 9.76 Hz, 1H), 7.60 (dd, J = 2,4, 8.84 Hz, 1H), 7.50 (d, J = 4.60 Hz, 1H), 7.47-7.20 (m, 3H), 4.43 (t, J = 4.80 Hz, 2H), 4.26 (t, J = 4.88 Hz, 2H), 1.83 (s, 3H) |
| 303 | MS (ESI) m/z 613.08 [M + 1]+; 1H NMR (400 MHz, DMSO-d6) δ 12.03 (s, 1H), 8.78 (d, J = 4.84 Hz, 1H), 8.32 (s, 1H), 8.05 (s, J = 9.60, 1H), 7.59 (dd, J = 8.96, 2.56 Hz, 1H), 7.49-7.35 (m, 4H), 4.41 (m, 2H), 4.27 (m, 2H), 3.86 (s, 3H), 1.89 (s, 3H) |
| 304 | MS (ESI) m/z 583.20 [M + 1]+; 1H NMR (400 MHz, DMSO-d6) δ 12.96 (s,1H), 7.95 (s, 1H), 7.86-7.85 (m, 3H), 7.53 (d, J = 7.96, 1H), 7.43-7.38 (m, 2H), 7.28 (d, J = 2.6, 1H), 7.20 (d, J = 8.8 Hz, 1H), 4.30 (s, 4H), 2.18 (s, 3H) |
| 305 | MS (ESI) m/z 638.07 [M + 1]+; 1H NMR (400 MHz, DMSO-d6) δ 13.21 (bs, 1H), 8.83 (s, 1H), 8.35 (s, 1H), 7.94 (s, 1H), 7.71 (s, 1H), 7.58 (dd, J = 2.44, 8.88 Hz, 1H), 7.47 (bs, 1H), 7.43 (s, 1H), 7.33 (d, J = 8.96 Hz, 1H), 4.35 (t, J = 5.32 Hz, 2H), 4.18 (t, J = 5.08 Hz, 2H), 1.71 (s, 3H) |

TABLE 3-continued

Other Compounds

| Compound | Characterization |
|---|---|
| 306 | MS (ESI) m/z 577.08 [M + 1]+; 1H NMR (400 MHz, DMSO-d6) δ 8.90 (d, J = 4.68 Hz, 1H), 8.39 (s, 1H), 7.61-7.58 (m, 1H), 7.48 (d, J = 4.64 Hz, 1H), 7.44-7.35 (m, 3H), 4.40 (t, J = 5.18 Hz, 2H), 4.22 (t, J = 4.48 Hz, 2H), 1.73 (s, 3H) |
| 307 | MS (ESI) m/z 629.98 [M + 1]+; 1H NMR (400 MHz, DMSO-d6) δ 12.68 (s, 1H), 8.90 (d, J = 4.80 Hz, 1H), 8.53 (s, 1H), 7.72 (dd, J = 7.60, 10.68 Hz, 1H), 7.61 (dd, J = 2.56, 8.88 Hz, 1H), 7.56 (d, J = 4.84 Hz, 1H), 7.44 (d, J = 2.64 Hz, 1H), 7.37 (d, J = 9.0 Hz, 1H), 4.41 (t, J = 4.56 Hz, 2H), 4.23 (t, J = 4.60 Hz, 2H), 3.57 (s, 3H), 1.74 (s, 3H) |
| 308 | MS (ESI) m/z 581.97 [M + 1]+; 1H NMR (400 MHz, DMSO-d6) δ 12.09 (s, 1H), 8.83 (d, J = 4.76 Hz, 1H), 8.26 (s, 1H), 7.73 (dd, J = 7.24, 10.48 Hz, 1H), 7.59 (dd, J = 2.48, 8.88 Hz, 1H), 7.44 (d, J = 4.72 Hz, 1H), 7.40 (d, J = 2.52 Hz, 1H), 7.35 (d, J = 9.04 Hz, 1H), 4.38 (t, J = 4.28 Hz, 2H), 4.22 (t, J = 4.56 Hz, 2H), 3.88 (s, 3H), 1.75 (s, 3H) |
| 309 | MS (ESI) m/z 614.07 [M + 1]+. 1H NMR (400 MHz, DMSO-D2O) δ 8.76 (s, 1H), 8.21 (s, 1H), 8.03 (s, 1H), 7.87 (s, 1H), 7.53 (d, J = 12 Hz, 1H), 7.41 (s, 1H), 7.30-7.26 (m, 2H), 4.34 (s, 2H), 4.17 (s, 2H), 3.41 (s, 3H), 1.50 (s, 3H) |

TABLE 3-continued
| Compound | | Characterization |
|---|---|---|
| 310 | 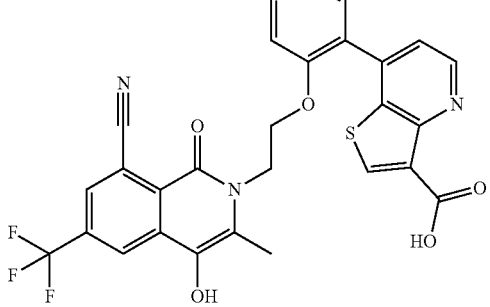 | MS (ESI) m/z 600.23 [M + 1]+; 1H NMR (400 MHz, DMSO-d6) δ 8.84 (d, J = 4.8 Hz, 1H), 8.41 (s, 1H), 8.32 (s, 1H), 8.29 (s, 1H), 8.11 (s, 1H), 7.58 (dd, J = 2.5 Hz, 2.6 Hz, 1H), 7.52 (d, J = 4.7 Hz, 1H), 7.42 (d, J = 2.6 Hz, 1H), 7.36 (d, J = 8 Hz, 1H), 4.41 (t, J = 5.2 Hz, 2H), 4.21 (t, J = 5.5 Hz, 2H), 1.54 (s, 3H) |
| 311 | 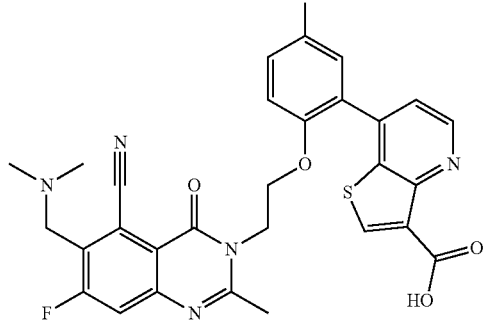 | MS (ESI) m/z 592.10 [M + 1]+; 1H NMR (400 MHz, DMSO-d6) δ 8.83 (d, J = 4.72 Hz, 1H), 8.29 (s, 1H), 7.62-7.60 (m, 2H), 7.48 (d, J = 4.76 Hz, 1H), 7.43 (d, J = 2.60 Hz, 1H), 7.37 (d, J = 8.96 Hz, 1H), 4.59 (s, 2H), 4.41 (t, J = 4.68 Hz, 2H), 4.25 (t, J = 4.68 Hz, 2H), 2.95 (s, 6H), 1.81 (s, 3H) |
| 312 | 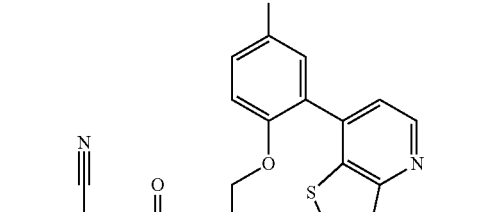 | MS (ESI) m/z 541.97 [M + 1]+; 1H NMR (400 MHz, DMSO-d6) δ 13.23 (bs, 1H), 8.8 (d, J = 4.8 Hz, 1H), 8.52 (s, 1H), 8.4 (d, J = 7.8 Hz, 1H), 8.06 (d, J = 7.8 Hz, 1H), 7.59 (dd, J = 8.9, 2.6 Hz, 1H), 7.46 (d, J = 4.8 Hz, 1H), 7.44 (d, J = 2.5 Hz, 1H), 7.36 (d, J = 8.9 Hz, 1H), 4.42 (t, J = 4.6 Hz, 2H), 4.28 (t, J = 4.9 Hz, 2H), 1.97 (s, 3H). |

TABLE 3-continued
| | Compound | Characterization |
|---|---|---|
| 313 | 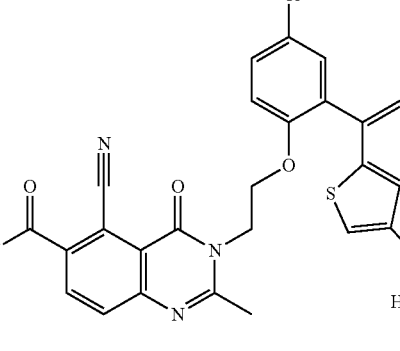 | MS (ESI) m/z 600.97 [M + 1]+; 1H NMR (400 MHz, DMSO-d6) δ 13.23 (bs, 1H), 8.77 (d, J = 4.76 Hz, 1H), 8.55 (s, 1H), 8.02 (d, J = 8.28 Hz, 1H), 7.92 (d, J = 7.24 Hz, 1H), 7.58 (dd, J = 2.56, 8.88 Hz, 1H), 7.46-7.44 (m, 2H), 7.35 (d, J = 8.96 Hz, 1H), 4.41 (t, J = 5.32 Hz, 2H), 4.26 (t, J = 4.52 Hz, 2H), 1.90 (s, 3H). |
| 316 | 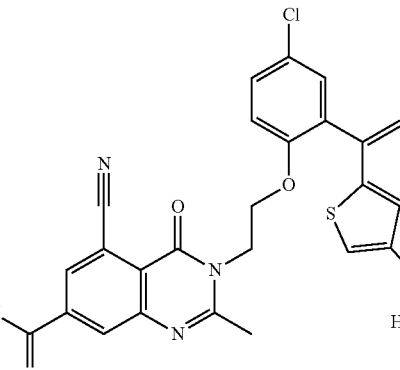 | MS (ESI) m/z 560.39 [M + 1]+; 1H NMR (400 MHz, DMSO-d6) δ 8.83 (d, J = 4.8 Hz, 1H), 8.40 (s, 1H), 8.17 (s, 1H), 7.92 (d, J = 8.36 Hz, 2H), 7.69 (d, J = 8.52 Hz, 1H), 7.60-7.58 (m, 1H), 7.48 (d, J = 4.84 Hz, 1H), 7.44 (d, J = 2.68 Hz, 1H), 7.35 (d, J = 8.96 Hz, 1H), 4.39 (t, J = 4.48 Hz, 2H), 4.23 (t, J = 4.48 Hz, 2H), 1.72 (s, 3H) |
| 317 | | MS (ESI) m/z 559.99 [M + 1]+; 1H NMR (400 MHz, DMSO-d6) δ 13.34 (bs, 1H), 8.81 (d, J = 4.4 Hz, 1H), 8.45 (s, 1H), 8.28 (s, 2H), 8.20 (s, 1H), 7.87 (s, 1H), 7.59-7.57 (m, 1H), 7.50-7.40 (m, 2H), 7.35 (d, J = 8.8 Hz, 1H), 4.49-4.30 (m, 2H), 4.29-4.15 (m, 2H), 1.77 (s, 3H) |

TABLE 3-continued

Other Compounds

| Compound | Characterization |
|---|---|
| 318 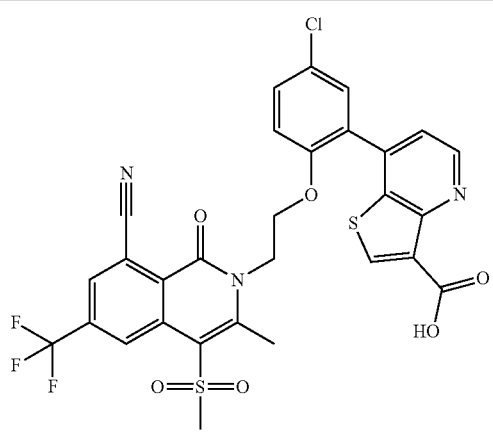 [SMILES: Cc1c(S(C)(=O)=O)c2cc(C(F)(F)F)cc(C#N)c2c(=O)n1CCOc1ccc(Cl)cc1-c1ccnc2c(C(=O)O)csc12] | MS (ESI) m/z 662.04 [M + 1]+; 1H NMR (400 MHz, DMSO-d6) δ 9.03 (s, 1H), 8.78 (d, J = 4.76 Hz, 1H), 8.47 (s, 1H), 8.43 (s, 1H), 7.60-7.58 (m, 1H), 7.47-7.44 (m, 2H), 7.38 (d, J = 8.92 Hz, 1H), 4.44 (s, 4H), 3.27 (s, 3H), 2.33 (s, 3H) |
| 334 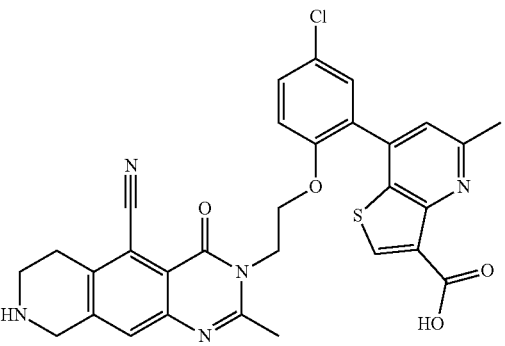 [SMILES: Cc1cc(-c2cc(Cl)ccc2OCCn2c(C)nc3cc4c(c(C#N)c3c2=O)CCNC4)c2scc(C(=O)O)c2n1] | MS (ESI) m/z 586.3 [M + 1]+; 1H-NMR (400 MHz, d6-DMSO) δ/ppm = 9.20 (b, 2H), 8.30 (s, 1H), 7.60 (dd, J = 8.9, 2.7 Hz, 1H), 7.55 (s, 1H), 7.44 (s, 1H), 7.39-7.35 (m, 2H), 4.53-4.48 (m, 2H), 4.41 (bt, 2H), 4.26 (bt, 2H), 3.57 (2H; observed by HSQC, signal is obscured by water peak in 1H-NMR), 3.22 (bt, 2H), 2.73 (s, 3H), 1.97 (s, 3H) |
| 335 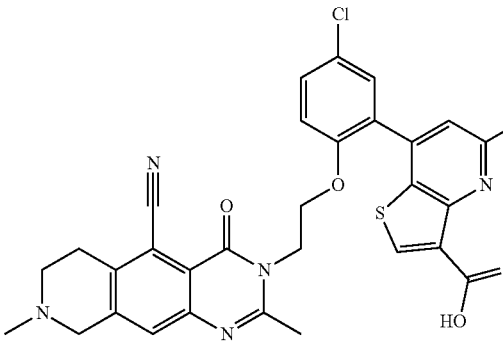 | MS (ESI) m/z 600.7 [M + 1]+; 1H-NMR (400 MHz, d6-DMSO) δ/ppm = 10.30 (b, 1H), 8.27 (bs, 1H), 7.63-7.58 (m, 1H), 7.52 (bs, 1H), 7.45-7.34 (m, 4H), 4.88-4.12 (m, 6H), 3.04 (s, 3H), 2.72 (s, 3H), 1.92 (s, 3H) [remaining signals obscured by water or solvent peak] |
| 336 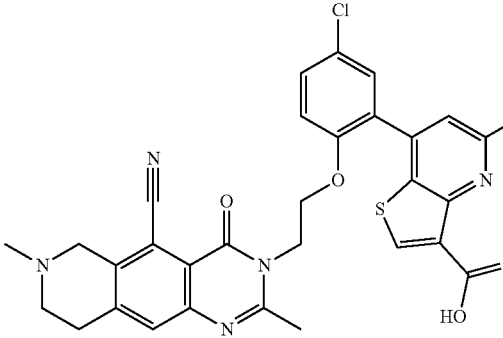 | MS (ESI) m/z 600.3 [M + 1]+; 1H-NMR (400 MHz, d6-DMSO) δ/ppm = 10.46-10.14 (b, 1H), 8.26 (s, 1H), 7.60 (dd, J = 9.0, 2.8 Hz, 1H), 7.54 (s, 1H), 7.43 (s, 1H), 7.40-7.35 (m, 2H), 4.93-3.38 (m, 6H; partially obscured by water peak), 4.43-4.35 (b, 2H), 3.38-3.27 (b, 2H), 3.10 (s, 3H), 2.73 (s, 3H), 1.93 (s, 3H) |

TABLE 3-continued

| Compound | Characterization |
|---|---|
| 337 | MS (ESI) m/z 575.0 [M + 1]+; 1H-NMR (400 MHz, d6-DMSO) δ/ppm = 9.07 (d, J = 1.9 Hz, 1H), 8.30 (s, 1H), 8.16 (d, J = 1.9 Hz, 1H), 7.59 (dd, J = 8.9, 2.6 Hz, 1H), 7.43-7.41 (m, 2H), 7.35 (d, J = 8.9 Hz, 1H), 4.39 (t, J = 5.0 Hz, 2H), 4.26 (t, J = 5.0 Hz, 2H), 2.70 (s, 3H), 1.80 (s, 3H) |
| 345a | MS (ESI) m/z 676.6 [M + 1]+; 1H-NMR (400 MHz, d6-DMSO) δ/ppm = 8.31 (s, 1H), 8.19 (s, 1H), 8.07-8.04 (m, 1H), 7.93-7.88 (m, 1H), 7.80-7.74 (m, 2H), 7.59 (dd, J = 8.9, 2.6 Hz, 1H), 7.45 (s, 1H), 7.42 (d, J = 2.6 Hz, 1H), 7.35 (d, J = 8.9 Hz, 1H), 4.41 (t, J = 4.8 Hz, 2H), 4.27 (t, J = 4.8 Hz, 2H), 2.74 (s, 3H), 1.82 (s, 3H) |
| 345b | MS (ESI) m/z 694.1 [M + 1]+; 1H-NMR (400 MHz, d6-DMSO) δ/ppm = 8.29 (s, 1H), 8.07 (s, 1H), 8.01-7.95 (b, 1H), 7.88 (dd, J = 7.7, 1.7 Hz, 1H), 7.65-7.55 (m, 3H), 7.46-7.39 (m, 3H), 7.33 (d, J = 9.0 Hz, 1H), 7.21-7.15 (b, 1H), 4.40 (t, J = 4.7 Hz, 2H), 4.27-4.20 (b, 2H), 2.74 (s, 3H), 1.74 (s, 3H) |
| 346 | MS (ESI) m/z 681.3 [M + 1]+; 1H-NMR (400 MHz, d6-DMSO) δ/ppm = 8.33 (s, 1H), 8.23 (s, 1H), 7.62-7.56 (m, 2H), 7.51 (dt, J = 7.6, 1.4 Hz, 1H), 7.46-7.42 (m, 2H), 7.40-7.35 (m, 1H), 7.35 (d, J = 9.0 Hz, 1H), 7.32-7.28 (m, 1H), 4.43-4.34 (m, 2H), 4.29-4.18 (m, 4H), 2.73 (s, 3H), 1.81 (s, 3H) |

TABLE 3-continued

Other Compounds

| | Compound | Characterization |
|---|---|---|
| 351a | | MS (ESI) m/z 590.0 [M + 1]+; 1H-NMR (400 MHz, d6-DMSO) d/ppm = 11.72 (s, 1H), 8.44 (s, 1H), 7.59 (dd, J = 8.9, 2.7 Hz, 1H), 7.42 (d, J = 2.7 Hz, 1H), 7.40 (s, 1H), 7.34 (d, J = 8.9 Hz, 1H), 7.17-7.16 (m, 1H), 7.07-7.05 (m, 1H), 4.40 (t, J = 4.9 Hz, 1H), 4.25 (t, J = 4.9 Hz, 2H), 2.68 (s, 3H), 1.88 (s, 3H) |
| 351b | | MS (ESI) m/z 574.0 [M + 1]+; 1H-NMR (400 MHz, d6-DMSO) d/ppm = 8.35 (s, 1H), 8.18-8.14 (m, 1H), 7.76-7.71 (m, 1H), 7.58 (dd, J = 8.9, 2.8 Hz, 1H), 7.42 (d, J = 2.8 Hz, 1H), 7.40 (s, 1H), 7.34 (d, J = 8.9 Hz, 1H), 4.38 (t, J = 4.9 Hz, 2H), 4.24 (t, J = 4.9 Hz, 2H), 2.69 (s, 3H), 1.84 (s, 3H) |
| 353 | | MS (ESI) m/z 584.2 [M + 1]+; 1H NMR (400 MHz, DMSO-d6) δ 8.77 (d, J = 4.9 Hz, 1H), 8.61 (s, 1H), 8.18-8.17 (m, 1H), 8.16-8.15 (m, 1H), 7.67 (s, 1H), 7.59 (dd, J = 8.9, 2.7 Hz, 1H), 7.47 (s, 1H), 7.46 (d, J = 2.3 Hz, 1H), 7.38 (d, J = 9.0 Hz, 1H), 4.30 (t, J = 6.2 Hz, 2H), 3.70 (s, 3H), 2.71 (t, J = 6.2 Hz, 2H) |
| 355 | | MS (ESI) m/z 615.0 [M + 1]+; 1H NMR (400 MHz, DMSO-d6) δ 8.87-8.84 (m, 2H), 7.61-7.57 (m, 2H), 7.53-7.51 (m, 2H), 7.38 (d, J = 9.0 Hz, 1H), 7.35 (s, 1H), 4.23 (t, J = 5.5 Hz, 2H), 3.74 (t, J = 5.4 Hz, 2H), 2.75 (s, 3H), 1.07 (s, 6H) |

TABLE 3-continued
Other Compounds
| Compound | Characterization |
|---|---|
| 357 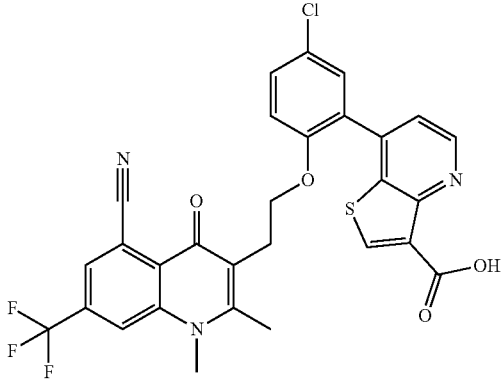 [SMILES: Cc1c(CCOc2ccc(Cl)cc2-c2ccnc3c(C(=O)O)csc23)c(=O)c2c(C#N)cc(C(F)(F)F)cc2n1C] | MS (ESI) m/z 598.1 [M + 1]+; 1H NMR (400 MHz, DMSO-d6) δ 8.83 (d, J = 4.8 Hz, 1H), 8.51 (s, 1H), 8.27-8.26 (m, 1H), 8.16 (dd, J = 1.5, 0.6 Hz, 1H), 7.56 (dd, J = 8.9, 2.7 Hz, 1H), 7.49 (d, J = 4.8 Hz, 1H), 7.41 (d, J = 2.7 Hz, 1H), 7.37 (d, J = 9.0 Hz, 1H), 4.23 (t, J = 6.1 Hz, 2H), 3.62 (s, 3H), 2.89 (t, J = 6.1 Hz, 2H), 1.85 (s, 3H) |
| 358 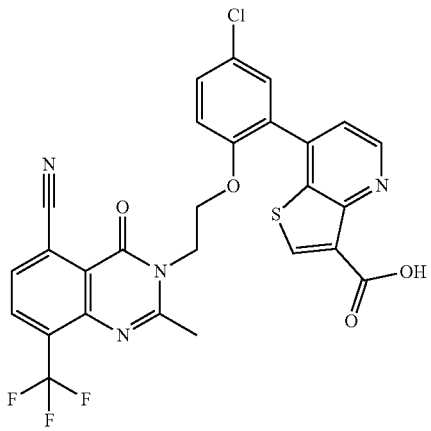 [SMILES: Cc1nc2c(C(F)(F)F)ccc(C#N)c2c(=O)n1CCOc1ccc(Cl)cc1-c1ccnc2c(C(=O)O)csc12] | MS (ESI) m/z 585.2 [M + 1]+; 1H NMR (400 MHz, DMSO-d6) δ 8.76 (d, J = 4.8 Hz, 1H), 8.63 (s, 1H), 8.24 (d, J = 7.9 Hz, 1H), 8.06 (d, J = 7.8 Hz, 1H), 7.59 (dd, J = 8.9, 2.7 Hz, 1H), 7.48-7.43 (m, 2H), 7.37 (d, J = 9.0 Hz, 1H), 4.44 (t, J = 5.1 Hz, 2H), 4.29 (t, J = 5.1 Hz, 2H), 1.98 (s, 3H). |
| 359 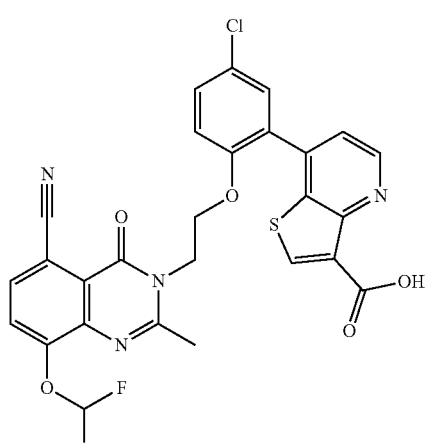 | MS (ESI) m/z 583.1 [M + 1]+; 1H NMR (400 MHz, DMSO-d6) δ 8.78 (d, J = 4.3 Hz, 1H), 8.55 (s, 1H), 7.97 (d, J = 8.3 Hz, 1H), 7.67 (d, J = 8.2 Hz, 1H), 7.60 (dd, J = 9.0, 2.6 Hz, 1H), 7.52-7.29 (m, 4H), 4.42 (t, J = 4.2 Hz, 2H), 4.26 (t, J = 4.4 Hz, 2H), 1.92 (s, 3H) |

TABLE 3-continued

Other Compounds

| Compound | Characterization |
|---|---|
| 360 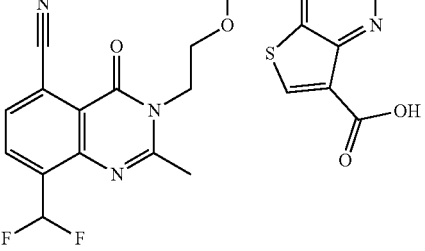 | MS (ESI) m/z 567.1 [M + 1]+; 1H NMR (400 MHz, DMSO-d6) δ 8.77 (d, J = 4.8 Hz, 1H), 8.55 (s, 1H), 8.12 (d, J = 7.9 Hz, 1H), 8.06 (d, J = 7.8 Hz, 1H), 7.59 (dd, J = 8.9, 2.7 Hz, 1H), 7.51 (t, J = 54.6 Hz, 1H). 7.44 (d, J = 2.7 Hz, 1H), 7.43 (d, J = 4.7 Hz, 1H), 7.36 (d, J = 9.0 Hz, 1H), 4.42 (t, J = 5.0 Hz, 2H), 4.25 (t, J = 5.0 Hz, 2H), 1.84 (s, 3H) |
| 361  | MS (ESI) m/z 632.2 [M + 1]+; 1H NMR (400 MHz, DMSO-d6) δ 8.83 (d, J = 4.8 Hz, 1H), 8.45 (s, 1H), 8.28 (s, 1H), 7.57 (dd, J = 8.9, 2.7 Hz, 1H), 7.48 (d, J = 4.8 Hz, 1H), 7.39 (d, J = 2.7 Hz, 1H), 7.36 (d, J = 9.0 Hz, 1H), 4.24 (t, J = 5.9 Hz, 2H), 3.60 (s, 3H), 2.89 (t, J = 5.9 Hz, 2H), 1.80 (s, 3H) |
| 362  | MS (ESI) m/z 630.2 [M + 1]+; 1H NMR (400 MHz, DMSO-d6) δ 8.83 (d, J = 4.8 Hz, 1H), 8.71 (s, 1H), 8.36 (s, 1H), 8.18 (d, J = 1.2 Hz, 1H), 7.57 (dd, J = 8.9, 2.7 Hz, 1H), 7.53 (d, J = 4.8 Hz, 1H), 7.46 (d, J = 2.7 Hz, 1H), 7.38 (d, J = 9.0 Hz, 1H), 4.76 (t, J = 4.4 Hz, 1H), 4.73-4.66 (m, 1H), 4.64 (s, 2H), 4.21 (t, J = 6.3 Hz, 2H), 2.93 (t, J = 6.3 Hz, 2H), 2.02 (s, 3H) |

TABLE 3-continued

| Compound | Characterization |
|---|---|
| 366 | MS (ESI) m/z 661.1 [M + 1]+; 1H NMR (400 MHz, DMSO-d6) δ 9.43 (s, 1H), 8.34 (s, 1H), 7.60 (dd, J = 8.9, 2.6 Hz, 1H), 7.48 (d, J = 10.1 Hz, 1H), 7.46-7.39 (m, 2H), 7.36 (d, J = 8.9 Hz, 1H), 4.39 (t, J = 4.9 Hz, 2H), 4.24 (t, J = 5.0 Hz, 2H), 3.83 (s, 2H), 3.06-2.92 (m, 4H), 2.77 (d, J = 4.0 Hz, 3H), 2.71 (s, 3H), 1.88 (s, 3H) |
| 367 | MS (ESI) m/z 648.3 [M + 1]+; 1H NMR (400 MHz, DMSO-d6) δ 8.34 (s, 1H), 7.60 (dd, J = 8.9, 2.7 Hz, 1H), 7.55 (d, J = 10.1 Hz, 1H), 7.43 (s, 1H), 7.42 (d, J = 2.6 Hz, 1H), 7.36 (d, J = 9.0 Hz, 1H), 4.40 (t, J = 5.1 Hz, 2H), 4.25 (t, J = 5.1 Hz, 3H), 3.70 (bs, 4H), 2.99 (bs, 4H), 2.72 (s, 3H), 1.88 (s, 3H) |
| 368 | MS (ESI) m/z 563.3 [M + 1]+; 1H NMR (400 MHz, DMSO-d6) δ 8.39 (s, 1H), 7.60 (dd, J = 9.0, 2.7 Hz, 1H), 7.44-7.39 (m, 3H), 7.36 (d, J = 9.0 Hz, 1H), 4.39 (t, J = 5.1 Hz, 2H), 4.24 (t, J = 5.1 Hz, 2H), 2.72 (s, 3H), 2.50 (s, 3H), 1.91 (s, 3H) |
| 369 | MS (ESI) m/z 618.4 [M + 1]+; 1H NMR (400 MHz, DMSO-d6) δ 9.37 (s, 1H), 8.50 (s, 1H), 7.96 (s, 1H), 7.60 (dd, J = 8.9, 2.7 Hz, 1H), 7.44 (s, 1H), 7.41 (d, J = 2.6 Hz, 1H), 7.38 (d, J = 9.0 Hz, 1H), 4.64 (d, J = 4.6 Hz, 2H), 4.43 (t, J = 5.0 Hz, 2H), 4.27 (t, J = 4.9 Hz, 2H), 2.79 (d, J = 4.0 Hz, 6H), 2.70 (s, 3H), 1.99 (s, 3H) |

TABLE 3-continued

Other Compounds

| Compound | Characterization |
|---|---|
| 370 | MS (ESI) m/z 646.3 [M + 1]+; 1H NMR (400 MHz, DMSO-d6) δ 9.36 (s, 1H), 8.53 (s, 1H), 7.96 (s, 1H), 7.60 (dd, J = 8.9, 2.7 Hz, 1H), 7.44 (s, 1H), 7.42 (d, J = 2.6 Hz, 1H), 7.38 (d, J = 9.0 Hz, 1H), 4.89 (hept, J = 6.0 Hz, 1H), 4.62 (d, J = 4.9 Hz, 2H), 4.42 (t, J = 5.0 Hz, 2H), 4.26 (t, J = 5.0 Hz, 2H), 2.78 (d, J = 4.3 Hz, 6H), 2.69 (s, 3H), 1.93 (s, 3H), 1.42 (d, J = 6.0 Hz, 6H) |
| 371 | MS (ESI) m/z 589.1 [M + 1]+; 1H NMR (400 MHz, DMSO-d6) δ 8.42 (s, 1H), 7.76 (d, J = 9.4 Hz, 1H), 7.63 (d, J = 9.2 Hz, 1H), 7.59 (dd, J = 8.9, 2.7 Hz, 1H), 7.44-7.39 (m, 2H), 7.36 (d, J = 9.0 Hz, 1H), 4.92 (hept, J = 6.0 Hz, 1H), 4.38 (t, J = 5.1 Hz, 2H), 4.21 (t, J = 5.1 Hz, 2H), 2.71 (s, 3H), 1.79 (s, 3H), 1.37 (d, J = 6.0 Hz, 6H) |
| 390 | MS (ESI) m/z 666.3 [M + 1]+; 1H NMR (400 MHz, DMSO-d6) δ 8.29 (s, 1H), 8.17 (s, 1H), 8.03 (s, 1H), 7.58 (dd, J = 8.9, 2.7 Hz, 1H), 7.51 (s, 1H), 7.43-7.39 (m, 2H), 7.33 (d, J = 9.0 Hz, 1H), 4.68 (s, 2H), 4.37 (t, J = 4.4 Hz, 2H), 4.21 (t, J = 4.5 Hz, 2H), 2.71 (s, 3H), 1.79 (s, 3H) |
| 391 | MS (ESI) m/z 631.1 [M + 1]+; 1H NMR (400 MHz, DMSO-d6) δ 8.31 (s, 1H), 8.05 (s, 1H), 7.59 (dd, J = 8.9, 2.7 Hz, 1H), 7.45 (s, 1H), 7.42 (d, J = 2.7 Hz, 1H), 7.36 (d, J = 9.0 Hz, 1H), 4.40 (t, J = 5.0 Hz, 2H), 4.24 (t, J = 5.0 Hz, 2H), 3.01-2.93 (m, 2H), 2.71 (s, 3H), 1.81 (s, 3H), 1.79-1.70 (m, 2H), 1.42 (h, J = 7.4 Hz, 2H), 0.93 (t, J = 7.3 Hz, 3H) |

TABLE 3-continued

| | Other Compounds | |
|---|---|---|
| | Compound | Characterization |
| 392 | | MS (ESI) m/z 674.1 [M + 1]+; 1H NMR (400 MHz, DMSO-d6) δ 8.66 (d, J = 2.8 Hz, 1H), 8.40 (s, 1H), 7.98 (dd, J = 9.1, 2.9 Hz, 1H), 7.90 (s, 1H), 7.60 (dd, J = 8.9, 2.7 Hz, 1H), 7.45 (s, 1H), 7.43 (d, J = 2.6 Hz, 1H), 7.37 (d, J = 9.0 Hz, 1H), 4.42 (t, J = 5.1 Hz, 2H), 4.35-4.17 (m, 2H), 2.74 (s, 3H), 2.25 (s, 3H), 1.89 (s, 3H) |
| 393 | | MS (ESI) m/z 656.0 [M + 1]+; 1H NMR (400 MHz, DMSO-d6) δ 8.76 (s, 1H), 8.42 (s, 1H), 7.86 (s, 1H), 7.64-7.56 (m, 2H), 7.52 (d, J = 5.0 Hz, 1H), 7.43 (s, 1H), 7.42 (d, J = 2.6 Hz, 1H), 7.37 (d, J = 9.0 Hz, 1H), 4.41 (t, J = 5.1 Hz, 2H), 4.26 (t, J = 5.0 Hz, 2H), 2.73 (s, 3H), 2.64 (s, 3H), 1.90 (s, 3H) |
| 394 | | MS (ESI) m/z 660.1 [M + 1]+; 1H NMR (400 MHz, DMSO-d6) δ 8.80 (d, J = 2.8 Hz, 1H), 8.63 (t, J = 1.7 Hz, 1H), 8.43 (s, 1H), 8.12 (ddd, J = 9.6, 2.8, 1.7 Hz, 1H), 7.87 (s, 1H), 7.60 (dd, J = 8.9, 2.7 Hz, 1H), 7.43 (s, 1H), 7.41 (d, J = 2.6 Hz, 1H), 7.37 (d, J = 9.0 Hz, 1H), 4.41 (t, J = 5.1 Hz, 2H), 4.31-4.23 (m, 3H), 2.73 (s, 3H), 1.94 (s, 3H) |
| 395 | | MS (ESI) m/z 656.1 [M + 1]+; 1H NMR (400 MHz, DMSO-d6) δ 8.66 (dd, J = 5.0, 1.7 Hz, 1H), 8.41 (s, 1H), 7.92-7.87 (m, 2H), 7.60 (dd, J = 8.9, 2.7 Hz, 1H), 7.52 (dd, J = 7.7, 4.9 Hz, 1H), 7.45 (s, 1H), 7.44 (d, J = 2.7 Hz, 1H), 7.37 (d, J = 9.0 Hz, 1H), 4.41 (t, J = 5.0 Hz, 2H), 4.32-4.18 (m, 2H), 2.73 (s, 3H), 2.29 (s, 3H), 1.86 (s, 3H) |

TABLE 3-continued

Other Compounds

| Compound | Characterization |
|---|---|
| 396 | MS (ESI) m/z 670.0 [M + 1]+; 1H NMR (400 MHz, DMSO-d6) δ 8.39 (s, 1H), 7.87 (s, 1H), 7.69 (s, 2H), 7.60 (dd, J = 8.9, 2.7 Hz, 1H), 7.44 (s, 1H), 7.42 (d, J = 2.7 Hz, 1H), 7.37 (d, J = 9.0 Hz, 1H), 4.41 (t, J = 5.1 Hz, 2H), 4.27 (t, J = 5.0 Hz, 2H), 2.73 (s, 3H), 2.70 (s, 6H), 1.91 (s, 3H) |
| 397 | MS (ESI) m/z 685.1 [M + 1]+; 1H NMR (400 MHz, DMSO-d6) δ 8.44 (s, 1H), 8.24 (d, J = 2.0 Hz, 1H), 7.88 (d, J = 9.6 Hz, 1H), 7.83 (s, 1H), 7.60 (dd, J = 8.9, 2.7 Hz, 1H), 7.43 (s, 1H), 7.41 (d, J = 2.6 Hz, 1H), 7.37 (d, J = 9.0 Hz, 1H), 7.10 (d, J = 9.2 Hz, 1H), 4.40 (t, J = 5.1 Hz, 2H), 4.26 (t, J = 5.0 Hz, 2H), 3.21 (s, 6H), 2.73 (s, 3H), 1.92 (s, 3H) |
| 399 | MS (ESI) 699.3 m/z [M + 1]+; 1H NMR (400 MHz, DMSO-d6) δ 9.02-8.95 (m, 2H), 8.67 (tt, J = 7.7, 1.3 Hz, 1H), 8.36 (s, 1H), 8.22-8.15 (m, 2H), 7.85 (s, 1H), 7.59 (dd, J = 8.9, 2.7 Hz, 1H), 7.45-7.40 (m, 2H), 7.35 (d, J = 9.0 Hz, 1H), 6.22 (s, 2H), 4.37 (t, J = 4.9 Hz, 2H), 4.22 (t, J = 5.0 Hz, 2H), 2.71 (s, 3H), 1.87 (s, 3H) |
| 403 | MS (ESI) m/z 547.1 [M + 1]+; 1H NMR (400 MHz, DMSO-d6) δ 8.82 (d, J = 4.8 Hz, 1H), 8.33 (s, 1H), 7.88 (d, J = 8.4 Hz, 1H), 7.59 (dd, J = 8.9, 2.7 Hz, 1H), 7.48 (d, J = 4.8 Hz, 1H), 7.41 (d, J = 2.6 Hz, 1H), 7.37 (dd, J = 8.9, 2.9 Hz, 2H), 4.42 (t, J = 5.1 Hz, 2H), 4.24 (t, J = 5.1 Hz, 2H), 3.97 (s, 3H), 1.83 (s, 3H) |

TABLE 3-continued

| | Other Compounds | |
|---|---|---|
| | Compound | Characterization |
| 404 | | MS (ESI) m/z 547.2 [M + 1]+; 1H NMR (400 MHz, DMSO-d6) δ 8.82 (d, J = 4.8 Hz, 1H), 8.41 (s, 1H), 7.76 (d, J = 9.3 Hz, 1H), 7.70 (d, J = 9.3 Hz, 1H), 7.59 (dd, J = 8.9, 2.7 Hz, 1H), 7.47 (d, J = 4.8 Hz, 1H), 7.42 (d, J = 2.6 Hz, 1H), 7.36 (d, J = 8.9 Hz, 1H), 4.39 (t, J = 5.0 Hz, 2H), 4.21 (t, J = 5.0 Hz, 2H), 4.04 (s, 3H), 1.74 (s, 3H) |
| 405 | | MS (ESI) m/z 547.2 [M + 1]+; 1H NMR (400 MHz, DMSO-d6) δ 8.86 (d, J = 4.9 Hz, 1H), 8.38 (s, 1H), 7.60 (dd, J = 8.9, 2.6 Hz, 1H), 7.57 (d, J = 2.5 Hz, 1H), 7.54 (d, J = 4.9 Hz, 1H), 7.43 (d, J = 2.7 Hz, 1H), 7.36 (d, J = 9.0 Hz, 1H), 7.11 (d, J = 2.5 Hz, 1H), 4.39 (t, J = 5.0 Hz, 2H), 4.20 (t, J = 5.0 Hz, 2H), 3.99 (s, 3H), 1.72 (s, 3H). |
| 406 | | MS (ESI) m/z 601.1 [M + 1]+; 1H NMR (400 MHz, DMSO-d6) δ 8.83 (d, J = 4.9 Hz, 1H), 8.44 (s, 1H), 8.05-8.00 (m, 1H), 7.84 (d, J = 9.1 Hz, 1H), 7.60 (dd, J = 8.9, 2.7 Hz, 1H), 7.51 (d, J = 4.9 Hz, 1H), 7.45 (d, J = 2.6 Hz, 1H), 7.36 (d, J = 9.0 Hz, 1H), 4.41 (t, J = 4.9 Hz, 2H), 4.25 (t, J = 4.9 Hz, 2H), 1.78 (s, 3H) |
| 407 | | MS (ESI) m/z 569.1 [M + 1]+; 1H NMR (400 MHz, DMSO-d6) δ 8.82 (d, J = 4.8 Hz, 1H), 8.48 (s, 1H), 8.17 (d, J = 9.5 Hz, 1H), 7.60 (dd, J = 8.9, 2.6 Hz, 1H), 7.50 (d, J = 4.8 Hz, 1H), 7.43 (d, J = 2.7 Hz, 1H), 7.37 (d, J = 9.0 Hz, 1H), 4.42 (t, J = 5.0 Hz, 2H), 4.26 (t, J = 5.0 Hz, 2H), 1.84 (s, 3H) |

TABLE 3-continued

| | Other Compounds | |
|---|---|---|
| | Compound | Characterization |
| 408 | | MS (ESI) m/z 617.2 [M + 1]+; 1H NMR (400 MHz, DMSO-d6) δ 8.83 (d, J = 4.8 Hz, 1H), 8.54 (s, 1H), 8.19 (s, 1H), 7.80 (s, 1H), 7.60 (dd, J = 8.9, 2.7 Hz, 1H), 7.47 (d, J = 4.8 Hz, 1H), 7.43 (d, J = 2.7 Hz, 1H), 7.36 (d, J = 8.9 Hz, 1H), 4.57 (bs, 2H), 4.40 (t, J = 5.0 Hz, 2H), 4.26 (t, J = 5.0 Hz, 2H), 2.87 (s, 6H), 1.80 (s, 3H) |
| 409 | | MS (ESI) m/z 612.2 [M + 1]+; 1H NMR (400 MHz, DMSO-d6) δ 8.55 (s, 1H), 8.26 (s, 1H), 8.16 (bd, J = 1.1 Hz, 1H), 7.56 (dd, J = 8.9, 2.7 Hz, 1H), 7.44 (s, 1H), 7.40 (d, J = 2.6 Hz, 1H), 7.37 (d, J = 9.0 Hz, 1H), 4.23 (t, J = 6.1 Hz, 2H), 3.63 (s, 3H), 2.90 (t, J = 6.1 Hz, 2H), 2.70 (s, 3H), 1.94 (s, 3H). |
| 412 | | MS (ESI) m/z 573.9 [M + 1]+; 1H NMR (400 MHz, DMSO-d6) δ 8.81 (d, J = 4.9 Hz, 2H), 8.45 (s, 1H), 8.26 (bs, 1H), 8.16 (bs, 1H), 7.59 (dd, J = 8.8, 2.6 Hz, 1H), 7.46 (bs, 1H), 7.44 (bs, 1H), 7.35 (d, J = 9.0 Hz, 1H), 4.40 (t, J = 5.3 Hz, 2H), 4.24 (t, J = 5.3 Hz, 2H), 2.87 (d, J = 4.5 Hz, 3H), 1.78 (s, 3H) |
| 413 | | MS (ESI) m/z 588.2 [M + 1]+; 1H NMR (400 MHz, DMSO-d6) δ 8.83 (d, J = 4.8 Hz, 1H), 8.37 (s, 1H), 7.98 (d, J = 1.4 Hz, 1H), 7.65 (d, J = 2.0 Hz, 1H), 7.60 (dd, J = 8.9, 2.6 Hz, 1H), 7.48 (d, J = 4.8 Hz, 1H), 7.45 (d, J = 2.7 Hz, 1H), 7.35 (d, J = 9.0 Hz, 1H), 4.40 (t, J = 5.3 Hz, 2H), 4.23 (t, J = 5.3 Hz, 2H), 3.05 (s, 3H), 3.01 (s, 3H), 1.69 (s, 3H) |

TABLE 3-continued

Other Compounds

| Compound | Characterization |
|---|---|
| 426 | MS (ESI) m/z 651.6 [M + 1]+; 1H NMR (400 MHz, DMSO-d6) δ 8.70 (m, 1H), 8.41 (s, 1H), 8.03 (s, 1H), 7.99 (tdd, J = 7.7, 3.1, 1.8 Hz, 1H), 7.85 (s, 1H), 7.66 (d, J = 7.8 Hz, 1H), 7.59 (dd, J = 8.9, 2.7 Hz, 1H), 7.51 (m, 1H), 7.43 (d, J = 2.6 Hz, 1H), 7.42 (d, J = 2.7 Hz, 1H), 7.34 (d, J = 9.0 Hz, 1H), 4.39 (t, J = 5.0 Hz, 2H), 4.26 (t, J = 5.0 Hz, 2H), 2.69 (s, 3H), 1.85 (s, 3H) |
| 427 | MS (ESI) m/z 672.5 [M + 1]+; 1H NMR (400 MHz, DMSO-d6) δ 8.27 (s, 1H), 7.98 (s, 1H), 7.70 (s, 1H), 7.59 (dd, J = 8.9, 2.7 Hz, 1H), 7.41 (d, J = 2.6 Hz, 1H), 7.39 (s, 1H), 7.35 (d, J = 9.0 Hz, 1H), 4.39 (t, J = 5.1 Hz, 2H), 4.24 (t, J = 5.0 Hz, 3H), 3.59-3.50 (m, 2H), 3.26-3.10 (m, 6H), 2.93 (s, 3H), 2.69 (s, 3H), 1.84 (s, 3H) |
| 436 | MS (ESI) m/z 666.5 [M + 1]+; 1H NMR (400 MHz, DMSO-d6) δ 8.71 (bs, 2H), 8.33 (s, 1H), 8.32 (s, 1H), 7.59 (dd, J = 8.9, 2.7 Hz, 1H), 7.54 (br, 1H), 7.45 (s, 1H), 7.44 (d, J = 2.6 Hz, 1H), 7.36 (d, J = 9.0 Hz, 1H), 4.40 (t, J = 4.5 Hz, 2H), 4.27 (d, J = 4.5 Hz, 2H), 2.74 (s, 3H), 2.06 (bs, 3H), 1.84 (s, 3H) |
| 438 | MS (ESI) m/z 690.2 [M + 1]+; 1H NMR (400 MHz, DMSO-d6) δ 8.65 (d, J = 2.9 Hz, 1H), 8.41 (s, 1H), 7.98 (s, 1H), 7.88 (dd, J = 9.0, 2.9 Hz, 1H), 7.60 (dd, J = 8.9, 2.7 Hz, 1H), 7.45 (s, 1H), 7.43 (d, J = 2.7 Hz, 1H), 7.37 (d, J = 9.0 Hz, 1H), 6.89 (t, J = 53.7 Hz, 1H), 4.48-4.38 (m, 2H), 4.37-4.19 (m, 2H), 2.73 (s, 3H), 2.18 (s, 3H), 1.89 (s, 3H) |

TABLE 3-continued

Other Compounds

| Compound | Characterization |
| --- | --- |
| 439a | MS (ESI) m/z 624.1 [M + 1]+; 1H NMR (400 MHz, DMSO-d6) δ 8.44 (s, 1H), 7.77 (s, 1H), 7.59 (dd, J = 8.9, 2.7 Hz, 1H), 7.42 (d, J = 2.7 Hz, 1H), 7.41 (s, 1H), 7.36 (d, J = 9.0 Hz, 1H), 7.16 (t, J = 54.4 Hz, 1H), 4.39 (t, J = 5.0 Hz, 2H), 4.22 (t, J = 5.0 Hz, 2H), 2.97 (s, 6H), 2.69 (s, 3H), 1.82 (s, 3H) |
| 439b | MS (ESI) m/z 597.0 [M + 1]+; 1H NMR (400 MHz, DMSO-d6) δ 8.44 (s, 1H), 7.72 (s, 1H), 7.59 (dd, J = 8.9, 2.7 Hz, 1H), 7.42 (d, J = 2.7 Hz, 1H), 7.41 (s, 1H), 7.35 (d, J = 9.0 Hz, 1H), 7.15 (t, J = 54.2 Hz, 1H), 4.38 (t, J = 5.0 Hz, 3H), 4.21 (t, J = 5.0 Hz, 3H), 2.69 (s, 3H), 1.78 (s, 3H) |
| 440 | MS (ESI) m/z 671.9 [M + 1]+; 1H NMR (400 MHz, DMSO-d6) δ 8.73 (dd, J = 5.2, 1.7 Hz, 1H), 8.41 (s, 1H), 7.98 (bd, J = 5.9 Hz, 2H), 7.64-7.56 (m, 2H), 7.45 (s, 1H), 7.44 (d, J = 2.7 Hz, 1H), 7.37 (d, J = 9.0 Hz, 1H), 6.84 (t, J = 53.7 Hz, 1H), 4.48-4.37 (m, 2H), 4.37-4.16 (m, 2H), 2.72 (s, 3H), 2.27 (s, 3H), 1.87 (s, 3H). |
| 449 | MS (ESI) m/z 656.6 [M + 1]+; 1H NMR (400 MHz, DMSO-d6) δ 8.36 (s, 1H), 8.05 (s, 1H), 7.70-7.17 (m, 5H), 4.49 (s, 2H), 4.42 (t, J = 5.0 Hz, 2H), 4.27 (t, J = 5.0 Hz, 2H), 2.86 (s, 6H), 2.72 (s, 3H), 1.87 (s, 3H) |

TABLE 3-continued

Other Compounds

| Compound | Characterization |
|---|---|
| 451 | MS (ESI) m/z 731.3 [M + 1]+; 1H NMR (400 MHz, DMSO-d6) δ 13.08 (s, 1H), 9.79 (s, 1H), 8.40 (s, 1H), 7.97 (s, 1H), 7.62 (dd, J = 8.9, 2.7 Hz, 1H), 7.51 (s, 1H), 7.44-7.36 (m, 2H), 7.25 (s, 1H), 4.51 (s, 2H), 4.43 (d, J = 5.3 Hz, 2H), 4.27 (d, J = 5.1 Hz, 2H), 3.56 (s, 3H), 2.85 (s, 6H), 2.74 (s, 3H), 1.83 (s, 3H) |
| 456 | MS (ESI) m/z 601.2 [M + 1]+; 1H NMR (400 MHz, DMSO-d6) δ 8.80 (d, J = 4.7 Hz, 1H), 8.35 (s, 1H), 8.07-8.03 (m, 1H), 7.60-7.56 (m, 1H), 7.55 (d, J = 2.7 Hz, 1H), 7.45 (d, J = 4.8 Hz, 1H), 7.41 (d, J = 2.7 Hz, 1H), 7.32 (d, J = 9.0 Hz, 1H), 4.36 (t, J = 5.0 Hz, 2H), 4.20 (t, J = 5.0 Hz, 2H), 1.70 (s, 3H) |
| 457 | MS (ESI) m/z 604.2 [M + 1]+; 1H NMR (400 MHz, DMSO-d6) δ 8.78 (d, J = 4.8 Hz, 1H), 8.36 (s, 1H), 7.78 (d, J = 9.3 Hz, 1H), 7.70 (d, J = 9.2 Hz, 1H), 7.57 (dd, J = 9.0, 2.7 Hz, 1H), 7.44 (d, J = 4.8 Hz, 1H), 7.39 (d, J = 2.7 Hz, 1H), 7.33 (d, J = 9.0 Hz, 1H), 4.68-4.55 (m, 2H), 4.36 (t, J = 5.1 Hz, 2H), 4.20 (d, J = 5.2 Hz, 2H), 3.62 (s, 2H), 2.96-2.87 (m, 7H), 1.77 (s, 3H) |
| 458 | MS (ESI) m/z 640.1 [M + 1]+; 1H NMR (400 MHz, DMSO-d6) δ 8.78 (d, J = 4.8 Hz, 1H), 8.39 (s, 1H), 8.04 (s, 1H), 7.63-7.17 (m, 5H), 4.54-4.42 (m, 2H), 4.39 (t, J = 5.0 Hz, 2H), 4.24 (t, J = 5.0 Hz, 2H), 2.83 (s, 6H), 1.79 (s, 3H) |

TABLE 3-continued

Other Compounds

| Compound | Characterization |
|---|---|
| 460 | LCMS: 708.6 [M + H]+; 1H NMR (400 MHz, DMSO-d6) δ 8.25 (s, 1H), 8.05 (s, 1H), 7.59 (dd, J = 8.9, 2.7 Hz, 1H), 7.44-7.38 (m, 2H), 7.35 (d, J = 8.9 Hz, 1H), 4.38 (t, J = 5.0 Hz, 2H), 4.24 (t, J = 5.0 Hz, 2H), 2.75 (d, J = 1.6 Hz, 3H), 2.69 (s, 3H), 1.78 (s, 3H) |
| 461 | LCMS: 652.5 [M + H]+; 1H NMR (400 MHz, DMSO-d6) δ 8.76 (s, 2H), 8.34 (s, 1H), 8.28 (s, 1H), 8.01 (d, J = 7.9 Hz, 1H), 7.61 (d, J = 11.7, 8.4, 3.8 Hz, 2H), 7.46-7.41 (m, 2H), 7.36 (d, J = 9.0 Hz, 1H), 4.41 (t, J = 5.0 Hz, 2H), 4.27 (t, J = 5.0 Hz, 2H), 2.72 (s, 3H), 1.84 (s, 3H) |
| 462 | LCMS: 652.5.6 [M + H]+; 1H NMR (400 MHz, DMSO-d6) δ 8.69 (dd, J = 4.9, 1.6 Hz, 1H), 8.40 (s, 1H), 8.30 (s, 1H), 8.03 (td, J = 7.7, 1.8 Hz, 1H), 7.84 (d, J = 8.0 Hz, 1H), 7.61-7.52 (m, 2H), 7.45-7.41 (m, 2H), 7.35 (d, J = 9.0 Hz, 1H), 4.40 (t, J = 5.0 Hz, 2H), 4.27 (t, J = 5.1 Hz, 2H), 2.70 (s, 3H), 1.82 (s, 3H) |
| 463 | LCMS: 666.6 [M + H]+; 1H NMR (400 MHz, DMSO-d6) δ 8.76 (d, J = 5.5 Hz, 1H), 8.31 (d, J = 6.8 Hz, 2H), 7.67 (s, 1H), 7.59 (dd, J = 8.9, 2.8 Hz, 2H), 7.45-7.41 (m, 2H), 7.35 (d, J = 9.0 Hz, 1H), 4.40 (t, J = 5.0 Hz, 2H), 4.27 (t, J = 5.0 Hz, 2H), 2.73 (s, 3H), 2.67 (s, 3H), 1.84 (s, 3H) |

TABLE 3-continued

Other Compounds

| Compound | Characterization |
|---|---|
| 464 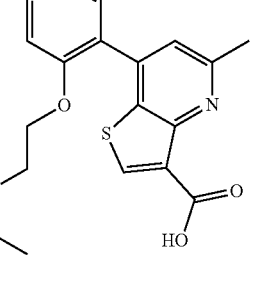 | LCMS: 652.5 [M + H]+; 1H NMR (400 MHz, DMSO-d6); 1H NMR (400 MHz, DMSO-d6) δ 8.84 (s, 2H), 8.35 (s, 1H), 8.30 (s, 1H), 7.69 (d, J = 5.5 Hz, 2H), 7.59 (dd, J = 8.9, 2.7 Hz, 1H), 7.46-7.41 (m, 2H), 7.36 (d, J = 9.0 Hz, 1H), 4.40 (t, J = 4.9 Hz, 2H), 4.27 (t, J = 4.9 Hz, 2H), 2.73 (s, 3H), 1.84 (s, 3H) |
| 467 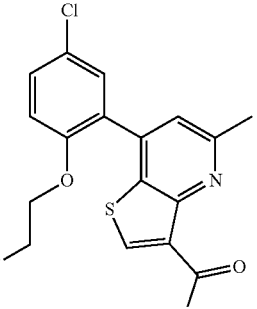 | LCMS: 651.8 [M + H]+; 1H NMR (400 MHz, DMSO-d6) δ 8.36 (s, 1H), 8.24 (s, 1H), 7.59 (dd, J = 8.9, 2.7 Hz, 1H), 7.53 (s, 5H), 7.43 (d, J = 3.1 Hz, 2H), 7.36 (d, J = 9.0 Hz, 1H), 4.40 (t, J = 5.0 Hz, 2H), 4.26 (t, J = 4.9 Hz, 2H), 2.71 (s, 3H), 1.83 (s, 3H) |
| 488 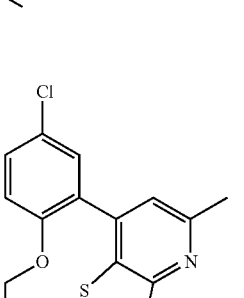 | LCMS: 635.9 [M + H]+; 1H NMR (400 MHz, Methanol-d4) δ 8.40 (s, 1H), 7.93 (d, J = 9.8 Hz, 1H), 7.58-7.51 (m, 2H), 7.42 (d, J = 2.6 Hz, 1H), 7.29 (d, J = 8.9 Hz, 1H), 7.23 (s, 1H), 4.48 (t, J = 4.8 Hz, 2H), 4.40 (t, J = 4.7 Hz, 2H), 2.91 (s, 3H), 2.11 (s, 3H) |
| 490 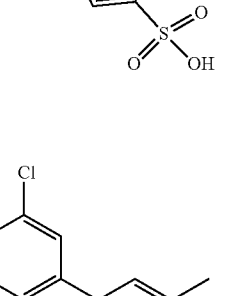 | MS (ESI) m/z 593.7 [M + 1]+; 1H NMR (400 MHz, DMSO-d6) δ 8.14 (dd, J = 7.3, 1.5 Hz, 1H), 8.04 (d, J = 9.7 Hz, 1H), 7.61 (dd, J = 8.9, 2.7 Hz, 1H), 7.58 (s, 1H), 7.51-7.46 (m, 1H), 7.39 (s, 1H), 7.36 (d, J = 4.1 Hz, 1H), 7.33 (d, J = 2.6 Hz, 1H), 7.31-7.25 (m, 1H), 7.22 (s, 0H), 4.50-4.08 (m, 4H), 2.78 (s, 3H), 1.84 (s, 3H) |

TABLE 3-continued

Other Compounds

| Compound | Characterization |
|---|---|
| 493 | MS (ESI) m/z 627.12 [M − 1]−; 1H NMR (400 MHz, DMSO-d6) δ 13.29 (bs, 1H), 8.84 (d, J = 4.68, 1H), 8.38 (s, 1H), 7.89 (s, 1H), 7.60 (dd, J = 2.56, 9.3 Hz, 1H), 7.47 (d, J = 4.6 Hz, 1H), 7.42 (d, J = 1.96 Hz, 1H), 7.34 (d, J = 8.84 Hz, 1H) 4.39 (t, J = 4.7 Hz, 2H), 4.23 (t, J = 4.76, 2H), 3.60 (s, 3H), 1.75 (s, 3H) |
| 497 | MS (ESI) m/z 619.47 [M + 1]+; 1H NMR (400 MHz, DMSO-d6) δ 8.80 (d, J = 4.8 Hz, 1H), 8.54 (s, 1H), 8.28 (s, 1H), 7.60 (dd, J = 8.88, 2.68 Hz 1H), 7.47-7.21 (m, 4H), 4.42 (t, J = 5.12, 2H), 4.28 (t, J = 4.88 Hz, 2H), 1.89 (s, 3H) |
| 498 | MS (ESI) m/z 619.47 [M + 1]+. 1H NMR (400 MHz, DMSO-d6) δ 8.82 (d, J = 4.8 Hz, 1H), 8.44 (s, 1H), 7.66-7.59 (m, 5H), 4.42 (t, J = 9.04 Hz, 2H), 4.27 (t, J = 8.6 Hz, 2H), 1.84 (s, 3H) |
| 499 | MS (ESI) m/z 593.13 [M + 1]+; 1H NMR (400 MHz, DMSO-d6) δ 9.03 (s, 1 H), 8.85 (d, J = 4.8 Hz, 1H), 7.83 (d, J = 3.6 Hz, 2H), 7.64 (s, 1H), 7.60 (dd, J = 8.8 Hz, 2.46 Hz, 1H), 7.32 (d, J = 8.8 Hz, 1H), 6.98 (s, 1H), 3.63 (t, J = 6.8 Hz, 2H), 2.90 (t, J = 7.2 Hz, 2H), 2.39 (s, 3H) |

TABLE 3-continued

Other Compounds

| Compound | Characterization |
|---|---|
| 500 | MS (ESI) m/z 599.53 [M + 1]+; 1H NMR (400 MHz, DMSO-d6) δ 8.77 (d, J = 4.92 Hz, 1H), 8.08 (d, J = 9.72 Hz, 1H), 7.61 (dd, J = 8.80, 2.64 Hz, 1H), 7.53 (d, J = 4.96 Hz, 1H), 7.49-7.22 (m, 3H), 4.44 (t, J = 5.40 Hz, 2H), 4.29 (t, J = 4.84 Hz, 2H). 2.60-2.40 (merged, 3H), 1.96 (s, 3H) |
| 504 | MS (ESI) m/z 603.0 [M + 1]+; 1H NMR (400 MHz, DMSO-d6) δ 8.82 (d, J = 4.80 Hz, 1H), 8.46 (s, 1H), 8.05 (d, J = 9.60 Hz, 1H), 7.65 (d, J = 8.32 Hz, 1H), 7.56 (d, J = 11.32 Hz, 1H), 7.51-7.36 (m, 2H), 4.45 (t, J = 4.72 Hz, 2H), 4.28 (t, J = 6.96 Hz, 2H), 1.86 (s, 3H) |
| 506 | MS (ESI) m/z 571.10 [M + 1]+; 1H NMR (400 MHz, DMSO-d6) δ 8.84 (d, J = 4.48 Hz, 1H), 8.41 (s, 1H), 7.74-7.70 (m, 1H), 7.62 (d, J = 8.36 Hz, 1H), 7.55 (d, J = 11.28 Hz, 1H), 7.48 (d, J = 4.48 Hz, 1H), 4.42 (t, J = 4.20 Hz, 2H). 4.23 (t, J = 4.20 Hz, 2H), 1.75 (s, 3H) |
| 507 | MS (ESI) m/z 588.17 [M + 1]+; 1H-NMR (400 MHz, DMSO-d6) δ 13.30 (bs, 1H), 9.71 (bs, 1H), 8.81 (d, J = 4.76 Hz ,1H), 8.35 (s, 1H), 7.91(d, J = 8.52 Hz, 1H),7.68 (d, J = 8.4 Hz, 1H), 7.60 (dd, J = 2.40, 8.84 Hz, 1H), 7.46 (d, J = 4.72 Hz, 1H), 7.42 (d, J = 2.5 Hz, 1H), 7.37 (d, J = 8.88 Hz, 1H), 4.40 (s, 2H), 4.25 (s, 2H), 3.4-3.41 (m, 2H), 3.33 (t, J = 3.84 Hz ,2H), 2.92 (s, 6H) ,1.83 (s, 3H) |

TABLE 3-continued

Other Compounds

| Compound | Characterization |
|---|---|
| 508 | MS (ESI) m/z 592.16 [M + 1]+; 1H NMR (400 MHz, DMSO-d6) δ 10.23 (bs, 1H), 8.81 (d, J = 4.60 Hz, 1H), 8.34 (s, 1H), 8.09 (d, J = 10.08 Hz, 1H), 7.61-7.58 (m, 1H), 7.48 (d, J = 4.64 Hz, 1H), 7.42 (d, J = 2.0 Hz, 1H), 7.38 (d, J = 8.88 Hz, 1H), 4.58 (bs, 2H), 4.43 (t, J = 6.08 Hz, 2H), 4.28 (t, J = 5.24 Hz, 2H), 2.90 (s, 6H), 1.87 (s, 3H) |
| 509 | MS (ESI) m/z 608.16 [M + 1]+; 1H NMR (400 MHz, DMSO-d6) δ 13.24 (bs, 1H), 8.82 (d, J = 4.72 Hz, 1H), 8.35 (bs, 1H), 7.79 (bs, 1H), 7.60 (dd, J = 2.44, 8.84 Hz, 1H), 7.47 (d, J = 4.72 Hz, 1H), 7.42 (d, J = 2.56 Hz, 1H), 7.35 (d, J = 8.92 Hz, 1H), 4.39 (t, J = 5.4 Hz, 2H), 4.23 (t, J = 6.12 Hz, 2H), 3.75 (bs, 2H), 2.26 (bs, 6H), 1.77 (s, 3H) |
| 510 | MS (ESI) m/z 599.1 [M + 1]+; 1H NMR (400 MHz, DMSO-d6) δ 8.84 (d, J = 4.76 Hz, 1H), 8.26 (s, 2H), 7.61 (dd, J = 8.84, 2.52 Hz, 1H), 7.48 (d, J = 4.76, Hz, 1H), 7.43 (d, J = 2.56 Hz, 1H), 7.37 (d, J = 8.96 Hz, 1H), 4.55 (bs, 2H), 4.42 (bs, 2H), 4.27 (b s, 2H), 2.90 (bs, 6H), 1.82 (s, 3H) |
| 511 | MS (ESI) m/z 598.21 [M + 1]+; 1H-NMR (400 MHz, DMSO-d6) δ 8.84 (d, J = 4.72 Hz,1H), 8.32 (s, 1H), 8.24 (s, 1H), 7.59 (dd, J = 2.44, 2.48 Hz, 1H), 7.45 (d, J = 4.72 Hz, 1H), 7.40-7.36 (m, 2H), 6.06 (s, 1H), 4.59 (bs, 2H), 4.43 (t, J = 4.36 Hz, 2H), 4.24 (t, J = 4.68 Hz, 2H), 2.93 (bs, 6H), 1.69 (s, 3H) |

TABLE 3-continued

| | Other Compounds | |
|---|---|---|
| | Compound | Characterization |
| 512 | | MS (ESI) m/z 574.38. [M + 1]+; 1H-NMR (400 MHz, DMSO-d6) δ 9.96 (bs, 1H), 8.82 (d, J = 4.72 Hz ,1H), 8.36 (s, 1H), 8.08 (s, 1H), 7.83 (s, 1H), 7.61 (dd, J = 2.32, 8.84 Hz, 1H), 7.49 (d, J = 4.68 Hz), 7.44 (d, J = 2.32, 1H), 7.38 (d = 8.96 Hz), 4.46 (s, 2H), 4.41 (t, J = 5.12 Hz, 2H), 4.25 (t, J = 5.08 Hz, 2H), 2.83 (s, 6H), 1.79 (s, 3H) |
| 513 | | MS (ESI) m/z 588.22 [M + 1]+. 1H-NMR (400 MHz, DMSO-d6) δ 9.49 (bs, 1H), 8.86 (dd, J = 4.76, 8.85 Hz, 1H), 8.28 (s, 1H), 7.97 (s, 1H), 7.60 (s, 1H),7.59 (d, J = 7.59 Hz, 1H), 7.45 (d, J = 2.28, Hz, 1H), 7.42 (d, J = 2.52 Hz, 1H), 7.35 (d, J = 8.92 Hz, 1H), 4.40 (t, J = 5.76 Hz, 2H), 4.22 (t, J = 6.32 Hz, 2H), 3.51 (t, J = 4.56. Hz, 2H), 3.18 (t, J = 8.0 Hz, 2H), 2.88 (s, 6H), 1.75 (s, 3H) |
| 514 | | MS (ESI) m/z 623.97 [M + 1]+; 1H NMR (400 MHz, DMSO-d6) δ 8.82 (bs, 1H), 8.20 (s, 1H), 8.08 (s, 1H), 7.88 (s, 1H), 7.56 (d, J = 9.0 Hz, 1H), 7.45-7.36 (m, 2H), 7.32 (d, J = 8.92 Hz, 1H), 4.37 (t, J = 4.44 Hz, 2H) 4.23 (t, J = 4.08 Hz, 2H), 3.21 (t, J = 14.48 Hz, 2H), 2.25 (s, 6H), 1.75 (s, 3H). |
| 515 | | MS (ESI) m/z 624.14 [M + 1]+. 1H-NMR (400 MHz, DMSO-d6) δ 9.69 (bs, 1H), 8.80 (d, J = 4.4 Hz, 1H), 8.46 (s, 1H), 8.05 (bs, 1H), 7.68-7.35 (m, 5H), 4.64 (bs, 2H), 4.41 (s, 2H), 4.26 (s, 2H), 2.83 (bs, 6H), 1.79 (s, 3H) |

TABLE 3-continued

Other Compounds

| Compound | Characterization |
|---|---|
| 516 | MS (ESI) m/z 607.9 [M + 1]+; 1H NMR (400 MHz, DMSO-d6) δ 8.81 (d, J = 4.76 Hz, 1H), 8.39 (s, 1H), 7.75 (s, 1H), 7.59 (dd, J = 8.8, 2.4 Hz, 1H), 7.46 (d, J = 4.76 Hz, 1H), 7.42 (d, J = 2.56 Hz, 1H), 7.35 (d, J = 9.0 Hz, 1H), 4.39 (t, J = 5.8 Hz, 2H), 4.23 (t, J = 5.3 Hz, 2H), 3.63 (s, 2H), 2.28 (s, 6H), 1.77 (s, 3H) |
| 517 | MS (ESI) m/z 592.02 [M + 1]+; 1H NMR (400 MHz, DMSO-d6) δ 9.98 (bs, 1H), 8.81 (d, J = 4.68 Hz, 1H), 8.41 (s, 1H), 8.00 (d, J = 6.56 Hz, 1H), 7.60 (dd, J = 8.76, 2.28 Hz, 1H), 7.47 (d, J = 4.68 Hz, 1H), 7.42 (d, J = 2.23 Hz, 1H), 7.37 (d, J = 8.96 Hz, 1H), 4.53 (s, 2H), 4.41 (t, J = 6.24 Hz, 2H), 4.26 (t, J = 6.28 Hz, 2H), 2.89 (s, 6H), 1.80 (s, 3H) |
| 518 | MS (ESI) m/z 642.14 [M + 1]+; 1H NMR (400 MHz, DMSO-d6) δ 8.79 (d, J = 4.4 Hz, 1H), 8.45 (s, 1H), 7.49 (m, 5H), 4.63 (bs, 2H), 4.43 (bs, 2H), 4.29 (bs, 2H), 2.83 (bs, 6H), 1.86 (s, 3H) |
| 520 | MS (ESI) m/z 678.03 [M + 1]+. 1H NMR (400 MHz, DMSO-d6) δ 12.65 (bs, 1H), 8.89 (d, J = 4.12 Hz, 1H), 8.48 (s, 1H), 7.90 (s, 1H), 7.65-7.35 (m, 5H), 4.40 (t, J = 5.18 Hz, 2H), 4.23 (t, J = 6.72 Hz, 2H), 3.56 (s, 3H), 1.71 (s, 3H) |

TABLE 3-continued

Other Compounds

| Compound | Characterization |
|---|---|
| 529 | MS (ESI) m/z 638.20 [M + 1]+; 1H NMR (400 MHz, DMSO-d6) δ 13.59 (bs, 1H), 8.38 (s, 1H), 8.04 (d, J = 8.72 Hz, 1H), 7.77 (d, J = 8.20 Hz, 1H), 7.80-7.55 (m, 1H), 7.42-7.40 (m, 2H), 7.35 (d, J = 9.00 Hz, 1H), 4.40 (t, J = 4.52 Hz, 2H), 4.25 (t, J = 5.16 Hz, 2H), 2.69 (s, 3H), 2.60-2.20 (merged, 8H), 1.83 (s, 3H) |
| 530 | MS (ESI) m/z 623.97 [M + 1]+; 1H NMR (400 MHz, DMSO-d6) δ 13.28 (bs, 1H), 8.80 (d, J = 4.72 Hz, 1H), 8.27 (s, 1H), 7.95 (s, 1H), 7.62-7.32 (m, 5H), 4.62 (s, 2H), 4.41 (t, J = 4.92 Hz, 2H), 4.26 (t, J = 5.40 Hz, 2H), 2.87 (s, 6H), 1.79 (s, 3H) |
| 531 | MS (ESI) m/z 640.12 [M + 1]+; 1H-NMR (400 MHz, DMSO-d6) δ 13.40 (bs, 1H), 9.88 (bs, 1H), 8.83 (d, J = 4.48 Hz ,1H), 8.34 (s, 1H),7.74-7.35 (m, 6H), 4.54 (s, 2H), 4.41 (t, J = 5.6 Hz, 2H), 4.25 (t, J = 5.6 Hz, 2H), 2.94 (s, 6H), 1.76 (s, 3H) |
| 532 | MS (ESI) m/z 658.20 [M + 1]+. 1H NMR (400 MHz, DMSO-d6) δ 10.03 (bs, 1H), 8.84 (d, J = 3.04 Hz, 1H), 8.28 (s, 1H), 7.60 (bs, 2H), 7.47-7.35 (m, 3H), 4.59 (s, 2H), 4.41 (t, J = 4.92 Hz, 2H), 4.26 (t, J = 4.72 Hz, 2H), 2.90 (s, 6H), 1.76 (s, 3H) |

TABLE 3-continued

Other Compounds

| Compound | Characterization |
|---|---|
| 533 | MS (ESI) m/z 578.18 [M + 1]+; 1H NMR (400 MHz, DMSO-d6) δ 8.82 (d, J = 4.76 Hz, 1H), 8.37 (s, 1H), 7.67 (d, J = 10.08 Hz, 1H), 7.59-7.56 (dd, J = 2.6, 2.56 Hz, 1H), 7.45 (d, J = 4.64 Hz, 1H), 7.40-7.35 (m, 2H), 5.97 (s, 1H), 4.69 (s, 2H), 4.40 (t, J = 4.64 Hz, 2H), 4.21 (t, J = 4.64 Hz, 2H), 3.42 (s, 3H), 1.68 (s, 3H) |
| 534 | MS (ESI) m/z 594.04. [M + 1]+; 1H NMR (400 MHz, DMSO-d6) δ 8.81 (d, J = 4.72 Hz, 1H), 8.37 (s, 1H), 7.73 (d, J = 10.16 Hz, 1H), 7.58-7.56 (dd, J = 2.48, 2.28 Hz, 1H), 7.44-7.37 (m, 3H), 5.98 (s, 1H) 4.40 (t, J = 5.30 Hz, 2H), 4.20 (t, J = 4.54 Hz, 2H), 3.98 (s, 2H), 2.04 (s, 3H), 1.66 (s, 3H) |
| 536 | MS (ESI) m/z 601.05 [M + 1]+. 1H NMR (400 MHz, DMSO-d6) δ 8.85 (d, J = 4.72 Hz, 1H), 8.47 (s, 1H), 7.72-7.34 (m, 6H), 4.39 (t, J = 6.4 Hz, 2H), 4.22 (t, J = 6.4 Hz, 2H), 1.71 (s, 3H) |
| 537 | MS (ESI) m/z 615.03 [M − 1]; 1H NMR (400 MHz, DMSO-d6) δ 8.85 (d, J = 4.5 Hz, 1H), 8.49 (s, 1H), 7.76-7.33 (m, 6H), 4.88 (t, J = 5.4 Hz, 2H), 4.23 (t, J = 6.1 Hz, 2H), 1.69 (s, 3H) |

TABLE 3-continued

Other Compounds

| Compound | Characterization |
|---|---|
| 538 | MS (ESI) m/z 608.15 [M + 1]+; 1H NMR (400 MHz, DMSO-d6) δ 13.39 (bs, 1H), 8.85 (d, J = 4.7 Hz, 1H), 8.43 (s, 1H), 7.83-7.33 (m, 6H), 4.39 (bs, 2H), 4.25 (bs, 2H), 1.72 (s, 3H) |
| 539 | MS (ESI) m/z 633.2 [M + 1]+. 1H NMR (400 MHz, DMSO-d6) δ 13.49 (bs, 1H), 8.84 (d, J = 4.8 Hz, 1H), 8.49 (s, 1H), 7.75-7.24 (m, 7H), 4.39 (t, J = 4.16 Hz, 2H), 4.24 (t, J = 5.0 Hz, 2H), 1.70 (s, 3H) |
| 540 | MS (ESI) m/z 651.13 [M + 1]+; 1H NMR (400 MHz, DMSO-d6) δ 8.85 (d, J = 4.76 Hz, 1H), 8.48 (s, 1H), 7.78-7.48 ( m, 4H), 7.44 (d, J = 2.6 Hz, 1H), 7.36 (d, J = 9.0 Hz, 1H), 4.39 (t, J = 4.56 Hz, 2H), 4.29 (t, J = 4.52 Hz, 2H), 1.70 (s, 3H) |
| 541 | MS (ESI) m/z 649.16 [M + 1]+; 1H NMR (400 MHz, DMSO-d6) δ 8.85 (d, J = 4.76, 1H), 8.47 (s, 1H), 7.93 (s, 1H), 7.93 (s, 1H), 7.59 (dd, J = 8.88, 2.52 ,1H), 7.48-6.83 (m, 5H), 4.38 (t, J = 5.48 Hz, 2H), 4.22 (t, J = 4.84, 2H), 1.73 (s, 3H) |

TABLE 3-continued

| | Other Compounds | |
|---|---|---|
| | Compound | Characterization |

542

MS (ESI) m/z 635.09 [M + 1]+; 1H NMR (400 MHz, DMSO-d6) δ 13.33 (bs, 1H), 8.83 (d, J = 4.76 Hz, 1H), 8.367 (s, 1H), 7.76 (d, J = 1.32, 1H), 7.58 (dd, J = 2.6 Hz, J = 8.88 Hz, 1H), 7.48 (d, J = 4.76 Hz, 1H), 7.43 (d, J = 1.76 Hz, 1H) 7.34 (d, J = 8.92 Hz, 1H), 4.39 (s, 2H), 4.23 (s, 2H), 1.74 (s, 3H)

543

MS (ESI) m/z 626.11 [M + 1]+; 1H-NMR (400 MHz, DMSO-d6) δ 8.85 (d, J = 4.76 Hz, 1H), 8.34 (s, 1H), 7.76 (s, 1H), 7.60 (dd, J = 8.80, 2.44 Hz, 1H), 7.49 (d, J = 4.68 Hz, 1H), 7.43 (d, J = 2.48 Hz, 1H), 7.35 (d, J = 8.96 Hz, 1H) 4.40 (t, J = 4.32 Hz, 2H), 4.25 (t, J = 4.12 Hz, 2H), 1.74 (s, 3H)

544

MS (ESI) m/z 626.11 [M + 1]+; 1H-NMR (400 MHz, DMSO-d6) δ 8.85 (d, J = 4.76 Hz, 1H), 8.34 (s, 1H), 7.76 (s, 1H), 7.60 (dd, J = 8.80, 2.44 Hz, 1H), 7.49 (d, J = 4.68 Hz, 1H), 7.43 (d, J = 2.48 Hz, 1H), 7.35 (d, J = 8.96 Hz, 1H) 4.40 (t, J = 4.32 Hz, 2H), 4.25 (t, J = 4.12 Hz, 2H), 1.74 (s, 3H)

TABLE 3-continued

Other Compounds

| Compound | Characterization |
|---|---|
| 545 | MS (ESI) m/z 601.18 [M + 1]+; 1H NMR (400 MHz, DMSO-d6) δ 8.82 (d, J = 4.76 Hz, 1H), 8.44 (s, 1H), 7.69 (d, J = 10.76 Hz, 1H), 7.60 (dd, J = 2.64, 8.76 Hz, 1H), 7.48 (d, J = 4.68 Hz, 1H), 7.42 (d, J = 2.68 Hz, 1H), 7.41 (t, J = 71.52 Hz, 1H), 7.35 (d, J = 8.92 Hz, 1H), 4.38 (t, J = 4.44 Hz, 2H), 4.23 (t, J = 4.44 Hz, 2H), 1.77 (s, 3H) |
| 546 | MS (ESI) m/z 617.13 [M + 1]+. 1H NMR (400 MHz, DMSO-d6) δ 8.84 (d, J = 4.68 Hz, 1H), 8.41 (s, 1H), 7.92 (s, 1H), 7.60 (dd, J = 2.60, 9.52 Hz, 1H), 7.50 (d, J = 4.56 Hz, 1H), 7.42 (d, J = 1.84 Hz, 1H), 7.36 (bs, 1H), 7.35 (t, J = 71.96 Hz, 1H), 4.39 (t, J = 5.08 Hz, 2H), 4.23 (t, J = 5.08 Hz, 2H), 1.76 (s, 3H) |
| 547 | MS (ESI) m/z 608.10 [M + 1]+; 1H NMR (400 MHz, DMSO-d6) δ 13.25 (bs, 1H), 8.86-8.79 (m, 1H), 8.60-8.49 (m, 2H), 7.72-7.33 (m, 5H), 4.46-4.36 (m, 2H), 4.33-4.24 (m, 2H), 1.94 (s, 3H) |
| 548 | MS (ESI) m/z 633.07 [M + 1]+; 1H NMR (400 MHz, DMSO-d6) δ 8.77 (d, J = 4.76 Hz, 1H), 8.57 (s, 1H), 8.04 (s, 1H), 7.81-7.35 (m, 6H), 4.41 (t, J = 5.04 Hz, 2H), 4.25 (t, J = 4.84 Hz, 2H), 1.81 (s, 3H) |

TABLE 3-continued

Other Compounds

| Compound | Characterization |
|---|---|
| 550 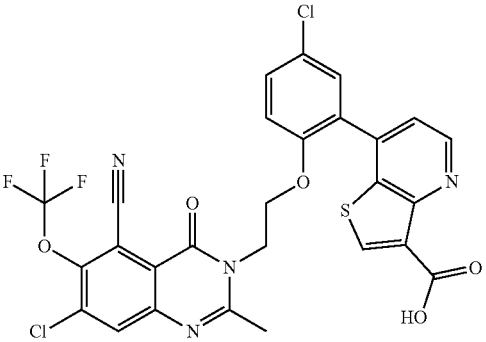 [SMILES: Cc1nc2cc(Cl)c(OC(F)(F)F)c(C#N)c2c(=O)n1CCOc1ccc(Cl)cc1-c1ccnc2c(C(=O)O)csc12] | MS (ESI) m/z 635.09 [M + 1]+; 1H NMR (400 MHz, DMSO-d6) δ 8.84 (d, J = 4.8 Hz, 1H), 8.41 (s, 1H), 8.00 (s, 1H), 7.60 (dd, J = 2.52 Hz, 8.84 Hz, 1H), 7.50 (d, J = 4.76, 1H), 7.45 (d, J = 2.48, 1H), 7.36 (d, J = 8.96 Hz, 1H), 4.40 (t, J = 4.48 Hz, 2H), 4.24 (t, J = 4.32 Hz, 2H), 1.75 (s, 3H) |
| 551 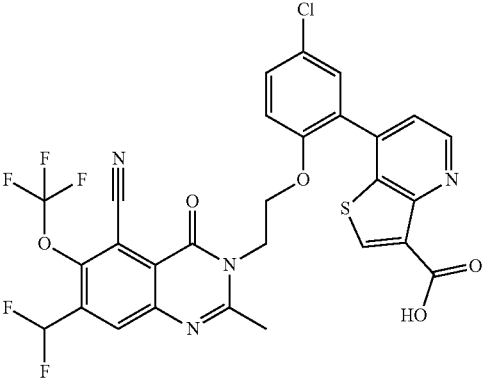 [SMILES: Cc1nc2cc(C(F)F)c(OC(F)(F)F)c(C#N)c2c(=O)n1CCOc1ccc(Cl)cc1-c1ccnc2c(C(=O)O)csc12] | MS (ESI) m/z 650.9 [M + 1]+; 1H NMR (400 MHz, DMSO-d6) δ 8.82 (d, J = 4.76 Hz, 1H), 8.38 (s, 1H), 8.04 (s, 1H), 7.59 (dd, J = 8.92, 2.40 Hz, 1H), 7.48-7.19 (m, 4H), 4.40 (t, J = 5.6 Hz, 2H), 4.25 (t, J = 5.6 Hz, 2), 1.76 (s, 3H). |
| 552 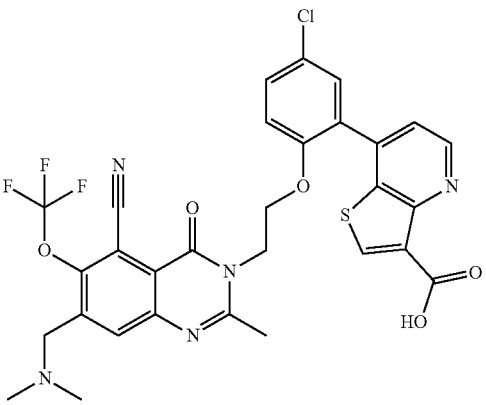 [SMILES: Cc1nc2cc(CN(C)C)c(OC(F)(F)F)c(C#N)c2c(=O)n1CCOc1ccc(Cl)cc1-c1ccnc2c(C(=O)O)csc12] | MS (ESI) m/z 658.16 [M + 1]+; 1H NMR (400 MHz, DMSO-d6) δ 8.80 (d, J = 4.7Hz, 1H), 8.48 (s, 1H), 8.17 (s, 1H), 7.62-7.59 (m, 1H), 7.46 (t, J = 4.2 Hz, 2H), 7.37 (d, J = 8.9 Hz, 1H), 4.5 (bs, 2H), 4.41 (t, J = 4.3 Hz, 2H), 4.26 (t, J = 4.3 Hz, 2H), 2.86 (s, 6H), 1.80 (s, 3H). |
| 557 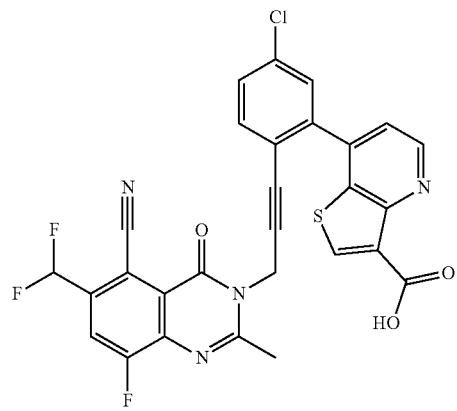 [SMILES: Cc1nc2c(F)cc(C(F)F)c(C#N)c2c(=O)n1CC#Cc1ccc(Cl)cc1-c1ccnc2c(C(=O)O)csc12] | MS (ESI) m/z 579.03 [M + 1]+; 1H NMR (400 MHz, DMSO-d6) δ 12.96 (bs, 1H), 8.73 (d, J = 4.7 Hz, 1H), 8.66 (s, 1H), 8.13 (d, J = 9.7 Hz, 1H), 7.76 (d, J = 9.0 Hz, 1H), 7.68 (m, 2H), 7.53 (d, J = 4.7 Hz, 1H), 7.37 (t, J = 53.7 Hz, 1H), 4.88 (s, 2H), 2.22 (s, 3H) |

TABLE 3-continued

Other Compounds

| Compound | Characterization |
|---|---|
| 566 | MS (ESI) m/z 676.15 [M + 1]+. 1H NMR (400 MHz, DMSO-d6) δ 12.93 (bs, 1H), 8.06 (d, J = 9.72 Hz, 1H), 7.60 (dd, J = 8.80, 2.40 Hz, 1H), 7.48-7.22 (m, 4H), 4.43 (t, J = 4.6 Hz, 2H), 4.28 (t, J = 4.8 Hz, 2H), 3.5 (s, 3H), 2.69 (s, 3H), 1.94 (s, 3H) |
| 567 | MS (ESI) m/z 644.09 [M + 1]+; 1H NMR (400 MHz, DMSO-d6) δ 12.99 (s, 1H), 8.48 (s, 1H), 7.73 (dd, J = 7.88, 10.80 Hz, 1H), 7.60 (dd, J = 2.44, 8.88 Hz, 1H), 7.48 (s, 1H), 7.40 (d, J = 2.60 Hz, 1H), 7.36 (d, J = 9.2 Hz, 1H), 4.41 (t, J = 5.12 Hz, 2H), 4.23 (t, J = 4.28 Hz, 2H), 3.57 (s, 3H), 2.71 (s, 3H), 1.80 (s, 3H) |
| 570 | MS (ESI) m/z 676.14 [M + 1]+; 1H NMR (400 MHz, DMSO-d6) δ 12.34 (bs, 1H), 8.80 (s, 1H), 8.12 (d, J = 10.0 Hz, 1H), 7.56 (dd, J = 8.8 Hz 2.80 Hz, 1H), 7.49-7.22 (m, 4H), 4.38 (t, J = 5.20 Hz, 2H), 4.245 (t, J = 4.40 Hz, 2H), 2.63 (s, 3H). 1.98 (s, 3 H), 1.75 (s, 3H) |
| 572 | MS (ESI) m/z 531.22 [M + 1]+; 1H NMR (400 MHz, DMSO-d6) δ 8.80 (d, J = 4.72 Hz, 1H), 8.39 (s, 1H), 7.83 (d, J = 8.64 Hz, 1H), 7.58 (d, J = 8.64 Hz, 2H), 7.48 (d, J = 4.84 Hz, 1H), 7.42 (d, J = 2.52 Hz, 1H), 7.35 (d, J = 9.0 Hz, 1H), 4.41-4.38 (m, 2H), 4.24-4.23 (m, 2H), 2.60 (s, 3H), 1.79 (s, 3H) |

TABLE 3-continued

| | Other Compounds | |
|---|---|---|
| | Compound | Characterization |
| 573 | | MS (ESI) m/z 531.18 [M + 1]+; 1H-NMR (400 MHz, DMSO-d6) δ 8.82 (d, J = 4.04 Hz ,1H), 8.30 (s, 1H), 7.79 (s, 1H), 7.58 (d, J = 8.88 Hz, 1H), 7.46 (m, 2H), 7.41 (m, 2H), 7.35 (d, J = 9.08 Hz, 1H), 4.35 (s, 2H), 4.19 (s, 2H), 2.49 (s, 3H), 1.81 (s, 3H) |
| 574 | | MS (ESI) m/z 531.2 [M + 1]+; 1H NMR (400 MHz, DMSO-d6) δ 13.26 (bs, 1H), 8.80 (d, J = 4.68 Hz, 1H), 8.43 (s, 1H), 7.82 (d, J = 7.56 Hz, 1H), 7.55 (d, J = 7.68, 1H), 7.59 (dd, J = 2.44, 2.48 Hz,1H), 7.46 (d, J = 4.68 Hz, 1H), 7.41 (d, J = 2.4 Hz, 1H), 7.37 (d, J = 8.96 Hz, 1H), 4.42 (s, 2H), 4.23 (s, 2H), 3.38 (s, 3H), 1.815 (s, 3H) |
| 575 | | MS (ESI) m/z 654.14 [M + 1]+. 1H NMR (400 MHz, DMSO-d6) δ, 8.27 (s, 1H), 8.04-7.67 (3, 2H), 7.63 (d, J = 8.4 Hz, 1H), 7.59-7.56 (m, 1H), 7.42 (m, 1H), 7.35 (d, J = 9.2 Hz, 1H), 7.10 (s, 1H), 4.39 (t, J = 4.8 Hz, 2H), 4.24 (t, J = 5.6 Hz, 2H), 3.07(t, J = 7.2 Hz, 2H), 2.58 (t, J = 7.2 Hz, 2H), 2.22 (s, 6H), 1.75 (s, 3H) |
| 576 | | MS (ESI) m/z 601.30 [M + 1]+., 1H-NMR (400 MHz, DMSO-d6) δ 12.96 (bs, 1H), 7.90 (d, J = 8.44 Hz, 1H), 7.83 (s, 1H), 7.78 (d, J = 8.44 Hz, 1H),7.48 (dd, J = 2.44, 8.76 Hz,1H), 7.27-7.22 (m, 3H), 7.10 (d, J = 7.28 Hz, 1H), 4.32 (t, J = 4.8 Hz, 2H), 4.20 (t, J = 4.8 Hz, 2H), 2.86 (s, 6H), 2.68 (s, 3H), 1.72 (s, 3H) |

TABLE 3-continued

Other Compounds

| Compound | Characterization |
|---|---|
| 577 | MS (ESI) m/z 637.22 [M + 1]+; 1H NMR (400 MHz, DMSO-d6) δ 8.16-7.87 (m, 3H), 7.33 (d, J = 9.2 Hz, 1H), 7.66 (d, J = 8.5 Hz, 1H), 7.53 (dd, J = 2.6, 8.8 Hz, 1H), 7.37-7.30 (m, 3H), 4.31 (t, J = 5.6 Hz, 2H), 4.17 (t, J = 5.6 Hz, 2H), 3.09 (t, J = 6.9 Hz, 2H), 2.56 (t, J = 6.8 Hz, 2H), 2.32 (s, 6H), 1.73 (s, 3H) |
| 578 | MS (ESI) m/z 655.24 [M + 1]+; 1H NMR (400 MHz, DMSO-d6) δ 8.00 (s, 1H), 7.88-7.85 (m, 2H), 7.68 (d, J = 8.48 Hz, 1H), 7.54 (dd, J = 2.60, 8.88 Hz, 1H), 7.41-7.38 (m, 2H), 7.30 (d, J = 8.92 Hz, 1H), 4.34 (t, J = 4.36 Hz, 2H), 4.19 (t, J = 4.96 Hz, 2H), 3.07 (t, J = 7.20 Hz, 2H), 2.65-2.62 (m, 2H), 2.27 (s, 6H), 1.66 (s, 3H) |
| 579 | MS (ESI) m/z 597.17 [M + 1]+; 1H NMR (400 MHz, DMSO-d6) δ 13.66 (bs, 1H), 8.43 (s, 1H), 7.84 (s, 1H), 7.71-7.33 (m, 6H), 4.39-4.37 (m, 2H), 4.23-4.21 (m, 2H), 2.70 (s, 3H), 1.81 (s, 3H) |
| 580 | MS (ESI) m/z 674.19 [M + 1]+; 1H NMR (400 MHz, DMSO-d6) δ 13.07 (bs, 1H), 8.44 (s, 1H), 7.85 (s, 1H), 7.71 to 7.41 (m, 4H), 7.36 to 7.32 (m, 2H), 4.4 (bs, 2H), 4.21 (bs, 2H), 3.56 (s, 3H), 2.71 (s, 3H), 1.79 (s, 3H) |

TABLE 3-continued

| | Other Compounds | |
|---|---|---|
| | Compound | Characterization |
| 581 | | MS (ESI) m/z 674.19 [M + 1]+; 1H NMR (400 MHz, DMSO-d6) δ 13.07 (bs, 1H), 8.44 (s, 1H), 7.85 (s, 1H), 7.71 to 7.41 (m, 4H), 7.36 to 7.32 (m, 2H), 4.4 (bs, 2H), 4.21 (bs, 2H), 3.56 (s, 3H), 2.71 (s, 3H), 1.79 (s, 3H) |
| 582 | | MS (ESI) m/z 599.27 [M + 1]+; 1H NMR (400 MHz, DMSO-d6) δ 13.55 (bs, 1H), 8.37 (s, 1H), 7.89 (s, 1H), 7.60 (dd, J = 1.88 Hz, 8.84 Hz, 1H), 7.41 (s, 2H), 7.35 (d, J = 8.84 Hz, 1H), 4.40-4.38 (m, 2H), 4.24-4.22 (m, 2H), 2.70 (s, 3H), 1.82 (s, 3H) |
| 583 | | MS (ESI) m/z 615.05 [M + 1]+; 1H NMR (400 MHz, DMSO-d6) δ 13.5 (bs, 1H), 8.41 (s, 1H), 8.02 (d, J = 8.8 Hz, 1H), 7.81 (d, J = 9.08, 1H), 7.59 (dd, J = 2.44, 8.80, 1H), 7.42-7.41 (m, 1H), 7.35 (d, J = 8.96, 1H), 4.39 (t, J = 5.08 Hz, 2H), 4.24 (t, J = 4.52, 2H), 2.69 (s, 3H), 1.83 (s, 3H) |
| 584 | | MS (ESI) m/z 602.18 [M + 1]+; 1H NMR (400 MHz, DMSO-d6) δ 9.74 (bs, 1H), 8.33 (s, 1H), 7.91 (d, J = 8.8 Hz, 1H), 7.67 (d, J = 8.4 Hz, 1H), 7.61-7.58 (m, 1H), 7.41-7.35 (m, 3H), 4.41 (t, J = 4.8 Hz, 2H), 4.26 (t, J = 5.6 Hz, 2H), 3.41 (t, J = 9.6 Hz, 2H), 3.37 (t, J = 3.2 Hz, 2H), 2.91 (s, 6H), 2.70 (s, 3H), 1.87 (s, 3H) |

TABLE 3-continued

Other Compounds

| Compound | Characterization |
|---|---|
| 585 | MS (ESI) m/z 615.29 [M + 1]+; 1H NMR (400 MHz, DMSO-d6) δ 13.68 (bs, 1H), 8.43 (s, 1H), 7.60-7.55 (m, 2H), 7.54 (t, J = 71.72 Hz, 1H), 7.43 (s, 1H), 7.40 (d, J = 4.00 Hz, 1H), 7.34 (d, J = 9.04 Hz, 1H), 4.38 (t, J = 4.68 Hz, 2H), 4.23 (t, J = 4.60 Hz, 2H), 2.71 (s, 3H), 1.78 (s, 3H) |
| 586 | MS (ESI) m/z 615.07 [M + 1]+. 1H-NMR (400 MHz, DMSO-d6) δ 8.39 (s, 1H), 7.83 (s, 1H), 7.63-7.34 (m, 5H), 4.40 (t, J = 4.0 Hz, 2H), 4.25 (t, J = 4.4 Hz, 2H), 2.70 (s, 3H), 1.83 (s, 3H) |
| 587 | MS (ESI) m/z 599.20 [M + 1]+; 1H NMR (400 MHz, DMSO-d6) δ 13.5 (s, 1H), 8.44 (s, 1H), 8.04 (d, J = 9.24 Hz, 1H), 7.62-7.58 (m, 1H), 7.47-7.21 (m, 4H), 4.41 (bs, 2H), 4.28 (bs, 2H), 2.69 (s, 3H), 1.94 (s, 3H) |
| 588 | MS (ESI) m/z 581.17 [M − 1]−; 1H NMR (400 MHz, DMSO-d6) δ 8.47 (s, 1H), 8.15 (d, J = 9.32 Hz, 1H), 7.59 (dd, J = 2.44, 8.88 Hz, 1H), 7.40-7.35 (m, 3H), 4.41 (t, J = 6.24 Hz, 2H), 4.27 (t, J = 5.44 Hz, 2H), 2.70 (s, 3H), 1.93 (s, 3H) |

TABLE 3-continued

| | Other Compounds | |
|---|---|---|
| | Compound | Characterization |
| 592 | | MS (ESI) m/z 668.20 [M + 1]+; UPLC: 92.22%; 1H NMR (400 MHz, DMSO-d6) 6: 8.32 (s, 1H), 7.78-7.33 (m, 6H), 4.38 (t, J = 4.7 Hz, 2H), 4.22 (t, J = 4.3 Hz, 2H), 3.06-3.04 (m, 2H), 2.76-2.69 (m, 5H), 2.23 (s, 6H), 1.82 (s, 3H) |
| 593 | | MS (ESI) m/z [M + 1]+; 1H NMR (400 MHz, DMSO-d6) δ 8.61 (s, 1H), 8.01 (d, J = 9.60 Hz, 1H), 7.88 (s, 1H), 7.67 (dd, J = 8.96, 2.52 Hz, 1H), 7.51 (d, J = 2.52 Hz, 1H), 7.49-7.22 (m, 2H), 4.46 (t, J = 4.84 Hz, 2H), 4.33 (t, J = 4.52 Hz, 2H), 2.94 (s, 3H), 2.07 (s, 3H) |
| 594 | | MS (ESI) m/z 669 [M + 1]+; 1H NMR (400 MHz, DMSO-d6) δ 11.93 (s, 1H), 8.45 (s, 1H), 8.01 (d, J = 9.76 Hz, 1H), 7.59 (dd, J = 8.88, 2.40, 1H), 7.47-7.20 (m, 4H), 4.40 (t, J = 4.36 Hz, 2H), 4.28 (t, J = 4.76 Hz, 2H), 3.11 (bs, 6H), 2.67 (s, 3H), 1.99 (s, 3H) |

| Compound | Characterization |
|---|---|
| 596 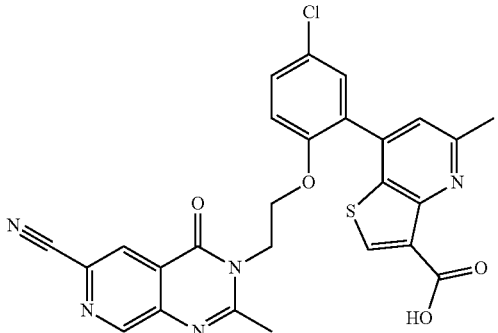 | MS (ESI) m/z 532.14 [M + 1]+; 1H NMR (400 MHz, DMSO-d6) δ 8.85 (s, 1H), 8.42 (s, 1H), 8.37 (s, 1H), 7.59 (dd, J = 8.84 Hz, 2.56 Hz, 1H), 7.41 (t, J = 4.44 Hz, 2H), 7.33 (d, J = 8.92, 1H), 4.38 (t, J = 6.12 Hz, 2H), 4.27 (t, J = 6.2 Hz, 2H), 2.70 (s, 3H), 1.86 (s, 3H) |
| 598 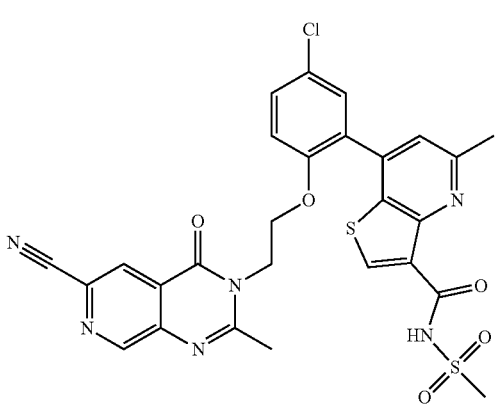 [SMILES: Cc1cc(-c2cc(Cl)ccc2OCCn2c(C)nc3cnc(C#N)cc3c2=O)c2scc(C(=O)NS(C)(=O)=O)c2n1] | MS (ESI) m/z 608.90 [M + 1]+; 1H NMR (400 MHz, DMSO-d6) δ 12.95 (s, 1H), 8.86 (s, 1H), 8.50 (s, 1H), 8.42 (s, 1H), 7.60 (dd, J = 7.24 Hz, 2.64Hz, 1H), 7.45 (s, 1H), 7.41 (d, J = 2.6 Hz, 1H), 7.35 (d, J = 8.96 Hz, 1H), 4.26 (t, J = 6.04 Hz, 2H), 4.26 (t, J = 4.52 Hz, 2H), 3.59 (s, 3H), 2.71 (s, 3H), 1.88 (s, 3H) |
| 599 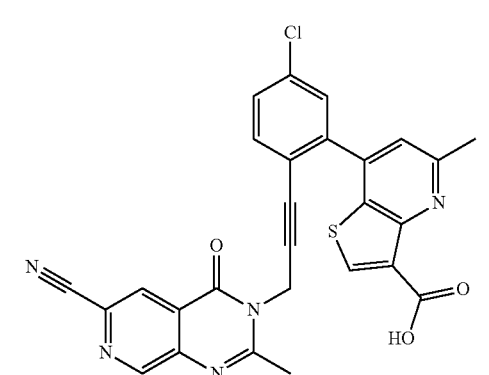 | MS (ESI) m/z 526.15 [M + 1]+; 1H NMR (400 MHz, DMSO-d6) δ 9.02 (bs, 1H), 8.45 (bs, 2H), 7.74 (s, 1H), 7.67 (d, J = 8.4 Hz, 2H), 7.40 (bs, 1H), 4.88 (s, 2H), 2.66 (s, 3H), 2.19 (s, 3H), |
| 606 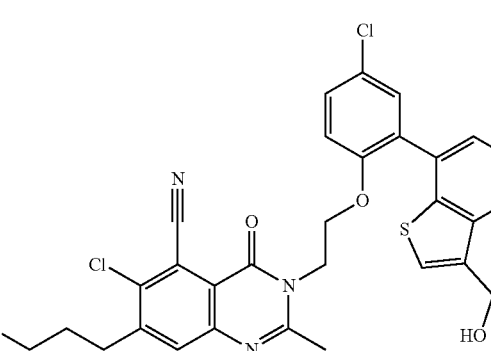 | MS (ESI) m/z 650.24 [M + 1]+; 1H NMR (400 MHz, DMSO-d6) δ 13.75 (bs, 1H), 9.50-9.30 (m, 1H), 8.29 (s, 1H), 7.64 (s, 1H), 7.60 (dd, J = 8.92, 2.56 Hz, 1H), 7.45 (s, 1H), 7.40 (d, J = 2.56 Hz, 1H), 7.36 (d, J = 9.0 Hz, 1H), 4.40 (t, J = 5.04 Hz, 2H), 4.24 (t, J = 4.48 Hz, 2H), 3.28-3.15 (m, 2H), 2.93 (t, J = 7.64 Hz, 2H), 2.83 (d, J = 4.60, 6H), 2.72 (s, 3H), 2.18-2.07 (m, 2H), 1.84 (s, 3H) |

TABLE 3-continued

| | Compound | Characterization |
|---|---|---|
| 607 | | MS (ESI) m/z 668.24 [M + 1]+; UPLC: 97.83%; 1H NMR (400 MHz, DMSO-d6) δ 8.25 (s, 1H), 7.66 (s, 1H), 7.58 (dd, J = 8.68 Hz, J = 2.36 Hz, 1H), 7.47-7.12 (m, 4H), 4.41 (t, J = 4.5 Hz, 2H), 4.24 (t, J = 4.3 Hz, 2H), 3.46 (t, J = 6.0 Hz, 2H), 3.18 (t, J = 8.0 Hz, 2H), 2.89 (s, 6H), 2.70 (s, 3H), 1.81 (s, 3H) |
| 608 | | MS (ESI) m/z 620.22 [M + 1]+; 1H NMR (400 MHz, DMSO-d6) δ 8.44 (s, 1H), 7.81 (d, J = 10.8 Hz, 1H), 7.58 (dd, J = 2.36 Hz, 9.0 Hz, 1H), 7.39-7.35 (m, 3H), 4.40 (t, J = 4.88 Hz, 2H), 4.25 (t, J = 4.44 Hz, 2H), 3.07 (t, J = 7.36 HZ, 2H), 2.69 (s, 5H), 2.28 (s, 6H), 1.94 (s, 3H) |
| 609 | | MS (ESI) m/z 636.04 [M + 1]+: 1H NMR (400 MHz, DMSO-d6) δ 8.32 (s, 1H), 7.74 (s, 1H), 7.59-7.57 (m, 1H), 7.40-7.33 (m, 3H), 4.38 (t, J = 5.0 Hz, 2H), 4.22 (t, J = 3.92 Hz, 2H), 3.50 (s, 2H), 3.21 (t, J = 7.96 Hz, 2H) 2.69 (s, 3H), 2.26 (s, 6H), 1.84 (s, 3H) |
| 611 | | MS (ESI) m/z 614.21 [M + 1]+; 1H NMR (400 MHz, DMSO-d6) δ 8.24 (s, 1H), 7.61 (dd, J1 = 2.5 Hz, J2 = 8.8 Hz, 1H), 7.48 (s, 1H), 7.42 (s, 1H),7.38 (s, 1H), 7.36 (S, 1H), 4.40 (S, 2H), 4.39-4.30 (m, 1H),4.20 (s, 2H), 3.61-3.54 (m, 2H), 3.45-3.20 (m, 2H), 2.9 (s, 6H), 2.71 (s, 3H), 1.93 (s, 3H) |

TABLE 3-continued
Other Compounds
| Compound | Characterization |
|---|---|
| 612 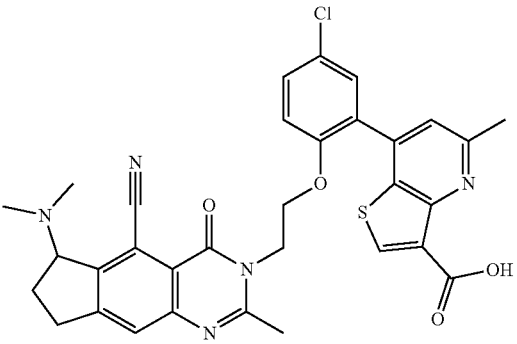 | MS (ESI) m/z 614.2 [M + 1]+; 1H NMR (400 MHz, DMSO-d6) δ 13.63 (bs, 1H), 9.72 (bs, 1H), 8.16 (s, 1H), 7.61-7.59 (m, 2H), 7.44-7.36 (m, 3H), 5.19-5.08 (m, 1H), 4.50-4.35 (m, 2H), 4.35-4.18 (m, 2H), 3.23-3.07 (m, 2H), 2.93-2.73 (m, 6H), 2.73 (s, 3H), 1.90 (s, 1H) |
| 613 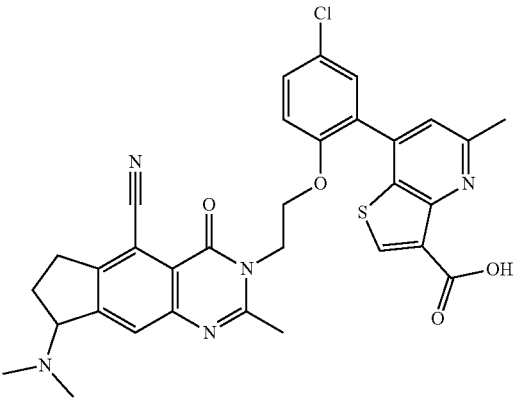 | MS (ESI) m/z 614.24 [M + 1]+; 1H NMR (400 MHz, DMSO-d6) δ 8.35 (s, 1H), 7.59-7.56 (dd, J = 2.52, 2.56 Hz, 1H), 7.48 (s, 1H), 7.40 (d, J = 2.4 Hz, 1H), 7.36-7.33 (m, 2H), 4.49 (t, J = 7.52 Hz, 1H), 4.41-4.19 (m, 4H), 3.14-2.98 (m, 2H), 2.67. (s, 3H), 2.20 (s, 6H), 2.12-2.05 (m, 2H), 1.89 (s, 3H) |
| 618 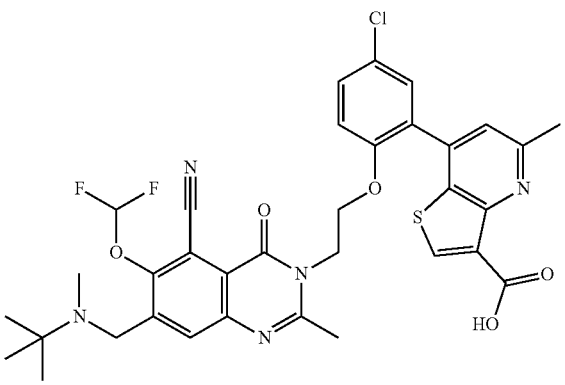 [SMILES: Cc1cc(-c2cc(Cl)ccc2OCCn2c(C)nc3cc(CN(C)C(C)(C)C)c(OC(F)F)c(C#N)c3c2=O)c2scc(C(=O)O)c2n1] | MS (ESI) m/z 696.40 [M + 1]+; 1H-NMR (400 MHz, DMSO-d6) δ 13.57 (bs, 1H), 8.41 (s ,1H), 7.90 (s, 1H), 7.60-7.57 (dd, J = 2.25, 8.8 Hz, 1H), 7.41-7.32 (m, 4H), 4.39 (t, J = 5.28 Hz, 2H), 4.23 (t, J = 5.28 Hz, 2H), 3.71 (s, 2H), 2.68 (s, 3H), 2.11 (s, 3H), 1.82 (s, 3H), 1.15 (s, 9H) |
| 619 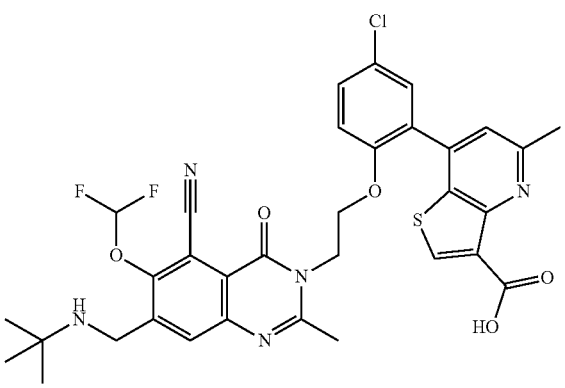 [SMILES: Cc1cc(-c2cc(Cl)ccc2OCCn2c(C)nc3cc(CNC(C)(C)C)c(OC(F)F)c(C#N)c3c2=O)c2scc(C(=O)O)c2n1] | MS (ESI) m/z 682.24 [M + 1]+; 1H-NMR (400 MHz, DMSO-d6) δ 8.83 (bs, 1H), 8.36 (s ,1H), 8.01 (s, 1H), 7.69-7.33 (m, 5H), 4.42 (t, J = 4.72 Hz, 2H), 4.28 (m, 4H), 2.72 (s, 3H). 1.92 (s, 3H). 1.42 (s, 9H) |

TABLE 3-continued

Other Compounds

| Compound | | Characterization |
|---|---|---|
| 620 | | MS (ESI) m/z 631.21 [M + 1]+; 1H NMR (400 MHz, DMSO-d6) δ 8.82 (d, J = 4.76 Hz, 1H), 8.24 (s, 1H), 7.67 (s, 1H), 7.61 (dd, J = 2.64, J = 8.88 Hz, 1H), 7.47 (d, J = 4.80 Hz, 1H), 7.43 (d, J = 2.64 Hz, 1H), 7.35 (d, J = 9.04 Hz, 1H), 4.65 (s, 2H), 4.39 (t, J = 4.48 Hz, 2H), 4.21 (t, J = 4.32 Hz, 2H), 2.87 (s, 6H), 1.77 (s, 3H) |
| 621 | | MS (ESI) m/z 634.99 [M + 1]+; 1H NMR (400 MHz, DMSO-d6) δ 8.84 (d, J = 4.74 Hz, 1H), 8.25 (s, 1H), 7.65 (s, 1H), 7.60 (dd, J = 8.84, 2.48 Hz, 1H), 7.48 (d, J = 4.72 Hz, 1H), 7.43 (d, J = 2.48 Hz, 1H), 7.35 (d, J = 8.96 Hz, 1H), 4.55 (2H), 4.39 (bs, 2H), 4.24 (bs, 2H), 2.92 (s, 6H), 1.78 (s, 3H). |
| 622 | | MS (ESI) m/z 617.93 [M + 1]+; 1H NMR (400 MHz, DMSO-d6) δ 8.72 (d, J = 4.72 Hz, 1H), 8.60 (s, 1H), 8.09 (s, 1H), 7.76 (d, J = 8.92 Hz, 1H), 7.69-7.65 (m, 2H), 7.54-7.38 (m, 2H), 4.90 (s, 2H), 4.63 (bs, 2H), 2.88 (s, 6H), 2.14 (s, 3H) |

TABLE 3-continued

Other Compounds

| | Compound | Characterization |
|---|---|---|
| 623 | (structure) | MS (ESI) m/z 636.00 [M + 1]+; 1H NMR (400 MHz, DMSO-d6) δ 8.76 (s, 1H), 8.59 (s, 1H), 8.06 (s, 1H), 7.76 (d, J = 8.92, 1H), 7.68 (d, J = 1.8 Hz, 2H), 7.53 (s, 1H), 4.87 (s, 2H), 3.70 (s, 2H), 2.23 (s, 6H), 2.12 (s, 3H) |
| 625 | (structure) | MS (ESI) m/z 512.12 [M + 1]+; 1H NMR (400 MHz, DMSO-d6) δ 9.0 (s, 1H), 8.74 (d, J = 4.8 Hz, 1H), 8.6 (s, 1H), 8.43 (s, 1H), 7.75 (d, J = 8.9 Hz, 1H), 7.68 (m, 2H), 7.51 (d, J = 4.6 Hz, 1H), 4.87 (s, 2H), 2.17 (s, 3H) |
| 626 | (structure) | MS (ESI) m/z 634.10 [M + 1]+; 1H NMR (400 MHz, DMSO-d6) δ 13.14 (bs, 1H), 8.74 (d, J = 4.72 Hz, 1H), 8.65 (s, 1H), 8.19 (s, 1H), 7.77-7.60 (m, 3H), 7.57-7.24 (m, 2H), 4.88 (s, 2H), 4.53 (s, 2H), 2.88 (s, 6H), 2.16 (s, 3H) |
| 627 | (structure) | MS (ESI) m/z 594.95 [M + 1]+; 1H NMR (400 MHz, DMSO-d6) δ 8.36 (s, 1H), 7.80 (s, 1H), 7.60 (dd, J = 2.36, J = 2.52, 1H), 7.20-7.40 (m, 4H), 4.40 (bs, 2H), 4.25 (bs, 2H), 2.68 (s, 3H), 2.65 (s, 3H), 1.88 (s, 3H) |

TABLE 3-continued

Other Compounds

| Compound | Characterization |
|---|---|
| 628 | MS (ESI) m/z 559.06 [M + 1]+; 1H NMR (400 MHz, DMSO-d6) δ 8.34 (s, 1H), 7.59 (dd, J = 2.6 Hz, 2.56 Hz, 1H), 7.44 (s, 1H), 7.35-7.39 (m, 3H), 4.39 (s, 2H), 4.23 (s, 2H), 2.70 (s, 3H), 2.51 (s, 3H), 2.437 (s, 3H), 1.9 (s, 3H) |
| 635 | MS (ESI) m/z 656.12 [M + 1]+; 1H NMR (400 MHz, DMSO-d6) δ 13.48 (s, 1H), 8.38 (s, 1H), 7.92 (s, 1H), 7.59 (dd, J = 8.88, 2.52 Hz, 1H), 7.40-7.34 (m, 3H), 4.39 (t, J = 4.6 Hz, 2H), 4.25 (t, J = 4.6 Hz, 2H), 3.68 (s, 2H), 2.69 (s, 3H), 2.22 (s, 6H), 1.90 (s, 3H) |
| 639 | MS (ESI) m/z 667.15 [M + 1]+. 1H NMR (400 MHz, DMSO-d6) δ 8.35 (s, 1H), 7.74 (bs, 1H), 7.59 (dd, J = 2.46, 8.88 Hz, 1H), 7.49-7.31 (m, 4H), 4.39 (bs, 2H), 4.23 (bs, 2H), 3.58 (bs, 2H), 3.02 (q, J = 7.52 Hz, 2H), 2.25 ( s, 6H), 1.78 (s, 3H), 1.35 (t, J = 7.24 Hz, 3H) |
| 646 | MS (ESI) m/z 693.21 [M + 1]+; 1H NMR (400 MHz, DMSO-d6) δ, 9.41 (bs, 1H), 8.33 (s, 1H), 7.86 (s, 1H), 7.69-7.35 (m, 5H), 4.41 (t, J = 6.4 Hz, 2H), 4.26 (t, J = 6.4 Hz, 2H), 4.00 (s, 2H), 3.41 (d, J = 12.0 Hz, 2H), 3.02-2.94 (m, 4H), 2.79 (d, J = 3.6 Hz, 3H), 2.64 (s, 3H),2.49 (bs, 2H), 1.85 (s, 3H) |

TABLE 3-continued

| | Compound | Characterization |
|---|---|---|
| 647 | | MS (ESI) m/z 642.99 [M + 1]+; 1H-NMR (400 MHz, DMSO-d6) δ 8.37 (s, 1H), 7.92 (d, J = 8.52 Hz, 1H), 7.64 (d, J = 8.48 Hz, 1H), 7.58 (dd, J = 8.84, 2.44 Hz, 1H), 7.41-7.34 (m, 3H), 4.42-4.37 (m, 2H), 4.27-4.21 (m, 2H), 3.75 (s, 3H), 2.68 (s, 3H), 2.50-2.30 (m, 6H), 2.21-2.16 (s, 4H), 1.85 (s, 3H) |
| 648 | | MS (ESI) m/z 599.20 [M + 1]+; 1H NMR (400 MHz, DMSO-d6) δ 8.45 (s, 1H), 7.77 (d, J = 10.56 Hz, 1H), 7.60 (m, 1H), 7.40-7.35 (m, 3H), 4.41 (bs, 2H), 4.26 (bs, 2H), 2.69 (s, 3H), 2.58 (s, 3H), 1.98 (s, 3H) |
| 650 | | MS (ESI) m/z 602.03 [M + 1]+; 1H NMR (400 MHz, DMSO-d6) δ 8.36 (s, 1H), 7.86 (s, 1H), 7.61 (dd, J = 8.92 Hz, 2.48 Hz, 1H), 7.43 (s, 1H), 7.41 (d, J = 2.52, 1H), 7.38 (d, J = 9.00 Hz, 1H), 4.54 (s, 2H), 4.43 (t, J = 5.72, 2H), 4.27 (t, J = 4.2 Hz, 2H), 2.87 (s, 6H), 2.71 (s, 3H), 2.67 (s, 3H), 1.95 (s, 3H) |
| 651 | | MS (ESI) m/z 721.31 [M + 1]+; 1H-NMR (400 MHz, DMSO-d6) δ 8.81 (d, J = 8.80 Hz, 1H), 8.47 (s ,1H), 8.23 (s, 1H), 8.03 (s, 1H), 7.61 (dd, J = 2.52, 8.84 Hz 1H), 7.47-7.19 (m, 4H), 4.41-4.40 (m, 6H), 4.21 (s, 2H), 4.10 (s, 3H), 2.67 (s, 3H). 1.82 (s, 3H) |

TABLE 3-continued

Other Compounds

| Compound | Characterization |
|---|---|
| 653 | MS (ESI) m/z 642.01 [M + 1]+; 1H NMR (400 MHz, DMSO-d6) 8.76-8.73 (m, 2H), 8.45 (s, 1H), 8.03 (d, J = 7.84 Hz, 1H), 7.86 (s,1H), 7.67-7.64 (m, 1H), 7.59 (dd, J = 8.8, 2.44 Hz, 1H), 7.45-7.40 (m, 2H), 7.36 (d, J = 8.96 Hz, 1H), 4.40 (t, J = 4.28 Hz, 2H), 4.26 (t, J = 3.76 Hz, 2H), 2.72 (s, 3H), 1.90 (s, 3H) |
| 654 | MS (ESI) m/z 608.35 [M + 1]+; 1H-NMR (400 MHz, DMSO-d6) δ 9.20 (bs, 1H), 8.74 (bs ,1H), 8.45 (d, J = 7.96 Hz, 1H), 8.39 (s, 1H), 8.32 (s, 1H), 8.00 (s, 1H), 7.66 (m, 1H), 7.61-7.57 (dd, J = 2.26, 8.56 Hz, 1H),7.45 (s, 1H), 7.41 (d, J = 2.48 Hz, 1H), 7.38 (d, J = 8.96 Hz, 1H), 4.44 (t, J = 5.20 Hz, 2H), 4.26 (t, J = 4.60 2H), 2.71 (s, 3H), 1.84 (s, 3H), |
| 657 | LCMS (ESI) m/z 552.3 [M + H]+; 1H NMR (400 MHz, DMSO-d6) δ 8.70 (dd, J = 8.7, 1.1 Hz, 1H), 8.62 (d, J = 4.8 Hz, 1H), 8.25 (d, J = 8.6 Hz, 1H), 8.16 (s, 1H), 8.07 (dd, J = 7.4, 1.1 Hz, 1H), 7.95 (dd, J = 8.3, 7.4 Hz, 1H), 7.55 (dd, J = 8.9, 2.7 Hz, 1H), 7.38 (d, J = 1Hz, 1H), 7.36 (d, J = 5.2 Hz, 1H), 7.33 (d, J = 2.3 Hz, 1H), 7.16-7.06 (m, 2H), 7.01-6.92 (m, 1H), 4.56-4.50 (m, 4H) |
| 658 | LCMS (ESI) m/z 529.1 [M + 1]+; 1H NMR (400 MHz, DMSO-d6) δ 9.78 (s, 1H), 9.10 (s, 1H), 8.62-8.51 (m, 2H), 8.25 (dd, J = 8.0, 1.3 Hz, 1H), 8.08 (s, 1H), 7.95 (ddd, J = 8.3, 7.2, 1.4 Hz, 1H), 7.80 (ddd, J = 8.1, 7.3, 1.1 Hz, 1H), 7.56 (dd, J = 9.0, 2.7 Hz, 1H), 7.37 (d, J = 9.0 Hz, 1H), 7.33-7.26 (m, 2H), 4.61 (t, J = 5.2 Hz, 2H), 4.50 (t, J = 5.1 Hz, 2H) |

TABLE 3-continued
| | Other Compounds | |
|---|---|---|
| | Compound | Characterization |
659 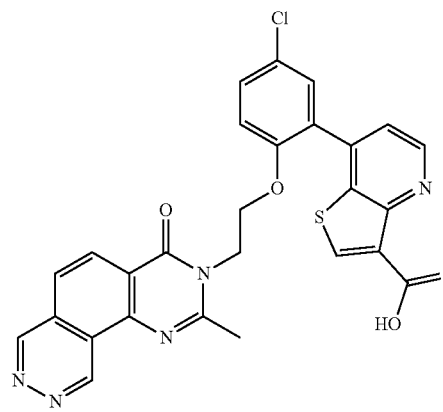
LCMS (ESI) m/z 543.9 [M + 1]+; 1H NMR (400 MHz, DMSO-d6) δ 10.20-10.15 (m, 1H), 9.83 (s, 1H), 8.76 (d, J = 4.8 Hz, 1H), 8.36 (d, J = 8.5 Hz, 1H), 8.21 (s, 1H), 8.03 (d, J = 8.5 Hz, 1H), 7.55 (dd, J = 8.9, 2.7 Hz, 1H), 7.43-7.30 (m, 2H), 4.42 (d, J = 5.1 Hz, 1H), 4.30 (t, J = 4.9 Hz, 1H), 2.44-2.38 (m, 1H), 1.94 (s, 3H)
665 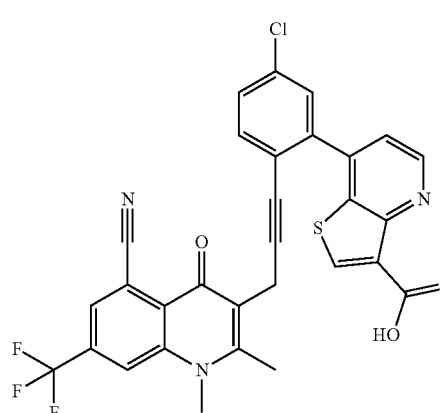
LCMS (ESI) m/z 592.1 [M + 1]+; 1H NMR (400 MHz, DMSO-d6) δ 8.68 (d, J = 4.8 Hz, 1H), 8.67 (s, 1H), 8.33 (s, 1H), 8.17 (s, 1H), 7.64 (d, J = 8.4 Hz, 1H), 7.62-7.56 (m, 2H), 7.46 (d, J = 4.8 Hz, 1H), 3.76 (s, 3H), 3.49 (s, 2H), 2.03 (s, 4H)
669 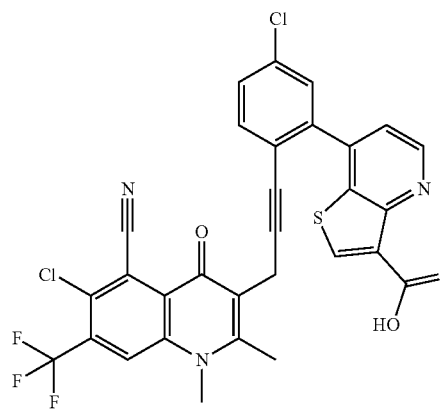
LCMS (ESI) m/z 626.1 [M + 1]+; 1H NMR (400 MHz, DMSO-d6) δ 8.73-8.63 (m, 2H), 8.35 (s, 1H), 7.68-7.53 (m, 3H), 7.47 (d, J = 4.8 Hz, 1H), 3.77 (s, 1H), 2.05 (d, J = 4.3 Hz, 1H), 2.04 (s, 1H)

TABLE 3-continued

Other Compounds

| Compound | Characterization |
|---|---|
| 671 | LCMS (ESI) m/z 558.1 [M + 1]+; 1H NMR (400 MHz, DMSO-d6) δ 10.23 (d, J = 0.7 Hz, 1H), 9.92 (d, J = 1.5 Hz, 1H), 8.41 (d, J = 8.5 Hz, 1H), 8.28 (s, 1H), 8.09 (dd, J = 8.6, 0.7 Hz, 1H), 7.59 (dd, J = 8.9, 2.7 Hz, 1H), 7.47-7.34 (m, 3H), 4.46 (s, 5H), 4.34 (s, 5H), 2.65 (s, 3H), 2.04 (s, 3H) |
| 676 | LCMS (ESI) m/z 673.1 [M + 1]+; 1H NMR (400 MHz, DMSO-d6) δ 8.30 (s, 1H), 8.10 (s, 1H), 7.56 (dd, J = 8.9, 2.7 Hz, 1H), 7.42-7.35 (m, 2H), 7.31 (d, J = 9.0 Hz, 1H), 4.35 (t, J = 5.1 Hz, 2H), 4.19 (t, J = 4.9 Hz, 2H), 3.19 (m, 4H), 2.88 (d, J = 4.1 Hz, 3H), 2.67 (s, 3H), 1.75 (s, 3H) |
| 677 | LCMS (ESI) m/z 673.2 [M + 1]+; 1H NMR (400 MHz, DMSO-d6) δ 9.78 (s, 1H), 8.31 (s, 1H), 8.09 (s, 1H), 7.56 (dd, J = 8.9, 2.7 Hz, 1H), 7.42-7.35 (m, 2H), 7.31 (d, J = 9.0 Hz, 1H), 4.35 (t, J = 5.0 Hz, 2H), 4.19 (d, J = 10.1 Hz, 1H), 3.58 (d, J = 11.8 Hz, 4H), 3.29-3.13 (m, 4H), 2.88 (d, J = 3.4 Hz, 3H), 2.67 (s, 3H), 1.75 (s, 3H) |
| 678 | LCMS (ESI) m/z 605.0 [M + 1]+; 1H NMR (400 MHz, DMSO-d6) δ 9.78 (s, 1H), 7.66-7.51 (m, 1H), 7.47-7.36 (m, 1H), 7.37-7.27 (m, 1H), 4.52 (d, J = 13.9 Hz, 1H), 4.33 (t, J = 5.1 Hz, 1H), 4.16 (t, J = 5.1 Hz, 1H), 3.54 (d, J = 11.8 Hz, 1H), 3.20 (d, J = 13.0 Hz, 1H), 3.18-3.03 (m, 1H), 2.84 (d, J = 3.6 Hz, 2H), 2.67 (s, 1H), 1.73 (s, 1H) |

| Compound | Characterization |
|---|---|
| 679 | LCMS (ESI) m/z 550.2 [M + 1]+; 1H NMR (400 MHz, DMSO-d6) δ 8.50 (s, 1H), 7.62-7.52 (m, 2H), 7.43 (d, J = 2.7 Hz, 1H), 7.40-7.30 (m, 2H), 7.19 (d, J = 9.2 Hz, 1H), 4.36 (t, J = 5.0 Hz, 2H), 4.18 (t, J = 5.0 Hz, 2H), 3.12 (s, 6H), 2.70 (s, 3H), 1.73 (s, 3H) |
| 680 | LCMS (ESI) m/z 609.0 [M + 1]+; 1H NMR (400 MHz, DMSO-d6) δ 8.59 (s, 1H), 8.16 (s, 1H), 7.56 (dd, J = 8.9, 2.6 Hz, 1H), 7.45-7.38 (m, 2H), 7.33 (d, J = 9.0 Hz, 1H), 4.40 (t, J = 5.0 Hz, 2H), 4.24 (t, J = 5.1 Hz, 2H), 4.11 (s, 1H), 2.67 (s, 3H), 1.96 (s, 3H (m, 2H), 7.43 (d, J = 2.7 Hz, 1H), 7.40-7.30 (m, 2H), 7.19 (d, J = 9.2 Hz, 1H), 4.36 (t, J = 5.0 Hz, 2H), 4.18 (t, J = 5.0 Hz, 2H), 3.12 (s, 6H), 2.70 (s, 3H), 1.73 (s, 3H) |
| 681 | LCMS (ESI) m/z 650.7 [M + 1]+; 1H NMR (400 MHz, DMSO-d6) δ 8.69 (s, 1H), 8.00 (s, 1H), 7.96 (t, J = 7.8 Hz, 1H), 7.75 (d, J = 8.3 Hz, 1H), 7.71-7.63 (m, 2H), 7.54 (d, J = 7.7 Hz, 1H), 7.48 (s, 1H), 7.44 (d, J = 7.8 Hz, 1H), 4.86 (s, 2H), 2.64 (s, 3H), 2.56 (s, 3H), 2.17 (s, 3H) |
| 682 | LCMS (ESI) m/z 653.2 [M + 1]+; 1H NMR (400 MHz, DMSO-d6) δ 9.86 (s, 1H), 8.75 (d, J = 4.8 Hz, 1H), 8.60 (s, 1H), 8.29 (s, 1H), 7.75 (d, J = 9.2 Hz, 1H), 7.71-7.65 (m, 2H), 7.54 (d, J = 4.8 Hz, 1H), 4.86 (s, 2H), 3.64 (dd, J = 24.2, 12.1 Hz, 5H), 3.30 (d, J = 13.5 Hz, 7H), 2.92 (s, 3H), 2.12 (s, 3H) |

TABLE 3-continued

| Other Compounds | |
|---|---|
| Compound | Characterization |

683 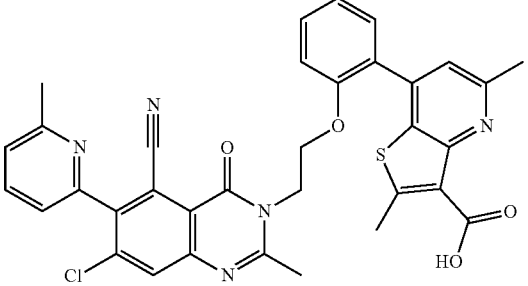

LCMS (ESI) m/z 670.1 [M + 1]+; 1H NMR (400 MHz, DMSO-d6) δ 7.89 (t, J = 7.8 Hz, 1H), 7.78 (s, 1H), 7.56 (dd, J = 8.9, 2.7 Hz, 1H), 7.45-7.35 (m, 4H), 7.33 (d, J = 9.0 Hz, 1H), 4.38 (t, J = 5.0 Hz, 2H), 2.68 (s, 3H), 2.53 (d, J = 11.1 Hz, 6H), 1.93 (s, 3H)

685 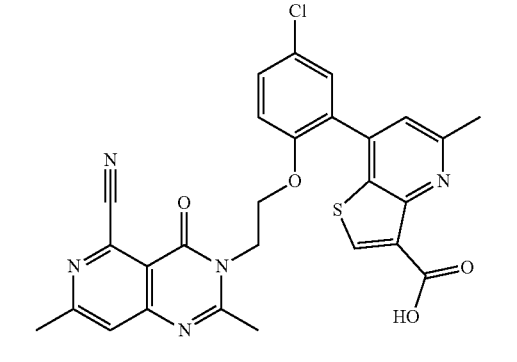

LCMS (ESI) m/z 546.9 [M + 1]+; 1H NMR (400 MHz, DMSO-d6) δ 8.36 (s, 1H), 7.60 (dd, J = 8.9, 2.7 Hz, 1H), 7.45-7.38 (m, 3H), 7.36 (d, J = 9.0 Hz, 1H), 4.39 (d, J = 5.1 Hz, 2H), 4.26 (d, J = 5.1 Hz, 2H), 2.71 (s, 3H), 2.64 (s, 3H), 1.90 (s, 3H)

688 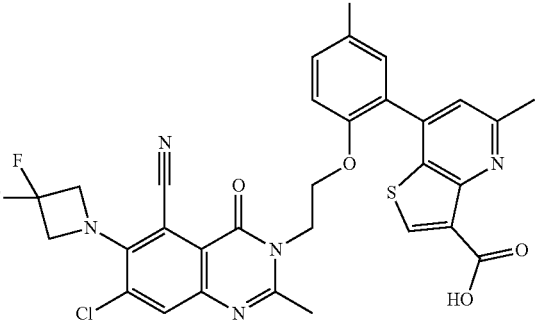

LCMS (ESI) m/z 656.1, 658.1 [M + 1]+; 1H NMR (400 MHz, DMSO-d6) δ 8.44 (s, 1H), 7.59 (dd, J = 8.9, 2.7 Hz, 1H), 7.55 (s, 1H), 7.43-7.38 (m, 2H), 7.36 (d, J = 9.0 Hz, 1H), 5.03 (t, J = 12.6 Hz, 4H), 4.38 (m, 2H), 4.19 (m, 2H), 2.72 (s, 3H), 1.83 (s, 3H)

689 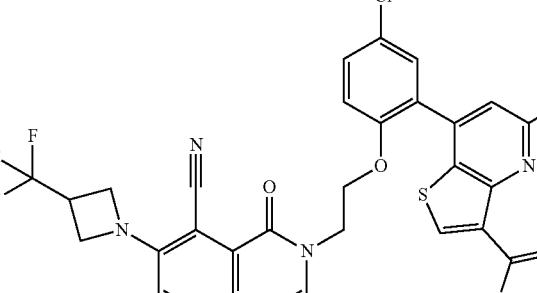

LCMS (ESI) m/z 688.0 [M + 1]+; 1H NMR (400 MHz, DMSO-d6) δ 8.47 (d, J = 0.4 Hz, 1H), 7.59 (dd, J = 8.9, 2.7 Hz, 1H), 7.51 (s, 1H), 7.42 (s, 1H), 7.41 (d, J = 2.7 Hz, 1H), 7.36 (d, J = 8.9 Hz, 1H), 4.84 (t, J = 9.3 Hz, 2H), 4.63 (dd, J = 9.6, 5.0 Hz, 2H), 4.37 (t, J = 5.1 Hz, 2H), 4.18 (t, J = 5.1 Hz, 2H), 3.67 (d, J = 9.1 Hz, 0H), 2.73 (s, 3H), 1.81 (s, 3H)

TABLE 3-continued

Other Compounds

| Compound | | Characterization |
|---|---|---|
| 690 | 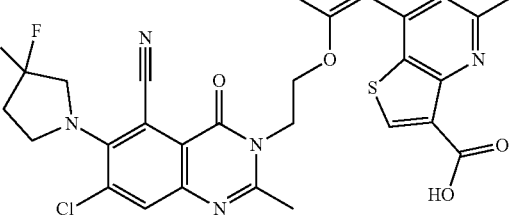 | LCMS (ESI) m/z 670.2 [M + 1]+; 1H NMR (400 MHz, DMSO-d6) δ 8.47 (d, J = 0.4 Hz, 1H), 7.59 (dd, J = 8.9, 2.7 Hz, 1H), 7.51 (s, 1H), 7.42 (s, 1H), 7.41 (d, J = 2.7 Hz, 1H), 7.36 (d, J = 8.9 Hz, 1H), 4.84 (t, J = 9.3 Hz, 2H), 4.63 (dd, J = 9.6, 5.0 Hz, 2H), 4.37 (t, J = 5.1 Hz, 2H), 4.18 (t, J = 5.1 Hz, 2H), 3.67 (d, J = 9.1 Hz, 0H), 2.73 (s, 3H), 1.81 (s, 3H) |
| 691 | 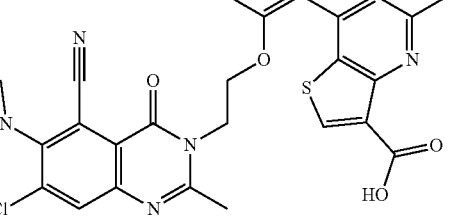 | LCMS (ESI) m/z 648.2 [M + 1]+; 1H NMR (400 MHz, DMSO-d6) δ 7.56 (dd, J = 8.9, 2.7 Hz, 1H), 7.45-7.27 (m, 3H), 4.33 (t, J = 5.0 Hz, 2H), 4.28 (bs, 2H), 4.14 (t, J = 5.0 Hz, 2H), 2.69 (s, 2H), 1.76 (s, 2H), 1.27 (s, 3H) |
| 692 | 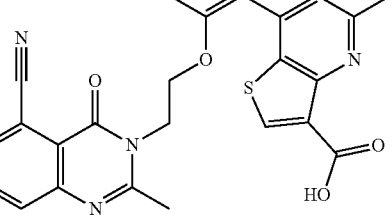 | LCMS (ESI) m/z 580.1 [M + 1]+; 1H NMR (400 MHz, DMSO-d6) δ 8.41 (s, 1H), 7.60-7.51 (m, 2H), 7.43-7.34 (m, 2H), 7.31 (d, J = 9.0 Hz, 1H), 6.45 (s, 2H), 4.33 (t, J = 5.0 Hz, 2H), 4.15 (t, J = 4.9 Hz, 2H), 2.67 (s, 3H), 1.69 (s, 3H) |
| 693 | 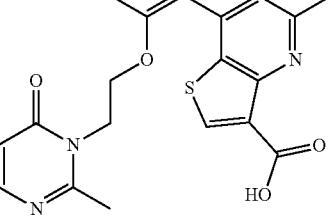 | LCMS (ESI) m/z 567.0 [M + 1]+; 1H NMR (400 MHz, DMSO-d6) δ 8.39 (s, 1H), 8.10 (d, J = 2.1 Hz, 1H), 7.71 (d, J = 2.0 Hz, 1H), 7.59 (dd, J = 8.9, 2.7 Hz, 1H), 7.44-7.40 (m, 2H), 7.35 (d, J = 9.0 Hz, 1H), 4.39 (t, J = 5.1 Hz, 2H), 4.23 (t, J = 5.1 Hz, 2H), 2.71 (s, 3H), 1.83 (s, 3H) |

TABLE 3-continued

Other Compounds

| Compound | Characterization |
|---|---|
| 694 | LCMS (ESI) m/z 594.2 [M + 1]+; 1H NMR (400 MHz, DMSO-d6) δ 8.46 (d, J = 0.4 Hz, 1H), 7.59 (dd, J = 8.9, 2.7 Hz, 1H), 7.54 (s, 1H), 7.44-7.40 (m, 2H), 7.35 (d, J = 8.9 Hz, 1H), 6.57 (d, J = 13.4 Hz, 1H), 4.37 (t, J = 5.0 Hz, 4H), 4.18 (t, J = 5.0 Hz, 2H), 3.24 (s, 3H), 2.72 (s, 3H), 1.74 (s, 3H) |
| 695 | LCMS (ESI) m/z 581.2 [M + 1]+; 1H NMR (400 MHz, DMSO-d6) δ 8.42 (s, 1H), 7.69 (s, 1H), 7.59 (dd, J = 8.9, 2.7 Hz, 1H), 7.43-7.39 (m, 2H), 7.35 (d, J = 9.0 Hz, 1H), 4.37 (t, J = 5.0 Hz, 2H), 4.20 (d, J = 5.1 Hz, 2H), 2.70 (s, 3H), 1.74 (s, 3H) |
| 696 | LCMS (ESI) m/z 608.0 ]M + 1]; +1H NMR (400 MHz, DMSO-d6) δ 8.44 (d, J = 0.4 Hz, 1H), 7.65 (s, 1H), 7.59 (dd, J = 8.9, 2.7 Hz, 1H), 7.46-7.39 (m, 2H), 7.36 (d, J = 9.0 Hz, 1H), 4.38 (s, 2H), 4.20 (s, 2H), 3.03 (s, 6H), 2.72 (s, 3H), 1.81 (s, 3H) |
| 697 | LCMS (ESI) m/z 648.2 [M + 1]+; 1H NMR (400 MHz, Methanol-d4) δ 8.44 (s, 1H), 7.83 (s, 1H), 7.54 (dd, J = 8.9, 2.6 Hz, 1H), 7.52 (s, 1H), 7.33 (d, J = 2.6 Hz, 1H), 7.29 (d, J = 8.9 Hz, 1H), 4.53-4.28 (m, 2H), 4.06-3.97 (m, 2H), 3.92-3.84 (m, 2H), 2.87 (s, 3H), 2.65 (t, J = 7.8 Hz, 2H), 2.40 (q, J = 7.5 Hz, 2H), 2.04 (s, 3H) |

TABLE 3-continued

| | Other Compounds | |
|---|---|---|
| | Compound | Characterization |
| 698 | | LCMS (ESI) m/z 636.3 [M + 1]+; 1H NMR (400 MHz, DMSO-d6) δ 8.45 (s, 1H), 7.55 (dd, J = 8.9, 2.7 Hz, 1H), 7.43 (s, 1H), 7.41-7.28 (m, 3H), 4.79 (ddd, J = 9.4, 6.7, 1.3 Hz, 2H), 4.43 (tt, J = 6.7, 4.2 Hz, 1H), 4.36-4.24 (m, 4H), 4.14 (t, J = 5.1 Hz, 2H), 2.68 (s, 3H), 1.74 (s, 3H) |
| 699 | | LCMS (ESI) m/z 659.3 [M + 1]+; 1H NMR (400 MHz, DMSO-d6) δ 8.48 (s, 1H), 7.59 (dd, J = 8.9, 2.7 Hz, 1H), 7.46 (s, 1H), 7.44-7.39 (m, 2H), 7.35 (d, J = 9.0 Hz, 1H), 4.89-4.75 (m, 2H), 4.50-4.45 (m, 2H), 4.36 (t, J = 5.0 Hz, 2H), 4.31 (dd, J = 10.5, 4.2 Hz, 2H), 4.17 (t, J = 5.1 Hz, 2H), 2.72 (s, 3H), 1.77 (s, 3H) |
| 700 | | LCMS (ESI) m/z 656.9 [M + 1]+; 1H NMR (400 MHz, DMSO-d6) δ 9.31 (s, 1H), 8.46 (s, 1H), 8.32 (s, 1H), 8.25 (s, 1H), 7.87 (s, 1H), 7.66-7.60 (m, 2H), 7.60 (dd, J = 8.9, 2.7 Hz, 1H), 7.47-7.40 (m, 2H), 7.36 (d, J = 9.0 Hz, 1H), 4.40 (t, J = 5.0 Hz, 2H), 4.24 (t, J = 4.9 Hz, 2H), 2.71 (s, 3H), 1.80 (s, 3H) |
| 701 | | LCMS (ESI) m/z 650.1 [M + 1]+; 1H NMR (400 MHz, DMSO-d6) δ 8.44 (s, 1H), 7.55 (dd, J = 8.9, 2.7 Hz, 1H), 7.44 (s, 1H), 7.40-7.28 (m, 3H), 4.76 (dd, J = 10.0, 6.5 Hz, 2H), 4.38 (dd, J = 9.8, 3.5 Hz, 2H), 4.32 (d, J = 5.3 Hz, 2H), 4.22-4.12 (m, 3H), 3.25 (s, 3H), 2.68 (s, 3H), 1.75 (s, 3H) |

TABLE 3-continued

| | Other Compounds | |
|---|---|---|
| | Compound | Characterization |
| 702 | | LCMS (ESI) m/z 698.1 [M + 1]+; 1H NMR (400 MHz, DMSO-d6) δ 8.48 (s, 1H), 7.59 (dd, J = 8.9, 2.6 Hz, 1H), 7.52 (s, 1H), 7.44-7.32 (m, 3H), 4.90 (t, J = 9.4 Hz, 2H), 4.79 (dd, J = 10.1, 4.9 Hz, 2H), 4.43-4.31 (m, 3H), 4.18 (t, J = 5.0 Hz, 2H), 3.12 (s, 3H), 2.72 (s, 3H), 1.80 (s, 3H) |
| 703 | | LCMS (ESI) m/z 664.1 [M + 1]+; 1H NMR (400 MHz, DMSO-d6) δ 8.43 (s, 1H), 7.55 (dd, J = 8.9, 2.7 Hz, 1H), 7.41 (s, 1H), 7.40-7.34 (m, 2H), 7.31 (d, J = 9.0 Hz, 1H), 4.40 (d, J = 8.7 Hz, 2H), 4.32 (t, J = 5.0 Hz, 2H), 4.19-4.09 (m, 4H), 3.40 (s, 2H), 2.67 (s, 3H), 1.72 (s, 3H), 1.22 (s, 3H) |
| 704 | | LCMS (ESI) m/z 666.4 [M + 1]+; 1H NMR (400 MHz, DMSO-d6) δ 7.58 (s, 1H), 7.51 (d, J = 9.8 Hz, 2H), 7.34 (s, 1H), 7.28 (d, J = 9.1 Hz, 1H), 7.17 (s, 1H), 6.66 (bs, 1H), 4.89 (t, J = 8.8 Hz, 2H), 4.39 (s, 2H), 4.93-4.36 (m, 2H), 4.30 (s, 2H), 4.15 (s, 3H), 3.72 (s, 1H), 2.62 (s, 3H), 2.51 (s, 2H), 2.12 (s, 3H), 1.84 (s, 4H), 1.73 (d, J = 8.4 Hz, 3H) |
| 710 | | MS (ESI) m/z 668.20 [M + 1]+; 1H NMR (400 MHz, DMSO-d6) δ 10.10 (bs, 1H), 8.35 (s, 1H), 8.12 (s, 1H), 7.61 (dd, J = 2.56, 8.84 Hz, 1H), 7.56-7.21 (m, 4H), 4.84-4.82 (m, 1H), 4.47-4.17 (m, 4H), 2.90 (s, 3H), 2.71 (s, 3H), 2.66 (s, 3H), 1.78 (s, 6H) |

TABLE 3-continued

Other Compounds

| Compound | Characterization |
|---|---|
| 712 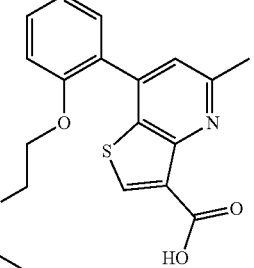 | MS (ESI) m/z 586.04 [M + 1]+; 1H NMR (400 MHz, DMSO-d6) δ 10.95 (bs, 1H), 8.30 (s, 1H), 7.66 (s, 1H), 7.60 (dd, J = 8.84, 2.56 Hz, 1H), 7.42 (s, 1H), 7.39-7.35 (m, 2H), 4.92 (bs, 4H), 4.40 (t, J = 4.40 Hz, 2H), 4.26 (t, J = 4.80 Hz, 2H), 3.13 (s, 3H), 2.71 (s, 3H), 1.93 (s, 3H) |
| 715 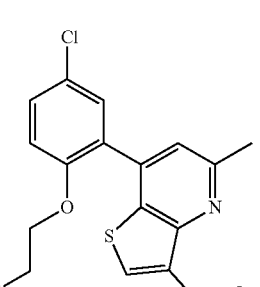 | MS (ESI) m/z 786.00 [M + 1]+; 1H NMR (400 MHz, DMSO-d6) δ 8.27 (s, 1H), 7.70 (s, 1H), 7.54 (dd, J = 8.84, 2.48 Hz, 1H), 7.36 (d, J = 2.52 Hz, 1H), 7.30 (d, J = 8.96 Hz, 1H), 7.20 (s, 1H), 5.09 (t, J = 4.6 Hz, 1H), 4.89 (d, J = 3.88 Hz, 2H), 4.33 (d, J = 4.52 Hz, 2H), 4.19 (s, 2H), 2.62 (s, 3H), 1.69 (s, 3H), 1.61 (s, 9H) |
| 716 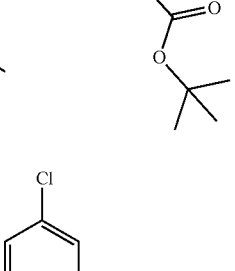 | MS (ESI) m/z 784.32 [M + 1]+; 1H NMR (400 MHz, DMSO-d6) δ 10.10 (s, 1H), 8.29 (s, 1H), 7.79 (s, 1H), 7.54 (dd, J = 8.8, 2.5 Hz, 1H), 7.36 (d, J = 2.52 Hz, 1H), 7.30 (d, J = 8.92 Hz, 1H), 7.21 (s, 1H), 4.35 (t, J = 4.28 Hz, 2H), 4.20 (t, J = 4.0 Hz, 2H), 2.62 (s, 3H), 1.73 (s, 3H), 1.61 (s, 9H) |
| 718 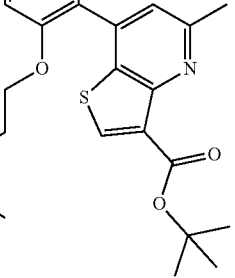 | MS (ESI) m/z 657.11 [M + 1]+; 1H NMR (400 MHz, DMSO-d6) δ 13.54 (bs, 1H), 8.30 (s, 1H), 7.58 (dd, J = 8.92 Hz, 2.6 Hz, 1H), 7.48 (s, 1H), 7.39-7.34 (m, 3H), 4.38 (t, J = 5.88 Hz, 2H), 4.22 (t, J = 4.32 Hz, 2H), 3.75 (s, 2H), 2.68 (s, 3H), 2.56 (s, 3H), 2.45 (bs, 4H,), 2.28 (bs, 4H), 2.12 (s, 3H), 1.89 (s, 3H) |

TABLE 3-continued

Other Compounds

| Compound | Characterization |
|---|---|
| 720 | MS (ESI) m/z 579.93 [M + 1]+; 1H NMR (400 MHz, DMSO-d6) δ 8.80 (d, J = 4.88 Hz, 1H), 8.48 (s, 1H), 8.32 (s, 1H), 7.59 (dd, J = 8.92, 2.68 Hz, 1H), 7.50-7.44 (m, 2H), 7.40 (d, J = 2.6 Hz, 1H), 7.35 (d, J = 8.96 Hz, 1H), 4.49-4.38 (m, 5H), 4.33-4.27 (m, 2H), 1.85 (s, 3H) |
| 724 | MS (ESI) m/z 577.00 [M + 1]+; 1H NMR (400 MHz, DMSO-d6) δ 8.36 (s, 1H), 7.64 (s, 1H), 7.59 (dd, J = 8.8 Hz, 2.56 Hz, 1H), 7.39-7.35 (m, 3H), 5.68 (d, 46.72 Hz, 2H), 4.40 (t, 4.40 Hz, 2H), 4.25 (t, 4.56 Hz, 2H), 2.69 (s, 3H), 2.53 (s, 3H), 1.95 (s, 3H) |
| 729 | MS (ESI) m/z 622.01 [M + 1]+; 1H NMR (400 MHz, DMSO-d6) δ 8.82 (bs, 1H), 8.71 (bs, 1H), 8.07 (d, J = 7.84 Hz, 1H), 7.93 (s, 1H), 7.62-7.56 (m, 1H), 7.53-7.49 (m, 1H), 7.30-7.28 (m, 3H), 7.12 (d, J = 7.6 Hz, 1H), 4.42 (t, J = 4.76 Hz, 2H), 4.21 (t, J = 6.16 Hz, 2H), 2.72 (s, 3H), 2.66 (s, 3H), 1.93 (s, 3H) |
| 741 | MS (ESI) m/z 677.17 [M + 1]+; 1H NMR (400 MHz, DMSO-d6) δ 14.31 (bs, 1H), 7.71 (bs, 1H), 7.60 (dd, J = 2.48, 8.8 Hz 1H), 7.41 (s, 1H), 7.39-7.18 (m, 2H), 4.38 (t, J = 4.12 Hz, 2H), 4.24 (t, J = 4.6 Hz, 2 H), 3.81-3.21 (m, 8H), 2.93 (s, 3H), 2.71 (s, 3H), 2.50 (s, 3H), 2.02 (s, 3H) |

TABLE 3-continued

Other Compounds

| Compound | Characterization |
|---|---|
| 743 | MS (ESI) m/z 622.01 [M + 1]+; 1H NMR (400 MHz, DMSO-d6) δ 8.69 (d, J = 3.88 Hz, 1H), 8.02 (t, J = 6.20 Hz, 1H), 7.81 (d, J = 7.76 Hz, 2H), 7.51-7.47 (m, 2H), 7.30-7.08 (m, 3H), 7.03 (bs, 1H), 4.32 (t, J = 6.04 Hz, 2H), 4.21 (t, J = 5.4 Hz, 2H), 2.76 (s, 3H), 2.66 (s, 3H), 1.93 (s, 3H) |
| 744 | MS (ESI) m/z 579.36 [M + 1]+; 1H-NMR (400 MHz, DMSO-d6) δ 13.59 (bs, 1H), 8.90 (s, 1H), 8.44 (s, 1H), 7.57 (d, J = 8.84 Hz, 1H), 7.41 (s, 1H), 7.38 (s, 1H), 7.33 (d, J = 8.84 Hz, 1H), 4.39 (t, J = 5.4 Hz, 2H), 4.21 ((t, J = 4.32 Hz, 2H)), 2.68 (s, 3H), 2.35-2.32 (m, 1H), 1.78 (s, 3H), 1.29-1.07 (m, 4H) |
| 745 | MS (ESI) m/z 522.26 [M + 1]+; 1H NMR (400 MHz, DMSO-d6) δ 13.58 (bs, 1H), 9.04 (s, 1H), 8.47 (s, 1H), 7.59 (dd, J = 2.48, 8.88 Hz, 1H), 7.40 (t, J = 2.68 Hz, 2H), 7.35 (d, J = 8.92 Hz, 1H), 4.40 (t, J = 4.32 Hz, 2H), 4.23 (t, J = 5.04 Hz, 2H), 2.69 (s, 6H), 1.81 (s, 3H) |
| 746 | MS (ESI) m/z 536.27 [M + 1]+; 1H-NMR NMR (400 MHz, DMSO-d6) δ 13.58 (bs, 1H), 8.49 (s, 1H), 7.59 (d, J = 8.72 Hz, 1H), 7.40-7.38 (m, 2H), 7.35 (d, J = 8.84 Hz, 1H), 4.39 (bs, 2H), 4.22 (bs, 2H), 2.69 (s, 3H), 2.67 (s, 3H), 2.65 (s, 3H), 1.82 (s, 3H) |

TABLE 3-continued

| | Other Compounds | |
|---|---|---|
| | Compound | Characterization |
| 748 | | MS (ESI) m/z 571.01 [M + 1]+. 1H-NMR (400 MHz, DMSO-d6) δ 8.34 (s, 1H), 7.59 (dd, J = 8.80, 2.80 Hz 1H), 7.44-7.40 (m, 2H), 7.40-7.34 (m, 2H), 4.39 (t, J = 4.96 Hz, 2H), 4.24 (t, J = 4.52 Hz, 2H), 3.10 (t, J = 7.12 Hz, 4H), 2.71 (s, 3H), 2.21-2.14 (m, 2H), 1.96 (s, 3H) |
| 750 | | MS (ESI) m/z 695.96 [M + 1]+; 1H NMR (400 MHz, DMSO-d6) δ 8.48 (s, 1H), 7.62 (s, 1H), 7.69-7.56 (m, 1H), 7.42 (d, J = 2.44 Hz, 1H), 7.39 (s, 1H), 7.34 (d, J = 8.84 Hz, 1H), 4.35 (t, J = 4.84 Hz, 2H), 4.26 (t, J = 7.52 Hz, 4H), 4.16 (t, J = 4.36 Hz, 2H), 2.70 (s, 3H), 2.31-2.27 (m, 2H), 1.73 (s, 3H) |
| 752 | | MS (ESI) m/z 620.00 [M + 1]+; 1H NMR (400 MHz, DMSO-d6) δ 8.45 (s, 1H), 7.58 (dd, J = 2.56, 8.80 Hz, 1H), 7.46 (s, 1H), 7.40 (d, J = 2.56 Hz, 1H), 7.38 (s, 1H), 7.34 (d, J = 9.04 Hz, 1H), 4.60 (t, J = 7.60 Hz, 4H), 4.35 (t, J = 5.12 Hz, 2H), 4.16 (t, J = 4.12 Hz, 2H), 2.70 (s, 3H), 2.32-2.26 (m, 2H), 1.77 (s, 3H) |
| 755 | | MS (ESI) m/z 1136.89 [M + 1]+; 1H NMR (400 MHz, DMSO-d6) δ 8.81 (d, J = 4.8 Hz, 1H), 8.41 (s, 1H), 8.20 (s, 1H), 7.98 (s, 1H), 7.72 (bs, 1H), 7.61-7.58 (m, 1H), 7.54-7.35 (m, 5H), 6.40 (s, 1H), 6.35 (s, 1H), 4.46-4.12 (m, 11H), 3.47-3.33 (m, 13H), 3.04-3.01 (m, 4H), 2.66-2.50 (m, 4H), 2.03-2.00 (m, 4H), 1.81 (s, 3H), 1.58-1.55 (m, 4H), 1.47-1.43 (m, 4H), 1.25-1.20 (m, 2H) |

TABLE 3-continued

Other Compounds

| Compound | Characterization |
|---|---|
| | |

| 758 | MS (ESI) m/z 692.00 [M + 1]+; 1H NMR (400 MHz, DMSO-d6) δ 13.56 (bs, 1H), 8.47 (s, 1H), 8.28 (t, J = 7.84 Hz, 1H), 7.94 (d, J = 7.72 Hz, 1H), 7.91-7.86 (m, 2H), 7.59 (dd, J = 8.88, 2.56 Hz, 1H), 7.44-7.39 (m, 2H), 7.35 (d, J = 8.96 Hz, 1H), 7.04 (t, J = 54.68 Hz, 1H), 4.39 (t, J = 4.64 Hz, 2H), 4.25 (t, J = 5.44 Hz, 2H), 2.71 (s, 3H), 1.86 (s, 3H) |

| 761 | MS (ESI) m/z 651.05 [M + 1]+; 1H NMR (400 MHz, DMSO-d6) δ 13.49 (s, 1H), 8.80 (d, J = 5.8 Hz, 2H), 8.57 (s, 1H), 7.63 (d J = 5.56 Hz, 2H), 7.59 (dd, J = 8.92 Hz, 2.56, 1H), 7.44 (d, J = 2.6 Hz, 1H), 7.40 (s, 1H), 7.36 (d, J = 8.96 Hz, 1H), 4.42 (t, J = 5.4 Hz, 2H), 4.32 (t, J = 4.24 Hz, 2H), 2.71 (s, 3H), 2.00 (s, 3H) |

| 759 | MS (ESI) m/z 622.07 [M + 1]+; 1H NMR (400 MHz, DMSO-d6) δ 13.63 (bs, 1H), 8.77 (s, 1H), 8.71 (s, 1H), 8.35 (s, 1H), 8.03 (d, J = 6.96 Hz, 1H), 7.61-7.59 (m, 2H), 7.52 (s, 1H), 7.43-7.36 (m, 3H), 4.42 (t, J = 5.76 Hz, 2H), 4.26 (t, J = 5.48 Hz, 2H), 2.71 (s, 3H), 2.5 (s, 3H, not visible, merged with moisture peak), 1.87 (s, 3H) |

TABLE 3-continued

Other Compounds

| Compound | Characterization |
|---|---|
| 760 | MS (ESI) m/z 589.98 [M + 1]+; 1H NMR (400 MHz, DMSO-d6) δ 8.51 (s, 1H), 7.59 (dd, J = 8.88, 2.6 Hz, 1H), 7.42 (d J = 2.56 Hz, 1H), 7.39 (s, 1H), 7.35 (d, J = 8.96 Hz, 1H), 4.40 (t, J = 4.72 Hz, 2H), 4.28 (t, J = 4.8 Hz, 2H), 2.79 (s, 3H), 2.69 (s, 3H), 1.98 (s, 3H) |
| 766 | MS (ESI) m/z 630.01 [M + 1]+; 1H NMR (400 MHz, DMSO-d6) δ 8.40 (s, 1H), 7.89 (s, 1H), 7.59 (dd, J = 90.20, 2.52 Hz, 1H), 7.42 (s, 2H), 7.34 (d, J = 8.96 Hz, 1H), 4.36 (t, J = 5.64 Hz, 2H), 4.22-4.18 (m, 6H), 2.70 (s, 3H), 2.36-2.30 (m, 2H), 1.72 (s, 3H) |
| 764 | MS (ESI) m/z 652.95 [M + 1]+, 1H NMR (400 MHz, DMSO-d6) δ 13.57 (bs, 1H), 9.09 (s, 1H), 8.84 (d, J = 2.44 Hz, 1H), 8.80 (bs, 1H), 8.37 (s, 1H), 8.35 (s, 1H), 7.58 (dd, J = 2.56, 8.88 Hz, 1H), 7.43 (bs, 2H), 7.35 (d, J = 8.96 Hz, 1H), 4.41 (t, J = 4.96 Hz, 2H), 4.28 (t, J = 4.36 Hz, 2H), 2.70 (s, 3H), 1.83 (s, 3H) |
| 765 | MS (ESI) m/z 652.95 [M + 1]+; 1H NMR (400 MHz, DMSO-d6) δ 13.61 (bs, 1H), 9.02 (d, J = 4.92 Hz, 2H), 8.40 (s, 1H), 8.34 (s, 1H), 7.70 (t, J = 4.92 Hz, 1H), 7.58 (dd, J = 8.92, 2.52 Hz, 1H), 7.43 (d, J = 2.48 Hz, 1H), 7.41 (s, 1H), 7.34 (d, J = 8.96 Hz, 1H), 4.39-4.37 (m, 2H), 4.30-4.23 (m, 2H), 2.69 (s, 3H), 1.80 (s, 3H) |

TABLE 3-continued

Other Compounds

| Compound | | Characterization |
|---|---|---|
| 769 | | MS (ESI) m/z 667.07 [M + 1]+; 1H NMR (400 MHz, DMSO-d6) δ 13.57 (bs, 1H), 8.95 (d, J = 5.12 Hz, 1H), 8.37 (s, 1H), 8.33 (s, 1H), 7.75 (d, J = 5.08 Hz, 1H), 7.59 (dd, J = 2.52, 8.84 Hz, 1H), 7.42 (t, J = 2.64 Hz, 2H), 7.35 (d, J = 8.96 Hz, 1H), 4.40 (t, J = 6.64 Hz, 2H), 4.27 (t, J = 6.6 Hz, 2H), 2.71 (s, 6H), 1.81 (s, 3H) |
| 767 | | MS (ESI) m/z 652.92 [M + 1]+; 1H NMR (400 MHz, DMSO-d6) δ 13.57 (bs, 1H) 9.35 (d, J = 0.88 Hz, 1H), 9.08 (d, J = 5.16 Hz, 1H), 8.37 (s, 1H), 8.35 (s, 1H), 7.98 (dd, J = 4.04, 1.52 Hz, 1H), 7.59 (dd, J = 9.20, 2.40, Hz, 1H), 7.43-7.41 (m, 2H), 7.35 (d, J = 8.96 Hz, 1H), 4.40 (t, J = 3.76 Hz, 2H), 4.27 (t, J = 4.48 Hz, 2H), 2.70 (s, 3H), 1.83 (s, 3H) |
| 768 | | MS (ESI) m/z 653.01 [M + 1]+; 1H NMR (400 MHz, DMSO-d6) δ 13.55 (bs, 1H), 9.38 (s, 1H), 9.03 (s, 2H), 8.31 (d, J = 2.88 Hz, 1H), 7.59 (dd, J = 8.80, 2.40 Hz, 1H), 7.43-7.41 (m, 2H), 7.35 (d, J = 8.96 Hz, 1H), 4.41 (t, J = 4.80 Hz, 2H), 4.27 (t, J = 4.80 Hz, 2H), 2.72 (s, 3H), 1.85 (s, 3H) |
| 781 | | MS (ESI) m/z 646.02 [M + 1]+; 1H NMR (400 MHz, DMSO-d6) δ 8.38 (s, 1H), 8.27 (s, 1H), 7.62-7.57 (dd, J = 2.6, 8.8 Hz, 1H), 7.44-7.43 (m, 2H), 7.36 (d, J = 9.2 Hz, 1H), 4.39 (t, J = 4.4 Hz, 2H), 4.25 (t, J = 4.4 Hz, 2H), 3.06 (s, 3H), 2.79 (s, 3H), 2.71 (s, 3H), 1.78 (s, 3H) |

TABLE 3-continued

Other Compounds

| Compound | Characterization |
|---|---|
| 778 | MS (ESI) m/z 639.97 [M + 1]+; 1H NMR (400 MHz, DMSO-d6) δ 8.80 (d, J = 5.28 Hz, 1H), 8.43 (s, 1H), 7.76 (s, 1H), 7.70 (d, J = 4.88, 1H), 7.61-7.58 (m, 2H), 7.43 (s, 1H), 7.41 (d, J = 2.48 Hz, 1H), 7.37 (d, J = 8.96 Hz, 1H), 4.41 (t, J = 5.32 Hz, 2H), 4.27 (t, J = 4.28 Hz, 2H), 2.73 (s, 3H), 2.67 (s, 3H), 1.94 (s, 3H) |
| 780 | MS (ESI) m/z 616.97 [M + 1]+; 1H NMR (400 MHz, DMSO-d6) δ 13.58 (s, 1H), 8.32 (s, 1H), 8.25 (s, 1H), 7.60 (dd, J = 2.56, 8.84 Hz 1H), 7.42-7.41 (m, 2H), 7.36 (d, J = 8.96 Hz, 1H), 4.41 (t, J = 4.56 Hz, 2H), 4.28 (t, J = 4.28 Hz, 2H), 2.72 (s, 3H), 2.71 (s, 3H), 1.81 (s, 3H) |
| 784 | MS (ESI) m/z 612.97 [M + 1]+; 1H-NMR (400 MHz, DMSO-d6) δ 8.28 (s, 1H), 8.08 (s ,1H), 7.59 (dd, J = 2.48, 8.88 Hz, 1H), 7.41 (d, J = 2.6 Hz, 2H), 7.35 (d, J = 8.96 Hz, 1H), 4.37 (t, J = 4.48 Hz, 2H), 4.23 (t, J = 4.92 Hz, 2H), 2.69 (s, 3H), 2.19 (s, 3H), 1.76 (s, 3H) |
| 782 | MS (ESI) m/z 653.03 [M + 1]+. 1H NMR (400 MHz, DMSO-d6) δ 13.5 (bs, 1H), 8.40 (s, 1H), 8.32 (s, 1H), 7.59 (d, J = 8.0 Hz, 1H), 7.41 (s, 2H), 7.33 (d, J = 9.0 Hz, 1H), 4.40 (bs, 2H), 4.27 (bs, 2H), 3.54 (s, 3H), 2.70 (s, 3H), 1.78 (s, 3H) |

TABLE 3-continued

Other Compounds

| Compound | Characterization |
|---|---|
| 783 | MS (ESI) m/z 598.95 [M + 1]+; 1H NMR (400 MHz, DMSO-d6) δ 13.57 (bs, 1H), 8.29 (s, 1H), 8.13 (s, 1H), 7.60-7.57 (dd, J = 8.84, 2.4 Hz, 2H), 7.41 (d, J = 3.48 Hz 1H), 7.34 (d, J = 8.92 Hz, 1H), 4.89 (s, 1H), 4.38 (t, J = 3.84 Hz, 2H), 4.24 (t, J = 4.52 Hz, 2H), 2.69 (s, 3H), 1.76 (s, 3H) |
| 787 | MS (ESI) m/z 654.99 [M + 1]+; 1H NMR (400 MHz, DMSO-d6) δ 13.60 (bs, 1H), 8.35 (s, 1H), 8.20 (s, 1H), 7.82 (d, J = 1.96 Hz, 1H), 7.58 (dd, J = 8.88, 2.48 Hz, 1H), 7.42 (d, J = 2.52 Hz, 1H), 7.40 (s, 1H), 7.34 (d, J = 8.96 Hz, 1H), 6.70 (d, J = 2.0 Hz, 1H), 4.39 (t, J = 4.40 Hz, 2H), 4.25 (t, J = 4.00 Hz, 2H), 3.94 (s, 3H), 2.68 (s, 3H), 1.77 (s, 3H) |
| 785 | MS (ESI) m/z 600.0 [M + 1]+. 1H-NMR (400 MHz, DMSO-d6) ) δ 8.33 (s, 1H), 8.24 (s ,1H), 7.60 (dd, J = 2.52, 8.84 Hz, 1H), 7.43 (s, 1H), 7.41 (d, J = 2.52 Hz, 1H), 7.35 (d, J = 8.96 Hz, 1H), 4.40 (t, J = 4.4 Hz, 2H), 4.27 (t, J = 6.0 Hz, 2H), 2.70 (s, 3H), 1.75 (s, 3H) |
| 786 | MS (ESI) m/z 615.29 [M + 1]+; 1H NMR (400 MHz, DMSO-d6) δ 8.41 (s, 1H), 8.00 (s, 1H), 7.59 (d, J = 7.72 Hz, 1H), 7.42 (d, J = 1.92 Hz, 1H), 7.40 (s, 1H), 7.34 (d, J = 9.04 Hz, 1H), 4.37 (t, J = 4.12 Hz, 2H), 4.19 (t, J = 5.04 Hz, 2H), 3.01 (s, 6H), 2.69 (s, 1H), 1.72 (s, 3H) |

TABLE 3-continued

Other Compounds

| Compound | | Characterization |
|---|---|---|
| 795 | 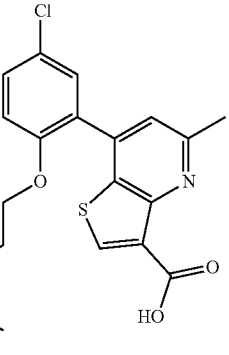 | MS (ESI) m/z 615.04 [M + 1]+; 1H NMR (400 MHz, DMSO-d6) δ 13.58 (bs, 1H), 8.32 (s, 1H), 8.03 (s, 1H), 7.59 (dd, J = 2.40, 8.76 Hz, 1H), 7.42 (d, J = 2.52 Hz, 1H), 7.39 (s, 1H), 7.33 (d, J = 8.96 Hz, 1H), 4.37 (bs, 2H), 4.21 (bs, 2H), 2.68 (s, 3H), 2.37-2.32 (m, 1H), 1.76 (s, 3H), 1.19-1.13 (m, 4H) |
| 788Fa | 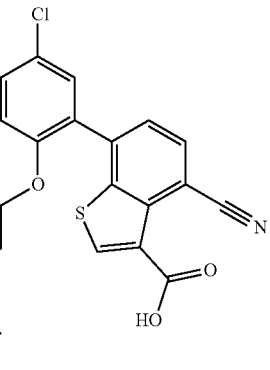 | MS (ESI) m/z 676.01 [M + 1]+; 1H NMR (400 MHz, DMSO-d6) δ 11.58 (s, 1H), 8.43 (d, J = 5.0 Hz, 1H), 8.21 (d, J = 6.6 Hz, 2H), 8.11 (d, J = 7.56 Hz, 1H), 7.62 (s, 1H), 7.60-7.56 (m, 1H), 7.43 (d, J = 2.6 Hz, 2H), 7.35 (d, J = 8.8 Hz, 2H), 4.40 (t, J = 6.7 Hz, 2H), 4.24 (t, J = 5.0 Hz, 2H), 2.58 (s, 3H), 1.71 (s, 3H) |
| 788Fb | 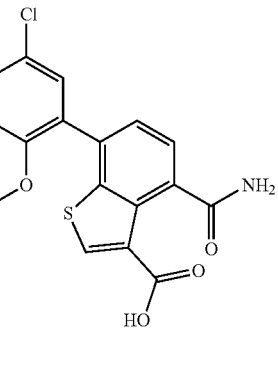 | MS (ESI) m/z 694.03 [M + 1]+; 1H NMR (400 MHz, DMSO-d6) δ 12.69 (s, 1H), 8.63 (d, J = 4.9 Hz, 1H), 8.40 (s, 1H), 7.80 (s, 1H), 7.75 (s, 1H), 7.61 (d, J = 7.4 Hz, 1H), 7.52 (dd, J = 2.4, 4.9 Hz, 1H), 7.45 (s, 1H), 7.37 (s, 2H), 7.31-7.29 (m, 1H), 7.26 (s, 2H), 4.35 (bs, 2H), 4.24 (bs, 2H), 2.58 (s, 3H), 1.75 (s, 3H) |
| 798 | 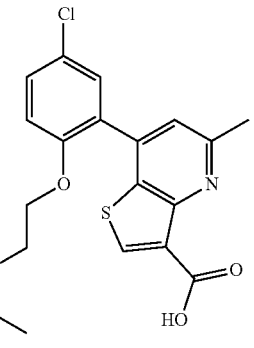 | MS (ESI) m/z 725.97 [M + 1]+; 1H NMR (400 MHz, DMSO-d6) δ 8.45 (s, 1H), 7.66 (s, 1H), 7.58 (dd, J = 8.88, 2.56 Hz 1H), 7.43-7.38 (m, 2H), 7.35 (d, J = 8.96 Hz, 1H), 4.37 (t, J = 6.00 Hz, 2H), 4.20 (t, J = 4.28 Hz, 2H), 3.55-3.44 (m, 4H), 2.70 (s, 3H), 2.05-1.94 (m, 4H), 1.81 (s, 3H) |

TABLE 3-continued

Other Compounds

| Compound | Characterization |
|---|---|
| 796 | MS (ESI) m/z 644.27 [M + 1]+; 1H-NMR (400 MHz, DMSO-d6) δ 13.60 (bs, 1H), 8.34 (s, 1H), 8.02 (s ,1H), 7.59 (dd, J = 2.52, 8.88 Hz, 1H), 7.41 (d, J = 2.52 Hz, 1H),7.39 (s, 1H), 7.35 (d, J = 8.96 Hz, 1H), 5.03 (s, 4H), 4.37 (t, J = 5.28 Hz, 2H), 4.23 (t, J = 6.32 Hz, 2H), 2.70 (s, 3H), 1.75 (s, 3H) |
| 797 | MS (ESI) m/z 644.0 [M − 1]−; 1H-NMR (400 MHz, DMSO-d6) ) δ 13.59 (bs, 1H), 8.39 (s, 1H), 7.90 (s ,1H), 7.59 (dd, J = 2.44, 8.88 Hz, 1H), 7.41 (d, J = 2.48 Hz, 1H), 7.38 (s, 1H), 7.33 (d, J = 8.96 Hz, 1H), 5.70 (d, J = 5.84 Hz, 1H), 4.57-4.56 (m, 1H), 4.38-4.32 (m, 4H), 4.18 (d, J = 4.2 Hz, 2H), 3.96-3.92 (m, 2H), 2.68 (s, 3H), 1.71 (s, 3H) |
| 801 | MS (ESI) m/z 686.30 [M + 1]+; 1H NMR (400 MHz, DMSO-d6) δ 13.58 (bs, 1H), 8.38 (s, 1H), 8.02 (s, 1H), 7.59 (dd, J = 2.60, 8.92 Hz, 1H), 7.42 (d, J = 2.56 Hz, 1H), 7.39 (s, 1H), 7.33 (d, J = 8.96 Hz, 1H), 4.37 (t, J = 4.64 Hz, 2H), 4.20 (t, J = 5.56 Hz, 2H), 3.23 (t, J = 5.16 Hz, 4H), 2.68 (s, 3H), 1.78 (s, 3H), 1.48 (t, J = 5.2 Hz, 4H), 0.99 (s, 6H) |
| 799 | MS (ESI) m/z 671.94 [M + 1]+; 1H NMR (400 MHz, DMSO-d6) δ 13.55 (bs, 1H), 8.42 (s, 1H), 7.69 (s, 1H), 7.58 (dd, J = 2.36, 8.84 Hz, 1H), 7.40 (d, J = 2.52 Hz, 1H), 7.39 (s, 1H), 7.35 (d, J = 9.00 Hz, 1H), 7.33 (t, J = 54.04 Hz, 1H), 4.92 (t, J = 12.44 Hz, 4H), 4.38 (t, J = 5.36 Hz, 2H), 4.20 (t, J = 5.80 Hz, 2H), 2.70 (s, 3H), 1.82 (s, 3H) |

TABLE 3-continued

Other Compounds

| Compound | Characterization |
|---|---|
| 800 | MS (ESI) m/z 672.15 [M + 1]+; 1H NMR (400 MHz, DMSO-d6) δ 8.38 (s, 1H), 8.03 (s, 1H), 7.59 (dd, J = 2.56, 8.88 Hz, 1H), 7.42 (d, J = 2.56 Hz, 1H), 7.39 (s, 1H), 7.33 (d, J = 8.96 Hz, 1H), 4.37 (t, J = 5.48 Hz, 2H), 4.20 (t, J = 4.32 Hz, 2H), 3.55 (d, J = 12.44 Hz, 2H), 2.90 (t, J = 11.90 Hz, 2H), 2.68 (s, 3H), 1.74-1.72 (m, 5H), 1.58 (bs, 1H), 1.31-1.23 (m, 2H), 0.97 (d, J = 6.44 Hz, 3H) |
| 804 | MS (ESI) m/z 681.96 [M + 1]+; 1H NMR (400 MHz, DMSO-d6) δ 13.56 (s, 1H), 8.59 (d, J = 3.56, 1H), 8.35 (s, 1H), 8.14 (s, 1H) 7.87 (t, J = 6.92 Hz, 1H), 7.59-7.53 (m, 2H), 7.42-7.40 (m, 2H), 7.38-7.33 (m, 2H), 5.66 (s, 2H), 4.39 (t, J = 4.36 Hz, 2H), 4.22 (t, J = 4.04 Hz, 2H), 2.70 (s, 3H), 1.75 (s, 3H) |
| 802 | MS (ESI) m/z 694.06 [M + 1]+; 1H NMR (400 MHz, DMSO-d6) δ 13.57 (bs, 1H), 8.33 (s, 1H), 8.10 (s, 1H), 7.58 (d, J = 7.08, 1H), 7.41-7.32 (m, 3H), 4.38 (t, J = 3.64 Hz, 2H), 4.21 (t, J = 5.68 Hz, 2H), 3.35 (t, J = 5.08 Hz, 4H), 2.68 (s, 3H), 2.14 (t, J = 13.4 Hz, 4H), 1.76 (s, 3H) |
| 803 | MS (ESI) m/z 725.97 [M + 1]+; 1H NMR (400 MHz, DMSO-d6) δ 8.38 (s, 1H), 8.06 (s, 1H), 7.58 (d, J = 8.60 Hz, 1H), 7.41 (s, 2H), 7.34 (d, J = 8.96 Hz, 1H), 4.38 (t, J = 5.16 Hz, 2H), 4.21 (t, J = 5.52 Hz, 2H), 3.62 (d, J = 12.52 Hz, 2H), 2.97 (t, J = 12.12 Hz, 2H), 2.70 (s, 3H), 1.94 (d, J = 11.96 Hz, 2H), 1.76 (s, 3H), 1.64-159 (m, 2H) |

TABLE 3-continued

| Other Compounds | |
|---|---|
| Compound | Characterization |
| 810 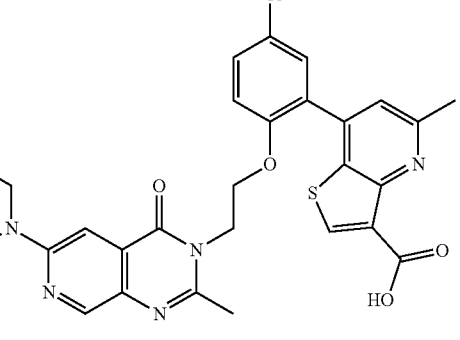 | MS (ESI) m/z 605.8 [M + 1]+; 1H NMR (400 MHz, DMSO-d6) δ 8.49 (d, J = 0.8 Hz, 1H), 8.44 (s, 1H), 7.58 (dd, J = 8.9, 2.7 Hz, 1H), 7.42 (d, J = 2.7 Hz, 1H), 7.36 (s, 1H), 7.34 (d, J = 9.0 Hz, 1H), 7.11 (d, J = 0.9 Hz, 1H), 4.48 (d, J = 12.6 Hz, 2H), 4.36 (t, J = 5.1 Hz, 2H), 4.21 (t, J = 5.1 Hz, 2H), 3.56 (bd, J = 11.0 Hz, 2H), 3.25-3.04 (m, 4H), 2.88 (d, J = 3.5 Hz, 3H), 2.69 (s, 3H), 1.83 (s, 3H) |
| 805 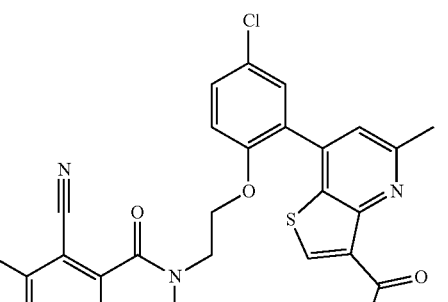 | MS (ESI) m/z 614.99 [M + 1]+; 1H NMR (400 MHz, DMSO-d6) δ 8.44 (s, 1H), 7.59 (dd, J = 8.80, 2.40 Hz, 1H), 7.43-7.41 (m, 3H), 7.36 (d, J = 8.80 Hz, 1H), 6.19 (s, 1H), 4.38 (t, J = 4.92 Hz, 2H), 4.22 (t, J = 6.00 Hz, 2H), 2.78-2.50 (m, 5H), 2.09-2.01 (m, 4H), 1.86 (s, 3H) |
| 806 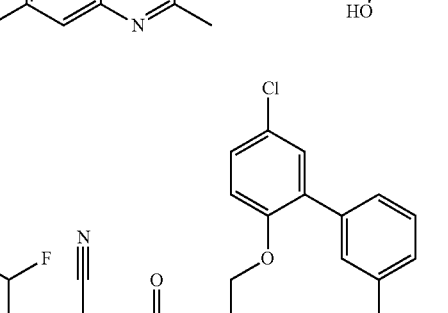 | MS (ESI) m/z 583.01 [M + 1]+; 1H NMR (400 MHz, DMSO-d6) δ 12.89 (bs, 1H), 8.07 (bs, 1H), 7.89 (d, J = 7.6 Hz, 1H), 7.85 (s, 1H), 7.52-7.12 (m, 6H), 4.35 (s, 4H), 4.13 (s, 2H), 2.56 (bs, 6H), 2.14 (s, 3H) |
| 841 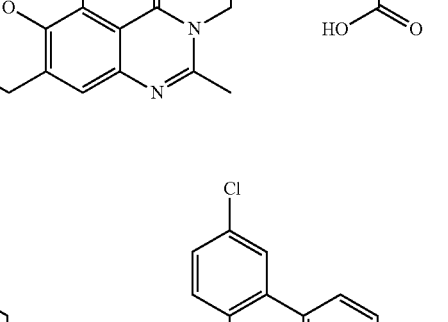 | MS (ESI) m/z = 580.3 [M + 1]+; 1H-NMR (400 MHz, d6-DMSO) δ/ppm = 9.74-9.62 (b, 1H), 8.84 (d, J = 4.7 Hz, 1H), 8.52 (s, 1H), 8.44 (s, 1H), 8.38 (s, 1H), 7.59 (dd, J = 8.9, 2.7 Hz, 1H), 7.46-7.43 (m, 2H), 7.32 (d, J = 8.9 Hz, 1H), 4.54 (t, J = 4.4 Hz, 2H), 4.34 (t, J = 4.9 Hz, 2H), 4.18 (t, J = 4.9 Hz, 2H), 3.61-3.56 (m, 2H), 2.98 (d, J = 4.4 Hz, 6H), 1.80 (s, 3H) |

TABLE 3-continued

Other Compounds

| Compound | Characterization |
|---|---|
| 811 | MS (ESI) m/z 604.8 [M + 1]+; 1H NMR (400 MHz, DMSO-d6) δ 8.44 (s, 1H), 7.57 (td, J = 8.9, 2.8 Hz, 2H), 7.42 (d, J = 2.7 Hz, 1H), 7.39-7.27 (m, 4H), 4.36 (t, J = 5.1 Hz, 2H), 4.22 (t, J = 5.0 Hz, 2H), 3.97 (d, J = 13.2 Hz, 2H), 3.57 (d, J = 12.3 Hz, 2H) 3.29-3.13 (m, 2H), 3.04 (t, J = 12.6 Hz, 2H), 2.89 (d, J = 4.0 Hz, 3H), 2.68 (s, 3H), 1.82 (s, 3H). |
| 812 | MS (ESI) m/z 643.6 [M + 1]+; 1H NMR (400 MHz, DMSO-d6) δ 7.70 (d, J = 9.0 Hz, 1H), 7.64-7.57 (m, 2H), 7.43-7.34 (m, 3H), 4.41 (t, J = 5.0 Hz, 2H), 4.24 (t, J = 5.1 Hz, 2H), 3.82-3.55 (m, 4H), 3.25 (bd, J = 9.1 Hz, 4H), 2.92 (s, 3H), 2.70 (s, 3H), 2.48 (s, 3H), 1.95 (s, 3H) |
| 877 | LCMS (ESI) m/z 671.1 [M + 1]+. 1H NMR (400 MHz, DMSO-d6) δ 8.62 (s, 1H), 8.18 (d, J = 8.8 Hz, 1H), 8.07 (s, 1H), 7.63 (s, 1H), 7.56 (dd, J = 8.9, 2.7 Hz, 1H), 7.41-7.28 (m, 2H), 4.37 (t, J = 5.0 Hz, 1H), 4.22 (d, J = 5.0 Hz, 1H), 3.38 (d, J = 12.0 Hz, 1H), 3.09 (d, J = 12.0 Hz, 1H), 2.67 (s, 2H), 2.17 (s, 2H), 1.94 (t, J = 11.8 Hz, 1H), 1.81 (s, 3H) |
| 849 | LCMS: 672.9 [M + H]+; 1H NMR (400 MHz, DMSO-d6) δ 9.79 (s, 1H), 8.48 (s, 1H), 8.41 (s, 1H), 7.60 (dd, J = 8.9, 2.7 Hz, 1H), 7.43 (d, J = 2.7 Hz, 1H), 7.40-7.31 (m, 2H), 4.41 (t, J = 5.1 Hz, 2H), 4.27 (t, J = 5.2 Hz, 2H), 3.37-3.12 (m, 6H), 2.93 (d, J = 2.7 Hz, 3H), 2.69 (s, 3H), 1.99 (s, 3H) |

TABLE 3-continued

Other Compounds

| Compound | Characterization |
|---|---|
| 858 | LCMS: 631.4 [M + H]+; 1H NMR (400 MHz, DMSO-d6) δ 9.77-9.57 (m, 1H), 8.79 (d, J = 4.8 Hz, 1H), 8.19 (s, 1H), 8.11 (s, 1H), 7.70 (s, 1H), 7.56 (dd, J = 8.9, 2.7 Hz, 1H), 7.41 (dd, J = 12.9, 3.7 Hz, 2H), 7.32 (d, J = 9.0 Hz, 1H), 4.36 (t, J = 5.1 Hz, 2H), 4.22 (t, J = 5.0 Hz, 2H), 3.34 (t, J = 6.2 Hz, 2H), 3.20 (dd, J = 11.3, 5.4 Hz, 2H), 2.88 (d, J = 4.3 Hz, 6H), 1.78 (s, 3H) |
| 896 | MS (ESI) m/z 668.21 [M + 1]+; 1H NMR (400 MHz, DMSO-d6) δ 8.34 (s, 1H), 7.74 (bs, 1H), 7.60 (dd, J = 2.4, 8.8 Hz, 1H), 7.49-7.13 (m, 4H), 4.39 (bs, 2H), 4.23 (bs, 2H), 3.58 (bs, 2H), 3.03-2.98 (m, 2H), 2.25 (bs, 6H), 1.78 (s, 3H), 1.37 (t, J = 7.6 Hz, 3H) |
| 880 | LCMS (ESI) m/z 643.1 [M + 1]+. 1H NMR (400 MHz, DMSO-d6) δ 8.77 (d, J = 4.8 Hz, 1H), 8.26 (s, 1H), 8.20 (s, 1H), 8.06 (s, 1H), 7.70 (s, 1H), 7.56 (dd, J = 8.9, 2.7 Hz, 1H), 7.45-7.37 (m, 2H), 7.32 (d, J = 9.0 Hz, 1H), 4.36 (t, J = 5.0 Hz, 2H), 4.21 (t, J = 5.1 Hz, 2H), 3.19 (s, 1H), 3.09 (d, J = 11.9 Hz, 2H), 1.94 (q, J = 13.5, 12.6 Hz, 4H), 1.79 (s, 3H) |
| 881 | LCMS (ESI) m/z 657.0 [M + 1]+; 1H NMR (400 MHz, DMSO-d6) δ 8.78 (d, J = 4.8 Hz, 1H), 8.24 (s, 1H), 8.02 (s, 1H), 7.70 (s, 1H), 7.56 (dd, J = 8.9, 2.7 Hz, 1H), 7.45-7.37 (m, 2H), 7.32 (d, J = 9.0 Hz, 1H), 4.36 (t, J = 5.0 Hz, 2H), 4.21 (t, J = 5.0 Hz, 2H), 3.21-3.11 (m, 3H), 2.82 (d, J = 4.6 Hz, 3H), 1.99 (s, 3H), 1.78 (s, 3H) |

TABLE 3-continued

Other Compounds

| Compound | Characterization |
|---|---|
| 920  | MS (ESI) m/z 662.15 [M + 1]+; 1H NMR (400 MHz, DMSO-d6) δ 8.38 (s, 1H), 7.74 (d, J = 8.72 Hz, 1H), 7.57 (dd, J = 2.12, 8.76 Hz, 1H), 7.41 (d, J = 2.08 Hz, 1H), 7.39 (bs, 1H), 7.34(d, J = 8.92 Hz, 1H), 4.37 (bs, 2H), 4.19 (bs, 2H), 3.60-3.57 (m, 1H), 3.47-3.41 (m, 1H), 2.69 (s, 3H), 2.10-2.05 (m, 2H), 1.89-1.86 (m, 2H), 1.79 (s, 3H), 1.25 (s, 3H), 1.12 (s, 3H) |
| 918  | MS (ESI) m/z 648.12 [M + 1]+; 1H NMR (400 MHz, DMSO-d6) δ 13.32 (bs, 1H), 8.37 (s, 1H), 7.62-7.57 (m, 2H), 7.42-7.33 (m, 3H), 4.41-4.37 (m, 4H), 4.18 (s, 2H), 2.69 (s, 3H), 2.25 (t, J = 7.52 Hz, 2H), 1.74 (s, 3H), 1.53 (s, 6H). |
| 919  | MS (ESI) m/z 684.04 [M + 1]+; 1H NMR (400 MHz, DMSO-d6) δ 8.40 (s, 1H), 7.68 (s, 1H), 7.59 (dd, J = 2.48, 8.84 Hz, 1H), 7.40 (bs, 2H), 7.35 (d, J = 8.92 Hz, 1H), 4.38 (t, J = 5.92 Hz, 2H), 4.22 (t, J = 6.52 Hz, 2H), 3.45 (t, J = 5.96 Hz, 4H), 2.71 (s, 3H), 2.21-2.16 (m, 4H), 1.86 (s, 3H) |
| 933  | MS (ESI) m/z 668.23 [M + 1]+; 1H NMR (400 MHz, DMSO-d6) δ 8.39 (s, 1H), 7.79 (s, 1H), 7.60 (dd, J = 8.84, 2.6 Hz, 1H), 7.51 (bs, 2H), 7.42 (s, 1H), 7.40 (d, J = 2.56 Hz, 1H), 7.37 (d, J = 9 Hz, 1H), 5.32 (d, J = 46.4 Hz, 2H), 4.41 (t, J = 3.04 Hz, 2H), 4.27 (t, J = 5.12 Hz, 2H), 2.72 (s, 3H), 2.64 (s, 6H), 1.96 (s, 3H) |

TABLE 3-continued
| | Other Compounds | |
|---|---|---|
| | Compound | Characterization |
| 921 | 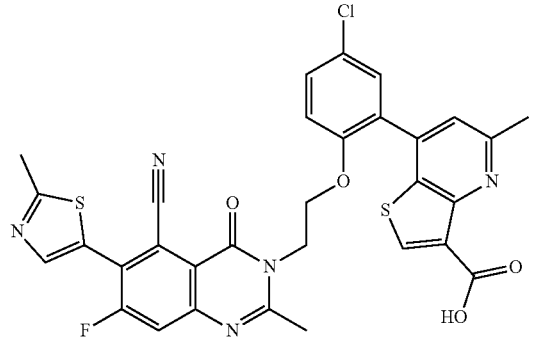 [SMILES: Cc1cc(-c2cc(Cl)ccc2OCCn2c(C)nc3cc(F)c(-c4cnc(C)s4)c(C#N)c3c2=O)c2scc(C(=O)O)c2n1] | MS (ESI) m/z 646.03 [M + 1]+; 1H NMR (400 MHz, DMSO-d6) δ 8.45 (s, 1H), 8.02 (s, 1H), 7.59 (dd, J = 2.56 Hz, J = 8.88 Hz, 1H), 7.55 (d, J = 10.16 Hz, 1H), 7.43 (s, 1H), 7.41 (d, J = 2.56 Hz, 1H), 7.36 (d, J = 8.96 Hz, 1H), 4.40 (t, J = 5.88 Hz, 2H), 4.25 (t, J = 4.44 Hz, 2H), 2.79 (s, 3H), 2.72 (s, 3H), 1.90 (s, 3H) |
| 932 | 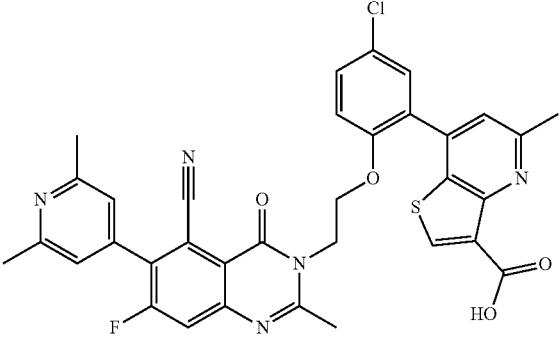 | MS (ESI) m/z 654.10 [M + 1]+; 1H NMR (400 MHz, DMSO-d6) δ 8.41 (s, 1H), 7.69-7.55 (m, 4H), 7.43 (s, 1H), 7.40 (d, J = 2.52 Hz, 1H), 7.32 (d, J = 8.96 Hz, 1H), 4.44-4.38 (m, 2H) 4.26 (t, J = 5.40 Hz, 2H), 2.73 (s, 3H), 2.65 (s, 6H), 1.93 (s, 3H) |
| 938 | 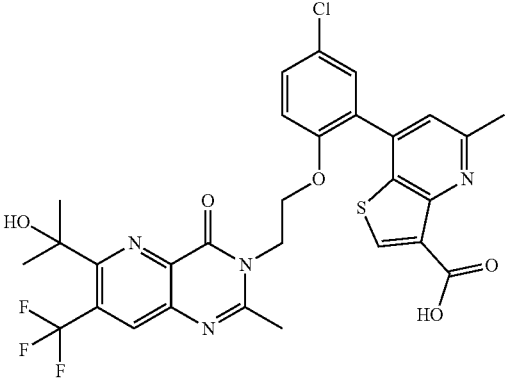 [SMILES: Cc1cc(-c2cc(Cl)ccc2OCCn2c(C)nc3cc(C(F)(F)F)c(C(C)(C)O)nc3c2=O)c2scc(C(=O)O)c2n1] | MS (ESI) m/z 633.05 [M + 1]+.1H NMR (400 MHz, DMSO-d6) δ 13.56 (s, 1H), 8.38 (s, 1H), 8.14 (s, 1H), 7.57 (bs, 1H), 7.42-7.33 (m, 3H), 5.36 (bs, 1H), 4.39 (bs, 2H), 4.23 (bs, 2H), 2.67 (s, 3H), 1.79 (s, 3H), 1.58 (s, 6H) |
| 935 | 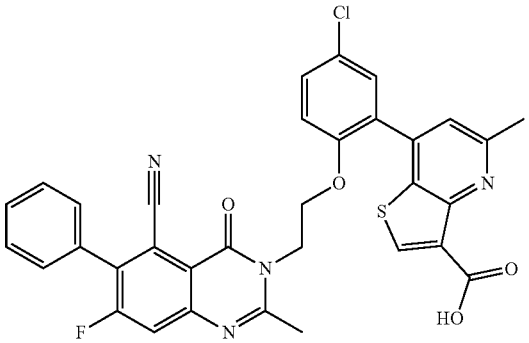 [SMILES: Cc1cc(-c2cc(Cl)ccc2OCCn2c(C)nc3cc(F)c(-c4ccccc4)c(C#N)c3c2=O)c2scc(C(=O)O)c2n1] | MS (ESI) m/z 625.09 [M + 1]+; 1H NMR (400 MHz, DMSO-d6) δ 13.59 (bs, 1H), 8.46 (s, 1H), 7.58-7.51 (m, 7H), 7.42 (s, 2H), 7.37 (d, J = 8.44 Hz, 1H), 4.40 (t, J = 3.72 Hz, 2H), 4.25 (t, J = 5.12 Hz, 2H), 2.72 (s, 3H), 1.85 (s, 3H). |

TABLE 3-continued

| | Other Compounds | |
|---|---|---|
| | Compound | Characterization |
| 936 | | MS (ESI) m/z 646.04 [M + 1]+, 1H NMR (400 MHz, DMSO-d6) δ 9.29 (s, 1H), 8.45 (s, 1H), 7.61-7.57 (m, 2H), 7.43 (bs, 2H), 7.33 (t, J = 19.2Hz, 1H), 4.40 (t, J = 5.68 Hz, 2H), 4.25 (d, J = 4.48 Hz, 2H), 2.72 (s, 3H), 2.30 (s, 3H), 1.85 (s, 3H). |
| 956 | | MS (ESI) m/z 636.11 [M + 1]+; 1H NMR (400 MHz, DMSO-d6) δ 13.47 (s, 1H), 8.38 (s, 1H), 7.73 (s, 1H), 7.58 (dd, J = 2.32 Hz, J = 8.80 Hz, 1H), 7.43 (d, J = 2.28 Hz, 1H), 7.40 (s, 1H), 7.35 (d, J = 8.96 Hz, 1H), 4.55 (s, 1H), 4.37 (t, J = 5.12 Hz, 2H), 4.19 (t, J = 6.04 Hz, 2H), 2.69 (s, 3H), 1.74 (s, 3H), 1.32 (s, 9H) |
| 939 | | MS (ESI) m/z 671.98 [M + 1]+; 1H NMR (400 MHz, DMSO-d6) δ 13.61 (bs, 1H), 9.19 (s, 1H), 8.35 (s, 1H), 7.58 (dd, J = 8.88, 2.56 Hz, 1H), 7.44 (s, 2H), 7.35 (d, J = 9.0 Hz, 1H), 4.40 (t, J = 5.0 Hz, 2H), 4.26 (t, J = 5.44 Hz, 2H), 2.72 (s, 3H), 2.20 (s, 3H), 1.81 (s, 3H) |
| 955 | | MS (ESI) m/z 650.12 [M + 1]+; 1H NMR (400 MHz, DMSO-d6) δ 13.54 (s, 1H), 8.34 (s, 1H), 7.72 (s, 1H), 7.58 (dd, J = 1.48 Hz, J = 7.80 Hz, 1H), 7.42 (d, J = 1.76 Hz, 1H), 7.40 (s, 1H), 7.50 (d, J = 8.88 Hz, 1H), 4.38 (t, J = 5.80, 2H), 4.20 (t, J = 4.32, 2H), 2.90 (s, 3H), 2.70 (s, 3H), 1.77 (s, 3H), 1.25 (s, 9H) |

TABLE 3-continued

Other Compounds

| Compound | Characterization |
|---|---|
| 959 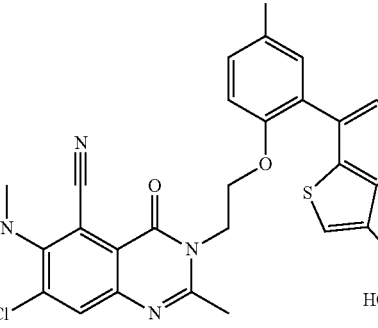 | MS (ESI) m/z 685.17 [M + 1]+; 1H NMR (400 MHz, DMSO-d6) δ 13.58 (s, 1H), 8.41 (s, 1H), 8.17 (s, 1H), 7.92 (s, 1H), 7.62-7.59 (m, 3H), 7.44 (s, 2H), 7.37 (d, J = 8.96 Hz, 1H), 4.40 (t, J = 2.76 Hz, 2H), 4.26 (t, J = 3.72 Hz, 2H), 3.44 (s, 3H), 2.73 (s, 3H), 2.57 (s, 3H), 1.85 (s, 3H) |
| 957 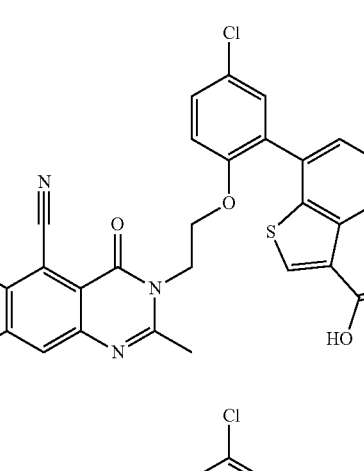 | MS (ESI) m/z 634.13 [M + 1]+; 1H NMR (400 MHz, DMSO-d6) δ 13.4 (s, 1H), 8.39 (s, 1H), 7.69 (s, 1H), 7.59 (dd, J = 8.84, 2.44 Hz, 1H), 7.42 (d, J = 2.4 Hz, 1H), 7.38 (s, 1H), 7.35 (d, J = 8.92 Hz, 1H), 4.37 (bs, 2H), 4.19 (bs, 2H), 3.08 (t, J = 10.36 Hz, 1H), 3.02 (s, 3H), 2.69 (s, 3H), 1.78 (s, 3H), 0.63 (d, J = 4.92 Hz, 2H), 0.37 (bs, 2H) |
| 958 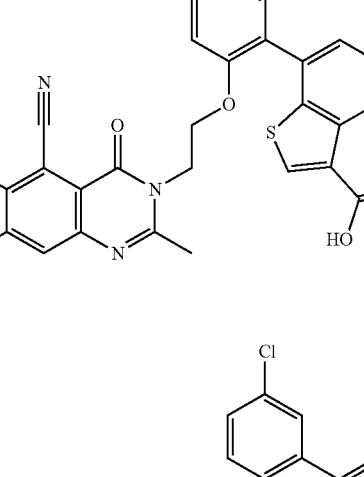 | MS (ESI) m/z 620.03 [M + 1]+; 1H NMR (400 MHz, DMSO-d6) δ 8.46 (s, 1H), 7.59 (d, J = 2.2 Hz, 1H), 7.54 (s, 1H), 7.43 (d, J = 2.4 Hz, 2H), 7.36 (d, J = 8.92 Hz, 1H), 6.66 (s, 1H), 4.36 (bs, 2H), 4.10 (bs, 2H), 3.16 (d, J = 6.84 Hz, 1H), 2.70 (s, 3H), 1.80 (s, 3H), 0.867-0.82 (m, 2H), 0.65-0.62 (m, 2H) |
| 962 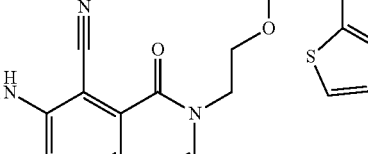 | MS (ESI) m/z 675.07 [M + 1]+; 1H NMR (400 MHz, DMSO-d6) δ 9.07 (s, 1H), 8.45 (s, 1H), 8.09 (s, 1H), 8.03 (d, J = 2.04, 1H), 7.85 (s, 1H), 7.59 (dd, J = 8.84 Hz, 2.36 Hz, 1H), 7.44 (s, 2H), 7.36 (d, J = 8.92 Hz, 1H), 7.04 (d, J = 11.12 Hz, 1H), 4.39 (t, J = 4.64 Hz, 2H), 4.22 (t, J = 4.48 Hz, 2H), 2.72 (s, 3H), 1.75 (s, 3H) |

TABLE 3-continued

| | Other Compounds | |
|---|---|---|
| | Compound | Characterization |
| 960 | 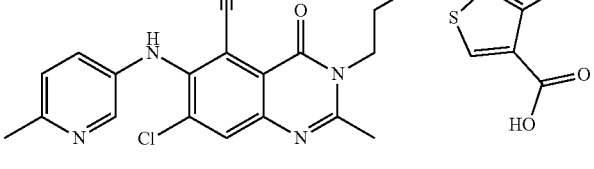 | MS (ESI) m/z 671.27 [M + 1]+; 1H NMR (400 MHz, DMSO-d6) δ 9.25 (s, 1H), 8.45 (s, 1H), 8.20 (d, J = 2.20, 1H), 7.86 (s, 1H), 7.69 (s, 1H), 7.60 (dd, J = 2.32 Hz, J = 8.72 Hz, 2H), 7.43-7.42 (m, 2H), 7.36 (d, J = 8.92 Hz, 1H), 4.39 (t, J = 5.56 Hz, 2H), 4.24 (t, J = 3.56 Hz, 2H), 2.71 (s, 3H), 2.55 (s, 3H), 1.81 (s, 3H) |
| 961 | 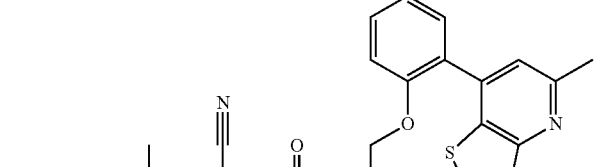 | MS (ESI) m/z 689.15 [M + 1]+; 1H NMR (400 MHz, DMSO-d6) δ 8.43 (s, 1H), 8.01 (s, 1H), 7.91 (s, 1H), 7.79 (s, 1H), 7.59 (d, J = 8.80 Hz, 1H), 7.44 (s, 2H), 7.36 (d, J = 8.80 Hz, 1H), 7.04 (d, J = 12.04 Hz, 1H), 4.39 (s, 2H), 4.25 (s, 2H), 3.39 (s, 3H), 2.73 (s, 3H), 1.80 (s, 3H) |
| 1001 | 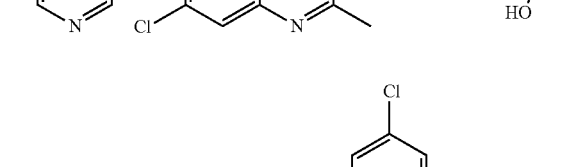 | MS (ESI) m/z [M + 1]+, 1H NMR (400 MHz, DMSO-d6) δ 9.08 (s, 1H), 8.64 (s, 1H), 8.38 (s, 1H), 8.02 (d, J = 6.96 Hz,1H), 7.59 (d, J = 6.76 Hz, 1H), 7.39-7.35 (m, 3H), 6.18 (s, 1H), 4.37 (s, 2H), 4.22 (s, 2H), 2.68 (s, 3H), 2.30 (s, 3H), 1.78 (s, 3H), 1.05 (t, J = 7.16 Hz, 1H). |
| 990 | 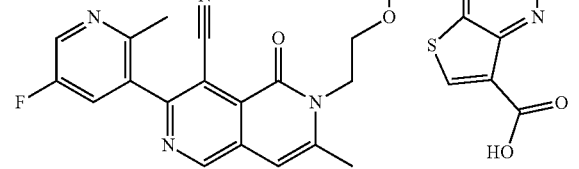 | MS (ESI) m/z 721.31 [M + 1]+; 1H NMR (400 MHz, DMSO-d6) δ 13.63 (bs, 1H), 9.18 (s, 1H), 9.13 (s, 1H), 8.46 (s, 1H), 8.32 (s, 1H), 7.58 (dd, J = 2.52, 8.88 Hz, 1H), 7.44-7.43 (m, 2H), 7.34 (d, J = 8.96 Hz, 1H), 4.39 (t, J = 5.00 Hz, 2H), 4.26 (t, J = 4.36 Hz, 2H), 2.70 (s, 3H), 1.82 (s, 3H) |

TABLE 3-continued

| | Other Compounds | |
|---|---|---|
| | Compound | Characterization |
| 1000 | | MS (ESI) m/z [M + 1]+; 1H NMR (400 MHz, DMSO-d6) δ 9.12 (s, 1H), 8.49 (s, 1H), 7.86 (t, J = 9.12 Hz, 1H), 7.74-7.66 (m, 2H), 7.54-7.38 (m, 3H), 6.21 (s, 1H), 4.40 (t, J = 4.48, 2H), 4.24 (t, J = 4.64, 2H), 2.69 (s, 3H), 2.54 (s, 3H), 1.69 (s, 3H). |
| 1005 | | MS (ESI) m/z 562.18 [M + 1]+; 1H NMR (400 MHz, DMSO-d6) δ 13.64 (bs, 1H), 8.58 (s, 1H), 8.56 (s, 1H), 7.62-7.56 (m, 1H), 7.43-.7.39 (m, 2H), 7.34 (d, J = 8.92 Hz, 1H), 4.35 (t, J = 4.68 Hz, 2H), 4.41 (t, J = 4.48 Hz, 2H), 3.70 (s, 3H), 2.72 (s, 3H), 1.71 (s, 3H) |
| 1002 | | MS (ESI) m/z 574 [M + 1]+; 1H NMR (400 MHz, DMSO-d6) δ 13.52 (bs, 1H), 8.57 (s, 1H), 8.49 (s, 1H), 7.57 (d, J = 8.52 Hz, 1H), 7.39-7.33 (m, 3H), 5.91 (s, 1H), 4.37 (t, J = 5.08 Hz, 2H), 4.16 (t, J = 4.04 Hz, 2H), 3.21 (s, 6H), 2.70 (s, 3H), 1.63 (s, 3H) |
| 1003 | | MS (ESI) m/z 586.13 [M + 1]+; 1H NMR (400 MHz, DMSO-d6) δ 13.49 (bs, 1H), 8.56 (s, 1H), 8.48 (s, 1H), 7.56 (d, J = 8.84 Hz, 1H), 7.39 (s, 1H), 7.40-7.33 (m, 2H), 5.89 (s, 1H), 4.37-4.32 (m, 6H), 4.15 (t, J = 5.36 Hz, 2H), 2.69 (s, 3H), 1.69 (s, 3H), 2.38-2.32 (m, 2H) |

TABLE 3-continued

| | Other Compounds | |
|---|---|---|
| | Compound | Characterization |
| 1018 | (structure) | MS (ESI) m/z 667.06 [M + 1]+; 1H NMR (400 MHz, DMSO-d6) δ 13.58 (bs, 1H), 8.95 (s, 1H), 8.68 (s, 1H), 8.36 (s, 1H), 8.32 (s, 1H), 7.58 (dd, J = 8.92, 2.40 Hz, 1H), 7.42 (s, 2H), 7.35 (d, J = 8.92 Hz, 1H), 4.40 (s, 2H), 4.27 (s, 2H), 2.70 (s, 3H), 2.62 (s, 3H), 1.81 (s, 3H) |
| 1006 | (structure) | MS (ESI) m/z 632.03 [M + 1]+; 1H NMR (400 MHz, DMSO-d6) δ 8.51 (s, 1H), 8.48 (s, 1H), 7.91 (s, 1H), 7.63-7.56 (m, 2H), 7.46-7.40 (m, 2H), 7.35 (d, J = 8.96 Hz, 1H), 4.39 (t, J = 5.96 Hz, 2H), 4.24 (t, J = 5.44 Hz, 2H), 2.71 (s, 3H), 1.81 (s, 3H) |
| 1007 | (structure) | MS (ESI) m/z 591.10 [M + 1]+; 1H NMR (400 MHz, DMSO-d6) δ 13.58 (bs, 1H), 8.69 (s, 1H), 8.46 (s, 1H), 7.59 (dd, J = 2.52, 8.64 Hz, 1H), 7.43-7.42 (m, 3H), 7.34 (s, 1H), 7.32 (s, 1H), 4.34 (t, J = 5.04 Hz, 2H), 4.15 (t, J = 4.68 Hz, 2H), 2.70 (s, 3H), 1.69 (s, 3H) |
| 1021 | (structure) | MS (ESI) m/z 721.05 [M − 1]−; 1H NMR (400 MHz, DMSO-d6) δ 9.51 (s, 1H), 9.41 (s, 1H), 8.39 (s, 1H), 8.36 (s, 1H), 7.59 (dd, J = 2.0, 8.8 Hz, 1H), 7.42 (s, 1H), 7.36 (d, J = 8.8 Hz, 1H, 4.41 (bs, 2H), 4.29 (bs, 2H), 2.69 (s, 3H), 1.83 (s, 3H) |

TABLE 3-continued

Other Compounds

| Compound | Characterization |
|---|---|
| 1019 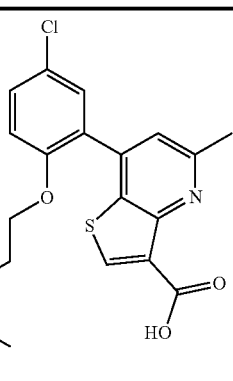 | MS (ESI) m/z 667.16 [M + 1]+; 1H NMR (400 MHz, DMSO-d6) 13.60 (s,1H), 8.72 (d, J = 2.36 Hz, 1H), 8.61 (s, 1H), 8.39 (s, 1H), 8.37 (s, 1H), 7.58 (dd, J = 8.76, 2.36 Hz, 1H), 7.47-7.40 (m, 2H), 7.35 (d, J = 8.96 Hz, 1H), 4.40 (t, J = 4.3 Hz, 2H), 4.26 (t, J = 4.8 Hz, 2H), 2.71 (s, 3H), 2.35 (s, 3H), 1.82 (s, 3H) |
| 1020 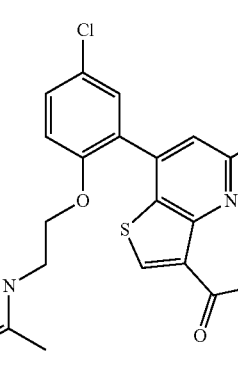 | MS (ESI) m/z 703.10 [M + 1]+; 1H NMR (400 MHz, DMSO-d6) δ 13.56 (bs, 1H), 9.24 (s, 1H), 9.12 (s, 1H), 8.37 (d, J = 7.00 Hz, 2H), 7.60 (dd, J = 2.44, 8.88 Hz, 1H), 7.42-7.13 (m, 4H), 4.42 (t, J = 5.68 Hz, 2H), 4.28 (t, J = 5.16 Hz, 2H), 2.71 (s, 3H) 1.84 (s, 3H) |
| 1024 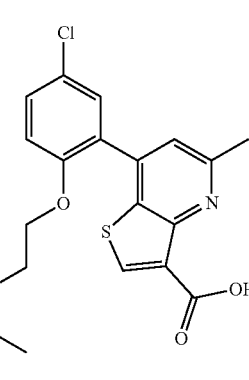 | MS (ESI) m/z 701.10 [M + 1]+; 1H NMR (400 MHz, DMSO-d6) δ 8.74 (s, 1H), 8.39 (s, 1H), 8.35 (s, 1H), 7.58 (dd, J = 8.9, 2.3 Hz, 1H), 7.44 (s, 2H), 7.34 (d, J = 8.9 Hz, 1H), 4.39 (t, J = 9.5 Hz, 2H), 4.26 (t, J = 4.5 Hz, 2H), 3.21 (s, 3H), 2.64 (s, 3H), 1.82 (s, 3H) |
| 1022 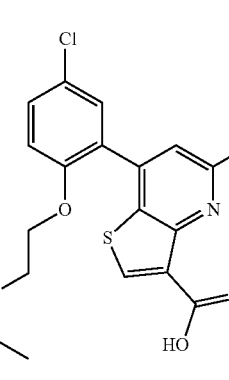 | MS (ESI) m/z 681.06. [M + 1]+; 1H NMR (400 MHz, DMSO-d6) δ 13.62 (bs, 1H), 8.59 (s, 1H), 8.40 (s, 1H), 8.35 (s, 1H), 7.58 (dd, J = 2.48, 8.88 Hz, 1H), 7.43 (d, J = 2.5 Hz, 1H),7.43 (s, 1H), 7.34 (d, J = 8.96 Hz, 1H), 4.39 (t, J = 4.39 Hz, 2H), 4.26 (t, J = 4.12 Hz, 2H), 2.71 (s, 6H), 2.29 (s, 3H), 1.81 (s, 1H) |

TABLE 3-continued

| Compound | | Characterization |
|---|---|---|
| 1023 | (structure) | MS (ESI) m/z 681.21 [M + 1]+; 1H NMR (400 MHz, DMSO-d6) δ 8.48 (s, 1H), 8.39 (s, 1H), 8.34 (s, 1H), 7.58 (dd, J = 8.88, 2.56 Hz, 1H), 7.44 (d, J = 2.84 Hz, 2H), 7.35 (d, J = 8.92 Hz, 1H), 4.39 (t, J = 9.4 Hz, 2H), 4.26 (t, J = 8.32 Hz, 2H), 2.71 (s, 3H), 2.57 (s, 3H), 2.30 (s, 3H), 1.81 (s, 3H) |
| 1048 | (structure) | MS (ESI) m/z 621.09 [M + 1]+; 1H NMR (400 MHz, DMSO-d6) ) δ 13.49 (bs, 1H), 8.34 (s, 1H), 7.76 (s, 1H), 7.65-7.34 (m, 5H), 4.39 (t, J = 5.8 Hz, 2H), 4.23 (t, J = 5.2 Hz, 2H), 2.69 (s, 3H), 2.20-2.09 (m, 1H), 1.85 (s, 3H), 1.25-1.18 (m, 2H), 0.97-0.88 (m, 2H) |
| 1040 | (structure) | MS (ESI) m/z 650.13 [M + 1]+; 1H NMR (400 MHz, DMSO-d6) δ 13.54 (bs, 1H), 8.34 (s, 1H), 7.59-7.52 (m, 1H), 7.50-7.45 (m, 5H), 7.40 (bs, 2H), 7.35 (d, J = 8.92 Hz, 1H), 6.99 (s, 1H), 4.36 (t, J = 5.24 Hz, 2H), 4.18 (t, J = 4.84 Hz, 2H), 2.71 (s, 3H), 2.70 (s, 6H), 1.79 (s, 3H) |
| 1047 | (structure) | MS (ESI) m/z 619.12 [M + 1]+; 1H NMR (400 MHz, DMSO-d6) δ 13.50 (s, 1H), 8.37 (s, 1H), 7.66 (s, 1H), 7.57 (dd, J = 2.32 Hz, J = 6.64 Hz, 1H), 7.41-7.34 (m, 3H), 4.37 (bs, 2H), 4.33-4.28 (m, 1H), 4.22 (bs, 2H), 2.81-2.73 (m, 2H), 2.69 (s, 3H), 2.50-2.48 (m, 2H), 2.10-2.03 (m, 1H), 2.01-1.84 (m, 1H), 1.84 (s, 3H) |

TABLE 3-continued

Other Compounds

| Compound | Characterization |
|---|---|
| 1061 | MS (ESI) m/z 672.07 [M + 1]+; 1H NMR (400 MHz, DMSO-d6) δ 13.50 (bs, 1H), 8.44 (s, 1H), 8.30 (s, 1H), 7.88 (dd, J = 8.56, 2.16 Hz, 1H), 7.87 (s, 1H), 7.59 (dd, J = 8.88, 2.16 Hz, 1H), 7.42 (s, 2H), 7.36 (d, J = 8.88 Hz, 1H), 7.03 (d, J = 8.52 Hz, 1H), 4.40 (t, J = 5.56 Hz, 2H), 4.25 (t, J = 5.20 Hz, 2H), 3.95 (s, 3H), 2.71 (s, 3H), 1.89 (s, 3H) |
| 1050 | MS (ESI) m/z 605.09 [M + 1]+; 1H NMR (400 MHz, DMSO-d6) δ 13.51 (bs, 1H), 8.34 (s, 1H), 7.68 (s, 1H), 7.58 (dd, J = 8.64, 1.96 Hz, 1H), 7.44-7.38 (m, 2H), 7.35 (d, J = 8.92 Hz, 1H), 4.37 (s, 2H), 4.21 (s, 2H), 2.69 (s, 3H), 2.08-2.03 (m, 1H), 1.84 (s, 3H), 1.26-1.20 (m, 2H), 0.92-0.86 (m, 2H) |
| 1054 | MS (ESI) m/z 650.08 [M + 1]+; 1H NMR (400 MHz, DMSO-d6) δ 13.01 (s, 1H), 8.42 (s, 1H), 7.65 (s, 1H), 7.59 (dd, J = 10.96 Hz, 8.88 Hz, 1H), 7.33-7.41 (m, 3H), 5.02 (s, 1H), 4.44 (s, 1H), 4.36 (bs, 2H), 4.19 (bs, 2H), 3.74-3.79 (m, 2H), 3.43-3.47 (m, 1H), 3.33 (s, 1H), 2.69 (s, 3H), 2.07-2.15 (m, 1H), 1.75-1.86 (m, 1H), 1.80 (s, 3H) |
| 1083 | MS (ESI) m/z 686.21 [M + 1]+; 1H NMR (400 MHz, DMSO-d6) δ 8.23 (s, 1H), 7.98 (s, 1H), 7.67 (s, 1H), 7.59 (dd, J = 2.52 Hz, J = 8.84 Hz, 1H), 7.43 (bs, 2H), 7.35 (d, J = 8.96 Hz, 1H), 4.39 (t, J = 6.20 Hz, 2H), 4.23 (t, J = 6.32 Hz, 2H), 3.56 (d, J = 9.80 Hz, 2H), 3.25-3.13 (m, 6H), 2.99 (q, J = 7.52 Hz, J = 15.04 Hz, 2H), 2.93 (bs, 3H), 1.79 (s, 3H), 1.35 (t, 7.56 Hz, 3H) |

TABLE 3-continued

Other Compounds

| Compound | Characterization |
|---|---|
| 1077 | MS (ESI) m/z, 580.08 [M + 1]+; 1H NMR (400 MHz, DMSO-d6) δ 13.85 (s, 1H), 8.50 (s, 1H), 7.58 (dd, J = 2.56, 11.44 Hz, 1H), 7.48 (d, J = 1.76 Hz, 1H), 7.42-7.41 (m, 2H), 7.34 (d, J = 8.96 Hz, 1H), 7.23 (d, J = 2.56 Hz, 1H), 7.18 (bs, 2H), 4.35 (t, J = 5.28 Hz, 2H), 4.24 (t, J = 4.76 Hz, 2H), 2.99 (q, J = 7.48 Hz, 2H), 1.34 (t, J = 7.52 Hz, 3H) |
| 1078 | MS (ESI) m/z 581.07 [M + 1]+; 1H NMR (400 MHz, DMSO-d6) δ 13.75 (bs, 1H), 8.53 (s, 1H), 7.72 (d, J = 1.60 Hz, 1H), 7.58 (dd, J = 2.56, 8.88 Hz, 1H), 7.46 (bs, 1H), 7.42 (d, J = 2.56 Hz, 2H), 7.34 (d, J = 8.96 Hz, 1H), 7.30 (d, J = 1.76 Hz, 1H), 4.35 (t, J = 5.16 Hz, 2H), 4.10 (t, J = 5.04 Hz, 2H), 2.99 (q, J = 7.48 Hz, 2H), 1.34 (t, J = 7.56 Hz, 3H) |
| 1090b | MS (ESI) m/z 689.25 [M + 1]+; 1H NMR (400 MHz, DMSO-d6) δ 14.28 (bs, 1H), 7.58 (dd, J = 2.28, 8.84 Hz, 1H), 7.41 (bs, 1H), 7.38 (d, J = 2.36 Hz, 1H), 7.34 (d, J = 8.92 Hz, 1H), 6.99 (d, J = 8.28 Hz, 1H), 4.38 (t, J = 5.04 Hz, 2H), 4.19 (t, J = 4.68 Hz, 2H), 3.55 (d, J = 11.64 Hz, 2H), 2.79-2.73 (m, 2H), 2.70 (s, 3H), 2.39 (s, 3H), 2.37-2.34 (m, 2H), 2.23 (s, 3H), 1.86 (s, 3H), 1.10 (d, J = 6.00 Hz, 6H) |
| 1084 | MS (ESI) m/z 687.16 [M + 1]+; 1H NMR (400 MHz, DMSO-d6) δ 13.72 (bs, 1H), 8.30 (s, 1H), 8.10 (s, 1H), 7.59 (dd, J = 2.5, 9.1 Hz, 1H), 7.45 (s, 2H), 7.34 (d, J = 8.9 Hz, 1H), 4.38 (bs, 2H), 4.21 (bs, 2H), 3.59 (bs, 4H), 3.25 (bs, 4H), 3.03-2.97 (m, 2H), 2.90 (s, 3H), 1.72 (s, 3H), 1.34 (t, J = 7.52 Hz, 3H) |

TABLE 3-continued

| Compound | Characterization |
|---|---|
| 1090a | MS (ESI) m/z 705.26 [M + 1]+; 1H NMR (400 MHz, DMSO-d6) δ 14.28 (bs, 1H), 7.60 (bs, 1H), 7.58 (dd, J = 2.64, 8.96 Hz, 1H), 7.39 (bs, 1H), 7.38 (d, J = 2.60 Hz, 1H), 7.35 (d, J = 9.00 Hz, 1H), 4.37 (t, J = 4.56 Hz, 2H), 4.23 (t, J = 4.16 Hz, 2H), 3.17-3.12 (m, 5H), 2.70 (s, 3H), 2.43-2.38 (m, 4H), 2.22 (s, 3H), 1.96 (s, 3H), 1.03 (d, J = 6.08 Hz, 6H) |
| 1096 | MS (ESI) m/z 687.25 [M + 1]+; 1H NMR (400 MHz, DMSO-d6) δ 14.36 (bs, 1H), 8.00 (s, 1H), 8.32 (s, 1H), 7.60 (dd, J = 2.20, 8.68 Hz, 1H), 7.41 (s, 1H), 7.34 (d, J = 8.92 Hz, 1H), 4.40 (t, J = 4.32 Hz, 2H), 4.20 (t, J = 3.92 Hz, 2H), 3.23 (bs, 4H), 2.69 (s, 3H), 2.49 (bs, 4H), 2.35 (s, 3H), 2.23 (s, 3H), 1.77 (s, 3H) |
| 1094 | MS (ESI) m/z 675.07 [M + 1]+; 1H NMR (400 MHz, DMSO-d6) δ 13.57 (s, 1H), 8.38 (s, 1H), 7.58 (s, 2H), 7.41-7.33 (m, 3H), 4.36 (s, 2H), 4.21 (s, 2H), 3.55 (bs, 4H), 3.24 (bs, 2H), 3.06 (bs, 2H), 2.91 (s, 3H), 2.69 (s, 3H), 1.82 (s, 3H) |
| 1095 | MS (ESI) m/z 711.15 [M + 1]+; 1H NMR (400 MHz, DMSO-d6) δ 8.42 (s, 1H), 7.57 (dd, J = 8.8, 2.5 Hz, 1H), 7.45-7.41 (m, 2H), 7.36-7.32 (m, 2H), 7.12 (d, J = 13.2 Hz, 1H), 4.35 (t, J = 9.2 Hz, 2H), 4.20 (t, J = 9.3 Hz, 2H), 3.14 (bs, 4H), 2.69 (s, 3H), 2.50 (bs, 4H), 1.79 (s, 3H), 1.23 (s, 3H) |

TABLE 3-continued

Other Compounds

| Compound | Characterization |
|---|---|
| 1138 | MS (ESI) m/z 679.1 [M + 1]+; 1H NMR (400 MHz, DMSO-d6) δ 12.98 (s, 1H), 8.41 (s, 1H), 7.88 (d, J = 8.5 Hz, 1H), 7.67 (d, J = 8.5 Hz, 1H), 7.61 (dd, J = 8.9, 2.7 Hz, 1H), 7.46-7.37 (m, 3H), 4.42 (t, J = 5.1 Hz, 2H), 4.25 (t, J = 5.1 Hz, 2H), 3.56 (s, 3H), 3.45-3.37 (m, 2H), 3.37-3.29 (m, 2H), 2.91 (d, J = 4.5 Hz, 6H), 2.70 (s, 3H), 1.91 (s, 3H) |
| 1098 | MS (ESI) m/z 642.01 [M + 1]+; 1H NMR (400 MHz, DMSO-d6) δ 8.84 (s, 1H), 8.73 (d, J = 3.7 Hz, 1H), 8.24 (s, 1H), 8.13 (d, J = 7.8 Hz 1H), 7.75 (s, 1H), 7.63-7.57 (m, 2H), 7.40-7.35 (m, 3H), 4.42 (t, J = 5.1 Hz, 2H), 4.27 (t, J = 4.8 Hz, 2H), 2.69 (s, 3H), 1.83 (s, 3H) |
| 1114 | MS (ESI) m/z 683.3 [M + 1]+; 1H NMR (400 MHz, Chloroform-d) δ 8.79 (d, J = 4.9 Hz, 1H), 8.66 (d, J = 0.9 Hz, 1H), 8.30 (s, 1H), 7.48 (dd, J = 8.9, 2.6 Hz, 1H), 7.32 (d, J = 4.9 Hz, 1H), 7.24 (d, J = 2.6 Hz, 1H), 7.07 (d, J = 8.9 Hz, 1H), 6.87 (d, J = 0.9 Hz, 1H), 5.23-5.13 (m, 1H), 4.37 (t, J = 5.0 Hz, 2H), 4.28 (t, J = 5.0 Hz, 2H), 3.88 (d, J = 12.0 Hz, 2H), 3.57 (t, J = 14.3 Hz, 2H), 3.34-3.24 (m, 2H), 2.97 (s, 3H), 2.51-2.36 (m, 2H), 2.08-2.02 (m, 5H), 1.80 (t, J = 19.0 Hz, 3H) |
| 1155 | MS (ESI) m/z 735.80 [M + 1]; 1H NMR (400 MHz, DMSO-d6) δ 12.50 (bs, 1H), 8.87 (d, J = 4.7 Hz, 1H), 8.47 (s, 1H), 8.12 (s, 1H), 7.60 (dd, J = 2.4, 8.9 Hz, 1H), 7.53 (d, J = 4.7 Hz, 1H), 7.45 (d, J = 2.4 Hz, 1H), 7.35 (d, J = 8.9 Hz, 1H), 4.39 (t, J = 5.1 Hz, 2H), 4.20 (t, J = 4.5 Hz, 2H), 3.51 (s, 3H), 3.28 (bs, 4H), 2.55 (bs, 4H), 2.28 (s, 3H), 1.69 (s, 3H) |

TABLE 3-continued

Other Compounds

| Compound | Characterization |
|---|---|
| 1147 | MS (ESI) m/z 460.1 [M + 1]+; 1H NMR (300 MHz, DMSO-d6) δ 12.95 (s, 1H), 8.00-7.82 (m, 5H), 7.56-7.49 (m, 1H), 7.45-7.36 (m, 2H), 7.29 (d, J = 2.7 Hz, 1H), 7.21 (d, J = 8.9 Hz, 1H), 4.34 (s, 4H), 2.19 (s, 3H) |
| 1150 | MS (ESI) m/z 721.29 [M + 1]+; 1H NMR (400 MHz, DMSO-d6) δ 14.35 (s, 1H), 9.78 (s, 1H), 8.12 (s, 1H), 7.62 (dd, J = 8.8, 2.5 Hz, 1H), 7.45-7.42 (m, 2H), 7.38 (d, 1H), 4.41 (t, J = 4.5 Hz, 2H), 4.26 (t, J = 8.9 Hz, 2H), 3.90 (m, 2H), 3.57 (s, 5H), 3.23 (m, 4H), 2.90 (s, 3H), 2.72 (s, 3H), 2.47 (s, 3H), 1.99 (s, 3H) |
| 1205 | MS (ESI) m/z 661.24 [M + 1]+. 1H NMR (400 MHz, DMSO-d6) δ 14.29 (bs, 1H), 7.58 (d, J = 6.8 Hz, 1H), 7.44-7.34 (m, 4H), 4.38 (t, J = 4.8 Hz, 2H), 4.26 (t, J = 5.2 Hz, 2H), 2.68 (s, 3H), 2.54 (s, 3H), 2.52-2.45 (m, 8H), 2.24 (s, 3H), 1.98 (s, 3H) |
| 1193 | MS (ESI) m/z 639.26 [M + 1]+; 1H NMR (400 MHz, DMSO-d6) δ 8.68 (s, 1H), 7.59-7.58 (m, 6H), 7.42-7.36 (m, 3H), 4.41 (t, J = 4.0 Hz, 2H), 4.25 (t, J = 4.0, Hz, 2H), 3.20 (s, 3H), 2.66 (s, 3H), 2.03 (s, 3H) |

TABLE 3-continued

Other Compounds

| | Compound | Characterization |
|---|---|---|
| 1201 | | MS (ESI) m/z 719.23 [M + 1]+; 1H NMR (400 MHz, DMSO-d6) δ 14.24 (bs, 1H), 7.65 (s, 1H), 7.57 (d, J = 7.2 Hz, 1H), 7.37-7.33 (m, 3H), 4.38 (s, 2H), 4.26 (s, 2H), 2.68 (s, 6H), 2.5-2.47 (m, 8H), 1.93 (s, 3H), 1.06 (s, 9H) |
| 1210 | | MS (ESI) m/z 672.17 [M + 1]+; 1H NMR (400 MHz, DMSO-d6), δ 8.79 (d, J = 4.8 Hz, 1H), 8.02 (s, 1H), 7.68 (s, 1H), 7.59 (dd, J = 9.2 Hz, 2.4 Hz, 1H), 7.51 (d, J = 4.8 Hz, 1H), 7.42 (d, J = 2.4 Hz, 1H), 7.35 (d, J = 9.2 Hz, 1H), 4.40 (bs, 2H), 4.24 (bs, 2H), 3.56-3.54 (m, 2H), 3.20-3.12 (m, 6H), 2.93 (s, 3H), 2.23 (s, 3H), 1.78 (s, 3H) |
| 1208 | | MS (ESI) m/z 673.30 [M + 1]+; 1H NMR (400 MHz, DMSO-d6) δ 14.41 (bs, 1H), 7.59 (dd, J = 8.8, 2.4 Hz, 1H), 7.41 (s, 1H), 7.40-7.32 (m, 2H), 6.96 (s, 1H), 4.39 (s, 2H), 4.19 (s, 2H), 4.00 (s, 3H), 3.26 (s, 4H), 2.71 (s, 3H), 2.55-2.45 (merged, 4H), 2.40 (s, 3H), 2.28 (s, 3H), 1.91 (s, 3H) |
| 1209 | | MS (ESI) m/z 682.30 [M + 1]+; 1H NMR (400 MHz, DMSO-d6) δ 8.43 (s, 1H), 7.96 (s, 1H), 7.93 (s, 1H), 7.58 (dd, J = 8.8, 2.4 Hz, 1H), 7.42-7.34 (m, 3H), 4.39 (s, 2H), 4.22 (s, 2H), 3.52 (s, 3H), 3.04 (s, 4H), 2.68 (s, 3H), 2.50 (merged, 4H), 2.26 (s, 3H), 1.87 (s, 3H) |

TABLE 3-continued

Other Compounds

| Compound | Characterization |
|---|---|
| 1240 | MS (ESI) m/z 682.34 [M + 1]+; 1H NMR (400 MHz, DMSO-d6) δ 13.14 (bs, 1H), 8.82 (d, J = 4.8, 1H), 8.32 (s, 1H), 8.05 (s, 1H), 7.57 (d, J = 6.4 Hz, 1H), 7.42 (d, J = 5.2 Hz, 2H), 7.35 (d, J = 9.2 Hz, 1H), 6.07 (s, 1H), 4.39 (s, 2H), 4.19 (s, 2H), 3.67 (bs, 4H), 2.87 (bs, 4H), 2.23 (s, 3H), 1.61 (s, 3H) |
| 1211 | MS (ESI) m/z 656.26 [M + 1]+; 1H NMR (400 MHz, DMSO-d6) δ 13.24 (s, 1H), 8.27 (s, 1H), 8.08 (s, 1H), 7.56 (dd, J = 8.4 Hz, 2.4 Hz, 1H), 7.40 (s, 1H), 7.33 (s, 1H), 7.30 (d, J = 14.8 Hz, 1H), 7.25 (s, 1H), 4.53-3.38 (m, 4H), 4.25-3.16 (m, 4H), 3.01-2.98 (m, 2H), 2.89 (s, 3H), 2.86 (s, 3H), 2.69-2.60 (m, 2H), 2.26 (s, 3H) |
| 1230 | MS (ESI) m/z 660.24 [M + 2]+; 1H NMR (400 MHz, DMSO-d6), δ 8.1 (d, J = 4.8 Hz, 1H), 8.30 (s, 1H), 7.95 (s, 1H), 7.70 (s, 1H), 7.58 (dd, J = 8.8, 2.4 Hz, 1H), 7.45-7.42 (m, 2H), 7.34 (d, J = 9.2 Hz, 1H), 4.38 (bs, 2H), 4.23 (bs, 2H), 3.0 (bs, 8H), 2.50 (bs, 3H), 1.78 (bs, 3H) |
| 1278 | MS (ESI) m/z 672.23 [M + 1]+; 1H NMR (400 MHz, DMSO-d6) δ 13.29 (bs, 1H), 8.81 (d, J = 4.8 Hz, 1H), 8.39 (s, 1H), 7.82 (s, 1H), 7.58 (dd, J = 8.8, 6.4 Hz 1H), 7.52-7.15 (m, 4H), 4.59 (d, J = 47.2 Hz, 2H), 4.40 (s, 2H), 4.23 (s, 2H), 3.76 (s, 2H), 2.89-2.71 (m, 2H), 2.30 (s, 3H), 1.79 (s, 3H) |

TABLE 3-continued

Other Compounds

| Compound | | Characterization |
|---|---|---|
| 1267 | | MS (ESI) m/z 683.35 [M + 1]+; 1H NMR (400 MHz, DMSO-d6) δ 10.14 (bs, 1H), 8.83 (d, J = 4.8 Hz, 1H), 8.54 (s, 1H), 8.52 (d, J = 2.8 Hz, 1H), 7.91 (s, 1H), 7.62-7.55 (m, 2H), 7.46-7.43 (m, 2H), 7.30 (d, J = 8.9 Hz, 1H), 4.66-4.56 (m, 2H), 4.22 (s, 2H), 4.15-4.06 (m, 2H), 2.96 (s, 6H), 2.06 (s, 3H), 1.77 (s, 3H) |
| 1277 | | MS (ESI) m/z 688.19 [M + 1]+; 1H NMR (400 MHz, DMSO-d6) δ 8.82 (d, J = 4.8 Hz, 1H), 8.38 (s, 1H), 7.76 (s, 1H), 7.59 (dd, J = 2.4, 8.8 Hz, 1H), 7.50-7.20 (m, 4H), 4.39 (d, J = 4.4 Hz, 2H), 4.23 (bs, 2H), 4.05 (s, 2H), 3.85 (t, J = 12.4 Hz, 4H), 1.78 (s, 3H) |
| 1285 | | MS (ESI) m/z 696.35 [M + 1]+; 1H NMR (400 MHz, DMSO-d6) δ 13.93 (bs, 1H), 8.78 (d, J = 4.8 Hz, 1H), 8.10 (s, 1H), 7.59 (dd, J = 8.8 Hz, 2.8 Hz, 1H), 7.48 (d, J = 4.8 Hz, 1H), 7.41 (d, J = 2.8 Hz, 1H), 7.36 (d, J = 8.8 Hz, 1H), 6.13 (s, 1H), 4.41 (bs, 2H), 4.22 (bs, 2H), 3.93-3.87 (m, 2H), 3.54 (d, J = 10.8 Hz, 2H), 3.16 (d, J = 12.8 Hz, 2H), 3.09-3.06 (m, 2H), 2.90 (s, 3H), 2.37 (s, 3H), 1.70 (s, 3H) |
| 1280 | | MS (ESI) m/z 616.25 [M + 1]+; 1H NMR (400 MHz, DMSO-d6) δ 8.50 (s, 1H), 7.58 (dd, J = 8.8, 2.4 Hz, 1H), 7.44-7.31 (m, 5H), 4.46-4.34 (m, 3H), 4.19 (s, 2H), 3.87-3.77 (m, 2H), 3.54 (t, J = 7.20, 1H), 3.36 (d, J = 10.4 Hz, 1H), 2.70 (s, 3H), 2.08-1.86 (m, 2H), 1.78 (s, 3H) |

TABLE 3-continued

| | Other Compounds | |
|---|---|---|
| | Compound | Characterization |
| 1284 | (structure) | MS (ESI) m/z 697.27 [M + 1]+; 1H NMR (400 MHz, DMSO-d6) δ 14.00 (bs, 1H), 10.10 (bs, 1H), 8.77 (d, J = 4.8 Hz, 1H), 8.53 (d, J = 2.4 Hz, 1H), 7.96 (s, 1H), 7.64-7.54 (m, 2H), 7.47-7.46 (m, 2H), 7.29 (d, J = 8.9 Hz, 1H), 4.65-4.56 (m, 2H), 4.23 (s, 2H), 4.15-4.10 (m, 2H), 2.94 (s, 6H), 2.57 (s, 3H), 2.06 (s, 3H), 1.83 (s, 3H) |
| 1295 | (structure) | MS (ESI) m/z 707.34 [M + 1]+; 1H NMR (400 MHz, DMSO-d6) δ 13.58 (bs, 1H), 8.39 (s, 1H), 8.10 (s, 1H), 7.61-7.58 (dd, J = 2.8, 8.8 Hz, 1H), 7.42 (s, 2H), 7.38 (d, J = 9.2 Hz, 1H), 4.41 (t, J = 4.8 Hz, 2H), 4.24 (t, J = 4.4 Hz, 2H), 3.74 (bs, 2H), 3.57 (s, 3H), 3.08 (bs, 4H), 2.87 (m, 2H), 2.71 (s, 3H), 2.32 (s, 3H), 1.87 (s, 3H) |
| 1290 | (structure) | MS (ESI) m/z 703.31 [M + 1]+; 1H NMR (400 MHz, DMSO-d6) δ 8.75 (d, J = 4.8 Hz, 1H), 8.62 (s, 1H), 8.25 (s, 1H), 7.75 (d, J = 8.8 Hz, 1H), 7.69 (t, J = 3.2 Hz, 2H), 7.55 (d, J = 4.8 Hz, 1H), 6.43 (t, J = 54.4 Hz, 1H), 4.85 (s, 2H), 3.44 (s, 6H), 3.18 (bs, 4H), 2.09 (s, 3H) |

TABLE 3-continued

Other Compounds

| Compound | Characterization |
|---|---|
| 1294 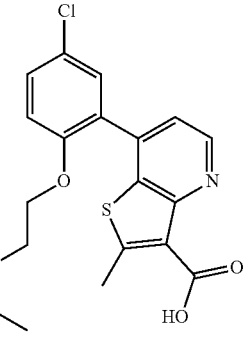 | MS (ESI) m/z 707.32 [M + 1]+; 1H NMR (400 MHz, DMSO-d6) δ 14.03 (bs, 1H), 9.79 (bs, 1H), 8.79 (d, J = 4.8 Hz, 1H), 8.13 (s, 1H), 7.63-7.60 (dd, J = 2.4, 8.8 Hz, 1H), 7.53 (d, J = 4.8 Hz, 1H), 7.44 (d, J = 2.4 Hz, 1H), 7.38 (d, J = 8.8 Hz, 1H), 4.42 (bs, 2H), 4.25 (bs, 2H), 3.93 (t, J = 12.0 Hz, 2H), 3.59-3.57 (m, 5H), 3.34-23 (m, 4H), 2.91 (s, 3H), 2.44 (s, 3H), 1.88 (s, 3H) |
| 1300 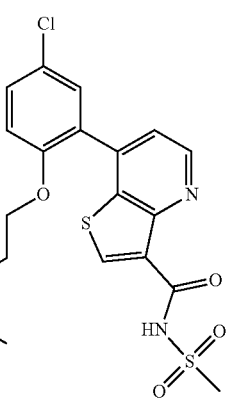 | MS (ESI) m/z 735.80 [M + 1]+; 1H NMR (400 MHz, DMSO-d6) δ 12.50 (bs, 1H), 8.87 (d, J = 4.7 Hz, 1H), 8.47 (s, 1H), 8.12 (s, 1H), 7.60 (dd, J = 2.4, 8.9 Hz, 1H), 7.53 (d, J = 4.7 Hz, 1H), 7.45 (d, J = 2.4 Hz, 1H), 7.35 (d, J = 9.0 Hz, 1H), 4.39 (t, J = 5.1 Hz, 2H), 4.20 (t, J = 4.6 Hz, 2H), 3.51 (s, 3H), 3.28 (bs, 4H), 2.55 (bs, 4H), 2.28 (s, 3H), 1.69 (s, 3H) |
| 1296 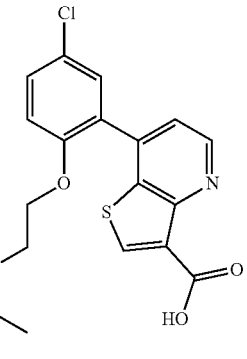 | MS (ESI) m/z 693.35; 1H NMR (400 MHz, DMSO-d6) δ 13.50 (bs, 1H), 9.78 (bs, 1H), 8.84 (d, J = 4.8 Hz, 1H), 8.33 (s, 1H), 8.13 (s, 1H), 7.61 (dd, J = 8.4, 2.4, Hz, 1H), 7.49 (d, J = 4.7 Hz, 1H), 7.44 (d, J = 2.4 Hz, 1H), 7.36 (d, J = 8.1 Hz, 1H), 4.49-4.39 (m, 2H), 4.30-4.20 (m, 2H), 3.95-3.85 (m, 2 Hz), 3.62-3.50 (m, 5H), 3.40 (d, J = 12.0 Hz, 2H), 3.29-3.19 (m, 2H), 2.92 (s, 3H), 1.79 (s, 3H) |
| 1299 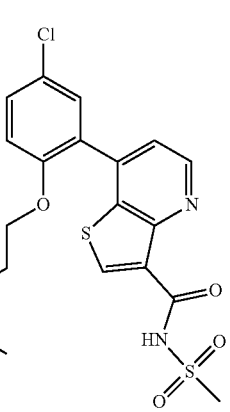 | MS (ESI) m/z 735.36 [M + 1]+; 1H NMR (400 MHz, DMSO-d6) δ 12.58 (bs, 1H), 8.83 (d, J = 4.8 Hz, 1H), 8.36 (s, 1H), 7.97 (s, 1H), 7.74 (s, 1H), 7.56 (d, J = 8.4 Hz, 1H), 7.44 (d, J = 8.4 Hz, 2H), 7.33 (d, J = 8.8 Hz, 1H), 4.39 (s, 2H), 4.22 (s, 2H), 3.42 (s, 2H), 3.31 (m, 4H), 2.95 (m, 4H), 2.10 (s, 3H), 1.77 (s, 3H) |

TABLE 3-continued

Other Compounds

| Compound | Characterization |
|---|---|
| 1379 | MS (ESI) m/z 602.3 [M + 1]+; 1H NMR (400 MHz, DMSO-d6) δ 9.57 (s, 1H), 8.16 (s, 1H), 7.66-7.51 (m, 2H), 7.49-7.33 (m, 3H), 4.63 (s, 2H), 4.42 (t, J = 5.1 Hz, 2H), 4.25 (t, J = 5.0 Hz, 2H), 2.96 (s, 6H), 2.73 (s, 3H), 2.62 (s, 3H), 1.90 (s, 3H) |
| 1331 | MS (ESI) m/z 596.2 [M + 1]+; 1H NMR (400 MHz, DMSO-d6) δ 13.39 (bs, 1H), 9.59 (s, 1H), 8.82 (d, J = 4.8 Hz, 1H), 8.54 (s, 1H), 8.45 (s, 1H), 8.44 (s, 1H), 7.60-7.57 (dd, J = 2.4, 8.8 Hz, 1H), 7.44 (t, J = 8.3 Hz, 2H), 7.33 (d, J = 8.8 Hz, 1H), 4.34 (d, J = 4.4 Hz, 2H), 4.19 (s, 2H), 3.43 (s, 4H), 2.90 (s, 6H), 1.83 (s, 3H) |
| 1373 | MS (ESI) m/z 535.0 [M + 1]+; 1H NMR (400 MHz, DMSO-d6) δ 8.82 (d, J = 4.8 Hz, 1H), 8.44 (s, 1H), 7.99 (dd, J = 8.4, 4.5 Hz, 1H), 7.77 (dd, J = 9.6, 8.4 Hz, 1H), 7.60 (dd, J = 8.9, 2.7 Hz, 1H), 7.49 (d, J = 4.8 Hz, 1H), 7.43 (d, J = 2.7 Hz, 1H), 7.37 (d, J = 9.0 Hz, 1H), 4.42 (t, J = 5.1 Hz, 2H), 4.26 (t, J = 5.1 Hz, 2H), 1.87 (s, 3H) |
| 1387 | MS (ESI) m/z 676.1 [M + 1]+; 1H NMR (400 MHz, DMSO-d6) δ 8.80 (d, J = 2.6 Hz, 1H), 8.57 (s, 1H), 8.40 (s, 1H), 8.04 (ddd, J = 9.4, 2.8, 1.7 Hz, 1H), 7.95 (s, 1H), 7.60 (dd, J = 8.9, 2.7 Hz, 1H), 7.47-7.32 (m, 3H), 6.93 (t, J = 53.7 Hz, 1H), 4.42 (t, J = 5.0 Hz, 2H), 4.29 (dd, J = 5.3, 1.9 Hz, 2H), 2.73 (s, 3H), 1.92 (s, 3H) |

TABLE 3-continued

Other Compounds

| Compound | Characterization |
|---|---|
| 1385 | MS (ESI) m/z 686.1 [M + 1]+; 1H NMR (400 MHz, DMSO-d6) δ 8.36 (s, 1H), 7.95 (s, 1H), 7.63-7.51 (m, 3H), 7.44-7.40 (m, 2H), 7.36 (d, J = 9.0 Hz, 1H), 6.90 (t, J = 53.7 Hz, 3H), 4.42 (t, J = 5.0 Hz, 2H), 4.28 (t, J = 5.0 Hz, 2H), 2.72 (s, 3H), 2.66 (s, 6H), 1.89 (s, 3H) |
| 1386 | MS (ESI) m/z 672.0 [M + 1]+; 1H NMR (400 MHz, DMSO-d6) δ 8.76 (d, J = 5.4 Hz, 1H), 8.39 (s, 1H), 7.95 (s, 1H), 7.62-7.57 (m, 2H), 7.56-7.51 (m, 1H), 7.44-7.40 (m, 2H), 7.36 (d, J = 9.0 Hz, 1H), 6.88 (t, J = 53.8 Hz, 1H), 4.41 (t, J = 5.0 Hz, 2H), 4.28 (t, J = 4.8 Hz, 2H), 2.72 (s, 3H), 2.65 (s, 3H), 1.89 (s, 3H) |
| 1935 | |
| 1936 | |

TABLE 3-continued

Other Compounds

| Compound | Characterization |
|---|---|

1937

1940

1943

1946

TABLE 3-continued

Other Compounds

| Compound | Characterization |
|---|---|

1938

1939

1949

1941

TABLE 3-continued
Other Compounds
| Compound | Characterization |
|---|---|
| 1942 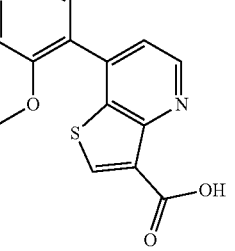 | |
| 1952 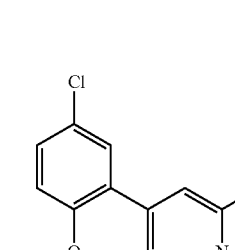 | |
| 1944 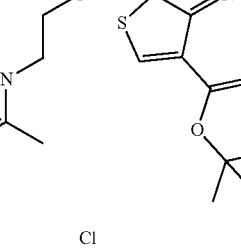 | |
| 1945 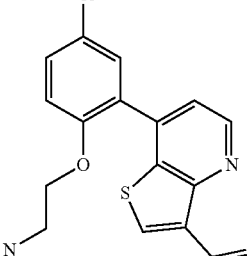 | |

TABLE 3-continued
| Other Compounds | |
|---|---|
| Compound | Characterization |
1955 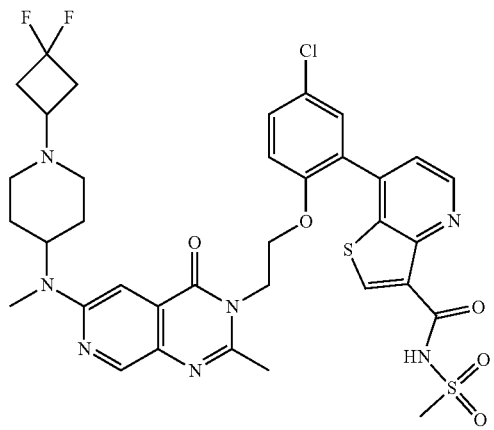 [SMILES: Cc1nc2cnc(N(C)C3CCN(C4CC(F)(F)C4)CC3)cc2c(=O)n1CCOc1ccc(Cl)cc1-c1ccnc2c(C(=O)NS(C)(=O)=O)csc12]
1947 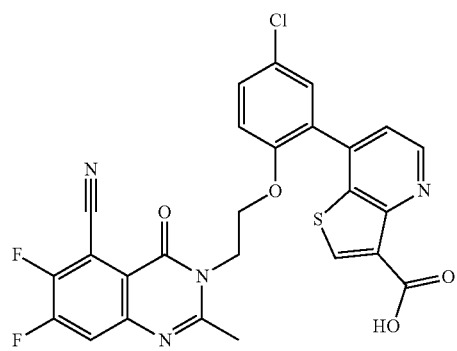 [SMILES: Cc1nc2cc(F)c(F)c(C#N)c2c(=O)n1CCOc1ccc(Cl)cc1-c1ccnc2c(C(=O)O)csc12]
1948 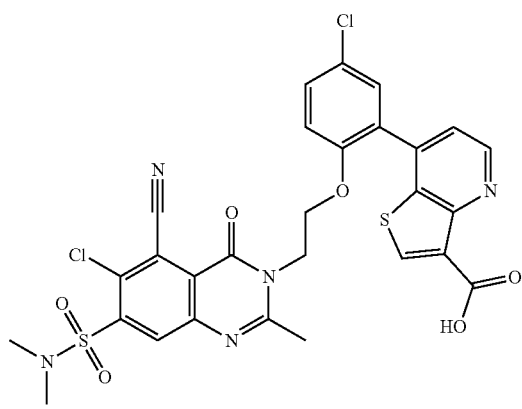 [SMILES: Cc1nc2cc(S(=O)(=O)N(C)C)c(Cl)c(C#N)c2c(=O)n1CCOc1ccc(Cl)cc1-c1ccnc2c(C(=O)O)csc12]

TABLE 3-continued

| Other Compounds | |
|---|---|
| Compound | Characterization |

1958

1950

1951

1961

TABLE 3-continued
Other Compounds
| Compound | Characterization |
|---|---|
| 1953 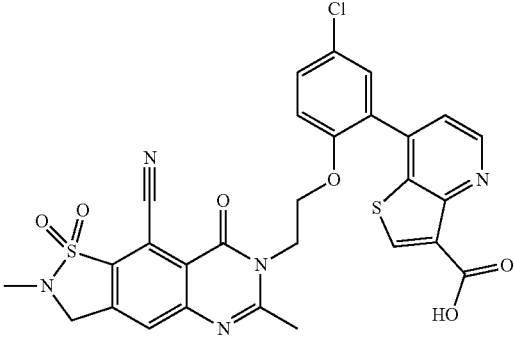 [SMILES: Cc1nc2cc3c(c(C#N)c2c(=O)n1CCOc1ccc(Cl)cc1-c1ccnc2c(C(=O)O)csc12)S(=O)(=O)N(C)C3] | |
| 1954 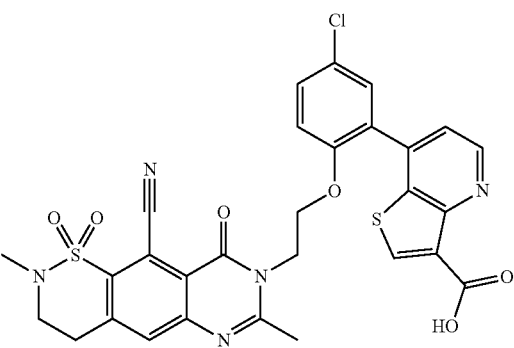 [SMILES: Cc1nc2cc3c(c(C#N)c2c(=O)n1CCOc1ccc(Cl)cc1-c1ccnc2c(C(=O)O)csc12)S(=O)(=O)N(C)CC3] | |
| 1964 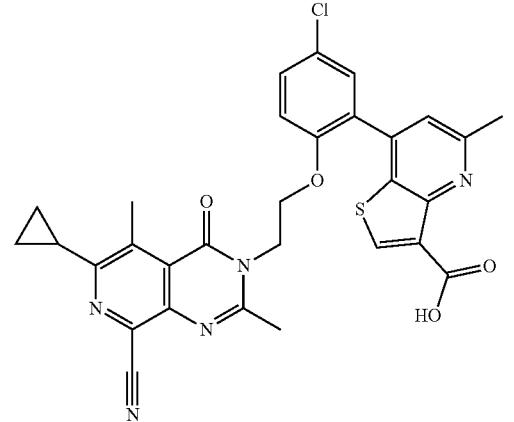 [SMILES: Cc1cc(-c2cc(Cl)ccc2OCCn2c(C)nc3c(C#N)nc(C4CC4)c(C)c3c2=O)c2scc(C(=O)O)c2n1] | |
| 1956 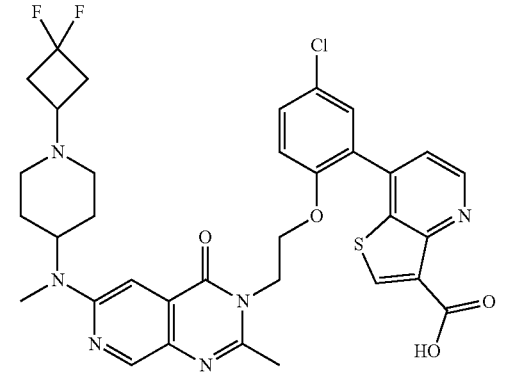 [SMILES: Cc1nc2cnc(N(C)C3CCN(C4CC(F)(F)C4)CC3)cc2c(=O)n1CCOc1ccc(Cl)cc1-c1ccnc2c(C(=O)O)csc12] | |

TABLE 3-continued
Other Compounds
| Compound | Characterization |
|---|---|
| 1957 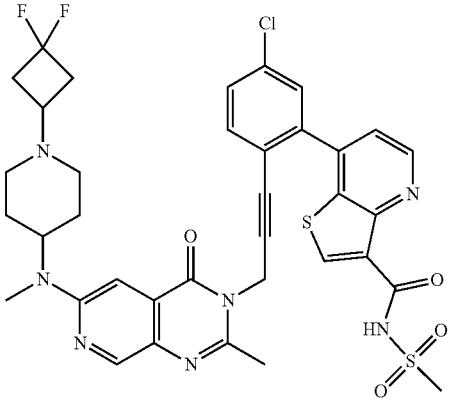 [SMILES: Cc1nc2cnc(N(C)C3CCN(C4CC(F)(F)C4)CC3)cc2c(=O)n1CC#Cc1ccc(Cl)cc1-c1ccnc2c(C(=O)NS(C)(=O)=O)csc12] | |
| 1967 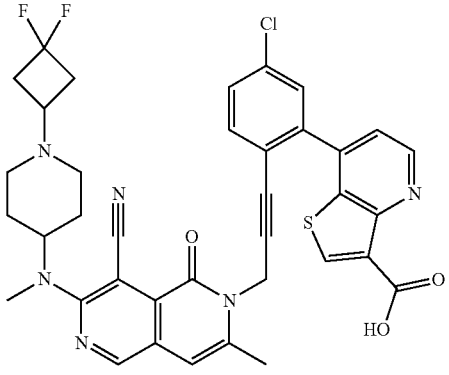 [SMILES: Cc1cc2cnc(N(C)C3CCN(C4CC(F)(F)C4)CC3)c(C#N)c2c(=O)n1CC#Cc1ccc(Cl)cc1-c1ccnc2c(C(=O)O)csc12] | |
| 1959 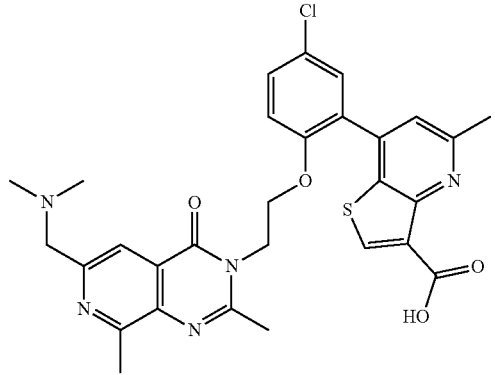 | |
| 1960 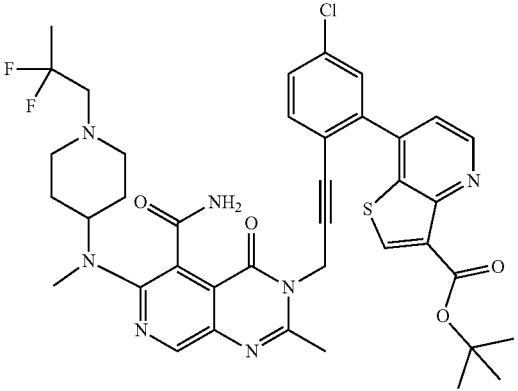 [SMILES: Cc1nc2cnc(N(C)C3CCN(CC(C)(F)F)CC3)c(C(N)=O)c2c(=O)n1CC#Cc1ccc(Cl)cc1-c1ccnc2c(C(=O)OC(C)(C)C)csc12] | |

TABLE 3-continued
| Other Compounds | |
|---|---|
| Compound | Characterization |
1970
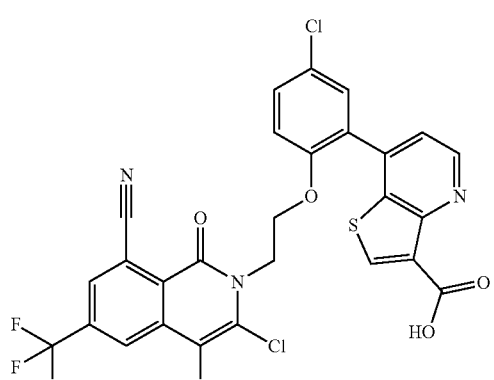
1962
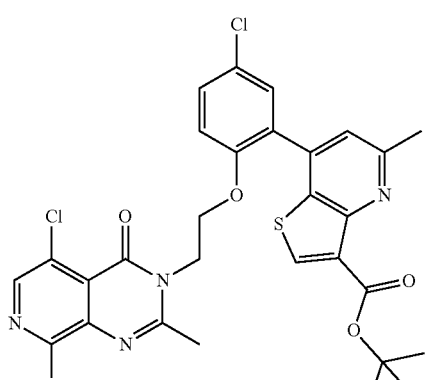
1963
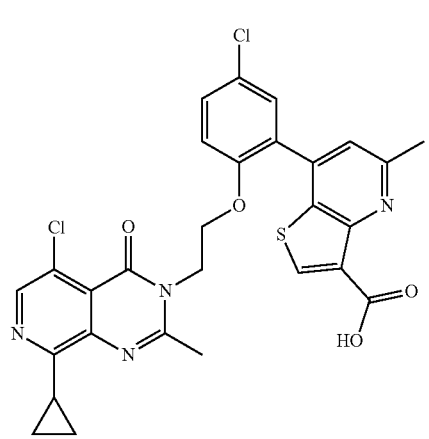 [SMILES: Cc1cc(-c2cc(Cl)ccc2OCCn2c(C)nc3c(C4CC4)ncc(Cl)c3c2=O)c2scc(C(=O)O)c2n1]

TABLE 3-continued

| Other Compounds | |
|---|---|
| Compound | Characterization |

2026

1965

1966

TABLE 3-continued

| Other Compounds | |
|---|---|
| Compound | Characterization |

1976

1968

1969

TABLE 3-continued
Other Compounds
| Compound | Characterization |
|---|---|
| 1979 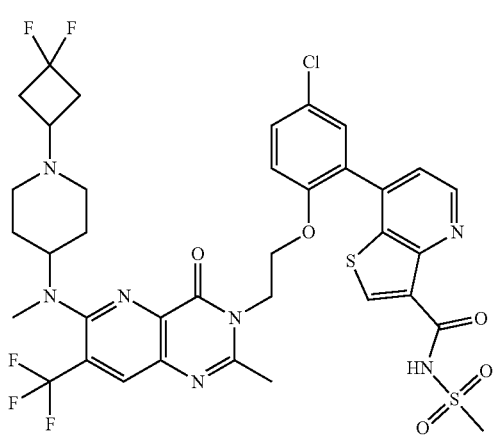 [SMILES: Cc1nc2cc(C(F)(F)F)c(N(C)C3CCN(C4CC(F)(F)C4)CC3)nc2c(=O)n1CCOc1ccc(Cl)cc1-c1ccnc2c(C(=O)NS(C)(=O)=O)csc12] | |
| 1971 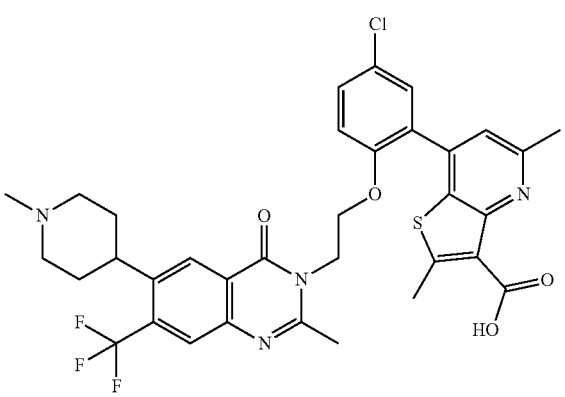 | |
| 1972 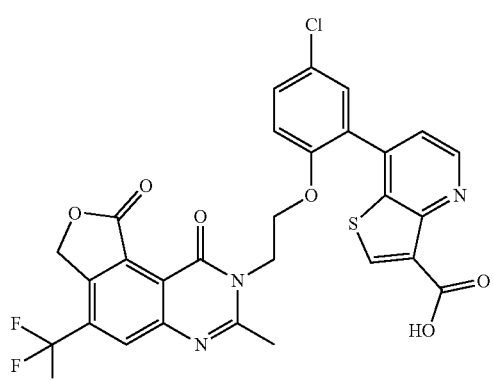 | |

TABLE 3-continued

Other Compounds

| Compound | Characterization |
|---|---|

1986

1974

1975

1989

TABLE 3-continued

Other Compounds

| Compound | Characterization |
|---|---|
| 1977 | |
| 1978 | |
| 1992 | |
| 1980 | |

TABLE 3-continued
| Other Compounds | |
|---|---|
| Compound | Characterization |
1981
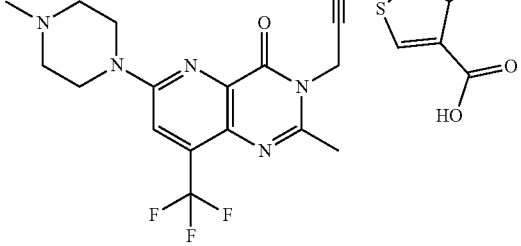
1996
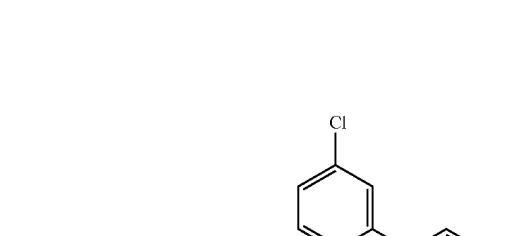
1987
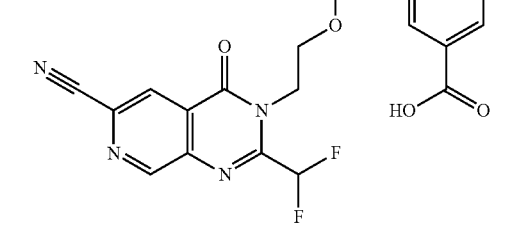

TABLE 3-continued

Other Compounds

| Compound | Characterization |
|---|---|

1988

1999

1990

1991

TABLE 3-continued

Other Compounds

| Compound | Characterization |
|---|---|
| 2002 | |
| 1993 | |
| 1995 | |
| 2005 | |

TABLE 3-continued

| Other Compounds | |
|---|---|
| Compound | Characterization |
| 1997 | |
| 1998 | |
| 2008 | |

TABLE 3-continued

Other Compounds

| Compound | Characterization |
|---|---|

2000

2001

2011

TABLE 3-continued

Other Compounds

| Compound | Characterization |
|---|---|
| 2003 | |
| 2004 | |
| 2014 | |
| 2006 | |

TABLE 3-continued
Other Compounds
| Compound | Characterization |
|---|---|
| 2007 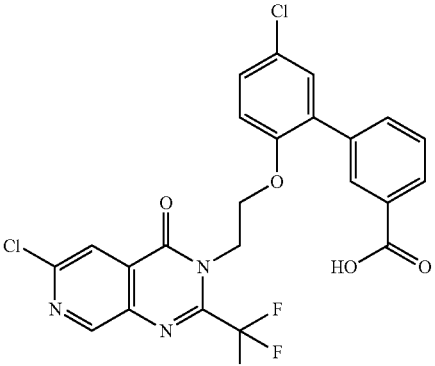 | |
| 2017 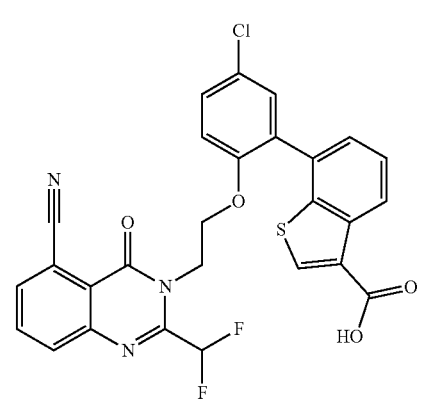 [SMILES: N#Cc1cccc2nc(C(F)F)n(CCOc3ccc(Cl)cc3-c3cccc4c(C(=O)O)csc34)c(=O)c12] | |
| 2009 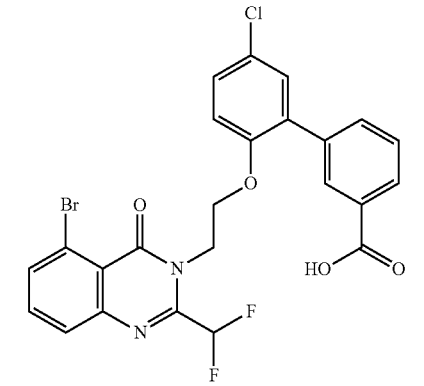 [SMILES: O=C(O)c1cccc(-c2cc(Cl)ccc2OCCn2c(C(F)F)nc3cccc(Br)c3c2=O)c1] | |
| 2010 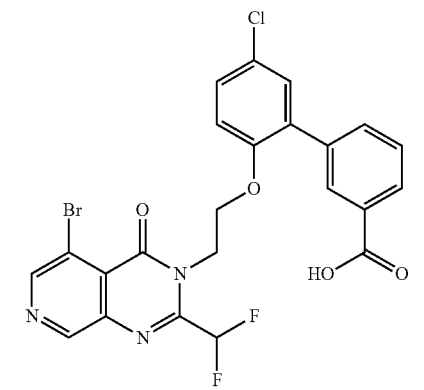 [SMILES: O=C(O)c1cccc(-c2cc(Cl)ccc2OCCn2c(C(F)F)nc3cncc(Br)c3c2=O)c1] | |

TABLE 3-continued
Other Compounds
| Compound | Characterization |
|---|---|
| 2027 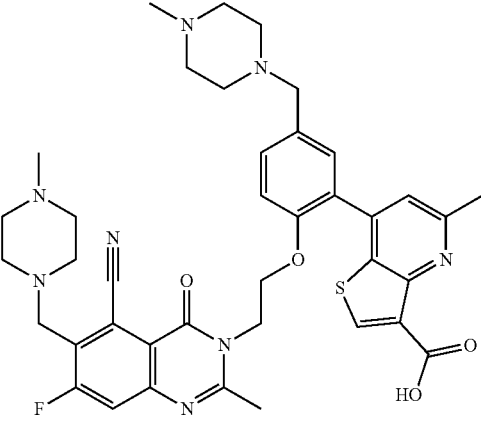 [SMILES: Cc1cc(-c2cc(CN3CCN(C)CC3)ccc2OCCn2c(C)nc3cc(F)c(CN4CCN(C)CC4)c(C#N)c3c2=O)c2scc(C(=O)O)c2n1] | |
| 2012 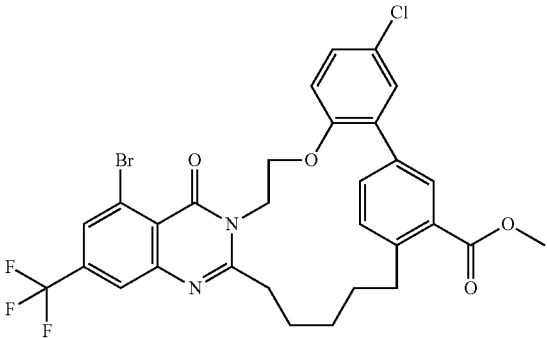 [SMILES: COC(=O)c1cc2ccc1CCCCCc1nc3cc(C(F)(F)F)cc(Br)c3c(=O)n1CCOc1ccc(Cl)cc1-2] | |
| 2013 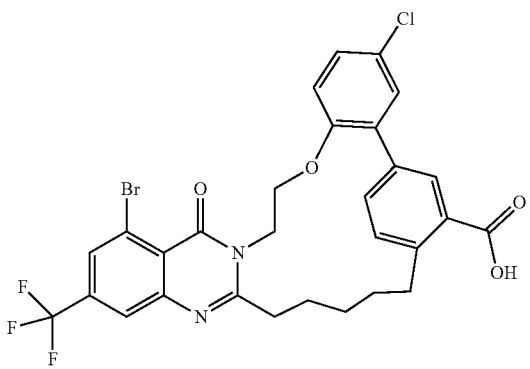 [SMILES: O=C(O)c1cc2ccc1CCCCCc1nc3cc(C(F)(F)F)cc(Br)c3c(=O)n1CCOc1ccc(Cl)cc1-2] | |
| 2026 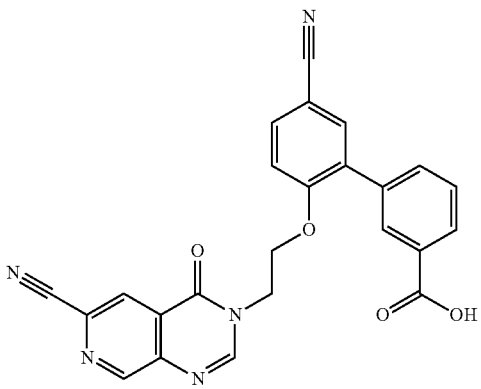 [SMILES: N#Cc1ccc(OCCn2cnc3cnc(C#N)cc3c2=O)c(-c2cccc(C(=O)O)c2)c1] | |

TABLE 3-continued

Other Compounds

| Compound | | Characterization |
|---|---|---|
| 2034 | (structure) | MS (ESI) m/z 526.15 [M + 1]+ |
| 2035 | (structure) | MS (ESI) m/z 553.33 [M + 1]+ |

Example 5. Biological Studies

Example 5A. Fluorescence Polarization

Compounds were screened for eIF4E binding potency using a fluorescence polarization competition assay. All binding reactions were performed in fluorescence polarization buffer (FPB) containing 20 mM Tris pH 7.5, 100 mM NaCl, 1 mM DTT, and 0.02% Tween-20. Final binding reactions contained 75 nM recombinant eIF4E (Beryllium, custom order), 20 nM EDA-m$^7$GDP-ATTO-550 (Jena Bioscience, NU-827-550) and varying concentrations of the inhibitory compound of interest. Final DMSO concentration in each reaction was 1%.

eIF4E protein was pre-incubated with EDA-m$^7$GDP-ATTO-550 in FPB at 2× concentrations for 5 minutes prior to the addition of compounds. Compounds (100×) were prepared using 3-fold serial dilutions in 100% DMSO, and subsequently diluted 1:50 in FPB to produce 2× stocks. 50 µl of 2× eIF4E/EDA-m$^7$GDP-ATTO-550 were transferred to the wells of a 96-well half-area black flat bottom polystyrene plate. 50 µl of 2× test compound were added, and binding reactions were allowed to equilibrate for 30 minutes at room temperature while protected from light. The fluorescent polarization signal was detected using a Victor 2 multi-label counter (Perkin Elmer) and the concentration necessary to achieve inhibition of eIF4E/EDA-m$^7$GDP-ATTO-550 binding by 50% (IC$_{50}$) was calculated using data from an 8-point compound dilution series.

The results of these assays are set forth in Tables 4A and 4B, below. In Table 4A, IC$_{50}$ values of less than 0.05 µM are labelled as "+++", from 1 to 0.05 µM are labelled as "++", and greater than 1 µM are labelled as "+". Calculated IC$_{50}$ values are shown in Table 4B. ND=not determined.

TABLE 4A

| Compound | eIF4E FP |
|---|---|
| 1 | ++ |
| 2 | + |
| 3 | + |
| 4 | + |
| 5 | + |
| 6 | + |
| 7 | + |
| 8 | +++ |
| 9 | + |
| 10 | + |
| 11 | + |
| 12 | + |
| 13 | + |
| 14 | + |
| 15 | + |
| 16 | ++++ |
| 17 | ++ |
| 18 | ++ |
| 19 | ++ |
| 20 | + |
| 21 | ++ |
| 22 | +++ |
| 23 | ++ |

TABLE 4A-continued

| Compound | eIF4E FP |
|---|---|
| 24 | ++ |
| 25 | + |
| 26 | ++ |
| 27 | ++ |
| 28 | ++ |
| 29 | ++ |
| 30 | ++ |
| 31 | ++ |
| 32 | ++ |
| 33 | ++ |
| 34 | ++ |
| 35 | +++ |
| 36 | ND |
| 37 | +++ |
| 38 | ++ |
| 39 | ++ |
| 40 | +++ |
| 41 | + |
| 42 | + |
| 43 | + |
| 44 | ++ |
| 45 | + |
| 46 | ++ |
| 47 | +++ |
| 48 | ++ |
| 49 | +++ |
| 50 | +++ |
| 51 | +++ |
| 52 | + |
| 53 | ++ |
| 54 | + |
| 55 | +++ |
| 56 | +++ |
| 57 | +++ |
| 58 | ++ |
| 59 | +++ |
| 60 | +++ |
| 61 | +++ |
| 62 | +++ |
| 63 | +++ |
| 64 | ++ |
| 65 | +++ |
| 66 | ++ |
| 67 | + |
| 68 | + |
| 69 | + |
| 70 | ++ |
| 71 | ++ |
| 72 | + |
| 73 | ++ |
| 74 | ++ |
| 75 | + |
| 76 | + |
| 77 | + |
| 78 | + |
| 79 | + |
| 80 | ++ |
| 81 | + |
| 82 | + |
| 83 | + |
| 84 | + |
| 85 | + |
| 86 | + |
| 87 | + |
| 88 | + |
| 89 | + |
| 90 | + |
| 91 | ++ |
| 92 | + |
| 93 | + |
| 94 | + |
| 95 | + |
| 96 | + |
| 97 | + |
| 98 | ++ |
| 99 | + |
| 100 | + |

TABLE 4A-continued

| Compound | eIF4E FP |
|---|---|
| 101 | + |
| 102 | + |
| 103 | ++ |
| 104 | ++ |
| 105 | + |
| 106 | + |
| 107 | + |
| 108 | + |
| 109 | + |
| 110 | + |
| 111 | ++ |
| 112 | + |
| 113 | ++ |
| 114 | ++ |
| 115 | + |
| 116 | + |
| 117 | + |
| 118 | ++ |
| 119 | +++ |
| 120 | +++ |
| 121 | +++ |
| 122 | +++ |
| 123 | +++ |
| 124 | + |
| 125 | + |
| 126 | + |
| 127 | ++ |
| 128 | ++ |
| 129 | + |
| 130 | + |
| 131 | ++ |
| 132 | ++ |
| 133 | ++ |
| 134 | ++ |
| 135 | ND |
| 136 | ++ |
| 137 | ++ |
| 138 | ++ |
| 139 | +++ |
| 140 | ++ |
| 141 | +++ |
| 142 | ++ |
| 143 | +++ |
| 144 | +++ |
| 145 | ++ |
| 146 | ++ |
| 147 | +++ |
| 148 | +++ |
| 149 | ++ |
| 150A | ++ |
| 150B | ++ |
| 150C | ++ |
| 151 | +++ |
| 152 | +++ |
| 153 | ++ |
| 154 | ++ |
| 155 | +++ |
| 156 | +++ |
| 157 | ND |
| 158 | +++ |
| 159 | +++ |
| 160 | +++ |
| 161 | ++ |
| 162 | +++ |
| 163 | ++ |
| 164 | ND |
| 165 | ++ |
| 166 | +++ |
| 167 | ++ |
| 168 | +++ |
| 169 | ++ |
| 170 | ++ |
| 171 | ++ |
| 172 | ++ |
| 173 | ++ |
| 174 | ++ |
| 175 | +++ |

TABLE 4A-continued

| Compound | eIF4E FP |
|---|---|
| 176 | +++ |
| 177 | +++ |
| 178 | ++ |
| 179 | +++ |
| 180 | +++ |
| 181 | ++ |
| 182 | +++ |
| 183 | ++ |
| 184 | ++ |
| 185 | ++ |
| 186 | ++ |
| 187 | +++ |
| 188 | ++ |
| 189 | + |
| 190 | ++ |
| 191 | ++ |
| 192 | + |
| 193 | +++ |
| 194 | +++ |
| 195 | +++ |
| 196 | +++ |
| 197 | ++ |
| 198 | ++ |
| 199 | ++ |
| 200 | +++ |
| 201 | ++ |
| 202 | +++ |
| 203 | ++ |
| 204 | +++ |
| 205 | ++ |
| 206 | ++ |
| 207 | +++ |
| 208 | ++ |
| 209 | +++ |
| 210 | ++ |
| 211 | +++ |
| 212 | +++ |
| 213 | +++ |
| 214 | +++ |
| 215 | ++ |
| 216 | ++ |
| 217 | ++ |
| 218 | +++ |
| 219 | ++ |
| 220 | ++ |
| 221 | ++ |
| 222 | ++ |
| 223 | ++ |
| 224 | +++ |
| 225 | ++ |
| 226 | ++ |
| 227 | ++ |
| 228 | +++ |
| 229 | +++ |
| 230 | +++ |
| 231 | +++ |
| 232 | +++ |
| 233 | +++ |
| 234 | +++ |
| 235 | +++ |
| 236 | +++ |
| 237 | ++ |
| 238 | +++ |
| 239 | +++ |
| 240 | +++ |
| 241 | +++ |
| 242 | +++ |
| 243 | +++ |
| 244 | +++ |
| 245 | +++ |
| 246 | +++ |
| 247 | ++ |
| 248 | ++ |
| 249 | +++ |
| 250 | +++ |
| 251 | +++ |
| 252 | +++ |

TABLE 4A-continued

| Compound | eIF4E FP |
|---|---|
| 253 | +++ |
| 254 | +++ |
| 255 | ++ |
| 256 | ++ |
| 257 | ++ |
| 258 | +++ |
| 259 | ++ |
| 260 | +++ |
| 261 | +++ |
| 262 | +++ |
| 263 | +++ |
| 264 | +++ |
| 265 | ++ |
| 266 | +++ |
| 267 | ++ |
| 268 | +++ |
| 269 | +++ |
| 270 | +++ |
| 271 | +++ |
| 272 | +++ |
| 273 | +++ |
| 274 | +++ |
| 275 | +++ |
| 276 | +++ |
| 277 | +++ |
| 278 | +++ |
| 279 | +++ |
| 280 | +++ |
| 281 | +++ |
| 282 | +++ |
| 283 | +++ |
| 284 | +++ |
| 285 | ++ |
| 286 | ++ |
| 287 | +++ |
| 288 | +++ |
| 289 | +++ |
| 290 | +++ |
| 291 | ++ |
| 292 | ++ |
| 293 | ++ |
| 294 | +++ |
| 295 | ++ |
| 296 | +++ |
| 297 | +++ |
| 298 | ++ |
| 299 | +++ |
| 300 | +++ |
| 301 | ++ |
| 302 | ++ |
| 303 | ++ |
| 304 | + |
| 305 | ++ |
| 306 | ++ |
| 307 | ++ |
| 308 | ++ |
| 309 | ++ |
| 310 | ++ |
| 311 | ++ |
| 312 | ++ |
| 313 | +++ |
| 314 | +++ |
| 315 | ++ |
| 316 | +++ |
| 317 | +++ |
| 318 | +++ |
| 319 | ++ |
| 320 | +++ |
| 321 | +++ |
| 322 | ++ |
| 323 | ++ |
| 324 | ++ |
| 325 | ++ |
| 326 | + |
| 327 | +++ |
| 328 | + |
| 329 | +++ |

TABLE 4A-continued

| Compound | eIF4E FP |
|---|---|
| 330 | +++ |
| 331 | ND |
| 332 | +++ |
| 333 | ND |
| 334 | +++ |
| 335 | ++ |
| 336 | +++ |
| 337 | +++ |
| 338 | +++ |
| 339 | +++ |
| 340 | +++ |
| 341 | +++ |
| 342 | +++ |
| 343 | +++ |
| 344 | +++ |
| 345 | +++ |
| 345 | +++ |
| 346 | +++ |
| 347 | +++ |
| 348 | +++ |
| 349 | +++ |
| 350 | +++ |
| 351 | ++ |
| 351 | ++ |
| 352 | + |
| 353 | ++ |
| 354 | ++ |
| 355 | ++ |
| 356 | + |
| 357 | +++ |
| 358 | ++ |
| 359 | +++ |
| 360 | +++ |
| 361 | ++ |
| 362 | ++ |
| 363 | +++ |
| 364 | ++ |
| 365 | +++ |
| 366 | +++ |
| 367 | +++ |
| 368 | +++ |
| 369 | +++ |
| 370 | +++ |
| 371 | +++ |
| 372 | +++ |
| 373 | +++ |
| 374 | +++ |
| 375 | ++ |
| 376 | +++ |
| 377 | ++ |
| 378 | +++ |
| 379 | +++ |
| 380 | +++ |
| 381 | ND |
| 382 | ND |
| 383 | ND |
| 384 | +++ |
| 385 | +++ |
| 386 | +++ |
| 387 | ++ |
| 388 | +++ |
| 389 | +++ |
| 390 | +++ |
| 391 | +++ |
| 392 | +++ |
| 393 | +++ |
| 394 | +++ |
| 395 | +++ |
| 396 | +++ |
| 397 | +++ |
| 398 | ++ |
| 399 | ++ |
| 400 | +++ |
| 401 | +++ |
| 402 | ++ |
| 403 | +++ |
| 404 | +++ |

TABLE 4A-continued

| Compound | eIF4E FP |
|---|---|
| 405 | +++ |
| 406 | +++ |
| 407 | +++ |
| 408 | +++ |
| 409 | +++ |
| 410 | ++ |
| 411 | ++ |
| 412 | ++ |
| 413 | +++ |
| 414 | +++ |
| 415 | +++ |
| 416 | +++ |
| 417 | +++ |
| 418 | +++ |
| 419 | +++ |
| 420 | +++ |
| 421 | +++ |
| 422 | +++ |
| 423 | +++ |
| 424 | +++ |
| 425 | +++ |
| 426 | +++ |
| 427 | +++ |
| 428 | +++ |
| 429 | +++ |
| 430 | +++ |
| 431 | ++ |
| 432 | +++ |
| 433 | +++ |
| 434 | +++ |
| 435 | +++ |
| 436 | +++ |
| 437 | +++ |
| 438 | +++ |
| 439 | +++ |
| 439 | +++ |
| 440 | +++ |
| 441 | +++ |
| 442 | +++ |
| 443 | ++ |
| 444 | +++ |
| 445 | ++ |
| 446 | ++ |
| 447 | ++ |
| 448 | +++ |
| 449 | +++ |
| 450 | +++ |
| 451 | +++ |
| 452 | +++ |
| 453 | + |
| 454 | ++ |
| 455 | ++ |
| 456 | +++ |
| 457 | +++ |
| 458 | +++ |
| 459 | +++ |
| 460 | +++ |
| 461 | +++ |
| 462 | +++ |
| 463 | +++ |
| 464 | +++ |
| 465 | +++ |
| 466 | +++ |
| 467 | +++ |
| 468 | +++ |
| 469 | +++ |
| 470 | +++ |
| 471 | +++ |
| 472 | +++ |
| 473 | +++ |
| 474 | +++ |
| 475 | +++ |
| 476 | +++ |
| 477 | +++ |
| 478 | +++ |
| 479 | +++ |
| 480 | +++ |

TABLE 4A-continued

| Compound | eIF4E FP |
|---|---|
| 481 | +++ |
| 482 | +++ |
| 483 | +++ |
| 484 | +++ |
| 485 | +++ |
| 486 | +++ |
| 487 | ++ |
| 488 | +++ |
| 489 | +++ |
| 490 | ++ |
| 491 | +++ |
| 492 | +++ |
| 493 | ++ |
| 494 | ++ |
| 495 | ++ |
| 496 | + |
| 497 | +++ |
| 498 | +++ |
| 499 | ++ |
| 500 | +++ |
| 501 | +++ |
| 502 | +++ |
| 503 | +++ |
| 504 | +++ |
| 505 | +++ |
| 506 | ++ |
| 507 | +++ |
| 508 | +++ |
| 509 | ++ |
| 510 | ++ |
| 511 | ++ |
| 512 | ++ |
| 513 | +++ |
| 514 | +++ |
| 515 | +++ |
| 516 | +++ |
| 517 | +++ |
| 518 | +++ |
| 519 | +++ |
| 520 | +++ |
| 521 | ++ |
| 522 | +++ |
| 523 | +++ |
| 524 | +++ |
| 525 | +++ |
| 526 | ++ |
| 527 | +++ |
| 528 | +++ |
| 529 | +++ |
| 530 | +++ |
| 531 | +++ |
| 532 | +++ |
| 533 | ++ |
| 534 | +++ |
| 535 | ++ |
| 536 | +++ |
| 537 | +++ |
| 538 | +++ |
| 539 | +++ |
| 540 | +++ |
| 541 | +++ |
| 542 | +++ |
| 543 | +++ |
| 544 | +++ |
| 545 | +++ |
| 546 | +++ |
| 547 | ++ |
| 548 | +++ |
| 549 | +++ |
| 550 | ++ |
| 551 | +++ |
| 552 | ++ |
| 553 | +++ |
| 554 | +++ |
| 555 | +++ |
| 556 | +++ |
| 557 | +++ |

TABLE 4A-continued

| Compound | eIF4E FP |
|---|---|
| 558 | +++ |
| 559 | +++ |
| 560 | +++ |
| 561 | ++ |
| 562 | +++ |
| 563 | +++ |
| 564 | +++ |
| 565 | +++ |
| 566 | +++ |
| 567 | +++ |
| 568 | +++ |
| 569 | +++ |
| 570 | +++ |
| 571 | ++ |
| 572 | +++ |
| 573 | ++ |
| 574 | ++ |
| 575 | +++ |
| 576 | +++ |
| 577 | +++ |
| 578 | +++ |
| 579 | +++ |
| 580 | +++ |
| 581 | +++ |
| 582 | +++ |
| 583 | +++ |
| 584 | +++ |
| 585 | +++ |
| 586 | +++ |
| 587 | +++ |
| 588 | +++ |
| 589 | +++ |
| 590 | +++ |
| 591 | +++ |
| 592 | +++ |
| 593 | +++ |
| 594 | + |
| 595 | +++ |
| 596 | +++ |
| 597 | +++ |
| 598 | ++ |
| 599 | ++ |
| 600 | +++ |
| 601 | ++ |
| 602 | +++ |
| 603 | +++ |
| 604 | ++ |
| 605 | ND |
| 606 | +++ |
| 607 | +++ |
| 608 | +++ |
| 609 | +++ |
| 610 | +++ |
| 611 | +++ |
| 612 | +++ |
| 613 | +++ |
| 614 | ++ |
| 615 | +++ |
| 616 | +++ |
| 617 | +++ |
| 618 | +++ |
| 619 | +++ |
| 620 | +++ |
| 621 | ++ |
| 622 | +++ |
| 623 | +++ |
| 624 | +++ |
| 625 | ++ |
| 626 | +++ |
| 627 | +++ |
| 628 | +++ |
| 629 | +++ |
| 630 | ++ |
| 631 | +++ |
| 632 | +++ |
| 633 | +++ |
| 634 | +++ |

TABLE 4A-continued

| Compound | eIF4E FP |
|---|---|
| 635 | +++ |
| 636 | +++ |
| 637 | +++ |
| 638 | +++ |
| 639 | +++ |
| 640 | +++ |
| 641 | +++ |
| 642 | +++ |
| 643 | +++ |
| 644 | +++ |
| 645 | +++ |
| 646 | +++ |
| 647 | +++ |
| 648 | +++ |
| 649 | +++ |
| 650 | +++ |
| 651 | +++ |
| 652 | +++ |
| 653 | +++ |
| 654 | +++ |
| 655 | +++ |
| 656 | +++ |
| 657 | +++ |
| 658 | + |
| 659 | +++ |
| 660 | ++ |
| 661 | +++ |
| 662 | ++ |
| 663 | ++ |
| 664 | ++ |
| 665 | +++ |
| 666 | ++ |
| 667 | +++ |
| 668 | +++ |
| 669 | +++ |
| 670 | +++ |
| 671 | ++ |
| 672 | ++ |
| 673 | +++ |
| 674 | +++ |
| 675 | +++ |
| 676 | +++ |
| 677 | +++ |
| 678 | ++ |
| 679 | ++ |
| 680 | ++ |
| 681 | +++ |
| 682 | +++ |
| 683 | +++ |
| 684 | +++ |
| 685 | +++ |
| 686 | +++ |
| 687 | +++ |
| 688 | +++ |
| 689 | +++ |
| 690 | +++ |
| 691 | +++ |
| 692 | +++ |
| 693 | +++ |
| 694 | +++ |
| 695 | +++ |
| 696 | +++ |
| 697 | +++ |
| 698 | +++ |
| 699 | +++ |
| 700 | +++ |
| 701 | +++ |
| 702 | +++ |
| 703 | +++ |
| 704 | ++ |
| 705 | +++ |
| 706 | ++ |
| 707 | +++ |
| 708 | ++ |
| 709 | ++ |
| 710 | +++ |
| 711 | ++ |
| 712 | +++ |
| 713 | +++ |
| 714 | +++ |
| 715 | ND |
| 716 | ND |
| 717 | ++ |
| 718 | +++ |
| 719 | +++ |
| 720 | ++ |
| 721 | +++ |
| 722 | +++ |
| 723 | +++ |
| 724 | +++ |
| 725 | +++ |
| 726 | ++ |
| 727 | +++ |
| 728 | +++ |
| 729 | ++ |
| 730 | ++ |
| 731 | +++ |
| 732 | ++ |
| 733 | + |
| 734 | +++ |
| 735 | ++ |
| 736 | +++ |
| 737 | +++ |
| 738 | +++ |
| 739 | +++ |
| 740 | +++ |
| 741 | +++ |
| 742 | +++ |
| 743 | ++ |
| 744 | +++ |
| 745 | +++ |
| 746 | +++ |
| 747 | +++ |
| 748 | +++ |
| 749 | + |
| 750 | +++ |
| 751 | ++ |
| 752 | +++ |
| 753 | +++ |
| 754 | +++ |
| 755 | +++ |
| 756 | +++ |
| 757 | ++ |
| 758 | +++ |
| 759 | ++ |
| 760 | +++ |
| 761 | +++ |
| 762 | +++ |
| 763 | +++ |
| 764 | +++ |
| 765 | +++ |
| 766 | +++ |
| 767 | +++ |
| 768 | +++ |
| 769 | +++ |
| 770 | +++ |
| 771 | +++ |
| 772 | +++ |
| 773 | +++ |
| 774 | +++ |
| 775 | +++ |
| 776 | +++ |
| 777 | ++ |
| 778 | +++ |
| 779 | +++ |
| 780 | +++ |
| 781 | +++ |
| 782 | +++ |
| 783 | +++ |
| 784 | +++ |
| 785 | +++ |
| 786 | +++ |
| 787 | +++ |
| 788Fa | + |

TABLE 4A-continued

| Compound | eIF4E FP |
|---|---|
| 788Fb | +++ |
| 789 | +++ |
| 790 | +++ |
| 791 | +++ |
| 792 | +++ |
| 793 | +++ |
| 794 | +++ |
| 795 | +++ |
| 796 | +++ |
| 797 | +++ |
| 798 | +++ |
| 799 | +++ |
| 800 | +++ |
| 801 | +++ |
| 802 | +++ |
| 803 | ++ |
| 804 | +++ |
| 805 | +++ |
| 806 | +++ |
| 807 | +++ |
| 808 | ++ |
| 809 | +++ |
| 810 | +++ |
| 811 | ++ |
| 812 | +++ |
| 813 | +++ |
| 814 | ND |
| 815 | +++ |
| 816 | +++ |
| 817 | +++ |
| 818 | +++ |
| 819 | +++ |
| 820 | +++ |
| 821 | +++ |
| 822 | +++ |
| 823 | +++ |
| 824 | +++ |
| 825 | +++ |
| 826 | +++ |
| 827 | +++ |
| 828 | +++ |
| 829 | +++ |
| 830 | +++ |
| 831 | +++ |
| 832 | ND |
| 833 | ++ |
| 834 | +++ |
| 835 | +++ |
| 836 | +++ |
| 837 | +++ |
| 838 | +++ |
| 839 | +++ |
| 840 | +++ |
| 841 | ++ |
| 842 | +++ |
| 843 | +++ |
| 844 | +++ |
| 845 | +++ |
| 846 | +++ |
| 847 | +++ |
| 848 | +++ |
| 849 | +++ |
| 850 | +++ |
| 851 | +++ |
| 852 | +++ |
| 853 | +++ |
| 854 | +++ |
| 855 | +++ |
| 856 | +++ |
| 857 | +++ |
| 858 | +++ |
| 859 | +++ |
| 860 | +++ |
| 861 | +++ |
| 862 | +++ |
| 863 | +++ |
| 864 | +++ |
| 865 | +++ |
| 866 | +++ |
| 867 | +++ |
| 868 | +++ |
| 869 | +++ |
| 870 | ++ |
| 871 | +++ |
| 872 | +++ |
| 873 | +++ |
| 874 | +++ |
| 875 | +++ |
| 876 | ++ |
| 877 | ++ |
| 878 | +++ |
| 879 | +++ |
| 880 | ++ |
| 881 | +++ |
| 882 | +++ |
| 883 | +++ |
| 884 | +++ |
| 885 | +++ |
| 886 | +++ |
| 887 | +++ |
| 888 | +++ |
| 889 | +++ |
| 890 | +++ |
| 891 | +++ |
| 892 | +++ |
| 893 | +++ |
| 894 | +++ |
| 895 | +++ |
| 896 | +++ |
| 897 | +++ |
| 898 | +++ |
| 899 | +++ |
| 900 | +++ |
| 901 | +++ |
| 902 | +++ |
| 903 | +++ |
| 904 | +++ |
| 905 | +++ |
| 906 | +++ |
| 907 | +++ |
| 908 | +++ |
| 909 | +++ |
| 910 | +++ |
| 911 | +++ |
| 912 | +++ |
| 913 | +++ |
| 914 | +++ |
| 915 | +++ |
| 916 | +++ |
| 917 | +++ |
| 918 | +++ |
| 919 | +++ |
| 920 | +++ |
| 921 | ++ |
| 922 | ++ |
| 923 | +++ |
| 924 | +++ |
| 925 | +++ |
| 926 | +++ |
| 927 | +++ |
| 928 | +++ |
| 929 | +++ |
| 930 | +++ |
| 931 | +++ |
| 932 | +++ |
| 933 | ++ |
| 934 | +++ |
| 935 | +++ |
| 936 | ND |
| 937 | +++ |
| 938 | +++ |
| 939 | +++ |
| 940 | ++ |
| 941 | +++ |

TABLE 4A-continued

| Compound | eIF4E FP |
|---|---|
| 942 | +++ |
| 943 | +++ |
| 944 | +++ |
| 945 | +++ |
| 946 | +++ |
| 947 | +++ |
| 948 | +++ |
| 949 | +++ |
| 950 | +++ |
| 951 | +++ |
| 952 | +++ |
| 953 | +++ |
| 954 | +++ |
| 955 | +++ |
| 956 | +++ |
| 957 | +++ |
| 958 | +++ |
| 959 | +++ |
| 960 | +++ |
| 961 | +++ |
| 962 | +++ |
| 963 | +++ |
| 964 | +++ |
| 965 | ++ |
| 966 | +++ |
| 967 | +++ |
| 968 | +++ |
| 969 | +++ |
| 970 | ++ |
| 971 | ++ |
| 972 | +++ |
| 973 | ++ |
| 974 | +++ |
| 975 | +++ |
| 976 | +++ |
| 977 | +++ |
| 978 | +++ |
| 979 | +++ |
| 980 | +++ |
| 981 | +++ |
| 982 | +++ |
| 983 | +++ |
| 984 | +++ |
| 985 | +++ |
| 986 | +++ |
| 987 | +++ |
| 988 | +++ |
| 989 | +++ |
| 990 | +++ |
| 991 | +++ |
| 992 | ++ |
| 993 | +++ |
| 994 | +++ |
| 995 | +++ |
| 996 | +++ |
| 997 | +++ |
| 998 | +++ |
| 999 | +++ |
| 1000 | +++ |
| 1001 | +++ |
| 1002 | +++ |
| 1003 | +++ |
| 1004 | +++ |
| 1005 | +++ |
| 1006 | +++ |
| 1007 | +++ |
| 1008 | +++ |
| 1009 | +++ |
| 1010 | +++ |
| 1011 | +++ |
| 1012 | +++ |
| 1013 | +++ |
| 1014 | +++ |
| 1015 | +++ |
| 1016 | +++ |
| 1017 | +++ |
| 1018 | +++ |
| 1019 | +++ |
| 1020 | +++ |
| 1021 | +++ |
| 1022 | +++ |
| 1023 | +++ |
| 1024 | +++ |
| 1025 | +++ |
| 1026 | +++ |
| 1027 | +++ |
| 1028 | +++ |
| 1029 | +++ |
| 1030 | +++ |
| 1031 | +++ |
| 1032 | +++ |
| 1033 | +++ |
| 1034 | +++ |
| 1035 | +++ |
| 1036 | +++ |
| 1037 | +++ |
| 1038 | +++ |
| 1039 | +++ |
| 1040 | +++ |
| 1041 | +++ |
| 1042 | +++ |
| 1043 | +++ |
| 1044 | +++ |
| 1045 | +++ |
| 1046 | +++ |
| 1047 | +++ |
| 1048 | +++ |
| 1049 | +++ |
| 1050 | +++ |
| 1051 | +++ |
| 1052 | +++ |
| 1053 | +++ |
| 1054 | +++ |
| 1055 | +++ |
| 1056 | +++ |
| 1057 | +++ |
| 1058 | +++ |
| 1059 | +++ |
| 1060 | ++ |
| 1061 | +++ |
| 1062 | +++ |
| 1063 | +++ |
| 1064 | +++ |
| 1065 | +++ |
| 1066 | ++ |
| 1067 | +++ |
| 1068 | +++ |
| 1069 | +++ |
| 1070 | +++ |
| 1071 | ++ |
| 1072 | +++ |
| 1073 | ++ |
| 1074 | +++ |
| 1075 | +++ |
| 1076 | +++ |
| 1077 | ++ |
| 1078 | ++ |
| 1079 | ND |
| 1080 | ++ |
| 1081 | + |
| 1082 | ++ |
| 1083 | +++ |
| 1084 | +++ |
| 1085 | ++ |
| 1086 | +++ |
| 1087 | +++ |
| 1088 | ++ |
| 1089 | ++ |
| 1090 | +++ |
| 1090 | ++ |
| 1091 | ++ |
| 1092 | +++ |
| 1093 | ++ |
| 1094 | ++ |

TABLE 4A-continued

| Compound | eIF4E FP |
|---|---|
| 1095 | +++ |
| 1096 | +++ |
| 1097 | +++ |
| 1098 | +++ |
| 1099 | +++ |
| 1100 | +++ |
| 1101 | +++ |
| 1102 | +++ |
| 1103 | +++ |
| 1104 | ++ |
| 1105 | +++ |
| 1106 | +++ |
| 1107 | +++ |
| 1108 | +++ |
| 1109 | +++ |
| 1110 | +++ |
| 1111 | +++ |
| 1112 | +++ |
| 1113 | ++ |
| 1114 | +++ |
| 1115 | +++ |
| 1116 | +++ |
| 1117 | +++ |
| 1118 | +++ |
| 1119 | +++ |
| 1120 | +++ |
| 1121 | +++ |
| 1122 | +++ |
| 1123 | +++ |
| 1124 | +++ |
| 1125 | +++ |
| 1126 | +++ |
| 1127 | +++ |
| 1128 | +++ |
| 1129 | +++ |
| 1130 | +++ |
| 1131 | +++ |
| 1132 | +++ |
| 1133 | +++ |
| 1134 | +++ |
| 1135 | +++ |
| 1136 | +++ |
| 1137 | +++ |
| 1138 | +++ |
| 1139 | ND |
| 1140 | +++ |
| 1141 | +++ |
| 1142 | +++ |
| 1143 | +++ |
| 1144 | +++ |
| 1145 | +++ |
| 1146 | +++ |
| 1147 | +++ |
| 1148 | +++ |
| 1149 | +++ |
| 1150 | +++ |
| 1151 | +++ |
| 1152 | +++ |
| 1153 | +++ |
| 1154 | +++ |
| 1155 | +++ |
| 1156 | +++ |
| 1157 | +++ |
| 1158 | +++ |
| 1159 | +++ |
| 1160 | +++ |
| 1161 | +++ |
| 1162 | +++ |
| 1163 | +++ |
| 1164 | +++ |
| 1165 | +++ |
| 1166 | +++ |
| 1167 | +++ |
| 1168 | +++ |
| 1169 | +++ |
| 1170 | +++ |
| 1171 | +++ |

TABLE 4A-continued

| Compound | eIF4E FP |
|---|---|
| 1172 | +++ |
| 1173 | +++ |
| 1173 | +++ |
| 1174 | +++ |
| 1175 | +++ |
| 1176 | +++ |
| 1177 | +++ |
| 1178 | +++ |
| 1179 | +++ |
| 1180 | +++ |
| 1181 | +++ |
| 1182 | +++ |
| 1183 | +++ |
| 1184 | +++ |
| 1185 | +++ |
| 1186 | +++ |
| 1187 | +++ |
| 1188 | +++ |
| 1189 | +++ |
| 1190 | +++ |
| 1191 | +++ |
| 1192 | +++ |
| 1193 | +++ |
| 1194 | +++ |
| 1195 | +++ |
| 1196 | +++ |
| 1197 | +++ |
| 1198 | +++ |
| 1199 | +++ |
| 1200 | +++ |
| 1201 | +++ |
| 1202 | +++ |
| 1203 | +++ |
| 1204 | ++ |
| 1205 | ++ |
| 1206 | +++ |
| 1207 | ++ |
| 1208 | +++ |
| 1209 | ++ |
| 1210 | +++ |
| 1211 | ++ |
| 1212 | +++ |
| 1213 | +++ |
| 1214 | +++ |
| 1215 | +++ |
| 1216 | +++ |
| 1217 | +++ |
| 1218 | +++ |
| 1219 | +++ |
| 1220 | +++ |
| 1221 | +++ |
| 1222 | +++ |
| 1223 | +++ |
| 1224 | ++ |
| 1225 | +++ |
| 1226 | +++ |
| 1227 | +++ |
| 1228 | +++ |
| 1229 | +++ |
| 1230 | +++ |
| 1231 | ND |
| 1232 | +++ |
| 1233 | ND |
| 1234 | +++ |
| 1235 | +++ |
| 1236 | +++ |
| 1237 | +++ |
| 1238 | +++ |
| 1239 | +++ |
| 1240 | +++ |
| 1241 | +++ |
| 1242 | +++ |
| 1243 | +++ |
| 1244 | +++ |
| 1245 | +++ |
| 1246 | ++ |
| 1247 | +++ |

TABLE 4A-continued

| Compound | eIF4E FP |
|---|---|
| 1248 | ++ |
| 1249 | ++ |
| 1250 | ++ |

TABLE 4B

| Cmpd. | IC$_{50}$ (µM) |
|---|---|
| 1 | 0.281 |
| 2 | 3.10 |
| 3 | 4.72 |
| 4 | 3.52 |
| 5 | 7.64 |
| 6 | 7.39 |
| 7 | 12.0 |
| 8 | >30.0 |
| 9 | >30.0 |
| 10 | 6.51 |
| 11 | 6.85 |
| 12 | 2.39 |
| 13 | 1.07 |
| 14 | >3.00 |
| 15 | 1.74 |
| 16 | 46.1 |
| 17 | 0.721 |
| 18 | 0.832 |
| 19 | 0.838 |
| 20 | 1.07 |
| 21 | 0.575 |
| 22 | 0.0249 |
| 23 | 0.624 |
| 24 | 0.184 |
| 25 | 12.6 |
| 26 | 0.919 |
| 27 | 0.149 |
| 28 | 0.0616 |
| 29 | 0.211 |
| 30 | 0.164 |
| 31 | 0.751 |
| 32 | 0.190 |
| 33 | 0.203 |
| 34 | 0.0885 |
| 35 | 0.0443 |
| 36 | ND |
| 37 | 0.0396 |
| 38 | 0.0555 |
| 39 | 0.116 |
| 40 | 0.540 |
| 41 | 3.44 |
| 42 | 19.8 |
| 43 | >10.0 |
| 44 | 0.0731 |
| 45 | 2.89 |
| 46 | 0.0672 |
| 47 | 0.0224 |
| 48 | 0.631 |
| 49 | >3.00 |
| 50 | >3.00 |
| 51 | 0.0213 |
| 52 | >3.00 |
| 53 | 0.931 |
| 54 | 2.28 |
| 55 | 0.0216 |
| 56 | 0.00789 |
| 57 | 0.0128 |
| 58 | 0.0502 |
| 59 | 0.0215 |
| 60 | 0.0147 |
| 61 | 0.0265 |
| 62 | 0.0249 |
| 63 | 0.0258 |
| 64 | 0.0625 |
| 65 | 0.0241 |
| 66 | 0.187 |

TABLE 4B-continued

| Cmpd. | IC$_{50}$ (µM) |
|---|---|
| 67 | 3.22 |
| 68 | 64.3 |
| 69 | 26.8 |
| 70 | 0.432 |
| 71 | 0.636 |
| 72 | 3.10 |
| 73 | 0.0832 |
| 74 | 0.423 |
| 75 | 1.40 |
| 76 | 2.30 |
| 77 | 1.44 |
| 78 | 1.63 |
| 79 | 1.65 |
| 80 | 0.110 |
| 81 | 4.22 |
| 82 | 1.66 |
| 83 | 2.56 |
| 84 | 1.25 |
| 85 | 1.85 |
| 86 | 49.7 |
| 87 | 1.16 |
| 88 | 1.68 |
| 89 | >3.00 |
| 90 | 1.23 |
| 91 | 0.287 |
| 92 | >3.00 |
| 93 | 1.40 |
| 94 | 1.42 |
| 95 | 2.86 |
| 96 | 2.10 |
| 97 | >3.00 |
| 98 | 0.564 |
| 99 | 3.42 |
| 100 | 3.48 |
| 101 | 43.8 |
| 102 | 4.82 |
| 103 | 0.747 |
| 104 | 0.586 |
| 105 | >3.00 |
| 106 | 1.38 |
| 107 | 3.82 |
| 108 | 11.2 |
| 109 | 19.2 |
| 110 | 26.9 |
| 111 | 0.434 |
| 112 | >3.00 |
| 113 | 0.804 |
| 114 | 0.333 |
| 115 | >3.00 |
| 116 | >3.00 |
| 117 | >3.00 |
| 118 | 0.416 |
| 119 | 0.0199 |
| 120 | 0.0357 |
| 121 | 0.0375 |
| 122 | 0.0244 |
| 123 | 0.0365 |
| 124 | 9.13 |
| 125 | >3.00 |
| 126 | 8.36 |
| 127 | 0.0770 |
| 128 | 0.970 |
| 129 | 3.10 |
| 130 | 1.42 |
| 131 | 0.600 |
| 132 | 0.624 |
| 133 | 0.0665 |
| 134 | 0.116 |
| 135 | ND |
| 136 | 0.199 |
| 137 | 0.904 |
| 138 | 0.279 |
| 139 | 0.0346 |
| 140 | 0.0500 |
| 141 | 0.0442 |
| 142 | 0.152 |
| 143 | 0.0167 |
| 144 | 0.132 |

TABLE 4B-continued

| Cmpd. | IC$_{50}$ (μM) |
|---|---|
| 145 | 0.0959 |
| 146 | 0.259 |
| 147 | 0.0147 |
| 148 | 0.0205 |
| 149 | 0.110 |
| 150FA | 0.0631 |
| 150FB | 0.143 |
| 150FC | 0.124 |
| 151 | 1.05 |
| 152 | >3.00 |
| 153 | 0.0540 |
| 154 | 0.0972 |
| 155 | 0.0455 |
| 156 | 0.00420 |
| 157 | ND |
| 158 | 0.0483 |
| 159 | 0.0309 |
| 160 | 0.00883 |
| 161 | 0.0904 |
| 162 | 0.0287 |
| 163 | 0.0955 |
| 164 | 0.0164 |
| 165 | 0.106 |
| 166 | 0.0350 |
| 167 | 0.101 |
| 168 | 0.0372 |
| 169 | 0.234 |
| 170 | 0.845 |
| 171 | 0.194 |
| 172 | 0.0923 |
| 173 | 0.141 |
| 174 | 0.0521 |
| 175 | 0.0204 |
| 176 | 0.0415 |
| 177 | 0.0268 |
| 178 | 0.140 |
| 179 | 0.0206 |
| 180 | 0.0477 |
| 181 | 0.0623 |
| 182 | 0.0438 |
| 183 | 0.0502 |
| 184 | 0.144 |
| 185 | 0.0949 |
| 186 | 0.344 |
| 187 | 0.0483 |
| 188 | 0.0632 |
| 189 | 1.57 |
| 190 | 0.301 |
| 191 | 0.144 |
| 192 | 1.31 |
| 193 | 0.0209 |
| 194 | 0.0358 |
| 195 | 0.0274 |
| 196 | 0.0257 |
| 197 | 0.0524 |
| 198 | 0.124 |
| 199 | 0.143 |
| 200 | 0.0435 |
| 201 | 0.354 |
| 202 | 0.0474 |
| 203 | 0.0806 |
| 204 | 0.0444 |
| 205 | 0.101 |
| 206 | 0.229 |
| 207 | 0.0213 |
| 208 | 0.103 |
| 209 | 0.0470 |
| 210 | 0.0910 |
| 211 | 0.0354 |
| 212 | 0.0400 |
| 213 | 0.0356 |
| 214 | 0.0122 |
| 215 | 0.137 |
| 216 | 0.0628 |
| 217 | 0.0554 |
| 218 | 0.0169 |
| 219 | 0.109 |
| 220 | 0.213 |
| 221 | 0.113 |
| 222 | 0.0674 |
| 223 | 0.950 |
| 224 | 0.0110 |
| 225 | 0.147 |
| 226 | 0.0707 |
| 227 | 0.507 |
| 228 | 0.0235 |
| 229 | 0.0222 |
| 230 | 0.0149 |
| 231 | 0.0129 |
| 232 | 0.0163 |
| 233 | 0.0289 |
| 234 | 0.0185 |
| 235 | 0.0166 |
| 236 | 0.0203 |
| 237 | 0.0548 |
| 238 | 0.0380 |
| 239 | 0.0286 |
| 240 | 0.00978 |
| 241 | 0.00487 |
| 242 | 0.0203 |
| 243 | 0.0432 |
| 244 | 0.0312 |
| 245 | 0.0256 |
| 246 | 0.0430 |
| 247 | 0.0611 |
| 248 | 0.0523 |
| 249 | 0.0198 |
| 250 | 0.0437 |
| 251 | 0.0311 |
| 252 | 0.0420 |
| 253 | 0.0460 |
| 254 | 0.0204 |
| 255 | 0.0785 |
| 256 | 0.104 |
| 257 | 0.0692 |
| 258 | 0.0377 |
| 259 | >1.00 |
| 260 | 0.0204 |
| 261 | 0.0420 |
| 262 | 0.0224 |
| 263 | 0.0127 |
| 264 | 0.0246 |
| 265 | 0.0771 |
| 266 | 0.0266 |
| 267 | 0.0741 |
| 268 | 0.0341 |
| 269 | 0.0156 |
| 270 | 0.0464 |
| 271 | 0.0132 |
| 272 | 0.0229 |
| 273 | 0.0302 |
| 274 | 0.0188 |
| 275 | 0.0365 |
| 276 | 0.0228 |
| 277 | 0.0307 |
| 278 | 0.0127 |
| 279 | 0.0178 |
| 280 | 0.0412 |
| 281 | 0.0375 |
| 282 | 0.0171 |
| 283 | 0.0406 |
| 284 | 0.0196 |
| 285 | 0.0725 |
| 286 | 0.183 |
| 287 | 0.0478 |
| 288 | 0.0461 |
| 289 | 0.0191 |
| 290 | 0.0427 |
| 291 | 0.0995 |
| 292 | 0.203 |
| 293 | 0.0639 |
| 294 | 0.0229 |
| 295 | 0.167 |
| 296 | 0.0375 |
| 297 | 0.0363 |
| 298 | 0.101 |

TABLE 4B-continued

| Cmpd. | IC$_{50}$ (μM) |
|---|---|
| 299 | 0.0223 |
| 300 | 0.0243 |
| 301 | 0.0576 |
| 302 | 0.0776 |
| 303 | 0.498 |
| 304 | 1.60 |
| 305 | 0.431 |
| 306 | 0.0912 |
| 307 | 0.0594 |
| 308 | 0.811 |
| 309 | 0.0525 |
| 310 | 0.0977 |
| 311 | 0.0555 |
| 312 | 0.0756 |
| 313 | 0.0345 |
| 314 | 0.0428 |
| 315 | 0.582 |
| 316 | 0.0204 |
| 317 | 0.0171 |
| 318 | 0.00292 |
| 319 | 0.0535 |
| 320 | 0.0435 |
| 321 | 0.00489 |
| 322 | 0.116 |
| 323 | 0.0826 |
| 324 | 0.0933 |
| 325 | 0.0520 |
| 326 | 1.44 |
| 327 | 0.0437 |
| 328 | 1.32 |
| 329 | 0.0464 |
| 330 | 0.0477 |
| 331 | ND |
| 332 | 0.0377 |
| 333 | 0.0249 |
| 334 | 0.0104 |
| 335 | 0.0569 |
| 336 | 0.0279 |
| 337 | 0.0257 |
| 338 | 0.0453 |
| 339 | 0.0268 |
| 340 | 0.00501 |
| 341 | 0.0450 |
| 342 | 0.0474 |
| 343 | 0.0418 |
| 344 | 0.0321 |
| 345a | 0.0432 |
| 345b | 0.0253 |
| 346 | 0.0181 |
| 347 | 0.0321 |
| 348 | 0.0154 |
| 349 | 0.00584 |
| 350 | 0.0142 |
| 351a | 0.885 |
| 351b | 0.0936 |
| 352 | 1.27 |
| 353 | 0.101 |
| 354 | >1.00 |
| 355 | 0.146 |
| 356 | 1.22 |
| 357 | 0.0477 |
| 358 | 0.0863 |
| 359 | 0.0489 |
| 360 | 0.0426 |
| 361 | 0.0684 |
| 362 | 0.0722 |
| 363 | 0.0228 |
| 364 | 0.107 |
| 365 | 0.0190 |
| 366 | 0.00666 |
| 367 | 0.00287 |
| 368 | 0.0411 |
| 369 | 0.00132 |
| 370 | 0.0121 |
| 371 | 0.0200 |
| 372 | 0.00734 |
| 373 | 0.00643 |
| 374 | 0.0205 |
| 375 | 0.0580 |
| 376 | 0.0127 |
| 377 | 0.0612 |
| 378 | 0.0451 |
| 379 | 0.0267 |
| 380 | 0.0297 |
| 381 | ND |
| 382 | ND |
| 383 | ND |
| 384 | 0.0209 |
| 385 | 0.0395 |
| 386 | 0.0254 |
| 387 | 0.619 |
| 388 | 0.00629 |
| 389 | 0.0123 |
| 390 | 0.00175 |
| 391 | 0.00352 |
| 392 | 0.0251 |
| 393 | 0.0118 |
| 394 | 0.0218 |
| 395 | 0.00968 |
| 396 | 0.0181 |
| 397 | 0.0105 |
| 398 | 0.149 |
| 399 | 0.0699 |
| 400 | 0.00468 |
| 401 | 0.0474 |
| 402 | 0.124 |
| 403 | 0.0126 |
| 404 | 0.0101 |
| 405 | 0.0197 |
| 406 | 0.0114 |
| 407 | 0.0331 |
| 408 | 0.0311 |
| 409 | 0.0133 |
| 410 | 0.0626 |
| 411 | 0.193 |
| 412 | 0.0701 |
| 413 | 0.0346 |
| 414 | 0.0205 |
| 415 | 0.0143 |
| 416 | 0.0230 |
| 417 | 0.0197 |
| 418 | 0.00907 |
| 419 | 0.00108 |
| 420 | 0.00960 |
| 421 | 0.0171 |
| 422 | 0.0115 |
| 423 | 0.00884 |
| 424 | 0.00408 |
| 425 | 0.0112 |
| 426 | 0.0412 |
| 427 | 0.0250 |
| 428 | 0.00745 |
| 429 | 0.0382 |
| 430 | 0.00900 |
| 431 | 0.226 |
| 432 | 0.0258 |
| 433 | 0.00415 |
| 434 | 0.00776 |
| 435 | 0.0167 |
| 436 | 0.00717 |
| 437 | 0.00621 |
| 438 | 0.00916 |
| 439a | 0.00287 |
| 439b | 0.0320 |
| 440 | 0.00499 |
| 441 | 0.0204 |
| 442 | 0.0177 |
| 443 | 0.128 |
| 444 | 0.0308 |
| 445 | 0.0931 |
| 446 | 0.0573 |
| 447 | 0.0848 |
| 448 | 0.00420 |
| 449 | 0.0196 |
| 450 | 0.00784 |
| 451 | 0.0360 |

TABLE 4B-continued

| Cmpd. | IC$_{50}$ (μM) |
|---|---|
| 452 | 0.0466 |
| 453 | 2.32 |
| 454 | 0.0511 |
| 455 | 0.473 |
| 456 | 0.0109 |
| 457 | 0.0112 |
| 458 | 0.0368 |
| 459 | 0.0415 |
| 460 | 0.0255 |
| 461 | 0.00615 |
| 462 | 0.0105 |
| 463 | 0.00886 |
| 464 | 0.0214 |
| 465 | 0.0151 |
| 466 | 0.00930 |
| 467 | 0.0180 |
| 468 | 0.00436 |
| 469 | 0.00225 |
| 470 | 0.0128 |
| 471 | 0.0288 |
| 472 | 0.0236 |
| 473 | 0.0145 |
| 474 | 0.0135 |
| 475 | 0.0170 |
| 476 | 0.0339 |
| 477 | 0.00973 |
| 478 | 0.0132 |
| 479 | 0.0135 |
| 480 | 0.00739 |
| 481 | 0.0105 |
| 482 | 0.0354 |
| 483 | 0.0421 |
| 484 | 0.0116 |
| 485 | 0.00859 |
| 486 | 0.0305 |
| 487 | 0.114 |
| 488 | 0.0265 |
| 489 | 0.0208 |
| 490 | 0.178 |
| 491 | 0.0229 |
| 492 | 0.0297 |
| 493 | 0.0942 |
| 494 | 0.0856 |
| 495 | 0.237 |
| 496 | 1.06 |
| 497 | 0.0397 |
| 498 | 0.0242 |
| 499 | >1.00 |
| 500 | 0.0365 |
| 501 | 0.0257 |
| 502 | 0.0384 |
| 503 | 0.00867 |
| 504 | 0.0229 |
| 505 | 0.0436 |
| 506 | 0.0689 |
| 507 | 0.0490 |
| 508 | 0.0152 |
| 509 | 0.125 |
| 510 | 0.0505 |
| 511 | 0.0880 |
| 512 | 0.0718 |
| 513 | 0.0116 |
| 514 | 0.0399 |
| 515 | 0.0460 |
| 516 | 0.0344 |
| 517 | 0.0357 |
| 518 | 0.0164 |
| 519 | 0.0378 |
| 520 | 0.0183 |
| 521 | 0.623 |
| 522 | 0.0227 |
| 523 | 0.0239 |
| 524 | 0.0128 |
| 525 | 0.0347 |
| 526 | 0.0641 |
| 527 | 0.0248 |
| 528 | 0.0271 |
| 529 | 0.00578 |
| 530 | 0.00665 |
| 531 | 0.0429 |
| 532 | 0.0451 |
| 533 | 0.0627 |
| 534 | 0.0302 |
| 535 | 0.244 |
| 536 | 0.0488 |
| 537 | 0.0466 |
| 538 | 0.0223 |
| 539 | 0.0472 |
| 540 | 0.0140 |
| 541 | 0.0491 |
| 542 | 0.0202 |
| 543 | 0.0382 |
| 544 | 0.0282 |
| 545 | 0.00781 |
| 546 | 0.0436 |
| 547 | 0.134 |
| 548 | 0.0472 |
| 549 | 0.0193 |
| 550 | 0.0878 |
| 551 | 0.0292 |
| 552 | 0.0509 |
| 553 | 0.0134 |
| 554 | 0.0318 |
| 555 | 0.0108 |
| 556 | 0.0227 |
| 557 | 0.00640 |
| 558 | 0.0272 |
| 559 | 0.00869 |
| 560 | 0.00477 |
| 561 | 0.0562 |
| 562 | 0.00878 |
| 563 | 0.0144 |
| 564 | 0.0405 |
| 565 | 0.0297 |
| 566 | 0.0164 |
| 567 | 0.0117 |
| 568 | 0.0141 |
| 569 | 0.00200 |
| 570 | 0.00557 |
| 571 | 0.0548 |
| 572 | 0.0306 |
| 573 | 0.0547 |
| 574 | 0.0575 |
| 575 | 0.0257 |
| 576 | 0.0177 |
| 577 | 0.0394 |
| 578 | 0.0320 |
| 579 | 0.0302 |
| 580 | 0.0242 |
| 581 | 0.00608 |
| 582 | 0.0127 |
| 583 | 0.0159 |
| 584 | 0.0235 |
| 585 | 0.0296 |
| 586 | 0.0500 |
| 587 | 0.0255 |
| 588 | 0.0493 |
| 589 | 0.00445 |
| 590 | 0.00226 |
| 591 | 0.0449 |
| 592 | 0.0103 |
| 593 | 0.0329 |
| 594 | 1.35 |
| 595 | 0.0248 |
| 596 | 0.0377 |
| 597 | 0.0468 |
| 598 | 0.0572 |
| 599 | 0.0616 |
| 600 | 0.0142 |
| 601 | 0.0520 |
| 602 | 0.0102 |
| 603 | 0.0117 |
| 604 | 0.0707 |
| 605 | ND |
| 606 | 0.00412 |
| 607 | 0.00550 |

TABLE 4B-continued

| Cmpd. | IC$_{50}$ (µM) |
|---|---|
| 608 | 0.0186 |
| 609 | 0.0331 |
| 610 | 0.0139 |
| 611 | 0.00776 |
| 612 | 0.0438 |
| 613 | 0.00789 |
| 614 | 0.167 |
| 615 | 0.0163 |
| 616 | 0.00245 |
| 617 | 0.0397 |
| 618 | 0.00298 |
| 619 | 0.00634 |
| 620 | 0.0369 |
| 621 | 0.0600 |
| 622 | 0.0438 |
| 623 | 0.00477 |
| 624 | 0.00402 |
| 625 | 0.0780 |
| 626 | 0.0104 |
| 627 | 0.00672 |
| 628 | 0.0285 |
| 629 | 0.00639 |
| 630 | 0.0502 |
| 631 | 0.00341 |
| 632 | 0.0120 |
| 633 | 0.0129 |
| 634 | 0.00562 |
| 635 | 0.0106 |
| 636 | 0.0332 |
| 637 | 0.0166 |
| 638 | 0.00446 |
| 639 | 0.00157 |
| 640 | 0.0240 |
| 641 | 0.0333 |
| 642 | 0.00363 |
| 643 | 0.000832 |
| 644 | 0.00497 |
| 645 | 0.0313 |
| 646 | 0.0414 |
| 647 | 0.0198 |
| 648 | 0.0246 |
| 649 | 0.0150 |
| 650 | 0.0283 |
| 651 | 0.0218 |
| 652 | 0.00668 |
| 653 | 0.0227 |
| 654 | 0.00312 |
| 655 | 0.0135 |
| 656 | 0.0334 |
| 657 | 0.0457 |
| 658 | 1.29 |
| 659 | 0.0264 |
| 660 | 0.258 |
| 661 | 0.0121 |
| 662 | 0.144 |
| 663 | 0.332 |
| 664 | 0.153 |
| 665 | 0.0165 |
| 666 | 0.268 |
| 667 | 0.0467 |
| 668 | 0.00776 |
| 669 | 0.0364 |
| 670 | 0.0180 |
| 671 | 0.0777 |
| 672 | 0.106 |
| 673 | 0.0253 |
| 674 | 0.00927 |
| 675 | 0.00777 |
| 676 | 0.00622 |
| 677 | 0.00544 |
| 678 | 0.0538 |
| 679 | 0.160 |
| 680 | 0.0566 |
| 681 | 0.0174 |
| 682 | 0.00621 |
| 683 | 0.0403 |
| 684 | 0.0150 |
| 685 | 0.0176 |
| 686 | 0.0265 |
| 687 | 0.0135 |
| 688 | 0.0228 |
| 689 | 0.0115 |
| 690 | 0.00595 |
| 691 | 0.00717 |
| 692 | 0.00597 |
| 693 | 0.0150 |
| 694 | 0.0191 |
| 695 | 0.00105 |
| 696 | 0.00894 |
| 697 | 0.0102 |
| 698 | 0.00340 |
| 699 | 0.0121 |
| 700 | 0.0224 |
| 701 | 0.0192 |
| 702 | 0.0127 |
| 703 | 0.00318 |
| 704 | 0.0890 |
| 705 | 0.0191 |
| 706 | 0.140 |
| 707 | 0.0178 |
| 708 | 0.0878 |
| 709 | 0.0567 |
| 710 | 0.0316 |
| 711 | 0.0775 |
| 712 | 0.0196 |
| 713 | 0.0314 |
| 714 | 0.0472 |
| 715 | ND |
| 716 | ND |
| 717 | 0.0730 |
| 718 | 0.0201 |
| 719 | 0.0285 |
| 720 | 0.199 |
| 721 | 0.0206 |
| 722 | 0.0380 |
| 723 | 0.0287 |
| 724 | 0.0377 |
| 725 | 0.0382 |
| 726 | 0.0530 |
| 727 | 0.0294 |
| 728 | 0.0310 |
| 729 | 0.0925 |
| 730 | 0.0510 |
| 731 | 0.00597 |
| 732 | 0.874 |
| 733 | 1.73 |
| 734 | 0.00468 |
| 735 | 0.0580 |
| 736 | 0.0170 |
| 737 | 0.0123 |
| 738 | 0.0193 |
| 739 | 0.0308 |
| 740 | 0.0392 |
| 741 | 0.0152 |
| 742 | 0.0325 |
| 743 | 0.188 |
| 744 | 0.0133 |
| 745 | 0.0333 |
| 746 | 0.0367 |
| 747 | 0.0189 |
| 748 | 0.0163 |
| 749 | >100 |
| 750 | 0.0415 |
| 751 | 0.0698 |
| 752 | 0.0276 |
| 753 | 0.0138 |
| 754 | 0.0172 |
| 755 | 0.0101 |
| 756 | 0.0432 |
| 757 | 0.137 |
| 758 | 0.0131 |
| 759 | 0.0529 |
| 760 | 0.00644 |
| 761 | 0.0258 |
| 762 | 0.0337 |
| 763 | 0.00519 |

TABLE 4B-continued

| Cmpd. | IC$_{50}$ (μM) |
|---|---|
| 764 | 0.0106 |
| 765 | 0.00919 |
| 766 | 0.0451 |
| 767 | 0.00751 |
| 768 | 0.0224 |
| 769 | 0.0239 |
| 770 | 0.0140 |
| 771 | 0.0128 |
| 772 | 0.0141 |
| 773 | 0.0102 |
| 774 | 0.00829 |
| 775 | 0.0483 |
| 776 | 0.0365 |
| 777 | 0.0533 |
| 778 | 0.0000702 |
| 779 | 0.00954 |
| 780 | 0.00960 |
| 781 | 0.00312 |
| 782 | 0.00403 |
| 783 | 0.0148 |
| 784 | 0.0137 |
| 785 | 0.0182 |
| 786 | 0.0192 |
| 787 | 0.0109 |
| 788Fa | 1.94 |
| 788Fb | 0.00435 |
| 789 | 0.00896 |
| 790 | 0.0178 |
| 791 | 0.00359 |
| 792 | 0.00244 |
| 793 | 0.00481 |
| 794 | 0.00341 |
| 795 | 0.0121 |
| 796 | 0.00327 |
| 797 | 0.00679 |
| 798 | 0.00986 |
| 799 | 0.00935 |
| 800 | 0.0324 |
| 801 | 0.0170 |
| 802 | 0.0359 |
| 803 | 0.161 |
| 804 | 0.0188 |
| 805 | 0.0136 |
| 806 | 0.00358 |
| 807 | 0.0210 |
| 808 | 0.0524 |
| 809 | 0.0160 |
| 810 | 0.00547 |
| 811 | 0.157 |
| 812 | 0.0300 |
| 813 | 0.00404 |
| 814 | ND |
| 815 | 0.00331 |
| 816 | 0.00687 |
| 817 | 0.00724 |
| 818 | 0.0131 |
| 819 | 0.0282 |
| 820 | 0.0136 |
| 821 | 0.0142 |
| 822 | 0.0107 |
| 823 | 0.0115 |
| 824 | 0.0136 |
| 825 | 0.0143 |
| 826 | 0.0124 |
| 827 | 0.00572 |
| 828 | 0.00572 |
| 829 | 0.00453 |
| 830 | 0.0128 |
| 831 | 0.0123 |
| 832 | ND |
| 833 | 0.111 |
| 834 | 0.0316 |
| 835 | 0.0293 |
| 836 | 0.00233 |
| 837 | 0.0134 |
| 838 | 0.0387 |
| 839 | 0.0296 |
| 840 | 0.0104 |

TABLE 4B-continued

| Cmpd. | IC$_{50}$ (μM) |
|---|---|
| 841 | >1.00 |
| 842 | 0.0209 |
| 843 | 0.0131 |
| 844 | 0.0233 |
| 845 | 0.0127 |
| 846 | 0.0379 |
| 847 | 0.0440 |
| 848 | 0.0269 |
| 849 | 0.0145 |
| 850 | 0.0177 |
| 851 | 0.00602 |
| 852 | 0.0214 |
| 853 | 0.0319 |
| 854 | 0.0119 |
| 855 | 0.00477 |
| 856 | 0.0137 |
| 857 | 0.00462 |
| 858 | 0.00728 |
| 859 | 0.00559 |
| 860 | 0.0103 |
| 861 | 0.0246 |
| 862 | 0.0209 |
| 863 | 0.0455 |
| 864 | 0.0479 |
| 865 | 0.0284 |
| 866 | 0.0168 |
| 867 | 0.00661 |
| 868 | 0.0172 |
| 869 | 0.0254 |
| 870 | 0.140 |
| 871 | 0.0164 |
| 872 | 0.0204 |
| 873 | 0.0157 |
| 874 | 0.0415 |
| 875 | ND |
| 876 | 0.0733 |
| 877 | 0.234 |
| 878 | 0.00963 |
| 879 | 0.00731 |
| 880 | 0.0679 |
| 881 | 0.0204 |
| 882 | 0.00662 |
| 883 | 0.0128 |
| 884 | 0.00585 |
| 885 | 0.0307 |
| 886 | 0.0105 |
| 887 | 0.0201 |
| 888 | 0.0402 |
| 889 | 0.0124 |
| 890 | 0.0125 |
| 891 | 0.0137 |
| 892 | 0.0360 |
| 893 | 0.0201 |
| 894 | 0.0216 |
| 895 | 0.0229 |
| 896 | 0.00157 |
| 897 | 0.00140 |
| 898 | 0.0325 |
| 899 | 0.00744 |
| 900 | 0.0112 |
| 901 | 0.0456 |
| 902 | 0.0142 |
| 903 | 0.0112 |
| 904 | 0.00419 |
| 905 | 0.00938 |
| 906 | 0.0176 |
| 907 | 0.00776 |
| 908 | 0.00326 |
| 909 | 0.0132 |
| 910 | 0.0175 |
| 911 | 0.0171 |
| 912 | 0.00898 |
| 913 | 0.0162 |
| 914 | 0.0207 |
| 915 | 0.0184 |
| 916 | 0.00481 |
| 917 | 0.0110 |
| 918 | 0.00437 |

TABLE 4B-continued

| Cmpd. | IC$_{50}$ (μM) |
|---|---|
| 919 | 0.0177 |
| 920 | 0.00576 |
| 921 | 0.0696 |
| 922 | 0.0894 |
| 923 | 0.00371 |
| 924 | 0.0143 |
| 925 | 0.0431 |
| 926 | 0.0183 |
| 927 | 0.00634 |
| 928 | 0.0387 |
| 929 | 0.0225 |
| 930 | 0.00688 |
| 931 | 0.0137 |
| 932 | 0.0178 |
| 933 | 0.122 |
| 934 | 0.0136 |
| 935 | 0.0196 |
| 936 | ND |
| 937 | 0.00136 |
| 938 | 0.00244 |
| 939 | 0.0121 |
| 940 | 0.470 |
| 941 | 0.0200 |
| 942 | 0.00693 |
| 943 | 0.0147 |
| 944 | 0.0462 |
| 945 | 0.0389 |
| 946 | 0.0277 |
| 947 | 0.0237 |
| 948 | 0.0183 |
| 949 | 0.0373 |
| 950 | 0.0172 |
| 951 | 0.0436 |
| 952 | 0.0450 |
| 953 | 0.0134 |
| 954 | 0.00829 |
| 955 | 0.0102 |
| 956 | 0.0165 |
| 957 | 0.00581 |
| 958 | 0.0135 |
| 959 | 0.0148 |
| 960 | 0.0396 |
| 961 | 0.0211 |
| 962 | 0.00315 |
| 963 | 0.00784 |
| 964 | 0.00332 |
| 965 | 0.118 |
| 966 | 0.00358 |
| 967 | 0.0122 |
| 968 | 0.00895 |
| 969 | 0.00556 |
| 970 | 0.166 |
| 971 | 0.0578 |
| 972 | 0.00977 |
| 973 | 0.0850 |
| 974 | 0.0236 |
| 975 | 0.0148 |
| 976 | 0.0190 |
| 977 | 0.0144 |
| 978 | 0.0207 |
| 979 | 0.00948 |
| 980 | 0.0156 |
| 981 | 0.0416 |
| 982 | 0.0204 |
| 983 | 0.0189 |
| 984 | 0.0115 |
| 985 | 0.00669 |
| 986 | 0.0169 |
| 987 | 0.0136 |
| 988 | 0.0219 |
| 989 | 0.0198 |
| 990 | 0.0322 |
| 991 | 0.0121 |
| 992 | 0.0561 |
| 993 | 0.0156 |
| 994 | 0.0234 |
| 995 | 0.0157 |
| 996 | 0.0316 |
| 997 | 0.0122 |
| 998 | 0.0451 |
| 999 | 0.0163 |
| 1000 | 0.0167 |
| 1001 | 0.0312 |
| 1002 | 0.00237 |
| 1003 | 0.0134 |
| 1004 | 0.0225 |
| 1005 | 0.0334 |
| 1006 | 0.0182 |
| 1007 | 0.0482 |
| 1008 | 0.0153 |
| 1009 | 0.00623 |
| 1010 | 0.00529 |
| 1011 | 0.00715 |
| 1012 | 0.00894 |
| 1013 | 0.0185 |
| 1014 | 0.0256 |
| 1015 | 0.0197 |
| 1016 | 0.00111 |
| 1017 | 0.00826 |
| 1018 | 0.00671 |
| 1019 | 0.0308 |
| 1020 | 0.0234 |
| 1021 | 0.0211 |
| 1022 | 0.0424 |
| 1023 | 0.0498 |
| 1024 | 0.0242 |
| 1025 | 0.0300 |
| 1026 | 0.0155 |
| 1027 | 0.0315 |
| 1028 | 0.00614 |
| 1029 | 0.00766 |
| 1030 | 0.0144 |
| 1031 | 0.0116 |
| 1032 | 0.00620 |
| 1033 | 0.0200 |
| 1034 | 0.0379 |
| 1035 | 0.0197 |
| 1036 | 0.00351 |
| 1037 | 0.0119 |
| 1038 | 0.0389 |
| 1039 | 0.0217 |
| 1040 | 0.0300 |
| 1041 | 0.00621 |
| 1042 | 0.0265 |
| 1043 | 0.00398 |
| 1044 | 0.00531 |
| 1045 | 0.0382 |
| 1046 | 0.0380 |
| 1047 | 0.0212 |
| 1048 | 0.0137 |
| 1049 | 0.00935 |
| 1050 | 0.0195 |
| 1051 | 0.00502 |
| 1052 | 0.00546 |
| 1053 | 0.00508 |
| 1054 | 0.0186 |
| 1055 | 0.0117 |
| 1056 | 0.0161 |
| 1057 | 0.0125 |
| 1058 | 0.0397 |
| 1059 | 0.0111 |
| 1060 | 0.0509 |
| 1061 | 0.00854 |
| 1062 | 0.00663 |
| 1063 | 0.0312 |
| 1064 | 0.0162 |
| 1065 | 0.0186 |
| 1066 | 0.0574 |
| 1067 | 0.0105 |
| 1068 | 0.0278 |
| 1069 | 0.00152 |
| 1070 | 0.0320 |
| 1071 | 0.0540 |
| 1072 | 0.0372 |
| 1073 | 0.0581 |
| 1074 | 0.0174 |

TABLE 4B-continued

| Cmpd. | IC$_{50}$ (μM) |
|---|---|
| 1075 | 0.00664 |
| 1076 | 0.0245 |
| 1077 | 0.245 |
| 1078 | 0.347 |
| 1079 | 0.0559 |
| 1080 | 0.105 |
| 1081 | 1.04 |
| 1082 | 0.903 |
| 1083 | 0.0440 |
| 1084 | 0.0150 |
| 1085 | 0.0543 |
| 1086 | 0.0384 |
| 1087 | 0.0392 |
| 1088 | 0.0533 |
| 1089 | 0.618 |
| 1090a | 0.0383 |
| 1090b | 0.503 |
| 1091 | 0.0914 |
| 1092 | 0.0427 |
| 1093 | 0.0586 |
| 1094 | 0.0716 |
| 1095 | 0.0465 |
| 1096 | 0.0335 |
| 1097 | 0.0388 |
| 1098 | 0.0156 |
| 1099 | 0.0375 |
| 1100 | 0.0335 |
| 1101 | 0.00720 |
| 1102 | 0.0192 |
| 1103 | 0.0148 |
| 1104 | 0.631 |
| 1105 | 0.0217 |
| 1106 | 0.0174 |
| 1107 | 0.0105 |
| 1108 | 0.0291 |
| 1109 | 0.0134 |
| 1110 | 0.00720 |
| 1111 | 0.00571 |
| 1112 | 0.0199 |
| 1113 | 0.140 |
| 1114 | 0.0499 |
| 1115 | 0.00677 |
| 1116 | 0.0171 |
| 1117 | 0.0134 |
| 1118 | 0.0140 |
| 1119 | 0.0146 |
| 1120 | 0.00951 |
| 1121 | 0.00926 |
| 1122 | 0.0146 |
| 1123 | 0.0215 |
| 1124 | 0.0132 |
| 1125 | 0.0145 |
| 1126 | 0.0266 |
| 1127 | 0.0129 |
| 1128 | 0.0239 |
| 1129 | 0.0107 |
| 1130 | 0.00439 |
| 1131 | 0.0147 |
| 1132 | 0.0133 |
| 1133 | 0.0170 |
| 1134 | 0.0153 |
| 1135 | 0.0343 |
| 1136 | 0.0170 |
| 1137 | 0.0174 |
| 1138 | 0.0237 |
| 1139 | ND |
| 1140 | 0.00614 |
| 1141 | 0.0189 |
| 1142 | 0.0130 |
| 1143 | 0.0246 |
| 1144 | 0.0344 |
| 1145 | 0.0331 |
| 1146 | 0.0144 |
| 1147 | 0.0446 |
| 1148 | 0.0356 |
| 1149 | 0.00419 |
| 1150 | 0.00460 |
| 1151 | 0.0190 |
| 1152 | 0.00380 |
| 1153 | 0.0380 |
| 1154 | 0.0140 |
| 1155 | 0.0181 |
| 1156 | 0.0351 |
| 1157 | 0.0220 |
| 1158 | 0.0158 |
| 1159 | 0.0147 |
| 1160 | 0.0172 |
| 1161 | 0.0195 |
| 1162 | 0.0216 |
| 1163 | 0.0248 |
| 1164 | 0.0267 |
| 1165 | 0.0223 |
| 1166 | 0.0286 |
| 1167 | 0.0173 |
| 1168 | 0.0130 |
| 1169 | 0.0153 |
| 1170 | 0.0171 |
| 1171 | 0.0130 |
| 1172 | 0.0142 |
| 1173a | 0.0192 |
| 1173b | 0.0130 |
| 1174 | 0.00932 |
| 1175 | 0.0221 |
| 1176 | 0.0343 |
| 1177 | 0.0342 |
| 1178 | 0.0229 |
| 1179 | 0.0147 |
| 1180 | 0.0162 |
| 1181 | 0.0137 |
| 1182 | 0.0136 |
| 1183 | 0.0232 |
| 1184 | 0.00932 |
| 1185 | 0.0176 |
| 1186 | 0.0201 |
| 1187 | 0.0186 |
| 1188 | 0.0124 |
| 1189 | 0.0134 |
| 1190 | 0.00730 |
| 1191 | 0.0128 |
| 1192 | 0.0488 |
| 1193 | 0.0102 |
| 1194 | 0.0153 |
| 1195 | 0.0131 |
| 1196 | 0.0306 |
| 1197 | 0.00593 |
| 1198 | 0.0130 |
| 1199 | 0.0182 |
| 1200 | 0.0148 |
| 1201 | 0.0228 |
| 1202 | 0.0197 |
| 1203 | 0.00915 |
| 1204 | 0.150 |
| 1205 | 0.199 |
| 1206 | 0.0325 |
| 1207 | 0.121 |
| 1208 | 0.0489 |
| 1209 | 0.0980 |
| 1210 | 0.0483 |
| 1211 | >1.00 |
| 1212 | 0.0442 |
| 1213 | 0.0427 |
| 1214 | 0.00508 |
| 1215 | 0.0257 |
| 1216 | 0.0103 |
| 1217 | 0.0242 |
| 1218 | 0.0131 |
| 1219 | 0.00399 |
| 1220 | 0.0131 |
| 1221 | 0.0300 |
| 1222 | 0.00302 |
| 1223 | 0.00279 |
| 1224 | 0.0760 |
| 1225 | 0.00312 |
| 1226 | 0.00663 |
| 1227 | 0.0128 |
| 1228 | 0.00111 |

TABLE 4B-continued

| Cmpd. | IC$_{50}$ (μM) |
|---|---|
| 1229 | 0.0107 |
| 1230 | 0.0103 |
| 1231 | ND |
| 1232 | 0.00449 |
| 1233 | ND |
| 1234 | 0.0302 |
| 1235 | 0.00632 |
| 1236 | 0.0339 |
| 1237 | 0.00668 |
| 1238 | 0.0130 |
| 1239 | 0.0182 |
| 1240 | 0.0155 |
| 1241 | 0.0173 |
| 1242 | 0.00885 |
| 1243 | 0.00555 |
| 1244 | 0.0194 |
| 1245 | 0.0156 |
| 1246 | 0.106 |
| 1247 | 0.0355 |
| 1248 | 0.0607 |
| 1249 | 0.0759 |
| 1250 | 0.0758 |
| 1251 | 0.00477 |
| 1252 | 0.222 |
| 1253 | 0.00840 |
| 1254 | 0.0265 |
| 1255 | 0.150 |
| 1256 | 0.0247 |
| 1257 | 0.0525 |
| 1258 | 0.0615 |
| 1259 | 0.00538 |
| 1260 | 0.0130 |
| 1261 | 0.0336 |
| 1262 | 0.0106 |
| 1263 | 0.0106 |
| 1264 | 0.0124 |
| 1265 | 0.0115 |
| 1266 | 0.00907 |
| 1267 | >1.00 |
| 1268 | 0.472 |
| 1269 | 0.0666 |
| 1270 | 0.0399 |
| 1271 | 0.0131 |
| 1272 | 0.0281 |
| 1273 | 0.00748 |
| 1274 | 0.0402 |
| 1275 | 0.0587 |
| 1276 | 0.0135 |
| 1277 | 0.0384 |
| 1278 | 0.0106 |
| 1279 | 0.00891 |
| 1280 | 0.00426 |
| 1281 | 0.117 |
| 1282 | 0.0382 |
| 1283 | 0.0335 |
| 1284 | >1.00 |
| 1285 | 0.0413 |
| 1286 | 0.0342 |
| 1287 | 0.0424 |
| 1288 | 0.0367 |
| 1289 | 0.0140 |
| 1290 | 0.149 |
| 1291 | 0.0412 |
| 1292 | 0.0523 |
| 1293 | 0.0351 |
| 1294 | 0.0559 |
| 1295 | 0.0134 |
| 1296 | 0.0270 |
| 1297 | 0.0378 |
| 1298 | 0.0383 |
| 1299 | 0.0321 |
| 1300 | 0.0181 |
| 1301 | 0.0155 |
| 1302 | 0.0307 |
| 1303 | 0.0366 |
| 1304 | 0.0185 |
| 1305 | 0.0265 |
| 1306 | 0.0389 |
| 1307 | 0.0542 |
| 1308 | 0.0415 |
| 1309 | 0.0372 |
| 1310 | 0.0213 |
| 1311 | 0.0133 |
| 1312 | 0.00829 |
| 1313 | 0.0426 |
| 1314 | 0.0181 |
| 1315 | 0.0131 |
| 1316 | 0.0328 |
| 1317 | 0.0335 |
| 1318 | 0.0344 |
| 1319 | 0.0136 |
| 1320 | 0.0277 |
| 1321 | 0.0602 |
| 1322 | 0.0112 |
| 1323 | 0.0730 |
| 1324 | 0.0237 |
| 1325 | 0.0271 |
| 1326 | 0.0128 |
| 1327 | 0.0193 |
| 1328 | 0.0248 |
| 1329 | 0.0352 |
| 1330 | 0.0130 |
| 1331 | 0.0918 |
| 1332 | 0.0345 |
| 1333 | 0.0262 |
| 1334 | 0.0513 |
| 1335 | 0.0128 |
| 1336 | 0.0130 |
| 1337 | 0.0519 |
| 1338 | 0.00950 |
| 1339 | 0.0364 |
| 1340 | 0.0442 |
| 1341 | 0.0215 |
| 1342 | 0.0304 |
| 1343 | 0.0406 |
| 1344 | 0.0183 |
| 1345 | 0.0345 |
| 1346 | 0.0197 |
| 1347 | 0.0414 |
| 1348 | 0.0122 |
| 1349 | 0.0365 |
| 1350 | 0.0351 |
| 1351 | 0.0160 |
| 1352 | 0.0216 |
| 1353 | 0.0172 |
| 1354 | 0.0216 |
| 1355 | 0.0248 |
| 1356 | 0.0232 |
| 1357 | 0.0159 |
| 1358 | 0.0183 |
| 1359 | 0.0397 |
| 1360 | 0.0168 |
| 1361 | 0.0213 |
| 1362 | 0.0141 |
| 1363 | 0.0429 |
| 1364 | 0.0247 |
| 1365 | 0.0341 |
| 1366 | 0.0143 |
| 1367 | 0.0149 |
| 1368 | 0.0199 |
| 1369 | 0.0132 |
| 1370 | 0.0199 |
| 1371 | 0.0151 |
| 1372 | 0.0807 |
| 1373 | 0.0267 |
| 1374 | 0.0561 |
| 1375 | 0.0839 |
| 1376 | 0.0136 |
| 1377 | 0.0440 |
| 1378 | 0.0300 |
| 1379 | 0.0180 |
| 1380 | 0.0266 |
| 1381 | 0.00796 |
| 1382 | 0.0216 |
| 1383 | 0.00503 |
| 1384 | 0.00686 |

TABLE 4B-continued

| Cmpd. | IC$_{50}$ (μM) |
|---|---|
| 1385 | 0.00724 |
| 1386 | 0.0128 |
| 1387 | 0.0228 |
| 1388 | 0.0362 |
| 1389 | 1.19 |
| 1390 | ND |
| 1391 | 0.0376 |
| 1392 | 0.0265 |
| 1393 | 0.0132 |
| 1394 | 0.00474 |
| 1395 | 0.0296 |
| 1396 | 0.0195 |
| 1397 | 0.0147 |
| 1398 | 0.0140 |
| 1399 | 0.0144 |
| 1400 | 0.0278 |
| 1401 | 0.0127 |
| 1402 | 0.00658 |
| 1403 | 0.00876 |
| 1404 | 0.482 |
| 1405 | 0.631 |
| 1406 | 0.0266 |
| 1407 | 0.0247 |
| 1408 | 0.0176 |
| 1409 | 0.0108 |
| 1410 | 0.0180 |
| 1411 | 0.0175 |
| 1412 | 0.00671 |
| 1413 | 0.0517 |
| 1414 | 0.0153 |
| 1415 | 0.0168 |
| 1416 | 0.0127 |
| 1417 | 0.0249 |
| 1418 | 0.00910 |
| 1419 | 0.00676 |
| 1420 | 0.00633 |
| 1421 | 0.0366 |
| 1422 | 0.0335 |
| 1423 | 0.0232 |
| 1424 | 0.0292 |
| 1425 | 0.0130 |
| 1426 | 0.0117 |
| 1427 | 0.0143 |
| 1428 | 0.0122 |
| 1429 | 0.0178 |
| 1430 | 0.0228 |
| 1431 | 0.0198 |
| 1432 | 0.0212 |
| 1433 | 0.0274 |
| 1434 | 0.0290 |
| 1435 | 0.0264 |
| 1436 | 0.0295 |
| 1437 | 0.0373 |
| 1438 | 0.0408 |
| 1439 | 0.0128 |
| 1440 | 0.0690 |
| 1441 | 0.0298 |
| 1443 | 0.0316 |
| 1444 | 0.0252 |
| 1445 | 0.0320 |
| 1446 | 0.0140 |
| 1447 | 0.0316 |
| 1448 | 0.0260 |
| 1449 | 0.0170 |
| 1450 | 0.0134 |
| 1451 | 0.0217 |
| 1452 | 0.0391 |
| 1453 | 0.0146 |
| 1454 | 0.00615 |
| 1455 | 0.0211 |
| 1456 | 0.0184 |
| 1457 | 0.0180 |
| 1458 | 0.0191 |
| 1459 | 0.0207 |
| 1460 | 0.00799 |
| 1461 | 0.0138 |
| 1462 | 0.0201 |
| 1463 | 0.0229 |
| 1464 | 0.0134 |
| 1465 | 0.0236 |
| 1466 | 0.0179 |
| 1467 | 0.0110 |
| 1468 | 0.0350 |
| 1469 | 0.0230 |
| 1470 | 0.0308 |
| 1471 | 0.0142 |
| 1472 | 0.0289 |
| 1473 | 0.0169 |
| 1474 | 0.0138 |
| 1475 | 0.00720 |
| 1476 | 0.0162 |
| 1477 | 0.0181 |
| 1478 | 0.0130 |
| 1479 | 0.0167 |
| 1480 | ND |
| 1481 | 0.0208 |
| 1482 | 0.0166 |
| 1483 | 0.0137 |
| 1484 | 0.0229 |
| 1485 | 0.0229 |
| 1486 | 0.0107 |
| 1487 | 0.0254 |
| 1488 | 0.0123 |
| 1489 | 0.0137 |
| 1490 | 0.0291 |
| 1491 | 0.0290 |
| 1492 | 0.0201 |
| 1493 | 0.00683 |
| 1494 | 0.0247 |
| 1495 | 0.00709 |
| 1496 | 0.0325 |
| 1497 | 0.0129 |
| 1498 | 0.0291 |
| 1499 | 0.0275 |
| 1500 | 0.0170 |
| 1501 | 0.0205 |
| 1502 | 0.0262 |
| 1503 | 0.0192 |
| 1504 | 0.0136 |
| 1505 | 0.0130 |
| 1506 | 0.0274 |
| 1507 | 0.0160 |
| 1508 | 0.0174 |
| 1509 | 0.0375 |
| 1510 | 0.0201 |
| 1511 | 0.0232 |
| 1512 | 0.0122 |
| 1513 | 0.0134 |
| 1514 | 0.0517 |
| 1515 | 0.0321 |
| 1516 | 0.0170 |
| 1518 | 0.0107 |
| 1519 | 0.0153 |
| 1520 | 0.0179 |
| 1521 | 0.0183 |
| 1522 | 0.0177 |
| 1523 | 0.0131 |
| 1524 | 0.0125 |
| 1525 | 0.0151 |
| 1526 | 0.0112 |
| 1527 | 0.0156 |
| 1528 | 0.00631 |
| 1529 | 0.0201 |
| 1530 | 0.0335 |
| 1531 | 0.0134 |
| 1532 | 0.0112 |
| 1533 | 0.0217 |
| 1534 | 0.0158 |
| 1535 | 0.0174 |
| 1536 | 0.0183 |
| 1537 | 0.0189 |
| 1538 | 0.0145 |
| 1539 | 0.0125 |
| 1540 | 0.0195 |
| 1541 | 0.0106 |
| 1542 | 0.0186 |

TABLE 4B-continued

| Cmpd. | IC$_{50}$ (μM) |
|---|---|
| 1543 | 0.0205 |
| 1544 | 0.0131 |
| 1545 | 0.0275 |
| 1546 | 0.0134 |
| 1547 | 0.0152 |
| 1548 | 0.0362 |
| 1549 | 0.0262 |
| 1550 | 0.0229 |
| 1551 | 0.0220 |
| 1553 | 0.0129 |
| 1554 | 0.0151 |
| 1555 | 0.0239 |
| 1556 | 0.0499 |
| 1557 | 0.00677 |
| 1558 | 0.0690 |
| 1559 | 0.0134 |
| 1560 | 0.00631 |
| 1561 | 0.0130 |
| 1562 | 0.0168 |
| 1563 | 0.0130 |
| 1564 | 0.0106 |
| 1565 | 0.00799 |
| 1566 | 0.00439 |
| 1568 | 0.0216 |
| 1569 | 0.0195 |
| 1570 | 0.0229 |
| 1571 | 0.0205 |
| 1572 | 0.0200 |
| 1573 | 0.0222 |
| 1574 | 0.0134 |
| 1575 | 0.0147 |
| 1576 | 0.0179 |
| 1577 | 0.0133 |
| 1578 | 0.0203 |
| 1579 | 0.0303 |
| 1581 | 0.0143 |
| 1582 | 0.0192 |
| 1583 | 0.0582 |
| 1584 | 0.0369 |
| 1585 | 0.0152 |
| 1586 | 0.0318 |
| 1587 | 0.0397 |
| 1588 | 0.0264 |
| 1589 | 0.0124 |
| 1590 | 0.0360 |
| 1591 | 0.0362 |
| 1592 | 0.0203 |
| 1593 | 0.0616 |
| 1594 | 0.442 |
| 1595 | 0.0548 |
| 1596 | 0.654 |
| 1597 | 0.0221 |
| 1598 | 0.0375 |
| 1599 | 0.0167 |
| 1600 | 0.0203 |
| 1601 | 0.00805 |
| 1602 | 0.00388 |
| 1603 | 0.00212 |
| 1604 | 0.00396 |
| 1605 | 0.00378 |
| 1606 | 0.00460 |
| 1607 | 0.0146 |
| 1608 | 0.00659 |
| 1609 | 0.00488 |
| 1610 | 0.00602 |
| 1611 | 0.00385 |
| 1612 | 0.0137 |
| 1613 | 0.0161 |
| 1614 | 0.0314 |
| 1615 | 0.0147 |
| 1616 | 0.0115 |
| 1617 | 0.0156 |
| 1618 | 0.0124 |
| 1619 | 0.0316 |
| 1620 | 0.0179 |
| 1621 | 0.0721 |
| 1622 | 0.0173 |
| 1623 | ND |

TABLE 4B-continued

| Cmpd. | IC$_{50}$ (μM) |
|---|---|
| 1624 | 0.00417 |
| 1625 | ND |
| 1626 | 0.0303 |
| 1627 | ND |
| 1628 | ND |
| 1629 | ND |
| 1630 | ND |
| 1631 | 0.0161 |
| 1632 | 0.0424 |
| 1633 | 0.0526 |
| 1634 | 0.0174 |
| 1635 | 0.0215 |
| 1636 | 0.0388 |
| 1637 | 0.0177 |
| 1638 | 0.0388 |
| 1639 | 0.0305 |
| 1640 | ND |
| 1641 | 0.0189 |
| 1642 | 0.0245 |
| 1643 | 0.0188 |
| 1644 | 0.0145 |
| 1645 | 0.0232 |
| 1646 | 0.0263 |
| 1647 | 0.0196 |
| 1648 | 0.0133 |
| 1649 | 0.0183 |
| 1650 | 0.0107 |
| 1651 | ND |
| 1652 | ND |
| 1653 | 0.0265 |
| 1654 | 0.0210 |
| 1655 | 0.0134 |
| 1656 | ND |
| 1657 | ND |
| 1658 | ND |
| 1659 | ND |
| 1660 | ND |
| 1661 | ND |
| 1662 | 0.0221 |
| 1663 | 0.0141 |
| 1664 | ND |
| 1665 | 0.0146 |
| 1666 | ND |
| 1667 | 0.0122 |
| 1668 | 0.00567 |
| 1669 | 0.00917 |
| 1670 | 0.00568 |
| 1671 | 0.00414 |
| 1672 | 0.0132 |
| 1673 | 0.00722 |
| 1674 | 0.00650 |
| 1675 | 0.00411 |
| 1676 | 0.00433 |
| 1677 | 0.0129 |
| 1678 | 0.0280 |
| 1679 | 0.0293 |
| 1680 | 0.0233 |
| 1681 | 0.00827 |
| 1682 | 0.0151 |
| 1683 | 0.0183 |
| 1684 | ND |
| 1685 | ND |
| 1686 | ND |
| 1687 | ND |
| 1688 | 0.0127 |
| 1689 | 0.0222 |
| 1690 | 0.0274 |
| 1691 | 0.0179 |
| 1692 | ND |
| 1693 | ND |
| 1694 | ND |
| 1695 | ND |
| 1696 | ND |
| 1697 | ND |
| 1698 | ND |
| 1699 | ND |
| 1700 | ND |
| 1701 | ND |

TABLE 4B-continued

| Cmpd. | IC$_{50}$ (μM) |
|---|---|
| 1702 | ND |
| 1703 | 0.00600 |
| 1704 | 0.00654 |
| 1705 | 0.00480 |
| 1706 | 0.0121 |
| 1707 | 0.0157 |
| 1708 | 0.0162 |
| 1709 | 0.0284 |
| 1710 | ND |
| 1711 | ND |
| 1712 | ND |
| 1713 | 0.0158 |
| 1714 | ND |
| 1715 | ND |
| 1716 | ND |
| 1717 | 0.0134 |
| 1718 | ND |
| 1719 | ND |
| 1720 | ND |
| 1721 | ND |
| 1722 | ND |
| 1723 | ND |
| 1724 | 0.00407 |
| 1725 | ND |
| 1726 | ND |
| 1727 | 0.00384 |
| 1728 | ND |
| 1729 | ND |
| 1730 | ND |
| 1731 | ND |
| 1732 | ND |
| 1733 | 0.00811 |
| 1734 | 0.0194 |
| 1735 | 0.0336 |
| 1736 | 0.0126 |
| 1737 | 0.0143 |
| 1738 | 0.0255 |
| 1739 | 0.0333 |
| 1740 | 0.0126 |
| 1741 | 0.0110 |
| 1742 | 0.00543 |
| 1743 | 0.00687 |
| 1744 | 0.0115 |
| 1745 | 0.0110 |
| 1746 | 0.0108 |
| 1747 | 0.0165 |
| 1748 | 0.0175 |
| 1749 | 0.0164 |
| 1750 | 0.0161 |
| 1751 | ND |
| 1752 | ND |
| 1753 | ND |
| 1754 | ND |
| 1755 | ND |
| 1756 | ND |
| 1757 | ND |
| 1758 | ND |
| 1759 | ND |
| 1760 | ND |
| 1761 | 0.00565 |
| 1762 | 0.0250 |
| 1763 | 0.0233 |
| 1764 | 0.0190 |
| 1765 | 0.0123 |
| 1766 | ND |
| 1767 | 0.0174 |
| 1768 | 0.0313 |
| 1769 | 0.0164 |
| 1770 | 0.0175 |
| 1771 | 0.0266 |
| 1772 | 0.00607 |
| 1773 | 0.0475 |
| 1774 | 0.0450 |
| 1775 | 0.0321 |
| 1776 | 0.00365 |
| 1777 | ND |
| 1778 | ND |
| 1779 | 0.0351 |
| 1780 | 0.0109 |
| 1781 | 0.00832 |
| 1782 | ND |
| 1783 | ND |
| 1784 | ND |
| 1785 | ND |
| 1786 | ND |
| 1787 | ND |
| 1788 | ND |
| 1789 | ND |
| 1790 | ND |
| 1791 | 0.0101 |
| 1792 | 0.00924 |
| 1793 | 0.00729 |
| 1794 | 0.00928 |
| 1795 | 0.00896 |
| 1796 | ND |
| 1797 | ND |
| 1798 | ND |
| 1799 | ND |
| 1800 | ND |
| 1801 | ND |
| 1802 | ND |
| 1803 | ND |
| 1804 | ND |
| 1805 | ND |
| 1806 | ND |
| 1807 | 0.0104 |
| 1808 | 0.00540 |
| 1809 | 0.00757 |
| 1810 | 0.0129 |
| 1811 | 0.0127 |
| 1812 | 0.0184 |
| 1813 | ND |
| 1814 | ND |
| 1815 | ND |
| 1816 | ND |
| 1817 | 0.0258 |
| 1818 | 0.0130 |
| 1819 | 0.00440 |
| 1820 | 0.0122 |
| 1821 | ND |
| 1822 | ND |
| 1823 | ND |
| 1824 | ND |
| 1825 | 0.0171 |
| 1826 | 0.0184 |
| 1827 | 0.0148 |
| 1828 | ND |
| 1829 | 0.00627 |
| 1830 | 0.00806 |
| 1831 | 0.00500 |
| 1832 | 0.0205 |
| 1833 | 0.0148 |
| 1834 | ND |
| 1835 | ND |
| 1836 | ND |
| 1837 | ND |
| 1838 | 0.0123 |
| 1839 | 0.0345 |
| 1840 | 0.0264 |
| 1841 | ND |
| 1842 | ND |
| 1843 | ND |
| 1844 | ND |
| 1845 | ND |
| 1846 | ND |
| 1847 | ND |
| 1848 | ND |
| 1849 | ND |
| 1850 | ND |
| 1851 | ND |
| 1852 | ND |
| 1853 | ND |
| 1854 | ND |
| 1855 | ND |
| 1856 | ND |
| 1857 | ND |

TABLE 4B-continued

| Cmpd. | IC$_{50}$ (μM) |
|---|---|
| 1858 | ND |
| 1859 | ND |
| 1860 | ND |
| 1861 | ND |
| 1862 | ND |
| 1863 | ND |
| 1864 | ND |
| 1865 | ND |
| 1866 | ND |
| 1867 | ND |
| 1868 | ND |
| 1869 | ND |
| 1870 | ND |
| 1871 | ND |
| 1872 | ND |
| 1873 | ND |
| 1874 | ND |
| 1875 | ND |
| 1876 | ND |
| 1877 | ND |
| 1878 | ND |
| 1879 | ND |
| 1880 | ND |
| 1881 | ND |
| 1882 | ND |
| 1883 | ND |
| 1884 | ND |
| 1885 | ND |
| 1886 | ND |
| 1887 | ND |
| 1888 | ND |
| 1889 | ND |
| 1890 | ND |
| 1891 | ND |
| 1892 | ND |
| 1893 | ND |
| 1894 | ND |
| 1895 | 0.0127 |
| 1896 | 0.0122 |
| 1897 | 0.0131 |
| 1898 | 0.0613 |
| 1899 | 0.0164 |
| 1900 | 2.70 |
| 1901 | 0.0357 |
| 1902 | 0.0842 |
| 1903 | 0.0298 |
| 1904 | 0.0369 |
| 1905 | 0.881 |
| 1906 | ND |
| 1907 | 0.405 |
| 1908 | 0.00517 |
| 1909 | 0.0292 |
| 1910 | 0.0474 |
| 1911 | 0.00403 |
| 1912 | 0.00596 |
| 1913 | 0.0229 |
| 1914 | ND |
| 1915 | ND |
| 1916 | ND |
| 1917 | ND |
| 1918 | ND |
| 1919 | ND |
| 1920 | ND |
| 1921 | ND |
| 1922 | ND |
| 1923 | ND |
| 1924 | ND |
| 1925 | ND |
| 1926 | ND |
| 1927 | ND |
| 1928 | ND |
| 1929 | ND |
| 1930 | 0.00481 |
| 1931 | 0.0197 |
| 1932 | 0.00840 |
| 1933 | 0.0346 |
| 1934 | 0.0385 |
| 1935 | 0.0801 |

TABLE 4B-continued

| Cmpd. | IC$_{50}$ (μM) |
|---|---|
| 1936 | 0.0374 |
| 1937 | 0.0382 |
| 1938 | 0.0463 |
| 1939 | 0.0245 |
| 1940 | 0.0349 |
| 1941 | 0.0616 |
| 1942 | 0.182 |
| 1943 | 0.0424 |
| 1944 | 0.0249 |
| 1945 | 0.0449 |
| 1946 | 0.0447 |
| 1947 | 0.0297 |
| 1948 | 0.0356 |
| 1949 | 0.0216 |
| 1950 | 0.0417 |
| 1951 | 0.0199 |
| 1952 | ND |
| 1953 | 0.0893 |
| 1954 | 0.0170 |
| 1955 | ND |
| 1956 | ND |
| 1957 | ND |
| 1958 | ND |
| 1959 | 0.0463 |
| 1960 | 43.2 |
| 1961 | 0.211 |
| 1962 | ND |
| 1963 | 0.241 |
| 1964 | 0.0498 |
| 1965 | 0.0864 |
| 1966 | ND |
| 1967 | ND |
| 1968 | ND |
| 1969 | ND |
| 1970 | 0.0672 |
| 1971 | 0.0519 |
| 1972 | 0.0180 |
| 1973 | 0.0143 |
| 1974 | 0.0513 |
| 1975 | 0.109 |
| 1976 | 1.85 |
| 1977 | >1.00 |
| 1978 | 0.0253 |
| 1979 | ND |
| 1980 | ND |
| 1981 | 0.0238 |
| 1982 | 0.0364 |
| 1983 | 0.0826 |
| 1984 | ND |
| 1985 | ND |
| 1986 | 0.0785 |
| 1987 | 1.29 |
| 1988 | 0.0495 |
| 1989 | 0.0890 |
| 1990 | 0.0581 |
| 1991 | >300 |
| 1992 | 0.490 |
| 1993 | 0.412 |
| 1994 | 0.0418 |
| 1995 | 0.0593 |
| 1996 | 0.189 |
| 1997 | 0.0775 |
| 1998 | 0.409 |
| 1999 | 0.482 |
| 2000 | 18.2 |
| 2001 | 65.8 |
| 2002 | 0.259 |
| 2003 | 0.264 |
| 2004 | 0.639 |
| 2005 | 0.364 |
| 2006 | 0.611 |
| 2007 | >300 |
| 2008 | 0.0961 |
| 2009 | 2.15 |
| 2010 | 1.19 |
| 2011 | 0.529 |
| 2012 | ND |
| 2013 | >10.0 |

TABLE 4B-continued

| Cmpd. | IC$_{50}$ (µM) |
|---|---|
| 2014 | 12.2 |
| 2015 | 0.0511 |
| 2016 | 0.613 |
| 2017 | 0.0506 |
| 2018 | 0.0244 |
| 2019 | 0.0249 |
| 2020 | 0.0330 |
| 2021 | ND |
| 2022 | ND |
| 2023 | ND |
| 2024 | ND |
| 2025 | ND |
| 2026 | 0.656 |
| 2027 | >1.00 |
| 2028 | >1.00 |
| 2029 | ND |
| 2030 | ND |
| 2031 | ND |
| 2032 | ND |
| 2034 | 0.00620 |
| 2035 | 0.0723 |
| 2036 | 0.0384 |
| 2037 | >1.00 |
| 2038 | ND |
| 2039 | ND |
| 2041 | ND |
| 2042 | ND |

Example 5B. Cell Proliferation Assays

MDA-MB-361 cells were maintained in DMEM supplemented with 10% FBS and 1× penicillin/streptomycin solution at 370° C. in a CO$_2$ incubator. For cell proliferation assays, exponentially growing cells were seeded at 2,000 cells per well in 96-well flat bottom white polystyrene plates (ThermoFisher) and cultured overnight. The following day, compound was added in a 9 point 3-fold dilution series starting from a top concentration of 1 or 10 µM (as indicated) together with a DMSO control. The final DMSO concentration in samples was 0.1%.

Figure 2:
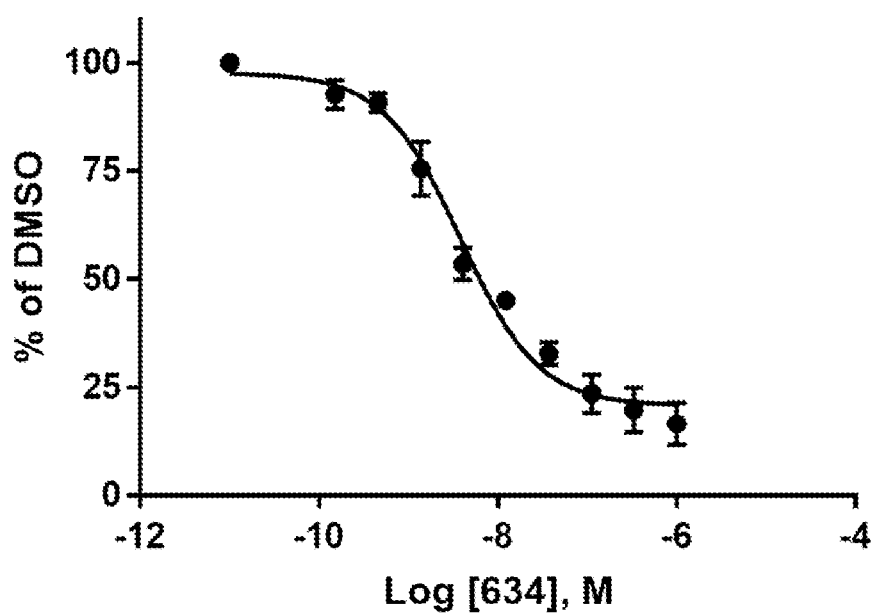
FIG. 2, graph showing the results of a cell proliferation assay using compound 634.
Figure 3:
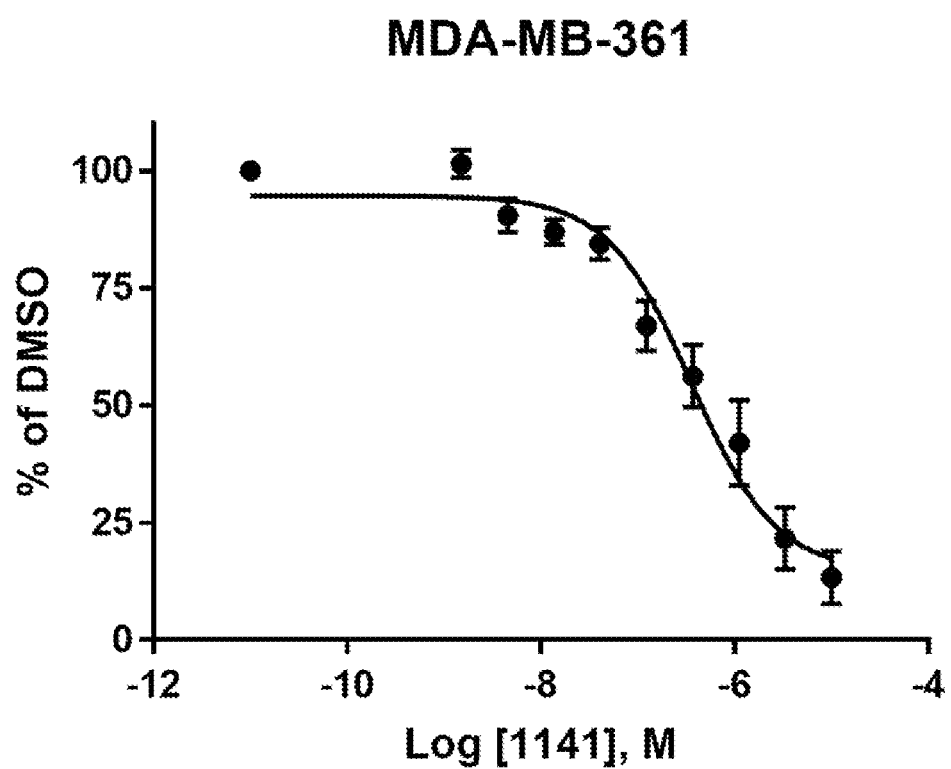
FIG. 3, graph showing the results of a cell proliferation assay using compound 1141.

Cells were incubated for up to 6 days hours at 37° C. in a CO$_2$ incubator. Baseline viability of untreated cells was measured on the day of treatment and proliferation was measured after 6 days hours of treatment using CELLTITER-GLO® reagent from Promega (Madison, Wis.) according to the manufacturer's instructions. Response to compound was calculated relative to the DMSO control (% of control) using the formula, % of control (DMSO)= [(CTG$_{cells}$+inhibitor)/(CTG$_{DMSO\ control}$)]×100. Data were plotted using Prism (GraphPad software), and IC$_{50}$ and E$_{max}$ values were calculated from a 4 parameter, variable slope non-linear regression model. Results are shown below and in FIGS. 1-3.

| Compound | Mean IC50 (nM) | n |
|---|---|---|
| 1188 | 46.8* | 7 |
| 634 | 3.8 | 3 |
| 1141 | 361 | 2 |

*95% CI (nM) 35.1-62.2, E$_{max}$ (%), 90.2

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A compound of Formula III:

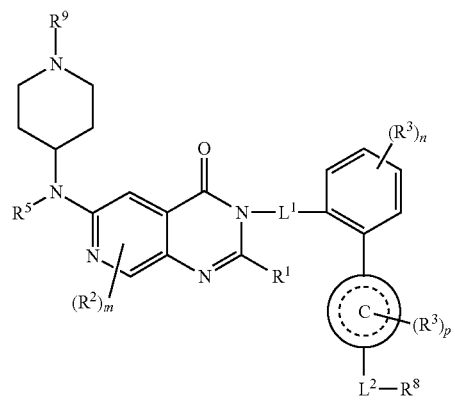

or a pharmaceutically acceptable salt thereof, wherein:
L$^1$ is —(CH$_2$)—, —(CH$_2$)$_2$—, —(CH$_2$)$_3$—, —CH((C$_1$-C$_8$)alkyl)(CH$_2$)—, —CH((C$_1$-C$_8$)alkyl)(CH$_2$)$_2$—, —(CH$_2$)$_2$—O—, —CH$_2$CH═CH—, —CH$_2$C≡C— or —CH$_2$(cyclopropyl)-;
L$^2$ is —C(R$^6$)(R$^6$)—, —C(R$^6$)(R$^6$)C(R$^6$)(R$^6$)—, —C(R$^6$)═C(R$^6$)—, —N(R$^5$)C(R$^6$)(R$^6$)—, —OC(R$^6$)(R$^6$)—, —C(═O)—, —C(═O)N(R$^5$)C(R$^6$)(R$^6$)— or a bond;
Ring C is a heteroaryl;
R$^1$ is H, OH, halo, CN, (C$_1$-C$_8$)alkyl, (C$_1$-C$_8$)haloalkyl, (C$_3$-C$_6$)cycloalkyl or NR$^5$R$^5$;
R$^2$ is independently H, halo, CN, NO, NO$_2$, C≡CH, (C$_1$-C$_8$)alkyl, (C$_1$-C$_8$)haloalkyl, CH$_2$SR$^5$, OR$^5$, NHR$^5$, NR$^5$R$^5$, [(C$_1$-C$_8$)alkylene]heterocyclyl, [(C$_1$-C$_8$)alkylene]heteroaryl, [(C$_1$-C$_8$)alkylene]NHR$^5$, [(C$_1$-C$_8$)alkylene]NR$^5$R$^5$, C(O)R$^5$, C(O)OR$^5$, C(O)NHR$^5$, C(O)NR$^5$R$^5$, SR$^5$, S(O)R$^5$, SO$_2$R$^5$, SO$_2$NHR$^5$, SO$_2$NR$^5$R$^5$, NH(CO)R$^6$, NR$^5$(CO)R$^6$, aryl, heteroaryl, cycloalkyl or heterocyclyl;
R$^3$ is independently OH, halo, CN, NO$_2$, (C$_1$-C$_6$)alkyl, (C$_1$-C$_6$)haloalkyl, (C$_1$-C$_6$)alkoxy, C≡CH, NHR$^7$, NR$^7$R$^7$, CO$_2$H, CO$_2$R$^7$, [(C$_1$-C$_3$)alkylene] (C$_1$-C$_3$)alkoxy, [(C$_1$-C$_3$)alkylene]CO$_2$H, (C$_3$-C$_5$)cycloalkyl, ═O, ═S, SR$^7$, SO$_2$R$^7$, NH(CO)R$^7$ or NR$^7$(CO)R$^7$;
R$^5$ is independently H, (C$_1$-C$_3$)alkyl, (C$_1$-C$_3$)haloalkyl, (C$_3$-C$_5$)cycloalkyl or heterocyclyl;
R$^6$ is independently H, OH, halo, CN, (C$_1$-C$_3$)alkyl, (C$_1$-C$_3$)haloalkyl, (C$_1$-C$_3$)alkoxy, NHR$^7$, NR$^7$R$^7$, CO$_2$H, [(C$_1$-C$_3$)alkylene]CO$_2$H, (C$_3$-C$_5$)cycloalkyl, SR$^7$, NH(CO)R$^7$ or NR$^7$(CO)R$^7$;
R$^7$ is independently H, (C$_1$-C$_8$)alkyl, (C$_1$-C$_8$)haloalkyl, cycloalkyl, heterocyclyl, aryl or heteroaryl;

R$^8$ is H, OH, CO$_2$H, CO$_2$R$^7$, CF$_2$C(R$^6$)$_2$OH, C(R$^6$)$_2$OH, C(CF$_3$)$_2$OH, SO$_2$H, SO$_3$H, CF$_2$SO$_2$C(R$^6$)$_3$, CF$_2$SO$_2$N(H)R$^5$, SO$_2$N(H)R$^5$, SO$_2$N(H)C(O)R$^6$, C(O)N(H)SO$_2$R$^5$, C(O)haloalkyl, C(O)N(H)OR$^5$, C(O)N(R$^5$)OH, C(O)N(H)R$^5$, C(O)NR$^5$C(O)N(R$^5$)$_2$, P(O)(OR$^5$)OH, P(O)(C(R$^6$)$_3$)C(R$^6$)$_3$, B(OH)$_2$, heterocyclyl or heteroaryl;

R$^9$ is H, (C$_1$-C$_8$)alkyl, (C$_1$-C$_8$)haloalkyl, cycloalkyl or heterocyclyl;

m is 0, 1, or 2;

n is 0, 1, 2 or 3;

p is 0, 1, 2 or 3;

wherein any alkyl, alkylene, cycloalkyl, heterocyclyl, heteroaryl or aryl is optionally substituted with 1, 2 or 3 groups selected from OH, CN, SH, SCH$_3$, SO$_2$CH$_3$, SO$_2$NH$_2$, SO$_2$NH(C$_1$-C$_4$)alkyl, halogen, NH$_2$, NH(C$_1$-C$_4$)alkyl, N[(C$_1$-C$_4$)alkyl]$_2$, NH(aryl), C(O)NH$_2$, C(O)NH(alkyl), CH$_2$C(O)NH(alkyl), COOH, COOMe, acetyl, (C$_1$-C$_8$)alkyl, (C$_1$-C$_8$)haloalkyl, O(C$_1$-C$_8$)alkyl, O(C$_1$-C$_8$)haloalkyl, (C$_2$-C$_5$)alkenyl, (C$_2$-C$_5$)alkynyl, thioalkyl, cyanomethylene, alkylaminyl, alkylene-C(O)NH$_2$, alkylene-C(O)—NH(Me), NHC(O)alkyl, CH$_2$—C(O)—(C$_1$-C$_8$)alkyl, C(O)—(C$_1$-C$_8$)alkyl, and alkylcarbonylaminyl.

2. The compound or the salt of claim 1, wherein L$^2$ is a bond.

3. The compound or the salt of claim 1, wherein Ring C is heteroaryl.

4. The compound or the salt of claim 1, wherein Ring C is

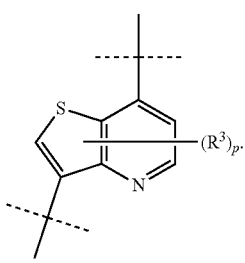

5. The compound or the salt of claim 1, wherein R$^1$ is H, (C$_1$-C$_8$)alkyl or (C$_1$-C$_8$)haloalkyl.

6. The compound or the salt of claim 1, wherein R$^2$ is halo, CN, (C$_1$-C$_8$)alkyl, (C$_1$-C$_8$)haloalkyl or OR$^5$.

7. The compound or the salt of claim 1, wherein R$^2$ is halo, CN or (C$_1$-C$_8$)haloalkyl.

8. The compound or the salt of claim 1, wherein R$^5$ is H, (C$_1$-C$_3$)alkyl or (C$_1$-C$_3$)haloalkyl.

9. The compound or the salt of claim 1, wherein R$^8$ is CO$_2$H or C(O)N(H)SO$_2$R$^5$.

10. The compound or the salt of claim 1, wherein R$^9$ is cycloalkyl or heterocyclyl.

11. The compound or the salt of claim 1, wherein p=0 or 1.

12. A compound having the formula:

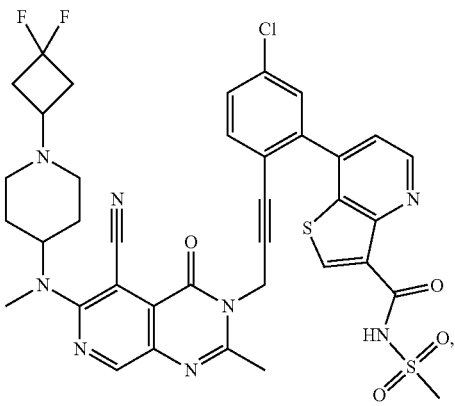 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(C)(=O)=O)csc12]

or a pharmaceutically acceptable salt thereof.

13. A compound having the formula:

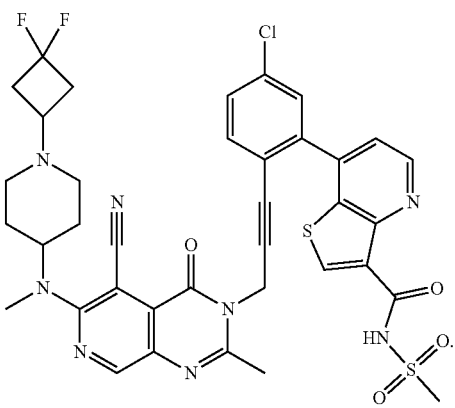 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(C)(=O)=O)csc12]

14. A pharmaceutically acceptable salt of a compound having the formula:

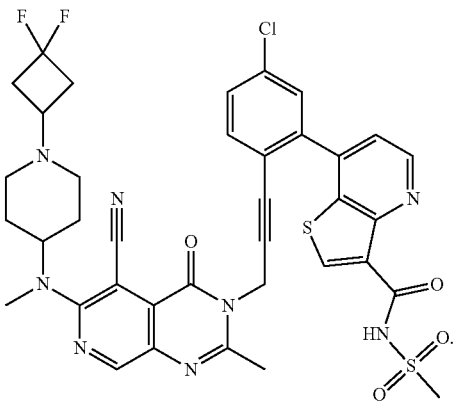 [SMILES: Cc1nc2cnc(N(C)C3CCN(C4CC(F)(F)C4)CC3)c(C#N)c2c(=O)n1CC#Cc1ccc(Cl)cc1-c1ccnc2c(C(=O)NS(C)(=O)=O)csc12]

15. A compound having the formula:

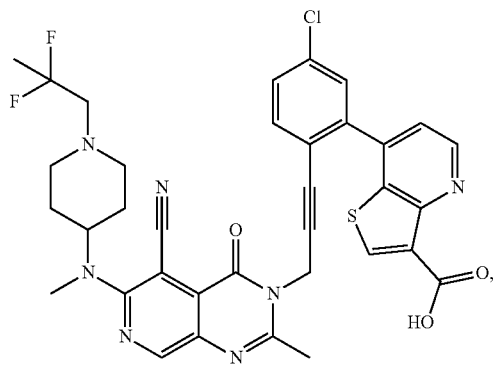

or a pharmaceutically acceptable salt thereof.

16. A compound having the formula:

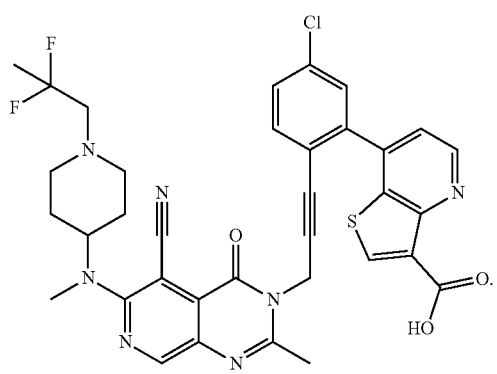 [SMILES: Cc1nc2cnc(N(C)C3CCN(CC(C)(F)F)CC3)c(C#N)c2c(=O)n1CC#Cc1ccc(Cl)cc1-c1ccnc2c(C(=O)O)csc12]

17. A pharmaceutically acceptable salt of a compound having the formula:

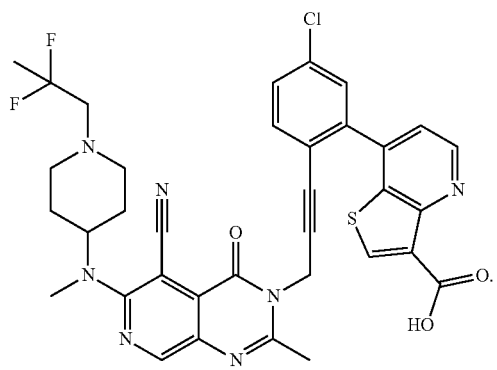 [SMILES: Cc1nc2cnc(N(C)C3CCN(CC(C)(F)F)CC3)c(C#N)c2c(=O)n1CC#Cc1ccc(Cl)cc1-c1ccnc2c(C(=O)O)csc12]

18. A compound having the formula:

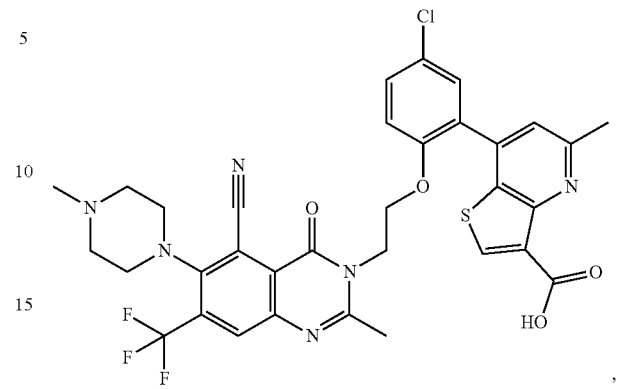

or a pharmaceutically acceptable salt thereof.

19. A compound having the formula:

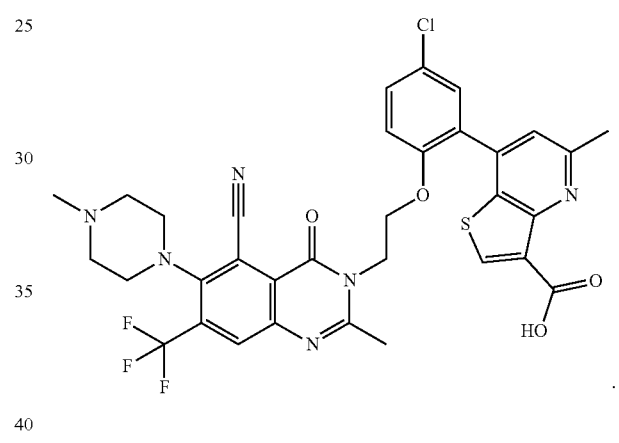

20. A pharmaceutically acceptable salt of a compound having the formula:

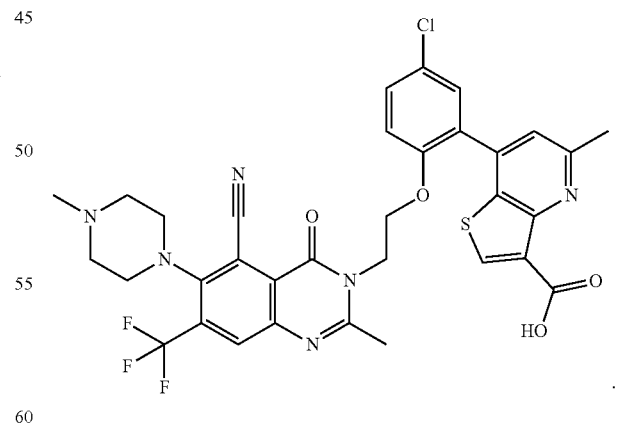

21. A pharmaceutical composition comprising:
(a) a compound or a salt of claim 1; and
(b) a pharmaceutically acceptable carrier, diluent, or excipient.

22. The pharmaceutical composition of claim 21, wherein the compound has the formula

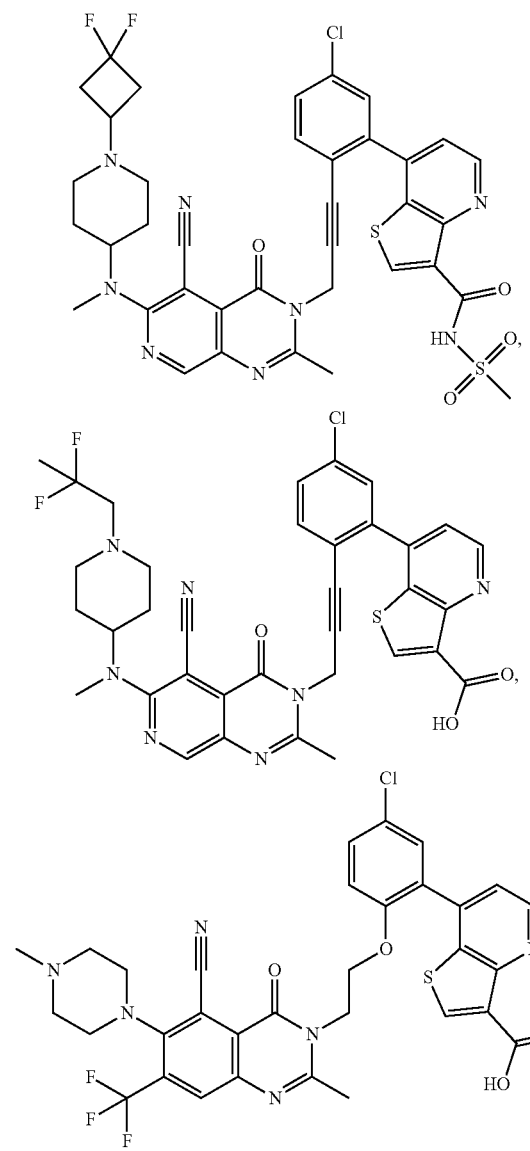

23. A method of treating cancer, comprising administering to an individual in need thereof a therapeutically effective amount of a compound or a salt of claim 1, wherein the cancer is colon cancer, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, brain cancer, CNS cancer, renal cancer, prostate cancer, ovarian cancer, or breast cancer.

24. The method of claim 23, wherein the compound has the formula

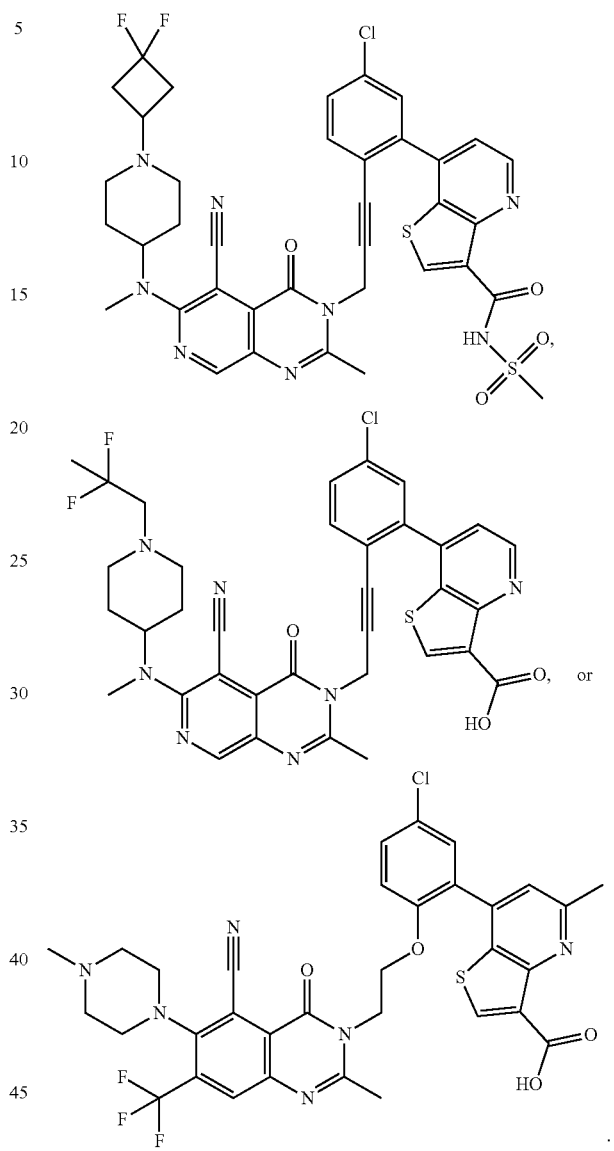

25. The method of claim 23, wherein the cancer is a metastatic cancer.

26. The method of claim 23, wherein the cancer is breast cancer, prostate cancer, or lung cancer.

27. The method of claim 26, wherein the cancer is breast cancer.

28. The method of claim 27, wherein the breast cancer is hormone receptor positive breast cancer.

* * * * *